United States Patent
Gu et al.

(10) Patent No.: US 12,410,436 B2
(45) Date of Patent: Sep. 9, 2025

(54) ADENO-ASSOCIATED VIRUS (AAV) PRODUCER CELL LINES

(71) Applicant: LONZA HOUSTON, INC., Pearland, TX (US)

(72) Inventors: Bingnan Gu, Pearland, TX (US); Gang Li, Pearland, TX (US); Caitlin Tripp, Pearland, TX (US)

(73) Assignee: LONZA HOUSTON, INC., Pearland, TX (US)

( * ) Notice: Subject to any disclaimer, the term of this patent is extended or adjusted under 35 U.S.C. 154(b) by 0 days.

(21) Appl. No.: 18/498,577

(22) Filed: Oct. 31, 2023

(65) Prior Publication Data
US 2025/0136999 A1 May 1, 2025

(51) Int. Cl.
*C12N 15/63* (2006.01)
*C07K 14/005* (2006.01)
*C12N 15/85* (2006.01)

(52) U.S. Cl.
CPC .......... *C12N 15/635* (2013.01); *C07K 14/005* (2013.01); *C12N 15/85* (2013.01); *C12N 2710/16222* (2013.01); *C12N 2760/14122* (2013.01); *C12N 2830/003* (2013.01)

(58) Field of Classification Search
CPC .................. C12N 15/635; C12N 15/85; C12N 2710/16222; C12N 2760/14122; C12N 2830/003; C07K 14/005
See application file for complete search history.

(56) References Cited

U.S. PATENT DOCUMENTS

| 5,622,856 | A | 4/1997 | Natsoulis |
| 2021/0062161 | A1* | 3/2021 | Vink ..................... C07K 14/005 |

FOREIGN PATENT DOCUMENTS

| WO | WO-2006083800 A2 * | 8/2006 | ............... A61P 25/28 |
| WO | 2015/162211 A1 | 10/2015 | |
| WO | 2018/136566 A1 | 7/2018 | |
| WO | 2018/192982 A2 | 10/2018 | |

OTHER PUBLICATIONS

Mi, Jing, et al. "H1 Rna polymerase III promoter-driven expression of an RNA aptamer leads to high-level inhibition of intracellular protein activity." Nucleic acids research 34.12 (2006): 3577-3584. (Year: 2006).*
Chu et al., "SV40 DNA Transfection of Cells in Suspension: Analysis of the Efficiency of Transcription and Translation of T Antigen," Gene 13(2): 197-202 (1981).
Clark et al., "Cell Lines for the Production of Recombinant Adeno-Associated Virus," Human Gene Therapy 6:1329-1341 (1995).
Bianchi et al., "A potent enhancer element in the 5'-UTR intron is crucial for transcriptional regulation of the human ubiquitin C gene," Gene. 448(1):88-101 (2009).
Deuschle et al., "Tetracycline-Reversible Silencing of Eukaryotic Promoters," Mol. Cell Biol. 15(4): 1907-1914 (1995).
Farris and Pintel, "Improved splicing of Adeno-associated viral (AAV) capsid protein-supplying pre-mRNAs leads to increased recombinant AAV vector production," Hum Gene Ther. 19(12): 1421-1427 (2008).
Feng et al., "The VP35 protein of Ebola virus inhibits the antiviral effect mediated by double-stranded RNA-dependent protein kinase PKR," J Virol. 81(1):182-192 (2007).
Graham et al., "A New Technique for the Assay of Infectivity of Human Adenovirus 5 DNA," Virology, 52(2):456-457 (1973).
Guido et al., "Human bocavirus: Current knowledge and future challenges," World J. Gateroenterol 22:8684-8697.
Huang et al., "Adenovirus early region 4 encodes two gene products with redundant effects in lytic infection," Journal of Virology 63(6):2605-2615 (1989).
Ishibashi et al., "Adenoviruses of animals," The Adenoviruses, Ginsberg, ed., Plenum Press, New York, N.Y., pp. 497-562 (1984).
Kotin, R. M., "Prospects for the Use of Adeno-Associated Virus as a Vector for Human Gene Therapy," Human Gene Therapy 5:793-801 (1994).
Langland et al., "Inhibition of PKR by RNA and DNA viruses," Virus Res. 119(1):100-110 (2006).
Li et al., "Role for Highly Regulated rep Gene Expression in Adeno-Associated Virus Vector Production," Journal of Virology 71:5236-5243 (1997).
Machitani et al., "Development of an adenovirus vector lacking the expression of virus-associates RNAs," Journal of Controlled Release 154(3):285-289 (2011).
Mullick et al., "The cumate gene-switch: a system for regulated expression in mammalian cells," BMC Biotechnology 6:43 (1-18) (2006).
Muzyczka, N., "Use of Adeno-Associated Virus as a General Transduction Vector for Mammalian Cells," Current Topics in Microbiol. and Immunol. 158:97-129 (1992).
Nakamura et al., "Development of packaging cell lines for generation of adeno-associated virus vectors by lentiviral gene transfer of trans-complementary components," Eur. J. Haematol. 73:285-294 (2004).
Robert et al., "Manufacturing of Recombinant Adeno-Associated Viruses Using Mammalian Expression Platforms," Biotechnology Journal 12(1600193): 1-16 (2017).
Smith and Katin, "An adeno-associated virus (AAV) initiator protein, Rep 78, catalyzes the cleavage and ligation of single-stranded AAV ori DNA," J. Viral. 74(7):3122-3129 (2002).
Strauss, "Adenovirus infections in humans," In The Adenoviruses, Ginsberg, ed., Plenum Press, New York, N.Y., pp. 451-596 (1984).
Szulc et al., "A versatile tool for conditional gene expression and knockdown," Nature Methods 3:109-116 (2006).

(Continued)

*Primary Examiner* — Ekaterina Poliakova-Georgantas
*Assistant Examiner* — John Charles McKillop
(74) *Attorney, Agent, or Firm* — MEDLER FERRO WOODHOUSE & MILLS PLLC

(57) ABSTRACT

The present disclosure relates to nucleic acids encoding helper genes and adeno-associated virus (AAV) genes, under the control of inducible promoters. The disclosure also relates to a mammalian cell line for producing AAV as well as methods of using the mammalian cells for producing AAVs.

3 Claims, 24 Drawing Sheets

Specification includes a Sequence Listing.

(56) References Cited

OTHER PUBLICATIONS

Tetracycline On, "Tetracycline (Tet) Inducible Expression", Addgene. Retrieved from https://www.addgene.org/collections/tetracycline/ on Jun. 2, 2023.

Tordo et al., "A Novel Adeno-Associated Virus Capsid with Enhanced Neurotropism Corrects a Lysosomal Transmembrane Enzyme Deficiency," Brain ePub 141(7): 2014-2031 (2018).

Urabe et al., "Insect Cells as a Factory to Produce Adeno-Associated Virus Type 2 Vectors," Human Gene Therapy 13: 193501943 (2002).

Wiederschain et al., "Single-vector inducible lentiviral RNAi system for oncology target validation," Cell Cycle 8:498-504 (2009).

Yao et al., "Tetracycline Repressor, tetR, rather than the tetR-Mammalian Cell Transcription Factor Fusion Derivatives, Regulates Inducible Gene Expression in Mammalian Cells," Human Gene Therapy 9:1939-1950 (1998).

Zhou et al., "A New Vector System with Inducible E2a Cell Line for Production of Higher Titer and Safer Adenoviral Vectors," Virology 275(2):348-357 (2000).

\* cited by examiner

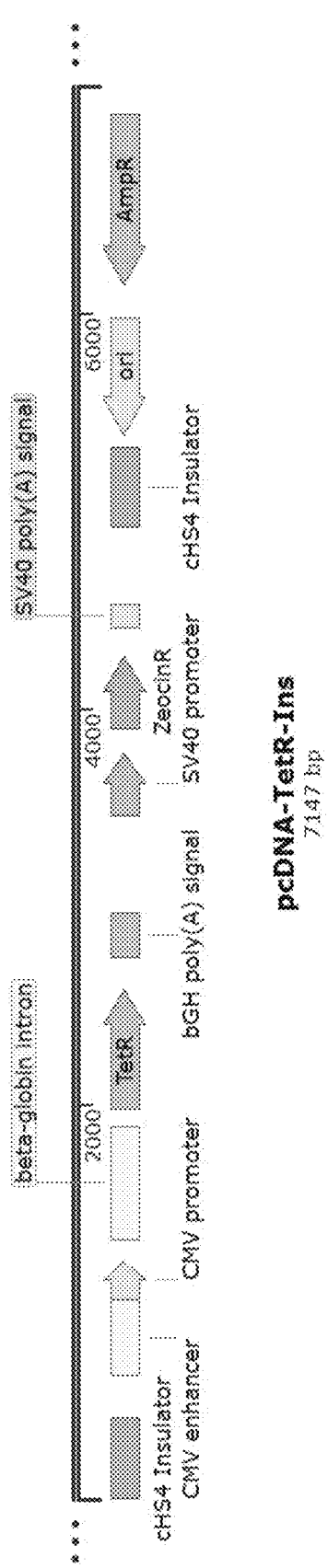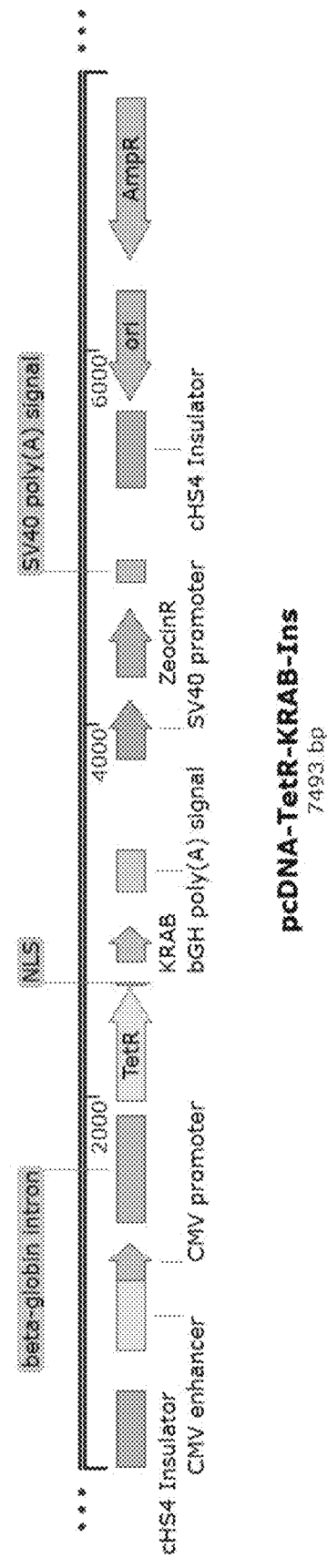
FIG. 2A  pcDNA-TetR-Ins 7147 bp
FIG. 2B  pcDNA-TetR-KRAB-Ins 7493 bp

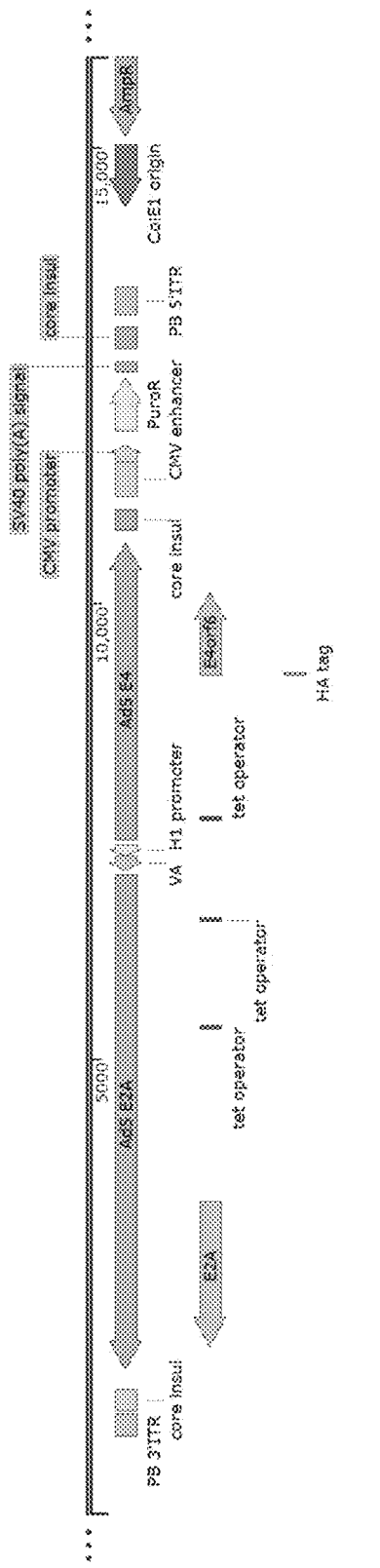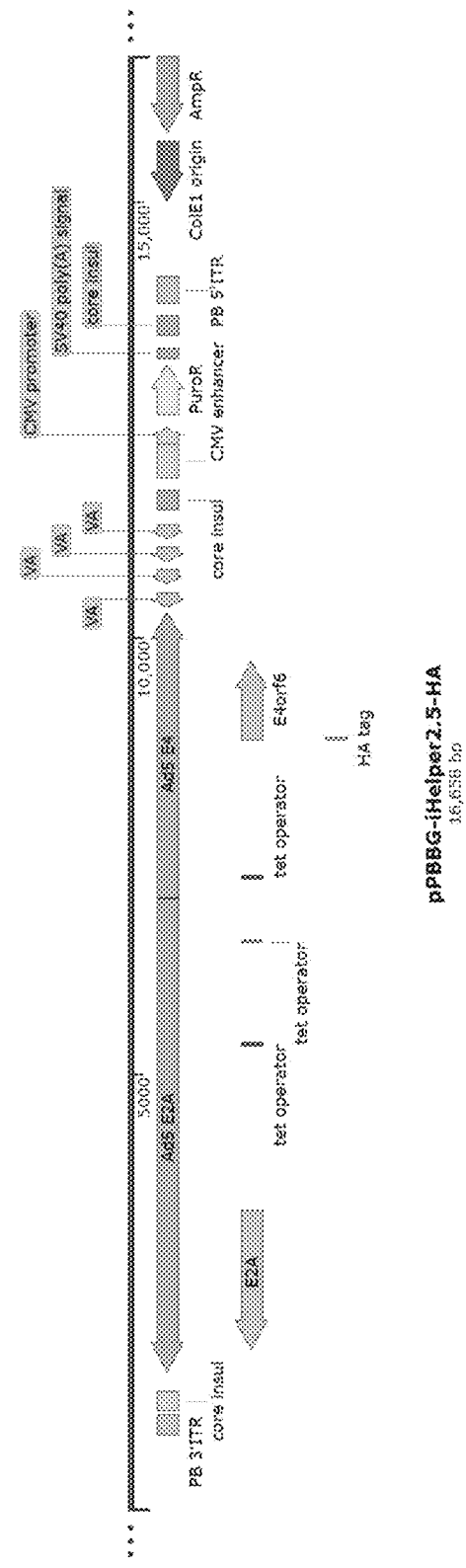

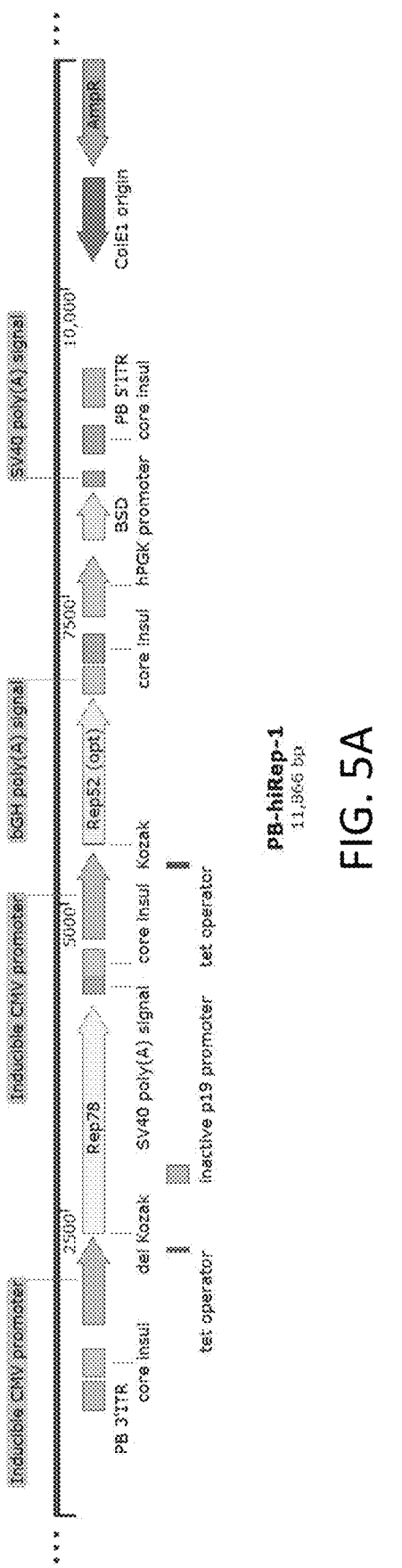
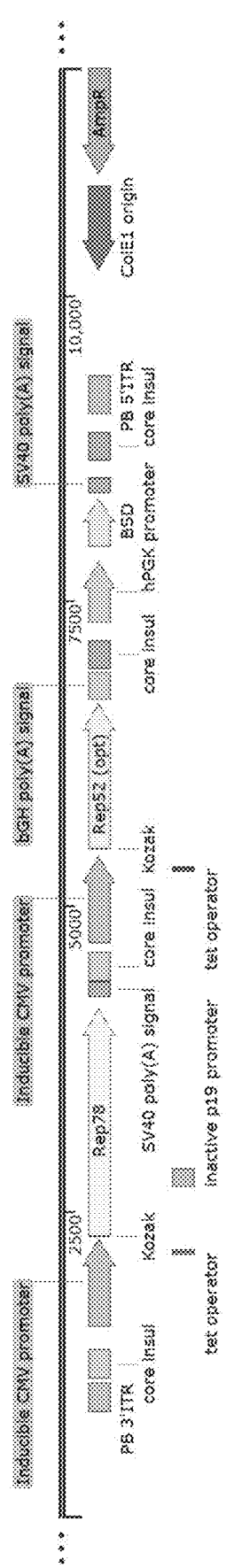
FIG. 5A
FIG. 5B

PB-hiRep-3
11,580 bp

PB-hiRep-4
11,702 bp

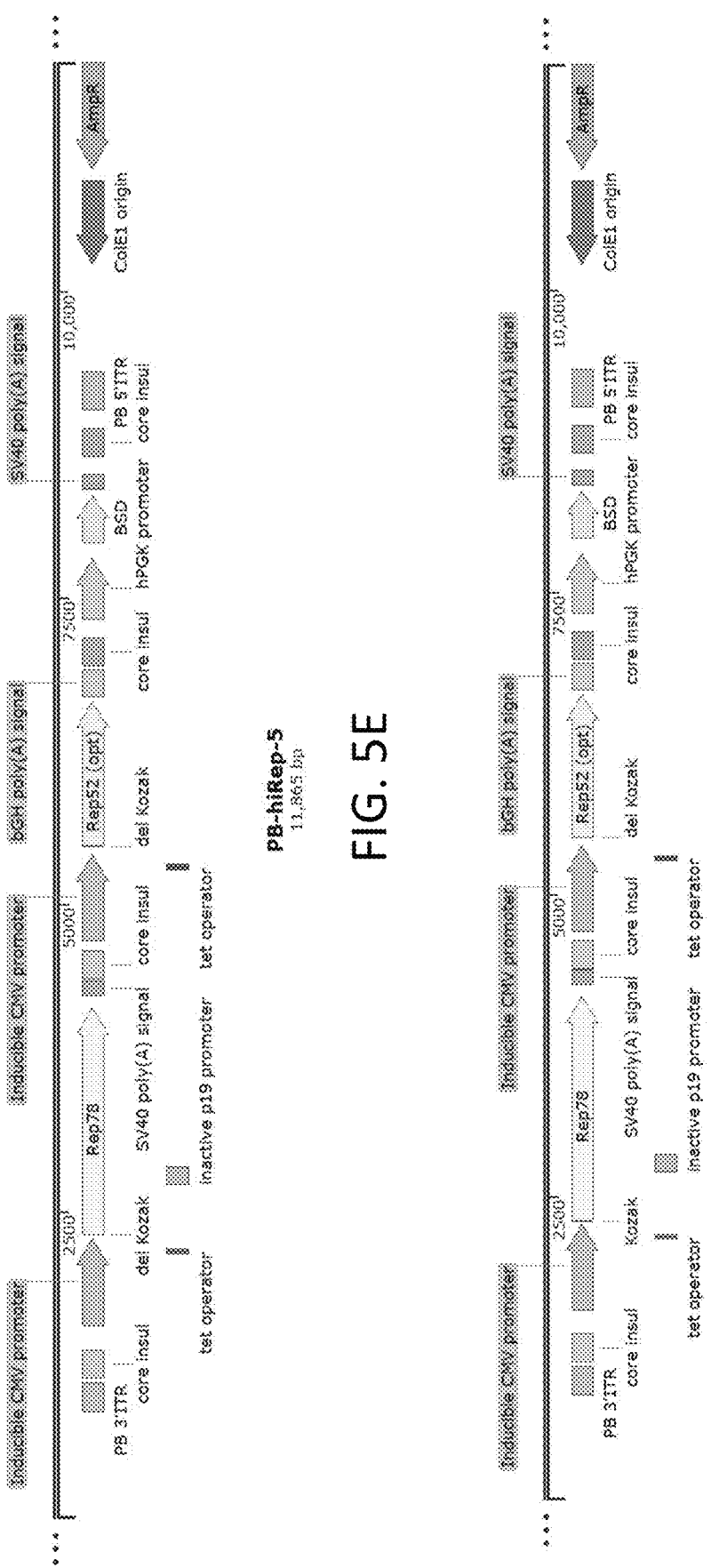

PB-hiRep-9
11,861 bp

PB-hiRep-10
11,580 bp

PB-hiRep-11
11,702 bp

PB-hiRep-12
11,859 bp

PB-hiRep-13
11,654 bp

PB-hiRep-14
11,573 bp

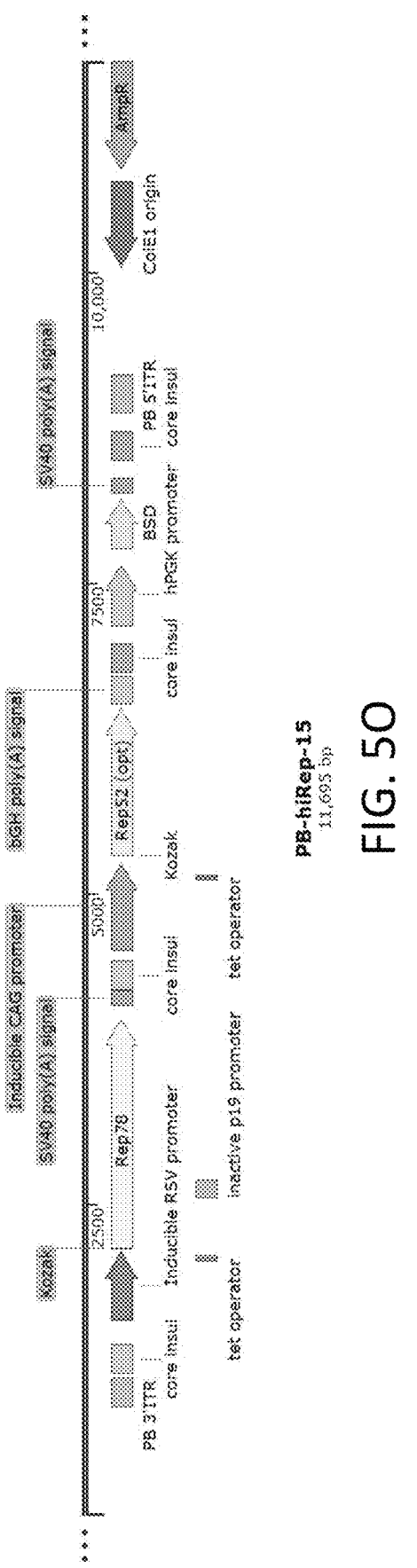
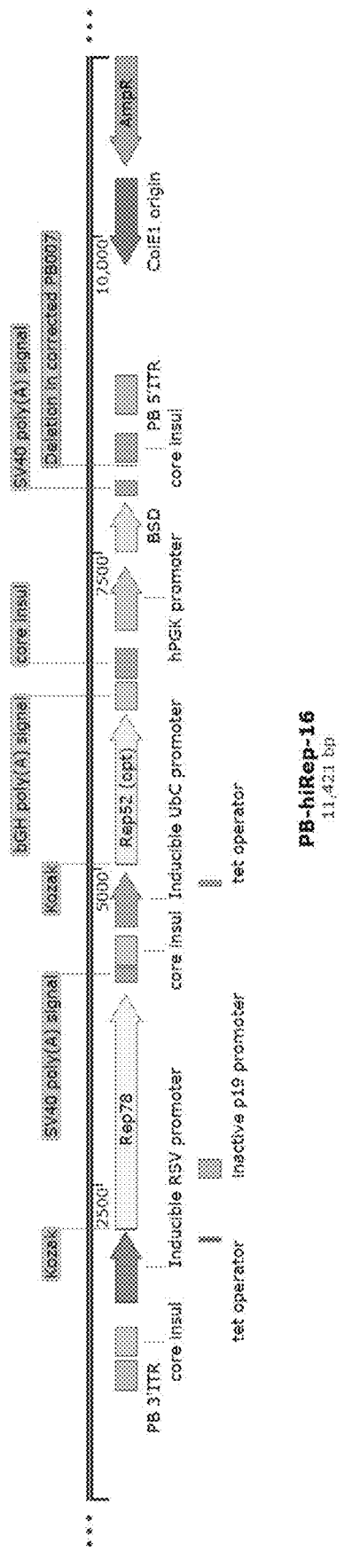
FIG. 5O
FIG. 5P

ADENO-ASSOCIATED VIRUS (AAV) PRODUCER CELL LINES

REFERENCE TO SEQUENCE LISTING

The application contains a Sequence Listing which has been submitted electronically in .XML format and is hereby incorporated by reference in its entirety. Said .XML copy, created on Oct. 30, 2023, is named "0132-0318US1.xml" and is 513,568 bytes in size. The sequence listing contained in this .XML file is part of the specification and is hereby incorporated by reference herein in its entirety.

FIELD OF THE INVENTION

The present disclosure provides mammalian cell lines for producing adeno-associated virus (AAV). The cells suitably include isolated nucleic acids encoding helper genes and AAV genes, under the control of inducible promoters. The disclosure also relates to methods of producing AAVs using the mammalian cells and nucleic acids described herein.

BACKGROUND

Recombinant adeno-associated virus (rAAV) has emerged as an important gene therapy vector for broad clinical application due to its high safety profile and strong potency for delivering functional genes into a variety of tissues with long-term therapeutic benefits. Multiple AAV-based gene therapies have been approved by the US Food and Drug Administration (FDA) and European Medicines Agency (EMA). With 25 viral-vector therapeutics in late-stage development and approximately 120 in Phase II trials as of February 2022, the number of approved therapies is only expected to grow.

However, the challenges of current AAV manufacturing processes include low productivity and scalability, low batch-to-batch reproducibility, high cost and complex supply chain issues, which significantly limit the access to the gene delivery platform for the treatment of a variety of human diseases. Additionally, constitutive expression of both helper and Rep genes required for AAV production can be cytotoxic. AAV stable producer cell lines (PCLs) and vectors that are designed to tightly control the expression of helper and Rep genes can overcome these limitations and bolster large-scale current good manufacturing practice (cGMP) manufacturing for AAV gene therapy.

SUMMARY OF THE INVENTION

In some embodiments, the present disclosure is directed to an isolated nucleic acid molecule operably comprising a first inducible promoter with two tetracycline operator sequences (a $TetO_2$ sequence), an E2A gene under control of the first inducible promoter, a viral associated (VA) non-coding RNA under control of a second inducible promoter, a third inducible promoter with a $TetO_2$ sequence, an E4 gene under control of the third inducible promoter, and an antibiotic resistance gene.

In further embodiments, the disclosure provides an isolated nucleic acid molecule operably comprising, a first inducible promoter with a $TetO_2$ sequence, an E2A gene under control of the first inducible promoter, a viral associated (VA) non-coding RNA under control of a second inducible promoter, a third inducible promoter with a $TetO_2$ sequence, an E4 gene under control of the third inducible promoter, an expression cassette encoding a protein ortholog of the VA RNA and a peptide protein tag under the control of a depressible promoter comprising a human Cytomegalovirus (CMV) promoter and a $TetO_2$ sequence, a termination sequence, and an antibiotic resistance gene.

In still further embodiments, the present disclosure is directed to an isolated nucleic acid molecule operably comprising a plasmid encoding a first inducible promoter with a $TetO_2$ sequence, a Rep78 gene, including a silenced p19 promoter located within the Rep78 gene coding region, wherein the silenced p19 promoter comprises mutations in SP1, TATA-1, and/or TATA-2 sites, a second inducible promoter and a $TetO_2$ sequence, a Rep52 gene under control of the second inducible promoter, termination sequence and an antibiotic resistance gene.

In still further embodiments, the present disclosure is directed to a mammalian cell for producing an adeno-associated virus (AAV), comprising any of isolated nucleic acid molecules disclosed herein integrated into its genome. In some embodiments, the mammalian cell further comprises a nucleic acid encoding a transcriptional repression domain in frame with a nucleic acid encoding a tetracycline repressor protein. In some embodiments, the mammalian cell comprises a nucleic acid molecule encoding a gene of interest.

In still further embodiments, the disclosure provides a method for producing an adeno-associated virus (AAV), comprising inducing production of the genomically integrated nucleic acid sequence of any of the mammalian cells disclosed herein, culturing the mammalian cell, and harvesting the AAV.

BRIEF DESCRIPTION OF THE FIGURES

FIGS. 2A and 2B show an exemplary TetR and TetR-KRAB fusion system.

FIGS. 3A-3I show exemplary nucleic acid molecules for production of helper genes in accordance with embodiments hereof.

DETAILED DESCRIPTION OF THE INVENTION

Figure 1:
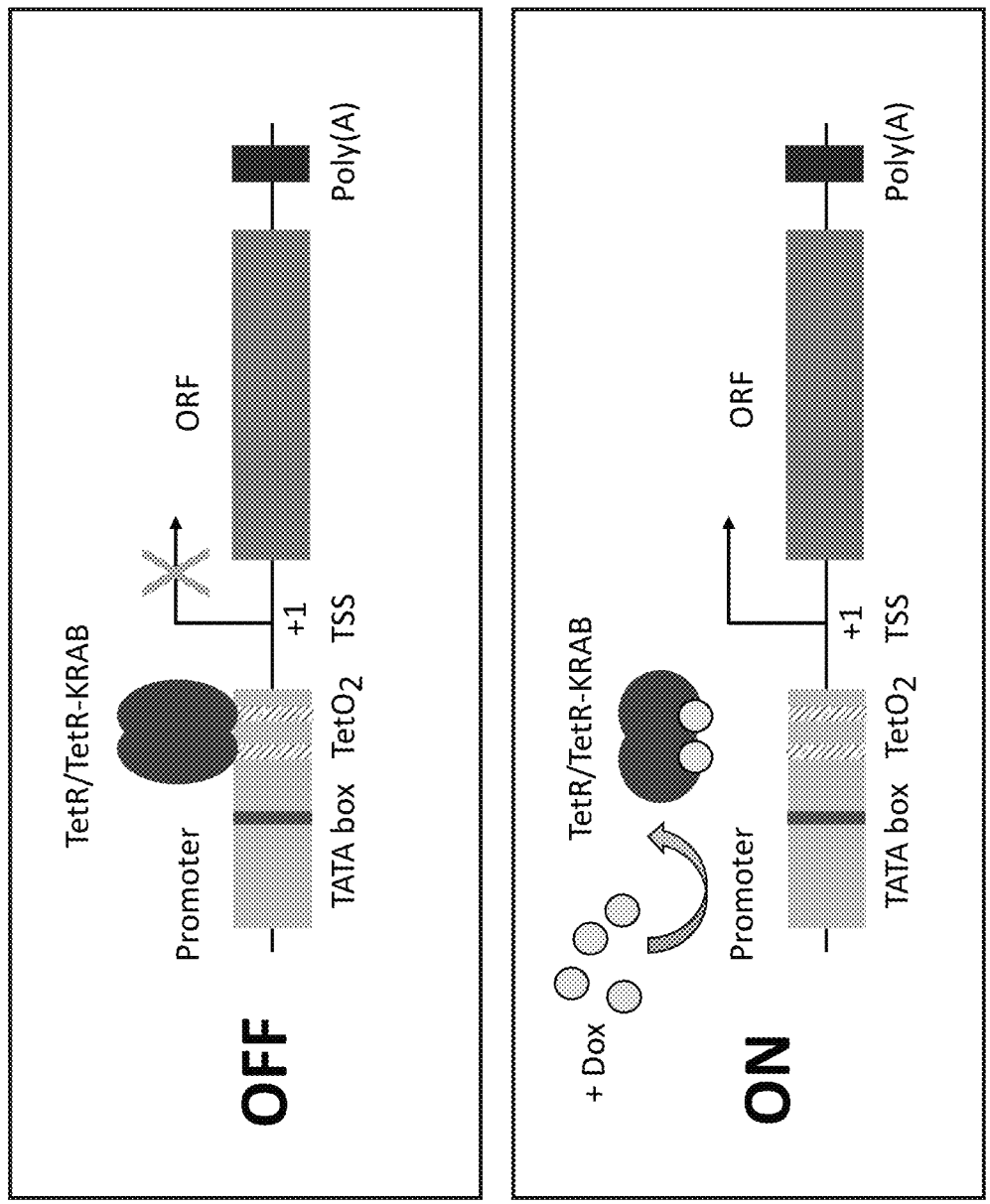
FIG. 1 shows a schematic of the use of the Tet-On inducible system utilizing the tetracycline repressor protein to repress and activate expression of a protein.

Unless otherwise defined herein, scientific and technical terms used in the present disclosure shall have the meanings that are commonly understood by one of ordinary skill in the art. Further, unless otherwise required by context, singular terms shall include pluralities and plural terms shall include the singular. The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the method/device being employed to determine the value. Typically, the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer only to alternatives or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited, elements or method steps. It is contemplated that any embodiment discussed in this specification can be implemented with respect to any method, system, host cells, expression vectors, and/or composition of the invention. Furthermore, compositions, systems, cells, and/or nucleic acids of the invention can be used to achieve any of the methods as described herein.

The use of the term "for example" and its corresponding abbreviation "e.g." (whether italicized or not) means that the specific terms recited are representative examples and embodiments of the disclosure that are not intended to be limited to the specific examples referenced or cited unless explicitly stated otherwise.

As used herein, "between" is a range inclusive of the ends of the range. For example, a number between x and y explicitly includes the numbers x and y, and any numbers that fall within x and y.

As used herein, the term "adeno-associated virus (AAV)" refers to a small sized, replicative-defective nonenveloped virus containing a single stranded DNA of the family Parvoviridae and the genus Dependoparvovirus. Over 10 adeno-associated virus serotypes have been identified so far, with serotype AAV2 being the best characterized. Other non-limiting examples of AAV serotypes are ANC80, AAV1, AAV3, AAV4, AAV5, AAV6, AAV7, AAV8, AAV9, AAV10, and AAV11. In addition to these serotypes, AAV pseudotypes have been developed. An AAV pseudotype contains the capsid of a first serotype and the genome of a second serotype (e.g., the pseudotype AAV2/5 would correspond to an AAV with the genome of serotype AAV2 and the capsid of AAV5).

As referred to herein, the term "adenovirus" refers to a nonenveloped virus with an icosahedral nucleocapsid containing a double stranded DNA of the family Adenoviridae. Over 50 adenoviral subtypes have been isolated from humans and many additional subtypes have been isolated from other mammals and birds. Birds. See, e.g., Ishibashi et al., "Adenoviruses of animals," In The Adenoviruses, Ginsberg, ed., Plenum Press, New York, N.Y., pp. 497-562 (1984); Strauss, "Adenovirus infections in humans," In The Adenoviruses, Ginsberg, ed., Plenum Press, New York, N.Y., pp. 451-596 (1984). These subtypes belong to the family Adenoviridae, which is currently divided into two genera, namely Mastadenovirus and Aviadenovirus. All adenoviruses are morphologically and structurally similar. In humans, however, adenoviruses show diverging immunological properties and are, therefore, divided into serotypes. Two human serotypes of adenovirus, namely AV2 and AV5, have been studied intensively and have provided the majority of general information about adenoviruses.

Adeno-associated virus (AAV) has emerged as the vector of choice for gene therapy in over 120 clinical trials worldwide. The fast-growing demand of recombinant AAV requires highly efficient and robust manufacturing platforms. However, current methods for AAV production, including transient transfection and helper virus systems, are extremely costly and lab-intensive. Thus, described herein are isolated nucleic acid molecules for producing an adeno-associated virus (AAV) and plasmid/helper virus-free AAV producer cell lines, and methods of use thereof, that provide efficient AAV manufacturing for a long-term solution at significantly reduced cost. The AAV producer cell line described herein represents a next generation platform for both clinical and commercial AAV manufacturing.

As used herein, a "vector" or "expression vector" refers to a nucleic acid replicon, such as a plasmid, phage, virus, or cosmid, to which another nucleic acid segment may be attached to bring about the replication and/or expression of the attached nucleic acid segment in a host cell. The term "vector" includes episomal (e.g., plasmids) and non episomal vectors. The term "vector" may also include synthetic vectors. Non-limiting examples of vectors include baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (e.g., mammalian cells such as the E1 complementary producer cells described herein, including but not limited to HEK293 cells, PER.C6 cells, CAP® cells, and derivatives thereof). Vectors may be introduced into the desired host cells, e.g., HEK293 cells, PER.C6 cells, CAP® cells, or derivatives thereof, by well-known methods, including, but not limited to, transfection, transduction, cell fusion, and lipofection. Vectors can comprise various regulatory elements including, e.g., constitutive and inducible promoters, transcription enhancers, transcription terminators, and the like.

As used herein an "isolated nucleic acid molecule" includes vectors and plasmids that can contain the isolated nucleic acid molecule, as well as similar structures where the isolated nucleic acid molecule can be manipulated, stored, shipped, and ultimately utilized in various cell transfection systems. The isolated nucleic acid molecules described herein can be used for production of AAVs as described herein, but can also be utilized in various non-AAV producing cell lines (including transient transfection systems). The isolated nucleic acid molecules described herein suitably further include various additional elements and sequences as required to allow for use in the cellular systems, including mammalian cells, described herein.

A "nucleic acid," "nucleic acid molecule," or "oligonucleotide" means a polymeric compound comprising covalently linked nucleotides. The term "nucleic acid" includes polyribonucleic acid (RNA) and polydeoxyribonucleic acid (DNA), both of which may be single- or double-stranded.

DNA includes, but is not limited to, complimentary DNA (cDNA), genomic DNA, plasmid or vector DNA, and synthetic DNA. RNA includes, but is not limited to, mRNA, tRNA, rRNA, snRNA, microRNA, miRNA, or MIRNA.

A "gene" refers to an assembly of nucleotides that encode a polypeptide, and includes cDNA and genomic DNA nucleic acid molecules. "Gene" also refers to a nucleic acid fragment that can act as a regulatory sequence preceding (5' non-coding sequences) and following (3' non-coding sequences) the coding sequence. In some embodiments, genes are integrated with multiple copies. In some embodiments, genes are integrated at predefined copy numbers.

As referred to herein, the term "heterologous gene" or "HG" as it relates to nucleic acid sequences such as a coding sequence or a control sequence, denotes a nucleic acid sequence, e.g., a gene, that is not normally joined together, and/or are not normally associated with a particular cell. In some embodiments, a heterologous gene is a construct where the coding sequence itself is not found in nature (e.g., synthetic sequences having codons different from the native gene). Allelic variation or naturally occurring mutational events do not give rise to heterologous DNA, as used herein.

In the various embodiments described herein, the nucleic acid molecules are capable of encoding the various genes. That is the nucleic acid molecules, when transcribed, produce mRNA for the genes described herein, which is then translated to the desired or required proteins.

The various nucleic acid molecules encoding the various genes described herein are suitably under control of a promoter. As used herein "under control" refers to a gene being regulated by a "promoter," "promoter sequence," or "promoter region," which refers to a DNA regulatory region/sequence capable of binding RNA polymerase and initiating transcription of a downstream coding or non-coding gene sequence. In other words, the promoter and the gene are in operable combination or operably linked. As referred to herein, the terms "in operable combination", "in operable order", "operably linked" and "operably" refer to the linkage of nucleic acid sequences in such a manner that a promoter capable of directing the transcription of a given gene and/or the synthesis of a desired protein molecule is produced.

In some examples of the present disclosure, the promoter sequence includes the transcription initiation site and extends upstream to include the minimum number of bases or elements necessary to initiate transcription at levels detectable above background. In some embodiments, the promoter sequence includes a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the gene expression, e.g., in the host cell or vectors of the present disclosure. In some embodiments, the promoter is not a leaky promoter, i.e., the promoter is not constitutively expressing any of the gene products as described herein. In other embodiments as described herein, the promoter is a constitutive promoter, which initiates mRNA synthesis independent of the influence of an external regulation.

Suitably, the promoters used to control the transcription of the various genes for producing the AAVs described herein are derepressible promoters. As used herein, a "derepressible promoter" refers to a structure that includes an inducible or a functional promoter and additional elements or sequences capable of binding to a repressor element to cause repression of the inducible or functional promoter. "Repression" refers to the decrease or inhibition of the initiation of transcription of a downstream coding or non-coding gene sequence by a promoter. A "repressor element" refers to a protein or polypeptide that is capable of binding to a promoter (or near a promoter) so as to decrease or inhibit the activity of the promoter. A repressor element can interact with a substrate or binding partner of the repressor element, such that the repressor element undergoes a conformation change. This conformation change in the repressor element takes away the ability of the repressor element to decrease or inhibit the promoter, resulting in the "derepression" of the promoter, thereby allowing the promoter to proceed with the initiation of transcription.

In some embodiments, the derepressible promoter comprises an inducible or functional promoter and one or more tetracycline operator sequences ($TetO_2$). An "inducible promoter" regulates (e.g., activates or inactivates) transcriptional activity of a nucleic acid to which it is operably linked when the promoter is influenced by or contacted by a corresponding regulatory protein or other external stimuli such as chemicals, stress, or biotic stimuli. A "functional promoter" refers to a promoter, that absent the action of the repressor element, would be capable of initiation transcription. Various inducible and functional promoters that can be used in the practice of the present invention are known in the art, and include for example, PCMV, PHI, P19, P5, P40 and promoters of Adenovirus helper genes (e.g., E1A, E1B, E2A, E4Orf6, and VA).

The term "Tet operator sequence", "Tet operator sequence motif", "Tet operator", "$TetO_2$" or "TetO" as used herein is intended to encompass all classes of Tet operator sequences, e.g., TetO(A), TetO(B), TetO(C), TetO(D), TetO(E), TetO (G), TetO(H), TetO(J) and TetO(Z). The nucleotide sequences of Tet repressors of members of the A, B, C, D, E, G, H, J and Z classes, and their corresponding Tet operator sequences are well known in the art, see, for example, Waters 1983, Null. Acids Res 11:6089-6105, Hillen 1983, Nucl. Acids Res. 11:525-539, Postle 1984, Nucl. Acids Res. 12:4849-4863, Unger 1984, Gene 31:103-108, Unger 1984, Nucl Acids Res. 12:7693-7703 and Tovar 1988, Mol. Gen. Genet. 215:76-80, which are incorporated herewith by reference with respect to the specifically disclosed Tet operator sequences and in their entireties. Tet operator sequences are also disclosed in U.S. Pat. No. 5,464,758.

Exemplary repressor elements and their corresponding binding partners that can be used as derepressible promoters are known in the art, and include systems such as the cumate gene-switch system (CuO operator, CymR repressor and cumate binding partner) (see, e.g., Mullick et al., "The cumate gene-switch: a system for regulated expression in mammalian cells," *BMC Biotechnology* 6:43 (1-18) (2006), the disclosure of which is incorporated by reference herein in its entirety, including the disclosure of the derepressible promoter system described therein) and the TetO/TetR system described herein (see, e.g., Yao et al., "Tetracycline Repressor, tetR, rather than the tetR-Mammalian Cell Transcription Factor Fusion Derivatives, Regulates Inducible Gene Expression in Mammalian Cells," Human Gene Therapy 9:1939-1950 (1998), the disclosure of which is incorporated by reference herein in its entirety).

VA (virus-associated) RNA is a non-coding type found in adenoviruses. It plays a role in the regulation of translation. There are two copies of this RNA called VAI or RNA I VA and VAII or RNA II VA. The two RNA VA genes are distinct genes in the adenovirus genome. RNA I VA is the main species with RNA II VA expressed at a lower level. Neither transcript is polyadenylated and both are transcribed by PolIII.

As described herein, the nucleic acid molecules suitably encode viral helper gene. Viral helper genes include various adenoviral virus genes, herpes virus genes and bocavirus genes (see, e.g., Guido et al., "Human bocavirus: Current knowledge and future challenges," World J. Gateroenterol 22:8684-8697, the disclosure of which is incorporated by reference herein in its entirety). In exemplary embodiments, the viral helper gene is an adenovirus helper gene. As referred to herein, the term "adenovirus helper gene" or "AV helper gene" refers to a gene that is composed of one or more nucleic acid sequences derived from one or more adenovirus subtypes or serotypes that contributes to Adeno-associated virus replication and packaging. In some embodiments, the Adenovirus helper gene is E1A, E1B, E2A, E4 (including E4Orf6), VA, or a combination thereof or any other adenovirus helper gene. In exemplary embodiments, the adenovirus helper gene comprises both E2A and E4Orf6 genes.

In still further embodiments, provided herein is an isolated nucleic acid molecule operably comprising a first inducible promoter and two tetracycline operator sequences (a $TetO_2$ sequence), an E2A gene under control of the first inducible promoter, a viral associated (VA) non-coding RNA under control of a second inducible promoter, a third inducible promoter and a $TetO_2$ sequence, an E4 gene under control of the third inducible promoter, and an antibiotic resistance gene.

In other embodiments, the present disclosure provides an isolated nucleic acid molecule operably comprising, a first inducible promoter and a $TetO_2$ sequence, an E2A gene under control of the first inducible promoter, a viral associated (VA) non-coding RNA under control of a second inducible promoter, a third inducible promoter and a $TetO_2$ sequence, an E4 gene under control of the third inducible promoter, an expression cassette encoding a protein ortholog of the VA RNA and a peptide protein tag under the control of a depressible promoter comprising a human Cytomegalovirus (CMV) promoter and a $TetO_2$ sequence, a termination sequence, and an antibiotic resistance gene.

As described herein, in exemplary embodiments, the E2A gene that is encoded by the nucleic acid molecules is suitably under the control of a first inducible promoter that is native to the E2A gene. In some embodiments, the VA non-coding RNA that is encoded by the nucleic acid molecules is suitably under the control of a second inducible promoter that is native to the VA non-coding RNA. In some embodiments, the second inducible promoter is an H1 promoter. In some embodiments, the E4 gene that is encoded by the nucleic acid molecules is suitably under the control of a third inducible promoter that is native to the E4 gene.

As used herein, protein orthologs refer to proteins that have the same specificity in different organisms, e.g., bind the same ligand and similar DNA sites in related genomes. Hence, orthologous proteins carry the same or similar specificity determining residues. In some embodiments, the isolated nucleic acid molecule described herein comprises a protein ortholog of the of the VA RNA. In some embodiments, the protein ortholog is an influenza non-structural 1 protein (NS1), Ebola viral protein 35 (VP35), orthoreovirus sigma 3 protein (σ3), group C rotavirus non-structural protein 3 (NSP3), vaccinia virus E3L protein (E3L), herpes simplex virus type 1 US11 protein (US11), Epstein-Barr virus SM protein (SM), baculovirus PK2 protein (PK2), hepatitis C virus non-structural protein 5A protein (NS5A), human herpes virus-8 protein vIRF-2 (vIRF-2), human immunodeficiency virus protein Tat, vaccinia virus K3L protein (K3L), Herpes Simplex virus protein γ134.5/ICP34.5, or human papilloma virus-18 E6 protein (E6). In some embodiments, the protein ortholog is VP35. In some embodiments, the protein ortholog is SM.

Alternatively, or in addition, the protein ortholog of the VA RNA of any isolated nucleic acid molecule of the present invention may be operably linked to a peptide tag to assist in its isolation and detection, or to assist in the identification and expression of the encoded protein. A variety of peptide tags can be used in the context of the present invention, including PK tags, FLAG tags, MYC tags, hemagglutinin (HA) tags and polyhistidine tags. Peptide tags can be diagnosed by immunodetection tests, which use anti-tag antibodies. In some embodiments, the peptide tag is located individually at the N-terminus of the protein ortholog of the VA RNA. In some embodiments, the isolated nucleic acid molecule comprises a peptide protein tag. In some embodiments, the peptide protein tag is an HA tag. In some embodiments, the peptide protein tag is a FLAG-tag. In some embodiments, the FLAG-tag is an N-terminal flag tag.

As used herein, the role of the termination sequence is to define the end of a transcriptional unit (such as a gene) and initiate the process of releasing the newly synthesized RNA from the transcription machinery. Terminators are found downstream of the gene to be transcribed, and typically occur directly after any 3' regulatory elements, such as the polyadenylation or poly(A) signal. In some embodiments, any of the nucleic acid molecules disclosed herein comprise a termination sequence. In some embodiments, the termination sequence is a bovine growth hormone polyadenylation (bgh-PolyA) signal.

As referred to herein, a "reporter gene" is a gene whose expression confers a phenotype upon a cell that can be easily identified and measured. In some embodiments, the reporter gene comprises a fluorescent protein gene. In some embodiments, the reporter gene comprises a selection gene.

In some embodiments, the isolated nucleic acid molecules comprise a selection gene. As referred to herein, the term "selection gene" refers to the use of a gene which encodes an enzymatic activity that confers the ability to grow in medium lacking what would otherwise be an essential nutrient; in addition, a selection gene may confer resistance to an antibiotic or drug upon the cell in which the selection gene is expressed. A selection gene may be used to confer a particular phenotype upon a host cell. When a host cell must express a selection gene to grow in selective medium, the gene is said to be a positive selection gene. A selection gene can also be used to select against host cells containing a particular gene; a selection gene used in this manner is referred to as a negative selection gene. In some embodiments, the selection gene is an antibiotic resistance gene. In some embodiments, the antibiotic resistance gene is a puromycin resistance gene. In some embodiments, the antibiotic resistance gene is a blasticidin resistance gene. In some embodiments, the antibiotic resistance gene is a hygromycin resistance gene. In some embodiments, the antibiotic resistance gene is a zeocin resistance gene.

In exemplary embodiments, the nucleic acid molecules include two inverted terminal repeat (ITR) sequences. As known in the art, these ITR sequences (i.e., AAV2 ITR) are single stranded sequence of nucleotides, followed downstream by its reverse compliment. ITR sequences represent the minimal sequence required for replication, rescue, packaging and integration of the AAV genome. Suitably, these ITR sequences flank a gene of interest. Thus, in embodiments, the nucleic acid molecules further encode a gene of interest. This gene of interest can be, for example, a reporter gene, a selection gene, or a gene of therapeutic interest, for example. In some embodiments, the nucleic acid sequence is flanked on both the 5' and 3' ends by transposon-specific inverted terminal repeats (ITR).

As used herein, "core insulator" refers to a gene boundary element that blocks the interaction between an enhancer and a promoter. The presence of the core insulator between the enhancer and the promoter allows the insulator to block subsequent interactions. The core insulator can determine the set of genes that the enhancer can influence. Insulators are required when two adjacent genes on a chromosome have very different transcriptional patterns and it is necessary to induce or suppress one mechanism without inhibiting the adjacent genes. In some embodiments, any of the nucleic acid sequences disclosed herein comprise a core insulator sequence inserted downstream of the ITR on the 3' end and upstream of the ITR on the 5' end. In some embodiments, the nucleic acid molecule comprises a core insulator sequence inserted between the termination sequence and the antibiotic resistance gene.

As referred to herein, the term "Rep" gene refers to the art-recognized region of the AAV genome which encodes the replication proteins of the virus which are collectively required for replicating the viral genome, or functional homologues thereof such as the human herpesvirus 6 (HHV-6) rep gene which is also known to mediate AAV2 DNA replication. Thus, the Rep coding region can include the genes encoding for AAV Rep78 and Rep68 (the "long forms of Rep"), and Rep52 and Rep40 (the "short forms of Rep"), or functional homologues thereof. The Rep coding region, as used herein, can be derived from any viral serotype, such as the AAV serotypes described herein. The region need not include all wild-type genes but may be altered, (e.g., by insertion, deletion or substitution of nucleotides), so long as the Rep genes present provide for sufficient integration functions when expressed in a suitable target cell. See, e.g., Muzyczka, N., Current Topics in Microbiol. and Immunol. 158:97-129 (1992); and Kotin, R. M., Human Gene Therapy 5:793-801 (1994).

In still further embodiments, provided herein is an isolated nucleic acid molecule comprising a plasmid encoding a first inducible promoter and a $TetO_2$ sequence, a Rep78 gene, including a silenced p19 promoter located within the Rep78 gene coding region, wherein the silenced p19 promoter comprises mutations in SP1, TATA-1, and/or TATA-2 sites, a second inducible promoter and a $TetO_2$ sequence, a Rep52 gene under control of the second inducible promoter, termination sequence and an antibiotic resistance gene.

The terms "sequence identity" or "% identity" in the context of nucleic acid sequences described herein refer to the percentage of residues in the compared sequences that are the same when the sequences are aligned over a specified comparison window. A comparison window can be a segment of at least 10 to over 1000 residues in which the sequences can be aligned and compared. Methods of alignment for determination of sequence identity are well-known and can be performed using publicly available databases such as BLAST (blast.ncbi.nlm.nih.gov/Blast. CGI.).

The Kozak consensus sequence, Kozak consensus or Kozak sequence, is known as a sequence which occurs on eukaryotic mRNA and has the consensus (gcc)gccRccAUGG, where R is a purine (adenine or guanine) three bases upstream of the start codon (AUG), which is followed by another "G." In some embodiments, the isolated nucleic acid molecules disclosed herein comprise a Kozak consensus sequence. In some embodiments, the nucleic acid molecules comprise a consensus sequence that has at least about 70%, at least about 80%, at least about 90% sequence identity, or more identity to the Kozak consensus sequence. In some embodiments, the isolated nucleic acid molecule includes a Kozak consensus sequence after the gene cassette encoding one or more proteins of interest is inserted into the vector, e.g., at the restriction site downstream of the promoter. For example, the isolated nucleic acid molecule can include a nucleotide sequence of GCCGCCATG, where the ATG is the start codon of the protein of interest. In some embodiments, the isolated nucleic acid molecule comprises a nucleotide sequence of GCGGCCGCCATG, where the ATG is the start codon of the protein of interest. In some embodiments, the Rep78 gene of the isolated nucleic acid molecule further comprises a Kozak consensus sequence. In some embodiments, the Rep52 gene of the isolated nucleic acid molecule further comprises a Kozak consensus sequence.

To control the production of Rep proteins more effectively, non-canonical start codons or non-canonical translational initiation codons can be used. In some embodiments, the Rep78 gene of the isolated nucleic acid molecules further comprises a non-canonical start codon. In some embodiments, the Rep52 gene of the isolated nucleic acid molecule further comprises a non-canonical start codon. In some embodiments, the non-canonical translation initiation codon is GTG, CTG, ACG or TTG. In some embodiments, the non-canonical translation initiation codon is CTG.

Non-limiting examples of gene modifications that can be used in the present invention include codon optimization aimed at, for example, modifying a non-CTG leucine codon to CTG, or modifying a non-AAG lysine codon to AAG. Another example of a nucleic acid codon-optimizing modification is to increase GC content. To increase the vector stability and Rep52 expression, the DNA sequence of coding region of Rep52 was optimized for human cell codon usage while retaining the same protein sequence, which significantly reduced the DNA sequence identity of the Rep52 coding sequence to the Rep78 coding sequence, from 100% sequence identity to 80.1% sequence identity. In some embodiments, the Rep52 of any of the nucleic acid molecules disclosed herein is codon optimized. In some embodiments, the VP1 gene of any of the nucleic acid molecules disclosed herein, excluding the first 439 bp of the coding region, is optimized.

In further embodiments, the first inducible promoter of the nucleic acid molecules disclosed herein is a human cytomegalovirus (CMV) immediate early enhancer-promoter, CMV immediate early enhancer fused chicken β-actin promoter (CAG), human ubiquitin C (UbC) promoter or Rous sarcoma virus (RSV) promoter. In some embodiments, the first inducible promoter is an RSV promoter. In some embodiments, the first inducible promoter is an UbC promoter. As described herein, the use of an artificial intron allows for removal of an inducible promoter following induction of the promoter and prior to the producing the AAV. In some embodiments, the nucleic acid molecule further comprises an intron of the UbC promoter inserted upstream of the UbC promoter.

In some embodiments, the second inducible promoter of the nucleic acid molecules disclosed herein is human CMV immediate early enhancer-promoter, CMV immediate early enhancer fused chicken β-actin promoter (CAG), human ubiquitin C (UbC) promoter or Rous sarcoma virus (RSV) promoter. In some embodiments, the second inducible promoter is a CAG promoter. In some embodiments, the second inducible promoter is a CMV promoter.

As referred to herein, the term "Cap" gene refers to the art-recognized region of the AAV genome which encodes the capsid proteins of the virus. Illustrative (non-limiting) examples of these capsid proteins are the AAV capsid proteins VP1, VP2, and VP3. Cap genes used in this disclosure can come from any AAV serotype or a combination of AAV serotypes.

In still further embodiments, the present disclosure provides an isolated nucleic acid molecule operably comprising a first inducible promoter and a $TetO_2$ sequence, a VP1 gene, a second inducible promoter and a $TetO_2$ sequence, a VP2 gene and a VP3 gene, and an antibiotic resistance gene. In some embodiments, the nucleic acid sequence comprises a core insulator sequence inserted between the 1) VP1 gene and 2) the second inducible promoter and $TetO_2$ sequence. In some embodiments, the nucleic acid sequence comprises a core insulator sequence inserted between 1) the VP2 and VP3 gene and 2) the antibiotic resistance gene.

As referred to herein, the term "gene of interest", or "gene of therapeutic interest" or "GOI" is used to describe a heterologous gene. The GOI of the present disclosure can comprise any desired gene that encodes a protein that is defective or missing from a target cell genome or that encodes a non-native protein having a desired biological or therapeutic effect (e.g., an antiviral function), or the sequence can correspond to a molecule having an antisense or ribozyme function. Representative (non-limiting) examples of suitable genes of therapeutic interest include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemias and hemophilia; genetic defects such as cystic fibrosis, Gaucher's Disease, adenosine deaminase (ADA) deficiency, emphysema, etc. Several antisense oligonucleotides (e.g., short oligonucleotides complementary to sequences around the translational initiation site (AUG codon) of an mRNA) that are useful in antisense therapy for cancer and for viral diseases have been described in the art and are also examples of suitable genes of therapeutic interest.

In further embodiments, the nucleic acid molecule comprises a gene of interest (GOI) downstream of the VP2 and VP3 gene and upstream of the antibiotic resistance gene. In some embodiments, the nucleic acid molecule comprises a core insulator sequence inserted between the VP3 gene and the GOI. In some embodiments, the nucleic acid molecule comprises a core insulator sequence inserted between the GOI and the antibiotic resistance gene. In some embodiments, the nucleic acid molecule comprises a core insulator sequence inserted between the VP3 gene and the GOI, and between the GOI and the antibiotic resistance gene. In some embodiments, the GOI is a therapeutic gene.

In some embodiments, the present disclosure provides a mammalian cell for producing an adeno-associated virus (AAV), comprising any of the isolated nucleic acid molecules disclosed herein integrated into its genome. In some embodiments, the mammalian cell further comprises a nucleic acid encoding a transcriptional repression domain in frame with a nucleic acid encoding a tetracycline repressor protein. In some embodiments, the mammalian cell disclosed herein further comprises a nucleic acid molecule encoding a gene of interest.

The AAV producer cells described herein provide a long-term and cost-effective solution for large scale AAV manufacturing. As constitutive expression of either helper or Rep proteins can be cytotoxic, the strategies described herein allow for control of their expression by engineered, derepressible promoters.

As used herein, the term "mammalian cell" includes cells from any member of the order Mammalia, such as, for example, human cells, mouse cells, rat cells, monkey cells, hamster cells, and the like. In some embodiments, the cell is a mouse cell, a human cell, a Chinese hamster ovary (CHO) cell, a CHOK1 cell, a CHO-DXB11 cell, a CHO-DG44 cell, a CHOK1SV cell including all variants (e.g., POTELLIGENT®, Lonza, Slough, UK), a CHOK1SV GS-KO (glutamine synthetase knockout) cell including all variants (e.g., XCEED™ Lonza, Slough, UK). In some embodiments, the mammalian cell is a Chinese hamster ovary (CHO) cell. In some embodiments, the mammalian cell is a human cell.

Exemplary human cells include human embryonic kidney (HEK) cells, such as HEK293, a HeLa cell, or a HT1080 cell. As used herein, the term "human embryonic kidney 293 (HEK293) cell" refers to a cell line originally derived from human embryonic kidney cells and containing approximately 4.5 kb of Ad5 genome. Variants of HEK293 cells have been developed and include, e.g., HEK293S, HEK293T, HEK293F, HEK293FT, HEK293FTM, HEK293SG, HEK293SGGD, HEK293H, HEK293E, HEK293MSR, and HEK293A. The term "HEK293 cell" as used herein encompasses all HEK293 cell variants and derivatives, including but not limited to the variants described herein. See, e.g., Yuan et al., "The Scattered Twelve Tribes of HEK293," Biomed Pharmacol J 2018; 11 (2). In some embodiments, the human cell is an HEK cell. In some embodiments, the HEK cell is an HEK293 cell.

As described herein, suitably the mammalian cells are mammalian cell cultures, and in embodiments, can be suspension cultures. As described herein, the use of suspension cell cultures allows for increased scalability and production of AAV. Adherent cultures refer to cells that are grown on a substrate surface, for example a plastic plate, dish or other suitable cell culture growth platform, and may be anchorage dependent. Suspension cultures refer to cells that can be maintained in, for example, culture flasks or large suspension vats, which allows for a large surface area for gas and nutrient exchange. Suspension cell cultures often utilize a stirring or agitation mechanism to provide appropriate mixing. Media and conditions for maintaining cells in suspension are generally known in the art. An exemplary suspension cell culture includes human HEK293 clonal cells.

"Transfection" as used herein means the introduction of an exogenous nucleic acid molecule, including a vector, into a cell. A "transfected" cell comprises an exogenous nucleic acid molecule inside the cell and a "transformed" cell is one in which the exogenous nucleic acid molecule within the cell induces a phenotypic change in the cell. The transfected nucleic acid molecule can be integrated into the host cell's genomic DNA and/or can be maintained by the cell, temporarily or for a prolonged period of time, extra-chromosomally. Host cells or organisms that express exogenous nucleic acid molecules or fragments are referred to as "recombinant," "transformed," or "transgenic" organisms. A number of transfection techniques are generally known in the art. See, e.g., Graham et al., Virology, 52:456 (1973); Sambrook et al., Molecular Cloning, a laboratory manual, Cold Spring Harbor Laboratories, New York (1989); Davis et al., Basic Methods in Molecular Biology, Elsevier (1986); and Chu et al., Gene 13:197 (1981). Such techniques can be used to introduce one or more exogenous DNA moieties, such as an AAV vector cassette, AAV helper constructs, and other nucleic acid molecules, into suitable host cells.

Various methods of transfecting the mammalian cells with the isolated nucleic acid molecules described herein (i.e., vectors), are known in the art and include various chemical and physical methods, for example, electroporation, cell injection, calcium phosphate exposure, liposome or polymer-based carrier systems, etc.

In still further embodiments, the present disclosure provides a method for producing an adeno-associated virus (AAV), comprising inducing production of the genomically integrated nucleic acid sequence of any of the mammalian cells disclosed herein, culturing the mammalian cell, and harvesting the AAV.

As discussed herein, the methods of producing and the mammalian cells of the present disclosure advantageously provide a high titer of the AAV produced by the mammalian cells. In some embodiments, the amount of the AAV produced is about $10^{10}$ to about $10^{11}$ viral genomes per mL (vg/mL). In some embodiments, the amount of the AAV produced is at least about $10^{10}$ viral genomes per mL (vg/mL). In some embodiments, the amount of the AAV produced is at least about $10^{11}$ viral genomes per mL (vg/mL).

In some embodiments, the mammalian cells provided herein are substantially free of helper virus. As referred to herein, a "helper virus" is any non-AAV virus that is added to enable the replication and packaging of adeno-associated virus. Representative (non-limiting) examples of helper viruses are adenovirus and herpes virus. In some embodiments, the term substantially free of helper virus refers to a cell that has fewer than 100, fewer than 10, or fewer than 1 helper virus per cell. In some embodiments, the term substantially free of helper virus refers to a cell in which no helper viruses are present or to a population of cells in which no helper viruses are present using detection methods known to those skilled in the art. In some embodiments, no wild-type helper virus is in the cell. In some embodiments, the term wild-type virus refers to any complete-non-AAV virus that can replicate in the cell independently of any other virus.

The methods of producing the AAVs can be used in a continuous manufacturing system. In exemplary embodiments, the use of a suspension cell culture allows for the production of large volumes of AAV, with high productivity and prolonged culture conditions to allow for multiple harvests of AAV for each batch of starting cells.

Production methods can utilize any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermenter or fermentation unit, or any other reaction vessel and the term "reactor" is used interchangeably with "fermenter." The term fermenter or fermentation refers to both microbial and mammalian cultures. For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and $CO_2$ levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

ADDITIONAL EXEMPLARY EMBODIMENTS

Embodiment 1 is an isolated nucleic acid molecule operably comprising a first inducible promoter and two tetracycline operator sequences (a $TetO_2$ sequence), an E2A gene under control of the first inducible promoter, a viral associated (VA) non-coding RNA under control of a second inducible promoter, a third inducible promoter and a $TetO_2$ sequence, an E4 gene under control of the third inducible promoter, and an antibiotic resistance gene.

Embodiment 2 includes the nucleic acid molecule of embodiment 1, wherein the first inducible promoter is native to the E2A gene.

Embodiment 3 includes the nucleic acid molecule of embodiment 1 or 2, wherein the second inducible promoter is a promoter native to the VA non-coding RNA.

Embodiment 4 includes the nucleic acid molecule of any one of embodiments 1 to 3, wherein the second inducible promoter is an H1 promoter.

Embodiment 5 includes the nucleic acid molecule of any one of embodiments 1 to 4, wherein the third inducible promoter is native to the E4 gene.

Embodiment 6 includes the nucleic acid molecule of any one of embodiments 1 to 5, wherein the antibiotic resistance gene is a puromycin resistance gene.

Embodiment 7 includes the nucleic acid molecule of any one of embodiments 1 to 6, wherein the nucleic acid sequence comprises a core insulator sequence inserted between the E4 gene and the antibiotic resistance gene.

Embodiment 8 includes the nucleic acid molecule of any one of embodiments 1 to 7, wherein the nucleic acid sequence is flanked on both the 5' and 3' ends by transposon-specific inverted terminal repeats (ITR).

Embodiment 9 includes the nucleic acid molecule of embodiment 8, wherein the nucleic acid sequence comprises a core insulator sequence inserted downstream of the ITR on the 3' end and upstream of the ITR on the 5' end.

Embodiment 10 includes the nucleic acid molecule of any one of embodiments 1 to 9, further comprising multiple copies of VA non-coding RNA.

Embodiment 11 is an isolated nucleic acid molecule operably comprising a first inducible promoter and a $TetO_2$ sequence, an E2A gene under control of the first inducible promoter, a viral associated (VA) non-coding RNA under control of a second inducible promoter, a third inducible promoter and a TetO$_2$ sequence, an E4 gene under control of the third inducible promoter, an expression cassette encoding a protein ortholog of the VA RNA and a peptide protein tag under the control of a depressible promoter comprising a human Cytomegalovirus (CMV) promoter and a TetO$_2$ sequence, a termination sequence, and an antibiotic resistance gene.

Embodiment 12 includes the nucleic acid molecule of embodiment 11, wherein the first inducible promoter is native to the E2A gene.

Embodiment 13 includes the nucleic acid molecule of embodiment 11 or 12, wherein the second inducible promoter is a promoter native to the VA non-coding RNA.

Embodiment 14 includes the nucleic acid molecule of any one of embodiments 11 to 13, wherein the second inducible promoter is an H1 promoter.

Embodiment 15 includes the isolated nucleic acid molecule of any one of embodiments 12 to 14, wherein the third inducible promoter is native to the E4 gene.

Embodiment 16 includes the isolated nucleic acid molecule of any one of embodiments 11 to 15, wherein the protein ortholog is an influenza non-structural 1 protein (NS1), Ebola viral protein 35 (VP35), orthoreovirus sigma 3 protein (σ3), group C rotavirus non-structural protein 3 (NSP3), vaccinia virus E3L protein (E3L), herpes simplex virus type 1 US11 protein (US11), Epstein-Barr virus SM protein (SM), baculovirus PK2 protein (PK2), hepatitis C virus non-structural protein 5A protein (NS5A), human herpes virus-8 protein vIRF-2 (vIRF-2), human immunodeficiency virus protein Tat, vaccinia virus K3L protein (K3L), Herpes Simplex virus protein γ134.5/ICP34.5, and human papilloma virus-18 E6 protein (E6).

Embodiment 17 includes the isolated nucleic acid molecule of embodiment 16, wherein the protein ortholog is VP35.

Embodiment 18 includes the isolated nucleic acid molecule of embodiment 16, wherein the protein ortholog is SM.

Embodiment 19 includes the isolated nucleic acid molecule of any one of embodiments 11 to 18, wherein the peptide protein tag is a FLAG-tag.

Embodiment 20 includes the isolated nucleic acid molecule of embodiment 19, wherein the FLAG-tag is a N-terminal Flag tag.

Embodiment 21 includes the isolated nucleic acid molecule of any one of embodiments 11 to 20, wherein the termination sequence is a bovine growth hormone polyadenylation (bgh-PolyA) signal.

Embodiment 22 includes the nucleic acid molecule of any one of embodiments 11 to 21, wherein the antibiotic resistance gene is a puromycin resistance gene.

Embodiment 23 includes the nucleic acid molecule of any one of embodiments 11 to 22, wherein the nucleic acid sequence comprises a core insulator sequence inserted between the E4 gene and the expression cassette.

Embodiment 24 includes the nucleic acid molecule of any one of embodiments 11 to 23, wherein the nucleic acid sequence is flanked on both the 5' and 3' ends by transposon-specific inverted terminal repeats (ITR).

Embodiment 25 includes the nucleic acid molecule of embodiment 24, wherein the nucleic acid sequence comprises a core insulator sequence inserted downstream of the ITR on the 3' end and upstream of the ITR on the 5' end.

Embodiment 26 is an isolated nucleic acid molecule operably comprising a plasmid encoding a first inducible promoter and a TetO$_2$ sequence, a Rep78 gene, including a silenced p19 promoter located within the Rep78 gene coding region, wherein the silenced p19 promoter comprises mutations in SP1, TATA-1, and/or TATA-2 sites, a second inducible promoter and a TetO$_2$ sequence, a Rep52 gene under control of the second inducible promoter, termination sequence and, an antibiotic resistance gene.

Embodiment 27 includes the isolated nucleic acid molecule of embodiment 26, wherein the Rep78 gene further comprises a Kozak consensus sequence or a non-canonical start codon.

Embodiment 28 includes the nucleic acid molecule of embodiment 26, wherein the Rep52 gene further comprises a Kozak consensus sequence or a non-canonical start codon.

Embodiment 29 includes the isolated nucleic acid molecule of any one of embodiments 26 to 28, wherein the first inducible promoter is human cytomegalovirus (CMV) immediate early enhancer-promoter, CMV immediate early enhancer fused chicken β-actin promoter (CAG), human ubiquitin C (UbC) promoter or Rous sarcoma virus (RSV) promoter.

Embodiment 30 includes the isolated nucleic acid molecule of embodiment 29, wherein the first inducible promoter is an RSV promoter.

Embodiment 31 includes the isolated nucleic acid molecule of any one of embodiments 26 to 30, wherein the second inducible promoter is human CMV immediate early enhancer-promoter, CMV immediate early enhancer fused chicken β-actin promoter (CAG), human ubiquitin C (UbC) promoter or Rous sarcoma virus (RSV) promoter.

Embodiment 32 includes the isolated nucleic acid molecule of embodiment 31, wherein the second inducible promoter is a CAG promoter.

Embodiment 33 includes the isolated nucleic acid molecule of any one of embodiments 26 to 32, wherein the termination sequence is a bovine growth hormone polyadenylation (bgh-PolyA) signal.

Embodiment 34 includes the nucleic acid molecule of any one of embodiments 26 to 33, wherein the antibiotic resistance gene is a blasticidin resistance gene.

Embodiment 35 includes the nucleic acid molecule of any one of embodiments 26 to 34, wherein the nucleic acid sequence comprises a core insulator sequence inserted between the termination sequence and the antibiotic resistance gene.

Embodiment 36 includes the nucleic acid molecule of any one of embodiments 26 to 35, wherein the Rep52 is codon optimized.

Embodiment 37 includes the nucleic acid molecule of any one of embodiments 26 to 36, wherein the nucleic acid sequence is flanked on both the 5' and 3' ends by transposon-specific inverted terminal repeats (ITR).

Embodiment 38 includes the nucleic acid molecule of embodiment 37, wherein the nucleic acid sequence comprises a core insulator sequence inserted downstream of the ITR on the 3' end and upstream of the ITR on the 5' end.

Embodiment 39 is an isolated nucleic acid molecule operably comprising a first inducible promoter and a TetO$_2$ sequence, a VP1 gene, a second inducible promoter and a TetO$_2$ sequence, a VP2 gene and a VP3 gene, and an antibiotic resistance gene.

Embodiment 40 includes the isolated nucleic acid molecule of embodiment 39, wherein the VP1 gene, excluding the first 439 bp of the coding region, is optimized.

Embodiment 41 includes the isolated nucleic acid molecule of embodiment 39 or 40, wherein the first inducible promoter is human cytomegalovirus (CMV) immediate early enhancer-promoter, CMV immediate early enhancer fused chicken β-actin promoter (CAG), human ubiquitin C (UbC) promoter or Rous sarcoma virus (RSV) promoter.

Embodiment 42 includes the isolated nucleic acid molecule of embodiment 41, wherein the first inducible promoter is an UbC promoter.

Embodiment 43 includes the isolated nucleic acid molecule of embodiment 42, further comprising an intron of the UbC promoter inserted upstream of the UbC promoter.

Embodiment 44 includes the isolated nucleic acid molecule of any one of embodiments 37 to 43, wherein the second inducible promoter is human CMV immediate early enhancer-promoter, CMV immediate early enhancer fused chicken β-actin promoter (CAG), human ubiquitin C (UbC) promoter or Rous sarcoma virus (RSV) promoter.

Embodiment 45 includes the isolated nucleic acid molecule of embodiment 44, wherein the second inducible promoter is a CMV promoter.

Embodiment 46 includes the isolated nucleic acid molecule of any one of embodiments 39 to 45, further comprising a gene of interest (GOI) downstream of the VP3 gene and upstream of the antibiotic resistance gene.

Embodiment 47 includes the isolated nucleic acid molecule of embodiment 46, wherein the nucleic acid molecule comprises a core insulator sequence inserted between the VP3 gene and the GOI and between the GOI and the antibiotic resistance gene.

Embodiment 48 includes the isolated nucleic acid molecule of embodiment 47, wherein the GOI is a therapeutic gene.

Embodiment 49 includes the nucleic acid molecule of any one of embodiments 39 to 48, wherein the nucleic acid sequence comprises a core insulator sequence inserted between the VP1 gene and the second inducible promoter and TetO$_2$ sequence.

Embodiment 50 includes the nucleic acid molecule of any one of embodiments 39 to 49, wherein the nucleic acid sequence comprises a core insulator sequence inserted between the VP2 and VP3 gene of d) and the antibiotic resistance gene of e).

Embodiment 51 includes the nucleic acid molecule of any one of embodiments 39 to 50, wherein the nucleic acid sequence is flanked on both the 5' and 3' ends by transposon-specific inverted terminal repeats (ITR).

Embodiment 52 includes the nucleic acid molecule of embodiment 51, wherein the nucleic acid sequence comprises a core insulator sequence inserted downstream of the ITR on the 3' end and upstream of the ITR on the 5' end.

Embodiment 53 includes the mammalian cell for producing an adeno-associated virus (AAV), comprising the isolated nucleic acid molecule of any one of embodiments 1 to 52 integrated into its genome.

Embodiment 54 includes the mammalian cell of embodiment 53, further comprising a nucleic acid encoding a transcriptional repression domain in frame with a nucleic acid encoding a tetracycline repressor protein.

Embodiment 55 includes the mammalian cell of embodiment 53 or 54, wherein the mammalian cell is a mammalian cell culture.

Embodiment 56 includes the mammalian cell any one of embodiments 53 to 55, wherein the mammalian cell is a Chinese hamster ovary (CHO) cell.

Embodiment 57 includes the mammalian cell of any one of embodiments 53 to 55, wherein the mammalian cell is a human cell.

Embodiment 58 includes the mammalian of embodiment 57, wherein the human cell is a human embryonic kidney (HEK) cell.

Embodiment 59 includes the mammalian cell of embodiment 58, wherein the HEK cell is an HEK293 cell.

Embodiment 60 includes the mammalian cell of any one of embodiments 53 to 59, further comprising a nucleic acid molecule encoding a gene of interest.

Embodiment 61 includes a method for producing an adeno-associated virus (AAV), comprising inducing production of the genomically integrated nucleic acid sequence of any of the mammalian cells of embodiments 53 to 60, culturing the mammalian cell, and harvesting the AAV.

Embodiment 62 includes the method of embodiment 61, wherein an amount of the AAV produced is about $10^{10}$ to about $10^{11}$ viral genomes per mL (vg/mL).

Embodiment 63 includes the method of embodiment 62, wherein an amount of the AAV produced is at least about $10^{10}$ viral genomes per mL (vg/mL).

EXAMPLES

Example 1: Preparation of HEK293 Stable Clonal Cells for TetR-KRAB Expression

One of the original Tet-On inducible systems utilizes the tetracycline repressor protein (TetR) to silence the human cytomegalovirus (CMV) promoter with an insertion of two tetracycline operator sequences (TetO$_2$) between the TATA box and transcriptional start site (TSS) (Yao et al., "Tetracycline repressor, tetR, rather than the tetR-mammalian cell transcription factor fusion derivatives, regulates inducible gene expression in mammalian cells," Hum Gene Ther. 9 (13): 1939-50 (1998)). In the absence of doxycycline, transcription initiation is blocked by the binding of TetR on the TetO$_2$ sites. When doxycycline is added into the medium, it competitively binds to TetR and changes its conformation. This leads to the release of TetR and derepression/activation of the CMV promoter and results in induced gene expression (See FIG. 1). However, the high level of leaky expression of toxic proteins before induction in the original system poses a major challenge for the stability of the generated inducible cell lines and limits its application for an AAV producer cell line.

Improvements of the Tet-On inducible system were implemented to minimize the leakiness level. First, an enhanced version of TetR was applied as described in Suzlc et al., "A versatile tool for conditional gene expression and knockdown," Nat Methods 3 (2): 109-16 (2006). Briefly, a strong repressive domain of KRAB was fused in-frame to the C-terminus of original TetR, which dramatically improved its repressive activity and minimized basal gene expression before induction. An SV40 nuclear localization signal (NLS) was inserted as well to facilitate the nuclear entry of the larger TetR-KRAB fusion protein (See FIGS. 2A and 2B). Second, the expression cassette was optimized for high level expression of TetR-KRAB protein, including the strong human CMV promoter to drive a high level of mRNA expression, the consensus Kozak sequence to boost the initiation of the protein translation, and the rabbit beta-globin intron to increase mRNA level. The expression cassette was further protected on both ends by two chicken hypersensitive site-4 (cHS4) extended core chromatin insulators, which can prevent undesired silencing of the CMV promoter from the spreading of neighboring heterochromatin. An SV40 promoter driven Zeocin antibiotic resistance gene was included for stable selection. Third, a stable TetR-KRAB overexpression clonal HEK293 cell line, C20, was established using this optimized construct by plasmid random integration. When compared to a commercially available TetR stable HEK293 cell line in a transient transfection test, the C20 cell line reduced the leaky production of AAV by approximately 200-fold.

Sequence Listings

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The sequence of the pcDNA-TetR-Ins vector is provided below:

```
pcDNA-TetR-Ins (7147 bp)
                                                                    (SEQ ID NO: 1)
gacggatcgggagatctgagctcacggggacagccccccccaaagccccagggatgtaattacgtccctcccccgcta gggggcagcagcgagccgcccggggctccgctccggtccggcgctcccccgcatccccgagccggcagcgtgcggggacagccc gggcacggggaaggtggcacgggatcgctttcctctgaacgcttctcgctgctctttgagcctgcagacacctgggggatacggggaaa aagctttaggctgaaagagagatttagaatgacagaatcatagaacggcctgggttgcaaaggagcacagtgctcatccagatccaacccc ctgctatgtgcagggtcatcaaccagcagcccaggctgcccagagccacatccagcctggccttgaatgcctgcaggcccgatcccctat ggtcgactctcagtacaatctgctctgatgccgcatagttaagccagtatctgctccctgcttgtgtgttggaggtcgctgagtagtgcgcgag caaaatttaagctacaacaaggcaaggcttgaccgacaattgcatgaagaatctgcttagggttaggcgttttgcgctgcttcgcgatgtacg ggccagatatacgcgttgacattgattattgactagttattaatagtaatcaattacggggtcattagttcatagcccatatggagttccgcg ttacataacttacggtaaatggcccgcctggctgaccgcccaacgaccccgcccattgacgtcaataatgacgtatgttcccatagtaacgcc aatagggactttccattgacgtcaatgggtggactatttacggtaaactgcccacttggcagtacatcaagtgtatcatatgccaagtacgccc cctattgacgtcaatgacggtaaatggcccgcctggcattatgcccagtacatgaccttatgggactttcctacttggcagtacatctacgtatt agtcatcgctattaccatggtgatgcggttttggcagtacatcaatgggcgtggatagcggtttgactcacggggatttccaagtctccacccc attgacgtcaatgggagtttgttttggcaccaaaatcaacgggactttccaaaatgtcgtaacaactccgcccattgacgcaaatgggcggt aggcgtgtacggtgggaggtctatataagcagagctctctggctaactagagaacccactgcttactggcttatcgaaattaatacgactcac tatagggagacccaagctggctagcgtttaaacttaagctttctgtgagtttggggacccttgattgttctttcttttttcgctattgtaaaattc atgttatatggaggggggcaaagttttcagggtgttgtttagaatgggaagatgtcccttgtatcaccatggaccctcatgataattttgtttctt tcactttctactctgttgacaaccattgtctcctcttatttcttttcatttttctgtaacttttttcgttaaactttagcttgcatttgtaacgaa tttttaaaattcacttttgtttatttgtcagattgtaagtactttctctaatcactttttttttcaaggcaatcagggtatattatattgtacttca gcacagttttagagaacaattgttataattaaatgataaggtagaatatttctgcatataaattctggctggcgtggaaatattcttattggtag aaacaactacatcctggtcatcatcctgcctttctctttatggttacaatgatatacactgtttgagatgaggataaaatactctgagtccaaac cgggcccctctgctaaccatgttcatgccttcttcttttcctacagctcctgggcaacgtgctggttattgtgctgtctcatcatttttggcaaa gaattgtaatacgactcactatagggcgagccaccatggctagattagataaaagtaaagtgattaacagcgcattagagctgcttaatgaggtc ggaatcgaaggtttaacaacccgtaaactcgcccagaagctaggtgtagagcagcctacattgtattggcatgtaaaaaataagcgggctttgct cgacgccttagccattgagatgttagataggcaccatactcacttttgcccttttagaaggggaaagctggcaagatttttttacgtaataacgcta aaagttttagatgtgctttactaagtcatcgcgatggagcaaaagtacatttaggtacacggcctacagaaaaacagtatgaaactctcgaaaat caattagccttttatgccaacaaggttttttcactagagaatgccttatatgcactcagcgccgtggggcatttttactttaggttgcgtattgga agatcaagagcatcaagtcgctaaagaagaaagggaaacacctactactgatagtatgccgccattattacgacaagctatcgaattatttgatc accaaggtgcagagccagccttcttattcggccttgaattgatcatatgcggattagaaaaacaacttaaatgtgaaagtgggtccccaaaaaag aagagaaaggtcgacggcggtggttcagtttaagcgtacagcgggatccactagtccagtgtggtggaattctgcagatatccagcacagtggcg gccgctcgagtctagagggcccgtttaaacccgctgatcagcctcgactgtgccttctagttgccagccatctgttgtttgcccctcccccgtg
```

-continued ccttccttgaccctggaaggtgccactcccactgtcctttcctaataaaatgaggaaattgcatcgcattgtctgagtaggtgtcattctattct gggggggtggggggggcaggacagcaaggggggaggattgggaagacaatagcaggcatgctggggatgcggtgggctctatggcttctgaggcgg aaagaaccagctggggctctaggggggtatccccacgcgccctgtagcggcgcattaagcgcggcgggtgtggtggttacgcgcagcgtgaccgc tacacttgccagcgccctagcgcccgctcctttcgctttcttcccttccttctcgccacgttcgccggctttccccgtcaagctctaaatcggg gcatccctttagggttccgatttagtgctttacggcacctcgaccccaaaaaacttgattagggtgatggttcacgtagtgggccatcgccctga tagacggttttttcgcccttgacgttggagtccacgttcttaatagtggactcttgttccaaactggaacaacactcaaccctatctcggtcta ttcttttgatttataagggattttgggg atttcggcctattggttaaaaaatgagctgatttaacaaaaatttaacgcgaattaattctgtggaa tgtgtgtcagttagggtgtggaaagtccccaggctccccaggcaggcagaagtatgcaaagcatgcatctcaattagtcagcaaccaggtgtgga aagtccccaggctccccagcaggcagaagtatgcaaagcatgcatctcaattagtcagcaaccatagtcccgcccctaactccgcccatcccgc ccctaactccgccagttccgccattctccgccccatggctgactaattttttttatttatgcagaggccgaggccgcctctgcctctgagcta ttccagaagtagtgaggaggcttttttggaggcctaggcttttgcaaaaagctcccgggagcttgtatatccattttcggatctgatcagcacgt gttgacaattaatcatcggcatagtatatcggcatagtataatacgacaaggtgaggaactaaaccatggccaagttgaccagtgccgttccggt gctcaccgcgcgcgacgtcgccggagcggtcgagttctggaccgaccggctcgggttctcccgggacttcgtggaggacgacttcgccggtgt ggtccgggacgacgtgaccctgttcatcagcgcggtccaggaccaggtggtgccggacaacaccctggcctgggtgtgggtgcgcggc ctggacgagctgtacgccgagtggtcggaggtcgtgtccacgaacttccgggacgcctccgggccggccatgaccgagatcggcgagc agccgtgggggggagttcgccctgcgcgacccggccggcaactgcgtgcacttcgtggccgaggagcaggactgacacgtgctac gagatttcgattccaccgccgccttctatgaaaggttgggcttcggaatcgttttccgggacgccggctggatgatcctccagcgcgggat ctcatgctggagttcttcgcccaccccaacttgtttattgcagcttataatggttacaaataaagcaatagcatcacaaatttcacaaataaagc attttttttcactgcattctagttgtggtttgtccaaactcatcaatgtatcttatcatgtctgtataccgtcgacctctagctagagcttggcgt aatcatggtcatagctgtttcctgtgtgaaattgttatccgctcacaattccacacaacatacgagccggaagcataaagtgtaaagcctgggt gcctaatgagtgagctaactcacattaattgcgttgcgctcactgcccgctttccagtcgggaaacctgtcgtgccagctgcattaatgaatcgg ccaacgcgcggggagaggcggtttgcgtattgggcgctcttccgcttcctcgctcactgactcgctgcgctcggtcgttcggctgcggcgagcgg tatcagctcactcaaaggcggtaatacggttatccacagaatcagggg ataacgcaggaaagagagctcacgggg acagcccccccccca aagcccccagggatgtaattacgtccctcccccgctagggggcagcagcgagccgcccggggctccgctccggtccggcgctccccccc gcatccccgagccggcagcgtgcgggg acagcccgggcacgggg aaggtggcacggg atcgctttcctctgaacgcttctcgctgctct ttgagcctgcagacacctgggggg atacggggaaaaagctttaggctgaaagagagatttagaatgacagaatcatagaacggcctgggt tgcaaaggagcacagtgctcatccagatccaaccccctgctatgtgcagggtcatcaaccagcagcccaggctgcccagagccacatcca gcctggccttgaatgcctgcaggacatgtgagcaaaaggccagcaaaaggccaggaaccgtaaaaaggccgcgttgctggcgttttttcca taggctccgcccccctgacgagcatcacaaaaatcgacgctcaagtcagaggtggcgaaacccgacaggactataaagataccaggcgt ttccccctggaagctccctcgtgcgctctcctgttccgaccctgccgcttaccggatacctgtccgcctttctcccttcgggaagcgtggcgct ttctcaatgctcacgctgtaggtatctcagttcggtgtaggtcgttcgctccaagctgggctgtgtgcacgaaccccccgttcagcccgaccg ctgcgccttatccggtaactatcgtcttgagtccaacccggtaagacacgacttatcgccactggcagcagccactggtaacaggattagca gagcgaggtatgtaggcggtgctacagagttcttgaagtggtggcctaactacggctacactagaaggacagtatttggtatctgcgctctgc tgaagccagttaccttcggaaaaagagttggtagctcttgatccggcaaacaaaccaccgctggtagcggtggtttttttgtttgcaagcagca gattacgcgcagaaaaaaaggatctcaagaagatcctttgatcttttctacggggtctgacgctcagtggaacgaaaactcacgttaagggat tttggtcatgagattatcaaaaaggatcttcacctagatcctttttaaattaaaaatgaagttttaaatcaatctaaagtatatatgagtaaactt ggtctgacagttaccaatgcttaatcagtgaggcacctatctcagcgatctgtctatttcgttcatccatagttgcctgactccccgtcgtgtag ataactacgatacggg agggcttaccatctggccccagtgctgcaatgataccgcgagacccacgctcaccggctccagatttatcagcaataaa ccagccagccggaagggccgagcgcagaagtggtcctgcaacttatccgcctccatccagtctattaattgttgccgggaagctagagtaagt agttcgccagttaatagtttgcgcaacgttgttgccattgctacaggcatcgtggtgtcacgctcgtcgtttggtatggcttcattcagctccgg -continued

```
ttcccaacgatcaaggcgagttacatgatcccccatgttgtgcaaaaaagcggttagctccttcggtcctccgatcgttgtcagaagtaagttg gccgcagtgttatcactcatggttatggcagcactgcataattctcttactgtcatgccatccgtaagatgcttttctgtgactggtgagtact caaccaagtcattctgagaatagtgtatgcggcgaccgagttgctcttgcccggcgtcaatacgggataataccgcgccacatagcagaacttta aaagtgctcatcattggaaaacgttcttcggggcgaaaactctcaaggatcttaccgctgttgagatccagttcgatgtaacccactcgtgcac ccaactgatcttcagcatcttttactttcaccagcgtttctgggtgagcaaaaacaggaaggcaaatgccgcaaaaaagggaataagggcg acacggaaatgttgaatactcatactcttccttttttcaatattattgaagcatttatcagggttattgtctcatgagcggatacatatttgaatg tatttagaaaaataaacaaatagggggttccgcgcacatttccccgaaaagtgccacctgacgtc
```

The sequence of the pcDNA-TetR-KRAB-Ins vector is provided below:

pcDNA-TetR-KRAB-Ins (7493 bp)

(SEQ ID NO: 2)

```
gacggatcgggagatctgagctcacggggacagcccccccccaaagcccccagggatgtaattacgtccctccccgctaggggcag cagcgagccgcccggggctccgctccggtccggcgctcccccgcatccccgagccggcagcgtgcggggacagcccgggcacgg ggaaggtggcacgggatcgctttcctctgaacgcttctcgctgctctttgagcctgcagacacctgggggatacggggaaaaagctttag gctgaaagagagatttagaatgacagaatcatagaacggcctgggttgcaaaggagcacagtgctcatccagatccaaccccctgctatgt gcagggtcatcaaccagcagcccaggctgcccagagccacatccagcctggccttgaatgcctgcaggcccgatcccctatggtcgactc tcagtacaatctgctctgatgccgcatagttaagccagtatctgctccctgcttgtgtgttggaggtcgctgagtagtgcgcgagcaaaattta gctacaacaaggcaaggcttgaccgacaattgcatgaagaatctgcttagggttaggcgttttgcgctgcttcgcgatgtacgggccagatat acgcgttgacattgattattgactagttattaatagtaatcaattacggggtcattagttcatagcccatatatggagttccgcgttacataact tacggtaaatggcccgcctggctgaccgcccaacgaccccgcccattgacgtcaataatgacgtatgttcccatagtaacgccaatagggact ttccattgacgtcaatgggtggactatttacggtaaactgcccacttggcagtacatcaagtgtatcatatgccaagtacgccccctattgacgt caatgacggtaaatggcccgcctggcattatgcccagtacatgacctatgggactttcctacttggcagtacatctacgtattagtcatcgcta ttaccatggtgatgcggttttggcagtacatcaatgggcgtggatagcggtttgactcacggggatttccaagtctccacccattgacgtcaa tgggagtttgttttggcaccaaaatcaacgggactttccaaaatgtcgtaacaactccgccccattgacgcaaatgggcggtaggcgtgtac ggtgggaggtctatataagcagagctctctggctaactagagaacccactgcttactggcttatcgaaattaatacgactcactatagggaga cccaagctggctagcgtttaaacttaagcttctgtgagtttggggaccccttgattgttcttctttttcgctattgtaaaattcatgttatatg gagggggcaaagttttcagggtgttgtttagaatgggaagatgtcccttgtatcaccatggaccctcatgataattttgtttctttcactttcta ctctgttgacaaccattgtctcctcttattttctttcattttctgtaacttttcgttaaactttagcttgcatttgtaacgaattttttaaatt cacttttgttatttgtcagattgtaagtactttctctaatcacttttttttcaaggcaatcagggtatattatattgtacttcagcacagtttt agagaacaattgttataattaaatgataaggtagaatatttctgcatataaattctggctggcgtggaaatattcttattggtagaaacaactac atcctggtcatcatcctgcctttctctttatggttacaatgatatacactgtttgagatgaggataaaatactctgagtccaaaccgggcccctc tgctaaccatgttcatgccttcttcttttttcctacagctcctgggcaacgtgctggttattgtgctgtctcatcattttggcaaagaattgtaat acgactcactatagggcgagccaccatggctagattagataaaagtaaagtgattaacagcgcattagagctgcttaatgaggtcggaatcgaa ggtttaacaacccgtaaactcgcccagaagctaggtgtagagcagcctacattgtattggcatgtaaaaaataagcgggctttgctcgacgcctt agccattgagatgttagataggcaccatactcacttttgccctttagaagggaaagctggcaagatttttttacgtaataacgctaaagttttta gatgtgctttactaagtcatcgcgatggagcaaaagtacatttaggtacacggcctacagaaaaacagtatgaaactctcgaaaatcaattagc cttttatgccaacaaggttttcactagagaatgccttatatgcactcagcgccgtggggcattttactttaggttgcgtattggaagatcaag agcatcaagtcgctaaagaagaaagggaaacacctactactgatagtatgccgccattattacgacaagctatcgaattatttgatcaccaaggt gcagagccagccttcttattcggccttgaattgatcatatgcggattagaaaaacaacttaaatgtgaaagtgggtcccaaaaaagaagagaa aggtcgacggcggtggtgctttgtctcctcagcactctgctgtcactcaaggaagatcatcaagaacaaggagggcatggatgctaagtcact aactgcctggtcccggacactggtgaccttcaaggatgtatttgtggacttcaccagggaggagtggaagctgctggacactgctcagcagatc
```

-continued gtgtacagaaatgtgatgctggagaactataagaacctggtttccttgggttatcagcttactaagccagatgtgatcctccggttggagaagg gagaagagccctggctggtggagagagaaattcaccaagagacccatcctgattcagagactgcatttgaaatcaaatcatcagtttaagcgtac agcggggatccactagtccagtgtggtggaattctgcagatatccagcacagtggcggccgctcgagtctagagggcccgtttaaacccgctgat cagcctcgactgtgccttctagttgccagccatctgttgtttgcccctcccccgtgccttccttgaccctggaaggtgccactcccactgtcctt tcctaataaaatgaggaaattgcatcgcattgtctgagtaggtgtcattctattctgggggggggtggggcaggacagcaaggggggaggattgg gaagacaatagcaggcatgctggggatgcggtgggctctatggcttctgaggcggaaagaaccagctggggctctaggggggtatccccacgcgcc ctgtagcggcgcattaagcgcggcgggtgtggtggttacgcgcagcgtgaccgctacacttgccagcgccctagcgcccgctcctttcgcttt cttccttcctttctcgccacgttcgccggctttccccgtcaagctctaaatcggggcatccctttagggttccgatttagtgctttacggcacc tcgaccccaaaaaacttgattagggtgatggttcacgtagtgggccatcgccctgatagacggttttttcgccctttgacgttggagtccacgttc tttaatagtggactcttgttccaaactggaacaacactcaacccatctcggtctattcttttgatttataagggattttgggggatttcggccta ttggttaaaaaatgagctgatttaacaaaaatttaacgcgaattaattctgtggaatgtgtgtcagttagggtgtggaaagtccccaggctcccc aggcaggcagaagtatgcaaagcatgcatctcaattagtcagcaaccaggtgtggaaagtccccaggctccccagcaggcagaagtatgcaaag catgcatctcaattagtcagcaaccatagtcccgcccctaactccgcccatcccgcccctaactccgcccagttccgcccattctccgcccca tggctgactaatttttttatttatgcagaggccgaggccgcctctgcctctgagctattccagaagtagtgaggaggcttttttggaggcctag gcttttgcaaaaagctcccgggagcttgtatatccattttcggatctgatcagcacgtgttgacaattaatcatcggcatagtatatcggcatag tataatacgacaaggtgaggaactaaaccatggccaagttgaccagtgccgttccggtgctcaccgcgcgcgacgtcgccggagcggtcg agttctggaccgaccggctcgggttctcccgggacttcgtggaggacgacttcgccggtgtggtccgggacgacgtgaccctgttcatcag cgcggtccaggaccaggtggtgccggacaacaccctggcctgggtgtgggtgcgcggcctggacgagctgtacgccgagtggtcgga ggtcgtgtccacgaacttccgggacgcctccgggccggccatgaccgagatcggcgagcagccgtggggggggagttcgccctgcg cgacccggccgcaactgcgtgcacttcgtggccgaggagcaggactgacacgtgctacgagatttcgattccaccgccgccttctatga aaggttgggcttcggaatcgttttccgggacgccggctggatgatcctccagcgcggggatctcatgctggagttcttcgcccaccccaact tgttattgcagcttataatggttacaaataaagcaatagcatcacaaatttcacaaataaagcattttttcactgcattctagttgtggtttg tccaaactcatcaatgtatcttatcatgtctgtataccgtcgacctctagctagagcttggcgtaatcatggtcatagctgtttcctgtgtgaa attgttatccgctcacaattccacacaacatacgagccggaagcataaagtgtaaagcctggggtgcctaatgagtgagctaactcacattaatt gcgttgcgctcactgcccgctttccagtcgggaaacctgtcgtgccagctgcattaatgaatcggccaacgcgcggggagaggcggtttgcgtat tgggcgctcttccgcttcctcgctcactgactcgctgcgctcggtcgttcggctgcggcgagcggtatcagctcactcaaaggcggtaatacg gttatccacagaatcaggggataacgcaggaaagagagctcacgggacagcccccccccaaagcccccagggatgtaattacgtccct ccccgctaggggggcagcagcgagccgcccgggggctccgctccggtccggcgctcccccgcatccccgagccggcagcgtgcggg gacagcccgggcacgggaaggtggcacgggatcgctttcctctgaacgcttctcgctgctctttgagcctgcagacacctgggggggata cggggaaaaagctttaggctgaaagagagatttagaatgacagaatcatagaacggcctgggttgcaaaggagcacagtgctcatccaga tccaaccccctgctatgtgcagggtcatcaaccagcagcccaggctgcccagagccacatccagcctggccttgaatgcctgcaggacat gtgagcaaaaggccagcaaaaggccaggaaccgtaaaaaggccgcgttgctggcgtttttccataggctccgcccccctgacgagcatc acaaaaatcgacgctcaagtcagaggtggcgaaacccgacaggactataaagataccaggcgtttccccctggaagctccctcgtgcgct ctcctgttccgaccctgccgcttaccggatacctgtccgcctttctcccttcgggaagcgtggcgctttctcaatgctcacgctgtaggtatctc agttcggtgtaggtcgttcgctccaagctgggctgtgtgcacgaaccccccgttcagcccgaccgctgcgccttatccggtaactatcgtctt gagtccaacccggtaagacacgacttatcgccactggcagcagccactggtaacaggattagcagagcgaggtatgtaggcggtgctaca gagttcttgaagtggtggcctaactacggctacactagaaggacagtatttggtatctgcgctctgctgaagccagttaccttcggaaaaaga gttggtagctcttgatccggcaaacaaaccaccgctggtagcggtggtttttttgtttgcaagcagcagattacgcgcagaaaaaaaggatct caagaagatcctttgatcttttctacggggtctgacgctcagtggaacgaaaactcacgttaagggattttggtcatgagattatcaaaaggat cttcacctagatccttttaaattaaaaatgaagttttaaatcaatctaaagtatatatgagtaaacttggtctgacagttaccaatgcttaatca -continued

```
gtgaggcacctatctcagcgatctgtctatttcgttcatccatagttgcctgactccccgtcgtgtagataactacgatacgggagggcttacca tctggcccagtgctgcaatgataccgcgagaccacgctcaccggctccagatttatcagcaataaaccagccagccggaagggccgagc gcagaagtggtcctgcaactttatccgcctccatccagtctattaattgttgccgggaagctagagtaagtagttcgccagttaatagtttgcgc aacgttgttgccattgctacaggcatcgtggtgtcacgctcgtcgtttggtatggcttcattcagctccggttcccaacgatcaaggcgagttac atgatcccccatgttgtgcaaaaaagcggttagctccttcggtcctccgatcgttgtcagaagtaagttggccgcagtgttatcactcatggtta tggcagcactgcataattctcttactgtcatgccatccgtaagatgcttttctgtgactggtgagtactcaaccaagtcattctgagaatagtgt atgcggcgaccgagttgctcttgcccggcgtcaatacgggataataccgcgccacatagcagaactttaaaagtgctcatcattggaaaacgtt cttcggggcgaaaactctcaaggatcttaccgctgttgagatccagttcgatgtaaaccactcgtgcacccaactgatcttcagcatcttttact ttcaccagcgtttctgggtgagcaaaaacaggaaggcaaaatgccgcaaaaaagggaataagggcgacacggaaatgttgaatactcatac tcttccttttcaatattattgaagcatttatcagggttattgtctcatgagcggatacatatttgaatgtatttagaaaaataaacaaatagggg gttccgcgcacatttccccgaaaagtgccacctgacgtc
```

Figure 3A:
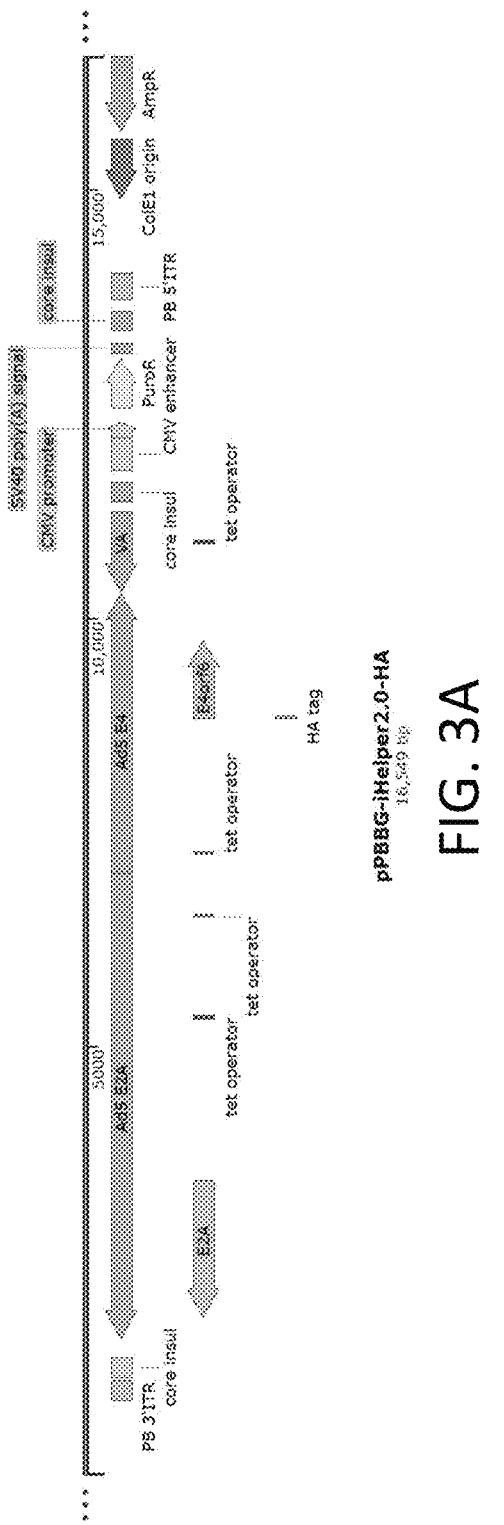

Example 2: Design and Validation of Derepressible Helper Genes pPBBG-iHelper2.0-HA Vector To drive the expression of Adenovirus Helper Genes E2A and E4Orf6, two tetracycline operator sequences (TetO₂) were inserted between the TATA box and transcriptional start site (TSS) in the native promoters of the E2A and E4 genes. Expression of the VA RNA is driven by its native promoter or H1 promoter with or without TetO₂ insertion. The VA gene promoter is embedded in the gene body of the non-coding RNA, and the TetO₂ sequences were added upstream of the VA gene. To facilitate the detection of E4orf6 protein expression, an HA tag was fused in frame to the N-terminus of E4orf6 coding sequence. The expression cassettes of inducible E2A, E4 and VA as one gene block was flanked by core insulator sequences, long-range regulatory sequences to prevent the activation or silencing of the gene promoters from neighboring distal enhancers or spreading heterochromatin, respectively. The sequence was fully synthesized and subcloned into a piggyBac transposon vector between the transposon-specific ITRs on 5' and 3' ends. To allow the antibiotic selection of the recombinant transposon in cells, the puromycin antibiotic resistance gene driven by a CMV promoter was also included and flanked by core insulators inside the ITRs, which resulted in the pPBBG-iHelper2.0-HA vector (See FIG. 3A).

To enhance the VA RNA expression of the pPBBG-iHelper2.0-HA vector design, a series of modifications were applied to the VA cassettes in the pPBBG-iHelper2.0-HA vector design.

Figure 3B:
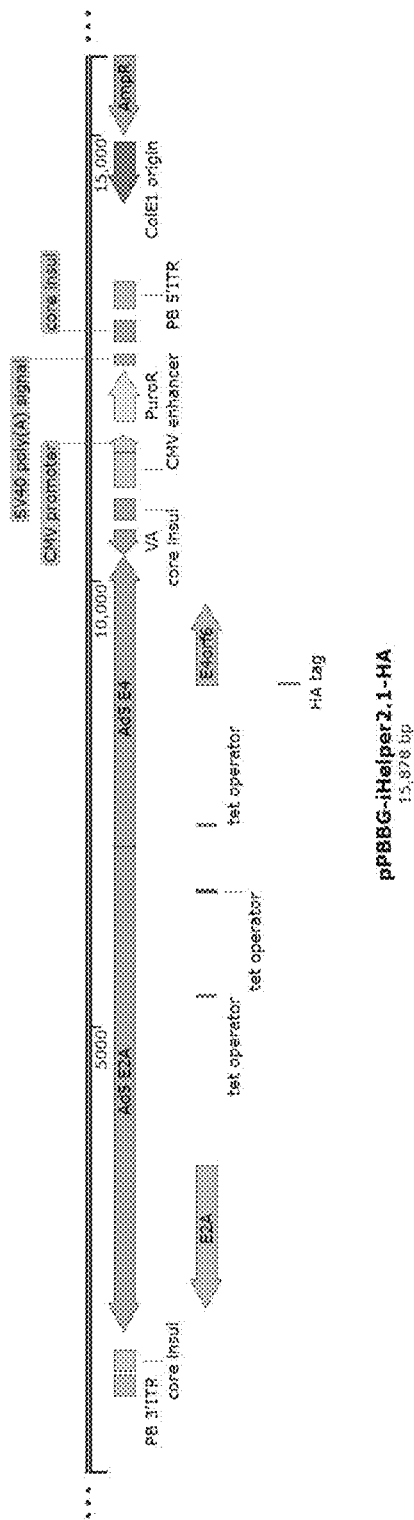
Figure 3C:
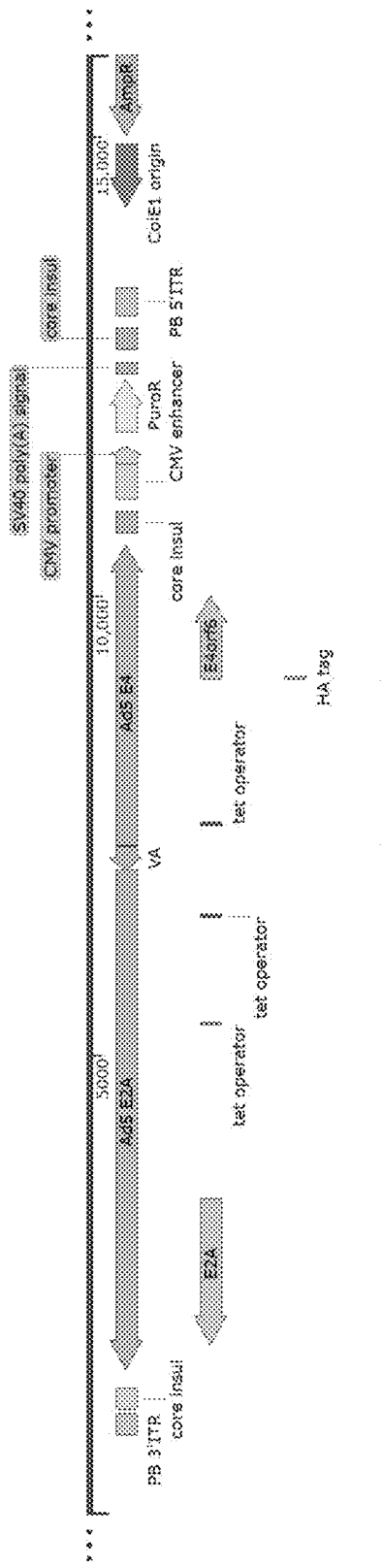
Figure 3D:
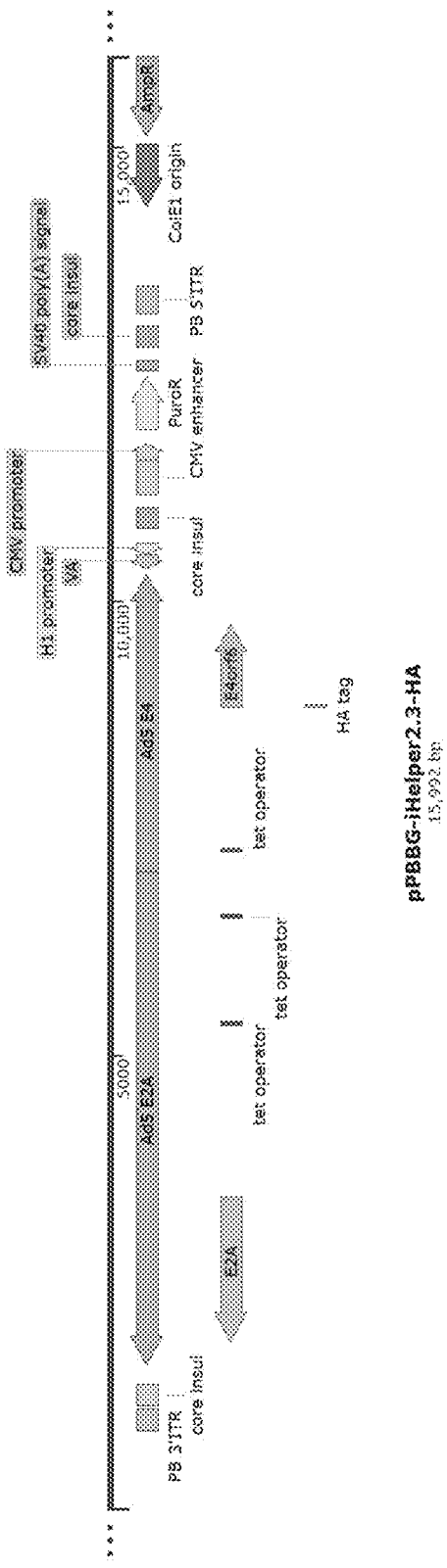
Figure 3G:
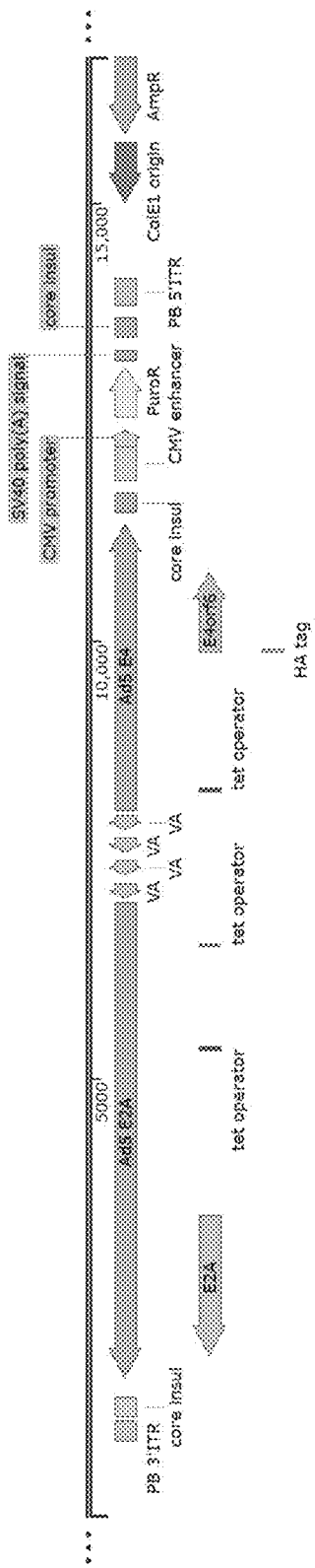
Figure 3H:
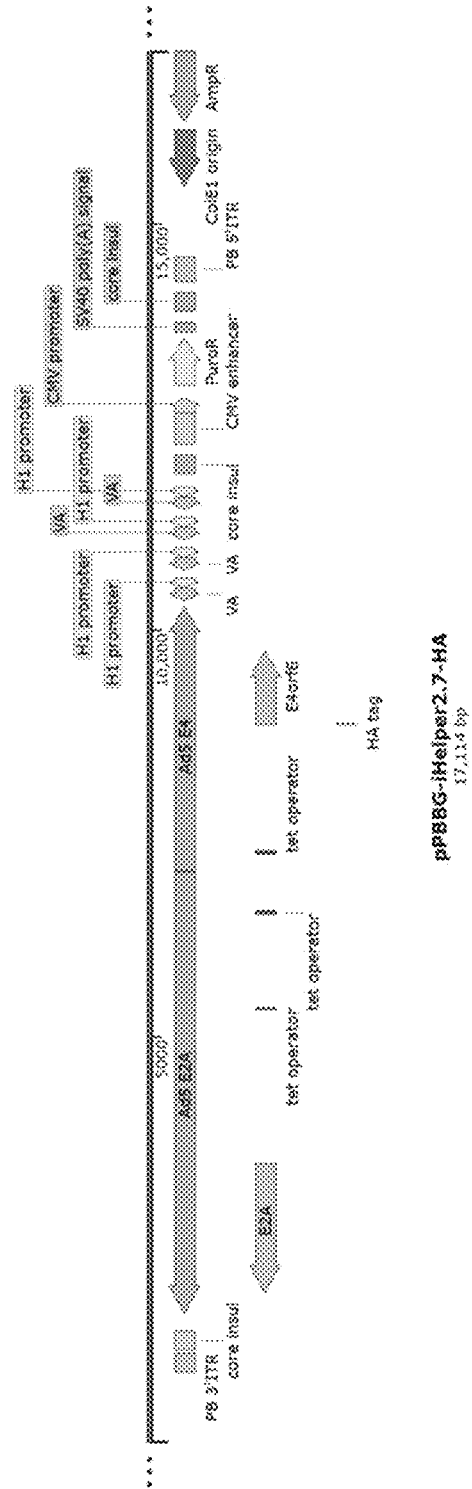
Figure 31:
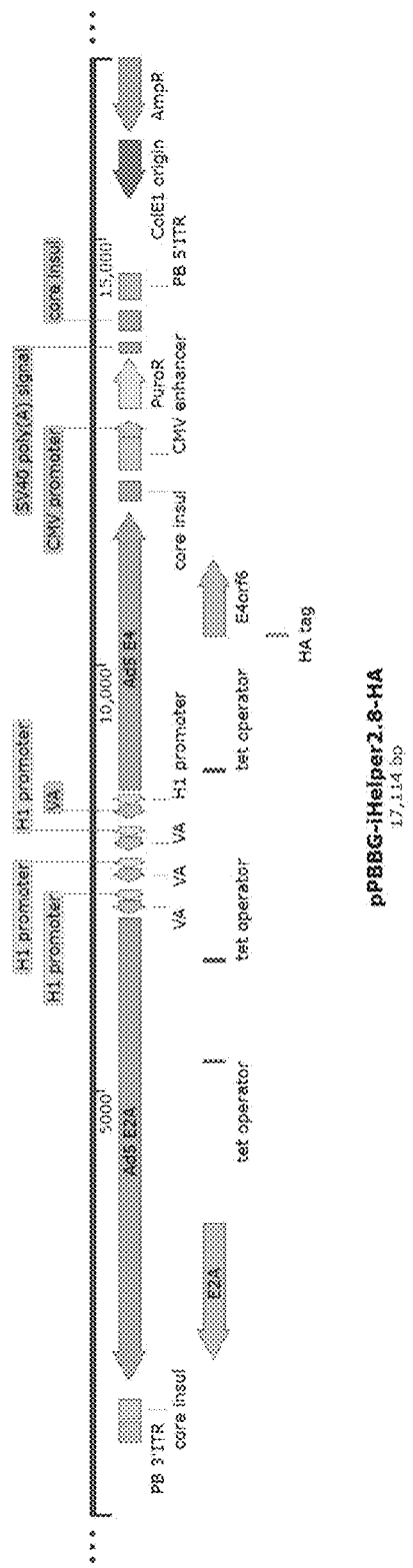

In the iHelper2.1 vector, both the TetO₂ and VAII regions originally in the pPBBG-iHelper2.0-HA vector design were removed (see FIG. 3B). In the iHelper2.2 vector, the VAI cassette in iHelper2.1 was relocated between E2A and E4 cassettes to achieve inducibility from neighboring TetO₂ sequences (See FIG. 3C). In the iHelper2.3 vector, the constitutive H1 promoter was added upstream of VAI cassette in the iHelper2.1 to increase the VA expression (see FIG. 3D). In iHelper2.4 vector, the VAI and H1 promoter in iHelper2.3 was relocated between E2A and E4 cassettes (see FIG. 3E). To further augment the VA expression, the VA cassette was increased from a single copy in the iHelper 2.1, 2.2, 2.3 and 2.4 vectors to four tandem repeats in the iHelper 2.5, 2.6, 2.7 and 2.8, accordingly. The addition of further promoters (H1) in various locations was also investigated. (See FIGS. 3F-3I).

Figure 4A:
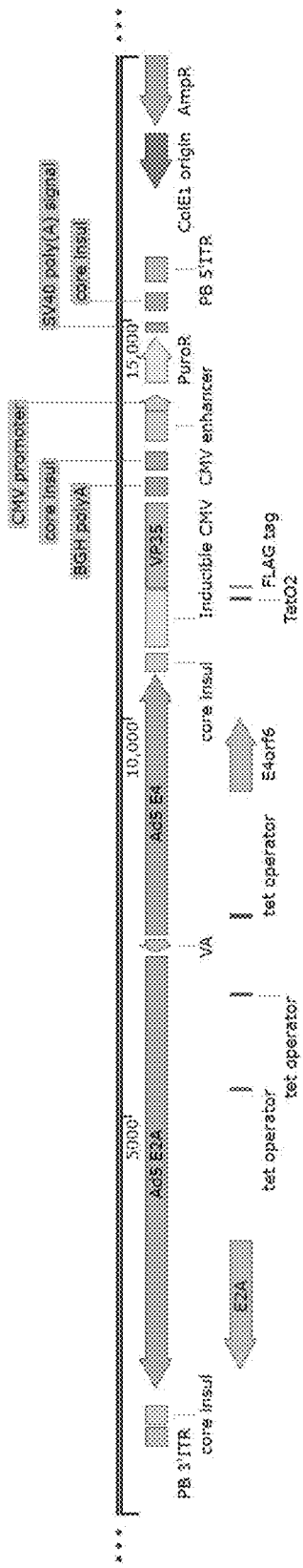
FIGS. 4A and 4B show exemplary nucleic acid molecules for production of helper genes in accordance with embodiments hereof.
Figure 4B:
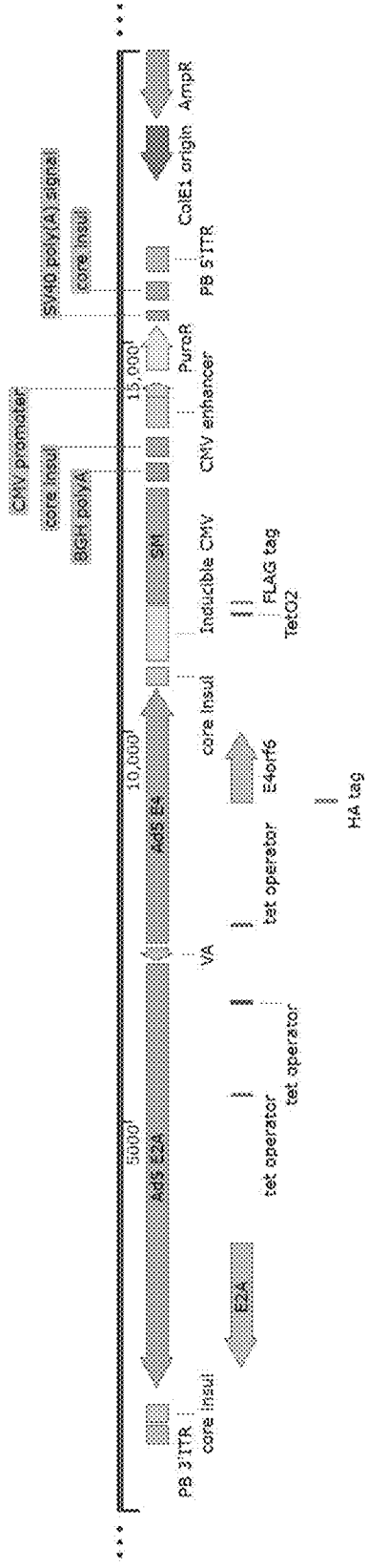

To further enhance the helper function, functional protein orthologs to VA RNA were screened to enhance AAV production. These protein-encoding genes are derived from different viruses with reported function as inhibitors of protein kinase R (PKR), a key function of VA RNA (Langland et al., "Inhibition of PKR by RNA and DNA viruses," Virus Res. 119 (1): 100-10 (2006) and Feng et al., "The VP35 protein of Ebola virus inhibits the antiviral effect mediated by double-stranded RNA-dependent protein kinase PKR," J Virol. 81 (1): 182-92 (2007). Two candidates boosted AAV production, VP35 from Ebola virus and SM from Epstein-Barr virus. To incorporate the protein orthologs into the iHelper2.2 vector, a VP35 or SM gene was fused in frame to an N-terminal Flag tag, and placed under an inducible human CMV promoter with an insertion of TetO₂, followed by a BGH Poly(A) signal. The expression cassette was then inserted into the region between E4 and puromycin resistance gene in the iHelper2.2, flanked by core insulators. The iHelper3.1 vector with a VP35 gene is shown in FIG. 4A and the iHelper3.2 vector with a SM gene is shown in FIG. 4B.

Sequence Listings

The sequence of the pPBBG-iHelper2.0-HA vector is provided below:

pPBBG-iHelper2.0-HA (16,549 bp)

(SEQ ID NO: 3)

```
ACTCTTCCTTTTTCAATATTATTGAAGCATTTATCAGGGTTATTGTCTCATGA

GCGGATACATATTTGAATGTATTTAGAAAAATAAACAAATAGGGGTTCCGCGCACA

TTTCCCCGAAAAGTGCCACCTAAATTGTAAGCGTTAATATTTTGTTAAAATTCGCGTT

AAATTTTTGTTAAATCAGCTCATTTTTTAACCAATAGGCCGAAATCGGCAAAATCCC

TTATAAATCAAAAGAATAGACCGAGATAGGGTTGAGTGTTGTTCCAGTTTGGAACA
```

-continued

```
AGAGTCCACTATTAAAGAACGTGGACTCCAACGTCAAAGGGCGAAAAACCGTCTAT
CAGGGCGATGGCCCACTACGTGAACCATCACCCTAATCAAGTTTTTTGGGGTCGAGG
TGCCGTAAAGCACTAAATCGGAACCCTAAAGGGAGCCCCCGATTTAGAGCTTGACG
GGGAAAGCCGGCGAACGTGGCGAGAAAGGAAGGGAAGAAAGCGAAAGGAGCGGG
CGCTAGGGCGCTGGCAAGTGTAGCGGTCACGCTGCGCGTAACCACCACACCCGCCG
CGCTTAATGCGCCGCTACAGGGCGCGTCCCATTCGCCATTCAGGCTGCGCAACTGTT
GGGAAGGGCGATCGGTGCGGGCCTCTTCGCTATTACGCCAGCTGGCGAAAGGGGGA
TGTGCTGCAAGGCGATTAAGTTGGGTAACGCCAGGGTTTTCCCAGTCACGACGTTGT
AAAACGACGGCCAGTGAGCGCGCCTCGTTCATTCACGTTTTTGAACCCGTGGAGGAC
GGGCAGACTCGCGGTGCAAATGTGTTTTACAGCGTGATGGAGCAGATGAAGATGCT
CGACACGCTGCAGAACACGCAGCTAGATTAACCCTAGAAAGATAATCATATTGTGA
CGTACGTTAAAGATAATCATGCGTAAAATTGACGCATGTGTTTTATCGGTCTGTATA
TCGAGGTTTATTTATTAATTTGAATAGATATTAAGTTTTATTATATTTACACTTACAT
ACTAATAATAAATTCAACAAACAATTTATTTATGTTTATTTATTTATTAAAAAAAAA
CAAAAACTCAAAATTTCTTCTATAAAGTAACAAAACTTTTATCGAATTCCTGCAGCC
CGGGGGATCCACTAGTTCTAGAGGGACAGCCCCCCCCCAAAGCCCCCAGGGATGTA
ATTACGTCCCTCCCCCGCTAGGGGGCAGCAGCGAGCCGCCCGGGGCTCCGCTCCGGT
CCGGCGCTCCCCCCGCATCCCCGAGCCGGCAGCGTGCGGGGACAGCCCGGGCACGG
GGAAGGTGGCACGGGATCGCTTTCCTCTGAACGCTTCTCGCTGCTCTTTGAGCCTGC
AGACACCTGGGGGGATACGGGGAAAAGGCCTCCAAGGCCAGCTTCCCACAATAAGT
TGGGTGAATTTTGGCTCATTCCTCCTTTCTATAGGATTGAGGTCAGAGCTTTGTGATG
GGAATTCTGTGGAATGTGTGTCAGTTAGGGTGTGGAAAGTCCCgcGATCgcTAGcGTTT
AAACTTAAGCTTGGTACCGAGCTCGGATCCACTAGTCCAGTGTGGTGGAATTCCTGC
TTCGCGATGTACGGGCCggtacccaactccatgcttaacagtccccaggtacagccaccctgcgtcgcaaccaggaaca
gctctacagcttcctggagcgccactcgccctacttccgcagccacagtgcgcagattaggagcgccacttcttttgtcacttgaaaaacat
gtaaaaataatgtactaggagacactttcaataaaggcaaatgttttttatttgtacactctcgggtgattatttaccccccaccttgccgtctg
cgccgtttaaaaatcaaagggttctgccgcgcatcgctatgcgccactggcagggacacgttgcgatactggtgtttagtgctccacttaaact
caggcacaaccatccgcggcagctcggtgaagttttcactccacaggctgcgcaccatcaccaacgcgtttagcaggtcgggcgccgata
tcttgaagtcgcagttgggggcctccgccctgcgcgcgcgagttgcgatacacaggggttgcagcactggaacactatcagcgccgggtggt
gcacgctggccagcacgctcttgtcggagatcagatccgcgtccaggtcctccgcgttgctcagggcgaacggagtcaactttggtagctg
ccttcccaaaaagggtgcatgcccaggctttgagttgcactcgcaccgtagtggcatcagaaggtgaccgtgcccggtctgggcgttagga
tacagcgcctgcatgaaagccttgatctgcttaaaagccacctgagcctttgcgccttcagagaagaacatgccgcaagacttgccggaaa
actgattggccggacaggccgcgtcatgcacgcagcaccttgcgtcggtgttggagatctgcaccacatttcggccccaccggttcttcacg
atcttggccttgctagactgctccttcagcgcgcgctgcccgttttcgctcgtcacatccatttcaatcacgtgctccttatttatcataatgct
cccgtgtagacacttaagctcgccttcgatctcagcgcagcggtgcagccacaacgcgcagcccgtgggctcgtggtgcttgtaggttacctctg
caaacgactgcaggtacgcctgcaggaatcgccccatcatcgtcacaaaggtcttgttgctggtgaaggtcagctgcaacccgcggtgctc
ctcgtttagccaggtcttgcatacggccgccagagcttccacttggtcaggcagtagcttgaagtttgcctttagatcgttatccacgtggtact
tgtccatcaacgcgcgcgcagcctccatgcccttctcccacgcagacacgatcggcaggctcagcgggtttatcaccgtgctttcactttccg
cttcactggactcttccttttcctcttgcgtccgcataccccgcgccactgggtcgtcttcattcagccgccgcaccgtgcgcttacctcccttg
ccgtgcttgattagcaccggtgggttgctgaaacccaccatttgtagcgccacatcttctctttcttcctcgctgtccacgatcacctctgggga
```

-continued

```
tggcgggcgctcgggcttgggagaggggcgcttcttttttcttttttggacgcaatggccaaatccgccgtcgaggtcgatggccgcgggctgg gtgtgcgcggcaccagcgcatcttgtgacgagtcttcttcgtcctcggactcgagacgccgcctcagccgcttttttggggcgcgcggggg aggcggcggcgacggcgacggggacgacacgtcctccatggttggtggacgtcgcgccgcaccgcgtccgcgctcggggtggtttc gcgctgctcctcttcccgactggccatttccttctcctataggcagaaaaagatcatggagtcagtcgagaaggaggacagcctaaccgccc cctttgagttcgccaccaccgcctccaccgatgccgccaacgcgcctaccaccttccccgtcgaggcaccccgcttgaggaggaggaa gtgattatcgagcaggacccaggttttgtaagcgaagacgacgaggatcgctcagtaccaacagaggataaaaagcaagaccaggacga cgcagaggcaaacgaggaacaagtcgggcggggggaccaaaggcatggcgactacctagatgtgggagacgacgtgctgttgaagca tctgcagcgccagtgcgccattatctgcgacgcgttgcaagagcgcagcgatgtgcccctcgccatagcggatgtcagccttgcctacgaa cgccacctgttctcaccgcgcgtaccccccaaacgccaagaaaacggcacatgcgagcccaacccgcgcctcaacttctaccccgtatttg ccgtgccagaggtgcttgccacctatcacatcttttttccaaaactgcaagataccccctatcctgccgtgccaaccgcagccgagcggacaag cagctggccttgcggcagggcgctgtcatacctgatatcgcctcgctcgacgaagtgccaaaaatctttgagggtcttggacgcgacgaga aacgcgcggcaaacgctctgcaacaagaaaacagcgaaaatgaaagtcactgtggagtgctggtggaacttgagggtgacaacgcgcg cctagccgtgctgaaacgcagcatcgaggtcacccactttgcctaccggcacttaacctaccccccaaggttatgagcacagtcatgagc gagctgatcgtgcgccgtgcacgacccctggagagggatgcaaacttgcaagaacaaaccgaggagggcctacccgcagttggcgatg agcagctggcgcgctggcttgagacgcgcgagcctgccgacttggaggagcgacgcaagctaatgatggccgcagtgcttgttaccgtg gagcttgagtgcatgcagcggttctttgctgacccggagatgcagcgcaagctagaggaaacgttgcactacacctttcgccagggctacg tgcgccaggcctgcaaaatttccaacgtggagctctgcaacctggtctcctaccttggaattttgcacgaaaaccgcctcgggcaaaacgtg cttcattccacgctcaagggcgaggcgcgccgcgactacgtccgcgactgcgtttacttatttctgtgctacacctggcaaacggccatggg cgtgtggcagcaatgcctggaggagcgcaacctaaaggagctgcagaagctgctaaagcaaaacttgaaggacctatggacggccttca acgagcgctccgtggccgcgcacctggcggacattatcttccccgaacgcctgcttaaaaccctgcaacagggtctgccagacttcaccag tcaaagcatgttgcaaaactttaggaactttatcctagagcgttcaggaattctgcccgccacctgctgtgcgcttcctagcgactttgtgccca ttaagtaccgtgaatgccctccgccgctttggggtcactgctaccttctgcagctagccaactaccttgcctaccactccgacatcatggaaga cgtgagcggtgacggcctactggagtgtcactgtcgctgcaacctatgcaccccgcaccgctccctggtctgcaattcgcaactgcttagcg aaagtcaaattatcggtacctttgagctgcagggtccctcgcctgacgaaaagtccgcggctccggggttgaaactcactccggggctgtg gacgtcCGATCTCTATCACTGATAGGGAGATCTCTATCACTGATAGGGAGAGggcttaccttcg caaatttgtacctgaggactaccacgcccacgagattaggttctacgaagaccaatcccgcccgccaaatgcggagcttaccgcctgcgtc attacccagggccacatccttggccaattgcaagccatcaacaaagcccgccaagagtttctgctacgaaagggacgggggggtttacctgg accccagtccggcgaggagctcaacccaatcccccgccgccgcagccctatcagcagccgcgggcccttgcttcccaggatggcac ccaaaaagaagctgcagctgccgccgccgccacccacggacgaggaggaatactgggacagtcaggcagaggaggttttggacgagg aggaggagatgatggaagactgggacagcctagacgaagcttccgaggccgaagaggtgtcagacgaaacaccgtcaccctcggtcgc attcccctcgccggcgccccagaaattggcaaccgttcccagcatcgctacaacctccgctcctcaggcgccgccggcactgcctgttcgc cgacccaaccgtagatgggacaccactggaaccagggccggtaagtctaagcagccgccgccgttagcccaagagcaacaacagcgc caaggctaccgctcgtggcgcgggcacaagaacgccatagttgcttgcttgcaagactgtggggcaacatctccttcgcccgccgctttct tctctaccatcacggcgtggccttccccgtaacatcctgcattactaccgtcatctctacagccctactgcaccggcggcagcggcagcg gcagcaacagcagcggtcacacagaagcaaaggcgaccggatagcaagactctgacaaagcccaagaaatccacagcggcggcagc agcaggaggaggagcgctcgtctggcgcccaacgaacccgtatcgacccgcgagcttagaaataggattttttcccactctgtatgctatat ttcaacaaagcaggggccaagaacaagagctgaaaataaaaaacaggtctctgcgctccctcacccgcagctgcctgtatcacaaaagcg aagatcagcttcggcgcacgctggaagacgcggaggctctcttcagcaaCGATCTCTATCACTGATAGGGAGATC TCTATCACTGATAGGGAGAGatactgcgcgctgactcttaaggactagtttcgcgccctttctcaaatttaagcgcgaaaa ctacgtcatctccagcggccacacccggcgccagcacctgtcgtcagcgccattatgagcaaggaaattcccacgccctacatgtggagtt accagccacaaatgggacttgcggctggagctgcccaagactactcaacccgaataaaactacatgagcgcgggaccccacatgatatccc
```

-continued gggtcaacggaatccgcgcccaccgaaaccgaattctcctcgaacaggcggctattaccaccacacctcgtaataaccttaatccccgtagt tggcccgctgccctggtgtaccaggaaagtcccgctcccaccactgtggtacttcccagagacgcccaggccgaagttcagatgactaact caggggcgcagcttgcgggcggctttcgtcacagggtgcggtcgcccgggcgttttagggcggagtaacttgcatgtattgggaattgtag ttttttaaaatgggaagtgacgtatcgtgggaaaacggaagtgaagatttgaggaagttgtgggttttttggctttcgtttctgggcgtaggtt cgcgtgcggttttctgggtgttttttgtggactttaaccgttacgtcattttttagtcctatatatactcgctctgtaCTCTCCCTATCAGT GATAGAGATCTCCCTATCAGTGATAGAGATCGcttggcccttttttacactgtgactgattgagctggtgccgtgt cgagtggtgtttttttaataggttttttttactggtaaggctgactgttatggctgccgctgtggaagcgctgtatgttgttctggagcgggagggt gctattttgcctaggcaggagggttttttcaggtgtttatgtgttttttctctcctattaatttgttatacctcctatggggctgtaatgttgtc tctacgcctgcgggtatgtattccccgggctatttcggtcgcttttagcactgaccgatgttaaccaacctgatgtgtttaccgagtcttaca ttatgactccggacatgaccgaggaactgtcggtggtgcttttaatcacggtgaccagttttttttacggtcacgccggcatggccgtagtccgt cttatgcttataagggttgttttttcctgttgtaagacaggcttctaatgtttaaatgttttttttttttgttattttattttgtgtttaatgcagg aacccgcagacatgtttgagagaaaaatggtgtcttttttctgtggtggttccggaacttacctgcctttatctgcatgagcatgactacgatgtg cttgcttttttgcgcgaggctttgcctgatttttttgagcagcaccttgcattttatatcgccgcccatgcaacaagcttacatagggctacgct ggttagcatagctccgagtatgcgtgtcataatcagtgtgggttcttttgtcatggttcctggcggggaagtggccgcgctggtccgtcagacc tgcacgattatgttcagctggccctgcgaagggacctacgggatcgcggtattttttgttaatgttccgcttttgaatcttatacaggtctgtgag gaacctgaattttttgcaatcatgattcgctgcttgaggctgaaggtggagggcgctctggagcagattttttacaatggccggacttaatattcgg gatttgcttagagacatattgataaggtggcgagatgaaaattatttgggcatggttgaaggtgctggaatgtttatagaggagattcaccctga agggtttagcctttacgtccacttggacgtgagggcagtttgccttttggaagccattgtgcaacatcttacaaatgccattatctgttctttgg ctgtagagtttgaccacgccaccggaggggagcgcgttcacttaatagatcttcattttgaggttttggataatcttttggaataaaaaaaaaa aacatggttcttccagctcttcccgctcctcccgtgtgtgactcgcagaacgaatgtgtaggttggctgggtgtggcttattctgcggtggtgga tgttatcagggcagcggcgcatgaaggagtttacatagaacccgaagccaggggcgcctggatgctttgagagagtggatatactacaactact acacagagcgagctaagcgacgagaccggagacgcagatctgtttgtcacgcccgcacctggttttgcttcaggaaatatgTACCCATACGATGT TCCAGATTACGCTGGAGGAGGCGGAGGCactacgtccggcgttccatttggcatgacactacgaccaacacgatct cggttgtctcggcgcactccgtacagtagggatcgcctacctccttttgagacagagacccgcgctaccatactggaggatcatccgctgct gcccgaatgtaacactttgacaatgcacaacgtgagttacgtgcgaggtcttccctgcagtgtgggatttacgctgattcaggaatgggttgtt ccctgggatatggttctgacgcgggaggagcttgtaatcctgaggaagtgtatgcacgtgtgcctgtgttgtgccaacattgatatcatgacg agcatgatgatccatggttacgagtcctgggctctccactgtcattgttccagtcccggttccctgcagtgcatagccggcgggcaggttttgg ccagctggtttaggatggtggtggatggcgccatgtttaatcagaggtttatatggtaccgggaggtggtgaattacaacatgccaaaagag gtaatgtttatgtccagcgtgtttatgaggggtcgccacttaatctacctgcgcttgtggtatgatggcacgtgggttctgtggtccccgccat gagctttggatacagcgccttgcactgtgggattttgaacaatattgtggtgctgtgctgcagttactgtgctgatttaagtgagatcagggtgc gctgctgtgcccggaggacaaggcgtctcatgctgcgggcggtgcgaatcatcgctgaggagaccactgccatgttgtattcctgcaggac ggagcggcggcggcagcagtttattcgcgcgctgctgcagcaccaccgccctatcctgatgcacgattatgactctaccccatgtaggcg tggacttcccctttcgccgcccgttgagcaaccgcaagttggacagcagcctgtggctcagcagctggacagcgacatgaacttaagcgag ctgcccggggagtttattaatatcactgatgagcgtttggctcgacaggaaaccgtgtggaatataacacctaagaatatgtctgttacccatg atatgatgcttttttaaggccagccggggagaaaggactgtgtactctgtgtgttgggagggaggtggcaggttgaatactagggttctgtgag tttgattaaggtacggtgatcaatataagctatgtggtggtgggctatactactgaatgaaaaatgacttgaaattttctgcaattgaaaaata aacacgttgaaacataacatgcaacaggttcacgattctttattcctgggcaatgtaggagaaggtgaagagttggtagcaaaagtttcagtgg tgtattttccactttcccaggaccatgtaaaagacatagagtaagtgcttacctcgctagtttctgtggattcactagaatcgatgtaggatgtt gcccctcctgacgcggtaggagaagggggagggtgccctgcatgtctgccgctgctcttgctcttgccgctgctgaggaggggggcgcatctg ccgcagcaccggatgcatctgggaaaagcaaaaaggggctcgtccctgtttccggaggaatttgcaagcggggtcttgcatgacgggg -continued aggcaaaccccgttcgccgcagtccggccggcccgagactcgaaccgggggtcctgcgactcaacccttggaaaataaccctccggct acagggagcgagccacttaatgctttcgctttccagcctaaccgcttacgccgcgcgcggccagtggccaaaaaagctagcgcagcagcc gccgcgcctggaaggaagccaaaaggagcgctccccgttgtctgacgtcgcacacctgggttcgacacgcgggggtaaccgcatgg atcacggcggacggccggatccggggttcgaaccccggtcgtccgccatgatacccttgcgaatttatccaccagaccacggaagagtgc ccgcttacaCGATCTCTATCACTGATAGGGAGATCTCTATCACTGATAGGGAGAGggctctcctt ttgcacggtctagagcgtcaacgactgcgcacgcctcaccgccagagcgtcccgaccatggagcacttttttgccgctgcgcaacatctgg aaccgcgtccgcgactttccgcgcgcctccaccaccgccgccggcatcacctggatgtccaggtacatctacggattacgtcgacgtttaa accatatgatcagctcactcaaaggcggtaatacggttatccacagaatcagggggataacgcaggaaagaacatgtgagcaaaaggccag caaaaggccaggaaccgtaaaaaggccgcgttgctggcgtttccactttggccgcggctcgagTGAGCTATTCCAGAAGT

AGTGAAGAGGCTTTTTTGGAGGCCTAGGCTTTTGCAAAAAGCTCCGGATCGATGCCC

GGGGGATCCACTAGTTCTAGAGGGACAGCCCCCCCCCAAAGCCCCCAGGGATGTAA

TTACGTCCCTCCCCCGCTAGGGGGCAGCAGCGAGCCGCCCGGGGCTCCGCTCCGGTC

CGGCGCTCCCCCCGCATCCCCGAGCCGGCAGCGTGCGGGGACAGCCCGGGCACGGG

GAAGGTGGCACGGGATCGCTTTCCTCTGAACGCTTCTCGCTGCTCTTTGAGCCTGCA

GACACCTGGGGGGATACGGGGAAAAGGCCTCCAAGGCCAGCTTCCCACAATAAGTT

GGGTGAATTTTGGCTGAGCTATTCCAGAAGTAGTGAAGAGGCTTTTTTGGAGGCCTA

GGCTTTTGCAAAAAGCTCCGGATCGATCATATATGGCAGATATACGCGTTGACATTG

ATTATTGACTAGTTATTAATAGTAATCAATTACGGGGTCATTAGTTCATAGCCCATAT

ATGGAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAGGG

ACTTTCCATTGACGTCAATGGGTGGAGTATTTACGGTAAACTGCCCACTTGGCAGTA

CATCAAGTGTATCATATGCCAAGTACGCCCCCTATTGACGTCAATGACGGTAAATGG

CCCGCCTGGCATTATGCCCAGTACATGACCTTATGGGACTTTCCTACTTGGCAGTAC

ATCTACGTATTAGTCATCGCTATTACCATGGTGATGCGGTTTTGGCAGTACATCAAT

GGGCGTGGATAGCGGTTTGACTCACGGGGATTTCCAAGTCTCCACCCCATTGACGTC

AATGGGAGTTTGTTTTGGCACCAAAATCAACGGGACTTTCCAAAATGTCGTAACAAC

TCCGCCCCATTGACGCAAATGGGCGGTAGGCGTGTACGGTGGGAGGTCTATATAAG

CAGAGCTCTCTGGCTAACTATCGTCGACGAGCTCGTTTAGTGAACCGTCAGATCGCC

TGGAGACGCCATCCACGCTGTTTTGACCTCCATAGAAGACACCGGGACCGATCCAG

CCTCCGGACTCTAGCGTTTAAACTTAAGCTTGCCACCatgaccgagtacaagcccacggtgcgcctcgc cacccgcgacgacgtccccagggccgtacgcaccctcgccgccgcgttcgccgactaccccgccacgcgccacaccgtcgatccggac cgccacatcgagcgggtcaccgagctgcaagaactcttcctcacgcgcgtcgggctcgacatcggcaaggtgtgggtcgcggacgacg gcgccgcggtggcggtctggaccacgccggagagcgtcgaagcggggcggtgttcgccgagatcggcccgcgcatggccgagttga gcggttcccggctggccgcgcagcaacagatggaaggcctcctggcgccgcaccggcccaaggagcccgcgtggttcctggccaccgt cggcgtctcgcccgaccaccagggcaagggtctgggcagcgccgtcgtgctccccggagtggaggcggccgagcgcgccggggtgc ccgccttcctggagacctccgcgccccgcaacctccccttctacgagcggctcggcttcaccgtcaccgccgacgtcgaggtgcccgaag gaccgcgcacctggtgcatgacccgcaagcccggtgcctgaAGCGCGGGGATCTCATGCTGGAGTTCTTCG

CCCACCCCAACTTGTTTATTGCAGCTTATAATGGTTACAAATAAAGCAATAGCATCA

CAAATTTCACAAATAAAGCATTTTTTTCACTGCATTCTAGTTGTGGTTTGTCCAAACT

CATCAATGTATCTTATCATGTCTGTAGCtGATgtATAcCTAggATCCGGCCGGccTGCAgg

TGTCCTCACAGGAACGAAGTCCCTAAAGAAACAGTGGCAGCCAGGTTTAGCCCCGG

-continued

```
AATTGACTGGATTCCTTTTTTAGGGCCCATTGGTATGGCTTTTTCCCCGTATCCCCCC
AGGTGTCTGCAGGCTCAAAGAGCAGCGAGAAGCGTTCAGAGGAAAGCGATCCCGTG
CCACCTTCCCCGTGCCCGGGCTGTCCCCGCACGCTGCCGGCTCGGGGATGCGGGGGG
AGCGCCGGACCGGAGCGGAGCCCCGGGCGGCTCGCTGCTGCCCCCTAGCGGGGGAG
GGACGTAATTACATCCCTGGGGGCTTTGGGGGGGGGCTGTCCCTCTAGAGCGGCCGC
CACCGCGGTGGAGCTCCAGCTTTTGTTCCCTTTAGTGAGGGTTAATTAGATCTTAATA
CGACTCACTATAGGGCGAATTGGGTACCGGGCCCCCCCTCGAGGTCGACGGTATCG
ATAAGCTTGATATCTATAACAAGAAAATATATATATAATAAGTTATCACGTAAGTAG
AACATGAAATAACAATATAATTATCGTATGAGTTAAATCTTAAAAGTCACGTAAAA
GATAATCATGCGTCATTTTGACTCACGCGGTCGTTATAGTTCAAAATCAGTGACACT
TACCGCATTGACAAGCACGCCTCACGGGAGCTCCAAGCGGCGACTGAGATGTCCTA
AATGCACAGCGACGGATTCGCGCTATTTAGAAAGAGAGAGCAATATTTCAAGAATG
CATGCGTCAATTTTACGCAGACTATCTTTCTAGGGTTAATCTAGCTGCATCAGGATC
ATATCGTCGGGTCTTTTTTCCGGCTCAGTCATCGCCCAAGCTGGCGCTATCTGGGCAT
CGGGGAGGAAGAAGCCCGTGCCTTTTCCCGCGAGGTTGAAGCGGCATGGAAAGAGT
TTGCCGAGGATGACTGCTGCTGCATTGACGTTGAGCGAAAACGCACGTTTACCATGA
TGATTCGGGAAGGTGTGGCCATGCACGCCTTTAACGGTGAACTGTTCGTTCAGGCCA
CCTGGGATACCAGTTCGTCGCGGCTTTTCCGGACACAGTTCCGGATGGTCAGCCCGA
AGCGCATCAGCAACCCGAACAATACCGGCGACAGCCGGAACTGCCGTGCCGGTGTG
CAGATTAATGACAGCGGTGCGGCGCTGGGATATTACGTCAGCGAGGACGGGTATCC
TGGCTGGATGCCGCAGAAATGGACATGGATACCCCGTGAGTTACCCGGCGGGCGCG
CTTGGCGTAATCATGGTCATAGCTGTTTCCTGTGTGAAATTGTTATCCGCTCACAATT
CCACACAACATACGAGCCGGAAGCATAAAGTGTAAAGCCTGGGGTGCCTAATGAGT
GAGCTAACTCACATTAATTGCGTTGCGCTCACTGCCCGCTTTCCAGTCGGGAAACCT
GTCGTGCCAGCTGCATTAATGAATCGGCCAACGCGCGGGGAGAGGCGGTTTGCGTA
TTGGGCGCTCTTCCGCTTCCTCGCTCACTGACTCGCTGCGCTCGGTCGTTCGGCTGCG
GCGAGCGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACCGTAA
AAAGGCCGCGTTGCTGGCGTTTTTCCATAGGCTCCGCCCCCCTGACGAGCATCACAA
AAATCGACGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCCGCTTACCGG
ATACCTGTCCGCCTTTCTCCCTTCGGGAAGCGTGGCGCTTTCTCATAGCTCACGCTGT
AGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCG
GTAAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTACAC
TAGAAGGACAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGTTTTTTGT
TTGCAAGCAGCAGATTACGCGCAGAAAAAAAGGATCTCAAGAAGATCCTTTGATCT
TTTCTACGGGGTCTGACGCTCAGTGGAACGAAAACTCACGTTAAGGGATTTTGGTCA
```

```
TGAGATTATCAAAAAGGATCTTCACCTAGATCCTTTTAAATTAAAAATGAAGTTTTA

AATCAATCTAAAGTATATATGAGTAAACTTGGTCTGACAGTTACCAATGCTTAATCA

GTGAGGCACCTATCTCAGCGATCTGTCTATTTCGTTCATCCATAGTTGCCTGACTCCC

CGTCGTGTAGATAACTACGATACGGGAGGGCTTACCATCTGGCCCCAGTGCTGCAAT

GATACCGCGAGACCCACGCTCACCGGCTCCAGATTTATCAGCAATAAACCAGCCAG

CCGGAAGGGCCGAGCGCAGAAGTGGTCCTGCAACTTTATCCGCCTCCATCCAGTCTA

TTAATTGTTGCCGGGAAGCTAGAGTAAGTAGTTCGCCAGTTAATAGTTTGCGCAACG

TTGTTGCCATTGCTACAGGCATCGTGGTGTCACGCTCGTCGTTTGGTATGGCTTCATT

CAGCTCCGGTTCCCAACGATCAAGGCGAGTTACATGATCCCCCATGTTGTGCAAAAA

AGCGGTTAGCTCCTTCGGTCCTCCGATCGTTGTCAGAAGTAAGTTGGCCGCAGTGTT

ATCACTCATGGTTATGGCAGCACTGCATAATTCTCTTACTGTCATGCCATCCGTAAG

ATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGA

TCTTACCGCTGTTGAGATCCAGTTCGATGTAACCCACTCGTGCACCCAACTGATCTTC

AGCATCTTTTACTTTCACCAGCGTTTCTGGGTGAGCAAAAACAGGAAGGCAAAATGC

CGCAAAAAAGGGAATAAGGGCGACACGGAAATGTTGAATACTCAT
```

The sequence of the pPBBG-iHelper2.1-HA vector is provided below:

pPBBG-iHelper2.1-HA (15,878 bp)   (SEQ ID NO: 4)

```
ACTCTTCCTTTTTCAATATTATTGAAGCATTTATCAGGGTTATTGTCTCATGA

GCGGATACATATTTGAATGTATTTAGAAAAATAAACAAATAGGGGTTCCGCGCACA

TTTCCCCGAAAAGTGCCACCTAAATTGTAAGCGTTAATATTTTGTTAAAATTCGCGTT

AAATTTTTGTTAAATCAGCTCATTTTTTAACCAATAGGCCGAAATCGGCAAAATCCC

TTATAAATCAAAAGAATAGACCGAGATAGGGTTGAGTGTTGTTCCAGTTTGGAACA

AGAGTCCACTATTAAAGAACGTGGACTCCAACGTCAAAGGGCGAAAAACCGTCTAT

CAGGGCGATGGCCCACTACGTGAACCATCACCCTAATCAAGTTTTTTGGGGTCGAGG

TGCCGTAAAGCACTAAATCGGAACCCTAAAGGGAGCCCCCGATTTAGAGCTTGACG

GGGAAAGCCGGCGAACGTGGCGAGAAAGGAAGGGAAGAAAGCGAAAGGAGCGGG

CGCTAGGGCGCTGGCAAGTGTAGCGGTCACGCTGCGCGTAACCACCACACCCGCCG

CGCTTAATGCGCCGCTACAGGGCGCGTCCCATTCGCCATTCAGGCTGCGCAACTGTT

GGGAAGGGCGATCGGTGCGGGCCTCTTCGCTATTACGCCAGCTGGCGAAAGGGGGA

TGTGCTGCAAGGCGATTAAGTTGGGTAACGCCAGGGTTTTCCCAGTCACGACGTTGT

AAAACGACGGCCAGTGAGCGCGCCTCGTTCATTCACGTTTTTGAACCCGTGGAGGAC

GGGCAGACTCGCGGTGCAAATGTGTTTTACAGCGTGATGGAGCAGATGAAGATGCT

CGACACGCTGCAGAACACGCAGCTAGATTAACCCTAGAAAGATAATCATATTGTGA

CGTACGTTAAAGATAATCATGCGTAAAATTGACGCATGTGTTTTATCGGTCTGTATA

TCGAGGTTTATTTATTAATTTGAATAGATATTAAGTTTTATTATATTTACACTTACAT

ACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC
```

```
CGGGGGATCCACTAGTTCTAGAGGGACAGCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCggtacccaactccatgcttaacagtccccaggtacagcccaccctgcgtcgcaaccaggaaca gctctacagcttcctggagcgccactcgccctacttccgcagccacagtgcgcagattaggagcgccacttcttttttgtcacttgaaaaacat gtaaaaataatgtactaggagacactttcaataaaggcaaatgttttttatttgtacactctcgggtgattatttaccccccaccctttgccgtctg cgccgtttaaaaatcaaaggggttctgccgcgcatcgctatgcgccactggcagggacacgttgcgatactggtgtttagtgctccacttaaact caggcacaaccatccgcggcagctcggtgaagttttcactccacaggctgcgcaccatcaccaacgcgtttagcaggtcgggcgccgata tcttgaagtcgcagttgggccctccgccctgcgcgcgcgagttgcgatacacaggggttgcagcactggaacactatcagcgccgggtggt gcacgctggccagcacgctcttgtcggagatcagatccgcgtccaggtcctccgcgttgctcagggcgaacggagtcaactttggtagctg ccttcccaaaaagggtgcatgcccaggctttgagttgcactcgcaccgtagtggcatcagaaggtgaccgtgcccggtctgggcgttagga tacagcgcctgcatgaaagccttgatctgcttaaaagccacctgagcctttgcgccttcagagaagaacatgccgcaagacttgccggaaa actgattggccggacaggccgcgtcatgcacgcagcaccttgcgtcggtgttggagatctgcaccacatttcggccccaccggttcttcacg atcttggccttgctagactgctccttcagcgcgcgctgcccgttttcgctcgtcacatccatttcaatcacgtgctccttatttatcataatgct cccgtgtagacacttaagctcgccttcgatctcagcgcagcggtgcagccacaacgcgcagcccgtgggctcgtggtgcttgtaggttacctctg caaacgactgcaggtacgcctgcaggaatcgcccatcatcgtcacaaaggtcttgttgctggtgaaggtcagctgcaacccgcggtgctc ctcgtttagccaggtcttgcatacggccgccagagcttccacttggtcaggcagtagcttgaagtttgcctttagatcgttatccacgtggtact tgtccatcaacgcgcgcgcagcctccatgcccttctcccacgcagacacgatcggcaggctcagcgggtttatcaccgtgctttcactttccg cttcactggactcttccttttcctcttgcgtccgcataccccgcgccactgggtcgtcttcattcagccgccgcaccgtgcgcttacctcccttg ccgtgcttgattagcaccggtgggttgctgaaacccaccatttgtagcgccacatcttctctttcttcctcgctgtccacgatcacctctgggga tggcgggcgctcgggcttgggagaggggcgcttcttttctttttggacgcaatggccaaatccgccgtcgaggtcgatggccgcgggctgg gtgtgcgcggcaccagcgcatcttgtgacgagtcttcttcgtcctcggactcgagacgccgcctcagccgcttttttgggggcgcgcggggg aggcggcggcgacggcgacggggacgacacgtcctccatggttggtggacgtcgcgccgcaccgcgtccgcgctcggggtggtttc gcgctgctcctcttcccgactggccatttccttctcctataggcagaaaaagatcatggagtcagtcgagaaggaggacagcctaaccgccc cctttgagttcgccaccaccgcctccaccgatgccgccaacgcgcctaccaccttccccgtcgaggcacccccgcttgaggaggaggaa gtgattatcgagcaggacccaggttttgtaagcgaagacgacgaggatcgctcagtaccaacagaggataaaaagcaagaccaggacga cgcagaggcaaacgaggaacaagtcgggcgggggaccaaaggcatggcgactacctagatgtgggagacgacgtgctgttgaagca tctgcagcgccagtgcgccattatctgcgacgcgttgcaagagcgcagcgatgtgcccctcgccatagcggatgtcagccttgcctacgaa cgccacctgttctcaccgcgcgtaccccccaaacgccaagaaaacggcacatgcgagcccaacccgcgcctcaacttctaccccgtatttg ccgtgccagaggtgcttgccacctatcacatcttttttccaaaactgcaagataccccctatcctgccgtgccaaccgcagccgagcggacaag cagctggccttgcggcagggcgctgtcatacctgatatcgcctcgctcgacgaagtgccaaaaatctttgagggtcttggacgcgacgaga aacgcgcggcaaacgctctgcaacaagaaaacagcgaaaatgaaagtcactgtggagtgctggtggaacttgagggtgacaacgcgcg cctagccgtgctgaaacgcagcatcgaggtcacccactttgcctacccggcacttaacctaccccccaaggttatgagcacagtcatgagc gagctgatcgtgcgccgtgcacgacccctggagagggatgcaaacttgcaagaacaaaccgaggagggcctaccccgcagttggcgatg agcagctggcgcgctggcttgagacgcgcgagcctgccgacttggaggagcgacgcaagctaatgatggccgcagtgcttgttaccgtg
```

-continued

```
gagcttgagtgcatgcagcggttctttgctgacccggagatgcagcgcaagctagaggaaacgttgcactacacctttcgccagggctacg tgcgccaggcctgcaaaatttccaacgtggagctctgcaacctggtctcctaccttggaattttgcacgaaaaccgcctcgggcaaaacgtg cttcattccacgctcaagggcgaggcgcgccgcgactacgtccgcgactgcgtttacttatttctgtgctacacctggcaaacggccatggg cgtgtggcagcaatgcctggaggagcgcaacctaaaggagctgcagaagctgctaaagcaaaacttgaaggacctatggacggccttca acgagcgctccgtggccgcgcacctggcggacattatcttccccgaacgcctgcttaaaaccctgcaacagggtctgccagacttcaccag tcaaagcatgttgcaaaactttaggaactttatcctagagcgttcaggaattctgcccgccacctgctgtgcgcttcctagcgactttgtgccca ttaagtaccgtgaatgccctccgccgctttggggtcactgctaccttctgcagctagccaactaccttgcctaccactccgacatcatggaaga cgtgagcggtgacggcctactggagtgtcactgtcgctgcaacctatgcaccccgcaccgctccctggtctgcaattcgcaactgcttagcg aaagtcaaattatcggtacctttgagctgcagggtccctcgcctgacgaaaagtccgcggctccggggttgaaactcactccggggctgtg gacgtcCGATCTCTATCACTGATAGGGAGATCTCTATCACTGATAGGGAGAggcttaccttcg caaatttgtacctgaggactaccacgcccacgagattaggttctacgaagaccaatcccgcccgccaaatgcggagcttaccgcctgcgtc attcccagggccacatccttggccaattgcaagccatcaacaaagcccgccaagagtttctgctacgaaagggacgggggggtttacctgg accccagtccggcgaggagctcaacccaatcccccgccgccgcagccctatcagcagccgcgggcccttgcttcccaggatggcac ccaaaaagaagctgcagctgccgccgccgccaccccacggacgaggaggaatactgggacagtcaggcagaggaggttttggacgagg aggaggagatgatgaagactgggacagcctagacgaagcttccgaggccgaagaggtgtcagacgaaacaccgtcaccctcggtcgc attcccctcgccggcgccccagaaattggcaaccgttcccagcatcgctacaacctccgctcctcaggcgccgccggcactgcctgttcgc cgacccaaccgtagatgggacaccactggaaccagggccggtaagtctaagcagccgccgccgttagcccaagagcaacaacagcgc caaggctaccgctcgtggcgcgggcacaagaacgccatagttgcttgcttgcaagactgtgggggcaacatctccttcgcccgccgctttct tctctaccatcacggcgtggccttcccccgtaacatcctgcattactaccgtcatctctacagccctactgcaccggcggcagcggcagcg gcagcaacagcagcggtcacacagaagcaaaggcgaccggatagcaagactctgacaaagcccaagaaatccacagcggcggcagc agcaggaggaggagcgctgcgtctggcgcccaacgaacccgtatcgacccgcgagcttagaaataggattttttcccactctgtatgctatat ttcaacaaagcaggggccaagaacaagagctgaaaaaaaaacaggtctctgcgctccctcacccgcagctgcctgtatcacaaaagcg aagatcagcttcggcgcacgctggaagacgcggaggctctcttcagcaaCGATCTCTATCACTGATAGGGAGATC TCTATCACTGATAGGGAGAgatactgcgcgctgactcttaaggactagtttcgcgccctttctcaaatttaagcgcgaaaa ctacgtcatctccagcggccacacccggcgccagcacctgtcgtcagcgccattatgagcaaggaaattcccacgccctacatgtggagtt accagccacaaatgggacttgcggctggagctgcccaagactactcaacccgaataaaactacatgagcgcgggaccccacatgatatccc gggtcaacggaatccgcgcccaccgaaaccgaattctcctcgaacaggcggctattaccaccacacctcgtaataaccttaatcccgtagt tggcccgctgccctggtgtaccaggaaagtcccgctcccaccactgtggtacttcccagagacgcccaggccgaagttcagatgactaact cagggggcgcagcttgcgggcggctttcgtcacagggtgcggtcgcccggcgttttagggcggagtaacttgcatgtattgggaattgtag ttttttttaaaatgggaagtgacgtatcgtgggaaaacggaagtgaagatttgaggaagttgtgggttttttggctttcgtttctgggcgtaggtt cgcgtgcggttttctgggtgttttttgtggactttaaccgttacgtcattttttagtcctatatatactcgctctgtaCTCTCCCTATCAGT GATAGAGATCTCCCTATCAGTGATAGAGATCGcttggcccttttttacactgtgactgattgagctggtgccgtgt cgagtggtgttttttaataggtttttttactggtaaggctgactgttatggctgccgctgtggaagcgctgtatgttgttctggagcgggagggt gctattttgcctaggcaggagggttttttcaggtgtttatgtgttttttctctcctattaattttgttatacctcctatgggggctgtaatgttgtc tctacgcctgcgggtatgtattccccgggctatttcggtcgcttttttagcactgaccgatgttaaccaacctgatgtgtttaccgagtcttaca ttatgactccggacatgaccgaggaactgtcgtggtgcttttaatcacggtgaccagttttttttacggtcacgccggcatggccgtagtccg tcttatgcttataagggttgttttttcctgttgtaagacaggcttctaatgtttaaatgtttttttttttttgttattttattttgtgtttaatgcag gaacccgcagacatgtttgagagaaaaatggtgtctttttctgtggtggttccggaacttacctgcctttatctgcatgagcatgactacgatgt gcttgcttttttgcgcgaggctttgcctgattttttgagcagcaccttgcattttatatcgccgcccatgcaacaagcttacatagggctacgc tggttagcatagctccgagtatgcgtgtcataatcagtgtgggttcttttgtcatggttcctggcggggaagtggccgcgctggtccgtgcaga cctgcacgattatgttcagctggccctgcgaagggacctacgggatcgcggtattttttgttaatgttccgcttttgaatcttatacaggtctgtg
```

-continued aggaacctgaattttttgcaatcatgattcgctgcttgaggctgaaggtggagggcgctctggagcagattttttacaatggccggacttaatattc
gggatttgcttagagacatattgataaggtggcgagatgaaaattatttgggcatggttgaaggtgctggaatgtttatagaggagattcaccct
gaagggtttagcctttacgtccacttggacgtgagggcagtttgccttttggaagccattgtgcaacatcttacaaatgccattatctgttcttt
ggctgtagagtttgaccacgccaccggaggggagcgcgttcacttaatagatcttcattttgaggttttggataatcttttggaataaaaaaaaa
aaaacatggttcttccagctcttcccgctcctcccgtgtgtgactcgcagaacgaatgtgtaggttggctgggtgtggcttattctgcggtggtg
gatgttatcagggcagcggcgcatgaaggagtttacatagaacccgaagccaggggggcgcctggatgctttgagagagtggatatactacaacta
ctacacagagcgagctaagcgacgagaccggagacgcagatctgtttgtcacgcccgcacctggttttgcttcaggaaatatgTACCCATACGAT
GTTCCAGATTACGCTGGAGGAGGCGGAGGCactacgtccggcgttccatttggcatgacactacgaccaacacgatct
cggttgtctcggcgcactccgtacagtagggatcgcctacctccttttgagacagagacccgcgctaccatactggaggatcatccgctgct
gcccgaatgtaacactttgacaatgcacaacgtgagttacgtgcgaggtcttccctgcagtgtgggatttacgctgattcaggaatgggttgtt
ccctgggatatggttctgacgcgggaggagcttgtaatcctgaggaagtgtatgcacgtgtgcctgtgttgtgccaacattgatatcatgacg
agcatgatgatccatggttacgagtcctgggctctccactgtcattgttccagtcccggttccctgcagtgcatagccggcgggcaggttttgg
ccagctggtttaggatggtggtggatggcgccatgtttaatcagaggtttatatggtaccgggaggtggtgaattacaacatgccaaaagag
gtaatgtttatgtccagcgtgtttatgaggggtcgccacttaatctacctgcgcttgtggtatgatggcacgtgggttctgtggtccccgccat
gagctttggatacagcgccttgcactgtgggattttgaacaatattgtggtgctgtgctgcagttactgtgctgatttaagtgagatcagggtgc
gctgctgtgcccggaggacaaggcgtctcatgctgcgggcggtgcgaatcatcgctgaggagaccactgccatgttgtattcctgcaggac
ggagcggcggcggcagcagtttattcgcgcgctgctgcagcaccaccgccctatcctgatgcacgattatgactctaccccatgtaggcg
tggacttccccttcgccgcccgttgagcaaccgcaagttggacagcagcctgtggctcagcagctggacagcgacatgaacttaagcgag
ctgcccggggagtttattaatatcactgatgagcgtttggctcgacaggaaaccgtgtggaatataacacctaagaatatgtctgttacccatg
atatgatgcttttttaaggccagccggggagaaaggactgtgtactctgtgtgttgggagggaggtggcaggttgaatactagggttctgtgag
tttgattaaggtacggtgatcaatataagctatgtggtggtggggctatactactgaatgaaaaatgacttgaaattttctgcaattgaaaaata
aacacgttgaaacataacatgcaacaggttcacgattctttattcctgggcaatgtaggagaaggtgtaagagttggtagcaaaagtttcagtgg
tgtattttccactttcccaggaccatgtaaaagacatagagtaagtgcttacctcgctagtttctgtggattcactagaaccagtggccaaaaa
gctagcgcagcagccgccgcgcctggaaggaagcaaaaggagcgctcccccgttgtctgacgtcgcacacctgggttcgacacgcgg
gcggtaaccgcatggatcacggcggacggccggatccgggggttcgaaccccggtcgtccgccatgataccctgcgaatttatccaccag
accacgaagagtgcccgcttacaggctctccttttgcacggtctagagcgtcaacgactgcgcacgtccactttggccgcggctcgagT
GAGCTATTCCAGAAGTAGTGAAGAGGCTTTTTTGGAGGCCTAGGCTTTTGCAAAAAG
CTCCGGATCGATGCCCGGGGGATCCACTAGTTCTAGAGGGACAGCCCCCCCCCCAAA
GCCCCCAGGGATGTAATTACGTCCCTCCCCCGCTAGGGGGCAGCAGCGAGCCGCCC
GGGGCTCCGCTCCGGTCCGGCGCTCCCCCCGCATCCCCGAGCCGGCAGCGTGCGGG
GACAGCCCGGGCACGGGGAAGGTGGCACGGGATCGCTTTCCTCTGAACGCTTCTCG
CTGCTCTTTGAGCCTGCAGACACCTGGGGGGATACGGGGAAAAGGCCTCCAAGGCC
AGCTTCCCACAATAAGTTGGGTGAATTTTGGCTGAGCTATTCCAGAAGTAGTGAAGA
GGCTTTTTTGGAGGCCTAGGCTTTTGCAAAAAGCTCCGGATCGATCATATATGGCAG
ATATACGCGTTGACATTGATTATTGACTAGTTATTAATAGTAATCAATTACGGGGTC
ATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTCC
CATAGTAACGCCAATAGGGACTTTCCATTGACGTCAATGGGTGGAGTATTTACGGTA
AACTGCCCACTTGGCAGTACATCAAGTGTATCATATGCCAAGTACGCCCCCTATTGA
CGTCAATGACGGTAAATGGCCCGCCTGGCATTATGCCCAGTACATGACCTTATGGGA -continued

```
CTTTCCTACTTGGCAGTACATCTACGTATTAGTCATCGCTATTACCATGGTGATGCGG

TTTTGGCAGTACATCAATGGGCGTGGATAGCGGTTTGACTCACGGGGATTTCCAAGT

CTCCACCCCATTGACGTCAATGGGAGTTTGTTTTGGCACCAAAATCAACGGGACTTT

CCAAAATGTCGTAACAACTCCGCCCCATTGACGCAAATGGGCGGTAGGCGTGTACG

GTGGGAGGTCTATATAAGCAGAGCTCTCTGGCTAACTATCGTCGACGAGCTCGTTTA

GTGAACCGTCAGATCGCCTGGAGACGCCATCCACGCTGTTTTGACCTCCATAGAAGA

CACCGGGACCGATCCAGCCTCCGGACTCTAGCGTTTAAACTTAAGCTTGCCACCatgac cgagtacaagcccacggtgcgcctcgccacccgcgacgacgtccccagggccgtacgcaccctcgccgccggttcgccgactacccc gccacgcgccacaccgtcgatccggaccgccacatcgagcgggtcaccgagctgcaagaactcttcctcacgcgcgtcgggctcgacat cggcaaggtgtgggtcgcggacgacgcgccgcggtggcggtctggaccacgccggagagcgtcgaagcgggggcggtgttcgccg agatcggcccgcgcatggccgagttgagcggttcccggctggccgcgcagcaacagatggaaggcctcctggcgccgcaccggccca aggagcccgcgtggttcctggccaccgtcggcgtctcgcccgaccaccagggcaagggtctgggcagcgccgtcgtgctccccggagt ggaggcggccgagcgcgccggggtgcccgccttcctggagacctccgcgccccgcaacctccccttctacgagcggctcggcttcacc gtcaccgccgacgtcgaggtgcccgaaggaccgcgcacctggtgcatgacccgcaagcccggtgcctgaAGCGCGGGGATC

TCATGCTGGAGTTCTTCGCCCACCCCAACTTGTTTATTGCAGCTTATAATGGTTACAA

ATAAAGCAATAGCATCACAAATTTCACAAATAAAGCATTTTTTTCACTGCATTCTAG

TTGTGGTTTGTCCAAACTCATCAATGTATCTTATCATGTCTGTAGCtGATgtATAcCTAg gATCCGGCCGGccTGCAggTGTCCTCACAGGAACGAAGTCCCTAAAGAAACAGTGGCA

GCCAGGTTTAGCCCCGGAATTGACTGGATTCCTTTTTTAGGGCCCATTGGTATGGCTT

TTTCCCCGTATCCCCCCAGGTGTCTGCAGGCTCAAAGAGCAGCGAGAAGCGTTCAGA

GGAAAGCGATCCCGTGCCACCTTCCCCGTGCCCGGGCTGTCCCCGCACGCTGCCGGC

TCGGGGATGCGGGGGGAGCGCCGGACCGGAGCGGAGCCCCGGGCGGCTCGCTGCTG

CCCCCTAGCGGGGGAGGGACGTAATTACATCCCTGGGGGCTTTGGGGGGGGGCTGT

CCCTCTAGAGCGGCCGCCACCGCGGTGGAGCTCCAGCTTTTGTTCCCTTTAGTGAGG

GTTAATTAGATCTTAATACGACTCACTATAGGGCGAATTGGGTACCGGGCCCCCCCT

CGAGGTCGACGGTATCGATAAGCTTGATATCTATAACAAGAAAATATATATATAATA

AGTTATCACGTAAGTAGAACATGAAATAACAATATAATTATCGTATGAGTTAAATCT

TAAAAGTCACGTAAAAGATAATCATGCGTCATTTTGACTCACGCGGTCGTTATAGTT

CAAAATCAGTGACACTTACCGCATTGACAAGCACGCCTCACGGGAGCTCCAAGCGG

CGACTGAGATGTCCTAAATGCACAGCGACGGATTCGCGCTATTTAGAAAGAGAGAG

CAATATTTCAAGAATGCATGCGTCAATTTTACGCAGACTATCTTTCTAGGGTTAATCT

AGCTGCATCAGGATCATATCGTCGGGTCTTTTTTCCGGCTCAGTCATCGCCCAAGCT

GGCGCTATCTGGGCATCGGGGAGGAAGAAGCCCGTGCCTTTTCCCGCGAGGTTGAA

GCGGCATGGAAAGAGTTTGCCGAGGATGACTGCTGCTGCATTGACGTTGAGCGAAA

ACGCACGTTTACCATGATGATTCGGGAAGGTGTGGCCATGCACGCCTTTAACGGTGA

ACTGTTCGTTCAGGCCACCTGGGATACCAGTTCGTCGCGGCTTTTCCGGACACAGTT

CCGGATGGTCAGCCCGAAGCGCATCAGCAACCCGAACAATACCGGCGACAGCCGGA

ACTGCCGTGCCGGTGTGCAGATTAATGACAGCGGTGCGGCGCTGGGATATTACGTCA

GCGAGGACGGGTATCCTGGCTGGATGCCGCAGAAATGGACATGGATACCCCGTGAG

TTACCCGGCGGGCGCGCTTGGCGTAATCATGGTCATAGCTGTTTCCTGTGTGAAATT

GTTATCCGCTCACAATTCCACACAACATACGAGCCGGAAGCATAAAGTGTAAAGCC
```

-continued

```
TGGGGTGCCTAATGAGTGAGCTAACTCACATTAATTGCGTTGCGCTCACTGCCCGCT

TTCCAGTCGGGAAACCTGTCGTGCCAGCTGCATTAATGAATCGGCCAACGCGCGGG

GAGAGGCGGTTTGCGTATTGGGCGCTCTTCCGCTTCCTCGCTCACTGACTCGCTGCG

CTCGGTCGTTCGGCTGCGGCGAGCGGTATCAGCTCACTCAAAGGCGGTAATACGGTT

ATCCACAGAATCAGGGGATAACGCAGGAAAGAACATGTGAGCAAAAGGCCAGCAA

AAGGCCAGGAACCGTAAAAAGGCCGCGTTGCTGGCGTTTTTCCATAGGCTCCGCCCC

CCTGACGAGCATCACAAAAATCGACGCTCAAGTCAGAGGTGGCGAAACCCGACAGG

ACTATAAAGATACCAGGCGTTTCCCCCTGGAAGCTCCCTCGTGCGCTCTCCTGTTCC

GACCCTGCCGCTTACCGGATACCTGTCCGCCTTTCTCCCTTCGGGAAGCGTGGCGCT

TTCTCATAGCTCACGCTGTAGGTATCTCAGTTCGGTGTAGGTCGTTCGCTCCAAGCTG

GGCTGTGTGCACGAACCCCCCGTTCAGCCCGACCGCTGCGCCTTATCCGGTAACTAT

CGTCTTGAGTCCAACCCGGTAAGACACGACTTATCGCCACTGGCAGCAGCCACTGGT

AACAGGATTAGCAGAGCGAGGTATGTAGGCGGTGCTACAGAGTTCTTGAAGTGGTG

GCCTAACTACGGCTACACTAGAAGGACAGTATTTGGTATCTGCGCTCTGCTGAAGCC

AGTTACCTTCGGAAAAAGAGTTGGTAGCTCTTGATCCGGCAAACAAACCACCGCTG

GTAGCGGTGGTTTTTTTGTTTGCAAGCAGCAGATTACGCGCAGAAAAAAAGGATCTC

AAGAAGATCCTTTGATCTTTTCTACGGGGTCTGACGCTCAGTGGAACGAAAACTCAC

GTTAAGGGATTTTGGTCATGAGATTATCAAAAAGGATCTTCACCTAGATCCTTTTAA

ATTAAAAATGAAGTTTTAAATCAATCTAAAGTATATATGAGTAAACTTGGTCTGACA

GTTACCAATGCTTAATCAGTGAGGCACCTATCTCAGCGATCTGTCTATTTCGTTCATC

CATAGTTGCCTGACTCCCCGTCGTGTAGATAACTACGATACGGGAGGGCTTACCATC

TGGCCCCAGTGCTGCAATGATACCGCGAGACCCACGCTCACCGGCTCCAGATTTATC

AGCAATAAACCAGCCAGCCGGAAGGGCCGAGCGCAGAAGTGGTCCTGCAACTTTAT

CCGCCTCCATCCAGTCTATTAATTGTTGCCGGGAAGCTAGAGTAAGTAGTTCGCCAG

TTAATAGTTTGCGCAACGTTGTTGCCATTGCTACAGGCATCGTGGTGTCACGCTCGTC

GTTTGGTATGGCTTCATTCAGCTCCGGTTCCCAACGATCAAGGCGAGTTACATGATC

CCCCATGTTGTGCAAAAAAGCGGTTAGCTCCTTCGGTCCTCCGATCGTTGTCAGAAG

TAAGTTGGCCGCAGTGTTATCACTCATGGTTATGGCAGCACTGCATAATTCTCTTACT

GTCATGCCATCCGTAAGATGCTTTTCTGTGACTGGTGAGTACTCAACCAAGTCATTCT

GAGAATAGTGTATGCGGCGACCGAGTTGCTCTTGCCCGGCGTCAATACGGGATAAT

ACCGCGCCACATAGCAGAACTTTAAAAGTGCTCATCATTGGAAAACGTTCTTCGGGG

CGAAAACTCTCAAGGATCTTACCGCTGTTGAGATCCAGTTCGATGTAACCCACTCGT

GCACCCAACTGATCTTCAGCATCTTTTACTTTCACCAGCGTTTCTGGGTGAGCAAAA

ACAGGAAGGCAAAATGCCGCAAAAAAGGGAATAAGGGCGACACGGAAATGTTGAA

TACTCAT
```

The sequence of the pPBBG-iHelper2.2-HA vector is provided below:

pPBBG-iHelper2.2-HA (15,878 bp)

(SEQ ID NO: 5)

ACTCTTCCTTTTTCAATATTATTGAAGCATTTATCAGGGTTATTGTCTCATGA

GCGGATACATATTTGAATGTATTTAGAAAAATAAACAAATAGGGGTTCCGCGCACA

TTTCCCCGAAAAGTGCCACCTAAATTGTAAGCGTTAATATTTTGTTAAAATTCGCGTT

AAATTTTTGTTAAATCAGCTCATTTTTTAACCAATAGGCCGAAATCGGCAAAATCCC

TTATAAATCAAAAGAATAGACCGAGATAGGGTTGAGTGTTGTTCCAGTTTGGAACA

AGAGTCCACTATTAAAGAACGTGGACTCCAACGTCAAAGGGCGAAAAACCGTCTAT

CAGGGCGATGGCCCACTACGTGAACCATCACCCTAATCAAGTTTTTTGGGGTCGAGG

TGCCGTAAAGCACTAAATCGGAACCCTAAAGGGAGCCCCCGATTTAGAGCTTGACG

GGGAAAGCCGGCGAACGTGGCGAGAAAGGAAGGGAAGAAAGCGAAAGGAGCGGG

CGCTAGGGCGCTGGCAAGTGTAGCGGTCACGCTGCGCGTAACCACCACACCCGCCG

CGCTTAATGCGCCGCTACAGGGCGCGTCCCATTCGCCATTCAGGCTGCGCAACTGTT

GGGAAGGGCGATCGGTGCGGGCCTCTTCGCTATTACGCCAGCTGGCGAAAGGGGGA

TGTGCTGCAAGGCGATTAAGTTGGGTAACGCCAGGGTTTTCCCAGTCACGACGTTGT

AAAACGACGGCCAGTGAGCGCGCCTCGTTCATTCACGTTTTTGAACCCGTGGAGGAC

GGGCAGACTCGCGGTGCAAATGTGTTTTACAGCGTGATGGAGCAGATGAAGATGCT

CGACACGCTGCAGAACACGCAGCTAGATTAACCCTAGAAAGATAATCATATTGTGA

CGTACGTTAAAGATAATCATGCGTAAAATTGACGCATGTGTTTTATCGGTCTGTATA

TCGAGGTTTATTTATTAATTTGAATAGATATTAAGTTTTATTATATTTACACTTACAT

ACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCggtacccaactccatgcttaacagtccccaggtacagcccaccctgcgtcgcaaccaggaaca gctctacagcttcctggagcgccactcgccctacttccgcagccacagtgcgcagattaggagcgccacttcttttgtcacttgaaaaacat gtaaaaataatgtactaggagacactttcaataaaggcaaatgttttattgtacactctcgggtgattatttacccccaccttgccgtctg cgccgtttaaaaatcaaaggggttctgccgcgcatcgctatgcgccactggcagggacacgttgcgatactggtgtttagtgctccacttaaact caggcacaaccatccgcggcagctcggtgaagttttcactccacaggctgcgcaccatcaccaacgcgtttagcaggtcgggcgccgata tcttgaagtcgcagttggggcctccgccctgcgcgcgcgagttgcgatacacagggttgcagcactggaacactatcagcgccgggtggt gcacgctggccagcacgctcttgtcggagatcagatccgcgtccaggtcctccgcgttgctcagggcgaacggagtcaactttggtagctg ccttcccaaaaagggtgcatgcccaggctttgagttgcactcgcaccgtagtggcatcagaaggtgaccgtgcccggtctgggcgttagga tacagcgcctgcatgaaagccttgatctgcttaaaagccacctgagcctttgcgccttcagagaagaacatgccgcaagacttgccggaaa actgattggccggacaggccgcgtcatgcacgcagcaccttgcgtcggtgttggagatctgcaccacatttcggccccaccggttcttcacg -continued

```
atcttggccttgctagactgctccttcagcgcgcgctgcccgttttcgctcgtcacatccatttcaatcacgtgctccttatttatcataatgct
cccgtgtagacacttaagctcgccttcgatctcagcgcagcggtgcagccacaacgcgcagcccgtgggctcgtggtgcttgtaggttacctctg
caaacgactgcaggtacgcctgcaggaatcgccccatcatcgtcacaaaggtcttgttgctggtgaaggtcagctgcaacccgcggtgctc
ctcgtttagccaggtcttgcatacggccgccagagcttccacttggtcaggcagtagcttgaagtttgcctttagatcgttatccacgtggtact
tgtccatcaacgcgcgcgcagcctccatgccttctcccacgcagacacgatcggcaggctcagcgggtttatcaccgtgctttcactttccg
cttcactggactcttccttttcctcttgcgtccgcatacccgcgccactgggtcgtcttcattcagccgccgcaccgtgcgcttacctcccttg
ccgtgcttgattagcaccggtgggttgctgaaacccaccatttgtagcgccacatcttctctttcttcctcgctgtccacgatcacctctgggga
tggcgggcgctcgggcttgggagaggggcgcttctttttcttttttggacgcaatggccaaatccgccgtcgaggtcgatggccgcgggctgg
gtgtgcgcggcaccagcgcatcttgtgacgagtcttcttcgtcctcggactcgagacgccgcctcagccgcttttttgggggcgcgcggg
aggcggcggcgacggcgacggggacgacacgtcctccatggttggtggacgtcgcgccgcaccgcgtccgcgctcggggtggtttc
gcgctgctcctcttcccgactggccatttccttctcctataggcagaaaaagatcatggagtcagtcgagaaggaggacagcctaaccgccc
cctttgagttcgccaccaccgcctccaccgatgccgccaacgcgcctaccaccttcccgtcgaggcaccccgcttgaggaggaggaa
gtgattatcgagcaggacccaggttttgtaagcgaagacgacgaggatcgctcagtaccaacagaggataaaaagcaagaccaggacga
cgcagaggcaaacgaggaacaagtcgggcgggggaccaaaggcatggcgactacctagatgtgggagacgacgtgctgttgaagca
tctgcagcgccagtgcgccattatctgcgacgcgttgcaagagcgcagcgatgtgcccctcgccatagcggatgtcagccttgcctacgaa
cgccacctgttctcaccgcgcgtacccccaaacgccaagaaaacggcacatgcgagcccaacccgcgcctcaacttctaccccgtatttg
ccgtgccagaggtgcttgccacctatcacatcttttttccaaaactgcaagatacccctatcctgccgtgccaaccgcagccgagcggacaag
cagctggccttgcggcagggcgctgtcatacctgatatcgcctcgctcgacgaagtgccaaaaatctttgagggtcttggacgcgacgaga
aacgcgcggcaaacgctctgcaacaagaaaacagcgaaatgaaagtcactgtggagtgctggtggaacttgagggtgacaacgcgcg
cctagccgtgctgaaacgcagcatcgaggtcacccactttgcctacccggcacttaacctacccccaaggttatgagcacagtcatgagc
gagctgatcgtgcgccgtgcacgaccccctggagagggatgcaaacttgcaagaacaaaccgaggagggcctacccgcagttggcgatg
agcagctggcgcgctggcttgagacgcgcgagcctgccgacttggaggagcgacgcaagctaatgatggccgcagtgcttgttaccgtg
gagcttgagtgcatgcagcggttctttgctgacccggagatgcagcgcaagctagaggaaacgttgcactacacctttcgccagggctacg
tgcgccaggcctgcaaaatttccaacgtggagctctgcaacctggtctcctaccttggaattttgcacgaaaaccgcctcgggcaaaacgtg
cttcattccacgctcaagggcgaggcgcgccgcgactacgtccgcgactgcgtttacttatttctgtgctacacctggcaaacggccatggg
cgtgtggcagcaatgcctggaggagcgcaacctaaaggagctgcagaagctgctaaagcaaaacttgaaggacctatggacggccttca
acgagcgctccgtggccgcgcacctggcggacattatcttccccgaacgcctgcttaaaaccctgcaacagggtctgccagacttcaccag
tcaaagcatgttgcaaaactttaggaacttatcctagagcgttcaggaattctgcccgccacctgctgtgcgcttcctagcgactttgtgccca
ttaagtaccgtgaatgccctccgccgctttggggtcactgctaccttctgcagctagccaactaccttgcctaccactccgacatcatggaaga
cgtgagcggtgacggcctactggagtgtcactgtcgctgcaacctatgcaccccgcaccgctccctggtctgcaattcgcaactgcttagcg
aaagtcaaattatcggtacctttgagctgcagggtccctcgcctgacgaaaagtccgcggctccgggggttgaaactcactccggggctgtg
gacgtcCGATCTCTATCACTGATAGGGAGATCTCTATCACTGATAGGGAGAGgcttaccttcg
caaatttgtacctgaggactaccacgcccacgagattaggttctacgaagaccaatcccgcccgccaaatgcggagcttaccgcctgcgtc
attacccagggccacatccttggccaattgcaagccatcaacaaagcccgccaagagtttctgctacgaaagggacgggggtttacctgg
accccagtccggcgaggagctcaacccaatcccccgccgccgcagccctatcagcagccgcgggcccttgcttcccaggatggcac
ccaaaaagaagctgcagctgccgccgccgccacccacggacgaggaggaatactgggacagtcaggcagaggaggttttggacgagg
aggaggagatgatggaagactgggacagcctagacgaagcttccgaggccgaagaggtgtcagacgaaacaccgtcaccctcggtcgc
attcccctcgccggcgcccagaaattggcaaccgttcccagcatcgctacaacctccgctcctcaggcgccgccggcactgctgttcgc
cgacccaaccgtagatgggacaccactggaaccagggccggtaagtctaagcagccgccgccgttagcccaagagcaacaacagcgc
caaggctaccgctcgtggcgcgggcacaagaacgccatagttgcttgcttgcaagactgtggggcaacatctccttcgcccgccgctttct
tctctaccatcacggcgtggccttcccccgtaacatcctgcattactaccgtcatctctacagcccctactgcaccggcggcagcggcagcg
``` gcagcaacagcagcggtcacacagaagcaaaggcgaccggatagcaagactctgacaaagcccaagaaatccacagcggcggcagc agcaggaggaggagcgctgcgtctggcgcccaacgaacccgtatcgacccgcgagcttagaaataggattttcccactctgtatgctatat ttcaacaaagcaggggccaagaacaagagctgaaaaaaaaaacaggtctctgcgctccctcacccgcagctgcctgtatcacaaaagcg aagatcagcttcggcgcacgctggaagacgcggaggctctcttcagcaaCGATCTCTATCACTGATAGGGAGATC TCTATCACTGATAGGGAGAGatactgcgcgctgactcttaaggactagtttcgcgccctttctcaaatttaagcgcgaaaa ctacgtcatctccagcggccacacccggcgccagcacctgtcgtcagcgccattatgagcaaggaaattcccacgccctacatgtggagtt accagccacaaatgggacttgcggctggagctgcccaagactactcaacccgaataaactacatgagcgcgggaccccacatgatatccc gggtcaacggaatccgcgccaccgaaaccgaattctcctcgaacaggcggctattaccaccacacctcgtaataaccttaatcccgtagt tggcccgctgccctggtgtaccaggaaagtcccgctccaccactgtggtacttcccagagacgcccaggccgaagttcagatgactaact caggggcgcagcttgcgggcggctttcgtcacagggtgcggtcgccccagtggccaaaaagctagcgcagcagccgccgcgcctg gaaggaagccaaaaggagcgctccccgttgtctgacgtcgcacacctgggttcgacacgcgggcggtaaccgcatggatcacggcgg acggccggatccggggttcgaaccccggtcgtccgccatgatacccctgcgaatttatccaccagaccacggaagagtgcccgcttacag gctctccttttgcacggtctagagcgtcaacgactgcgcacggggcgttttagggcggagtaacttgcatgtattgggaattgtagtttttttaa aatgggaagtgacgtatcgtgggaaaacggaagtgaagatttgaggaagttgtgggttttttggctttcgtttctgggcgtaggttcgcgtgcg gttttctgggtgttttttgtggactttaaccgttacgtcattttttagtcctatatatactcgctctgtaCTCTCCCTATCAGTGATAG AGATCTCCCTATCAGTGATAGAGATCGcttggccctttttacactgtgactgattgagctggtgccgtgtcgagtggt gttttttaataggtttttttactggtaaggctgactgttatggctgccgctgtggaagcgctgtatgttgttctggagcgggagggtgctatttt gcctaggcaggagggttttcaggtgtttatgtgttttctctcctattaattttgttataccctctatgggggctgtaatgttgtctctacgcc tgcgggtatgtattccccgggctatttcggtcgcttttagcactgaccgatgttaaccaacctgatgtgtttaccgagtcttacattatgact ccggacatgaccgaggaactgtcggtggtgcttttaatcacggtgaccagttttttacggtcacgccggcatggccgtagtccgtcttatgct tataagggttgttttcctgttgtaagacaggcttctaatgtttaaatgttttttttttgttattttattttgtgtttaatgcaggaacccgca gacatgtttgagagaaaaatggtgtctttttctgtggtggttccggaacttacctgcctttatctgcatgagcatgactacgatgtgcttgcttt tttgcgcgaggctttgcctgatttttttgagcagcaccttgcatttttatatcgccgcccatgcaacaagcttacataggggctacgctggttagca tagctccgagtatgcgtgtcataatcagtgtgggttcttttgtcatggttcctggcggggaagtggccgcgctggtccgtgcagacctgcacgat tatgttcagctggccctgcgaagggacctacgggatcgcggtattttgttaatgttccgcttttgaatcttatacaggtctgtgaggaacctga attttttgcaatcatgattcgctgcttgaggctgaaggtggagggcgctctggagcagattttacaatggccggacttaatattcgggatttgct tagagacatattgataaggtggcgagatgaaaattatttgggcatggttgaaggtgctggaatgtttatagaggagattcaccctgaagggttta gcctttacgtccacttggacgtgagggcagtttgccttttggaagccattgtgcaacatcttacaaatgccattatctgttctttggctgtagag tttgaccacgccaccggaggggagcgcgttcacttaatagatcttcattttgaggttttggataatcttttggaataaaaaaaaaaaaacatggt tcttccagctcttcccgctcctcccgtgtgtgactcgcagaacgaatgtgtaggttggctgggtgtggcttattctgcggtggtggatgttatca gggcagcggcgcatgaaggagtttacatagaacccgaagccaggggcgcctggatgctttgagagagtggatatactacaactactacacagag cgagctaagcgacgagaccggagacgcagatctgtttgtcacgcccgcacctggttttgcttcaggaaatatgTACCCATACGATGTTCCAGA TTACGCTGGAGGAGGCGGAGGCactacgtccggcgttccatttggcatgacactacgaccaacacgatctcggttgtct cggcgcactccgtacagtagggatcgcctacctccttttgagacagagaccgcgctaccatactggaggatcatccgctgctgcccgaat gtaacactttgacaatgcacaacgtgagttacgtgcgaggtcttcctgcagtgtgggatttacgctgattcaggaatggggttgttcctggga tatggttctgacgcgggaggagcttgtaatcctgaggaagtgtatgcacgtgtgcctgtgttgtgccaacattgatatcatgacgagcatgatg atccatggttacgagtcctgggctctccactgtcattgttccagtcccggttccctgcagtgcatagccggcgggcaggttttggccagctggt ttaggatggtggtgatggcgccatgtttaatcagaggtttatatggtaccgggaggtggtgaattacaacatgccaaaagaggtaatgtttat gtccagcgtgtttatgaggggtcgccacttaatctacctgcgcttgtggtatgatggccacgtgggttctgtggtccccgccatgagctttgga tacagcgccttgcactgtgggattttgaacaatattgtggtgctgtgctgcagttactgtgctgatttaagtgagatcagggtgcgctgctgtgc -continued

```
ccggaggacaaggcgtctcatgctgcgggcggtgcgaatcatcgctgaggagaccactgccatgttgtattcctgcaggacggagcggc
ggcggcagcagtttattcgcgcgctgctgcagcaccaccgccctatcctgatgcacgattatgactctaccccatgtaggcgtggacttcc
ccttcgccgcccgttgagcaaccgcaagttggacagcagcctgtggctcagcagctggacagcgacatgaacttaagcgagctgcccgg
ggagtttattaatatcactgatgagcgtttggctcgacaggaaaccgtgtggaatataacacctaagaatatgtctgttacccatgatatgatgc
tttttaaggccagccggggagaaaggactgtgtactctgtgtgttgggagggaggtggcaggttgaatactagggttctgtgagtttgattaa
ggtacggtgatcaatataagctatgtggtggtggggctatactactgaatgaaaaatgacttgaaattttctgcaattgaaaaataaacacgttg
aaacataacatgcaacaggttcacgattctttattcctgggcaatgtaggagaaggtgtaagagttggtagcaaaagtttcagtggtgtattttc
cactttcccaggaccatgtaaaagacatagagtaagtgcttacctcgctagtttctgtggattcactagaatccactttggccgcggctcgagT
GAGCTATTCCAGAAGTAGTGAAGAGGCTTTTTTGGAGGCCTAGGCTTTTGCAAAAAG
CTCCGGATCGATGCCCGGGGGATCCACTAGTTCTAGAGGGACAGCCCCCCCCCCAAA
GCCCCCAGGGATGTAATTACGTCCCTCCCCCGCTAGGGGGCAGCAGCGAGCCGCCC
GGGGCTCCGCTCCGGTCCGGCGCTCCCCCCGCATCCCCGAGCCGGCAGCGTGCGGG
GACAGCCCGGGCACGGGGAAGGTGGCACGGGATCGCTTTCCTCTGAACGCTTCTCG
CTGCTCTTTGAGCCTGCAGACACCTGGGGGGATACGGGGAAAAGGCCTCCAAGGCC
AGCTTCCCACAATAAGTTGGGTGAATTTTGGCTGAGCTATTCCAGAAGTAGTGAAGA
GGCTTTTTTGGAGGCCTAGGCTTTTGCAAAAAGCTCCGGATCGATCATATATGGCAG
ATATACGCGTTGACATTGATTATTGACTAGTTATTAATAGTAATCAATTACGGGGTC
ATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTCC
CATAGTAACGCCAATAGGGACTTTCCATTGACGTCAATGGGTGGAGTATTTACGGTA
AACTGCCCACTTGGCAGTACATCAAGTGTATCATATGCCAAGTACGCCCCCTATTGA
CGTCAATGACGGTAAATGGCCCGCCTGGCATTATGCCCAGTACATGACCTTATGGGA
CTTTCCTACTTGGCAGTACATCTACGTATTAGTCATCGCTATTACCATGGTGATGCGG
TTTTGGCAGTACATCAATGGGCGTGGATAGCGGTTTGACTCACGGGGATTTCCAAGT
CTCCACCCCATTGACGTCAATGGGAGTTTGTTTTGGCACCAAAATCAACGGGACTTT
CCAAAATGTCGTAACAACTCCGCCCCATTGACGCAAATGGGCGGTAGGCGTGTACG
GTGGGAGGTCTATATAAGCAGAGCTCTCTGGCTAACTATCGTCGACGAGCTCGTTTA
GTGAACCGTCAGATCGCCTGGAGACGCCATCCACGCTGTTTTGACCTCCATAGAAGA
CACCGGGACCGATCCAGCCTCCGGACTCTAGCGTTTAAACTTAAGCTTGCCACCatgac
cgagtacaagcccacggtgcgcctcgccaccgcgacgacgtccccagggccgtacgcaccctcgccgccgcgttcgccgactacccc
gccacgcgccacaccgtcgatccggaccgccacatcgagcgggtcaccgagctgcaagaactcttcctcacgcgcgtcgggctcgacat
cggcaaggtgtgggtcgcggacgacggcgccgcggtggcggtctggaccacgccggagagcgtcgaagcgggggcggtgttcgccg
agatcggcccgcgcatggccgagttgagcggttcccggctggccgcgcagcaacagatggaaggcctcctggcgccgcaccggccca
aggagcccgcgtggttcctggccaccgtcggcgtctcgcccgaccaccagggcaagggtctgggcagcgccgtcgtgctccccggagt
ggaggcggccgagcgcgccggggtgcccgccttcctggagacctccgcgccccgcaacctcccttctacgagcggctcggcttcacc
gtcaccgccgacgtcgaggtgcccgaaggaccgcgcacctggtgcatgacccgcaagcccggtgcctgaAGCGCGGGGATC
TCATGCTGGAGTTCTTCGCCCACCCCAACTTGTTTATTGCAGCTTATAATGGTTACAA
ATAAAGCAATAGCATCACAAATTTCACAAATAAAGCATTTTTTTCACTGCATTCTAG
TTGTGGTTTGTCCAAACTCATCAATGTATCTTATCATGTCTGTAGCtGATgtATAcCTAg
gATCCGGCCGGccTgCAggTGTCCTCACAGGAACGAAGTCCCTAAAGAAACAGTGGCA
GCCAGGTTTAGCCCCGGAATTGACTGGATTCCTTTTTTAGGGCCCATTGGTATGGCTT
```

-continued

```
TTTCCCCGTATCCCCCCAGGTGTCTGCAGGCTCAAAGAGCAGCGAGAAGCGTTCAGA
GGAAAGCGATCCCGTGCCACCTTCCCCGTGCCCGGGCTGTCCCCGCACGCTGCCGGC
TCGGGGATGCGGGGGGAGCGCCGGACCGGAGCGGAGCCCCGGGCGGCTCGCTGCTG
CCCCCTAGCGGGGGAGGGACGTAATTACATCCCTGGGGGCTTTGGGGGGGGCTGT
CCCTCTAGAGCGGCCGCCACCGCGGTGGAGCTCCAGCTTTTGTTCCCTTTAGTGAGG
GTTAATTAGATCTTAATACGACTCACTATAGGGCGAATTGGGTACCGGGCCCCCCCT
CGAGGTCGACGGTATCGATAAGCTTGATATCTATAACAAGAAAATATATATATAATA
AGTTATCACGTAAGTAGAACATGAAATAACAATATAATTATCGTATGAGTTAAATCT
TAAAAGTCACGTAAAAGATAATCATGCGTCATTTTGACTCACGCGGTCGTTATAGTT
CAAAATCAGTGACACTTACCGCATTGACAAGCACGCCTCACGGGAGCTCCAAGCGG
CGACTGAGATGTCCTAAATGCACAGCGACGGATTCGCGCTATTTAGAAAGAGAGAG
CAATATTTCAAGAATGCATGCGTCAATTTTACGCAGACTATCTTTCTAGGGTTAATCT
AGCTGCATCAGGATCATATCGTCGGGTCTTTTTTCCGGCTCAGTCATCGCCCAAGCT
GGCGCTATCTGGGCATCGGGGAGGAAGAAGCCCGTGCCTTTTCCCGCGAGGTTGAA
GCGGCATGGAAAGAGTTTGCCGAGGATGACTGCTGCTGCATTGACGTTGAGCGAAA
ACGCACGTTTACCATGATGATTCGGGAAGGTGTGGCCATGCACGCCTTTAACGGTGA
ACTGTTCGTTCAGGCCACCTGGGATACCAGTTCGTCGCGGCTTTTCCGGACACAGTT
CCGGATGGTCAGCCCGAAGCGCATCAGCAACCCGAACAATACCGGCGACAGCCGGA
ACTGCCGTGCCGGTGTGCAGATTAATGACAGCGGTGCGGCGCTGGGATATTACGTCA
GCGAGGACGGGTATCCTGGCTGGATGCCGCAGAAATGGACATGGATACCCCGTGAG
TTACCCGGCGGGCGCGCTTGGCGTAATCATGGTCATAGCTGTTTCCTGTGTGAAATT
GTTATCCGCTCACAATTCCACACAACATACGAGCCGGAAGCATAAAGTGTAAAGCC
TGGGGTGCCTAATGAGTGAGCTAACTCACATTAATTGCGTTGCGCTCACTGCCCGCT
TTCCAGTCGGGAAACCTGTCGTGCCAGCTGCATTAATGAATCGGCCAACGCGCGGG
GAGAGGCGGTTTGCGTATTGGGCGCTCTTCCGCTTCCTCGCTCACTGACTCGCTGCG
CTCGGTCGTTCGGCTGCGGCGAGCGGTATCAGCTCACTCAAAGGCGGTAATACGGTT
ATCCACAGAATCAGGGGATAACGCAGGAAAGAACATGTGAGCAAAAGGCCAGCAA
AAGGCCAGGAACCGTAAAAAGGCCGCGTTGCTGGCGTTTTTCCATAGGCTCCGCCCC
CCTGACGAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTCCTGTTCC
GACCCTGCCGCTTACCGGATACCTGTCCGCCTTTCTCCCTTCGGGAAGCGTGGCGCT
TTCTCATAGCTCACGCTGTAGGTATCTCAGTTCGGTGTAGGTCGTTCGCTCCAAGCTG
GGCTGTGTGCACGAACCCCCCGTTCAGCCCGACCGCTGCGCCTTATCCGGTAACTAT
CGTCTTGAGTCCAACCCGGTAAGACACGACTTATCGCCACTGGCAGCAGCCACTGGT
AACAGGATTAGCAGAGCGAGGTATGTAGGCGGTGCTACAGAGTTCTTGAAGTGGTG
GCCTAACTACGGCTACACTAGAAGGACAGTATTTGGTATCTGCGCTCTGCTGAAGCC
AGTTACCTTCGGAAAAAGAGTTGGTAGCTCTTGATCCGGCAAACAAACCACCGCTG
GTAGCGGTGGTTTTTTGTTTGCAAGCAGCAGATTACGCGCAGAAAAAAAGGATCTC
AAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCCTTTTAA
```

-continued

```
ATTAAAAATGAAGTTTTAAATCAATCTAAAGTATATATGAGTAAACTTGGTCTGACA

GTTACCAATGCTTAATCAGTGAGGCACCTATCTCAGCGATCTGTCTATTTCGTTCATC

CATAGTTGCCTGACTCCCCGTCGTGTAGATAACTACGATACGGGAGGGCTTACCATC

TGGCCCCAGTGCTGCAATGATACCGCGAGACCCACGCTCACCGGCTCCAGATTTATC

AGCAATAAACCAGCCAGCCGGAAGGGCCGAGCGCAGAAGTGGTCCTGCAACTTTAT

CCGCCTCCATCCAGTCTATTAATTGTTGCCGGGAAGCTAGAGTAAGTAGTTCGCCAG

TTAATAGTTTGCGCAACGTTGTTGCCATTGCTACAGGCATCGTGGTGTCACGCTCGTC

GTTTGGTATGGCTTCATTCAGCTCCGGTTCCCAACGATCAAGGCGAGTTACATGATC

CCCCATGTTGTGCAAAAAAGCGGTTAGCTCCTTCGGTCCTCCGATCGTTGTCAGAAG

TAAGTTGGCCGCAGTGTTATCACTCATGGTTATGGCAGCACTGCATAATTCTCTTACT

GTCATGCCATCCGTAAGATGCTTTTCTGTGACTGGTGAGTACTCAACCAAGTCATTCT

GAGAATAGTGTATGCGGCGACCGAGTTGCTCTTGCCCGGCGTCAATACGGGATAAT

ACCGCGCCACATAGCAGAACTTTAAAAGTGCTCATCATTGGAAAACGTTCTTCGGGG

CGAAAACTCTCAAGGATCTTACCGCTGTTGAGATCCAGTTCGATGTAACCCACTCGT

GCACCCAACTGATCTTCAGCATCTTTTACTTTCACCAGCGTTTCTGGGTGAGCAAAA

ACAGGAAGGCAAAATGCCGCAAAAAAGGGAATAAGGGCGACACGGAAATGTTGAA

TACTCAT
```

The sequence of the pPBBG-iHelper2.3-HA vector is provided below:

pPBBG-iHelper2.3-HA (15,992 bp)    (SEQ ID NO: 6)

```
ACTCTTCCTTTTTCAATATTATTGAAGCATTTATCAGGGTTATTGTCTCATGA

GCGGATACATATTTGAATGTATTTAGAAAAATAAACAAATAGGGGTTCCGCGCACA

TTTCCCCGAAAAGTGCCACCTAAATTGTAAGCGTTAATATTTTGTTAAAATTCGCGTT

AAATTTTTGTTAAATCAGCTCATTTTTTAACCAATAGGCCGAAATCGGCAAAATCCC

TTATAAATCAAAAGAATAGACCGAGATAGGGTTGAGTGTTGTTCCAGTTTGGAACA

AGAGTCCACTATTAAAGAACGTGGACTCCAACGTCAAAGGGCGAAAAACCGTCTAT

CAGGGCGATGGCCCACTACGTGAACCATCACCCTAATCAAGTTTTTTGGGGTCGAGG

TGCCGTAAAGCACTAAATCGGAACCCTAAAGGGAGCCCCCGATTTAGAGCTTGACG

GGGAAAGCCGGCGAACGTGGCGAGAAAGGAAGGGAAGAAAGCGAAAGGAGCGGG

CGCTAGGGCGCTGGCAAGTGTAGCGGTCACGCTGCGCGTAACCACCACACCCGCCG

CGCTTAATGCGCCGCTACAGGGCGCGTCCCATTCGCCATTCAGGCTGCGCAACTGTT

GGGAAGGGCGATCGGTGCGGGCCTCTTCGCTATTACGCCAGCTGGCGAAAGGGGGA

TGTGCTGCAAGGCGATTAAGTTGGGTAACGCCAGGGTTTTCCCAGTCACGACGTTGT

AAAACGACGGCCAGTGAGCGCGCCTCGTTCATTCACGTTTTTGAACCCGTGGAGGAC

GGGCAGACTCGCGGTGCAAATGTGTTTTACAGCGTGATGGAGCAGATGAAGATGCT

CGACACGCTGCAGAACACGCAGCTAGATTAACCCTAGAAAGATAATCATATTGTGA

CGTACGTTAAAGATAATCATGCGTAAAATTGACGCATGTGTTTTATCGGTCTGTATA

TCGAGGTTTATTTATTAATTTGAATAGATATTAAGTTTTATTATATTTACACTTACAT

ACTAATAATAAATTCAACAAACAATTTATTTATGTTTATTTATTTATTAAAAAAAA

CAAAAACTCAAAATTTCTTCTATAAAGTAACAAAACTTTTATCGAATTCCTGCAGCC
```

```
CGGGGGATCCACTAGTTCTAGAGGGACAGCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCggtacccaactccatgcttaacagtccccaggtacagcccaccctgcgtcgcaaccaggaaca gctctacagcttcctggagcgccactcgccctacttccgcagccacagtgcgcagattaggagcgccacttcttttttgtcacttgaaaaacat gtaaaaataatgtactaggagacactttcaataaaggcaaatgttttttatttgtacactctcgggtgattatttaccccccaccttgccgtctg cgccgtttaaaaatcaaaggggttctgccgcgcatcgctatgcgccactggcagggacacgttgcgatactggtgtttagtgctccacttaaact caggcacaaccatccgcggcagctcggtgaagttttcactccacaggctgcgcaccatcaccaacgcgtttagcaggtcgggcgccgata tcttgaagtcgcagttggggcctccgccctgcgcgcgcgagttgcgatacacaggggttgcagcactggaacactatcagcgccgggtggt gcacgctggccagcacgctcttgtcggagatcagatccgcgtccaggtcctccgcgttgctcagggcgaacggagtcaactttggtagctg ccttcccaaaagggtgcatgcccaggctttgagttgcactcgcaccgtagtggcatcagaaggtgaccgtgcccggtctgggcgttagga tacagcgcctgcatgaaagccttgatctgcttaaaagccacctgagcctttgcgccttcagagaagaacatgccgcaagacttgccggaaa actgattggccggacaggccgcgtcatgcacgcagcaccttgcgtcggtgttggagatctgcaccacatttcggccccaccggttcttcacg atcttggccttgctagactgctccttcagcgcgcgctgcccgttttcgctcgtcacatccatttcaatcacgtgctccttatttatcataatgct cccgtgtagacacttaagctcgccttcgatctcagcgcagcggtgcagccacaacgcgcagcccgtgggctcgtggtgcttgtaggttacctctg caaacgactgcaggtacgcctgcaggaatcgcccatcatcgtcacaaaggtcttgttgctggtgaaggtcagctgcaacccgcggtgctc ctcgtttagccaggtcttgcatacggccgccagagcttccacttggtcaggcagtagcttgaagtttgcctttagatcgttatccacgtggtact tgtccatcaacgcgcgcgcagcctccatgcccttctcccacgcagacacgatcggcaggctcagcgggtttatcaccgtgctttcactttccg cttcactggactcttccttttcctcttgcgtccgcataccccgcgccactgggtcgtcttcattcagccgccgcaccgtgcgcttacctcccttg ccgtgcttgattagcaccggtgggttgctgaaacccaccattgtagcgccacatcttctctttcttcctcgctgtccacgatcacctctgggga tggcgggcgctcgggcttgggagaggggcgcttctttttcttttggacgcaatggccaaatccgccgtcgaggtcgatggccgcgggctgg gtgtgcgcggcaccagcgcatcttgtgacgagtcttcttcgtcctcggactcgagacgccgcctcagccgcttttttgggggcgcgcggggg aggcggcggcgacggcgacggggacgacacgtcctccatggttggtggacgtcgcgccgcaccgcgtccgcgctcggggtggtttc gcgctgctcctcttcccgactggccatttccttctcctataggcagaaaaagatcatggagtcagtcgaaggaggacagcctaaccgccc cctttgagttcgccaccaccgcctccaccgatgccgccaacgcgcctaccaccttccccgtcgaggcaccccccgcttgaggaggaggaa gtgattatcgagcaggacccaggttttgtaagcgaagacgacgaggatcgctcagtaccaacagaggataaaaagcaagaccaggacga cgcagaggcaaacgaggaacaagtcgggcgggggaccaaaggcatggcgactacctagatgtgggagacgacgtgctgttgaagca tctgcagcgccagtgcgccattatctgcgacgcgttgcaagagcgcagcgatgtgcccctcgccatagcggatgtcagccttgcctacgaa cgccacctgttctcaccgcgcgtaccccccaaacgccaagaaaacggcacatgcgagcccaacccgcgcctcaacttctaccccgtatttg ccgtgccagaggtgcttgccacctatcacatcttttttccaaaactgcaagataccccctatcctgccgtgccaaccgcagccgagcggacaag cagctggccttgcggcagggcgctgtcatacctgatatcgcctcgctcgacgaagtgccaaaaatctttgagggtcttggacgcgacgaga aacgcgcggcaaacgctctgcaacaagaaaacagcgaaaatgaaagtcactgtggagtgctggtggaacttgagggtgacaacgcgcg cctagccgtgctgaaacgcagcatcgaggtcacccactttgcctaccggcacttaacctaccccccaaggttatgagcacagtcatgagc gagctgatcgtgcgccgtgcacgacccctggagagggatgcaaacttgcaagaacaaaccgaggagggcctaccccgcagttggcgatg agcagctggcgcgctggcttgagacgcgcgagcctgccgacttggaggagcgacgcaagctaatgatggccgcagtgcttgttaccgtg
```

-continued gagcttgagtgcatgcagcggttctttgctgacccggagatgcagcgcaagctagaggaaacgttgcactacacctttcgccagggctacg tgcgccaggcctgcaaaatttccaacgtggagctctgcaacctggtctcctaccttggaattttgcacgaaaaccgcctcgggcaaaacgtg cttcattccacgctcaagggcgaggcgcgccgcgactacgtccgcgactgcgtttacttatttctgtgctacacctggcaaacggccatggg cgtgtggcagcaatgcctggaggagcgcaacctaaaggagctgcagaagctgctaaagcaaaacttgaaggacctatggacggccttca acgagcgctccgtggccgcgcacctggcggacattatcttccccgaacgcctgcttaaaaccctgcaacagggtctgccagacttcaccag tcaaagcatgttgcaaaactttaggaactttatcctagagcgttcaggaattctgcccgccacctgctgtgcgcttcctagcgactttgtgccca ttaagtaccgtgaatgccctccgccgctttggggtcactgctaccttctgcagctagccaactaccttgcctaccactccgacatcatggaaga cgtgagcggtgacggcctactggagtgtcactgtcgctgcaacctatgcaccccgcaccgctccctggtctgcaattcgcaactgcttagcg aaagtcaaattatcggtacctttgagctgcagggtccctcgcctgacgaaaagtccgcggctccggggttgaaactcactccggggctgtg gacgtcCGATCTCTATCACTGATAGGGAGATCTCTATCACTGATAGGGAGAGggcttaccttcg caaatttgtacctgaggactaccacgcccacgagattaggttctacgaagaccaatcccgcccgccaaatgcggagcttaccgcctgcgtc attcccagggccacatccttggccaattgcaagccatcaacaaagcccgccaagagtttctgctacgaaagggacgggggggtttacctgg acccccagtccggcgaggagctcaaccccaatccccccgccgcgcagccctatcagcagccgcgggcccttgcttcccaggatggcac ccaaaaagaagctgcagctgccgccgccgccacccacggacgaggaggaatactgggacagtcaggcagaggaggttttggacgagg aggaggagatgatgaagactgggacagcctagacgaagcttccgaggccgaagaggtgtcagacgaaacaccgtcaccctcggtcgc attcccctcgccggcgccccagaaattggcaaccgttcccagcatcgctacaacctccgctcctcaggcgccgccggcactgcctgttcgc cgacccaaccgtagatgggacaccactggaaccagggccggtaagtctaagcagccgccgccgttagcccaagagcaacaacagcgc caaggctaccgctcgtggcgcgggcacaagaacgccatagttgcttgcttgcaagactgtgggggcaacatctccttcgcccgccgctttct tctctaccatcacgcgtggccttcccccgtaacatcctgcattactaccgtcatctctacagcccctactgcaccggcggcagcggcagcg gcagcaacagcagcggtcacacagaagcaaaggcgaccggatagcaagactctgacaaagcccaagaaatccacagcggcggcagc agcaggaggaggagcgctgcgtctggcgcccaacgaacccgtatcgacccgcgagcttagaaataggattttttcccactctgtatgctatat ttcaacaaagcaggggccaagaacaagagctgaaaataaaaaacaggtctctgcgctccctcacccgcagctgcctgtatcacaaaagcg aagatcagcttcggcgcacgctggaagacgcggaggctctcttcagcaaCGATCTCTATCACTGATAGGGAGATC TCTATCACTGATAGGGAGAGatactgcgcgctgactcttaaggactagtttcgcgcccttttctcaaatttaagcgcgaaaa ctacgtcatctccagcggccacacccggcgccagcacctgtcgtcagcgccattatgagcaaggaaattcccacgccctacatgtggagtt accagccacaaatgggacttgcggctggagctgcccaagactactcaacccgaataaaactacatgagcgcgggacccacatgatatccc gggtcaacggaatccgcgcccaccgaaaccgaattctcctcgaacaggcggctattaccaccacacctcgtaataaccttaatcccgtagt tggcccgctgccctggtgtaccaggaaagtcccgctcccaccactgtggtacttcccagagacgcccaggccgaagttcagatgactaact caggggcgcagcttgcgggcggctttcgtcacagggtgcggtcgcccggcgttttagggcggagtaacttgcatgtattgggaattgtag tttttttaaaatgggaagtgacgtatcgtgggaaaacggaagtgaagatttgaggaagttgtgggtttttttggctttcgtttctgggcgtaggtt cgcgtgcggttttctgggtgttttttgtggactttaaccgttacgtcattttttagtcctatatatactcgctctgtaCTCTCCCTATCAGT GATAGAGATCTCCCTATCAGTGATAGAGATCGcttggcccttttttacactgtgactgattgagctggtgccgtgt cgagtggtgtttttttaataggtttttttactggtaaggctgactgttatggctgccgctgtggaagcgctgtatgttgttctggagcgggagggt gctattttgcctaggcaggagggttttttcaggtgtttatgtgttttttctctcctattaattttgttatacctcctatgggggctgtaatgttgt ctctacgcctgcgggtatgtattcccccgggctatttcggtcgcttttttagcactgaccgatgttaaccaacctgatgtgtttaccgagtcttac attatgactccggacatgaccgaggaactgtcggtggtgcttttaatcacggtgaccagttttttttacggtcacgccggcatgccgtagtcc gtcttatgcttataaggggttgttttttcctgttgtaagacaggcttctaatgttaaatgtttttttttttgttatttatttgtgtttaatgca ggaacccgcagacatgtttgagagaaaaatggtgtcttttttctgtggtggttccggaacttacctgcctttatctgcatgagcatgactacgatg tgcttgcttttttgcgcgaggctttgcctgattttttgagcagcaccttgcattttatatcgccgcccatgcaacaagcttacataggggctac gctggttagcatagctccgagtatgcgtgtcataatcagtgtgggttcttttgtcatggttcctggcggggaagtggccgcgctggtccgtgcag acctgcacgattatgttcagctggccctgcgaagggacctacgggatcgcggtattttttgttaatgttccgcttttgaatcttatacaggtctgt -continued

```
gaggaacctgaattttttgcaatcatgattcgctgcttgaggctgaaggtggagggcgctctggagcagattttacaatggccggacttaatatt
cgggatttgcttagagacatattgataaggtggcgagatgaaaattatttgggcatggttgaaggtgctggaatgtttatagaggagattcaccc
tgaagggtttagcctttacgtccacttggacgtgagggcagtttgccttttggaagccattgtgcaacatcttacaaatgccattatctgttctt
tggctgtagagtttgaccacgccaccggaggggagcgcgttcacttaatagatcttcattttgaggttttggataatcttttggaataaaaaaa
aaaaaacatggttcttccagctcttcccgctcctcccgtgtgtgactcgcagaacgaatgtgtaggttggctgggtgtggcttattctgcggtgg
tggatgttatcagggcagcggcgcatgaaggagtttacatagaacccgaagccagggggcgcctggatgctttgagagagtggatatactacaa
ctactacacagagcgagctaagcgacgagaccggagacgcagatctgtttgtcacgcccgcacctggttttgcttcaggaaatatgTACCCATAC
GATGTTCCAGATTACGCTGGAGGAGGCGGAGGCactacgtccggcgttccatttggcatgacactacgaccaacacgatct
cggttgtctcggcgcactccgtacagtagggatcgcctacctccttttgagacagagacccgcgctaccatactggaggatcatccgctgct
gcccgaatgtaacactttgacaatgcacaacgtgagttacgtgcgaggtcttccctgcagtgtgggatttacgctgattcaggaatgggttgtt
ccctgggatatggttctgacgcgggaggagcttgtaatcctgaggaagtgtatgcacgtgtgcctgtgttgtgccaacattgatatcatgacg
agcatgatgatccatggttacgagtcctgggctctccactgtcattgttccagtcccggttccctgcagtgcatagccggcgggcaggttttgg
ccagctggtttaggatggtggtggatggcgccatgtttaatcagaggtttatatggtaccgggaggtggtgaattacaacatgccaaagag
gtaatgtttatgtccagcgtgtttatgaggggtcgccacttaatctacctgcgcttgtggtatgatggcacgtgggttctgtggtccccgccat
gagctttggatacagcgccttgcactgtgggattttgaacaatattgtggtgctgtgctgcagttactgtgctgatttaagtgagatcagggtgc
gctgctgtgcccggaggacaaggcgtctcatgctgcgggcggtgcgaatcatcgctgaggagaccactgccatgttgtattcctgcaggac
ggagcggcggcggcagcagtttattcgcgcgctgctgcagcaccaccgccctatcctgatgcacgattatgactctaccccatgtaggcg
tggacttccccttcgccgcccgttgagcaaccgcaagttggacagcagcctgtggctcagcagctggacagcgacatgaacttaagcgag
ctgcccggggagtttattaatatcactgatgagcgtttggctcgacaggaaaccgtgtggaatataacacctaagaatatgtctgttacccatg
atatgatgcttttaaggccagccggggagaaaggactgtgtactctgtgtgttgggagggaggtggcaggttgaatactagggttctgtgag
tttgattaaggtacggtgatcaatataagctatgtggtggtgggctatactactgaatgaaaaatgacttgaaattttctgcaattgaaaaata
aacacgttgaaacataacatgcaacaggttcacgattctttattcctgggcaatgtaggagaaggtgtaagagttggtagcaaaagtttcagtgg
tgtattttccactttcccaggaccatgtaaaagacatagagtaagtgcttacctcgctagtttctgtggattcactagaaccagtggccaaaaa
gctagcgcagcagccgccgcgcctggaaggaagcaaaaggagcgctcccccgttgtctgacgtcgcacacctgggttcgacacgcgg
gcggtaaccgcatggatcacggcggacggccggatccggggttcgaaccccggtcgtccgccatgataccctttgcgaattatccaccag
accacggaagagtgcccgcttacagGTGGTCTCATACAGAACTTATAAGATTCCCAAATCCAAAGA
CATTTCACGTTTATGGTGATTTCCCAGAACACATAGCGACATGCAAATATTGCAGGG
CGCCACTCCCCTGTCCgctctccttttgcacggtctagagcgtcaacgactgcgcacgtccactttggccgcggctcgagTG
AGCTATTCCAGAAGTAGTGAAGAGGCTTTTTTGGAGGCCTAGGCTTTTGCAAAAAGC
TCCGGATCGATGCCCGGGGGATCCACTAGTTCTAGAGGGACAGCCCCCCCCCAAAG
CCCCCAGGGATGTAATTACGTCCCTCCCCCGCTAGGGGGCAGCAGCGAGCCGCCCG
GGGCTCCGCTCCGGTCCGGCGCTCCCCCCGCATCCCCGAGCCGGCAGCGTGCGGGG
ACAGCCCGGGCACGGGAAGGTGGCACGGGATCGCTTTCCTCTGAACGCTTCTCGCT
GCTCTTTGAGCCTGCAGACACCTGGGGGATACGGGAAAAGGCCTCCAAGGCCAG
CTTCCCACAATAAGTTGGGTGAATTTTGGCTGAGCTATTCCAGAAGTAGTGAAGAGG
CTTTTTTGGAGGCCTAGGCTTTTGCAAAAAGCTCCGGATCGATCATATATGGCAGAT
ATACGCGTTGACATTGATTATTGACTAGTTATTAATAGTAATCAATTACGGGGTCAT
TAGTTCATAGCCCATATATGGAGTTCCGCGTTACATAACTTACGGTAAATGGCCCGC
CTGGCTGACCGCCCAACGACCCCCGCCCATTGACGTCAATAATGACGTATGTTCCCA
TAGTAACGCCAATAGGGACTTTCCATTGACGTCAATGGGTGGAGTATTTACGGTAAA
```

-continued

```
CTGCCCACTTGGCAGTACATCAAGTGTATCATATGCCAAGTACGCCCCCTATTGACG

TCAATGACGGTAAATGGCCCGCCTGGCATTATGCCCAGTACATGACCTTATGGGACT

TTCCTACTTGGCAGTACATCTACGTATTAGTCATCGCTATTACCATGGTGATGCGGTT

TTGGCAGTACATCAATGGGCGTGGATAGCGGTTTGACTCACGGGGATTTCCAAGTCT

CCACCCCATTGACGTCAATGGGAGTTTGTTTTGGCACCAAAATCAACGGGACTTTCC

AAAATGTCGTAACAACTCCGCCCCATTGACGCAAATGGGCGGTAGGCGTGTACGGT

GGGAGGTCTATATAAGCAGAGCTCTCTGGCTAACTATCGTCGACGAGCTCGTTTAGT

GAACCGTCAGATCGCCTGGAGACGCCATCCACGCTGTTTTGACCTCCATAGAAGACA

CCGGGACCGATCCAGCCTCCGGACTCTAGCGTTTAAACTTAAGCTTGCCACCatgaccga gtacaagcccacggtgcgcctcgccaccgcgacgacgtccccagggccgtacgcaccctcgccgccgcgttcgccgactacccgcc acgcgccacaccgtcgatccggaccgccacatcgagcgggtcaccgagctgcaagaactcttcctcacgcgcgtcgggctcgacatcgg caaggtgtgggtcgcggacgacggcgccgcggtggcggtctggaccacgccggagagcgtcgaagcgggggcggtgttcgccgaga tcggcccgcgcatggccgagttgagcggttcccggctggccgcgcagcaacagatggaaggcctcctggcgccgcaccggcccaagg agcccgcgtggttcctggccaccgtcggcgtctcgcccgaccaccagggcaagggtctgggcagcgccgtcgtgctccccggagtgga ggcggccgagcgcgccggggtgcccgccttcctggagacctccgcgccccgcaacctccccttctacgagcggctcggcttcaccgtca ccgccgacgtcgaggtgcccgaaggaccgcgcacctggtgcatgacccgcaagcccggtgcctgaAGCGCGGGGATCTC

ATGCTGGAGTTCTTCGCCCACCCCAACTTGTTTATTGCAGCTTATAATGGTTACAAAT

AAAGCAATAGCATCACAAATTTCACAAATAAAGCATTTTTTTCACTGCATTCTAGTT

GTGGTTTGTCCAAACTCATCAATGTATCTTATCATGTCTGTAGCtGATgtATAcCTAggA

TCCGGCCGGccTGCAggTGTCCTCACAGGAACGAAGTCCCTAAAGAAACAGTGGCAG

CCAGGTTTAGCCCCGGAATTGACTGGATTCCTTTTTTAGGGCCCATTGGTATGGCTTT

TTCCCCGTATCCCCCCAGGTGTCTGCAGGCTCAAAGAGCAGCGAGAAGCGTTCAGA

GGAAAGCGATCCCGTGCCACCTTCCCCGTGCCCGGGCTGTCCCCGCACGCTGCCGGC

TCGGGGATGCGGGGGGAGCGCCGGACCGGAGCGGAGCCCCGGGCGGCTCGCTGCTG

CCCCCTAGCGGGGGAGGGACGTAATTACATCCCTGGGGGCTTTGGGGGGGGGCTGT

CCCTCTAGAGCGGCCGCCACCGCGGTGGAGCTCCAGCTTTTGTTCCCTTTAGTGAGG

GTTAATTAGATCTTAATACGACTCACTATAGGGCGAATTGGGTACCGGGCCCCCCCT

CGAGGTCGACGGTATCGATAAGCTTGATATCTATAACAAGAAAATATATATATAATA

AGTTATCACGTAAGTAGAACATGAAATAACAATATAATTATCGTATGAGTTAAATCT

TAAAAGTCACGTAAAAGATAATCATGCGTCATTTTGACTCACGCGGTCGTTATAGTT

CAAAATCAGTGACACTTACCGCATTGACAAGCACGCCTCACGGGAGCTCCAAGCGG

CGACTGAGATGTCCTAAATGCACAGCGACGGATTCGCGCTATTTAGAAAGAGAGAG

CAATATTTCAAGAATGCATGCGTCAATTTTACGCAGACTATCTTTCTAGGGTTAATCT

AGCTGCATCAGGATCATATCGTCGGGTCTTTTTCCGGCTCAGTCATCGCCCAAGCT

GGCGCTATCTGGGCATCGGGGAGGAAGAAGCCCGTGCCTTTTCCCGCGAGGTTGAA

GCGGCATGGAAAGAGTTTGCCGAGGATGACTGCTGCTGCATTGACGTTGAGCGAAA

ACGCACGTTTACCATGATGATTCGGGAAGGTGTGGCCATGCACGCCTTTAACGGTGA

ACTGTTCGTTCAGGCCACCTGGGATACCAGTTCGTCGCGGCTTTTCCGGACACAGTT

CCGGATGGTCAGCCCGAAGCGCATCAGCAACCCGAACAATACCGGCGACAGCCGGA

ACTGCCGTGCCGGTGTGCAGATTAATGACAGCGGTGCGGCGCTGGGATATTACGTCA

GCGAGGACGGGTATCCTGGCTGGATGCCGCAGAAATGGACATGGATACCCCGTGAG
```

-continued

```
TTACCCGGCGGGCGCGCTTGGCGTAATCATGGTCATAGCTGTTTCCTGTGTGAAATT
GTTATCCGCTCACAATTCCACACAACATACGAGCCGGAAGCATAAAGTGTAAAGCC
TGGGGTGCCTAATGAGTGAGCTAACTCACATTAATTGCGTTGCGCTCACTGCCCGCT
TTCCAGTCGGGAAACCTGTCGTGCCAGCTGCATTAATGAATCGGCCAACGCGCGGG
GAGAGGCGGTTTGCGTATTGGGCGCTCTTCCGCTTCCTCGCTCACTGACTCGCTGCG
CTCGGTCGTTCGGCTGCGGCGAGCGGTATCAGCTCACTCAAAGGCGGTAATACGGTT
ATCCACAGAATCAGGGGATAACGCAGGAAAGAACATGTGAGCAAAAGGCCAGCAA
AAGGCCAGGAACCGTAAAAAGGCCGCGTTGCTGGCGTTTTTCCATAGGCTCCGCCCC
CCTGACGAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTCCTGTTCC
GACCCTGCCGCTTACCGGATACCTGTCCGCCTTTCTCCCTTCGGGAAGCGTGGCGCT
TTCTCATAGCTCACGCTGTAGGTATCTCAGTTCGGTGTAGGTCGTTCGCTCCAAGCTG
GGCTGTGTGCACGAACCCCCCGTTCAGCCCGACCGCTGCGCCTTATCCGGTAACTAT
CGTCTTGAGTCCAACCCGGTAAGACACGACTTATCGCCACTGGCAGCAGCCACTGGT
AACAGGATTAGCAGAGCGAGGTATGTAGGCGGTGCTACAGAGTTCTTGAAGTGGTG
GCCTAACTACGGCTACACTAGAAGGACAGTATTTGGTATCTGCGCTCTGCTGAAGCC
AGTTACCTTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCCTTTTAA
ATTAAAAATGAAGTTTTAAATCAATCTAAAGTATATATGAGTAAACTTGGTCTGACA
GTTACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACCATC
TGGCCCCAGTGCTGCAATGATACCGCGAGACCCACGCTCACCGGCTCCAGATTTATC
AGCAATAAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGTTCGCCAG
TTAATAGTTTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTACATGATC
CCCCATGTTGTGCAAAAAAGCGGTTAGCTCCTTCGGTCCTCCGATCGTTGTCAGAAG
TAAGTTGGCCGCAGTGTTATCACTCATGGTTATGGCAGCACTGCATAATTCTCTTACT
GTCATGCCATCCGTAAGATGCTTTTCTGTGACTGGTGAGTACTCAACCAAGTCATTCT
GAGAATAGTGTATGCGGCGACCGAGTTGCTCTTGCCCGGCGTCAATACGGGATAAT
ACCGCGCCACATAGCAGAACTTTAAAAGTGCTCATCATTGGAAAACGTTCTTCGGGG
CGAAAACTCTCAAGGATCTTACCGCTGTTGAGATCCAGTTCGATGTAACCCACTCGT
GCACCCAACTGATCTTCAGCATCTTTTACTTTCACCAGCGTTTCTGGGTGAGCAAAA
ACAGGAAGGCAAAATGCCGCAAAAAAGGGAATAAGGGCGACACGGAAATGTTGAA
TACTCAT
```

The sequence of the pPBBG-iHelper2.4-HA vector is provided below:

pPBBG-iHelper2.4-HA (15,992 bp)

(SEQ ID NO: 7)

ACTCTTCCTTTTTCAATATTATTGAAGCATTTATCAGGGTTATTGTCTCATGA

GCGGATACATATTTGAATGTATTTAGAAAAATAAACAAATAGGGGTTCCGCGCACA

TTTCCCCGAAAAGTGCCACCTAAATTGTAAGCGTTAATATTTTGTTAAAATTCGCGTT

AAATTTTTGTTAAATCAGCTCATTTTTTAACCAATAGGCCGAAATCGGCAAAATCCC

TTATAAATCAAAAGAATAGACCGAGATAGGGTTGAGTGTTGTTCCAGTTTGGAACA

AGAGTCCACTATTAAAGAACGTGGACTCCAACGTCAAAGGGCGAAAAACCGTCTAT

CAGGGCGATGGCCCACTACGTGAACCATCACCCTAATCAAGTTTTTTGGGGTCGAGG

TGCCGTAAAGCACTAAATCGGAACCCTAAAGGGAGCCCCCGATTTAGAGCTTGACG

GGGAAAGCCGGCGAACGTGGCGAGAAAGGAAGGGAAGAAAGCGAAAGGAGCGGG

CGCTAGGGCGCTGGCAAGTGTAGCGGTCACGCTGCGCGTAACCACCACACCCGCCG

CGCTTAATGCGCCGCTACAGGGCGCGTCCCATTCGCCATTCAGGCTGCGCAACTGTT

GGGAAGGGCGATCGGTGCGGGCCTCTTCGCTATTACGCCAGCTGGCGAAAGGGGGA

TGTGCTGCAAGGCGATTAAGTTGGGTAACGCCAGGGTTTTCCCAGTCACGACGTTGT

AAAACGACGGCCAGTGAGCGCGCCTCGTTCATTCACGTTTTTGAACCCGTGGAGGAC

GGGCAGACTCGCGGTGCAAATGTGTTTTACAGCGTGATGGAGCAGATGAAGATGCT

CGACACGCTGCAGAACACGCAGCTAGATTAACCCTAGAAAGATAATCATATTGTGA

CGTACGTTAAAGATAATCATGCGTAAAATTGACGCATGTGTTTTATCGGTCTGTATA

TCGAGGTTTATTTATTAATTTGAATAGATATTAAGTTTTATTATATTTACACTTACAT

ACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCggtacccaactccatgcttaacagtccccaggtacagcccaccctgcgtcgcaaccaggaaca gctctacagcttcctggagcgccactcgccctacttccgcagccacagtgcgcagattaggagcgccacttcttttttgtcacttgaaaaacat gtaaaaataatgtactaggagacactttcaataaaggcaaatgttttttatttgtacactctcgggtgattatttaccccccacccttgccgtctg cgccgtttaaaaatcaaaggggttctgccgcgcatcgctatgcgccactggcagggacacgttgcgatactggtgtttagtgctccacttaaact caggcacaaccatccgcggcagctcggtgaagttttcactccacaggctgcgcaccatcaccaacgcgtttagcaggtcgggcgccgata tcttgaagtcgcagttggggcctccgccctgcgcgcgcgagttgcgatacacagggttgcagcactggaacactatcagcgccgggtggt gcacgctggccagcacgctcttgtcggagatcagatccgcgtccaggtcctccgcgttgctcagggcgaacggagtcaactttggtagctg ccttcccaaaaagggtgcatgcccaggctttgagttgcactcgcaccgtagtggcatcagaaggtgaccgtgcccggtctgggcgttagga tacagcgcctgcatgaaagccttgatctgcttaaaagccacctgagcctttgcgccttcagagaagaacatgccgcaagacttgccggaaa actgattggccggacaggccgcgtcatgcacgcagcaccttgcgtcggtgttggagatctgcaccacatttcggccccaccggttcttcacg -continued

```
atcttggccttgctagactgctccttcagcgcgcgctgcccgttttcgctcgtcacatccatttcaatcacgtgctccttatttatcataatgc tcccgtgtagacacttaagctcgccttcgatctcagcgcagcggtgcagccacaacgcgcagcccgtgggctcgtggtcgttgtaggttacctct gcaaacgactgcaggtacgcctgcaggaatcgccccatcatcgtcacaaaggtcttgttgctggtgaaggtcagctgcaacccgcggtgctc ctcgtttagccaggtcttgcatacggccgccagagcttccacttggtcaggcagtagcttgaagtttgcctttagatcgttatccacgtggtact tgtccatcaacgcgcgcgcagcctccatgcccttctcccacgcagacacgatcggcaggctcagcgggtttatcaccgtgctttcactttccg cttcactggactcttccttttcctcttgcgtccgcataccccgcgccactgggtcgtcttcattcagccgccgcaccgtgcgcttacctcccttg ccgtgcttgattagcaccggtgggttgctgaaacccaccatttgtagcgccacatcttctctttcttcctcgctgtccacgatcacctctgggga tggcgggcgctcgggcttgggagaggggcgcttcttttcttttttggacgcaatggccaaatccgccgtcgaggtcgatggccgcgggctgg gtgtgcgcggcaccagcgcatcttgtgacgagtcttcttcgtcctcggactcgagacgccgcctcagccgcttttttggggggcgcgcggggg aggcggcggcgacggcgacggggacgacacgtcctccatggttggtggacgtcgcgccgcaccgcgtccgcgctcggggggtggtttc gcgctgctcctcttcccgactggccatttccttctcctataggcagaaaaagatcatggagtcagtcgagaaggaggacagcctaaccgccc cctttgagttcgccaccaccgcctccaccgatgccgccaacgcgcctaccaccttccccgtcgaggcaccccgcttgaggaggaggaa gtgattatcgagcaggacccaggttttgtaagcgaagacgacgaggatcgctcagtaccaacagaggataaaaagcaagaccaggacga cgcagaggcaaacgaggaacaagtcgggcgggggggaccaaaggcatggcgactacctagatgtgggagacgacgtgctgttgaagca tctgcagcgccagtgcgccattatctgcgacgcgttgcaagagcgcagcgatgtgcccctcgccatagcggatgtcagccttgcctacgaa cgccacctgttctcaccgcgcgtaccccccaaacgccaagaaaacggcacatgcgagcccaacccgcgcctcaacttctaccccgtatttg ccgtgccagaggtgcttgccacctatcacatcttttttccaaaactgcaagataccctatcctgccgtgccaaccgcagccgagcggacaag cagctggccttgcggcagggcgctgtcatacctgatatcgcctcgctcgacgaagtgccaaaaatctttgagggtcttggacgcgacgaga aacgcgcggcaaacgctctgcaacaagaaaacagcgaaatgaaagtcactgtggagtgctggtggaacttgagggtgacaacgcgcg cctagccgtgctgaaacgcagcatcgaggtcacccactttgcctacccggcacttaacctaccccccaaggttatgagcacagtcatgagc gagctgatcgtgcgccgtgcacgacccctggagagggatgcaaacttgcaagaacaaaccgaggagggcctaccccgcagttggcgatg agcagctggcgcgctggcttgagacgcgcgagcctgccgacttggaggagcgacgcaagctaatgatggccgcagtgcttgttaccgtg gagcttgagtgcatgcagcggttcttttgctgacccggagatgcagcgcaagctagaggaaacgttgcactacacctttcgccagggctacg tgcgccaggcctgcaaaatttccaacgtggagctctgcaacctggtctcctaccttggaattttgcacgaaaaccgcctcgggcaaaacgtg cttcattccacgctcaagggcgaggcgcgccgcgactacgtccgcgactgcgtttacttatttctgtgctacacctggcaaacggccatggg cgtgtggcagcaatgcctggaggagcgcaacctaaaggagctgcagaagctgctaaagcaaaacttgaaggacctatggacggccttca acgagcgctccgtggccgcgcacctggcggacattatcttccccgaacgcctgcttaaaaccctgcaacagggtctgccagacttcaccag tcaaagcatgttgcaaaactttaggaacttatcctagagcgttcaggaattctgcccgccacctgctgtgcgcttcctagcgactttgtgccca ttaagtaccgtgaatgccctccgccgctttggggtcactgctaccttctgcagctagccaactaccttgcctaccactccgacatcatggaaga cgtgagcggtgacggcctactggagtgtcactgtcgctgcaacctatgcaccccgcaccgctccctggtctgcaattcgcaactgcttagcg aaagtcaaattatcggtacctttgagctgcagggtccctcgcctgacgaaaagtccgcggctccgggggttgaaactcactccggggctgtg gacgtcCGATCTCTATCACTGATAGGGAGATCTCTATCACTGATAGGGAGAGgcttaccttcg caaatttgtacctgaggactaccacgcccacgagattaggttctacgaagaccaatcccgcccgccaaatgcggagcttaccgcctgcgtc attacccagggccacatccttggccaattgcaagccatcaacaaagcccgccaagagtttctgctacgaaagggacgggggttacctgg accccagtccggcgaggagctcaacccaatccccccgccgccagccctatcagcagccgcgggcccttgcttcccaggatggcac ccaaaaagaagctgcagctgccgccgccgccacccacggacgaggaggaatactgggacagtcaggcagaggaggttttggacgagg aggaggagatgatggaagactgggacagcctagacgaagcttccgaggccgaagaggtgtcagacgaaacaccgtcaccctcggtcgc attccctcgccggcgcccagaaattggcaaccgttcccagcatcgctacaacctccgctcctcaggcgccgccggcactgctgttcgc cgacccaaccgtagatgggacaccactggaaccagggccggtaagtctaagcagccgccgccgttagcccaagagcaacaacagcgc caaggctaccgctcgtggcgcgggcacaagaacgccatagttgcttgcttgcaagactgtggggcaacatctccttcgcccgccgctttct tctctaccatcacggcgtggccttcccccgtaacatcctgcattactaccgtcatctctacagcccctactgcaccggcggcagcggcagcg
```

```
gcagcaacagcagcggtcacacagaagcaaaggcgaccggatagcaagactctgacaaagcccaagaaatccacagcggcggcagc
agcaggaggaggagcgctgcgtctggcgcccaacgaacccgtatcgacccgcgagcttagaaataggattttttcccactctgtatgctatat
ttcaacaaagcaggggccaagaacaagagctgaaaaaaaaaacaggtctctgcgctccctcacccgcagctgcctgtatcacaaaagcg
aagatcagcttcggcgcacgctggaagacgcggaggctctcttcagcaaCGATCTCTATCACTGATAGGGAGATC
TCTATCACTGATAGGGAGAGatactgcgcgctgactcttaaggactagtttcgcgccctttctcaaatttaagcgcgaaaa
ctacgtcatctccagcggccacacccggcgccagcacctgtcgtcagcgccattatgagcaaggaaattcccacgccctacatgtggagtt
accagccacaaatgggacttgcggctggagctgcccaagactactcaacccgaataaactacatgagcgcgggaccccacatgatatccc
gggtcaacggaatccgcgccaccgaaaccgaattctcctcgaacaggcggctattaccaccacacctcgtaataaccttaatcccgtagt
tggcccgctgccctggtgtaccaggaaagtcccgctccaccactgtggtacttcccagagacgcccaggccgaagttcagatgactaact
caggggcgcagcttgcgggcggctttcgtcacagggtgcggtcgcccccagtggccaaaaaagctagcgcagcagccgccgcgcctg
gaaggaagccaaaaggagcgctccccgttgtctgacgtcgcacacctgggttcgacacgcgggcggtaaccgcatggatcacggcgg
acggccggatccggggttcgaaccccggtcgtccgccatgatacccttgcgaatttatccaccagaccacggaagagtgcccgcttacag
GTGGTCTCATACAGAACTTATAAGATTCCCAAATCCAAGACATTTCACGTTTATGG
TGATTTCCCAGAACACATAGCGACATGCAAATATTGCAGGGCGCCACTCCCCTGTCC
gctctccttttgcacggtctagagcgtcaacgactgcgcacggggcgttttagggcggagtaacttgcatgtattgggaattgtagttttttttaa
aatgggaagtgacgtatcgtgggaaaacggaagtgaagatttgaggaagttgtgggttttttggctttcgtttctgggcgtaggttcgcgtgcg
gttttctgggtgttttttgtggactttaaccgttacgtcattttttagtcctatatatactcgctctgtaCTCTCCCTATCAGTGATAG
AGATCTCCCTATCAGTGATAGAGATCGcttggcccttttttacactgtgactgattgagctggtgccgtgtcgagtggt
gtttttttaataggttttttttactggtaaggctgactgttatggctgccgctgtggaagcgctgtatgttgttctggagcgggagggtgctatttt
gcctaggcaggagggttttttcaggtgtttatgtgttttttctctcctattaattttgttataacctcctatgggggctgtaatgttgtctctacgcc
tgcgggtatgtattccccccgggctatttcggtcgcttttttagcactgaccgatgttaaccaacctgatgtgtttaccgagtcttacattatgact
ccggacatgaccgaggaactgtcggtggtgcttttttaatcacggtgaccagtttttttacggtcacgccggcatggccgtagtccgtcttatgct
tataagggttgtttttcctgttgtaagacaggcttctaatgtttaaatgttttttttttttgttatttttatttttgtgtttaatgcaggaacccgca
gacatgtttgagagaaaaatggtgtcttttttctgtggtggttccggaacttacctgcctttatctgcatgagcatgactacgatgtgcttgctttt
tttgcgcgaggctttgcctgatttttttgagcagcaccttgcattttatatcgccgcccatgcaacaagcttacataggggctacgctggttagca
tagctccgagtatgcgtgtcataatcagtgtgggttcttttgtcatggttcctggcggggaagtggccgcgctggtccgtgcagacctgcacgat
tatgttcagctggccctgcgaagggacctacgggatcgcggtattttgttaatgttccgcttttgaatcttatacaggtctgtgaggaacctga
atttttgcaatcatgattcgctgcttgaggctgaaggtggagggcgctctggagcagattttttacaatggccggacttaatattcgggatttgct
tagagacatattgataaggtggcgagatgaaaattatttgggcatggttgaaggtgctggaatgtttatagaggagattcaccctgaagggttta
gcctttacgtccacttggacgtgagggcagtttgccttttggaagccattgtgcaacatcttacaaatgccattatctgttctttggctgtagag
tttgaccacgccaccggaggggagcgcgttcacttaatagatcttcattttgaggttttggataatcttttggaataaaaaaaaaaaacatggt
tcttccagctcttcccgctcctcccgtgtgtgactcgcagaacgaatgtgtaggttggctgggtgtggcttattctgcggtggtggatgttatca
gggcagcggcgcatgaaggagtttacatagaacccgaagccaggggcgcctggatgctttgagagagtggatatactacaactactacacagag
cgagctaagcgacgagaccggagacgcagatctgtttgtcacgcccgcacctggttttgcttcaggaaatatgTACCCATACGATGTTCCAGA
TTACGCTGGAGGAGGCGGAGGCactacgtccggcgttccatttggcatgacactacgaccaacacgatctcggttgtct
cggcgcactccgtacagtagggatcgcctacctccttttgagacagagaccgcgctaccatactggaggatcatccgctgctgcccgaat
gtaacactttgacaatgcacaacgtgagttacgtgcgaggtcttccctgcagtgtgggatttacgctgattcaggaatggggttgttcctggga
tatggttctgacgcgggaggagcttgtaatcctgaggaagtgtatgcacgtgtgcctgtgttgtgccaacattgatatcatgacgagcatgatg
atccatggttacgagtcctgggctctccactgtcattgttccagtcccggttccctgcagtgcatagccggcgggcaggttttggccagctggt
ttaggatggtggtggatggcgccatgtttaatcagagggtttatatggtaccgggaggtggtgaattacaacatgccaaaagaggtaatgtttat
```

-continued gtccagcgtgtttatgaggggtcgccacttaatctacctgcgcttgtggtatgatggccacgtgggttctgtggtccccgccatgagctttgga tacagcgccttgcactgtgggattttgaacaatattgtggtgctgtgctgcagttactgtgctgatttaagtgagatcagggtgcgctgctgtgc ccggaggacaaggcgtctcatgctgcgggcggtgcgaatcatcgctgaggagaccactgccatgttgtattcctgcaggacggagcggc ggcggcagcagtttattcgcgcgctgctgcagcaccaccgccctatcctgatgcacgattatgactctaccccatgtaggcgtggacttcc ccttcgccgcccgttgagcaaccgcaagttggacagcagcctgtggctcagcagctggacagcgacatgaacttaagcgagctgcccgg ggagtttattaatatcactgatgagcgtttggctcgacaggaaccgtgtggaatataaacacctaagaatatgtctgttacccatgatatgatgc tttttaaggccagccggggagaaaggactgtgtactctgtgtgttgggagggaggtggcaggttgaatactaggggttctgtgagtttgattaa ggtacggtgatcaatataagctatgtggtggtggggctatactactgaatgaaaaatgacttgaaattttctgcaattgaaaaataaacacgttg aaacataacatgcaacaggttcacgattctttattcctgggcaatgtaggagaaggtgtaagagttggtagcaaaagtttcagtggtgtattttc cactttcccaggaccatgtaaaagacatagagtaagtgcttacctcgctagtttctgtggattcactagaatccactttggccgcggctcgagT

GAGCTATTCCAGAAGTAGTGAAGAGGCTTTTTTGGAGGCCTAGGCTTTTGCAAAAAG

CTCCGGATCGATGCCCGGGGGATCCACTAGTTCTAGAGGGACAGCCCCCCCCCAAA

GCCCCCAGGGATGTAATTACGTCCCTCCCCCGCTAGGGGGCAGCAGCGAGCCGCCC

GGGGCTCCGCTCCGGTCCGGCGCTCCCCCCGCATCCCCGAGCCGGCAGCGTGCGGG

GACAGCCCGGGCACGGGGAAGGTGGCACGGGATCGCTTTCCTCTGAACGCTTCTCG

CTGCTCTTTGAGCCTGCAGACACCTGGGGGGATACGGGGAAAAGGCCTCCAAGGCC

AGCTTCCCACAATAAGTTGGGTGAATTTTGGCTGAGCTATTCCAGAAGTAGTGAAGA

GGCTTTTTTGGAGGCCTAGGCTTTTGCAAAAAGCTCCGGATCGATCATATATGGCAG

ATATACGCGTTGACATTGATTATTGACTAGTTATTAATAGTAATCAATTACGGGGTC

ATTAGTTCATAGCCCATATATGGAGTTCCGCGTTACATAACTTACGGTAAATGGCCC

GCCTGGCTGACCGCCCAACGACCCCCGCCCATTGACGTCAATAATGACGTATGTTCC

CATAGTAACGCCAATAGGGACTTTCCATTGACGTCAATGGGTGGAGTATTTACGGTA

AACTGCCCACTTGGCAGTACATCAAGTGTATCATATGCCAAGTACGCCCCCTATTGA

CGTCAATGACGGTAAATGGCCCGCCTGGCATTATGCCCAGTACATGACCTTATGGGA

CTTTCCTACTTGGCAGTACATCTACGTATTAGTCATCGCTATTACCATGGTGATGCGG

TTTTGGCAGTACATCAATGGGCGTGGATAGCGGTTTGACTCACGGGGATTTCCAAGT

CTCCACCCCATTGACGTCAATGGGAGTTTGTTTTGGCACCAAAATCAACGGGACTTT

CCAAAATGTCGTAACAACTCCGCCCCATTGACGCAAATGGGCGGTAGGCGTGTACG

GTGGGAGGTCTATATAAGCAGAGCTCTCTGGCTAACTATCGTCGACGAGCTCGTTTA

GTGAACCGTCAGATCGCCTGGAGACGCCATCCACGCTGTTTTGACCTCCATAGAAGA

CACCGGGACCGATCCAGCCTCCGGACTCTAGCGTTTAAACTTAAGCTTGCCACCatgac cgagtacaagcccacggtgcgcctcgccacccgcgacgacgtccccagggccgtacgcaccctcgccgccgcgttcgccgactacccc gccacgcgccacaccgtcgatccggaccgccacatcgagcgggtcaccgagctgcaagaactcttcctcacgcgcgtcgggctcgacat cggcaaggtgtgggtcgcggacgacggcgccgcggtggcggtctggaccacgccggagagcgtcgaagcgggggcggtgttcgccg agatcggcccgcgcatggccgagttgagcggttcccggctggccgcgcagcaacagatggaaggcctcctggcgccgcaccggccca aggagccgcgtggttcctggccaccgtcggcgtctcgcccgaccaccagggcaaggtctgggcagcgccgtcgtgctcccgggagt ggaggcggccgagcgcgccggggtgcccgccttcctggagacctccgcgccccgcaacctccccttctacgagcggctcggcttcacc gtcaccgccgacgtcgaggtgcccgaaggaccgcgcacctggtgcatgacccgcaagcccggtgcctgaAGCGCGGGGATC

TCATGCTGGAGTTCTTCGCCCACCCCAACTTGTTTATTGCAGCTTATAATGGTTACAA

ATAAAGCAATAGCATCACAAATTTCACAAATAAAGCATTTTTTTCACTGCATTCTAG

TTGTGGTTTGTCCAAACTCATCAATGTATCTTATCATGTCTGTAGCtGATgtATAcCTAg

-continued gATCCGGCCGGccTGCAggTGTCCTCACAGGAACGAAGTCCCTAAAGAAACAGTGGCA

GCCAGGTTTAGCCCCGGAATTGACTGGATTCCTTTTTTAGGGCCCATTGGTATGGCTT

TTTCCCCGTATCCCCCCAGGTGTCTGCAGGCTCAAAGAGCAGCGAGAAGCGTTCAGA

GGAAAGCGATCCCGTGCCACCTTCCCCGTGCCCGGGCTGTCCCCGCACGCTGCCGGC

TCGGGGATGCGGGGGGAGCGCCGGACCGGAGCGGAGCCCCGGGCGGCTCGCTGCTG

CCCCCTAGCGGGGGAGGGACGTAATTACATCCCTGGGGGCTTTGGGGGGGGCTGT

CCCTCTAGAGCGGCCGCCACCGCGGTGGAGCTCCAGCTTTTGTTCCCTTTAGTGAGG

GTTAATTAGATCTTAATACGACTCACTATAGGGCGAATTGGGTACCGGGCCCCCCCT

CGAGGTCGACGGTATCGATAAGCTTGATATCTATAACAAGAAAATATATATATAATA

AGTTATCACGTAAGTAGAACATGAAATAACAATATAATTATCGTATGAGTTAAATCT

TAAAAGTCACGTAAAAGATAATCATGCGTCATTTTGACTCACGCGGTCGTTATAGTT

CAAAATCAGTGACACTTACCGCATTGACAAGCACGCCTCACGGGAGCTCCAAGCGG

CGACTGAGATGTCCTAAATGCACAGCGACGGATTCGCGCTATTTAGAAAGAGAGAG

CAATATTTCAAGAATGCATGCGTCAATTTTACGCAGACTATCTTTCTAGGGTTAATCT

AGCTGCATCAGGATCATATCGTCGGGTCTTTTTTCCGGCTCAGTCATCGCCCAAGCT

GGCGCTATCTGGGCATCGGGGAGGAAGAAGCCCGTGCCTTTTCCCGCGAGGTTGAA

GCGGCATGGAAAGAGTTTGCCGAGGATGACTGCTGCTGCATTGACGTTGAGCGAAA

ACGCACGTTTACCATGATGATTCGGGAAGGTGTGGCCATGCACGCCTTTAACGGTGA

ACTGTTCGTTCAGGCCACCTGGGATACCAGTTCGTCGCGGCTTTTCCGGACACAGTT

CCGGATGGTCAGCCCGAAGCGCATCAGCAACCCGAACAATACCGGCGACAGCCGGA

ACTGCCGTGCCGGTGTGCAGATTAATGACAGCGGTGCGGCGCTGGGATATTACGTCA

GCGAGGACGGGTATCCTGGCTGGATGCCGCAGAAATGGACATGGATACCCCGTGAG

TTACCCGGCGGGCGCGCTTGGCGTAATCATGGTCATAGCTGTTTCCTGTGTGAAATT

GTTATCCGCTCACAATTCCACACAACATACGAGCCGGAAGCATAAAGTGTAAAGCC

TGGGGTGCCTAATGAGTGAGCTAACTCACATTAATTGCGTTGCGCTCACTGCCCGCT

TTCCAGTCGGGAAACCTGTCGTGCCAGCTGCATTAATGAATCGGCCAACGCGCGGG

GAGAGGCGGTTTGCGTATTGGGCGCTCTTCCGCTTCCTCGCTCACTGACTCGCTGCG

CTCGGTCGTTCGGCTGCGGCGAGCGGTATCAGCTCACTCAAAGGCGGTAATACGGTT

ATCCACAGAATCAGGGGATAACGCAGGAAAGAACATGTGAGCAAAAGGCCAGCAA

AAGGCCAGGAACCGTAAAAAGGCCGCGTTGCTGGCGTTTTTCCATAGGCTCCGCCCC

CCTGACGAGCATCACAAAAATCGACGCTCAAGTCAGAGGTGGCGAAACCCGACAGG

ACTATAAAGATACCAGGCGTTTCCCCCTGGAAGCTCCCTCGTGCGCTCTCCTGTTCC

GACCCTGCCGCTTACCGGATACCTGTCCGCCTTTCTCCCTTCGGGAAGCGTGGCGCT

TTCTCATAGCTCACGCTGTAGGTATCTCAGTTCGGTGTAGGTCGTTCGCTCCAAGCTG

GGCTGTGTGCACGAACCCCCCGTTCAGCCCGACCGCTGCGCCTTATCCGGTAACTAT

CGTCTTGAGTCCAACCCGGTAAGACACGACTTATCGCCACTGGCAGCAGCCACTGGT

AACAGGATTAGCAGAGCGAGGTATGTAGGCGGTGCTACAGAGTTCTTGAAGTGGTG

GCCTAACTACGGCTACACTAGAAGGACAGTATTTGGTATCTGCGCTCTGCTGAAGCC

AGTTACCTTCGGAAAAAGAGTTGGTAGCTCTTGATCCGGCAAACAAACCACCGCTG

GTAGCGGTGGTTTTTTTGTTTGCAAGCAGCAGATTACGCGCAGAAAAAAAGGATCTC

-continued

```
AAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCCTTTTAA
ATTAAAAATGAAGTTTTAAATCAATCTAAAGTATATATGAGTAAACTTGGTCTGACA
GTTACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACCATC
TGGCCCCAGTGCTGCAATGATACCGCGAGACCCACGCTCACCGGCTCCAGATTTATC
AGCAATAAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGTTCGCCAG
TTAATAGTTTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTACATGATC
CCCCATGTTGTGCAAAAAAGCGGTTAGCTCCTTCGGTCCTCCGATCGTTGTCAGAAG
TAAGTTGGCCGCAGTGTTATCACTCATGGTTATGGCAGCACTGCATAATTCTCTTACT
GTCATGCCATCCGTAAGATGCTTTTCTGTGACTGGTGAGTACTCAACCAAGTCATTCT
GAGAATAGTGTATGCGGCGACCGAGTTGCTCTTGCCCGGCGTCAATACGGGATAAT
ACCGCGCCACATAGCAGAACTTTAAAAGTGCTCATCATTGGAAAACGTTCTTCGGGG
CGAAAACTCTCAAGGATCTTACCGCTGTTGAGATCCAGTTCGATGTAACCCACTCGT
GCACCCAACTGATCTTCAGCATCTTTTACTTTCACCAGCGTTTCTGGGTGAGCAAAA
ACAGGAAGGCAAAATGCCGCAAAAAAGGGAATAAGGGCGACACGGAAATGTTGAA
TACTCAT
```

The sequence of the pPBBG-iHelper2.5-HA vector is provided below:

pPBBG-iHelper2.5-HA (16,658 bp)            (SEQ ID NO: 8)

```
ACTCTTCCTTTTTCAATATTATTGAAGCATTTATCAGGGTTATTGTCTCATGA
GCGGATACATATTTGAATGTATTTAGAAAAATAAACAAATAGGGGTTCCGCGCACA
TTTCCCCGAAAAGTGCCACCTAAATTGTAAGCGTTAATATTTTGTTAAAATTCGCGTT
AAATTTTTGTTAAATCAGCTCATTTTTTAACCAATAGGCCGAAATCGGCAAAATCCC
TTATAAATCAAAAGAATAGACCGAGATAGGGTTGAGTGTTGTTCCAGTTTGGAACA
AGAGTCCACTATTAAAGAACGTGGACTCCAACGTCAAAGGGCGAAAAACCGTCTAT
CAGGGCGATGGCCCACTACGTGAACCATCACCCTAATCAAGTTTTTTGGGGTCGAGG
TGCCGTAAAGCACTAAATCGGAACCCTAAAGGGAGCCCCCGATTTAGAGCTTGACG
GGGAAAGCCGGCGAACGTGGCGAGAAAGGAAGGGAAGAAAGCGAAAGGAGCGGG
CGCTAGGGCGCTGGCAAGTGTAGCGGTCACGCTGCGCGTAACCACCACACCCGCCG
CGCTTAATGCGCCGCTACAGGGCGCGTCCCATTCGCCATTCAGGCTGCGCAACTGTT
GGGAAGGGCGATCGGTGCGGGCCTCTTCGCTATTACGCCAGCTGGCGAAAGGGGGA
TGTGCTGCAAGGCGATTAAGTTGGGTAACGCCAGGGTTTTCCCAGTCACGACGTTGT
AAAACGACGGCCAGTGAGCGCGCCTCGTTCATTCACGTTTTTGAACCCGTGGAGGAC
GGGCAGACTCGCGGTGCAAATGTGTTTTACAGCGTGATGGAGCAGATGAAGATGCT
CGACACGCTGCAGAACACGCAGCTAGATTAACCCTAGAAAGATAATCATATTGTGA
CGTACGTTAAAGATAATCATGCGTAAAATTGACGCATGTGTTTTATCGGTCTGTATA
TCGAGGTTTATTTATTAATTTGAATAGATATTAAGTTTTATTATATTTACACTTACAT
```

-continued

```
ACTAATAATAAATTCAACAAACAATTTATTTATGTTTATTTATTTATTAAAAAAAAA
CAAAAACTCAAAATTTCTTCTATAAAGTAACAAAACTTTTATCGAATTCCTGCAGCC
CGGGGGATCCACTAGTTCTAGAGGGACAGCCCCCCCCAAAGCCCCAGGGATGTA
ATTACGTCCCTCCCCCGCTAGGGGCAGCAGCGAGCCGCCCGGGGCTCCGCTCCGGT
CCGGCGCTCCCCCCGCATCCCCGAGCCGGCAGCGTGCGGGACAGCCCGGGCACGG
GGAAGGTGGCACGGGATCGCTTTCCTCTGAACGCTTCTCGCTGCTCTTTGAGCCTGC
AGACACCTGGGGGGATACGGGGAAAAGGCCTCCAAGGCCAGCTTCCCACAATAAGT
TGGGTGAATTTTGGCTCATTCCTCCTTTCTATAGGATTGAGGTCAGAGCTTTGTGATG
GGAATTCTGTGGAATGTGTGTCAGTTAGGGTGTGGAAAGTCCCgcGATCgcTAGcGTTT
AAACTTAAGCTTGGTACCGAGCTCGGATCCACTAGTCCAGTGTGGTGGAATTCCTGC
TTCGCGATGTACGGGCCggtacccaactccatgcttaacagtccccaggtacagcccaccctgcgtcgcaaccaggaaca
gctctacagcttcctggagcgccactcgccctacttccgcagccacagtgcgcagattaggagcgccacttcttttttgtcacttgaaaaacat
gtaaaaataatgtactaggagacactttcaataaaggcaaatgtttttatttgtacactctcgggtgattatttaccccccaccctgccgtctg
cgccgtttaaaaatcaaagggttctgccgcgcatcgctatgcgccactggcagggacacgttgcgatactggtgtttagtgctccacttaaact
caggcacaaccatccgcggcagctcggtgaagttttcactccacaggctgcgcaccatcaccaacgcgtttagcaggtcgggcgccgata
tcttgaagtcgcagttgggcctccgccctgcgcgcgcgagttgcgatacacaggggttgcagcactggaacactatcagcgccgggtggt
gcacgctggccagcacgctcttgtcggagatcagatccgcgtccaggtcctccgcgttgctcagggcgaacggagtcaactttggtagctg
ccttcccaaaaagggtgcatgcccaggctttgagttgcactcgcaccgtagtggcatcagaaggtgaccgtgcccggtctgggcgttagga
tacagcgcctgcatgaaagccttgatctgcttaaaagccacctgagcctttgcgccttcagagaagaacatgccgcaagacttgccggaaa
actgattggccggacaggccgcgtcatgcacgcagccacttgcgtcggtgttggagatctgcaccacatttcggccccaccggttcttcacg
atcttggccttgctagactgctccttcagcgcgcgctgcccgttttcgctcgtcacatccatttcaatcacgtgctccttatttatcataatgc
tcccgtgtagacacttaagctcgccttcgatctcagcgcagcggtgcagccacaacgcgcagcccgtgggctcgtggtgcttgtaggttacctct
gcaaacgactgcaggtacgcctgcaggaatcgccccatcatcgtcacaaaggtcttgttgctggtgaaggtcagctgcaacccgcggtgctc
ctcgtttagccaggtcttgcatacggccgccagagcttccacttggtcaggcagtagcttgaagtttgcctttagatcgttatccacgtggtact
tgtccatcaacgcgcgcgcagcctccatgcccttctcccacgcagacacgatcggcaggctcagcgggtttatcaccgtgctttcactttccg
cttcactggactcttccttttcctcttgcgtccgcatacccgcgccactgggtcgtcttcattcagccgccgcaccgtgcgcttacctcccttg
ccgtgcttgattagcaccggtgggttgctgaaacccaccatttgtagcgccacatcttctctttcttcctcgctgtccacgatcacctctgggga
tggcgggcgctcgggcttgggagaggggcgcttcttttctttttggacgcaatggccaaatccgccgtcgaggtcgatggccgcgggctgg
gtgtgcgcggcaccagcgcatcttgtgacgagtcttcttcgtcctcggactcgagacgccgcctcagccgcttttttgggggcgcgcggggg
aggcggcggcgacggcgacggggacgacacgtcctccatggttggtggacgtcgcgccgcaccgcgtccgcgctcggggtggtttc
gcgctgctcctcttcccgactggccatttccttctcctataggcagaaaaagatcatggagtcagtcgaaggaggacagcctaaccgccc
cctttgagttcgccaccaccgcctccaccgatgccgccaacgcgcctaccaccttccccgtcgaggcaccccgcttgaggaggaggaa
gtgattatcgagcaggacccaggttttgtaagcgaagacgacgaggatcgctcagtaccaacagaggataaaaagcaagaccaggacga
cgcagaggcaaacgaggaacaagtcgggcgggggggaccaaaggcatggcgactacctagatgtgggagacgacgtgctgttgaagca
tctgcagcgccagtgcgccattatctgcgacgcgttgcaagagcgcagcgatgtgcccctcgccatagcggatgtcagccttgcctacgaa
cgccacctgttctcaccgcgcgtaccccccaaacgccaagaaaacggcacatgcgagcccaacccgcgcctcaacttctaccccgtatttg
ccgtgccagaggtgcttgccacctatcacatcttttttccaaaactgcaagataccctatcctgccgtgccaaccgcagccgagcggacaag
cagctggccttgcggcagggcgctgtcatacctgatatcgcctcgctcgacgaagtgccaaaaatctttgagggtcttggacgcgacgaga
aacgcgcggcaaacgctctgcaacaagaaaacagcgaaaatgaaagtcactgtggagtgctggtggaacttgagggtgacaacgcgcg
cctagccgtgctgaaacgcagcatcgaggtcacccactttgcctaccggcacttaacctaccccccaaggttatgagcacagtcatgagc
```

-continued gagctgatcgtgcgccgtgcacgaccccctggagagggatgcaaacttgcaagaacaaaccgaggagggcctacccgcagttggcgatg
agcagctggcgcgctggcttgagacgcgcgagcctgccgacttggaggagcgacgcaagctaatgatggccgcagtgcttgttaccgtg
gagcttgagtgcatgcagcggttctttgctgacccggagatgcagcgcaagctagaggaaacgttgcactacacctttcgccagggctacg
tgcgccaggcctgcaaaatttccaacgtggagctctgcaacctggtctcctaccttggaattttgcacgaaaaccgcctcgggcaaaacgtg
cttcattccacgctcaagggcgaggcgcgccgcgactacgtccgcgactgcgtttacttatttctgtgctacacctggcaaacggccatggg
cgtgtggcagcaatgcctggaggagcgcaacctaaaggagctgcagaagctgctaaagcaaaacttgaaggacctatggacggccttca
acgagcgctccgtggccgcgcacctggggacattatcttccccgaacgcctgcttaaaaccctgcaacagggtctgccagacttcaccag
tcaaagcatgttgcaaaactttaggaactttatcctagagcgttcaggaattctgcccgccacctgctgtgcgcttcctagcgactttgtgccca
ttaagtaccgtgaatgccctccgccgctttggggtcactgctaccttctgcagctagccaactaccttgcctaccactccgacatcatggaaga
cgtgagcggtgacggcctactggagtgtcactgtcgctgcaacctatgcaccccgcaccgctccctggtctgcaattcgcaactgcttagcg
aaagtcaaattatcggtacctttgagctgcagggtccctcgcctgacgaaaagtccgcggctccggggttgaaactcactccggggctgtg
gacgtcCGATCTCTATCACTGATAGGGAGATCTCTATCACTGATAGGGAGAGggcttaccttcg
caaatttgtacctgaggactaccacgcccacgagattaggttctacgaagaccaatcccgcccgccaaatgcggagcttaccgcctgcgtc
attcccagggccacatccttggccaattgcaagccatcaacaaagcccgccaagagtttctgctacgaaagggacggggggtttacctgg
acccccagtccggcgaggagctcaacccaatcccccgccgccgcagccctatcagcagccgcgggcccttgcttccaggatggcac
ccaaaaagaagctgcagctgccgccgccgccacccacggacgaggaggaatactgggacagtcaggcagaggaggttttggacgagg
aggaggagatgatgaagactgggacagcctagacgaagcttccgaggccgaagaggtgtcagacgaaacaccgtcaccctcggtcgc
attcccctcgccggcgccccagaaattggcaaccgttcccagcatcgctacaacctccgctcctcaggcgccgccggcactgctgttcgc
cgacccaaccgtagatgggacaccactggaaccagggccggtaagtctaagcagccgccgccgttagcccaagagcaacaacagcgc
caaggctaccgctcgtggcgcgggcacaagaacgccatagttgcttgcttgcaagactgtggggcaacatctccttcgcccgccgctttct
tctctaccatcacggcgtggccttcccccgtaacatcctgcattactaccgtcatctctacagcccctactgcaccggcggcagcggcagcg
gcagcaacagcagcggtcacacagaagcaaaggcgaccggatagcaagactctgacaaagcccaagaaatccacagcggcggcagc
agcaggaggaggagcgctgcgtctggcgcccaacgaacccgtatcgacccgcgagcttagaaataggattttttcccactctgtatgctatat
ttcaacaaagcaggggccaagaacaagagctgaaaataaaaaacaggtctctgcgctccctcacccgcagctgcctgtatcacaaaagcg
aagatcagcttcggcgcacgctggaagacgcggaggctctcttcagcaaCGATCTCTATCACTGATAGGGAGATC
TCTATCACTGATAGGGAGAGatactgcgcgctgactcttaaggactagtttcgcgcccttttctcaaatttaagcgcgaaaa
ctacgtcatctccagcggccacacccggcgccagcacctgtcgtcagcgccattatgagcaaggaaattcccacgccctacatgtggagtt
accagccacaaatgggacttgcggctggagctgcccaagactactcaacccgaataaaactacatgagcgcgggacccacatgatatccc
gggtcaacggaatccgcgcccaccgaaaccgaattctcctcgaacaggcggctattaccaccacacctcgtaataaccttaatcccccgtagt
tggcccgctgccctggtgtaccaggaaagtcccgctcccaccactgtggtacttcccagagacgcccaggccgaagttcagatgactaact
caggggcgcagcttgcgggcggctttcgtcacagggtgcggtcgcccgggcgttttagggcggagtaacttgcatgtattgggaattgtag
tttttttaaaatgggaagtgacgtatcgtgggaaaacggaagtgaagatttgaggaagttgtgggttttttggctttcgtttctgggcgtaggtt
cgcgtgcggttttctgggtgttttttgtggactttaaccgttacgtcatttttagtcctatatatactcgctctgtaCTCTCCCTATCAGT
GATAGAGATCTCCCTATCAGTGATAGAGATCGcttggccctttttacactgtgactgattgagctggtgccgtgt
cgagtggtgtttttaataggttttttttactggtaaggctgactgttatggctgccgctgtggaagcgctgtatgttgttctggagcgggagggt
gctattttgcctaggcaggagggttttttcaggtgtttatgtgttttttctctcctattaatttgttataccctctatgggggctgtaatgttgtc
tctacgcctgcgggtatgtattcccccgggctatttcggtcgcttttagcactgaccgatgttaaccaacctgatgtgtttaccgagtcttaca
ttatgactccggacatgaccgaggaactgtcggtggtgcttttaatcacggtgaccagtttttttacggtcacgccggcatggccgtagtccgt
cttatgcttataagggttgttttttcctgttgtaagacaggcttctaatgtttaaatgttttttttttttgttattttattttgtgtttaatgcagg
aacccgcagacatgtttgagagaaaaatggtgtcttttttctgtggtggttccggaacttacctgcctttatctgcatgagcatgactacgatgtg
cttgcttttttgcgcgaggctttgcctgattttttgagcagcaccttgcattttatatcgccgcccatgcaacaagcttacatagggggctacgct -continued ggttagcatagctccgagtatgcgtgtcataatcagtgtgggttcttttgtcatggttcctggcggggaagtggccgcgctggtccgtgcagac ctgcacgattatgttcagctggccctgcgaagggacctacggatcgcggtattttgttaatgttccgcttttgaatcttatacaggtctgtg aggaacctgaattttgcaatcatgattcgctgcttgaggctgaaggtggagggcgctctggagcagattttacaatggccggacttaatattc gggatttgcttagagacatattgataaggtggcgagatgaaaattatttgggcatggttgaaggtgctggaatgtttatagaggagattcaccct gaagggtttagcctttacgtccacttggacgtgagggcagtttgccttttggaagccattgtgcaacatcttacaaatgccattatctgttcttt ggctgtagagtttgaccacgccaccggaggggagcgcgttcacttaatagatcttcattttgaggttttggataatcttttggaataaaaaaaaa aaaacatggttcttccagctcttcccgctcctcccgtgtgtgactcgcagaacgaatgtgtaggttggctgggtgtggcttattctgcggtggt ggatgttatcagggcagcggcgcatgaaggagtttacatagaacccgaagccaggggggcgcctggatgctttgagagagtggatatactacaact actacacagagcgagctaagcgacgagaccggagacgcagatctgtttgtcacgcccgcacctggttttgcttcaggaaatatgTACCCATACGA TGTTCCAGATTACGCTGGAGGAGGCGGAGGCactacgtccggcgttccatttggcatgacactacgaccaacacgatct cggttgtctcggcgcactccgtacagtagggatcgcctacctccttttgagacagagacccgcgctaccatactggaggatcatccgctgct gcccgaatgtaacactttgacaatgcacaacgtgagttacgtgcgaggtcttccctgcagtgtgggatttacgctgattcaggaatgggttgtt ccctgggatatggttctgacgcgggaggagcttgtaatcctgaggaagtgtatgcacgtgtgcctgtgttgtgccaacattgatatcatgacg agcatgatgatccatggttacgagtcctgggctctccactgtcattgttccagtcccggttcctgcagtgcatagccggcgggcaggttttgg ccagctggtttaggatggtggtggatggcgccatgtttaatcagaggtttatatggtaccgggaggtggtgaattacaacatgccaaaagag gtaatgtttatgtccagcgtgtttatgaggggtcgccacttaatctacctgcgcttgtggtatgatggcacgtgggttctgtggtccccgccat gagctttggatacagcgccttgcactgtgggattttgaacaatattgtggtgctgtgctgcagttactgtgctgatttaagtgagatcagggtgc gctgctgtgcccggaggacaaggcgtctcatgctgcgggcggtgcgaatcatcgctgaggagaccactgccatgttgtattcctgcaggac ggagcggcggcggcagcagtttattcgcgcgctgctgcagcaccaccgcccatcctgatgcacgattatgactctaccccatgtaggcg tggacttcccccttcgccgcccgttgagcaaccgcaagttggacagcagcctgtggctcagcagctggacagcgacatgaacttaagcgag ctgcccggggagtttattaatatcactgatgagcgtttggctcgacaggaaaccgtgtggaatataacacctaagaatatgtctgttacccatg atatgatgctttttaaggccagccggggagaaaggactgtgtactctgtgtgttgggagggaggtggcaggttgaatactagggttctgtgag tttgattaaggtacggtgatcaatataagctatgtggtggtggggctatactactgaatgaaaaatgacttgaaattttctgcaattgaaaaata aacacgttgaaacataacatgcaacaggttcacgattctttattcctgggcaatgtaggagaaggtgtaagagttggtagcaaaagtttcagtgg tgtattttccactttcccaggaccatgtaaaagacatagagtaagtgcttacctcgctagtttctgtggattcactagaaccagtggccaaaaa gctagcgcagcagccgccgcgcctggaaggaagccaaaaggagcgctccccgttgtctgacgtcgcacacctgggttcgacacgcgg gcggtaaccgcatggatcacggcggacggccggatccgggggttcgaaccccggtcgtccgccatgataccttgcgaattttatccaccag accacggaagagtgcccgcttacaggctctccttttgcacggtctagagcgtcaacgactgcgcacgccagtggccaaaaaagctagcgc agcagccgccgcgcctggaaggaagccaaaaggagcgctccccgttgtctgacgtcgcacacctgggttcgacacgcgggcggtaac cgcatggatcacggcggacggccggatccgggggttcgaaccccggtcgtccgccatgataccttgcgaatttatccaccagaccacgga agagtgcccgcttacaggctctccttttgcacggtctagagcgtcaacgactgcgcacgccagtggccaaaaaagctagcgcagcagccg ccgcgcctggaaggaagccaaaaggagcgctccccgttgtctgacgtcgcacacctgggttcgacacgcgggggtaaccgcatggat cacggcggacggccggatccgggggttcgaaccccggtcgtccgccatgataccttgcgaatttatccaccagaccacggaagagtgcc cgcttacaggctctccttttgcacggtctagagcgtcaacgactgcgcacgccagtggccaaaaaagctagcgcagcagccgccgcgcct ggaaggaagccaaaaggagcgctccccgttgtctgacgtcgcacacctgggttcgacacgcgggcggtaaccgcatggatcacggcg gacggccggatccgggggttcgaaccccggtcgtccgccatgataccttgcgaatttatccaccagaccacggaagagtgcccgcttaca ggctctccttttgcacggtctagagcgtcaacgactgcgcacgtccactttggccgcggctcgagTGAGCTATTCCAGAAGT

AGTGAAGAGGCTTTTTTGGAGGCCTAGGCTTTTGCAAAAAGCTCCGGATCGATGCCC

GGGGGATCCACTAGTTCTAGAGGGACAGCCCCCCCCCAAAGCCCCCAGGGATGTAA

TTACGTCCCTCCCCCGCTAGGGGGCAGCAGCGAGCCGCCCGGGGCTCCGCTCCGGTC

-continued

```
CGGCGCTCCCCCCGCATCCCCGAGCCGGCAGCGTGCGGGACAGCCCGGGCACGGG

GAAGGTGGCACGGGATCGCTTTCCTCTGAACGCTTCTCGCTGCTCTTTGAGCCTGCA

GACACCTGGGGGATACGGGGAAAAGGCCTCCAAGGCCAGCTTCCCACAATAAGTT

GGGTGAATTTTGGCTGAGCTATTCCAGAAGTAGTGAAGAGGCTTTTTTGGAGGCCTA

GGCTTTTGCAAAAAGCTCCGGATCGATCATATATGGCAGATATACGCGTTGACATTG

ATTATTGACTAGTTATTAATAGTAATCAATTACGGGGTCATTAGTTCATAGCCCATAT

ATGGAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAGGG

ACTTTCCATTGACGTCAATGGGTGGAGTATTTACGGTAAACTGCCCACTTGGCAGTA

CATCAAGTGTATCATATGCCAAGTACGCCCCCTATTGACGTCAATGACGGTAAATGG

CCCGCCTGGCATTATGCCCAGTACATGACCTTATGGGACTTTCCTACTTGGCAGTAC

ATCTACGTATTAGTCATCGCTATTACCATGGTGATGCGGTTTTGGCAGTACATCAAT

GGGCGTGGATAGCGGTTTGACTCACGGGGATTTCCAAGTCTCCACCCCATTGACGTC

AATGGGAGTTTGTTTTGGCACCAAAATCAACGGGACTTTCCAAAATGTCGTAACAAC

TCCGCCCCATTGACGCAAATGGGCGGTAGGCGTGTACGGTGGGAGGTCTATATAAG

CAGAGCTCTCTGGCTAACTATCGTCGACGAGCTCGTTTAGTGAACCGTCAGATCGCC

TGGAGACGCCATCCACGCTGTTTTGACCTCCATAGAAGACACCGGGACCGATCCAG

CCTCCGGACTCTAGCGTTTAAACTTAAGCTTGCCACCatgaccgagtacaagcccacggtgcgcctcgc cacccgcgacgacgtccccagggccgtacgcaccctcgccgccgcgttcgccgactaccccgccacgcgccacaccgtcgatccggac cgccacatcgagcgggtcaccgagctgcaagaactcttcctcacgcgcgtcgggctcgacatcggcaaggtgtgggtcgcggacgacg gcgccgcggtggcggtctggaccacgccggagagcgtcgaagcggggcggtgttcgccgagatcggcccgcgcatggccgagttga gcggttcccggctggccgcgcagcaacagatggaaggcctcctggcgccgcaccggcccaaggagcccgcgtggttcctggccaccgt cggcgtctcgcccgaccaccagggcaagggtctgggcagcgccgtcgtgctccccggagtggaggcggccgagcgcgccggggtgc ccgccttcctggagacctccgcgccccgcaacctccccttctacgagcggctcggcttcaccgtcaccgccgacgtcgaggtgcccgaag gaccgcgcacctggtgcatgacccgcaagcccggtgcctgaAGCGCGGGGATCTCATGCTGGAGTTCTTCG

CCCACCCCAACTTGTTTATTGCAGCTTATAATGGTTACAAATAAAGCAATAGCATCA

CAAATTTCACAAATAAAGCATTTTTTTCACTGCATTCTAGTTGTGGTTTGTCCAAACT

CATCAATGTATCTTATCATGTCTGTAGCtGATgtATAcCTAggATCCGGCCGGccTGCAgg

TGTCCTCACAGGAACGAAGTCCCTAAAGAAACAGTGGCAGCCAGGTTTAGCCCCGG

AATTGACTGGATTCCTTTTTTAGGGCCCATTGGTATGGCTTTTTCCCCGTATCCCCCC

AGGTGTCTGCAGGCTCAAAGAGCAGCGAGAAGCGTTCAGAGGAAAGCGATCCCGTG

CCACCTTCCCCGTGCCCGGGCTGTCCCCGCACGCTGCCGGCTCGGGGATGCGGGGGG

AGCGCCGGACCGGAGCGGAGCCCCGGGCGGCTCGCTGCTGCCCCCTAGCGGGGGAG

GGACGTAATTACATCCCTGGGGGCTTTGGGGGGGGCTGTCCCTCTAGAGCGGCCGC

CACCGCGGTGGAGCTCCAGCTTTTGTTCCCTTTAGTGAGGGTTAATTAGATCTTAATA

CGACTCACTATAGGGCGAATTGGGTACCGGGCCCCCCCTCGAGGTCGACGGTATCG

ATAAGCTTGATATCTATAACAAGAAAATATATATATAATAAGTTATCACGTAAGTAG

AACATGAAATAACAATATAATTATCGTATGAGTTAAATCTTAAAAGTCACGTAAAA

GATAATCATGCGTCATTTTGACTCACGCGGTCGTTATAGTTCAAAATCAGTGACACT

TACCGCATTGACAAGCACGCCTCACGGGAGCTCCAAGCGGCGACTGAGATGTCCTA

AATGCACAGCGACGGATTCGCGCTATTTAGAAAGAGAGAGCAATATTTCAAGAATG
```

-continued

```
CATGCGTCAATTTTACGCAGACTATCTTTCTAGGGTTAATCTAGCTGCATCAGGATC
ATATCGTCGGGTCTTTTTTCCGGCTCAGTCATCGCCCAAGCTGGCGCTATCTGGGCAT
CGGGGAGGAAGAAGCCCGTGCCTTTTCCCGCGAGGTTGAAGCGGCATGGAAAGAGT
TTGCCGAGGATGACTGCTGCTGCATTGACGTTGAGCGAAAACGCACGTTTACCATGA
TGATTCGGGAAGGTGTGGCCATGCACGCCTTTAACGGTGAACTGTTCGTTCAGGCCA
CCTGGGATACCAGTTCGTCGCGGCTTTTCCGGACACAGTTCCGGATGGTCAGCCCGA
AGCGCATCAGCAACCCGAACAATACCGGCGACAGCCGGAACTGCCGTGCCGGTGTG
CAGATTAATGACAGCGGTGCGGCGCTGGGATATTACGTCAGCGAGGACGGGTATCC
TGGCTGGATGCCGCAGAAATGGACATGGATACCCCGTGAGTTACCCGGCGGGCGCG
CTTGGCGTAATCATGGTCATAGCTGTTTCCTGTGTGAAATTGTTATCCGCTCACAATT
CCACACAACATACGAGCCGGAAGCATAAAGTGTAAAGCCTGGGGTGCCTAATGAGT
GAGCTAACTCACATTAATTGCGTTGCGCTCACTGCCCGCTTTCCAGTCGGGAAACCT
GTCGTGCCAGCTGCATTAATGAATCGGCCAACGCGCGGGGAGAGGCGGTTTGCGTA
TTGGGCGCTCTTCCGCTTCCTCGCTCACTGACTCGCTGCGCTCGGTCGTTCGGCTGCG
GCGAGCGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACCGTAA
AAAGGCCGCGTTGCTGGCGTTTTTCCATAGGCTCCGCCCCCCTGACGAGCATCACAA
AAATCGACGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCCGCTTACCGG
ATACCTGTCCGCCTTTCTCCCTTCGGGAAGCGTGGCGCTTTCTCATAGCTCACGCTGT
AGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCG
GTAAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTACAC
TAGAAGGACAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGTTTTTTTGT
TTGCAAGCAGCAGATTACGCGCAGAAAAAAAGGATCTCAAGAAGATCCTTTGATCT
TTTCTACGGGGTCTGACGCTCAGTGGAACGAAAACTCACGTTAAGGGATTTTGGTCA
TGAGATTATCAAAAAGGATCTTCACCTAGATCCTTTTAAATTAAAAATGAAGTTTTA
AATCAATCTAAAGTATATATGAGTAAACTTGGTCTGACAGTTACCAATGCTTAATCA
GTGAGGCACCTATCTCAGCGATCTGTCTATTTCGTTCATCCATAGTTGCCTGACTCCC
CGTCGTGTAGATAACTACGATACGGGAGGGCTTACCATCTGGCCCCAGTGCTGCAAT
GATACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGTCTA
TTAATTGTTGCCGGGAAGCTAGAGTAAGTAGTTCGCCAGTTAATAGTTTGCGCAACG
TTGTTGCCATTGCTACAGGCATCGTGGTGTCACGCTCGTCGTTTGGTATGGCTTCATT
CAGCTCCGGTTCCCAACGATCAAGGCGAGTTACATGATCCCCCATGTTGTGCAAAAA
AGCGGTTAGCTCCTTCGGTCCTCCGATCGTTGTCAGAAGTAAGTTGGCCGCAGTGTT
ATCACTCATGGTTATGGCAGCACTGCATAATTCTCTTACTGTCATGCCATCCGTAAG
ATGCTTTTCTGTGACTGGTGAGTACTCAACCAAGTCATTCTGAGAATAGTGTATGCG
```

-continued

GCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGA

TCTTACCGCTGTTGAGATCCAGTTCGATGTAACCCACTCGTGCACCCAACTGATCTTC

AGCATCTTTTACTTTCACCAGCGTTTCTGGGTGAGCAAAAACAGGAAGGCAAAATGC

CGCAAAAAAGGGAATAAGGGCGACACGGAAATGTTGAATACTCAT

The sequence of the pPBBG-iHelper2.6-HA vector is provided below:

pPBBG-iHelper2.6-HA (16,658 bp)  (SEQ ID NO: 9)

ACTCTTCCTTTTTCAATATTATTGAAGCATTTATCAGGGTTATTGTCTCATGA

GCGGATACATATTTGAATGTATTTAGAAAAATAAACAAATAGGGGTTCCGCGCACA

TTTCCCCGAAAAGTGCCACCTAAATTGTAAGCGTTAATATTTTGTTAAAATTCGCGTT

AAATTTTTGTTAAATCAGCTCATTTTTTAACCAATAGGCCGAAATCGGCAAAATCCC

TTATAAATCAAAAGAATAGACCGAGATAGGGTTGAGTGTTGTTCCAGTTTGGAACA

AGAGTCCACTATTAAAGAACGTGGACTCCAACGTCAAAGGGCGAAAAACCGTCTAT

CAGGGCGATGGCCCACTACGTGAACCATCACCCTAATCAAGTTTTTTGGGGTCGAGG

TGCCGTAAAGCACTAAATCGGAACCCTAAAGGGAGCCCCCGATTTAGAGCTTGACG

GGGAAAGCCGGCGAACGTGGCGAGAAAGGAAGGGAAGAAAGCGAAAGGAGCGGG

CGCTAGGGCGCTGGCAAGTGTAGCGGTCACGCTGCGCGTAACCACCACACCCGCCG

CGCTTAATGCGCCGCTACAGGGCGCGTCCCATTCGCCATTCAGGCTGCGCAACTGTT

GGGAAGGGCGATCGGTGCGGGCCTCTTCGCTATTACGCCAGCTGGCGAAAGGGGGA

TGTGCTGCAAGGCGATTAAGTTGGGTAACGCCAGGGTTTTCCCAGTCACGACGTTGT

AAAACGACGGCCAGTGAGCGCGCCTCGTTCATTCACGTTTTTGAACCCGTGGAGGAC

GGGCAGACTCGCGGTGCAAATGTGTTTTACAGCGTGATGGAGCAGATGAAGATGCT

CGACACGCTGCAGAACACGCAGCTAGATTAACCCTAGAAAGATAATCATATTGTGA

CGTACGTTAAAGATAATCATGCGTAAAATTGACGCATGTGTTTTATCGGTCTGTATA

TCGAGGTTTATTTATTAATTTGAATAGATATTAAGTTTTATTATATTTACACTTACAT

ACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCggtacccaactccatgcttaacagtccccaggtacagcccaccctgcgtcgcaaccaggaaca gctctacagcttcctggagcgccactcgccctacttccgcagccacagtgcgcagattaggagcgccacttcttttgtcacttgaaaaacat gtaaaataatgtactaggagacactttcaataaaggcaaatgttttttatttgtacactctcgggtgattatttaccccccacccttgccgtctg cgccgtttaaaaatcaaagggggttctgccgcgcatcgctatgcgccactggcagggacacgttgcgatactggtgtttagtgctccacttaaact -continued

```
caggcacaaccatccgcggcagctcggtgaagttttcactccacaggctgcgcaccatcaccaacgcgtttagcaggtcgggcgccgata tcttgaagtcgcagttggggcctccgccctgcgcgcgcgagttgcgatacacaggggttgcagcactggaacactatcagcgccgggtggt gcacgctggccagcacgctcttgtcggagatcagatccgcgtccaggtcctccgcgttgctcagggcgaacggagtcaactttggtagctg ccttcccaaaaagggtgcatgcccaggctttgagttgcactcgcaccgtagtggcatcagaaggtgaccgtgcccggtctgggcgttagga tacagcgcctgcatgaaagccttgatctgcttaaaagccacctgagcctttgcgccttcagagaagaacatgccgcaagacttgccggaaa actgattggccggacaggccgcgtcatgcacgcagccacccttgcgtcggtgttggagatctgcaccacatttcggccccaccggttcttcacg atcttggccttgctagactgctccttcagcgcgcgctgcccgttttcgctcgtcacatccatttcaatcacgtgctccttatttatcataatgct cccgtgtagacacttaagctcgccttcgatctcagcgcagcggtgcagccacaacgcgcagcccgtgggctcgtggtgcttgtaggttacctctg caaacgactgcaggtacgcctgcaggaatcgcccatcatcgtcacaaggtcttgttgctggtgaaggtcagctgcaacccgcggtgctc ctcgtttagccaggtcttgcatacggccgccagagcttccacttggtcaggcagtagcttgaagtttgcctttagatcgttatccacgtggtact tgtccatcaacgcgcgcgcagcctccatgcccttctcccacgcagacacgatcggcaggctcagcgggtttatcaccgtgctttcactttccg cttcactggactcttcctttttcctcttgcgtccgcataccccgcgccactgggtcgtcttcattcagccgccgcaccgtgcgcttacctcccttg ccgtgcttgattagcaccggtgggttgctgaaacccaccatttgtagcgccacatcttctctttcttcctcgctgtccacgatcacctctgggga tggcgggcgctcgggcttgggagaggggcgcttcttttttcttttttggacgcaatggccaaatccgccgtcgaggtcgatggccgcgggctgg gtgtgcgcggcaccagcgcatcttgtgacgagtcttcttcgtcctcggactcgagacgccgcctcagccgcttttttgggggcgcgcgggg aggcggcggcgacggcgacggggacgacacgtcctccatggttggtggacgtcgcgccgcaccgcgtccgcgctcggggtggtttc gcgctgctcctcttcccgactggccatttccttctcctataggcagaaaaagatcatggagtcagtcgagaaggaggacagcctaaccgccc cctttgagttcgccaccaccgcctccaccgatgccgccaacgcgcctaccaccttccccgtcgaggcaccccgcttgaggaggaggaa gtgattatcgagcaggacccaggttttgtaagcgaagacgacgaggatcgctcagtaccaacagaggataaaaagcaagaccaggacga cgcagaggcaaacgaggaacaagtcgggcgggggggaccaaaggcatggcgactacctagatgtgggagacgacgtgctgttgaagca tctgcagcgccagtgcgccattatctgcgacgcgttgcaagagcgcagcgatgtgcccctcgccatagcggatgtcagccttgcctacgaa cgccacctgttctcaccgcgcgtaccccccaaacgccaagaaaacggcacatgcgagcccaacccgcgcctcaacttctaccccgtatttg ccgtgccagaggtgcttgccacctatcacatcttttttccaaaactgcaagatacccctatcctgccgtgccaaccgcagccgagcggacaag cagctggccttgcggcagggcgctgtcatacctgatatcgcctcgctcgacgaagtgccaaaaatctttgagggtcttggacgcgacgaga aacgcgcggcaaacgctctgcaacaagaaaacagcgaaaatgaaagtcactgtggagtgctggtggaacttgagggtgacaacgcgcg cctagccgtgctgaaacgcagcatcgaggtcacccactttgcctacccggcacttaacctaccccccaaggttatgagcacagtcatgagc gagctgatcgtgcgccgtgcacgaccccctggagagggatgcaaacttgcaagaacaaaccgaggagggcctaccccgcagttggcgatg agcagctggcgcgctggcttgagacgcgcgagcctgccgacttggaggagcgacgcaagctaatgatggccgcagtgcttgttaccgtg gagcttgagtgcatgcagcggttctttgctgacccggagatgcagcgcaagctagaggaaacgttgcactacaccttcgccagggctacg tgcgccaggcctgcaaaatttccaacgtggagctctgcaacctggtctcctaccttggaattttgcacgaaaaccgcctcgggcaaaacgtg cttcattccacgctcaagggcgaggcgcgccgcgactacgtccgcgactgcgtttacttattctgtgctacacctggcaaacggccatggg cgtgtggcagcaatgcctggaggagcgcaacctaaaggagctgcagaagctgctaaagcaaaacttgaaggacctatggacggccttca acgagcgctccgtggccgcgcacctggcggacattatcttccccgaacgcctgcttaaaccctgcaacagggtctgccagacttcaccag tcaaagcatgttgcaaaactttaggaactttatcctagagcgttcaggaattctgcccgccacctgctgtgcgcttcctagcgactttgtgccca ttaagtaccgtgaatgccctccgccgctttgggtcactgctaccttctgcagctagccaactaccttgcctaccactccgacatcatggaaga cgtgagcggtgacggcctactggagtgtcactgtcgctgcaacctatgcaccccgcaccgctccctggtctgcaattcgcaactgcttagcg aaagtcaaattatcggtacctttgagctgcagggtccctcgcctgacgaaaagtccgcggctccggggttgaaactcactccggggctgtg gacgtcCGATCTCTATCACTGATAGGGAGATCTCTATCACTGATAGGGAGAGggcttaccttcg caaatttgtacctgaggactaccacgcccacgagattaggttctacgaagaccaatcccgcccgccaaatgcggagcttaccgcctgcgtc attacccagggccacatccttggccaattgcaagccatcaacaaagcccgccaagagtttctgctacgaaagggacggggggtttacctgg
```

-continued accccccagtccggcgaggagctcaacccaatccccccgccgccgcagccctatcagcagccgcgggcccttgcttcccaggatggcac ccaaaaagaagctgcagctgccgccgccgccaccccacggacgaggaggaatactgggacagtcaggcagaggaggttttggacgagg aggaggagatgatggaagactgggacagcctagacgaagcttccgaggccgaagaggtgtcagacgaaacaccgtcaccctcggtcgc attcccctcgccggcgccccagaaattggcaaccgttcccagcatcgctacaacctccgctcctcaggcgccgccggcactgcctgttcgc cgacccaaccgtagatgggacaccactggaaccagggccggtaagtctaagcagccgccgccgttagcccaagagcaacaacagcgc caaggctaccgctcgtggcgcgggcacaagaacgccatagttgcttgcttgcaagactgtggggcaacatctccttcgcccgccgctttct tctctaccatcacggcgtggccttcccccgtaacatcctgcattactaccgtcatctctacagccctactgcaccggcggcagcggcagcg gcagcaacagcagcggtcacacagaagcaaaggcgaccggatagcaagactctgacaaagcccaagaaatccacagcggcggcagc agcaggaggaggagcgctgcgtctggcgcccaacgaacccgtatcgacccgcgagcttagaaataggattttttcccactctgtatgctatat ttcaacaaagcaggggccaagaacaagagctgaaaataaaaaacaggtctctgcgctccctcacccgcagctgcctgtatcacaaaagcg aagatcagcttcggcgcacgctggaagacgcggaggctctcttcagcaaCGATCTCTATCACTGATAGGGAGATC TCTATCACTGATAGGGAGAGatactgcgcgctgactcttaaggactagtttcgcgcccttctcaaatttaagcgcgaaaa ctacgtcatctccagcggccacacccggcgccagcacctgtcgtcagcgccattatgagcaaggaaattcccacgccctacatgtggagtt accagccacaaatgggacttgcggctggagctgcccaagactactcaacccgaataaactacatgagcgcgggaccccacatgatatccc gggtcaacggaatccgcgccaccgaaaccgaattctcctcgaacaggcggctattaccaccacacctcgtaataaccttaatccccgtagt tggcccgctgccctggtgtaccaggaaagtcccgctcccaccactgtggtacttcccagagacgcccaggccgaagttcagatgactaact caggggcgcagcttgcgggcggctttcgtcacagggtgcggtcgcccccagtggccaaaaaagctagcgcagcagccgccgcgcctg gaaggaagccaaaaggagcgctcccccgttgtctgacgtcgcacacctgggttcgacacgcgggcggtaaccgcatggatcacggcgg acggccggatccggggttcgaaccccggtcgtccgccatgataccctttgcgaatttatccaccagaccacggaagagtgcccgcttacag gctctccttttgcacggtctagagcgtcaacgactgcgcacgccagtggccaaaaaagctagcgcagcagccgccgcgcctggaaggaa gccaaaaggagcgctcccccgttgtctgacgtcgcacacctgggttcgacacgcgggcggtaaccgcatggatcacggcggacggccg gatccggggttcgaaccccggtcgtccgccatgataccctttgcgaatttatccaccagaccacggaagagtgcccgcttacaggctctcctt ttgcacggtctagagcgtcaacgactgcgcacgccagtggccaaaaaagctagcgcagcagccgccgcgcctggaaggaagccaaaa ggagcgctcccccgttgtctgacgtcgcacacctgggttcgacacgcgggcggtaaccgcatggatcacggcggacggccggatccgg ggttcgaaccccggtcgtccgccatgataccctttgcgaatttatccaccagaccacggaagagtgcccgcttacaggctctccttttgcacg gtctagagcgtcaacgactgcgcacgccagtggccaaaaaagctagcgcagcagccgccgcgcctggaaggaagccaaaaggagcg ctcccccgttgtctgacgtcgcacacctgggttcgacacgcgggcggtaaccgcatggatcacggcggacggccggatccggggttcga accccggtcgtccgccatgataccctttgcgaatttatccaccagaccacggaagagtgcccgcttacaggctctccttttgcacggtctagag cgtcaacgactgcgcacggggcgttttagggcggagtaacttgcatgtattgggaattgtagttttttttaaaatgggaagtgacgtatcgtggg aaaacggaagtgaagatttgaggaagttgtgggttttttggctttcgtttctgggcgtaggttcgcgtgcggttttctgggtgttttttgtggac tttaaccgttacgtcatttttttagtcctatatatactcgctctgtaCTCTCCCTATCAGTGATAGAGATCTCCCTATCA GTGATAGAGATCGcttggcccttttttacactgtgactgattgagctggtgccgtgtcgagtggtgttttttaataggttttttttactggt aaggctgactgttatggctgccgctgtggaagcgctgtatgttgttctggagcgggagggtgctattttgcctaggcaggagggttttttcaggt gtttatgtgtttttctctcctattaattttgttatacctcctatgggggctgtaatgttgtctctacgcctgcgggtatgtattcccccgggcta tttcggtcgcttttttagcactgaccgatgttaaccaacctgatgtgtttaccgagtcttacattatgactccggacatgaccgaggaactgtcg gtggtgcttttttaatcacggtgaccagttttttttacggtcacgccggcatggccgtagtccgtcttatgcttataagggttgttttttcctgttg taagacaggcttctaatgtttaaatgtttttttttttttgttatttttattttgtgtttaatgcaggaacccgcagacatgtttgagagaaaaatgg tgtcttttctgtggtggttccggaacttacctgcctttatctgcatgagcatgactacgatgtgcttgcttttttgcgcgaggctttgcctga ttttttgagcagcaccttgcatttatatcgccgcccatgcaacaagcttacatagggcgtacgctggttagcatagctccgagtatgcgtgtca taatcagtgtgggtctttttgtcatggttcctggcggggaagtggccgcgctggtccgtgcagacctgcacgattatgttcagctggccctgcg aagggacctacgggatcgcggtatttttgttaatgttccgcttttgaatcttatacaggtctgtgaggaacctgaattttttgcaatcatgattcg ctgcttgaggctgaaggtggagggcgctctggagcagattttttacaatggccggacttaatattcgggatttgcttagagacatattgataaggt ggcgagatgaaaattatttgggcatggttgaaggtgctggaatgtttatagaggagattcaccctgaagggtttagcctttacgtccacttggac gtgagggcagtttgccttttggaagccattgtgcaacatcttacaaatgccattatctgttctttggctgtagagtttgaccacgccaccggagg ggagcgcgttcacttaatagatcttcattttgaggttttggataatcttttggaataaaaaaaaaaaaacatggttcttccagctcttcccgctc ctcccgtgtgtgactcgcagaacgaatgtgtaggttggctgggtgtggcttattctgcggtggtggatgttatcagggcagcggcgcatgaagg agtttacatagaacccgaagccagggggcgcctggatgctttgagagagtggatatactacaactactacacagagcgagctaagcgacgagacc ggagacgcagatctgtttgtcacgcccgcacctggttttgcttcaggaaatatgTACCCATACGATGTTCCAGATTACGCTGGAGGAGG CGGAGGCactacgtccggcgttccatttggcatgacactacgaccaacacgatctcggttgtctcggcgcactccgtacagtagggat cgcctacctccttttgagacagagacccgcgctaccatactggaggatcatccgctgctgcccgaatgtaacactttgacaatgcacaacgt gagttacgtgcgaggtcttccctgcagtgtgggatttacgctgattcaggaatgggttgttccctgggatatggttctgacgcgggaggagctt gtaatcctgaggaagtgtatgcacgtgtgcctgtgttgtgccaacattgatatcatgacgagcatgatgatccatggttacgagtcctgggctc tccactgtcattgttccagtcccggttccctgcagtgcatagccggcgggcaggttttggccagctggtttaggatggtggtggatggcgcca tgtttaatcagaggtttatatggtaccggaggtggtgaattacaacatgccaaaagaggtaatgtttatgtccagcgtgtttatgagggtcgc cacttaatctacctgcgcttgtggtatgatggccacgtgggtctgtggtccccgccatgagctttggatacagcgccttgcactgtgggattttt gaacaatattgtggtgctgtgctgcagttactgtgctgatttaagtgagatcagggtgcgctgctgtgcccggaggacaaggcgtctcatgct gcgggcggtgcgaatcatcgctgaggagaccactgccatgttgtattcctgcaggacggagcggcggcggcagcagtttattcgcgcgct gctgcagcaccaccgccctatcctgatgcacgattatgactctaccccatgtaggcgtggacttcccctttcgccgcccgttgagcaaccgc aagttggacagcagcctgtggctcagcagctggacagcgacatgaacttaagcgagctgcccggggagtttattaatatcactgatgagcg tttggctcgacaggaaaccgtgtggaatataacacctaagaatatgtctgttacccatgatatgatgcttttttaaggccagccggggagaaag gactgtgtactctgtgtgttgggagggaggtggcaggttgaatactagggttctgtgagtttgattaaggtacggtgatcaatataagctatgtg gtggtggggctatactactgaatgaaaaatgacttgaaattttctgcaattgaaaaataaacacgttgaaacataacatgcaacaggttcacga ttctttattcctgggcaatgtaggagaaggtgtaagagttggtagcaaaagtttcagtggtgtattttccactttcccaggaccatgtaaaagac atagagtaagtgcttacctcgctagtttctgtggattcactagaatccactttggccgcggctcgagTGAGCTATTCCAGAAGT

AGTGAAGAGGCTTTTTTGGAGGCCTAGGCTTTTGCAAAAAGCTCCGGATCGATGCCC

GGGGGATCCACTAGTTCTAGAGGGACAGCCCCCCCCCAAAGCCCCCAGGGATGTAA

TTACGTCCCTCCCCCGCTAGGGGGCAGCAGCGAGCCGCCCGGGGCTCCGCTCCGGTC

CGGCGCTCCCCCCGCATCCCCGAGCCGGCAGCGTGCGGGACAGCCCGGGCACGGG

GAAGGTGGCACGGGATCGCTTTCCTCTGAACGCTTCTCGCTGCTCTTTGAGCCTGCA

GACACCTGGGGGATACGGGGAAAAGGCCTCCAAGGCCAGCTTCCCACAATAAGTT

GGGTGAATTTTGGCTGAGCTATTCCAGAAGTAGTGAAGAGGCTTTTTTGGAGGCCTA

GGCTTTTGCAAAAAGCTCCGGATCGATCATATATGGCAGATATACGCGTTGACATTG

ATTATTGACTAGTTATTAATAGTAATCAATTACGGGGTCATTAGTTCATAGCCCATAT

ATGGAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAGGG

ACTTTCCATTGACGTCAATGGGTGGAGTATTTACGGTAAACTGCCCACTTGGCAGTA

CATCAAGTGTATCATATGCCAAGTACGCCCCCTATTGACGTCAATGACGGTAAATGG

CCCGCCTGGCATTATGCCCAGTACATGACCTTATGGGACTTTCCTACTTGGCAGTAC

ATCTACGTATTAGTCATCGCTATTACCATGGTGATGCGGTTTTGGCAGTACATCAAT

GGGCGTGGATAGCGGTTTGACTCACGGGGATTTCCAAGTCTCCACCCCATTGACGTC

AATGGGAGTTTGTTTTGGCACCAAAATCAACGGGACTTTCCAAAATGTCGTAACAAC

```
TCCGCCCCATTGACGCAAATGGGCGGTAGGCGTGTACGGTGGGAGGTCTATATAAG

CAGAGCTCTCTGGCTAACTATCGTCGACGAGCTCGTTTAGTGAACCGTCAGATCGCC

TGGAGACGCCATCCACGCTGTTTTGACCTCCATAGAAGACACCGGGACCGATCCAG

CCTCCGGACTCTAGCGTTTAAACTTAAGCTTGCCACCatgaccgagtacaagcccacggtgcgcctcgc cacccgcgacgacgtccccagggccgtacgcaccctcgccgccgcgttcgccgactaccccgccacgcgccacaccgtcgatccggac cgccacatcgagcgggtcaccgagctgcaagaactcttcctcacgcgcgtcgggctcgacatcggcaaggtgtgggtcgcggacgacg gcgccgcggtggcggtctggaccacgccggagagcgtcgaagcggggcggtgttcgccgagatcggcccgcgcatggccgagttga gcggttcccggctggccgcgcagcaacagatggaaggcctcctggccgccaccggcccaaggagcccgcgtggttcctggccaccgt cggcgtctcgcccgaccaccagggcaagggtctgggcagcgccgtcgtgctccccggagtggaggcggccgagcgcgccggggtgc ccgccttcctggagacctccgcgccccgcaacctccccttctacgagcggctcggcttcaccgtcaccgccgacgtcgaggtgcccgaag gaccgcgcacctggtgcatgacccgcaagcccggtgcctgaAGCGCGGGGATCTCATGCTGGAGTTCTTCG

CCCACCCCAACTTGTTTATTGCAGCTTATAATGGTTACAAATAAAGCAATAGCATCA

CAAATTTCACAAATAAAGCATTTTTTTCACTGCATTCTAGTTGTGGTTTGTCCAAACT

CATCAATGTATCTTATCATGTCTGTAGCtGATgtATAcCTAggATCCGGCCGGccTGCAgg

TGTCCTCACAGGAACGAAGTCCCTAAAGAAACAGTGGCAGCCAGGTTTAGCCCCGG

AATTGACTGGATTCCTTTTTTAGGGCCCATTGGTATGGCTTTTTCCCCGTATCCCCCC

AGGTGTCTGCAGGCTCAAAGAGCAGCGAGAAGCGTTCAGAGGAAAGCGATCCCGTG

CCACCTTCCCCGTGCCCGGGCTGTCCCCGCACGCTGCCGGCTCGGGGATGCGGGGGG

AGCGCCGGACCGGAGCGGAGCCCCGGGCGGCTCGCTGCTGCCCCCTAGCGGGGGAG

GGACGTAATTACATCCCTGGGGGCTTTGGGGGGGGGCTGTCCCTCTAGAGCGGCCGC

CACCGCGGTGGAGCTCCAGCTTTTGTTCCCTTTAGTGAGGGTTAATTAGATCTTAATA

CGACTCACTATAGGGCGAATTGGGTACCGGGCCCCCCCTCGAGGTCGACGGTATCG

ATAAGCTTGATATCTATAACAAGAAAATATATATATAATAAGTTATCACGTAAGTAG

AACATGAAATAACAATATAATTATCGTATGAGTTAAATCTTAAAAGTCACGTAAAA

GATAATCATGCGTCATTTTGACTCACGCGGTCGTTATAGTTCAAAATCAGTGACACT

TACCGCATTGACAAGCACGCCTCACGGGAGCTCCAAGCGGCGACTGAGATGTCCTA

AATGCACAGCGACGGATTCGCGCTATTTAGAAAGAGAGAGCAATATTTCAAGAATG

CATGCGTCAATTTTACGCAGACTATCTTTCTAGGGTTAATCTAGCTGCATCAGGATC

ATATCGTCGGGTCTTTTTTCCGGCTCAGTCATCGCCCAAGCTGGCGCTATCTGGGCAT

CGGGGAGGAAGAAGCCCGTGCCTTTTCCCGCGAGGTTGAAGCGGCATGGAAAGAGT

TTGCCGAGGATGACTGCTGCTGCATTGACGTTGAGCGAAAACGCACGTTTACCATGA

TGATTCGGGAAGGTGTGGCCATGCACGCCTTTAACGGTGAACTGTTCGTTCAGGCCA

CCTGGGATACCAGTTCGTCGCGGCTTTTCCGGACACAGTTCCGGATGGTCAGCCCGA

AGCGCATCAGCAACCCGAACAATACCGGCGACAGCCGGAACTGCCGTGCCGGTGTG

CAGATTAATGACAGCGGTGCGGCGCTGGGATATTACGTCAGCGAGGACGGGTATCC

TGGCTGGATGCCGCAGAAATGGACATGGATACCCCGTGAGTTACCCGGCGGGCGCG

CTTGGCGTAATCATGGTCATAGCTGTTTCCTGTGTGAAATTGTTATCCGCTCACAATT

CCACACAACATACGAGCCGGAAGCATAAAGTGTAAAGCCTGGGGTGCCTAATGAGT

GAGCTAACTCACATTAATTGCGTTGCGCTCACTGCCCGCTTTCCAGTCGGGAAACCT

GTCGTGCCAGCTGCATTAATGAATCGGCCAACGCGCGGGGAGAGGCGGTTTGCGTA

TTGGGCGCTCTTCCGCTTCCTCGCTCACTGACTCGCTGCGCTCGGTCGTTCGGCTGCG
```

-continued

```
GCGAGCGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACCGTAA
AAAGGCCGCGTTGCTGGCGTTTTTCCATAGGCTCCGCCCCCCTGACGAGCATCACAA
AAATCGACGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCCGCTTACCGG
ATACCTGTCCGCCTTTCTCCCTTCGGGAAGCGTGGCGCTTTCTCATAGCTCACGCTGT
AGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCG
GTAAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTACAC
TAGAAGGACAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGTTTTTTTGT
TTGCAAGCAGCAGATTACGCGCAGAAAAAAAGGATCTCAAGAAGATCCTTTGATCT
TTTCTACGGGGTCTGACGCTCAGTGGAACGAAAACTCACGTTAAGGGATTTTGGTCA
TGAGATTATCAAAAAGGATCTTCACCTAGATCCTTTTAAATTAAAAATGAAGTTTTA
AATCAATCTAAAGTATATATGAGTAAACTTGGTCTGACAGTTACCAATGCTTAATCA
GTGAGGCACCTATCTCAGCGATCTGTCTATTTCGTTCATCCATAGTTGCCTGACTCCC
CGTCGTGTAGATAACTACGATACGGGAGGGCTTACCATCTGGCCCCAGTGCTGCAAT
GATACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGTCTA
TTAATTGTTGCCGGGAAGCTAGAGTAAGTAGTTCGCCAGTTAATAGTTTGCGCAACG
TTGTTGCCATTGCTACAGGCATCGTGGTGTCACGCTCGTCGTTTGGTATGGCTTCATT
CAGCTCCGGTTCCCAACGATCAAGGCGAGTTACATGATCCCCCATGTTGTGCAAAAA
AGCGGTTAGCTCCTTCGGTCCTCCGATCGTTGTCAGAAGTAAGTTGGCCGCAGTGTT
ATCACTCATGGTTATGGCAGCACTGCATAATTCTCTTACTGTCATGCCATCCGTAAG
ATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCA
GAACTTTAAAAGTGCTCATCATTGGAAAACGTTCTTCGGGGCGAAAACTCTCAAGGA
TCTTACCGCTGTTGAGATCCAGTTCGATGTAACCCACTCGTGCACCCAACTGATCTTC
AGCATCTTTTACTTTCACCAGCGTTTCTGGGTGAGCAAAAACAGGAAGGCAAAATGC
CGCAAAAAAGGGAATAAGGGCGACACGGAAATGTTGAATACTCAT
```

The sequence of the pPBBG-iHelper2.7-HA vector is provided below:

pPBBG-iHelper2.7-HA (17,114 bp)

(SEQ ID NO: 10)

```
ACTCTTCCTTTTTCAATATTATTGAAGCATTTATCAGGGTTATTGTCTCATGA
GCGGATACATATTTGAATGTATTTAGAAAAATAAACAATAGGGGTTCCGCGCACA
TTTCCCCGAAAAGTGCCACCTAAATTGTAAGCGTTAATATTTTGTTAAAATTCGCGTT
AAATTTTGTTAAATCAGCTCATTTTTTAACCAATAGGCCGAAATCGGCAAAATCCC
TTATAAATCAAAAGAATAGACCGAGATAGGGTTGAGTGTTGTTCCAGTTTGGAACA
```

```
AGAGTCCACTATTAAAGAACGTGGACTCCAACGTCAAAGGGCGAAAAACCGTCTAT
CAGGGCGATGGCCCACTACGTGAACCATCACCCTAATCAAGTTTTTTGGGGTCGAGG
TGCCGTAAAGCACTAAATCGGAACCCTAAAGGGAGCCCCCGATTTAGAGCTTGACG
GGGAAAGCCGGCGAACGTGGCGAGAAAGGAAGGGAAGAAAGCGAAAGGAGCGGG
CGCTAGGGCGCTGGCAAGTGTAGCGGTCACGCTGCGCGTAACCACCACACCCGCCG
CGCTTAATGCGCCGCTACAGGGCGCGTCCCATTCGCCATTCAGGCTGCGCAACTGTT
GGGAAGGGCGATCGGTGCGGGCCTCTTCGCTATTACGCCAGCTGGCGAAAGGGGGA
TGTGCTGCAAGGCGATTAAGTTGGGTAACGCCAGGGTTTTCCCAGTCACGACGTTGT
AAAACGACGGCCAGTGAGCGCGCCTCGTTCATTCACGTTTTTGAACCCGTGGAGGAC
GGGCAGACTCGCGGTGCAAATGTGTTTTACAGCGTGATGGAGCAGATGAAGATGCT
CGACACGCTGCAGAACACGCAGCTAGATTAACCCTAGAAAGATAATCATATTGTGA
CGTACGTTAAAGATAATCATGCGTAAAATTGACGCATGTGTTTTATCGGTCTGTATA
TCGAGGTTTATTTATTAATTTGAATAGATATTAAGTTTTATTATATTTACACTTACAT
ACTAATAATAAATTCAACAAACAATTTATTTATGTTTATTTATTTATTAAAAAAAAA
CAAAAACTCAAAATTTCTTCTATAAAGTAACAAAACTTTTATCGAATTCCTGCAGCC
CGGGGGATCCACTAGTTCTAGAGGGACAGCCCCCCCCCAAAGCCCCCAGGGATGTA
ATTACGTCCCTCCCCCGCTAGGGGGCAGCAGCGAGCCGCCCGGGGCTCCGCTCCGGT
CCGGCGCTCCCCCCGCATCCCCGAGCCGGCAGCGTGCGGGGACAGCCCGGGCACGG
GGAAGGTGGCACGGGATCGCTTTCCTCTGAACGCTTCTCGCTGCTCTTTGAGCCTGC
AGACACCTGGGGGGATACGGGGAAAAGGCCTCCAAGGCCAGCTTCCCACAATAAGT
TGGGTGAATTTTGGCTCATTCCTCCTTTCTATAGGATTGAGGTCAGAGCTTTGTGATG
GGAATTCTGTGGAATGTGTGTCAGTTAGGGTGTGGAAAGTCCCgcGATCgcTAGcGTTT
AAACTTAAGCTTGGTACCGAGCTCGGATCCACTAGTCCAGTGTGGTGGAATTCCTGC
TTCGCGATGTACGGGCCggtacccaactccatgcttaacagtccccaggtacagcccaccctgcgtcgcaaccaggaaca
gctctacagcttcctggagcgccactcgcccacttccgcagccacagtgcgcagattaggagcgccacttcttttgtcacttgaaaaacat
gtaaaaataatgtactaggagacactttcaataaaggcaaatgttttatttgtacactctcgggtgattatttaccccccaccttgccgtctg
cgccgtttaaaaatcaaaggggttctgccgcgcatcgctatgcgccactggcagggacacgttgcgatactggtgtttagtgctccacttaaact
caggcacaaccatccgcggcagctcggtgaagttttcactccacaggctgcgcaccatcaccaacgcgtttagcaggtcgggcgccgata
tcttgaagtcgcagttgggcctccgccctgcgcgcgcgagttgcgatacacaggggttgcagcactggaacactatcagcgccgggtggt
gcacgctggccagcacgctcttgtcggagatcagatccgcgtccaggtcctccgcgttgctcagggcgaacggagtcaactttggtagctg
ccttcccaaaaagggtgcatgcccaggctttgagttgcactcgcaccgtagtggcatcagaaggtgaccgtgcccggtctgggcgttagga
tacagcgcctgcatgaaagccttgatctgcttaaaagccacctgagcctttgcgccttcagagaagaacatgccgcaagacttgccggaaa
actgattggccggacaggccgcgtcatgcacgcagcaccttgcgtcggtgttggagatctgcaccacatttcggccccaccggttcttcacg
atcttggccttgctagactgctccttcagcgcgcgctgcccgttttcgctcgtcacatccatttcaatcacgtgctccttatttatcataatgc
tcccgtgtagacacttaagctcgccttcgatctcagcgcagcggtgcagccacaacgcgcagcccgtgggctcgtggtgcttgtaggttacctct
gcaaacgactgcaggtacgcctgcaggaatcgccccatcatcgtcacaaaggtcttgttgctggtgaaggtcagctgcaacccgcggtgctc
ctcgtttagccaggtcttgcatacggccgccagagcttccacttggtcaggcagtagcttgaagtttgcctttagatcgttatccacgtggtact
tgtccatcaacgcgcgcgcagcctccatgcccttctcccacgcagacacgatcggcaggctcagcgggtttatcaccgtgctttcactttccg
cttcactggactcttcctttcctcttgcgtccgcatacccgcgccactgggtcgtcttcattcagccgccgcaccgtgcgcttacctcccttg
ccgtgcttgattagcaccggtgggttgctgaaacccaccatttgtagcgccacatcttctctttcttcctcgctgtccacgatcacctctgggga
tggcgggcgctcgggcttgggagaggggcgcttcttttttcttttttggacgcaatggccaaatccgccgtcgaggtcgatggccgcgggctgg
```

-continued

```
gtgtgcgcggcaccagcgcatcttgtgacgagtcttcttcgtcctcggactcgagacgccgcctcagccgcttttttgggggcgcgcgggg aggcggcggcgacggcgacggggacgacacgtcctccatggttggtggacgtcgcgccgcaccgcgtccgcgctcggggtggtttc gcgctgctcctcttcccgactggccatttccttctcctataggcagaaaaagatcatggagtcagtcgagaaggaggacagcctaaccgccc cctttgagttcgccaccaccgcctccaccgatgccgccaacgcgcctaccaccttccccgtcgaggcaccccgcttgaggaggaggaa gtgattatcgagcaggacccaggttttgtaagcgaagacgacgaggatcgctcagtaccaacagaggataaaaagcaagaccaggacga cgcagaggcaaacgaggaacaagtcgggcggggggaccaaaggcatggcgactacctagatgtgggagacgacgtgctgttgaagca tctgcagcgccagtgcgccattatctgcgacgcgttgcaagagcgcagcgatgtgcccctcgccatagcggatgtcagccttgcctacgaa cgccacctgttctcaccgcgcgtaccccccaaacgccaagaaaacgcacatgcgagcccaacccgcgcctcaacttctaccccgtatttg ccgtgccagaggtgcttgccacctatcacatcttttccaaaactgcaagataccctatcctgccgtgccaaccgcagccgagcggacaag cagctggccttgcggcagggcgctgtcatacctgatatcgcctcgctcgacgaagtgccaaaaatctttgagggtcttggacgcgacgaga aacgcgcggcaaacgctctgcaacaagaaaacagcgaaaatgaaagtcactgtggagtgctggtggaacttgagggtgacaacgcgcg cctagccgtgctgaaacgcagcatcgaggtcacccactttgcctacccggcacttaacctaccccccaaggttatgagcacagtcatgagc gagctgatcgtgcgccgtgcacgacccctggagagggatgcaaacttgcaagaacaaaccgaggagggcctacccgcagttggcgatg agcagctggcgcgctggcttgagacgcgcgagcctgccgacttggaggagcgacgcaagctaatgatggccgcagtgcttgttaccgtg gagcttgagtgcatgcagcggttctttgctgacccggagatgcagcgcaagctagaggaaacgttgcactacacctttcgccagggctacg tgcgccaggcctgcaaaatttccaacgtggagctctgcaacctggtctcctaccttggaattttgcacgaaaaccgcctcgggcaaaacgtg cttcattccacgctcaagggcgaggcgcgccgcgactacgtccgcgactgcgtttacttatttctgtgctacacctggcaaacggccatggg cgtgtggcagcaatgcctggaggagcgcaacctaaaggagctgcagaagctgctaaagcaaaacttgaaggacctatggacggccttca acgagcgctccgtggccgcgcacctggcggacattatcttccccgaacgcctgcttaaaaccctgcaacagggtctgccagacttcaccag tcaaagcatgttgcaaaacttttaggaactttatcctagagcgttcaggaattctgcccgccacctgctgtgcgcttcctagcgactttgtgccca ttaagtaccgtgaatgccctccgccgctttggggtcactgctaccttctgcagctagccaactaccttgcctaccactccgacatcatggaaga cgtgagcggtgacggcctactggagtgtcactgtcgctgcaacctatgcaccccgcaccgctccctggtctgcaattcgcaactgcttagcg aaagtcaaattatcggtacctttgagctgcagggtccctcgcctgacgaaaagtccgcggctccggggttgaaactcactccggggctgtg gacgtcCGATCTCTATCACTGATAGGGAGATCTCTATCACTGATAGGGAGAGggcttaccttcg caaatttgtacctgaggactaccacgcccacgagattaggttctacgaagaccaatcccgcccgccaaatgcggagcttaccgcctgcgtc attacccagggccacatccttggccaattgcaagccatcaacaaagcccgccaagagtttctgctacgaaagggacggggggtttacctgg acccccagtccggcgaggagctcaacccaatcccccgccgccgcagccctatcagcagccgcgggcccttgcttccaggatggcac ccaaaaagaagctgcagctgccgccgccgccaccacggacgaggaggaatactgggacagtcaggcagaggaggttttggacgagg aggaggagatgatgaagactgggacagcctagacgaagcttccgaggccgaagaggtgtcagacgaaacaccgtcaccctcggtcgc attcccctcgccggcgccccagaaattggcaaccgttcccagcatcgctacaacctccgctcctcaggcgccgccggcactgctgttcgc cgacccaaccgtagatgggacaccactggaaccagggccggtaagtctaagcagccgccgccgttagcccaagagcaacaacagcgc caaggctaccgctcgtggcgcgggcacaagaacgccatagttgcttgcttgcaagactgtggggcaacatctccttcgcccgccgctttct tctctaccatcacgcgtggccttcccccgtaacatcctgcattactaccgtcatctctacagccctactgcaccggcggcagcggcagcg gcagcaacagcagcggtcacacagaagcaaaggcgaccggatagcaagactctgacaaagcccaagaaatccacagcggcggcagc agcaggaggaggagcgctgcgtctggcgcccaacgaacccgtatcgacccgcgagcttagaaataggattttttcccactctgtatgctatat ttcaacaaagcaggggccaagaacaagagctgaaaataaaaaacaggtctctgcgctccctcacccgcagctgcctgtatcacaaaagcg aagatcagcttcggcgcacgctggaagacgcggaggctctcttcagcaaCGATCTCTATCACTGATAGGGAGATC TCTATCACTGATAGGGAGAGatactgcgcgctgactcttaaggactagtttcgcgcccttttctcaaatttaagcgcgaaaa ctacgtcatctccagcggccacacccggcgccagcacctgtcgtcagcgccattatgagcaaggaaattcccacgccctacatgtggagtt accagccacaaatgggacttgcggctggagctgcccaagactactcaacccgaataaactacatgagcgcgggaccccacatgatatccc
```

-continued

```
gggtcaacggaatccgcgcccaccgaaaccgaattctcctcgaacaggcggctattaccaccacacctcgtaataaccttaatcccgtagt tggcccgctgccctggtgtaccaggaaagtcccgctccaccactgtggtacttcccagagacgcccaggccgaagttcagatgactaact caggggcgcagcttgcgggcggctttcgtcacagggtgcggtcgcccgggcgttttagggcggagtaacttgcatgtattgggaattgtag ttttttaaaatgggaagtgacgtatcgtgggaaaacggaagtgaagatttgaggaagttgtgggttttttggctttcgtttctgggcgtaggtt cgcgtgcggttttctgggtgtttttgtggactttaaccgttacgtcattttttagtcctatatatactcgctctgtaCTCTCCCTATCAGT GATAGAGATCTCCCTATCAGTGATAGAGATCGcttggcccttttttacactgtgactgattgagctggtgccgtgt cgagtggtgtttttaataggttttttttactggtaaggctgactgttatggctgccgctgtggaagcgctgtatgttgttctggagcgggagggt gctattttgcctaggcaggaggttttttcaggtgtttatgtgttttttctctcctattaattttgttatacctcctatgggggctgtaatgttgt ctctacgcctgcgggtatgtattcccccgggctatttcggtcgcttttagcactgaccgatgttaaccaacctgatgtgtttaccgagtcttac attatgactccggacatgaccgaggaactgtcggtggtgcttttaatcacggtgaccagtttttttacggtcacgccggcatggccgtagtcc gtcttatgcttataaggggttgttttcctgttgtaagacaggcttctaatgtttaaatgttttttttttttgttatttttattttgtgtttaatgc aggaacccgcagacatgtttgagagaaaaatggtgtcttttctgtggtggttccggaacttacctgcctttatctgcatgagcatgactacga tgtgcttgctttttgcgcgaggctttgcctgattttttgagcagcaccttgcattttatatcgccgcccatgcaacaagcttacataggggcta cgctggttagcatagctccgagtatgcgtgtcataatcagtgtgggttcttttgtcatggttcctggcggggaagtggccgcgctggtccgtgca gacctgcacgattatgttcagctggccctgcgaagggacctacgggatcgcggtattttgttaatgttccgcttttgaatcttatacaggtctg tgaggaacctgaattttttgcaatcatgattcgctgcttgaggctgaaggtggagggcgctctggagcagattttttacaatggccggacttaatat tcgggatttgcttagagacatattgataaggtggcgagatgaaaattatttgggcatggttgaaggtgctggaatgtttatagaggagattcacc ctgaagggtttagcctttacgtccacttggacgtgagggcagtttgccttttggaagccattgtgcaacatcttacaaatgccattatctgttc tttggctgtagagtttgaccacgccaccggaggggagcgcgttcacttaatagatcttcattttgaggttttggataatcttttggaataaaaaa aaaaaaacatggttcttccagctcttcccgctcctcccgtgtgtgactcgcagaacgaatgtgtaggttggctgggtgtggcttattctgcggt ggtggatgttatcagggcagcggcgcatgaaggagtttacatagaacccgaagccagggggcgcctggatgctttgagagagtggatatactaca actactacacagagcgagctaagcgacgagaccggagacgcagatctgtttgtcacgcccgcacctggttttgcttcaggaaatatgTACCCATA CGATGTTCCAGATTACGCTGGAGGAGGCGGAGGCactacgtccggcgttccatttggcatgacactacgaccaacacgatct cggttgtctcggcgcactccgtacagtagggatcgcctacctccttttgagacagagacccgcgctaccatactggaggatcatccgctgct gcccgaatgtaacactttgacaatgcacaacgtgagttacgtgcgaggtcttccctgcagtgtgggatttacgctgattcaggaatgggttgtt ccctgggatatggttctgacgcgggaggagcttgtaatcctgaggaagtgtatgcacgtgtgcctgtgttgtgccaacattgatatcatgacg agcatgatgatccatggttacgagtcctgggctctccactgtcattgttccagtcccggttccctgcagtgcatagccggggcaggttttgg ccagctggtttaggatggtggtggatggcgccatgtttaatcagaggtttatatggtaccgggaggtggtgaattacaacatgccaaaagag gtaatgtttatgtccagcgtgtttatgaggggtcgccacttaatctacctgcgcttgtggtatgatggccacgtgggttctgtggtccccgccat gagctttggatacagcgccttgcactgtgggattttgaacaatattgtggtgctgtgctgcagttactgtgctgatttaagtgagatcagggtgc gctgctgtgcccggaggacaaggcgtctcatgctgcgggcggtgcgaatcatcgctgaggagaccactgccatgttgtattcctgcaggac ggagcggcggcggcagcagtttattcgcgcgctgctgcagcaccaccgccctatcctgatgcacgattatgactctaccccatgtaggcg tggacttccccttcgccgcccgttgagcaaccgcaagttggacagcagcctgtggctcagcagctggacagcgacatgaacttaagcgag ctgcccggggagtttattaatatcactgatgagcgtttggctcgacaggaaaccgtgtggaatataacacctaagaatatgtctgttacccatg atatgatgcttttaaggccagccggggagaaaggactgtgtactctgtgtgttgggagggaggtggcaggttgaatactagggttctgtgag tttgattaaggtacggtgatcaatataagctatgtggtggtgggctatactactgaatgaaaaatgacttgaaattttctgcaattgaaaaata aacacgttgaaacataacatgcaacaggttcacgattctttattcctgggcaatgtaggagaaggtgtaagagttggtagcaaaagtttcagtgg tgtattttccactttcccaggaccatgtaaaagacatagagtaagtgcttacctcgctagttttctgtggattcactagaaccagtggccaaaaaa gctagcgcagcagccgccgcgcctggaaggaagccaaaaggagcgctccccgttgtctgacgtcgcacacctgggttcgacacgcgg gcggtaaccgcatggatcacggcggacggccggatccggggttcgaaccccggtcgtccgccatgataccttgcgaatttatccaccag accacggaagagtgcccgcttacagGTGGTCTCATACAGAACTTATAAGATTCCCAAATCCAAAGA
```

CATTTCACGTTTATGGTGATTTCCCAGAACACATAGCGACATGCAAATATTGCAGGG

CGCCACTCCCCTGTCCgctctccttttgcacggtctagagcgtcaacgactgcgcacgccagtggccaaaaaagctagcgca gcagccgccgcgcctggaaggaagccaaaaggagcgctccccgttgtctgacgtcgcacacctgggttcgacacgcgggcggtaacc gcatggatcacggcggacggccggatccggggttcgaaccccggtcgtccgccatgatacccttgcgaatttatccaccagaccacggaa gagtgcccgcttacagGTGGTCTCATACAGAACTTATAAGATTCCCAAATCCAAGACATTTC

ACGTTTATGGTGATTTCCCAGAACACATAGCGACATGCAAATATTGCAGGGCGCCAC

TCCCCTGTCCgctctccttttgcacggtctagagcgtcaacgactgcgcacgccagtggccaaaaaagctagcgcagcagccgcc gcgcctggaaggaagccaaaaggagcgctccccgttgtctgacgtcgcacacctgggttcgacacgcgggcggtaaccgcatggatca cggcggacggccggatccggggttcgaaccccggtcgtccgccatgatacccttgcgaatttatccaccagaccacggaagagtgcccg cttacagGTGGTCTCATACAGAACTTATAAGATTCCCAAATCCAAGACATTTCACGTTT

ATGGTGATTTCCCAGAACACATAGCGACATGCAAATATTGCAGGGCGCCACTCCCCT

GTCCgctctccttttgcacggtctagagcgtcaacgactgcgcacgccagtggccaaaaaagctagcgcagcagccgccgcgcctgg aaggaagccaaaaggagcgctccccgttgtctgacgtcgcacacctgggttcgacacgcgggggtaaccgcatggatcacggcgga cggccggatccggggttcgaaccccggtcgtccgccatgatacccttgcgaatttatccaccagaccacggaagagtgcccgcttacagG

TGGTCTCATACAGAACTTATAAGATTCCCAAATCCAAGACATTTCACGTTTATGGT

GATTTCCCAGAACACATAGCGACATGCAAATATTGCAGGGCGCCACTCCCCTGTCCg ctctccttttgcacggtctagagcgtcaacgactgcgcacgtccactttggccgcggctcgagTGAGCTATTCCAGAAGTA

GTGAAGAGGCTTTTTTGGAGGCCTAGGCTTTTGCAAAAAGCTCCGGATCGATGCCCG

GGGGATCCACTAGTTCTAGAGGGACAGCCCCCCCCCAAAGCCCCCAGGGATGTAAT

TACGTCCCTCCCCCGCTAGGGGGCAGCAGCGAGCCGCCCGGGGCTCCGCTCCGGTCC

GGCGCTCCCCCCGCATCCCCGAGCCGGCAGCGTGCGGGGACAGCCCGGGCACGGGG

AAGGTGGCACGGGATCGCTTTCCTCTGAACGCTTCTCGCTGCTCTTTGAGCCTGCAG

ACACCTGGGGGATACGGGAAAAGGCCTCCAAGGCCAGCTTCCCACAATAAGTTG

GGTGAATTTTGGCTGAGCTATTCCAGAAGTAGTGAAGAGGCTTTTTTGGAGGCCTAG

GCTTTTGCAAAAAGCTCCGGATCGATCATATATGGCAGATATACGCGTTGACATTGA

TTATTGACTAGTTATTAATAGTAATCAATTACGGGGTCATTAGTTCATAGCCCATATA

TGGAGTTCCGCGTTACATAACTTACGGTAAATGGCCCGCCTGGCTGACCGCCCAACG

ACCCCCGCCCATTGACGTCAATAATGACGTATGTTCCCATAGTAACGCCAATAGGGA

CTTTCCATTGACGTCAATGGGTGGAGTATTTACGGTAAACTGCCCACTTGGCAGTAC

ATCAAGTGTATCATATGCCAAGTACGCCCCCTATTGACGTCAATGACGGTAAATGGC

CCGCCTGGCATTATGCCCAGTACATGACCTTATGGGACTTTCCTACTTGGCAGTACA

TCTACGTATTAGTCATCGCTATTACCATGGTGATGCGGTTTTGGCAGTACATCAATG

GGCGTGGATAGCGGTTTGACTCACGGGGATTTCCAAGTCTCCACCCCATTGACGTCA

ATGGGAGTTTGTTTTGGCACCAAAATCAACGGGACTTTCCAAAATGTCGTAACAACT

CCGCCCCATTGACGCAAATGGGCGGTAGGCGTGTACGGTGGGAGGTCTATATAAGC

AGAGCTCTCTGGCTAACTATCGTCGACGAGCTCGTTTAGTGAACCGTCAGATCGCCT

GGAGACGCCATCCACGCTGTTTTGACCTCCATAGAAGACACCGGGACCGATCCAGC

CTCCGGACTCTAGCGTTTAAACTTAAGCTTGCCACCatgaccgagtacaagcccacggtgcgcctcgcc acccgcgacgacgtccccagggccgtacgcacccgcgccgcgcgttcgccgactacccgccacgcgccacaccgtcgatccggacc gccacatcgagcgggtcaccgagctgcaagaactcttcctcacgcgcgtcgggctcgacatcggcaaggtgtgggtcgcggacgacgg -continued cgccgcggtggcggtctggaccacgccggagagcgtcgaagcgggggcggtgttcgccgagatcggcccgcgcatggccgagttgag cggttcccggctggccgcgcagcaacagatggaaggcctcctggcgccgcaccggcccaaggagcccgcgtggttcctggccaccgtc ggcgtctcgcccgaccaccagggcaaggg tctgggcagcgccgtcgtgctccccggagtggaggcggccgagcgcgccggggtgcc cgccttcctggagacctccgcgccccgcaacctccccttctacgagcggctcggcttcaccgtcaccgccgacgtcgaggtgcccgaagg accgcgcacctggtgcatgacccgcaagcccggtgcctgaAGCGCGGGGATCTCATGCTGGAGTTCTTCGC

CCACCCCAACTTGTTTATTGCAGCTTATAATGGTTACAAATAAAGCAATAGCATCAC

AAATTTCACAAATAAAGCATTTTTTTCACTGCATTCTAGTTGTGGTTTGTCCAAACTC

ATCAATGTATCTTATCATGTCTGTAGCtGATgtATAcCTAggATCCGGCCGGccTGCAggT

GTCCTCACAGGAACGAAGTCCCTAAAGAAACAGTGGCAGCCAGGTTTAGCCCCGGA

ATTGACTGGATTCCTTTTTTAGGGCCCATTGGTATGGCTTTTTCCCCGTATCCCCCCA

GGTGTCTGCAGGCTCAAAGAGCAGCGAGAAGCGTTCAGAGGAAAGCGATCCCGTGC

CACCTTCCCCGTGCCCGGGCTGTCCCCGCACGCTGCCGGCTCGGGGATGCGGGGGG

AGCGCCGGACCGGAGCGGAGCCCCGGGCGGCTCGCTGCTGCCCCCTAGCGGGGGAG

GGACGTAATTACATCCCTGGGGGCTTTGGGGGGGGGCTGTCCCTCTAGAGCGGCCGC

CACCGCGGTGGAGCTCCAGCTTTTGTTCCCTTTAGTGAGGGTTAATTAGATCTTAATA

CGACTCACTATAGGGCGAATTGGGTACCGGGCCCCCCCTCGAGGTCGACGGTATCG

ATAAGCTTGATATCTATAACAAGAAAATATATATATAATAAGTTATCACGTAAGTAG

AACATGAAATAACAATATAATTATCGTATGAGTTAAATCTTAAAAGTCACGTAAAA

GATAATCATGCGTCATTTTGACTCACGCGGTCGTTATAGTTCAAAATCAGTGACACT

TACCGCATTGACAAGCACGCCTCACGGGAGCTCCAAGCGGCGACTGAGATGTCCTA

AATGCACAGCGACGGATTCGCGCTATTTAGAAAGAGAGAGCAATATTTCAAGAATG

CATGCGTCAATTTTACGCAGACTATCTTTCTAGGGTTAATCTAGCTGCATCAGGATC

ATATCGTCGGGTCTTTTTTCCGGCTCAGTCATCGCCCAAGCTGGCGCTATCTGGGCAT

CGGGGAGGAAGAAGCCCGTGCCTTTTCCCGCGAGGTTGAAGCGGCATGGAAAGAGT

TTGCCGAGGATGACTGCTGCTGCATTGACGTTGAGCGAAAACGCACGTTTACCATGA

TGATTCGGGAAGGTGTGGCCATGCACGCCTTTAACGGTGAACTGTTCGTTCAGGCCA

CCTGGGATACCAGTTCGTCGCGGCTTTTCCGGACACAGTTCCGGATGGTCAGCCCGA

AGCGCATCAGCAACCCGAACAATACCGGCGACAGCCGGAACTGCCGTGCCGGTGTG

CAGATTAATGACAGCGGTGCGGCGCTGGGATATTACGTCAGCGAGGACGGGTATCC

TGGCTGGATGCCGCAGAAATGGACATGGATACCCCGTGAGTTACCCGGCGGGCGCG

CTTGGCGTAATCATGGTCATAGCTGTTTCCTGTGTGAAATTGTTATCCGCTCACAATT

CCACACAACATACGAGCCGGAAGCATAAAGTGTAAAGCCTGGGGTGCCTAATGAGT

GAGCTAACTCACATTAATTGCGTTGCGCTCACTGCCCGCTTTCCAGTCGGGAAACCT

GTCGTGCCAGCTGCATTAATGAATCGGCCAACGCGCGGGGAGAGGCGGTTTGCGTA

TTGGGCGCTCTTCCGCTTCCTCGCTCACTGACTCGCTGCGCTCGGTCGTTCGGCTGCG

GCGAGCGGTATCAGCTCACTCAAAGGCGGTAATACGGTTATCCACAGAATCAGGGG

ATAACGCAGGAAAGAACATGTGAGCAAAAGGCCAGCAAAAGGCCAGGAACCGTAA

AAAGGCCGCGTTGCTGGCGTTTTTCCATAGGCTCCGCCCCCCTGACGAGCATCACAA

AAATCGACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCGCTTACCGG

ATACCTGTCCGCCTTTCTCCCTTCGGGAAGCGTGGCGCTTTCTCATAGCTCACGCTGT

-continued

```
AGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCG
GTAAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTACAC
TAGAAGGACAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGTTTTTTTGT
TTGCAAGCAGCAGATTACGCGCAGAAAAAAAGGATCTCAAGAAGATCCTTTGATCT
TTTCTACGGGGTCTGACGCTCAGTGGAACGAAAACTCACGTTAAGGGATTTTGGTCA
TGAGATTATCAAAAAGGATCTTCACCTAGATCCTTTTAAATTAAAAATGAAGTTTTA
AATCAATCTAAAGTATATATGAGTAAACTTGGTCTGACAGTTACCAATGCTTAATCA
GTGAGGCACCTATCTCAGCGATCTGTCTATTTCGTTCATCCATAGTTGCCTGACTCCC
CGTCGTGTAGATAACTACGATACGGGAGGGCTTACCATCTGGCCCCAGTGCTGCAAT
GATACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGTCTA
TTAATTGTTGCCGGGAAGCTAGAGTAAGTAGTTCGCCAGTTAATAGTTTGCGCAACG
TTGTTGCCATTGCTACAGGCATCGTGGTGTCACGCTCGTCGTTTGGTATGGCTTCATT
CAGCTCCGGTTCCCAACGATCAAGGCGAGTTACATGATCCCCCATGTTGTGCAAAAA
AGCGGTTAGCTCCTTCGGTCCTCCGATCGTTGTCAGAAGTAAGTTGGCCGCAGTGTT
ATCACTCATGGTTATGGCAGCACTGCATAATTCTCTTACTGTCATGCCATCCGTAAG
ATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCA
GAACTTTAAAAGTGCTCATCATTGGAAAACGTTCTTCGGGGCGAAAACTCTCAAGGA
TCTTACCGCTGTTGAGATCCAGTTCGATGTAACCCACTCGTGCACCCAACTGATCTTC
AGCATCTTTTACTTTCACCAGCGTTTCTGGGTGAGCAAAAACAGGAAGGCAAAATGC
CGCAAAAAAGGGAATAAGGGCGACACGGAAATGTTGAATACTCAT
```

The sequence of the pPBBG-iHelper2.8-HA vector is provided below:

pPBBG-iHelper2.8-HA (17,114 bp)    (SEQ ID NO: 11)

```
ACTCTTCCTTTTTCAATATTATTGAAGCATTTATCAGGGTTATTGTCTCATGA
GCGGATACATATTTGAATGTATTTAGAAAAATAAACAAATAGGGGTTCCGCGCACA
TTTCCCCGAAAAGTGCCACCTAAATTGTAAGCGTTAATATTTTGTTAAAATTCGCGTT
AAATTTTGTTAAATCAGCTCATTTTTTAACCAATAGGCCGAAATCGGCAAAATCCC
TTATAAATCAAAAGAATAGACCGAGATAGGGTTGAGTGTTGTTCCAGTTTGGAACA
AGAGTCCACTATTAAAGAACGTGGACTCCAACGTCAAAGGGCGAAAAACCGTCTAT
CAGGGCGATGGCCCACTACGTGAACCATCACCCTAATCAAGTTTTTTGGGGTCGAGG
TGCCGTAAAGCACTAAATCGGAACCCTAAAGGGAGCCCCCGATTTAGAGCTTGACG
GGGAAAGCCGGCGAACGTGGCGAGAAAGGAAGGGAAGAAAGCGAAAGGAGCGGG
CGCTAGGGCGCTGGCAAGTGTAGCGGTCACGCTGCGCGTAACCACCACACCCGCCG
CGCTTAATGCGCCGCTACAGGGCGCGTCCCATTCGCCATTCAGGCTGCGCAACTGTT
```

-continued

```
GGGAAGGGCGATCGGTGCGGGCCTCTTCGCTATTACGCCAGCTGGCGAAAGGGGGA

TGTGCTGCAAGGCGATTAAGTTGGGTAACGCCAGGGTTTTCCCAGTCACGACGTTGT

AAAACGACGGCCAGTGAGCGCGCCTCGTTCATTCACGTTTTTGAACCCGTGGAGGAC

GGGCAGACTCGCGGTGCAAATGTGTTTTACAGCGTGATGGAGCAGATGAAGATGCT

CGACACGCTGCAGAACACGCAGCTAGATTAACCCTAGAAAGATAATCATATTGTGA

CGTACGTTAAAGATAATCATGCGTAAAATTGACGCATGTGTTTTATCGGTCTGTATA

TCGAGGTTTATTTATTAATTTGAATAGATATTAAGTTTTATTATATTTACACTTACAT

ACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCggtacccaactccatgcttaacagtccccaggtacagcccaccctgcgtcgcaaccaggaaca gctctacagcttcctggagcgccactcgccctacttccgcagccacagtgcgcagattaggagcgccacttcttttgtcacttgaaaaacat gtaaaaataatgtactaggagacactttcaataaaggcaaatgttttatttgtacactctcgggtgattatttacccccaccttgccgtctgcg ccgtttaaaaatcaaagggtcgtgccgcgcatcgctatgcgccactggcagggacacgttgcgatactggtgtttagtgctccacttaaact caggcacaaccatccgcggcagctcggtgaagttttcactccacaggctgcgcaccatcaccaacgcgtttagcaggtcgggcgccgata tcttgaagtcgcagttggggcctccgccctgcgcgcgcgagttgcgatacacaggggttgcagcactggaacactatcagcgccgggtggt gcacgctggccagcacgctcttgtcggagatcagatccgcgtccaggtcctccgcgttgctcagggcgaacggagtcaactttggtagctg ccttcccaaaaaggggtgcatgcccaggctttgagttgcactcgcaccgtagtggcatcagaaggtgaccgtgcccggtctgggcgttagga tacagcgcctgcatgaaagccttgatctgcttaaaagccacctgagcctttgcgccttcagagaagaacatgccgcaagacttgccggaaa actgattggccggacaggccgcgtcatgcacgcagcaccttgcgtcggtgttggagatctgcaccacatttcggccccaccggttcttcacg atcttggccttgctagactgctccttcagcgcgcgctgcccgttttcgctcgtcacatccatttcaatcacgtgctccttatttatcataatgctccc gtgtagacacttaagctcgccttcgatctcagcgcagcggtgcagccacaacgcgcagcccgtgggctcgtggtgcttgtaggttacctctg caaacgactgcaggtacgcctgcaggaatcgcccatcatcgtcacaaaggtcttgttgctggtgaaggtcagctgcaacccgcggtgctc ctcgtttagccaggtcttgcatacggccgccagagcttccacttggtcaggcagtagcttgaagtttgcctttagatcgttatccacgtggtactt gtccatcaacgcgcgcgcagcctccatgcccttctcccacgcagacacgatcggcaggctcagcgggtttatcaccgtgctttcactttccg cttcactggactcttccttttcctcttgcgtccgcataccccgcgccactgggtcgtcttcattcagccgccgcaccgtgcgcttacctcccttgc cgtgcttgattagcaccggtgggttgctgaaacccaccatttgtagcgccacatcttctctttcttcctcgctgtccacgatcacctctgggat ggcgggcgctcgggcttgggagaggggcgcttcttttctttttggacgcaatggccaaatccgccgtcgaggtcgatggccgcgggctgg gtgtgcgcggcaccagcgcatcttgtgacgagtcttcttcgtcctcggactcgagacgccgcctcagccgcttttttgggggcgcgcgggg aggcggcggcgacggcgacggggacgacacgtcctccatggttggtggacgtcgcgccgcaccgcgtccgcgctcggggtggtttc gcgctgctcctcttcccgactggccatttccttctcctataggcagaaaaagatcatggagtcagtcgagaaggaggacagcctaaccgcc cctttgagttcgccaccaccgcctccaccgatgccgccaacgcgcctaccaccttccccgtcgaggcacccccgcttgaggaggaggaa gtgattatcgagcaggacccaggttttgtaagcgaagacgacgaggatcgctcagtaccaacagaggataaaaagcaagaccaggacga cgcagaggcaaacgaggaacaagtcgggcgggggaccaaaggcatggcgactacctagatgtgggagacgacgtgctgttgaagca
``` tctgcagcgccagtgcgccattatctgcgacgcgttgcaagagcgcagcgatgtgccctcgccatagcggatgtcagccttgcctacgaa cgccacctgttctcaccgcgcgtaccccccaaacgccaagaaaacgcgcacatgcgagcccaacccgcgcctcaacttctaccccgtatttg ccgtgccagaggtgcttgccacctatcacatcttttccaaaactgcaagataccctatcctgccgtgccaaccgcagccgagcggacaag cagctggccttgcggcagggcgctgtcatacctgatatcgcctcgctcgacgaagtgccaaaaatctttgagggtcttggacgcgacgaga aacgcgcggcaaacgctctgcaacaagaaaacagcgaaaatgaaagtcactgtggagtgctggtggaacttgagggtgacaacgcgcg cctagccgtgctgaaacgcagcatcgaggtcacccactttgcctacccggcacttaacctacccccaaggttatgagcacagtcatgagc gagctgatcgtgcgccgtgcacgacccctggagagggatgcaaacttgcaagaacaaaccgaggagggcctacccgcagttggcgatg agcagctggcgcgctggcttgagacgcgcgagcctgccgacttggaggagcgacgcaagctaatgatggccgcagtgcttgttaccgtg gagcttgagtgcatgcagcggttctttgctgacccggagatgcagcgcaagctagaggaaacgttgcactacacctttcgccagggctacg tgcgccaggcctgcaaaatttccaacgtggagctctgcaacctggtctcctaccttggaattttgcacgaaaaccgcctcgggcaaaacgtg cttcattccacgctcaagggcgaggcgcgccgcgactacgtccgcgactgcgtttacttatttctgtgctacacctggcaaacggccatggg cgtgtggcagcaatgcctggaggagcgcaacctaaaggagctgcagaagctgctaaagcaaaacttgaaggacctatggacggccttca acgagcgctccgtggccgcgcacctggcggacattatcttccccgaacgcctgcttaaaaccctgcaacagggtctgccagacttcaccag tcaaagcatgttgcaaaactttaggaactttatcctagagcgttcaggaattctgcccgccacctgctgtgcgcttcctagcgactttgtgccca ttaagtaccgtgaatgccctccgccgctttggggtcactgctaccttctgcagctagccaactaccttgcctaccactccgacatcatggaaga cgtgagcggtgacggcctactggagtgtcactgtcgctgcaacctatgcaccccgcaccgctccctggtctgcaattcgcaactgcttagcg aaagtcaaattatcggtacctttgagctgcagggtccctcgcctgacgaaaagtccgcggctccggggttgaaactcactccggggctgtg gacgtcCGATCTCTATCACTGATAGGGAGATCTCTATCACTGATAGGGAGAGggcttaccttcg caaatttgtacctgaggactaccacgcccacgagattaggttctacgaagaccaatcccgcccgccaaatgcggagcttaccgcctgcgtc attacccagggccacatccttggccaattgcaagccatcaacaaagcccgccaagagtttctgctacgaaagggacggggggtttacctgg accccagtccggcgaggagctcaacccaatcccccgccgccgcagccctatcagcagccgcgggcccttgcttccaggatggcac ccaaaaagaagctgcagctgccgccgccgccacccacggacgaggaggaatactgggacagtcaggcagaggaggttttggacgagg aggaggagatgatgaagactgggacagcctagacgaagcttccgaggccgaagaggtgtcagacgaaacaccgtcaccctcggtcgc attcccctcgccggcgccccagaaattggcaaccgttcccagcatcgctacaacctccgctcctcaggcgccgccggcactgcctgttcgc cgacccaaccgtagatgggacaccactggaaccagggccggtaagtctaagcagccgccgccgttagcccaagagcaacaacagcgc caaggctaccgctcgtggcgcgggcacaagaacgccatagttgcttgcttgcaagactgtgggggcaacatctccttcgcccgccgctttct tctctaccatcacggcgtggccttcccccgtaacatcctgcattactaccgtcatctctacagccccactgcaccggcggcagcggcagcg gcagcaacagcagcggtcacacagaagcaaaggcgaccggatagcaagactctgacaaagcccaagaaatccacagcggcggcagc agcaggaggaggagcgctgcgtctggcgcccaacgaacccgtatcgacccgcgagcttagaaataggattttttcccactctgtatgctatat ttcaacaaagcaggggccaagaacaagagctgaaaataaaaaacaggtctctgcgctccctcacccgcagctgcctgtatcacaaaagcg aagatcagcttcggcgcacgctggaagacgcggaggctctcttcagcaaCGATCTCTATCACTGATAGGGAGATC TCTATCACTGATAGGGAGAGatactgcgcgctgactcttaaggactagtttcgcgcccttttctcaaatttaagcgcgaaaa ctacgtcatctccagcggccacacccggcgccagcacctgtcgtcagcgccattatgagcaaggaaattcccacgccctacatgtggagtt accagccacaaatgggacttgcggctggagctgcccaagactactcaacccgaataaactacatgagcgcgggaccccacatgatatccc gggtcaacggaatccgcgcccaccgaaaccgaattctcctcgaacaggcggctattaccaccacacctcgtaataaccttaatcccccgtagt tggcccgctgccctggtgtaccaggaaagtcccgctcccaccactgtggtacttcccagagacgcccaggccgaagttcagatgactaact caggggcgcagcttgcgggcggctttcgtcacagggtgcggtcgccccagtggccaaaaaagctagcgcagcagccgccgcgcctg gaaggaagccaaaaggagcgctccccgttgtctgacgtcgcacacctgggttcgacacgcgggcggtaaccgcatggatcacgcgg acggccggatccggggttcgaaccccggtcgtccgccatgataccttgcgaatttatccaccagaccacggaagagtgcccgcttacag

GTGGTCTCATACAGAACTTATAAGATTCCCAAATCCAAGACATTTCACGTTTATGG

```
TGATTTCCCAGAACACATAGCGACATGCAAATATTGCAGGGCGCCACTCCCCTGTCC gctctccttttgcacggtctagagcgtcaacgactgcgcacgccagtggccaaaaaagctagcgcagcagccgccgcgcctggaaggaa gccaaaaggagcgctccccgttgtctgacgtcgcacacctgggttcgacacgcgggcggtaaccgcatggatcacggcggacggccg gatccggggttcgaaccccggtcgtccgccatgatacccttgcgaatttatccaccagaccacggaagagtgcccgcttacagGTGGT

CTCATACAGAACTTATAAGATTCCCAAATCCAAAGACATTTCACGTTTATGGTGATT

TCCCAGAACACATAGCGACATGCAAATATTGCAGGGCGCCACTCCCCTGTCCgctctcctt ttgcacggtctagagcgtcaacgactgcgcacgccagtggccaaaaaagctagcgcagcagccgccgcgcctggaaggaagccaaaa ggagcgctccccgttgtctgacgtcgcacacctgggttcgacacgcgggcggtaaccgcatggatcacggcggacggccggatccgg ggttcgaaccccggtcgtccgccatgatacccttgcgaatttatccaccagaccacggaagagtgcccgcttacagGTGGTCTCAT

ACAGAACTTATAAGATTCCCAAATCCAAAGACATTTCACGTTTATGGTGATTTCCCA

GAACACATAGCGACATGCAAATATTGCAGGGCGCCACTCCCCTGTCCgctctccttttgcacgg tctagagcgtcaacgactgcgcacgccagtggccaaaaaagctagcgcagcagccgccgcgcctggaaggaagccaaaaggagcgct ccccgttgtctgacgtcgcacacctgggttcgacacgcgggcggtaaccgcatggatcacggcggacggccggatccggggttcgaac cccggtcgtccgccatgatacccttgcgaatttatccaccagaccacggaagagtgcccgcttacagGTGGTCTCATACAGA

ACTTATAAGATTCCCAAATCCAAAGACATTTCACGTTTATGGTGATTTCCCAGAACA

CATAGCGACATGCAAATATTGCAGGGCGCCACTCCCCTGTCCgctctccttttgcacggtctagagc gtcaacgactgcgcacggggcgttttaggcggagtaacttgcatgtattgggaattgtagttttttaaaatgggaagtgacgtatcgtggga aaacggaagtgaagatttgaggaagttgtgggttttttggctttcgtttctgggcgtaggttcgcgtgcggttttctgggtgttttttgtggacttta accgttacgtcattttttagtcctatatatactcgctctgtaCTCTCCCTATCAGTGATAGAGATCTCCCTATCAG TGATAGAGATCGcttggccctttttacactgtgactgattgagctggtgccgtgtcgagtggtgttttttaataggtttttttactggtaa ggctgactgttatggctgccgctgtgaagcgctgtatgttgttctggagcgggagggtgctatttttgcctaggcaggagggttttcaggtgt ttatgtgttttttctctcctattaattttgttatacctcctatgggggctgtaatgttgtctctacgcctgcgggtatgtattccccggctatttcg gtcgcttttagcactgaccgatgttaaccaacctgatgtgtttaccgagtcttacattatgactccggacatgaccgaggaactgtcggtggtgctt tttaatcacggtgaccagtttttttacggtcacgccggcatggccgtagtccgtcttatgcttataagggttgttttcctgttgtaagacaggcttc taatgtttaaatgtttttttttttgttattttattttgtgtttaatgcaggaacccgcagacatgtttgagagaaaaatggtgtcttttctgtggtg gttccggaacttacctgcctttatctgcatgagcatgactacgatgtgcttgctttttgcgcgaggctttgcctgattttttgagcagcaccttgca ttttatatcgccgccatgcaacaagcttacatagggggctacgctggttagcatagctccgagtatgcgtgtcataatcagtgtgggttcttttgtca tggttcctggcggggaagtggccgcgctggtccgtgcagacctgcacgattatgttcagctggccctgcgaagggacctacgggatcgcggt attttttgttaatgttccgcttttgaatcttatacaggtctgtgaggaacctgaatttttgcaatcatgattcgctgcttgaggctgaaggtggagggc gctctggagcagattttttacaatggccggacttaatattcgggatttgcttagagacatattgataaggtggcgagatgaaaattatttgggcat ggttgaaggtgctggaatgtttatagaggagattcaccctgaagggtttagcctttacgtccacttggacgtgagggcagtttgccttttggaa gccattgtgcaacatcttacaaatgccattatctgttctttggctgtagagtttgaccacgccaccggaggggagcgcgttcacttaatagatct tcattttgaggttttggataatcttttggaataaaaaaaaaaaacatggttcttccagctcttcccgctcctcccgtgtgtgactcgcagaacga atgtgtaggttggctgggtgtggcttattctgcggtggtggatgttatcagggcagcggcgcatgaaggagtttacatagaacccgaagcca gggggcgcctggatgctttgagagagtggatatactacaactactacacagagcgagctaagcgacgagaccggagacgcagatctgttt gtcacgcccgcacctggttttgcttcaggaaatatgTACCCATACGATGTTCCAGATTACGCTGGAGGAGG CGGAGGCactacgtccggcgttccatttggcatgacactacgaccaacacgatctcggttgtctcggcgcactccgtacagtagggat cgcctacctccttttgagacagagacccgcgctaccatactggaggatcatccgctgctgcccgaatgtaacactttgacaatgcacaacgt gagttacgtgcgaggtcttccctgcagtgtgggatttacgctgattcaggaatgggttgttccctgggatatggttctgacgcgggaggagctt gtaatcctgaggaagtgtatgcacgtgtgcctgtgttgtgccaacattgatatcatgacgagcatgatgatccatggttacgagtcctgggctc tccactgtcattgttccagtcccggttccctgcagtgcatagccggcgggcaggttttggccagctggtttaggatggtggtggatggcgcca
```

```
tgtttaatcagaggtttatatggtaccgggaggtggtgaattacaacatgccaaaagaggtaatgtttatgtccagcgtgtttatgaggggtcgc
cacttaatctacctgcgcttgtggtatgatggccacgtgggttctgtggtccccgccatgagctttggatacagcgccttgcactgtgggatttt
gaacaatattgtggtgctgtgctgcagttactgtgctgatttaagtgagatcagggtgcgctgctgtgcccggaggacaaggcgtctcatgct
gcgggcggtgcgaatcatcgctgaggagaccactgccatgttgtattcctgcaggacggagcggcggcggcagcagtttattcgcgcgct
gctgcagcaccaccgccctatcctgatgcacgattatgactctaccccatgtaggcgtggacttccccttcgccgcccgttgagcaaccgc
aagttggacagcagcctgtggctcagcagctggacagcgacatgaacttaagcgagctgcccggggagtttattaatatcactgatgagcg
tttggctcgacaggaaaccgtgtggaatataacacctaagaatatgtctgttacccatgatatgatgcttttttaaggccagccggggagaaag
gactgtgtactctgtgtgttgggagggaggtggcaggttgaatactagggttctgtgagtttgattaaggtacggtgatcaatataagctatgtg
gtggtggggctatactactgaatgaaaaatgacttgaaattttctgcaattgaaaaataaacacgttgaaacataacatgcaacaggttcacga
ttctttattcctgggcaatgtaggagaaggtgtaagagttggtagcaaaagtttcagtggtgtattttccactttcccaggaccatgtaaaagaca
tagagtaagtgcttacctcgctagtttctgtggattcactagaatccactttggccgcggctcgagTGAGCTATTCCAGAAGT
AGTGAAGAGGCTTTTTTGGAGGCCTAGGCTTTTGCAAAAAGCTCCGGATCGATGCCC
GGGGGATCCACTAGTTCTAGAGGGACAGCCCCCCCCCAAAGCCCCCAGGGATGTAA
TTACGTCCCTCCCCCGCTAGGGGGCAGCAGCGAGCCGCCCGGGGCTCCGCTCCGGTC
CGGCGCTCCCCCCGCATCCCCGAGCCGGCAGCGTGCGGGACAGCCCGGGCACGGG
GAAGGTGGCACGGGATCGCTTTCCTCTGAACGCTTCTCGCTGCTCTTTGAGCCTGCA
GACACCTGGGGGATACGGGGAAAAGGCCTCCAAGGCCAGCTTCCCACAATAAGTT
GGGTGAATTTTGGCTGAGCTATTCCAGAAGTAGTGAAGAGGCTTTTTTGGAGGCCTA
GGCTTTTGCAAAAAGCTCCGGATCGATCATATATGGCAGATATACGCGTTGACATTG
ATTATTGACTAGTTATTAATAGTAATCAATTACGGGGTCATTAGTTCATAGCCCATAT
ATGGAGTTCCGCGTTACATAACTTACGGTAAATGGCCCGCCTGGCTGACCGCCCAAC
GACCCCCGCCCATTGACGTCAATAATGACGTATGTTCCCATAGTAACGCCAATAGGG
ACTTTCCATTGACGTCAATGGGTGGAGTATTTACGGTAAACTGCCCACTTGGCAGTA
CATCAAGTGTATCATATGCCAAGTACGCCCCCTATTGACGTCAATGACGGTAAATGG
CCCGCCTGGCATTATGCCCAGTACATGACCTTATGGGACTTTCCTACTTGGCAGTAC
ATCTACGTATTAGTCATCGCTATTACCATGGTGATGCGGTTTTGGCAGTACATCAAT
GGGCGTGGATAGCGGTTTGACTCACGGGGATTTCCAAGTCTCCACCCCATTGACGTC
AATGGGAGTTTGTTTTGGCACCAAAATCAACGGGACTTTCCAAAATGTCGTAACAAC
TCCGCCCCATTGACGCAAATGGGCGGTAGGCGTGTACGGTGGGAGGTCTATATAAG
CAGAGCTCTCTGGCTAACTATCGTCGACGAGCTCGTTTAGTGAACCGTCAGATCGCC
TGGAGACGCCATCCACGCTGTTTTGACCTCCATAGAAGACACCGGGACCGATCCAG
CCTCCGGACTCTAGCGTTTAAACTTAAGCTTGCCACCatgaccgagtacaagcccacggtgcgcctcgc
cacccgcgacgacgtccccagggccgtacgcaccctcgccgccgcgttcgccgactaccccgccacgcgccacaccgtcgatccggac
cgccacatcgagcgggtcaccgagctgcaagaactcttcctcacgcgcgtcgggctcgacatcggcaaggtgtgggtcgcggacgacg
gcgccgcggtggcggtctggaccacgccggagagcgtcgaagcggggcggtgttcgccgagatcggcccgcgcatggccgagttga
gcggttcccggctggccgcgcagcaacagatggaaggcctcctggcgccgcaccggcccaaggagcccgcgtggttcctggccaccgt
cggcgtctcgcccgaccaccagggcaagggtctgggcagcgccgtcgtgctccccggagtggaggcggccgagcgcgccggggtgc
ccgccttcctggagacctcgcgcccgcaacctccccttctacgagcggctcggcttcaccgtcaccgccgacgtcgaggtgcccgaag
gaccgcgcacctggtgcatgacccgcaagcccggtgcctgaAGCGCGGGGATCTCATGCTGGAGTTCTTCG
CCCACCCCAACTTGTTTATTGCAGCTTATAATGGTTACAAATAAAGCAATAGCATCA
```

-continued

```
CAAATTTCACAAATAAAGCATTTTTTTCACTGCATTCTAGTTGTGGTTTGTCCAAACT

CATCAATGTATCTTATCATGTCTGTAGCtGATgtATAcCTAggATCCGGCCGGccTGCAgg

TGTCCTCACAGGAACGAAGTCCCTAAAGAAACAGTGGCAGCCAGGTTTAGCCCCGG

AATTGACTGGATTCCTTTTTTAGGGCCCATTGGTATGGCTTTTTCCCCGTATCCCCCC

AGGTGTCTGCAGGCTCAAAGAGCAGCGAGAAGCGTTCAGAGGAAAGCGATCCCGTG

CCACCTTCCCCGTGCCCGGGCTGTCCCCGCACGCTGCCGGCTCGGGGATGCGGGGGG

AGCGCCGGACCGGAGCGGAGCCCCGGGCGGCTCGCTGCTGCCCCCTAGCGGGGAG

GGACGTAATTACATCCCTGGGGGCTTTGGGGGGGGCTGTCCCTCTAGAGCGGCCGC

CACCGCGGTGGAGCTCCAGCTTTTGTTCCCTTTAGTGAGGGTTAATTAGATCTTAATA

CGACTCACTATAGGGCGAATTGGGTACCGGGCCCCCCCTCGAGGTCGACGGTATCG

ATAAGCTTGATATCTATAACAAGAAAATATATATATAATAAGTTATCACGTAAGTAG

AACATGAAATAACAATATAATTATCGTATGAGTTAAATCTTAAAAGTCACGTAAAA

GATAATCATGCGTCATTTTGACTCACGCGGTCGTTATAGTTCAAAATCAGTGACACT

TACCGCATTGACAAGCACGCCTCACGGGAGCTCCAAGCGGCGACTGAGATGTCCTA

AATGCACAGCGACGGATTCGCGCTATTTAGAAAGAGAGCAATATTTCAAGAATG

CATGCGTCAATTTTACGCAGACTATCTTTCTAGGGTTAATCTAGCTGCATCAGGATC

ATATCGTCGGGTCTTTTTTCCGGCTCAGTCATCGCCCAAGCTGGCGCTATCTGGGCAT

CGGGGAGGAAGAAGCCCGTGCCTTTTCCCGCGAGGTTGAAGCGGCATGGAAAGAGT

TTGCCGAGGATGACTGCTGCTGCATTGACGTTGAGCGAAAACGCACGTTTACCATGA

TGATTCGGGAAGGTGTGGCCATGCACGCCTTTAACGGTGAACTGTTCGTTCAGGCCA

CCTGGGATACCAGTTCGTCGCGGCTTTTCCGGACACAGTTCCGGATGGTCAGCCCGA

AGCGCATCAGCAACCCGAACAATACCGGCGACAGCCGGAACTGCCGTGCCGGTGTG

CAGATTAATGACAGCGGTGCGGCGCTGGGATATTACGTCAGCGAGGACGGGTATCC

TGGCTGGATGCCGCAGAAATGGACATGGATACCCCGTGAGTTACCCGGCGGGCGCG

CTTGGCGTAATCATGGTCATAGCTGTTTCCTGTGTGAAATTGTTATCCGCTCACAATT

CCACACAACATACGAGCCGGAAGCATAAAGTGTAAAGCCTGGGGTGCCTAATGAGT

GAGCTAACTCACATTAATTGCGTTGCGCTCACTGCCCGCTTTCCAGTCGGGAAACCT

GTCGTGCCAGCTGCATTAATGAATCGGCCAACGCGCGGGGAGAGGCGGTTTGCGTA

TTGGGCGCTCTTCCGCTTCCTCGCTCACTGACTCGCTGCGCTCGGTCGTTCGGCTGCG

GCGAGCGGTATCAGCTCACTCAAAGGCGGTAATACGGTTATCCACAGAATCAGGGG

ATAACGCAGGAAAGAACATGTGAGCAAAAGGCCAGCAAAAGGCCAGGAACCGTAA

AAAGGCCGCGTTGCTGGCGTTTTTCCATAGGCTCCGCCCCCCTGACGAGCATCACAA

AAATCGACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCGCTTACCGG

ATACCTGTCCGCCTTTCTCCCTTCGGGAAGCGTGGCGCTTTCTCATAGCTCACGCTGT

AGGTATCTCAGTTCGGTGTAGGTCGTTCGCTCCAAGCTGGGCTGTGTGCACGAACCC

CCCGTTCAGCCCGACCGCTGCGCCTTATCCGGTAACTATCGTCTTGAGTCCAACCCG

GTAAGACACGACTTATCGCCACTGGCAGCAGCCACTGGTAACAGGATTAGCAGAGC

GAGGTATGTAGGCGGTGCTACAGAGTTCTTGAAGTGGTGGCCTAACTACGGCTACAC

TAGAAGGACAGTATTTGGTATCTGCGCTCTGCTGAAGCCAGTTACCTTCGGAAAAAG

AGTTGGTAGCTCTTGATCCGGCAAACAAACCACCGCTGGTAGCGGTGGTTTTTTTGT
```

-continued

```
TTGCAAGCAGCAGATTACGCGCAGAAAAAAAGGATCTCAAGAAGATCCTTTGATCT

TTTCTACGGGGTCTGACGCTCAGTGGAACGAAAACTCACGTTAAGGGATTTTGGTCA

TGAGATTATCAAAAAGGATCTTCACCTAGATCCTTTTAAATTAAAAATGAAGTTTTA

AATCAATCTAAAGTATATATGAGTAAACTTGGTCTGACAGTTACCAATGCTTAATCA

GTGAGGCACCTATCTCAGCGATCTGTCTATTTCGTTCATCCATAGTTGCCTGACTCCC

CGTCGTGTAGATAACTACGATACGGGAGGGCTTACCATCTGGCCCCAGTGCTGCAAT

GATACCGCGAGACCCACGCTCACCGGCTCCAGATTTATCAGCAATAAACCAGCCAG

CCGGAAGGGCCGAGCGCAGAAGTGGTCCTGCAACTTTATCCGCCTCCATCCAGTCTA

TTAATTGTTGCCGGGAAGCTAGAGTAAGTAGTTCGCCAGTTAATAGTTTGCGCAACG

TTGTTGCCATTGCTACAGGCATCGTGGTGTCACGCTCGTCGTTTGGTATGGCTTCATT

CAGCTCCGGTTCCCAACGATCAAGGCGAGTTACATGATCCCCCATGTTGTGCAAAAA

AGCGGTTAGCTCCTTCGGTCCTCCGATCGTTGTCAGAAGTAAGTTGGCCGCAGTGTT

ATCACTCATGGTTATGGCAGCACTGCATAATTCTCTTACTGTCATGCCATCCGTAAG

ATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGA

TCTTACCGCTGTTGAGATCCAGTTCGATGTAACCCACTCGTGCACCCAACTGATCTTC

AGCATCTTTTACTTTCACCAGCGTTTCTGGGTGAGCAAAAACAGGAAGGCAAAATGC

CGCAAAAAAGGGAATAAGGGCGACACGGAAATGTTGAATACTCAT
```

The sequence of the pPBBG-iHelper3.1-HA vector is provided below:

pPBBG-iHelper3.1-HA (18,311 bp)

(SEQ ID NO: 12)

```
ACTCTTCCTTTTTCAATATTATTGAAGCATTTATCAGGGTTATTGTCTCATGA

GCGGATACATATTTGAATGTATTTAGAAAAATAAACAAATAGGGGTTCCGCGCACA

TTTCCCCGAAAAGTGCCACCTAAATTGTAAGCGTTAATATTTTGTTAAAATTCGCGTT

AAATTTTTGTTAAATCAGCTCATTTTTTAACCAATAGGCCGAAATCGGCAAAATCCC

TTATAAATCAAAAGAATAGACCGAGATAGGGTTGAGTGTTGTTCCAGTTTGGAACA

AGAGTCCACTATTAAAGAACGTGGACTCCAACGTCAAAGGGCGAAAAACCGTCTAT

CAGGGCGATGGCCCACTACGTGAACCATCACCCTAATCAAGTTTTTTGGGGTCGAGG

TGCCGTAAAGCACTAAATCGGAACCCTAAAGGGAGCCCCCGATTTAGAGCTTGACG

GGGAAAGCCGGCGAACGTGGCGAGAAAGGAAGGGAAGAAAGCGAAAGGAGCGGG

CGCTAGGGCGCTGGCAAGTGTAGCGGTCACGCTGCGCGTAACCACCACACCCGCCG

CGCTTAATGCGCCGCTACAGGGCGCGTCCCATTCGCCATTCAGGCTGCGCAACTGTT

GGGAAGGGCGATCGGTGCGGGCCTCTTCGCTATTACGCCAGCTGGCGAAAGGGGGA

TGTGCTGCAAGGCGATTAAGTTGGGTAACGCCAGGGTTTTCCCAGTCACGACGTTGT

AAAACGACGGCCAGTGAGCGCGCCTCGTTCATTCACGTTTTTGAACCCGTGGAGGAC

GGGCAGACTCGCGGTGCAAATGTGTTTTACAGCGTGATGGAGCAGATGAAGATGCT

CGACACGCTGCAGAACACGCAGCTAGATTAACCCTAGAAAGATAATCATATTGTGA

CGTACGTTAAAGATAATCATGCGTAAAATTGACGCATGTGTTTTATCGGTCTGTATA
```

```
TCGAGGTTTATTTATTAATTTGAATAGATATTAAGTTTTATTATATTTACACTTACAT

ACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCggtacccaactccatgcttaacagtccccaggtacagcccaccctgcgtcgcaaccaggaaca gctctacagcttcctggagcgccactcgccctacttccgcagccacagtgcgcagattaggagcgccacttcttttttgtcacttgaaaaacat gtaaaaataatgtactaggagacacttttcaataaaggcaaatgttttttatttgtacactctcgggtgattatttacccccccaccccttgccgtctgcg ccgtttaaaaatcaaaggggttctgccgcgcatcgctatgcgccactggcagggacacgttgcgatactggtgtttagtgctccacttaaact caggcacaaccatccgcggcagctcggtgaagttttcactccacaggctgcgcaccatcaccaacgcgtttagcaggtcgggcgccgata tcttgaagtcgcagttggggcctccgccctgcgcgcgcgagttgcgatacacaggggttgcagcactggaacactatcagcgccgggtggt gcacgctggccagcacgctcttgtcggagatcagatccgcgtccaggtcctccgcgttgctcagggcgaacggagtcaactttggtagctg ccttcccaaaaagggtgcatgcccaggctttgagttgcactcgcaccgtagtggcatcagaaggtgaccgtgcccggtctgggcgttagga tacagcgcctgcatgaaagccttgatctgcttaaaagccacctgagcctttgcgccttcagagaagaacatgccgcaagacttgccggaaa actgattggccggacaggccgcgtcatgcacgcagcaccttgcgtcggtgttggagatctgcaccacatttcggcccaccggttcttcacg atcttggccttgctagactgctccttcagcgcgcgctgcccgttttcgctcgtcacatccatttcaatcacgtgctccttatttatcataatgctccc gtgtagacacttaagctcgccttcgatctcagcgcagcggtgcagccacaacgcgcagcccgtgggctcgtggtgcttgtaggttacctctg caaacgactgcaggtacgcctgcaggaatcgcccatcatcgtcacaaaggtcttgttgctggtgaaggtcagctgcaacccgcggtgctc ctcgtttagccaggtcttgcatacggccgccagagcttccacttggtcaggcagtagcttgaagtttgcctttagatcgttatccacgtggtactt gtccatcaacgcgcgcgcagcctccatgcccttctcccacgcagacacgatcggcaggctcagcgggtttatcaccgtgctttcactttccg cttcactggactcttccttttcctcttgcgtccgcataccccgcgccactgggtcgtcttcattcagccgccgcaccgtgcgcttacctcccttgc cgtgcttgattagcaccggtgggttgctgaaacccaccatttgtagcgccacatcttctctttcttcctcgctgtccacgatcacctctggggat ggcgggcgctcgggcttgggagaggggcgcttcttttttcttttttggacgcaatggccaaatccgccgtcgaggtcgatggccgcgggctgg gtgtgcgcggcaccagcgcatcttgtgacgagtcttcttcgtcctcggactcgagacgccgcctcagccgcttttttgggggcgcgcgggg aggcggcggcgacggcgacggggacgacacgtcctccatggttggtggacgtcgcgccgcaccgcgtccgcgctcggggtggtttc gcgctgctcctcttcccgactggccatttccttctcctataggcagaaaaagatcatggagtcagtcgagaaggaggacagcctaaccgccc cctttgagttcgccaccaccgcctccaccgatgccgccaacgcgcctaccaccttcccgtcgaggcaccccgcttgaggaggaggaa gtgattatcgagcaggacccaggttttgtaagcgaagacgacgaggatcgctcagtaccaacagaggataaaaagcaagaccaggacga cgcagaggcaaacgaggaacaagtcgggcgggggggaccaaaggcatggcgactacctagatgtgggagacgacgtgctgttgaagca tctgcagcgccagtgcgccattatctgcgacgcgttgcaagagcgcagcgatgtgccccctcgccatagcggatgtcagccttgcctacgaa cgccacctgttctcaccgcgcgtaccccccaaacgccaagaaaacggcacatgcgagcccaacccgcgcctcaacttctaccccgtatttg ccgtgccagaggtgcttgccacctatcacatcttttttccaaaactgcaagataccccctatcctgccgtgccaaccgcagccgagcggacaag cagctggccttgcggcagggcgctgtcatacctgatatcgcctcgctcgacgaagtgccaaaaatctttgagggtcttggacgcgacgaga aacgcgcggcaaacgctctgcaacaagaaaacagcgaaaatgaaagtcactgtggagtgctggtggaacttgagggtgacaacgcgcg cctagccgtgctgaaacgcagcatcgaggtcacccactttgcctacccggcacttaacctaccccccaaggttatgagcacagtcatgagc
```

```
gagctgatcgtgcgccgtgcacgaccccctggagagggatgcaaacttgcaagaacaaaccgaggagggcctacccgcagttggcgatg
agcagctggcgcgctggcttgagacgcgcgagcctgccgacttggaggagcgacgcaagctaatgatggccgcagtgcttgttaccgtg
gagcttgagtgcatgcagcggttctttgctgacccggagatgcagcgcaagctagaggaaacgttgcactacacctttcgccagggctacg
tgcgccaggcctgcaaaatttccaacgtggagctctgcaacctggtctcctaccttggaattttgcacgaaaaccgcctcgggcaaaacgtg
cttcattccacgctcaagggcgaggcgcgccgcgactacgtccgcgactgcgtttacttatttctgtgctacacctggcaaacggccatggg
cgtgtggcagcaatgcctggaggagcgcaacctaaaggagctgcagaagctgctaaagcaaaacttgaaggacctatggacggcttca
acgagcgctccgtggccgcgcacctggcggacattatcttccccgaacgcctgcttaaaaccctgcaacagggtctgccagacttcaccag
tcaaagcatgttgcaaaactttaggaactttatcctagagcgttcaggaattctgcccgccacctgctgtgcgcttcctagcgactttgtgccca
ttaagtaccgtgaatgccctccgccgctttggggtcactgctaccttctgcagctagccaactaccttgcctaccactccgacatcatggaaga
cgtgagcggtgacggcctactggagtgtcactgtcgctgcaacctatgcaccccgcaccgctccctggtctgcaattcgcaactgcttagcg
aaagtcaaattatcggtacctttgagctgcagggtccctcgcctgacgaaaagtccgcggctccggggttgaaactcactccggggctgtg
gacgtcCGATCTCTATCACTGATAGGGAGATCTCTATCACTGATAGGGAGAGggcttaccttcg
caaatttgtacctgaggactaccacgcccacgagattaggttctacgaagaccaatcccgcccgccaaatgcggagcttaccgcctgcgtc
attacccagggccacatccttggccaattgcaagccatcaacaaagcccgccaagagtttctgctacgaaagggacgggggggtttacctgg
accccagtccggcgaggagctcaacccaatcccccgccgccgcagccctatcagcagccgcgggcccttgcttcccaggatggcac
ccaaaaagaagctgcagctgccgccgccgccacccacggacgaggaggaatactgggacagtcaggcagaggaggttttggacgagg
aggaggagatgatggaagactgggacagcctagacgaagcttccgaggccgaagaggtgtcagacgaaacaccgtcaccctcggtcgc
attcccctcgccggcgccccagaaattggcaaccgttcccagcatcgctacaacctccgctcctcaggcgccgccggcactgcctgttcgc
cgacccaaccgtagatgggacaccactggaaccagggccggtaagtctaagcagccgccgccgttagcccaagagcaacaacagcgc
caaggctaccgctcgtggcgcgggcacaagaacgccatagttgcttgcttgcaagactgtggggcaacatctccttcgcccgccgctttct
tctctaccatcacggcgtggccttcccccgtaacatcctgcattactaccgtcatctctacagcccctactgcaccggcggcagcggcagcg
gcagcaacagcagcggtcacacagaagcaaaggcgaccggatagcaagactctgacaaagcccaagaaatccacagcggcggcagc
agcaggaggaggagcgctgcgtctggcgcccaacgaacccgtatcgacccgcgagcttagaaataggattttttcccactctgtatgctatat
ttcaacaaagcagggaaagaacaagagctgaaaaaaaaaacaggtctctgcgctccctcacccgcagctgcctgtatcacaaagcg
aagatcagcttcggcgcacgctggaagacgcggaggctctcttcagcaaCGATCTCTATCACTGATAGGGAGATC
TCTATCACTGATAGGGAGAGatactgcgcgctgactcttaaggactagtttcgcgccctttctcaaatttaagcgcgaaaa
ctacgtcatctccagcggccacacccggcgccagcacctgtcgtcagcgccattatgagcaaggaaattcccacgccctacatgtggagtt
accagccacaaatgggacttgcggctggagctgcccaagactactcaacccgaataaactacatgagcgcgggaccccacatgatatccc
gggtcaacgaatccgcgccaccgaaaccgaattctcctcgaacaggggctattaccaccacacctcgtaataaccttaatccccgtagt
tggcccgctgccctggtgtaccaggaaagtcccgctcccaccactgtggtacttcccagagacgcccaggccgaagttcagatgactaact
caggggcgcagcttgcgggcggctttcgtcacagggtgcggtcgcccccagtggccaaaaaagctagcgcagcagccgccgcgcctg
gaaggaagccaaaaggagcgctcccccgttgtctgacgtcgcacacctgggttcgacacgcgggcggtaaccgcatggatcacggcgg
acggccggatccggggttcgaaccccggtcgtccgccatgataccctttgcgaatttatccaccagaccacggaagagtgcccgcttacag
gctctccttttgcacggtctagagcgtcaacgactgcgcacgggggcgttttagggcggagtaacttgcatgtattgggaattgtagttttttttaa
aatgggaagtgacgtatcgtgggaaaacggaagtgaagatttgaggaagttgtgggttttttggctttcgtttctgggcgtaggttcgcgtgcg
gttttctgggtgttttttgtggactttaaccgttacgtcatttttttagtcctatatatactcgctctgtaCTCTCCCTATCAGTGATAG
AGATCTCCCTATCAGTGATAGAGATCGcttggcccttttttacactgtgactgattgagctggtgccgtgtcgagtggt
gttttttaataggttttttttactggtaaggctgactgttatggctgccgctgtggaagcgctgtatgttgttctggagcgggagggtgctattttgcc
taggcaggagggttttttcaggtgtttatgtgtttttctctcctattaattttgttatacctcctatgggggctgtaatgttgtctctacgcctgcggg
tatgtattccccgggctatttcggtcgcttttttagcactgaccgatgttaaccaacctgatgtgtttaccgagtcttacattatgactccggacatg
```

-continued

```
accgaggaactgtcggtggtgcttttttaatcacggtgaccagttttttttacggtcacgccggcatggccgtagtccgtcttatgcttataagggtt
gttttttcctgttgtaagacaggcttctaatgtttaaatgtttttttttttgttattttattttgtgtttaatgcaggaaccgcagacatgtttgaga
gaaaaatggtgtcttttctgtggtggttccggaacttacctgcctttatctgcatgagcatgactacgatgtgcttgcttttttgcgcgaggctttg
cctgattttttgagcagcaccttgcattttatatcgccgcccatgcaacaagcttacatagggctacgctggttagcatagctccgagtatgcgtgt
cataatcagtgtgggttcttttgtcatggttcctggcggggaagtggccgcgctggtccgtgcagacctgcacgattatgttcagctggccctgc
gaagggacctacggatcgcggtattttgttaatgttccgcttttgaatcttatacaggtctgtgaggaacctgaatttttgcaatcatgattcgc
tgcttgaggctgaaggtggagggcgctctggagcagattttacaatggccggacttaatattcgggatttgcttagagacatattgataaggt
ggcgagatgaaaattatttgggcatggttgaaggtgctggaatgtttatagaggagattcaccctgaagggtttagcctttacgtccacttgga
cgtgagggcagtttgccttttggaagccattgtgcaacatcttacaaatgccattatctgttctttggctgtagagtttgaccacgccaccggag
gggagcgcgttcacttaatagatcttcattttgaggttttggataatcttttggaataaaaaaaaaaaaacatggttcttccagctcttcccgctcc
tcccgtgtgtgactcgcagaacgaatgtgtaggttggctgggtgtggcttattctgcggtggtggatgttatcagggcagcggcgcatgaag
gagtttacatagaacccgaagccaggggcgcctggatgctttgagagagtggatatactacaactactacacagagcgagctaagcgac
gagaccggagacgcagatctgtttgtcacgcccgcacctggttttgcttcaggaaatatgTACCCATACGATGTTCCAGA
TTACGCTGGAGGAGGCGGAGGCactacgtccggcgttccatttggcatgacactacgaccaacacgatctcggttgtct
cggcgcactccgtacagtagggatcgcctacctccttttgagacagagaccgcgctaccatactggaggatcatccgctgctgcccgaat
gtaacactttgacaatgcacaacgtgagttacgtgcgaggtcttccctgcagtgtgggatttacgctgattcaggaatgggttgttccctggga
tatggttctgacgcggggaggagcttgtaatcctgaggaagtgtatgcacgtgtgcctgtgttgtgccaacattgatatcatgacgagcatgatg
atccatggttacgagtcctgggctctccactgtcattgttccagtcccggttccctgcagtgcatagccggcgggcaggttttggccagctggt
ttaggatggtggtggatggcgccatgtttaatcagaggtttatatggtaccgggaggtggtgaattacaacatgccaaaagaggtaatgtttat
gtccagcgtgtttatgaggggtcgccacttaatctacctgcgcttgtggtatgatggccacgtgggttctgtggtccccgccatgagctttgga
tacagcgccttgcactgtgggattttgaacaatattgtggtgctgtgctgcagttactgtgctgatttaagtgagatcagggtgcgctgctgtgc
ccggaggacaaggcgtctcatgctgcgggcggtgcgaatcatcgctgaggagaccactgccatgttgtattcctgcaggacggagcggc
ggcggcagcagtttattcgcgcgctgctgcagcaccaccgccctatcctgatgcacgattatgactctaccccatgtaggcgtggacttcc
ccttcgccgcccgttgagcaaccgcaagttggacagcagcctgtggctcagcagctggacagcgacatgaacttaagcgagctgcccgg
ggagtttattaatatcactgatgagcgtttggctcgacaggaaaccgtgtggaatataacacctaagaatatgtctgttacccatgatatgatgc
tttttaaggccagccggggagaaaggactgtgtactctgtgtgttgggagggaggtggcaggttgaatactagggttctgtgagtttgattaa
ggtacggtgatcaatataagctatgtggtggtggggctatactactgaatgaaaaatgacttgaaattttctgcaattgaaaaataaacacgttg
aaacataacatgcaacaggttcacgattctttattcctgggcaatgtaggagaaggtgtaagagttggtagcaaaagtttcagtggtgtattttc
cactttcccaggaccatgtaaaagacatagagtaagtgcttacctcgctagtttctgtggattcactagaatccactttggccgcggctcgagg
agggacagccccccccaaagccccagggatgtaattacgtccctcccccgctaggggcagcagcgagccgcccggggctccgct
ccggtccggcgctcccccgcatccccgagccggcagcgtgcggggacagcccgggcacggggaaggtggcacgggatcgctttcct
ctgaacgcttctcgctgctctttgagcctgcagacacctgggggatacggggaaaaggcctccaaggccagcttcccacaataagttggg
tgaattttggctcattcctcctttctataggattgaggtcagagcGACATTGATTATTGACTAGTTATTAATAGTA
ATCAATTACGGGGTCATTAGTTCATAGCCCATATATGGAGTTCCGCGTTACATAACT
TACGGTAAATGGCCCGCCTGGCTGACCGCCCAACGACCCCCGCCCATTGACGTCAAT
AATGACGTATGTTCCCATAGTAACGCCAATAGGGACTTTCCATTGACGTCAATGGGT
GGAGTATTTACGGTAAACTGCCCACTTGGCAGTACATCAAGTGTATCATATGCCAAG
TACGCCCCCTATTGACGTCAATGACGGTAAATGGCCCGCCTGGCATTATGCCCAGTA
CATGACCTTATGGGACTTTCCTACTTGGCAGTACATCTACGTATTAGTCATCGCTATT
ACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGAACCAA
```

```
AATCAACGGGACTTTCCAAAATGTCGTAACAACTCCGCCCCATTGACGCAAATGGG
CGGTAGGCGTGTACGGTGGGAGGTCTATATAAGCAGAGCTCTCCCTATCAGTGATAG
AGATCTCCCTATCAGTGATAGAGATCGTCGACGAGCTCGTTTAGTGAACCGTCAGAT
CGCCTGGAGACGCCATCCACGCTGTTTTGACCTCCATAGAAGACACCGGGACCGATC
CAGCCTgaacgcgcagccgccatgGACTACAAAGACGATGACGACAAGGGAGGAGGCGGAG
GCacaactagaacaaagggcaggggccatactgcggccacgactcaaaacgacagaatgccaggccctgagctttcgggctggatctc
tgagcagctaatgaccggaagaattcctgtaagcgacatcttctgtgatattgagaacaatccaggattatgctacgcatcccaaatgcaaca
aacgaagccaaacccgaagacgcgcaacagtcaaacccaaacggacccaatttgcaatcatagttttgaggaggtagtacaaacattggct
tcattggctactgttgtgcaacaacaaaccatcgcatcagaatcattagaacaacgcattacgagtcttgagaatggtctaaagccagtttatg
atatggcaaaaacaatctcctcattgaacagggtttgtgctgagatggttgcaaaatatgatcttctggtgatgacaaccggtcgggcaacag
caaccgctgcggcaactgaggcttattgggccgaacatggtcaaccaccacctggaccatcactttatgaagaaagtgcgattcggggtaa
gattgaatctagagatgagaccgtccctcaaagtgttagggaggcattcaacaatctaaacagtaccacttcactaactgaggaaaattttgg
gaaacctgacatttcggcaaaggatttgagaaacattatgtatgatcacttgcctggttttggaactgctttccaccaattagtacaagtgatttgt
aaattgggaaaagatagcaactcattggacatcattcatgctgagttccaggccagcctggctgaaggagactctcctcaatgtgccctaatt
caaattacaaaaagagttccaatcttccaagatgctgctccacctgtcatccacatccgctctcgaggtgacattccccgagcttgccagaaa
agcttgcgtccagtcccaccatcgcccaagattgatcgaggttgggtatgtgttttttcagcttcaagatggtaaaacacttggactcaaaatttg
aGGATCCACTAGTCCAGTGTGGTGGAATTCTGCAGATATCCAGCACAGTGGCGGCCG
CTCGAGTCTAGAGGGCCCGTTTAAACCCGCTGATCAGCCTCGACTGTGCCTTCTAGT
TGCCAGCCATCTGTTGTTTGCCCCTCCCCCGTGCCTTCCTTGACCCTGGAAGGTGCCA
CTCCCACTGTCCTTTCCTAATAAAATGAGGAAATTGCATCGCATTGTCTGAGTAGGT
GTCATTCTATTCTGGGGGGTGGGGTGGGGCAGGACAGCAAGGGGGAGGATTGGGAA
GACAATAGCAGGCATGCTGGGGATGCGGTGGGCTCTATGGTGAGCTATTCCAGAAG
TAGTGAAGAGGCTTTTTTGGAGGCCTAGGCTTTTGCAAAAAGCTCCGGATCGATGCC
CGGGGGATCCACTAGTTCTAGAGGGACAGCCCCCCCCCAAAGCCCCCAGGGATGTA
ATTACGTCCCTCCCCCGCTAGGGGGCAGCAGCGAGCCGCCCGGGGCTCCGCTCCGGT
CCGGCGCTCCCCCCGCATCCCCGAGCCGGCAGCGTGCGGGGACAGCCCGGGCACGG
GGAAGGTGGCACGGGATCGCTTTCCTCTGAACGCTTCTCGCTGCTCTTTGAGCCTGC
AGACACCTGGGGGGATACGGGGAAAAGGCCTCCAAGGCCAGCTTCCCACAATAAGT
TGGGTGAATTTTGGCTGAGCTATTCCAGAAGTAGTGAAGAGGCTTTTTTGGAGGCCT
AGGCTTTTGCAAAAAGCTCCGGATCGATCATATATGGCAGATATACGCGTTGACATT
GATTATTGACTAGTTATTAATAGTAATCAATTACGGGGTCATTAGTTCATAGCCCAT
ATATGGAGTTCCGCGTTACATAACTTACGGTAAATGGCCCGCCTGGCTGACCGCCCA
ACGACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGCAG
TACATCAAGTGTATCATATGCCAAGTACGCCCCCTATTGACGTCAATGACGGTAAAT
GGCCCGCCTGGCATTATGCCCAGTACATGACCTTATGGGACTTTCCTACTTGGCAGT
ACATCTACGTATTAGTCATCGCTATTACCATGGTGATGCGGTTTTGGCAGTACATCA
ATGGGCGTGGATAGCGGTTTGACTCACGGGGATTTCCAAGTCTCCACCCCATTGACG
TCAATGGGAGTTTGTTTTGGCACCAAAATCAACGGGACTTTCCAAAATGTCGTAACA
ACTCCGCCCCATTGACGCAAATGGGCGGTAGGCGTGTACGGTGGGAGGTCTATATA
```

-continued

AGCAGAGCTCTCTGGCTAACTATCGTCGACGAGCTCGTTTAGTGAACCGTCAGATCG

CCTGGAGACGCCATCCACGCTGTTTTGACCTCCATAGAAGACACCGGGACCGATCCA

GCCTCCGGACTCTAGCGTTTAAACTTAAGCTTGCCACCatgaccgagtacaagcccacggtgcgcctc gccaccgcgacgacgtccccagggccgtacgcaccctcgccgccgcgttcgccgactaccccgccacgcgccacaccgtcgatccg gaccgccacatcgagcgggtcaccgagctgcaagaactcttcctcacgcgcgtcgggctcgacatcggcaaggtgtgggtcgcggacg acggcgccgcggtggcggtctggaccacgccggagagcgtcgaagcgggggcggtgttcgccgagatcggcccgcgcatggccgag ttgagcggttcccggctggccgcgcagcaacagatggaaggcctcctggcgccgcaccggcccaaggagcccgcgtggttcctggcca ccgtcggcgtctcgcccgaccaccagggcaagggtctgggcagcgccgtcgtgctccccggagtggaggcggccgagcgcgccggg gtgcccgccttcctggagacctccgcgccccgcaacctcccccttctacgagcggctcggcttcaccgtcaccgccgacgtcgaggtgccc gaaggaccgcgcacctggtgcatgacccgcaagcccggtgcctgaAGCGCGGGGATCTCATGCTGGAGTTCTT

CGCCCACCCCAACTTGTTTATTGCAGCTTATAATGGTTACAAATAAAGCAATAGCAT

CACAAATTTCACAAATAAAGCATTTTTTTCACTGCATTCTAGTTGTGGTTTGTCCAAA

CTCATCAATGTATCTTATCATGTCTGTAGCtGATgtATAcCTAggATCCGGCCGGccTGC

AggTGTCCTCACAGGAACGAAGTCCCTAAAGAAACAGTGGCAGCCAGGTTTAGCCCC

GGAATTGACTGGATTCCTTTTTTAGGGCCCATTGGTATGGCTTTTTCCCCGTATCCCC

CCAGGTGTCTGCAGGCTCAAAGAGCAGCGAGAAGCGTTCAGAGGAAAGCGATCCCG

TGCCACCTTCCCCGTGCCCGGGCTGTCCCCGCACGCTGCCGGCTCGGGGATGCGGGG

GGAGCGCCGGACCGGAGCGGAGCCCCGGGCGGCTCGCTGCTGCCCCCTAGCGGGGG

AGGGACGTAATTACATCCCTGGGGGCTTTGGGGGGGGGCTGTCCCTCTAGAGCGGC

CGCCACCGCGGTGGAGCTCCAGCTTTTGTTCCCTTTAGTGAGGGTTAATTAGATCTTA

ATACGACTCACTATAGGGCGAATTGGGTACCGGGCCCCCCCTCGAGGTCGACGGTA

TCGATAAGCTTGATATCTATAACAAGAAAATATATATATAATAAGTTATCACGTAAG

TAGAACATGAAATAACAATATAATTATCGTATGAGTTAAATCTTAAAAGTCACGTAA

AAGATAATCATGCGTCATTTTGACTCACGCGGTCGTTATAGTTCAAAATCAGTGACA

CTTACCGCATTGACAAGCACGCCTCACGGGAGCTCCAAGCGGCGACTGAGATGTCC

TAAATGCACAGCGACGGATTCGCGCTATTTAGAAAGAGAGCAATATTTCAAGAA

TGCATGCGTCAATTTTACGCAGACTATCTTTCTAGGGTTAATCTAGCTGCATCAGGAT

CATATCGTCGGGTCTTTTTTCCGGCTCAGTCATCGCCCAAGCTGGCGCTATCTGGGCA

TCGGGGAGGAAGAAGCCCGTGCCTTTTCCCGCGAGGTTGAAGCGGCATGGAAAGAG

TTTGCCGAGGATGACTGCTGCTGCATTGACGTTGAGCGAAAACGCACGTTTACCATG

ATGATTCGGGAAGGTGTGGCCATGCACGCCTTTAACGGTGAACTGTTCGTTCAGGCC

ACCTGGGATACCAGTTCGTCGCGGCTTTTCCGGACACAGTTCCGGATGGTCAGCCCG

AAGCGCATCAGCAACCCGAACAATACCGGCGACAGCCGGAACTGCCGTGCCGGTGT

GCAGATTAATGACAGCGGTGCGGCGCTGGGATATTACGTCAGCGAGGACGGGTATC

CTGGCTGGATGCCGCAGAAATGGACATGGATACCCCGTGAGTTACCCGGCGGGCGC

GCTTGGCGTAATCATGGTCATAGCTGTTTCCTGTGTGAAATTGTTATCCGCTCACAAT

TCCACACAACATACGAGCCGGAAGCATAAAGTGTAAAGCCTGGGGTGCCTAATGAG

TGAGCTAACTCACATTAATTGCGTTGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTTCCGCTTCCTCGCTCACTGACTCGCTGCGCTCGGTCGTTCGGCTGC

GGCGAGCGGTATCAGCTCACTCAAAGGCGGTAATACGGTTATCCACAGAATCAGGG

-continued

```
GATAACGCAGGAAAGAACATGTGAGCAAAAGGCCAGCAAAAGGCCAGGAACCGTA

AAAAGGCCGCGTTGCTGGCGTTTTTCCATAGGCTCCGCCCCCCTGACGAGCATCACA

AAAATCGACGCTCAAGTCAGAGGTGGCGAAACCCGACAGGACTATAAAGATACCAG

GCGTTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACGCTG

TAGGTATCTCAGTTCGGTGTAGGTCGTTCGCTCCAAGCTGGGCTGTGTGCACGAACC

CCCCGTTCAGCCCGACCGCTGCGCCTTATCCGGTAACTATCGTCTTGAGTCCAACCC

GGTAAGACACGACTTATCGCCACTGGCAGCAGCCACTGGTAACAGGATTAGCAGAG

CGAGGTATGTAGGCGGTGCTACAGAGTTCTTGAAGTGGTGGCCTAACTACGGCTACA

CTAGAAGGACAGTATTTGGTATCTGCGCTCTGCTGAAGCCAGTTACCTTCGGAAAAA

GAGTTGGTAGCTCTTGATCCGGCAAACAAACCACCGCTGGTAGCGGTGGTTTTTTTG

TTTGCAAGCAGCAGATTACGCGCAGAAAAAAAGGATCTCAAGAAGATCCTTTGATC

TTTTCTACGGGGTCTGACGCTCAGTGGAACGAAAACTCACGTTAAGGGATTTTGGTC

ATGAGATTATCAAAAAGGATCTTCACCTAGATCCTTTTAAATTAAAAATGAAGTTTT

AAATCAATCTAAAGTATATATGAGTAAACTTGGTCTGACAGTTACCAATGCTTAATC

AGTGAGGCACCTATCTCAGCGATCTGTCTATTTCGTTCATCCATAGTTGCCTGACTCC

CCGTCGTGTAGATAACTACGATACGGGAGGGCTTACCATCTGGCCCCAGTGCTGCAA

TGATACCGCGAGACCCACGCTCACCGGCTCCAGATTTATCAGCAATAAACCAGCCA

GCCGGAAGGGCCGAGCGCAGAAGTGGTCCTGCAACTTTATCCGCCTCCATCCAGTCT

ATTAATTGTTGCCGGGAAGCTAGAGTAAGTAGTTCGCCAGTTAATAGTTTGCGCAAC

GTTGTTGCCATTGCTACAGGCATCGTGGTGTCACGCTCGTCGTTTGGTATGGCTTCAT

TCAGCTCCGGTTCCCAACGATCAAGGCGAGTTACATGATCCCCCATGTTGTGCAAAA

AAGCGGTTAGCTCCTTCGGTCCTCCGATCGTTGTCAGAAGTAAGTTGGCCGCAGTGT

TATCACTCATGGTTATGGCAGCACTGCATAATTCTCTTACTGTCATGCCATCCGTAAG

ATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGA

TCTTACCGCTGTTGAGATCCAGTTCGATGTAACCCACTCGTGCACCCAACTGATCTTC

AGCATCTTTTACTTTCACCAGCGTTTCTGGGTGAGCAAAAACAGGAAGGCAAAATGC

CGCAAAAAAGGGAATAAGGGCGACACGGAAATGTTGAATACTCAT
```

The sequence of the pPBBG-iHelper3.2-HA vector is provided below:

pPBBG-iHelper3.2-HA (18,728 bp)   (SEQ ID NO: 13)

```
ACTCTTCCTTTTTCAATATTATTGAAGCATTTATCAGGGTTATTGTCTCATGA

GCGGATACATATTTGAATGTATTTAGAAAAATAAACAAATAGGGGTTCCGCGCACA

TTTCCCCGAAAAGTGCCACCTAAATTGTAAGCGTTAATATTTTGTTAAAATTCGCGTT

AAATTTTTGTTAAATCAGCTCATTTTTTAACCAATAGGCCGAAATCGGCAAAATCCC

TTATAAATCAAAAGAATAGACCGAGATAGGGTTGAGTGTTGTTCCAGTTTGGAACA

AGAGTCCACTATTAAAGAACGTGGACTCCAACGTCAAAGGGCGAAAAACCGTCTAT
```

```
CAGGGCGATGGCCCACTACGTGAACCATCACCCTAATCAAGTTTTTTGGGGTCGAGG

TGCCGTAAAGCACTAAATCGGAACCCTAAAGGGAGCCCCCGATTTAGAGCTTGACG

GGGAAAGCCGGCGAACGTGGCGAGAAAGGAAGGGAAGAAAGCGAAAGGAGCGGG

CGCTAGGGCGCTGGCAAGTGTAGCGGTCACGCTGCGCGTAACCACCACACCCGCCG

CGCTTAATGCGCCGCTACAGGGCGCGTCCCATTCGCCATTCAGGCTGCGCAACTGTT

GGGAAGGGCGATCGGTGCGGGCCTCTTCGCTATTACGCCAGCTGGCGAAAGGGGGA

TGTGCTGCAAGGCGATTAAGTTGGGTAACGCCAGGGTTTTCCCAGTCACGACGTTGT

AAAACGACGGCCAGTGAGCGCGCCTCGTTCATTCACGTTTTTGAACCCGTGGAGGAC

GGGCAGACTCGCGGTGCAAATGTGTTTTACAGCGTGATGGAGCAGATGAAGATGCT

CGACACGCTGCAGAACACGCAGCTAGATTAACCCTAGAAAGATAATCATATTGTGA

CGTACGTTAAAGATAATCATGCGTAAAATTGACGCATGTGTTTTATCGGTCTGTATA

TCGAGGTTTATTTATTAATTTGAATAGATATTAAGTTTTATTATATTTACACTTACAT

ACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCggtacccaactccatgcttaacagtccccaggtacagcccaccctgcgtcgcaaccaggaaca gctctacagcttcctggagcgccactcgccctacttccgcagccacagtgcgcagattaggagcgccacttcttttttgtcacttgaaaaacat gtaaaaataatgtactaggagacacttcaataaaggcaaatgttttttattttgtacactctcgggtgattatttaccccccaccttgccgtctgcg ccgtttaaaaatcaaaggggttctgccgcgcatcgctatgcgccactggcagggacacgttgcgatactggtgtttagtgctccacttaaact caggcacaaccatccgcggcagctcggtgaagttttcactccacaggctgcgcaccatcaccaacgcgtttagcaggtcgggcgccgata tcttgaagtcgcagttggggcctccgccctgcgcgcgcgagttgcgatacacagggttgcagcactggaacactatcagcgccgggtggt gcacgctggccagcacgctcttgtcggagatcagatccgcgtccaggtcctccgcgttgctcagggcgaacggagtcaactttggtagctg ccttcccaaaaagggtgcatgcccaggctttgagttgcactcgcaccgtagtggcatcagaaggtgaccgtgcccggtctgggcgttagga tacagcgcctgcatgaaagccttgatctgcttaaaagccacctgagcctttgcgccttcagagaagaacatgccgcaagacttgccggaaa actgattggccggacaggccgcgtcatgcacgcagcaccttgcgtcggtgttggagatctgcaccacatttcggcccaccggttcttcacg atcttggccttgctagactgctccttcagcgcgcgctgcccgttttcgctcgtcacatccatttcaatcacgtgctccttatttatcataatgctccc gtgtagacacttaagctcgccttcgatctcagcgcagcggtgcagccacaacgcgcagcccgtgggctcgtggtgcttgtaggttacctctg caaacgactgcaggtacgcctgcaggaatcgcccccatcatcgtcacaaaggtcttgttgctggtgaaggtcagctgcaacccgcggtgctc ctcgtttagccaggtcttgcatacggccgccagagcttccacttggtcaggcagtagcttgaagtttgcctttagatcgttatccacgtggtactt gtccatcaacgcgcgcgcagcctccatgcccttctcccacgcagacacgatcggcaggctcagcgggtttatcaccgtgctttcactttccg cttcactggactcttcctttcctcttgcgtccgcataccccgcgccactgggtcgtcttcattcagccgccgcaccgtgcgcttacctcccttgc cgtgcttgattagcaccggtgggttgctgaaacccaccatttgtagcgccacatcttctctttcttcctcgctgtccacgatcacctctggggat ggcgggcgctcgggcttgggagaggggcgcttctttttcttttggacgcaatggccaaatccgccgtcgaggtcgatggccgcgggctgg gtgtgcgcggcaccagcgcatcttgtgacgagtcttcttcgtcctcggactcgagacgccgcctcagccgcttttttgggggcgcgcgggg
```

-continued aggcggcggcgacggcgacggggacgacacgtcctccatggttggtggacgtcgcgccgcaccgcgtccgcgctcggggggtggtttc gcgctgctcctcttcccgactggccatttccttctcctataggcagaaaaagatcatggagtcagtcgagaaggaggacagcctaaccgccc cctttgagttcgccaccaccgcctccaccgatgccgccaacgcgcctaccaccttcccgtcgaggcaccccgcttgaggaggaggaa gtgattatcgagcaggacccaggttttgtaagcgaagacgacgaggatcgctcagtaccaacagaggataaaaagcaagaccaggacga cgcagaggcaaacgaggaacaagtcgggcgggggaccaaaggcatggcgactacctagatgtgggagacgacgtgctgttgaagca tctgcagcgccagtgcgccattatctgcgacgcgttgcaagagcgcagcgatgtgccctcgccatagcggatgtcagccttgcctacgaa cgccacctgttctcaccgcgcgtaccccccaaacgccaagaaaacggcacatgcgagcccaacccgcgcctcaacttctaccccgtatttg ccgtgccagaggtgcttgccacctatcacatcttttttccaaaactgcaagataccctatcctgccgtgccaaccgcagccgagcggacaag cagctggccttgcggcagggcgctgtcatacctgatatcgcctcgctcgacgaagtgccaaaaatctttgagggtcttggacgcgacgaga aacgcgcggcaaacgctctgcaacaagaaaacagcgaaaatgaaagtcactgtggagtgctggtggaacttgagggtgacaacgcgcg cctagccgtgctgaaacgcagcatcgaggtcacccactttgcctacccggcacttaacctaccccccaaggttatgagcacagtcatgagc gagctgatcgtgcgccgtgcacgacccctggagagggatgcaaacttgcaagaacaaaccgaggagggcctacccgcagttggcgatg agcagctggcgcgctggcttgagacgcgcgagcctgccgacttggaggagcgacgcaagctaatgatggccgcagtgcttgttaccgtg gagcttgagtgcatgcagcggttctttgctgacccggagatgcagcgcaagctagaggaaacgttgcactacacctttcgccagggctacg tgcgccaggcctgcaaaatttccaacgtggagctctgcaacctggtctcctaccttggaattttgcacgaaaaccgcctcgggcaaaacgtg cttcattccacgctcaagggcgaggcgcgccgcgactacgtccgcgactgcgtttacttattctgtgctacacctggcaaacggccatggg cgtgtggcagcaatgcctggaggagcgcaacctaaaggagctgcagaagctgctaaagcaaaacttgaaggacctatggacggccttca acgagcgctccgtggccgcgcacctggcggacattatcttccccgaacgcctgcttaaaaccctgcaacagggtctgccagacttcaccag tcaaagcatgttgcaaaactttaggaactttatcctagagcgttcaggaattctgcccgccacctgctgtgcgcttcctagcgactttgtgccca ttaagtaccgtgaatgccctccgccgctttgggtcactgctaccttctgcagctagccaactaccttgcctaccactccgacatcatggaaga cgtgagcggtgacggcctactggagtgtcactgtcgctgcaacctatgcaccccgcaccgctccctggtctgcaattcgcaactgcttagcg aaagtcaaattatcggtacctttgagctgcagggtccctcgcctgacgaaaagtccgcggctccggggttgaaactcactccggggctgtg gacgtcCGATCTCTATCACTGATAGGGAGATCTCTATCACTGATAGGGAGAGgcttaccttcg caaatttgtacctgaggactaccacgcccacgagattaggttctacgaagaccaatcccgcccgccaaatgcggagcttaccgcctgcgtc attacccagggccacatccttggccaattgcaagccatcaacaaagcccgccaagagtttctgctacgaaagggacgggggggtttacctgg accccagtccggcgaggagctcaacccaatccccccgccgccgcagccctatcagcagccgcgggcccttgcttcccaggatggcac ccaaaaagaagctgcagctgccgccgccgccaccccacggacgaggaggaatactgggacagtcaggcagaggaggttttggacgagg aggaggagatgatggaagactgggacagcctagacgaagcttccgaggccgaagaggtgtcagacgaaacaccgtcaccctcggtcgc attcccctcgccggcgcccagaaattggcaaccgttcccagcatcgctacaacctccgctcctcaggcgccgccggcactgctgttcgc cgacccaaccgtagatgggacaccactggaaccagggccggtaagtctaagcagccgccgccgttagcccaagagcaacaacagcgc caaggctaccgctcgtggcgcgggcacaagaacgccatagttgcttgcttgcaagactgtggggcaacatctccttcgcccgccgctttct tctctaccatcacggcgtggccttcccccgtaacatcctgcattactaccgtcatctctacagcccctactgcaccggcggcagcggcagcg gcagcaacagcagcggtcacacagaagcaaaggcgaccggatagcaagactctgacaaagcccaagaaatccacagcggcggcagc agcaggaggaggagcgctgcgtctggcgcccaacgaacccgtatcgacccgcgagcttagaaataggattttttcccactctgtatgctatat ttcaacaaagcaggggccaagaacaagagctgaaaataaaaaacaggtctctgcgctccctcacccgcagctgcctgtatcacaaaagcg aagatcagcttcggcgcacgctggaagacgcggaggctctcttcagcaaCGATCTCTATCACTGATAGGGAGATC TCTATCACTGATAGGGAGAGactgcgcgctgactcttaaggactagtttcgcgccctttctcaaatttaagcgcgaaaa ctacgtcatctccagcggccacacccggcgccagcacctgtcgtcagcgccattatgagcaaggaaattcccacgccctacatgtggagtt accagccacaaatgggacttgcggctggagctgcccaagactactcaacccgaataaaactacatgagcgcgggaccccacatgatatccc gggtcaacggaatccgcgcccaccgaaaccgaattctcctcgaacaggcggctattaccaccacacctcgtaataaccttaatccccgtagt -continued

```
tggcccgctgccctggtgtaccaggaaagtcccgctcccaccactgtggtacttcccagagacgcccaggccgaagttcagatgactaact
cagggggcgcagcttgcgggcggctttcgtcacagggtgcggtcgcccccagtggccaaaaaagctagcgcagcagccgccgcgcctg
gaaggaagccaaaaggagcgctccccgttgtctgacgtcgcacacctgggttcgacacgcgggggtaaccgcatggatcacggcgg
acggccggatccggggttcgaaccccggtcgtccgccatgataccccttgcgaatttatccaccagaccacggaagagtgcccgcttacag
gctctccttttgcacggtctagagcgtcaacgactgcgcacggggcgttttagggcggagtaacttgcatgtattgggaattgtagtttttttaa
aatgggaagtgacgtatcgtgggaaaacggaagtgaagatttgaggaagttgtggtttttttggctttcgtttctgggcgtaggttcgcgtgcg
gttttctgggtgttttttgtggactttaaccgttacgtcatttttttagtcctatatatactcgctctgtaCTCTCCCTATCAGTGATAG
AGATCTCCCTATCAGTGATAGAGATCGcttggccctttttacactgtgactgattgagctggtgccgtgtcgagtggt
gttttttaataggtttttttactggtaaggctgactgttatggctgccgctgtggaagcgctgtatgttgttctggagcgggagggtgctattttgcc
taggcaggagggttttttcaggtgtttatgtgttttttctctcctattaattttgttatacctcctatgggggctgtaatgttgtctctacgcctgcggg
tatgtattccccgggctatttcggtcgcttttagcactgaccgatgttaaccaacctgatgtgtttaccgagtcttacattatgactccggacatg
accgaggaactgtcggtggtgcttttaatcacggtgaccagttttttacggtcacgccggcatggccgtagtccgtcttatgcttataagggtt
gtttttcctgttgtaagacaggcttctaatgtttaaatgtttttttttttgttattttattttgtgtttaatgcaggaacccgcagacatgtttgaga
gaaaatggtgtcttttctgtggtggttccggaacttacctgcctttatctgcatgagcatgactacgatgtgcttgctttttgcgcgaggctttg
cctgatttttgagcagcaccttgcattttatatcgccgcccatgcaacaagcttacatagggctacgctggttagcatagctccgagtatgcgtgt
cataatcagtgtgggttcttttgtcatggttcctggcggggaagtggccgcgctggtccgtgcagacctgcacgattatgttcagctggccctgc
gaagggacctacgggatcgcggtatttttgttaatgttccgcttttgaatcttatacaggtctgtgaggaacctgaattttttgcaatcatgattcgc
tgcttgaggctgaaggtggagggcgctctggagcagattttttacaatggccggacttaatattcgggatttgcttagagacatattgataaggt
ggcgagatgaaaattatttgggcatggttgaaggtgctggaatgtttatagaggagattcaccctgaagggtttagcctttacgtccacttgga
cgtgagggcagtttgccttttggaagccattgtgcaacatcttacaaatgccattatctgttctttggctgtagagtttgaccacgccaccggag
gggagcgcgttcacttaatagatcttcattttgaggttttggataatcttttggaataaaaaaaaaaaacatggttcttccagctcttcccgctcc
tcccgtgtgtgactcgcagaacgaatgtgtaggttggctgggtgtggcttattctgcggtggtggatgttatcagggcagcggcgcatgaag
gagtttacatagaacccgaagccaggggcgcctggatgctttgagagagtggatatactacaactactacacagagcgagctaagcgac
gagaccggagacgcagatctgtttgtcacgcccgcacctggttttgcttcaggaaatatgTACCCATACGATGTTCCAGA
TTACGCTGGAGGAGGCGGAGGCactacgtccggcgttccatttggcatgacactacgaccaacacgatctcggttgtct
cggcgcactccgtacagtagggatcgcctacctccttttgagacagagaccgcgctaccatactggaggatcatccgctgctgcccgaat
gtaacactttgacaatgcacaacgtgagttacgtgcgaggtcttccctgcagtgtgggatttacgctgattcaggaatgggttgttccctggga
tatggttctgacgcgggaggagcttgtaatcctgaggaagtgtatgcacgtgtgcctgtgttgtgccaacattgatatcatgacgagcatgatg
atccatggttacgagtcctgggctctccactgtcattgttccagtcccggttccctgcagtgcatagccggcgggcaggttttggccagctggt
ttaggatggtggtggatggcgccatgtttaatcagaggtttatatggtaccgggaggtggtgaattacaacatgccaaaagaggtaatgtttat
gtccagcgtgtttatgagggtcgccacttaatctacctgcgcttgtggtatgatggccacgtgggttctgtggtccccgccatgagctttgga
tacagcgccttgcactgtgggattttgaacaatattgtggtgctgtgctgcagttactgtgctgatttaagtgagatcagggtgcgctgctgtgc
ccggaggacaaggcgtctcatgctgcgggcggtgcgaatcatcgctgaggagaccactgccatgttgtattcctgcaggacggagcggc
ggcggcagcagtttattcgcgcgctgctgcagcaccaccgccctatcctgatgcacgattatgactctaccccatgtaggcgtggacttcc
ccttcgccgcccgttgagcaaccgcaagttggacagcagcctgtggctcagcagctggacagcgacatgaacttaagcgagctgcccgg
ggagtttattaatatcactgatgagcgtttggctcgacaggaaaccgtgtggaatataacacctaagaatatgtctgttacccatgatatgatgc
tttttaaggccagccggggagaaaggactgtgtactctgtgtgttgggagggaggtggcaggttgaatactagggttctgtgagtttgattaa
ggtacggtgatcaatataagctatgtggtggtgggctatactactgaatgaaaaatgacttgaaattttctgcaattgaaaaataaacacgttg
aaacataacatgcaacaggttcacgattctttattcctgggcaatgtaggagaaggtgtaagagttggtagcaaaagtttcagtggtgtattttc
cactttcccaggaccatgtaaaagacatagagtaagtgcttacctcgctagtttctgtggattcactagaatccactttggccgcggctcgagg
agggacagccccccccaaagcccccagggatgtaattacgtccctcccccgctagggggcagcagcgagccgcccggggctccgct
``` ccggtccggcgctcccccgcatcccgagccggcagcgtgcggggacagcccgggcacggggaaggtggcacgggatcgctttcct ctgaacgcttctcgctgctcttgagcctgcagacacctgggggatacggggaaaaggcctccaaggccagcttcccacaataagttggg tgaattttggctcattcctcctttctataggattgaggtcagagcGACATTGATTATTGACTAGTTATTAATAGTA

ATCAATTACGGGGTCATTAGTTCATAGCCCATATATGGAGTTCCGCGTTACATAACT

TACGGTAAATGGCCCGCCTGGCTGACCGCCCAACGACCCCCGCCCATTGACGTCAAT

AATGACGTATGTTCCCATAGTAACGCCAATAGGGACTTTCCATTGACGTCAATGGGT

GGAGTATTTACGGTAAACTGCCCACTTGGCAGTACATCAAGTGTATCATATGCCAAG

TACGCCCCCTATTGACGTCAATGACGGTAAATGGCCCGCCTGGCATTATGCCCAGTA

CATGACCTTATGGGACTTTCCTACTTGGCAGTACATCTACGTATTAGTCATCGCTATT

ACCATGGTGATGCGGTTTTGGCAGTACATCAATGGGCGTGGATAGCGGTTTGACTCA

CGGGGATTTCCAAGTCTCCACCCCATTGACGTCAATGGGAGTTTGTTTTGGAACCAA

AATCAACGGGACTTTCCAAAATGTCGTAACAACTCCGCCCCATTGACGCAAATGGG

CGGTAGGCGTGTACGGTGGGAGGTCTATATAAGCAGAGCTCTCCCTATCAGTGATAG

AGATCTCCCTATCAGTGATAGAGATCGTCGACGAGCTCGTTTAGTGAACCGTCAGAT

CGCCTGGAGACGCCATCCACGCTGTTTTGACCTCCATAGAAGACACCGGGACCGATC

CAGCCTgaacgcgcagccgccatgGACTACAAAGACGATGACGACAAGGGAGGAGGCGGAG

GCgttccttctcagagactctcccgaactagcagcatttcctccaacgaggatcccgcagagagccacattctggaactcgaagcggtctc agacaccaacacagactgcgatctggaccctatggagggcagcgaagaacactccacagatggagagatttcatcctcagaggaggagg atgaagatccaactccggcccacgccatacctgcacggccctccagcgtggtcataaccctacctcggcatcgtttgtgattcccagaaag aagtgggacctacaggacaagacagtcacattgcatcgctcacccctgtgcagggacgaggacgagaaggagggagactggcaactcct cttacaccagaggccacaaaaggcgacgcggagaggtccatggctgcaccgatgaaagttatggcaagcgccgacacctgcccccggg agcaagagcgcccagagccccaagggcccccaggtgcctagagcaccgaggtctccaagagctccccgaagcaacagagcaacca gaggtccccggtcagaatctcgaggggccggcaggagcacaaggaagcaggcgaggcaagaacgcagccagaggcccctgccgaa caaaccgtggtttgacatgagtctggttaagcctgtctccaagattacatttgtcaccttgcccagcccctggcctctctgacccctagagccc atccaagacccgttcctacagtcgatgctggcggtggccgcccatccagagattggagcctggcagaaagtgcaacccagacacgagct gcgcaggagctacaagacactacgtgagttttttcaccaagtcaaccaacaaggacacatggctggatgcacgcatgcaggcgatccagaa cgcgggctctgcaccctggtggccatgctagaagagaccatcttttggctccaggagatcacctaccacggcgacctgcccctagctccc gcggaagacatcctcctggcctgcgccatgagtcttagcaaggtgatcctgaccaagctcaaagagctggcaccctgcttccttcctaacac gcgagactacaactttgtgaagcaactcttctacatcacctgtgccacgcccgtcaaaacaaggtggtggagaccctgagcagctcatatg tgaagcagcccctctgtctcttggcagcatatgcggcagtagccccagcctacattaacgccaactgcagacggagacacgatgaagttga attcctgggccactacatcaagaattacaaccctggcacgctaagctccttttgacagaggccgtggagactcacacacgtgactgccgaa gtgcatcatgcagccgacttgtcagggccattctctctccgggcactgggtcactaggactgttttttgttcctggattaaatcaataaGGAT

CCACTAGTCCAGTGTGGTGGAATTCTGCAGATATCCAGCACAGTGGCGGCCGCTCGA

GTCTAGAGGGCCCGTTTAAACCCGCTGATCAGCCTCGACTGTGCCTTCTAGTTGCCA

GCCATCTGTTGTTTGCCCCTCCCCCGTGCCTTCCTTGACCCTGGAAGGTGCCACTCCC

ACTGTCCTTTCCTAATAAAATGAGGAAATTGCATCGCATTGTCTGAGTAGGTGTCAT

TCTATTCTGGGGGGTGGGGTGGGGCAGGACAGCAAGGGGGAGGATTGGGAAGACA

ATAGCAGGCATGCTGGGGATGCGGTGGGCTCTATGGTGAGCTATTCCAGAAGTAGT

GAAGAGGCTTTTTTGGAGGCCTAGGCTTTTGCAAAAAGCTCCGGATCGATGCCCGGG

GGATCCACTAGTTCTAGAGGGACAGCCCCCCCCCAAAGCCCCCAGGGATGTAATTA

-continued

```
CGTCCCTCCCCCGCTAGGGGGCAGCAGCGAGCCGCCCGGGGCTCCGCTCCGGTCCG

GCGCTCCCCCGCATCCCCGAGCCGGCAGCGTGCGGGGACAGCCCGGGCACGGGGA

AGGTGGCACGGGATCGCTTTCCTCTGAACGCTTCTCGCTGCTCTTTGAGCCTGCAGA

CACCTGGGGGGATACGGGGAAAAGGCCTCCAAGGCCAGCTTCCCACAATAAGTTGG

GTGAATTTTGGCTGAGCTATTCCAGAAGTAGTGAAGAGGCTTTTTTGGAGGCCTAGG

CTTTTGCAAAAAGCTCCGGATCGATCATATATGGCAGATATACGCGTTGACATTGAT

TATTGACTAGTTATTAATAGTAATCAATTACGGGGTCATTAGTTCATAGCCCATATAT

GGAGTTCCGCGTTACATAACTTACGGTAAATGGCCCGCCTGGCTGACCGCCCAACGA

CCCCCGCCCATTGACGTCAATAATGACGTATGTTCCCATAGTAACGCCAATAGGGAC

TTTCCATTGACGTCAATGGGTGGAGTATTTACGGTAAACTGCCCACTTGGCAGTACA

TCAAGTGTATCATATGCCAAGTACGCCCCCTATTGACGTCAATGACGGTAAATGGCC

CGCCTGGCATTATGCCCAGTACATGACCTTATGGGACTTTCCTACTTGGCAGTACAT

CTACGTATTAGTCATCGCTATTACCATGGTGATGCGGTTTTGGCAGTACATCAATGG

GCGTGGATAGCGGTTTGACTCACGGGGATTTCCAAGTCTCCACCCCATTGACGTCAA

TGGGAGTTTGTTTTGGCACCAAAATCAACGGGACTTTCCAAAATGTCGTAACAACTC

CGCCCCATTGACGCAAATGGGCGGTAGGCGTGTACGGTGGGAGGTCTATATAAGCA

GAGCTCTCTGGCTAACTATCGTCGACGAGCTCGTTTAGTGAACCGTCAGATCGCCTG

GAGACGCCATCCACGCTGTTTTGACCTCCATAGAAGACACCGGGACCGATCCAGCCT

CCGGACTCTAGCGTTTAAACTTAAGCTTGCCACCatgaccgagtacaagcccacggtgcgcctcgccacc cgcgacgacgtccccagggccgtacgcaccctcgccgccgcgttcgccgactaccccgccacgcgccacaccgtcgatccggaccgc cacatcgagcgggtcaccgagctgcaagaactcttcctcacgcgcgtcgggctcgacatcggcaaggtgtgggtcgggacgacggcg ccgcggtggcggtctggaccacgccggagagcgtcgaagcggggcggtgttcgccgagatcggcccgcgcatggccgagttgagcg gttcccggctggccgcgcagcaacagatggaaggcctcctggccgcgcaccggcccaaggagcccgcgtggttcctggccaccgtcgg cgtctcgcccgaccaccagggcaagggtctgggcagcgccgtcgtgctccccggagtggaggcggccgagcgcgccggggtgcccg ccttcctggagacctccgcgccccgcaacctccccttctacgagcggctcggcttcaccgtcaccgccgacgtcgaggtgcccgaaggac cgcgcacctggtgcatgacccgcaagcccggtgcctgaAGCGCGGGGATCTCATGCTGGAGTTCTTCGCC

CACCCCAACTTGTTTATTGCAGCTTATAATGGTTACAAATAAAGCAATAGCATCACA

AATTTCACAAATAAAGCATTTTTTTCACTGCATTCTAGTTGTGGTTTGTCCAAACTCA

TCAATGTATCTTATCATGTCTGTAGCtGATgtATAcCTAggATCCGGCCGGccTGCAggTG

TCCTCACAGGAACGAAGTCCCTAAAGAAACAGTGGCAGCCAGGTTTAGCCCCGGAA

TTGACTGGATTCCTTTTTAGGGCCCATTGGTATGGCTTTTTCCCCGTATCCCCCCAG

GTGTCTGCAGGCTCAAAGAGCAGCGAGAAGCGTTCAGAGGAAAGCGATCCCGTGCC

ACCTTCCCCGTGCCCGGGCTGTCCCCGCACGCTGCCGGCTCGGGGATGCGGGGGA

GCGCCGGACCGGAGCGGAGCCCCGGGCGGCTCGCTGCTGCCCCCTAGCGGGGAGG

GACGTAATTACATCCCTGGGGGCTTTGGGGGGGGCTGTCCCTCTAGAGCGGCCGCC

ACCGCGGTGGAGCTCCAGCTTTTGTTCCCTTTAGTGAGGGTTAATTAGATCTTAATAC

GACTCACTATAGGGCGAATTGGGTACCGGGCCCCCCCTCGAGGTCGACGGTATCGA

TAAGCTTGATATCTATAACAAGAAAATATATATATAATAAGTTATCACGTAAGTAGA

ACATGAAATAACAATATAATTATCGTATGAGTTAAATCTTAAAAGTCACGTAAAAG

ATAATCATGCGTCATTTTGACTCACGCGGTCGTTATAGTTCAAAATCAGTGACACTT

ACCGCATTGACAAGCACGCCTCACGGGAGCTCCAAGCGGCGACTGAGATGTCCTAA
```

```
ATGCACAGCGACGGATTCGCGCTATTTAGAAAGAGAGAGCAATATTTCAAGAATGC

ATGCGTCAATTTTACGCAGACTATCTTTCTAGGGTTAATCTAGCTGCATCAGGATCAT

ATCGTCGGGTCTTTTTTCCGGCTCAGTCATCGCCCAAGCTGGCGCTATCTGGGCATCG

GGGAGGAAGAAGCCCGTGCCTTTTCCCGCGAGGTTGAAGCGGCATGGAAAGAGTTT

GCCGAGGATGACTGCTGCTGCATTGACGTTGAGCGAAAACGCACGTTTACCATGATG

ATTCGGGAAGGTGTGGCCATGCACGCCTTTAACGGTGAACTGTTCGTTCAGGCCACC

TGGGATACCAGTTCGTCGCGGCTTTTCCGGACACAGTTCCGGATGGTCAGCCCGAAG

CGCATCAGCAACCCGAACAATACCGGCGACAGCCGGAACTGCCGTGCCGGTGTGCA

GATTAATGACAGCGGTGCGGCGCTGGGATATTACGTCAGCGAGGACGGGTATCCTG

GCTGGATGCCGCAGAAATGGACATGGATACCCCGTGAGTTACCCGGCGGGCGCGCT

TGGCGTAATCATGGTCATAGCTGTTTCCTGTGTGAAATTGTTATCCGCTCACAATTCC

ACACAACATACGAGCCGGAAGCATAAAGTGTAAAGCCTGGGGTGCCTAATGAGTGA

GCTAACTCACATTAATTGCGTTGCGCTCACTGCCCGCTTTCCAGTCGGGAAACCTGT

CGTGCCAGCTGCATTAATGAATCGGCCAACGCGCGGGGAGAGGCGGTTTGCGTATT

GGGCGCTCTTCCGCTTCCTCGCTCACTGACTCGCTGCGCTCGGTCGTTCGGCTGCGGC

GAGCGGTATCAGCTCACTCAAAGGCGGTAATACGGTTATCCACAGAATCAGGGGAT

AACGCAGGAAAGAACATGTGAGCAAAAGGCCAGCAAAAGGCCAGGAACCGTAAAA

AGGCCGCGTTGCTGGCGTTTTTCCATAGGCTCCGCCCCCCTGACGAGCATCACAAAA

ATCGACGCTCAAGTCAGAGGTGGCGAAACCCGACAGGACTATAAAGATACCAGGCG

TTTCCCCCTGGAAGCTCCCTCGTGCGCTCTCCTGTTCCGACCCTGCCGCTTACCGGAT

ACCTGTCCGCCTTTCTCCCTTCGGGAAGCGTGGCGCTTTCTCATAGCTCACGCTGTAG

GTATCTCAGTTCGGTGTAGGTCGTTCGCTCCAAGCTGGGCTGTGTGCACGAACCCCC

CGTTCAGCCCGACCGCTGCGCCTTATCCGGTAACTATCGTCTTGAGTCCAACCCGGT

AAGACACGACTTATCGCCACTGGCAGCAGCCACTGGTAACAGGATTAGCAGAGCGA

GGTATGTAGGCGGTGCTACAGAGTTCTTGAAGTGGTGGCCTAACTACGGCTACACTA

GAAGGACAGTATTTGGTATCTGCGCTCTGCTGAAGCCAGTTACCTTCGGAAAAAGAG

TTGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCAGTGGAACGAAAACTCACGTTAAGGGATTTTGGTCATGA

GATTATCAAAAAGGATCTTCACCTAGATCCTTTTAAATTAAAAATGAAGTTTTAAAT

CAATCTAAAGTATATATGAGTAAACTTGGTCTGACAGTTACCAATGCTTAATCAGTG

AGGCACCTATCTCAGCGATCTGTCTATTTCGTTCATCCATAGTTGCCTGACTCCCCGT

CGTGTAGATAACTACGATACGGGAGGGCTTACCATCTGGCCCCAGTGCTGCAATGAT

ACCGCGAGACCCACGCTCACCGGCTCCAGATTTATCAGCAATAAACCAGCCAGCCG

GAAGGGCCGAGCGCAGAAGTGGTCCTGCAACTTTATCCGCCTCCATCCAGTCTATTA

ATTGTTGCCGGGAAGCTAGAGTAAGTAGTTCGCCAGTTAATAGTTTGCGCAACGTTG

TTGCCATTGCTACAGGCATCGTGGTGTCACGCTCGTCGTTTGGTATGGCTTCATTCAG

CTCCGGTTCCCAACGATCAAGGCGAGTTACATGATCCCCCATGTTGTGCAAAAAAGC

GGTTAGCTCCTTCGGTCCTCCGATCGTTGTCAGAAGTAAGTTGGCCGCAGTGTTATC

ACTCATGGTTATGGCAGCACTGCATAATTCTCTTACTGTCATGCCATCCGTAAGATG
```

```
CTTTTCTGTGACTGGTGAGTACTCAACCAAGTCATTCTGAGAATAGTGTATGCGGCG

ACCGAGTTGCTCTTGCCCGGCGTCAATACGGGATAATACCGCGCCACATAGCAGAA

CTTTAAAAGTGCTCATCATTGGAAAACGTTCTTCGGGGCGAAAACTCTCAAGGATCT

TACCGCTGTTGAGATCCAGTTCGATGTAACCCACTCGTGCACCCAACTGATCTTCAG

CATCTTTTACTTTCACCAGCGTTTCTGGGTGAGCAAAAACAGGAAGGCAAAATGCCG

CAAAAAAGGGAATAAGGGCGACACGGAAATGTTGAATACTCAT
```

Example 3: Design and Validation of Inducible Rep Genes

Producing inducible Rep proteins can be challenging due to the critical maintenance of the ratio of Rep78 and Rep52 protein expression needed for high titer AAV quality and quantity. In addition, the p19 promoter required for Rep52 expression is embedded in the coding region of Rep78, which is difficult for direct promoter engineering. To overcome these challenges, two strategies were developed.

First, the expression cassettes of Rep78 and Rep52 were split from overlapped genes into two separate ones, each of which was driven by one of the following viral or non-viral promoters with diverse strength, including human cytomegalovirus (CMV) immediate early enhancer-promoter, CMV immediate early enhancer fused chicken β-actin promoter (CAG), human ubiquitin C (UbC) promoter and Rous sarcoma virus (RSV) promoter. To convert these constitutive promoters into inducible versions, two tetracycline operator sequences (TetO$_2$) were inserted between the TATA box and transcriptional start site (TSS).

The original p19 promoter in the Rep78 open reading frame (ORF) was silenced by changing six nucleotides in three core regulatory elements required for p19 activity (SP1, TATA-1, and TATA-2 sites). These changes did not alter the Rep78 protein sequence. To increase vector stability and Rep52 expression, the DNA sequence of coding region of Rep52 was optimized for human cell codon usage while retaining the same protein sequence, which significantly reduced the sequence identity of the Rep52 sequence with the Rep78 sequence, from 100% to 80.1%.

Figures 5C, 5D:
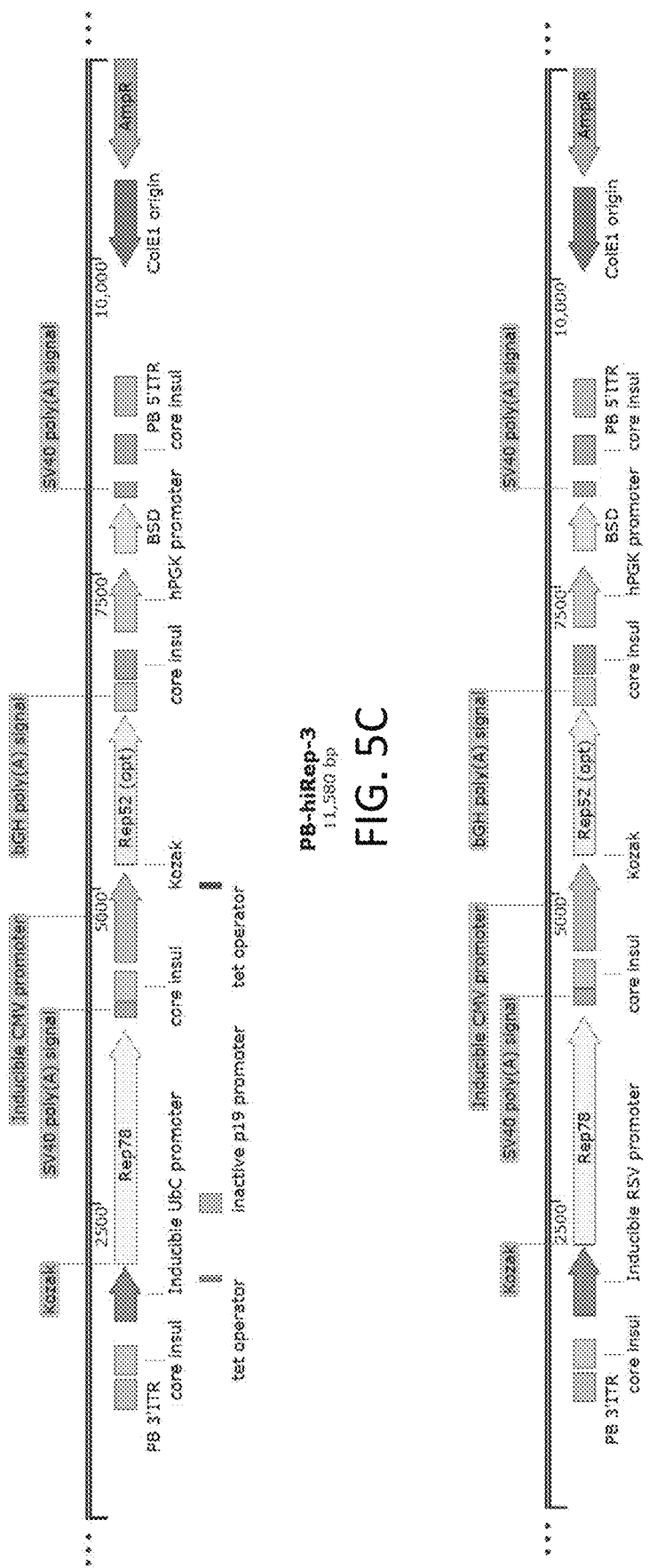
FIGS. 5A-5P show exemplary nucleic acid molecules for production of Rep genes in accordance with embodiments hereof.
Figures 5G, 5H:
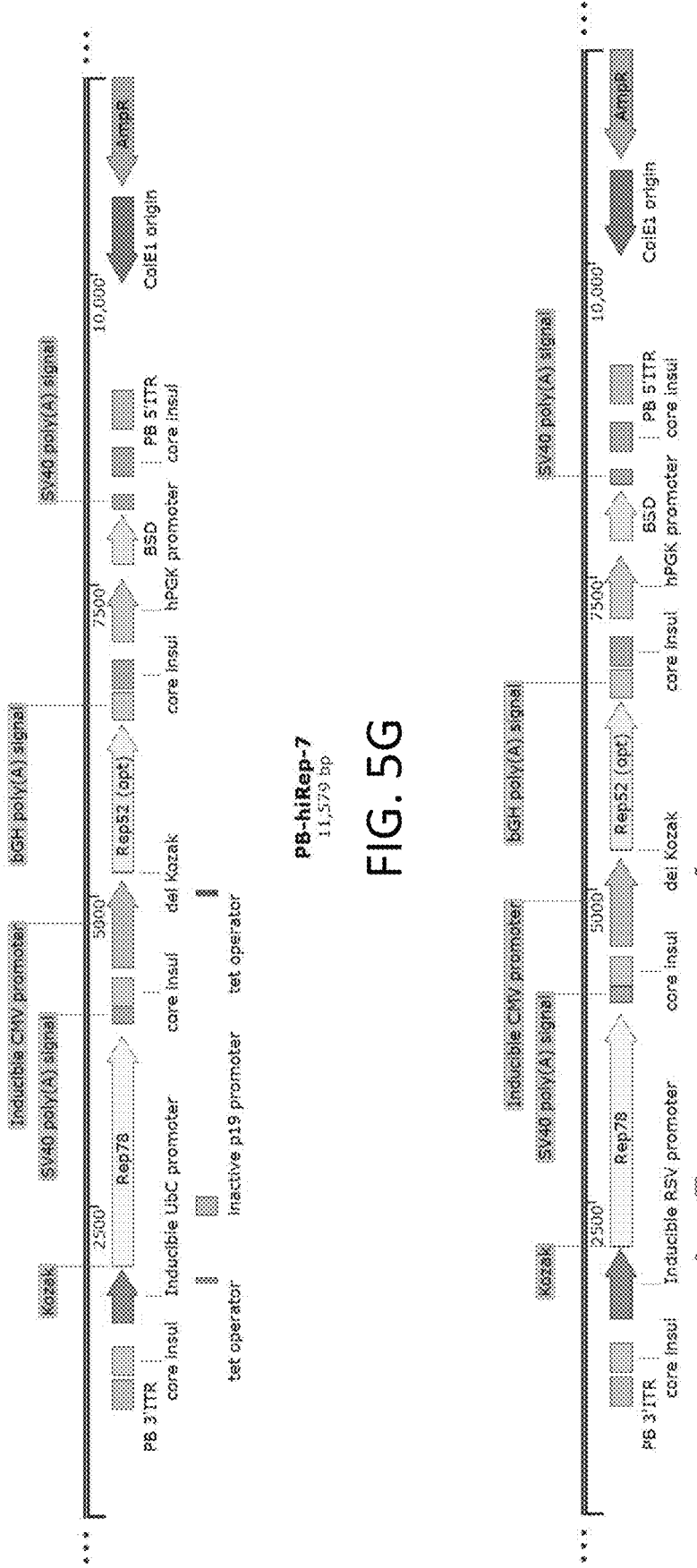
Figure 5I:
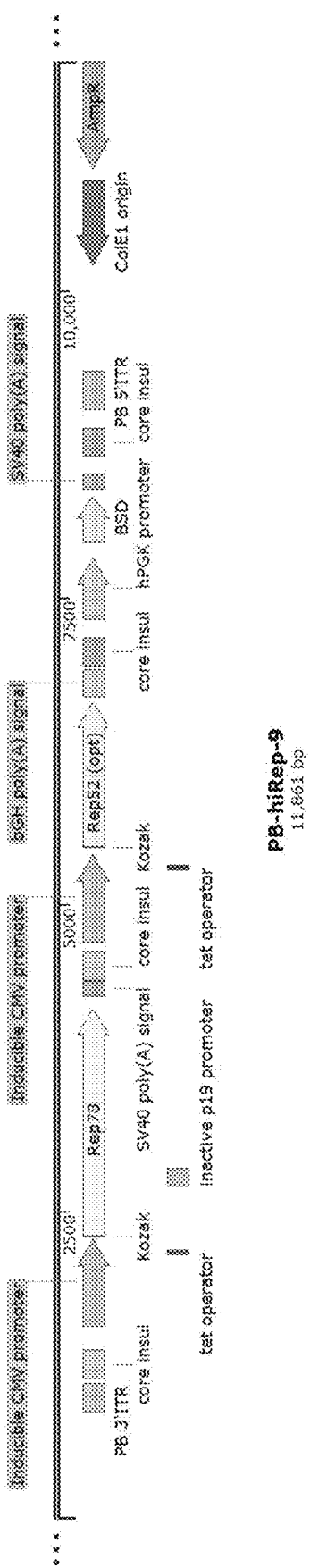
Figure 5J:
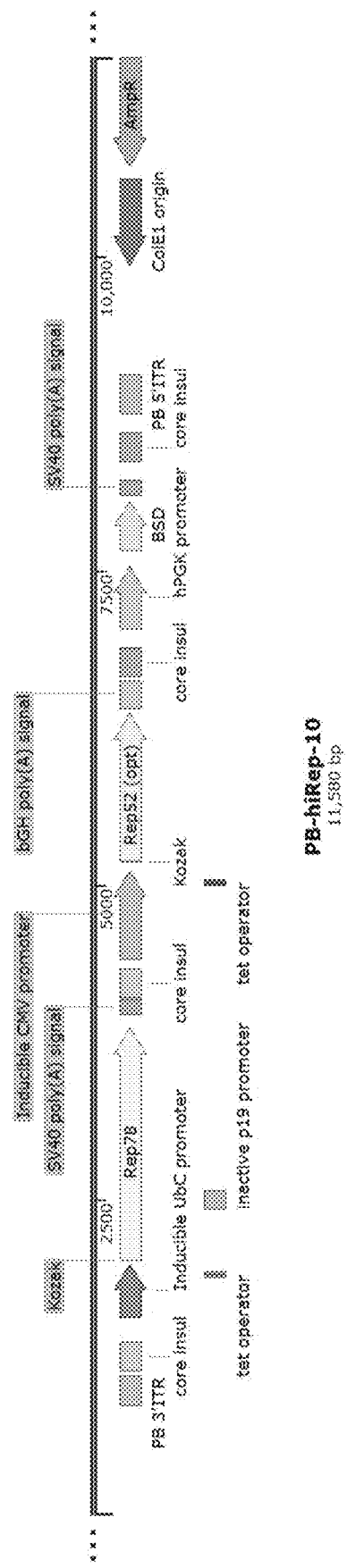
Figure 5K:
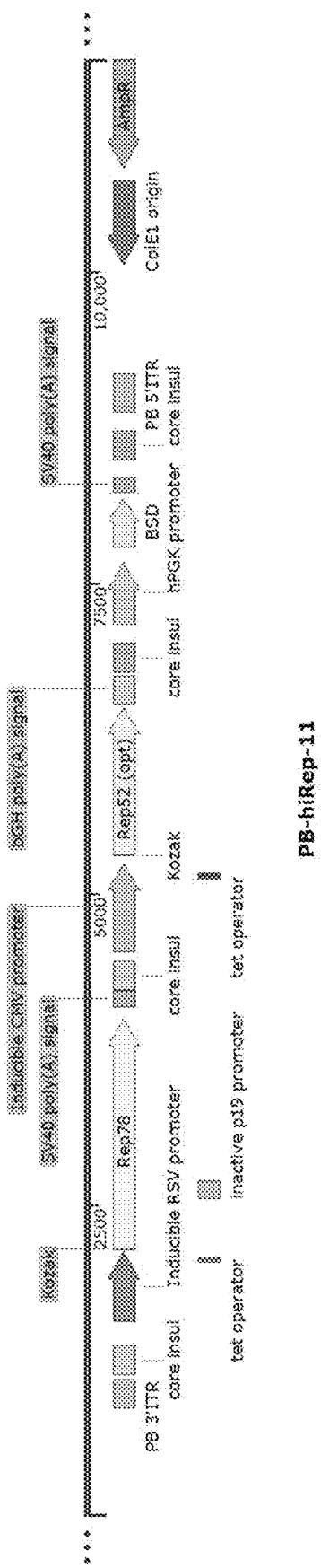
Figure 5L:
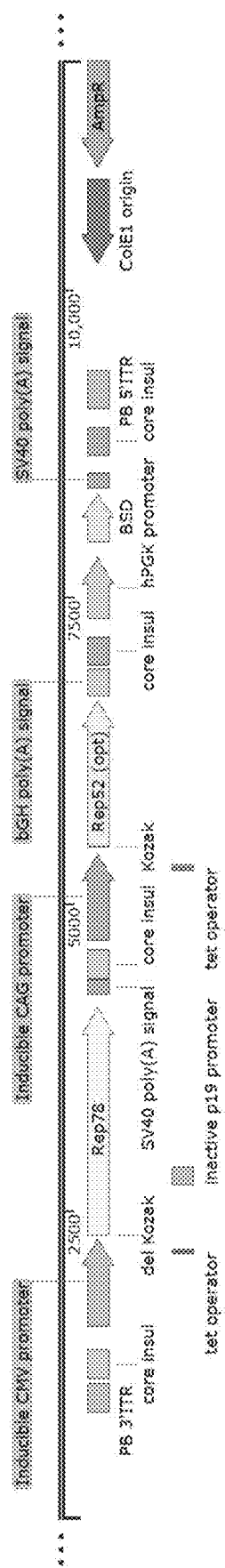
Figure 5M:
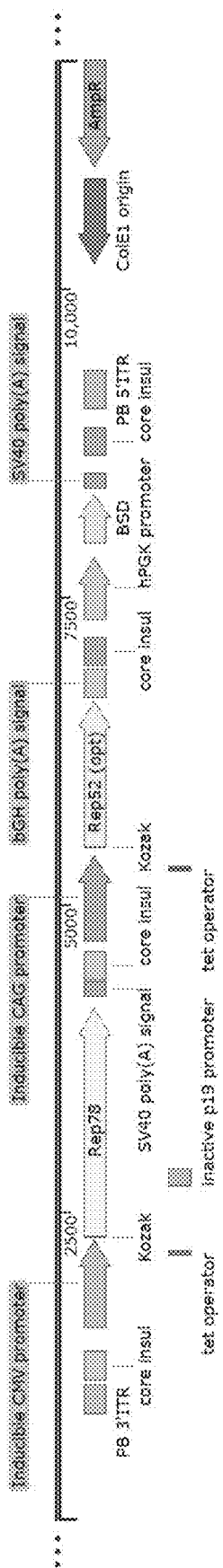
Figure 5N:
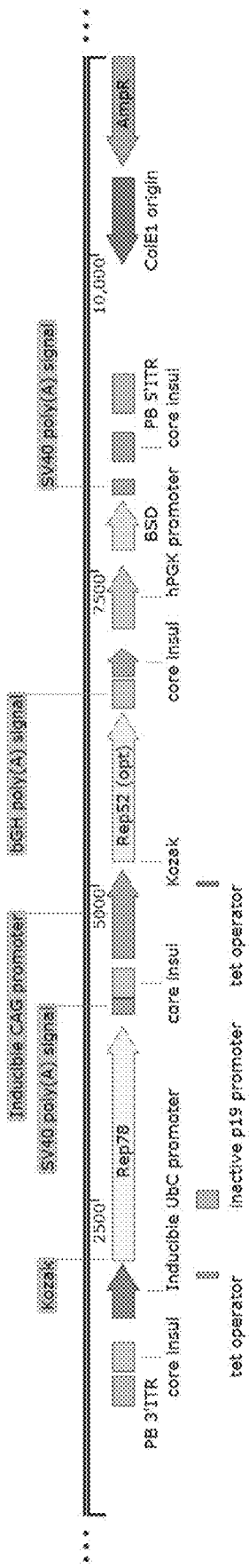

To improve the expression of Rep genes, a Kozak sequence or non-canonical start codon ACG was applied to enhance or reduce the protein expression, respectively. Sixteen inducible Rep vectors were designed in piggyBac transposon vectors with core insulators flanking the Rep78 and Rep52 cassettes, as well as an expression cassette for human PGK promoter driven blasticidin antibiotic resistance gene (BSD) (See FIG. 5A-5P). A summary of the inducible promoter designs for Rep genes are shown in Table 1.

TABLE 1

| | | iCMV | iCMV/no Kozak | iCMV/ACG | iCAG | iUbC | iRSV |
|---|---|---|---|---|---|---|---|
| PB-hiRep-1 | Rep78 | x | | | | | |
| | Rep52 | x | | | | | |
| PB-hiRep-2 | Rep78 | | | x | | | |
| | Rep52 | x | | | | | |
| PB-hiRep-3 | Rep78 | | | | | x | |
| | Rep52 | x | | | | | |
| PB-hiRep-4 | Rep78 | | | | | | x |
| | Rep52 | x | | | | | |
| PB-hiRep-5 | Rep78 | | x | | | | |
| | Rep52 | | x | | | | |
| PB-hiRep-6 | Rep78 | | | x | | | |
| | Rep52 | | x | | | | |
| PB-hiRep-7 | Rep78 | | | | | x | |
| | Rep52 | | x | | | | |
| PB-hiRep-8 | Rep78 | | | | | | x |
| | Rep52 | | x | | | | |
| PB-hiRep-9 | Rep78 | | | x | | | |
| | Rep52 | | | x | | | |
| PB-hiRep-10 | Rep78 | | | | x | | |
| | Rep52 | | | x | | | |
| PB-hiRep-11 | Rep78 | | | | | | x |
| | Rep52 | | | x | | | |
| PB-hiRep-12 | Rep78 | | x | | | | |
| | Rep52 | | | | x | | |
| PB-hiRep-13 | Rep78 | | | x | | | |
| | Rep52 | | | | x | | |
| PB-hiRep-14 | Rep78 | | | | | x | |
| | Rep52 | | | | x | | |
| PB-hiRep-15 | Rep78 | | | | | | x |
| | Rep52 | | | | x | | |
| PB-hiRep-16 | Rep78 | | | | | | x |
| | Rep52 | | | | | x | |

The sequence of the PB-hiRep-1 #(11,866 bp) vector is provided below:

PB-hiRep-1# (11,866 bp)

(SEQ ID NO: 14)

```
actcttccttttcaatattattgaagcatttatcagggttattgtctcatgagcggatacatatttgaatgtatttagaaaaataaaca aataggggttccgcgcacatttccccgaaaagtgccacctaaattgtaagcgttaatattttgttaaaattcgcgttaaattttgttaaatcagc tcatttttaaccaataggccgaaatcggcaaaatccctataaatcaaaagaatagaccgagatagggttgagtgttgttccagtttggaacaag agtccactattaaagaacgtggactccaacgtcaaagggcgaaaaaccgtctatcagggcgatggcccactacgtgaaccatcaccctaat caagttttttggggtcgaggtgccgtaaagcactaaatcggaacccctaaagggagcccccgatttagagcttgacggggaaagccggcga acgtggcgagaaaggaagggaagaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc
```

-continued

```
ctcttcgctattacgccagctggcgaaaggggggatgtgctgcaaggcgattaagttgggtaacgccagggttttcccagtcacgacgttgta aaacgacggccagtgagcgcgcctcgttcattcacgttttttgaacccgtggaggacgggcagactcgcggtgcaaatgtgttttacagcgtg atggagcagatgaagatgctcgacacgctgcagaacacgcagctagattaaccctagaaagataatcatattgtgacgtacgttaaagataa tcatgcgtaaaattgacgcatgtgttttatcggtctgtatatcgaggtttatttattaatttgaatagatattaagttttattatatttacactta catactaataataaattcaacaaacaatttatttatgttttatttatttattaaaaaaaaacaaaaactcaaaatttcttctataaagtaacaaaac ttttatcgaattcctgcagcccggggggatccactagttctagagggacagccccccccaaagccccagggatgtaattacgtccctcccccgct agggggcagcagcgagccgcccggggctccgctccggtccggcgctcccccgcatcccgagccggcagcgtgcggggacagcccgggca cggggaaggtggcacgggatcgctttcctctgaacgcttctcgctgctctttgagcctgcagacacctgggggataggggaaaaggcc tccaaggccagcttcccacaataagttgggtgaattttggctcattcctcctttctataggattgaggtcagagctttgtgatgggaattctgtgg aatgtgtgtcagttagggtgtggaaagtcccgcgatcgctagcttaagcgctgatcaattggcgcgccgaattcgttatctgcagaattcggct tgacattgattattgactagttattaatagtaatcaattacggggtcattagttcatagcccatatatggagttccgcgttacataacttacggta aatggcccgcctggctgaccgcccaacgacccccgcccattgacgtcaataatgacgtatgttcccatagtaacgccaatagggactttccatt gacgtcaatgggtggagtatttacggtaaactgcccacttggcagtacatcaagtgtatcatatgccaagtacgccccctattgacgtcaatga cggtaaatggcccgcctggcattatgcccagtacatgaccttatgggactttcctacttggcagtacatctacgtattagtcatcgctattaccat ggtgatgcggttttggcagtacatcaatgggcgtggatagcggtttgactcacggggatttccaagtctccaccccattgacgtcaatgggag tttgttttggaaccaaaatcaacgggactttccaaaatgtcgtaacaactccgccccattgacgcaaatgggcggtaggcgtgtacggtggg aggtctatataagcagagctctccctatcagtgatagagatctccctatcagtgatagagatcgtcgacgagctcgtttagtgaaccgtcagat cgcctggagacgccatccacgctgttttgacctccatagaagacaccgggaccgatccagcctgaacgcgcagccgccaatggatgccg gggttttacgagattgtgattaaggtccccagcgaccttgacgagcatctgcccggcatttctgacagctttgtgaactgggtggccgagaag gaatgggagttgccgccagattctgacatggatctgaatctgattgagcaggcacccctgaccgtggccgagaagctgcagcgcgactttc tgacggaatggcgccgtgtgagtaaggccccggaggctcttttctttgtgcaatttgagaagggagagagctacttccacatgcacgtgctc gtggaaaccaccggggtgaaatccatggttttgggacgtttcctgagtcagattcgcgaaaaactgattcagagaatttaccgcgggatcga gccgactttgccaaactggttcgcggtcacaaagaccagaaatggcgccggaggggggaacaaggtggtggatgagtgctacatcccca attacttgctccccaaaacccagcctgagctccaatgggcatggaccaacatggaacagtacctcagcgcctgtttgaatctcacggagcgt aaacggttggtggcgcagcatctgacgcacgtgtcgcagacgcaggagcagaacaaagagaatcagaatcccaattctgatgcgccggt gatcagatcaaaaacttcagccaggtacatggagctggtcgggtggctcgtggacaaggggattacctcggagaagcagtggatccagg aggaccaggcctcatacatctccttcaatgcggcctccaactcgcggtcccaaatcaaggctgccttggacaatgcgggaaagattatgag cctgactaaaaccgccccgactacctggtgggccagcagcccgtggaggacatttccagcaatcggattttataaaattttggaactaaacg ggtacgatcccaatatgcggcttccgtctttctgggatgggccacgaaaaagttcggcaagaggaacaccatctggctgtttgggcctgca actaccgggaagaccaacatcgcggaggccatagcccacactgtgcccttctacgggtgcgtaaactggaccaatgagaactttcccttca acgactgtgtcgacaagatggtgatctggtgggaggagggggaagatgaccgccaaggtcgtggagtcggccaaagccattctcggagga agcaaggtgcgcgtggaccagaaatgcaagtcctcggcccagatagacccgactcccgtgatcgtcacctccaacaccaacatgtgcgc cgtgattgacgggaactcaacgaccttcgaacaccagcagccgttgcaagaccggatgttcaaatttgaactcacccgccgtctggatcatg actttgggaaggtcaccaagcaggaagtcaaagacttttttccggtgggcaaaggatcacgtggttgaggtggagcatgaattctacgtcaaa aagggtggagccaagaaaagacccgccccccagtgacgcagatataagtgagcccaaacgggtgcgcgagtcagttgcgcagccatcga cgtcagacgcggaagcttcgatcaactacgcagacaggtaccaaaacaaatgttctcgtcacgtgggcatgaatctgatgctgtttccctgc agacaatgcgagagaatgaatcagaattcaaatatctgcttcactcacggacagaaagactgtttagagtgctttcccgtgtcagaatctcaac ccgtttctgtcgtcaaaaaggcgtatcagaaactgtgctacattcatcatatcatgggaaaggtgccagacgcttgcactgcctgcgatctggt caatgtggatttggatgactgcatctttgaacaataaaatggctaggatccggccgcctgcaggtgtcctcacaggaacgaagtccctaaa gaaacagtggcagccaggtttagccccggaaaacttgtttattgcagcttataatggttacaaataaagcaatagcatcacaaatttcacaaat
```

-continued aaagcatttttttcactgcattctagttgtggtttgtccaaactcatcaatgtatcttattgactggattgagggacagccccccccaaagcccc cagggatgtaattacgtccctcccccgctagggggcagcagcgagccgcccggggctccgctccggtccggcgctcccccgcatccc cgagccggcagcgtgcgggacagcccgggcacggggaaggtggcacgggatcgctttcctctgaacgcttctcgctgctctttgagcct gcagacacctgggggatacggggaaaaggcctccaaggccagcttcccacaataagttgggtgaattttggctcattcctcctttctatag gattgaggtcagagcGACATTGATTATTGACTAGTTATTAATAGTAATCAATTACGGGGTCAT

TAGTTCATAGCCCATATATGGAGTTCCGCGTTACATAACTTACGGTAAATGGCCCGC

CTGGCTGACCGCCCAACGACCCCCGCCCATTGACGTCAATAATGACGTATGTTCCCA

TAGTAACGCCAATAGGGACTTTCCATTGACGTCAATGGGTGGAGTATTTACGGTAAA

CTGCCCACTTGGCAGTACATCAAGTGTATCATATGCCAAGTACGCCCCCTATTGACG

TCAATGACGGTAAATGGCCCGCCTGGCATTATGCCCAGTACATGACCTTATGGGACT

TTCCTACTTGGCAGTACATCTACGTATTAGTCATCGCTATTACCATGGTGATGCGGTT

TTGGCAGTACATCAATGGGCGTGGATAGCGGTTTGACTCACGGGGATTTCCAAGTCT

CCACCCCATTGACGTCAATGGGAGTTTGTTTTGGAACCAAAATCAACGGGACTTTCC

AAAATGTCGTAACAACTCCGCCCCATTGACGCAAATGGGCGGTAGGCGTGTACGGT

GGGAGGTCTATATAAGCAGAGCTCTCCCTATCAGTGATAGAGATCTCCCTATCAGTG

ATAGAGATCGTCGACGAGCTCGTTTAGTGAACCGTCAGATCGCCTGGAGACGCCATC

CACGCTGTTTTGACCTCCATAGAAGACACCGGGACCGATCCAGCCTatcccaattctgatgcgc cggtgatcagatcaaaaacttcagccaggtacgccaccatggaactggtcggatggctggtggataagggcatcacaagcgagaagcaat ggatccaggaggaccaggcctcatatatttcttttaacgccgctagcaattccagaagccagatcaaggctgctctggacaacgccggcaa aatcatgagcctgaccaagaccgcccctgactacctggtgggacagcagcctgtggaagatatcagcagcaacagaatctataagatcctg gaactgaacggctacgaccccagtacgccgcctccgtgttcctgggctgggctacaaagaagttcggcaagcggaacaccatctggctg ttcggacctgccaccacaggcaaaaccaatatcgccgaggccatcgcccacaccgtgcctttctacggctgcgtgaactggacaaacgag aacttccccttcaacgactgtgtggacaagatggtgatctggtgggaggaaggcaaaatgacagctaaggtggtggaatctgccaaggcta tcctgggaggctctaaggtcagggtggatcagaagtgtaaaagcagcgcccagattgaccctacccctgtgatcgtgaccagcaataccaa catgtgcgccgtgatcgacggcaacagcaccaccttcgagcatcagcagcctctgcaggaccggatgttcaagtttgagctcaccagacg gctggatcacgacttcggcaaggtgaccaagcaggaggtgaaggatttcttcagatgggccaaagaccacgttgttgaggtggaacacga gttctacgtgaagaagggcggcgccaagaaaagaccggcccctagcgacgccgacatcagcgagcctaagagagtgcgggaaagcgt ggcccagcccagcacatctgatgctgaggccagcatcaactacgccgatagataccaaaacaagtgcagccgccacgtgggcatgaacc tgatgctgtttccctgcagacagtgtgaaagaatgaaccagaattctaatatctgctttacacacggccagaaagattgcctggaatgcttccct gtgtccgagagccaaccagtgtctgtggtgaaaaaggcctaccagaagctgtgctacatccaccacatcatgggcaaggtgccagacgcc tgtaccgcctgcgacctggtcaacgtggacctggacgactgcatcttcgagcagtgatttgtgatgggaattctgtgctgtgccttctagttgc cagccatctgttgtttgcccctcccccgtgccttccttgaccctggaaggtgccactcccactgtcctttcctaataaaatgaggaaattgcatc gcattgtctgagtaggtgtcattctattctggggggtggggtggggcaggacagcaaggggaggattgggaagacaatagcaggcatgc tggggatgcggtgggctctatgggaccttttttagggcccattggtatggctttttcccgtatcccccaggtgtctgcaggctcaaagagca gcgagaagcgttcagaggaaagcgatcccgtgccaccttccccgtgcccgggctgtccccgcacgctgccggctcggggatgcgggg gagcgccggaccggagcggagcccggcggctcgctgctgcccctagcggggggggacgtaattacatccctgggggctttggg gggggctgtccctctagagcggccgccaccgcggtggagctccagcttttgttccctttagtgagggttaattagatcttaatacgactcact ataggcgaattgggtaccgggccccctgaggcggaaagaaccagctgggctctagggggtatccccggggttgggttgcgccttt ccaaggcagccctgggtttgcgcagggacgcggctgctctgggcgtggttccgggaaacgcagcggcgccgaccctggtctcgcaca ttcttcacgtccgttcgcagcgtcacccggatcttcgccgctacccttgtgggcccccggcgacgcttcctgctccgccctaagtcggga aggttccttgcggttcgcggcgtgccggacgtgacaaacggaagccgcacgtctcactagtaccctcgcagacggacagcgccaggga -continued

```
gcaatggcagcgcgccgaccgcgatgggctgtggccaatagcggctgctcagcagggcgcgccgagagcagcggccgggaaggg
cggtgcgggaggcggggtgtggggcggtagtgtgggccctgttcctgcccgcgcggtgttccgcattctgcaagcctccggagcgcacg
tcggcagtcggctccctcgttgaccgaatcaccgacctctctcccagaagctcccgggagcttgtatatccattttcggatctgatcagcac
gtgttgacaattaatcatcggcatagtatatcggcatagtataatacgacaaggtgaggaacgccaccatggccaagcctttgtctcaagaag
aatccaccctcattgaaagagcaacggctacaatcaacagcatccccatctctgaagactacagcgtcgccagcgcagctctctctagcga
cggccgcatcttcactggtgtcaatgtatatcattttactggggaccttgtgcagaactcgtggtgctgggcactgctgctgctgcggcagct
ggcaacctgacttgtatcgtcgcgatcggaaatgagaacaggggcatcttgagccctgcggacggtgccgacaggtgcttctcgatctgc
atcctgggatcaaagccatagtgaaggacagtgatggacagccgacggcagttgggattcgtgaattgctgccctctggttatgtgtgggag
ggctaaagcgcgggatctcatgctggagttcttcgcccaccccaacttgtttattgcagcttataatggttacaaataaagcaatagcatcac
aaatttcacaaataaagcatttttttcactgcattctagttgtggtttgtccaaactcatcaatgtatcttatcatgtctgtagctgatgtatacc
taggatccggccggcctgcaggtgtcctcacaggaacgaagtccctaaagaaacagtggcagccaggtttagccccggaattgactggattcctt
ttttagggcccattggtatggcttttccccgtatcccccaggtgtctgcaggctcaaagagcagcgagaagcgttcagaggaaagcgatc
ccgtgccaccttccccgtgcccggctgtcccgcacgctgccggctcggggatgcggggggagcgccggaccggagcggagcccc
gggcggctcgctgctgcccctagcggggagggacgtaattacatccctgggggctttgggggggggctgtccctctagagcggccgc
caccgcggtggagctccagcttttgttccctttagtgagggttaattagatcttaatacgactcactatagggcgaattgggtaccgggcccc
cctcgaggtcgacggtatcctcgaggtcgacggtatcgataagcttgatatctataacaagaaatatatatataataagttatcacgtaagtag
aacatgaaataacaatataattatcgtatgagtttaaatcttaaaagtcacgtaaaagataatcatgcgtcattttgactcacgcggtcgttatagt
tcaaaatcagtgacacttaccgcattgacaagcacgcctcacgggagctccaagcggcgactgagatgtcctaaatgcacagcgacggatt
cgcgctatttagaaagagagagcaatatttcaagaatgcatgcgtcaattttacgcagactatctttctagggttaatctagctgcatcaggatc
atatcgtcgggtcttttttccggctcagtcatcgcccaagctggcgctatctgggcatcggggaggaagaagcccgtgccttttcccgcgag
gttgaagcggcatggaaagagtttgccgaggatgactgctgctgcattgacgttgagcgaaaacgcacgtttaccatgatgattcggaag
gtgtggccatgcacgcctttaacggtgaactgttcgttcaggccacctgggataccagttcgtcgcggcttttccggacacagttccggatgg
tcagcccgaagcgcatcagcaacccgaacaataccggcgacagccggaactgccgtgccggtgtgcagattaatgacagcggtgcggc
gctgggatattacgtcagcgaggacgggtatcctggctgatgccgcagaaatggacatggataccccgtgagttacccggcgggcgcg
cttggcgtaatcatggtcatagctgtttcctgtgtgaaattgttatccgctcacaattccacacaacatacgagccggaagcataaagtgtaaag
cctggggtgcctaatgagtgagctaactcacattaattgcgttgcgctcactgcccgctttccagtcgggaaacctgtcgtgccagctgcatta
atgaatcggccaacgcgcggggagaggcggtttgcgtattgggcgctcttccgcttcctcgctcactgactcgctgcgctcggtcgttcggc
tgcggcgagcggtatcagctcactcaaaggcggtaatacggttatccacagaatcaggggataacgcaggaaagaacatgtgagcaaaa
ggccagcaaaaggccaggaaccgtaaaaaggccgcgttgctggcgtttttccataggctccgcccccctgacgagcatcacaaaaatcga
cgctcaagtcagaggtggcgaaacccgacaggactataaagataccaggcgtttccccctggaagctccctcgtgcgctctcctgttccga
ccctgccgcttaccggatacctgtccgcctttctcccttcgggaagcgtggcgctttctcatagctcacgctgtaggtatctcagttcggtgtag
gtcgttcgctccaagctgggctgtgtgcacgaaccccccgttcagcccgaccgctgcgccttatccggtaactatcgtcttgagtccaaccc
ggtaagacacgacttatcgccactggcagcagccactggtaacaggattagcagagcgaggtatgtaggcggtgctacagagttcttgaa
gtggtggcctaactacggctacactagaaggacagtatttggtatctgcgctctgctgaagccagttaccttcggaaaaagagttggtagctc
ttgatccggcaaacaaaccaccgctggtagcggtggtttttttgtttgcaagcagcagattacgcgcagaaaaaaaggatctcaagaagatc
ctttgatcttttctacggggtctgacgctcagtggaacgaaaactcacgttaagggattttggtcatgagattatcaaaaaggatcttcacctag
atccttttaaattaaaaatgaagttttaaatcaatctaaagtatatatgagtaaacttggtctgacagttaccaatgcttaatcagtgaggcacct
atctcagcgatctgtctatttcgttcatccatagttgcctgactccccgtcgtgtagataactacgatacgggagggcttaccatctggccccagt
gctgcaatgataccgcgagacccacgctcaccggctccagatttatcagcaataaaccagccagccggaagggccgagcgcagaagtggt
cctgcaactttatccgcctccatccagtctattaattgttgccgggaagctagagtaagtagttcgccagttaatagtttgcgcaacgttgttgcc
```

-continued

```
attgctacaggcatcgtggtgtcacgctcgtcgtttggtatggcttcattcagctccggttcccaacgatcaaggcgagttacatgatcccccat
gttgtgcaaaaaagcggttagctccttcggtcctccgatcgttgtcagaagtaagttggccgcagtgttatcactcatggttatggcagcactg
cataattctcttactgtcatgccatccgtaagatgcttttctgtgactggtgagtactcaaccaagtcattctgagaatagtgtatgcggcgaccg
agttgctcttgcccggcgtcaatacgggataataccgcgccacatagcagaactttaaaagtgctcatcattggaaaacgttcttcggggcga
aaactctcaaggatcttaccgctgttgagatccagttcgatgtaacccactcgtgcacccaactgatcttcagcatcttttactttcaccagcgtt
tctgggtgagcaaaaacaggaaggcaaaatgccgcaaaaaagggaataagggcgacacggaaatgttgaatactcat
```

The sequence of the PB-hiRep-2 #vector is provided below:

PB-hiRep-2# (11,861 bp)

(SEQ ID NO: 15)

```
actcttcctttttcaatattattgaagcatttatcagggttattgtctcatgagcggatacatatttgaatgtatttagaaaaataaaca
aatagggttccgcgcacatttccccgaaaagtgccacctaaattgtaagcgttaatattttgttaaaattcgcgttaaattttgttaaatcagc
tcattttttaaccaataggccgaaatcggcaaaatcccttataaatcaaaagaatagaccgagatagggttgagtgttgttccagtttggaacaag
agtccactattaaagaacgtggactccaacgtcaaagggcgaaaaaccgtctatcagggcgatggcccactacgtgaaccatcaccctaat
caagttttttggggtcgaggtgccgtaaagcactaaatcggaaccctaaagggagccccgatttagagcttgacggggaaagccggcga
acgtggcgagaaaggaagggaagaaagcgaaggagcgggcgctagggcgctggcaagtgtagcggtcacgctgcgcgtaaccacc
acaccgccgcgcttaatgcgccgctacagggcgcgtcccattcgccattcaggctgcgcaactgttgggaagggcgatcggtgcgggc
ctcttcgctattacgccagctggcgaaaggggatgtgctgcaaggcgattaagttgggtaacgccagggttttcccagtcacgacgttgta
aaacgacggccagtgagcgcgcctcgttcattcacgttttgaacccgtggaggacgggcagactcgcggtgcaaatgtgttttacagcgtg
atggagcagatgaagatgctcgacacgctgcagaacacgcagctagattaaccctagaaagataatcatattgtgacgtacgttaaagataa
tcatgcgtaaaattgacgcatgtgtttatcggtctgtatatcgaggtttatttattaatttgaatagatattaagttttattatatttacactta
catactaataataaattcaacaaacaatttatttatgtttattttattaaaaaaaaacaaaaactcaaaatttcttctataaagtaacaaaa
cttttatcgaattcctgcagcccgggggatccactagttctagagggacagcccccccaaagccccagggatgtaattacgtccctcccccgc
taggggcagcagcgagccgcccggggctccgctccggtccggcgctcccccgcatccccgagccggcagcgtgcggggacagcccgggca
cggggaaggtggcacgggatcgctttcctctgaacgcttctcgctgctctttgagcctgcagacacctgggggatacggggaaaggcc
tccaaggccagcttcccacaataagttgggtgaattttggctcattcctcctttctataggattgaggtcagagctttgtgatgggaattctgtgg
aatgtgtgtcagttagggtgtggaaagtcccgcgatcgctagcttaagcgctgatcaattggcgcgccgaattcgttatctgcagaattcggct
tgacattgattattgactagttattaatagtaatcaattacgggtcattagttcatagcccatatatggagttccgcgttacataacttacggta
aatggcccgcctggctgaccgcccaacgacccccgcccattgacgtcaataatgacgtatgttcccatagtaacgccaatagggactttccatt
gacgtcaatgggtggagtatttacggtaaactgcccacttggcagtacatcaagtgtatcatatgccaagtacgccccctattgacgtcaatga
cggtaaatggcccgcctggcattatgcccagtacatgaccttatgggactttcctacttggcagtacatctacgtattagtcatcgctattaccat
ggtgatgcggttttggcagtacatcaatgggcgtggatagcggtttgactcacggggatttccaagtctccaccccattgacgtcaatgggag
tttgttttggaaccaaaatcaacgggactttccaaaatgtcgtaacaactccgccccattgacgcaaatgggcggtaggcgtgtacggtggg
aggtctatataagcagagctctccctatcagtgatagagatctccctatcagtgatagagatcgtcgacgagctcgtttagtgaaccgtcagat
cgcctggagacgccatccacgctgttttgacctccatagaagacaccgggaccgatccagcctgaacgcgcagcgcacgcgggtt
ttacgagattgtgattaaggtccccagcgaccttgacgagcatctgcccggcatttctgacagctttgtgaactgggtggccgagaaggaat
gggagttgccgccagatctgacatggatctgaatctgattgagcaggcacccctgaccgtggccgagaagctgcagcgcgactttctgac
ggaatggcgccgtgtgagtaaggccccggaggctcttttctttgtgcaatttgagaagggagagagctacttccacatgcacgtgctcgtgg
aaaccaccggggtgaaatccatggttttgggacgtttcctgagtcagattcgcgaaaaactgattcagagaatttaccgcgggatcgagccg
actttgccaaactggttcgcggtcacaaagaccagaaatggcgccggaggcgggaacaaggtggtggatgagtgctacatcccccaattac
ttgctccccaaaacccagcctgagctccaatgggcatggaccaacatggaacagtacctcagcgcctgtttgaatctcacggagcgtaaac
```

-continued

```
ggttggtggcgcagcatctgacgcacgtgtcgcagacgcaggagcagaacaaagagaatcagaatcccaattctgatgcgccggtgatc
agatcaaaaacttcagccaggtacatggagctggtcgggtggctcgtggacaaggggattacctcggagaagcagtggatccaggagga
ccaggcctcatacatctccttcaatgcggcctccaactcgcggtcccaaatcaaggctgccttggacaatgcgggaaagattatgagcctga
ctaaaaccgcccccgactacctgggggccagcagcccgtggaggacatttccagcaatcggatttataaaattttggaactaaacgggtac
gatccccaatatgcggcttccgtctttctgggatgggccacgaaaaagttcggcaagaggaacaccatctggctgtttgggcctgcaactac
cgggaagaccaacatcgcggaggccatagcccacactgtgcccttctacgggtgcgtaaactggaccaatgagaactttcccttcaacgac
tgtgtcgacaagatggtgatctggtgggaggagggaagatgaccgccaaggtcgtggagtcggccaaagccattctcggaggaagcaa
ggtgcgcgtggaccagaaatgcaagtcctcggcccagatagacccgactcccgtgatcgtcacctccaacaccaacatgtgcgccgtgat
tgacgggaactcaacgaccttcgaacaccagcagccgttgcaagaccggatgttcaaatttgaactcacccgccgtctggatcatgactttg
ggaaggtcaccaagcaggaagtcaaagacttttttccggtgggcaaaggatcacgtggttgaggtggagcatgaattctacgtcaaaaagg
gtggagccaagaaaagacccgcccccagtgacgcagatataagtgagcccaaacgggtgcgcgagtcagttgcgcagccatcgacgtc
agacgcggaagcttcgatcaactacgcagacaggtaccaaaacaaatgttctcgtcacgtgggcatgaatctgatgctgtttccctgcagac
aatgcgagagaatgaatcagaattcaaatatctgcttcactcacggacagaaagactgtttagagtgctttcccgtgtcagaatctcaacccgt
ttctgtcgtcaaaaaggcgtatcagaaactgtgctacattcatcatatcatgggaaaggtgccagacgcttgcactgcctgcgatctggtcaat
gtggatttggatgactgcatctttgaacaataaaatggctaggatccggccggcctgcaggtgtcctcacaggaacgaagtccctaaagaaa
cagtggcagccaggtttagccccgaaaacttgtttattgcagcttataatggttacaaataaagcaatagcatcacaaatttcacaaataaag
cattttttttcactgcattctagttgtggtttgtccaaactcatcaatgtatcttattgactggattgagggacagccccccccaaagcccccagg
gatgtaattacgtccctcccccgctaggggggcagcagcgagccgccggggctccgctccggtccggcgctcccccgcatcccgag
ccggcagcgtgcggggacagcccgggcacggggaaggtggcacggatcgctttcctctgaacgcttctcgctgctctttgagcctgcag
acacctgggggatacggggaaaaggcctccaaggccagcttcccacaataagttgggtgaattttggctcattcctccttttctataggattg
aggtcagagcGACATTGATTATTGACTAGTTATTAATAGTAATCAATTACGGGGTCATTAG
TTCATAGCCCATATATGGAGTTCCGCGTTACATAACTTACGGTAAATGGCCCGCCTG
GCTGACCGCCCAACGACCCCCGCCCATTGACGTCAATAATGACGTATGTTCCCATAG
TAACGCCAATAGGGACTTTCCATTGACGTCAATGGGTGGAGTATTTACGGTAAACTG
CCCACTTGGCAGTACATCAAGTGTATCATATGCCAAGTACGCCCCCTATTGACGTCA
ATGACGGTAAATGGCCCGCCTGGCATTATGCCCAGTACATGACCTTATGGGACTTTC
CTACTTGGCAGTACATCTACGTATTAGTCATCGCTATTACCATGGTGATGCGGTTTTG
GCAGTACATCAATGGGCGTGGATAGCGGTTTGACTCACGGGGATTTCCAAGTCTCCA
CCCCATTGACGTCAATGGGAGTTTGTTTTGGAACCAAAATCAACGGGACTTTCCAAA
ATGTCGTAACAACTCCGCCCCATTGACGCAAATGGGCGGTAGGCGTGTACGGTGGG
AGGTCTATATAAGCAGAGCTCTCCCTATCAGTGATAGAGATCTCCCTATCAGTGATA
GAGATCGTCGACGAGCTCGTTTAGTGAACCGTCAGATCGCCTGGAGACGCCATCCA
CGCTGTTTTGACCTCCATAGAAGACACCGGGACCGATCCAGCCTatcccaattctgatgcgccggt
gatcagatcaaaaacttcagccaggtacgccaccatggaactggtcggatggctggtggataagggcatcacaagcgagaagcaatggat
ccaggaggaccaggcctcatatatttcttttaacgccgctagcaattccagaagccagatcaaggctgctctggacaacgccggcaaaatca
tgagcctgaccaagaccgcccctgactacctggtgggacagcagcctgtggaagatatcagcagcaacagaatctataagatcctggaac
tgaacggctacgaccccagtacgccgcctccgtgttcctgggctgggctacaaagaagttcggcaagcggaacaccatctggctgttcg
gacctgccaccacaggcaaaaccaatatcgccgaggccatcgcccacaccgtgcctttctacggctgcgtgaactggacaaacgagaact
tccccttcaacgactgtgtggacaagatggtgatctggtgggaggaaggcaaaatgacagctaaggtggtggaatctgccaaggctatcct
gggaggctctaaggtcagggtggatcagaagtgtaaaagcagcgcccagattgaccctacccctgtgatcgtgaccagcaataccaacat
```

-continued

```
gtgcgccgtgatcgacggcaacagcaccaccttcgagcatcagcagcctctgcaggaccggatgttcaagtttgagctcaccagacggct
ggatcacgacttcggcaaggtgaccaagcaggaggtgaaggatttcttcagatgggccaaagaccacgttgttgaggtggaacacgagtt
ctacgtgaagaagggcggcgccaagaaagacccgcccctagcgacgccgacatcagcgagcctaagagagtgcgggaaagcgtgg
cccagcccagcacatctgatgctgaggccagcatcaactacgccgatagataccaaaacaagtgcagccgccacgtgggcatgaacctg
atgctgtttccctgcagacagtgtgaaagaatgaaccagaattctaatatctgctttacacacggccagaaagattgcctggaatgcttccctgt
gtccgagagccaaccagtgtctgtggtgaaaaaggcctaccagaagctgtgctacatccaccacatcatgggcaaggtgccagacgcctg
taccgcctgcgacctggtcaacgtggacctggacgactgcatcttcgagcagtgatttgtgatgggaattctgtgctgtgccttctagttgcca
gccatctgttgtttgccccctcccccgtgccttccttgaccctggaaggtgccactcccactgtcctttcctaataaaatgaggaaattgcatcgc
attgtctgagtaggtgtcattctattctgggggtgggggggcaggacagcaaggggaggattgggaagacaatagcaggcatgctg
gggatgcggtgggctctatgggacctttttagggcccattggtatggcttttccccgtatcccccaggtgtctgcaggctcaaagagcag
cgagaagcgttcagaggaaagcgatcccgtgccaccttccccgtgcccgggctgtccccgcacgctgccggctcggggatgcgggggg
agcgccggaccggagcggagcccgggcggctcgctgctgcccctagcggggagggacgtaattacatccctgggggctttgggg
gggggctgtccctctagagcggccgccaccgcggtggagctccagcttttgttcccttagtgagggttaattagatcttaatacgactcacta
tagggcgaattgggtaccgggccccctgaggcggaaagaaccagctggggctctagggggtatccccgggttggggttgcgccttttc
caaggcagccctgggtttgcgcagggacgcggctgctctgggcgtggttccgggaaacgcagcggcgccgaccctgggtctcgcacatt
cttcacgtccgttcgcagcgtcaccggatcttcgccgctaccttgtgggccccggcgacgcttcctgctccgcccctaagtcgggaa
ggttccttgcggttcgcggcgtgccggacgtgacaaacggaagccgcacgtctcactagtaccctcgcagacggacagcgccagggag
caatggcagcgcgccgaccgcgatgggctgtggccaatagcggctgctcagcagggcgcgccgagagcagcggccgggaagggc
ggtgcgggaggcggggtgtgggcggtagtgtgggccctgttcctgcccgcgcggtgttccgcattctgcaagcctccggagcgcacgt
cggcagtcggctccctcgttgaccgaatcaccgacctctctccccagaagctcccgggagcttgtatatccattttcggatctgatcagcacg
tgttgacaattaatcatcggcatagtatatcggcatagtataatacgacaaggtgaggaacgccaccatggccaagcctttgtctcaagaaga
atccaccctcattgaaagagcaacggctacaatcaacagcatcccatctctgaagactacagcgtcgccagcgcagctctctctagcgac
ggccgcatcttcactggtgtcaatgtatatcattttactgggggaccttgtgcagaactcgtggtgctgggcactgctgctgctgcggcagctg
gcaacctgacttgtatcgtcgcgatcggaaatgagaacaggggcatcttgagcccctgcggacggtgccgacaggtgcttctcgatctgca
tcctgggatcaaagccatagtgaaggacagtgatggacagccgacggcagttgggattcgtgaattgctgccctctggttatgtgtgggag
ggctaaagcgcggggatctcatgctggagttcttcgcccaccccaacttgtttattgcagcttataatggttacaaataaagcaatagcatcac
aaatttcacaaataaagcatttttttcactgcattctagttgtggtttgtccaaactcatcaatgtatcttatcatgtctgtagctgatgtatac
ctaggatccggccggcctgcaggtgtcctcacaggaacgaagtccctaaagaaacagtggcagccaggtttagccccggaattgactggattccctt
ttttagggcccattggtatggcttttccccgtatcccccaggtgtctgcaggctcaaagagcagcgagaagcgttcagaggaaagcgatc
ccgtgccaccttccccgtgcccgggctgtccccgcacgctgccggctcggggatgcgggggagcgccggaccggagcggagcccc
gggcggctcgctgctgcccctagcggggagggacgtaattacatccctgggggctttgggggggctgtccctctagagcggccgc
caccgcggtggagctccagcttttgttcccttagtgagggttaattagatcttaatacgactcactatagggcgaattgggtaccgggccccc
cctcgaggtcgacggtatcctcgaggtcgacggtatcgataagcttgatatctaaacaagaaatatatatataataagttatcacgtaagtag
aacatgaaataacaatataattatcgtatgagttaaatcttaaaagtcacgtaaaagataatcatgcgtcattttgactcacgcggtcgttatagt
tcaaaatcagtgacacttaccgcattgacaagcacgcctcacgggagctccaagcggcgactgagatgtcctaaatgcacagcgacggatt
cgcgctatttagaaagagagcaatatttcaagaatgcatgcgtcaattttacgcagactatctttctagggttaatctagctgcatcaggatc
atatcgtcgggtcttttttccggctcagtcatcgcccaagctggcgctatctgggcatcggggaggaagaagcccgtgccttttcccgcgag
gttgaagcggcatggaaagagtttgccgaggatgactgctgctgcattgacgttgagcgaaaacgcacgtttaccatgatgattcggaag
gtgtggccatgcacgcctttaacggtgaactgttcgttcaggccacctgggataccagttcgtcgcggcttttccggacacagttccggatgg
tcagcccgaagcgcatcagcaacccgaacaataccggcgacagccggaactgccgtgccggtgtgcagattaatgacagcggtgcggc
gctgggatattacgtcagcgaggacgggtatcctggctggatgccgcagaaatggacatggataccccgtgagttacccggcgggcgcg
```

-continued

```
cttggcgtaatcatggtcatagctgtttcctgtgtgaaattgttatccgctcacaattccacacaacatacgagccggaagcataaagtgtaaag cctggggtgcctaatgagtgagctaactcacattaattgcgttgcgctcactgcccgctttccagtcgggaaacctgtcgtgccagctgcatta atgaatcggccaacgcgcggggagaggcggtttgcgtattgggcgctcttccgcttcctcgctcactgactcgctgcgctcggtcgttcggc tgcggcgagcggtatcagctcactcaaaggcggtaatacggttatccacagaatcaggggataacgcaggaaagaacatgtgagcaaaa ggccagcaaaaggccaggaaccgtaaaaaggccgcgttgctggcgtttttccataggctccgcccccctgacgagcatcacaaaaatcga cgctcaagtcagaggtggcgaaacccgacaggactataaagataccaggcgtttccccctggaagctccctcgtgcgctctcctgttccga ccctgccgcttaccggatacctgtccgcctttctcccttcgggaagcgtggcgctttctcatagctcacgctgtaggtatctcagttcggtgtag gtcgttcgctccaagctgggctgtgtgcacgaaccccccgttcagcccgaccgctgcgccttatccggtaactatcgtcttgagtccaaccc ggtaagacacgacttatcgccactggcagcagccactggtaacaggattagcagagcgaggtatgtaggcggtgctacagagttcttgaa gtggtggcctaactacggctacactagaaggacagtatttggtatctgcgctctgctgaagccagttaccttcggaaaaagagttggtagctc ttgatccggcaaacaaaccaccgctggtagcggtggtttttttgtttgcaagcagcagattacgcgcagaaaaaaaggatctcaagaagatc ctttgatcttttctacggggtctgacgctcagtggaacgaaaactcacgttaagggattttggtcatgagattatcaaaaaggatcttcacctag atccttttaaattaaaaatgaagttttaaatcaatctaaagtatatatgagtaaacttggtctgacagttaccaatgcttaatcagtgaggcacct atctcagcgatctgtctatttcgttcatccatagttgcctgactccccgtcgtgtagataactacgatacgggagggcttaccatctggccccag tgctgcaatgataccgcgagacccacgctcaccggctccagatttatcagcaataaaccagccagccggaagggccgagcgcagaagtggt cctgcaactttatccgcctccatccagtctattaattgttgccgggaagctagagtaagtagttcgccagttaatagtttgcgcaacgttgttgcc attgctacaggcatcgtggtgtcacgctcgtcgtttggtatggcttcattcagctccggttcccaacgatcaaggcgagttacatgatccccat gttgtgcaaaaaagcggttagctccttcggtcctccgatcgttgtcagaagtaagttggccgcagtgttatcactcatggttatggcagcactg cataattctcttactgtcatgccatccgtaagatgcttttctgtgactggtgagtactcaaccaagtcattctgagaatagtgtatgcggcgaccg agttgctcttgcccggcgtcaatacgggataataccgcgccacatagcagaactttaaaagtgctcatcattggaaaacgttcttcggggcga aaactctcaaggatcttaccgctgttgagatccagttcgatgtaacccactcgtgcacccaactgatcttcagcatcttttactttcaccagcgtt tctgggtgagcaaaaacaggaaggcaaaatgccgcaaaaaagggaataagggcgacacggaaatgttgaatactcat
```

The sequence of the PB-hiRep-3 #vector is provided below:

PB-hiRep-3# (11,580 bp)

(SEQ ID NO: 16)

```
actcttcctttttcaatattattgaagcatttatcagggttattgtctcatgagcggatacatatttgaatgtatttagaaaaataaaca aataggggttccgcgcacatttccccgaaaagtgccacctaaattgtaagcgttaatattttgttaaaattcgcgttaaattttgttaaatcagc tcattttttaaccaataggccgaaatcggcaaaatcccttataaatcaaaagaatagaccgagatagggttgagtgttgttccagtttggaacaag agtccactattaaagaacgtggactccaacgtcaaagggcgaaaaccgtctatcagggcgatggcccactacgtgaaccatcaccctaat caagttttttggggtcgaggtgccgtaaagcactaaatcggaaccctaaagggagccccgatttagagcttgacggggaaagccggcga acgtggcgagaaagcgaaagggaagaaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc ctcttcgctattacgccagctggcgaaaggggatgtgctgcaaggcgattaagttgggtaacgccagggttttcccagtcacgacgttgta aaacgacggccagtgagcgcgcctcgttcattcacgttttt gaacccgtggaggacgggcagactcgcggtgcaaatgtgttttacagcgtg atggagcagatgaagatgctcgacacgctgcagaacacgcagctagattaacctagaaagataatcatattgtgacgtacgttaaagataa tcatgcgtaaaattgacgcatgtgttttatcggtctgtatatcgaggtttatttattaatttgaatagatattaagttttattatatttacactta catactaataataaaattcaacaaacaatttatttatgtttatttatttattaaaaaaaaacaaaaactcaaaatttcttctataaagtaacaaaac ttttatcgaattcctgcagcccggggatccactagttctagagggacagcccccccccaaagccccagggatgtaattacgtccctcccccgct aggggcagcagcgagccgcccggggctccgctccggtccggcgctcccccgcatcccgagccggcagcgtgcggggacagcccgggca
```

-continued cggggaaggtggcacgggatcgctttcctctgaacgcttctcgctgctctttgagcctgcagacacctgggggatacggggaaaaggcc tccaaggccagcttcccacaataagttgggtgaattttggctcattcctcctttctataggattgaggtcagagctttgtgatgggaattctgtgg aatgtgtgtcagttagggtgtggaaagtcccgcgatcgctagcttaagcgctgatcaattggcgcgccgaattcgttatctgcagaattcggct tggcctccgcgccgggttttggcgcctcccgcgggcgccccctcctcacgcgagcgctgccacgtcagacgaagggcgcagcgagc gtcctgatccttccgcccggacgctcaggacagcggcccgctgctcataagactcggccttagaaccccagtatcagcagaaggacatttt aggacgggacttgggtgactctagggcactggttttcttccagagagcggaacaggcgaggaaaagtagtcccttctcggcgattctgcg gagggatctccgtggggcggtgaacgccgatgattatataaggacgcgccggtccctatcagtgatagagatctccctatcagtgatagag agtgtggcacagctagttccgtcgcagccgggatttgggtcgcggttcttgtttgtggatcgctgtgatcgtcacttgacgaacgcgcagccg ccatgccggggttttacgagattgtgattaaggtccccagcgaccttgacgagcatctgcccggcatttctgacagctttgtgaactgggggg ccgagaaggaatgggagttgccgccagattctgacatggatctgaatctgattgagcaggcacccctgaccgtggccgagaagctgcagc gcgactttctgacgaatggcgccgtgtgagtaaggccccggaggctcttttctttgtgcaatttgagaagggagagagctacttccacatgc acgtgctcgtggaaaccaccggggtgaaatccatggttttgggacgtttcctgagtcagattcgcgaaaaactgattcagagaatttaccgcg ggatcgagccgactttgccaaactggttcgcggtcacaaagaccagaaatggcgccggaggcgggaacaaggtggtggatgagtgctac atccccaattacttgctccccaaaacccagcctgagctccaatgggcatggaccaacatggaacagtacctcagcgcctgtttgaatctcac ggagcgtaaacggttggtggcgcagcatctgacgcacgtgtcgcagacgcaggagcagaacaaagagaatcagaatcccaattctgatg cgccggtgatcagatcaaaaacttcagccaggtacatggagctggtcgggggctcgtggacaaggggattacctcggagaagcagtgg atccaggaggaccaggcctcatacatctccttcaatgcggcctccaactcgcggtcccaaatcaaggctgccttggacaatgcgggaaaga ttatgagcctgactaaaaccgcccccgactacctggtgggccagcagcccgtggaggacatttccagcaatcggatttataaaattttggaa ctaaacgggtacgatccccaatatgcggcttccgtctttctgggatgggccacgaaaaagttcggcaagaggaacaccatctggctgtttgg gcctgcaactaccgggaagaccaacatcgcggaggccatagcccacactgtgcccttctacgggtgcgtaaactggaccaatgagaactt tcccttcaacgactgtgtcgacaagatggtgatctggtgggaggaggggaagatgaccgccaaggtcgtggagtcggccaaagccattct cggaggaagcaaggtgcgcgtggaccagaaatgcaagtcctcggcccagatagacccgactcccgtgatcgtcacctccaacaccaaca tgtgcgccgtgattgacgggaactcaacgaccttcgaacaccagcagccgttgcaagaccggatgttcaaatttgaactcacccgccgtctg gatcatgactttgggaaggtcaccaagcaggaagtcaaagacttttttccggtgggcaaaggatcacgtggttgaggtggagcatgaattcta cgtcaaaaagggtggagccaagaaaagacccgcccccagtgacgcagatataagtgagcccaaacgggtgcgcgagtcagttgcgcag ccatcgacgtcagacgcggaagcttcgatcaactacgcagacaggtaccaaaacaaatgttctcgtcacgtgggcatgaatctgatgctgtt tccctgcagacaatgcgagagaatgaatcagaattcaaatatctgcttcactcacggacagaaagactgtttagagtgcttccccgtgtcaga atctcaacccgtttctgtcgtcaaaaaggcgtatcagaaactgtgctacattcatcatatcatgggaaaggtgccagacgcttgcactgcctgc gatctggtcaatgtggatttggatgactgcatctttgaacaataaaatggctaggatccggccggcctgcaggtgtcctcacaggaacgaagt ccctaaagaaacagtggcagccaggtttagccccggaaaacttgtttattgcagcttataatggttacaaataaagcaatagcatcacaaattt cacaaataaagcattttttcactgcattctagttgtggtttgtccaaactcatcaatgtatcttattgactggattgagggacagcccccccccca aagcccccagggatgtaattacgtccctcccccgctaggggcagcagcgagccgccgggctccgctccggtccggcgctcccccg catcccgagccggcagcgtgcggggacagcccgggcacggggaaggtggcacgggatcgctttcctctgaacgcttctcgctgctcttt gagcctgcagacacctgggggatacggggaaaaggcctccaaggccagcttcccacaataagttgggtgaattttggctcattcctcctttt ctataggattgaggtcagagcGACATTGATTATTGACTAGTTATTAATAGTAATCAATTACGGGG

TCATTAGTTCATAGCCCATATATGGAGTTCCGCGTTACATAACTTACGGTAAATGGC

CCGCCTGGCTGACCGCCCAACGACCCCCGCCCATTGACGTCAATAATGACGTATGTT

CCCATAGTAACGCCAATAGGGACTTTCCATTGACGTCAATGGGTGGAGTATTTACGG

TAAACTGCCCACTTGGCAGTACATCAAGTGTATCATATGCCAAGTACGCCCCCTATT

GACGTCAATGACGGTAAATGGCCCGCCTGGCATTATGCCCAGTACATGACCTTATGG

GACTTTCCTACTTGGCAGTACATCTACGTATTAGTCATCGCTATTACCATGGTGATGC

```
GGTTTTGGCAGTACATCAATGGGCGTGGATAGCGGTTTGACTCACGGGGATTTCCAA

GTCTCCACCCCATTGACGTCAATGGGAGTTTGTTTTGGAACCAAAATCAACGGGACT

TTCCAAAATGTCGTAACAACTCCGCCCCATTGACGCAAATGGGCGGTAGGCGTGTAC

GGTGGGAGGTCTATATAAGCAGAGCTCTCCCTATCAGTGATAGAGATCTCCCTATCA

GTGATAGAGATCGTCGACGAGCTCGTTTAGTGAACCGTCAGATCGCCTGGAGACGC

CATCCACGCTGTTTTGACCTCCATAGAAGACACCGGGACCGATCCAGCCTatcccaattctg atgcgccggtgatcagatcaaaaacttcagccaggtacgccaccatggaactggtcggatggctggtggataagggcatcacaagcgag aagcaatggatccaggaggaccaggcctcatatatttcttttaacgccgctagcaattccagaagccagatcaaggctgctctggacaacgc cggcaaaatcatgagcctgaccaagaccgcccctgactacctggtgggacagcagcctgtggaagatatcagcagcaacagaatctataa gatcctggaactgaacggctacgaccccagtacgccgcctccgtgttcctgggctgggctacaaagaagttcggcaagcggaacaccat ctggctgttcggacctgccaccacaggcaaaaccaatatcgccgaggccatcgcccacaccgtgcctttctacggctgcgtgaactggaca aacgagaacttccccttcaacgactgtgtggacaagatggtgatctggtgggaggaaggcaaaatgacagctaaggtggtggaatctgcc aaggctatcctgggaggctctaaggtcagggtggatcagaagtgtaaaagcagcgcccagattgaccctacccctgtgatcgtgaccagc aataccaacatgtgcgccgtgatcgacggcaacagcaccaccttcgagcatcagcagcctctgcaggaccggatgttcaagtttgagctca ccagacggctggatcacgacttcggcaaggtgaccaagcaggaggtgaaggatttcttcagatgggccaaagaccacgttgttgaggtgg aacacgagttctacgtgaagaagggcggcgccaagaaaaagacccgcccctagcgacgccgacatcagcgagcctaagagagtgcggg aaagcgtggcccagcccagcacatctgatgctgaggccagcatcaactacgccgatagataccaaaacaagtgcagccgccacgtgggc atgaacctgatgctgtttccctgcagacagtgtgaaagaatgaaccagaattctaatatctgctttacacacgccagaaagattgcctggaat gcttccctgtgtccgagagccaaccagtgtctgtggtgaaaaaggcctaccagaagctgtgctacatccaccacatcatgggcaaggtgcc agacgcctgtaccgcctgcgacctggtcaacgtggacctggacgactgcatcttcgagcagtgatttgtgatgggaattctgtgctgtgcctt ctagttgccagccatctgttgtttgccctcccccgtgccttccttgaccctggaaggtgccactcccactgtcctttcctaataaaatgaggaa attgcatcgcattgtctgagtaggtgtcattctattctgggggggtgggggggcaggacagcaaggggaggattgggaagacaatagca ggcatgctggggatgcggtgggctctatgggacctttttagggcccattggtatggcttttcccgtatcccccaggtgtctgcaggctca aagagcagcgagaagcgttcagaggaaagcgatcccgtgccaccttccccgtgcccgggctgtccccgcacgctgccggctcggggat gcgggggagcgccggaccggagcggagcccgggcggctcgctgctgcccctagcggggaggacgtaattacatcctgggg gctttggggggggctgtccctctagagcggccgccaccgcggtggagctccagcttttgttcccttttagtgagggttaattagatcttaatac gactcactatagggcgaattgggtaccgggccccctgaggcggaaagaaccagctggggctctaggggtatccccgggggtgggt gcgccttttccaaggcagccctgggtttgcgcagggacgcggctgctctgggcgtggttccgggaaacgcagcggcgccgaccctgggt ctcgcacattcttcacgtccgttcgcagcgtcacccggatcttcgccgctacccttgtgggcccccggcgacgcttcctgctccgcccctaa gtcgggaaggttccttgcggttcgcggcgtgccggacgtgacaaacggaagccgcacgtctcactagtaccctcgcagacggacagcgc cagggagcaatggcagcgcgccgaccgcgatgggctgtggcaatagcggctgctcagcagggcgcgccgagagcagcggccggg aaggggcggtgcgggaggcggggtgtgggcggtagtgtgggccctgttcctgcccgcgcggtgttccgcattctgcaagcctccggag cgcacgtcggcagtcggctccctcgttgaccgaatcaccgacctctctcccagaagctcccgggagcttgtatatccattttcggatctgat cagcacgtgttgacaattaatcatcggcatagtatatcggcatagtataatacgacaaggtgaggaacgccaccatggccaagcctttgtctc aagaagaatccaccctcattgaaagagcaacggctacaatcaacagcatcccatctctgaagactacagcgtcgccagcgcagctctctc tagcgacggccgcatcttcactggtgtcaatgtatatcattttactggggaccttgtgcagaactcgtggtgctgggcactgctgctgctgcg gcagctggcaacctgacttgtatcgtcgcgatcggaaatgagaacaggggcatcttgagcccctgcggacggtgccgacaggtgcttctc gatctgcatcctgggatcaaagccatagtgaaggacagtgatggacagccgacggcagttgggattcgtgaattgctgccctctggttatgt gtgggagggctaaagcgcggggatctcatgctggagttcttcgcccaccccaacttgtttattgcagcttataatggttacaaataaagcaata gcatcacaaatttcacaaataaagcattttttttcactgcattctagttgtggtttgtccaaactcatcaatgtatcttatcatgtctgtagctg
```

-continued

```
atgtatacctaggatccggccggcctgcaggtgtcctcacaggaacgaagtccctaaagaaacagtggcagccaggtttagccccggaattgactg
gattccttttttagggcccattggtatggcttttcccgtatccccccaggtgtctgcaggctcaaagagcagcgagaagcgttcagaggaaa
gcgatcccgtgccaccttcccgtgcccggctgtcccgcacgctgccggctcggggatgcgggggagcgccggaccggagcgga
gccccgggcggctcgctgctgccccctagcggggagggacgtaattacatccctgggggctttggggggggctgtccctctagagcg
gccgccaccgcggtggagctccagcttttgttccctttagtgagggttaattagatcttaatacgactcactatagggcgaattgggtaccggg
ccccccctcgaggtcgacggtatcctcgaggtcgacggtatcgataagcttgatatctataacaagaaaatatatatataataagttatcacgt
aagtagaacatgaaataacaatataattatcgtatgagttaaatcttaaaagtcacgtaaaagataatcatgcgtcattttgactcacgcggtcgt
tatagttcaaaatcagtgacacttaccgcattgacaagcacgcctcacgggagctccaagcggcgactgagatgtcctaaatgcacagcga
cggattcgcgctatttagaaagagagagcaatatttcaagaatgcatgcgtcaattttacgcagactatctttctagggttaatctagctgcatca
ggatcatatcgtcgggtcttttttccggctcagtcatcgcccaagctggcgctatctgggcatcggggaggaagaagcccgtgccttttcccg
cgaggttgaagcggcatggaaagagtttgccgaggatgactgctgctgcattgacgttgagcgaaaacgcacgtttaccatgatgattcgg
gaaggtgtggccatgcacgcctttaacggtgaactgttcgttcaggccacctgggataccagttcgtcgcggcttttccggacacagttccg
gatggtcagcccgaagcgcatcagcaacccgaacaataccggcgacagccggaactgccgtgccggtgtgcagattaatgacagcggt
gcggcgctgggatattacgtcagcgaggacgggtatcctggctggatgccgcagaaatggacatggatacccgtgagttacccggcgg
gcgcgcttggcgtaatcatggtcatagctgtttcctgtgtgaaattgttatccgctcacaattccacacaacatacgagccggaagcataaagt
gtaaagcctggggtgcctaatgagtgagctaactcacattaattgcgttgcgctcactgcccgctttccagtcgggaaacctgtcgtgccagc
tgcattaatgaatcggccaacgcgcggggagaggcggtttgcgtattgggcgctcttccgcttcctcgctcactgactcgctgcgctcggtc
gttcggctgcggcgagcggtatcagctcactcaaaggcggtaatacggttatccacagaatcaggggataacgcaggaaagaacatgtga
gcaaaaggccagcaaaaggccaggaaccgtaaaaaggccgcgttgctggcgtttttccataggctccgcccccctgacgagcatcacaa
aaatcgacgctcaagtcagaggtggcgaaacccgacaggactataaagataccaggcgtttccccctggaagctccctcgtgcgctctcct
gttccgaccctgccgcttaccggatacctgtccgcctttctcccttcgggaagcgtggcgctttctcatagctcacgctgtaggtatctcagttc
ggtgtaggtcgttcgctccaagctgggctgtgtgcacgaaccccccgttcagcccgaccgctgcgccttatccggtaactatcgtcttgagtc
caacccggtaagacacgacttatcgccactggcagcagccactggtaacaggattagcagagcgaggtatgtaggcggtgctacagagtt
cttgaagtggtggcctaactacggctacactagaaggacagtatttggtatctgcgctctgctgaagccagttaccttcggaaaaagagttgg
tagctcttgatccggcaaacaaaccaccgctggtagcggtggtttttttgtttgcaagcagcagattacgcgcagaaaaaaaggatctcaaga
agatcctttgatcttttctacggggtctgacgctcagtggaacgaaaactcacgttaagggattttggtcatgagattatcaaaaaggatcttca
cctagatccttttaaattaaaaatgaagttttaaatcaatctaaagtatatatgagtaaacttggtctgacagttaccaatgcttaatcagtgag
gcacctatctcagcgatctgtctatttcgttcatccatagttgcctgactccccgtcgtgtagataactacgatacgggagggcttaccatctggc
cccagtgctgcaatgataccgcgagacccacgctcaccggctccagatttatcagcaataaaccagccagccggaagggccgagcgcaga
agtggtcctgcaactttatccgcctccatccagtctattaattgttgccgggaagctagagtaagtagttcgccagttaatagtttgcgcaacgtt
gttgccattgctacaggcatcgtggtgtcacgctcgtcgtttggtatggcttcattcagctccggttcccaacgatcaaggcgagttacatgatc
ccccatgttgtgcaaaaaagcggttagctccttcggtcctccgatcgttgtcagaagtaagttggccgcagtgttatcactcatggttatggca
gcactgcataattctcttactgtcatgccatccgtaagatgcttttctgtgactggtgagtactcaaccaagtcattctgagaatagtgtatgcgg
cgaccgagttgctcttgcccggcgtcaatacgggataataccgcgccacatagcagaactttaaaagtgctcatcattggaaaacgttcttcg
gggcgaaaactctcaaggatcttaccgctgttgagatccagttcgatgtaacccactcgtgcacccaactgatcttcagcatcttttactttcac
cagcgtttctgggtgagcaaaaacaggaaggcaaaatgccgcaaaaaagggaataagggcgacacggaaatgttgaatactcat
```

The sequence of the PB-hiRep-4 #vector is provided below:

PB-hiRep-4# (11,702 bp)

(SEQ ID NO: 17)

actcttccttttcaatattattgaagcatttatcagggttattgtctcatgagcggatacatatttgaatgtatttagaaaaataaaca aatagggttccgcgcacatttccccgaaaagtgccacctaaattgtaagcgttaatattttgttaaaattcgcgttaaattttgttaaatcagc tcattttttaaccaataggccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtgaaccatcaccctaat caagttttttggggtcgaggtgccgtaaagcactaaatcggaaccctaaagggagcccccgatttagagcttgacggggaaagccggcga acgtggcgagaaaggaagggaagaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc ctcttcgctattacgccagctggcgaaaggggatgtgctgcaaggcgattaagttgggtaacgccagggttttcccagtcacgacgttgta aaacgacggccagtgagcgcgcctcgttcattcacgttttgaacccgtggaggacgggcagactcgcggtgcaaatgtgttttacagcgtg atggagcagatgaagatgctcgacacgctgcagaacacgcagctagattaaccctagaaagataatcatattgtgacgtacgttaaagataa tcatgcgtaaaattgacgcatgtgttttatcggtctgtatatcgaggtttatttattaatttgaatagatattaagttttattatatttacactta catactaataataaattcaacaaacaatttatttatgttttattttatttattaaaaaaaaacaaaaactcaaaatttcttctataaagtaacaaaa cttttatcgaattcctgcagcccgggggatccactagttctagagggacagccccccccaaagccccaggatgtaattacgtccctcccccg ctaggggcagcagcgagccgcccgggcctccgctccggtccggcgctcccccgcatcccgagccggcagcgtgcggggacagcccgggca cggggaaggtggcacgggatcgctttcctctgaacgcttctcgctgctctttgagcctgcagacacctgggggataacgggggaaaaggcc tccaaggccagcttcccacaataagttgggtgaattttggctcattcctcctttctataggattgaggtcagagctttgtgatgggaattctgtgg aatgtgtgtcagttagggtgtggaaagtcccgcgatcgctagcttaagcgctgatcaattggcgcgccgaattcgttatctgcagaattcggct tctgctccctgcttgtgtgttggaggtcgctgagtagtgcgcgagcaaaatttaagctacaacaaggcaaggcttgaccgacaattgcatgaa gaatctgcttagggttaggcgttttgcgctgcttcgcgatgtacgggccagatatacgcgtatctgagggactagggtgtgtttaggcgaaa agcgggcttcggttgtacgcggttaggagtcccctcaggatatagtagtttcgcttttgcatagggagggggaaatgtagtcttatgcaatac acttgtagtcttgcaacatggtaacgatgagttagcaacatgccttacaaggagagaaaaagcaccgtgcatgccgattggtggaagtaagg tggtacgatcgtgccttattaggaaggcaacagacaggtctgacatggattggacgaaccactgaattccgcattgcagagataattgtattta agtgcctagctccctatcagtgatagagatctccctatcagtgatagagatcgatacaataaacgccatttgaccattcaccacattggtgtgc accgaacgcgcagccgccatgccgggttttacgagattgtgattaaggtccccagcgaccttgacgagcatctgcccggcatttctgaca gctttgtgaactgggtggccgagaaggaatgggagttgccgccagattctgacatggatctgaatctgattgagcaggcacccctgaccgt ggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgccggaggcgggaaca aggtggtggatgagtgctacatccccaattacttgctccccaaaacccagcctgagctccaatgggcatggaccaacatggaacagtacct cagcgcctgtttgaatctcacggagcgtaaacggttggtggcgcagcatctgacgcacgtgtcgcagacgcaggagcagaacaaagaga atcagaatcccaattctgatgcgccggtgatcagatcaaaaacttcagccaggtacatggagctggtcgggtggctcgtggacaaggggat tacctcggagaagcagtggatccaggaggaccaggcctcatacatctccttcaatgcggcctccaactcgcggtcccaaatcaaggctgcc ttggacaatgcgggaaagattatgagcctgactaaaaccgccccgactacctggtgggccagcagcccgtggaggacatttccagcaat cggatttataaaattttggaactaaacgggtacgatcccaatatgcggcttccgtctttctgggatgggccacgaaaaagttcggcaagagg aacaccatctggctgtttgggcctgcaactaccgggaagaccaacatcgcggaggccatagcccacactgtgcccttctacgggtgcgtaa actggaccaatgagaactttcccttcaacgactgtgtcgacaagatggtgatctggtgggaggagggaagatgaccgccaaggtcgtgg agtcggccaaagccattctcggaggaagcaaggtgcgcgtggaccagaaatgcaagtcctcggcccagatagacccgactcccgtgatc gtcacctccaacaccaacatgtgcgccgtgattgacgggaactcaacgaccttcgaacaccagcagccgttgcaagaccggatgttcaaat -continued

```
ttgaactcacccgccgtctggatcatgactttgggaaggtcaccaagcaggaagtcaaagacttttttccggtgggcaaaggatcacgtggtt gaggtggagcatgaattctacgtcaaaaagggtggagccaagaaaagacccgcccccagtgacgcagatataagtgagcccaaacggg tgcgcgagtcagttgcgcagccatcgacgtcagacgcggaagcttcgatcaactacgcagacaggtaccaaaacaaatgttctcgtcacgt gggcatgaatctgatgctgtttccctgcagacaatgcgagagaatgaatcagaattcaaatatctgcttcactcacggacagaaagactgttta gagtgctttcccgtgtcagaatctcaacccgtttctgtcgtcaaaaaggcgtatcagaaactgtgctacattcatcatatcatgggaaaggtgc cagacgcttgcactgcctgcgatctggtcaatgtggatttggatgactgcatctttgaacaataaaatggctaggatccggccggcctgcagg tgtcctcacaggaacgaagtccctaaagaaacagtggcagccaggtttagccccggaaaacttgtttattgcagcttataatggttacaaata aagcaatagcatcacaaatttcacaaataaagcattttttttcactgcattctagttgtggtttgtccaaactcatcaatgtatcttattgactgg attgagggacagccccccccaaagccccagggatgtaattacgtccctccccgctaggggcagcagcgagccgcccggggctccgct ccggtccggcgctcccccgcatccccgagccggcagcgtgcggggacagcccgggcacggggaaggtggcacgggatcgctttcct ctgaacgcttctcgctgctctttgagcctgcagacacctgggggatacggggaaaaggcctccaaggccagcttcccacaataagttggg tgaattttggctcattcctcctttctataggattgaggtcagagcGACATTGATTATTGACTAGTTATTAATAGTA

ATCAATTACGGGGTCATTAGTTCATAGCCCATATATGGAGTTCCGCGTTACATAACT

TACGGTAAATGGCCCGCCTGGCTGACCGCCCAACGACCCCCGCCCATTGACGTCAAT

AATGACGTATGTTCCCATAGTAACGCCAATAGGGACTTTCCATTGACGTCAATGGGT

GGAGTATTTACGGTAAACTGCCCACTTGGCAGTACATCAAGTGTATCATATGCCAAG

TACGCCCCCTATTGACGTCAATGACGGTAAATGGCCCGCCTGGCATTATGCCCAGTA

CATGACCTTATGGGACTTTCCTACTTGGCAGTACATCTACGTATTAGTCATCGCTATT

ACCATGGTGATGCGGTTTTGGCAGTACATCAATGGGCGTGGATAGCGGTTTGACTCA

CGGGGATTTCCAAGTCTCCACCCCATTGACGTCAATGGGAGTTTGTTTTGGAACCAA

AATCAACGGGACTTTCCAAAATGTCGTAACAACTCCGCCCCATTGACGCAAATGGG

CGGTAGGCGTGTACGGTGGGAGGTCTATATAAGCAGAGCTCTCCCTATCAGTGATAG

AGATCTCCCTATCAGTGATAGAGATCGTCGACGAGCTCGTTTAGTGAACCGTCAGAT

CGCCTGGAGACGCCATCCACGCTGTTTTGACCTCCATAGAAGACACCGGGACCGATC

CAGCCTatcccaattctgatgcgccggtgatcagatcaaaaacttcagccaggtacgccaccatggaactggtcggatggctggtgga taagggcatcacaagcgagaagcaatggatccaggaggaccaggcctcatatatttcttttaacgccgctagcaattccagaagccagatc aaggctgctctggacaacgccggcaaaatcatgagcctgaccaagaccgcccctgactacctggtgggacagcagcctgtggaagatat cagcagcaacagaatctataagatcctggaactgaacggctacgaccccagtacgccgcctccgtgttcctgggctgggctacaaagaa gttcggcaagcggaacaccatctggctgttcggacctgccaccacaggcaaaaccaatatcgccgaggccatcgcccacaccgtgcctt ctacggctgcgtgaactggacaaacgagaacttccccttcaacgactgtgtggacaagatggtgatctggtgggaggaaggcaaaatgac agctaaggtggtggaatctgccaaggctatcctgggaggctctaaggtcagggtggatcagaagtgtaaaagcagcgcccagattgaccc taccctgtgatcgtgaccagcaataccaacatgtgcgccgtgatcgacggcaacagcaccaccttcgagcatcagcagcctctgcagga ccggatgttcaagtttgagctcaccagacggctggatcacgacttcggcaaggtgaccaagcaggaggtgaaggatttcttcagatgggcc aaagaccacgttgttgaggtggaacacgagttctacgtgaagaagggcggcgccaagaaaagacccgcccctagcgacgccgacatca gcgagcctaagagagtgcgggaaagcgtggcccagcccagcacatctgatgctgaggccagcatcaactacgccgatagataccaaaa caagtgcagccgccacgtgggcatgaacctgatgctgtttccctgcagacagtgtgaaagaatgaaccagaattctaatatctgctttacaca cggccagaaagattgcctggaatgcttccctgtgtccgagagccaaccagtgtctgtggtgaaaaaggcctaccagaagctgtgctacatc caccacatcatgggcaaggtgccagacgcctgtaccgcctgcgacctggtcaacgtggacctggacgactgcatcttcgagcagtgatttg tgatgggaattctgtgctgtgccttctagttgccagccatctgttgtttgcccctcccccgtgccttccttgaccctggaaggtgccactcccact gtccttttcctaataaaatgaggaaattgcatcgcattgtctgagtaggtgtcattctattctgggggtggggggggcaggacagcaagggg gaggattgggaagacaatagcaggcatgctggggatgcggtgggctctatgggacctttttttagggcccattggtatggcttttttccccgtat
```

-continued

```
cccccccaggtgtctgcaggctcaaagagcagcgagaagcgttcagaggaaagcgatcccgtgccaccttccccgtgcccgggctgtccc cgcacgctgccggctcggggatgcggggggagcgccggaccggagcggaccccgggcggctcgctgctgcccccctagcggggga gggacgtaattacatccctgggggctttggggggggctgtccctctagagcggccgccaccgcggtggagctccagcttttgttcccttta gtgagggttaattagatcttaatacgactcactatagggcgaattgggtaccgggccccctgaggcggaaagaaccagctggggctctag ggggtatccccggggttgggggttgcgccttttccaaggcagccctgggtttgcgcagggacgcggctgctctgggcgtggttccgggaaa cgcagcggcgccgaccctgggtctcgcacattcttcacgtccgttcgcagcgtcacccggatcttcgccgctacccttgtgggcccccccgg cgacgcttcctgctccgcccctaagtcgggaaggttccttgcggttcgcggcgtgccggacgtgacaaacggaagccgcacgtctcacta gtaccctcgcagacggacagcgccagggagcaatggcagcgcgccgaccgcgatgggctgtggccaatagcggctgctcagcagggc gcgccgagagcagcggccgggaaggggcggtgcgggaggcggggtgtggggcggtagtgtgggccctgttcctgcccgcgcggtgt tccgcattctgcaagcctccggagcgcacgtcggcagtcggctccctcgttgaccgaatcaccgacctctctccccagaagctcccggga gcttgtatatccattttcggatctgatcagcacgtgttgacaattaatcatcggcatagtatatcggcatagtataatacgacaaggtgaggaac gccaccatggccaagcctttgtctcaagaagaatccaccctcattgaaagagcaacggctacaatcaacagcatcccatctctgaagacta cagcgtcgccagcgcagctctctctagcgacggccgcatcttcactggtgtcaatgtatatcattttactgggggaccttgtgcagaactcgtg gtgctgggcactgctgctgctgcggcagctggcaacctgacttgtatcgtcgcgatcggaaatgagaacaggggcatcttgagcccctgcg gacggtgccgacaggtgcttctcgatctgcatcctgggatcaaagccatagtgaaggacagtgatggacagccgacggcagttgggattc gtgaattgctgccctctggttatgtgtgggagggctaaagcgcgggatctcatgctggagttcttcgcccaccccaacttgtttattgcagctt ataatggttacaaataaagcaatagcatcacaaatttcacaaataaagcattttttttcactgcattctagttgtggtttgtccaaactcatcaatg tatcttatcatgtctgtagctgatgtataccaggatccggccggctgcaggtgtcctcacaggaacgaagtccctaaagaaacagtggcagcc aggtttagccccggaattgactggattccttttttagggcccattggtatggcttttccccgtatcccccaggtgtctgcaggctcaaagagc agcgagaagcgttcagaggaaagcgatcccgtgccaccttccccgtgcccgggctgtccccgcacgctgccggctcggggatgcgggg ggagcgccggaccggagcggagccccgggcggctcgctgctgcccccctagcggggagggacgtaattacatccctgggggctttgg ggggggctgtccctctagagcggccgccaccgcggtggagctccagcttttgttccctttagtgagggttaattagatcttaatacgactca ctatagggcgaattgggtaccgggccccccctcgaggtcgacggtatcctcgaggtcgacggtatcgataagcttgatatctataacaagaa aatatatatataataagttatcacgtaagtagaacatgaaataacaatataattatcgtatgagttaaatcttaaaagtcacgtaaaagataatc atgcgtcattttgactcacgcggtcgttatagttcaaaatcagtgacacttaccgcattgacaagcacgcctcacggagctccaagcggcgac tgagatgtcctaaatgcacagcgacggattcgcgctatttagaaagagagagcaatatttcaagaatgcatgcgtcaattttacgcagactatc tttctagggttaatctagctgcatcaggatcatatcgtcgggtcttttttccggctcagtcatcgcccaagctggcgctatctgggcatcggggga ggaagaagcccgtgccttttcccgcgaggttgaagcggcatggaaagagtttgccgaggatgactgctgctgcattgacgttgagcgaaaa cgcacgtttaccatgatgattcggaaggtgtggccatgcacgcctttaacggtgaactgttcgttcaggccacctgggataccagttcgtcg cggcttttccggacacagttccggatggtcagcccgaagcgcatcagcaacccgaacaataccggcgacagccggaactgccgtgccgg tgtgcagattaatgacagcggtgcggcgctgggatattacgtcagcgaggacgggtatcctggctggatgccgcagaaatggacatggat accccgtgagttacccggcgggcgcgcttggcgtaatcatggtcatagctgtttcctgtgtgaaattgttatccgctcacaattccacacaaca tacgagccggaagcataaagtgtaaagcctggggtgcctaatgagtgagctaactcacattaattgcgttgcgctcactgcccgctttccagt cgggaaacctgtcgtgccagctgcattaatgaatcggccaacgcgcggggagaggcggtttgcgtattgggcgctcttccgcttcctcgct cactgactcgctgcgctcggtcgttcggctgcggcgagcggtatcagctcactcaaaggcggtaatacggttatccacagaatcaggggat aacgcaggaaagaacatgtgagcaaaaggccagcaaaaggccaggaaccgtaaaaaggccgcgttgctggcgtttttccataggctccg ccccctgacgagcatcacaaaaatcgacgctcaagtcagaggtggcgaaacccgacaggactataaagataccaggcgtttccccctgg aagctccctcgtgcgctctcctgttccgaccctgccgcttaccggatacctgtccgcctttctcccttcgggaagcgtggcgctttctcatagct cacgctgtaggtatctcagttcggtgtaggtcgttcgctccaagctgggctgtgtgcacgaaccccccgttcagcccgaccgctgcgcctat ccggtaactatcgtcttgagtccaacccggtaagacacgacttatcgccactggcagcagccactggtaacaggattagcagagcgaggta
```

-continued

```
tgtaggcggtgctacagagttcttgaagtggtggcctaactacggctacactagaaggacagtatttggtatctgcgctctgctgaagccagtt accttcggaaaaagagttggtagctcttgatccggcaaacaaaccaccgctggtagcggtggttttttttgtttgcaagcagcagattacgcgc agaaaaaaggatctcaagaagatcctttgatcttttctacggggtctgacgctcagtggaacgaaaactcacgttaagggattttggtcatga gattatcaaaaaggatcttcacctagatccttttaaattaaaaatgaagttttaaatcaatctaaagtatatatgagtaaacttggtctgacagtt accaatgcttaatcagtgaggcacctatctcagcgatctgtctatttcgttcatccatagttgcctgactcccgtcgtgtagataactacgatac gggagggcttaccatctggccccagtgctgcaatgataccgcgagacccacgctcaccggctccagatttatcagcaataaaccagccagcc ggaagggccgagcgcagaagtggtcctgcaactttatccgcctccatccagtctattaattgttgccgggaagctagagtaagtagttcgcc agttaatagtttgcgcaacgttgttgccattgctacaggcatcgtggtgtcacgctcgtcgtttggtatggcttcattcagctccggttcccaacg atcaaggcgagttacatgatccccatgttgtgcaaaaaagcggttagctccttcggtcctccgatcgttgtcagaagtaagttggccgcagt gttatcactcatggttatggcagcactgcataattctcttactgtcatgccatccgtaagatgcttttctgtgactggtgagtactcaaccaagtc attctgagaatagtgtatgcggcgaccgagttgctcttgcccggcgtcaatacgggataataccgcgccacatagcagaactttaaaagtgctc atcattggaaaacgttcttcggggcgaaaactctcaaggatcttaccgctgttgagatccagttcgatgtaacccactcgtgcacccaactgat cttcagcatcttttactttcaccagcgtttctgggtgagcaaaaacaggaaggcaaaatgccgcaaaaaagggaataagggcgacacggaa atgttgaatactcat
```

The sequence of the PB-hiRep-5 #vector is provided below:

PB-hiRep-5# (11,865 bp)
(SEQ ID NO: 18)

```
actcttcctttttcaatattattgaagcatttatcagggttattgtctcatgagcggatacatatttgaatgtatttagaaaaataaaca aatagggttccgcgcacatttccccgaaaagtgccacctaaattgtaagcgttaatattttgttaaaattcgcgttaaattttgttaaatcagc tcattttttaaccaataggccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtgaaccatcaccctaat caagttttttggggtcgaggtgccgtaaagcactaaatcggaaccctaaagggagccccgatttagagcttgacggggaaagccggcga acgtggcgagaaaggaagggaagaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc ctcttcgctattacgccagctggcgaaaggggatgtgctgcaaggcgattaagttgggtaacgccagggttttcccagtcacgacgttgta aaacgacggccagtgagcgcgcctcgttcattcacgttttgaacccgtggaggacgggcagactcgcggtgcaaatgtgttttacagcgtg atggagcagatgaagatgctcgacacgctgcagaacacgcagctagattaaccctagaaagataatcatattgtgacgtacgttaaagataa tcatgcgtaaaattgacgcatgtgttttatcggtctgtatatcgaggtttatttattaatttgaatagatattaagttttattatatttacactta catactaataataaattcaacaaacaatttatttatgtttatttatttattaaaaaaaaacaaaaactcaaaatttcttctataaagtaacaaaac ttttatcgaattcctgcagcccggggatccactagttctagaggacagcccccccaaagccccagggatgtaattacgtccctcccccgct aggggcagcagcgagccgcccggggctccgctccggtccggcgctcccccgcatccccgagccggcagcgtgcggggacagcccgggca cggggaaggtggcacgggatcgctttcctctgaacgcttctcgctgctctttgagcctgcagacacctgggggataggggaaaggcc tccaaggccagcttcccacaataagttgggtgaattttggctcattcctcctttctataggattgaggtcagagctttgtgatgggaattctgtgg aatgtgtgtcagttagggtgtggaaagtcccgcgatcgctagcttaagcgctgatcaattggcgcgccgaattcgttatctgcagaattcggct
``` tGACATTGATTATTGACTAGTTATTAATAGTAATCAATTACGGGGTCATTAGTTCATA

GCCCATATATGGAGTTCCGCGTTACATAACTTACGGTAAATGGCCCGCCTGGCTGAC

CGCCCAACGACCCCCGCCCATTGACGTCAATAATGACGTATGTTCCCATAGTAACGC

CAATAGGGACTTTCCATTGACGTCAATGGGTGGAGTATTTACGGTAAACTGCCCACT

TGGCAGTACATCAAGTGTATCATATGCCAAGTACGCCCCCTATTGACGTCAATGACG

GTAAATGGCCCGCCTGGCATTATGCCCAGTACATGACCTTATGGGACTTTCCTACTT

-continued

```
GGCAGTACATCTACGTATTAGTCATCGCTATTACCATGGTGATGCGGTTTTGGCAGT
ACATCAATGGGCGTGGATAGCGGTTTGACTCACGGGGATTTCCAAGTCTCCACCCCA
TTGACGTCAATGGGAGTTTGTTTTGGAACCAAAATCAACGGGACTTTCCAAAATGTC
GTAACAACTCCGCCCCATTGACGCAAATGGGCGGTAGGCGTGTACGGTGGGAGGTC
TATATAAGCAGAGCTCTCCCTATCAGTGATAGAGATCTCCCTATCAGTGATAGAGAT
CGTCGACGAGCTCGTTTAGTGAACCGTCAGATCGCCTGGAGACGCCATCCACGCTGT
TTTGACCTCCATAGAAGACACCGGGACCGATCCAGCCTgAACGCGCAGCCGCCaatgg
ATGccggggttttacgagattgtgattaaggtccccagcgaccttgacgagcatctgcccggcatttctgacagctttgtgaactgggtgg
ccgagaaggaatgggagttgccgccagattctgacatggatctgaatctgattgagcaggcacccctgaccgtggccgagaagctgcagc
gcgactttctgacggaatggcgccgtgtgagtaaggccccggaggctcttttctttgtgcaatttgagaaggagagagctacttccacatgc
acgtgctcgtggaaaccaccggggtgaaatccatggttttgggacgtttcctgagtcagattcgcgaaaaactgattcagagaatttaccgcg
ggatcgagccgactttgccaaactggttcgcggtcacaaagaccagaaatggcgccggaggcgggaacaaggtggtggatgagtgctac
atccccaattacttgctccccaaaacccagcctgagctccaatgggcatggaccaacatggaacagtacctcagcgcctgtttgaatctcac
ggagcgtaaacggttggtggcgcagcatctgacgcacgtgtcgcagacgcaggagcagaacaaagagaatcagaatcccaattctgatg
cgccggtgatcagatcaaaaacttcagccaggtacatggagctggtcgggtggctcgtggacaaggggattacctcggagaagcagtgg
atccaggaggaccaggcctcatacatctccttcaatgcggcctccaactcgcggtcccaaatcaaggctgccttggacaatgcgggaaaga
ttatgagcctgactaaaaccgcccccgactacctggtgggccagcagcccgtggaggacatttccagcaatcggatttataaaattttggaa
ctaaacgggtacgatccccaatatgcggcttccgtctttctgggatgggccacgaaaaagttcggcaagaggaacaccatctggctgtttgg
gcctgcaactaccgggaagaccaacatcgcggaggccatagcccacactgtgcccttctacgggtgcgtaaactggaccaatgagaactt
tcccttcaacgactgtgtcgacaagatggtgatctggtggggaggaggggaagatgaccgccaaggtcgtggagtcggccaaagccattct
cggaggaagcaaggtgcgcgtggaccagaaatgcaagtcctcggcccagatagacccgactcccgtgatcgtcacctccaacaccaaca
tgtgcgccgtgattgacgggaactcaacgaccttcgaacaccagcagccgttgcaagaccggatgttcaaatttgaactcacccgccgtctg
gatcatgactttgggaaggtcaccaagcaggaagtcaaagacttttttccggtgggcaaaggatcacgtggttgaggtggagcatgaattcta
cgtcaaaaagggtggagccaagaaaagacccgcccccagtgacgcagatataagtgagcccaaacgggtgcgcgagtcagttgcgcag
ccatcgacgtcagacgcggaagcttcgatcaactacgcagacaggtaccaaaacaaatgttctcgtcacgtgggcatgaatctgatgctgtt
tccctgcagacaatgcgagagaatgaatcagaattcaaatatctgcttcactcacggacagaaagactgtttagagtgctttcccgtgtcaga
atctcaacccgtttctgtcgtcaaaaaggcgtatcagaaactgtgctacattcatcatatcatgggaaaggtgccagacgcttgcactgcctgc
gatctggtcaatgtggatttggatgactgcatctttgaacaataaaatggctaggatccggccggcctgcaggtgtcctcacaggaacgaagt
ccctaaagaaacagtggcagccaggtttagccccggaaaacttgtttattgcagcttataatggttacaaataaagcaatagcatcacaaattt
cacaaataaagcattttttttcactgcattctagttgtggtttgtccaaactcatcaatgtatcttattgactggattgagggacagccccccccca
aagccccagggatgtaattacgtccctccccgctaggggcagcagcgagccgcccggggctccgctccggtccggcgctcccccg
catcccgagccggcagcgtgcggggacagcccgggcacggggaaggtggcacgggatcgctttcctctgaacgcttctcgctgctcttt
gagcctgcagacacctggggggatacggggaaaaggcctccaaggccagcttcccacaataagttgggtgaattttggctcattcctccttt
ctataggattgaggtcagagcgacattgattattgactagttattaatagtaatcaattacggggtcattagttcatagcccatatatggagttcc
gcgttacataacttacggtaaatggcccgcctggctgaccgcccaacgacccccgcccattgacgtcaataatgacgtatgttcccatagtaac
gccaatagggactttccattgacgtcaatgggtggagtatttacggtaaactgcccacttggcagtacatcaagtgtatcatatgccaagtacg
ccccctattgacgtcaatgacggtaaatggcccgcctggcattatgcccagtacatgaccttatgggactttcctacttggcagtacatctacgt
attagtcatcgctattaccatggtgatgcggttttggcagtacatcaatgggcgtggatagcggtttgactcacggggatttccaagtctccacc
ccattgacgtcaatgggagtttgttttggaaccaaaatcaacgggactttccaaaatgtcgtaacaactccgccccattgacgcaaatgggcg
gtaggcgtgtacggtgggaggtctatataagcagagctctccctatcagtgatagagatctccctatcagtgatagagatcgtcgacgagctc
```

-continued

```
gtttagtgaaccgtcagatcgcctggagacgccatccacgctgttttgacctccatagaagacaccgggaccgatccagcctatcccaattct
gatgcgccggtgatcagatcaaaaacttcagccaggtacaatggatggaactggtcggatggctggtggataagggcatcacaagcgaga
agcaatggatccaggaggaccaggcctcatatatttcttttaacgccgctagcaattccagaagccagatcaaggctgctctggacaacgcc
ggcaaaatcatgagcctgaccaagaccgcccctgactacctggtgggacagcagcctgtggaagatatcagcagcaacagaatctataag
atcctggaactgaacggctacgaccccagtacgccgcctccgtgttcctgggctgggctacaaagaagttcggcaagcggaacaccatc
tggctgttcggacctgccaccacaggcaaaaccaatatcgccgaggccatcgcccacaccgtgcctttctacggctgcgtgaactggacaa
acgagaacttccccttcaacgactgtgtggacaagatggtgatctggtgggaggaaggcaaaatgacagctaaggtggtggaatctgcca
aggctatcctgggaggctctaaggtcagggtggatcagaagtgtaaaagcagcgcccagattgaccctacccctgtgatcgtgaccagca
ataccaacatgtgcgccgtgatcgacggcaacagcaccaccttcgagcatcagcagcctctgcaggaccggatgttcaagtttgagctcac
cagacggctggatcacgacttcggcaaggtgaccaagcaggaggtgaaggatttcttcagatgggccaaagaccacgttgttgaggtgga
acacgagttctacgtgaagaagggcggcgccaagaaaagacccgcccctagcgacgccgacatcagcgagcctaagagagtgcggga
aagcgtggcccagcccagcacatctgatgctgaggccagcatcaactacgccgatagataccaaaacaagtgcagccgccacgtgggca
tgaacctgatgctgtttccctgcagacagtgtgaaagaatgaaccagaattctaatatctgctttacacacggccagaaagattgcctggaatg
cttccctgtgtccgagagccaaccagtgtctgtggtgaaaaaggcctaccagaagctgtgctacatccaccacatcatgggcaaggtgcca
gacgcctgtaccgcctgcgacctggtcaacgtggacctggacgactgcatcttcgagcagtgatttgtgatgggaattctgtgctgtgccttct
agttgccagccatctgttgtttgccccctccccgtgccttccttgaccctggaaggtgccactcccactgtcctttcctaataaaatgaggaaatt
gcatcgcattgtctgagtaggtgtcattctattctgggggtggggggggcaggacagcaaggggaggattgggaagacaatagcagg
catgctggggatgcggtgggctctatgggacctttttagggcccattggtatggcttttcccgtatccccccaggtgtctgcaggctcaaa
gagcagcgagaagcgttcagaggaaagcgatcccgtgccaccttccccgtgcccgggctgtccccgcacgctgccggctcggggatgc
gggggagcgccggaccggagcggagccccgggcggctcgctgctgccccctagcggggagggacgtaattacatccctgggggc
tttggggggggctgtccctctagagcggccgccaccgcggtggagctccagcttttgttccctttagtgagggttaattagatcttaatacga
ctcactatagggcgaattgggtaccgggccccctgaggcggaaagaaccagctggggctctaggggggtatccccggggttggggttgc
gccttttccaaggcagccctgggttttgcgcagggacgcggctgctctgggcgtggttccgggaaacgcagcggcgccgaccctgggtct
cgcacattcttcacgtccgttcgcagcgtcacccggatcttcgccgctaccttgtgggcccccggcgacgcttcctgctccgcccctaagt
cgggaaggttccttgcggttcgcggcgtgccggacgtgacaaacggaagccgcacgtctcactagtaccctcgcagacggacagcgcca
gggagcaatggcagcgcgccgaccgcgatgggctgtggccaatagcggctgctcagcagggcgcgccgagagcagcggccgggaa
ggggcggtgcgggaggcggggtgtgggcggtagtgtgggccctgttcctgcccgcgcggtgttccgcattctgcaagcctccggagc
gcacgtcggcagtcggctccctcgttgaccgaatcaccgacctctctccccagaagctcccgggagcttgtatatccattttcggatctgatc
agcacgtgttgacaattaatcatcggcatagtatatcggcatagtataatacgacaaggtgaggaacgccaccatggccaagcctttgtctca
agaagaatccaccctcattgaaagagcaacggctacaatcaacagcatcccatctctgaagactacagcgtcgccagcgcagctctctct
agcgacggccgcatcttcactggtgtcaatgtatatcattttactggggaccttgtgcagaactcgtggtgctgggcactgctgctgctgcg
gcagctggcaacctgacttgtatcgtcgcgatcggaaatgagaacaggggcatcttgagccctgcggacggtgccgacaggtgcttctc
gatctgcatcctgggatcaaagccatagtgaaggacagtgatggacagccgacggcagttgggattcgtgaattgctgccctctggttatgt
gtgggagggctaaagcgcggggatctcatgctggagttcttcgcccaccccaacttgtttattgcagcttataatggttacaaataaagcaata
gcatcacaaatttcacaaataaagcattttttcactgcattctagttgtggtttgtccaaactcatcaatgtatcttatcatgtctgtagctga
tgtatacctaggatccggccggcctgcaggtgtcctcacaggaacgaagtccctaaagaaacagtggcagccaggtttagccccggaattgactg
gattcctttttagggcccattggtatggcttttcccgtatccccccaggtgtctgcaggctcaaagagcagcgagaagcgttcagaggaaa
gcgatcccgtgccaccttccccgtgcccgggctgtccccgcacgctgccggctcggggatgcgggggagcgccggaccggagcgga
gcccgggcggctcgctgctgccccctagcggggagggacgtaattacatccctgggggctttggggggggctgtccctctagagcg
gccgccaccgcggtggagctccagcttttgttccctttagtgagggttaattagatcttaatacgactcactatagggcgaattgggtaccggg
cccccctcgaggtcgacggtatcctcgaggtcgacggtatcgataagcttgatatctataacaagaaaatatatatataataagttatcacgt
```

-continued

```
aagtagaacatgaaataacaatataattatcgtatgagttaaatcttaaaagtcacgtaaaagataatcatgcgtcattttgactcacgcggtcgt tatagttcaaaatcagtgacacttaccgcattgacaagcacgcctcacgggagctccaagcggcgactgagatgtcctaaatgcacagcga cggattcgcgctatttagaaagagagagcaatatttcaagaatgcatgcgtcaattttacgcagactatctttctagggttaatctagctgcatca ggatcatatcgtcgggtcttttttccggctcagtcatcgcccaagctggcgctatctgggcatcggggaggaagaagcccgtgccttttcccg cgaggttgaagcggcatggaaagagtttgccgaggatgactgctgctgcattgacgttgagcgaaaacgcacgtttaccatgatgattcgg gaaggtgtggccatgcacgcctttaacggtgaactgttcgttcaggccacctgggataccagttcgtcgcggcttttccggacacagttccg gatggtcagcccgaagcgcatcagcaacccgaacaataccggcgacagccggaactgccgtgccggtgtgcagattaatgacagcggt gcggcgctgggatattacgtcagcgaggacgggtatcctggctgatgccgcagaaatggacatggataccccgtgagttacccggcgg gcgcgcttggcgtaatcatggtcatagctgtttcctgtgtgaaattgttatccgctcacaattccacacaacatacgagccggaagcataaagt gtaaagcctggggtgcctaatgagtgagctaactcacattaattgcgttgcgctcactgcccgctttccagtcgggaaacctgtcgtgccagc tgcattaatgaatcggccaacgcgcggggagaggcggtttgcgtattgggcgctcttccgcttcctcgctcactgactcgctgcgctcggtc gttcggctgcggcgagcggtatcagctcactcaaaggcggtaatacggttatccacagaatcaggggataacgcaggaaagaacatgtga gcaaaaggccagcaaaaggccaggaaccgtaaaaaggccgcgttgctggcgtttttccataggctccgcccccctgacgagcatcacaa aaatcgacgctcaagtcagaggtggcgaaacccgacaggactataaagataccaggcgtttccccctggaagctccctcgtgcgctctcct gttccgaccctgccgcttaccggatacctgtccgcctttctcccttcgggaagcgtggcgctttctcatagctcacgctgtaggtatctcagttc ggtgtaggtcgttcgctccaagctgggctgtgtgcacgaaccccccgttcagcccgaccgctgcgccttatccggtaactatcgtcttgagtc caacccggtaagacacgacttatcgccactggcagcagccactggtaacaggattagcagagcgaggtatgtaggcggtgctacagagtt cttgaagtggtggcctaactacggctacactagaaggacagtatttggtatctgcgctctgctgaagccagttaccttcggaaaaagagttgg tagctcttgatccggcaaacaaaccaccgctggtagcggtggtttttttgtttgcaagcagcagattacgcgcagaaaaaaaggatctcaaga agatcctttgatcttttctacggggtctgacgctcagtggaacgaaaactcacgttaagggattttggtcatgagattatcaaaaaggatcttca cctagatccttttaaattaaaaatgaagttttaaatcaatctaaagtatatatgagtaaacttggtctgacagttaccaatgcttaatcagtgagg cacctatctcagcgatctgtctatttcgttcatccatagttgcctgactccccgtcgtgtagataactacgatacgggagggcttaccatctggcc ccagtgctgcaatgataccgcgagacccacgctcaccggctccagatttatcagcaataaaccagccagccggaagggccgagcgcaga agtggtcctgcaactttatccgcctccatccagtctattaattgttgccgggaagctagagtaagtagttcgccagttaatagtttgcgcaacgtt gttgccattgctacaggcatcgtggtgtcacgctcgtcgtttggtatggcttcattcagctccggttcccaacgatcaaggcgagttacatgatc ccccatgttgtgcaaaaaagcggttagctccttcggtcctccgatcgttgtcagaagtaagttggccgcagtgttatcactcatggttatggca gcactgcataattctcttactgtcatgccatccgtaagatgcttttctgtgactggtgagtactcaaccaagtcattctgagaatagtgtatgcgg cgaccgagttgctcttgcccggcgtcaatacgggataataccgcgccacatagcagaactttaaaagtgctcatcattggaaaacgttcttcg gggcgaaaactctcaaggatcttaccgctgttgagatccagttcgatgtaacccactcgtgcacccaactgatcttcagcatcttttactttcac cagcgtttctgggtgagcaaaaacaggaaggcaaaatgccgcaaaaaagggaataagggcgacacggaaatgttgaatactcat
```

The sequence of the PB-hiRep-6 #vector is provided below:

PB-hiRep-6# (11,860 bp)

(SEQ ID NO: 19)

```
actcttcctttttcaatattattgaagcatttatcagggttattgtctcatgagcggatacatatttgaatgtatttagaaaaataaaca aataggggttccgcgcacatttccccgaaaagtgccacctaaattgtaagcgttaatattttgttaaaattcgcgttaaattttgttaaatcagc tcattttttaaccaataggccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtgaaccatcaccctaat caagtttttggggtcgaggtgccgtaaagcactaaatcggaaccctaaaggagccccgatttagagcttgacggggaaagccggcga acgtggcgagaaaggaagggaagaaagcgaaaggagcgggcgctagggcgctggcaagtgtagcggtcacgctgcgcgtaaccacc
```

-continued

```
acacccgccgcgcttaatgcgccgctacagggcgcgtcccattcgccattcaggctgcgcaactgttgggaagggcgatcggtgcgggc ctcttcgctattacgccagctggcgaaaggggatgtgctgcaaggcgattaagttgggtaacgccagggttttcccagtcacgacgttgta aaacgacggccagtgagcgcgcctcgttcattcacgttttgaacccgtggaggacgggcagactcgcggtgcaaatgtgttttacagcgtg atggagcagatgaagatgctcgacacgctgcagaacacgcagctagattaaccctagaaagataatcatattgtgacgtacgttaaagataa tcatgcgtaaaattgacgcatgtgttttatcggtctgtatatcgaggtttatttattaatttgaatagatattaagttttattatatttacactt acatactaataataaattcaacaaacaattttatttatgtttatttatttattaaaaaaaaacaaaaactcaaaatttcttctataaagtaacaaaa cttttatcgaattcctgcagcccgggggatccactagttctagagggacagccccccccaaagccccagggatgtaattacgtccctcccccgc taggggggcagcagcgagccgcccggggctccgctccggtccggcgctcccccgcatccccgagccggcagcgtgcggggacagcccgggca cggggaaggtggcacgggatcgctttcctctgaacgcttctcgctgctctttgagcctgcagacacctgggggggatacggggaaaaggcc tccaaggccagcttcccacaataagttgggtgaattttggctcattcctccttctataggattgaggtcagagctttgtgatgggaattctgtgg aatgtgtgtcagttagggtgtggaaagtcccgcgatcgctagcttaagcgctgatcaattggcgcgccgaattcgttatctgcagaattcggct tGACATTGATTATTGACTAGTTATTAATAGTAATCAATTACGGGGTCATTAGTTCATA

GCCCATATATGGAGTTCCGCGTTACATAACTTACGGTAAATGGCCCGCCTGGCTGAC

CGCCCAACGACCCCCGCCCATTGACGTCAATAATGACGTATGTTCCCATAGTAACGC

CAATAGGGACTTTCCATTGACGTCAATGGGTGGAGTATTTACGGTAAACTGCCCACT

TGGCAGTACATCAAGTGTATCATATGCCAAGTACGCCCCCTATTGACGTCAATGACG

GTAAATGGCCCGCCTGGCATTATGCCCAGTACATGACCTTATGGGACTTTCCTACTT

GGCAGTACATCTACGTATTAGTCATCGCTATTACCATGGTGATGCGGTTTTGGCAGT

ACATCAATGGGCGTGGATAGCGGTTTGACTCACGGGGATTTCCAAGTCTCCACCCCA

TTGACGTCAATGGGAGTTTGTTTTGGAACCAAAATCAACGGGACTTTCCAAAATGTC

GTAACAACTCCGCCCCATTGACGCAAATGGGCGGTAGGCGTGTACGGTGGGAGGTC

TATATAAGCAGAGCTCTCCCTATCAGTGATAGAGATCTCCCTATCAGTGATAGAGAT

CGTCGACGAGCTCGTTTAGTGAACCGTCAGATCGCCTGGAGACGCCATCCACGCTGT

TTTGACCTCCATAGAAGACACCGGGACCGATCCAGCCTgAACGCGCAGCCGCCacgccg gggttttacgagattgtgattaaggtccccagcgaccttgacgagcatctgcccggcatttctgacagctttgtgaactgggtggccgagaag gaatgggagttgccgccagattctgacatggatctgaatctgattgagcaggcacccctgaccgtggccgagaagctgcagcgcgactttc tgacggaatggcgccgtgtgagtaaggccccggaggctcttttcttgtgcaatttgagaagggagagagctacttccacatgcacgtgctc gtggaaaccaccggggtgaaatccatggttttgggacgtttcctgagtcagattcgcgaaaaactgattcagagaatttaccgcgggatcga gccgactttgccaaactggttcgcggtcacaaagaccagaaatggcgccggaggcgggaacaaggtggtggatgagtgctacatcccca attacttgctccccaaaacccagcctgagctccaatgggcatggaccaacatggaacagtacctcagcgcctgtttgaatctcacggagcgt aaacggttggtggcgcagcatctgacgcacgtgtcgcagacgcaggagcagaacaaagaatcagaatcccaattctgatgcgccggt gatcagatcaaaaacttcagccaggtacatggagctggtcgggtggctcgtggacaaggggattacctcggagaagcagtggatccagg aggaccaggcctcatacatctccttcaatgcggcctccaactcgcggtcccaaatcaaggctgccttggacaatgcgggaaagattatgag cctgactaaaaccgcccccgactacctggtgggccagcagcccgtggaggacatttccagcaatcggatttataaaattttggaactaaacg ggtacgatcccaatatgcggcttccgtctttctgggatgggccacgaaaaagttcggcaagaggaacaccatctggctgtttgggcctgca actaccgggaagaccaacatcgcggaggccatagcccacactgtgcccttctacgggtgcgtaaactggaccaatgagaactttcccttca acgactgtgtcgacaagatggtgatctggtgggaggagggaagatgaccgccaaggtcgtggagtcggccaaagccattctcggagga agcaaggtgcgcgtggaccagaaatgcaagtcctcggcccagatagacccgactcccgtgatcgtcacctccaacaccaacatgtgcgc cgtgattgacgggaactcaacgaccttcgaacaccagcagccgttgcaagaccggatgttcaaatttgaactcacccgccgtctggatcatg actttgggaaggtcaccaagcaggaagtcaaagactttttccggtgggcaaaggatcacgtggttgaggtggagcatgaattctacgtcaaa aagggtggagccaagaaaagacccgcccccagtgacgcagatataagtgagcccaaacgggtgcgcgagtcagttgcgcagccatcga
```

-continued cgtcagacgcggaagcttcgatcaactacgcagacaggtaccaaaacaaatgttctcgtcacgtgggcatgaatctgatgctgtttccctgc agacaatgcgagagaatgaatcagaattcaaatatctgcttcactcacggacagaaagactgtttagagtgctttcccgtgtcagaatctcaac ccgtttctgtcgtcaaaaaggcgtatcagaaactgtgctacattcatcatatcatgggaaaggtgccagacgcttgcactgcctgcgatctggt caatgtggatttggatgactgcatctttgaacaataaaatggctaggatccggccggcctgcaggtgtcctcacaggaacgaagtccctaaa gaaacagtggcagccaggtttagccccggaaaacttgtttattgcagcttataatggttacaaataaagcaatagcatcacaaatttcacaaat aaagcattttttcactgcattctagttgtggtttgtccaaactcatcaatgtatcttattgactggattgagggacagccccccccaaagcccc cagggatgtaattacgtccctcccccgctaggggggcagcagcgagccgcccggggctccgctccggtccggcgctcccccgcatccc cgagccggcagcgtgcgggacagcccgggcacggggaaggtggcacgggatcgctttcctctgaacgcttctcgctgctctttgagcct gcagacacctgggggatacggggaaaaggcctccaaggccagcttcccacaataagttgggtgaattttggctcattcctcctttctatag gattgaggtcagagcgacattgattattgactagttattaatagtaatcaattacggggtcattagttcatagcccatatatggagttccgcgtta ataacttacggtaaatggcccgcctggctgaccgcccaacgacccccgcccattgacgtcaataatgacgtatgttcccatagtaacgccaa ctagggactttccattgacgtcaatgggtggagtatttacggtaaactgcccacttggcagtacatcaagtgtatcatatgccaagtacgcccc tattgacgtcaatgacggtaaatggcccgcctggcattatgcccagtacatgaccttatgggactttcctacttggcagtacatctacgtattagt catcgctattaccatggtgatgcggttttggcagtacatcaatgggcgtggatagcggtttgactcacggggatttccaagtctccacccccatt gacgtcaatgggagtttgttttggaaccaaaatcaacgggactttccaaaatgtcgtaacaactccgccccattgacgcaaatgggcggtag gcgtgtacggtgggaggtctatataagcagagctctccctatcagtgatagagatctccctatcagtgatagagatcgtcgacgagctcgttt agtgaaccgtcagatcgcctggagacgccatccacgctgttttgacctccatagaagacaccgggaccgatccagcctatcccaattctgat gcgccggtgatcagatcaaaaacttcagccaggtacaatggatgaactggtcggatggctggtggataagggcatcacaagcgagaag caatggatccaggaggaccaggcctcatatatttcttttaacgccgctagcaattccagaagccagatcaaggctgctctggacaacgccgg caaaatcatgagcctgaccaagaccgcccctgactacctggtgggacagcagcctgtggaagatatcagcagcaacagaatctataagat cctggaactgaacggctacgaccccccagtacgccgcctccgtgttcctgggctgggctacaaagaagttcggcaagcggaacaccatctg gctgttcggacctgccaccacaggcaaaaccaatatcgccgaggccatcgcccacaccgtgcctttctacggctgcgtgaactggacaaa cgagaacttccccttcaacgactgtgtggacaagatggtgatctggtgggaggaaggcaaaatgacagctaaggtggtggaatctgccaa ggctatcctgggaggctctaaggtcagggtggatcagaagtgtaaaagcagcgcccagattgaccctacccctgtgatcgtgaccagcaat accaacatgtgcgccgtgatcgacggcaacagcaccaccttcgagcatcagcagcctctgcaggaccggatgttcaagtttgagctcacca gacggctggatcacgacttcggcaaggtgaccaagcaggaggtgaaggatttcttcagatgggccaaagaccacgttgttgaggtggaac acgagttctacgtgaagaagggcggcgccaagaaaagacccgcccctagcgacgccgacatcagcgagcctaagagagtgcgggaaa gcgtggcccagcccagcacatctgatgctgaggccagcatcaactacgccgatagataccaaaacaagtgcagccgccacgtgggcatg aacctgatgctgtttccctgcagacagtgtgaaagaatgaaccagaattctaatatctgcttacacacggccagaaagattgcctggaatgct tccctgtgtccgagagccaaccagtgtctgtggtgaaaaaggcctaccagaagctgtgctacatccaccacatcatgggcaaggtgccaga cgcctgtaccgcctgcgacctggtcaacgtggacctggacgactgcatcttcgagcagtgatttgtgatgggaattctgtgctgtgccttctag ttgccagccatctgttgtttgcccctcccccgtgccttccttgaccctggaaggtgccactcccactgtcctttcctaataaaatgaggaaattgc atcgcattgtctgagtaggtgtcattctattctggggggtgggggggcaggacagcaaggggaggattgggaagacaatagcaggca tgctgggatgcggtgggctctatgggacctttttagggcccattggtatggcttttccccgtatcccccaggtgtctgcaggctcaaaga gcagcgagaagcgttcagaggaaagcgatcccgtgccaccttccccgtgcccgggctgtcccgcacgctgccggctcggggatgcgg ggggagcgccggaccggagcggagccccgggcggctcgctgctgcccctagcggggagggacgtaattacatccctggggctt ggggggggctgtccctctagagcggccgccaccgcggtggagctccagcttttgttccctttagtgagggttaattagatcttaatacgact cactatagggcgaattgggtaccgggccccctgaggcggaaagaaccagctggggctctaggggtatccccgggttggggttgcg ccttttccaaggcagccctgggtttgcgcagggacgcggctgctctgggcgtggttccgggaaacgcagcggcgccgaccctgggtctc gcacattcttcacgtccgttcgcagcgtcacccggatcttcgccgctaccttgtgggccccccggcgacgcttcctgctccgcccctaagtc -continued

```
gggaaggttccttgcggttcgcggcgtgccggacgtgacaaacggaagccgcacgtctcactagtaccctcgcagacggacagcgcca gggagcaatggcagcgcgccgaccgcgatgggctgtggccaatagcggctgctcagcagggcgcgccgagagcagcggccgggaa ggggcggtgcgggaggcggggtgtggggcggtagtgtgggccctgttcctgcccgcgcggtgttccgcattctgcaagcctccggagc gcacgtcggcagtcggctccctcgttgaccgaatcaccgacctctctccccagaagctcccgggagcttgtatatccattttcggatctgatc agcacgtgttgacaattaatcatcggcatagtatatcggcatagtataatacgacaaggtgaggaacgccaccatggccaagcctttgtctca agaagaatccaccctcattgaaagagcaacggctacaatcaacagcatcccatctctgaagactacagcgtcgccagcgcagctctctct agcgacggccgcatcttcactggtgtcaatgtatatcattttactggggaccttgtgcagaactcgtggtgctgggcactgctgctgctgcg gcagctggcaacctgacttgtatcgtcgcgatcggaaatgagaacaggggcatcttgagcccctgcggacggtgccgacaggtgcttctc gatctgcatcctgggatcaaagccatagtgaaggacagtgatggacagccgacggcagttgggattcgtgaattgctgccctctggttatgt gtgggagggctaaagcgcgggatctcatgctggagttcttcgcccaccccaacttgtttattgcagcttataatggttacaaataaagcaata gcatcacaaatttcacaaataaagcatttttttcactgcattctagttgtggtttgtccaaactcatcaatgtatcttatcatgtctgtagctga tgtatacctaggatccggccggcctgcaggtgtcctcacaggaacgaagtccctaaagaaacagtggcagccaggtttagccccggaattgactg gattcctttttagggcccattggtatggcttttccccgtatcccccaggtgtctgcaggctcaaagagcagcgagaagcgttcagaggaaa gcgatcccgtgccaccttccccgtgcccgggctgtcccgcacgctgccggctcggggatgcgggggagcgccggaccggagcgga gccccggcggctcgctgctgcccctagcggggagggacgtaattacatccctgggggctttgggggggggctgtccctctagagcg gccgccaccgcggtggagctccagcttttgttccctttagtgagggttaattagatcttaatacgactcactatagggcgaattgggtaccggg cccccctcgaggtcgacggtatcctcgaggtcgacggtatcgataagcttgatatctataacaagaaatatatatataataagttatcacgt aagtagaacatgaaataacaatataattatcgtatgagttaaatcttaaaagtcacgtaaaagataatcatgcgtcattttgactcacgcggtcgt tatagttcaaaatcagtgacacttaccgcattgacaagcacgcctcacgggagctccaagcggcgactgagatgtcctaaatgcacagcga cggattcgcgctatttagaaagagagagcaatatttcaagaatgcatgcgtcaattttacgcagactatctttctagggttaatctagctgcatca ggatcatatcgtcgggtcttttttccggctcagtcatcgcccaagctggcgctatctgggcatcggggaggaagaagcccgtgccttttcccg cgaggttgaagcggcatggaaagagtttgccgaggatgactgctgctgcattgacgttgagcgaaaacgcacgtttaccatgatgattcgg gaaggtgtggccatgcacgcctttaacgtgaactgttcgttcaggccacctgggataccagttcgtcgcggcttttccggacacagttccg gatggtcagcccgaagcgcatcagcaacccgaacaataccggcgacagccggaactgccgtgccggtgtgcagattaatgacagcggt gcggcgctgggatattacgtcagcgaggacgggtatcctggctggatgccgcagaaatggacatggataccccgtgagttacccggcgg gcgcgcttggcgtaatcatggtcatagctgtttcctgtgtgaaattgttatccgctcacaattccacacaacatacgagccggaagcataaagt gtaaagcctggggtgcctaatgagtgagctaactcacattaattgcgttgcgctcactgcccgctttccagtcgggaaacctgtcgtgccagc tgcattaatgaatcggccaacgcgcggggagaggcggtttgcgtattgggcgctcttccgcttcctcgctcactgactcgctgcgctcggtc gttcggctgcggcgagcggtatcagctcactcaaaggcggtaatacggttatccacagaatcaggggataacgcaggaaagaacatgtga gcaaaaggccagcaaaaggccaggaaccgtaaaaaggccgcgttgctggcgtttttccataggctccgcccccctgacgagcatcacaa aaatcgacgctcaagtcagaggtggcgaaacccgacaggactataaagataccaggcgtttccccctggaagctccctcgtgcgctctcct gttccgaccctgccgcttaccggatacctgtccgcctttctcccttcgggaagcgtggcgctttctcatagctcacgctgtaggtatctcagttc ggtgtaggtcgttcgctccaagctgggctgtgtgcacgaaccccccgttcagcccgaccgctgcgccttatccggtaactatcgtcttgagtc caacccggtaagacacgacttatcgccactggcagcagccactggtaacaggattagcagagcgaggtatgtaggcggtgctacagagtt cttgaagtggtggcctaactacggctacactagaaggacagtatttggtatctgcgctctgctgaagccagttaccttcggaaaaagagttgg tagctcttgatccggcaaacaaaccaccgctggtagcggtggtttttttgttgcaagcagcagattacgcgcagaaaaaaaggatctcaaga agatcctttgatcttttctacggggtctgacgctcagtggaacgaaaactcacgttaagggattttggtcatgagattatcaaaaaggatcttca cctagatccttttaaattaaaaatgaagttttaaatcaatctaaagtatatatgagtaaacttggtctgacagttaccaatgcttaatcagtgagg cacctatctcagcgatctgtctatttcgttcatccatagttgcctgactccccgtcgtgtagataactacgatacgggagggcttaccatctggcc ccagtgctgcaatgataccgcgagacccacgctcaccggctccagatttatcagcaataaaccagccagccggaagggccgagcgcaga agtggtcctgcaactttatccgcctccatccagtctattaattgttgccgggaagctagagtaagtagttcgccagttaatagtttgcgcaacgtt
```

-continued

```
gttgccattgctacaggcatcgtggtgtcacgctcgtcgtttggtatggcttcattcagctccggttcccaacgatcaaggcgagttacatgatc ccccatgttgtgcaaaaaagcggttagctccttcggtcctccgatcgttgtcagaagtaagttggccgcagtgttatcactcatggttatggca gcactgcataattctcttactgtcatgccatccgtaagatgcttttctgtgactggtgagtactcaaccaagtcattctgagaatagtgtatgcgg cgaccgagttgctcttgcccggcgtcaatacgggataataccgcgccacatagcagaactttaaaagtgctcatcattgaaaacgttcttcg gggcgaaaactctcaaggatcttaccgctgttgagatccagttcgatgtaacccactcgtgcacccaactgatcttcagcatcttttactttcac cagcgtttctgggtgagcaaaaacaggaaggcaaaatgccgcaaaaaagggaataagggcgacacggaaatgttgaatactcat
```

The sequence of the PB-hiRep-7 #vector is provided below:

PB-hiRep-7# (11,579 bp)

(SEQ ID NO: 20)

```
actcttccttttttcaatattattgaagcatttatcagggttattgtctcatgagcggatacatatttgaatgtatttagaaaaataaaca aatagggggttccgcgcacatttccccgaaaagtgccacctaaattgtaagcgttaatattttgttaaaattcgcgttaaatttttgttaaatcagc tcatttttaaccaataggccgaaatcggcaaaatcccttataaatcaaaagaatagaccgagatagggttgagtgttgttccagtttggaacaag agtccactattaaagaacgtggactccaacgtcaaagggcgaaaaccgtctatcaggggatggcccactacgtgaaccatcaccctaat caagttttttggggtcgaggtgccgtaaagcactaaatcggaaccctaaaggggagccccgatttagagcttgacggggaaagccggcga acgtggcgagaaaggaagggaagaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc ctcttcgctattacgccagctggcgaaaggggggatgtgctgcaaggcgattaagttgggtaacgccagggttttcccagtcacgacgttgta aaacgacggccagtgagcgcgcctcgttcattcacgttttgaaccgtggaggacgggcagactcgcggtgcaaatgtgttttacagcgtg atggagcagatgaagatgctcgacacgctgcagaacacgcagctagattaaccctagaaagataatcatattgtgacgtacgttaaagataa tcatgcgtaaaattgacgcatgtgttttatcggtctgtatatcgaggtttatttattaatttgaatagatattaagttttattatatttacactta catactaataataaattcaacaaacaatttatttatgtttatttatttattaaaaaaaaacaaaaactcaaaatttcttctataaagtaacaaaa cttttatcgaattcctgcagcccgggggatccactagttctagagggacagcccccccaaagccccagggatgtaattacgtccctcccccg ctaggggcagcagcgagccgcccgggctccgctccggtccggcgctccccgcatcccgagccggcagcgtgcggggacagcccgggca cggggaaggtggcacgggatcgctttcctctgaacgcttctcgctgctctttgagcctgcagacacctgggggatacggggaaaaggcc tccaaggccagcttcccacaataagttgggtgaattttggctcattcctcctttctataggattgaggtcagagctttgtgatgggaattctgtgg aatgtgtgtcagttagggtgtggaaagtcccgcgatcgctagcttaagcgctgatcaattggcgcgccgaattcgttatctgcagaattcggct tggcctccgcgccgggttttggcgcctcccgcgggcgccccctcctcacgcgagcgctgccacgtcagacgaagggcgcagcgagc gtcctgatccttccgcccggacgctcaggacagcggcccgctgctcataagactcggccttagaaccccagtatcagcagaaggacatttt aggacgggacttgggtgactctagggcactggttttctttccagagagcggaacaggcgaggaaaagtagtcccttctcggcgattctgcg gagggatctccgtggggcggtgaacgccgatgattatataaggacgcgccggTCCCTATCAGTGATAGAGAtcTCC CTATCAGTGATAGAGAgtgtggcacagctagttccgtcgcagccgggatttgggtcgcggttcttgtttgtggatcgctgtgat cgtcacttgacGAACGCGCAGCCGCCATGccgggggttttacgagattgtgattaaggtccccagcgaccttgacgagcatc tgcccggcatttctgacagctttgtgaactgggtggccgagaaggaatgggagttgccgccagattctgacatggatctgaatctgattgagc aggcacccctgaccgtggccgagaagctgcagcgcgactttctgacggaatggcgccgtgtgagtaaggccccggaggctcttttctttgt gcaatttgagaaggagagagctacttccacatgcacgtgctcgtggaaaccaccggggtgaaatccatggttttgggacgtttcctgagtc agattcgcgaaaaactgattcagagaatttaccgcggatcgagccgactttgccaaactggttcgcggtcacaaagaccagaaatggcgc cggaggcgggaacaaggtggtggatgagtgctacatccccaattacttgctccccaaaacccagcctgagctccaatgggcatggaccaa catggaacagtacctcagcgcctgtttgaatctcacggagcgtaaacgttggtggcgcagcatctgacgcacgtgtcgcagacgcagga gcagaacaaagagaatcagaatcccaattctgatgcgccggtgatcagatcaaaaacttcagccaggtacatggagctggtcgggtggctc
```

-continued

```
gtggacaaggggattacctcggagaagcagtggatccaggaggaccaggcctcatacatctccttcaatgcggcctccaactcgcggtcc
caaatcaaggctgccttggacaatgcgggaaagattatgagcctgactaaaaccgccccgactacctggtgggccagcagcccgtgga
ggacatttccagcaatcggatttataaaattttggaactaaacgggtacgatccccaatatgcggcttccgtctttctgggatgggccacgaaa
aagttcggcaagaggaacaccatctggctgtttgggcctgcaactaccgggaagaccaacatcgcggaggccatagcccacactgtgcc
cttctacgggtgcgtaaactggaccaatgagaactttccccttcaacgactgtgtcgacaagatggtgatctggtgggaggaggggaagatg
accgccaaggtcgtggagtcggccaaagccattctcggaggaagcaaggtgcgcgtggaccagaaatgcaagtcctcggcccagatag
acccgactcccgtgatcgtcacctccaacaccaacatgtgcgccgtgattgacgggaactcaacgaccttcgaacaccagcagccgttgca
agaccggatgttcaaatttgaactcacccgccgtctggatcatgactttgggaaggtcaccaagcaggaagtcaaagacttttttccggtggg
caaaggatcacgtggttgaggtggagcatgaattctacgtcaaaaaggggagccaagaaaagacccgcccccagtgacgcagatata
agtgagcccaaacgggtgcgcgagtcagttgcgcagccatcgacgtcagacgcggaagcttcgatcaactacgcagacaggtaccaaaa
caaatgttctcgtcacgtgggcatgaatctgatgctgtttccctgcagacaatgcgagagaatgaatcagaattcaaatatctgcttcactcacg
gacagaaagactgtttagagtgctttcccgtgtcagaatctcaacccgtttctgtcgtcaaaaaggcgtatcagaaactgtgctacattcatcat
atcatggaaaggtgccagacgcttgcactgcctgcgatctggtcaatgtggatttggatgactgcatctttgaacaataaaatggctaggat
ccggccggcctgcaggtgtcctcacaggaacgaagtccctaaagaaacagtggcagccaggtttagccccggaaaacttgtttattgcagc
ttataatggttacaaataaagcaatagcatcacaaatttcacaaataaagcattttttttcactgcattctagttgtggtttgtccaaactcatcaa
tgtatcttattgactggattgagggacagcccccccccaaagcccccagggatgtaattacgtccctcccccgctaggggcagcagcgagcc
gcccggggctccgctccggtccggcgctcccccgcatcccccgagccggcagcgtgcggggacagcccgggcacggggaaggtggc
acgggatcgctttcctctgaacgcttctcgctgctctttgagcctgcagacacctgggggggatacggggaaaaggcctccaaggccagctt
cccacaataagttgggtgaattttggctcattcctcctttctataggattgaggtcagagcgacattgattattgactagttattaatagtaatca
attacgggtgtcattagttcatagcccatatatggagttccgcgttacataacttacggtaaatggcccgcctggctgaccgcccaacgacccc
gcccattgacgtcaataatgacgtatgttcccatagtaacgccaatagggactttccattgacgtcaatgggtggagtatttacggtaaactgc
ccacttggcagtacatcaagtgtatcatatgccaagtacgccccctattgacgtcaatgacggtaaatggcccgcctggcattatgcccagta
catgaccttatgggactttcctacttggcagtacatctacgtattagtcatcgctattaccatggtgatgcggttttggcagtacatcaatgggcg
tggatagcggtttgactcacggggatttccaagtctccacccattgacgtcaatgggagtttgttttggaaccaaaatcaacgggactttcca
aaatgtcgtaacaactccgccccattgacgcaaatgggcggtaggcgtgtacggtgggaggtctatataagcagagctctccctatcagtga
tagagatctccctatcagtgatagagatcgtcgacgagctcgtttagtgaaccgtcagatcgcctggagacgccatccacgctgttttgacct
ccatagaagacaccgggaccgatccagcctatcccaattctgatgcgccggtgatcagatcaaaaacttcagccaggtacaatggatgaa
ctggtcggatggctggtggataagggcatcacaagcgagaagcaatggatccaggaggaccaggcctcatatatttcttttaacgccgcta
gcaattccagaagccagatcaaggctgctctggacaacgccggcaaaatcatgagcctgaccaagaccgcccctgactacctggtggga
cagcagcctgtggaagatatcagcagcaacagaatctataagatcctggaactgaacggctacgaccccagtacgccgcctccgtgttcc
tgggctgggctacaaagaagttcggcaagcggaacaccatctggctgttcggacctgccaccacaggcaaaaccaatatcgccgaggcc
atcgcccacaccgtgcctttctacggctgcgtgaactggacaaacgagaacttccccttcaacgactgtgtggacaagatggtgatctggtg
ggaggaaggcaaaatgacagctaaggtggtggaatctgccaaggctatcctgggaggctctaaggtcagggtggatcagaagtgtaaaa
gcagcgcccagattgaccctacccctgtgatcgtgaccagcaataccaacatgtgcgccgtgatcgacggcaacagcaccaccttcgagc
atcagcagcctctgcaggaccggatgttcaagtttgagctcaccagacggctggatcacgacttcggcaaggtgaccaagcaggaggtga
aggatttcttcagatgggccaaagaccacgttgttgaggtggaacacgagttctacgtgaagaagggcggcgccaagaaaagacccgcc
cctagcgacgccgacatcagcgagcctaagagagtgcgggaaagcgtggcccagcccagcacatctgatgctgaggccagcatcaact
acgccgatagataccaaaacaagtgcagccgccacgtgggcatgaacctgatgctgtttcctgcagacagtgtgaaagaatgaaccaga
attctaatatctgctttacacacggccagaaagattgcctggaatgcttccctgtgtccgagagccaaccagtgtctgtggtgaaaaggccta
ccagaagctgtgctacatccaccacatcatgggcaaggtgccagacgcctgtaccgcctgcgacctggtcaacgtggacctggacgactg
catcttcgagcagtgatttgtgatgggaattctgtgctgtgccttctagttgccagccatctgttgtttgcccctcccccgtgccttccttgaccc
```

-continued

```
tggaaggtgccactcccactgtcctttcctaataaaatgaggaaattgcatcgcattgtctgagtaggtgtcattctattctggggggggggtg
gggcaggacagcaaggggaggattgggaagacaatagcaggcatgctgggatgcggtgggctctatgggaccttttttagggcccat
tggtatggcttttccccgtatcccccaggtgtctgcaggctcaaagagcagcgagaagcgttcagaggaaagcgatcccgtgccaccttc
cccgtgcccgggctgtccccgcacgctgccggctcggggatgcggggggagcgccggaccggagcggagccccgggcggctcgct
gctgcccctagcggggagggacgtaattacatccctgggggctttggggggggctgtccctctagagcggccgccaccgcggtgg
agctccagcttttgttcccttagtgagggttaattagatcttaatacgactcactatagggcgaattgggtaccgggccccccctgaggcggaa
agaaccagctggggctctaggggtatccccggggttggggttgcgccttttccaaggcagccctgggtttgcgcagggacgcggctgct
ctgggcgtggttccggaaaacgcagcggcgccgaccctgggtctcgcacattcttcacgtccgttcgcagcgtcaccggatcttcgccgc
taccttgtgggcccccggcgacgcttcctgctccgcccctaagtcgggaaggttccttgcggttcgcggcgtgccggacgtgacaaac
ggaagccgcacgtctcactagtaccctcgcagacggacagcgccaggagcaatggcagcgcgccgaccgcgatgggctgtggccaa
tagcggctgctcagcagggcgcgccgagagcagcggccgggaaggggcggtgcgggaggcgggtgtgggcggtagtgtgggcc
ctgttcctgcccgcgcggtgttccgcattctgcaagcctccggagcgcacgtcggcagtcggctccctcgttgaccgaatcaccgacctctc
tccccagaagctcccgggagcttgtatatccattttcggatctgatcagcacgtgttgacaattaatcatcggcatagtatatcggcatagtata
atacgacaaggtgaggaacgccaccatggccaagcctttgtctcaagaagaatccaccctcattgaaagagcaacggctacaatcaacag
catcccatctctgaagactacagcgtcgccagcgcagctctctctagcgacggccgcatcttcactggtgtcaatgtatatcattttactggg
ggaccttgtgcagaactcgtggtgctgggcactgctgctgctgcggcagctggcaacctgacttgtatcgtcgcgatcggaaatgagaaca
ggggcatcttgagccctgcggacggtgccgacaggtgcttctcgatctgcatcctgggatcaaagccatagtgaaggacagtgatggac
agccgacggcagttgggattcgtgaattgctgccctctggttatgtgtgggagggctaaagcgcggggatctcatgctggagttcttcgccc
accccaacttgtttattgcagcttataatggttacaaataaagcaatagcatcacaaatttcacaaataaagcatttttttcactgcattctagt
tgtggtttgtccaaactcatcaatgtatcttatcatgtctgtagctgatgtatacctaggatccggccggcctgcaggtgtcctcacaggaacga
agtccctaaagaaacagtggcagccaggtttagccccggaattgactggattcctttttagggcccattggtatggcttttccccgtatccccc
caggtgtctgcaggctcaaagagcagcgagaagcgttcagaggaaagcgatcccgtgccaccttcccgtgcccgggctgtccccgcacgct
gccggctcggggatgcggggggagcgccggaccggagcggagccccgggcggctcgctgctgcccctagcggggagggacgta
attacatccctgggggctttggggggggctgtccctctagagcggccgccaccgcggtggagctccagcttttgttcccttagtgagggtt
aattagatcttaatacgactcactatagggcgaattgggtaccgggccccccctcgaggtcgacggtatcctcgaggtcgacggtatcgata
agcttgatatctataacaagaaatatatatataatgagttatcacgtaagtagaacatgaaataacaatataattatcgtatgagttaaatctta
aaagtcacgtaaaagataatcatgcgtcattttgactcacgcggtcgttatagttcaaaatcagtgacacttaccgcattgacaagcacgcctcac
gggagctccaagcggcgactgagatgtcctaaatgcacagcgacggattcgcgctatttagaaagagagagcaatatttcaagaatgcatg
cgtcaatttacgcagactatcttctcagggttaatctagctgcatcaggatcatatcgtcgggtcttttttccggctcagtcatcgcccaagctg
gcgctatctgggcatcggggaggaagaagcccgtgccttttcccgcgaggttgaagcggcatggaaagagtttgccgaggatgactgctgc
tgcattgacgttgagcgaaaacgcacgtttaccatgatgattcgggaaggtgtggccatgcacgcctttaacggtgaactgttcgttcaggcc
acctgggataccagttcgtcgcggcttttccggacacagttccggatggtcagcccgaagcgcatcagcaacccgaacaataccggcgac
agccggaactgccgtgccggtgtgcagattaatgacagcggtgcggcgctggatattacgtcagcgaggacgggtatcctggctggatg
ccgcagaaatggacatggataccccgtgagttacccggggggcgcgcttggcgtaatcatggtcatagctgtttcctgtgtgaaattgttatc
cgctcacaattccacacaacatacgagccggaagcataaagtgtaaagcctggggtgcctaatgagtgagctaactcacattaattgcgttg
cgctcactgcccgctttccagtcgggaaacctgtcgtgccagctgcattaatgaatcggccaacgcgcggggagaggcggtttgcgtattg
ggcgctcttccgcttcctcgctcactgactcgctgcgctcggtcgttcggctgcggcgagcggtatcagctcactcaaaggcggtaatacgg
ttatccacagaatcaggggataacgcaggaaagaacatgtgagcaaaaggccagcaaaaggccaggaaccgtaaaaaggccgcgttgc
tggcgttttccataggctccgcccccctgacgagcatcacaaaaatcgacgctcaagtcagaggtggcgaaacccgacaggactataaag
ataccaggcgtttccccctggaagctccctcgtgcgctctcctgttccgaccctgccgcttaccggatacctgtccgcctttctcccttcggga
```

-continued

```
agcgtggcgctttctcatagctcacgctgtaggtatctcagttcggtgtaggtcgttcgctccaagctgggctgtgtgcacgaaccccccgttc agcccgaccgctgcgccttatccggtaactatcgtcttgagtccaacccggtaagacacgacttatcgccactggcagcagccactggtaa caggattagcagagcgaggtatgtaggcggtgctacagagttcttgaagtggtggcctaactacggctacactagaaggacagtatttggta tctgcgctctgctgaagccagttaccttcggaaaaagagttggtagctcttgatccggcaaacaaaccaccgctggtagcggtggttttttttgtt tgcaagcagcagattacgcgcagaaaaaaggatctcaagaagatcctttgatcttttctacggggtctgacgctcagtggaacgaaaactc acgttaagggattttggtcatgagattatcaaaaaggatcttcacctagatccttttaaattaaaaatgaagttttaaatcaatctaaagtatata tgagtaaacttggtctgacagttaccaatgcttaatcagtgaggcacctatctcagcgatctgtctatttcgttcatccatagttgcctgactccc cgtcgtgtagataactacgatacgggagggcttaccatctggccccagtgctgcaatgataccgcgagacccacgctcaccggctccagatttat cagcaataaaccagccagccggaagggccgagcgcagaagtggtcctgcaactttatccgcctccatccagtctattaattgttgccggga agctagagtaagtagttcgccagttaatagtttgcgcaacgttgttgccattgctacaggcatcgtggtgtcacgctcgtcgtttggtatggcttc attcagctccggttcccaacgatcaaggcgagttacatgatccccatgttgtgcaaaaaagcggttagctccttcggtcctccgatcgttgtc agaagtaagttggccgcagtgttatcactcatggttatggcagcactgcataattctcttactgtcatgccatccgtaagatgcttttctgtgact ggtgagtactcaaccaagtcattctgagaatagtgtatgcggcgaccgagttgctcttgcccggcgtcaatacgggataataccgcgccacat agcagaactttaaaagtgctcatcattggaaaacgttcttcggggcgaaaactctcaaggatcttaccgctgttgagatccagttcgatgtaac ccactcgtgcacccaactgatcttcagcatcttttactttcaccagcgtttctgggtgagcaaaaacaggaaggcaaatgccgcaaaaaag ggaataagggcgacacggaaatgttgaatactcat
```

The sequence of the PB-hiRep-8 #vector is provided below:

PB-hiRep-8# (11,701 bp)

(SEQ ID NO: 21)

```
actcttcctttttcaatattattgaagcatttatcagggttattgtctcatgagcggatacatatttgaatgtatttagaaaaataaaca aatagggggttccgcgcacatttccccgaaaagtgccacctaaattgtaagcgttaatattttgttaaaattcgcgttaaattttttgttaaatcagc tcattttttaaccaataggccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtgaaccatcaccctaat caagttttttggggtcgaggtgccgtaaagcactaaatcggaaccctaaagggagccccccgatttagagcttgacggggaaagccggcga acgtggcgagaaaggaagggaagaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc ctcttcgctattacgccagctggcgaaaggggggatgtgctgcaaggcgattaagttgggtaacgccagggttttcccagtcacgacgttgta aaacgacggccagtgagcgcgcctcgttcattcacgttttttgaacccgtggaggacgggcagactcgcggtgcaaatgtgttttacagcgtg atggagcagatgaagatgctcgacacgctgcagaacacgcagctagattaaccctagaaagataatcatattgtgacgtacgttaaagataa tcatgcgtaaaattgacgcatgtgttttatcggtctgtatatcgaggtttatttattaatttgaatagatattaagttttattatatttacactta catactaataataaattcaacaaacaatttatttatgtttatttatttattaaaaaaaaacaaaactcaaaatttcttctataaagtaacaaaac ttttatcgaattcctgcagcccggggatccactagttctagaggacagccccccccaaagccccagggatgtaattacgtccctccccgct aggggggcagcagcgagccgcccggggctccgctccggtccggcgctcccccgcatcccgagccggcagcgtgcggggacagcccgggca cggggaaggtggcacgggatcgctttcctctgaacgcttctcgctgctctttgagcctgcagacacctgggggatacggggaaaggcc tccaaggccagcttcccacaataagttgggtgaattttggctcattcctcctttctataggattgaggtcagagctttgtgatgggaattctgtgg aatgtgtgtcagttagggtgtggaaagtcccgcgatcgctagcttaagcgctgatcaattggcgcgccgaattcgttatctgcagaattcggct tctgctccctgcttgtgtgttggaggtcgctgagtagtgcgcgagcaaaatttaagctacaacaaggcaaggcttgaccgacaattgcatgaa gaatctgcttagggttaggcgttttgcgctgcttcgcgatgtacgggccagatatacgcgtatctgagggggactagggtgtgtttaggcgaaa agcggggcttcggttgtacgcggttaggagtcccctcaggatatagtagtttcgcttttgcatagggaggggaaatgtagtcttatgcaatac acttgtagtcttgcaacatggtaacgatgagttagcaacatgccttacaaggagagaaaaagcaccgtgcatgccgattggtggaagtaagg
```

-continued tggtacgatcgtgccttattaggaaggcaacagacaggtctgacatggattggacgaaccactgaattccgcattgcagagataattgtattta agtgcctagcTCCCTATCAGTGATAGAGAtcTCCCTATCAGTGATAGAGAtcgatacaataaacgccat ttgaccattcaccacattggtgtgcaccGAACGCGCAGCCGCCATGccggggttttacgagattgtgattaaggtccccagc gaccttgacgagcatctgcccggcatttctgacagctttgtgaactgggtggccgagaaggaatgggagttgccgccagattctgacatgg atctgaatctgattgagcaggcacccctgaccgtggccgagaagctgcagcgcgactttctgacggaatggcgccgtgtgagtaaggccc cggaggctcttttctttgtgcaatttgagaagggagagagctacttccacatgcacgtgctcgtggaaaccaccggggtgaaatccatggtttt gggacgtttcctgagtcagattcgcgaaaaactgattcagagaatttaccgcgggatcgagccgactttgccaaactggttcgcggtcacaa agaccagaaatggcgccggaggcgggaacaaggtggtggatgagtgctacatccccaattacttgctccccaaaacccagcctgagctc caatgggcatggaccaacatggaacagtacctcagcgcctgtttgaatctcacggagcgtaaacggttggtggcgcagcatctgacgcac gtgtcgcagacgcaggagcagaacaaagagaatcagaatcccaattctgatgcgccggtgatcagatcaaaaacttcagccaggtacatg gagctggtcgggtggctcgtggacaaggggattacctcggagaagcagtggatccaggaggaccaggcctcatacatctccttcaatgcg gcctccaactcgcggtcccaaatcaaggctgccttggacaatgcgggaaagattatgagcctgactaaaaccgcccccgactacctggtg ggccagcagcccgtggaggacatttccagcaatcggatttataaaattttggaactaaacgggtacgatccccaatatgcggcttccgtctttc tgggatgggccacgaaaaagttcggcaagaggaacaccatctggctgtttgggcctgcaactaccgggaagaccaacatcgcggaggcc atagcccacactgtgcccttctacgggtgcgtaaactggaccaatgagaactttcccttcaacgactgtgtcgacaagatggtgatctggtgg gaggaggggaagatgaccgccaaggtcgtggagtcggccaaagccattctcggaggaagcaaggtgcgcgtggaccagaaatgcaag tcctcggcccagatagacccgactcccgtgatcgtcacctccaacaccaacatgtgcgccgtgattgacgggaactcaacgaccttcgaac accagcagccgttgcaagaccggatgttcaaatttgaactcacccgccgtctggatcatgactttgggaaggtcaccaagcaggaagtcaa agacttttccggtgggcaaaggatcacgtggttgaggtggagcatgaattctacgtcaaaaagggtggagccaagaaaagacccgcccc cagtgacgcagatataagtgagcccaaacgggtgcgcgagtcagttgcgcagccatcgacgtcagacgcggaagcttcgatcaactacg cagacaggtaccaaaacaaatgttctcgtcacgtgggcatgaatctgatgctgtttccctgcagacaatgcgagagaatgaatcagaattcaa atatctgcttcactcacggacagaaagactgtttagagtgctttcccgtgtcagaatctcaacccgtttctgtcgtcaaaaaggcgtatcagaaa ctgtgctacattcatcatatcatgggaaaggtgccagacgcttgcactgcctgcgatctggtcaatgtggatttggatgactgcatctttgaaca ataaaatggctaggatccggccggcctgcaggtgtcctcacaggaacgaagtccctaaagaaacagtggcagccaggtttagccccgga aaacttgtttattgcagcttataatggttacaaataaagcaatagcatcacaaatttcacaaataaagcattttttcactgcattctagttgtg gtttgtccaaactcatcaatgtatcttattgactggattgagggacagccccccccaaagcccccagggatgtaattacgtccctcccccgctag ggggcagcagcgagccgcccggggctccgctccggtccggcgctccccccgcatccccgagccggcagcgtgcggggacagcccg ggcacggggaaggtggcacgggatcgctttcctctgaacgcttctcgctgctctttgagcctgcagacacctgggggatacggggaaaa ggcctccaaggccagcttcccacaataagttgggtgaattttggctcattcctcctttctataggattgaggtcagagcgacattgattattgact agttattaatagtaatcaattacggggtcattagttcatagcccatatatggagttccgcgttacataacttacggtaaatggcccgcctggctga ccgcccaacgaccccgcccattgacgtcaataatgacgtatgttcccatagtaacgccaataggactttccattgacgtcaatgggtgga gtatttacggtaaactgcccacttggcagtacatcaagtgtatcatatgccaagtacgccccctattgacgtcaatgacggtaaatggcccgc ctggcattatgcccagtacatgaccttatgggactttcctacttggcagtacatctacgtattagtcatcgctattaccatggtgatgcggttttg gcagtacatcaatgggcgtggatagcggtttgactcacggggatttccaagtctccaccccattgacgtcaatgggagtttgttttggaaccaaa atcaacgggactttccaaaatgtcgtaacaactccgccccattgacgcaaatgggggtaggcgtgtacggtggaggtctatataagcag agctctccctatcagtgatagagatctccctatcagtgatagagatcgtcgacgagctcgtttagtgaaccgtcagatcgcctggagacgcca tccacgctgttttgacctccatagaagacaccgggaccgatccagcctatcccaattctgatgcgccggtgatcagatcaaaaacttcagcca ggtacaatggatggaactggtcggatggctggtggataagggcatcacaagcgagaagcaatggatccaggaggaccaggcctcatata tttcttttaacgccgctagcaattccagaagccagatcaaggctgctctggacaacgccggcaaaatcatgagcctgaccaagaccgcccct gactacctggtgggacagcagcctgtggaagatatcagcagcaacagaatctataagatcctggaactgaacggctacgaccccccagtac -continued

```
gccgcctccgtgttcctgggctgggctacaaagaagttcggcaagcggaacaccatctggctgttcggacctgccaccacaggcaaaacc aatatcgccgaggccatcgcccacaccgtgcctttctacggctgcgtgaactggacaaacgagaacttcccccttcaacgactgtgtggaca agatggtgatctggtgggaggaaggcaaaatgacagctaaggtggtggaatctgccaaggctatcctgggaggctctaaggtcagggtgg atcagaagtgtaaaagcagcgcccagattgaccctaccctgtgatcgtgaccagcaataccaacatgtgcgccgtgatcgacggcaaca gcaccaccttcgagcatcagcagcctctgcaggaccggatgttcaagtttgagctcaccagacggctggatcacgacttcggcaaggtgac caagcaggaggtgaaggatttcttcagatgggccaaagaccacgttgttgaggtggaacacgagttctacgtgaagaagggcggcgcca agaaaagacccgcccctagcgacgccgacatcagcgagcctaagagagtgcgggaaagcgtggcccagcccagcacatctgatgctg aggccagcatcaactacgccgatagataccaaaacaagtgcagccgccacgtgggcatgaacctgatgctgtttccctgcagacagtgtg aaagaatgaaccagaattctaatatctgctttacacacggccagaaagattgcctggaatgcttccctgtgtccgagagccaaccagtgtctg tggtgaaaaaggcctaccagaagctgtgctacatccaccacatcatgggcaaggtgccagacgcctgtaccgcctgcgacctggtcaacg tggacctggacgactgcatcttcgagcagtgatttgtgatgggaattctgtgctgtgccttctagttgccagccatctgttgtttgcccctccccc gtgccttccttgaccctggaaggtgccactcccactgtccttcctaataaaatgaggaaattgcatcgcattgtctgagtaggtgtcattctatt ctgggggtggggtggggcaggacagcaaggggggaggattgggaagacaatagcaggcatgctggggatgcggtgggctctatggga cctttttttagggcccattggtatggcttttttccccgtatcccccaggtgtctgcaggctcaaagagcagcgagaagcgttcagaggaaagcg atcccgtgccaccttccccgtgcccggctgtccccgcacgctgccggctcggggatgcggggggagcgccggaccggagcggagcc ccgggcggctcgctgctgcccctagcggggagggacgtaattacatccctgggggctttggggggggctgtccctctagagcggcc gccaccgcggtggagctccagcttttgttcccttagtgagggttaattagatcttaatacgactcactatagggcgaattgggtaccgggccc ccctgaggcggaaagaaccagctggggctctaggggtatccccggggttgggttgcgccttttccaaggcagccctgggtttgcgcag ggacgcggctgctctgggcgtggttccggaaacgcagcggcgccgaccctgggtctcgcacattcttcacgtccgttcgcagcgtcacc cggatcttcgccgctaccttgtgggcccccggcgacgcttcctgctccgcccctaagtcgggaaggttccttgcggttcgcggcgtgcc ggacgtgacaaacggaagccgcacgtctcactagtaccctcgcagacggacagcgccagggagcaatggcagcgcgccgaccgcgat gggctgtggccaatagcggctgctcagcagggcgcgccgagagcagcggccgggaaggggcggtgcgggaggcggggtgtgggc ggtagtgtgggccctgttcctgcccgcgcggtgttccgcattctgcaagcctccggagcgcacgtcggcagtcggctccctcgttgaccga atcaccgacctctctccccagaagctcccgggagcttgtatatccattttcggatctgatcagcacgtgttgacaattaatcatcggcatagtat atcggcatagtataatacgacaaggtgaggaacgccaccatggccaagcctttgtctcaagaagaatccaccctcattgaaagagcaacgg ctacaatcaacagcatcccatctctgaagactacagcgtcgccagcgcagctctctctagcgacggccgcatcttcactggtgtcaatgtat atcattttactgggggaccttgtgcagaactcgtggtgctgggcactgctgctgctgcggcagctggcaacctgacttgtatcgtcgcgatcg gaaatgagaacaggggcatcttgagcccctgcggacggtgccgacaggtgcttctcgatctgcatcctgggatcaaagccatagtgaagg acagtgatggacagccgacggcagttgggattcgtgaattgctgccctctggttatgtgtggagggctaaagcgcgggatctcatgctg gagttcttcgcccaccccaacttgtttattgcagcttataatggttacaaataaagcaatagcatcacaaatttcacaaataaagcattttttttca ctgcattctagttgtggtttgtccaaactcatcaatgtatcttatcatgtctgtagctgatgtatacctaggatccggccggcctgcaggtgtcc tcacaggaacgaagtccctaaagaaacagtggcagccaggtttagccccggaattgactggattcctttttttagggcccattggtatggcttttt ccccgtatcccccaggtgtctgcaggctcaaagagcagcgagaagcgttcagaggaaagcgatcccgtgccaccttccccgtgcccgggct gtccccgcacgctgccggctcggggatgcggggggagcgccggaccggagcggagccccgggcggctcgctgctgcccctagcgg gggagggacgtaattacatccctgggggctttggggggggctgtccctctagagcggccgccaccgcggtggagctccagcttttgttc cctttagtgagggttaattagatcttaatacgactcactatagggcgaattgggtaccgggccccccctcgaggtcgacggtatcctcgaggt cgacggtatcgataagcttgatatctataacaagaaatatatatataatagttatcacgtaagtagaacatgaataacaatataattatcgta tgagttaaatcttaaaagtcacgtaaaagataatcatgcgtcattttgactcacgcggtcgttatagttcaaaatcagtgacacttaccgcattga caagcacgcctcacgggagctccaagcggcgactgagatgtcctaaatgcacagcgacggattcgcgctatttagaaagagagagcaatat ttcaagaatgcatgcgtcaattttacgcagactatctttctagggttaatctagctgcatcaggatcatatcgtcgggtcttttttccggctcagt catcgcccaagctggcgctatctgggcatcggggaggaagaagcccgtgccttttcccgcgaggttgaagcggcatggaaagagtttgccga
```

-continued

```
ggatgactgctgctgcattgacgttgagcgaaaacgcacgtttaccatgatgattcgggaaggtgtggccatgcacgcctttaacggtgaac tgttcgttcaggccacctgggataccagttcgtcgcggcttttccggacacagttccggatggtcagcccgaagcgcatcagcaacccgaa caataccggcgacagccggaactgccgtgccggtgtgcagattaatgacagcggtgcggcgctgggatattacgtcagcgaggacgggt atcctggctggatgccgcagaaatggacatggataccccgtgagttaccggcgggcgcgcttggcgtaatcatggtcatagctgtttcctg tgtgaaattgttatccgctcacaattccacacaacatacgagccggaagcataaagtgtaaagcctggggtgcctaatgagtgagctaactca cattaattgcgttgcgctcactgcccgctttccagtcgggaaacctgtcgtgccagctgcattaatgaatcggccaacgcgcgggggagagg cggtttgcgtattgggcgctcttccgcttcctcgctcactgactcgctgcgctcggtcgttcggctgcggcgagcggtatcagctcactcaaa ggcggtaatacggttatccacagaatcaggggataacgcaggaaagaacatgtgagcaaaaggccagcaaaaggccaggaaccgtaaa aaggccgcgttgctggcgtttttccataggctccgcccccctgacgagcatcacaaaaatcgacgctcaagtcagaggtggcgaaacccg acaggactataaagataccaggcgtttccccctggaagctccctcgtgcgctctcctgttccgaccctgccgcttaccggatacctgtccgcc tttctcccttcgggaagcgtggcgctttctcatagctcacgctgtaggtatctcagttcggtgtaggtcgttcgctccaagctgggctgtgtgca cgaaccccccgttcagcccgaccgctgcgccttatccggtaactatcgtcttgagtccaacccggtaagacacgacttatcgccactggcag cagccactggtaacaggattagcagagcgaggtatgtaggcggtgctacagagttcttgaagtggtggcctaactacggctacactagaag gacagtatttggtatctgcgctctgctgaagccagttaccttcggaaaaagagttggtagctcttgatccggcaaacaaaccaccgctggtag cggtggtttttttgtttgcaagcagcagattacgcgcagaaaaaaaggatctcaagaagatcctttgatcttttctacggggtctgacgctcagt ggaacgaaaactcacgttaagggattttggtcatgagattatcaaaaaggatcttcacctagatccttttaaattaaaaatgaagttttaaatcaa tctaaagtatatatgagtaaacttggtctgacagttaccaatgcttaatcagtgaggcacctatctcagcgatctgtctatttcgttcatccatag ttgcctgactccccgtcgtgtagataactacgatacgggagggcttaccatctggccccagtgctgcaatgataccgcgagacccacgctcac cggctccagatttatcagcaataaaccagccagccggaagggccgagcgcagaagtggtcctgcaactttatccgcctccatccagtctatt aattgttgccgggaagctagagtaagtagttcgccagttaatagtttgcgcaacgttgttgccattgctacaggcatcgtggtgtcacgctcgt cgtttggtatggcttcattcagctccggttcccaacgatcaaggcgagttacatgatccccatgttgtgcaaaaaagcggttagctccttcggt cctccgatcgttgtcagaagtaagttggccgcagtgttatcactcatggttatggcagcactgcataattctcttactgtcatgccatccgtaaga tgcttttctgtgactggtgagtactcaaccaagtcattctgagaatagtgtatgcggcgaccgagttgctcttgcccggcgtcaatacgggata ataccgcgccacatagcagaactttaaaagtgctcatcattggaaaacgttcttcggggcgaaaactctcaaggatcttaccgctgttgagat ccagttcgatgtaacccactcgtgcacccaactgatcttcagcatcttttactttcaccagcgtttctgggtgagcaaaaacaggaaggcaaaa tgccgcaaaaaagggaataagggcgacacggaaatgttgaatactcat
```

The sequence of the PB-hiRep-9#vector is provided below:

PB-hiRep-9# (11, 861 bp)

(SEQ ID NO: 22)

```
actcttcctttttcaatattattgaagcatttatcagggttattgtctcatgagcggatacatatttgaatgtatttagaaaaataaaca aatagggggttccgcgcacatttccccgaaaagtgccacctaaattgtaagcgttaatattttgttaaaattcgcgttaaattttgttaaatcagc tcattttttaaccaataggccgaaatcggcaaaatcccttataaatcaaaagaatagaccgagatagggttgagtgttgttccagtttggaacaag agtccactattaaagaacgtggactccaacgtcaaagggcgaaaaccgtctatcagggcgatggcccactacgtgaaccatcaccctaat caagttttttggggtcgaggtgccgtaaagcactaaatcggaaccctaaagggagcccccgatttagagcttgacggggaaagccggcga acgtggcgagaaaggaagggaagaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc ctcttcgctattacgccagctggcgaaaggggatgtgctgcaaggcgattaagttgggtaacgccagggttttcccagtcacgacgttgta aaacgacggccagtgagcgcgcctcgttcattcacgttttgaacccgtggaggacgggcagactcgcggtgcaaatgtgttttacagcgtg atggagcagatgaagatgctcgacacgctgcagaacacgcagctagattaaccctagaaagataatcatattgtgacgtacgttaaagataa
```

-continued

```
tcatgcgtaaaattgacgcatgtgttttatcggtctgtatatcgagggtttatttattaatttgaatagatattaagttttattatattacactt
acatactaataataaattcaacaaacaatttatttatgtttatttattttattaaaaaaaaacaaaaactcaaaatttcttctataaagtaacaaa
acttttatcgaattcctgcagcccggggatccactagttctagagggacagccccccccaaagccccagggatgtaattacgtccctccccc
gctaggggggcagcagcgagccgccgggctccgctccggtccggcgctcccccgcatcccgagccggcagcgtgcgggacagcccgggca
cggggaaggtggcacgggatcgctttcctctgaacgcttctcgctgctctttgagcctgcagacacctgggggggatacggggaaaaggcc
tccaaggccagcttcccacaataagttgggtgaatttttggctcattcctcctttctataggattgaggtcagagctttgtgatgggaattctgtgg
aatgtgtgtcagttagggtgtggaaagtcccgcgatcgctagcttaagcgctgatcaattggcgcgccgaattcgttatctgcagaattcggct
tGACATTGATTATTGACTAGTTATTAATAGTAATCAATTACGGGGTCATTAGTTCATA
GCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGC
CAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACG
GTAAATGGCCCGCCTGGCATTATGCCCAGTACATGACCTTATGGGACTTTCCTACTT
GGCAGTACATCTACGTATTAGTCATCGCTATTACCATGGTGATGCGGTTTTGGCAGT
ACATCAATGGGCGTGGATAGCGGTTTGACTCACGGGGATTTCCAAGTCTCCACCCCA
TTGACGTCAATGGGAGTTTGTTTTGGAACCAAAATCAACGGGACTTTCCAAAATGTC
GTAACAACTCCGCCCCATTGACGCAAATGGGCGGTAGGCGTGTACGGTGGGAGGTC
TATATAAGCAGAGCTCTCCCTATCAGTGATAGAGATCTCCCTATCAGTGATAGAGAT
CGTCGACGAGCTCGTTTAGTGAACCGTCAGATCGCCTGGAGACGCCATCCACGCTGT
TTTGACCTCCATAGAAGACACCGGGACCGATCCAGCCTgAACGCGCAGCCGCCacgccg
gggttttacgagattgtgattaaggtccccagcgaccttgacgagcatctgcccggcatttctgacagctttgtgaactgggtggccgagaag
gaatgggagttgccgccagattctgacatggatctgaatctgattgagcaggcacccctgaccgtggccgagaagctgcagcgcgactttc
tgacggaatggcgccgtgtgagtaaggcccggaggctcttttctttgtgcaatttgagaagggagagagctacttccacatgcacgtgctc
gtggaaaccaccggggtgaaatccatggttttgggacgtttcctgagtcagattcgcgaaaaactgattcagagaatttaccgcgggatcga
gccgactttgccaaactggttcgcggtcacaaagaccagaaatggcgccggaggggggaacaaggtggtgatgagtgctacatcccca
attacttgctccccaaaacccagcctgagctccaatgggcatggaccaacatggaacagtacctcagcgcctgtttgaatctcacggagcgt
aaacggttggtggcgcagcatctgacgcacgtgtcgcagacgcaggagcagaacaaagagaatcagaatcccaattctgatgcgccggt
gatcagatcaaaaacttcagccaggtacatggagctggtcgggtggctcgtggacaagggggattacctcggagaagcagtggatccagg
aggaccaggcctcatacatctccttcaatgcggcctccaactcgcggtcccaaatcaaggctgccttggacaatgcgggaaagattatgag
cctgactaaaaccgcccccgactacctggtgggccagcagcccgtggaggacatttccagcaatcggatttataaaattttggaactaaacg
ggtacgatcccaatatgcggcttccgtctttctgggatgggccacgaaaaagttcggcaagaggaacaccatctggctgtttgggcctgca
actaccgggaagaccaacatcgcggaggccatagcccacactgtgcccttctacgggtgcgtaaactggaccaatgagaactttcccttca
acgactgtgtcgacaagatggtgatctggtgggaggaggggaagatgaccgccaaggtcgtggagtcggccaaagccattctcggagga
agcaaggtgcgcgtggaccagaaatgcaagtcctcggcccagatagacccgactcccgtgatcgtcacctccaacaccaacatgtgcgc
cgtgattgacgggaactcaacgaccttcgaacaccagcagccgttgcaagaccggatgttcaaatttgaactcacccgccgtctggatcatg
actttgggaaggtcaccaagcaggaagtcaaagacttttttccggtgggcaaaggatcacgtggttgaggtggagcatgaattctacgtcaaa
aagggtggagccaagaaaagacccgcccccagtgacgcagatataagtgagcccaaacgggtgcgcgagtcagttgcgcagccatcga
cgtcagacgcggaagcttcgatcaactacgcagacaggtaccaaaacaaatgttctcgtcacgtgggcatgaatctgatgctgtttccctgc
agacaatgcgagagaatgaatcagaattcaaatatctgcttcactcacggacagaaagactgtttagagtgctttcccgtgtcagaatctcaac
ccgtttctgtcgtcaaaaaggcgtatcagaaactgtgctacattcatcatatcatgggaaaggtgccagacgcttgcactgcctgcgatctggt
caatgtggatttggatgactgcatctttgaacaataaaaatggctaggatccggccggcctgcaggtgtcctcacaggaacgaagtccctaaa
```

-continued

```
gaaacagtggcagccaggtttagccccggaaaacttgtttattgcagcttataatggttacaaataaagcaatagcatcacaaatttcacaaat aaagcatttttttcactgcattctagttgtggtttgtccaaactcatcaatgtatcttattgactggattgagggacagccccccccaaagcccc cagggatgtaattacgtccctcccccgctagggggcagcagcgagccgcccggggctccgctccggtccggcgctcccccgcatccc cgagccggcagcgtgcgggacagcccgggcacgggaaggtggcacgggatcgctttcctctgaacgcttctcgctgctctttgagcct gcagacacctgggggatacggggaaaaggcctccaaggccagcttcccacaataagttgggtgaattttggctcattcctcctttctatag gattgaggtcagagcgacattgattattgactagttattaatagtaatcaattacggggtcattagttcatagcccatatatggagttccgcgtta cataacttacggtaaatggcccgcctggctgaccgcccaacgaccccgcccattgacgtcaataatgacgtatgttcccatagtaacgccaa tagggactttccattgacgtcaatgggtggagtatttacggtaaactgcccacttggcagtacatcaagtgtatcatatgccaagtacgcccc tattgacgtcaatgacggtaaatggcccgcctggcattatgcccagtacatgaccttatgggactttcctacttggcagtacatctacgtattagt catcgctattaccatggtgatgcggttttggcagtacatcaatgggcgtggatagcggtttgactcacggggatttccaagtctccacccatt gacgtcaatgggagtttgttttggaaccaaaatcaacgggactttccaaaatgtcgtaacaactccgccccattgacgcaaatggggtag gcgtgtacggtgggaggtctatataagcagagctctccctatcagtgatagagatctccctatcagtgatagagatcgtcgacgagctcgttt agtgaaccgtcagatcgcctggagacgccatccacgctgttttgacctccatagaagacaccgggaccgatccagcctatcccaattctgat gcgccggtgatcagatcaaaaacttcagccaggtacgccaccAcGgaactggtcggatggctggtggataagggcatcacaagcgaga agcaatggatccaggaggaccaggcctcatatatttcttttaacgccgctagcaattccagaagccagatcaaggctgctctggacaacgcc ggcaaaatcatgagcctgaccaagaccgcccctgactacctggtgggacagcagcctgtggaagatatcagcagcaacagaatctataag atcctggaactgaacggctacgaccccagtacgccgcctccgtgttcctgggctgggctacaaagaagttcggcaagcggaacaccatc tggctgttcggacctgccaccacaggcaaaaccaatatcgccgaggccatcgcccacaccgtgcctttctacggctgcgtgaactggacaa acgagaacttccccttcaacgactgtgtggacaagatggtgatctggtgggaggaaggcaaaatgacagctaaggtggtggaatctgcca aggctatcctgggaggctctaaggtcaggtggatcagaagtgtaaaagcagcgcccagattgaccctacccctgtgatcgtgaccagca ataccaacatgtgcgccgtgatcgacggcaacagcaccaccttcgagcatcagcagcctctgcaggaccggatgttcaagtttgagctcac cagacggctggatcacgacttcggcaaggtgaccaagcaggaggtgaaggatttcttcagatgggccaaagaccacgttgttgaggtgga acacgagttctacgtgaagaagggcggcgccaagaaaagacccgcccctagcgacgccgacatcagcgagcctaagagagtgcggga aagcgtggcccagcccagcacatctgatgctgaggcagcatcaactacgccgatagataccaaaacaagtgcagccgccacgtgggca tgaacctgatgctgtttccctgcagacagtgtgaaagaatgaaccagaattctaatatctgctttacacacggccagaaagattgcctggaatg cttccctgtgtccgagagccaaccagtgtctgtggtgaaaaaggcctaccagaagctgtgctacatccaccacatcatgggcaaggtgcca gacgcctgtaccgcctgcgacctggtcaacgtggacctggacgactgcatcttcgagcagtgatttgtgatgggaattctgtgctgtgccttct agttgccagccatctgttgtttgccctccccgtgccttccttgaccctggaaggtgccactcccactgtcctttcctaataaaatgaggaaatt gcatcgcattgtctgagtaggtgtcattctattctggggggggggggggcaggacagcaaggggggaggattgggaagacaatagcagg catgctggggatgcggtgggctctatgggaccttttttagggcccattggtatggcttttttccccgtatcccccaggtgtctgcaggctcaaa gagcagcgagaagcgttcagaggaaagcgatcccgtgccaccttcccgtgcccgggctgtcccgcacgctgccggctcggggatgc gggggagcgccggaccggagcggagcccgggcggctcgctgctgcccctagcggggggggacgtaattacatccctggggc tttgggggggggctgtccctctagagcggccgccaccgcggtggagctccagcttttgttccctttagtgagggttaattagatcttaatacga ctcactatagggcgaattgggtaccgggccccctgaggcggaaagaaccagctggggctctaggggtatcccggggttgggttgc gccttttccaaggcagccctgggtttgcgcagggacgcggctgctctgggcgtggttccgggaaacgcagcggcgccgaccctgggtct cgcacattcttcacgtccgttcgcagcgtcacccggatcttcgccgctaccttgtgggccccggcgacgcttcctgctccgcccctaagt cgggaaggttccttgccggttcgcggcgtgccggacgtgacaaacggaagccgcacgtctcactagtaccctcgcagacggacagcgcca gggagcaatggcagcgcgccgaccgcgatgggctgtggccaatagcggctgctcagcagggcgcgccgagagcagcggccgggaa ggggcggtgcgggaggggggtgtgggcggtagtgtgggccctgttcctgcccgcgcggtgttccgcattctgcaagcctccggagc gcacgtcggcagtcggctccctcgttgaccgaataccgacctctctccccagaagctcccgggagcttgtatatccattttcggatctgatc
```

-continued

```
agcacgtgttgacaattaatcatcggcatagtatatcggcatagtataatacgacaaggtgaggaacgccaccatggccaagcctttgtctca agaagaatccaccctcattgaaagagcaacggctacaatcaacagcatcccatctctgaagactacagcgtcgccagcgcagctctctct agcgacggccgcatcttcactggtgtcaatgtatatcattttactgggggaccttgtgcagaactcgtggtgctgggcactgctgctgctgcg gcagctggcaacctgacttgtatcgtcgcgatcggaaatgagaacaggggcatcttgagcccctgcggacggtgccgacaggtgcttctc gatctgcatcctgggatcaaagccatagtgaaggacagtgatggacagccgacggcagttgggattcgtgaattgctgccctctggttatgt gtgggagggctaaagcgcgggatctcatgctggagttcttcgcccaccccaacttgtttattgcagcttataatggttacaaataaagcaata gcatcacaaatttcacaaataaagcatttttttcactgcattctagttgtggtttgtccaaactcatcaatgtatcttatcatgtctgtagctga tgtatacctaggatccggccggcctgcaggtgtcctcacaggaacgaagtccctaaagaaacagtggcagccaggtttagccccggaattgactg gattccttttttagggcccattggtatggcttttccccgtatcccccaggtgtctgcaggctcaaagagcagcgagaagcgttcagaggaaa gcgatcccgtgccaccttcccgtgcccgggctgtcccgcacgctgccggctcggggatgcgggggagcgccggaccggagcgga gccccgggcggctcgctgctgcccctagcggggagggacgtaattacatccctgggggctttgggggggggctgtccctctagagcg gccgccaccgcggtggagctccagcttttgttcccttagtgagggttaattagatcttaatacgactcactatagggcgaattgggtaccggg ccccccctcgaggtcgacggtatcctcgaggtcgacggtatcgataagcttgatatctataacaagaaaatatatatataataagttatcacgt aagtagaacatgaaataacaatataattatcgtatgagttaaatcttaaaagtcacgtaaaagataatcatgcgtcattttgactcacgcggtcgt tatagttcaaaatcagtgacacttaccgcattgacaagcacgcctcacgggagctccaagcggcgactgagatgtcctaaatgcacagcga cggattcgcgctatttagaaagagagagcaatatttcaagaatgcatgcgtcaattttacgcagactatctttctagggttaatctagctgcatca ggatcatatcgtcgggtcttttttccggctcagtcatcgcccaagctggcgctatctgggcatcggggaggaagaagcccgtgccttttcccg cgaggttgaagcggcatggaaagagtttgccgaggatgactgctgctgcattgacgttgagcgaaaacgcacgtttaccatgatgattcgg gaaggtgtggccatgcacgcctttaacggtgaactgttcgttcaggccacctgggataccagttcgtcgcggcttttccggacacagttccg gatggtcagcccgaagcgcatcagcaacccgaacaataccggcgacagccggaactgccgtgccggtgtgcagattaatgacagcggt gcggcgctgggatattacgtcagcgaggacgggtatcctggctggatgccgcagaaatggacatggatacccgtgagttacccggcgg gcgcgcttggcgtaatcatggtcatagctgtttcctgtgtgaaattgttatccgctcacaattccacacaacatacgagccggaagcataaagt gtaaagcctggggtgcctaatgagtgagctaactcacattaattgcgttgcgctcactgcccgctttccagtcgggaaacctgtcgtgccagc tgcattaatgaatcggccaacgcgcggggagaggcggtttgcgtattgggcgctcttccgcttcctcgctcactgactcgctgcgctcggtc gttcggctgcggcgagcggtatcagctcactcaaaggcggtaatacggttatccacagaatcaggggataacgcaggaaagaacatgtga gcaaaaggccagcaaaaggccaggaaccgtaaaaaggccgcgttgctggcgtttttccataggctccgcccccctgacgagcatcacaa aaatcgacgctcaagtcagaggtggcgaaacccgacaggactataaagataccaggcgtttccccctggaagctccctcgtgcgctctcct gttccgaccctgccgcttaccggatacctgtccgcctttctcccttcgggaagcgtggcgctttctcatagctcacgctgtaggtatctcagttc ggtgtaggtcgttcgctccaagctgggctgtgtgcacgaaccccccgttcagcccgaccgctgcgccttatccggtaactatcgtcttgagtc caacccggtaagacacgacttatcgccactggcagcagccactggtaacaggattagcagagcgaggtatgtaggcggtgctacagagtt cttgaagtggtggcctaactacggctacactagaaggacagtatttggtatctgcgctctgctgaagccagttaccttcggaaaaagagttgg tagctcttgatccggcaaacaaaccaccgctggtagcggtggtttttttgtttgcaagcagcagattacgcgcagaaaaaaggatctcaaga agatcctttgatcttttctacggggtctgacgctcagtggaacgaaaactcacgttaagggattttggtcatgagattatcaaaaaggatcttca cctagatccttttaaattaaaaatgaagttttaaatcaatctaaagtatatatgagtaaacttggtctgacagttaccaatgcttaatcagtgagg cacctatctcagcgatctgtctatttcgttcatccatagttgcctgactccccgtcgtgtagataactacgatacgggagggcttaccatctggcc ccagtgctgcaatgataccgcgagacccacgctcaccggctccagatttatcagcaataaaccagccagccggaagggccgagcgcaga agtggtcctgcaactttatccgcctccatccagtctattaattgttgccgggaagctagagtaagtagttcgccagttaatagtttgcgcaacgtt gttgccattgctacaggcatcgtggtgtcacgctcgtcgtttggtatggcttcattcagctccggttcccaacgatcaaggcgagttacatgatc ccccatgttgtgcaaaaaagcggttagctccttcggtcctccgatcgttgtcagaagtaagttggccgcagtgttatcactcatggttatggca gcactgcataattctcttactgtcatgccatccgtaagatgcttttctgtgactggtgagtactcaaccaagtcattctgagaatagtgtatgcgg cgaccgagttgctcttgcccggcgtcaatacgggataataccgcgccacatagcagaactttaaaagtgctcatcattggaaaacgttcttcg
```

-continued gggcgaaaactctcaaggatcttaccgctgttgagatccagttcgatgtaacccactcgtgcacccaactgatcttcagcatcttttactttcac cagcgtttctgggtgagcaaaaacaggaaggcaaaatgccgcaaaaaagggaataagggcgacacggaaatgttgaatactcat The sequence of the PB-hiRep-10 #vector is provided below:

PB-hiRep-10# (11,580 bp)

(SEQ ID NO: 23)

actcttcctttttcaatattattgaagcatttatcagggttattgtctcatgagcggatacatatttgaatgtatttagaaaaataaaca aatagggggttccgcgcacatttccccgaaaagtgccacctaaattgtaagcgttaatattttgttaaaattcgcgttaaattttgttaaatcagc tcattttttaaccaataggccgaaatcggcaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtgaaccatcaccctaat caagttttttggggtcgaggtgccgtaaagcactaaatcggaaccctaaaggagccccccgatttagagcttgacggggaaagccggcga acgtggcgagaaaggaagggaagaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc ctcttcgctattacgccagctggcgaaaggggatgtgctgcaaggcgattaagttgggtaacgccagggttttcccagtcacgacgttgta aaacgacggccagtgagcgcgcctcgttcattcacgttttttgaacccgtggaggacgggcagactcgcggtgcaaatgtgttttacagcgtg atggagcagatgaagatgctcgacacgctgcagaacacgcagctagattaaccctagaaagataatcatattgtgacgtacgttaaagataa tcatgcgtaaaattgacgcatgtgttttatcggtctgtatatcgaggtttatttattaatttgaatagatattaagtttttattatatttacactt acatactaataataaattcaacaaacaatttatttatgtttatttatttattaaaaaaaaacaaaaactcaaaatttcttctataaagtaacaaa acttttatcgaattcctgcagcccggggatccactagttctagagggacagccccccccaaagccccagggatgtaattacgtccctcccccg ctaggggcagcagcgagccgcccggggctccgctccggtccggcgctcccccgcatccccgagccggcagcgtgcggggacagcccgggca cggggaaggtggcacgggatcgctttcctctgaacgcttctcgctgctctttgagcctgcagacacctgggggatacggggaaaggcc tccaaggccagcttcccacaataagttgggtgaattttggctcattcctcctttctataggattgaggtcagagctttgtgatgggaattctgtgg aatgtgtgtcagttagggtgtggaaagtcccgcgatcgctagcttaagcgctgatcaattggcgcgccgaattcgttatctgcagaattcggct tggcctccgcgccgggttttggcgcctcccgcgggcgccccctcctcacggcgagcgctgccacgtcagacgaagggcgcagcgagc gtcctgatccttccgcccggacgctcaggacagcggcccgctgctcataagactcggccttagaaccccagtatcagcagaaggacatttt aggacgggacttgggtgactctagggcactggttttctttccagagagcggaacaggcgaggaaaagtagtcccttctcggcgattctgcg gagggatctccgtggggcggtgaacgccgatgattatataaggacgcgccggTCCCTATCAGTGATAGAGAtcTCC CTATCAGTGATAGAGAgtgtggcacagctagttccgtcgcagccgggatttgggtcgcggttcttgtttgtggatcgctgtgat cgtcacttgacGAACGCGCAGCCGCCATGccgggggttttacgagattgtgattaaggtccccagcgaccttgacgagcatc tgcccggcatttctgacagctttgtgaactgggtggccgagaaggaatgggagttgccgccagattctgacatggatctgaatctgattgagc aggcacccctgaccgtggccgagaagctgcagcgcgactttctgacggaatggcgccgtgtgagtaaggccccggaggctcttttctttgt gcaatttgagaaggagagagctacttccacatgcacgtgctcgtggaaccaccgggggtgaaatccatggttttgggacgtttcctgagtc agattcgcgaaaactgattcagagaatttaccgcgggatcgagccgactttgccaaactggttcgcggtcacaaagaccagaaatggcgc cggaggcgggaacaaggtggtggatgagtgctacatccccaattacttgctccccaaaacccagcctgagctccaatgggcatggaccaa catggaacagtacctcagcgcctgtttgaatctcacgagcgtaaacggttggtggcgcagcatctgacgcacgtgtcgcagacgcagga gcagaacaaagagaatcagaatcccaattctgatgcgccggtgatcagatcaaaaacttcagccaggtacatggagctggtcgggtggctc gtggacaaggggattacctcggagaagcagtggatccaggaggaccaggcctcatacatctccttcaatgcggcctccaactcgcggtcc caaatcaaggctgccttggacaatgcgggaaagattatgagcctgactaaaaccgccccgactacctggtgggccagcagcccgtgga ggacatttccagcaatcggatttataaaattttggaactaaacgggtacgatccccaatatgcggcttccgtctttctgggatgggccacgaaa aagttcggcaagaggaacaccatctggctgtttgggcctgcaactaccgggaagaccaacatcgcggaggccatagcccacactgtgcc -continued

```
cttctacgggtgcgtaaactggaccaatgagaactttcccttcaacgactgtgtcgacaagatggtgatctggtgggaggaggggaagatg
accgccaaggtcgtggagtcggccaaagccattctcggaggaagcaaggtgcgcgtggaccagaaatgcaagtcctcggcccagatag
acccgactcccgtgatcgtcacctccaacaccaacatgtgcgccgtgattgacgggaactcaacgaccttcgaacaccagcagccgttgca
agaccggatgttcaaatttgaactcacccgccgtctggatcatgactttgggaaggtcaccaagcaggaagtcaaagacttttttccggtggg
caaaggatcacgtggttgaggtggagcatgaattctacgtcaaaaagggtggagccaagaaaagacccgcccccagtgacgcagatata
agtgagcccaaacgggtgcgcgagtcagttgcgcagccatcgacgtcagacgcggaagcttcgatcaactacgcagacaggtaccaaaa
caaatgttctcgtcacgtgggcatgaatctgatgctgtttccctgcagacaatgcgagagaatgaatcagaattcaaatatctgcttcactcacg
gacagaaagactgtttagagtgctttcccgtgtcagaatctcaacccgtttctgtcgtcaaaaaggcgtatcagaaactgtgctacattcatcat
atcatgggaaaggtgccagacgcttgcactgcctgcgatctggtcaatgtggatttggatgactgcatctttgaacaataaaatggctaggat
ccggccggcctgcaggtgtcctcacaggaacgaagtccctaaagaaacagtggcagccaggtttagcccgaaaacttgtttattgcagc
ttataatggttacaaataaagcaatagcatcacaaatttcacaaataaagcatttttttcactgcattctagttgtggtttgtccaaactcatca
atgtatcttattgactggattgagggacagccccccccaaagccccagggatgtaattacgtccctccccgctaggggcagcagcgagcc
gcccggggctccgctccggtccggcgctccccccgcatccccgagccggcagcgtgcggggacagcccgggcacggggaaggtggc
acgggatcgctttcctctgaacgcttctcgctgctctttgagcctgcagacacctgggggatacggggaaaaggcctccaaggccagctt
cccacaataagttgggtgaattttggctcattcctcctttctataggattgaggtcagagcgacattgattattgactagttattaatagtaatca
attacggggtcattagttcatagcccatatatggagttccgcgttacataacttacggtaaatggcccgcctggctgaccgcccaacgacccc
gcccattgacgtcaataatgacgtatgttcccatagtaacgccaatagggactttccattgacgtcaatgggtggagtatttacggtaaactgc
ccacttggcagtacatcaagtgtatcatatgccaagtacgccccctattgacgtcaatgacggtaaatggcccgcctggcattatgcccagta
catgaccttatgggactttcctacttggcagtacatctacgtattagtcatcgctattaccatggtgatgcggttttggcagtacatcaatgggcg
tggatagcggtttgactcacggggatttccaagtctccaccccattgacgtcaatgggagtttgttttggaaccaaaatcaacgggactttcca
aaatgtcgtaacaactccgccccattgacgcaaatgggcggtaggcgtgtacggtgggaggtctatataagcagagctctccctatcagtga
tagagatctccctatcagtgatagagatcgtcgacgagctcgtttagtgaaccgtcagatcgcctggagacgccatccacgctgttttgacct
ccatagaagacaccgggaccgatccagcctatcccaattctgatgcgccggtgatcagatcaaaaacttcagccaggtacgccaccAcG
gaactggtcggatggctggtggataagggcatcacaagcgagaagcaatggatccaggaggaccaggcctcatatatttcttttaacgccg
ctagcaattccagaagccagatcaaggctgctctggacaacgccggcaaaatcatgagcctgaccaagaccgcccctgactacctggtgg
gacagcagcctgtggaagatatcagcagcaacagaatctataagatcctggaactgaacggctacgaccccagtacgccgcctccgtgtt
cctgggctgggctacaaagaagttcggcaagcggaacaccatctggctgttcggacctgccaccacaggcaaaaccaatatcgccgagg
ccatcgcccacaccgtgcctttctacggctgcgtgaactggacaaacgagaacttcccccttcaacgactgtgtggacaagatggtgatctgg
tgggaggaaggcaaaatgacagctaaggtggtggaatctgccaaggctatcctgggaggctctaaggtcagggtggatcagaagtgtaaa
agcagcgcccagattgaccctacccctgtgatcgtgaccagcaataccaacatgtgcgccgtgatcgacggcaacagcaccaccttcgag
catcagcagcctctgcaggaccggatgttcaagtttgagctcaccagacggctggatcacgacttcggcaaggtgaccaagcaggaggtg
aaggatttcttcagatgggccaaagaccacgttgttgaggtggaacacgagttctacgtgaagaagggcggcgccaagaaaagacccgc
ccctagcgacgccgacatcagcgagcctaagagagtgcgggaaagcgtggcccagcccagcacatctgatgctgaggccagcatcaac
tacgccgatagataccaaaacaagtgcagccgccacgtgggcatgaacctgatgctgtttccctgcagacagtgtgaaagaatgaaccag
aattctaatatctgctttacacacggccagaaagattgcctggaatgcttccctgtgtccgagagccaaccagtgtctgtggtgaaaaaggcct
accagaagctgtgctacatccaccacatcatgggcaaggtgccagacgcctgaccgcctgcgacctggtcaacgtggacctggacgact
gcatcttcgagcagtgatttgtgatgggaattctgtgctgtgccttctagttgccagccatctgttgtttgcccctcccccgtgccttccttgacc
ctggaaggtgccactcccactgtcctttcctaataaaatgaggaaattgcatcgcattgtctgagtaggtgtcattctattctggggggtggggtg
gggcaggacagcaaggggaggattgggaagacaatagcaggcatgctggggatgcggtgggctctatggacctttttttagggcccat
tggtatggcttttttcccgtatcccccaggtgtctgcaggctcaaagagcagcgagaagcgttcagaggaaagcgatcccgtgccaccttc
cccgtgcccgggctgtccccgcacgctgccggctcggggatgcgggggagcgccggaccggagcggagccccgggcggctcgct
```

-continued

```
gctgcccctagcgggggagggacgtaattacatccctgggggctttggggggggctgtccctctagagcggccgccaccgcggtgg agctccagcttttgttccctttagtgagggttaattagatcttaatacgactcactatagggcgaattgggtaccgggccccctgaggcggaa agaaccagctggggctctaggggtatccccggggttgggttgcgccttttccaaggcagccctgggtttgcgcagggacgcggctgct ctgggcgtggttccgggaaacgcagcggcgccgaccctgggtctcgcacattcttcacgtccgttcgcagcgtcaccggatcttcgccgc tacccttgtgggcccccggcgacgcttcctgctccgcccctaagtcgggaaggttccttgcggttcgcggcgtgccggacgtgacaaac ggaagccgcacgtctcactagtaccctcgcagacggacagcgccagggagcaatggcagcgcgccgaccgcgatgggctgtggccaa tagcggctgctcagcagggcgcgccgagagcagcggccgggaaggggcggtgcgggaggcggggtgtggggcggtagtgtgggcc ctgttcctgcccgcgcggtgttccgcattctgcaagcctccggagcgcacgtcggcagtcggctccctcgttgaccgaatcaccgacctctc tccccagaagctcccgggagcttgtatatccattttcggatctgatcagcacgtgttgacaattaatcatcggcatagtatatcggcatagtata atacgacaaggtgaggaacgccaccatggccaagcctttgtctcaagaagaatccacccctcattgaaagagcaacgctacaatcaacag catcccatctctgaagactacagcgtcgccagcgcagctctctctagcgacggccgcatcttcactggtgtcaatgtatatcattttactggg ggaccttgtgcagaactcgtggtgctgggcactgctgctgctgcggcagctggcaacctgacttgtatcgtcgcgatcggaaatgagaaca ggggcatcttgagcccctgcggacggtgccgacaggtgcttctcgatctgcatcctgggatcaaagccatagtgaaggacagtgatggac agccgacggcagttgggattcgtgaattgctgccctctggttatgtgtgggagggctaaagcgcggggatctcatgctggagttcttcgccc accccaacttgtttattgcagcttataatggttacaaataaagcaatagcatcacaaatttcacaaataaagcatttttttcactgcattctagt tgtggtttgtccaaactcatcaatgtatcttatcatgtctgtagctgatgtatacctaggatccggccggcctgcaggtgtcctcacaggaacgaa gtccctaaagaaacagtggcagccaggtttagccccggaattgactggattccttttttagggcccattggtatggcttttcccgtatcccccc aggtgtctgcaggctcaaagagcagcgagaagcgttcagaggaaagcgatcccgtgccaccttcccgtgcccgggctgtccccgcacgct gccggctcggggatgcggggggagcgccggaccggagcggagccccggcggctcgctgctgcccccagcggggagggacgta attacatccctgggggctttggggggggctgtccctctagagcggccgccaccgcggtggagctccagcttttgttccctttagtgagggtt aattagatcttaatacgactcactatagggcgaattgggtaccgggccccccctcgaggtcgacggtatcctcgaggtcgacggtatcgata agcttgatatcctataacaagaaaatatatatataataagttatcacgtaagtagaacatgaaataacaatataattatcgtatgagttaaatctta aaagtcacgtaaaagataatcatgcgtcattttgactcacgcggtcgttatagttcaaaatcagtgacacttaccgcattgacaagcacgcctcac gggagctccaagcggcgactgagatgtcctaaatgcacagcgacggattcgcgctatttagaaagagagagcaatatttcaagaatgcatg cgtcaattttacgcagactatctttctagggttaatctagctgcatcaggatcatatcgtcggtctttttttccggctcagtcatcgcccaagctg gcgctatctgggcatcggggaggaagaagcccgtgccttttcccgcgaggttgaagcggcatggaaagagtttgccgaggatgactgctgc tgcattgacgttgagcgaaaacgcacgtttaccatgatgattcgggaaggtgtggccatgcacgcctttaacggtgaactgttcgttcaggcc acctgggataccagttcgtcgcggcttttccggacacagttccggatggtcagcccgaagcgcatcagcaacccgaacaataccggcgac agccggaactgccgtgccggtgtgcagattaatgacagcggtgcggcgctggatattacgtcagcgaggacgggtatcctggctggatg ccgcagaaatggacatggataccccgtgagttacccggcgggcgcgcttggcgtaatcatggtcatagctgtttcctgtgtgaaattgttatc cgctcacaattccacacaacatacgagccggaagcataaagtgtaaagcctggggtgcctaatgagtgagctaactcacattaattgcgttg cgctcactgcccgctttccagtcgggaaacctgtcgtgccagctgcattaatgaatcggccaacgcgcggggagaggcggtttgcgtattg ggcgctcttccgcttcctcgctcactgactcgctgcgctcggtcgttcggctgcggcgagcggtatcagctcactcaaaggcggtaatacgg ttatccacagaatcaggggataacgcaggaaagaacatgtgagcaaaaggccagcaaaaggccaggaaccgtaaaaaggccgcgttgc tggcgtttttccataggctccgcccccctgacgagcatcacaaaaatcgacgctcaagtcagaggtggcgaaacccgacaggactataaag ataccaggcgtttccccctggaagctccctcgtgcgctctcctgttccgaccctgccgcttaccggatacctgtccgcctttctcccttcggga agcgtggcgctttctcatagctcacgctgtaggtatctcagttcggtgtaggtcgttcgctccaagctgggctgtgtgcacgaaccccccgttc agcccgaccgctgcgccttatccggtaactatcgtcttgagtccaacccggtaagacacgacttatcgccactggcagcagccactggtaa caggattagcagagcgaggtatgtaggcggtgctacagagttcttgaagtggtggcctaactacggctacactagaaggacagtatttggta tctgcgctctgctgaagccagttaccttcggaaaaagagttggtagctcttgatccggcaaacaaaccaccgctggtagcggtggtttttttgtt
```

-continued

```
tgcaagcagcagattacgcgcagaaaaaaggatctcaagaagatcctttgatcttttctacggggtctgacgctcagtggaacgaaaactc
acgttaagggattttggtcatgagattatcaaaaaggatcttcacctagatccttttaaattaaaaatgaagttttaaatcaatctaaagtatata
tgagtaaacttggtctgacagttaccaatgcttaatcagtgaggcacctatctcagcgatctgtctatttcgttcatccatagttgcctgactccc
cgtcgtgtagataactacgatacgggagggcttaccatctggccccagtgctgcaatgataccgcgagacccacgctcaccggctccagatttat
cagcaataaaccagccagccggaagggccgagcgcagaagtggtcctgcaactttatccgcctccatccagtctattaattgttgccggga
agctagagtaagtagttcgccagttaatagtttgcgcaacgttgttgccattgctacaggcatcgtggtgtcacgctcgtcgtttggtatggcttc
attcagctccggttcccaacgatcaaggcgagttacatgatccccatgttgtgcaaaaaagcggttagctccttcggtcctccgatcgttgtc
agaagtaagttggccgcagtgttatcactcatggttatggcagcactgcataattctcttactgtcatgccatccgtaagatgcttttctgtgact
ggtgagtactcaaccaagtcattctgagaatagtgtatgcggcgaccgagttgctcttgcccggcgtcaatacgggataataccgcgccacat
agcagaactttaaaagtgctcatcattggaaaacgttcttcggggcgaaaactctcaaggatcttaccgctgttgagatccagttcgatgtaac
ccactcgtgcacccaactgatcttcagcatcttttactttcaccagcgtttctgggtgagcaaaaacaggaaggcaaatgccgcaaaaaag
ggaataagggcgacacggaaatgttgaatactcat
```

The sequence of the PB-hiRep-11 #vector is provided below:

PB-hiRep-11# (11,702 bp)

(SEQ ID NO: 24)

```
actcttcctttttcaatattattgaagcatttatcagggttattgtctcatgagcggatacatatttgaatgtatttagaaaaataaaca
aatagggggttccgcgcacatttccccgaaaagtgccacctaaattgtaagcgttaatattttgttaaaattcgcgttaaattttgttaaatcagct
cattttttaaccaataggccgaaatcggcaaaatcccttataaatcaaaagaatagaccgagatagggttgagtgttgttccagtttggaacaag
agtccactattaaagaacgtggactccaacgtcaaagggcgaaaaaccgtctatcagggcgatggcccactacgtgaaccatcaccctaat
caagttttttggggtcgaggtgccgtaaagcactaaatcggaaccctaaagggagccccgatttagagcttgacggggaaagccggcga
acgtggcgagaaaggaagggaagaaagcgaaggagcgggcgctagggcgctggcaagtgtagcggtcacgctgcgcgtaaccacc
acacccgccgcgcttaatgcgccgctacagggcgcgtcccattcgccattcaggctgcgcaactgttgggaagggcgatcggtgcgggc
ctcttcgctattacgccagctggcgaaaggggatgtgctgcaaggcgattaagttgggtaacgccagggttttcccagtcacgacgttgta
aaacgacggccagtgagcgcgcctcgttcattcacgttttgaacccgtggaggacgggcagactcgcggtgcaaatgtgttttacagcgtg
atggagcagatgaagatgctcgacacgctgcagaacacgcagctagattaacctagaaagataatcatattgtgacgtacgttaaagataa
tcatgcgtaaaattgacgcatgtgttttatcggtctgtatatcgaggtttatttattaatttgaatagatattaagttttattatatttacacttac
atactaataataaattcaacaaacaatttatttatgttttatttattaaaaaaaaacaaaaactcaaaatttcttctataaagtaacaaaactt
ttatcgaattcctgcagcccggggatccactagttctagagggacagccccccccaaagccccagggatgtaattacgtccctccccgctagg
gggcagcagcgagccgcccggggctccgctccggtccggcgctcccccgcatcccgagccggcagcgtgcggggacagcccgggca
cggggaaggtggcacgggatcgctttcctctgaacgcttctcgctgctctttgagcctgcagacacctgggggatacggggaaaggcc
tccaaggccagcttcccacaataagttgggtgaattttggctcattcctcctttctataggattgaggtcagagctttgtgatgggaattctgtgg
aatgtgtgtcagttagggtgtggaaagtcccgcgatcgctagcttaagcgctgatcaattggcgcgccgaattcgttatctgcagaattcggct
tctgctccctgcttgtgtgttggaggtcgctgagtagtgcgcgagcaaaatttaagctacaacaaggcaaggcttgaccgacaattgcatgaa
gaatctgcttagggttaggcgttttgcgctgcttcgcgatgtacgggccagatatacgcgtatctgaggggactagggtgtgtttaggcgaaa
agcggggcttcggttgtacgcggttaggagtcccctcaggatatagtagtttcgcttttgcatagggaggggaaatgtagtcttatgcaatac
acttgtagtcttgcaacatggtaacgatgagttagcaacatgccttacaaggagagaaaaagcaccgtgcatgccgattggtggaagtaagg
tggtacgatcgtgccttattaggaaggcaacagacaggtctgacatggattggacgaaccactgaattccgcattgcagagataattgtattta
agtgcctagcTCCCTATCAGTGATAGAGAtcTCCCTATCAGTGATAGAGAtcgatacaataaacgccat
ttgaccattcaccacattggtgtgcaccGAACGCGCAGCCGCCATGccgggggttttacgagattgtgattaaggtccccagc
gaccttgacgagcatctgcccggcatttctgacagctttgtgaactgggtggccgagaaggaatgggagttgccgccagattctgacatgg
```

-continued

```
atctgaatctgattgagcaggcacccctgaccgtggccgagaagctgcagcgcgactttctgacggaatggcgccgtgtgagtaaggccc
cggaggctcttttctttgtgcaatttgagaagggagagagctacttccacatgcacgtgctcgtggaaaccaccggggtgaaatccatggtttt
gggacgtttcctgagtcagattcgcgaaaaactgattcagagaatttaccgcgggatcgagccgactttgccaaactggttcgcggtcacaa
agaccagaaatggcgccggaggcgggaacaaggtggtggatgagtgctacatccccaattacttgctccccaaaacccagcctgagctc
caatgggcatggaccaacatggaacagtacctcagcgcctgtttgaatctcacggagcgtaaacggttggtggcgcagcatctgacgcac
gtgtcgcagacgcaggagcagaacaaagagaatcagaatcccaattctgatgcgccggtgatcagatcaaaaacttcagccaggtacatg
gagctggtcgggtggctcgtggacaaggggattacctcggagaagcagtggatccaggaggaccaggcctcatacatctccttcaatgcg
gcctccaactcgcggtcccaaatcaaggctgccttggacaatgcgggaaagattatgagcctgactaaaaccgccccgactacctggtg
ggccagcagcccgtggaggacatttccagcaatcggattttataaaattttggaactaaacgggtacgatccccaatatgcggcttccgtctttc
tgggatgggccacgaaaaagttcggcaagaggaacaccatctggctgtttgggcctgcaactaccgggaagaccaacatcgcggaggcc
atagcccacactgtgcccttctacgggtgcgtaaactggaccaatgagaactttcccttcaacgactgtgtcgacaagatggtgatctggtgg
gaggaggggaagatgaccgccaaggtcgtggagtcggccaaagccattctcggaggaagcaaggtgcgcgtggaccagaaatgcaag
tcctcggcccagatagacccgactcccgtgatcgtcacctccaacaccaacatgtgcgccgtgattgacgggaactcaacgaccttcgaac
accagcagccgttgcaagaccggatgttcaaatttgaactcacccgccgtctggatcatgactttgggaaggtcaccaagcaggaagtcaa
agacttttttccggtgggcaaaggatcacgtggttgaggtggagcatgaattctacgtcaaaaagggtggagccaagaaaagacccgcccc
cagtgacgcagatataagtgagcccaaacgggtgcgcgagtcagttgcgcagccatcgacgtcagacgcggaagcttcgatcaactacg
cagacaggtaccaaaacaaatgttctcgtcacgtgggcatgaatctgatgctgtttccctgcagacaatgcgagagaatgaatcagaattcaa
atatctgcttcactcacggacagaaagactgtttagagtgctttcccgtgtcagaatctcaaccgtttctgtcgtcaaaaaggcgtatcagaaa
ctgtgctacattcatcatatcatgggaaaggtgccagacgcttgcactgcctgcgatctggtcaatgtggatttggatgactgcatctttgaaca
ataaaatggctaggatccggccggcctgcaggtgtcctcacaggaacgaagtccctaaagaaacagtggcagccaggtttagccccgga
aaacttgtttattgcagcttataatggttacaaataaagcaatagcatcacaaatttcacaaataaagcatttttttcactgcattctagttgtggt
ttgtccaaactcatcaatgtatcttattgactggattgagggacagcccccccccaaagccccagggatgtaattacgtccctcccccgctag
ggggcagcagcgagccgccggggctccgctccggtccggcgctcccccgcatcccgagccggcagcgtgcggggacagcccg
ggcacggggaaggtggcacgggatcgctttcctctgaacgcttctcgctgctctttgagcctgcagacacctgggggatacggggaaaa
ggcctccaaggccagcttcccacaataagttgggtgaattttggctcattcctcctttctataggattgaggtcagagcgacattgattattgact
agttattaatagtaatcaattacggggtcattagttcatagcccatatatggagttccgcgttacataacttacggtaaatggcccgcctggctga
ccgcccaacgaccccgcccattgacgtcaataatgacgtatgttcccatagtaacgccaatagggactttccattgacgtcaatgggtgga
gtatttacggtaaactgcccacttggcagtacatcaagtgtatcatatgccaagtacgccccctattgacgtcaatgacggtaaatggcccgc
ctggcattatgcccagtacatgaccttatgggactttcctacttggcagtacatctacgtattagtcatcgctattaccatggtgatgcggttttgg
cagtacatcaatgggcgtggatagcggtttgactcacggggatttccaagtctccaccccattgacgtcaatgggagtttgttttggaaccaaa
atcaacgggactttccaaaatgtcgtaacaactccgccccattgacgcaaatgggcggtaggcgtgtacggtggaggtctatataagcag
agctctccctatcagtgatagagatctccctatcagtgatagagatcgtcgacgagctcgtttagtgaaccgtcagatcgcctggagacgcca
tccacgctgttttgacctccatagaagacaccgggaccgatccagcctatcccaattctgatgcgccggtgatcagatcaaaaacttcagcca
ggtacgccaccAcGgaactggtcggatggctggtggataagggcatcacaagcgagaagcaatggatccaggaggaccaggcctcat
atatttcttttaacgccgctagcaattccagaagccagatcaaggctgctctggacaacgccggcaaaatcatgagcctgaccaagaccgcc
cctgactacctggtgggacagcagcctgtggaagatatcagcagcaacagaatctataagatcctggaactgaacggctacgaccccag
tacgccgcctccgtgttcctgggctgggctacaaagaagttcggcaagcggaacaccatctggctgttcggacctgccaccacaggcaaa
accaatatcgccgaggccatcgcccacaccgtgcctttctacggctgcgtgaactggacaaacgagaacttcccttcaacgactgtgtgg
acaagatggtgatctggtgggaggaaggcaaaatgacagctaaggtggtggaatctgccaaggctatcctgggaggctctaaggtcagg
gtggatcagaagtgtaaaagcagcgcccagattgaccctaccctgtgatcgtgaccagcaataccaacatgtgcgccgtgatcgacggc
```

-continued

```
aacagcaccaccttcgagcatcagcagcctctgcaggaccggatgttcaagtttgagctcaccagacggctggatcacgacttcggcaag gtgaccaagcaggaggtgaaggatttcttcagatgggccaaagaccacgttgttgaggtggaacacgagttctacgtgaagaagggcggc gccaagaaaagacccgcccctagcgacgccgacatcagcgagcctaagagagtgcgggaaagcgtggcccagcccagcacatctgat gctgaggccagcatcaactacgccgatagataccaaaacaagtgcagccgccacgtgggcatgaacctgatgctgtttccctgcagacag tgtgaaagaatgaaccagaattctaatatctgctttacacacggccagaaagattgcctggaatgcttccctgtgtccgagagccaaccagtg tctgtggtgaaaaaggcctaccagaagctgtgctacatccaccacatcatgggcaaggtgccagacgcctgtaccgcctgcgacctggtca acgtggacctggacgactgcatcttcgagcagtgatttgtgatgggaattctgtgctgtgccttctagttgccagccatctgttgtttgcccctcc cccgtgccttccttgacccctggaaggtgccactcccactgtcctttcctaataaaatgaggaaattgcatcgcattgtctgagtaggtgtcattct attctggggggtggggggggcaggacagcaaggggggaggattgggaagacaatagcaggcatgctggggatgcggtgggctctatg ggaccttttttagggcccattggtatggcttttttcccgtatccccccaggtgtctgcaggctcaaagagcagcgagaagcgttcagaggaaa gcgatcccgtgccaccttccccgtgcccggggctgtccccgcacgctgccggctcggggatgcgggggagcgccggaccggagcgga gccccgggcggctcgctgctgccccctagcggggagggacgtaattacatccctgggggctttgggggggggctgtccctctagagcg gccgccaccgcggtggagctccagcttttgttccctttagtgagggttaattagatcttaatacgactcactatagggcgaattgggtaccggg cccccctgaggcggaaagaaccagctggggctctaggggtatccccgggttgggttgcgccttttccaaggcagccctgggtttgcg cagggacgcggctgctctgggcgtggttccgggaaacgcagcggcgccgaccctgggtctcgcacattcttcacgtccgttcgcagcgtc acccggatcttcgccgctacccttgtgggccccccggcgacgcttcctgctccgcccctaagtcgggaaggttccttgcggttcgcggcgt gccggacgtgacaaacggaagccgcacgtctcactagtaccctcgcagacggacagcgccagggagcaatggcagcgcgccaccg cgatgggctgtggccaatagcggctgctcagcagggcgcgccgagagcagcggccgggaaggggcggtgcgggaggcggggtgtg gggcggtagtgtgggccctgttcctgcccgcgcggtgttccgcattctgcaagcctccggagcgcacgtcggcagtcggctccctcgttga ccgaatcaccgacctctctccccagaagctcccgggagcttgtatatccattttcggatctgatcagcacgtgttgacaattaatcatcggcat agtatatcggcatagtataatacgacaaggtgaggaacgccaccatggccaagcctttgtctcaagaagaatccaccctcattgaaagagca acggctacaatcaacagcatccccatctctgaagactacagcgtcgccagcgcagctctctctagcgacggccgcatcttcactggtgtcaa tgtatatcattttactgggggaccttgtgcagaactcgtggtgctgggcactgctgctgctgcggcagctggcaacctgacttgtatcgtcgcg atcggaaatgagaacaggggcatcttgagcccctgcggacggtgccgacaggtgcttctcgatctgcatcctgggatcaaagccatagtga aggacagtgatggacagccgacggcagttgggattcgtgaattgctgccctctggttatgtgtgggagggctaaagcgcggggatctcatg ctggagttcttcgcccaccccaacttgttttattgcagcttataatggttacaaataaagcaatagcatcacaaatttcacaaataaagcatttttt cactgcattctagttgtggtttgtccaaactcatcaatgtatcttatcatgtctgtagctgatgtataccctaggatccgccggcctgcaggtgtcc tcacaggaacgaagtccctaaagaaacagtggcagccaggtttagccccgaattgactggattcctttttagggcccattggtatggcttttt cccgtatcccccaggtgtctgcaggctcaaagagcagcgagaagcgttcagaggaaagcgatcccgtgccaccttccccgtgcccgg gctgtccccgcacgctgccggctcggggatgcgggggagcgccggaccggagcggagccccgggggctcgctgctgcccctag cgggggagggacgtaattacatccctgggggctttgggggggggctgtccctctagagcggccgccaccgcggtggagctccagcttt gttccctttagtgagggttaattagatcttaatacgactcactatagggcgaattgggtaccgggccccccctcgaggtcgacggtatccgta ggtcgacggtatcgataagcttgatatctataacaagaaatatatatataataagttatcacgtaagtagaacatgaaataacaatataattatc gtatgagttaaatcttaaaagtcacgtaaaagataatcatgcgtcattttgactcacgcggtcgttatagttcaaaatcagtgacacttaccgcat tgacaagcacgcctcacgggagctccaagcggcgactgagatgtcctaaatgcacagcgacggattcgcgctatttagaaagagagagc aatatttcaagaatgcatgcgtcaattttacgcagactatctttctagggttaatctagctgcatcaggatcatatcgtcgggtcttttttccggct cagtcatcgcccaagctggcgctatctgggcatcggggaggaagaagcccgtgccttttcccgcgaggttgaagcggcatggaaagagttt gccgaggatgactgctgctgcattgacgttgagcgaaaacgcacgtttaccatgatgattcgggaaggtgtggccatgcacgcctttaacgg tgaactgttcgttcaggccacctgggataccagttcgtcgcggcttttccggacacagttccggatggtcagcccgaagcgcatcagcaacc cgaacaataccggcgacagccggaactgccgtgccggtgtgcagattaatgacagcggtgcggcgctgggatattacgtcagcgaggac gggtatcctggctggatgccgcagaaatggacatggataccccgtgagttacccggcgggcgcgcttggcgtaatcatggtcatagctgttt
```

-continued

```
cctgtgtgaaattgttatccgctcacaattccacacaacatacgagccggaagcataaagtgtaaagcctggggtgcctaatgagtgagcta actcacattaattgcgttgcgctcactgcccgctttccagtcgggaaacctgtcgtgccagctgcattaatgaatcggccaacgcgcgggga gaggcggtttgcgtattgggcgctcttccgcttcctcgctcactgactcgctgcgctcggtcgttcggctgcggcgagcggtatcagctcact caaaggcggtaatacggttatccacagaatcaggggataacgcaggaaagaacatgtgagcaaaaggccagcaaaaggccaggaacc gtaaaaaggccgcgttgctggcgtttttccataggctccgcccccctgacgagcatcacaaaaatcgacgctcaagtcagaggtggcgaaa cccgacaggactataaagataccaggcgtttccccctggaagctccctcgtgcgctctcctgttccgaccctgccgcttaccggatacctgtc cgcctttctcccttcgggaagcgtggcgctttctcatagctcacgctgtaggtatctcagttcggtgtaggtcgttcgctccaagctgggctgtg tgcacgaaccccccgttcagcccgaccgctgcgccttatccggtaactatcgtcttgagtccaacccggtaagacacgacttatcgccactg gcagcagccactggtaacaggattagcagagcgaggtatgtaggcggtgctacagagttcttgaagtggtggcctaactacggctacacta gaaggacagtatttggtatctgcgctctgctgaagccagttaccttcggaaaaagagttggtagctcttgatccggcaaacaaaccaccgctg gtagcggtggtttttttgtttgcaagcagcagattacgcgcagaaaaaaaggatctcaagaagatcctttgatcttttctacggggtctgacgct cagtggaacgaaaactcacgttaagggattttggtcatgagattatcaaaaaggatcttcacctagatccttttaaattaaaaatgaagttttaaa tcaatctaaagtatatatgagtaaacttggtctgacagttaccaatgcttaatcagtgaggcacctatctcagcgatctgtctatttcgttcatcca tagttgcctgactccccgtcgtgtagataactacgatacgggagggcttaccatctggccccagtgctgcaatgataccgcgagacccacgc tcaccggctccagatttatcagcaataaaccagccagccggaagggccgagcgcagaagtggtcctgcaactttatccgcctccatccagt ctattaattgttgccgggaagctagagtaagtagttcgccagttaatagtttgcgcaacgttgttgccattgctacaggcatcgtggtgtcacgc tcgtcgtttggtatggcttcattcagctccggttcccaacgatcaaggcgagttacatgatcccccatgttgtgcaaaaaagcggttagctcctt cggtcctccgatcgttgtcagaagtaagttggccgcagtgttatcactcatggttatggcagcactgcataattctcttactgtcatgccatccgt aagatgcttttctgtgactggtgagtactcaaccaagtcattctgagaatagtgtatgcggcgaccgagttgctcttgcccggcgtcaatacgg gataataccgcgccacatagcagaactttaaaagtgctcatcattggaaaacgttcttcggggcgaaaactctcaaggatcttaccgctgttg agatccagttcgatgtaacccactcgtgcacccaactgatcttcagcatcttttactttcaccagcgtttctgggtgagcaaaaacaggaaggc aaaatgccgcaaaaaagggaataagggcgacacggaaatgttgaatactcat
```

The sequence of the PB-hiRep-12 #vector is provided below:

PB-hiRep-12# (11,589 bp)

(SEQ ID NO: 25)

```
actcttcctttttcaatattattgaagcatttatcagggttattgtctcatgagcggatacatatttgaatgtatttagaaaaataaaca aatagggggttccgcgcacatttccccgaaaagtgccacctaaattgtaagcgttaatattttgttaaaattcgcgttaaattttttgttaaatcagct cattttttaaccaataggccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtgaaccatcaccctaat caagttttttggggtcgaggtgccgtaaagcactaaatcggaaccctaaagggagccccgatttagagcttgacggggaaagccggcga acgtggcgagaaaggaagggaagaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc ctcttcgctattacgccagctggcgaaaggggggatgtgctgcaaggcgattaagttgggtaacgccagggttttcccagtcacgacgttgta aaacgacggccagtgagcgcgcgcctcgttcattcacgttttgaacccgtggaggacgggcagactcgcggtgcaaatgtgttttacagcgtg atggagcagatgaagatgctcgacacgctgcagaacacgcagctagattaaccctagaaagataatcatattgtgacgtacgttaaagataa tcatgcgtaaaattgacgcatgtgttttatcggtctgtatatcgaggtttatttattaatttgaatagatattaagttttattatatttacacttac atactaataataaattcaacaaacaatttatttatgtttatttatttattaaaaaaaaacaaaaactcaaaattcttctataaagtaacaaaactt ttatcgaattcctgcagcccggggatccactagttctagagggacagccccccccaaagcccccaggatgtaattacgtccctcccccgctagg gggcagcagcgagccgcccggggctccgctccggtccggcgctccccccgcatcccgagccggcagcgtgcggggacagcccgggca
```

-continued cggggaaggtggcacgggatcgctttcctctgaacgcttctcgctgctctttgagcctgcagacacctggggggatacggggaaaaggcc tccaaggccagcttcccacaataagttgggtgaattttggctcattcctcctttctataggattgaggtcagagctttgtgatgggaattctgtgg aatgtgtgtcagttagggtgtggaaagtcccgcgatcgctagcttaagcgctgatcaattggcgcgccgaattcgttatctgcagaattcggct tgacattgattattgactagttattaatagtaatcaattacgggtcattagttcatagcccatatatggagttccgcgttacataacttacggtaa atggcccgcctggctgaccgcccaacgaccccgcccattgacgtcaataatgacgtatgttcccatagtaacgccaatagggactttccatt gacgtcaatgggtggagtatttacggtaaactgcccacttggcagtacatcaagtgtatcatatgccaagtacgccccctattgacgtcaatga cggtaaatggcccgcctggcattatgcccagtacatgaccttatgggactttcctacttggcagtacatctacgtattagtcatcgctattaccat ggtgatgcggttttggcagtacatcaatgggcgtggatagcggtttgactcacggggatttccaagtctccaccccattgacgtcaatgggag tttgttttggaaccaaaatcaacgggactttccaaaatgtcgtaacaactccgccccattgacgcaaatgggcggtaggcgtgtacggtggg aggtctatataagcagagctctccctatcagtgatagagatctccctatcagtgatagagatcgtcgacgagctcgtttagtgaaccgtcagat cgcctggagacgccatccacgctgttttgacctccatagaagacaccgggaccgatccagcctgaacgcgcagccgccaatggatgccg gggttttacgagattgtgattaaggtccccagcgaccttgacgagcatctgcccggcatttctgacagctttgtgaactgggtggccgagaag gaatgggagttgccgccagattctgacatggatctgaatctgattgagcaggcacccctgaccgtggccgagaagctgcagcgcgactttc tgacggaatggcgccgtgtgagtaaggccccggaggctcttttctttgtgcaatttgagaagggagagagctacttccacatgcacgtgctc gtggaaaccaccgggggtgaaatccatggttttgggacgtttcctgagtcagattcgcgaaaaactgattcagagaatttaccgcgggatcga gccgactttgccaaactggttcgcggtcacaaagaccagaaatggcgccggaggcgggaacaaggtggtggatgagtgctacatcccca attacttgctccccaaaacccagcctgagctccaatgggcatggaccaacatggaacagtacctcagcgcctgtttgaatctcacggagcgt aaacggttggtggcgcagcatctgacgcacgtgtcgcagacgcaggagcagaacaaagagaatcagaatcccaattctgatgcgccggt gatcagatcaaaaacttcagccaggtacatggagctggtcgggtggctcgtggacaaggggattacctcggagaagcagtggatccagg aggaccaggcctcatacatctccttcaatgcggcctccaactcgcggtcccaaatcaaggctgccttggacaatgcgggaaagattatgag cctgactaaaaccgccccgactacctggtgggccagcagccgtggaggacatttccagcaatcggatttataaaattttggaactaaacg ggtacgatccccaatatgcggcttccgtctttctgggatgggccacgaaaaagttcggcaagaggaacaccatctggctgtttgggcctgca actaccgggaagaccaacatcgcggaggccatagcccacactgtgcccttctacgggtgcgtaaactggaccaatgagaactttcccttca acgactgtgtcgacaagatggtgatctggtgggaggagggaagatgaccgccaaggtcgtggagtcggccaaagccattctcggagga agcaaggtgcgcgtggaccagaaatgcaagtcctcggcccagatagacccgactcccgtgatcgtcacctccaacaccaacatgtgcgc cgtgattgacgggaactcaacgaccttcgaacaccagcagccgttgcaagaccggatgttcaaatttgaactcacccgccgtctggatcatg actttgggaaggtcaccaagcaggaagtcaaagacttttttccggtgggcaaaggatcacgtggttgaggtggagcatgaattctacgtcaaa aagggtggagccaagaaaagacccgcccccagtgacgcagatataagtgagcccaaacgggtgcgcgagtcagttgcgcagccatcga cgtcagacgcggaagcttcgatcaactacgcagacaggtaccaaaacaaatgttctcgtcacgtgggcatgaatctgatgctgtttccctgc agacaatgcgagagaatgaatcagaattcaaatatctgcttcactcacggacagaaagactgtttagagtgctttcccgtgtcagaatctcaac ccgtttctgtcgtcaaaaaggcgtatcagaaactgtgctacattcatcatatcatgggaaaggtgccagacgcttgcactgcctgcgatctggt caatgtggatttggatgactgcatcttgaacaataaaatggctaggatccggccggcctgcaggtgtcctcacaggaacgaagtccctaaa gaaacagtggcagccaggtttagccccggaaaacttgtttattgcagcttataatggttacaaataaagcaatagcatcacaaatttcacaaat aaagcatttttttcactgcattctagttgtggtttgtccaaactcatcaatgtatcttattgactggattgagggacagccccccccaaagcccc cagggatgtaattacgtccctccccgctaggggcagcagcgagccgcccggggctccgctccggtccggcgctccccccgcatccc cgagccggcagcgtgcgggacagcccgggcacggggaaggtggcacgggatcgctttcctctgaacgcttctcgctgctctttgagcct gcagacacctggggggatacggggaaaaggcctccaaggccagcttcccacaataagttgggtgaattttggctcattcctcctttctatag gattgaggtcagagcGCGTTACATAACTTACGGTAAATGGCCCGCCTGGCTGACCGCCCAAC

GACCCCCGCCCATTGACGTCAATAATGACGTATGTTCCCATAGTAACGCCAATAGGG

ACTTTCCATTGACGTCAATGGGTGGAGTATTTACGGTAAACTGCCCACTTGGCAGTA

CATCAAGTGTATCATATGCCAAGTACGCCCCCTATTGACGTCAATGACGGTAAATGG

-continued

```
CCCGCCTGGCATTATGCCCAGTACATGACCTTATGGGACTTTCCTACTTGGCAGTAC

ATCTACGTATTAGTCATCGCTATTACCATGGTCGAGGTGAGCCCCACGTTCTGCTTCA

CTCTCCCCATCTCCCCCCCCTCCCCACCCCCAATTTTGTATTTATTTATTTTTTAATTA

TTTTGTGCAGCGATGGGGGCGGGGGGGGGGGGGGGCGCGCGCCAGGCGGGGCGG

GGCGGGGCGAGGGGCGGGGCGGGGCGAGGCGGAGAGGTGCGGCGGCAGCCAATCA

GAGCGGCGCGCTCCGAAAGTTTCCTTTTATGGCGAGGCGGCGGCGGCGGCGGCCCT

ATAAAAAGCGAAGCGTCCCTATCAGTGATAGAGAtcTCCCTATCAGTGATAGAGACG

CGGCGGGCGGGAGTCGCTGCGTTGCCTTCGCCCCGTGCCCCGCTCCGCGCCGCCTCG

CGCCGCCCGCCCCGGCTCTGACTGACCGCGTTACTCCCACAGatcccaattctgatgcgccggtgat cagatcaaaaacttcagccaggtacgccaccatggaactggtcggatggctggtggataagggcatcacaagcgagaagcaatggatcc aggaggaccaggcctcatatatttctttttaacgccgctagcaattccagaagccagatcaaggctgctctggacaacgccggcaaaatcatg agcctgaccaagaccgcccctgactacctggtgggacagcagcctgtggaagatatcagcagcaacagaatctataagatcctggaactg aacggctacgaccccagtacgccgcctccgtgttcctgggctgggctacaaagaagttcggcaagcggaacaccatctggctgttcgga cctgccaccacaggcaaaaccaatatcgccgaggccatcgcccacaccgtgccttcctacgctgcgtgaactggacaaacgagaacttc cccttcaacgactgtgtggacaagatggtgatctggtgggaggaaggcaaaatgacagctaaggtggtggaatctgccaaggctatcctgg gaggctctaaggtcagggtggatcagaagtgtaaaagcagcgcccagattgaccctaccctgtgatcgtgaccagcaataccaacatgtg cgccgtgatcgacggcaacagcaccaccttcgagcatcagcagcctctgcaggaccggatgttcaagtttgagctcaccagacggctgga tcacgacttcggcaaggtgaccaagcaggaggtgaaggatttcttcagatgggccaaagaccacgttgttgaggtggaacacgagttctac gtgaagaagggcggcgccaagaaaagacccgcccctagcgacgccgacatcagcgagcctaagagagtgcgggaaagcgtggccca gcccagcacatctgatgctgaggccagcatcaactacgccgatagataccaaaacaagtgcagccgccacgtgggcatgaacctgatgct gtttccctgcagacagtgtgaaagaatgaaccagaattctaatatctgctttacacacggccagaaagattgcctggaatgcttccctgtgtcc gagagccaaccagtgtctgtggtgaaaaaggcctaccagaagctgtgctacatccaccacatcatgggcaaggtgccagacgcctgtacc gcctgcgacctggtcaacgtggacctggacgactgcatcttcgagcagtgatttgtgatgggaattctgtgctgtgccttctagttgccagcca tctgttgtttgccctcccccgtgccttccttgaccctggaaggtgccactcccactgtcctttcctaataaaatgaggaaattgcatcgcattgt ctgagtaggtgtcattctattctgggggtggggggggcaggacagcaaggggaggattgggaagacaatagcaggcatgctgggga tgcggtgggctctatgggaccttttttagggcccattggtatggcttttccccgtatcccccaggtgtctgcaggctcaaagagcagcgaga agcgttcagaggaaagcgatcccgtgccaccttccccgtgcccgggctgtccccgcacgctgccggctcggggatgcgggggagcgc cggaccggagcggagccccgggcggctcgctgctgccccctagcggggagggacgtaattacatccctgggggctttggggggggg ctgtccctctagagcggccgccaccgcggtggagctccagcttttgttccctttagtgagggttaattagatcttaatacgactcactataggg cgaattgggtaccgggccccctgaggcggaaagaaccagctgggctaggggggtatccccggggttgggttgcgcctttccaag gcagccctgggtttgcgcagggacgcggctgctctgggcgtggttccgggaaacgcagcggcgccgacctggtctcgcacattcttca cgtccgttcgcagcgtcacccggatcttcgccgctaccttgtgggcccccggcgacgcttcctgctccgcccctaagtcgggaaggttc cttgcggttcgcggcgtgccggacgtgacaaacggaagccgcacgtctcactagtaccctcgcagacggacagcgccagggagcaatg gcagcgcgccgaccgcgatgggctgtggccaatagcggctgctcagcagggcgcgccgagagcagcggccgggaaggggcggtgc gggaggcggggtgtgggcggtagtgtgggccctgttcctgcccgcgcggtgttccgcattctgcaagcctccggagcgcacgtcggca gtcggctccctcgttgaccgaatcaccgacctctctccccagaagctcccgggagcttgtatatccattttcggatctgatcagcacgtgttga caattaatcatcggcatagtatatcggcatagtataatacgacaaggtgaggaacgccaccatggccaagccttgtctcaagaagaatcca ccctcattgaaagagcaacggctacaatcaacagcatccccatctctgaagactacagcgtcgccagcgcagctctctctagcgacggccg catcttcactggtgtcaatgtatatcattttactgggggaccttgtgcagaactcgtggtgctgggcactgctgctgcgcggcagctggcaac ctgacttgtatcgtcgcgatcggaaatgagaacaggggcatcttgagcccctgcggacggtgccgacaggtgcttctcgatctgcatcctgg
```

-continued

```
gatcaaagccatagtgaaggacagtgatggacagccgacggcagttgggattcgtgaattgctgccctctggttatgtgtgggagggctaa agcgcgggatctcatgctggagttcttcgcccaccccaacttgtttattgcagcttataatggttacaaataaagcaatagcatcacaaatttc acaaataaagcattttttttcactgcattctagttgtggtttgtccaaactcatcaatgtatcttatcatgtctgtagctgatgtatacctaggatcc ggccggcctgcaggtgtcctcacaggaacgaagtccctaaagaaacagtggcagccaggtttagccccggaattgactggattccttttttagg gcccattggtatggcttttccccgtatcccccaggtgtctgcaggctcaaagagcagcgagaagcgttcagaggaaagcgatcccgtgc caccttccccgtgcccgggctgtccccgcacgctgccggctcggggatgcgggggagcgccggaccggagcggagcccgggcgg ctcgctgctgcccctagcggggagggacgtaattacatccctgggggctttggggggggctgtccctctagagcggccgccaccgc ggtggagctccagcttttgttccctttagtgagggttaattagatcttaatacgactcactatagggcgaattgggtaccgggccccccctcga ggtcgacggtatcctcgaggtcgacggtatcgataagcttgatatctataacaagaaaatatatataataagttatcacgtaagtagaacatg aaataacaatataattatcgtatgagttaaatcttaaaagtcacgtaaaagataatcatgcgtcattttgactcacgcggtcgttatagttcaaaat cagtgacacttaccgcattgacaagcacgcctcacgggagctccaagcggcgactgagatgtcctaaatgcacagcgacggattcgcgct atttagaaagagagagcaatatttcaagaatgcatgcgtcaattttacgcagactatctttctagggttaatctagctgcatcaggatcatatcgt cgggtcttttttccggctcagtcatcgcccaagctggcgctatctgggcatcggggaggaagaagcccgtgccttttcccgcgaggttgaag cggcatggaaagagtttgccgaggatgactgctgctgcattgacgttgagcgaaaacgcacgtttaccatgatgattcgggaaggtgtggc catgcacgccttttaacggtgaactgttcgttcaggccacctgggataccagttcgtcgcggcttttccggacacagttccggatggtcagccc gaagcgcatcagcaacccgaacaataccggcgacagccggaactgccgtgccggtgtgcagattaatgacagcggtgcgcgctggga tattacgtcagcgaggacgggtatcctggctggatgccgcagaaatggacatggataccccgtgagttacccggcgggcgcgcttggcgt aatcatggtcatagctgtttcctgtgtgaaattgttatccgctcacaattccacacaacatacgagccggaagcataaagtgtaaagcctgggg tgcctaatgagtgagctaactcacattaattgcgttgcgctcactgcccgctttccagtcgggaaacctgtcgtgccagctgcattaatgaatc ggccaacgcgcggggagaggcggtttgcgtattgggcgctcttccgcttcctcgctcactgactcgctgcgctcggtcgttcggctgcggc gagcggtatcagctcactcaaaggcggtaatacggttatccacagaatcaggggataacgcaggaaagaacatgtgagcaaaaggccag caaaaggccaggaaccgtaaaaaggccgcgttgctggcgtttttccataggctccgcccccctgacgagcatcacaaaaatcgacgctca agtcagaggtggcgaaacccgacaggactataaagataccaggcgtttccccctggaagctccctcgtgcgctctcctgttccgaccctgc cgcttaccggatacctgtccgcctttctcccttcgggaagcgtggcgctttctcatagctcacgctgtaggtatctcagttcggtgtaggtcgtt cgctccaagctgggctgtgtgcacgaaccccccgttcagcccgaccgctgcgccttatccggtaactatcgtcttgagtccaacccggtaag acacgacttatcgccactggcagcagccactggtaacaggattagcagagcgaggtatgtaggcggtgctacagagttcttgaagtggtgg cctaactacggctacactagaaggacagtatttggtatctgcgctctgctgaagccagttaccttcggaaaaagagttggtagctcttgatccg gcaaacaaaccaccgctggtagcggtggtttttttgtttgcaagcagcagattacgcgcagaaaaaaaggatctcaagaagatcctttgatctt ttctacggggtctgacgctcagtggaacgaaaactcacgttaaggggattttggtcatgagattatcaaaaaggatcttcacctagatccttttaa attaaaaatgaagttttaaatcaatctaaagtatatatgagtaaacttggtctgacagttaccaatgcttaatcagtgaggcacctatctcagcgat ctgtctatttcgttcatccatagttgcctgactccccgtcgtgtagataactacgatacgggagggcttaccatctggccccagtgctgcaatga taccgcgagacccacgctcaccggctccagatttatcagcaataaaccagccagccggaagggccgagcgcagaagtggtcctgcaact ttatccgcctccatccagtctattaattgttgccgggaagctagagtaagtagttcgccagttaatagtttgcgcaacgttgttgccattgctaca ggcatcgtggtgtcacgctcgtcgtttggtatggcttcattcagctccggttcccaacgatcaaggcgagttacatgatcccccatgttgtgca aaaaagcggttagctccttcggtcctccgatcgttgtcagaagtaagttggccgcagtgttatcactcatggttatggcagcactgcataattct cttactgtcatgccatccgtaagatgcttttctgtgactggtgagtactcaaccaagtcattctgagaatagtgtatgcggcgaccgagttgctct tgcccggcgtcaatacgggataataccgcgccacatagcagaactttaaaagtgctcatcattggaaaacgttcttcggggcgaaaactctc aaggatcttaccgctgttgagatccagttcgatgtaacccactcgtgcacccaactgatcttcagcatcttttactttcaccagcgtttctgggtg agcaaaaacaggaaggcaaaatgccgcaaaaaagggaataagggcgacacggaaatgttgaatactcat
```

The sequence of the PB-hiRep-13 #vector is provided below:

PB-hiRep-13# (11, 854 bp)

(SEQ ID NO: 26)

actcttcctttttcaatattattgaagcatttatcagggttattgtctcatgagcggatacatatttgaatgtatttagaaaaataaaca aatagggttccgcgcacatttccccgaaaagtgccacctaaattgtaagcgttaatattttgttaaaattcgcgttaaattttgttaaatcagct cattttttaaccaataggccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtgaaccatcaccctaat caagttttttggggtcgaggtgccgtaaagcactaaatcggaaccctaaagggagcccccgatttagagcttgacggggaaagccggcga acgtggcgagaaaggaagggaagaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc ctcttcgctattacgccagctggcgaaaggggatgtgctgcaaggcgattaagttgggtaacgccagggttttcccagtcacgacgttgta aaacgacggccagtgagcgcgcctcgttcattcacgttttttgaacccgtggaggacgggcagactcgcggtgcaaatgtgttttacagcgtg atggagcagatgaagatgctcgacacgctgcagaacacgcagctagattaaccctagaaagataatcatattgtgacgtacgttaaagataa tcatgcgtaaaattgacgcatgtgttttatcggtctgtatatcgaggtttatttattaatttgaatagatattaagttttattatatttacacttac atactaataataaattcaacaaacaatttatttatgtttatttattttattaaaaaaaaacaaaaactcaaaatttcttctataaagtaacaaaactt ttatcgaattcctgcagcccgggggatccactagttctagagggacagccccccccaaagccccagggatgtaattacgtccctccccgctagg gggcagcagcgagccgcccgggctccgctccggtccggcgctcccccgcatcccgagccggcagcgtgcggggacagcccgggca cggggaaggtggcacgggatcgctttcctctgaacgcttctcgctgctctttgagcctgcagacacctgggggatacggggaaaaggcc tccaaggccagcttcccacaataagttgggtgaattttggctcattcctcctttctataggattgaggtcagagctttgtgatgggaattctgtgg aatgtgtgtcagttagggtgtggaaagtcccgcgatcgctagcttaagcgctgatcaattggcgcgccgaattcgttatctgcagaattcggct tgacattgattattgactagttattaatagtaatcaattacggggtcattagttcatagcccatatatggagttccgcgttacataacttacggtaa atggcccgcctggctgaccgcccaacgacccccgcccattgacgtcaataatgacgtatgttcccatagtaacgccaatagggactttccatt gacgtcaatgggtggagtatttacggtaaactgcccacttggcagtacatcaagtgtatcatatgccaagtacgccccctattgacgtcaatga cggtaaatggcccgcctggcattatgcccagtacatgaccttatgggactttcctacttggcagtacatctacgtattagtcatcgctattaccat ggtgatgcggttttggcagtacatcaatgggcgtggatagcggtttgactcacggggatttccaagtctccaccccattgacgtcaatgggag tttgttttggaaccaaaatcaacgggactttccaaaatgtcgtaacaactccgccccattgacgcaaatgggcggtaggcgtgtacggtggg aggtctatataagcagagctctccctatcagtgatagagatctccctatcagtgatagagatcgtcgacgagctcgtttagtgaaccgtcagat cgcctggagacgccatccacgctgttttgacctccatagaagacaccgggaccgatccagcctgaacgcgcagccgccacgccgggtt ttacgagattgtgattaaggtccccagcgaccttgacgagcatctgcccggcatttctgacagctttgtgaactgggtggccgagaaggaat gggagttgccgccagattctgacatggatctgaatctgattgagcaggcaccccctgaccgtggccgagaagctgcagcgcgactttctgac ggaatggcgccgtgtgagtaaggccccggaggctcttttctttgtgcaatttgagaagggagagagctacttccacatgcacgtgctcgtgg aaaccaccggggtgaaatccatggttttgggacgtttcctgagtcagattcgcgaaaaactgattcagagaatttaccgcgggatcgagccg actttgccaaactggttcgcggtcacaaagaccagaaatggcgccggaggcgggaacaaggtggtggatgagtgctacatccccaattac ttgctccccaaaacccagcctgagctccaatgggcatggaccaacatggaacagtacctcagcgcctgtttgaatctcacggagcgtaaac ggttggtggcgcagcatctgacgcacgtgtcgcagacgcaggagcagaacaaagagaatcagaatcccaattctgatgcgccggtgatc agatcaaaaacttcagccaggtacatggagctggtcgggtggctcgtggacaaggggattacctcggagaagcagtggatccaggagga ccaggcctcatacatctccttcaatgcggcctccaactcgcggtcccaaatcaaggctgccttggacaatgcgggaaagattatgagcctga ctaaaaccgccccgactacctggtgggccagcagcccgtggaggacatttccagcaatcggatttataaaatttggaactaaacgggtac gatcccaatatgcggcttccgtctttctgggatgggccacgaaaaagttcggcaagaggaacaccatctggctgtttgggcctgcaactac cgggaagaccaacatcgcggaggccatagcccacactgtgccccttctacgggtgcgtaaactggaccaatgagaactttccccttcaacgac tgtgtcgacaagatggtgatctggtgggaggagggggaagatgaccgccaaggtcgtggagtcggccaaagccattctcggaggaagcaa -continued ggtgcgcgtggaccagaaatgcaagtcctcggcccagatagacccgactcccgtgatcgtcacctccaacaccaacatgtgcgccgtgat tgacgggaactcaacgaccttcgaacaccagcagccgttgcaagaccggatgttcaaatttgaactcacccgccgtctggatcatgactttg ggaaggtcaccaagcaggaagtcaaagacttttccggtgggcaaaggatcacgtggttgaggtggagcatgaattctacgtcaaaaagg gtggagccaagaaaagacccgcccccagtgacgcagatataagtgagcccaaacgggtgcgcgagtcagttgcgcagccatcgacgtc agacgcggaagcttcgatcaactacgcagacaggtaccaaaacaaatgttctcgtcacgtgggcatgaatctgatgctgtttccctgcagac aatgcgagagaatgaatcagaattcaaatatctgcttcactcacggacagaaagactgtttagagtgctttcccgtgtcagaatctcaaccgt ttctgtcgtcaaaaaggcgtatcagaaactgtgctacattcatcatatcatgggaaaggtgccagacgcttgcactgcctgcgatctggtcaat gtggatttggatgactgcatctttgaacaataaaatggctaggatccggccggcctgcaggtgtcctcacaggaacgaagtccctaaagaaa cagtggcagccaggtttagccccggaaaacttgtttattgcagcttataatggttacaaataaagcaatagcatcacaaatttcacaaataaag cattttttcactgcattctagttgtggtttgtccaaactcatcaatgtatcttattgactggattgagggacagccccccccccaaagcccccagg gatgtaattacgtccctcccccgctagggggcagcagcgagccgcccggggctccgctccggtccggcgctccccccgcatccccgag ccggcagcgtgcgggacagcccgggcacggggaaggtggcacgggatcgctttcctctgaacgcttctcgctgctctttgagcctgcag acacctggggggatacggggaaaaggcctccaaggccagcttcccacaataagttgggtgaattttggctcattcctcctttctataggattg aggtcagagcGCGTTACATAACTTACGGTAAATGGCCCGCCTGGCTGACCGCCCAACGAC

CCCCGCCCATTGACGTCAATAATGACGTATGTTCCCATAGTAACGCCAATAGGGACT

TTCCATTGACGTCAATGGGTGGAGTATTTACGGTAAACTGCCCACTTGGCAGTACAT

CAAGTGTATCATATGCCAAGTACGCCCCCTATTGACGTCAATGACGGTAAATGGCCC

GCCTGGCATTATGCCCAGTACATGACCTTATGGGACTTTCCTACTTGGCAGTACATCT

ACGTATTAGTCATCGCTATTACCATGGTCGAGGTGAGCCCCACGTTCTGCTTCACTCT

CCCCATCTCCCCCCCCTCCCCACCCCCAATTTTGTATTTATTTATTTTTTAATTATTTT

GTGCAGCGATGGGGGCGGGGGGGGGGGGGGCGCGCGCCAGGCGGGGCGGGGCG

GGGCGAGGGGGGGCGGGGCGAGGCGGAGAGGTGCGGCGGCAGCCAATCAGAGC

GGCGCGCTCCGAAAGTTTCCTTTTATGGCGAGGCGGCGGCGGCGGCGGCCCTATAA

AAAGCGAAGCGTCCCTATCAGTGATAGAGAtcTCCCTATCAGTGATAGAGACGCGGC

GGGCGGGAGTCGCTGCGTTGCCTTCGCCCCGTGCCCCGCTCCGCGCCGCCTCGCGCC

GCCCGCCCCGGCTCTGACTGACCGCGTTACTCCCACAGatcccaattctgatgcgccggtgatcagatc aaaaacttcagccaggtacgccaccatggaactggtcggatggctggtggataagggcatcacaagcgagaagcaatggatccaggagg accaggcctcatatatttcttttaacgccgctagcaattccagaagccagatcaaggctgctctggacaacgccggcaaaatcatgagcctg accaagaccgcccctgactacctggtgggacagcagcctgtggaagatatcagcagcaacagaatctataagatcctggaactgaacggc tacgaccccagtacgccgcctccgtgttcctgggctggctacaaagaagttcggcaagcggaacaccatctggctgttcggacctgcca ccacaggcaaaaccaatatcgccgaggccatcgcccacaccgtgcctttctacggctgcgtgaactggacaaacgagaacttcccccttcaa cgactgtgtggacaagatggtgatctggtgggaggaaggcaaaatgacagctaaggtggtggaatctgccaaggctatcctgggaggctc taaggtcagggtggatcagaagtgtaaaagcagcgcccagattgaccctaccccctgtgatcgtgaccagcaataccaacatgtgcgccgtg atcgacggcaacagcaccaccttcgagcatcagcagcctctgcaggaccggatgttcaagtttgagctcaccagacggctggatcacgac ttcggcaaggtgaccaagcaggaggtgaaggatttcttcagatgggccaaagaccacgttgttgaggtggaacacgagttctacgtgaaga agggcggcgccaagaaaagacccgcccctagcgacgccgacatcagcgagcctaagagagtgcgggaaagcgtggcccagcccagc acatctgatgctgaggccagcatcaactacgccgatagataccaaaacaagtgcagccgccacgtgggcatgaacctgatgctgtttccct gcagacagtgtgaaagaatgaaccagaattctaatatctgctttacacacgccagaaagattgcctggaatgcttccctgtgtccgagagc caaccagtgtctgtggtgaaaaaggcctaccagaagctgtgctacatccaccacatcatgggcaaggtgccagacgcctgtaccgcctgc gacctggtcaacgtggacctggacgactgcatcttcgagcagtgatttgtgatgggaattctgtgctgtgccttctagttgccagccatctgttg tttgcccctcccccgtgccttccttgaccctggaaggtgccactcccactgtcctttcctaataaaatgaggaaattgcatcgcattgtctgagta -continued

```
ggtgtcattctattctgggggtgggggggcaggacagcaaggggaggattgggaagacaatagcaggcatgctggggatgcggt gggctctatgggaccttttttagggcccattggtatggcttttccccgtatcccccaggtgtctgcaggctcaaagagcagcgagaagcgtt cagaggaaagcgatcccgtgccaccttccccgtgcccgggctgtcccgcacgctgccggctcggggatgcgggggagcgccggac cggagcggagccccgggcggctcgctgctgccccctagcggggagggacgtaattacatccctgggggctttggggggggctgtcc ctctagagcggccgccaccgcggtggagctccagcttttgttccctttagtgagggttaattagatcttaatacgactcactatagggcgaatt gggtaccgggccccctgaggcggaaagaaccagctgggctctagggggtatcccggggttgggttgcgccttttccaaggcagcc ctgggtttgcgcagggacgcggctgctctgggcgtggttccgggaaacgcagcggcgccgaccctgggtctcgcacattcttcacgtccg ttcgcagcgtcacccggatcttcgccgctacccttgtgggcccccggcgacgcttcctgctccgcccctaagtcgggaaggttccttgcgg ttcgcggcgtgccggacgtgacaaacggaagccgcacgtctcactagtaccctcgcagacggacagcgccagggagcaatggcagcg cgccgaccgcgatgggctgtggccaatagcggctgctcagcagggcgcgccgagagcagcggccgggaagggcggtgcgggagg cggggtgtgggcggtagtgtgggccctgttcctgcccgcgcggtgttccgcattctgcaagcctccggagcgcacgtcggcagtcggct ccctcgttgaccgaatcaccgacctctctccccagaagctcccgggagcttgtatatccattttcggatctgatcagcacgtgttgacaattaat catcggcatagtatatcggcatagtataatacgacaaggtgaggaacgccaccatggccaagcctttgtctcaagaagaatccaccctcatt gaaagagcaacggctacaatcaacagcatcccctctctgaagactacagcgtcgccagcgcagctctctctagcgacggccgcatcttca ctggtgtcaatgtatatcattttactgggggaccttgtgcagaactcgtggtgctgggcactgctgctgctgcggcagctggcaacctgacttg tatcgtcgcgatcggaaatgagaacagggggcatcttgagcccctgcggacggtgccgacaggtgcttctcgatctgcatcctgggatcaaa gccatagtgaaggacagtgatggacagccgacggcagttgggattcgtgaattgctgccctctggttatgtgtggagggctaaagcgcg gggatctcatgctggagttcttcgcccaccccaacttgtttattgcagcttataatggttacaaataaagcaatagcatcacaaatttcacaaata aagcattttttcactgcattctagttgtggtttgtccaaactcatcaatgtatcttatcatgtctgtagctgatgtatacctaggatccggccggc ctgcaggtgtcctcacaggaacgaagtccctaaagaaacagtggcagccaggtttagccccggaattgactggattcctttttttagggcccatt ggtatggcttttccccgtatcccccaggtgtctgcaggctcaaagagcagcgagaagcgttcagaggaaagcgatcccgtgccaccttc cccgtgcccgggctgtcccgcacgctgccggctcggggatgcgggggagcgccgaccggagcggagccccgggcggctcgct gctgccccctagcggggagggacgtaattacatccctgggggctttggggggggctgtccctctagagcggccgccaccgcggtgg agctccagcttttgttccctttagtgagggttaattagatcttaatacgactcactatagggcgaattgggtaccgggccccctcgaggtcg acggtatcctcgaggtcgacggtatcgataagcttgatatctataacaagaaaatatatatataatataagttatcacgtaagtagaacatgaaata acaatataattatcgtatgagttaaatcttaaaagtcacgtaaaagataatcatgcgtcattttgactcacgcggtcgttatagttcaaaatcagtg acacttaccgcattgacaagcacgcctcacgggagctccaagcggcgactgagatgtcctaaatgcacagcgacggattcgcgctatttag aaagagagagcaatatttcaagaatgcatgcgtcaattttacgcagactatctttctagggttaatctagctgcatcaggatcatatcgtcgggt cttttttccggctcagtcatcgcccaagctggcgctatctgggcatcggggaggaagaagcccgtgccttttcccgcgaggttgaagcggca tggaaagagtttgccgaggatgactgctgctgcattgacgttgagcgaaaacgcacgtttaccatgatgattcgggaaggtgtggccatgca cgcctttaacggtgaactgttcgttcaggccacctgggataccagttcgtcgcggcttttccggacacagttccggatggtcagcccgaagc gcatcagcaacccgaacaataccggcgacagccggaactgccgtgccggtgtgcagattaatgacagcggtgcggcgctgggatattac gtcagcgaggacgggtatcctggctggatgccgcagaaatggacatggataccccgtgagttacccggcgggcgcgcttggcgtaatcat ggtcatagctgtttcctgtgtgaaattgttatccgctcacaattccacacaacatacgagccggaagcataaagtgtaaagcctggggtgccta atgagtgagctaactcacattaattgcgttgcgctcactgcccgctttccagtcgggaaacctgtcgtgccagctgcattaatgaateggccaa cgcgcggggagaggcggtttgcgtattggcgctcttccgcttcctcgctcactgactcgctgcgctcggtcgttcggctgcggcgagcgg tatcagctcactcaaaggcggtaatacggttatccacagaatcaggggataacgcaggaaagaacatgtgagcaaaaggccagcaaaag gccaggaaccgtaaaaaggccgcgttgctggcgttttccataggctccgcccccctgacgagcatcacaaaaatcgacgctcaagtcaga ggtggcgaaacccgacaggactataaagataccaggcgtttccccctggaagctccctcgtgcgctctcctgttccgaccctgccgcttacc ggatacctgtccgcctttctcccttcgggaagcgtggcgctttctcatagctcacgctgtaggtatctcagttcggtgtaggtcgttcgctccaa
```

-continued

```
gctgggctgtgtgcacgaaccccccgttcagcccgaccgctgcgccttatccggtaactatcgtcttgagtccaacccggtaagacacgact tatcgccactggcagcagccactggtaacaggattagcagagcgaggtatgtaggcggtgctacagagttcttgaagtggtggcctaacta cggctacactagaaggacagtatttggtatctgcgctctgctgaagccagttaccttcggaaaaagagttggtagctcttgatccggcaaaca aaccaccgctggtagcggtggttttttgtttgcaagcagcagattacgcgcagaaaaaaaggatctcaagaagatcctttgatcttttctacgg ggtctgacgctcagtggaacgaaaactcacgttaagggattttggtcatgagattatcaaaaaggatcttcacctagatccttttaaattaaaaa tgaagttttaaatcaatctaaagtatatatgagtaaacttggtctgacagttaccaatgcttaatcagtgaggcacctatctcagcgatctgtctat ttcgttcatccatagttgcctgactccccgtcgtgtagataactacgatacgggagggcttaccatctggccccagtgctgcaatgataccgcg agacccacgctcaccggctccagatttatcagcaataaaccagccagccggaagggccgagcgcagaagtggtcctgcaactttatccgc ctccatccagtctattaattgttgccgggaagctagagtaagtagttcgccagttaatagtttgcgcaacgttgttgccattgctacaggcatcgt ggtgtcacgctcgtcgtttggtatggcttcattcagctccggttcccaacgatcaaggcgagttacatgatcccccatgttgtgcaaaaaagcg gttagctccttcggtcctccgatcgttgtcagaagtaagttggccgcagtgttatcactcatggttatggcagcactgcataattctcttactgtca tgccatccgtaagatgcttttctgtgactggtgagtactcaaccaagtcattctgagaatagtgtatgcggcgaccgagttgctcttgcccggc gtcaatacgggataataccgcgccacatagcagaactttaaaagtgctcatcattggaaaacgttcttcggggcgaaaactctcaaggatctt accgctgttgagatccagttcgatgtaacccactcgtgcacccaactgatcttcagcatcttttactttcaccagcgtttctgggtgagcaaaaa caggaaggcaaaatgccgcaaaaaagggaataagggcgacacggaaatgttgaatactcat
```

The sequence of the PB-hiRep-14 #vector is provided below:

PB-hiRep-14# (11,573 bp)

(SEQ ID NO: 27)

```
actcttcctttttcaatattattgaagcatttatcagggttattgtctcatgagcggatacatatttgaatgtatttagaaaaataaaca aatagggggttccgcgcacatttccccgaaaagtgccacctaaattgtaagcgttaatattttgttaaaattcgcgttaaattttgttaaatcagct catttttaaccataggccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtgaaccatcaccctaat caagttttttggggtcgaggtgccgtaaagcactaaatcggaaccctaaaggagccccgatttagagcttgacggggaaagccggcga acgtggcgagaaaggaagggaagaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc ctcttcgctattacgccagctggcgaaaggggatgtgctgcaaggcgattaagttgggtaacgccagggttttcccagtcacgacgttgta aaacgacggccagtgagcgcgcctcgttcattcacgttttgaacccgtggaggacgggcagactcgcggtgcaaatgtgttttacagcgtg atggagcagatgaagatgctcgacacgctgcagaacacgcagctagattaaccctagaaagataatcatattgtgacgtacgttaaagataa tcatgcgtaaaattgacgcatgtgttttatcggtctgtatatcgaggtttatttattaatttgaatagatattaagttttattatatttacactta catactaataataaattcaacaaacaatttatttatgtttatttatttattaaaaaaaaacaaaaactcaaaatttcttctataaagtaacaaaac ttttatcgaattcctgcagcccggggggatccactagttctagagggacagcccccccaaagccccagggatgtaattacgtccctcccccgct agggggcagcagcgagccgcccggggctccgctccggtccggcgctcccccgcatcccgagccggcagcgtgcggggacagcccgggca cggggaaggtggcacgggatcgctttcctctgaacgcttctcgctgctctttgagcctgcagacacctgggggataggggaaagggccc tccaaggccagcttcccacaataagttgggtgaattttggctcattcctcctttctataggattgaggtcagagctttgtgatgggaattctgtgg aatgtgtgtcagttagggtgtggaaagtcccgcgatcgctagcttaagcgctgatcaattggcgcgccgaattcgttatctgcagaattcggct tggcctccgcgccgggttttggcgcctcccgcgggcgcccccctcctcacggcgagcgctgccacgtcagacgaagggcgcagcgagc gtcctgatccttccgcccggacgctcaggacagcggcccgctgctcataagactcggcttagaaccccagtatcagcagaaggacatttt aggacgggacttgggtgactctagggcactggttttcttccagagagcggaacaggcgaggaaaagtagtcccttctcggcgattctgcg gagggatctccgtggggcggtgaacgccgatgattatataaggacgcgcggtccctatcagtgatagagatctccctatcagtgatagag agtgtggcacagctagttccgtcgcagccgggatttgggtcgcggttcttgtttgtggatcgctgtgatcgtcacttgacgaacgcgcagccg
```

-continued

```
ccatgccggggttttacgagattgtgattaaggtccccagcgaccttgacgagcatctgcccggcatttctgacagctttgtgaactgggtgg ccgagaaggaatgggagttgccgccagattctgacatggatctgaatctgattgagcaggcacccctgaccgtggccgagaagctgcagc gcgactttctgacggaatggcgccgtgtgagtaaggccccggaggctcttttctttgtgcaatttgagaagggagagagctacttccacatgc acgtgctcgtggaaaccaccggggtgaaatccatggttttgggacgtttcctgagtcagattcgcgaaaaactgattcagagaatttaccgcg ggatcgagccgactttgccaaactggttcgcggtcacaaagaccagaaatggcgccggaggcgggaacaaggtggtggatgagtgctac atccccaattacttgctccccaaaacccagcctgagctccaatgggcatggaccaacatggaacagtacctcagcgcctgtttgaatctcac ggagcgtaaacggttggtggcgcagcatctgacgcacgtgtcgcagacgcaggagcagaacaaagagaatcagaatcccaattctgatg cgccggtgatcagatcaaaaacttcagccaggtacatggagctggtcggtggctcgtggacaagggggattacctcggagaagcagtgg atccaggaggaccaggcctcatacatctccttcaatgcggcctccaactcgcggtcccaaatcaaggctgccttggacaatgcgggaaaga ttatgagcctgactaaaaccgcccccgactacctggtgggccagcagcccgtggaggacatttccagcaatcggatttataaaattttggaa ctaaacgggtacgatccccaatatgcggcttccgtctttctgggatgggccacgaaaaagttcggcaagaggaacaccatctggctgtttgg gcctgcaactaccgggaagaccaacatcgcggaggccatagcccacactgtgccttctacgggtgcgtaaactggaccaatgagaactt tcccttcaacgactgtgtcgacaagatggtgatctggtgggaggagggaagatgaccgccaaggtcgtggagtcggccaaagccattct cggaggaagcaaggtgcgcgtggaccagaaatgcaagtcctcggcccagatagaccgactcccgtgatcgtcacctccaacaccaaca tgtgcgccgtgattgacgggaactcaacgaccttcgaacaccagcagccgttgcaagaccggatgttcaaatttgaactcacccgccgtctg gatcatgactttgggaaggtcaccaagcaggaagtcaaagacttttttccggtgggcaaaggatcacgtggttgaggtggagcatgaattcta cgtcaaaaagggtggagccaagaaaagacccgcccccagtgacgcagatataagtgagcccaaacgggtgcgcgagtcagttgcgcag ccatcgacgtcagacgcggaagcttcgatcaactacgcagacaggtaccaaaacaaatgttctcgtcacgtgggcatgaatctgatgctgtt tccctgcagacaatgcgagagaatgaatcagaattcaaatatctgcttcactcacggacagaaagactgtttagagtgctttcccgtgtcaga atctcaacccgtttctgtcgtcaaaaaggcgtatcagaaactgtgctacattcatcatatcatgggaaaggtgccagacgcttgcactgcctgc gatctggtcaatgtggatttggatgactgcatctttgaacaataaaatggctaggatccggccgcctgcaggtgtcctcacaggaacgaagt ccctaaagaaacagtggcagccaggtttagccccggaaaacttgttttattgcagcttataatggttacaaataaagcaatagcatcacaaattt cacaaataaagcatttttttcactgcattctagttgtggtttgtccaaactcatcaatgtatcttattgactggattgagggacagccccccccaa agccccagggatgtaattacgtccctcccccgctagggggcagcagcgagccgccggggctccgctccggtccggcgctcccccg catccccgagccggcagcgtgcggggacagcccgggcacggggaaggtggcacgggatcgctttcctctgaacgcttctcgctgctcttt gagcctgcagacacctgggggatacggggaaaaggcctccaaggccagcttcccacaataagttgggtgaattttggctcattcctccttt ctataggattgaggtcagagcGCGTTACATAACTTACGGTAAATGGCCCGCCTGGCTGACCGCCC

AACGACCCCCGCCCATTGACGTCAATAATGACGTATGTTCCCATAGTAACGCCAATA

GGGACTTTCCATTGACGTCAATGGGTGGAGTATTTACGGTAAACTGCCCACTTGGCA

GTACATCAAGTGTATCATATGCCAAGTACGCCCCCTATTGACGTCAATGACGGTAAA

TGGCCCGCCTGGCATTATGCCCAGTACATGACCTTATGGGACTTTCCTACTTGGCAG

TACATCTACGTATTAGTCATCGCTATTACCATGGTCGAGGTGAGCCCCACGTTCTGCT

TCACTCTCCCCATCTCCCCCCCCTCCCCACCCCCAATTTTGTATTTATTTATTTTTTAA

TTATTTTGTGCAGCGATGGGGGCGGGGGGGGGGGGGGCGCGCGCCAGGCGGGGC

GGGGCGGGGCGAGGGGCGGGGCGGGGCGAGGCGGAGAGGTGCGGCGGCAGCCAAT

CAGAGCGGCGCGCTCCGAAAGTTTCCTTTTATGGCGAGGCGGCGGCGGCGGCGGCC

CTATAAAAAGCGAAGCGTCCCTATCAGTGATAGAGAtcTCCCTATCAGTGATAGAGA

CGCGGCGGGCGGGAGTCGCTGCGTTGCCTTCGCCCCGTGCCCCGCTCCGCGCCGCCT

CGCGCCGCCCGCCCCGGCTCTGACTGACCGCGTTACTCCCACAGatcccaattctgatgcgccggt gatcagatcaaaaacttcagccaggtacgccaccatggaactggtcggatggctggtggataagggcatcacaagcgagaagcaatggat
```

-continued

```
ccaggaggaccaggcctcatatatttcttttaacgccgctagcaattccagaagccagatcaaggctgctctggacaacgccggcaaaatca
tgagcctgaccaagaccgcccctgactacctggtgggacagcagcctgtggaagatatcagcagcaacagaatctataagatcctggaac
tgaacggctacgaccccagtacgccgcctccgtgttcctgggctgggctacaaagaagttcggcaagcggaacaccatctggctgttcg
gacctgccaccacaggcaaaaccaatatcgccgaggccatcgcccacaccgtgcctttctacggctgcgtgaactggacaaacgagaact
tccccttcaacgactgtgtggacaagatggtgatctggtgggaggaaggcaaaatgacagctaaggtggtggaatctgccaaggctatcct
gggaggctctaaggtcaggtggatcagaagtgtaaaagcagcgcccagattgaccctacccctgtgatcgtgaccagcaataccaacat
gtgcgccgtgatcgacggcaacagcaccaccttcgagcatcagcagcctctgcaggaccggatgttcaagtttgagctcaccagacggct
ggatcacgacttcggcaaggtgaccaagcaggaggtgaaggatttcttcagatgggccaaagaccacgttgttgaggtggaacacgagtt
ctacgtgaagaagggcggcgccaagaaaagacccgccctagcgacgccgacatcagcgagcctaagagagtgcgggaaagcgtgg
cccagcccagcacatctgatgctgaggccagcatcaactacgccgatagataccaaaacaagtgcagccgccacgtgggcatgaacctg
atgctgtttccctgcagacagtgtgaaagaatgaaccagaattctaatatctgctttacacacggccagaaagattgcctggaatgcttccctgt
gtccgagagccaaccagtgtctgtggtgaaaaaggcctaccagaagctgtgctacatccaccacatcatgggcaaggtgccagacgcctg
taccgcctgcgacctggtcaacgtggacctggacgactgcatcttcgagcagtgatttgtgatggaattctgtgctgtgccttctagttgcca
gccatctgttgtttgcccctcccccgtgccttccttgaccctggaaggtgccactcccactgtcctttcctaataaaatgaggaaattgcatcgc
attgtctgagtaggtgtcattctattctggggggtgggggggcaggacagcaaggggaggattgggaagacaatagcaggcatgctg
gggatgcggtgggctctatgggacctttttagggcccattggtatggcttttccccgtatccccccaggtgtctgcaggctcaaagagcag
cgagaagcgttcagaggaaagcgatcccgtgccaccttccccgtgcccgggctgtccccgcacgctgccggctcggggatgcgggggg
agcgccggaccggagcggagccccgggcggctcgctgctgcccccctagcggggagggacgtaattacatccctgggggctttgggg
ggggctgtccctctagagcggccgccaccgcggtggagctccagcttttgttccctttagtgagggttaattagatcttaatacgactcacta
tagggcgaattgggtaccgggccccctgaggcggaaagaaccagctggggctctaggggtatcccgggttgggttgcgccttttc
caaggcagccctgggtttgcgcagggacgcggctgctctgggcgtggttccgggaaacgcagcggcgccgaccctgggtctcgcacatt
cttcacgtccgttcgcagcgtcaccggatcttcgccgctacccttgtgggccccggcgacgcttcctgctccgcccctaagtcgggaa
ggttccttgcggttcgcggcgtgccgacgtgacaaacggaagccgcacgtctcactagtaccctcgcagacggacagcgccagggag
caatggcagcgcgccgaccgcgatgggctgtggccaatagcggctgctcagcagggcgcgccgagagcagcggccgggaaggggc
ggtgcgggagggggtgtgggcggtagtgtgggccctgttcctgcccgcgcggtgttccgcattctgcaagcctccggagcgcacgt
cggcagtcggctccctcgttgaccgaatcaccgacctctctccccagaagctcccgggagcttgtatatccattttcggatctgatcagcacg
tgttgacaattaatcatcggcatagtatatcggcatagtataatacgacaaggtgaggaacgccaccatggccaagcctttgtctcaagaaga
atccaccctcattgaaagagcaacggctacaatcaacagcatccccatctctgaagactacagcgtcgccagcgcagctctctctagcgac
ggccgcatcttcactggtgtcaatgtatatcattttactggggggaccttgtgcagaactcgtggtgctgggcactgctgctgctgcggcagctg
gcaacctgacttgtatcgtcgcgatcggaaatgagaacaggggcatcttgagcccctgcggacggtgccgacaggtgcttctcgatctgca
tcctgggatcaaagccatagtgaaggacagtgatggacagccgacggcagttgggattcgtgaattgctgccctctggttatgtgtgggag
ggctaaagcgcggggatctcatgctggagttcttcgcccacccaacttgtttattgcagcttataatggttacaaataaagcaatagcatcac
aaatttcacaaataaagcattttttttcactgcattctagttgtggtttgtccaaactcatcaatgtatcttatcatgtctgtagctgatgtatacct
aggatccggccggcctgcaggtgtcctcacaggaacgaagtccctaaagaaacagtggcagccaggtttagcccggaattgactggattccttt
ttttagggcccattggtatggcttttccccgtatccccccaggtgtctgcaggctcaaagagcagcgagaagcgttcagaggaaagcgatc
ccgtgccaccttccccgtgcccgggctgtcccgcacgctgccggctcggggatgcggggggagcgccggaccggagcggagcccc
gggcggctcgctgctgcccccctagcggggagggacgtaattacatccctgggggctttggggggggctgtccctctagagcggccgc
caccgcggtggagctccagcttttgttccctttagtgagggttaattagatcttaatacgactcactatagggcgaattgggtaccgggcccc
cctcgaggtcgacggtatcctcgaggtcgacggtatcgataagcttgatatctataacaagaaaatatatatataataagttatcacgtaagtag
aacatgaaataacaatataattatcgtatgagttaaatcttaaaagtcacgtaaaagataatcatgcgtcattttgactcacgcggtcgttatagtt
caaaatcagtgacacttaccgcattgacaagcacgcctcacgggagctccaagcggcgactgagatgtcctaaatgcacagcgacggatt
```

-continued

```
cgcgctatttagaaagagagagcaatatttcaagaatgcatgcgtcaattttacgcagactatctttctagggttaatctagctgcatcaggatc atatcgtcgggtctttttttccggctcagtcatcgcccaagctggcgctatctgggcatcggggaggaagaagcccgtgccttttcccgcgag gttgaagcggcatggaaagagtttgccgaggatgactgctgctgcattgacgttgagcgaaaacgcacgtttaccatgatgattcgggaag gtgtggccatgcacgcctttaacggtgaactgttcgttcaggccacctgggataccagttcgtcgcggcttttccggacacagttccggatgg tcagcccgaagcgcatcagcaacccgaacaataccggcgacagccggaactgccgtgccggtgtgcagattaatgacagcggtgcggc gctgggatattacgtcagcgaggacgggtatcctggctgatgccgcagaaatggacatggatacccgtgagttacccggcgggcgcg cttggcgtaatcatggtcatagctgtttcctgtgtgaaattgttatccgctcacaattccacacaacatacgagccggaagcataaagtgtaaag cctggggtgcctaatgagtgagctaactcacattaattgcgttgcgctcactgcccgctttccagtcgggaaacctgtcgtgccagctgcatta atgaatcggccaacgcgcggggagaggcggtttgcgtattgggcgctcttccgcttcctcgctcactgactcgctgcgctcggtcgttcggc tgcggcgagcggtatcagctcactcaaaggcggtaatacggttatccacagaatcaggggataacgcaggaaagaacatgtgagcaaaa ggccagcaaaaggccaggaaccgtaaaaaggccgcgttgctggcgtttttccataggctccgcccccctgacgagcatcacaaaaatcga cgctcaagtcagaggtggcgaaacccgacaggactataaagataccaggcgtttccccctggaagctccctcgtgcgctctcctgttccga ccctgccgcttaccggatacctgtccgcctttctcccttcgggaagcgtggcgctttctcatagctcacgctgtaggtatctcagttcggtgtag gtcgttcgctccaagctgggctgtgtgcacgaaccccccgttcagcccgaccgctgcgccttatccggtaactatcgtcttgagtccaaccc ggtaagacacgacttatcgccactggcagcagccactggtaacaggattagcagagcgaggtatgtaggcggtgctacagagttcttgaa gtggtggcctaactacggctacactagaaggacagtatttggtatctgcgctctgctgaagccagttaccttcggaaaaagagttggtagctc ttgatccggcaaacaaaccaccgctggtagcggtggtttttttgtttgcaagcagcagattacgcgcagaaaaaaaggatctcaagaagatc ctttgatcttttctacggggtctgacgctcagtggaacgaaaactcacgttaagggattttggtcatgagattatcaaaaaggatcttcacctag atccttttaaattaaaaatgaagttttaaatcaatctaaagtatatatgagtaaacttggtctgacagttaccaatgcttaatcagtgaggcaccta tctcagcgatctgtctatttcgttcatccatagttgcctgactccccgtcgtgtagataactacgatacgggagggcttaccatctggccccagtg ctgcaatgataccgcgagacccacgctcaccggctccagatttatcagcaataaaccagccagccggaagggccgagcgcagaagtggt cctgcaactttatccgcctccatccagtctattaattgttgccgggaagctagagtaagtagttcgccagttaatagtttgcgcaacgttgttgcc attgctacaggcatcgtggtgtcacgctcgtcgtttggtatggcttcattcagctccggttcccaacgatcaaggcgagttacatgatcccccat gttgtgcaaaaaagcggttagctccttcggtcctccgatcgttgtcagaagtaagttggccgcagtgttatcactcatggttatggcagcactg cataattctcttactgtcatgccatccgtaagatgcttttctgtgactggtgagtactcaaccaagtcattctgagaatagtgtatgcggcgaccg agttgctcttgcccggcgtcaatacgggataataccgcgccacatagcagaactttaaaagtgctcatcattggaaaacgttcttcggggcga aaactctcaaggatcttaccgctgttgagatccagttcgatgtaacccactcgtgcacccaactgatcttcagcatcttttactttcaccagcgttt ctgggtgagcaaaaacaggaaggcaaaatgccgcaaaaaagggaataagggcgacacggaaatgttgaatactcat
```

The sequence of the PB-hiRep-15 #vector is provided below:

PB-hiRep-15# (11,695 bp)

(SEQ ID NO: 28)

```
actcttcctttttcaatattattgaagcatttatcagggttattgtctcatgagcggatacatatttgaatgtatttagaaaaataaaca aatagggggttccgcgcacatttccccgaaaagtgccacctaaattgtaagcgttaatattttgttaaaattcgcgttaaattttttgttaaatcagct cattttttaaccaataggccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtgaaccatcaccctaat caagttttttggggtcgaggtgccgtaaagcactaaatcggaaccctaaaggagccccccgatttagagcttgacggggaaagccggcga acgtggcgagaaaggaagggaagaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc ctcttcgctattacgccagctggcgaaagggggatgtgctgcaaggcgattaagttgggtaacgccagggttttcccagtcacgacgttgta
```

-continued

```
aaacgacggccagtgagcgcgcctcgttcattcacgttttgaacccgtggaggacgggcagactcgcggtgcaaatgtgttttacagcgtg
atggagcagatgaagatgctcgacacgctgcagaacacgcagctagattaaccctagaaagataatcatattgtgacgtacgttaaagataa
tcatgcgtaaaattgacgcatgtgttttatcggtctgtatatcgaggtttatttattaatttgaatagatattaagttttattatatttacactta
catactaataataaattcaacaaacaatttatttatgtttatttatttattaaaaaaaaacaaaaactcaaaatttcttctataaagtaacaaaact
tttatcgaattcctgcagcccgggggatccactagttctagagggacagccccccccaaagccccagggatgtaattacgtccctcccccgctag
ggggcagcagcgagccgccggggctccgctccggtccggcgctcccccgcatccccgagccggcagcgtgcgggacagcccgggca
cggggaaggtggcacgggatcgctttcctctgaacgcttctcgctgctctttgagcctgcagacacctggggggatacggggaaaaggcc
tccaaggccagcttcccacaataagttgggtgaattttggctcattcctcctttctataggattgaggtcagagctttgtgatgggaattctgtgg
aatgtgtgtcagttagggtgtggaaagtcccgcgatcgctagcttaagcgctgatcaattggcgcgccgaattcgttatctgcagaattcggct
tctgctccctgcttgtgtgttggaggtcgctgagtagtgcgcgagcaaaatttaagctacaacaaggcaaggcttgaccgacaattgcatgaa
gaatctgcttagggttaggcgttttgcgctgcttcgcgatgtacgggccagatatacgcgtatctgagggactagggtgtgtttaggcgaaa
agcggggcttcggttgtacgcggttaggagtcccctcaggatatagtagtttcgcttttgcatagggaggggaaatgtagtcttatgcaatac
acttgtagtcttgcaacatggtaacgatgagttagcaacatgccttacaaggagagaaaaagcaccgtgcatgccgattggtggaagtaagg
tggtacgatcgtgccttattaggaaggcaacagacaggtctgacatggattggacgaaccactgaattccgcattgcagagataattgtattta
agtgcctagctccctatcagtgatagagatctccctatcagtgatagagatcgatacaataaacgccatttgaccattcaccacattggtgtgc
accgaacgcgcagccgccatgccgggggttttacgagattgtgattaaggtccccagcgaccttgacgagcatctgcccggcatttctgaca
gctttgtgaactgggtggccgagaaggaatggagttgccgccagattctgacatggatctgaatctgattgagcaggcacccctgaccgt
ggccgagaagctgcagcgcgactttctgacggaatggcgccgtgtgagtaaggccccggaggctcttttctttgtgcaatttgagaaggga
gagagctacttccacatgcacgtgctcgtggaaaccaccggggtgaaatccatggttttgggacgtttcctgagtcagattcgcgaaaaact
gattcagagaatttaccgcgggatcgagccgactttgccaaactggttcgcggtcacaaagaccagaaatggcgccggaggcgggaaca
aggtggtggatgagtgctacatccccaattacttgctccccaaaacccagcctgagctccaatgggcatggaccaacatggaacagtacct
cagcgcctgtttgaatctcacggagcgtaaacggttggtggcgcagcatctgacgcacgtgtcgcagacgcaggagcagaacaaagaga
atcagaatcccaattctgatgcgccggtgatcagatcaaaaacttcagccaggtacatggagctggtcgggggctcgtggacaaggggat
tacctcggagaagcagtggatccaggaggaccaggcctcatacatctccttcaatgcggcctccaactcgcggtcccaaatcaaggctgcc
ttggacaatgcgggaaagattatgagcctgactaaaaccgccccgactacctggtgggccagcagcccgtggaggacatttccagcaat
cggatttataaaattttggaactaaacgggtacgatccccaatatgcggcttccgtctttctgggatgggccacgaaaaagttcggcaagagg
aacaccatctggctgtttgggcctgcaactaccgggaagaccaacatcgcggaggccatagcccacactgtgcccttctacgggtgcgtaa
actggaccaatgagaactttcccttcaacgactgtgtcgacaagatggtgatctggtgggaggaggggaagatgaccgccaaggtcgtgg
agtcggccaaagccattctcggaggaagcaaggtgcgcgtggaccagaaatgcaagtcctcggcccagatagacccgactcccgtgatc
gtcacctccaacaccaacatgtgcgccgtgattgacgggaactcaacgaccttcgaacaccagcagccgttgcaagaccggatgttcaaat
ttgaactcacccgccgtctggatcatgactttgggaaggtcaccaagcaggaagtcaaagacttttccggtgggcaaaggatcacgtggtt
gaggtggagcatgaattctacgtcaaaaagggtggagccaagaaaagacccgcccccagtgacgcagatataagtgagcccaaacggg
tgcgcgagtcagttgcgcagccatcgacgtcagacgcggaagcttcgatcaactacgcagacaggtaccaaaacaaatgttctcgtcacgt
gggcatgaatctgatgctgtttccctgcagacaatgcgagagaatgaatcagaattcaaatatctgcttcactcacggacagaaagactgttta
gagtgctttcccgtgtcagaatctcaacccgtttctgtcgtcaaaaaggcgtatcagaaactgtgctacattcatcatatcatgggaaaggtgc
cagacgcttgcactgcctgcgatctggtcaatgtggatttggatgactgcatcttgaacaataaaatggctaggatccggccgcctgcagg
tgtcctcacaggaacgaagtccctaaagaaacagtggcagccaggtttagccccggaaaacttgtttattgcagcttataatggttacaaata
aagcaatagcatcacaaatttcacaaataaagcatttttttcactgcattctagttgtggtttgtccaaactcatcaatgtatcttattgactggat
tgagggacagcccccccccaaagccccagggatgtaattacgtccctcccccgctagggggcagcagcgagccgcccggggctccgct
ccggtccggcgctcccccgcatccccgagccggcagcgtgcggggacagcccgggcacggggaaggtggcacgggatcgctttcct
ctgaacgcttctcgctgctctttgagcctgcagacacctggggggatacggggaaaaggcctccaaggccagcttcccacaataagttggg
```

-continued

```
tgaattttggctcattcctcctttctataggattgaggtcagagcGCGTTACATAACTTACGGTAAATGGCCCGCC

TGGCTGACCGCCCAACGACCCCCGCCCATTGACGTCAATAATGACGTATGTTCCCAT

AGTAACGCCAATAGGGACTTTCCATTGACGTCAATGGGTGGAGTATTTACGGTAAAC

TGCCCACTTGGCAGTACATCAAGTGTATCATATGCCAAGTACGCCCCCTATTGACGT

CAATGACGGTAAATGGCCCGCCTGGCATTATGCCCAGTACATGACCTTATGGGACTT

TCCTACTTGGCAGTACATCTACGTATTAGTCATCGCTATTACCATGGTCGAGGTGAG

CCCCACGTTCTGCTTCACTCTCCCCATCTCCCCCCCCTCCCCACCCCCAATTTTGTATT

TATTTATTTTTTAATTATTTTGTGCAGCGATGGGGGCGGGGGGGGGGGGGGGCGCG

CGCCAGGCGGGGCGGGGCGGGGCGAGGGGGGGGGGGGCGAGGCGGAGAGGTGC

GGCGGCAGCCAATCAGAGCGGCGCGCTCCGAAAGTTTCCTTTTATGGCGAGGCGGC

GGCGGCGGCGGCCCTATAAAAAGCGAAGCGTCCCTATCAGTGATAGAGAtcTCCCTA

TCAGTGATAGAGACGCGGCGGGCGGGAGTCGCTGCGTTGCCTTCGCCCCGTGCCCC

GCTCCGCGCCGCCTCGCGCCGCCCGCCCCGGCTCTGACTGACCGCGTTACTCCACA

Gatcccaattctgatgcgccggtgatcagatcaaaaacttcagccaggtacgccaccatggaactggtcggatggctggtggataagggc atcacaagcgagaagcaatggatccaggaggaccaggcctcatatatttcttttaacgccgctagcaattccagaagccagatcaaggctg ctctggacaacgccggcaaaatcatgagcctgaccaagaccgcccctgactacctggtgggacagcagcctgtggaagatatcagcagc aacagaatctataagatcctggaactgaacggctacgaccccagtacgccgcctccgtgttcctgggctgggctacaaagaagttcggca agcggaacaccatctggctgttcggacctgccaccacaggcaaaaccaatatcgccgaggccatcgcccacaccgtgcctttctacggct gcgtgaactggacaaacgagaacttcccccttcaacgactgtgtggacaagatggtgatctggtgggaggaaggcaaaatgacagctaagg tggtggaatctgccaaggctatcctgggaggctctaaggtcagggtggatcagaagtgtaaaagcagcgcccagattgaccctacccctgt gatcgtgaccagcaataccaacatgtgcgccgtgatcgacggcaacagcaccaccttcgagcatcagcagcctctgcaggaccggatgtt caagtttgagctcaccagacggctggatcacgacttcggcaaggtgaccaagcaggaggtgaaggatttcttcagatgggccaaagacca cgttgttgaggtggaacacgagttctacgtgaagaagggcggcgccaagaaaagacccgcccctagcgacgccgacatcagcgagcct aagagagtgcgggaaagcgtggcccagcccagcacatctgatgctgaggccagcatcaactacgccgatagataccaaaacaagtgca gccgccacgtgggcatgaacctgatgctgtttccctgcagacagtgtgaaagaatgaaccagaattctaatatctgctttacacacggccag aaagattgcctggaatgcttccctgtgtccgagagccaaccagtgtctgtggtgaaaaaggcctaccagaagctgtgctacatccaccacat catgggcaaggtgccagacgcctgtaccgcctgcgacctggtcaacgtggacctggacgactgcatcttcgagcagtgatttgtgatggga attctgtgctgtgccttctagttgccagccatctgttgtttgcccctccccgtgccttccttgaccctggaaggtgccactcccactgtcctttcc taataaaatgaggaaattgcatcgcattgtctgagtaggtgtcattctattctggggggggggtgggcaggacagcaaggggaggatt gggaagacaatagcaggcatgctggggatgcggtgggctctatgggaccttttttagggcccattggtatggcttttcccgtatccccca ggtgtctgcaggctcaaagagcagcgagaagcgttcagaggaaagcgatcccgtgccaccttccccgtgcccgggctgtcccgcacgc tgccggctcggggatgcgggggagcgccggaccggagcggagccccgggcggctcgctgctgcccctagcggggagggacgt aattacatccctgggggctttggggggggctgtccctctagagcggccgccaccgcggtggagctccagcttttgttccctttagtgaggg ttaattagatcttaatacgactcactataggggcgaattgggtaccgggccccctgaggcggaaagaaccagctggggctctaggggtat ccccggggttggggttgcgccttttccaaggcagccctgggtttgcgcagggacgcggctgctctgggcgtggttccgggaaacgcagc ggcgccgaccctgggtctcgcacattcttcacgtccgttcgcagcgtcacccggatcttcgccgctacccttgtgggccccccggcgacgc ttcctgctccgcccctaagtcgggaaggttccttgccggttcgcggcgtgccggacgtgacaaacggaagccgcacgtctcactagtaccct cgcagacggacagcgccagggagcaatggcagcgcgccgaccgcgatgggctgtggccaatagcggctgctcagcagggcgcgccg agagcagcggccggaaggggcggtgcgggaggcggggtgtgggcggtagtgtgggccctgttcctgcccgcgcggtgttccgcat tctgcaagcctccggagcgcacgtcggcagtcggctccctcgttgaccgaatcaccgacctctctccccagaagctcccgggagcttgtat
```

-continued

```
atccattttcggatctgatcagcacgtgttgacaattaatcatcggcatagtatatcggcatagtataatacgacaaggtgaggaacgccacca
tggccaagcctttgtctcaagaagaatccaccctcattgaaagagcaacggctacaatcaacagcatccccatctctgaagactacagcgtc
gccagcgcagctctctctagcgacggccgcatcttcactggtgtcaatgtatatcattttactggggaccttgtgcagaactcgtggtgctgg
gcactgctgctgctgcggcagctggcaacctgacttgtatcgtcgcgatcggaaatgagaacaggggcatcttgagcccctgcggacggt
gccgacaggtgcttctcgatctgcatcctgggatcaaagccatagtgaaggacagtgatggacagccgacggcagttgggattcgtgaatt
gctgccctctggttatgtgtgggagggctaaagcgcgggatctcatgctggagttcttcgcccacccaacttgtttattgcagcttataatg
gttacaaataaagcaatagcatcacaaatttcacaaataaagcatttttttcactgcattctagttgtggtttgtccaaactcatcaatgtatctt
atcatgtctgtagctgatgtataccta ggatccggccggcctgcaggtgtcctcacaggaacgaagtccctaaagaaacagtggcagccaggttt
agccccggaattgactggattccttttttagggcccattggtatggcttttccccgtatcccccaggtgtctgcaggctcaaagagcagcga
gaagcgttcagaggaaagcgatcccgtgccaccttccccgtgcccgggctgtccccgcacgctgccggctcggggatgcgggggagc
gccggaccggagcggagccccgggggctcgctgctgccccctagcggggagggacgtaattacatccctgggggctttgggggg
ggctgtccctctagagcggccgccaccgcggtggagctccagcttttgttccctttagtgagggttaattagatcttaatacgactcactatag
ggcgaattgggtaccggg cccccctcgaggtcgacggtatcctcgaggtcgacggtatcgataagcttgatatctataacaagaaaatata
tataataagttatcacgtaagtagaacatgaaataacaatataattatcgtatgagttaaatcttaaaagtcacgtaaaagataatcatgcgtc
attttgactcacgcggtcgttatagttcaaaatcagtgacacttaccgcattgacaagcacgcctcacgggagctccaagcggcgactgagat
gtcctaaatgcacagcgacggattcgcgctatttagaaagagagagcaatatttcaagaatgcatgcgtcaattttacgcagactatctttctag
ggttaatctagctgcatcaggatcatatcgtcggtcttttttccggctcagtcatcgcccaagctggcgctatctgggcatcggggaggaag
aagcccgtgccttttcccgcgaggttgaagcggcatggaaagagtttgccgaggatgactgctgctgcattgacgttgagcgaaaacgcac
gtttaccatgatgattcggaaggtgtggccatgcacgccttta acggtgaactgttcgttcaggccacctgggataccagttcgtcgcggctt
ttccggacacagttccggatggtcagcccgaagcgcatcagcaacccgaacaataccggcgacagccggaactgccgtgccggtgtgca
gattaatgacagcggtgcgcgctgggatattacgtcagcgaggacgggtatcctggctggatgccgcagaaatggacatggataccccg
tgagttaccggcgggcgcgcttggcgtaatcatggtcatagctgtttcctgtgtgaaattgttatccgctcacaattccacacaacatacgag
ccggaagcataaagtgtaaagcctggggtgcctaatgagtgagctaactcacattaattgcgttgcgctcactgcccgctttccagtcggga
aacctgtcgtgccagctgcattaatgaatcggccaacgcgcggggagaggcggtttgcgtattgggcgctcttccgcttcctcgctcactga
ctcgctgcgctcggtcgttcggctgcggcgagcggtatcagctcactcaaaggcggtaatacggttatccacagaatcagggggataacgca
ggaaagaacatgtgagcaaaaggccagcaaaaggccaggaaccgtaaaaaggccgcgttgctggcgtttttccataggctccgcccccc
tgacgagcatcacaaaaatcgacgctcaagtcagaggtggcgaaacccgacaggactataaagataccaggcgtttccccctggaagctc
cctcgtgcgctctcctgttccgaccctgccgcttaccggatacctgtccgcctttctcccttcgggaagcgtggcgctttctcatagctcacgct
gtaggtatctcagttcggtgtaggtcgttcgctccaagctgggctgtgtgcacgaaccccccgttcagcccgaccgctgcgccttatccggta
actatcgtcttgagtccaacccggtaagacacgacttatcgccactggcagcagccactggtaacaggattagcagagcgaggtatgtagg
cggtgctacagagttcttgaagtggtggcctaactacggctacactagaaggacagtatttggtatctgcgctctgctgaagccagttaccttc
ggaaaaagagttggtagctcttgatccggcaaacaaaccaccgctggtagcggtggtttttttgtttgcaagcagcagattacgcgcagaaa
aaaaggatctcaagaagatcctttgatcttttctacggggtctgacgctcagtggaacgaaaactcacgttaagggattttggtcatgagattat
caaaaaggatcttcacctagatccttttaaattaaaaatgaagttttaaatcaatctaaagtatatatgagtaaacttggtctgacagttaccaatg
cttaatcagtgaggcacctatctcagcgatctgtctatttcgttcatccatagttgcctgactccccgtcgtgtagataactacgatacgggagg
gcttaccatctggccccagtgctgcaatgataccgcgagacccacgctcaccggctccagatttatcagcaataaaccagccagccggaa
gggccgagcgcagaagtggtcctgcaactttatccgcctccatccagtctattaattgttgccgggaagctagagtaagtagttcgccagtta
atagtttgcgcaacgttgttgccattgctacaggcatcgtggtgtcacgctcgtcgtttggtatggcttcattcagctccggttcccaacgatcaa
ggcgagttacatgatcccccatgttgtgcaaaaaagcggttagctccttcggtcctccgatcgttgtcagaagtaagttggccgcagtgttatc
actcatggttatggcagcactgcataattctcttactgtcatgccatccgtaagatgcttttctgtgactggtgagtactcaaccaagtcattctga
gaatagtgtatgcggcgaccgagttgctcttgcccggcgtcaatacgggataataccgcgccacatagcagaactttaaaagtgctcatcatt
```

-continued ggaaaacgttcttcggggcgaaaactctcaaggatcttaccgctgttgagatccagttcgatgtaacccactcgtgcacccaactgatcttca gcatcttttactttcaccagcgtttctgggtgagcaaaaacaggaaggcaaaatgccgcaaaaaagggaataagggcgacacggaaatgtt gaatactcat The sequence of the PB-hiRep-16 #vector is provided below:

PB-hiRep-16# (11,421 bp)

(SEQ ID NO: 29)

actcttccttttcaatattattgaagcatttatcagggttattgtctcatgagcggatacatatttgaatgtatttagaaaaataaaca aatagggttccgcgcacatttccccgaaaagtgccacctaaatttgtaagcgttaatattttgttaaaattcgcgttaaattttgttaaatcagc tcattttttaaccaataggccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtgaaccatcaccctaat caagttttttggggtcgaggtgccgtaaagcactaaatcggaaccctaaagggagcccccgatttagagcttgacggggaaagccggcga acgtggcgagaaaggaagggaagaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc ctcttcgctattacgccagctggcgaaaggggatgtgctgcaaggcgattaagttgggtaacgccagggttttcccagtcacgacgttgta aaacgacggccagtgagcgcgcctcgttcattcacgttttgaacccgtggaggacgggcagactcgcggtgcaaatgtgttttacagcgtg atggagcagatgaagatgctcgacacgctgcagaacacgcagctagattaaccctagaaagataatcatattgtgacgtacgttaaagataa tcatgcgtaaaattgacgcatgtgttttatcggtctgtatatcgaggtttatttattaatttgaatagatattaagttttattatatttacacttac atactaataataaattcaacaaacaatttatttatgtttatttatttattaaaaaaaacaaaaactcaaaatttcttctataaagtaacaaaac ttttatcgaattcctgcagcccgggggatccactagttctagaggacagccccccccaaagccccagggatgtaattacgtccctccccgct aggggcagcagcgagccgcccggggctccgctccggtccggcgctccccccgcatcccgagccggcagcgtgcgggacagcccgggca cggggaaggtggcacgggatcgctttcctctgaacgcttctcgctgctctttgagcctgcagacacctgggggatacggggaaaaggcc tccaaggccagcttcccacaataagttgggtgaattttggctcattcctcctttctataggattgaggtcagagctttgtgatgggaattctgtgg aatgtgtgtcagttagggtgtggaaagtcccgcgatcgctagcttaagcgctgatcaattggcgcgccgaattcgttatctgcagaattcggct tctgctccctgcttgtgtgttggaggtcgctgagtagtgcgcgagcaaaatttaagctacaacaaggcaaggcttgaccgacaattgcatgaa gaatctgcttagggttaggcgttttgcgctgcttcgcgatgtacgggccagatatacgcgtatctgagggactagggtgtgtttaggcgaaa agcggggcttcggttgtacgcggttaggagtcccctcaggatatagtagtttcgcttttgcatagggaggggaaatgtagtcttatgcaatac acttgtagtcttgcaacatggtaacgatgagttagcaacatgccttacaaggagagaaaaagcaccgtgcatgccgattggtggaagtaagg tggtacgatcgtgccttattaggaaggcaacagacaggtctgacatggattggacgaaccactgaattccgcattgcagagataattgtattta agtgcctagctccctatcagtgatagagatctccctatcagtgatagagatcgatacaataaacgccatttgaccattcaccacattggtgtgc accgaacgcgcagccgccatgccggggttttacgagattgtgattaaggtccccagcgaccttgacgagcatctgcccggcatttctgaca gctttgtgaactgggtggccgagaaggaatggagttgccgccagattctgacatggatctgaatctgattgagcaggcaccctgaccgt ggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgccggaggcgggaaca aggtggtggatgagtgctacatccccaattacttgctccccaaaacccagcctgagctccaatgggcatggaccaacatggaacagtacct cagcgcctgtttgaatctcacggagcgtaaacggttggtggcgcagcatctgacgcacgtgtcgcagacgcaggagcagaacaaagaga atcagaatcccaattctgatgcgccggtgatcagatcaaaaacttcagccaggtacatggagctggtcgggtggctcgtggacaaggggat tacctcggagaagcagtggatccaggaggaccaggcctcatacatctccttcaatgcggcctccaactcgcggtcccaaatcaaggctgcc ttggacaatgcgggaaagattatgagcctgactaaaaccgcccccgactacctggtgggccagcagcccgtggaggacatttccagcaat -continued

```
cggatttataaaattttggaactaaacgggtacgatccccaatatgcggcttccgtctttctgggatgggccacgaaaaagttcggcaagagg aacaccatctggctgtttgggcctgcaactaccgggaagaccaacatcgcggaggccatagcccacactgtgcccttctacgggtgcgtaa actggaccaatgagaactttcccttcaacgactgtgtcgacaagatggtgatctggtgggaggaggggaagatgaccgccaaggtcgtgg agtcggccaaagccattctcggaggaagcaaggtgcgcgtggaccagaaatgcaagtcctcggcccagatagacccgactcccgtgatc gtcacctccaacaccaacatgtgcgccgtgattgacgggaactcaacgaccttcgaacaccagcagccgttgcaagaccggatgttcaaat ttgaactcacccgccgtctggatcatgactttggaaggtcaccaagcaggaagtcaaagacttttttccggtgggcaaaggatcacgtggtt gaggtggagcatgaattctacgtcaaaaaggggggagccaagaaaagacccgcccccagtgacgcagatataagtgagcccaaacggg tgcgcgagtcagttgcgcagccatcgacgtcagacgcggaagcttcgatcaactacgcagacaggtaccaaaacaaatgttctcgtcacgt gggcatgaatctgatgctgtttccctgcagacaatgcgagagaatgaatcagaattcaaatatctgcttcactcacggacagaaagactgttta gagtgctttcccgtgtcagaatctcaacccgtttctgtcgtcaaaaaggcgtatcagaaactgtgctacattcatcatatcatgggaaaggtgc cagacgcttgcactgcctgcgatctggtcaatgtggatttggatgactgcatctttgaacaataaaatggctaggatccggccggcctgcagg tgtcctcacaggaacgaagtccctaaagaaacagtggcagccaggtttagccccggaaaacttgtttattgcagcttataatggttacaaata aagcaatagcatcacaaatttcacaaataaagcattttttttcactgcattctagttgtgtttgtccaaactcatcaatgtatcttattgactgga ttgagggacagccccccccaaagccccagggatgtaattacgtccctccccgctagggggcagcagcgagccgcccggggctccgct ccggtccggcgctcccccgcatccccgagccggcagcgtgcggggacagcccgggcacggggaaggtggcacgggatcgctttcct ctgaacgcttctcgctgctctttgagcctgcagacacctgggggatacggggaaaaggcctccaaggccagcttcccacaataagttggg tgaattttggctcattcctcctttctataggattgaggtcagagcggcctccgcgccgggttttggcgcctcccgcgggcgccccctcctcac ggcgagcgctgccacgtcagacgaagggcgcagcgagcgtcctgatccttccgcccggacgctcaggacagcggcccgctgctcataa gactcggccttagaaccccagtatcagcagaaggacattttaggacgggacttgggtgactctagggcactggttttcttttccagagagcgg aacaggcgaggaaaagtagtcccttctcggcgattctgcggagggatctccgtgggcggtgaacgccgatgattatataaggacgcgcc ggTCCCTATCAGTGATAGAGAtcTCCCTATCAGTGATAGAGAgtgtggcacagctagttccgtcgcag ccgggatttgggtcgcggttcttgtttgtggatcgctgtgatcgtcacttgacatcccaattctgatgcgccggtgatcagatcaaaaacttcag ccaggtacgccaccatggaactggtcggatggctggtggataagggcatcacaagcgagaagcaatggatccaggaggaccaggcctc atatatttcttttaacgccgctagcaattccagaagccagatcaaggctgctctggacaacgccggcaaaatcatgagcctgaccaagaccg cccctgactacctggtgggacagcagcctgtggaagatatcagcagcaacagaatctataagatcctggaactgaacggctacgaccccc agtacgccgcctccgtgttcctgggctgggctacaaagaagttcggcaagcggaacaccatctggctgttcggacctgccaccacaggca aaaccaatatcgccgaggccatcgcccacaccgtgccttttctacggctgcgtgaactggacaaacgagaacttccccttcaacgactgtgtg gacaagatggtgatctggtgggaggaaggcaaaatgacagctaaggtggtggaatctgccaaggctatcctgggaggctctaaggtcag ggtggatcagaagtgtaaaagcagcgcccagattgaccctacccctgtgatcgtgaccagcaataccaacatgtgcgccgtgatcgacgg caacagcaccaccttcgagcatcagcagcctctgcaggaccggatgttcaagtttgagctcaccagacggctggatcacgacttcggcaa ggtgaccaagcaggaggtgaaggatttcttcagatgggccaaagaccacgttgttgaggtggaacacgagttctacgtgaagaagggcgg cgccaagaaaagacccgcccctagcgacgccgacatcagcgagcctaagagagtgcgggaaagcgtggcccagcccagcacatctga tgctgaggccagcatcaactacgccgatagataccaaaacaagtgcagccgccacgtgggcatgaacctgatgctgtttccctgcagaca gtgtgaaagaatgaaccagaattctaatatctgctttacacacggccagaaagattgcctggaatgcttccctgtgtccgagagccaaccagt gtctgtggtgaaaaaggcctaccagaagctgtgctacatccaccacatcatgggcaaggtgccagacgcctgtaccgcctgcgacctggtc aacgtggacctggacgactgcatcttcgagcagtgatttgtgatgggaattctgtgctgtgccttctagttgccagccatctgttgtttgcccctc ccccgtgccttccttgaccctggaaggtgccactcccactgtccttttcctaataaaatgaggaaattgcatcgcattgtctgagtaggtgtcatt ctattctggggggtggggtgggcaggacagcaaggggggaggattgggaagacaatagcaggcatgctggggatgcggtgggctctat gggacctttttagggccccattggtatggcttttttcccgtatcccccaggtgtctgcaggctcaaagagcagcgagaagcgttcagaggaa agcgatcccgtgccaccttccccgtgccccgggctgtccccgcacgctgccggctcggggatgcgggggggagcgccggaccggagcgg agccccgggcggctcgctgctgcccccctagcggggggagggacgtaattacatccctgggggctttgggggggggctgtccctctagagc
```

-continued ggccgccaccgcggtggagctccagcttttgttcccttagtgagggttaattagatcttaatacgactcactatagggcgaattgggtaccgg gcccccctgaggcggaaagaaccagctggggctctaggggggtatcccgggggttggggttgcgccttttccaaggcagccctgggtttgc gcagggacgcggctgctctgggcgtggttccgggaaacgcagcggcgccgaccctgggtctcgcacattcttcacgtccgttcgcagcgt cacccggatcttcgccgctaccttgtgggccccccggcgacgcttcctgctccgccctaagtcgggaaggttccttgcggttcgcggcg tgccggacgtgacaaacggaagccgcacgtctcactagtaccctcgcagacggacagcgccagggagcaatggcagcgcgccgaccg cgatgggctgtggccaatagcggctgctcagcagggcgcgccgagagcagcggccgggaaggggcggtgcgggaggcggggtgtg gggcggtagtgtgggccctgttcctgcccgcgcggtgttccgcattctgcaagcctccggagcgcacgtcggcagtcggctccctcgttga ccgaatcaccgacctctctccccagaagctcccgggagcttgtatatccattttcggatctgatcagcacgtgttgacaattaatcatcggcat agtatatcggcatagtataatacgacaaggtgaggaacgccaccatggccaagcctttgtctcaagaagaatccaccctcattgaaagagca acggctacaatcaacagcatcccatctctgaagactacagcgtcgccagcgcagctctctagcgacggccgcatcttcactggtgtcaa tgtatatcattttactgggggaccttgtgcagaactcgtggtgctgggcactgctgctgctgcggcagctggcaacctgacttgtatcgtcgcg atcggaaatgagaacaggggcatcttgagccctgcggacggtgccgacaggtgcttctcgatctgcatcctgggatcaaagccatagtga aggacagtgatggacagccgacggcagttgggattcgtgaattgctgccctctggttatgtgtgggagggctaaagcgcggggatctcatg ctggagttcttcgcccaccccaacttgtttattgcagcttataatggttacaaataaagcaatagcatcacaaatttcacaaataaagcattttt tcactgcattctagttgtggtttgtccaaactcatcaatgtatcttatcatgtctgtagctgatgtataccctaggatccggccggcctgcaggtgt cctcacaggaacgaagtccctaaagaaacagtggcagccaggtttagccccggaattgactggattccttttttagggcccattggtatggctttt tccccgtatccccccaggtgtctgcaggctcaaagagcagcgagaagcgttcagaggaaagcgatcccgtgccaccttcccgtgccgg gctgtccccgcacgctgccggctcgggatgcgggggagcgccggaccggagcggagcccggggctcgctgctgcccctag cggggagggacgtaattacatccctgggggctttgggggggggctgtccctctagagcggccgccaccgcggtggagctccagctttt gttcccttagtgagggttaattagatcttaatacgactcactatagggcgaattgggtaccgggcccccctcgaggtcgacggtatcctcga ggtcgacggtatcgataagcttgatatctataacaagaaatatatatataataagttatcacgtaagtagaacatgaaataacaatataattatc gtatgagttaaatcttaaaagtcacgtaaaagataatcatgcgtcattttgactcacgcggtcgttatagttcaaaatcagtgacacttaccgcat tgacaagcacgcctcacgggagctccaagcggcgactgagatgtcctaaatgcacagcgacggattcgcgctatttagaaagagagagc aatatttcaagaatgcatgcgtcaattttacgcagactatctttctagggttaatctagctgcatcaggatcatatcgtcgggtcttttttccggc tcagtcatcgcccaagctggcgctatctgggcatcggggaggaagaagcccgtgccttttcccgcgaggttgaagcggcatggaaagagttt gccgaggatgactgctgctgcattgacgttgagcgaaaacgcacgtttaccatgatgattcgggaaggtgtggccatgcacgcctttaacgg tgaactgttcgttcaggccacctgggataccagttcgtcgcggcttttccggacacagttccggatggtcagcccgaagcgcatcagcaacc cgaacaataccggcgacagccggaactgccgtgccggtgtgcagattaatgacagcggtgcggcgctgggatattcgtcagcgaggac gggtatcctggctggatgccgcagaaatggacatggataccccgtgagttacccggcgggcgcgcttggcgtaatcatggtcatagctgttt cctgtgtgaaattgttatccgctcacaattccacacaacatacgagccggaagcataaagtgtaaagcctggggtgcctaatgagtgagcta actcacattaattgcgttgcgctcactgcccgctttccagtcgggaaacctgtcgtgccagctgcattaatgaatcggccaacgcgcgggga gaggcggtttgcgtattgggcgctcttccgcttcctcgctcactgactcgctgcgctcggtcgttcggctgcggcgagcggtatcagctcact caaaggcggtaatacggttatccacagaatcaggggataacgcaggaaagaacatgtgagcaaaaggccagcaaaaggccaggaacc gtaaaaaggccgcgttgctggcgtttttccataggctccgcccccctgacgagcatcacaaaaatcgacgctcaagtcagaggtggcgaaa cccgacaggactataaagataccaggcgtttccccctggaagctccctcgtgcgctctcctgttccgaccctgccgcttaccggatacctgtc cgcctttctcccttcgggaagcgtggcgctttctcatagctcacgctgtaggtatctcagttcggtgtaggtcgttcgctccaagctgggctgtg tgcacgaaccccccgttcagcccgaccgctgcgccttatccggtaactatcgtcttgagtccaacccggtaagcacgacttatcgccactg gcagcagccactggtaacaggattagcagagcgaggtatgtaggcggtgctacagagttcttgaagtggtggcctaactacggctacacta gaaggacagtatttggtatctgcgctctgctgaagccagttaccttcggaaaaagagttggtagctcttgatccggcaaacaaaccaccgctg gtagcggtggtttttttgtttgcaagcagcagattacgcgcagaaaaaaaggatctcaagaagatcctttgatcttttctacggggtctgacgct -continued

```
cagtggaacgaaaactcacgttaagggattttggtcatgagattatcaaaaaggatcttcacctagatccttttaaattaaaaatgaagttttaaa tcaatctaaagtatatatgagtaaacttggtctgacagttaccaatgcttaatcagtgaggcacctatctcagcgatctgtctatttcgttcatcc atagttgcctgactcccgtcgtgtagataactacgatacgggagggcttaccatctggcccagtgctgcaatgataccgcgagacccacgc tcaccggctccagatttatcagcaataaaccagccagccggaagggccgagcgcagaagtggtcctgcaactttatccgcctccatccagt ctattaattgttgccgggaagctagagtaagtagttcgccagttaatagtttgcgcaacgttgttgccattgctacaggcatcgtggtgtcacgc tcgtcgtttggtatggcttcattcagctccggttcccaacgatcaaggcgagttacatgatcccccatgttgtgcaaaaaagcggttagctcctt cggtcctccgatcgttgtcagaagtaagttggccgcagtgttatcactcatggttatggcagcactgcataattctcttactgtcatgccatccgt aagatgcttttctgtgactggtgagtactcaaccaagtcattctgagaatagtgtatgcggcgaccgagttgctcttgcccggcgtcaatacgg gataataccgcgccacatagcagaactttaaaagtgctcatcattggaaaacgttcttcggggcgaaaactctcaaggatcttaccgctgttg agatccagttcgatgtaacccactcgtgcacccaactgatcttcagcatcttttactttcaccagcgtttctgggtgagcaaaaacaggaaggc aaaatgccgcaaaaaagggaataagggcgacacggaaatgttgaatactcat
```

Example 4: Design and Validation of Inducible Cap Genes and Gene of Interest

Two strategies were implemented for the inducible Cap gene expression. In the first strategy, the Cap genes were split into two cassettes, one for the VP1 expression, and the other for VP2 and VP3. To reduce the DNA sequence homology between VP1 and VP2/3 genes in order to increase the vector stability, the DNA sequence of VP1 coding region was optimized for human cell codon usage without change of protein sequence. To maintain the protein coding sequence of membrane-associated accessory protein (MAAP), the first 439 bp of VP1 coding region that included the MAAP gene was excluded for codon optimization. The DNA sequence identity between the optimized VP1 and the original VP2/3 gene was reduced to 80.7%.

An AAV ITR flanked transgene expression cassette, such as the GFP gene driven by CMV promoter, was also included in the vector as a representative of a gene of interest (GOI) inserted into the vector. In addition, the third antibiotic resistance gene for hygromycin driven by human PGK promoter was included. All the gene cassettes were subcloned into the piggyBac transposon vectors, and flanked by core insulators.

Figure 6A:
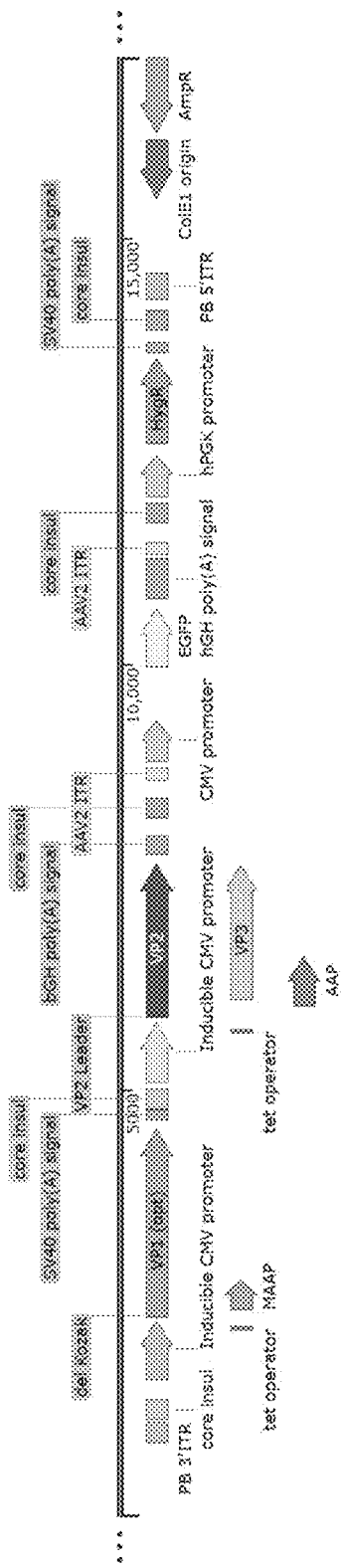
FIGS. 6A-6E show exemplary nucleic acid molecules for production of Cap genes and genes of interest in accordance with embodiments hereof.
Figure 6B:
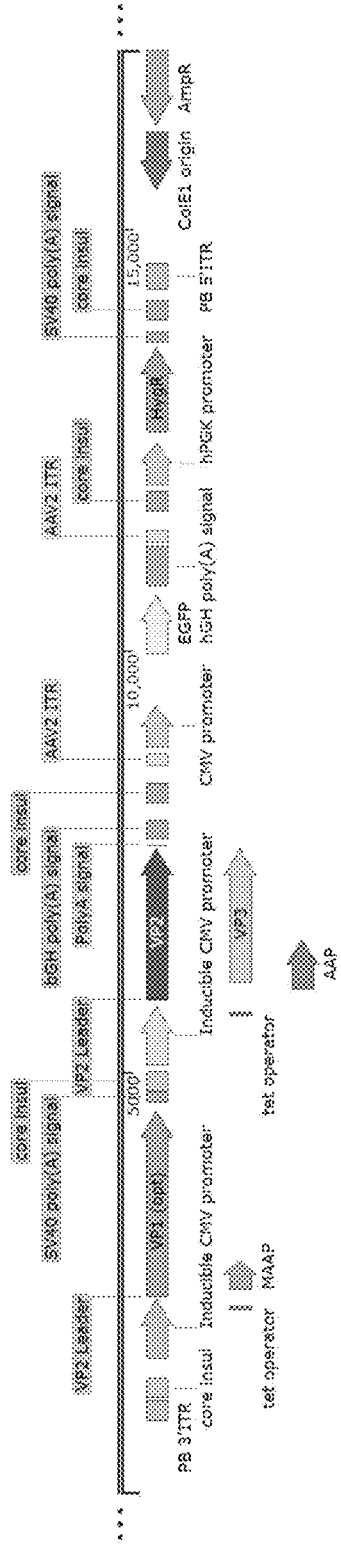
Figure 6C:
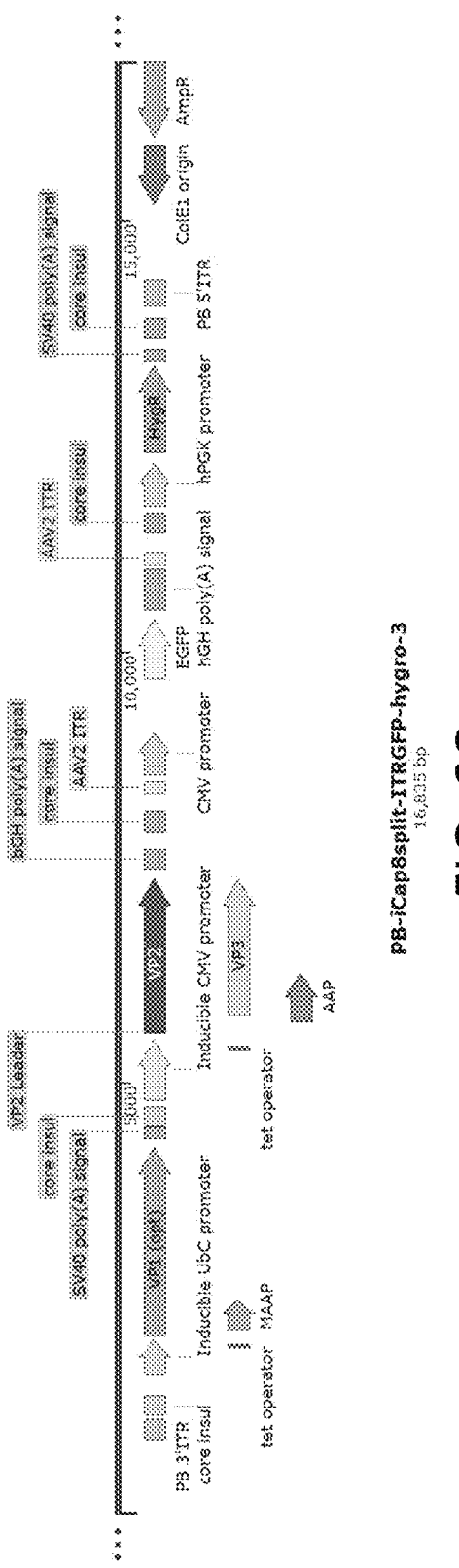
Figure 6D:
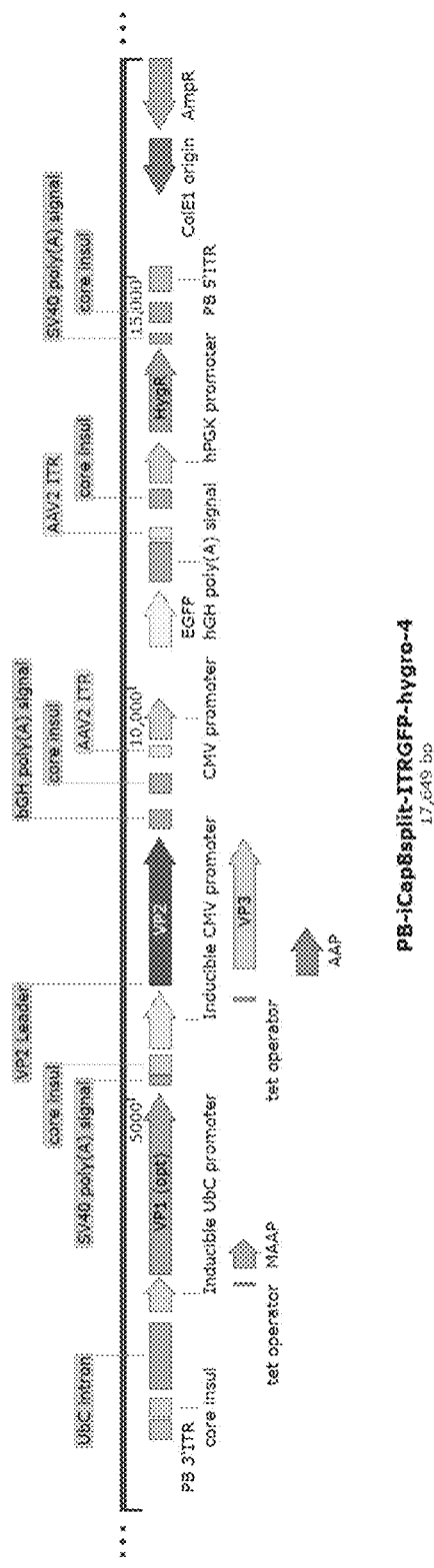

In the PB-iCapsplit-ITRGFP-hygro-1 vector, the previously described inducible CMV promoter was used to drive the VP1 gene expression without the Kozak sequence before ATG start codon of VP1, while the same promoter was also used for the expression of VP2 and VP3 gene expression by the native leader sequence (ggcgctaag) before the original ACG start codon (See FIG. 6A). In the PB-iCapsplit-ITRGFP-hygro-2 vector, the VP1 cassette was modified with the native VP2 leader sequence followed by the ACG start codon, while no other changes compared to PB-iCapsplit-ITRGFP-hygro-1 vector (See FIG. 6B). In the PB-iCapsplit-ITRGFP-hygro-3 vector, the promoter for VP1 cassette was switched to the inducible UbC promoter, and the Kozak sequence was added before the ATG start codon of VP1 gene, without other changes compared to PB-iCapsplit-ITRGFP-hygro-1 vector (See FIG. 6C). To increase the expression of VP1 protein, the 814 bp UbC intron that was identified as an enhancer (Bianchi et al., "A potent enhancer element in the 5'-UTR intron is crucial for transcriptional regulation of the human ubiquitin C gene," Gene 448 (1): 88-101 (2009) was inserted before the inducible UbC promoter in the PB-iCapsplit-ITRGFP-hygro-3 vector, and resulted in the PB-iCapsplit-ITRGFP-hygro-4 vector (See FIG. 6D).

Figure 6E:
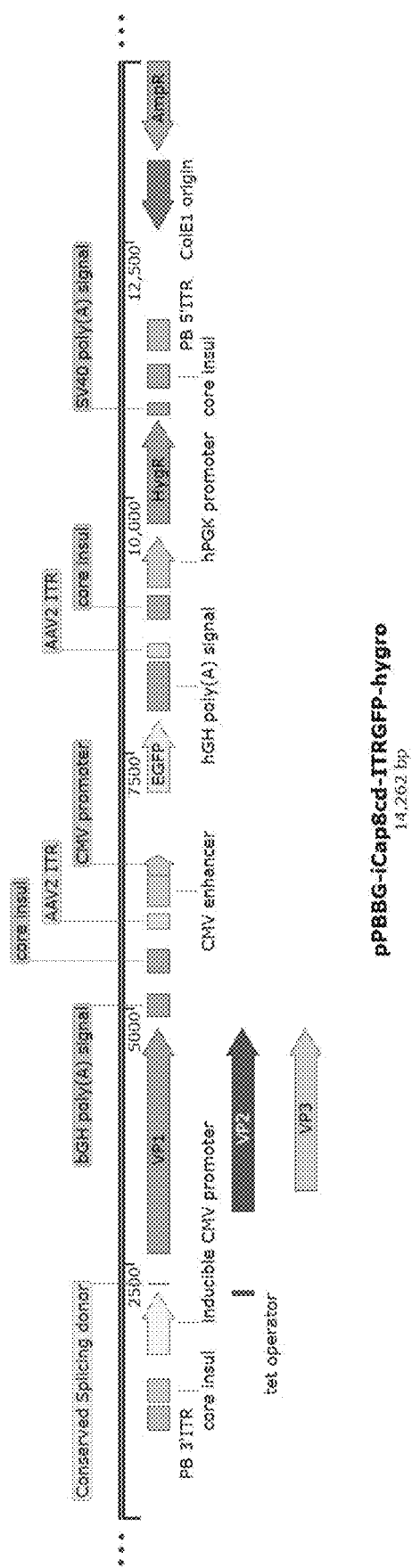

In the second strategy, the VP1, VP2 and VP3 genes remained in the original architecture in a single native DNA sequence. The strong inducible CMV promoter was applied to drive the Cap gene expression. To enhance the expression level of VP proteins, the original suboptimal splicing donor site for the VP genes was optimized to the conserved donor sequence (caggtaAGT from 2309 to 2317 bp) without affecting the ratios of VP proteins (Farris and Pintel, "Improved splicing of Adeno-associated viral (AAV) capsid protein-supplying pre-mRNAs leads to increased recombinant AAV vector production," Hum Gene Ther. 19 (12): 1421-1427 (2008). The pPBBG-iCap8cd-ITRGFP-hygro vector is shown in FIG. 6E.

The sequence of the PB-iCap8split-ITRGFP-hygro-1 vector is provided below:

PB-iCap8split-ITRGFP-hygro-1 (17,121 bp)

(SEQ ID NO: 30)

```
ACTCTTCCTTTTTCAATATTATTGAAGCATTTATCAGGGTTATTGTCTCATGA

GCGGATACATATTTGAATGTATTTAGAAAAATAAACAAATAGGGGTTCCGCGCACA

TTTCCCCGAAAAGTGCCACCTAAATTGTAAGCGTTAATATTTTGTTAAAATTCGCGTT

AAATTTTTGTTAAATCAGCTCATTTTTTAACCAATAGGCCGAAATCGGCAAAATCCC

TTATAAATCAAAAGAATAGACCGAGATAGGGTTGAGTGTTGTTCCAGTTTGGAACA

AGAGTCCACTATTAAAGAACGTGGACTCCAACGTCAAAGGGCGAAAAACCGTCTAT

CAGGGCGATGGCCCACTACGTGAACCATCACCCTAATCAAGTTTTTTGGGGTCGAGG

TGCCGTAAAGCACTAAATCGGAACCCTAAAGGGAGCCCCCGATTTAGAGCTTGACG
```

-continued

```
GGGAAAGCCGGCGAACGTGGCGAGAAAGGAAGGGAAGAAAGCGAAAGGAGCGGG
CGCTAGGGCGCTGGCAAGTGTAGCGGTCACGCTGCGCGTAACCACCACACCCGCCG
CGCTTAATGCGCCGCTACAGGGCGCGTCCCATTCGCCATTCAGGCTGCGCAACTGTT
GGGAAGGGCGATCGGTGCGGGCCTCTTCGCTATTACGCCAGCTGGCGAAAGGGGGA
TGTGCTGCAAGGCGATTAAGTTGGGTAACGCCAGGGTTTTCCCAGTCACGACGTTGT
AAAACGACGGCCAGTGAGCGCGCCTCGTTCATTCACGTTTTTGAACCCGTGGAGGAC
GGGCAGACTCGCGGTGCAAATGTGTTTTACAGCGTGATGGAGCAGATGAAGATGCT
CGACACGCTGCAGAACACGCAGCTAGATTAACCCTAGAAAGATAATCATATTGTGA
CGTACGTTAAAGATAATCATGCGTAAAATTGACGCATGTGTTTTATCGGTCTGTATA
TCGAGGTTTATTTATTAATTTGAATAGATATTAAGTTTTATTATATTTACACTTACAT
ACTAATAATAAATTCAACAAACAATTTATTTATGTTTATTTATTTATTAAAAAAAAA
CAAAAACTCAAAATTTCTTCTATAAAGTAACAAAACTTTTATCGAATTCCTGCAGCC
CGGGGGATCCACTAGTTCTAGAGGGACAGCCCCCCCCCAAAGCCCCCAGGGATGTA
ATTACGTCCCTCCCCCGCTAGGGGCAGCAGCGAGCCGCCCGGGGCTCCGCTCCGGT
CCGGCGCTCCCCCCGCATCCCCGAGCCGGCAGCGTGCGGGACAGCCCGGGCACGG
GGAAGGTGGCACGGGATCGCTTTCCTCTGAACGCTTCTCGCTGCTCTTTGAGCCTGC
AGACACCTGGGGGATACGGGAAAAGGCCTCCAAGGCCAGCTTCCCACAATAAGT
TGGGTGAATTTTGGCTCATTCCTCCTTTCTATAGGATTGAGGTCAGAGCTTTGTGATG
GGAATTCTGTGGAATGTGTGTCAGTTAGGGTGTGGAAAGTCCCgcGATCgcTAGcGTTT
AAACTTAAGCTTGGTACCGAGCTCGGATCCACTAGTCCAGTGTGGTGGAATTCCTGC
TTCGCGATGTACGGGCCAGATATACGCGTgacattgattattgactagttattaatagtaatcaattacgggtcatt
agttcatagcccatatatggagttccgcgttacataacttacggtaaatggcccgcctggctgaccgcccaacgaccccgcccattgacgt
caataatgacgtatgttcccatagtaacgccaatagggactttccattgacgtcaatgggtggagtatttacggtaaactgcccacttggcagt
acatcaagtgtatcatatgccaagtacgccccctattgacgtcaatgacggtaaatggcccgcctggcattatgcccagtacatgaccttatg
ggactttcctacttggcagtacatctacgtattagtcatcgctattaccatggtgatgcggttttggcagtacatcaatgggcgtggatagcggtt
tgactcacggggatttccaagtctccaccccattgacgtcaatgggagtttgttttggaaccaaaatcaacgggactttccaaaatgtcgtaac
aactccgccccattgacgcaaatgggcggtaggcgtgtacggtgggaggtctatataagcagagctctccctatcagtgatagagatctccc
tatcagtgatagagatcgtcgacgagctcgtttagtgaaccgtcagatcgcctggagacgccatccacgctgttttgacctccatagaagaca
ccgggaccgatccagcctgaacgcgcagccgccaatggATGGCCGCTGATGGCTATCTGCCTGATTGGCT
GGAAGATAACCTGAGTGAGGGCATCCGGGAATGGTGGGCCCTGAAGCctggagccccgaag
cccaaagccaaccagcaaaagcaggacgacgccggggtctggtgcttcctggctacaagtacctcggaccttcaacggactcgacaa
gggggagcccgtcaacgcggcggacgcagcggccctcgagcacgacaaggcctacgaccagcagctgcaggcgggtgacaatccgt
acctgcggtataaccacgccgacgccgagtttcaggagcgtctgcaagaagatacgtcttttgggggcaacctcgggcgagcagtcttcca
ggccaagaagcgggttctcgaacctctcggtctggttgaggaaggcgctaagacggctcctggaaagaagaggccggtagAACCT
AGCCCCCAGCGATCTCCAGATTCTTCTACCGGCATCGGCAAAAAGGGCCAACAGCC
TGCGAGAAAGCGGCTGAACTTCGGCCAGACCGGAGACAGCGAGAGCGTGCCCGACC
CTCAGCCTCTGGGCGAGCCCCCTGCCGCCCCTTCTGGCGTGGGCCCCAACACCATGG
CCGCCGGCGGCGGAGCCCCTATGGCCGACAACAACGAGGGCGCCGACGGCGTGGG
AAGCAGCAGCGGCAATTGGCACTGCGACTCCACCTGGCTGGGCGACAGAGTGATCA
CCACATCTACAAGAACCTGGGCCCTGCCCACCTACAACAATCACCTGTACAAGCAG
```

-continued

```
ATCAGCAATGGAACCTCTGGAGGCGCCACCAACGATAACACCTACTTTGGCTACAG

CACCCCTTGGGGATATTTCGACTTCAACCGGTTCCACTGTCACTTCAGCCCTCGGGA

CTGGCAGCGTCTCATTAACAATAACTGGGGCTTCAGACCAAAGAGACTGAGCTTCA

AGCTGTTCAACATCCAGGTGAAGGAAGTGACCCAAAACGAGGGCACCAAGACCATC

GCCAATAACCTCACCTCCACAATCCAAGTGTTCACCGATTCCGAGTACCAGCTGCCT

TACGTGCTGGGCTCCGCCCACCAGGGCTGCCTGCCACCATTCCCCGCCGACGTGTTC

ATGATCCCTCAGTACGGCTACCTGACACTGAACAACGGATCTCAAGCAGTGGGCAG

AAGCTCCTTCTACTGTCTGGAGTACTTCCCTAGCCAGATGCTGAGGACAGGCAACAA

TTTCCAGTTCACCTACACATTCGAGGACGTCCCTTTTCACAGCTCTTATGCCCATAGC

CAGAGCCTGGATAGACTGATGAACCCTCTGATCGACCAGTATCTGTATTACCTGAGC

AGAACGCAAACAACAGGCGGCACCGCTAATACCCAGACCCTGGGTTTCAGCCAAGG

CGGCCCTAACACAATGGCCAATCAGGCCAAAAACTGGCTTCCTGGCCCCTGCTACA

GACAGCAAAGAGTGAGCACAACCACCGGCCAGAACAACAACTCTAACTTCGCCTGG

ACAGCCGGCACCAAATACCACCTGAACGGCAGAAACAGCCTGGCCAACCCTGGAAT

CGCTATGGCTACACACAAGGACGATGAGGAACGGTTCTTCCCCAGCAACGGCATCC

TGATCTTCGGCAAGCAGAACGCCGCTCGCGACAACGCCGACTACAGCGACGTGATG

CTGACCAGCGAGGAAGAAATCAAGACAACAAACCCGGTCGCCACCGAGGAATACG

GCATTGTGGCCGATAACCTGCAGCAGCAGAATACCGCCCCTCAGATCGGCACCGTG

AACTCCCAGGGAGCCCTGCCTGGCATGGTGTGGCAGAACAGAGATGTGTACCTGCA

GGGCCCTATCTGGGCCAAGATCCCCCACACCGACGGAAATTTCCATCCAAGCCCTCT

GATGGGCGGATTTGGCCTGAAGCACCCCCCTCCACAGATTCTCATCAAAAACACACC

TGTGCCAGCCGACCCTCCCACAACATTTAATCAGTCTAAGCTGAATAGCTTCATCAC

CCAGTACAGCACCGGCCAGGTGTCCGTGGAAATCGAGTGGGAGCTGCAGAAAGAGA

ACAGCAAGAGATGGAACCCTGAGATCCAGTACACCAGCAACTACTACAAAAGCACA

AGCGTGGACTTCGCCGTTAATACTGAGGGCGTCTACTCAGAGCCTCGGCCCATCGGC

ACTCGGTACCTGACCAGAAACCTGaatggctaggatccggccggcctgcaggtgtcctcacaggaacgaagtccct aaagaaacagtggcagccaggtttagccccggaaaacttgtttattgcagcttataatggttacaaataaagcaatagcatcacaaatttcaca aataaagcattttttttcactgcattctagttgtggtttgtccaaactcatcaatgtatcttattgactggattgagggacagcccccccccaaagc ccccagggatgtaattacgtccctcccccgctaggggcagcagcgagccgcccggggctccgctccggtccggcgctcccccgcatc cccgagccggcagcgtgcgggacagcccgggcacggggaaggtggcacgggatcgctttcctctgaacgcttctcgctgctctttgag cctgcagacacctgggggatacggggaaaaggcctccaaggccagcttcccacaataagttgggtgaattttggctcattcctcctttctat aggattgaggtcagagcGACATTGATTATTGACTAGTTATTAATAGTAATCAATTACGGGGTC

ATTAGTTCATAGCCCATATATGGAGTTCCGCGTTACATAACTTACGGTAAATGGCCC

GCCTGGCTGACCGCCCAACGACCCCCGCCCATTGACGTCAATAATGACGTATGTTCC

CATAGTAACGCCAATAGGGACTTTCCATTGACGTCAATGGGTGGAGTATTTACGGTA

AACTGCCCACTTGGCAGTACATCAAGTGTATCATATGCCAAGTACGCCCCCTATTGA

CGTCAATGACGGTAAATGGCCCGCCTGGCATTATGCCCAGTACATGACCTTATGGGA

CTTTCCTACTTGGCAGTACATCTACGTATTAGTCATCGCTATTACCATGGTGATGCGG

TTTTGGCAGTACATCAATGGGCGTGGATAGCGGTTTGACTCACGGGGATTTCCAAGT

CTCCACCCCATTGACGTCAATGGGAGTTTGTTTTGGAACCAAAATCAACGGGACTTT

CCAAAATGTCGTAACAACTCCGCCCCATTGACGCAAATGGGCGGTAGGCGTGTACG
```

-continued

```
GTGGGAGGTCTATATAAGCAGAGCTCTCCCTATCAGTGATAGAGATCTCCCTATCAG

TGATAGAGATCGTCGACGAGCTCGTTTAGTGAACCGTCAGATCGCCTGGAGACGCC

ATCCACGCTGTTTTGACCTCCATAGAAGACACCGGGACCGATCCAGCCTatcccaattctgat gcgccggtgatcagatcaaaaacttcagccaggtacggcgctaagacggctcctggaaagaagaggccggtagagccatcaccccagc gttctccagactcctctacgggcatcggcaagaaaggccaacagcccgccagaaaaagactcaattttggtcagactggcgactcagagtc agttccagaccctcaacctctcggagaacctccagcagcgccctctggtgtgggacctaatacaatggctgcaggcggtggcgcaccaat ggcagacaataacgaaggcgccgacggagtgggtagttcctcgggaaattggcattgcgattccacatggctgggcgacagagtcatcac caccagcacccgaacctgggccctgcccacctacaacaaccacctctacaagcaaatctccaacgggacatcggaggagccaccaac gacaacacctacttcggctacagcacccctgggggtattttgactttaacagattccactgccacttttcaccacgtgactggcagcgactca tcaacaacaactggggattccggcccaagagactcagcttcaagctcttcaacatccaggtcaaggaggtcacgcagaatgaaggcacca agaccatcgccaataacctcaccagcaccatccaggtgtttacggactcggagtaccagctgccgtacgttctcggctctgcccaccaggg ctgcctgcctccgttcccggcggacgtgttcatgattccccagtacggctacctaacactcaacaacggtagtcaggccgtgggacgctcct ccttctactgcctggaatactttccttcgcagatgctgagaaccggcaacaacttccagtttacttacaccttcgaggacgtgcctttccacagc agctacgcccacagccagagcttggaccggctgatgaatcctctgattgaccagtacctgtactacttgtctcggactcaaacaacaggagg cacggcaaatacgcagactctgggcttcagccaaggtgggcctaatacaatggccaatcaggcaaagaactggctgccaggaccctgtta ccgccaacaacgcgtctcaacgacaaccgggcaaaacaacaatagcaactttgcctggactgctgggaccaaataccatctgaatggaag aaattcattggctaatcctggcatcgctatggcaacacacaaagacgacgaggagcgtttttttcccagtaacgggatcctgattttttggcaaa caaaatgctgccagagacaatgcggattacagcgatgtcatgctcaccagcgaggaagaaatcaaaaccactaaccctgtggctacagag gaatacggtatcgtggcagataacttgcagcagcaaaacacggctcctcaaattggaactgtcaacagccaggggggccttacccggtatgg tctggcagaaccgggacgtgtacctgcagggtcccatctgggccaagattcctcacacggacggcaacttccacccgtctccgctgatgg gcggctttggcctgaaacatcctccgcctcagatcctgatcaagaacacgcctgtacctgcggatcctccgaccaccttcaaccagtcaaag ctgaactctttcatcacgcaatacagcaccggacaggtcagcgtggaaattgaatgggagctgcagaaggaaaacagcaagcgctggaa ccccgagatccagtacacctccaactactacaaatctacaagtgtggactttgctgttaatacagaaggcgtgtactctgaaccccgccccatt ggcacccgttacctcacccgtaatctgtaaactagtttgcttgttaatcaataaaccgtttaattcgtttcagttgaGCGGCCGTCGAG

TCTAGAGGGCCCGTTTAAACCCGCTGATCAGCCTCGACTGTGCCTTCTAGTTGCCAG

CCATCTGTTGTTTGCCCCTCCCCCGTGCCTTCCTTGACCCTGGAAGGTGCCACTCCCA

CTGTCCTTTCCTAATAAAATGAGGAAATTGCATCGCATTGTCTGAGTAGGTGTCATT

CTATTCTGGGGGGTGGGTGGGGCAGGACAGCAAGGGGGAGGATTGGGAAGACAA

TAGCAGGCATGCTGGGGATGCGGTGGGCTCTATGGCTTCTGAGGCGGAAAGAACCA

GCTGGGGCTCTAGGGGGTATCCCCGGCGCGCCGAATTCGTTAACAAGCTtTAATTAaC

GCgtATAcCTAggATCCGGCCGGccTGCAggTGTCCTCACAGGAACGAAGTCCCTAAAG

AAACAGTGGCAGCCAGGTTTAGCCCCGGAATTGACTGGATTCCTTTTTTAGGGCCCA

TTGGTATGGCTTTTTCCCCGTATCCCCCCAGGTGTCTGCAGGCTCAAAGAGCAGCGA

GAAGCGTTCAGAGGAAAGCGATCCCGTGCCACCTTCCCCGTGCCCGGGCTGTCCCCG

CACGCTGCCGGCTCGGGGATGCGGGGGAGCGCCGGACCGGAGCGGAGCCCCGGG

CGGCTCGCTGCTGCCCCCTAGCGGGGAGGGACGTAATTACATCCCTGGGGGCTTTG

GGGGGGGCTGTCCCTGGCCTCCAAGGCCAGCTTCCCACAATAAGTTGGGTGAATTT

TGGCTCATTCCTCCTTTCTATAGGATTGAGGTCAGAGCTTTGTGATGGGAATTCTGTG

GAATGTGTGTCAGTTAGGGTGTGGAAAGTCCCgcGATCgcTAGcAAACGCCAGCAACG

CGGCCTTTTTACGGTTCCTGGCCTTTTGCTGGCCTTTTGCTCACATGTCCTGCAGGCA
```

-continued

```
GCTGCGCGCTCGCTCGCTCACTGAGGCCGCCCGGGCAAAGCCCGGGCGTCGGGCGA
CCTTTGGTCGCCCGGCCTCAGTGAGCGAGCGAGCGCGCAGAGAGGGAGTGGCCAAC
TCCATCACTAGGGGTTCCTGCGGCCGCACGCGTGGAGCTAGTTATTAATAGTAATCA
ATTACGGGGTCATTAGTTCATAGCCCATATATGGAGTTCCGCGTTACATAACTTACG
GTAAATGGCCCGCCTGGCTGACCGCCCAACGACCCCCGCCCATTGACGTCAATAATG
ACGTATGTTCCCATAGTAACGTCAATAGGGACTTTCCATTGACGTCAATGGGTGGAG
TATTTACGGTAAACTGCCCACTTGGCAGTACATCAAGTGTATCATATGCCAAGTACG
CCCCCTATTGACGTCAATGACGGTAAATGGCCCGCCTGGCATTATGCCCAGTACATG
ACCTTATGGGACTTTCCTACTTGGCAGTACATCTACGTATTAGTCATCGCTATTACCA
TGGTGATGCGGTTTTGGCAGTACATCAATGGGCGTGGATAGCGGTTTGACTCACGGG
GATTTCCAAGTCTCCACCCCATTGACGTCAATGGGAGTTTGTTTTGCACCAAAATCA
ACGGGACTTTCCAAAATGTCGTAACAACTCCGCCCCATTGACGCAAATGGGCGGTA
GGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCC
AGCCTCCGCGGATTCGAATCCCGGCCGGGAACGGTGCATTGGAACGCGGATTCCCC
GTGCCAAGAGTGACGTAAGTACCGCCTATAGAGTCTATAGGCCCACAAAAAATGCT
TTCTTCTTTTAATATACTTTTTTGTTTATCTTATTTCTAATACTTTCCCTAATCTCTTTC
TTTCAGGGCAATAATGATACAATGTATCATGCCTCTTTGCACCATTCTAAAGAATAA
CAGTGATAATTTCTGGGTTAAGGCAATAGCAATATTTCTGCATATAAATATTTCTGC
ATATAAATTGTAACTGATGTAAGAGGTTTCATATTGCTAATAGCAGCTACAATCCAG
CTACCATTCTGCTTTTATTTTATGGTTGGGATAAGGCTGGATTATTCTGAGTCCAAGC
TAGGCCCTTTTGCTAATCATGTTCATACCTCTTATCTTCCTCCCACAGCTCCTGGGCA
ACGTGCTGGTCTGTGTGCTGGCCCATCACTTTGGCAAAGAATTGGGATTCGAACATC
GATTGAATTCTGAATGGTGAGCAAGGGCGAGGAGCTGTTCACCGGGGTGGTGCCCA
TCCTGGTCGAGCTGGACGGCGACGTAAACGGCCACAAGTTCAGCGTGTCCGGCGAG
GGCGAGGGCGATGCCACCTACGGCAAGCTGACCCTGAAGTTCATCTGCACCACCGG
CAAGCTGCCCGTGCCCTGGCCCACCCTCGTGACCACCCTGACCTACGGCGTGCAGTG
CTTCAGCCGCTACCCCGACCACATGAAGCAGCACGACTTCTTCAAGTCCGCCATGCC
CGAAGGCTACGTCCAGGAGCGCACCATCTTCTTCAAGGACGACGGCAACTACAAGA
CCCGCGCCGAGGTGAAGTTCGAGGGCGACACCCTGGTGAACCGCATCGAGCTGAAG
GGCATCGACTTCAAGGAGGACGGCAACATCCTGGGGCACAAGCTGGAGTACAACTA
CAACAGCCACAACGTCTATATCATGGCCGACAAGCAGAAGAACGGCATCAAGGTGA
ACTTCAAGATCCGCCACAACATCGAGGACGGCAGCGTGCAGCTCGCCGACCACTAC
CAGCAGAACACCCCCATCGGCGACGGCCCCGTGCTGCTGCCCGACAACCACTACCT
GAGCACCCAGTCCGCCCTGAGCAAAGACCCCAACGAGAAGCGCGATCACATGGTCC
TGCTGGAGTTCGTGACCGCCGCCGGGATCACTCTCGGCATGGACGAGCTGTACAAGT
ACTCAGATCTCGAGCTCAAGTAGGGATCCTCTAGAGTCGACCTGCAGAAGCTTGCCT
CGAGCAGCGCTGCTCGAGAGATCTACGGGTGGCATCCCTGTGACCCCTCCCCAGTGC
CTCTCCTGGCCCTGGAAGTTGCCACTCCAGTGCCCACCAGCCTTGTCCTAATAAAAT
TAAGTTGCATCATTTTGTCTGACTAGGTGTCCTTCTATAATATTATGGGTGGAGGG
GGGTGGTATGGAGCAAGGGGCAAGTTGGGAAGACAACCTGTAGGGCCTGCGGGGTC
```

```
TATTGGGAACCAAGCTGGAGTGCAGTGGCACAATCTTGGCTCACTGCAATCTCCGCC
TCCTGGGTTCAAGCGATTCTCCTGCCTCAGCCTCCCGAGTTGTTGGGATTCCAGGCAT
GCATGACCAGGCTCAGCTAATTTTTGTTTTTTTGGTAGAGACGGGGTTTCACCATATT
GGCCAGGCTGGTCTCCAACTCCTAATCTCAGGTGATCTACCCACCTTGGCCTCCCAA
ATTGCTGGGATTACAGGCGTGAACCACTGCTCCCTTCCCTGTCCTTCTGATTTTGTAG
GTAACCACGTGCGGACCGAGCGGCCGCAGGAACCCCTAGTGATGGAGTTGGCCACT
CCCTCTCTGCGCGCTCGCTCGCTCACTGAGGCCGGGCGACCAAAGGTCGCCCGACGC
CCGGGCTTTGCCCGGGCGGCCTCAGTGAGCGAGCGAGCGCGCAGCTGCCTGCAGGG
GCGCCTGATGCGGTATTTTCTCCTTACGCATCTGTGCGGTATTTCACACCGCATACGT
CgtaGCtGATcaATTgGCGCGCCGAATTCGTTAACAAGCTtTAATTAaCGCgtATAcCTAgg
ATCCGGCCGGccTGCAggTGTCCTCACAGGAACGAAGTCCCTAAAGAAACAGTGGCA
GCCAGGTTTAGCCCCGGAATTGACTGGATTCCTTTTTTAGGGCCCATTGGTATGGCTT
TTTCCCCGTATCCCCCCAGGTGTCTGCAGGCTCAAAGAGCAGCGAGAAGCGTTCAGA
GGAAAGCGATCCCGTGCCACCTTCCCCGTGCCCGGGCTGTCCCCGCACGCTGCCGGC
TCGGGGATGCGGGGGGAGCGCCGGACCGGAGCGGAGCCCCGGGCGGCTCGCTGCTG
CCCCCTAGCGGGGGAGGGACGTAATTACATCCCTGGGGGCTTTGGGGGGGGGCTGT
CCCTGGCCTCCAAGGCCAGCTTCCCACAATAAGTTGGGTGAATTTTGGCTCATTCCT
CCTTTCTATAGGATTGAGGTCAGAGCgggggttgggggttgcgccttttccaaggcagccctgggtttgcgcagggac
gcggctgctctgggcgtggttccgggaaacgcagcggcgccgaccctgggtctcgcacattcttcacgtccgttcgcagcgtcacccgga
tcttcgccgctaccttgtgggcccccggcgacgcttcctgctccgccctaagtcgggaaggttccttgcggttcgcggcgtgccggac
gtgacaaacggaagccgcacgtctcactagtaccctcgcagacggacagcgccagggagcaatggcagcgcgccgaccgcgatgggc
tgtggccaatagcggctgctcagcagggcgcgccgagagcagcggccgggaaggggcggtgcgggaggcggggtgtgggcggta
gtgtgggccctgttcctgcccgcgcggtgttccgcattctgcaagcctccggagcgcacgtcggcagtcggctccctcgttgaccgaatca
ccgacctctctccccagAAGCTCCCGGGAGCTTGTATATCCATTTTCGGATCTGATCAGCACGT
GTTGACAATTAATCATCGGCATAGTATATCGGCATAGTATAATACGACAAGGTGAG
GAACgccaccATGAAAAAGCCTGAACTCACCGCGACGTCTGTCGAGAAGTTTCTGATC
GAAAAGTTCGACAGCGTCTCCGACCTGATGCAGCTCTCGGAGGGCGAAGAATCTCG
TGCTTTCAGCTTCGATGTAGGAGGGCGTGGATATGTCCTGCGGGTAAATAGCTGCGC
CGATGGTTTCTACAAAGATCGTTATGTTTATCGGCACTTTGCATCGGCCGCGCTCCCG
ATTCCGGAAGTGCTTGACATTGGGGAATTCAGCGAGAGCCTGACCTATTGCATCTCC
CGCCGTGCACAGGGTGTCACGTTGCAAGACCTGCCTGAAACCGAACTGCCCGCTGTT
CTGCAGCCGGTCGCGGAGGCCATGGATGCGATCGCTGCGGCCGATCTTAGCCAGAC
GAGCGGGTTCGGCCCATTCGGACCGCAAGGAATCGGTCAATACACTACATGGCGTG
ATTTCATATGCGCGATTGCTGATCCCCATGTGTATCACTGGCAAACTGTGATGGACG
ACACCGTCAGTGCGTCCGTCGCGCAGGCTCTCGATGAGCTGATGCTTTGGGCCGAGG
ACTGCCCCGAAGTCCGGCACCTCGTGCACGCGGATTTCGGCTCCAACAATGTCCTGA
CGGACAATGGCCGCATAACAGCGGTCATTGACTGGAGCGAGGCGATGTTCGGGGAT
TCCCAATACGAGGTCGCCAACATCTTCTTCTGGAGGCCGTGGTTGGCTTGTATGGAG
CAGCAGACGCGCTACTTCGAGCGGAGGCATCCGGAGCTTGCAGGATCGCCGCGGCT
CCGGGCGTATATGCTCCGCATTGGTCTTGACCAACTCTATCAGAGCTTGGTTGACGG
```

```
CAATTTCGATGATGCAGCTTGGGCGCAGGGTCGATGCGACGCAATCGTCCGATCCGG

AGCCGGGACTGTCGGGCGTACACAAATCGCCCGCAGAAGCGCGGCCGTCTGGACCG

ATGGCTGTGTAGAAGTACTCGCCGATAGTGGAAACCGACGCCCCAGCACTCGTCCG

AGGGCAAAGGAATAGAGCGCGGGATCTCATGCTGGAGTTCTTCGCCCACCCCAAC

TTGTTTATTGCAGCTTATAATGGTTACAAATAAAGCAATAGCATCACAAATTTCACA

AATAAAGCATTTTTTTCACTGCATTCTAGTTGTGGTTTGTCCAAACTCATCAATGTAT

CTTATCATGTCTGTAGCtGATgtATAcCTAggATCCGGCCGGccTGCAggTGTCCTCACAG

GAACGAAGTCCCTAAAGAAACAGTGGCAGCCAGGTTTAGCCCCGGAATTGACTGGA

TTCCTTTTTAGGGCCCATTGGTATGGCTTTTTCCCCGTATCCCCCCAGGTGTCTGCAG

GCTCAAAGAGCAGCGAGAAGCGTTCAGAGGAAAGCGATCCCGTGCCACCTTCCCCG

TGCCCGGGCTGTCCCCGCACGCTGCCGGCTCGGGGATGCGGGGGGAGCGCCGGACC

GGAGCGGAGCCCCGGGCGGCTCGCTGCTGCCCCCTAGCGGGGGAGGGACGTAATTA

CATCCCTGGGGCTTTGGGGGGGGCTGTCCCTCTAGAGCGGCCGCCACCGCGGTG

GAGCTCCAGCTTTTGTTCCCTTTAGTGAGGGTTAATTAGATCTTAATACGACTCACTA

TAGGGCGAATTGGGTACCGGGCCCCCCCTCGAGGTCGACGGTATCGATAAGCTTGAT

ATCTATAACAAGAAAATATATATATAATAAGTTATCACGTAAGTAGAACATGAAAT

AACAATATAATTATCGTATGAGTTAAATCTTAAAAGTCACGTAAAAGATAATCATGC

GTCATTTTGACTCACGCGGTCGTTATAGTTCAAAATCAGTGACACTTACCGCATTGA

CAAGCACGCCTCACGGGAGCTCCAAGCGGCGACTGAGATGTCCTAAATGCACAGCG

ACGGATTCGCGCTATTTAGAAAGAGAGCAATATTTCAAGAATGCATGCGTCAATT

TTACGCAGACTATCTTTCTAGGGTTAATCTAGCTGCATCAGGATCATATCGTCGGGT

CTTTTTTCCGGCTCAGTCATCGCCCAAGCTGGCGCTATCTGGGCATCGGGGAGGAAG

AAGCCCGTGCCTTTTCCCGCGAGGTTGAAGCGGCATGGAAAGAGTTTGCCGAGGAT

GACTGCTGCTGCATTGACGTTGAGCGAAAACGCACGTTTACCATGATGATTCGGGAA

GGTGTGGCCATGCACGCCTTTAACGGTGAACTGTTCGTTCAGGCCACCTGGGATACC

AGTTCGTCGCGGCTTTTCCGGACACAGTTCCGGATGGTCAGCCCGAAGCGCATCAGC

AACCCGAACAATACCGGCGACAGCCGGAACTGCCGTGCCGGTGTGCAGATTAATGA

CAGCGGTGCGGCGCTGGGATATTACGTCAGCGAGGACGGGTATCCTGGCTGGATGC

CGCAGAAATGGACATGGATACCCCGTGAGTTACCCGGCGGGCGCGCTTGGCGTAAT

CATGGTCATAGCTGTTTCCTGTGTGAAATTGTTATCCGCTCACAATTCCACACAACAT

ACGAGCCGGAAGCATAAAGTGTAAAGCCTGGGGTGCCTAATGAGTGAGCTAACTCA

CATTAATTGCGTTGCGCTCACTGCCCGCTTTCCAGTCGGGAAACCTGTCGTGCCAGC

TGCATTAATGAATCGGCCAACGCGCGGGGAGAGGCGGTTTGCGTATTGGGCGCTCTT

CCGCTTCCTCGCTCACTGACTCGCTGCGCTCGGTCGTTCGGCTGCGGCGAGCGGTAT

CAGCTCACTCAAAGGCGGTAATACGGTTATCCACAGAATCAGGGGATAACGCAGGA

AAGAACATGTGAGCAAAAGGCCAGCAAAAGGCCAGGAACCGTAAAAAGGCCGCGT

TGCTGGCGTTTTTCCATAGGCTCCGCCCCCCTGACGAGCATCACAAAAATCGACGCT

CAAGTCAGAGGTGGCGAAACCCGACAGGACTATAAAGATACCAGGCGTTTCCCCCT

GGAAGCTCCCTCGTGCGCTCTCCTGTTCCGACCCTGCCGCTTACCGGATACCTGTCC

GCCTTTCTCCCTTCGGGAAGCGTGGCGCTTTCTCATAGCTCACGCTGTAGGTATCTCA

GTTCGGTGTAGGTCGTTCGCTCCAAGCTGGGCTGTGTGCACGAACCCCCCGTTCAGC
```

-continued

```
CCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGGTAG
CTCTTGATCCGGCAAACAAACCACCGCTGGTAGCGGTGGTTTTTTTGTTTGCAAGCA
GCAGATTACGCGCAGAAAAAAGGATCTCAAGAAGATCCTTTGATCTTTTCTACGGG
GTCTGACGCTCAGTGGAACGAAAACTCACGTTAAGGGATTTTGGTCATGAGATTATC
AAAAAGGATCTTCACCTAGATCCTTTTAAATTAAAAATGAAGTTTTAAATCAATCTA
AAGTATATATGAGTAAACTTGGTCTGACAGTTACCAATGCTTAATCAGTGAGGCACC
TATCTCAGCGATCTGTCTATTTCGTTCATCCATAGTTGCCTGACTCCCCGTCGTGTAG
ATAACTACGATACGGGAGGGCTTACCATCTGGCCCCAGTGCTGCAATGATACCGCG
AGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTT
GCCGGGAAGCTAGAGTAAGTAGTTCGCCAGTTAATAGTTTGCGCAACGTTGTTGCCA
TTGCTACAGGCATCGTGGTGTCACGCTCGTCGTTTGGTATGGCTTCATTCAGCTCCGG
TTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATG
GTTATGGCAGCACTGCATAATTCTCTTACTGTCATGCCATCCGTAAGATGCTTTTCTG
TGACTGGTGAGTACTCAACCAAGTCATTCTGAGAATAGTGTATGCGGCGACCGAGTT
GCTCTTGCCCGGCGTCAATACGGGATAATACCGCGCCACATAGCAGAACTTTAAAA
GTGCTCATCATTGGAAAACGTTCTTCGGGGCGAAAACTCTCAAGGATCTTACCGCTG
TTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAG
GGAATAAGGGCGACACGGAAATGTTGAATACTCAT
```

The sequence of the PB-iCap8split-ITRGFP-hygro-2 vector is provided below:

PB-iCap8split-ITRGFP-hygro-2 (17,119 bp)

(SEQ ID NO: 31)

```
ACTCTTCCTTTTTCAATATTATTGAAGCATTTATCAGGGTTATTGTCTCATGA
GCGGATACATATTTGAATGTATTTAGAAAAATAAACAAATAGGGGTTCCGCGCACA
TTTCCCCGAAAAGTGCCACCTAAATTGTAAGCGTTAATATTTTGTTAAAATTCGCGTT
AAATTTTTGTTAAATCAGCTCATTTTTTAACCAATAGGCCGAAATCGGCAAAATCCC
TTATAAATCAAAAGAATAGACCGAGATAGGGTTGAGTGTTGTTCCAGTTTGGAACA
AGAGTCCACTATTAAAGAACGTGGACTCCAACGTCAAAGGGCGAAAAACCGTCTAT
CAGGGCGATGGCCCACTACGTGAACCATCACCCTAATCAAGTTTTTTGGGGTCGAGG
TGCCGTAAAGCACTAAATCGGAACCCTAAAGGGAGCCCCCGATTTAGAGCTTGACG
GGGAAAGCCGGCGAACGTGGCGAGAAAGGAAGGGAAGAAAGCGAAAGGAGCGGG
CGCTAGGGCGCTGGCAAGTGTAGCGGTCACGCTGCGCGTAACCACCACACCCGCCG
CGCTTAATGCGCCGCTACAGGGCGCGTCCCATTCGCCATTCAGGCTGCGCAACTGTT
GGGAAGGGCGATCGGTGCGGGCCTCTTCGCTATTACGCCAGCTGGCGAAAGGGGGA
```

-continued

```
TGTGCTGCAAGGCGATTAAGTTGGGTAACGCCAGGGTTTTCCCAGTCACGACGTTGT

AAAACGACGGCCAGTGAGCGCGCCTCGTTCATTCACGTTTTTGAACCCGTGGAGGAC

GGGCAGACTCGCGGTGCAAATGTGTTTTACAGCGTGATGGAGCAGATGAAGATGCT

CGACACGCTGCAGAACACGCAGCTAGATTAACCCTAGAAAGATAATCATATTGTGA

CGTACGTTAAAGATAATCATGCGTAAAATTGACGCATGTGTTTTATCGGTCTGTATA

TCGAGGTTTATTTATTAATTTGAATAGATATTAAGTTTTATTATATTTACACTTACAT

ACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCAAAGCCCCCAGGGATGTA

ATTACGTCCCTCCCCCGCTAGGGGCAGCAGCGAGCCGCCCGGGGCTCCGCTCCGGT

CCGGCGCTCCCCCCGCATCCCCGAGCCGGCAGCGTGCGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCAGATATACGCGTgacattgattattgactagttattaatagtaatcaattacgggtcatt agttcatagcccatatatggagttccgcgttacataacttacggtaaatggcccgcctggctgaccgcccaacgaccccgcccattgacgt caataatgacgtatgttcccatagtaacgccaatagggactttccattgacgtcaatgggtggagtatttacggtaaactgcccacttggcagt acatcaagtgtatcatatgccaagtacgccccctattgacgtcaatgacggtaaatggcccgcctggcattatgcccagtacatgaccttatg ggactttcctacttggcagtacatctacgtattagtcatcgctattaccatggtgatgcggttttggcagtacatcaatgggcgtggatagcgg tttgactcacggggatttccaagtctccaccccattgacgtcaatgggagtttgttttggaaccaaaatcaacgggactttccaaaatgtcgta acaactccgccccattgacgcaaatgggcggtaggcgtgtacggtgggaggtctatataagcagagctctccctatcagtgatagagatctccc tatcagtgatagagatcgtcgacgagctcgtttagtgaaccgtcagatcgcctggagacgccatccacgctgttttgacctccatagaagaca ccgggaccgatccagcctgaacgcgcaggcgctaagACGGCCGCTGATGGCTATCTGCCTGATTGGCTG GAAGATAACCTGAGTGAGGGCATCCGGGAATGGTGGGCCCTGAAGCctggagccccgaagc ccaaagccaaccagcaaaagcaggacgacggccggggtctggtgcttcctggctacaagtacctcggacccttcaacggactcgacaag ggggagcccgtcaacgcggcggacgcagcggccctcgagcacgacaaggcctacgaccagcagctgcaggcgggtgacaatccgta cctgcggtataaccacgccgacgccgagtttcaggagcgtctgcaagaagatacgtcttttgggggcaacctcgggcgagcagtcttccag gccaagaagcgggttctcgaacctctcggtctggttgaggaaggcgctaagacggctcctggaaagaagaggccggtagAACCTA

GCCCCCAGCGATCTCCAGATTCTTCTACCGGCATCGGCAAAAAGGGCCAACAGCCT

GCGAGAAAGCGGCTGAACTTCGGCCAGACCGGAGACAGCGAGAGCGTGCCCGACC

CTCAGCCTCTGGGCGAGCCCCCTGCCGCCCCTTCTGGCGTGGGCCCCAACACCATGG

CCGCCGGCGGCGGAGCCCCTATGGCCGACAACAACGAGGGCGCCGACGGCGTGGG

AAGCAGCAGCGGCAATTGGCACTGCGACTCCACCTGGCTGGGCGACAGAGTGATCA

CCACATCTACAAGAACCTGGGCCCTGCCCACCTACAACAATCACCTGTACAAGCAG

ATCAGCAATGGAACCTCTGGAGGCGCCACCAACGATAACACCTACTTTGGCTACAG

CACCCCTTGGGGATATTTCGACTTCAACCGGTTCCACTGTCACTTCAGCCCTCGGGA

CTGGCAGCGTCTCATTAACAATAACTGGGGCTTCAGACCAAAGAGACTGAGCTTCA

AGCTGTTCAACATCCAGGTGAAGGAAGTGACCCAAAACGAGGGCACCAAGACCATC

GCCAATAACCTCACCTCCACAATCCAAGTGTTCACCGATTCCGAGTACCAGCTGCCT
```

-continued

```
TACGTGCTGGGCTCCGCCCACCAGGGCTGCCTGCCACCATTCCCCGCCGACGTGTTC
ATGATCCCTCAGTACGGCTACCTGACACTGAACAACGGATCTCAAGCAGTGGGCAG
AAGCTCCTTCTACTGTCTGGAGTACTTCCCTAGCCAGATGCTGAGGACAGGCAACAA
TTTCCAGTTCACCTACACATTCGAGGACGTCCCTTTTCACAGCTCTTATGCCCATAGC
CAGAGCCTGGATAGACTGATGAACCCTCTGATCGACCAGTATCTGTATTACCTGAGC
AGAACGCAAACAACAGGCGGCACCGCTAATACCCAGACCCTGGGTTTCAGCCAAGG
CGGCCCTAACACAATGGCCAATCAGGCCAAAAACTGGCTTCCTGGCCCCTGCTACA
GACAGCAAAGAGTGAGCACAACCACCGGCCAGAACAACAACTCTAACTTCGCCTGG
ACAGCCGGCACCAAATACCACCTGAACGGCAGAAACAGCCTGGCCAACCCTGGAAT
CGCTATGGCTACACACAAGGACGATGAGGAACGGTTCTTCCCCAGCAACGGCATCC
TGATCTTCGGCAAGCAGAACGCCGCTCGCGACAACGCCGACTACAGCGACGTGATG
CTGACCAGCGAGGAAGAAATCAAGACAACAAACCCGGTCGCCACCGAGGAATACG
GCATTGTGGCCGATAACCTGCAGCAGCAGAATACCGCCCCTCAGATCGGCACCGTG
AACTCCCAGGGAGCCCTGCCTGGCATGGTGTGGCAGAACAGAGATGTGTACCTGCA
GGGCCCTATCTGGGCCAAGATCCCCCACACCGACGGAAATTTCCATCCAAGCCCTCT
GATGGGCGGATTTGGCCTGAAGCACCCCCCTCCACAGATTCTCATCAAAAACACACC
TGTGCCAGCCGACCCTCCCACAACATTTAATCAGTCTAAGCTGAATAGCTTCATCAC
CCAGTACAGCACCGGCCAGGTGTCCGTGGAAATCGAGTGGGAGCTGCAGAAAGAGA
ACAGCAAGAGATGGAACCCTGAGATCCAGTACACCAGCAACTACTACAAAAGCACA
AGCGTGGACTTCGCCGTTAATACTGAGGGCGTCTACTCAGAGCCTCGGCCCATCGGC
ACTCGGTACCTGACCAGAAACCTGaatggctaggatccggccggcctgcaggtgtcctcacaggaacgaagtccct
aaagaaacagtggcagccaggtttagcccccgaaaacttgtttattgcagcttataatggttacaaataaagcaatagcatcacaaatttcaca
aataaagcatttttttcactgcattctagttgtggtttgtccaaactcatcaatgtatcttattgactggattgagggacagcccccccccaaag
cccccagggatgtaattacgtccctcccccgctaggggggcagcagcgagccgcccggggctccgctccggtccggcgctcccccgcatc
cccgagccggcagcgtgcggggacagcccgggcacggggaaggtggcacgggatcgctttcctctgaacgcttctcgctgctctttgag
cctgcagacacctggggggatacggggaaaaggcctccaaggccagcttcccacaataagttgggtgaattttggctcattcctcctttctat
aggattgaggtcagagcGACATTGATTATTGACTAGTTATTAATAGTAATCAATTACGGGGTC
ATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTCC
CATAGTAACGCCAATAGGGACTTTCCATTGACGTCAATGGGTGGAGTATTTACGGTA
AACTGCCCACTTGGCAGTACATCAAGTGTATCATATGCCAAGTACGCCCCCTATTGA
CGTCAATGACGGTAAATGGCCCGCCTGGCATTATGCCCAGTACATGACCTTATGGGA
CTTTCCTACTTGGCAGTACATCTACGTATTAGTCATCGCTATTACCATGGTGATGCGG
TTTTGGCAGTACATCAATGGGCGTGGATAGCGGTTTGACTCACGGGGATTTCCAAGT
CTCCACCCCATTGACGTCAATGGGAGTTTGTTTTGGAACCAAAATCAACGGGACTTT
CCAAAATGTCGTAACAACTCCGCCCCATTGACGCAAATGGGCGGTAGGCGTGTACG
GTGGGAGGTCTATATAAGCAGAGCTCTCCCTATCAGTGATAGAGATCTCCCTATCAG
TGATAGAGATCGTCGACGAGCTCGTTTAGTGAACCGTCAGATCGCCTGGAGACGCC
ATCCACGCTGTTTTGACCTCCATAGAAGACACCGGGACCGATCCAGCCTatcccaattctgat
gcgccggtgatcagatcaaaaacttcagccaggtacggcgctaagacggctcctggaaagaagaggccggtagagccatcaccccagc
```

-continued

```
gttctccagactcctctacgggcatcggcaagaaaggccaacagcccgccagaaaaagactcaattttggtcagactggcgactcagagtc agttccagaccctcaacctctcggagaacctccagcagcgccctctggtgtgggacctaatacaatggctgcaggcggtggcgcaccaat ggcagacaataacgaaggcgccgacggagtgggtagttcctcgggaaattggcattgcgattccacatggctgggcgacagagtcatcac caccagcacccgaacctgggccctgcccacctacaacaaccacctctacaagcaaatctccaacgggacatcggaggagccaccaac gacaacacctacttcggctacagcaccccctgggggtattttgactttaacagattccactgccacttttcaccacgtgactggcagcgactca tcaacaacaactggggattccggcccaagagactcagcttcaagctcttcaacatccaggtcaaggaggtcacgcagaatgaaggcacca agaccatcgccaataacctcaccagcaccatccaggtgtttacggactcggagtaccagctgccgtacgttctcggctctgcccaccaggg ctgcctgcctccgttcccggcggacgtgttcatgattccccagtacggctacctaacactcaacaacggtagtcaggccgtgggacgctcct ccttctactgcctggaatactttccttcgcagatgctgagaaccggcaacaacttccagtttacttacaccttcgaggacgtgcctttccacagc agctacgcccacagccagagcttggaccggctgatgaatcctctgattgaccagtacctgtactacttgtctcggactcaaacaacaggagg cacggcaaatacgcagactctgggcttcagccaaggtgggcctaatacaatggccaatcaggcaaagaactggctgccaggaccctgtta ccgccaacaacgcgtctcaacgacaacccgggcaaaacaacaatagcaactttgcctggactgctgggaccaaataccatctgaatggaag aaattcattggctaatcctggcatcgctatggcaacacacaaagacgacgaggagcgttttttttcccagtaacgggatcctgattttttggcaaa caaaatgctgccagagacaatgcggattacagcgatgtcatgctcaccagcgaggaagaaatcaaaaccactaaccctgtggctacagag gaatacggtatcgtggcagataacttgcagcagcaaaacacggctcctcaaattggaactgtcaacagccaggggggccttacccggtatgg tctggcagaaccgggacgtgtacctgcagggtcccatctgggccaagattcctcacacggacggcaacttccacccgtctccgctgatgg gcggctttggcctgaaacatcctccgcctcagatcctgatcaagaacacgcctgtacctgcggatcctccgaccaccttcaaccagtcaaag ctgaactcttccatcacgcaatacagcaccggacaggtcagcgtggaaattgaatgggagctgcagaaggaaaacagcaagcgctggaa ccccgagatccagtacacctccaactactacaaatctacaagtgtggactttgctgttaatacagaaggcgtgtactctgaacccgccccatt ggcacccgttacctcacccgtaatctgtaaactagtttgcttgttaatcaataaaccgtttaattcgtttcagttgaGCGGCCGTCGAG

TCTAGAGGGCCCGTTTAAACCCGCTGATCAGCCTCGACTGTGCCTTCTAGTTGCCAG

CCATCTGTTGTTTGCCCCTCCCCCGTGCCTTCCTTGACCCTGGAAGGTGCCACTCCCA

CTGTCCTTTCCTAATAAAATGAGGAAATTGCATCGCATTGTCTGAGTAGGTGTCATT

CTATTCTGGGGGGTGGGGTGGGGCAGGACAGCAAGGGGGAGGATTGGGAAGACAA

TAGCAGGCATGCTGGGGATGCGGTGGGCTCTATGGCTTCTGAGGCGGAAAGAACCA

GCTGGGGCTCTAGGGGGTATCCCCGGCGCGCCGAATTCGTTAACAAGCTtTAATTAaC

GCgtATAcCTAggATCCGGCCGGccTGCAggTGTCCTCACAGGAACGAAGTCCCTAAAG

AAACAGTGGCAGCCAGGTTTAGCCCCGGAATTGACTGGATTCCTTTTTTAGGGCCCA

TTGGTATGGCTTTTTCCCCGTATCCCCCCAGGTGTCTGCAGGCTCAAAGAGCAGCGA

GAAGCGTTCAGAGGAAAGCGATCCCGTGCCACCTTCCCCGTGCCCGGCTGTCCCCG

CACGCTGCCGGCTCGGGGATGCGGGGGAGCGCCGGACCGGAGCGGAGCCCCGGG

CGGCTCGCTGCTGCCCCCTAGCGGGGGAGGGACGTAATTACATCCCTGGGGGCTTTG

GGGGGGGGCTGTCCCTGGCCTCCAAGGCCAGCTTCCCACAATAAGTTGGGTGAATTT

TGGCTCATTCCTCCTTTCTATAGGATTGAGGTCAGAGCTTTGTGATGGGAATTCTGTG

GAATGTGTGTCAGTTAGGGTGTGGAAAGTCCCgcGATCgcTAGcAAACGCCAGCAACG

CGGCCTTTTTACGGTTCCTGGCCTTTTGCTGGCCTTTTGCTCACATGTCCTGCAGGCA

GCTGCGCGCTCGCTCGCTCACTGAGGCCGCCCGGGCAAAGCCCGGGCGTCGGGCGA

CCTTTGGTCGCCCGGCCTCAGTGAGCGAGCGAGCGCGCAGAGAGGGAGTGGCCAAC

TCCATCACTAGGGGTTCCTGCGGCCGCACGCGTGGAGCTAGTTATTAATAGTAATCA

ATTACGGGGTCATTAGTTCATAGCCCATATATGGAGTTCCGCGTTACATAACTTACG

GTAAATGGCCCGCCTGGCTGACCGCCCAACGACCCCCGCCCATTGACGTCAATAATG
```

-continued

```
ACGTATGTTCCCATAGTAACGTCAATAGGGACTTTCCATTGACGTCAATGGGTGGAG
TATTTACGGTAAACTGCCCACTTGGCAGTACATCAAGTGTATCATATGCCAAGTACG
CCCCCTATTGACGTCAATGACGGTAAATGGCCCGCCTGGCATTATGCCCAGTACATG
ACCTTATGGGACTTTCCTACTTGGCAGTACATCTACGTATTAGTCATCGCTATTACCA
TGGTGATGCGGTTTTGGCAGTACATCAATGGGCGTGGATAGCGGTTTGACTCACGGG
GATTTCCAAGTCTCCACCCCATTGACGTCAATGGGAGTTTGTTTTGCACCAAAATCA
ACGGGACTTTCCAAAATGTCGTAACAACTCCGCCCCATTGACGCAAATGGGCGGTA
GGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCC
AGCCTCCGCGGATTCGAATCCCGGCCGGGAACGGTGCATTGGAACGCGGATTCCCC
GTGCCAAGAGTGACGTAAGTACCGCCTATAGAGTCTATAGGCCCACAAAAAATGCT
TTCTTCTTTTAATATACTTTTTTGTTTATCTTATTTCTAATACTTTCCCTAATCTCTTTC
TTTCAGGGCAATAATGATACAATGTATCATGCCTCTTTGCACCATTCTAAAGAATAA
CAGTGATAATTTCTGGGTTAAGGCAATAGCAATATTTCTGCATATAAATATTTCTGC
ATATAAATTGTAACTGATGTAAGAGGTTTCATATTGCTAATAGCAGCTACAATCCAG
CTACCATTCTGCTTTTATTTTATGGTTGGGATAAGGCTGGATTATTCTGAGTCCAAGC
TAGGCCCTTTTGCTAATCATGTTCATACCTCTTATCTTCCTCCCACAGCTCCTGGGCA
ACGTGCTGGTCTGTGTGCTGGCCCATCACTTTGGCAAAGAATTGGGATTCGAACATC
GATTGAATTCTGAATGGTGAGCAAGGGCGAGGAGCTGTTCACCGGGGTGGTGCCCA
TCCTGGTCGAGCTGGACGGCGACGTAAACGGCCACAAGTTCAGCGTGTCCGGCGAG
GGCGAGGGCGATGCCACCTACGGCAAGCTGACCCTGAAGTTCATCTGCACCACCGG
CAAGCTGCCCGTGCCCTGGCCCACCCTCGTGACCACCCTGACCTACGGCGTGCAGTG
CTTCAGCCGCTACCCCGACCACATGAAGCAGCACGACTTCTTCAAGTCCGCCATGCC
CGAAGGCTACGTCCAGGAGCGCACCATCTTCTTCAAGGACGACGGCAACTACAAGA
CCCGCGCCGAGGTGAAGTTCGAGGGCGACACCCTGGTGAACCGCATCGAGCTGAAG
GGCATCGACTTCAAGGAGGACGGCAACATCCTGGGGCACAAGCTGGAGTACAACTA
CAACAGCCACAACGTCTATATCATGGCCGACAAGCAGAAGAACGGCATCAAGGTGA
ACTTCAAGATCCGCCACAACATCGAGGACGGCAGCGTGCAGCTCGCCGACCACTAC
CAGCAGAACACCCCCATCGGCGACGGCCCCGTGCTGCTGCCCGACAACCACTACCT
GAGCACCCAGTCCGCCCTGAGCAAAGACCCCAACGAGAAGCGCGATCACATGGTCC
TGCTGGAGTTCGTGACCGCCGCCGGGATCACTCTCGGCATGGACGAGCTGTACAAGT
ACTCAGATCTCGAGCTCAAGTAGGGATCCTCTAGAGTCGACCTGCAGAAGCTTGCCT
CGAGCAGCGCTGCTCGAGAGATCTACGGGTGGCATCCCTGTGACCCCTCCCCAGTGC
CTCTCCTGGCCCTGGAAGTTGCCACTCCAGTGCCCACCAGCCTTGTCCTAATAAAAT
TAAGTTGCATCATTTTGTCTGACTAGGTGTCCTTCTATAATATTATGGGGGAGGG
GGGTGGTATGGAGCAAGGGGCAAGTTGGGAAGACAACCTGTAGGGCCTGCGGGGTC
TATTGGGAACCAAGCTGGAGTGCAGTGGCACAATCTTGGCTCACTGCAATCTCCGCC
TCCTGGGTTCAAGCGATTCTCCTGCCTCAGCCTCCCGAGTTGTTGGGATTCCAGGCAT
GCATGACCAGGCTCAGCTAATTTTTGTTTTTTTGGTAGAGACGGGGTTTCACCATATT
GGCCAGGCTGGTCTCCAACTCCTAATCTCAGGTGATCTACCCACCTTGGCCTCCCAA
```

-continued

ATTGCTGGGATTACAGGCGTGAACCACTGCTCCCTTCCCTGTCCTTCTGATTTTGTAG

GTAACCACGTGCGGACCGAGCGGCCGCAGGAACCCCTAGTGATGGAGTTGGCCACT

CCCTCTCTGCGCGCTCGCTCGCTCACTGAGGCCGGGCGACCAAAGGTCGCCCGACGC

CCGGGCTTTGCCCGGGCGGCCTCAGTGAGCGAGCGAGCGCGCAGCTGCCTGCAGGG

GCGCCTGATGCGGTATTTTCTCCTTACGCATCTGTGCGGTATTTCACACCGCATACGT

CgtaGCtGATcaATTgGCGCGCCGAATTCGTTAACAAGCTtTAATTAaCGCgtATAcCTAgg

ATCCGGCCGGccTGCAggTGTCCTCACAGGAACGAAGTCCCTAAAGAAACAGTGGCA

GCCAGGTTTAGCCCCGGAATTGACTGGATTCCTTTTTTAGGGCCCATTGGTATGGCTT

TTTCCCCGTATCCCCCCAGGTGTCTGCAGGCTCAAAGAGCAGCGAGAAGCGTTCAGA

GGAAAGCGATCCCGTGCCACCTTCCCCGTGCCCGGGCTGTCCCCGCACGCTGCCGGC

TCGGGATGCGGGGGGAGCGCCGGACCGGAGCGGAGCCCCGGGCGGCTCGCTGCTG

CCCCCTAGCGGGGGAGGGACGTAATTACATCCCTGGGGGCTTTGGGGGGGGCTGT

CCCTGGCCTCCAAGGCCAGCTTCCCACAATAAGTTGGGTGAATTTTGGCTCATTCCT

CCTTTCTATAGGATTGAGGTCAGAGCgggggttgggggttgcgccttttccaaggcagccctgggtttgcgcagggac gcggctgctctgggcgtggttccgggaaacgcagcggcgccgaccctgggtctcgcacattcttcacgtccgttcgcagcgtcacccgga tcttcgccgctaccccttgtgggcccccggcgacgcttcctgctccgcccctaagtcgggaaggttccttgcggttcgcggcgtgccggac gtgacaaacggaagccgcacgtctcactagtaccctcgcagacggacagcgccagggagcaatggcagcgcgccgaccgcgatgggc tgtggccaatagcggctgctcagcagggcgcgccgagagcagcggccgggaaggggcggtgcgggaggcggggtgtggggcggta gtgtgggccctgttcctgcccgcgcggtgttccgcattctgcaagcctccggagcgcacgtcggcagtcggctccctcgttgaccgaatca ccgacctctctccccagAAGCTCCCGGGAGCTTGTATATCCATTTTCGGATCTGATCAGCACGT

GTTGACAATTAATCATCGGCATAGTATATCGGCATAGTATAATACGACAAGGTGAG

GAACgccaccATGAAAAAGCCTGAACTCACCGCGACGTCTGTCGAGAAGTTTCTGATC

GAAAAGTTCGACAGCGTCTCCGACCTGATGCAGCTCTCGGAGGGCGAAGAATCTCG

TGCTTTCAGCTTCGATGTAGGAGGGCGTGGATATGTCCTGCGGGTAAATAGCTGCGC

CGATGGTTTCTACAAAGATCGTTATGTTTATCGGCACTTTGCATCGGCCGCGCTCCCG

ATTCCGGAAGTGCTTGACATTGGGGAATTCAGCGAGAGCCTGACCTATTGCATCTCC

CGCCGTGCACAGGGTGTCACGTTGCAAGACCTGCCTGAAACCGAACTGCCCGCTGTT

CTGCAGCCGGTCGCGGAGGCCATGGATGCGATCGCTGCGGCCGATCTTAGCCAGAC

GAGCGGGTTCGGCCCATTCGGACCGCAAGGAATCGGTCAATACACTACATGGCGTG

ATTTCATATGCGCGATTGCTGATCCCCATGTGTATCACTGGCAAACTGTGATGGACG

ACACCGTCAGTGCGTCCGTCGCGCAGGCTCTCGATGAGCTGATGCTTTGGGCCGAGG

ACTGCCCCGAAGTCCGGCACCTCGTGCACGCGGATTTCGGCTCCAACAATGTCCTGA

CGGACAATGGCCGCATAACAGCGGTCATTGACTGGAGCGAGGCGATGTTCGGGGAT

TCCCAATACGAGGTCGCCAACATCTTCTTCTGGAGGCCGTGGTTGGCTTGTATGGAG

CAGCAGACGCGCTACTTCGAGCGGAGGCATCCGGAGCTTGCAGGATCGCCGCGGCT

CCGGGCGTATATGCTCCGCATTGGTCTTGACCAACTCTATCAGAGCTTGGTTGACGG

CAATTTCGATGATGCAGCTTGGGCGCAGGGTCGATGCGACGCAATCGTCCGATCCGG

AGCCGGGACTGTCGGGCGTACACAAATCGCCCGCAGAAGCGCGGCCGTCTGGACCG

ATGGCTGTGTAGAAGTACTCGCCGATAGTGGAAACCGACGCCCCAGCACTCGTCCG

AGGGCAAAGGAATAGAGCGCGGGGATCTCATGCTGGAGTTCTTCGCCCACCCCAAC

TTGTTTATTGCAGCTTATAATGGTTACAAATAAAGCAATAGCATCACAAATTTCACA

```
AATAAAGCATTTTTTTCACTGCATTCTAGTTGTGGTTTGTCCAAACTCATCAATGTAT
CTTATCATGTCTGTAGCtGATgtATAcCTAggATCCGGCCGGccTGCAggTGTCCTCACAG
GAACGAAGTCCCTAAAGAAACAGTGGCAGCCAGGTTTAGCCCCGGAATTGACTGGA
TTCCTTTTTAGGGCCCATTGGTATGGCTTTTTCCCCGTATCCCCCCAGGTGTCTGCAG
GCTCAAAGAGCAGCGAGAAGCGTTCAGAGGAAAGCGATCCCGTGCCACCTTCCCCG
TGCCCGGGCTGTCCCCGCACGCTGCCGGCTCGGGGATGCGGGGGGAGCGCCGGACC
GGAGCGGAGCCCCGGGCGGCTCGCTGCTGCCCCCTAGCGGGGGAGGGACGTAATTA
CATCCCTGGGGCTTTGGGGGGGGCTGTCCCTCTAGAGCGGCCGCCACCGCGGTG
GAGCTCCAGCTTTTGTTCCCTTTAGTGAGGGTTAATTAGATCTTAATACGACTCACTA
TAGGGCGAATTGGGTACCGGGCCCCCCCTCGAGGTCGACGGTATCGATAAGCTTGAT
ATCTATAACAAGAAAATATATATATAATAAGTTATCACGTAAGTAGAACATGAAAT
AACAATATAATTATCGTATGAGTTAAATCTTAAAAGTCACGTAAAAGATAATCATGC
GTCATTTTGACTCACGCGGTCGTTATAGTTCAAAATCAGTGACACTTACCGCATTGA
CAAGCACGCCTCACGGGAGCTCCAAGCGGCGACTGAGATGTCCTAAATGCACAGCG
ACGGATTCGCGCTATTTAGAAAGAGAGCAATATTTCAAGAATGCATGCGTCAATT
TTACGCAGACTATCTTTCTAGGGTTAATCTAGCTGCATCAGGATCATATCGTCGGGT
CTTTTTTCCGGCTCAGTCATCGCCCAAGCTGGCGCTATCTGGGCATCGGGGAGGAAG
AAGCCCGTGCCTTTTCCCGCGAGGTTGAAGCGGCATGGAAAGAGTTTGCCGAGGAT
GACTGCTGCTGCATTGACGTTGAGCGAAAACGCACGTTTACCATGATGATTCGGGAA
GGTGTGGCCATGCACGCCTTTAACGGTGAACTGTTCGTTCAGGCCACCTGGGATACC
AGTTCGTCGCGGCTTTTCCGGACACAGTTCCGGATGGTCAGCCCGAAGCGCATCAGC
AACCCGAACAATACCGGCGACAGCCGGAACTGCCGTGCCGGTGTGCAGATTAATGA
CAGCGGTGCGGCGCTGGGATATTACGTCAGCGAGGACGGGTATCCTGGCTGGATGC
CGCAGAAATGGACATGGATACCCCGTGAGTTACCGGCGGGCGCGCTTGGCGTAAT
CATGGTCATAGCTGTTTCCTGTGTGAAATTGTTATCCGCTCACAATTCCACACAACAT
ACGAGCCGGAAGCATAAAGTGTAAAGCCTGGGGTGCCTAATGAGTGAGCTAACTCA
CATTAATTGCGTTGCGCTCACTGCCCGCTTTCCAGTCGGGAAACCTGTCGTGCCAGC
TGCATTAATGAATCGGCCAACGCGCGGGGAGAGGCGGTTTGCGTATTGGGCGCTCTT
CCGCTTCCTCGCTCACTGACTCGCTGCGCTCGGTCGTTCGGCTGCGGCGAGCGGTAT
CAGCTCACTCAAAGGCGGTAATACGGTTATCCACAGAATCAGGGGATAACGCAGGA
AAGAACATGTGAGCAAAAGGCCAGCAAAAGGCCAGGAACCGTAAAAAGGCCGCGT
TGCTGGCGTTTTTCCATAGGCTCCGCCCCCCTGACGAGCATCACAAAAATCGACGCT
CAAGTCAGAGGTGGCGAAACCCGACAGGACTATAAAGATACCAGGCGTTTCCCCCT
GGAAGCTCCCTCGTGCGCTCTCCTGTTCCGACCCTGCCGCTTACCGGATACCTGTCC
GCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGGTAG
```

-continued

```
CTCTTGATCCGGCAAACAAACCACCGCTGGTAGCGGTGGTTTTTTTGTTTGCAAGCA

GCAGATTACGCGCAGAAAAAAGGATCTCAAGAAGATCCTTTGATCTTTTCTACGGG

GTCTGACGCTCAGTGGAACGAAAACTCACGTTAAGGGATTTTGGTCATGAGATTATC

AAAAAGGATCTTCACCTAGATCCTTTTAAATTAAAAATGAAGTTTTAAATCAATCTA

AAGTATATATGAGTAAACTTGGTCTGACAGTTACCAATGCTTAATCAGTGAGGCACC

TATCTCAGCGATCTGTCTATTTCGTTCATCCATAGTTGCCTGACTCCCCGTCGTGTAG

ATAACTACGATACGGGAGGGCTTACCATCTGGCCCCAGTGCTGCAATGATACCGCG

AGACCCACGCTCACCGGCTCCAGATTTATCAGCAATAAACCAGCCAGCCGGAAGGG

CCGAGCGCAGAAGTGGTCCTGCAACTTTATCCGCCTCCATCCAGTCTATTAATTGTT

GCCGGGAAGCTAGAGTAAGTAGTTCGCCAGTTAATAGTTTGCGCAACGTTGTTGCCA

TTGCTACAGGCATCGTGGTGTCACGCTCGTCGTTTGGTATGGCTTCATTCAGCTCCGG

TTCCCAACGATCAAGGCGAGTTACATGATCCCCCATGTTGTGCAAAAAAGCGGTTAG

CTCCTTCGGTCCTCCGATCGTTGTCAGAAGTAAGTTGGCCGCAGTGTTATCACTCATG

GTTATGGCAGCACTGCATAATTCTCTTACTGTCATGCCATCCGTAAGATGCTTTTCTG

TGACTGGTGAGTACTCAACCAAGTCATTCTGAGAATAGTGTATGCGGCGACCGAGTT

GCTCTTGCCCGGCGTCAATACGGGATAATACCGCGCCACATAGCAGAACTTTAAAA

GTGCTCATCATTGGAAAACGTTCTTCGGGGCGAAAACTCTCAAGGATCTTACCGCTG

TTGAGATCCAGTTCGATGTAACCCACTCGTGCACCCAACTGATCTTCAGCATCTTTTA

CTTTCACCAGCGTTTCTGGGTGAGCAAAAACAGGAAGGCAAAATGCCGCAAAAAAG

GGAATAAGGGCGACACGGAAATGTTGAATACTCAT
```

The sequence of the PB-iCap8split-ITRGFP-hygro-3 vector is provided below:

```
PB-iCap8split-ITRGFP-hygro-3 (16,835 bp)                                    (SEQ ID NO: 32)

ACTCTTCCTTTTTCAATATTATTGAAGCATTTATCAGGGTTATTGTCTCATGA

GCGGATACATATTTGAATGTATTTAGAAAAATAAACAAATAGGGGTTCCGCGCACA

TTTCCCCGAAAAGTGCCACCTAAATTGTAAGCGTTAATATTTTGTTAAAATTCGCGTT

AAATTTTGTTAAATCAGCTCATTTTTTAACCAATAGGCCGAAATCGGCAAAATCCC

TTATAAATCAAAAGAATAGACCGAGATAGGGTTGAGTGTTGTTCCAGTTTGGAACA

AGAGTCCACTATTAAAGAACGTGGACTCCAACGTCAAAGGGCGAAAAACCGTCTAT

CAGGGCGATGGCCCACTACGTGAACCATCACCCTAATCAAGTTTTTTGGGGTCGAGG

TGCCGTAAAGCACTAAATCGGAACCCTAAAGGGAGCCCCCGATTTAGAGCTTGACG

GGGAAAGCCGGCGAACGTGGCGAGAAAGGAAGGGAAGAAAGCGAAAGGAGCGGG

CGCTAGGGCGCTGGCAAGTGTAGCGGTCACGCTGCGCGTAACCACCACACCCGCCG

CGCTTAATGCGCCGCTACAGGGCGCGTCCCATTCGCCATTCAGGCTGCGCAACTGTT

GGGAAGGGCGATCGGTGCGGGCCTCTTCGCTATTACGCCAGCTGGCGAAAGGGGGA

TGTGCTGCAAGGCGATTAAGTTGGGTAACGCCAGGGTTTTCCCAGTCACGACGTTGT

AAAACGACGGCCAGTGAGCGCGCCTCGTTCATTCACGTTTTTGAACCCGTGGAGGAC

GGGCAGACTCGCGGTGCAAATGTGTTTTACAGCGTGATGGAGCAGATGAAGATGCT

CGACACGCTGCAGAACACGCAGCTAGATTAACCCTAGAAAGATAATCATATTGTGA

CGTACGTTAAAGATAATCATGCGTAAAATTGACGCATGTGTTTTATCGGTCTGTATA
```

-continued

```
TCGAGGTTTATTTATTAATTTGAATAGATATTAAGTTTTATTATATTTACACTTACAT
ACTAATAATAAATTCAACAAACAATTTATTTATGTTTATTTATTTATTAAAAAAAAA
CAAAAACTCAAAATTTCTTCTATAAAGTAACAAAACTTTTATCGAATTCCTGCAGCC
CGGGGGATCCACTAGTTCTAGAGGGACAGCCCCCCCCAAAGCCCCCAGGGATGTA
ATTACGTCCCTCCCCCGCTAGGGGGCAGCAGCGAGCCGCCCGGGGCTCCGCTCCGGT
CCGGCGCTCCCCCCGCATCCCCGAGCCGGCAGCGTGCGGGGACAGCCCGGGCACGG
GGAAGGTGGCACGGGATCGCTTTCCTCTGAACGCTTCTCGCTGCTCTTTGAGCCTGC
AGACACCTGGGGGGATACGGGGAAAAGGCCTCCAAGGCCAGCTTCCCACAATAAGT
TGGGTGAATTTTGGCTCATTCCTCCTTTCTATAGGATTGAGGTCAGAGCTTTGTGATG
GGAATTCTGTGGAATGTGTGTCAGTTAGGGTGTGGAAAGTCCCgcGATCgcTAGcGTTT
AAACTTAAGCTTGGTACCGAGCTCGGATCCACTAGTCCAGTGTGGTGGAATTCCTGC
TTCGCGATGTACGGGCCAGATATACGCGTggcctccgcgccgggttttggcgcctcccgcgggcgcccccctc
ctcacggcgagcgctgccacgtcagacgaagggcgcagcgagcgtcctgatccttccgcccggacgctcaggacagcggcccgctgct
cataagactcggccttagaacccccagtatcagcagaaggacattttaggacgggacttgggtgactctagggcactggttttctttccagaga
gcggaacaggcgaggaaaagtagtcccttctcggcgattctgcggagggatctccgtggggcggtgaacgccgatgattatataaggacg
cgccggtccctatcagtgatagagatctccctatcagtgatagagagtgtggcacagctagttccgtcgcagccgggatttgggtcgcggtt
cttgtttgtggatcgctgtgatcgtcacttgacgaacgcgcagccgccATGGCCGCTGATGGCTATCTGCCTGATT
GGCTGGAAGATAACCTGAGTGAGGGCATCCGGGAATGGTGGGCCCTGAAGCctggagcc
ccgaagcccaaagccaaccagcaaaagcaggacgacggccggggtctggtgcttcctggctacaagtacctcggacccttcaacggact
cgacaagggggagcccgtcaacgcggcggacgcagcggccctcgagcacgacaaggcctacgaccagcagctgcaggcgggtgac
aatccgtacctgcggtataaccacgccgacgccgagtttcaggagcgtctgcaagaagatacgtcttttgggggcaacctcgggcgagca
gtcttccaggccaagaagcgggttctcgaacctctcggtctggttgaggaaggcgctaagacggctcctggaaagaagaggccggtagA
ACCTAGCCCCCAGCGATCTCCAGATTCTTCTACCGGCATCGGCAAAAAGGGCCAAC
AGCCTGCGAGAAAGCGGCTGAACTTCGGCCAGACCGGAGACAGCGAGAGCGTGCCC
GACCCTCAGCCTCTGGGCGAGCCCCCTGCCGCCCCTTCTGGCGTGGGCCCCAACACC
ATGGCCGCCGGCGGCGGAGCCCCTATGGCCGACAACAACGAGGGCGCCGACGGCGT
GGGAAGCAGCAGCGGCAATTGGCACTGCGACTCCACCTGGCTGGGCGACAGAGTGA
TCACCACATCTACAAGAACCTGGGCCCTGCCCACCTACAACAATCACCTGTACAAGC
AGATCAGCAATGGAACCTCTGGAGGCGCCACCAACGATAACACCTACTTTGGCTAC
AGCACCCCTTGGGGATATTTCGACTTCAACCGGTTCCACTGTCACTTCAGCCCTCGG
GACTGGCAGCGTCTCATTAACAATAACTGGGGCTTCAGACCAAAGAGACTGAGCTT
CAAGCTGTTCAACATCCAGGTGAAGGAAGTGACCCAAAACGAGGGCACCAAGACCA
TCGCCAATAACCTCACCTCCACAATCCAAGTGTTCACCGATTCCGAGTACCAGCTGC
CTTACGTGCTGGGCTCCGCCCACCAGGGCTGCCTGCCACCATTCCCCGCCGACGTGT
TCATGATCCCTCAGTACGGCTACCTGACACTGAACAACGGATCTCAAGCAGTGGGC
AGAAGCTCCTTCTACTGTCTGGAGTACTTCCCTAGCCAGATGCTGAGGACAGGCAAC
AATTTCCAGTTCACCTACACATTCGAGGACGTCCCTTTTCACAGCTCTTATGCCCATA
GCCAGAGCCTGGATAGACTGATGAACCCTCTGATCGACCAGTATCTGTATTACCTGA
GCAGAACGCAAACAACAGGCGGCACCGCTAATACCCAGACCCTGGGTTTCAGCCAA
GGCGGCCCTAACACAATGGCCAATCAGGCCAAAAACTGGCTTCCTGGCCCCTGCTA
```

```
CAGACAGCAAAGAGTGAGCACAACCACCGGCCAGAACAACAACTCTAACTTCGCCT
GGACAGCCGGCACCAAATACCACCTGAACGGCAGAAACAGCCTGGCCAACCCTGGA
ATCGCTATGGCTACACACAAGGACGATGAGGAACGGTTCTTCCCCAGCAACGGCAT
CCTGATCTTCGGCAAGCAGAACGCCGCTCGCGACAACGCCGACTACAGCGACGTGA
TGCTGACCAGCGAGGAAGAAATCAAGACAACAAACCCGGTCGCCACCGAGGAATA
CGGCATTGTGGCCGATAACCTGCAGCAGCAGAATACCGCCCCTCAGATCGGCACCG
TGAACTCCCAGGGAGCCCTGCCTGGCATGGTGTGGCAGAACAGAGATGTGTACCTG
CAGGGCCCTATCTGGGCCAAGATCCCCCACACCGACGGAAATTTCCATCCAAGCCCT
CTGATGGGCGGATTTGGCCTGAAGCACCCCCCTCCACAGATTCTCATCAAAAACACA
CCTGTGCCAGCCGACCCTCCCACAACATTTAATCAGTCTAAGCTGAATAGCTTCATC
ACCCAGTACAGCACCGGCCAGGTGTCCGTGGAAATCGAGTGGGAGCTGCAGAAAGA
GAACAGCAAGAGATGGAACCCTGAGATCCAGTACACCAGCAACTACTACAAAAGCA
CAAGCGTGGACTTCGCCGTTAATACTGAGGGCGTCTACTCAGAGCCTCGGCCCATCG
GCACTCGGTACCTGACCAGAAACCTGaatggctaggatccggccggcctgcaggtgtcctcacaggaacgaagt
ccctaaagaaacagtggcagccaggtttagccccggaaaacttgtttattgcagcttataatggttacaaataaagcaatagcatcacaaattt
cacaaataaagcattttttcactgcattctagttgtggtttgtccaaactcatcaatgtatcttattgactggattgagggacagcccccccc
caaagccccagggatgtaattacgtccctcccccgctagggggcagcagcgagccgccggggctccgctccggtccggcgctcccccg
catccccgagccggcagcgtgcggggacagcccgggcacggggaaggtggcacgggatcgctttcctctgaacgcttctcgctgctcttt
gagcctgcagacacctgggggatacgggaaaaggcctccaaggccagcttcccacaataagttgggtgaattttggctcattcctcctttt
ctataggattgaggtcagagcGACATTGATTATTGACTAGTTATTAATAGTAATCAATTACGGGG
TCATTAGTTCATAGCCCATATATGGAGTTCCGCGTTACATAACTTACGGTAAATGGC
CCGCCTGGCTGACCGCCCAACGACCCCCGCCCATTGACGTCAATAATGACGTATGTT
CCCATAGTAACGCCAATAGGGACTTTCCATTGACGTCAATGGGTGGAGTATTTACGG
TAAACTGCCCACTTGGCAGTACATCAAGTGTATCATATGCCAAGTACGCCCCCTATT
GACGTCAATGACGGTAAATGGCCCGCCTGGCATTATGCCCAGTACATGACCTTATGG
GACTTTCCTACTTGGCAGTACATCTACGTATTAGTCATCGCTATTACCATGGTGATGC
GGTTTTGGCAGTACATCAATGGGCGTGGATAGCGGTTTGACTCACGGGGATTTCCAA
GTCTCCACCCCATTGACGTCAATGGGAGTTTGTTTTGGAACCAAAATCAACGGGACT
TTCCAAAATGTCGTAACAACTCCGCCCCATTGACGCAAATGGGCGGTAGGCGTGTAC
GGTGGGAGGTCTATATAAGCAGAGCTCTCCCTATCAGTGATAGAGATCTCCCTATCA
GTGATAGAGATCGTCGACGAGCTCGTTTAGTGAACCGTCAGATCGCCTGGAGACGC
CATCCACGCTGTTTTGACCTCCATAGAAGACACCGGGACCGATCCAGCCTatcccaattctg
atgcgccggtgatcagatcaaaaacttcagccaggtacggcgctaagacggctcctggaaagaagaggccggtagagccatcacccccag
cgttctccagactcctctacgggcatcggcaagaaaggccaacagcccgccagaaaaagactcaattttggtcagactggcgactcagagt
cagttccagaccctcaacctctcggagaacctccagcagcgccctctggtgtgggacctaatacaatggctgcaggcggtggcgcaccaa
tggcagacaataacgaaggcgccgacggagtgggtagttcctcgggaaattggcattgcgattccacatggctgggcgacagagtcatca
ccaccagcacccgaacctgggcctgcccacctacaacaaccacctctacaagcaaatctccaacgggacatcggaggagccaccaa
cgacaacacctacttcggctacagcacccctgggggtattttgactttaacagattccactgccacttttcaccacgtgactggcagcgactc
atcaacaacaactggggattccggcccaagagactcagcttcaagctcttcaacatccaggtcaaggaggtcacgcagaatgaaggcacc
aagaccatcgccaataacctcaccagcaccatccaggtgtttacggactcggagtaccagctgccgtacgttctcggctctgcccaccagg
gctgcctgcctccgttcccggcggacgtgttcatgattccccagtacggctacctaacactcaacaacggtagtcaggccgtgggacgctc
```

-continued ctccttctactgcctggaatactttccttcgcagatgctgagaaccggcaacaacttccagtttacttacaccttcgaggacgtgcctttccac agcagctacgcccacagccagagcttggaccggctgatgaatcctctgattgaccagtacctgtactacttgtctcggactcaaacaacagga ggcacggcaaatacgcagactctgggcttcagccaaggtgggcctaatacaatggccaatcaggcaaagaactggctgccaggaccctg ttaccgccaacaacgcgtctcaacgacaaccgggcaaaacaacaatagcaactttgcctggactgctgggaccaaataccatctgaatgga agaaattcattggctaatcctggcatcgctatggcaacacacaaagacgacgaggagcgttttttttcccagtaacgggatcctgattttttggca aacaaaatgctgccagagacaatgcggattacagcgatgtcatgctcaccagcgaggaagaaatcaaaaccactaaccctgtggctacag aggaatacggtatcgtggcagataacttgcagcagcaaaacacggctcctcaaattggaactgtcaacagccagggggccttacccggtat ggtctggcagaaccgggacgtgtacctgcagggtcccatctgggccaagattcctcacacggacggcaacttccacccgtctccgctgat gggcggctttggcctgaaacatcctccgcctcagatcctgatcaagaacacgcctgtacctgcggatcctccgaccaccttcaaccagtcaa agctgaactctttcatcacgcaatacagcaccggacaggtcagcgtggaaattgaatgggagctgcagaaggaaaacagcaagcgctgg aaccccgagatccagtacacctccaactactacaaatctacaagtgtggactttgctgttaatacagaaggcgtgtactctgaaccccgcccc attggcacccgttacctcacccgtaatctgtaaactagtttgcttgttaatcaataaaccgtttaattcgtttcagttgaGCGGCCGTCGA

GTCTAGAGGGCCCGTTTAAACCCGCTGATCAGCCTCGACTGTGCCTTCTAGTTGCCA

GCCATCTGTTGTTTGCCCCTCCCCCGTGCCTTCCTTGACCCTGGAAGGTGCCACTCCC

ACTGTCCTTTCCTAATAAAATGAGGAAATTGCATCGCATTGTCTGAGTAGGTGTCAT

TCTATTCTGGGGGGTGGGGTGGGGCAGGACAGCAAGGGGGAGGATTGGGAAGACA

ATAGCAGGCATGCTGGGGATGCGGTGGGCTCTATGGCTTCTGAGGCGGAAAGAACC

AGCTGGGGCTCTAGGGGGTATCCCCGGCGCGCCGAATTCGTTAACAAGCTtTAATTAa

CGCgtATAcCTAggATCCGGCCGGccTGCAggTGTCCTCACAGGAACGAAGTCCCTAAA

GAAACAGTGGCAGCCAGGTTTAGCCCCGGAATTGACTGGATTCCTTTTTTAGGGCCC

ATTGGTATGGCTTTTTCCCCGTATCCCCCCAGGTGTCTGCAGGCTCAAAGAGCAGCG

AGAAGCGTTCAGAGGAAAGCGATCCCGTGCCACCTTCCCCGTGCCCGGGCTGTCCCC

GCACGCTGCCGGCTCGGGGATGCGGGGGGAGCGCCGGACCGGAGCGGAGCCCCGG

GCGGCTCGCTGCTGCCCCCTAGCGGGGAGGGACGTAATTACATCCCTGGGGGCTTT

GGGGGGGGGCTGTCCCTGGCCTCCAAGGCCAGCTTCCCACAATAAGTTGGGTGAATT

TTGGCTCATTCCTCCTTTCTATAGGATTGAGGTCAGAGCTTTGTGATGGGAATTCTGT

GGAATGTGTGTCAGTTAGGGTGTGGAAAGTCCCgcGATCgcTAGcAAACGCCAGCAAC

GCGGCCTTTTTACGGTTCCTGGCCTTTTGCTGGCCTTTTGCTCACATGTCCTGCAGGC

AGCTGCGCGCTCGCTCGCTCACTGAGGCCGCCCGGGCAAAGCCCGGGCGTCGGGCG

ACCTTTGGTCGCCCGGCCTCAGTGAGCGAGCGAGCGCGCAGAGAGGGAGTGGCCAA

CTCCATCACTAGGGGTTCCTGCGGCCGCACGCGTGGAGCTAGTTATTAATAGTAATC

AATTACGGGGTCATTAGTTCATAGCCCATATATGGAGTTCCGCGTTACATAACTTAC

GGTAAATGGCCCGCCTGGCTGACCGCCCAACGACCCCCGCCCATTGACGTCAATAAT

GACGTATGTTCCCATAGTAACGTCAATAGGGACTTTCCATTGACGTCAATGGGTGGA

GTATTTACGGTAAACTGCCCACTTGGCAGTACATCAAGTGTATCATATGCCAAGTAC

GCCCCCTATTGACGTCAATGACGGTAAATGGCCCGCCTGGCATTATGCCCAGTACAT

GACCTTATGGGACTTTCCTACTTGGCAGTACATCTACGTATTAGTCATCGCTATTACC

ATGGTGATGCGGTTTTGGCAGTACATCAATGGGCGTGGATAGCGGTTTGACTCACGG

GGATTTCCAAGTCTCCACCCCATTGACGTCAATGGGAGTTTGTTTTGCACCAAAATC

AACGGGACTTTCCAAAATGTCGTAACAACTCCGCCCCATTGACGCAAATGGGCGGT

-continued

```
AGGCGTGTACGGTGGGAGGTCTATATAAGCAGAGCTCGTTTAGTGAACCGTCAGAT
CGCCTGGAGACGCCATCCACGCTGTTTTGACCTCCATAGAAGACACCGGGACCGATC
CAGCCTCCGCGGATTCGAATCCCGGCCGGGAACGGTGCATTGGAACGCGGATTCCC
CGTGCCAAGAGTGACGTAAGTACCGCCTATAGAGTCTATAGGCCCACAAAAAATGC
TTTCTTCTTTTAATATACTTTTTTGTTTATCTTATTTCTAATACTTTCCCTAATCTCTTT
CTTTCAGGGCAATAATGATACAATGTATCATGCCTCTTTGCACCATTCTAAAGAATA
ACAGTGATAATTTCTGGGTTAAGGCAATAGCAATATTTCTGCATATAAATATTTCTG
CATATAAATTGTAACTGATGTAAGAGGTTTCATATTGCTAATAGCAGCTACAATCCA
GCTACCATTCTGCTTTTATTTTATGGTTGGGATAAGGCTGGATTATTCTGAGTCCAAG
CTAGGCCCTTTTGCTAATCATGTTCATACCTCTTATCTTCCTCCCACAGCTCCTGGGC
AACGTGCTGGTCTGTGTGCTGGCCCATCACTTTGGCAAAGAATTGGGATTCGAACAT
CGATTGAATTCTGAATGGTGAGCAAGGGCGAGGAGCTGTTCACCGGGGTGGTGCCC
ATCCTGGTCGAGCTGGACGGCGACGTAAACGGCCACAAGTTCAGCGTGTCCGGCGA
GGGCGAGGGCGATGCCACCTACGGCAAGCTGACCCTGAAGTTCATCTGCACCACCG
GCAAGCTGCCCGTGCCCTGGCCCACCCTCGTGACCACCCTGACCTACGGCGTGCAGT
GCTTCAGCCGCTACCCCGACCACATGAAGCAGCACGACTTCTTCAAGTCCGCCATGC
CCGAAGGCTACGTCCAGGAGCGCACCATCTTCTTCAAGGACGACGGCAACTACAAG
ACCCGCGCCGAGGTGAAGTTCGAGGGCGACACCCTGGTGAACCGCATCGAGCTGAA
GGGCATCGACTTCAAGGAGGACGGCAACATCCTGGGGCACAAGCTGGAGTACAACT
ACAACAGCCACAACGTCTATATCATGGCCGACAAGCAGAAGAACGGCATCAAGGTG
AACTTCAAGATCCGCCACAACATCGAGGACGGCAGCGTGCAGCTCGCCGACCACTA
CCAGCAGAACACCCCCATCGGCGACGGCCCCGTGCTGCTGCCCGACAACCACTACC
TGAGCACCCAGTCCGCCCTGAGCAAAGACCCCAACGAGAAGCGCGATCACATGGTC
CTGCTGGAGTTCGTGACCGCCGCCGGGATCACTCTCGGCATGGACGAGCTGTACAA
GTACTCAGATCTCGAGCTCAAGTAGGGATCCTCTAGAGTCGACCTGCAGAAGCTTGC
CTCGAGCAGCGCTGCTCGAGAGATCTACGGGTGGCATCCCTGTGACCCCTCCCCAGT
GCCTCTCCTGGCCCTGGAAGTTGCCACTCCAGTGCCCACCAGCCTTGTCCTAATAAA
ATTAAGTTGCATCATTTTGTCTGACTAGGTGTCCTTCTATAATATTATGGGGTGGAGG
GGGGTGGTATGGAGCAAGGGGCAAGTTGGGAAGACAACCTGTAGGGCCTGCGGGGT
CTATTGGGAACCAAGCTGGAGTGCAGTGGCACAATCTTGGCTCACTGCAATCTCCGC
CTCCTGGGTTCAAGCGATTCTCCTGCCTCAGCCTCCCGAGTTGTTGGGATTCCAGGC
ATGCATGACCAGGCTCAGCTAATTTTTGTTTTTTTGGTAGAGACGGGGTTTCACCATA
TTGGCCAGGCTGGTCTCCAACTCCTAATCTCAGGTGATCTACCCACCTTGGCCTCCC
AAATTGCTGGGATTACAGGCGTGAACCACTGCTCCCTTCCCTGTCCTTCTGATTTTGT
AGGTAACCACGTGCGGACCGAGCGGCCGCAGGAACCCCTAGTGATGGAGTTGGCCA
CTCCCTCTCTGCGCGCTCGCTCGCTCACTGAGGCCGGGCGACCAAAGGTCGCCCGAC
GCCCGGGCTTTGCCCGGGCGGCCTCAGTGAGCGAGCGAGCGCGCAGCTGCCTGCAG
GGGCGCCTGATGCGGTATTTTCTCCTTACGCATCTGTGCGGTATTTCACACCGCATAC
GTCgtaGCtGATcaATTggCGCGCCGAATTCGTTAACAAGCTtTAATTAacGCgtATAcCTA
ggATCCGGCCGGccTGCAggTGTCCTCACAGGAACGAAGTCCCTAAAGAAACAGTGGC
AGCCAGGTTTAGCCCCGGAATTGACTGGATTCCTTTTTTAGGGCCCATTGGTATGGC
```

-continued

```
TTTTTCCCCGTATCCCCCCAGGTGTCTGCAGGCTCAAAGAGCAGCGAGAAGCGTTCA
GAGGAAAGCGATCCCGTGCCACCTTCCCCGTGCCCGGGCTGTCCCCGCACGCTGCCG
GCTCGGGGATGCGGGGGAGCGCCGGACCGGAGCGGAGCCCCGGCGGCTCGCTG
CTGCCCCCTAGCGGGGGAGGGACGTAATTACATCCCTGGGGGCTTTGGGGGGGGC
TGTCCCTGGCCTCCAAGGCCAGCTTCCCACAATAAGTTGGGTGAATTTTGGCTCATT
CCTCCTTTCTATAGGATTGAGGTCAGAGCggggttggggttgcgccttttccaaggcagccctgggtttgcgca
gggacgcggctgctctgggcgtggttccgggaaacgcagcggcgccgaccctgggtctcgcacattcttcacgtccgttcgcagcgtcac
ccggatcttcgccgctaccttgtgggcccccggcgacgcttcctgctccgcccctaagtcgggaaggttccttgcggttcgcggcgtgc
cggacgtgacaaacggaagccgcacgtctcactagtaccctcgcagacggacagcgccagggagcaatggcagcgcgccgaccgcg
atgggctgtggccaatagcggctgctcagcagggcgcgccgagagcagcggccgggaaggggcggtgcgggagggggtgtggg
gcggtagtgtgggccctgttcctgcccgcgcggtgttccgcattctgcaagcctccggagcgcacgtcggcagtcggctccctcgttgacc
gaatcaccgacctctctccccagAAGCTCCCGGGAGCTTGTATATCCATTTTCGGATCTGATCAGC
ACGTGTTGACAATTAATCATCGGCATAGTATATCGGCATAGTATAATACGACAAGGT
GAGGAACgccaccATGAAAAAGCCTGAACTCACCGCGACGTCTGTCGAGAAGTTTCTG
ATCGAAAAGTTCGACAGCGTCTCCGACCTGATGCAGCTCTCGGAGGGCGAAGAATC
TCGTGCTTTCAGCTTCGATGTAGGAGGGCGTGGATATGTCCTGCGGGTAAATAGCTG
CGCCGATGGTTTCTACAAAGATCGTTATGTTTATCGGCACTTTGCATCGGCCGCGCTC
CCGATTCCGGAAGTGCTTGACATTGGGGAATTCAGCGAGAGCCTGACCTATTGCATC
TCCCGCCGTGCACAGGGTGTCACGTTGCAAGACCTGCCTGAAACCGAACTGCCCGCT
GTTCTGCAGCCGGTCGCGGAGGCCATGGATGCGATCGCTGCGGCCGATCTTAGCCA
GACGAGCGGGTTCGGCCCATTCGGACCGCAAGGAATCGGTCAATACACTACATGGC
GTGATTTCATATGCGCGATTGCTGATCCCCATGTGTATCACTGGCAAACTGTGATGG
ACGACACCGTCAGTGCGTCCGTCGCGCAGGCTCTCGATGAGCTGATGCTTTGGGCCG
AGGACTGCCCCGAAGTCCGGCACCTCGTGCACGCGGATTTCGGCTCCAACAATGTCC
TGACGGACAATGGCCGCATAACAGCGGTCATTGACTGGAGCGAGGCGATGTTCGGG
GATTCCCAATACGAGGTCGCCAACATCTTCTTCTGGAGGCCGTGGTTGGCTTGTATG
GAGCAGCAGACGCGCTACTTCGAGCGGAGGCATCCGGAGCTTGCAGGATCGCCGCG
GCTCCGGGCGTATATGCTCCGCATTGGTCTTGACCAACTCTATCAGAGCTTGGTTGA
CGGCAATTTCGATGATGCAGCTTGGGCGCAGGGTCGATGCGACGCAATCGTCCGATC
CGGAGCCGGGACTGTCGGGCGTACACAAATCGCCCGCAGAAGCGCGGCCGTCTGGA
CCGATGGCTGTGTAGAAGTACTCGCCGATAGTGGAAACCGACGCCCCAGCACTCGT
CCGAGGGCAAAGGAATAGAGCGCGGGGATCTCATGCTGGAGTTCTTCGCCCACCCC
AACTTGTTTATTGCAGCTTATAATGGTTACAAATAAAGCAATAGCATCACAAATTTC
ACAAATAAAGCATTTTTTTCACTGCATTCTAGTTGTGGTTTGTCCAAACTCATCAATG
TATCTTATCATGTCTGTAGCtGATgtATAcCTAggATCCGGCCGGccTGCAggTGTCCTCA
CAGGAACGAAGTCCCTAAAGAAACAGTGGCAGCCAGGTTTAGCCCCGGAATTGACT
GGATTCCTTTTTAGGGCCCATTGGTATGGCTTTTTCCCCGTATCCCCCCAGGTGTCTG
CAGGCTCAAAGAGCAGCGAGAAGCGTTCAGAGGAAAGCGATCCCGTGCCACCTTCC
CCGTGCCCGGGCTGTCCCCGCACGCTGCCGGCTCGGGGATGCGGGGGGAGCGCCGG
ACCGGAGCGGAGCCCCGGGCGGCTCGCTGCTGCCCCCTAGCGGGGGAGGGACGTAA
```

-continued

```
TTACATCCCTGGGGGCTTTGGGGGGGGGCTGTCCCTCTAGAGCGGCCGCCACCGCGG

TGGAGCTCCAGCTTTTGTTCCCTTTAGTGAGGGTTAATTAGATCTTAATACGACTCAC

TATAGGGCGAATTGGGTACCGGGCCCCCCCTCGAGGTCGACGGTATCGATAAGCTTG

ATATCTATAACAAGAAAATATATATATAATAAGTTATCACGTAAGTAGAACATGAA

ATAACAATATAATTATCGTATGAGTTAAATCTTAAAAGTCACGTAAAAGATAATCAT

GCGTCATTTTGACTCACGCGGTCGTTATAGTTCAAAATCAGTGACACTTACCGCATT

GACAAGCACGCCTCACGGGAGCTCCAAGCGGCGACTGAGATGTCCTAAATGCACAG

CGACGGATTCGCGCTATTTAGAAAGAGAGCAATATTTCAAGAATGCATGCGTCA

ATTTTACGCAGACTATCTTTCTAGGGTTAATCTAGCTGCATCAGGATCATATCGTCGG

GTCTTTTTTCCGGCTCAGTCATCGCCCAAGCTGGCGCTATCTGGGCATCGGGGAGGA

AGAAGCCCGTGCCTTTTCCCGCGAGGTTGAAGCGGCATGGAAAGAGTTTGCCGAGG

ATGACTGCTGCTGCATTGACGTTGAGCGAAAACGCACGTTTACCATGATGATTCGGG

AAGGTGTGGCCATGCACGCCTTTAACGGTGAACTGTTCGTTCAGGCCACCTGGGATA

CCAGTTCGTCGCGGCTTTTCCGGACACAGTTCCGGATGGTCAGCCCGAAGCGCATCA

GCAACCCGAACAATACCGGCGACAGCCGGAACTGCCGTGCCGGTGTGCAGATTAAT

GACAGCGGTGCGGCGCTGGGATATTACGTCAGCGAGGACGGGTATCCTGGCTGGAT

GCCGCAGAAATGGACATGGATACCCCGTGAGTTACCCGGCGGGCGCGCTTGGCGTA

ATCATGGTCATAGCTGTTTCCTGTGTGAAATTGTTATCCGCTCACAATTCCACACAAC

ATACGAGCCGGAAGCATAAAGTGTAAAGCCTGGGGTGCCTAATGAGTGAGCTAACT

CACATTAATTGCGTTGCGCTCACTGCCCGCTTTCCAGTCGGGAAACCTGTCGTGCCA

GCTGCATTAATGAATCGGCCAACGCGCGGGGAGAGGCGGTTTGCGTATTGGGCGCT

CTTCCGCTTCCTCGCTCACTGACTCGCTGCGCTCGGTCGTTCGGCTGCGGCGAGCGG

TATCAGCTCACTCAAAGGCGGTAATACGGTTATCCACAGAATCAGGGGATAACGCA

GGAAAGAACATGTGAGCAAAAGGCCAGCAAAAGGCCAGGAACCGTAAAAAGGCCG

CGTTGCTGGCGTTTTTCCATAGGCTCCGCCCCCCTGACGAGCATCACAAAAATCGAC

GCTCAAGTCAGAGGTGGCGAAACCCGACAGGACTATAAAGATACCAGGCGTTTCCC

CCTGGAAGCTCCCTCGTGCGCTCTCCTGTTCCGACCCTGCCGCTTACCGGATACCTGT

CCGCCTTTCTCCCTTCGGGAAGCGTGGCGCTTTCTCATAGCTCACGCTGTAGGTATCT

CAGTTCGGTGTAGGTCGTTCGCTCCAAGCTGGGCTGTGTGCACGAACCCCCCGTTCA

GCCCGACCGCTGCGCCTTATCCGGTAACTATCGTCTTGAGTCCAACCCGGTAAGACA

CGACTTATCGCCACTGGCAGCAGCCACTGGTAACAGGATTAGCAGAGCGAGGTATG

TAGGCGGTGCTACAGAGTTCTTGAAGTGGTGGCCTAACTACGGCTACACTAGAAGG

ACAGTATTTGGTATCTGCGCTCTGCTGAAGCCAGTTACCTTCGGAAAAAGAGTTGGT

AGCTCTTGATCCGGCAAACAAACCACCGCTGGTAGCGGTGGTTTTTTTGTTTGCAAG

CAGCAGATTACGCGCAGAAAAAAAGGATCTCAAGAAGATCCTTTGATCTTTTCTACG

GGGTCTGACGCTCAGTGGAACGAAAACTCACGTTAAGGGATTTTGGTCATGAGATTA

TCAAAAAGGATCTTCACCTAGATCCTTTTAAATTAAAAATGAAGTTTTAAATCAATC

TAAAGTATATATGAGTAAACTTGGTCTGACAGTTACCAATGCTTAATCAGTGAGGCA

CCTATCTCAGCGATCTGTCTATTTCGTTCATCCATAGTTGCCTGACTCCCCGTCGTGT

AGATAACTACGATACGGGAGGGCTTACCATCTGGCCCCAGTGCTGCAATGATACCG

CGAGACCCACGCTCACCGGCTCCAGATTTATCAGCAATAAACCAGCCAGCCGGAAG
```

```
GGCCGAGCGCAGAAGTGGTCCTGCAACTTTATCCGCCTCCATCCAGTCTATTAATTG

TTGCCGGGAAGCTAGAGTAAGTAGTTCGCCAGTTAATAGTTTGCGCAACGTTGTTGC

CATTGCTACAGGCATCGTGGTGTCACGCTCGTCGTTTGGTATGGCTTCATTCAGCTCC

GGTTCCCAACGATCAAGGCGAGTTACATGATCCCCCATGTTGTGCAAAAAAGCGGTT

AGCTCCTTCGGTCCTCCGATCGTTGTCAGAAGTAAGTTGGCCGCAGTGTTATCACTC

ATGGTTATGGCAGCACTGCATAATTCTCTTACTGTCATGCCATCCGTAAGATGCTTTT

CTGTGACTGGTGAGTACTCAACCAAGTCATTCTGAGAATAGTGTATGCGGCGACCGA

GTTGCTCTTGCCCGGCGTCAATACGGGATAATACCGCGCCACATAGCAGAACTTTAA

AAGTGCTCATCATTGGAAAACGTTCTTCGGGGCGAAAACTCTCAAGGATCTTACCGC

TGTTGAGATCCAGTTCGATGTAACCCACTCGTGCACCCAACTGATCTTCAGCATCTTT

TACTTTCACCAGCGTTTCTGGGTGAGCAAAAACAGGAAGGCAAAATGCCGCAAAAA

AGGGAATAAGGGCGACACGGAAATGTTGAATACTCAT
```

The sequence of the PB-iCap8split-ITRGFP-hygro-4 vector is provided below:

```
PB-iCap8split-ITRGFP-hygro-4 (17,649 bp)
                                                                    (SEQ ID NO: 33)
actcttcctttttcaatattattgaagcatttatcagggttattgtctcatgagcggatacatatttgaatgtatttagaaaaataaaca aatagggttccgcgcacatttccccgaaaagtgccacctaaattgtaagcgttaatattttgttaaaattcgcgttaaattttgttaaatca gctcatttttaaccaataggccgaaatcggcaaaatcccttataaatcaaaagaatagaccgagatagggttgagtgttgttccagtttggaa caagagtccactattaaagaacgtggactccaacgtcaaagggcgaaaaaccgtctatcagggcgatggcccactacgtgaaccatcaccctaa tcaagttttttggggtcgaggtgccgtaaagcactaaatcggaaccctaaagggagcccccgatttagagcttgacggggaaagccggcga acgtggcgagaaaggaagggaagaaagcgaaaggagcgggcgctagggcgctggcaagtgtagcggtcacgctgcgcgtaaccacc acacccgccgcgcttaatgcgccgctacagggcgcgtcccattcgccattcaggctgcgcaactgttgggaagggcgatcggtgcgggc ctcttcgctattacgccagctggcgaaaggggatgtgctgcaaggcgattaagttgggtaacgccaggttttcccagtcacgacgttgta aaacgacggccagtgagcgcgcctcgttcattcacgtttttgaacccgtggaggacgggcagactcgcggtgcaaatgtgttttacagcgtg atggagcagatgaagatgctcgacacgctgcagaacacgcagctagattaaccctagaaagataatcatattgtgacgtacgttaaagataa tcatgcgtaaaattgacgcatgtgttttatcggtctgtatatcgaggtttatttattaatttgaatagatattaagttttattatatttacact tacatactaataataaattcaacaaacaatttatttatgtttatttatttattaaaaaaaaacaaaaactcaaaatttcttctataaagtaaca aaacttttatcgaattcctgcagcccgggggatccactagttctagagggacagcccccccaaagccccagggatgtaattacgtccctcc cccgctagggggcagcagcgagccgcccggggctccgctccggtccggcgctcccccgcatccccgagccggcagcgtgggggacagcccggg cacggggaaggtggcacgggatcgctttcctctgaacgcttctcgctgctctttgagcctgcagacacctggggggatacggggaaaggcc tccaaggccagcttcccacaataagttgggtgaattttggctcattcctcctttctataggattgaggtcagagctttgtgatgggaattctgt ggaatgtggtgagtagcgggctgctgggctggccggggctttcgtggccgccgggccgctcggtgggacggaagcgtgtggagagaccgc caagggctgtagtctgggtccgcgagcaaggttgccctgaactgggggttgggggagcgcagcaaaatggcggctgttcccgagtctt gaatggaagacgcttgtgaggcgggctgtgaggtcgttgaaacaaggtgggggcatggtgggcggcaagaacccaaggtcttgaggc cttcgctaatgcgggaaagctcttattcgggtgagatgggctggggcaccatctggggaccctgacgtgaagtttgtcactgactggagaac tcggtttgtcgtctgttgcggggcggcagttatggcggtgccgttgggcagtgcacccgtaccttgggagcgcgcgccctcgtcgtgtcg tgacgtcacccgttctgttggcttataatgcagggtggggccacctgccggtaggtgtgcggtaggcttttctccgtcgcaggacgcagggtt cgggcctagggtaggctctcctgaatcgacaggcgccggacctctggtgagggagggataagtgaggcgtcagtttctttggtcggtttta tgtacctatcttcttaagtagctgaagctccggttttgaactatgcgctcggggttggcgagtgtgttttgtgaagttttttaggcacctttg
```

-continued

```
aaatgtaatcatttgggtcaatatgtaattttcagtgttagactagtaaattgtccgctaaattctggccgttttttggcttttttgttagactg
tcagttagggtgtggaaagtcccgcgatcgctagcgtttaaacttaagcttggtaccgagctcggatccactagtccagtgtggtggaattcct
gcttcgcgatgtacgggccagatatacgcgtggcctccgcgccgggttttggcgcctcccgcgggcgccccctcctcacggcgagcgctgcca
cgtcagacgaagggcgcagcgagcgtcctgatccttccgcccggacgctcaggacagcggcccgctgctcataagactcggccttagaacccca
gtatcagcagaaggacattttaggacgggacttgggtgactctagggcactggttttctttccagagagcggaacaggcgaggaaaagtag
tcccttctcggcgattctgcggagggatctccgtggggcggtgaacgccgatgattatataaggacgcgccggtccctatcagtgatagag
atctccctatcagtgatagagagtgtggcacagctagttccgtcgcagccgggatttgggtcgcggttcttgtttgtggatcgctgtgatcgtc
acttgacgaacgcgcagccgccatggccgctgatggctatctgcctgattggctggaagataacctgagtgagggcatccgggaatggtg
ggccctgaagcctggagccccgaagcccaaagccaaccagcaaaagcaggacgacggccggggtctggtgcttcctggctacaagtac
ctcggacccttcaacggactcgacaaggggggagcccgtcaacggggggacgcagcggccctcgagcacgacaaggcctacgacca
gcagctgcaggcgggtgacaatccgtacctgcggtataaccacgccgacgccgagtttcaggagcgtctgcaagaagatacgtcttttgg
gggcaacctcgggcgagcagtcttccaggccaagaagcgggttctcgaacctctcggtctggttgaggaaggcgctaagacggctcctg
gaaagaagaggccggtagaacctagccccagcgatctccagattcttctaccggcatcggcaaaaagggccaacagcctgcgagaaa
gcggctgaacttcggccagaccggagacagcgagagcgtgcccgaccctcagcctctgggcgagcccctgccgccccttctggcgtg
ggccccaacaccatggccgccggcggcggagcccctatggccgacaacaacgagggcgccgacggcgtgggaagcagcagcggca
attggcactgcgactccacctggctgggcgacagagtgatcaccacatctacaagaacctgggccctgcccacctacaacaatcacctgta
caagcagatcagcaatggaacctctgaggcgccaccaacgataacacctactttggctacagcacccccttggggatatttcgacttcaacc
ggttccactgtcacttcagccctcgggactggcagcgtctcattaacaataactggggcttcagaccaaagagactgagcttcaagctgttca
acatccaggtgaaggaagtgacccaaaacgagggcaccaagaccatcgccaataacctcacctccacaatccaagtgttcaccgattccg
agtaccagctgcccttacgtgctgggctccgcccaccagggctgcctgccaccattccccgccgacgtgttcatgatccctcagtacggctac
ctgacactgaacaacgggatctcaagcagtgggcagaagctcctttctactgtctggagtacttccctagccagatgctgaggacaggcaaca
atttccagttcacctacacattcgaggacgtccctttcacagctcttatgcccatagccagagcctggatagactgatgaaccctctgatcga
ccagtatctgtattacctgagcagaacgcaaacaacaggcggcaccgctaatacccagaccctgggtttcagccaaggcggccctaacaca
atggccaatcaggccaaaaactggcttcctggcccctgctacagacagcaaagagtgagcacaaccaccggccagaacaacaactctaa
cttcgcctggacagccggcaccaaataccacctgaacggcagaaacagcctggccaaccctggaatcgctatggctacacacaaggacg
atgaggaacggttcttccccagcaacggcatcctgatcttcggcaagcagaacgccgctcgcgacaacgccgactacagcgacgtgatgc
tgaccagcgaggaagaaatcaagacaacaaacccggtcgccaccgaggaatacggcattgtggccgataacctgcagcagcagaatac
cgcccctcagatcggcaccgtgaactcccagggagccctgcctggcatggtgtggcagaacagagatgtgtacctgcagggccctatctg
ggccaagatcccccacaccgacggaaatttccatccaagccctctgatggggatttggcctgaagcaccccctccacagattctcatc
aaaaacacacctgtgccagccgaccctcccacaacatttaatcagtctaagctgaatagcttcatcacccagtacagcaccggccaggtgtc
cgtggaaatcgagtgggagctgcagaaagagaacagcaagagatggaaccctgagatccagtacaccagcaactactacaaaagcaca
agcgtggacttcgccgttaatactgagggcgtctactcagagcctcggcccatcggcactcggtacctgaccagaaacctgaatggctagg
atccggccggcctgcaggtgtcctcacaggaacgaagtccctaaagaaacagtggcagccaggtttagccccggaaaacttgtttattgca
gcttataatggttacaaataaagcaatagcatcacaaatttcacaaataaagcattttttcactgcattctagttgtggtttgtccaaactca
tcaatgtatcttattgactggattgagggacagcccccccccaaagcccccaggggatgtaattacgtccctcccccgctaggggcagcagcga
gccgcccggggctccgctccggtccggcgctcccccgcatccccgagcggcagcgtgcggggacagcccgggcacggggaaggtg
gcacgggatcgctttcctctgaacgcttctcgctgctctttgagcctgcagacacctgggggatacggggaaaggcctccaaggccagc
ttcccacaataagttgggtgaattttggctcattcctcctttctataggattgaggtcagagcgacattgattattgactagttattaatagta
atcaattacggggtcattagttcatagcccatatatggagttccgcgttacataacttacggtaaatggcccgcctggctgaccgcccaacgac
ccccgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatgccca
```

-continued gtacatgaccttatgggactttcctacttggcagtacatctacgtattagtcatcgctattaccatggtgatgcggttttggcagtacatcaat gggcgtggatagcggtttgactcacggggattccaagtctccaccccattgacgtcaatgggagtttgttttggaaccaaaatcaacgggact ttccaaaatgtcgtaacaactccgccccattgacgcaaatgggcggtaggcgtgtacggtgggaggtctatataagcagagctctccctatcag tgatagagatctccctatcagtgatagagatcgtcgacgagctcgtttagtgaaccgtcagatcgcctgagacgccatccacgctgttttgac ctccatagaagacaccgggaccgatccagcctatcccaattctgatgcgccggtgatcagatcaaaaacttcagccaggtacggcgctaaga cggctcctggaaagaagaggccggtagagccatcaccccagcgttctccagactcctctacgggcatcggcaagaaaggccaacagcc cgccagaaaagactcaattttggtcagactggcgactcagagtcagttccagaccctcaacctctcggagaacctccagcagcgccctct ggtgtgggacctaatacaatggctgcaggcggtggcgcaccaatggcagacaataacgaaggcgccgacggagtgggtagttcctcgg gaaattggcattgcgattccacatggctgggcgacagagtcatcaccaccagcacccgaacctgggccctgcccacctacaacaaccacc tctacaagcaaatctccaacgggacatcggaggagccaccaacgacaacacctacttcggctacagcacccccctgggggtattttgactttt aacagattccactgccacttttcaccacgtgactggcagcgactcatcaacaacaactggggattccggcccaagagactcagcttcaagct cttcaacatccaggtcaaggaggtcacgcagaatgaaggcaccaagaccatcgccaataacctcaccagcaccatccaggtgtttacgga ctcggagtaccagctgccgtacgttctcggctctgcccaccagggctgcctgcctccgttccggcggacgtgttcatgattccccagtacg gctacctaacactcaacaacggtagtcaggccgtgggacgctcctccttctactgcctggaatactttccttcgcagatgctgagaaccggca acaacttccagtttacttacaccttcgaggacgtgcctttccacagcagctacgccacagccagagcttggaccggctgatgaatcctctga ttgaccagtacctgtactacttgtctcggactcaaacaacaggaggcacggcaaatacgcagactctgggcttcagccaaggtgggcctaat acaatggccaatcaggcaaagaactggctgccaggaccctgttaccgccaacaacgcgtctcaacgacaaccgggcaaaacaacaatag caactttgcctggactgctgggaccaaataccatctgaatgaagaaattcattggctaatcctggcatcgctatgcaacacacaaagacg acgaggagcgttttttccccagtaacgggatcctgatttttggcaaacaaaatgctgccagagacaatgcggattacagcgatgtcatgctca ccagcgaggaagaaatcaaaaccactaaccctgtggctacagaggaatacggtatcgtggcagataacttgcagcagcaaaacacggct cctcaaattggaactgtcaacagccaggggggccttacccggtatggtctggcagaaccgggacgtgtacctgcagggtcccatctgggcc aagattcctcacacggacggcaacttccaccgtctccgctgatgggcggctttggcctgaaacatcctccgcctcagatcctgatcaagaa cacgcctgtacctgcggatcctccgaccaccttcaaccagtcaaagctgaactctttcatcacgcaatacagcaccggacaggtcagcgtg gaaattgaatgggagctgcagaaggaaaacagcaagcgctggaaccccgagatccagtacacctccaactactacaaatctacaagtgtg gactttgctgttaatacagaaggcgtgtactctgaaccccgccccattggcacccgttacctcacccgtaatctgtaaactagtttgcttgtta atcaataaaccgtttaattcgtttcagttgagcggccgtcgagtctagagggcccgtttaaacccgctgatcagcctcgactgtgccttctagt tgccagccatctgttgtttgccctcccccgtgccttccttgaccctggaaggtgccactcccactgtcctttcctaataaaatgaggaaattg catcgcattgtctgagtaggtgtcattctattctggggggtggggggggcaggacagcaaggggaggattgggaagacaatagcaggcatgc tggggatgcggtgggctctatggcttctgaggcggaaagaaccagctggggctctagggggtatccccggcgcgccgaattcgttaacaa gctttaattaacgcgtataccctaggatccggccggcctgcaggtgtcctcacaggaacgaagtccctaaagaaacagtggcagccaggttt agccccggaattgactggattcctttttagggcccattggtatggcttttccccgtatccccccaggtgtctgcaggctcaaagagcagcga gaagcgttcagaggaaagcgatcccgtgccaccttccccgtgccgggctgtccccgcacgctgccggctcggggatgcgggggagc gccgaccggagcggagccccggcggctcgctgctgcccctagcgggagggacgtaattacatccctggggcttggggggg ggctgtccctggcctccaaggccagcttcccacaataagttgggtgaattttggctcattcctcctttctataggattgaggtcagagctttgt gatgggaattctgtggaatgtgtgtcagttagggtgtggaaagtcccgcgatcgctagcaaacgccagcaacgcggcctttttacggttcctgg ccttttgctggccttttgctcacatgtcctgcaggcagctgcgcgctcgctcgctcactgaggccgcccgggcaaagcccgggcgtcgggcg acctttggtcgcccggcctcagtgagcgagcgagcgcgcagagagggagtggccaactccatcactaggggttcctgcggccgcacgc gtggagctagttattaatagtaatcaattacggggtcattagttcatagcccatatatggagttccgcgttacataacttacggtaaatggccc gcctggctgaccgcccaacgacccccgcccattgacgtcaataatgacgtatgttcccatagtaacgtcaatagggactttccattgacgtcaa tgggtggagtatttacggtaaactgcccacttggcagtacatcaagtgtatcatatgccaagtacgccccctattgacgtcaatgacggtaaat -continued

```
ggcccgcctggcattatgcccagtacatgaccttatgggactttcctacttggcagtacatctacgtattagtcatcgctattaccatggtgat
gcggttttggcagtacatcaatgggcgtggatagcggtttgactcacggggattccaagtctccacccattgacgtcaatgggagtttgttt
tgcaccaaaatcaacgggactttccaaaatgtcgtaacaactccgccccattgacgcaaatgggcggtaggcgtgtacggtgggaggtctatat
aagcagagctcgtttagtgaaccgtcagatcgcctggagacgccatccacgctgttttgacctcatagaagacaccgggaccgatccagc
ctccgcggattcgaatcccggccgggaacggtgcattggaacgcggattccccgtgccaagagtgacgtaagtaccgcctatagagtctat
aggcccacaaaaaatgctttcttcttttaatatactttttgtttatcttatttctaatactttccctaatctctttctttcagggcaataatg
atacaatgtatcatgcctctttgcaccattctaaagaataacagtgataatttctgggttaaggcaatagcaatatttctgcatataaatattt
ctgcatataaattgtaactgatgtaagaggtttcatattgctaatagcagctacaatccagctaccattctgcttttattttatggttgggata
aggctggattattctgagtccaagctaggccttttgctaatcatgttcatacctcttatcttcctcccacagctcctgggcaacgtgctggtc
tgtgtgctggcccatcactttggcaaagaattgggattcgaacatcgattgaattctgaatggtgagcaagggcgaggagctgttcaccggggt
ggtgcccatcctggtcgagctggacggcgacgtaaacggccacaagttcagcgtgtccggcgagggcgagggcgatgccacctacggcaagctg
accctgaagttcatctgcaccaccggcaagctgcccgtgccctggcccaccctcgtgaccaccctgacctacggcgtgcagtgcttcagccgct
accccgaccacatgaagcagcacgacttcttcaagtccgccatgcccgaaggctacgtccaggagcgcaccatcttcttcaaggacgacggcaa
ctacaagacccgcgccgaggtgaagttcgagggcgacaccctggtgaaccgcatcgagctgaagggcatcgacttcaaggaggacggcaacat
cctggggcacaagctggagtacaactacaacagccacaacgtctatatcatggccgacaagcagaagaacggcatcaaggtgaacttcaa
gatccgccacaacatcgaggacggcagcgtgcagctcgccgaccactaccagcagaacacccccatcggcgacggccccgtgctgctg
cccgacaaccactacctgagcacccagtccgccctgagcaaagaccccaacgagaagcgcgatcacatggtcctgctggagttcgtgac
cgccgccgggatcactctcggcatggacgagctgtacaagtactcagatctcgagctcaagtagggatcctctagagtcgacctgcagaa
gcttgcctcgagcagcgctgctcgagagatctacgggtggcatccctgtgacccctccccagtgcctctcctggccctggaagttgccactc
cagtgcccaccagccttgtcctaataaaattaagttgcatcattttgtctgactaggtgtccttctataatattatgggtggaggggggtggt
atggagcaaggggcaagttgggaagacaacctgtagggcctgcggggtctattgggaaccaagctggagtgcagtggcacaatcttggctc
actgcaatctccgcctcctgggttcaagcgattctcctgcctcagcctcccgagttgttgggattccaggcatgcatgaccaggctcagctaat
ttttgtttttttggtagagacggggtttcaccatattggccaggctggtctccaactcctaatctcaggtgatctacccaccttggcctcccaa
attgctgggattacaggcgtgaaccactgctcccttccctgtccttctgattttgtaggtaaccacgtgcggaccgagcggccgcaggaacccc
tagtgatggagttggccactccctctctgcgcgctcgctcgctcactgaggccgggcgaccaaaggtcgcccgacgcccgggctttgcccg
ggcggcctcagtgagcgagcgagcgcgcagctgcctgcaggggcgcctgatgcggtattttctccttacgcatctgtgcggtatttcacac
cgcatacgtcgtagctgatcaattggcgcgccgaattcgttaacaagctttaattaacgcgtatacctaggatccgccggcctgcaggtgtc
ctcacaggaacgaagtccctaaagaaacagtggcagccaggtttagccccggaattgactggattccttttttagggcccattggtatggcttt
ttccccgtatcccccaggtgtctgcaggctcaaagagcagcgagaagcgttcagaggaaagcgatcccgtgccaccttcccgtgcccg
ggctgtcccgcacgctgccggctcggggatgcgggggagcgccggaccggagcggagcccgggcggctcgctgctgcccccta
gcggggagggacgtaattacatccctgggggctttgggggggggctgtccctggcctccaaggccagcttcccacaataagttgggtga
attttggctcattcctcctttctataggattgaggtcagagcggggttggggttgcgccttttccaaggcagccctgggtttgcgcagggacgc
ggctgctctgggcgtggttccgggaaacgcagcggcgccgacccggtctcgcacattcttcacgtccgttcgcagcgtcacccggatct
tcgccgctaccttgtgggccccccggcgacgcttcctgctccgcccctaagtcgggaaggttccttgccggttcgcggcgtgccggacgtg
acaaacggaagccgacgtctcactagtaccctcgcagacggacagcgccagggagcaatggcagcgcgccgaccgcgatgggctgt
ggccaatagcggctgctcagcagggcgcgccgagagcagcggccgggaaggggcggtgcgggaggcggggtgggggtagtg
tgggcccctgttcctgcccgcgcggtgttccgcattctgcaagcctccggagcgcacgtcggcagtcggctccctcgttgaccgaatcaccg
acctctctcccagaagctcccgggagcttgtatatccattttcggatctgatcagcacgtgttgacaattaatcatcggcatagtatatcggc
atagtataatacgacaaggtgaggaacgccaccatgaaaaagcctgaactcaccgcgacgtctgtcgagaagtttctgatcgaaaagttcga
cagcgtctccgacctgatgcagctctcggagggcgaagaatctcgtgctttcagcttcgatgtaggagggcgtggatatgtcctgcgggtaa
atagctgcgccgatggtttctacaaagatcgttatgtttatcggcactttgcatcggccgcgctcccgattccggaagtgcttgacattgggga
```

-continued

```
attcagcgagagcctgacctattgcatctcccgccgtgcacagggtgtcacgttgcaagacctgcctgaaaccgaactgcccgctgttctgc
agccggtcgcggaggccatggatgcgatcgctgcggccgatcttagccagacgagcgggttcggcccattcggaccgcaaggaatcgg
tcaatacactacatggcgtgatttcatatgcgcgattgctgatccccatgtgtatcactggcaaactgtgatggacgacaccgtcagtgcgtcc
gtcgcgcaggctctcgatgagctgatgctttgggccgaggactgccccgaagtccggcacctcgtgcacgcggatttcggctccaacaat
gtcctgacggacaatggccgcataacagcggtcattgactggagcgaggcgatgttcggggattcccaatacgaggtcgccaacatcttct
tctggaggccgtggttggcttgtatggagcagcagacgcgctacttcgagcggaggcatccggagcttgcaggatcgccgcggctccgg
gcgtatatgctccgcattggtcttgaccaactctatcagagcttggttgacggcaatttcgatgatgcagcttgggcgcagggtcgatgcgac
gcaatcgtccgatccggagccgggactgtcggcgtacacaaatcgcccgcagaagcgcggccgtctggaccgatggctgtgtagaagt
actcgccgatagtggaaaccgacgcccagcactcgtccgagggcaaaggaatagagcgcggggatctcatgctggagttcttcgccca
ccccaacttgtttattgcagcttataatggttacaaataaagcaatagcatcacaaatttcacaaataaagcattttttttcactgcattctagt
tgtggtttgtccaaactcatcaatgtatcttatcatgtctgtagctgatgtatacctaggatccggccggcctgcaggtgtcctcacaggaacg
aagtccctaaagaaacagtggcagccaggtttagcccccggaattgactggattcctttttagggcccattggtatggcttttcccccgtatccc
cccaggtgtctgcaggctcaaagagcagcgagaagcgttcagaggaaagcgatcccgtgccaccttcccgtgcccgggctgtcccgcacgct
gccggctcggggatgcgggggagcgccggaccggagcggagccccgggcggctcgctgctgcccectagcggggagggacgta
attacatccctgggggctttgggggggggctgtccctctagagcggccgccaccgcggtggagctccagcttttgttccctttagtgagggtt
aattagatcttaatacgactcactatagggcgaattgggtaccgggccccccctcgaggtcgacggtatcgataagcttgatatctataacaa
gaaaatatatatataataagttatcacgtaagtagaacatgaaataacaatataattatcgtatgagttaaatcttaaaagtcacgtaaaagat
aatcatgcgtcattttgactcacgcggtcgttatagttcaaaatcagtgacacttaccgcattgacaagcacgcctcacgggagctccaagcgg
cgactgagatgtcctaaatgcacagcgacggattcgcgctatttagaaagagagagcaatatttcaagaatgcatgcgtcaattttacgcagac
tatcttctaggggttaatctagctgcatcaggatcatatcgtcgggtctttttccggctcagtcatcgcccaagctggcgctatctgggcatc
ggggaggaagaagcccgtgccttttcccgcgaggttgaagcggcatggaaagagtttgccgaggatgactgctgctgcattgacgttgagcg
aaaacgcacgtttaccatgatgattcgggaaggtgtggccatgcacgcctttaacggtgaactgttcgttcaggccacctgggataccagttc
gtcgcggcttttccggacacagttccggatggtcagcccgaagcgcatcagcaacccgaacaataccggcgacaccggaactgccgtg
ccggtgtgcagattaatgacagcggtgcggcgctgggatattacgtcagcgaggacgggtatcctggctggatgccgcagaaatggacat
ggatacccgtgagttaccggcgggcgcgcttggcgtaatcatggtcatagctgtttcctgtgtgaaattgttatccgctcacaattccacac
aacatacgagccggaagcataaagtgtaaagcctggggtgcctaatgagtgagctaactcacattaattgcgttgcgctcactgcccgctttc
cagtcgggaaacctgtcgtgccagctgcattaatgaatcggccaacgcgcggggagaggcggtttgcgtattgggcgctcttccgcttcct
cgctcactgactcgctgcgctcggtcgttcggctgcggcgagcggtatcagctcactcaaaggcggtaatacggttatccacagaatcagg
ggataacgcaggaaagaacatgtgagcaaaaggccagcaaaaggccaggaaccgtaaaaaggccgcgttgctggcgtttttccataggc
tccgcccccctgacgagcatcacaaaaatcgacgctcaagtcagaggtggcgaaacccgacaggactataaagataccaggcgtttcccc
ctggaagctccctcgtgcgctctcctgttccgaccctgccgcttaccggatacctgtccgcctttctcccttcgggaagcgtggcgctttctca
tagctcacgctgtaggtatctcagttcggtgtaggtcgttcgctccaagctgggctgtgtgcacgaaccccccgttcagcccgaccgctgcgc
cttatccggtaactatcgtcttgagtccaacccggtaagacacgacttatcgccactggcagcagccactggtaacaggattagcagagcga
ggtatgtaggcggtgctacagagttcttgaagtggtggcctaactacggctacactagaaggacagtatttggtatctgcgctctgctgaagc
cagttaccttcggaaaaagagttggtagctcttgatccggcaaacaaaccaccgctggtagcggtggtttttttgtttgcaagcagcagattac
gcgcagaaaaaaaggatctcaagaagatcctttgatcttttctacggggtctgacgctcagtggaacgaaaactcacgttaagggattttggt
catgagattatcaaaaaggatcttcacctagatccttttaaattaaaaatgaagttttaaatcaatctaaagtatatatgagtaaacttggtct
gacagttaccaatgcttaatcagtgaggcacctatctcagcgatctgtctatttcgttcatccatagttgcctgactccccgtgtgtagataac
tacgatacgggagggcttaccatctggccccagtgctgcaatgataccgcgagacccacgctcaccggctccagatttatcagcaataaaccag
ccagccggaagggccgagcgcagaagtggtcctgcaactttatccgcctccatccagtctattaattgttgccgggaagctagagtaagtagtt
```

-continued

```
cgccagttaatagtttgcgcaacgttgttgccattgctacaggcatcgtggtgtcacgctcgtcgtttggtatggcttcattcagctccggttc ccaacgatcaaggcgagttacatgatcccccatgttgtgcaaaaaagcggttagctccttcggtcctccgatcgttgtcagaagtaagttggcc gcagtgttatcactcatggttatggcagcactgcataattctcttactgtcatgccatccgtaagatgcttttctgtgactggtgagtactcaa ccaagtcattctgagaatagtgtatgcggcgaccgagttgctcttgcccggcgtcaatacgggataataccgcgccacatagcagaactttaaa agtgctcatcattggaaaacgttcttcggggcgaaaactctcaaggatcttaccgctgttgagatccagttcgatgtaacccactcgtgcaccc aactgatcttcagcatcttttactttcaccagcgtttctgggtgagcaaaaacaggaaggcaaaatgccgcaaaaaagggaataagggcgacac ggaaatgttgaatactcat
```

The sequence of the pPBBG-iCap8cd-ITRGFP-hygro vector is provided below:

pPBBG-iCap8cd-ITRGFP-hygro (14,262 bp) (SEQ ID NO: 34)

```
ACTCTTCCTTTTTCAATATTATTGAAGCATTTATCAGGGTTATTGTCTCATGA

GCGGATACATATTTGAATGTATTTAGAAAAATAAACAAATAGGGGTTCCGCGCACA

TTTCCCCGAAAAGTGCCACCTAAATTGTAAGCGTTAATATTTTGTTAAAATTCGCGTT

AAATTTTTGTTAAATCAGCTCATTTTTTAACCAATAGGCCGAAATCGGCAAAATCCC

TTATAAATCAAAAGAATAGACCGAGATAGGGTTGAGTGTTGTTCCAGTTTGGAACA

AGAGTCCACTATTAAAGAACGTGGACTCCAACGTCAAAGGGCGAAAAACCGTCTAT

CAGGGCGATGGCCCACTACGTGAACCATCACCCTAATCAAGTTTTTTGGGGTCGAGG

TGCCGTAAAGCACTAAATCGGAACCCTAAAGGGAGCCCCCGATTTAGAGCTTGACG

GGGAAAGCCGGCGAACGTGGCGAGAAAGGAAGGGAAGAAAGCGAAAGGAGCGGG

CGCTAGGGCGCTGGCAAGTGTAGCGGTCACGCTGCGCGTAACCACCACACCCGCCG

CGCTTAATGCGCCGCTACAGGGCGCGTCCCATTCGCCATTCAGGCTGCGCAACTGTT

GGGAAGGGCGATCGGTGCGGGCCTCTTCGCTATTACGCCAGCTGGCGAAAGGGGGA

TGTGCTGCAAGGCGATTAAGTTGGGTAACGCCAGGGTTTTCCCAGTCACGACGTTGT

AAAACGACGGCCAGTGAGCGCGCCTCGTTCATTCACGTTTTTGAACCCGTGGAGGAC

GGGCAGACTCGCGGTGCAAATGTGTTTTACAGCGTGATGGAGCAGATGAAGATGCT

CGACACGCTGCAGAACACGCAGCTAGATTAACCCTAGAAAGATAATCATATTGTGA

CGTACGTTAAAGATAATCATGCGTAAAATTGACGCATGTGTTTTATCGGTCTGTATA

TCGAGGTTTATTTATTAATTTGAATAGATATTAAGTTTTATTATATTTACACTTACAT

ACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCAGATATACGCGTTGACATTGATTATTGACTAGTTATTAAT

AGTAATCAATTACGGGGTCATTAGTTCATAGCCCATATATGGAGTTCCGCGTTACAT
```

```
AACTTACGGTAAATGGCCCGCCTGGCTGACCGCCCAACGACCCCCGCCCATTGACGT

CAATAATGACGTATGTTCCCATAGTAACGCCAATAGGGACTTTCCATTGACGTCAAT

GGGTGGAGTATTTACGGTAAACTGCCCACTTGGCAGTACATCAAGTGTATCATATGC

CAAGTACGCCCCCTATTGACGTCAATGACGGTAAATGGCCCGCCTGGCATTATGCCC

AGTACATGACCTTATGGGACTTTCCTACTTGGCAGTACATCTACGTATTAGTCATCGC

TATTACCATGGTGATGCGGTTTTGGCAGTACATCAATGGGCGTGGATAGCGGTTTGA

CTCACGGGGATTTCCAAGTCTCCACCCCATTGACGTCAATGGGAGTTTGTTTTGGAA

CCAAAATCAACGGGACTTTCCAAAATGTCGTAACAACTCCGCCCCATTGACGCAAAT

GGGCGGTAGGCGTGTACGGTGGGAGGTCTATATAAGCAGAGCTCTCCCTATCAGTG

ATAGAGATCTCCCTATCAGTGATAGAGATCGTCGACGAGCTCGTTTAagttgcgcagccatcg acgtcagacgcggaagcttcgatcaactacgcagacaggtaAGTaaacaaatgttctcgtcacgtgggcatgaatctgatgctgtttccct gcagacaatgcgagagaatgaatcagaattcaaatatctgcttcactcacggacagaaagactgtttagagtgctttcccgtgtcagaatctc aacccgtttctgtcgtcaaaaaggcgtatcagaaactgtgctacattcatcatatcatgggaaaggtgccagacgcttgcactgcctgcgatct ggtcaatgtggatttggatgactgcatctttgaacaataaatgatttaaatcaggtatggctgccgatggttatcttccagattggctcgagga caacctctctgagggcattcgcgagtggtgggcgctgaaacctggagccccgaagcccaaagccaaccagcaaaagcaggacgacggc cggggtctggtgcttcctggctacaagtacctcggacccttcaacggactcgacaaggggagcccgtcaacgcggcggacgcagcgg ccctcgagcacgacaaggcctacgaccagcagctgcaggggtgacaatccgtacctgcggtataaccacgccgacgccgagtttcag gagcgtctgcaagaagatacgtcttttggggcaaccctcgggcgagcagtcttccaggccaagaagcgggttctcgaacctctcggtctgg ttgaggaaggcgctaagacggctcctggaaagaagaggccggtagagccatcaccccagcgttctccagactcctctacgggcatcggc aagaaaggccaacagcccgccagaaaagactcaattttggtcagactggcgactcagagtcagttccagaccctcaacctctggagaa cctccagcagcgccctctggtgtgggacctaatacaatggctgcaggcggtggcgcaccaatggcagacaataacgaaggcgccgacg gagtgggtagttcctcgggaaattggcattgcgattccacatggctgggcgacagagtcatcaccaccagcacccgaacctgggccctgc ccacctacaacaaccacctctacaagcaaatctccaacgggacatcgggaggagccaccaacgacaaacacctacttcggctacagcacc ccctgggggtattttgactttaacagattccactgccacttttcaccacgtgactggcagcgactcatcaacaacaactggggattccggccc aagagactcagcttcaagctcttcaacatccaggtcaaggaggtcacgcagaatgaaggcaccaagaccatcgccaataacctcaccagc accatccaggtgtttacggactcggagtaccagctgccgtacgttctcggctctgcccaccagggctgcctgcctccgttcccggcggacgt gttcatgattccccagtacggctacctaacactcaacaacgtagtcaggccgtgggacgctcctccttctactgcctggaatactttccttcg cagatgctgagaaccggcaacaacttccagtttacttacaccttcgaggacgtgcctttccacagcagctacgcccacagccagagcttgga ccggctgatgaatcctctgattgaccagtacctgtactacttgtctcggactcaaacaacaggaggcacggcaaatacgcagactctgggct tcagccaaggtgggcctaatacaatggccaatcaggcaaagaactggctgccaggaccctgttaccgccaacaacgcgtctcaacgacaa ccgggcaaaacaacaatagcaactttgcctggactgctgggaccaaataccatctgaatggaagaaattcattggctaatcctggcatcgct atggcaacacacaaagacgacgaggagcgttttttttcccagtaacgggatcctgatttttggcaaacaaatgctgccagagacaatgcgga ttacagcgatgtcatgctcaccagcgaggaagaaatcaaaaccactaaccctgtggctacagaggaatacggtatcgtggcagataacttg cagcagcaaaacacggctcctcaaattggaactgtcaacagccagggggccttacccggtatggtctggcagaacgggacgtgtacctg cagggtcccatctgggccaagattcctcacacgacggcaacttccaccgctctccgctgatgggcggctttggcctgaaacatcctccgc ctcagatcctgatcaagaacacgcctgtacctgcggatcctccgaccaccttcaaccagtcaaagctgaactcttcatcacgcaatacagca ccggacaggtcagcgtggaaattgaatgggagctgcagaaggaaaacagcaagcgctggaaccccgagatccagtacacctccaacta ctacaaatctacaagtgtggactttgctgttaatacagaaggcgtgtactctgaaccccgccccattggcacccgttacctcacccgtaatctg taaactagtttgcttgttaatcaataaaccgtttaattcgtttcagttgaGCGGCCGTCGAGTCTAGAGGGCCCGTTTA

AACCCGCTGATCAGCCTCGACTGTGCCTTCTAGTTGCCAGCCATCTGTTGTTTGCCCC
```

-continued

TCCCCCGTGCCTTCCTTGACCCTGGAAGGTGCCACTCCCACTGTCCTTTCCTAATAAA
ATGAGGAAATTGCATCGCATTGTCTGAGTAGGTGTCATTCTATTCTGGGGGGTGGGG
TGGGGCAGGACAGCAAGGGGGAGGATTGGGAAGACAATAGCAGGCATGCTGGGGA
TGCGGTGGGCTCTATGGCTTCTGAGGCGGAAAGAACCAGCTGGGGCTCTAGGGGGT
ATCCCCGGCGCGCCGAATTCGTTAACAAGCTtTAATTAaCGCgtATAcCTAggATCCGGC
CGGccTGCAggTGTCCTCACAGGAACGAAGTCCCTAAAGAAACAGTGGCAGCCAGGT
TTAGCCCCGGAATTGACTGGATTCCTTTTTTAGGGCCCATTGGTATGGCTTTTTCCCC
GTATCCCCCAGGTGTCTGCAGGCTCAAAGAGCAGCGAGAAGCGTTCAGAGGAAAG
CGATCCCGTGCCACCTTCCCCGTGCCCGGGCTGTCCCCGCACGCTGCCGGCTCGGGG
ATGCGGGGGAGCGCCGGACCGGAGCGGAGCCCCGGGCGGCTCGCTGCTGCCCCCT
AGCGGGGAGGGACGTAATTACATCCCTGGGGGCTTTGGGGGGGGCTGTCCCTGG
CCTCCAAGGCCAGCTTCCCACAATAAGTTGGGTGAATTTTGGCTCATTCCTCCTTTCT
ATAGGATTGAGGTCAGAGCTTTGTGATGGGAATTCTGTGGAATGTGTGTCAGTTAGG
GTGTGGAAAGTCCCgcGATCgcTAGcAAACGCCAGCAACGCGGCCTTTTTACGGTTCC
TGGCCTTTTGCTGGCCTTTTGCTCACATGTCCTGCAGGCAGCTGCGCGCTCGCTCGCT
CACTGAGGCCGCCCGGGCAAAGCCCGGGCGTCGGGCGACCTTTGGTCGCCCGGCCT
CAGTGAGCGAGCGAGCGCGCAGAGAGGGAGTGGCCAACTCCATCACTAGGGGTTCC
TGCGGCCGCACGCGTGGAGCTAGTTATTAATAGTAATCAATTACGGGGTCATTAGTT
CATAGCCCATATATGGAGTTCCGCGTTACATAACTTACGGTAAATGGCCCGCCTGGC
TGACCGCCCAACGACCCCCGCCCATTGACGTCAATAATGACGTATGTTCCCATAGTA
ACGTCAATAGGGACTTTCCATTGACGTCAATGGGTGGAGTATTTACGGTAAACTGCC
CACTTGGCAGTACATCAAGTGTATCATATGCCAAGTACGCCCCCTATTGACGTCAAT
GACGGTAAATGGCCCGCCTGGCATTATGCCCAGTACATGACCTTATGGGACTTTCCT
ACTTGGCAGTACATCTACGTATTAGTCATCGCTATTACCATGGTGATGCGGTTTTGGC
AGTACATCAATGGGCGTGGATAGCGGTTTGACTCACGGGGATTTCCAAGTCTCCACC
CCATTGACGTCAATGGGAGTTTGTTTTGCACCAAAATCAACGGGACTTTCCAAATG
TCGTAACAACTCCGCCCCATTGACGCAAATGGGCGGTAGGCGTGTACGGTGGGAGG
TCTATATAAGCAGAGCTCGTTTAGTGAACCGTCAGATCGCCTGGAGACGCCATCCAC
GCTGTTTTGACCTCCATAGAAGACACCGGGACCGATCCAGCCTCCGCGGATTCGAAT
CCCGGCCGGGAACGGTGCATTGGAACGCGGATTCCCCGTGCCAAGAGTGACGTAAG
TACCGCCTATAGAGTCTATAGGCCCACAAAAAATGCTTTCTTCTTTTAATATACTTTT
TTGTTTATCTTATTTCTAATACTTTCCCTAATCTCTTTCTTTCAGGGCAATAATGATAC
AATGTATCATGCCTCTTTGCACCATTCTAAAGAATAACAGTGATAATTTCTGGGTTA
AGGCAATAGCAATATTTCTGCATATAAATATTTCTGCATATAAATTGTAACTGATGT
AAGAGGTTTCATATTGCTAATAGCAGCTACAATCCAGCTACCATTCTGCTTTTATTTT
ATGGTTGGGATAAGGCTGGATTATTCTGAGTCCAAGCTAGGCCCTTTTGCTAATCAT
GTTCATACCTCTTATCTTCCTCCCACAGCTCCTGGGCAACGTGCTGGTCTGTGTGCTG
GCCCATCACTTTGGCAAAGAATTGGGATTCGAACATCGATTGAATTCTGAATGGTGA
GCAAGGGCGAGGAGCTGTTCACCGGGGTGGTGCCCATCCTGGTCGAGCTGGACGGC
GACGTAAACGGCCACAAGTTCAGCGTGTCCGGCGAGGGCGAGGGCGATGCCACCTA
CGGCAAGCTGACCCTGAAGTTCATCTGCACCACCGGCAAGCTGCCCGTGCCCTGGCC

```
CACCCTCGTGACCACCCTGACCTACGGCGTGCAGTGCTTCAGCCGCTACCCCGACCA
CATGAAGCAGCACGACTTCTTCAAGTCCGCCATGCCCGAAGGCTACGTCCAGGAGC
GCACCATCTTCTTCAAGGACGACGGCAACTACAAGACCCGCGCCGAGGTGAAGTTC
GAGGGCGACACCCTGGTGAACCGCATCGAGCTGAAGGGCATCGACTTCAAGGAGGA
CGGCAACATCCTGGGGCACAAGCTGGAGTACAACTACAACAGCCACAACGTCTATA
TCATGGCCGACAAGCAGAAGAACGGCATCAAGGTGAACTTCAAGATCCGCCACAAC
ATCGAGGACGGCAGCGTGCAGCTCGCCGACCACTACCAGCAGAACACCCCCATCGG
CGACGGCCCCGTGCTGCTGCCCGACAACCACTACCTGAGCACCCAGTCCGCCCTGAG
CAAAGACCCCAACGAGAAGCGCGATCACATGGTCCTGCTGGAGTTCGTGACCGCCG
CCGGGATCACTCTCGGCATGGACGAGCTGTACAAGTACTCAGATCTCGAGCTCAAGT
AGGGATCCTCTAGAGTCGACCTGCAGAAGCTTGCCTCGAGCAGCGCTGCTCGAGAG
ATCTACGGGTGGCATCCCTGTGACCCCTCCCCAGTGCCTCTCCTGGCCCTGGAAGTT
GCCACTCCAGTGCCCACCAGCCTTGTCCTAATAAAATTAAGTTGCATCATTTTGTCTG
ACTAGGTGTCCTTCTATAATATTATGGGTGGAGGGGGGTGGTATGGAGCAAGGGG
CAAGTTGGGAAGACAACCTGTAGGGCCTGCGGGGTCTATTGGGAACCAAGCTGGAG
TGCAGTGGCACAATCTTGGCTCACTGCAATCTCCGCCTCCTGGGTTCAAGCGATTCT
CCTGCCTCAGCCTCCCGAGTTGTTGGGATTCCAGGCATGCATGACCAGGCTCAGCTA
ATTTTTGTTTTTTTGGTAGAGACGGGGTTTCACCATATTGGCCAGGCTGGTCTCCAAC
TCCTAATCTCAGGTGATCTACCCACCTTGGCCTCCCAAATTGCTGGGATTACAGGCG
TGAACCACTGCTCCCTTCCCTGTCCTTCTGATTTTGTAGGTAACCACGTGCGGACCGA
GCGGCCGCAGGAACCCCTAGTGATGGAGTTGGCCACTCCCTCTCTGCGCGCTCGCTC
GCTCACTGAGGCCGGGCGACCAAAGGTCGCCCGACGCCCGGGCTTTGCCCGGGCGG
CCTCAGTGAGCGAGCGAGCGCGCAGCTGCCTGCAGGGGCGCCTGATGCGGTATTTT
CTCCTTACGCATCTGTGCGGTATTTCACACCGCATACGTCgtaGCtGATcaATTgGCGCG
CCGAATTCGTTAACAAGCTtTAATTAaCGCgtATAcCTAggATCCGGCCGGccTGCAggTG
TCCTCACAGGAACGAAGTCCCTAAAGAAACAGTGGCAGCCAGGTTTAGCCCCGGAA
TTGACTGGATTCCTTTTTTAGGGCCCATTGGTATGGCTTTTTCCCCGTATCCCCCCAG
GTGTCTGCAGGCTCAAAGAGCAGCGAGAAGCGTTCAGAGGAAAGCGATCCCGTGCC
ACCTTCCCCGTGCCCGGGCTGTCCCCGCACGCTGCCGGCTCGGGGATGCGGGGGGA
GCGCCGGACCGGAGCGGAGCCCCGGGCGGCTCGCTGCTGCCCCCTAGCGGGGGAGG
GACGTAATTACATCCCTGGGGGCTTTGGGGGGGGGCTGTCCCTGGCCTCCAAGGCCA
GCTTCCCACAATAAGTTGGGTGAATTTTGGCTCATTCCTCCTTTCTATAGGATTGAGG
TCAGAGCggggttggggttgcgccttttccaaggcagccctgggtttgcgcaggacgcggctgctctgggcgtggttccgggaaa
cgcagcggcgccgaccctgggtctcgcacattcttcacgtccgttcgcagcgtcacccggatcttcgccgctaccttgtgggcccccgg
cgacgcttcctgctccgccctaagtcgggaaggttccttgcggttcgcggcgtgccggacgtgacaaacggaagccgcacgtctcacta
gtaccctcgcagacggacagcgccagggagcaatggcagcgcgccgaccgcgatgggctgtggccaatagcggctgctcagcagggc
gcgccgagagcagcggccgggaaggggcggtgcgggaggcgggtgtggggcggtagtgtgggccctgttcctgcccgcgcggtgt
tccgcattctgcaagcctccggagcgcacgtcggcagtcggctccctcgttgaccgaatcaccgacctctctcccagAAGCTCCC
GGGAGCTTGTATATCCATTTTCGGATCTGATCAGCACGTGTTGACAATTAATCATCG
GCATAGTATATCGGCATAGTATAATACGACAAGGTGAGGAACgccaccATGAAAAAGC
```

-continued

```
CTGAACTCACCGCGACGTCTGTCGAGAAGTTTCTGATCGAAAAGTTCGACAGCGTCT
CCGACCTGATGCAGCTCTCGGAGGGCGAAGAATCTCGTGCTTTCAGCTTCGATGTAG
GAGGGCGTGGATATGTCCTGCGGGTAAATAGCTGCGCCGATGGTTTCTACAAAGATC
GTTATGTTTATCGGCACTTTGCATCGGCCGCGCTCCCGATTCCGGAAGTGCTTGACAT
TGGGGAATTCAGCGAGAGCCTGACCTATTGCATCTCCCGCCGTGCACAGGGTGTCAC
GTTGCAAGACCTGCCTGAAACCGAACTGCCCGCTGTTCTGCAGCCGGTCGCGGAGG
CCATGGATGCGATCGCTGCGGCCGATCTTAGCCAGACGAGCGGGTTCGGCCCATTCG
GACCGCAAGGAATCGGTCAATACACTACATGGCGTGATTTCATATGCGCGATTGCTG
ATCCCCATGTGTATCACTGGCAAACTGTGATGGACGACACCGTCAGTGCGTCCGTCG
CGCAGGCTCTCGATGAGCTGATGCTTTGGGCCGAGGACTGCCCCGAAGTCCGGCAC
CTCGTGCACGCGGATTTCGGCTCCAACAATGTCCTGACGGACAATGGCCGCATAACA
GCGGTCATTGACTGGAGCGAGGCGATGTTCGGGGATTCCCAATACGAGGTCGCCAA
CATCTTCTTCTGGAGGCCGTGGTTGGCTTGTATGGAGCAGCAGACGCGCTACTTCGA
GCGGAGGCATCCGGAGCTTGCAGGATCGCCGCGGCTCCGGGCGTATATGCTCCGCA
TTGGTCTTGACCAACTCTATCAGAGCTTGGTTGACGGCAATTTCGATGATGCAGCTT
GGGCGCAGGGTCGATGCGACGCAATCGTCCGATCCGGAGCCGGGACTGTCGGGCGT
ACACAAATCGCCCGCAGAAGCGCGGCCGTCTGGACCGATGGCTGTGTAGAAGTACT
CGCCGATAGTGGAAACCGACGCCCCAGCACTCGTCCGAGGGCAAAGGAATAGAGCG
CGGGGATCTCATGCTGGAGTTCTTCGCCCACCCCAACTTGTTTATTGCAGCTTATAAT
GGTTACAAATAAAGCAATAGCATCACAAATTTCACAAATAAAGCATTTTTTTCACTG
CATTCTAGTTGTGGTTTGTCCAAACTCATCAATGTATCTTATCATGTCTGTAGctGATg
tATAcCTAggATCCGGCCGGccTGCAggTGTCCTCACAGGAACGAAGTCCCTAAAGAAA
CAGTGGCAGCCAGGTTTAGCCCCGGAATTGACTGGATTCCTTTTTAGGGCCCATTGG
TATGGCTTTTTCCCCGTATCCCCCCAGGTGTCTGCAGGCTCAAAGAGCAGCGAGAAG
CGTTCAGAGGAAAGCGATCCCGTGCCACCTTCCCCGTGCCCGGGCTGTCCCCGCACG
CTGCCGGCTCGGGGATGCGGGGGAGCGCCGGACCGGAGCGGAGCCCCGGGCGGC
TCGCTGCTGCCCCCTAGCGGGGAGGGACGTAATTACATCCCTGGGGGCTTTGGGGG
GGGGCTGTCCCTCTAGAGCGGCCGCCACCGCGGTGGAGCTCCAGCTTTTGTTCCCTT
TAGTGAGGGTTAATTAGATCTTAATACGACTCACTATAGGGCGAATTGGGTACCGGG
CCCCCCCTCGAGGTCGACGGTATCGATAAGCTTGATATCTATAACAAGAAAATATAT
ATATAATAAGTTATCACGTAAGTAGAACATGAAATAACAATATAATTATCGTATGAG
TTAAATCTTAAAAGTCACGTAAAAGATAATCATGCGTCATTTTGACTCACGCGGTCG
TTATAGTTCAAAATCAGTGACACTTACCGCATTGACAAGCACGCCTCACGGGAGCTC
CAAGCGGCGACTGAGATGTCCTAAATGCACAGCGACGGATTCGCGCTATTTAGAAA
GAGAGAGCAATATTTCAAGAATGCATGCGTCAATTTTACGCAGACTATCTTTCTAGG
GTTAATCTAGCTGCATCAGGATCATATCGTCGGGTCTTTTTTCCGGCTCAGTCATCGC
CCAAGCTGGCGCTATCTGGGCATCGGGGAGGAAGAAGCCCGTGCCTTTTCCCGCGA
GGTTGAAGCGGCATGGAAAGAGTTTGCCGAGGATGACTGCTGCTGCATTGACGTTG
AGCGAAAACGCACGTTTACCATGATGATTCGGGAAGGTGTGGCCATGCACGCCTTTA
ACGGTGAACTGTTCGTTCAGGCCACCTGGGATACCAGTTCGTCGCGGCTTTTCCGGA
CACAGTTCCGGATGGTCAGCCCGAAGCGCATCAGCAACCCGAACAATACCGGCGAC
```

-continued

```
AGCCGGAACTGCCGTGCCGGTGTGCAGATTAATGACAGCGGTGCGGCGCTGGGATA

TTACGTCAGCGAGGACGGGTATCCTGGCTGGATGCCGCAGAAATGGACATGGATAC

CCCGTGAGTTACCCGGCGGGCGCGCTTGGCGTAATCATGGTCATAGCTGTTTCCTGT

GTGAAATTGTTATCCGCTCACAATTCCACACAACATACGAGCCGGAAGCATAAAGT

GTAAAGCCTGGGGTGCCTAATGAGTGAGCTAACTCACATTAATTGCGTTGCGCTCAC

TGCCCGCTTTCCAGTCGGGAAACCTGTCGTGCCAGCTGCATTAATGAATCGGCCAAC

GCGCGGGGAGAGGCGGTTTGCGTATTGGGCGCTCTTCCGCTTCCTCGCTCACTGACT

CGCTGCGCTCGGTCGTTCGGCTGCGGCGAGCGGTATCAGCTCACTCAAAGGCGGTA

ATACGGTTATCCACAGAATCAGGGGATAACGCAGGAAAGAACATGTGAGCAAAAG

GCCAGCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCGCTC

TCCTGTTCCGACCCTGCCGCTTACCGGATACCTGTCCGCCTTTCTCCCTTCGGGAAGC

GTGGCGCTTTCTCATAGCTCACGCTGTAGGTATCTCAGTTCGGTGTAGGTCGTTCGCT

CCAAGCTGGGCTGTGTGCACGAACCCCCCGTTCAGCCCGACCGCTGCGCCTTATCCG

GTAACTATCGTCTTGAGTCCAACCCGGTAAGACACGACTTATCGCCACTGGCAGCAG

CCACTGGTAACAGGATTAGCAGAGCGAGGTATGTAGGCGGTGCTACAGAGTTCTTG

AAGTGGTGGCCTAACTACGGCTACACTAGAAGGACAGTATTTGGTATCTGCGCTCTG

CTGAAGCCAGTTACCTTCGGAAAAAGAGTTGGTAGCTCTTGATCCGGCAAACAAAC

CACCGCTGGTAGCGGTGGTTTTTTTGTTTGCAAGCAGCAGATTACGCGCAGAAAAAA

AGGATCTCAAGAAGATCCTTTGATCTTTTCTACGGGGTCTGACGCTCAGTGGAACGA

AAACTCACGTTAAGGGATTTTGGTCATGAGATTATCAAAAAGGATCTTCACCTAGAT

CCTTTTAAATTAAAAATGAAGTTTTAAATCAATCTAAAGTATATATGAGTAAACTTG

GTCTGACAGTTACCAATGCTTAATCAGTGAGGCACCTATCTCAGCGATCTGTCTATTT

CGTTCATCCATAGTTGCCTGACTCCCCGTCGTGTAGATAACTACGATACGGGAGGGC

TTACCATCTGGCCCCAGTGCTGCAATGATACCGCGAGACCCACGCTCACCGGCTCCA

GATTTATCAGCAATAAACCAGCCAGCCGGAAGGGCCGAGCGCAGAAGTGGTCCTGC

AACTTTATCCGCCTCCATCCAGTCTATTAATTGTTGCCGGGAAGCTAGAGTAAGTAG

TTCGCCAGTTAATAGTTTGCGCAACGTTGTTGCCATTGCTACAGGCATCGTGGTGTC

ACGCTCGTCGTTTGGTATGGCTTCATTCAGCTCCGGTTCCCAACGATCAAGGCGAGT

TACATGATCCCCCATGTTGTGCAAAAAAGCGGTTAGCTCCTTCGGTCCTCCGATCGT

TGTCAGAAGTAAGTTGGCCGCAGTGTTATCACTCATGGTTATGGCAGCACTGCATAA

TTCTCTTACTGTCATGCCATCCGTAAGATGCTTTTCTGTGACTGGTGAGTACTCAACC

AAGTCATTCTGAGAATAGTGTATGCGGCGACCGAGTTGCTCTTGCCCGGCGTCAATA

CGGGATAATACCGCGCCACATAGCAGAACTTTAAAAGTGCTCATCATTGGAAAACG

TTCTTCGGGGCGAAAACTCTCAAGGATCTTACCGCTGTTGAGATCCAGTTCGATGTA

ACCCACTCGTGCACCCAACTGATCTTCAGCATCTTTTACTTTCACCAGCGTTTCTGGG

TGAGCAAAAACAGGAAGGCAAAATGCCGCAAAAAAGGGAATAAGGGCGACACGGA

AATGTTGAATACTCAT
```

Example 5: Performance of AAV Stable Producer Cell Lines

Figure 7:
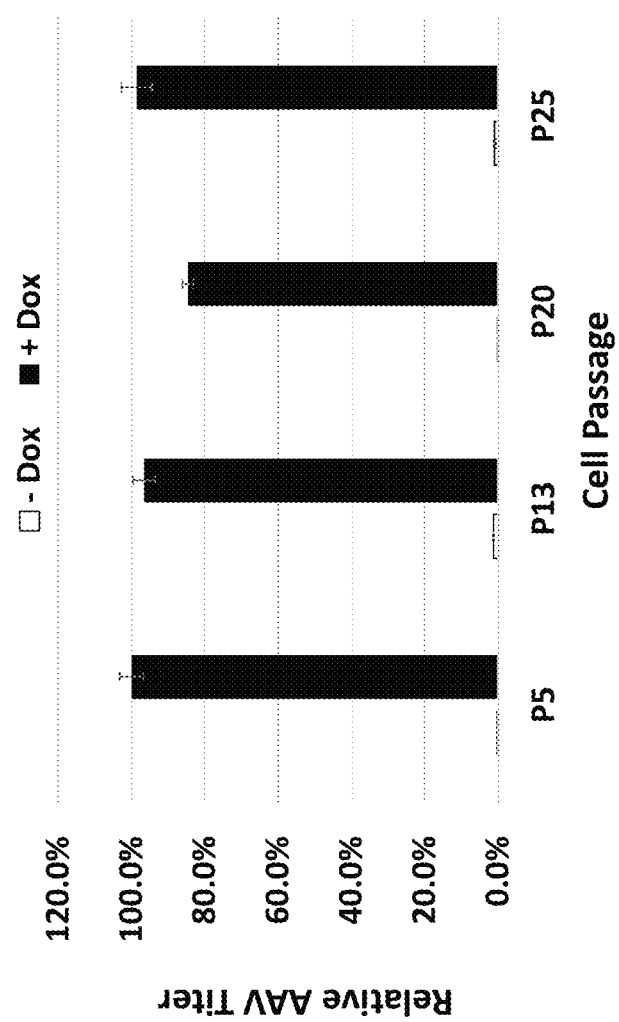
FIG. 7 shows the results of AAV titers using the Helper, Rep and Cap-GOI vectors, in accordance with embodiments hereof.

To generate stable AAV producer cell lines, one transposon from each group of iHelper, iRep and iCap-GOI was used to integrate into the genome of stable HEK293-TetR-KRAB C20 cell lines through a "cut and paste" mechanism by the co-transfection of these three transposon plasmids with mRNA encoding super piggyBac transposase (SPB-100). After transfection, three antibiotics including puromycin, blasticidin and hygromycin were added into the cell culture medium to select the transposon integrated cells. After stable cell pool generation and screening, one highly productive cell pool was selected to monitor the long-term stability of cells for AAV productivity. The suspension pool was left untreated or induced by doxycycline from cell passage 5 to passage 25 over three months. As shown in FIG. 7, the productivity of polyclonal pool of AAV producer cell line is stable for 25 passages upon induction by Dox. AAV production without Dox induction showed extremely low basal/leaky levels of AAVs.

Figure 8:
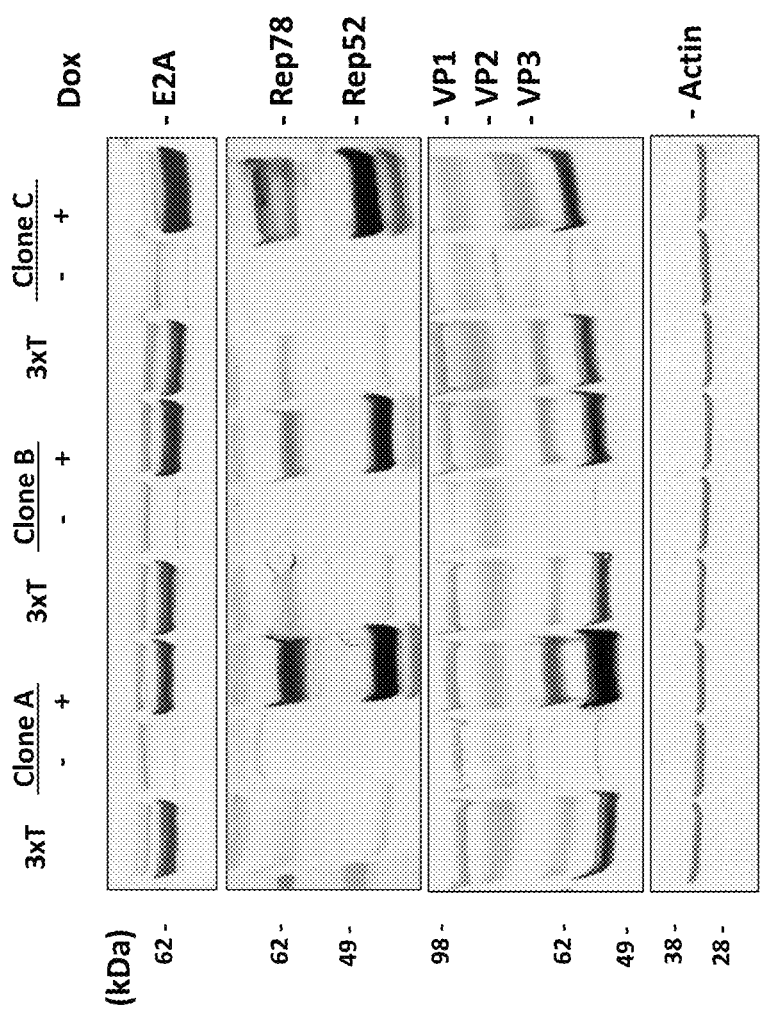
FIG. 8 shows a Western Blot image of the expression of helper, Rep and Cap proteins in accordance with embodiments hereof.

To evaluate the performance of AAV stable producer cell lines, multiple single cell clones were isolated by single cell printing and expanded for testing. First, the viral protein expression was evaluated by western blot analysis. Top three clonal cells (Clone A, B and C) were uninduced or induced by doxycycline for AAV production. Whole cell lysates were harvested three days post induction and prepared for the Western blot analysis. The whole cell lysate produced from a triple plasmid transfection process was used as positive control. The results show the robust induction of protein expression of helper, Rep and Cap genes in these clonal AAV producer cell lines, at the level similar or higher than the control samples, while showing undetectable level of leakiness protein expression in uninduced cells (See FIG. 8).

Figure 9:
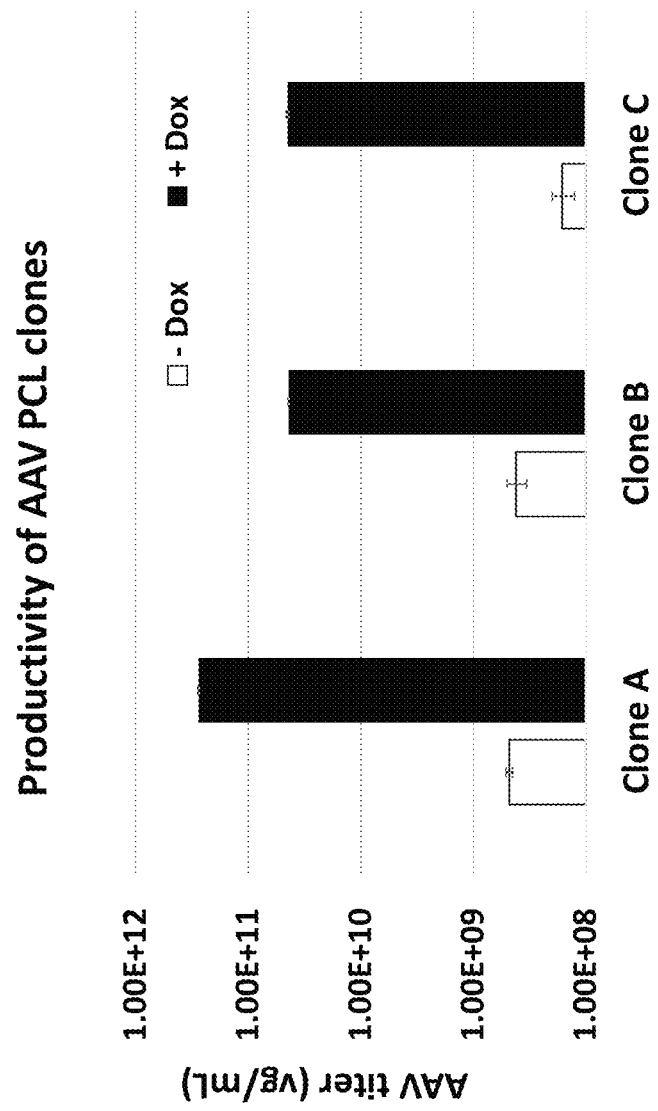
FIG. 9 shows the results of AAV production in 3 Liter single-use bioreactors in accordance with embodiments hereof.

The AAV productivity of the top three clones expressing Green Fluorescent Protein (GFP), a gene of interest, was examined in 3 Liter single-use bioreactors. The AAV genomic titer by ddPCR titer assay showed strong induction of AAV production in all clones in the range from $4.3 \times 10^{10}$ vg/mL to $2.8 \times 10^{11}$ vg/mL on day 5 harvest, which was comparable or higher than the AAV productivity using conventional triple transfection method (See FIG. 9).

Figure 10:
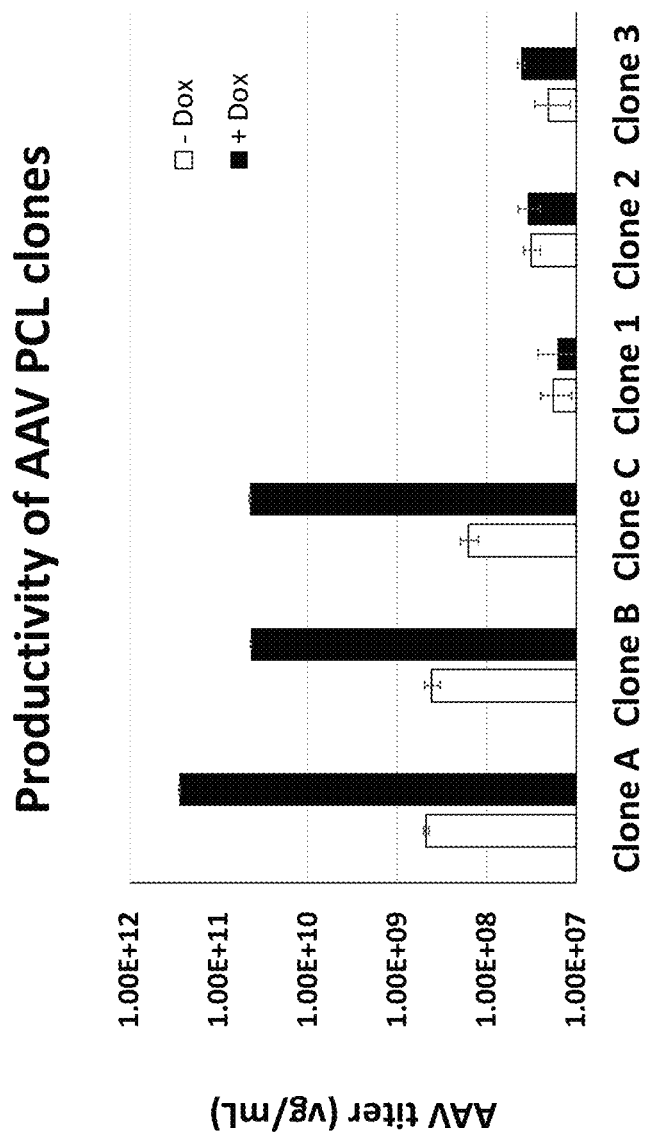
FIG. 10 shows comparative results of AAV production of PCL clones.

The productivity of Clones A, B and C expressing GFP was further compared to three representative clonal cells (Clone 1, Clone 2 and Clone 3) uninduced or induced by doxycycline. Clone 1, Clone 2 and Clone 3 comprise nucleic acid sequences disclosed in U.S. Pat. No. 11,739,347 B2 that were designed using E2A and E4 genes under control of an inducible CMV promoter, VA RNA under control of an H1 promoter, and Rep and Cap genes under control of a native promoter. The AAV productivity of Clones A, B and C was significantly higher than Clone 1, Clone 2 and Clone 3 after Dox induction (See FIG. 10).

Figure 11:
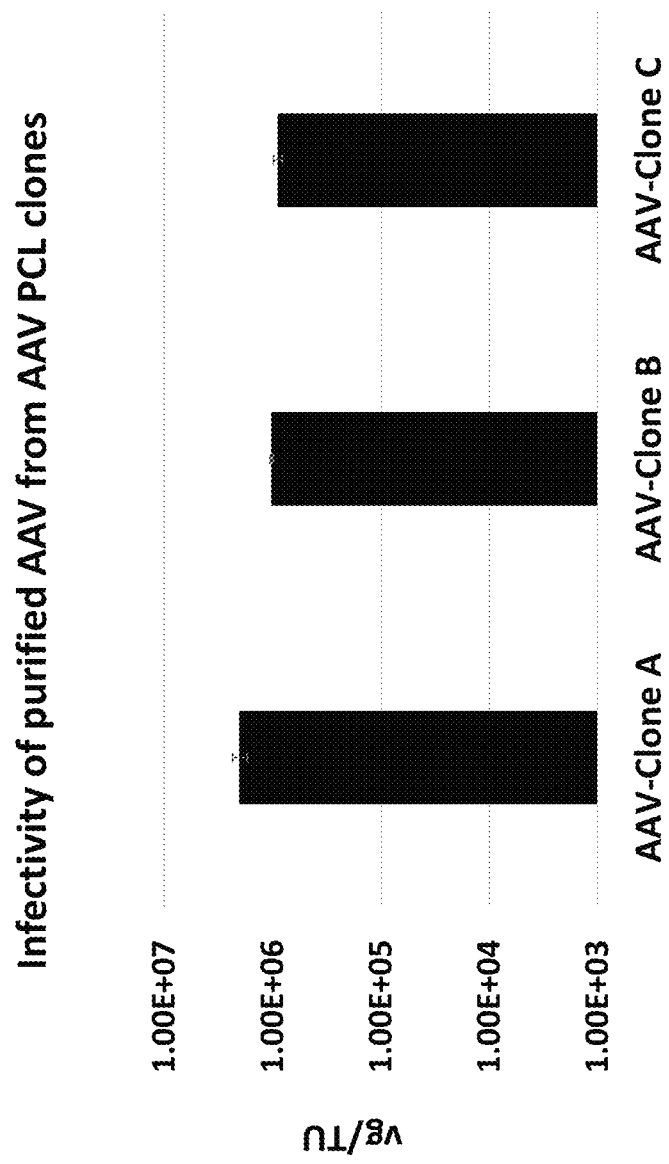
FIG. 11 shows the results of cell-based infectivity and potency assay of AAVs produced in accordance with embodiments hereof.

The functionality of the AAV produced from the bioreactors was tested by the cell-based infectivity and potency assay. The purified AAV was serially diluted and transduced to HT1080 cells in 96-well plates. The percentage of GFP-positive cells from transduced AAV was quantified by flow cytometry analysis and used to calculate the transduction unit (TU). The normalized viral genome per TU result suggests that the AAV produced from AAV producer cell lines are functional in infecting cells and expressing a gene of interest, such as GFP (See FIG. 11).

It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

All references cited herein, including patents, patent applications, papers, textbooks and the like, and the references cited therein, to the extent that they are not already, are hereby incorporated herein by reference in their entirety.

---

The invention claimed is:
1. An isolated nucleic acid molecule operably comprising:
a. a first transposon-specific inverted terminal repeat (ITR);
b. a first inducible promoter comprising a native E2A promoter and two tetracycline operator sequences (a first $TetO_2$ sequence);
c. an E2A coding sequence under control of the first inducible promoter;
d. a viral associated (VA) non-coding RNA under control of a second inducible promoter comprising a native VA promoter or a constitutive promoter comprising a native VA promoter;
e. a third inducible promoter comprising a promoter native to an E4 coding sequence and a second $TetO_2$ sequence;
f. the E4 coding sequence under control of the third inducible promoter;
g. an antibiotic resistance gene; and
h. a second ITR,
wherein the isolated nucleic acid molecule does not include a Rep gene and/or Cap gene.

2. The nucleic acid molecule of claim 1, wherein the nucleic acid molecule further comprises a core insulator sequence inserted between the E4 coding sequence and the antibiotic resistance gene.

3. The nucleic acid molecule of claim 1, further comprising a core insulator sequence inserted between the first ITR and the first inducible promoter.

* * * * *

SEQUENCE LISTING

```
Sequence total quantity: 34
SEQ ID NO: 1            moltype = DNA  length = 7147
FEATURE                 Location/Qualifiers
misc_feature            1..7147
                        note = Synthetic: pcDNA-TetR-Ins
source                  1..7147
                        mol_type = other DNA
                        organism = synthetic construct
SEQUENCE: 1
gacggatcgg gagatctgag ctcacgggga cagcccccccc ccaaagcccc cagggatgta    60
attacgtccc tcccccgcta gggggcagca gcgagccgcc cggggctccg ctccggtccg   120
gcgctccccc cgcatccccg agccggcagc gtgcgggac agcccgggca cggggaaggt   180
ggcacgggat cgctttcctc tgaacgcttc tcgctgctct ttgagcctgc agacacctgg   240
ggggatacgg ggaaaaagct ttaggctgaa agagagattt agaatgacag aatcatagaa   300
cggcctgggt tgcaaaggag cacagtgctc atccagatcc aacccctgc tatgtgcagg    360
gtcatcaacc agcagcccag gctgcccaga gccacatcca gcctggcctt gaatgcctgc   420
aggcccgatc ccctatggtc gactctcagt acaatctgct ctgatgccgc atagttaagc   480
cagtatctgc tccctgcttg tgtgttggag gtcgctgagt agtgcgcgag caaaatttaa   540
gctacaacaa ggcaaggctt gaccgacaat tgcatgaaga atctgcttag ggttaggcgt   600
tttgcgctgc ttcgcgatgt acgggccaga tatacgcgtt gacattgatt attgactagt   660
tattaatagt aatcaattac ggggtcatta gttcatagcc catatatgga gttccgcgtt   720
acataactta cggtaaatgg cccgcctggc tgaccgccca acgaccccg cccattgacg    780
tcaataatga cgtatgttcc catagtaacg ccaatagggaa ctttccattg acgtcaatgg   840
gtggactatt tacggtaaac tgcccacttg gcagtacatc aagtgtatca tatgccaagt   900
acgcccccta ttgacgtcaa tgacggtaaa tggcccgcct ggcattatgc ccagtacatg   960
```

```
accttatggg actttcctac ttggcagtac atctacgtat tagtcatcgc tattaccatg 1020
gtgatgcggt tttggcagta catcaatggg cgtggatagc ggtttgactc acggggattt 1080
ccaagtctcc accccattga cgtcaatggg agtttgtttt ggcaccaaaa tcaacgggac 1140
tttccaaaat gtcgtaacaa ctccgcccca ttgacgcaaa tgggcggtag gcgtgtacgg 1200
tgggaggtct atataagcag agctctctgg ctaactagag aacccactgc ttactggctt 1260
atcgaaatta atacgactca ctataggggag acccaagctg gctagcgttt aaacttaagc 1320
tttctgtgag tttggggacc cttgattgtt cttttctttt cgctattgta aaattcatgt 1380
tatatgagg gggcaaagtt ttcagggtgt tgtttagaat gggaagatgt cccttgtatc 1440
accatggacc ctcatgataa ttttgtttct ttcactttct actctgttga caaccattgt 1500
ctcctcttat tttcttttca ttttctgtaa cttttcgtt aaactttagc ttgcatttgt 1560
aacgaatttt taaattcact tttgtttatt tgtcagattg taagtacttt ctctaatcac 1620
tttttttca aggcaatcag ggtatattat attgtacttc agcacagttt tagagaacaa 1680
ttgttataat taaatgataa ggtagaatat ttctgcatat aaattctggc tggcgtggaa 1740
atattcttat tggtagaaac aactacatcc tggtcatcat cctgcctttc tctttatggt 1800
tacaatgata tacactgttt gagatgagga taaaatactc tgagtccaaa ccgggccct 1860
ctgctaacca tgttcatgcc ttcttctttt tcctacagct cctgggcaac gtgctggtta 1920
ttgtgctgtc tcatcatttt ggcaaagaat tgtaatacga ctcactatag ggcgagccac 1980
catggcctaga ttagataaaa gtaaagtgat taacagcgca ttagagctgc ttaatgaggt 2040
cggaatcgaa ggtttaacaa cccgtaaact cgcccagaag ctaggtgtag agcagcctac 2100
attgtattgg catgtaaaaa ataagcgggc tttgctcgac gccttagcca ttgagatgtt 2160
agataggcac catactcact tttgcccttt agaaggggaa agctggcaag atttttttacg 2220
taataacgct aaaagtttta gatgtgctttt actaagtcat cgcgatggga caaaagtaca 2280
tttaggtaca cggcctacag aaaaacagta tgaaactctc gaaaatcaat tagccttttt 2340
atgccaacaa ggttttttcac tagagaatgc cttatatgca ctcagcgccg tggggcattt 2400
tactttaggt tgcgtattgg aagatcaaga gcatcaagtc gctaaagaag aaagggaaac 2460
acctactact gatagtatgc cgccattatt acgacaagct atcgaattat ttgatcacca 2520
aggtgcagag ccagccttct tattcggcct tgaattgatc atatgcggat tagaaaaaca 2580
acttaaatgt gaaagtgggt ccccaaaaaa gaagagaaag gtcgacggcg gtggttcagt 2640
ttaagcgtac agcgggatcc actagtccag tgtggtggaa ttctgcagat atccagcaca 2700
gtggcggccg ctcgagtcta gagggcccgt ttaaacccgc tgatcagcct cgactgtgcc 2760
ttctagttgc cagccatctg ttgtttgccc ctccccgtg ccttccttga ccctggaagg 2820
tgccactccc actgtccttt cctaataaaa tgaggaaatt gcatcgcatt gtctgagtag 2880
gtgtcattct attctggggg gtggggtggg caggacagc aagggggagg attgggaaga 2940
caatagcagg catgctgggg atgcggtggg ctctgaggcgg aaagaaccag 3000
ctggggctcc aggggggtatc cccacgcgcc ctgtagcggc gcattaagcg cggcgggtgt 3060
ggtggttacg cgcagcgtga ccgctacact tgccagcgcc ctagcgcccg ctcctttcgc 3120
tttcttccct tcctttctcg ccacgttcgc cggctttccc cgtcaagctc taaatcgggg 3180
catccctta gggttccgat ttagtgcttt acggcaccctc gaccccaaaa aacttgatta 3240
gggtgatggt tcacgtagtg ggccatcgcc ctgatagacg gtttttcgcc ctttgacgtt 3300
ggagtccacg ttctttaata gtggactctt gttccaaact ggaacaacac tcaaccctat 3360
ctcggtctat tcttttgatt tataagggat tttgggggatt tcggcctatt ggttaaaaaa 3420
tgagctgatt taacaaaaat ttaacgcgaa ttaattctgt ggaatgtgtg tcagttaggg 3480
tgtggaaagt ccccaggctc cccaggcagg cagaagtatg caaagcatgc atctcaatta 3540
gtcagcaacc aggtgtggaa agtccccagg ctccccagca ggcagaagta tgcaaagcat 3600
gcatctcaat tagtcagcaa ccatagtccc gcccctaact ccgcccatcc cgcccctaac 3660
tccgcccagt tccgcccatt ctccgcccca tggctgacta ttttttttta tttatgcaga 3720
ggccgaggcc gcctctgcct ctgagctatt ccagaagtag tgaggaggct tttttggagg 3780
cctaggcttt tgcaaaaagc tcccgggagc ttgtatatcc attttcggat ctgatcagca 3840
cgtgttgaca attaatcatc ggcatagtat atcggcatag tataatacga caaggtgagg 3900
aactaaacca tggccaagtt gaccagtgcc gttccggtgc tcaccgcgcg cgacgtcgcc 3960
ggagcggtcg agttctggac cgaccggctc gggttctccc gggacttcgt ggaggacgac 4020
ttcgccggtg tggtccggga cgacgtgacc ctgttcatca gcgcggtcca ggaccaggtg 4080
gtgccggaca cacccctggc ctgggtgtgg gtgcgcggcc tggacgagct gtacgccgag 4140
tggtcggagg tcgtgtccac gaacttccgg gacgcctccg gccggccat gaccgagatc 4200
ggcgagcagc cgtgggggcg ggagttcgcc ctgcgcgacc cggccggcaa ctgcgtgcac 4260
ttcgtggccg aggagcagga ctgacacgtg ctacgagatt tcgattccac cgccgccttc 4320
tatgaaaggt tgggcttcgg aatcgttttc cgggacgccg gctggatgat cctccagcgc 4380
ggggatctca tgctggagtt cttcgcccac cccaacttgt ttattgcagc ttataatggt 4440
tacaaataaa gcaatagcat cacaaatttc acaaataaag cattttttc actgcattct 4500
agttgtggtt tgtccaaact catcaatgta tcttatcatg tctgtatacc gtcgacctct 4560
agctagagct tggcgtaatc atggtcatag ctgtttcctg tgtgaaattg ttatccgctc 4620
acaattccac acaacatacg agccggaagc ataaagtgta aagcctgggg tgcctaatga 4680
gtgagctaac tcacattaat tgcgttgcgc tcactgcccg ctttccagtc gggaaacctg 4740
tcgtgccagc tgcattaatg aatcggccaa cgcgcgggga gaggcggttt gcgtattggg 4800
cgctcttccg cttcctcgct cactgactcg ctgcgctcgg tcgttcggct gcggcgagcg 4860
gtatcagctc actcaaaggc ggtaatacgg ttatccacag aatcagggga taacgcagga 4920
aagaagagctc acgggacag cccccccca agcccccag ggatgtaatt acgtccctcc 4980
cccgctaggg ggcagcagcg agccgcccgg ggctccgctc cggtccggcg ctccccccgc 5040
atccccgagc cggcagcgtg cggggacagc ccgggtgtgg ggaaggtgcc acggagtcgg 5100
tttcctctga acgcttctcg ctgctctttg agcctgcaga cacctgggg gatacgggga 5160
aaaagcttta ggctgaaaga gagatttaga atgacagaat catagaacgg cctgggttgc 5220
aaaggagcac agtgctcatc cagatccaac ccctgctat gtgcagggtc atcaaccagc 5280
agcccaggct gcccagagcc acatccagcc tggccttgaa tgcctgcagg acatgtgagc 5340
aaaaggccag caaaaggcca ggaaccgtaa aaaggccgcg ttgctgggcgt ttttccatag 5400
gctccgcccc cctgacgagc atcacaaaaa tcgacgctca agtcagaggt ggcgaaaccc 5460
gacaggacta taaagatacc aggcgttttcc cctggaagc tccctcgtgc gctctcctgt 5520
tccgaccctg ccgcttaccg gatacctgtc cgcctttctc ccttcgggaa gcgtggcgct 5580
ttctcaatgc tcacgctgta ggtatctcag ttcggtgtag tcgttcgct ccaagctggg 5640
ctgtgtgcac gaaccccccg ttcagcccga ccgctgcgcc ttatccggta actatcgtct 5700
```

-continued

```
tgagtccaac ccggtaagac acgacttatc gccactggca gcagccactg gtaacaggat 5760
tagcagagcg aggtatgtag gcggtgctac agagttcttg aagtggtggc ctaactacgg 5820
ctacactaga aggacagtat ttggtatctg cgctctgctg aagccagtta ccttcggaaa 5880
aagagttggt agctcttgat ccggcaaaca aaccaccgct ggtagcggtg gttttttttgt 5940
ttgcaagcag cagattacgc gcagaaaaaa aggatccaa gaagatcctt tgatcttttc 6000
tacgggtct gacgctcagt ggaacgaaaa ctcacgttaa gggattttgg tcatgagatt 6060
atcaaaaagg atcttcacct agatcctttt aaattaaaaa tgaagtttta aatcaatcta 6120
aagtatatat gagtaaactt ggtctgacag ttaccaatgc ttaatcagtg aggcacctat 6180
ctcagcgatc tgtctatttc gttcatccat agttgcctga ctccccgtcg tgtagataac 6240
tacgatacgg gagggcttac catctgtgcc cagtgctgca atgataccgc gagacccacg 6300
ctcaccggct ccagatttat cagcaataaa ccagccagcc ggaagggccg agcgcagaag 6360
tggtcctgca actttatccg cctccatcca gtctattaat tgttgccggg aagctagagt 6420
aagtagttcg ccagttaata gtttgcgcaa cgttgttgcc attgctacag gcatcgtggt 6480
gtcacgctcg tcgtttggta tggcttcatt cagctccggt tcccaacgat caaggcgagt 6540
tacatgatcc cccatgttgt gcaaaaaagc ggttagctcc ttcggtcctc cgatcgttgt 6600
cagaagtaag ttggccgcag tgttatcact catggttatg gcagcactgc ataattctct 6660
tactgtcatg ccatccgtaa gatgcttttc tgtgactggt gagtactcaa ccaagtcatt 6720
ctgagaatag tgtatgcggc gaccgagttg ctcttgcccg gcgtcaatac gggataaatac 6780
cgcgccacat agcagaactt taaaagtgct catcattgga aaacgttctt cggggcgaaa 6840
actctcaagg atcttaccgc tgttgagatc cagttcgatg taacccactc gtgcacccaa 6900
ctgatcttca gcatctttta ctttcaccag cgtttctggg tgagcaaaaa caggaaggca 6960
aaatgccgca aaaaagggaa taagggcgac acggaaatgt tgaatactca tactcttcct 7020
ttttcaatat tattgaagca tttatcaggg ttattgtctc atgagcggat acatatttga 7080
atgtatttag aaaaataaac aaataggggt tccgcgcaca tttccccgaa aagtgccacc 7140
tgacgtc                                                            7147
```

SEQ ID NO: 2        moltype = DNA  length = 7493
FEATURE             Location/Qualifiers
misc_feature       1..7493
                    note = Synthetic: pcDNA-TetR-KRAB-Ins
source              1..7493
                    mol_type = other DNA
                    organism = synthetic construct
SEQUENCE: 2

```
gacggatcgg gagatctgag ctcacgggga cagccccccc ccaaagcccc cagggatgta 60
attacgtccc tccccgcta ggggggcagca gcgagccgcc cggggctccg ctccggtccg 120
gcgctccccc cgcatcccg agccggcagc gtgcggggac agcccgggca cggggaaggt 180
ggcacgggat cgctttcctc tgaacgcttc tcgctgctct ttgagcctgc agacacctgg 240
ggggatacgg ggaaaaagct ttaggctgaa agagagattt agaatgacag aatcatagaa 300
cggcctgggt tgcaaaggag cacagtgctc atccagatcc aacccctgc tatgtgcagg 360
gtcatcaacc agcagcccag gctgccagga gccacatcca gcctggcctt gaatgcctgc 420
aggcccgatc ccctatggtc gactctcagt acaatctgct ctgatgccgc atagttaagc 480
cagtatctgc tccctgcttg tgtgttggag gtcgctagt agtgcgcgaa caaaatttaa 540
gctacaacaa ggcaaggctt gaccgacaat tgcatgaaga atctgcttag ggttaggcgt 600
tttgcgctgc ttcgcgatgt acgggccaga tatacgcgtt gacattgatt attgactagt 660
tattaatagt aatcaattac ggggtcatta gttcatagcc catatatgga gttccgcgtt 720
acataactta cggtaaatgg cccgcctggc tgaccgccca acgaccccccg cccattgacg 780
tcaataatga cgtatgttcc catagtaacg ccaataggga ctttccattg acgtcaatgg 840
gtggactatt tacggtaaac tgcccacttg gcagtacatc aagtgtatca tatgccaagt 900
acgccccta ttgacgtcaa tgacggtaaa tggcccgcct ggcattatgc ccagtacatg 960
accttatggg actttcctac ttggcagtac atctacgtat tagtcatcgc tattaccatg 1020
gtgatgcggt tttggcagta catcaatggg cgtggatagc ggtttgactc acggggattt 1080
ccaagtctcc accccattga cgtcaatggg agtttgtttt ggcaccaaaa tcaacgggac 1140
tttccaaaat gtcgtaacaa ctccgcccca ttgacgcaaa tgggcggtag gcgtgtacgg 1200
tgggaggtct atataagcag agctctctgg ctaactagag aacccactgc ttactggctt 1260
atcgaaatta atacgactca ctataggga acccaagctg gctagcgttt aaacttaagc 1320
tttctgtgag tttggggacc cttgattgtt ctttctttt cgctattgta aaattcatgt 1380
tatatggagg gggcaaagtt ttcagggtgt tgtttagaat gggaagatgt cccttgtatc 1440
accatggacc ctcatgataa ttttgttttc ttcactttct actctgttga caaccattgt 1500
ctcctcttat tttctttttca ttttctgtaa cttttcgtt aaactttagc ttgcatttgt 1560
aacgaatttt taaattcact tttgtttatt tgtcagattg taagtacttt ctctaatcac 1620
ttttttttca aggcaatcag ggtatattat attgtacttc agcacagttt tagagaacaa 1680
ttgttataat taaatgataa ggtagaatat ttctgcatat aaattctggc tggcgtggaa 1740
atattcttat tggtagaaac aactacatcc tggtcatcat cctgcctttc tctttatggt 1800
tacaatgata tacactgttt gagatgagga taaatactc tgagtccaaa ccgggcccct 1860
ctgctaacca tgttcatgcc ttcttctttt cctacagct cctgggcaac gtgctggtta 1920
ttgtgctgtc tcatcatttt ggcaaagaat tgtaatacga ctcactatag ggcgagcac 1980
catggctaga ttagataaaa gtaaagtgat taacagcgca ttagagctgc ttaatgaggt 2040
cggaatcgaa ggtttaacaa cccgtaaact cgcccagaag ctaggtgtag agcagcctg 2100
attgtattgg catgtaaaaa ataagcgggc tttgctcgac gccttagcca ttgagatgtt 2160
agataggcac catactcact tttgcccttt agaaggggaa agctggcaag atttttttacg 2220
taataacgct aaaagtttta gatgtgcttt actaagtcat cgcgatggag caaaagtaca 2280
tttaggtaca cggcctacag aaaaacagta tgaaactctc gaaatcaat tagccttttt 2340
atgccaacaa ggttttctcac tagagaatgc cttatatgca ctcagcgcg tggggcattt 2400
tactttaggt tgcgtattgg aagatcaaga gcatcaagtc gctaaagaag aaagggaaac 2460
acctactact gatagtatgc cgccattatt acgacaagct atcgaattat tgatcacca 2520
aggtgcagag ccagccttct tattcggcct tgaattgatc atatgcggat tagaaaaaca 2580
acttaaatgt gaaagtgggt cccccaaaaa gaagagaaag gtcgacggcg tggtgctttt 2640
gtctcctcag cactctgctg tcactcaagg aagtatcatc aagaacaagg agggcatgga 2700
```

```
tgctaagtca ctaactgcct ggtcccggac actggtgacc ttcaaggatg tatttgtgga   2760
cttcaccagg gaggagtgga agctgctgga cactgctcag cagatcgtgt acagaaatgt   2820
gatgctggag aactataaga acctggtttc cttgggttat cagcttacta agccagatgt   2880
gatcctccgg ttgagaagg gagaagagcc ctggctggtg gagagagaaa ttcaccaaga    2940
gacccatcct gattcagaga ctgcatttga aatcaaatca tcagtttaag cgtacagcgg   3000
ggatccacta gtccagtgtg gtggaattct gcagatatcc agcacagtgg cggccgctcg   3060
agtctagagg gcccgtttaa acccgctgat cagcctcgac tgtgccttct agttgccagc   3120
catctgttgt ttgcccctcc cccgtgcctt ccttgaccct ggaaggtgcc actcccactg   3180
tcctttccta ataaaatgag gaaattgcat cgcattgtct gagtaggtgt cattctattc   3240
tggggggtgg ggtggggcag gacagcaagg gggaggattg ggaagacaat agcaggcatg   3300
ctggggatgc ggtgggctct atggcttctg aggcggaaag aaccagctgg ggctctaggg   3360
ggtatcccca cgcgccctgt agcggcgcat taagcgcggc gggtgtggtg gttacgcgca   3420
gcgtgaccgc tacacttgcc agcgccctag cgcccgctcc tttcgctttc ttcccttcct   3480
ttctcgccac gttcgccggc tttccccgtc aagctctaaa tcggggcatc cctttagggt   3540
tccgatttag tgctttacgg cacctcgacc ccaaaaaact tgattagggt gatggttcac   3600
gtagtgggcc atcgccctga tagacggttt ttcgcccttt gacgttggag tccacgttct   3660
ttaatagtgg actcttgttc caaactggaa caacactcaa ccctatctcg gtctattctt   3720
ttgatttata agggattttg gggatttcgg cctattggtt aaaaaatgag ctgatttaac   3780
aaaaatttaa cgcgaattaa ttctgtggaa tgtgtgtcag ttagggtgtg aaagtcccc    3840
aggctcccca ggcaggcaga agtatgcaaa gcatgcatct caattagtca gcaaccaggt   3900
gtggaaagtc cccaggctcc ccagcaggca gaagtatgca aagcatgcat ctcaattagt   3960
cagcaaccat agtcccgccc ctaactccgc ccatcccgcc ctaactccg cccagttccg    4020
cccattctcc gccccatggc tgactaattt ttttttattta tgcagaggcc gaggccgcct   4080
ctgcctctga gctattccag aagtagtgag gaggcttttt tggaggccta ggcttttgca   4140
aaaagctccc gggagcttgt atatccattt tcggatctga tcagcacgtg ttgacaatta   4200
atcatcggca tagtatatcg gcatagtata atacgacaag gtgaggaact aaaccatggc   4260
caagttgacc agtgccgttc cggtgctcac cgcgcgcgac gtcgccgag cggtcgagtt    4320
ctggaccgac cggctcgggt tctcccggga cttcgtggag gacgacttcg ccggtgtggt   4380
ccgggacgac gtgaccctgt tcatcagcgc ggtccaggac caggtggtgc cggacaacac   4440
cctggcctgg gtgtgggtgc gcggcctgga cgagctgtac gccgagtcgt cggaggtcgt   4500
gtccacgaac ttcgggacg cctccggccc ggccatgacc gagatcggcg agcagccgtg    4560
ggggcgggag ttcgccctgc gcgacccggc cggcaactgc gtgcacttcg tggccgagga   4620
gcaggactga cacgtgctac gagatttcga ttccaccgcc gccttctatg aaaggttggg   4680
cttcggaatc gttttccggg acgccggctg gatgatcctc cagcgcgggg atctcatgct   4740
ggagttcttc gcccaccccca acttgtttat tgcagcttat aatggttaca aataaagcaa   4800
tagcatcaca aatttcacaa ataaagcatt tttttcactg cattctagtt gtggtttgtc   4860
caaactcatc aatgtatctt atcatgtctg tataccgtcg acctctagct agagcttggc   4920
gtaatcatgg tcatagctgt ttcctgtgtg aaattgttat ccgctcacaa ttccacacaa   4980
catacgagcc ggaagcataa agtgtaaagc ctggggtgcc taatgagtga gctaactcac   5040
attaattgcg ttgcgctcac tgcccgcttt ccagtcggga aacctgtcgt gccagctgca   5100
ttaatgaatc ggccaacgcg cggggagagg cggtttgcgt attgggcgct cttccgcttc   5160
ctcgctcact gactcgctgc gctcggtcgt tcggctgcgg cgagcggtat cagctcactc   5220
aaaggcggta atacggttat ccacagaatc agggataac gcaggaaaga agctcacgg     5280
ggacagcccc cccccaaagc ccccaggat gtaattacga ccctccccccg ctaggggca     5340
gcagcgagcc gcccggggct ccgctccggt ccggcgctcc ccccgcatcc ccgagccggc   5400
agcgtgcggg gacagcccgg gcacgggaa ggtggcacgg gatcgctttc ctctgaacgc     5460
ttctcgctgc tctttgagcc tgcagacacc tgggggata cggggaaaaa gctttaggct     5520
gaaagagaga tttagaatga cagaatcata gaacggcctg ggttgcaaag gagcacagtg   5580
ctcatccaga tccaaccccc tgctatgtgc agggcatca accagcagcc caggctgccc     5640
agagccacat ccagcctggc cttgaatgcc tgcaggacat gtgagcaaaa ggccagcaaa   5700
aggccaggaa ccgtaaaaag gccgcgttgc tggcgttttt ccataggctc cgccccctg     5760
acgagcatca caaaaatcga cgctcaagtc agaggtggcg aaacccgaca ggactataaa   5820
gataccaggc gtttccccct ggaagctccc tcgtgcgctc tcctgttccg accctgccgc   5880
ttaccggata cctgtccgcc tttctccctt cgggaagcgt ggcgctttct caatgctcac   5940
gctgtaggta tctcagttcg gtgtaggtcg ttcgctccaa gctgggctgt gtgcacgaac   6000
ccccccgttca gcccgaccgc tgcgccttat ccggtaacta tcgtcttgag tccaacccgg    6060
taagacacga cttatcgcca ctggcagcag ccactggtaa caggattagc agagcgaggt   6120
atgtaggcgg tgctacagag ttcttgaagt ggtggcctaa ctacggctac actagaagga   6180
cagtatttgg tatctgcgct ctgctgaagc cagttaccttt cggaaaaaga gttggtagct   6240
cttgatccgg caaacaaacc accgctggta gcggtggttt tttttgtttgc aagcagcaga   6300
ttacgcgcag aaaaaaagga tctcaagaag atccttttgat cttttctacg gggtctgacg   6360
ctcagtggaa cgaaaactca cgttaaggga ttttggtcat gagattatca aaaaggatct   6420
tcacctagat cctttttaaat taaaaatgaa gttttaaatc aatctaaagt atatatgagt   6480
aaacttggtc tgacagttac caatgcttaa tcagtgaggc acctatctca gcgatctgtc   6540
tatttcgttc atccatagtt gcctgactcc ccgtcgtgta gataactacg atacgggagg   6600
gcttaccatc tggccccagt gctgcaatga taccgcgaga cccacgctca ccggctccag   6660
atttatcagc aataaaccag ccagccgaaa gggccgagcg cagaagtggt cctgcaactt   6720
tatccgcctc catccagtct attaattgtt gccgggaagc tagagtaagt agttcgccag   6780
ttaatagttt gcgcaacgtt gttgccattg ctacaggcat cgtggtgtca cgctcgtcgt   6840
ttggtatggc ttcattcagc tccggttccc aacgatcaag gcgagttaca tgatcccca     6900
tgttgtgcaa aaaagcggtt agctccttcg gtcctccgat cgttgtcaga agtaagttgg   6960
ccgcagtgtt atcactcatg gttatggcag cactgcataa ttctcttact gtcatgccat   7020
ccgtaagatg cttttctgtg actggtgagt actcaaccaa gtcattctga atagtgta      7080
tgcggcgacc gagttgctct tgcccggcgt caatacggga taataccgcg ccacatagca   7140
gaactttaaa agtgctcatc attggaaaac gttcttcggg gcgaaaactc tcaaggatct   7200
taccgctgtt gagatccagt tcgatgtaac ccactcgtgc acccaactga tcttcagcat   7260
cttttacttt caccagcgtt tctgggtgag caaaaacagg aaggcaaaat gccgcaaaaa   7320
agggaataag ggcgacacgg aaatgttgaa tactcatact cttccttttt caatattatt   7380
gaagcattta tcagggttat tgtctcatga gcggatacat atttgaatgt atttagaaaa   7440
```

```
ataaacaaat aggggttccg cgcacatttc cccgaaaagt gccacctgac gtc         7493

SEQ ID NO: 3           moltype = DNA  length = 16549
FEATURE                Location/Qualifiers
misc_feature           1..16549
                       note = Synthetic: pPBBG-iHelper2.0-HA
source                 1..16549
                       mol_type = other DNA
                       organism = synthetic construct
SEQUENCE: 3
actcttcctt tttcaatatt attgaagcat ttatcagggt tattgtctca tgagcggata   60
catatttgaa tgtatttaga aaaataaaca aatagggtt ccgcgcacat ttccccgaaa    120
agtgccacct aaattgtaag cgttaatatt ttgttaaaat tcgcgttaaa ttttgttaa    180
atcagctcat ttttaacca ataggccgaa atcggcaaa tcccttataa atcaaaagaa    240
tagaccgaga taggggttgag tgttgttcca gtttggaaca agagtccact attaaagaac 300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttggtaa cgccagggtt tcccagtca   720
cgacgttgta aaacgacggc cagtgagcgc gcctcgttca ttcacgtttt tgaacccgtg  780
gaggacgggg agactcgcgg tgcaaatgtg ttttacagcg tgatgcagca gatgaagatg  840
ctcgacacgc tgcagaacac gcagctagat taacccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata  1020
ataaattcaa caaacaattt attatgttt attatttat taaaaaaaaa caaaaactca    1080
aaatttcttc tataaagtaa caaaactttt atcgaattcc tgcagcccgg gggatccact  1140
agttctagag ggacagcccc cccccaaagc cccagggat gtaattacgt ccctccccg    1200
ctagggggca gcagcgagcc gcccgggggct ccgctccggt ccggcgctcc ccccgcatcc  1260
ccgagccggc agcgtgcggg gacagcccgg gcacggggaa ggtggcacgg gatcgctttc  1320
ctctgaacgc ttctcgctgc tctttgagcc tgcagacacc tgggggata cggggaaaag   1380
gcctccaagg ccagcttccc acaataagtt gggtgaattt tggctcattc ctcctttcta  1440
taggattgag gtcagagctt tgtgatggga atctgtggga atgtgtgtca gttagggtgt  1500
ggaaagtccc gcgatcgcta gcgtttaaac ttaagcttgg taccgagctc ggatccacta  1560
gtccagtgtg gtggaattcc tgcttcgcga tgtacgggcc ggtacccaac tccatgctta  1620
acagtcccca ggtacagccc accctgcgtc gcaaccagga acagctctac agcttcctgg  1680
agcgccactc gccctacttc cgcagccaca gtgcgcagat taggagcgcc acttctttt   1740
gtcacttgaa aaacatgtaa aaataatgta ctaggagaca ctttcaataa aggcaaatgt  1800
ttttatttgt acactctcgg gtgattattt accccccacc cttgccgtct gcgccgttta  1860
aaaatcaaag gggttctgcc gcgcatcgct atgcgccact ggcagggaca cgttgcgata  1920
ctggtgttta gtgctccact taaactcagg cacaaccatc gcgggcagct cgtgtgaagtt 1980
ttcactccac aggctgcgca ccatcaccaa cgcgtttagc aggtcgggcg ccgatatctt  2040
gaagtcgcag ttggggcctc cgccctgcgc gcgcgagttg cgatacacag ggttgcagca  2100
ctggaacact atcagcgccg ggtggtgcac gctggccagc acgctcttgt cggagatcag  2160
atccgcgtcc aggtcctccg cgttgctcag ggcgaacgga gtcaactttg gtagctgcct  2220
tcccaaaag ggtgcatgcc caggctttga gttgcactcg caccgtagtg gcatcagaag  2280
gtgaccgtgc ccggtctggg cgttaggata cagcgcctgc atgaaagcct tgatctgctt  2340
aaaagccacc tgagcctttg cgccttcaga gaagaacatg ccgcaagact tgccggaaaa  2400
ctgattggcc ggacaggccg cgtcatgcac gcagcacctt ggtcggtgt tggagatctg   2460
caccacattt cggccccacc ggttcttcac gatcttggcc ttgctagact gctccttcag  2520
cgcgcgctgc ccgttttcgc tcgtcacatc catttcaatc acgtgctcct tatttatcat  2580
aatgctcccg tgtagacact taagctcgcc ttcgatctca gcgcagcggt gcagccacaa  2640
cgcgcagccc gtgggctcgt ggtgcttgta ggttacctct gcaaacgact gcaggtacgc  2700
ctgcaggaat cgccccatca tcgtcacaaa ggtcttgttg ctggtgaagg tcagctgcaa  2760
cccgcggtgc tcctcgttta gccaggtctt gcatacggcc gccagagctt ccacttggtc  2820
aggcagtagc ttgaagtttg cctttagatc gttatccacg tggtacttgt ccatcaacgc  2880
gcgcgcagcc tccatgccct tctcccacgc agacacgatc ggcaggctca gcgggtttat  2940
caccgtgctt tcactttccg cttcactgga ctcttccttt tcctcttgcg tccgcatacc  3000
ccgcgccact gggtcgtctt cattcagccg ccgcaccgtg cgcttacctc ccttgccgtg  3060
cttgattagc accggtgggt tgctgaaacc caccatttgt agcgccacat cttctctttc  3120
ttcctcgctg tccacgatca cctctgggga tggcgggcgc tcgggcttgg gagaggggcg  3180
cttctttttc tttttggacg caatggccaa atccgccgtc gaggtcgatg gccgcgggtt  3240
gggtgtgcgc ggcaccagcg catcttgtga cgagtcttct tcgtcctcgg actcgagacg  3300
ccgcctcagc cgctttttg ggggcgcgcg gggaggcggc ggcgacggcg acggggacga   3360
cacgtcctcc atggttggtg gacgtcgcgc cgcaccgcgt ccgcgctcgg ggtggtttc   3420
gcgctgctcc tcttcccgac tggcatttc ctttctcctat aggcagaaaa agatcatgga  3480
gtcagtcgag aaggaggaca gcctaaccgc ccccttgag ttgccacca ccgcctccat   3540
cgatgccgcc aacgcgccta ccaccttccc cgtcgaggcc ccccgcttg aggaggagga   3600
agtgattatc gagcaggacc caggttttgt aagcgaagac gacagggatc gctcagtacc  3660
aacagaggat aaaagcaag accaggacga cgcagaggca aacgaggaac aagtcgggcg  3720
gggggaccaa aggcatggcg actacctaga tgtgggagac gacgtgctgt tgaagcatct  3780
gcagcgcgca tgccgcatta tctgcgacgc gttgcaagag cagcgcgatg tgccctcgc   3840
catgccggat gtcagccttg cctacgaacg ccacctgttc tcaccgcgcg tacccccaa   3900
acgccaagaa aacggcacat gcagcccaa cccgcgcctc aacttctacc ccgtatttgc  3960
cgtgccagag gtgcttgcca cctatcacat cttttttccaa aactgcaaga tacccctatc  4020
ctgccgtgcc aaccgcagcc gagcggacaa gcagctggcc ttgcggcagg gcgctgtcat  4080
acctgatatc gcctcgctcg acgaagtgcc aaaaatcttt gagggtcttg gacgcgacga  4140
```

```
gaaacgcgcg gcaaacgctc tgcaacaaga aaacagcgaa aatgaaagtc actgtggagt   4200
gctggtggaa cttgagggtg acaacgcgcg cctagccgtg ctgaaacgca gcatcgaggt   4260
cacccacttt gcctacccgg cacttaacct acccccaag gttatgagca cagtcatgag    4320
cgagctgatc gtgcgccgtg cacgacccct ggagagggat gcaaacttgc aagaacaaac   4380
cgaggagggc ctacccgcag ttggcgatga gcagctggcg cgctggcttg agacgcgcga   4440
gcctgccgac ttggaggagc gacgcaagct aatgatggcg gcagtggctt ttaccgtgga   4500
gcttgagtgc atgcagcggt tctttgctga cccggagatg cagcgcaagc tagaggaaac   4560
gttgcactac acctttcgcc agggctacgt gcgccaggcc tgcaaaattt ccaacgtgga   4620
gctctgcaac ctggtctcct accttggaat tttgcacgaa aaccgcctcg ggcaaaacgt   4680
gcttcattcc acgctcaagg gcgaggcgcg ccgcgactac gtccgcgact gcgtttactt   4740
atttctgtgc tacacctggc aaacggccat gggcgtgtgg cagcaatgcc tggaggagcg   4800
caacctaaag gagctgcaga agctgctaaa gcaaaacttg aaggacctat ggacggcctt   4860
caacgagcgc tccgtggccg cgcacctggc ggacattatc ttccccgaac gctgcttaa    4920
aaccctgcaa cagggtctgc cagacttcac cagtcaaagc atgttgcaaa acttaggaa    4980
ctttatccta gagcgttcag gaattctgcc cgccaccgtgc tgtgcgcttc ctagcgactt   5040
tgtgcccatt aagtaccgtg aatgcctcc gccgctttgg ggtcactgct accttctgca    5100
gctagccaac taccttgcct accactccga catcatggaa gacgtgagcg tgacggcct    5160
actgagtgt cactgtcgct gcaacctatg cacccccgac cgctccctgg tctgcaattc    5220
gcaactgctt agcgaaagtc aaattatcgg tacctttgag ctgcagggtc cctcgcctga   5280
cgaaagtcc gcggctccgg ggttgaaact cactccgggg ctgtgacgt ccgatctcta     5340
tcactgatag ggagatctct atcactgata gggagagggc ttaccttcgc aaatttgtac   5400
ctgaggacta ccacgcccac gagattaggt tctacgaaga ccaatcccgc ccgccaaatg   5460
cggagcttac cgcctgcgtc attacccagg gccacatcct tggccaattg caagccatca   5520
acaaagcccg ccaagagttt ctgctacgaa agggacgggg ggtttacctg acccccagt    5580
ccggcgagga gctcaaccca atccccccgc cgccgcagcc ctatcagcag ccgcgggccc   5640
ttgcttccca ggatggcacc caaaaagaag ctgcagctgc cgccgccgcc acccacggc    5700
gaggaggaat actgggacag tcaggcagag gaggttttgg acgaggagga ggagatgatg   5760
gaagactggg acagcctaga cgaagcttcc gaggccgaag aggtgtcaga cgaaacaccg   5820
tcaccctcgg tcgcattccc ctcgccgcg ccccagaaat tggcaaccgt tcccagcatc    5880
gctacaacct ccgctcctca ggccgccgcg gcactgctca ttcgccgacc caaccgtaga   5940
tgggacacca ctggaaccag ggccggtaag tctaagcagc cgccgccgtt agcccaagag   6000
caacaacagc gccaaggcta ccgctcgtgg cgcgggcaca agaacgccat agttgcttgc   6060
ttgcaagact gtggggcaa catctccttc gcccgccgct tcttctcta ccatcacggc     6120
gtggccttcc cccgtaacat cctgcattac taccgtcatc tctacagcgc ctactgcacc   6180
ggcggcagcg gcagcggcag caacagcagc ggtcacacag aagcaaaggc gaccggatag   6240
caagactctg acaaagccca agaaatccac agcggcggca gcagcaggag gaggagcgct   6300
gcgtctggcg cccaacgaac ccgtatcgac ccgcgagctt agaaatagga tttttcccac   6360
tctgtatgct atatttcaac aaagcagggg ccaagaacaa gagctgaaaa taaaaaacag   6420
gtctctgcgc tccctcaccc gcagctgcct gtatcacaaa agcgaagatc agcttcgcg    6480
cacgctggaa gacgcggagg ctctcttcag caacgatctc tatcactgat agggagatct   6540
ctatcactga tagggagaga tactgcgcgc tgactcttaa ggactagttt cgcgcccttt   6600
ctcaaattta agcgcgaaaa ctacgtcatc tccagcggcc acaccggcg ccagcacctg    6660
tcgtcagcgc cattatgagc aaggaaattc ccacgcccta catgtggagt taccagccac   6720
aaatgggact tgcggctgga gctgcccaag actactcaac ccgaataaac tacatgagcg   6780
cgggacccca catgatatcc cgggtcaacg gaatccgcgc ccaccgaaac cgaattctcc   6840
tcgaacaggc ggctattacc accacacctc gtaataacct taatcccgt agttggcccg    6900
ctgccctggt gtaccaggaa agtcccgctc ccaccactgt ggtacttcc agagacgccg    6960
aggccgaagt tcagatgact aactcagggg cgcagcttgc gggcggcttt cgtcacaggg   7020
tgcggtcgcc cgggcgtttt agggcggagt aacttgcatg tattgggaat gtagtttt     7080
ttaaaatggg aagtgacgta tcgtgggaaa acggaagtga agatttgagg aagttgtggg   7140
ttttttgct ttcgtttctg ggcgtaggtt cgcgtgcggt tttctgggtt gtttttgtgg    7200
actttaaccg ttacgtcatt ttttagtcct atatatactc gctctgtact ctccctatca   7260
gtgatagaga tctccctatc agtgatagag atcgcttggc cctttttaca ctgtgactga   7320
ttgagctggt gccgtgtcga gtggtgtttt taataggtt ttttactgg taaggctgac     7380
tgttatgct gccgctgtgg aagcgctgta tgttgttctg gagcgggag gtgctatttt    7440
gcctaggcag gagggttttt caggtgtttta tgtgttttc tctcctatta atttttgtat   7500
acctcctatg ggggctgtaa tgttgtctct acgcctgcgg gtatgtattc cccgggcta    7560
tttcggtcgc ttttttagcac tgaccgatgt taaccaacct gatgtgttta ccgagtctta   7620
cattatgact ccggacatga ccgaggaact gtcggtggtg cttttttaatc acggtgacca   7680
gtttttttac ggtcacgccg gcatggccgt agtccgtgct atgcttataa gggttgtttt   7740
tcctgttgta agacaggctt ctaatgttta aatgttttt ttttttgttat ttttattttgt   7800
gtttaatgca ggaacccgca gacatgtttg agagaaaaat ggtgtctttt tctgtggtgg   7860
ttccggaact tacctgcctt tatctgcatg agcatgacta cgatgtgctt gctttttgc    7920
gcgaggcttt gcctgatttt ttgagcagca cccttgcttt tatatcgccg catccatgcaa  7980
aagcttacat aggggctacg ctggttagca tagctccgag tatgcgtgtc ataatcagtg   8040
tgggttcttt tgtcatggtt cctgcggggg aagtggccgc gctggtccgt gcagacctgc   8100
acgattatgt tcagctggcc ctgcgaaggg acctacggga tcgcggtatt tttgttaatg   8160
ttccgctttt gaatcttata caggtctgtg aggaacctga attttttgcaa tcatgattcg   8220
ctgcttgagg ctgaaggtgg agggcgctct ggagcagatt tttacaatgg ccggacttaa   8280
tattcgggat ttgcttagag acatattgat aaggtggcga gatgaaaatt atttgggcat   8340
ggttgaaggt gctggaatgt ttatagagga gattcaccct gaagggttta gccttttacgt  8400
ccacttggac gtgagggcag tttgcctttt ggaagccatt tgcaacatc ttacaaatgc    8460
cattatctgt tctttggctg tagagtttga ccacgccacc gggggagc gcgttcactt    8520
aatagatctt cattttgagg ttttggataa taaaaaaaa aaacatggt                8580
tcttccagct cttcccgctc ctcccgtgtg tgactcgcag aacgaatgtg taggttggct   8640
gggtgtggct tattctgcgg tggtggatgt tatcagggca gcggcgcatg aaggagttta   8700
catagaaccc gaagccaggg ggcgcctgga tgctttgaga gagtggatat actcaaacta   8760
ctacacagag cgagctaagc gacgagaccg gagacgcaga tctgtttgtc acgcccgcac   8820
ctggtttgc ttcaggaaat atgtacccat acgatgttcc agattacgct ggaggaggcg    8880
```

```
gaggcactac gtccggcgtt ccatttggca tgacactacg accaacacga tctcggttgt  8940
ctcggcgcac tccgtacagt agggatcgcc tacctccttt tgagacagag acccgcgcta  9000
ccatactgga ggatcatccg ctgctgcccg aatgtaacac tttgacaatg cacaacgtga  9060
gttacgtgcg aggtcttccc tgcagtgtgg gatttacgct gattcaggaa tgggttgttc  9120
cctgggatat ggttctgacg cgggagggagc ttgtaatcct gaggaagtgt atgcacgtgt  9180
gcctgtgttg tgccaacatt gatatcatga cgagcatgat gatccatggt tacgagtcct  9240
gggctctcca ctgtcattgt tccagtcccg gttccctgca gtgcatagcc ggcgggcagg  9300
ttttggccag ctggtttagg atggtggtgg atggcgccat gtttaatcag aggtttatat  9360
ggtaccggga ggtggtgaat tacaaacatgc caaaagaggt aatgtttatg tccagcgtgt  9420
ttatgagggg tcgccactta atctacctgc gcttgtggta tgatggccac gtgggttctg  9480
tggtccccgc catgagcttt ggatacagcg ccttgcactg tgggattttg aacaatattg  9540
tggtgctgtg ctgcagttac tgtgctgatt taagtgagat cagggtgcgc tgctgtgccc  9600
ggaggacaag gcgtctcatg ctgcgggcgg tgcgaatcat cgctgaggag accactgcca  9660
tgttgtattc ctgcaggacg gagcggcggc ggcagcagtt tattcgcgcg ctgctgcagc  9720
accaccgccc tatcctgatg cacgattatg actctacccc catgtaggcg tggacttccc  9780
cttcgccgcc cgttgagcaa ccgcaagttg gacagcagcc tgtggctcag cagctggaca  9840
gcgacatgaa cttaagcgag ctgccgcggg agtttattaa tatcactgat gagcgtttgg  9900
ctcgacagga aaccgtgtgg aatataacac ctaagaatat gtctgttacc catgatatga  9960
tgcttttttaa ggccagccgg ggagaaagga ctgtgtactc tgtgtgttgg gagggaggtg 10020
gcaggttgaa tactagggtt ctgtgagttt gattaaggta cggtgatcaa tataagctat 10080
gtggtggtgg ggctatacta ctgaatgaaa aatgacttga aattttctgc aattgaaaaa 10140
taaacacgtt gaaacataac atgcaacagg ttcacgattc tttattcctg ggcaatgtag 10200
gagaaggtgt aagagttggt agcaaaagtt tcagtggtgt attttccact ttcccaggac 10260
catgtaaaag acatagagta agtgcttacc tcgctagttt ctgtggattc actagaatcg 10320
atgtaggatg ttgcccctcc tgacgcgta ggagaagggg agggtgccct gcatgtctgc 10380
cgctgctctt gctcttgccg ctgctgagga gggggcgga tctgccgcag caccggatgc 10440
atctgggaaa agcaaaaaag gggctcgtcc ctgtttccgg aggaatttgc aagcggggtc 10500
ttgcatgacg gggaggcaaa cccccgttcg ccgcagtccg gccggccgga gactcgaacc 10560
gggggtcctg cgactcaacc cttggaaaat aaccctccgg ctacagggag cgagccactt 10620
aatgctttcg ctttccagcc taaccgctta cgccgccgcg ggccagtggc caaaaaagct 10680
agcgcagcag ccgccgcgcc tggaaggaag ccaaaaggag cgctcccccg ttgtctgacg 10740
tcgcacacct gggttcgaca cgccgggcggt aaccgcatgg atcacggcgg acggccggat 10800
ccgggggttcg aaccccggtc gtccgccatg atacccttgc gaatttatcc accagaccac 10860
ggagagagtgc ccgcttacac gatctctatc actgataggg agatctctat cactgatagg 10920
gagagggctc tccttttgca cggtctagag cgtcaacgac tgcgcacgcc tcaccggcca 10980
gagcgtcccg accatggagc actttttgcc gctgcgcaac atctggaacc gcgtccgcga 11040
cttttccgcgc gcctccacca ccgccgccgg catcacctgg atgtccaggt acatctacgg 11100
attacgtcga cgtttaaacc atatgatcag ctcactcaaa ggcggtaata cggttatcca 11160
cagaatcagg ggataacgca ggaaagaaca tgtgagcaaa aggccagcaa aaggccagga 11220
accgtaaaaa ggccgcgttg ctggcgtttt cactttggcc gcggctcgag tgagctattc 11280
cagaagtagt gaagaggctt ttttggaggc ctaggctttt gcaaaaagct ccggatcgat 11340
gcccggggga tccactagtt ctagaggac agccccccccc caaagccccc aggatgtaaa 11400
ttacgtccct ccccgctag ggggcagcag cgagccgcc tccggtccgg 11460
cgctccccccc gcatcccga gccggcagcg tgcggggaca gccgggcac ggggaaggtg 11520
gcacgggatc gctttcctct gaacgcttct cgctgctctt tgagcctgca gacacctggg 11580
gggatacggg gaaaaggcct ccaaggccag cttcccacaa taagttgggt gaattttggc 11640
tgagctattc cagaagtagt gaagaggctt ttttggaggc ctaggcttt gcaaaagct 11700
ccggatcgat catatatggc agatatacgc gttgacattg attattgact agttattaat 11760
agtaatcaat tacgggggtca ttagttcata gcccatatat ggagttccgc gttacataac 11820
ttacggtaaa tggcccgcct ggctgaccgc ccaacgaccc ccgcccattg acgtcaataa 11880
tgacgtatgt tcccatagta acgccaatag ggactttcca ttgacgtcaa tgggtggagt 11940
atttacggta aactgcccac ttggcagtac atcaagtgta tcatatgcca agtacgcccc 12000
ctattgacgt caatgacggt aaatggcccg cctggcatta tgcccagtac atgaccttat 12060
gggactttcc tacttggcag tacatctacg tattagtcat cgctattacc atggtgatgc 12120
ggttttggca gtacatcaat gggcgtggat agcggtttga ctcacgggga tttccaagtc 12180
tccacccccat tgacgtcaat gggagtttgt tttggcacca aaatcaacgg gactttccaa 12240
aatgtcgtaa caactccgcc ccattgacgc aaatgggcgg taggcgtgta cggtgggagg 12300
tctatataag cagagctctc tggctaacta tcgtcgacga gctcgtttag tgaaccgtca 12360
gatcgcctgg agacgccatc cacgctgttt tgacctccat agaagacacc gggaccgatc 12420
cagcctccgg actcagcgt ttaaactaa gcttgccacc atgaccgagt acaagcccac 12480
ggtgcgcctc gccacccgcg acgacgtccc cagggccgta cgcaccctcg ccgccgcgtt 12540
cgccgactac cccgccacgc gccacaccgt cgatccggac cgccacatcg agcgggtcac 12600
cgagctgcaa gaactcttcc tcacgcgcgt cgggctcgac atcggcaagg tgtgggtcgc 12660
ggacgacggc gccgcggtgg cggtctggac cacgccggag cactcgaag cggggcggt 12720
gttcgccgag atcggcccgc gcatggccga gttgagcggt tccggctgg ccgcgcagca 12780
acagatggaa ggcctcctgg cgccgcaccg gcccaaggag cccgcgtggt tcctggccac 12840
cgtcggcgtc tcgccgacc accagggcaa gggtctgggc agcgccgtcg tgctccccgg 12900
agtggaggcg gccgagcgcg ccggggtgcc cgccttcctg gagacctccg cgcccgcaa 12960
cctccccttc tacgagcggc tcggcttcac cgtcagcgag gacgtcgaag tgcccgaagg 13020
accgcgcacc tggtgcatga cccgcaagcc cggtgcctga agcgcgggga tctcatgctg 13080
gagttcttcg cccaccccaa ctttgtttatt gcagcttata atggttacaa ataaagcaat 13140
agcatcacaca atttcacaaa taaagcattt ttttcactgc attctagttg tggtttgtcc 13200
aaactcatca atgtatctta tcatgtctgt agctgatgta tacctaggat ccggccggcc 13260
tgcaggtgtc ctcacaggaa cgaagtccct aaagaaacag tggcaccgag gtttagccccc 13320
ggaattgact ggattccttt tttaggggccc attggtatgg cttttttcccc gtatccccccc 13380
aggtgtctgc aggctcaaag agcagcgaga agcgttcaga ggaaagcgat cccgtgccac 13440
cttccccgtg cccgggctgt cccgcacgc tgccggctcg gggatgcggg gggagcgccg 13500
gaccggagcg gagcccgggg cggctcgctg ctgcccccta gcggggagg gacgtaatta 13560
catccctggg ggctttgggg gggggctgtc cctctagagc ggccgccacc gcggtggagc 13620
```

```
tccagcttttt gttcccttta gtgagggtta attagatctt aatacgactc actatagggc  13680
gaattgggta ccgggccccc cctcgaggtc gacggtatcg ataagcttga tatctataac  13740
aagaaaatat atatataata agttatcacg taagtagaac atgaaataac aatataatta  13800
tcgtatgagt taaatcttaa aagtcacgta aagataatc atgcgtcatt ttgactcacg   13860
cggtcgttat agttcaaaat cagtgacact taccgcattg acaagcacgc ctcacgggag  13920
ctccaagcgg cgactgagat gtcctaaatg cacagcgacg gattcgcgct atttagaaag  13980
agagagcaat atttcaagaa tgcatgcgtc aattttacgc agactatctt tctagggtta  14040
atctagctgc atcaggatca tatcgtcggg tctttttcc ggctcagtca tcgcccaagc   14100
tggcgctatc tgggcatcgg ggaggaagaa gcccgtgcct tttcccgcga ggttgaagcg  14160
gcatggaaag agtttgccga ggatgactgc tgctgcattg acgttgagcg aaaacgcacg  14220
tttaccatga tgattcggga aggtgtggcc atgcacgcct ttaacggtga actgttcgtt  14280
caggccacct gggataccag ttcgtcgcgg cttttccgga cacagttccg gatggtcagc  14340
ccgaagcgca tcagcaaccc gaacaatacc ggcgacagcc ggaactgccg tgccggtgtg  14400
cagattaatg acagcggtgc ggcgctggga tattacgtca gcgaggacgg gtatcctggc  14460
tggatgccgc agaaatggac atggataccc cgtgagttac ccggcgggcg cgcttggcgt  14520
aatcatggtc atagctgttt cctgtgtgaa attgttatcc gctcacaatt ccacacaaca  14580
tacgagccgg aagcataaag tgtaaagcct ggggtgccta atgagtgagc taactcacat  14640
taattgcgtt gcgctcactg cccgctttcc agtcgggaaa cctgtcgtgc cagctgcatt  14700
aatgaatcgg ccaacgcgcg gggagaggcg gtttgcgtat tgggcgctct tccgcttcct  14760
cgctcactga ctcgctgcgc tcggtcgttc ggctgcggcg agcggtatca gctcactcaa  14820
aggcggtaat acggttatcc acagaatcag gggataacgc aggaaagaac atgtgagcaa  14880
aaggccagca aaaggccagg aaccgtaaaa aggccgcgtt gctggcgttt ttccataggc  14940
tccgcccccc tgacgagcat cacaaaaatc gacgctcaag tcagaggtgg cgaaacccga  15000
caggactata aagataccag gcgtttcccc ctggaagctc cctcgtgcgc tctcctgttc  15060
cgaccctgcc gcttaccgga tacctgtccg cctttctccc ttcgggaagc gtggcgcttt  15120
ctcatagctc acgctgtagg tatctcagtt cggtgtaggt cgttcgctcc aagctgggct  15180
gtgtgcacga accccccgtt cagcccgacc gctgcgcctt atccggtaac tatcgtcttg  15240
agtccaaccc ggtaagacac gacttatcgc cactggcagc agccactggt aacaggatta  15300
gcagagcgag gtatgtaggc ggtgctacag agttcttgaa gtggtggcct aactacggct  15360
acactagaag gacagtattt ggtatctgcg ctctgctgaa gccagttacc ttcggaaaaa  15420
gagttggtag ctcttgatcc ggcaaacaaa ccaccgctgg tagcggtggt ttttttgttt  15480
gcaagcagca gattacgcgc agaaaaaaag gatctcaaga agatcctttg atcttttcta  15540
cggggtctga cgctcagtgg aacgaaaact cacgttaagg gattttggtc atgagattat  15600
caaaaaggat cttcacctag atccttttaa attaaaaatg aagttttaaa tcaatctaaa  15660
gtatatatga gtaaacttgg tctgacagtt accaatgctt aatcagtgag gcacctatct  15720
cagcgatctg tctatttcgt tcatccatag ttgcctgact ccccgtcgtg tagataacta  15780
cgatacggga gggcttacca tctggcccca gtgctgcaat gataccgcga cccacgct    15840
caccggctcc agatttatca gcaataaacc agccagccgg aagggccgag cgcagaagtg  15900
gtcctgcaac tttatccgcc tccatccagt ctattaattg ttgccgggaa gctagagtaa  15960
gtagttcgcc agttaatagt ttgcgcaacg ttgttgccat tgctacaggc atcgtggtgt  16020
cacgctcgtc gtttggtatg gcttcattca gctccggttc ccaacgatca aggcgagtta  16080
catgatcccc catgttgtgc aaaaaagcgg ttagctcctt cggtcctccg atcgttgtca  16140
gaagtaagtt ggccgcagtg ttatcactca tggttatggc agcactgcat aattctctta  16200
ctgtcatgcc atccgtaaga tgcttttctg tgactggtga gtactcaacc aagtcattct  16260
gagaatagtg tatgcggcga ccgagttgct cttgcccggc gtcaatacgg gataataccg  16320
cgccacatag cagaacttta aaagtgctca tcattggaaa acgttcttcg ggcgaaaac   16380
tctcaaggat cttaccgctg ttgagatcca gttcgatgta acccactcgt gcacccaact  16440
gatcttcagc atcttttact ttcaccagcg tttctgggtg agcaaaaaca ggaaggcaaa  16500
atgccgcaaa aaagggaata agggcgacac ggaaatgttg aatactcat              16549

SEQ ID NO: 4             moltype = DNA   length = 15878
FEATURE                  Location/Qualifiers
misc_feature             1..15878
                         note = Synthetic: pPBBG-iHelper2.1-HA
source                   1..15878
                         mol_type = other DNA
                         organism = synthetic construct
SEQUENCE: 4
actcttccttt tttcaatatt attgaagcat ttatcaggt tattgtctca tgagcggata    60
catatttgaa tgtatttaga aaaataaaca aataggggtt ccgcgcacat ttccccgaaa   120
agtgccacct aaattgtaag cgttaatatt tgttaaaat tcgcgttaaa ttttttgtta    180
atcagctcat ttttttaacca ataggccgaa atcggcaaaa tcccttataa atcaaaagaa   240
tagaccgaga tagggttgag tgttgttcca gtttggaaca agagtccact attaagaac    300
gtggactcca acgtcaaagg gcgaaaaacc gtctatcagg gcgatggccc actacgtgaa   360
ccatcacccc taatcaagttt tttggggtcg aggtgccgta aagcactaaa tcggaaccct   420
aaagggagcc cccgatttag agcttgacgg ggaaagccgg cgaacgtggc gagaaaggaa   480
gggaagaaag cgaaaggagc gggcgctagg gcgctggcaa gtgtagcggt cacgctgcgc   540
gtaaccacca cacccgccgc gcttaatgcg ccgctacagg gcgcgtccca ttcgccattc   600
aggctgcgca actgttggga agggcgatcg gtgcgggcct cttcgctatt acgccagctg   660
gcgaaagggg gatgtgctgc aaggcgatta agttgggtaa cgccagggtt ttcccagtca   720
cgacgttgta aaacgacggc cagtgagcgc gcctcgttca ttcacgtttt tgaacccgtg   780
gaggacgggc agactcgcgg tgcaaatgtg ttttacagcg tgatggagca gatgaagatg   840
ctcgacacgc tgcagaacac gcagctagat taaccctaga aagataatca tattgtgacg   900
tacgttaaag ataatcatgc gtaaaattga catgcatgtct gtatatcgag              960
gtttatttat taatttgaat agatattaag ttttattata tttacactta catactaata  1020
ataaattcaa caaacaattt atttatgttt attttattat taaaaaaaaa caaaaactca  1080
aaatttcttc tataaagtaa caaaactttt atcgaattcc tgcagcccgg ggatccact    1140
agttctagag ggcagccccc ccccaaagc ccccagggat gtaattacgt ccctcccccg    1200
ctaggggggca gcagcgagcc gcccggggct ccgctccggt ccgcgctccc cccgcatcc   1260
```

-continued

```
ccgagccggc agcgtgcggg gacagcccgg gcacgggaa ggtggcacgg gatcgcttc    1320
ctctgaacgc ttctcgctgc tctttgagcc tgcagacacc tggggggata cggggaaaag   1380
gcctccaagg ccagcttccc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcgtttaaac ttaagcttgg taccgagctc ggatccacta   1560
gtccagtgtg gtggaattcc tgcttcgcga tgtacgggcc ggtacccaac tccatgctta   1620
acagtcccca ggtacagccc accctgcgtc gcaaccagga acagctctac agcttcctgg   1680
agcgccactc gccctacttc cgcagccaca gtgcgcagat taggagcgcc acttcttttt   1740
gtcacttgaa aaacatgtaa aaataatgta ctaggagaca ctttcaataa aggcaaatgt   1800
ttttatttgt acactctcgg gtgattattt acccccacc cttgccgtct gcgccgttta    1860
aaaatcaaag gggttctgcc gcgcatcgct atgcgccact ggcagggaca cgttgcgata   1920
ctggtgttta gtgctccact taaactcagg cacaaccatc cgcggcagct cggtgaagtt   1980
ttcactccac aggctgcgca ccatcaccaa cgcgtttagc aggtcgggcg ccgatatctt   2040
gaagtcgcag ttgggggcctc cgccctgcgc gcgcgagttg cgatacacag ggttgcagca   2100
ctggaacact atcagcgccg ggtggtgcac gctggccagc acgctcttgt cggagatcag   2160
atccgcgtcc aggtcctccg cgttgctcag ggcgaacgga gtcaacttg gtagctgcct    2220
tcccaaaaag ggtgcatgcc caggctttga gttgcactcg caccgtagtg gcatcagaag   2280
gtgaccgtgc ccggtctggg cgttaggata cagcgcctgc atgaaagcct tgatctgctt   2340
aaaagccacc tgagcctttg cgccttcaga gaagaacatg ccgcaagact tgccggaaaa   2400
ctgattggcc ggacaggcg cgtcatgcac gcagcacctt gcgtcggtgt tggagatctg    2460
caccacattt cggccccacc ggttcttcac gatcttggcc ttgctagact gctccttcag   2520
cgcgcgctgc ccgttttcgc tcgtcacatc catttcaatc acgtgctcct tatttatcat   2580
aatgctcccg tgtagacact taagctcgcc ttcgatctca gcgcagcggt gcagccacaa   2640
cgcgcagccc gtgggctcgt ggtgcttgta ggttacctct gcaaacgact gcaggtacgc   2700
ctgcaggaat cgcccccatca tcgtcacaaa ggtcttgttg ctggtgaagg tcagctgcaa   2760
cccgcggctc tcctcgttta gccaggtctt gcatacgccg gccagagctt ccacttggtc   2820
aggcagtagc ttgaagtttg cctttagatc gttatccacg tggtacttgt ccatcaacgc   2880
gcgcgcagcc tccatgccct tctcccacgc agacacgatc ggcaggctca gcgggtttat   2940
caccgtgctt tcactttccg cttcactgga ctcttccttt tcctcttgcg tccgcatacc   3000
ccgcgccact gggtcgtctt cattcagccg ccgcaccgtg cgcttacctc ccttgccgtg   3060
cttgattagc accggtgggt tgctgaaacc caccatttgt agcgccacat cttctctttc    3120
ttcctcgctg tccacgatca cctctgggga tggcgggcgc tcgggcttgg gagaggggcg   3180
cttctttttc tttttggacg caatggccaa atccgccgtc gaggtcgatg gccgcgggct   3240
gggtgtgcgc ggcaccagcg catcttgtga cgagtcttct tcgtcctcgg actcgagacg   3300
ccgcctcagc cgcttttttg gggcgcgcg gggaggcggc ggcgacggcg acggggacga    3360
cacgtcctcc atggttggtg gacgtcgcgc gcaccgcgt ccgcgctcgg gggtggtttc    3420
gcgctgctcc tcttccgac tggccatttc cttctcctat aggcagaaaa agatcatgga   3480
gtcagtcgag aaggaggaca gcctaaccgc ccccttttgag ttcgcaccca ccgcctccac   3540
cgatgccgcc aacgcgccta ccaccttccc cgtcgaggca ccccccgcttg aggaggagga   3600
agtgattatc gagcaggacc caggttttgt aagcgaagac gacgaggatc gctcagtacc   3660
aacagaggat aaaaagcaag accaggacga cgcagaggca aacgaggaac aagtcgggcg   3720
gggggaccaa aggcatggcg actacctaga tgtgggagac gacgtgctgt tgaagcatct   3780
gcagcgccag tgcgccatta tctgcgacgc gttgcaagag cgcagcgatg tgcccctcga   3840
catagcggat gtcagccttg cctacgaacg ccacctgttc tcaccgcgcg tacccccaa    3900
acgccaagaa aacggcacat gcgagcccaa cccgcgcctc aacttctacc cgtatttgc    3960
cgtgccagag gtgcttgcca cctatcacat ctttttccaa aactgcaaga taccctatc    4020
ctgccgtgcc aaccgcagcc gagcggacaa gcagctggcc ttgccggcagg gcgctgtcat   4080
acctgatatc gcctcgctcg acgaagtgcc aaaaatcttt gagggtcttg gacgcgacga   4140
gaaacgcgcg gcaaacgctc tgcaacaaga aaacagcgaa aatgaaagtc actgtggagt   4200
gctggtggaa cttgagggtg acaacgcgcg cctagccgtg ctgaaacgca gcatcgaggt   4260
cacccacttt gcctacccgg cacttaacct acccccccaag gttatgagca cagtcatgag   4320
cgagctgatc gtgcgccgtg cacgacccct ggagagggat gcaaacttgc aagaacaaac   4380
cgaggagggc ctacccgcag ttggcgatga gcagctggcg cgctggcttg agacgcgcga   4440
gcctgccgac ttgaggagc gacgcaagct aatgatggcc gcagtgcttg ttaccgtgga   4500
gcttgagtgc atgcagcggt tctttgctga cccggagatg cagcgcaagc tagaggaaac   4560
gttgcactac accttcgcc agggctacgt gcgccaggcc tgcaaaattt ccaacgtgga   4620
gctctgcaac ctggtctcct accttggaat tttgcacgaa accgcctcg ggcaaaacgt    4680
gcttcattcc acgctcaagg gcgaggcgcg ccgcgactac gtccgcgact gcgtttactt   4740
atttctgtgc tacacctggc aaacggccat gggcgtgtg cagcaatgcc tggaggagcg    4800
caacctaaag gagctgcaga agctgctaaa gcaaaacttg aaggacctat ggacggcctt   4860
caacgagcgc tccgtggccg cgcacctggc ggacattatc ttccccgaac gcctgcttaa   4920
aacccctgcaa cagggtctgc cagacttcac cagtcaaagc atgttgcaaa actttaggaa   4980
cttttatccta gagcgttcag gaattctgcc cgccacctgc tgtgcgcttc ctagcgactt    5040
tgtgcccatt aagtaccgtg aatgccctcc gccgctttg ggtcactgct accttctgca    5100
gctagccaac taccttgcct accactccga catcatggaa gacgtgagcg gtgacgcct    5160
actggagtgt cactgtcgct gcaacctatg cacccgcac cgctccctgg tctgcaattc    5220
gcaactgctt agcgaaagtc aaattatcgg taccttgag ctgcagggtc cctcgcctga    5280
cgaaaagtcc gcggctccgg ggttgaaact cactccgggg ctgtggacgt ccgatctcta   5340
tcactgatag ggagatctct atcactgata gggagagctg ttaccttcgc aaatttgtac   5400
ctgaggacta ccacgcccac gagattaggt tctacgaaga ccaatcccgc cgcaaatg     5460
cggagcttac cgcctgcgtc attacccagg gccacatcct tggccaattg caagccatca   5520
acaaagcccg ccaagagttt ctgctacgaa agggacgggg gtttacctg gacccccagt    5580
ccggcgagga gctcaaccca atccccccgc cgccgcagcc ctatcagcag ccgcgggccc   5640
ttgcttccca ggatgcacc caaaaagaag ctgacgttcc acgccccgcc acccacgag    5700
gaggaggaat actgggacag tcaggcagag gaggttttgg acgaggagga ggagatgatg   5760
gaagactggg acagcctaga cgaagcttcc gaggccgaag aggtgtcaga cgaaacaccg   5820
tcaccctcgg tcgcattccc ctcgccgcg cccagaaat tggcaaccgt tcccagcatc    5880
gctacaacct ccgctcctca ggcgccgcg cactgcctg ttcgccgacc caaccgtaga    5940
tgggacacca ctggaaccag ggccggtaag tctaagcagc cgccgccgtt agcccaagag   6000
```

```
caacaacagc gccaaggcta ccgctcgtgg cgcgggcaca agaacgccat agttgcttgc   6060
ttgcaagact gtgggggcaa catctccttc gcccgccgct ttcttctcta ccatcacggc   6120
gtggccttcc cccgtaacat cctgcattac taccgtcatc tctacagccc ctactgcacc   6180
ggcggcagcg gcagcggcag caacagcagc ggtcacacag aagcaaaggc gaccggatag   6240
caagactctg acaaagccca agaaatccac agcggcggca gcagcaggag gaggagcgct   6300
gcgtctggcg cccaacgaac ccgtatcgac ccgcgagctt agaaatagga ttttttcccac  6360
tctgtatgct atatttcaac aaagcagggg ccaagaacaa gagctgaaaa taaaaaaacag   6420
gtctctgcgc tccctcaccc gcagctgcct gtatcacaaa agcgaagatc agcttcggcg   6480
cacgctggaa gacgcggagg ctctcttcag caacgatctc tatcactgat agggagatct   6540
ctatcactga tagggagaga tactgcgcgc tgactcttaa ggactagttt cgcgcccttt   6600
ctcaaattta agcgcgaaaa ctacgtcatc tccagcggcc acaccggcg ccagcacctg    6660
tcgtcagcgc cattatgagc aaggaaattc ccacgcccta catgtggagt taccagccac   6720
aaatgggact tgcggctgga gctgcccaag actactcaac ccgaataaac tacatgagcg   6780
cgggacccca catgatatcc cgggtcaacg gaatccgcgc ccaccgaaac cgaattctcc   6840
tcgaacaggc ggctattacc accacacctc gtaataacct taatcccgt agttggcccg    6900
ctgccctggt gtaccaggaa agtcccgctc ccaccactgt ggtacttccc agagacgccc   6960
aggccgaagt tcagatgact aactcagggg cgcagcttgc gggcggcttt cgtcacaggg   7020
tgcggtcgcc cgggcgtttt agggcggagt aacttgcatg tattgggaat tgtagttttt   7080
ttaaaatggg aagtgacgta tcgtgggaaa acgaagtga agatttgagg aagttgtggg    7140
ttttttggct ttcgtttctg ggcgtaggtt cgcgtgcggt tttctgggtg ttttttgtgg   7200
actttaaccg ttacgtcatt ttttagtcct atatatactc gctctgtact ctccctatca   7260
gtgatagaga tctccctatc agtgatagag atcgcttggc ccttttttaca ctgtgactga  7320
ttgagctggt gccgtgtcga gtggtgtttt ttaataggtt tttttactgg taaggctgac   7380
tgttatggct gccgctgtgg aagcgctgta tgttgttctg gagcgggagg gtgctatttt   7440
gcctaggcag gagggttttt caggtgttta tgtgtttttc tctcctatta attttgttat   7500
acctcctatg ggggctgtaa tgttgtctct acgcctgcgg gtatgtattc cccgggcta    7560
tttcggtcgc tttttagcac tgaccgatgt taaccaacct gatgtgttta ccgagtctta   7620
cattatgact ccgacatga ccgaggaact gtcggtggtg ctttttaatc acggtgacca    7680
gttttttttac ggtcacgccg gcatggccgt agtccgtctt atgcttataa gggttgtttt  7740
tcctgttgta agacaggctt ctaatgttta aatgttttt ttttttgttat tttatttgt    7800
gtttaatgca ggaacccgca gacatgtttg agagaaaaat ggtgtctttt tctgtggtga   7860
ttccggaact tacctgcctt tatctgcatg agcatgacta cgatgtgctt gcttttttgc   7920
gcgaggcttt gcctgatttt ttgagcagca ccttgcattt tatatcgccg cccatgcaac   7980
aagcttacat aggggctacg ctggttagca tagctccgag tatgcgtgtc ataatcagtg   8040
tgggttcttt tgtcatggtt cctggcgggg aagtggccgc gctggtccgt gcagacctgt   8100
acgattatgt tcagctggcc ctgcgaaggg acctacggga tcgggtatt tttgttaatg    8160
ttccgctttt gaatcttata caggtctgtg aggaacctga attttttgcaa tcatgattcg  8220
ctgcttgagg ctgaaggtgg agggcgctct ggagcagatt tttacaatgg ccggacttaa   8280
tattcgggat ttgcttagag acatattgat aaggtggcga gatgaaaatt atttgggcat   8340
ggttgaaggt gctggaatgt ttatagagga gattcaccct gaaggggttta gcctttacgt   8400
ccacttggac gtgagggcag tttgcctttt ggaagccatt gtgcaacatc ttacaaatgc   8460
cattatctgt tctttggctg tagagtttga ccacgccacc ggaggggagc gcgttcactt   8520
aatagatctt cattttgagg ttttggataa tctttttgaa taaaaaaaaa aaaacatggt   8580
tcttccagct cttcccgctc ctcccgtgtg tgactcgcag aacgaatgtg taggttggct   8640
gggtgtggct tattctgcgg tggtggatgt tatcagggca gcggcgcatg aaggagttta   8700
catagaaccc gaagccaggg ggcgcctgga tgctttgaga gagtggatat actcaacta    8760
ctacacagag cgagctaagc gacgaaccg gagacgcaga tctgttttgtc acgcccgcac   8820
ctggtttttgc ttcaggaaat atgtaccat acgatgttcc agattacgct ggaggaggcg   8880
gaggcactac gtccggcgtt ccatttggca tgacactacg accaacacga tctcggttgt   8940
ctcggcgcac tccgtacagt agggatcgcc tacctccttt tgagacagag acccgcgcta   9000
ccatactgga ggatcatccg ctgctgcccg aatgtaacac tttgacaatg cacaacgtga   9060
gttacgtgcg aggtcttccc tgcagtgtgg gatttacgct gattcaggaa tgggttgttc   9120
cctgggatat ggttctgacg cgggaggagc ttgtaatcct gaggaagtgt atgcacgtgt   9180
gcctgtgttg tgccaacatt gatatcatga cgagcatgat gatccatggt tacgagtcct   9240
gggctctcca ctgtcattgt tccagtcccg gttcctgca gtgcatagcc ggcgggcagg    9300
ttttggccaa ctggtttagg atggtggttgg atggcgccat gtttaatcag aggtttatat  9360
ggtaccggga ggtggtgaat tacaacatgc caaaagaggt aatgtttatg tccagcgtgt   9420
ttatgagggg tcgccactta atctacctgc gcttgtggta tgatggccac gtgggttctg   9480
tggtccccgc catgagcttt ggatacagcg ccttgcactg tgggattttg aacaatattg    9540
tggtgctgtg ctgcagttac tgtgctgatt taagtgagat cagggtgcgc tgctgtgccc   9600
ggaggacaag gcgtctcatg ctgcgggcgg tgcgaatcat cgctgaggag accactgcca   9660
tgttgtattc ctgcaggacg gagcggcggc ggcagcagtt tattcgcgcg ctgctgcagc   9720
accaccgcc tatcctgatg cacgattatg actctacccc catgtaggcg tggacttccc    9780
cttcgccgcc cgttgagcaa ccgcaagttg cacagcagcc tgtggctcag cagctggaca   9840
gcgacatgaa cttaagcgag ctgcccgggg agtttattaa tatcactgat gagcgtttgc   9900
ctcgacagga aaccgtgtgg aatataacac taagaatat gtctgttacc catgatatga    9960
tgctttttaa ggccagccgg ggagaaagga ctgtgtactc tgtgtgttgg gagggaggtg   10020
gcaggttgaa tactaggggtt ctgtgagttt gattaaggta cggtgatcaa tataagctat  10080
gtggtggtga tgctatacta ctgaatgaaa aatgacttga aattttctgc aattgaaaaa   10140
taaacacgtt gaaacataac atgcaacagg ttcacgattc tttattcctg ggcaatgtag   10200
gagaaggtgt aagagttggt agcaaaagtt tcagtggtgt attttccact ttcccaggac   10260
catgtaaaag acatagagta agtgcttacc tcgctagttt ctgtggattc actagaacca   10320
gtggccaaaa aagctagcgc agcagccgcc gcgcctggaa ggaagccaaa aggagcgctc   10380
ccccgttgtc tgacgtcgca cacctgggtt cgacacggca cggtaaccg catgatcac    10440
ggcggacggc cggatccggg gttcgaaccc cggtcgtccg ccatgatacc cttgcgaatt   10500
tatccaccag accacggaag agtgcccgct tacaggctct cctttttgcac ggtctagagc   10560
gtcaacgact gcgcacgtcc actttggccg cggctcgagt gagctattcc agaagtagtg   10620
aagaggcttt tttggaggcc taggcttttg caaaaagctc cggatcgatg cccgggggat   10680
ccactagttc tagagggaca gccccccccc aaagccccca gggatgtaat tacgtccctc   10740
```

```
ccccgctagg gggcagcagc gagccgcccg gggctccgct ccggtccggc gctcccccg    10800
catcccgag ccggcagcgt gcggggacag cccgggcacg gggaaggtgg cacgggatcg    10860
ctttcctctg aacgcttctc gctgctcttt gagcctgcag acacctgggg ggatacgggg    10920
aaaaggcctc caaggccagc ttcccacaat aagttgggtg aatttttggct gagctattcc    10980
agaagtagtg aagaggcttt tttggaggcc taggcttttg caaaaagctc cggatcgatc    11040
atatatggca gatatacgcg ttgacattga ttattgacta gttattaata gtaatcaatt    11100
acggggtcat tagttcatag cccatatatg gagttccgcg ttacataact tacggtaaat    11160
ggcccgcctg gctgaccgcc caacgacccc cgcccattga cgtcaataat gacgtatgtt    11220
cccatagtaa cgccaatagg gactttccat tgacgtcaat gggtggagta tttacggtaa    11280
actgcccact tggcagtaca tcaagtgtat catatgccaa gtacgccccc tattgacgtc    11340
aatgacggta aatggcccgc ctggcattat gcccagtaca tgaccttatg gactttcct    11400
acttggcagt acatctacgt attagtcatc gctattacca tggtgatgcg gttttggcag    11460
tacatcaatg ggcgtggata gcggtttgac tcacgggat ttccaagtct ccaccccatt    11520
gacgtcaatg ggagtttgtt ttggcaccaa aatcaacggg actttccaaa atgtcgtaac    11580
aactccgccc cattgacgca aatgggcggt aggcgtgtac ggtgggaggt ctatataagc    11640
agagctctct ggctaactat cgtcgacgag ctcgtttagt gaaccgtcag atcgcctgga    11700
gacgccatcc acgctgtttt gacctccata gaagacaccg ggaccgatcc agcctccgga    11760
ctctagcgtt taaacttaag cttgccacca tgaccgagta caagcccacg gtgcgcctcg    11820
ccacccgcga cgacgtcccc agggccgtac gcaccctcgc cgccgcgttc gccgactacc    11880
ccgccacgcg ccacaccgtc gatccggacc gccacatcga gcgggtcacc gagctgcaag    11940
aactcttcct cacgcgcgtc gggctcgaca tcggcaaggt gtgggtcgcg gacgacggcg    12000
ccgcggtggc ggtctggacc acgcgggaga gcgtcgaagc ggggcggtg ttcgccgaga    12060
tcggcccgcg catggccgag ttgagcggtt cccggctggc cgcgcagcaa cagatggaag    12120
gcctcctggc gccgcaccgg cccaaggagc ccgtggtt cctggccacc gtcggcgtct    12180
cgcccgacca ccagggcaag ggtctgggca gcgccgtcgt gctccccgga gtggaggcgg    12240
ccgagccggc cggggtgccc gccttcctgg agacctgag gccccgcaac ctcccctct    12300
acgagcggct cggcttcacc gtcaccgccg acgtcgaggt gccgaaggg ccgcgcacct    12360
ggtgcatgac ccgcaagccc ggtgcctgaa gcgcgggat ctcatgctgg agttcttcgc    12420
ccaccccaac ttgtttattg cagcttataa tggttacaaa taaagcaata gcatcacaaa    12480
tttcacaaat aaagcatttt tttcactgca ttctagttgt ggtttgtcca aactcatcaa    12540
tgtatcttat catgtctgta gctgatgtat acctaggatc cggccggcct gcaggtgtcc    12600
tcacaggaac gaagtcccta agaaacagt ggcagcagg tttagccccg gaattgactg    12660
gattcctttt ttagggccca ttggtatggc ttttttcccg tatcccccca ggtgtctgca    12720
ggctcaaaga gcagcgagaa gcgttcagag aaagcgatc ccgtgccacc ttcccgtgc    12780
ccgggctgtc cccgcacgct gccggctcgg ggatgcgggg ggagcgccgg accggagcgg    12840
agccccgggc ggctcgctgc tgcccccctag cggggaggg acgtaattac atccctgggg    12900
gctttggggg gggctgtcc ctctagagcg gccgccaccg cggtggagct ccagcttttg    12960
ttccctttag tgagggttaa ttagatctta atacgactca ctatagggcg aattgggtac    13020
cgggccccc ctcgaggtcg acggtatcga taagcttgat atctataaca agaaaatata    13080
tatataataa gttatcacgt aagtagaaca tgaaataaca ataaattat cgtatgagtt    13140
aaatcttaaa agtcacgtaa aagataatca tgcgtcattt tgactcacgc ggtcgttata    13200
gttcaaaatc agtgacactt accgcattga caagcacgcc tcacgggagc tccaagcggc    13260
gactgagatg tcctaaatgc acagcgacgg attcgcgcta tttagaaaga gagagcaata    13320
tttcaagaat gcatgcgtca attttacgca gactatcttt ctaggggttaa tctagctgca    13380
tcaggatcat atcgtcgggt cttttttccg gctcagtcat cgcccaagct ggcgctatct    13440
gggcatcggg gaggaagaag cccgtgcctt ttcccgcgag gttgaagcgg catggaaaga    13500
gtttgccgag gatgactgct gctgcattga cgttgagcga aaacgcacgt ttaccatgat    13560
gattcgggaa ggtgtggcca tgcacgcctt taacgtgaa ctgttcgttc aggccacctg    13620
ggataccagt tcgtcgcggc ttttccggac acagttccgg atggtcagcc cgaagcgcat    13680
cagcaacccg aacaataccg cgacagccg gaactgccgt gccggtgtgc agattaatga    13740
cagcggtgcg gcgctgggat attacgtcag cgaggacggg tatcctggct ggatgccgca    13800
gaaatggaca tggataccc gtgagttacc cggcgggcgc gcttggcgta atcatggtca    13860
tagctgtttc ctgtgtgaaa ttgttatccg ctcacaattc cacacaacat acgagccgga    13920
agcataaagt gtaaagcctg gggtgcctaa tgagtgagct aactcacatt aattgcgttg    13980
cgctcactgc ccgctttcca gtcgggaaac ctgtcgtgcc agctgcatta atgaatcggc    14040
caacgcgcgg ggagaggcgg tttgcgtatt gggcgctctt ccgcttcctc gctcactgac    14100
tcgctgcgct cggtcgttcg gctgcggcga gcggtatcag ctcactcaaa ggcggtaata    14160
cggttatcca cagaatcagg ggataacgca ggaaagaaca tgtgagcaaa aggccagcaa    14220
aaggccagga accgtaaaaa ggccgcgttg ctggcgtttt tccatagget ccgcccccct    14280
gacgagcatc acaaaaatcg acgctcaagt cagaggtggc gaaacccgac aggactataa    14340
agataccagg cgtttccccc tggaagctcc ctcgtgcgct ctcctgttcc gaccctgccg    14400
cttaccggat acctgtccgc ctttctccct tcgggaagcg tggcgctttc tcatagctca    14460
cgctgtaggt atctcagttc ggtgtaggtc gttcgctcca agctgggctg tgtgcacgaa    14520
ccccccgttc agcccgaccg ctgcgcctta tccggtaact atcgtcttga gtccaacccg    14580
gtaagacacg acttatcgcc actggcagca gccactggta acaggattag cagagcgagg    14640
tatgtaggcg gtgctacaga gttcttgaag tggtggccta actacggcta cactagaagg    14700
acagtatttg gtatctgcgc tctgctgaag ccagttacct tcggaaaaag agttggtagc    14760
tcttgatccg gcaaacaaac caccgctggt agcggtggtt ttttgtttg caagcagcag    14820
attacgcgca gaaaaaaagg atctcaagaa gatcctttga tcttttctac ggggtctgaa    14880
gctcagtgga acgaaaactc acgttaaggg attttggtca tgagattatc aaaaaggatc    14940
ttcacctaga tccttttaaa ttaaaaatga agttttaaat caatctaaag tatatatgag    15000
taaacttggt ctgacagtta ccaatgctta atcagtgagg cacctatctc agcgatctgt    15060
ctatttcgtt catccatagt tgcctgactc ccgtcgtgt agataactac gatacgggag    15120
ggcttaccat ctggccccag tgctgcaatg ataccgcgag acccacgctc accggctcca    15180
gatttatcag caataaacca gccagccgga aaggccgagc gcagaagtgg tcctgcaact    15240
ttatccgcct ccatccagtc tattaattgt tgccgggaag ctagagtaag tagttcgcca    15300
gttaatagtt tgcgcaacgt tgttgccatt gctacaggca tcgtggtgtc acgctcgtcg    15360
tttggtatgg cttcattcag ctccggttcc caacgatcaa ggcgagttac atgatccccc    15420
atgttgtgca aaaaagcggt tagctccttc ggtcctccga tcgttgtcag aagtaagttg    15480
```

```
gccgcagtgt tatcactcat ggttatggca gcactgcata attctcttac tgtcatgcca   15540
tccgtaagat gcttttctgt gactggtgag tactcaacca agtcattctg agaatagtgt   15600
atgcggcgac cgagttgctc ttgcccggcg tcaatacggg ataataccgc gccacatagc   15660
agaactttaa aagtgctcat cattggaaaa cgttcttcgg ggcgaaaact ctcaaggatc   15720
ttaccgctgt tgagatccag ttcgatgtaa cccactgtg cacccaactg atcttcagca    15780
tcttttactt tcaccagcgt ttctgggtga gcaaaaacag gaaggcaaaa tgccgcaaaa   15840
aagggaataa gggcgacacg gaaatgttga atactcat                          15878
```

| SEQ ID NO: 5 | moltype = DNA  length = 15878 |
|---|---|
| FEATURE | Location/Qualifiers |
| misc_feature | 1..15878 |
| | note = Synthetic: pPBBG-iHelper2.2-HA |
| source | 1..15878 |
| | mol_type = other DNA |
| | organism = synthetic construct |

SEQUENCE: 5

```
actcttcctt tttcaatatt attgaagcat ttatcagggt tattgtctca tgagcggata     60
catatttgaa tgtatttaga aaaataaaca aataggggtt ccgcgcacat ttccccgaaa    120
agtgccacct aaattgtaag cgttaatatt ttgttaaaat tcgcgttaaa ttttgttaa     180
atcagctcat tttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg cgaaaaaccg tctatcagg gcgatggccc actacgtgaa    360
ccatcaccct aatcaagttt ttgggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaa caaaaactca   1080
aaatttcttc tataaagtaa caaaactttt atcgaattcc tgcagcccgg ggatccact    1140
agttctagag ggacagcccc ccccaaagc cccagggat gtaattacgt ccctcccccg    1200
ctaggggca gcagcgagcc gcccgggct ccgtccggt ccggcgctcc cccgcatcc     1260
ccgagccggc agcgtgcggg gacagcccgg gcacggggaa ggtggcacgg gatcgctttc   1320
ctctgaacgc ttctcgctgc tctttgagcc tgcagacacc tggggggata cgggaaaag   1380
gcctccaagg ccagcttccc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcgtttaaac ttaagcttgg taccgagctc ggatccacta   1560
gtccagtgtg ttggaattcc tgcttcgcga tgtacgggcc ggtacccaac tccatgctta   1620
acagtcccca ggtacagccc accctgcgtc gcaaccagga acagctctac agcttcctgg   1680
agcgccactc gccctacttc cgcagccaca gtgcgcagat taggagcgcc acttcttttt   1740
gtcacttgaa aaacatgtaa aaataatgta ctaggagaca ctttcaataa aggcaaatgt   1800
ttttatttgt acactctcgg gtgattattt accccccacc ttgccgtct gcgccgttta    1860
aaaatcaaag gggttctgcc gcgcatcgct atgcgccact ggcaggga cgttgcgata    1920
ctggtgttta gtgctccact taaactcagg cacaaccatc gcggcagct cggtgaagtt    1980
ttcactccac aggctgcgca ccatcaccaa cgcgtttagc aggtcgggcg ccgatatctt   2040
gaagtcgcag ttgggggcctc cgccctgcgc gcgcgagttg cgatacacag ggttgcaga    2100
ctggaacact atcagcgccg ggtggtgcac gctggccagc acgtctcttgt cggagatcag   2160
atccgcgtcc aggtcctccg cgttgctcag ggcgaacgga gtcaacttg gtagctgcct    2220
tcccaaaaag ggtgcatgcc caggcttga gttgcactcg caccgtagtg gcatcagaag    2280
gtgaccgtgc ccggtctggg cgttaggata cagcgcctgc atgaaagcct tgatctgctt    2340
aaaagccacc tgagcctttg cgccttcaga gaagaacatg ccgcaagact tgccggaaaa    2400
ctgattggcc ggacaggcgc cgtcatgcac gcagcacctt gcgtcggtgt tggagatctg    2460
caccacattt cggccccacc ggttcttcac gatcttggcc ttgctagact gctccttcag   2520
cgcgcgctgc ccgtttctcgc tcgtcacatc catttcaatc acgtgctcct tattatcat    2580
aatgctcccg tgtagacact taagctcgcg ttcgatctca gcgcagcggt gcagccacaa    2640
cgcgcagccc gtgggctcgt ggtgcttgta ggttaccctct gcaaacgact gcaggtacgc    2700
ctgcaggaat cgccccatca tcgtcacaaa ggtcttgttg ctggtgaagg tcagctgcaa    2760
cccgcggtgc tcctcgttta gccaggtctt gcatacggcc gccagagctt ccacttggtc    2820
aggcagtagc ttgaagtttg cctttagatc gttatcgac tggtacttgt ccatccaacg    2880
gcgcgcagcc tccatgccct tctcccacgc agacacgatc ggcaggtcta gcggtttta    2940
caccgtgctt tcactttccg cttcactgga ctcttccttt tcctcttgcg tccgcatacc    3000
ccgcgccact gggtcgtctt cattcagccg ccgcaccgtg gcttacctc ccttgccgtg     3060
cttgattagc accggtgggt tgctgaaacc caccatttgt agcgccacat cttctcttt    3120
ttcctcgctg tccacgatca cctctgggga tggggggcgc tcgggcttgg gagaggggca   3180
cttctttttc tttttggacg caatggccaa atcgccgtc gaggtcgatg gccgcgggct    3240
gggtgtgcgc ggcaccagcg catcttgtga cgagtcttct tcgtcctcgg actcgagacg    3300
ccgcctcagc cgcttttttg ggggcgcgcg ggaggcggc ggcgacgcg acggggacga    3360
cacgtcctcc atggttggtg gacgtcgcgc cgcaccgcgt ccgcgctcgg gggtggttc    3420
gcgctgctcc tcttcccgac tggccatttc cttcctccat aggcagaaaa agatcatgga   3480
gtcagtcgag aaggaggaca gcctaaccgc ccccttgag ttcgccacca ccgcctccac    3540
cgatgccgcc aacgcgccta ccaccttccc cgtcgaggca ccccgcctg aggaggagga   3600
agtgattatc gagcaggacc caggttttgt aagcgagac gacgaggatc gctcagtacc    3660
aacagaggat aaaagcaag accaggacga cgcagaggca aacgaggaac aagtcggggcg    3720
gggggaccaa aggcatggcg actacctaga tgtgggagac gacgtgctgt tgaagcatct    3780
```

-continued

```
gcagcgccag tgcgccatta tctgcgacgc gttgcaagag cgcagcgatg tgccctcgc  3840
catagcggat gtcagccttg cctacgaacg ccacctgttc tcaccgcgcg tacccccaa  3900
acgccaagaa aacggcacat gcgagcccaa cccgcgcctc aacttctacc ccgtatttgc  3960
cgtgccagag gtgcttgcca cctatcacat ctttttccaa aactgcaaga taccccctatc  4020
ctgccgtgcc aaccgcagcc gagcggacaa gcagctggcc ttgcggcagg gcgctgtcat  4080
acctgatatc gcctcgctcg acgaagtgcc aaaaatcttt gagggtcttg gacgcgacga  4140
gaaacgcgcg gcaaacgctc tgcaacaaga aaacagcgaa aatgaaagtc actgtggagt  4200
gctggtggaa cttgagggtg acaacgcgcg cctagccgtg ctgaaacgca gcatcgaggt  4260
cacccacttt gcctacccgg cacttaacct accccccaag gttatgagca cagtcatgag  4320
cgagctgatc gtgcgccgtg cacgacccct ggagagggat gcaaacttgc aagaacaaac  4380
cgaggagggc ctacccgcag ttggcgatga gcagctggcg cgctggcttg agacgcgcga  4440
gcctgccgac ttggaggagc gacgcaagct aatgatggcc gcagtgcttg ttaccgtgga  4500
gcttgagtgc atgcagcggt tctttgctga cccgagatg cagcgcaagc tagaggaaac  4560
gttgcactac accttcgcc agggctacgt gcgccaagcc tgcaaaattt ccaacgtgga  4620
gctctgcaac ctggtctcct accttggaat tttgcacgaa aaccgcctcg ggcaaaacgt  4680
gcttcattcc acgctcaagg gcgaggcgcg ccgcgactac gtccgcgact gcgtttactt  4740
atttctgtgc tacacctggc aaacggccat gggcgtgtgg cagcaatgcc tggaggagcg  4800
caacctaaag gagctgcaga agctgctaaa gcaaaacttg aaggacctat ggacggcctt  4860
caacgagcgc tccgtggccg cgcacctggc ggacattatc ttccccgaac gcctgcttaa  4920
aaccctgcaa cagggtctgc cagacttcac cagtcaaagc atgttgcaaa actttaggaa  4980
cttatcccta gagcgttcag gaattctgcc cgccacctgc tgtgcgcttc ctagcgactt  5040
tgtgcccatt aagtaccgtg aatgccctcc gccgctttgg ggtcactgct accttctgca  5100
gctagccaac taccttgcct accactccga catcatggaa gacgtgagcg gtgacggcct  5160
actgagtgt cactgtcgct gcaacctatg caccccgcac cgctccctgg tctgcaattc  5220
gcaactgctt agcgaaagtc aaattatcgg tacctttgag ctgcagggtc cctgcctga  5280
cgaaaagtcc gcggctccgg ggttgaaact cactccgggc ctgtgacgt ccgatctcta  5340
tcactgatag ggagatctct atcactgata gggagagggc ttaccttcgc aaatttgtac  5400
ctgaggacta ccacgcccac gagattaggt tctacgaaga ccaatcccgc ccgcaaatg  5460
cggagcttac cgcctgcgtc attacccagg gccacatcct tggccaattg caagccatca  5520
acaaagcccg ccaagagttt ctgctacgaa agggacgggg ggtttacctg gacccccagt  5580
ccggcgagga gctcaaccca atccccccgc cgccgcagcc ctatcagcag ccgcgggccc  5640
ttgcttccca ggatggcacc caaaaagaag ctgcagctgc cgccgccgcc acccacggac  5700
gaggaggaat actgggacag tcaggcagag gaggttttgg acgaggagga ggagatgatg  5760
gaagactggg acagcctaga cgaagcttcc gaggccgaaa aggtgtcaga cgaaacaccg  5820
tcaccctcgg tcgcattccc ctcgccggcg ccccagaaat tggcaaccgt tccagcatc  5880
gctacaacct ccgctcctca ggcgccgccg gcactgcctg ttcgccgacc aaccgtaga  5940
tgggacacca ctggaaccag ggccggtaag tctaagcagc cgccgccgtt agcccaagag  6000
caacaacagc gccaaggcta ccgctcgtgg cgcgggcaca agaacgccat agttgcttgc  6060
ttgcaagact gtggggggcaa catctccttc gcccgccgct ttcttctcta ccatcacggc  6120
gtggccttcc cccgtaacat cctgcattac taccgtcatc tctacagccc ctactgcacc  6180
ggcggcagcg gcagcggcag caacagcagc ggtcacacag aagcaaaggc gaccggatag  6240
caagactctg acaaagccca agaaatccac agcggcggca gcagcaggag gaggagcgct  6300
gcgtctggcg cccaacgaac ccgtatcgac ccgcgagctt agaaatagga ttttttcccac  6360
tctgtatgct atatttcaac aaagcagggg ccaagaacaa gagctgaaaa taaaaaacag  6420
gtctctcgcg tccctcaccc gcagctgcct gtatcacaaa agcgaagatc agcttcggcg  6480
cacgctggaa gacgcggagg ctctcttcag caacgatctc tatcactgat agggagatct  6540
ctatcactga tagggagaga tactgcgcgc tgactcttaa ggactagttt cgcgccctt  6600
ctcaaattta agcgcgaaaa ctacgtcatc tccagcggcc acaccccgcg ccagcacctg  6660
tcgtcagcgc cattatgagc aaggaaattc ccacgcccta catgtggagt taccagccac  6720
aaaatgggact tgcggctgga gctgcccaag actactcaac ccgaataaac tacatgagcg  6780
cgggacccca catgatatcc cgggtcaacg gaatccgcgc ccaccgaaac cgaattcctc  6840
tcgaacaggc ggctattacc accacacctc gtaataacct taatcccgt agttggcccg  6900
ctgccctggt gtaccaggaa agtcccgctc ccaccactgt ggtacttccc agagacgccc  6960
aggccgaagt tcagatgact aactcagggg cgcagcttgc gggcggcttt cgtcacaggg  7020
tgcggtcgcc cccagtggcc aaaaaagcta gcgcagcagc cgccgcgcct ggaaggaagc  7080
caaaaggagc gctcccccgt tgtctgacgt cgcacacctg ggttcgacac gcgggcggta  7140
accgcatgga tcacgcgga cggccggatc cggggttcga accccggtcg tccgccatga  7200
tacccttgcg aatttatcca ccagaccacg gaagagtgcc cgcttacagg ctctcctttt  7260
gcacggtcta gagcgtcaac gactgcgcac gggggcgtttt agggcggagt aacttgcatg  7320
tattgggaat tgtagttttt ttaaaatggg aagtgacgta tcgtgggaaa acggaagtga  7380
agatttgagg aagttgtggg ttttttggct ttcgtttctg ggcgtaggtt cgcgtgcggt  7440
tttctgggtg ttttttgtgg actttaaccg ttacgtcatt ttttagtcct atatatactc  7500
gctctgtact ctccctatca gtgatagaga tctccctatc agtgatagag atcgcttggc  7560
ccttttaca ctgtgactga ttgagctggt gccgtgtcgg gttgttttt ttaataggtt  7620
tttttactgg taaggctgac tgttatggct gccgctgtgg aagcgctgta tgttgttctg  7680
gagcggagg gtgctatttt gcctaggcag gagggttttt caggtgttta tgtgttttc  7740
tctcctatta atttgttat acctcctatg ggggctgaa tgttgtctct acgcctgcgg  7800
gtatgtattc ccccggggcta tttcggtcgc tttttagcac tgaccgatgt taaccaacct  7860
gatgtgttta ccgagtctta cattatgact ccggacatga ccgaggaact gtcggtggtg  7920
cttttttaatc acggtgacca gttttttttac ggtcacgccg gcatggccgt agtccgtctt  7980
atgcttataa gggttgtttt tcctgttgta agacaggctt ctaatgttta aatgtttttt  8040
tttttgttat tttattttgt gtttaatgca ggaacccgca gacatgtttg agagaaaat  8100
ggtgtctttt tctgtggtgg ttccggaact tacctgcctt tatctgcatg agcatgacta  8160
cgatgtgctt gcttttttgc gcgaggcttt gcctgatttt ttgagcagca ccttgcattt  8220
tatatcgccg cccatgcaac aagcttacat aggggctacg ctggttagca tagctccgag  8280
tatgcgtgtc ataatcagtg tgggttcttt tgtcatggtt cctggcgggg aagtggccgc  8340
gctggtccgt gcagacctgc acgattatgt tcagctggcc ctgcgaaggg acctacggga  8400
tcgcggtatt tttgttaatg ttccgctttt gaatcttata caggtctgtg aggaacctga  8460
attttttgcaa tcatgattcg ctgcttgagg ctgaaggtgg agggcgctct ggagcagatt  8520
```

```
tttacaatgg ccggacttaa tattcgggat ttgcttagag acatattgat aaggtggcga   8580
gatgaaaatt atttgggcat ggttgaaggt gctggaatgt ttatagagga gattcaccct   8640
gaagggttta gcctttacgt ccacttggac gtgagggcag tttgccttt  ggaagccatt   8700
gtgcaacatc ttacaaatgc cattatctgt tctttggctg tagagtttga ccacgccacc   8760
ggaggggagc gcgttcactt aatagatctt cattttgagg ttttgaataa tcttttggaa   8820
taaaaaaaaa aaaacatggt tcttccagct cttcccgctc ctcccgtgtg tgactcgcag   8880
aacgaatgtg taggttggct gggtgtggct tattctgcgg tggtggatgt tatcagggca   8940
gcggcgcatg aaggagttta catagaaccc gaagccaggg ggcgcctgga tgctttgaga   9000
gagtggatat actacaacta ctacacagag cgagctaagc gacgagaccg gagacgcaga   9060
tctgttttgtc acgcccgcac ctggttttgc ttcaggaaat atgtacccat acgatgttcc   9120
agattacgct ggaggaggcg gaggcactac gtccggcgtt ccatttggca tgacactacg   9180
accaacacga tctcggttgt ctcggcgcac tccgtacagt agggatcgcc tacctccttt   9240
tgagacagag acccgcgcta ccatactgga ggatcatccg ctgctgcccg aatgtaacac   9300
ttgacaatg  cacaacgtga gttacgtgcg aggtcttccc tgcagtgtgg gatttacgct   9360
gattcaggaa tgggttgttc cctgggatat ggttctgacg cgggaggagc ttgtaatcct   9420
gaggaagtgt atgcacgtgt gcctgtgttg tgccaacatt gatatcatga cgagcatgat   9480
gatccatggt tacgagtcct gggctctcca ctgtcattgt tccagtcccg gttccctgca   9540
gtgcatagcc ggcgggcagg ttttggccag ctggtttagg atggtggtgg atggcgccat   9600
gtttaatcag aggtttatat ggtaccggga ggtggtgaat tacaacatgc caaaagaggt   9660
aatgtttatg tccagcgtgt ttatgagggg tcgccactta atctacctgc gcttgtggta   9720
tgatggccac gtgggttctg tggtcccgc  catgagcttt ggatacagcg ccttgcactg   9780
tgggatttg  aacaatattg tggtgctgtg ctgcagttac tgtgctgatt taagtgagat   9840
cagggtgcgc tgctgtgccc ggaggacaag gcgtctcatg ctgcgggcgg tgcgaatcat   9900
cgctgaggag accactgcca tgttgtattc ctgcaggacg gagcggcggc ggcagcagtt   9960
tattcgcgcg ctgctgcagc accaccgccc tatcctgatg cacgattatg actctacccc  10020
catgtaggcg tggacttccc cttcgccgcc cgttgagcaa ccgcaagttg gacagcagcc  10080
tgtggctcag cagctggaca gcgacatgaa cttaagcgag ctgcccgggg agttttattaa  10140
tatcactgat gagcgtttgg ctcgacagga aaccgtgtgg aatataacac ctaagaatat  10200
gtctgttacc catgatatga tgcttttaa  ggccagccgg ggagaaagga ctgtgtactc  10260
tgtgtgttgg gaggggaggtg gcaggttgaa tactagggt  ctgtgagttt gattaaggta  10320
cggtgatcaa tataagctat gtggtggtgg ggctatacta ctgaatgaaa aatgacttga  10380
aattttctgc aattgaaaaa taaacacgtt gaaacataac atgcaacagg ttcacgattc  10440
tttattcctg ggcaatgtag gagaaggtgt aagagttggt agcaaaagtt tcagtggtgt  10500
atttttccact ttcccaggac catgtaaaag acatagagta agtgcttacc tcgctagttt  10560
ctgtggattc actagaatcc actttggccg cggctcgagt gagctattcc agaagtagtg  10620
aagaggcttt tttggaggcc taggcttttg caaaaagctc cggatcgatg cccgggggat  10680
ccactagttc tagagggaca gcccccccc  aaagccccca gggatgtaat tacgtccctc  10740
ccccgctagg gggcagcagc gagccgcccg gggctccgct ccggtccggc gctcccccg   10800
catcccgag  ccggcagcgt gcggggacag cccgggcagg ggaaggtgg cacgggatcg  10860
ctttcctctg aacgcttctc gctgctcttt gagcctgcag acacctgggg ggatacgggg  10920
aaaaggcctc caaggccagc ttcccacaat aagttgggtg aatttggct  gagctattcc  10980
agaagtagtg aagaggcttt tttggaggcc taggcttttg caaaaagctc cggatcgatc  11040
atatatggca gatatacgcg ttgacattga ttattgacta gttattaata gtaatcaatt  11100
acggggtcat tagttcatag cccatatatg gagttccgcg ttacataact tacggtaaat  11160
ggcccgcctg gctgaccgcc caacgacccc cgcccattga cgtcaataat gacgtatgtt  11220
cccatagtaa cgccaatagg gactttccat tgacgtcaat gggtggagta tttacggtaa  11280
actgcccact tggcagtaca tcaagtgtat catatgccaa gtacgccccc tattgacgtc  11340
aatgacggta aatggcccgc ctggcattat gcccagtaca tgaccttatg gactttcct   11400
acttggcagt acatctacgt attagtcatc gctattacca tggtgatgcg gttttggcag  11460
tacatcaatg ggcgtggata gcggtttgac tcacggggat ttccaagtct ccacccatt   11520
gacgtcaatg ggagtttgtt ttggcaccaa aatcaacggg actttccaaa atgtcgtaac  11580
aactccgccc cattgacgca aatgggcggt aggcgtgtac ggtgggaggt ctatataagc  11640
agagctctct ggctaactat cgtcgacgag ctcgtttagt gaaccgtcag atcgcctgga  11700
gacgccatcc acgctgtttt gacctccata gaagacaccg ggaccgatcc agcctccgga  11760
ctctagcgtt taaacttaag cttgccacca tgaccgagta caagcccacg gtgcgcctcg  11820
ccacccgcga cgacgtcccc agggccgtac gcaccctcgc cgccgcgttc gccgactacc  11880
ccgcacgcgc ccacaccgtc gatccggacc gccacatcga gcgggtcacc gagctgcaag  11940
aactcttcct cacgcgcgtc gggctcgaca tcggcaaggt gtgggtcgcg gacgacggcg  12000
ccgcggtggc ggtctggacc acgccggaga gcgtcgaagc ggggcgggtg ttcgccgagg  12060
tcggcccgcg catggcgcga ttgagcggtt cccggctggc cgcgcagcaa cagatggaag  12120
gcctcctggc gccgcaccgg cccaaggagc ccgcgtggtt cctggccacc gtcggcgtct  12180
cgcccgacca ccagggcaag gtctgggcag cgccgtcgt  gctcccggga gtggaggcgg  12240
ccgagcgcgc cggggtgccc gccttcctgg agacctccgc gccccgcaac ctcccccttct  12300
acgagcgggct cggcttcacc gtcaccgccg acgtcgaggt gcccgaagga ccgcgcacct  12360
ggtgcatgac ccgcaagccc ggtgcctgaa gcgcgggat  ctcatgctgg agttcttcgc  12420
ccaccccaac ttgtttattg cagcttataa tggttacaaa taaagcaata gcatcacaaa  12480
tttcacaaat aaagcatttt tttcactgca ttctagttgt ggtttgtcca aactcatcaa  12540
tgtatcttat catgtctgta gctgatgtat acctaggatc cggccggcct gcaggtgtcc  12600
tcacaggaac gaagtcccta aagaaacagt ggcagccagg tttagccccg gaattgactg  12660
gattcctttt ttagggccca ttggtatggc ttttccccg  tatcccccca ggtgtctgca  12720
ggctcaaaga gcagcgagaa gcgttcagag gaaagcgatc ccgtgccacc ttccccgtgc  12780
ccgggctgtc cccgcacgct gccggctcgg ggatgcgggg ggagcgccgg accggagcgg  12840
agccccgggc ggctcgctgc tgcccccctag cggggaggg  acgtaattac atccctgggg  12900
gctttggggg gggctgtcc  ctctagageg gccgcccacc ggtcgccacc atggtgagca  12960
ttccctttag tgagggttaa ttagatctta atacgactca ctatagggcg aattgggtac  13020
cgggccccc  ctcgaggtcg acggtatcga taagcttgat atctataaca agaaaatata  13080
tatataataa gttatcacgt aagtagaaca tgaaataaca atataattat cgtatgagtt  13140
aaatcttaaa agtcacgtaa aagataatca tgcgtcattt tgactcacgc ggtcgttata  13200
gttcaaaatc agtgacactt accgcattga caagcacgcc tcacgggagc tccaagcggc  13260
```

```
gactgagatg tcctaaatgc acagcgacgg attcgcgcta tttagaaaga gagagcaata   13320
tttcaagaat gcatgcgtca attttacgca gactatcttt ctaggggttaa tctagctgca   13380
tcaggatcat atcgtcgggt ctttttttccg gctcagtcat cgcccaagct ggcgctatct   13440
gggcatcggg gaggaagaag cccgtgcctt ttcccgcgag gttgaagcgg catggaaaga   13500
gtttgccgag gtgactgct gctgcattga cgttgagcga aaacgcacgt ttaccatgat   13560
gattcgggaa ggtgtggcca tgcacgcctt taacggtgaa ctgttcgttc aggccacctg   13620
ggataccagt tcgtcgcggc ttttccggac acagttccgg atggtcagcc cgaagcgcat   13680
cagcaaccgg aacaataccg gcgacagccg gaactgccgt gccggtgtgc agattaatga   13740
cagcggtgcg gcgctgggat attacgtcag cgaggacggg tatcctggct ggatgccgca   13800
gaaatggaca tggataccc gtgagttacc cggcggggcgc gcttggcgta atcatggtca   13860
tagctgtttc ctgtgtgaaa ttgttatccg ctcacaattc cacacaacat acgagccgga   13920
agcataaagt gtaaagcctg gggtgcctaa tgagtgagct aactcacatt aattgcgttg   13980
cgctcactgc ccgctttcca gtcgggaaac ctgtcgtgcc agctgcatta atgaatcggc   14040
caacgcgcgg ggagaggcgg tttcgtatt gggcgctctt ccgcttcctc gctcactgac   14100
tcgctgcgct cggtcgttcg gctgcggcga gcggtatcag ctcactcaaa ggcggtaata   14160
cggttatcca cagaatcagg ggataacgca ggaaagaaca tgtgagcaaa aggccagcaa   14220
aaggccagga accgtaaaaa ggccgcgttg ctggcgtttt tccataggct ccgcccccct   14280
gacgagcatc acaaaaatcg acgctcaagt cagaggtggc gaaacccgac aggactataa   14340
agataccagg cgtttccccc tggaagctcc ctcgtgcgct ctcctgttcc gaccctgccg   14400
cttaccggat acctgtccgc ctttctccct tcgggaagcg tggcgctttc tcatagctca   14460
cgctgtaggt atctcagttc ggtgtaggtc gttcgctcca agctgggctg tgtgcacgaa   14520
ccccccgttc agcccgaccg ctgcgcctta tccggtaact atcgtcttga gtccaaccccg   14580
gtaagacacg acttatcgcc actggcagca gccactggta acaggattag cagagcgagg   14640
tatgtaggcg gtgctacaga gttcttgaag tggtggccta actacggcta cactagaagg   14700
acagtatttg gtatctgcgc tctgctgaag ccagttacct tcggaaaaag agttggtagc   14760
tcttgatccg gcaaacaaac caccgctggt agcggtggtt ttttttgttg caagcagcag   14820
attacgcgca gaaaaaaagg atctcaagaa gatcctttga tcttttctac ggggtctgac   14880
gctcagtgga acgaaaactc acgttaaggg attttggtca tgagattatc aaaaaggatc   14940
ttcacctaga tcctttttaaa ttaaaaatga agttttaaat caatctaaag tatatatgag   15000
taaacttggt ctgacagtta ccaatgctta atcagtgagg cacctatctc agcgatctgt   15060
ctatttcgtt catccatagt tgcctgactc cccgtcgtgt agataactac gatacgggga   15120
ggcttaccat ctggccccag tgctgcaatg ataccgcgag acccacgctc accggctcca   15180
gatttatcag caataaacca gccagccgga agggccgagc gcagaagtgg tcctgcaact   15240
ttatccgcct ccatccagtc tattaattgt tgccgggaag ctagagtaag tagttcgcca   15300
gttaatagtt tgcgcaacgt tgttgccatt gctacaggca tcgtggtgtc acgctcgtcg   15360
tttggtatgg cttcattcag ctccggttcc caacgatcaa ggcgagttac atgatccccc   15420
atgttgtgca aaaaagcggt tagctccttc ggtcctccga tcgttgtcag aagtaagttg   15480
gccgcagtgt tatcactcat ggttatggca gcactgcata attctcttac tgtcatgcca   15540
tccgtaagat gcttttctgt gactggtgag tactcaacca agtcattctg agaatagtgt   15600
atgcggcgac cgagttgctc ttgcccggcg tcaatacggg ataataccgc gccacatagc   15660
agaactttaa aagtgctcat cattggaaaa cgttcttcgg ggcgaaaact ctcaaggatc   15720
ttaccgctgt tgagatccag ttcgatgtaa cccactcgtg cacccaactg atcttcagca   15780
tcttttactt tcaccagcgt ttctgggtga gcaaaaacag gaaggcaaaa tgccgcaaaa   15840
aagggaataa gggcgacacg gaaatgttga atactcat                           15878
```

| | | |
|---|---|---|
| SEQ ID NO: 6 | moltype = DNA  length = 15992 | |
| FEATURE | Location/Qualifiers | |
| misc_feature | 1..15992 | |
| | note = Synthetic: pPBBG-iHelper2.3-HA | |
| source | 1..15992 | |
| | mol_type = other DNA | |
| | organism = synthetic construct | |

```
SEQUENCE: 6
actcttcctt tttcaatatt attgaagcat ttatcagggt tattgtctca tgagcggata     60
catatttgaa tgtatttaga aaaataaaca aataggggtt ccgcgcacat ttccccgaaa    120
agtgccacct aaattgtaag cgttaatatt ttgttaaaat tcgcgttaaa ttttttgttaa    180
atcagctcat tttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt ttttggggtcg aggtgccgta aagcactaaa tcggaacccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccaggtt    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggg agactcgcgg tgcaaatgtg ttttacagcg tgatggagca gatgaagatg    840
ctcgacacgc tgcagaacac gcagctagat taacccctaga aagataatca tattgtgacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttattat taaaaaaaa caaaaactca   1080
aaatttcttc tataaagtaa caaaacttt tcgaattcc tgcagcccgg ggatccact   1140
agttctagag ggacagcccc cccccaaagc cccaggggat gtaattacgt ccctccccg   1200
ctaggggca gcagcgagc ccggggct ccgtcccgg ccggcgctcc ccccgcatcc   1260
ccgagcggca agcgtgcggg gacagcccgg gcacggcaga ggtggcacgg atcgctttc   1320
ctctgaacgc ttccgctgc tctttgagcc tgcagacacc tggggggata cggggaaaag   1380
gcctccaagg ccagcttccc acaataagtt gggtgaattt tggctcattc ctcctttcta   1440
taggattgag tcagagcttt tgtgatggga attctgtgga atgtgtgtca gttagggtgt   1500
ggaaagtccc gcgatcgcta gcgtttaaac ttaagcttgg taccgagctc ggatccacta   1560
```

-continued

```
gtccagtgtg gtggaattcc tgcttcgcga tgtacgggcc ggtacccaac tccatgctta   1620
acagtcccca ggtacagccc accctgcgtc gcaaccagga acagctctac agcttcctgg   1680
agcgccactc gccctacttc cgcagccaca gtgcgcagat taggagcgcc acttcttttt   1740
gtcacttgaa aaacatgtaa aaataatgta ctaggagaca ctttcaataa aggcaaatgt   1800
ttttatttgt acactctcgg gtgattattt accccccacc cttgccgtct gcgccgttta   1860
aaaatcaaag gggttctgcc gcgcatcgct atgcgccact ggcagggaca cgttgcgata   1920
ctggtgttta gtgctccact taaactcagg cacaaccatc cgcggcagct cggtgaagtt   1980
ttcactccac aggctgcgca ccatcaccaa cgcgtttagc aggtcgggcg ccgatatctt   2040
gaagtcgcag ttggggcctc cgccctgcgc gcgcgagttg cgatacacag ggttgcagca   2100
ctggaacact atcagcgccg ggtggtgcac gctggccagc acgctcttgt cggagatcag   2160
atccgcgtcc aggtcctccg cgttgctcag ggcgaacgga gtcaactttg gtagctgcct   2220
tcccaaaaag ggtgcatgcc caggctttga gttgcactcg caccgtagtg gcatcagaag   2280
gtgaccgtgc ccggtctggg cgttaggata cagcgcctgc atgaaagcct tgatctgctt   2340
aaaagccacc tgagcctttg cgccttcaga gaagaacatg ccgcaagact tgccggaaaa   2400
ctgattggcc ggacaggccg cgtcatgcac gcagcacctt gcgtcggtgt tggagatctg   2460
caccacattt cggcccacc ggttcttcac gatcttggcc ttgctagact gctccttcag   2520
cgcgcgctgc ccgttttcgc tcgtcacatc catttcaatc acgtgctcct tatttatcat   2580
aatgctcccg tgtagacact taagctcgcc ttcgatctca gcgcagcggt gcagccacaa   2640
cgcgcagccc gtgggctcgt ggtgcttgta ggttacctct gcaaacgact gcaggtacgc   2700
ctgcaggaat cgccccatca tcgtcacaaa ggtcttgttg ctggtgaagg tcagctgcaa   2760
cccgcggtgc tcctcgttta gccaggtctt gcatacggcc gccagagctt ccacttggtc   2820
aggcagtagc ttgaagtttg cctttagatc gttatccacg tggtacttgt ccatcaacgc   2880
gcgcgcagcc tccatgccct tctcccacgc agacacgatc ggcaggctca gcgggtttat   2940
caccgtgctt tcactttccg cttcactgga ctcttccttt tcctcttgcg tccgcatacc   3000
ccgcgccact gggtcgtctt cattcagccg ccgcaccgtg cgcttacctc ccttgccgtg   3060
cttgattagc accggtgggt tgctgaaacc caccatttgt agcgccacat cttctctttc   3120
ttcctcgctg tccacgatca cctctgggga tggcgggcgc tcgggcttgg gagaggggcg   3180
cttcttttttc ttttttggacg caatggccaa atccgccgtc gaggtcgatg gccgcgggct   3240
gggtgtgcgc ggcaccagcg catcttgtga cgagtcttct tcgtcctcgg actcgagacg   3300
ccgcctcagc cgcttttttg ggggcgcgcg gggaggcggc gcgacggcg acggggacga   3360
cacgtcctcc atggttggtg gacgtcgcgc cgcaccgcgt ccgcgctcgg gggtggtttc   3420
gcgctgctcc tcttcccgac tggccatttc cttctcctat aggcagaaaa agatcatgga   3480
gtcagtcgag aaggaggaca gcctaaccgc cccctttgag ttcgcaccca ccgcctccac   3540
cgatgccgcc aacgcgccta ccaccttccc cgtcgaggca cccccgcttg aggaggagga   3600
agtgattatc gagcgaggacc caggttttgt aagcgaagac gacgaggatc gctcagtacc   3660
aacagaggat aaaaagcaag accaggacga cgcagaggca aacgaggaac aagtcgggcg   3720
ggggggaccaa aggcatggcg actacctaga tgtgggagac gacgtgctgt tgaagcatct   3780
gcagcgccag tgcgccatta tctgcgcgc gttgcaagag cgcagcgatg tgcccctcgc   3840
catgcggat gtcagccttg cctacgaacg ccacctgttc tcaccgcgcg taccccccaa   3900
acgccaagaa aacggcacat gcgagcccaa cccgcgcctc aacttctacc ccgtatttgc   3960
cgtgccagag gtgcttgcca cctatcacat ctttttttccaa aactgcaaga taccccctatc   4020
ctgccgtgcc aaccgcagcc gagcggacaa gcagctggcc ttgcggcagg gcgctgtcat   4080
acctgatatc gcctcgctcg acgaagtgcc aaaaatcttt gaggtgcttg gacgcgacga   4140
gaaacgcgcg gcaaacgctc tgcaacaaga aaacagcgaa aatgaaagtc actgtgagt   4200
gctggtggaa cttgagggtg acaacgcgcg cctagccgtg ctgaaacgca gcatcggagt   4260
cacccacttt gcctacccgg cacttaacct accccccaag gttatgagca cagtcatgag   4320
cgagctgatc gtgcgccgtg cacgaccct ggagagggat gcaaacttgc aagaacaaac   4380
cgaggagggc ctacccgcag ttggcgatga gcagctggcg cgctggcttg agacgcgcga   4440
gcctgccgac ttggagagc gacgcaagct aatgatggcc gcagtgcttg ttaccgtgga   4500
gcttgagtgc atgcagcggt tctttgctga cccgagatg cagcgcaagc tagggaaac   4560
gttgcactac accttttcgcc agggctacgt gcgccaggcc tgcaaaattt ccaacgtgga   4620
gctctgcaac ctggtctcct accttggaat tttgcacgaa aaccgcctcg gcaaaaacgt   4680
gcttcattcc acgtcaaggg gcgaggcgcg ccgcgactac gtccgcgact gcgtttactt   4740
atttctgtgc tacacctggc aaacggccat gggcgtgtgg cagcaatgcc tggaggagcg   4800
caacctaaag gagctgcaga agctgctaaa gcaaaacttg aaggacctat ggacggcctt   4860
caacgagcgc tccgtggccg cgcacctggc ggacattatc ttccccgaac gcctgcttaa   4920
aacccctgcaa cagggtctgc cagacttcac cagtcaaagc atgttgcaaa actttaggaa   4980
cttttatccta gagcgttcag gaattctgcc cgccacctgc tgtgcgcttc ctagcgactt   5040
tgtcccatt aagtaccgtg aatgccctcc gccgctttgg ggtcactgct accttctgca   5100
gctagccaac taccttgcct accactccga catcatggaa gacgtgagcg gtgacggcct   5160
actggagtgt cactgtcgct gcaacctatg caccccgcac cgctccctgg tctgcaattc   5220
gcaactgctt agcgaaagtc aaattatcgg taccttttgag ctgcagggtc cctgcctga   5280
cgaaaagtcc gcggctccgg ggttgaaact cactccgggg ctgtgacgt ccgatctcta   5340
tcactgatag ggagatctct atcactgata gggagagggc ttacctttcgc aaatttgtac   5400
ctgaggacta ccacgcccac gagattaggt tctacgaaga ccaatcccgc ccgcaaatg   5460
cggagcttac cgcctgcgtc attcccaggg gccacatcct tggccaattg caagccatca   5520
acaaagcccg ccaagagttt ctgctacgaa agggacgggg ggtttacctg acccccagt   5580
ccggcgagga gctcaaccca atcccccgc cgccagcagc ctatcagcag ccgcgggccc   5640
ttgcttccca ggatggcacc caaaaagaag ctgcagctgc cgccgccgcc acccaggac   5700
gaggaggaat actgggacag tcaggcagag gaggttttgg acgaggagga ggagatgatg   5760
gaagactggg acagcctaga cgaagcttcc gaggccgaag aggtgtcaga cgaaacaccg   5820
tcaccctcgg tcgcattccc ctcgccgcg ccccagaaat tggcaaccgt tcccagcatc   5880
gctacaacct ccgctcctca ggcgccgcg gcactgcctg ttcgccgacc caaccgtaga   5940
tgggacacca ctggaaccag ggcggttaag tctaagcagc gccaccaagag   6000
caacaacagc gccaaggcta ccgctcgtgg cgcgggcaca agaacgccat agttgcttgc   6060
ttgcaagact gtggggcaa catctccttc gcccgcgct tcttctcta ccatcacggc   6120
gtggccttcc cccgtaacat cctgcattac taccgtcatc tctacagccc ctactgcacc   6180
ggcgcagcg cagcggcag caacagcagc ggtcacacag aagcaaaggc gaccggatag   6240
caagactctg acaaagccca agaaatccac agcggcggca gcagcaggag gaggagcgct   6300
```

```
gcgtctggcg cccaacgaac ccgtatcgac ccgcgagctt agaaatagga ttttttcccac   6360
tctgtatgct atatttcaac aaagcagggg ccaagaacaa gagctgaaaa taaaaaacag   6420
gtctctcgcg tccctcaccc gcagctgcct gtatcacaaa agcgaagatc agcttcggcg   6480
cacgctggaa gacgcggagg ctctcttcag caacgatctc tatcactgat agggagatct   6540
ctatcactga tagggagaga tactgcgcgc tgactcttaa ggactagttt cgcgcccttt   6600
ctcaaattta agcgcgaaaa ctacgtcatc tccagcggcc acaccggcg ccagcacctg    6660
tcgtcagcgc cattatgagc aaggaaattc ccacgcccta catgtggagt taccagccac   6720
aaatgggact tgcggctgga gctgcccaag actactcaac ccgaataaac tacatgagcg   6780
cgggacccca catgatatcc cgggtcaacg gaatccgcgc ccaccgaaac cgaattctcc   6840
tcgaacaggc ggctattacc accacacctc gtaatacct taatcccgt agttggcccg      6900
ctgccctggt gtaccaggaa agtcccgctc ccaccactgt ggtacttccc agagacgccc   6960
aggccgaagt tcagatgact aactcagggg cgcagcttgc gggcggcttt cgtcacaggg   7020
tgcggtcgcc cgggcgtttt agggcggagt aacttgcatg tattgggaat tgtagttttt   7080
ttaaaatggg aagtgacgta tcgtgggaaa acggaagtga agatttgagg aagttgtggg   7140
tttttttggct ttcgtttctg ggcgtaggtt cgcgtgcggt tttctgggtg tttttttgtgg 7200
actttaaccg ttacgtcatt ttttagtcct atatatactc gctctgtact ctccctatca   7260
gtgatagaga tctcccctatc agtgatagag atcgcttggc cctttttaca ctgtgactga  7320
ttgagctggt gccgtgtcga gtggtgtttt ttaataggtt tttttactgg taaggctgac   7380
tgttatggct gccgctgtgg aagcgctgta tgttgttctg gagcgggagg gtgctatttt   7440
gcctaggcag gagggttttt caggtgttta tgtgttttc tctcctatta attttgttat    7500
acctcctatg ggggctgtaa tgttgtctct acgcctgcgg gtatgtattc cccgggcta    7560
tttcggtcgc tttttagcac tgaccgatgt taaccaacct gatgtgttta cgcagtctta   7620
cattatgact ccggacatga ccgaggaact gtcggtggtg cttttaatc acggtgacca    7680
gttttttac ggtcacgccg gcatggccgt agtccgtctt atgcttataa gggttgtttt    7740
tcctgttgta agacaggctt ctaatgttta aatgttttt ttttgttat tttattttgt     7800
gtttaatgca ggaacccgca gacatgtttg agagaaaaat ggtgtctttt tctgtggtgg   7860
ttccggaact tacctgcctt tatctgcatg agcatgacta cgatgtgctt gcttttttgc   7920
gcgaggcttt gcctgatttt ttgagcagca ccttgcattt tatatcgccg cccatgcaac   7980
aagcttacat aggggctacg ctggttagca tagctccgag tatgcgtgtc ataatcagtg   8040
tgggttcttt tgtcatggtt cctgccgggg aagtggccgc gctggtccgt gcagacctgc   8100
acgattatgt tcagctggcc ctgcgaaggg acctacggga tcgcggtatt tttgttaatg   8160
ttccgctttt gaatcttata caggtctgtg aggaacctga attttgcaa tcatgattcg    8220
ctgcttgagg ctgaaggtgg agggcgctct ggagcagatt tttacaatgg ccggacttaa   8280
tattcgggat ttgcttagag acatattgat aaggtggcga gatgaaaatt atttgggcat   8340
ggttaaggt gctggaatgt ttatagagga gattcaccct gaagggttta gccttttacgt   8400
ccacttggac gtgagggcag tttgccttt ggaagccatt gtgcaacatc ttacaaatgc    8460
cattatctgt tctttggctg tagagtttga ccacgccacc ggaggggagc gcgttcactt   8520
aatagatctt cattttgagg ttttggataa tcttttggaa taaaaaaaaa aaaacatggt   8580
tcttccagct cttcccgctc ctcccgtgt tgactgcgca acgaatgtg taggttgct      8640
gggtgtggct tattctgcgg tggtggatgt tatcaggtca gcggcgcatg aaggagttta   8700
catgaaccc gaagccaggg ggcgcctgga tgctttgaga gagtgtgatat actacaacta   8760
ctacacagag cgagctaagc gacgagaccg gagacgcaga tctgtttgtc acgcccgcac   8820
ctggttttgc ttcaggaaat atgtacccat acgatgttcc agattacgct ggaggaggcg   8880
gaggcactac gtccggcgtt ccatttggca tgacactacg accaacacga tctcggttgt   8940
ctcggcgcac tccgtacagt agggatcgcc tacctccttt tgagacagag acccgcgcta   9000
ccatactgga ggatcatccg ctgctgcccg aatgtaaacac tttgacaatg cacaacgtga   9060
gttacgtgcg aggtcttccc tgcagtgtgg gatttacgct gattcaggaa tgggttgttc    9120
cctgggatat ggttctgacg cgggaggagc ttgtaatcct gaggaagtgt atgcacgtgt   9180
gcctgtgttg tgccaacatt gatatcatga cgagcatgat gatccatggt tacgagtcct   9240
gggctctcca ctgtcattgt tccagtcccg gttccctgca gtgcatagcc ggcgggcagg   9300
ttttggccag ctggtttagg atggtggtgg atggcgccat gtttaatcag aggtttat      9360
ggtaccggga ggtggtgaat tacaacatgc caaaagaggt aatgtttatg tccagcgtgt   9420
ttatgagggg tcgccactta atctacctgc gcttgtggta tgatggccac gtgggttctg   9480
tggtccccgc catgagcttt ggatacagcg ccttgcactg tgggattttg aacaatattg   9540
tggtgctgtg ctgcagttac tgtgctgatt taagtgagat cagggtgcgc tgctgtgccc   9600
ggaggacaag gcgtctcatg ctgcgggcg tgcgaatcat cgctgaggag accactgcca    9660
tgttgtattc ctgcaggacg gagcggcggc ggcagcagtt tattcgcgcg ctgctgcagc   9720
accaccgccc tatcctgatg cacgattatg actctacccc catgtaggcg tggacttccc   9780
cttcgccgcc cgttgagcaa ccgcaagttg gacagcaggc tgtggctcag cagctggaca   9840
gcgacatgaa cttaagcgag ctgcccgggg agtttattaa tatcactgat gagcgtttgt   9900
ctcgacagga aaccgtgtgg aatataacac ctaagaatat gtctgttacc catgatatga   9960
tgcttttttaa ggccagccgg ggagaaagga ctgtgtactc tgtgtgttgg gagggaggtg  10020
gcaggttgaa tactagggtt ctgtgagttt gattaaggta cggtgatcaa tataagctat   10080
gtggtggtgg ggctatacta tgaatgaaa aatgcttga aatttctgc aattgaaaaa       10140
taaacacgtt gaaacataac atgcaacagg ttcacgattc tttattcctg ggcaatgtag   10200
gagaaggtgt aagagttggt agcaaaagtt tcagtggtgt attttccact ttcccaggac   10260
catgtaaaag acatagagta agtgcttacc tcgctagttt ctgtggattc actagaacca   10320
gtggccaaaa aagctagcgc agcagccgcc gcgcctggaa ggaagccaaa aggagcgctc   10380
cccgttgtc tgacgtcgca cacctgggtt cgacacggg gcgtaaccg catggatcac       10440
ggcggacggc cggatccggg gttcgaaccc cggtcgtccg ccatgatacc cttgcgaatt   10500
tatccaccag accacggaag agtgcccgct tacaggtggt ctcatacaga acttataaga   10560
ttcccaaatc caaagacatt tcacgttat ggtgatttcc cagaacacat agcgacatgc    10620
aaatattgca gggcgccact cccctgtccg ctctcctttt gcacggtcta gagcgtcaac   10680
gactgcgtac gtccactttg gccgcggctc gagtgagcta ttccagaagt agtgaagagg   10740
ctttttttgga ggcctaggct tttgcaaaaa gctccggatc gatgcccggg ggatccacta   10800
gttctagagg gacagccccc cccaaaagcc cccagggatg taattacgtc cctccccgc    10860
taggggggcag cagcgagccg cccggggctc cgctccggtc cggcgctccc cccgcatccc   10920
cgagccggca gcgtgcgggg acagcccggg cacggggaag gtggcacggg atcgctttcc   10980
tctgaacgct tctcgctgct ctttgagcct gcagacacct ggggggatac ggggaaaagg   11040
```

```
cctccaaggc cagcttccca caataagttg ggtgaatttt ggctgagcta ttccagaagt    11100
agtgaagagg ctttttttgga ggcctaggct tttgcaaaaa gctccggatc gatcatatat    11160
ggcagatata cgcgttgaca ttgattattg actagttatt aatagtaatc aattacgggg    11220
tcattagttc atagcccata tatggagttc cgcgttacat aacttacggt aaatggcccg    11280
cctggctgac cgcccaacga cccccgccca ttgacgtcaa taatgacgta tgttcccata    11340
gtaacgccaa tagggacttt ccattgacgt caatgggtgg agtatttacg gtaaactgcc    11400
cacttggcag tacatcaagt gtatcatatg ccaagtacgc cccctattga cgtcaatgac    11460
ggtaaatggc ccgcctggca ttatgcccag tacatgacct tatgggactt tcctacttgg    11520
cagtacatct acgtattagt catcgctatt accatggtga tgcggttttg gcagtacatc    11580
aatgggcgtg gatagcggtt tgactcacgg ggatttccaa gtctccaccc cattgacgtc    11640
aatgggagtt tgttttggca ccaaaatcaa cgggactttc caaaatgtcg taacaactcc    11700
gccccattga cgcaaatggg cggtaggcgt gtacggtggg aggtctatat aagcagagct    11760
ctctggctaa ctatcgtcga cgagctcgtt tagtgaaccg tcagatcgcc tggagacgcc    11820
atccacgctg ttttgacctc catagaagac accgggaccg atccagcctc cggactctag    11880
cgtttaaact taagcttgcc accatgaccg agtacaagcc cacggtgcgc ctcgccaccc    11940
gcgacgacgt ccccagggcc gtacgcaccc tcgccgccgc gttcgccgac taccccgcca    12000
cgcgccacac cgtcgatccg gaccgccaca tcgagcgggt caccgagctg caagaactct    12060
tcctcacgcg cgtcgggctc gacatcggca aggtgtgggt cgcggacgac ggcgccgcgg    12120
tggcggtctg gaccacgccg gagagcgtcg aagcgggggc ggtgttcgcc gagatcggcc    12180
cgcgcatggc cgagttgagc ggttcccggc tggccgcgca gcaacagatg gaaggcctcc    12240
tggcgccgca ccggcccaag gagcccgcgt ggttcctggc caccgtcggc gtctcgcccg    12300
accaccaggg caagggtctg gcagccgccg tcgtgctccg ggagtggag gcggccgagc    12360
gcgccggggt gcccgccttc ctggagacct ccgcgccccg caacctcccc ttctacgagc    12420
ggctcggctt caccgtcacc gccgacgtcg aggtgcccga aggaccgcgc acctggtgca    12480
tgacccgcaa gcccggtgcc tgaagcgcgg ggatctcatg ctggagttct tcgcccaccc    12540
caacttgttt attgcagctt ataatggtta caaataaagc aatagcatca caaatttcac    12600
aaataaagca tttttttcac tgcattctag ttgtggtttg tccaaactca tcaatgtatc    12660
ttatcatgtc tgtagctgat gtatacctag gatccggccg gcctgcaggt gtcctcacag    12720
gaacgaagtc cctaaagaaa cagtggcagc caggtttagc cccggaattg actggattcc    12780
ttttttaggg cccattggta tggcttttttc cccgtatccc caggtgtc tgcaggctca    12840
aagagcagcg agaagggttc agaggaaagc gatcccgtgc caccttcccc gtgcccgggc    12900
tgtccccgca cgctgccggc tcgggggatgc gggggggagcg ccggaccgga gcggagcccc    12960
gggcggctcg ctgctgcccc ctagcggggg aggacgtaa ttacatccct gggggctttg    13020
ggggggggct gtccctctag agcggccgcc accgcggtgg agctccagct tttgttcct    13080
ttagtgaggg ttaattagat cttaatacga ctcactatag ggcgaattgg gtaccgggcc    13140
cccctcgag gtcgacggta tcgataagct tgatatctat aacaagaaaa tatatatata    13200
ataagttatc acgtaagtag aacatgaaat aacaatataa ttatcgtatg agttaaatct    13260
taaaagtcac gtaaaagata atcatgcgtc attttgactc acgcggtcgt tatagttcaa    13320
aatcagtgac acttaccgca ttgacaagca cgcctcacgg gagctccaag cggcgactga    13380
gatgtcctaa atgcacagcg acggattcgc gctatttaga aagagagagc aatatttcaa    13440
gaatgcatgc gtcaatttta cgcagactat cttttctagg gttaatctagc tgcatcagga    13500
tcatatcgtc gggtcttttt tccggctcag tcatcgccca agctggcgct atctgggcat    13560
cggggaggaa gaagcccgtg ccttttcccg cgaggttgaa cgagcatgga aagagtttgc    13620
cgaggatgac tgctgctgca ttgacgttga gcgaaaacgc acgtttacca tgatgattcg    13680
ggaaggtgtg gccatgcacg cctttaacgg tgaactgttc gttcaggcca cctgggatac    13740
cagttcgtcg cggcttttcc ggacacagtt ccggatggtc agcccgaagc gcatcagcaa    13800
cccgaacaat accggcggaca gccgaactg ccgtgccggt cgagatta atgacagcgg    13860
tgcggcgctg ggatattacg tcagcgagga cgggtatcct ggctggatgc cgcagaaatg    13920
gacatggata ccccgtgagt tacccggcgg gcgcgcttgg cgtaatcatg gtcatagctg    13980
tttcctgtgt gaaattgtta tccgctcaca attccacaca acatacgagc cggaagcata    14040
aagtgtaaag cctggggtgc ctaatgagtg agctaactca cattaattgc gttgcgctca    14100
ctgcccgctt tccagtcggg aaacctgtcg tgccagctgc attaatgaat cggccaacgc    14160
gcggggagag gcggttttgcg tattgggcgc tcttccgctt cctcgctcac tgactcgctg    14220
cgctcggtcg ttcggctgcg gcgagcggta tcagctcact caaaggcggt aatacggtta    14280
tccacagaat caggggataa cgcaggaaag aacatgtgag caaaaggcca gcaaaaggcc    14340
aggaaccgta aaaaggccgc gttgctggcg ttttttccata ggctccgccc cctgacgag    14400
catcacaaaa atcgacgctc aagtcagagg tggcgaaacc cgacaggact ataaagatac    14460
caggcgtttc ccctggaag ctccctcgtg cgctctcctg ttccgaccct gccgcttacc    14520
ggatacctgt ccgcctttct cccttcggga agcgtggcgc tttctcatag ctcacgctgt    14580
aggtatctca gttcggtgta ggtcgttcgc tccaagctgg gctgtgtgca cgaaccccc    14640
gttcagcccg accgctgcgc cttatccggt aactatcgtc ttgagtccaa cccggtaaga    14700
cacgacttat cgccactggc agcagccact ggtaacagga ttagcagagc gaggtatgta    14760
ggcggtgcta cagagttctt gaagtggtgg cctaactacg gctacactag aaggacagta    14820
tttggtatct gcgctctgct gaagccagtt accttcggaa aaagagttgg tagctcttga    14880
tccggcaaac aaaccaccgc tggtagcggt ggtttttttg tttgcaagca gcagattacg    14940
cgcagaaaaa aaggatctca agaagatcct ttgatctttt ctacgggtc tgacgctcag    15000
tggaacgaaa actcacgtta agggattttg gtcatgagat tatcaaaag gatcttcacc    15060
tagatccttt taaattaaaa atgaagtttt aaatcaatct aaagtatata tgagtaaact    15120
tggtctgaca gttaccaatg cttaatcagt gaggcaccta tctcagcgat ctgtctattt    15180
cgttcatcca tagttgcctg actccccgtc gtgtagataa ctacgatacg ggagggctta    15240
ccatctggcc ccagtgctgc aatgataccg cgagacccac gctcaccggc tccagattta    15300
tcagcaataa accagccagc cggaagggcc gagcgcagaa gtggtcctgc aactttatcc    15360
gcctccatcc agtctattaa ttgttgccgg gaagctagag taagtagttc gccagttaat    15420
agtttgcgca acgttgttgc cattgctaca ggcatcgtgg tgtcacgctc gtcgtttggt    15480
atggcttcat tcagctccgg ttcccaacga tcaaggcgag ttacatgatc ccccatgttg    15540
tgcaaaaaag cggttagctc cttcggtcct ccgatcgttg tcagaagtaa gttggccgca    15600
gtgttatcac tcatggttat ggcagcactg cataattctc ttactgtcat gccatccgta    15660
agatgctttt ctgtgactgg tgagtactca accaagtcat tctgagaata gtgtatgcgg    15720
cgaccgagtt gctcttgccc ggcgtcaata cgggataata ccgcgccaca tagcagaact    15780
```

```
ttaaaagtgc tcatcattgg aaaacgttct tcggggcgaa aactctcaag gatcttaccg  15840
ctgttgagat ccagttcgat gtaacccact cgtgcaccca actgatcttc agcatctttt  15900
actttcacca gcgtttctgg gtgagcaaaa acaggaaggc aaaatgccgc aaaaaaggga  15960
ataagggcga cacggaaatg ttgaatactc at                                15992
```

```
SEQ ID NO: 7            moltype = DNA  length = 15992
FEATURE                 Location/Qualifiers
misc_feature            1..15992
                        note = Synthetic: pPBBG-iHelper2.4-HA
source                  1..15992
                        mol_type = other DNA
                        organism = synthetic construct
SEQUENCE: 7
actcttcctt tttcaatatt attgaagcat ttatcagggt tatttgtctca tgagcggata   60
catatttgaa tgtatttaga aaaataaaca aataggggtt ccgcgcacat ttccccgaaa  120
agtgccacct aaattgtaag cgttaatatt ttgttaaaat tcgcgttaaa ttttgttaa   180
atcagctcat tttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt ttttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccaggttt tcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
ctcgacacgc tgcagaacac gcagctagat aaccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata 1020
ataaattcaa caaacaattt atttatgttt atttatttat taaaaaaaaa caaaaactaa 1080
aaatttcttc tataaagtaa caaaacttttt atcgaattcc tgcagccggg ggatccact  1140
agttctagag ggacagcccc cccccaaagc ccccagggat gtaattacgt cccctcccccg 1200
ctaggggcga gcagcgagcc gcccggggct ccgctccggt ccggcgctcc ccccgcatcc 1260
ccgagccggc agcgtgcggg gacagcccgg gcacgggaca ggtggcacgg gatcgctttc 1320
ctctgaacgc ttctcgctgc tctttgagcc tgcagacacc tgggggggata cggggaaaag 1380
gcctccaagg ccagcttccc acaataagtt gggtgaattt tggctcattc ctcctttcta 1440
taggattgag gtcagagctt tgtgatggga attctgtgga atgtgtgtca gttagggtgt 1500
ggaaagtccc gcgatcgcta gcgtttaaac ttaagcttgg taccgagctc ggatccacta 1560
gtccagtgtg gtggaattcc tgcttcgcga tgtacgggcc ggtacccaac tccatgctta 1620
acagtcccca ggtacagccc accctgcgtc gcaaccagga acagctctac agcttcctgg 1680
agcgccactc gccctacttc cgcagccaca gtgcgcagat taggagcgcc acttcttttt 1740
gtcacttgaa aaacatgtaa aaataatgta ctaggaagca ctttcaataa aggcaaatgt 1800
ttttatttgt acactctcgg gtgattattt accccccacc cttgccgtct gcgccgttta 1860
aaaatcaaag gggttctgcc gcgcatcgct atgcgccact ggcagggaca cgttgcgata 1920
ctggtgtttg gtgctccact taaactcagg cacaaccatc cgcggcagct cggtgaagtt 1980
ttcactccac aggcttgcgca ccatcaccaa cgcgtttagc aggtcgggcg ccgatatctt 2040
gaagtcgcag ttggggcctc cgccctgcgc gcgcgagttg cgatacacag ggttgcagca 2100
ctggaacact atcagcgccg ggtggtgcac gctggccagc acgctcttgt cggagatcag 2160
atccgcgtcc aggtcctccg cgttgctcag ggcgaacgga gtcaactttg gtagctgcct 2220
tcccaaaaag ggtgcatgcc caggctttga gttgcactcg caccgtagtg gcatcagaag 2280
gtgaccgtgc ccggtctggg cgttaggata cagcgcctgc atgaaagcct tgatctgctt 2340
aaaagccacc tgagcctttg cgccttcaga gaagaacatg ccgcaagact tgccggaaaa 2400
ctgattggcc ggacaggccg cgtcatgcac gcagcacctt cgtcggtgt tggagatctg 2460
caccacattt cggccccacc ggttcttcac gatcttggcc ttgctagact gctccttcag 2520
cgcgcgctgc ccgttttcgc tcgtcacatc catttcaatc acgtgctcct tatttatcat 2580
aatgctcccg tgtagacact taagctcgcc ttcgatctca gcgcagcggt gcagccacaa 2640
cgcgcagccc gtgggctcgt ggtgcttgta ggttacctct gcaaacgact gcaggtacgc 2700
ctgcaggaat cgcccatca tcgtcacaaa ggtcttgttg ctggtgaagg tcagctgcaa 2760
cccgcggtgc tcctcgttta gccaggtctt gcatacggtc gccagagctt ccacttggtc 2820
aggcagtagc ttgaagtttg cctttagatc gttatccacg tggtacttgt ccatcaacgc 2880
gcgcgcagcc tccatgccct tctcccacgc agacacgatc ggcaggctca gcgggttat 2940
caccgtgctt tcactttccg cttcactgga ctcttccttt tcctcttgcg tccgcatacc 3000
ccgccact gggtcgtctt cattcagccg ccgcaccgtg cgcttacctc ccttgccgtg 3060
cttgattagc accggtgggt tgctgaaacc caccatttgt agcgccacat cttctcttcc 3120
ttcctcgctg tccacgatca cctctgggga tggcgggcgc tcgggcttgg gagaggggcg 3180
cttcttttc tttttggacg caatggccaa atccgccgtc gaggtcgatg gccgcgggct 3240
gggtgtgcgc ggcaccagcg catcttgtga cgagtcttct tcgtcctcgg actcgagacg 3300
ccgcctcagc cgctttttg gggcgcgcg gggaggcggc ggcgacgggcc acgggggaca 3360
cacgtcctcc atggttggtg gacgtcgcgc cgcaccgcgt ccgcgctcgg ggtggtttc 3420
gcgctgctcc tcttcccgac tggccatttc cttctcctat aggcagaaaa agatcatgga 3480
gtcagtcgag aaggaggaca gcctaaccgc ccccttgag ttcgccacca ccgcctccac 3540
cgatgccgcc aacgcgccta ccaccttccc cgtcgaggca ccccgcttg aggaggagga 3600
agtgattatc gagcaggacc caggtttttgt aagcgaagac aggtgctcagtacc gtcagtacc 3660
aacagaggat aaaaagcaag accaggacga cgcagaggca aacgaggaac aagtcgggcg 3720
gggggaccaa aggcatggcg actacctaga tgtgggagac gacgtgctgt tgaagcatct 3780
gcagcgccca tgcgccatta tctgcgacgc gttgcaagag cgcagcgatg tgcccctcgc 3840
catagcggat gtcagccttg cctacgaacg ccacctgttc tcaccgcgcg tacccccaa 3900
acgccaagaa aacggcacat gcgagcccaa cccgcgcctc aacttctacc ccgtatttgc 3960
```

```
cgtgccagag gtgcttgcca cctatcacat cttttccaa aactgcaaga taccccatc   4020
ctgccgtgcc aaccgcagcc gagcggacaa gcagctggcc ttgcggcagg gcgctgtcat  4080
acctgatatc gcctcgctcg acgaagtgcc aaaaatcttt gagggtcttg acgcgacga   4140
gaaacgcgcg gcaaacgctc tgcaacaaga aaacagcgaa aatgaaagtc actgtggagt  4200
gctggtggaa cttgagggtg acaacgcgcg cctagccgtg ctgaaacgca gcatcgaggt  4260
cacccacttt gcctacccgg cacttaacct acccccaag gttatgagca cagtcatgag   4320
cgagctgatc gtgcgccgtg cacgaccct ggagagggat gcaaacttgc aagaacaaac   4380
cgaggagggc ctacccgcag ttggcgatga gcagctggcg cgctggcttg agacgcgcga  4440
gcctgccgac ttggaggagc gacgcaagct aatgatggcg gcagtgcttg ttaccgtgga  4500
gcttgagtgc atgcagcggt tctttgctga cccggagatg cagcgcaagc tagaggaaac  4560
gttgcactac acctttcgcc agggctacgt gcgccaggcc tgcaaaattt ccaacgtgga  4620
gctctgcaac ctggtctcct accttggaat tttgcacgaa aaccgcctcg gcaaaacgt   4680
gcttcattcc acgctcaagg gcgaggcgcg ccgcgactac gtccgcgact gcgtttactt  4740
atttctgtgc tacacctggc aaacggccat gggcgtgtgg cagcaatgcc tggaggacg   4800
caacctaaag gagctgcaga gctgctaaa gcaaaacttg aaggacctat ggacggcctt   4860
caacgagcgc tccgtggccg cgcacctggc ggacattatc ttccccgaac gcctgcttaa  4920
aaccctgcaa cagggtctgc cagacttcac cagtcaaagc atgttgcaaa actttaggaa  4980
ctttatccta gagcgttcag gaattctgcc cgccacctgc tgtgcgcttc ctagcgactt  5040
tgtgccatt aagtaccgtg aatgccctcc gccgctttgg ggtcactgct accttctgca   5100
gctagccaac taccttgcct accactccga catcatggaa gacgtgagcg tgacggcct   5160
actggagtgt cactgtcgct gcaacctatg caccccgcac cgctccctgg tctgcaattc  5220
gcaactgctt agcgaaagtc aaattatcgg tacctttgag ctgcagggtc cctcgcctga  5280
cgaaaagtcc gcggctccgg ggttgaaact cactccgggg ctgtggacgt ccgatctcta  5340
tcactgatag ggagatctct atcactgata gggagagggc ttaccttcgc aaatttgtac  5400
ctgaggacta ccacgcccac gagattaggt tctacgaaga ccaatcccgc cgccaaatg   5460
cggagcttac cgcctgcgtc attacccagg gccacatcct tggccaattg caagccatca  5520
acaaagcccg ccaagagttt ctgctacgaa agggacgggg ggtttacctg gaccccagt   5580
ccggcgagga gctcaaccca atccccccgc cgccgcagcc ctatcagcag ccgcgggccc  5640
ttgcttccca ggatggcacc caaaaagaag ctgcagctgc cgccgccgcc acccacggac  5700
gaggaggaat actgggacag tcaggcagag gaggtttggg acgaggagga ggagatgatg  5760
gaagactggg acagcctaga cgaagcttcc gaggccgaag aggtgtcaga cgaaacaccg  5820
tcaccctcgg tcgcattccc ctcgccggcg ccccagaaat tggcaaccgt tcccagcatc  5880
gctacaacct ccgctcctca ggcgccgccg gcactgcctg ttcgccgacc caaccgtaga  5940
tgggacacca ctggaaccag ggccggtaag tctaagcagc cgccgccgtt agcccaagag  6000
caacaacagc gccaaggcta ccgctcgtgg cgcgggcaca agaacgccat agttgcttgc  6060
ttgcaagact gtgggggcaa catctccttc gcccgccgct tcttctctcta ccatcacggc  6120
gtggccttcc cccgtaacat cctgcattac taccgtcatc tctacagccc ctactgcacc  6180
ggcggcagcg gcagcggcag caacagcagc ggtcacacag aagcaaaggc gaccggatag   6240
caagactctg acaaagccca agaaatccac agcggccgca gcagcaggag gaggagcgct  6300
gcgtctggcg cccaacgaac ccgtatcgac ccgcgagctt agaaatagga ttttcccac   6360
tctgtatgct atatttcaac aaagcagggg ccaagaacaa gagctgaaaa taaaaaacag  6420
gtctctgcgc tccctcaccc gcagctgcct gtatcacaaa agcgaagatc agcttcggcg  6480
cacgctggaa gacgcggagg ctctcttcag caacgatctc tatcactgat agggagatct  6540
ctatcactga tagggagaga tactgcgcgc tgactcttaa ggactagttt cgcgcccttt  6600
ctcaaattta agcgcgaaaa ctacgtcatc tccagcggcc acaccggcg ccagcacctg   6660
tcgtcagcgc cattatgagc aaggaaattc ccacgcccta catgtggagt taccagccac  6720
aaatggact tgcggctgga gctgcccaag actactcaaa ccgaataaac tacatgagcg  6780
cgggacccca catgatatcc cgggtcaacg gaatccgcgc ccaccgaaac cgaattctcc  6840
tcgaacaggc ggctattacc accacactgt gtaataacct taatcccgt agttggccg    6900
ctgccctggt gtaccaggaa agtcccgctc ccaccactgt ggtacttccc agagacgccc  6960
aggccgaagt tcagatgact aactcagggg cgcagcttgc gggcggcttt cgtcacaggg  7020
tgcggtcgcc cccagtggcc aaaaaagcta gcgcagcagc cgccgcgcct ggaaggaagc  7080
caaaaggagc gctcccccgt tgtctgacgt cgcacacctg ggttcgacac gcgggcggta  7140
accgcatgga tcacgcgga cggccggatc cggggttcga accccggtcg tccgccatga    7200
taccccttgcg aatttatcca ccagaccacg gaagagtgcc cgcttacagg tggtctcata  7260
cagaacttat aagattccca aatccaaaga catttcacgt ttatggtgat ttcccagaac  7320
acatagcgac atgcaaatat tgcagggcgc cactccctg tccgctctcc ttttgcacgg   7380
tctagagcgt caacgactgc gcacggggcg ttttagggcg gagtaacttg catgtattgg  7440
gaattgtagt tttttaaaa tgggaagtga cgtatcgtgg gaaaacgaa gtgaagattt    7500
gaggaagttg tgggttttt ggctttcgtt tctgggcgta ggttcgcgtg cggttttctg   7560
ggtgttttt gtgactttta accgttacgt cattttttag tcctatatat actcgctctg   7620
tactctccct atcagtgata gagatctccc tatcagtgat agagatcgct tggccctttt  7680
tacactgtga ctgattgagc tggtgccgtg tcgagtggtg ttttttaata ggttttttta  7740
ctggtaaggc tgactgttat ggctgccgct gtggaagcgc tgtatgttgt tctggagcgg  7800
gaggggtgcta ttttgcctag gcaggagggt ttttcaggtg tttatgtgtt tttctctcct  7860
attaattttg ttatacctcc tatgggggct gtaatgttgt ctctacgcct gcgggtatgt  7920
attcccccgg gctatttcgg tcgcttttta gcactaccg atgttaacca acctgatgtg    7980
tttaccgagt cttacattat gactccggac atgaccgagg aactgtcggt ggtgcttttt  8040
aatcacgtg accagttttt ttaccgtcac gccgggcacg ccgtagtccg tcttatgctt  8100
ataagggttg ttttccctgt tgtaagacag gcttctaatg tttaaatgtt ttttttttg   8160
ttattttatt ttgtgtttaa tgcaggaacc cgcagacatg tttgagagaa aaatggtgtc  8220
tttttctgtg gtgggttccgg aacttacctg cctttatctg catgagcatg actacgatgt  8280
gcttgctttt ttgcgcgagg cttgcctga tttttgagc agcaccttgc atttttatc     8340
gccgcccatg caacaagctt acatagggc tacgctggtt agcatagctc cgagtatgac    8400
tgtcataatc agtgtgggtt ctttttgtcat ggttcctgct ggggaagtgg ccgcgctggt  8460
ccgtgcagac ctgcacgatt atgttcagct ggccctgcga agggacctac gggatcgcgg  8520
tattttttgtt aatgttccgc ttttgaatct tatacaggtc tgtgagaac ctgaattttt   8580
gcaatcatga ttcgctgctt gaggctgaag gtggagggcc ctctgagca gatttttaca   8640
atggccggac ttaatattcg ggatttgctt agagacatat tgataaggtg gcgagatgaa  8700
```

```
aattatttgg gcatggttga aggtgctgga atgtttatag aggagattca ccctgaaggg  8760
tttagccttt acgtccactt ggacgtgagg gcagtttgcc ttttggaagc cattgtgcaa  8820
catcttacaa atgccattat ctgttctttg gctgtagagt ttgaccacgc caccggaggg  8880
gagcgcgttc acttaataga tcttcatttt gaggttttgg ataatctttt ggaataaaaa  8940
aaaaaaaaca tggttcttcc agctcttccc gctcctcccg tgtgtgactc gcagaacgaa  9000
tgtgtaggtt ggctgggtgt ggcttattct gcggtggtgg atgttatcag ggcagcggcg  9060
catgaaggag tttacataga acccgaagcc aggggcgcc tggatgcttt gagagagtgg  9120
atatactaca actactacac agagcgagct aagcgacgag accggagacg cagatctgtt  9180
tgtcacgccc gcacctggtt ttgcttcagg aaatatgtac ccatacgatg ttccagatta  9240
cgctggagga ggcggaggca ctacgtccgg cgttccattt ggcatgacac tacgaccaac  9300
acgatctcgg ttgtctcggc gcactccgta cagtagggat cgcctacctc cttttgagac  9360
agagacccgc gctaccatac tggaggatca tccgctgctg cccgaatgta acactttgac  9420
aatgcacaac gtgagttacg tgcgaggtct tccctgcagt gtgggattta cgctgattca  9480
ggaatgggtt gttccctggg atatggttct gacgcgggag gagcttgtaa tcctgaggaa  9540
gtgtatgcac gtgtgcctgt gttgtgccaa cattgatatc atgacgagca tgatgatcca  9600
tggttacgag tcctgggctc tccactgtca ttgttccagt cccggttccc tgcagtgcat  9660
agccggcggg caggttttgg ccagctggtt taggatggtg gtggatggcg ccatgtttaa  9720
tcagaggttt atatggtacc ggggagtggt gaattacaac atgccaaaag aggtaatgtt  9780
tatgtccagc gtgtttatga gggggtcgcc acttaatctac ctgcgcttgt ggtatgatgg  9840
ccacgtgggg tctgtggtcc ccgccatgag ctttggatac agcgccttgc actgtgggat  9900
tttgaacaat attgtggtgc tgtgctgcag ttactgtgct gatttaagtg agatcagggt  9960
gcgctgctgt gcccggagga caaggcgtct catgctgcgg gcggtgcgaa tcatcgctgg 10020
ggagaccact gccatgttgt attcctgcag gacggagcgg cggcggcagc agtttattcg 10080
cgcgctgctg cagcaccacc gcccatcct gatgcacgat tatgactcta cccccatgta 10140
ggcgtggact tccccttcgc cgcccgttga gcaaccgcaa gttggacagc agcctgtggc 10200
tcagcagctg gacagcgaca tgaacttaag cgagctgccc ggggagttta ttaatatcac 10260
tgatgagcgt ttggctcgac aggaaaccgt gtggaatata acaccctaaga atatgtctgt 10320
tacccatgat atgatgcttt ttaaggccag ccggggagaa aggactgtgt actctgtgtg 10380
ttgggaggga ggtggcaggt tgaatactag ggttctgtga gtttgattaa ggtacgtgta 10440
tcaatataag ctatgtggtg gtgggcgtat actactgaat gaaaaatgac ttgaaatttt 10500
ctgcaattga aaaataaaca cgttgaaaca taacatgcaa caggttcacg attctttatt 10560
cctgggcaat gtaggagaag gtgtaagagt tggtagcaaa agtttcagtg gtgtattttc 10620
cactttccca ggaccatgta aaagacatag agtaagtgct tacctcgcta gtttctgtgg 10680
attcactaga atccactttg gccgcggctc gagtgagcta ttccagaagt agtgaagagg 10740
ctttttttga ggcctaggct tttgcaaaaa gctccggatc gatgccgggg ggatccacta 10800
gttctagagg gacagccccc ccccaaagcc cccaggatg taattacgtc cctcccccgc 10860
tagggggcag cagcgagccg cccggggctc cgctccggtc cggcgctccc cccgcatccc 10920
cgagccggca gcgtgcgggg acagcccggg cacggggaag gtgcacggg atcgctttcc 10980
tctgaacgct tctcgctgct cttttgagcct gcagacacct ggggggatac ggggaaaagg 11040
cctccaaggc cagcttccca caataagttg ggtgaatttt ggctgagcta ttccagaagt 11100
agtgaagagg cttttttgga ggcctaggct tttgcaaaaa gctccggatc gatcatatat 11160
ggcagatata cgcgttgaca ttgattattg actagttatt aatagtaatc aattacgggg 11220
tcattagttc atagcccata tatgagttc cgcgttacat aacttacgat aaatggcccg 11280
cctggctgac cgcccaacga ccccccgccca ttgacgtcaa taatgacgta tgttcccata 11340
gtaacgccaa tagggacttt ccattgacgt caatgggtgg agtatttacg gtaaactgcc 11400
cacttggcag tacatcaagt gtatcatatg ccaagtacgc ccctattga cgtcaatgac 11460
ggtaaatggc ccgcctggca ttatgcccag tacatgacct tatgggactt tcctacttgg 11520
cagtacatct acgtattagt catcgctatt accatggtga tgcggttttg gcagtacatc 11580
aatgggcgtg gatagcggtt tgactcacgg ggatttccaa gtctccaccc cattgacgtc 11640
aatgggagtt tgttttggca ccaaaatcaa cgggactttc caaaatgtcg taacaactcc 11700
gccccattga cgcaaatggg cggtaggcgt gtacggtggg aggtctatat aagcagagct 11760
ctctggctaa ctatcgtcga cgagctcgtt tagtgaaccg tcagatcgcc tggagacgcc 11820
atccacgctg ttttgacctc catagaagac accgggaccg atccagcctc cggactctag 11880
cgtttaaact taagcttgcc accatgaccg agtacaagcc cacggtgcgc ctcgccaccc 11940
gcgacgacgt ccccagggcc gtacgcaccc tcgccgcgac gttcgccgac tacccccgca 12000
cgcgccacac cgtcgatccg gaccgccaca tcgagcgggt caccgagctg caagaactcc 12060
tcctcacgcg cgtcgggctc gacatcggca aggtgtgggt cgcggacgac ggcgccgcgg 12120
tggcggtctg gaccacgccg gagagcgtcg aagcgggggc ggtgttcgcc gagatcggcc 12180
cgcgcatggc cgagttgagc ggttccggcc tggccgcgca gcaacagatg gaaggcctcc 12240
tggcgcgcgca ccgcccaag gagcccgcgt ggttcctggc caccgtcggc gtctcgcccg 12300
accaccaggg caagggtctg ggcagcgccg tcgtgctccc cggagtcgag gcggccgagc 12360
gcgcgggggt gcccgccttc ctggagacct ccgcgcccg caacctcccc ttctacgagc 12420
ggctcggctt caccgtcacc gccgacgtcg aggtgcccga aggaccgcgc acctggtgca 12480
tgacccgcaa gccgggtgcc tgaagcgcgg ggatctcatg ctggagttct tcgcccaccc 12540
caacttgttt attgcagctt ataatggtta caaataaagc aatagcatca caaatttcac 12600
aaataaagca tttttttcac tgcattctag ttgtggtttg tccaaactca tcaatgtatc 12660
ttatcatgtc tgtagctgat gtatacctag gatccgccg gcctgcaggt gtcctcacag 12720
gaacgaagtc cctaaagaaa cagtggcagc caggttagc cccggaattg actggattcc 12780
tttttaggg cccattggta tggctttttc cccgtatccc cccaggtgtc tgcaggctca 12840
aagagcagcg agaagcgttc agaggaaagc gatcccgtgc caccttcccc gtgcccgggc 12900
tgtccccgca cgctgccggc tcgggatgc gggggagcg ccggaccgga gcggagcccc 12960
gggcggctcg ctgctgcccc ctagcggggg agggacgtaa ttcatccct gggggctttg 13020
ggggggggct gtccctctag agcggccgcc accgcgtgg agctccagct tttgttccct 13080
ttagtgaggg ttaattagat cttaatacga ctcactatag ggcgaattgg gtaccgggcc 13140
ccccctcgag gtcgacggta tcgataagct tgatatctat aacaagaaaa tatatatata 13200
ataagttatc acgtaagtag aacatgaaat aacaatataa ttatcgtatg agttaaatct 13260
taaaagtcac gtaaaagata atcatgcgtc attttgactc acgcggtcgt tatagttcaa 13320
aatcagtgac acttaccgca ttgacaagca cgcctcacgg gagctccaag cggcgactga 13380
gatgtcctaa atgcacagcg acggattcgc gctatttaga aagagagagc aatatttcaa 13440
```

```
gaatgcatgc gtcaattta cgcagactat ctttctaggg ttaatctagc tgcatcagga   13500
tcatatcgtc gggtctttt tccggctcag tcatcgccca agctggcgct atctgggcat   13560
cggggaggaa gaagcccgtg ccttttcccg cgaggttgaa gcggcatgga aagagtttgc   13620
cgaggatgac tgctgctgca ttgacgttga gcgaaaacgc acgttacca  tgatgattcg   13680
ggaaggtgtg gccatgcacg cctttaacgg tgaactgttc gttcaggcca cctgggatac   13740
cagttcgtcg cggcttttcc ggacacagtt ccggatggtc agcccgaagc gcatcagcaa   13800
cccgaacaat accggcgaca gccggaactg ccgtgccggt gtgcagatta atgacagcgg   13860
tgcggcgctg ggatattacg tcagcgagga cgggtatcct ggctggatgc cgcagaaatg   13920
gacatggata cccgtgagt  tacccggcgg gcgcgcttgg cgtaatcatg gtcatagctg   13980
tttcctgtgt gaaattgtta tccgctcaca attccacaca acatacgagc cggaagcata   14040
aagtgtaaag cctggggtgc ctaatgagtg agctaactca cattaattgc gttgcgctca   14100
ctgcccgctt tccagtcggg aaacctgtcg tgccagctgc attaatgaat cggccaacgc   14160
gcggggagag gcggtttgcg tattgggcgc tcttccgctt cctcgctcac tgactcgctg   14220
cgctcgtcg  ttcggctgcg gcgagcggta tcagctcact caaaggcggt aatacggtta   14280
tccacagaat cagggggataa gcaggaaag  aacatgtgag caaaaggcca gcaaaaggcc   14340
aggaaccgta aaaaggccgc gttgctggcg ttttccata  ggctccgccc cctgacgag   14400
catcacaaaa atcgacgctc aagtcagagg tggcgaaacc cgacaggact ataaagatac   14460
caggcgtttc cccctggaag ctccctcgtg cgctctcctg ttccgaccct gccgcttacc   14520
ggatacctgt ccgcctttct cccttcggga agcgtggcgc tttctcatag ctcacgctgt   14580
aggtatctca gttcggtgta ggtcgttcgc tccaagctgg gctgtgtgca cgaaccccc    14640
gttcagcccg accgctgcgc cttatccggt aactatcgtc ttgagtccaa cccggtaaga   14700
cacgacttat cgccactggc agcagccact ggtaacagga ttacagagc  gaggtatgta   14760
ggcggtgcta cagagttctt gaagtggtgg cctaactacg gctacactag aaggacagta   14820
tttggtatct gcgctctgct gaagccagtt accttcggaa aaagagttgg tagctcttga   14880
tccggcaaac aaaccaccgc tggtagcggt ggtttttttg tttgcaagca gcagattacg   14940
cgcagaaaaa aaggatctca agaagatcct ttgatcttt  ctacggggtc tgacgctcag   15000
tggaacgaaa actcacgtta agggattttg gtcatgagat tatcaaaag  gatcttcacc   15060
tagatccttt taaattaaaa atgaagtttt aaatcaatct aaagtatata tgagtaaact   15120
tggtctgaca gttaccaatg cttaatcagt gaggcaccta tctcagcgat ctgtctattt   15180
cgttcatcca tagttgcctg actccccgtc gtgtagataa ctacgatacg ggagggctta   15240
ccatctggcc ccagtgctgc aatgatacgc gagacccac  gctcaccggc tccagattta   15300
tcagcaataa accagccagc cggaagggcc gagcgcagaa gtggtcctgc aactttatcc   15360
gcctccatcc agtctattaa ttgttgccgg gaagctagag taagtagttc gccagttaat   15420
agtttgcgca acgttgttgc cattgctaca ggcatcgtgg tgtcacgctc gtcgtttggt   15480
atggcttcat tcagctccgg ttcccaacga tcaaggcgag ttacatgatc cccatgttg   15540
tgcaaaaaag cggttagctc cttcggtcct ccgatcgttg tcagaagtaa gttggccgca   15600
gtgttatcac tcatggttat ggcagcactg cataattctc ttactgtcat gccatccgta   15660
agatgctttt ctgtgactgg tgagtactca accaagtcat tctgagaata gtgtatgcgg   15720
cgaccgagtt gctcttgccc ggcgtcaata cgggataata ccgcgccaca tagcagaact   15780
ttaaaagtgc tcatcattgg aaaacgttct cggggcgaa  aactctcaag gatcttaccg   15840
ctgttgagat ccagttcgat gtaacccact cgtgcaccca actgatcttc agcatctttt   15900
actttccacca gcgtttctgg gtgagcaaaa acaggaaggc aaaatgccgc aaaaaagga   15960
ataagggcga cacggaaatg ttgaatactc at                                15992
```

SEQ ID NO: 8           moltype = DNA    length = 16658
FEATURE                Location/Qualifiers
misc_feature           1..16658
                       note = Synthetic: pPBBG-iHelper2.5-HA
source                 1..16658
                       mol_type = other DNA
                       organism = synthetic construct
SEQUENCE: 8

```
actcttcctt tttcaatatt attgaagcat ttatcagggt tattgtctca tgagcggata    60
catatttgaa tgtatttaga aaaataaaca aatagggggtt ccgcgcacat ttccccgaaa   120
agtgccacct aaattgtaag cgttaatatt ttgttaaaat tcgcgttaaa tttttgttaa   180
atcagctcat ttttaacca  ataggccgaa atcggcaaaa tcccttataa atcaaaagaa   240
tagaccgaga tagggttgag tgttgttcca gtttggaaca agagtccact attaaagaac   300
gtggactcca acgtcaaagg gcgaaaaacc gtctatcagg gcgatggccc actacgtgaa   360
ccatcaccct aatcaagttt tttggggtcg aggtgccgta aagcactaaa tcggaaccct   420
aaagggagcc cccgatttag agcttgacgg ggaaagccgg cgaacgtggc gagaaaggaa   480
gggaagaaag cgaaaggagc gggcgctagg gcgctggcaa gtgtagcggt cacgctgcgc   540
gtaaccacca cacccgccgc gcttaatgcg ccgctacagg gcgcgtccca ttcgccattc   600
aggctgcgca actgttggga agggcgatcg gtgcgggcct cttcgctatt acgccagctg   660
gcgaaagga  gatgtgctgc aaggcgatta agttgggtaa ccgcagggtt tcccagtca    720
cgacgttgta aaacgacggc cagtgagcgc gcctcgttca ttcacgtttt tgaacccgtg   780
gaggacgggc agactcgcgg tgcaaatgtg ttttacagcg tgatggagca gatgaagatg   840
ctcgacacgc tgcagaacac gcagctagat taacccctaga aagataatca tattgtgacg   900
tacgttaaag ataatcatgc gtaaaattga cgcatgtgtt ttatcggtct gtatatcgag   960
gtttatttat taattgaat  agatattaag tttttatata tttacactta catactaata  1020
ataaattcaa caaacaattt atttatgtt  atttatttat taaaaaaaaa caaaactca   1080
aaatttcttc tataaagtaa caaaactttt atcgaattcc tgcagccggg ggatccact   1140
agttctagag gacagccccc ccccaaagc ccccagggat gtaattacgt ccctccccg    1200
ctaggggca  gcagcgagcc gcccggggct ccgctccggt ccggcgctcc cccgcatcc    1260
ccgagccgga gcgtgcggg  gacagcccgg cgacgggaga ggtggcgcag gatcgtttc    1320
ctctgaacgc ttctcgctgc tctttgagcc tgcagacacc tggggggata cggggaaaag   1380
gcctccaagg ccagcttccc acaataagtt gggtgaattt tggctcattc ctcctttcta   1440
taggattgag tcagagctt  tgtgatggga attctgtgga atgtgtgtca gttagggtgt   1500
ggaaagtccc gcgatcgcta gcgtttaaac ttaagcttgg taccgagctc ggatccacta   1560
gtccagtgtg gtggaattcc tgcttcgcga tgtacgggcc ggtacccaac tccatgctta   1620
```

```
acagtcccca ggtacagccc accctgcgtc gcaaccagga acagtctac agcttcctgg   1680
agcgccactc gccctacttc cgcagccaca gtgcgcagat taggagcgcc acttctttt   1740
gtcacttgaa aaacatgtaa aaataatgta ctaggagaca ctttcaataa aggcaaatgt   1800
tttttatttgt acactctcgg gtgattattt accccccacc cttgccgtct gcgccgttta   1860
aaaatcaaag gggttctgcc gcgcatcgct atgcgccact ggcaggggaca cgttgcgata   1920
ctggtgttta gtgctccact taaactcagg cacaaccatc cgcggcagct cggtgaagtt   1980
ttcactccac aggctgcgca ccatcaccaa cgcgtttagc aggtcgggcg ccgatatctt   2040
gaagtcgcag ttggggcctc cgccctgcgc gcgcgagttg cgatacacag ggttgcagca   2100
ctggaacact atcagcgccg ggtggtgcac gctggccagc acgctcttgt cggagatcag   2160
atccgcgtcc aggtcctccg cgttgctcag ggcgaacgga gtcaactttg gtagctgcct   2220
tcccaaaaag ggtgcatgcc caggctttga gttgcactcg caccgtagtg gcatcagaag   2280
gtgaccgtgc ccggtctggg cgttaggata cagcgcctgc atgaaagcct tgatctgctt   2340
aaaagccacc tgagcctttg cgccttcaga gaagaacatg ccgcaagact tgccggaaaa   2400
ctgattggcc ggacaggcg cgtcatgcac gcagcacctt ggcgtcggtgt tggagatctg   2460
caccacattt cggccccacc ggttcttcac gatcttggcc ttgctagact gctccttcag   2520
cgcgcgctgc ccgttttcgc tcgtcacatc catttcaatc acgtgctcct tatttatcat   2580
aatgctcccg tgtagacact taagctcgcc ttcgatctca gcgcagcggt gcagccacaa   2640
cgcgcagccc gtgggctcgt ggtgcttgta ggttaccctc gcaaacgact gcaggtacgc   2700
ctgcaggaat cgcccatca tcgtcacaaa ggtcttgttg ctggtgaagg tcagctgcaa   2760
cccgcggtgc tcctcgttta gccaggtctt gcatacggcc gccagagctt ccacttggtc   2820
aggcagtagc ttgaagtttg cctttagatc gttatccacg tggtacttgt ccatcaacgc   2880
gcgcgcagcc tccatgccct tctcccacgc agacacgatc ggcaggctca gcgggtttat   2940
caccgtgctt tcactttccg cttcactgga ctcttccttt tcctcttgcg tccgcatacc   3000
ccgcgccact gggtcgtctt cattcagccg ccgcaccgtg cgcttacctc ccttgccgtg   3060
cttgattagc accggtgggt tgctgaaacc caccattttgt agcgccacat cttctctttc   3120
ttcctcgctg tccacgatca cctctgggga tggcgggcga tggcttggag agagggcg   3180
cttcttttttc tttttggacg caatggccaa atccgccgtc gaggtcgatg gccgcgggct   3240
gggtgtgcgc ggcaccagcg catcttgtga cgagtcttct tcgtcctcgg actcgagacg   3300
ccgcctcagc cgctttttg ggggcgcgcg gggaggcggc ggcgacggcg acggggacga   3360
cacgtcctcc atggttggtg gacgtcgcgc cgcaccgcgt ccgcgctcgg gggtggttc   3420
gcgctgctcc tcttcccgac tggccatttc cttctcctat aggcagaaaa agatcatgga   3480
gtcagtcgag aaggaggaca gcctaaccgc cccctttgag ttcgccacca ccgcctccac   3540
cgatgccgcc aacgcgccta ccaccttccc cgtcgaggca ccccgcttg aggaggagga   3600
agtgattatc gagcaggacc caggttttgt aagcgaagac gacgaggatc gctcagtacc   3660
aacagaggat aaaaagcaag accaggacga cgcagaggca aacgaggaac aagtcgggcg   3720
gggggaccaa aggcatggcg actacctaga tgtgggagac gacgtgctgt tgaagcatct   3780
gcagcgccca tgcgccatta tctgcgacgc gttgcaagag cgcagcgatg tgcccctcgc   3840
catagcggat gtcagccttg cctacgaacg ccacctgttc tcaccgcgcg tacccccaa   3900
acgccaagaa aacggcacat gcgagcccaa cccgcgcctc aacttctacc ccgtatttgc   3960
cgtgccagaa gtgcttgcca cctatcacat cttttttccaa aactgcaaga taccccctatc   4020
ctgccgtgcc aaccgcagcc gagcggacaa gcagctggcc ttgcggcagg gcgctgtcat   4080
acctgatatc gcctcgctcg acgaagtgcc aaaaatcttt gagggtcttg gacgcgacga   4140
gaaacgcgcg gcaaacgctc tgcaacaaga aaacagcgaa aatgaaagtc actgtgggat   4200
gctggtggaa cttgagggtg acaacgcgcg cctagccgtg ctgaaacgca gcatcggaggt   4260
cacccacttt gcctacccgg cacttaacct acccccaag gttatgagca cagtcatgag   4320
cgagctgatc gtgcgccgtg cacgacccct ggagagggat gcaaacttgc aagaacaaac   4380
cgagggggc ctacccgcag ttggcgatga gcagctgggc cgctggcttg agacgcgcga   4440
gcctgccgac ttggaggagc gacgcaagct aatgatggcc gcagtgcttg ttaccgtgga   4500
gcttgagtgc atgcagcggt tctttgctga cccggagatg cagcgcaagc tagaggaaac   4560
gttgcactac acctttcgcc agggctacgt gcgccaggcc tgcaaaattt ccaacgtgga   4620
gctctgcaac ctggtctcct accttggaat tttgcacgaa aaccgcctcg ggcaaaacgt   4680
gcttcattcc acgctcaagg gcgaggcgcg ccgcgactac gtccgcgact gcgtttactt   4740
atttctgtgc tacacctggc aaacggccat gggcgtgtgg cagcaatgcc tggaggagcg   4800
caacctaaag gagctgcaga agctgctaaa gcaaaacttg aaggacctat ggacggcctt   4860
caacgacgtc tccgtggccg cgcacctggc ggacattact ttccccgaac gcctgcttaa   4920
aaccctgcaa cagggtctgc cagacttcac cagtcaaagc atgttgcaaa actttaggaa   4980
ctttatccta gagcgttcag gaattctgcc cgccaccctgc tgtgcgcttc ctagcgactt   5040
tgtgcccatt aagtaccgtg aatgccctcc gccgctttgg ggtcactgct accttctgca   5100
gctagcaaac taccttgcct accactccga catcatgaaa gacgtgagcg gtgacgggct   5160
actggagtgt cactgtcgct gcaacctatg caccccgcac cgctccctgg tctgcaattc   5220
gcaactgctt agcgaaagtc aaattatcgg taccttgag ctgcagggtc cctcgcctga   5280
cgaaaagtcc gcggctccgg ggttgaaact cactccgggg ctgtgacgt ccgatctcta   5340
tcactgatag ggagatctct atcactgata gggagaggc ttaccttcgc aaatttgtac   5400
ctgaggacta ccacgcccac gagattaggt tctacgaaga ccaatcccgc ccgccaaatg   5460
cggagcttac cgcctgcgtc attcccagg gccacatcct tggccaattg caagccatca   5520
acaaagcccg ccaagagttt ctgctacgaa agggacgggg ggtttacctg accccccagt   5580
ccggcgagga gctcaaccca atcccccgc cgccgcagcc ctatcagcag ccgcgggccc   5640
ttgcttccca ggatggcacc caaaagaag ctgcagctgc cgccgccgcc acccacggac   5700
gaggaggaat actgggacag tcaggcagga gggttttgg acgaggagga ggatgatgg   5760
gaagactggg acagcctaga cgaagcttcc gaggccgaag aggtgtcaga cgaaacaccg   5820
tcaccctcgg tcgcattccc ctcgccgcg ccccagaaat tggcaaccgt tcccagcatc   5880
gctacaacct ccgctcctca ggcgccgcg gcactgcctg tcgccgacc aaccgtaga   5940
tgggacacca ctggaaccag ggccggtaag tctaagcagc cgccgccgtt agcccaagag   6000
caacaacgc gccaaggcta ccgctcgtgg cgcgggcaca agaacgccat agttgcttgc   6060
ttgcaagact gtggggcaa catctccctc gcccgccgct tcttctcta ccatcacggc   6120
gtggccttcc cccgtaacat cctgcattac taccgtcatc tctacagccc ctactgcacc   6180
ggcggcagcg gcagcggcag caacagcagc ggtcacacag aagcaaaggc gaccggatag   6240
caagactctg acaaagccca agaaatccac agcggcggca gcagcaggag gaggagcgct   6300
gcgtctggcg cccaacgaac ccgtatcgac ccgcgagctt agaaatagga tttttcccac   6360
```

```
tctgtatgct atatttcaac aaagcagggg ccaagaacaa gagctgaaaa taaaaaacag  6420
gtctctgcgc tccctcaccc gcagctgcct gtatcacaaa agcgaagatc agcttcggcg  6480
cacgctggaa gacgcggagg ctctcttcag caacgatctc tatcactgat agggagatct  6540
ctatcactga tagggagaga tactgcgcgc tgactcttaa ggactagttt cgcgcccttt  6600
ctcaaattta agcgcgaaaa ctacgtcatc tccagcggcg acaccggcg ccagcacctg  6660
tcgtcagcgc cattatgagc aaggaaattc ccacgcccta catgtggagt taccagccac  6720
aaatgggact tgcggctgga gctgcccaag actactcaac ccgaataaac tacatgagcg  6780
cgggaccca catgatatcc cgggtcaacg gaatccgcgc ccaccgaaac cgaattctcc  6840
tcgaacaggc ggctattacc accacacctc gtaataacct taatcccgt agttggccgt  6900
ctgccctggt gtaccaggaa agtcccgctc ccaccactgt ggtacttccc agagacgccc  6960
aggccgaagt tcagatgact aactcagggg cgcagcttgc gggcggcttt cgtcacaggg  7020
tgcggtcgcc cgggcgtttt agggcggagt aacttgcatg tattgggaat tgtagttttt  7080
ttaaaatggg aagtgacgta tcgtgggaaa acggaagtga agatttgagg aagttgtggg  7140
tttttttggct ttcgtttctg ggcgtaggtt cgcgtgcggt tttctgggtg ttttttaatg  7200
actttaaccg ttacgtcatt ttttagtcct atatatactc gctctgtact ctccctatca  7260
gtgatagaga tctccctatc agtgatagag atcgcttggc ccttttttaca ctgtgactga  7320
ttgagctggt gccgtgtcga gtggtgtttt ttaataggtt tttttactgg taaggctgac  7380
tgttatgget gccgctgtgg aagcgctgta tgttgttctg gagcgggagg gtgctatttt  7440
gcctaggcag gagggttttt caggtgttta tgtgttttc tctcctatta atttttgttat  7500
acctcctatg ggggctgtaa tgttgtctct acgcctgcgg gtatgtattc ccccgggcta  7560
tttcggtcgc tttttagcac tgaccgatgt taaccaacct gatgtgttta ccgagtctta  7620
cattatgact ccggacatga ccgaggaact gtcggtgtg ctttttaatc acggtgacca  7680
gttttttac ggtcacgccg gcatggccgt agtccgtctt atgcttataa gggttgtttt  7740
tcctgttgta agacaggctt ctaatgttta aatgttttt ttttttgttat tttattttgt  7800
gtttaatgca ggaacccgca gacatgtttg agagaaaaat ggtgtctttt tctgtggtgg  7860
ttccggaact tacctgcctt tatctgcatg agcatgacta cgatgtgctt gcttttttgc  7920
gcgaggcttt gcctgatttt ttgagcagca ccttgcattt tatatcgccg cccatgcaac  7980
aagcttacat agggggctacg ctggttagca tagctccgag tatgcgtgtc ataatcagtg  8040
tgggttcttt tgtcatggtt cctggcgggg aagtggccgc gctggtccgt gcagacctgc  8100
acgattatgt tcagctggcc ctgcgaaggg acctacggga tcgcggtatt tttgttaatg  8160
ttccgctttt gaatcttata caggtctgtg aggaacctga attttttgcaa tcatgattcc  8220
ctgcttgagg ctgaaggtgg agggcgctct ggagcagatt tttacaatgg ccggacttaa  8280
tattcggat ttgcttagag acatattgat aaggtggcga atgaaaatt atttgggcat  8340
ggttgaaggt gctggaatgt ttatagagga gattcaccct gaagggttta gccttttacgt  8400
ccacttggac gtgagggcag tttgccttttt ggaagccatt gtgcaacatc ttacaaatgc  8460
cattatctgt tctttggctg tagagtttga ccacgccacc ggagggggagc gcgttcactt  8520
aatagatctt cattttgagg ttttggataa tcttttggaa taaaaaaaaa aaaacatggt  8580
tcttccagct ctcccgctc ctcccgtgtg tgactcgcag aacgaatgtg taggttggct  8640
gggtgtget tattctgcgg tggtggatgt tatcagggca gcggcgcatg aaggagttta  8700
catagaaccc gaagcaggg ggcgcctgga tgctttgaga gagtggatat actacaacta  8760
ctacacagag cgagctaagc gacgagaccg gagacgcaga tctgtttgtc acgcccgcac  8820
ctggttttgc ttcaggaaat atgtacccat acgatgttcc agattacgct ggaggaggcg  8880
gaggcactac gtccggcgtt ccatttggca tgacactacg accaacacga tctcggttgt  8940
ctcggcgcac tccgtacagt agggatcgcc tacctccttt tgagacagag accgcgcta  9000
ccatactgga ggatcatccg ctgctgcccg aatgtaacac tttgacaatg cacaacgtga  9060
gttacgtgcg aggtcttccc tgcagtgtgg gatttacgct gattcaggaa tgggttgttc  9120
cctggatat ggttctgacg cgggaggagc ttgtaatcct gaggaagtgt atgcacgtgt  9180
gcctgtgttg tgccaacatt gatatcatga cgagcatgat gatccatggt tacgagtcct  9240
gggctctcca ctgtcattgt tccagtcccg gttcctgca gtgcatagcc ggcgggcagg  9300
ttttggccag ctgtttagg atggtggtgg atggcgccat gtttaatcag aggttatat  9360
ggtaccgga ggtggtgaat tacaacatgc caaaagagt aatgtttatg tccagcgtgt  9420
ttatgagggg tcgccactta atctacctgc gcttgtggta tgatggccac gtgggttctg  9480
tggtccccgc catgagcttt ggatacagcg ccttgcactg tgggattttg aacaatattg  9540
tggtgctgtg ctgcagttac tgtgctgatt taagtgagat caggggtcgc tgctgtgccc  9600
ggaggacaag gcgtctcatg ctgcagggcg tgcgaatcat cgctgaggag accactgcca  9660
tgttgtattc ctgcaggacg gagcggcggc ggcagcagtt tattcgcgcg ctgctgcagc  9720
accaccgccc tatcctgatg cacgattatg actctacccc catgtaggcg tggacttccc  9780
cttcgccgcc cgttgagcaa ccgcaagttg gacagcagcc tgtggctcag cagctggaca  9840
gcgacatgaa cttaagcgag ctgcccgggg agtttattaa tatcactgat gagcgtttga  9900
ctcgacagga aaccgtgtgg aatataacac ctaagaatat gtctgttacc catgatatga  9960
tgcttttaa ggccagccgg ggagaaagga ctgtgtactc tgtgtgttgg gagggaggtg 10020
gcaggttgaa tactagggtt ctgtgagttt gattaaggta cggtgatcaa tataagctat 10080
gtggtggtgg ggctatacta ctgaatgaaa aatgacttga aattttctgc aattgaaaaa 10140
taaacacgtt gaaacataac atgcaacagg ttcacgattc tttattcctg ggcaatgtag 10200
gagaaggtgt aagagttggt agcaaaagtt tcagtggtgt attttccact ttcccaggac 10260
catgtaaaag acatagagta agtgcttacc tcgctagttt ctgtggattc actagaacca 10320
gtggccaaaa aagctagcgc agcagccgcc gcgcctggaa ggaagccaaa aggagcgctc 10380
ccccgttgtc tgacgtcgca cacctgggtt cgacacgcgg gcggtaaccg catggatcac 10440
ggcggacggc cggatccggg gttcgaaccc cggtcgtccg ccatgatacc cttgcgaatt 10500
tatccaccag accacggaag agtgcccgct tacaggctct ccttttgcac ggtctagagc 10560
gtcaacgact gcgcacgcca gtggccaaaa aagctagcgc agcagccgcc gcgcctggaa 10620
ggaagccaaa aggagcgctc ccccgttgtc tgacgtcgca cacctgggtt cgacacgcgg 10680
gcggtaaccg catggatcac ggcggacggc cggatccggg gttcgaaccc cggtcgtccg 10740
ccatgatacc cttgcgaatt tatccaccag accacggaag agtgcccgct tacaggctct 10800
ccttttgcac ggtctagagc gtcaacgact gcgcacgcca gtggccaaaa aagctagcgc 10860
agcagccgcc gcgcctggaa ggaagccaaa aggagcgctc ccccgttgtc tgacgtcgca 10920
cacctgggtt cgacacgcgg gcggtaaccg catggatcac ggcggacggc cggatccggg 10980
gttcgaaccc cggtcgtccg ccatgatacc cttgcgaatt tatccaccag accacggaag 11040
agtgcccgct tacaggctct ccttttgcac ggtctagagc gtcaacgact gcgcacgcca 11100
```

```
gtggccaaaa aagctagcgc agcagccgcc gcgcctggaa ggaagccaaa aggagcgctc   11160
ccccgttgtc tgacgtcgca cacctgggtt cgacacgcgg gcggtaaccg catggatcac   11220
ggcggacggc cggatccggg gttcgaaccc cggtcgtccg ccatgatacc cttgcgaatt   11280
tatccaccag accacggaag agtgcccgct tacaggctct ccttttgcac ggtctagagc   11340
gtcaacgact gcgcacgtcc actttggccg cggctcgagt gagctattcc agaagtagtg   11400
aagaggcttt tttggaggcc taggcttttg caaaaagctc cggatcgatg cccgggggat   11460
ccactagttc tagagggaca gccccccccc aaagccccca gggatgtaat tacgtccctc   11520
ccccgctagg gggcagcagc gagccgcccg gggctccgct ccggtccggc gctcccccg    11580
catcccgag ccggcagcgt gcggggacag cccgggcacg gggaaggtgg cacgggatcg    11640
ctttcctctg aacgcttctc gctgctcttt gagcctgcag acacctgggg ggatacgggg   11700
aaaaggcctc caaggccagc ttcccacaat aagttgggtg aatttttggct gagctattcc   11760
agaagtagtg aagaggcttt tttggaggcc taggcttttg caaaaagctc cggatcgatc   11820
atatatggca gatatacgcg ttgacattga ttattgacta gttattaata gtaatcaatt   11880
acggggtcat tagttcatag cccatatatg gagttccgcg ttacataact tacggtaaat   11940
ggcccgcctg gctgaccgcc caacgacccc gcccattga cgtcaataat gacgtatgtt    12000
cccatagtaa cgccaatagg gactttccat tgacgtcaat gggtggagta tttacggtaa   12060
actgcccact tggcagtaca tcaagtgtat catatgccaa gtacgccccc tattgacgtc   12120
aatgacggta aatggcccgc ctggcattat gcccagtaca tgaccttatg ggactttcct   12180
acttggcagt acatctacgt attagtcatc gctattacca tggtgatgcg gttttggcag   12240
tacatcaatg ggcgtggata gcggtttgac tcacggggat ttccaagtct ccaccccatt   12300
gacgtcaatg ggagtttgtt ttggcaccaa atcaacggg actttccaaa atgtcgtaac   12360
aactccgccc cattgacgca aatggccggt aggcgtgtac ggtgggaggt ctatataagc   12420
agagctctct ggctaactat cgtcgacgag ctcgtttagt gaaccgtcag atcgcctgga   12480
gacgccatcc acgctgtttt gacctccata aagacaccg ggaccgatcc agcctccgga    12540
ctctagcgtt taaacttaag cttgccacca tgaccgagta caagcccacg gtgcgcctcg   12600
ccaccgcgcga cgacgtccc agggccgtac gcaccctcgc gcgactacc gccgactacc    12660
ccgccacgcg ccacaccgtc gatccggacc gccacatcga gcgggtcacc gagctgcaag   12720
aactcttcct cacgcgcgtc gggctcgaca tcggcaaggt gtgggtcgcg gacgacggcg   12780
ccgcggtggc ggtctggacc acgccggaga gcgtcgaagc ggggggcggtg ttcgccgaga   12840
tcggccccgcg catggccgag ttgagcggtt cccggcctggc gccgcagcaa cagatggaag  12900
gcctcctggc gccgcaccgg cccaaggagc ccgcgtggtt cctggccacc gtcggcgtct   12960
cgcccgacca ccagggcaag ggtctgggca gcgccgtcgt gctccccgga gtggaggcgg   13020
ccgagcgcgc cggggtgccc gccttcctgg agacctccgc gccccgcaac ctcccttct    13080
acgagcggct cggcttcacc gtcaccgccg acgtcgaggg gccgaagga ccgcgcacct    13140
ggtgcatgac ccgcaagccc ggtgcctgaa gcgcggggat ctcatgctgg agttcttcgc   13200
ccaccccaac ttgtttattg cagcttataa tggttacaaa taaagcaata gcatcacaaa   13260
tttcacaaat aaagcatttt tttcactgca ttctagttgt ggtttgtcca aactcatcaa   13320
tgtatcttat catgtctgta gctgatgtat acctaggatc cggccggcct gcaggtgtcc   13380
tcacaggaac gaagtcccta aagaaacagt ggcagccagg tttagccccg gaattgactg   13440
gattccttttt ttagggccca ttggtatggc ttttttcccg tatcccccca ggtgtctgca   13500
ggctcaaaga gcagcgagaa gcgttcagag gaaagcgatc ccgtgccacc ttccccgtgc   13560
ccgggctgtc ccgcacgct gccggctcgg ggatgcgggg ggagcgccgg accggagcgg    13620
agcccggggc ggctcgctgc tgccccctag cgggggaggg acgtaattac atccctgggg   13680
gctttggggg gggctgtcc ctctagagcg gccgccaccg cggtggagct ccagcttttg    13740
ttccctttag tgagggttaa ttagatctta atacgactca ctatagggcg aattgggtac   13800
cgggcccccc ctcgaggtcg acggtatcga taagcttgat atctataaca agaaaatata   13860
tatataataa gttatcacgt aagtagaaca tgaaataaca atataattat cgtatgagtt   13920
aaatcttaaa agtcacgtaa aagataatca tgcgtcattt tgactcacgc ggtcgttata   13980
gttcaaaatc agtgacactt accgcattga caagcacgcc tcacgggagc tccaagcggc   14040
gactgagatg tcctaaatgc acagcgacgg attcgcgcta tttagaaaga gagagcaata   14100
tttcaagaat gcatgcgtca attttacgca gactatcttt ctaggggttaa tctagctgca   14160
tcaggatcat atcgtcgggt cttttttccg gctcagtcat cgcccaagct ggcgctatct   14220
gggcatcggg gaggaagaag cccgtgcctt ttcccgcgag gttgaagcgg catggaaaga   14280
gtttgccgag gatgactgct gctgcattga cgttgagcga aaacgcacgt ttaccatgat   14340
gattcgggaa ggtgtggcca tgcacgcctt taacgtcgga ctgttcgttc aggccacctg   14400
ggataccagt tcgtcgcggc ttttccggac acagttccgg atggtcagcc cgaagcgcat   14460
cagcaacccg aacaataccg gcgacagccg gaactgccgt gccggtgtgc agattaatga   14520
cagcggtgcg gcgctgggat attacgtcag cgaggacggg tatcctgcgt ggatgccgca   14580
gaaatggaca tggataccc gtgagttacc cggcggggcgc gcttggcgta atcatggtca   14640
tagctgtttc ctgtgtgaaa ttgttatccg ctcacaattc cacacaacat acgagccgga   14700
agcataaagt gtaaagcctg gggtgcctaa tgagtgagct aactcacatt aattgcgttg   14760
cgctcactgc ccgctttcca gtcgggaaac ctgtcgtgcc agctgcatta atgaatcggc   14820
caacgcgcgg ggagaggcgg tttgcgtatt gggcgctctt ccgcttcctc gctcactgac   14880
tcgctgcgct cggtcgttcg gctgcggcga gcggtatcag ctcactcaaa ggcggtaata   14940
cggttatcca cagaatcagg ggataacgca ggaaagaaca tgtgagcaaa aggccagcaa   15000
aaggccagga accgtaaaaa ggccgcgttg ctggcgtttt tccataggct ccgcccccct   15060
gacgagcatc acaaaaatcg acgctcaagt cagaggtggc gaaacccgac aggactataa   15120
agataccagg cgtttccccc tggaagctcc ctcgtgcgct ctcctgttcc gaccctgccg   15180
cttaccggat acctgtccgc ctttctccct tcgggaagcg tggcgctttc tcatagctca   15240
cgctgtaggt atctcagttc ggtgtaggtc gttcgctcca agctgggctg tgtgcacgaa   15300
ccccccgttc agcccgaccg ctgcgcctta tccggtaact atcgtcttga gtccaacccg   15360
gtaagacacg acttatcgcc actggcagca gccactggta acaggattag cagagcgagg   15420
tatgtaggcg gtgctacaga gttcttgaag tggtggccta actacggcta cactagaagg   15480
acagtatttg gtatctgcgc tctgctgaag ccagttacct tcggaaaaag agttggtagc   15540
tcttgatccg gcaaacaaac caccgctggt agcggtggtt tttttgtttg caagcagcag   15600
attacgcgca gaaaaaaagg atctcaagaa gatcctttga tcttttctac ggggtctgac   15660
gctcagtgga acgaaaactc acgttaaggg attttggtca tgagattatc aaaaaggatc   15720
ttcacctaga tccttttaaa ttaaaaatga agttttaaat caatctaaag tatatatgag   15780
taaacttggt ctgacagtta ccaatgctta atcagtgagg cacctatctc agcgatctgt   15840
```

```
ctatttcgtt catccatagt tgcctgactc cccgtcgtgt agataactac gatacgggag   15900
ggcttaccat ctggcccag tgctgcaatg ataccgcgag acccacgctc accggctcca   15960
gatttatcag caataaacca gccagccgga agggccgagc gcagaagtgg tcctgcaact   16020
ttatccgcct ccatccagtc tattaattgt tgccgggaag ctagagtaag tagttcgcca   16080
gttaatagtt tgcgcaacgt tgttgccatt gctacaggca tcgtggtgtc acgctcgtcg   16140
tttggtatgg cttcattcag ctccggttcc caacgatcaa ggcgagttac atgatccccc   16200
atgttgtgca aaaaagcggt tagctccttc ggtcctccga tcgttgtcag aagtaagttg   16260
gccgcagtgt tatcactcat ggttatggca gcactgcata attctcttac tgtcatgcca   16320
tccgtaagat gcttttctgt gactggtgag tactcaacca agtcattctg agaatagtgt   16380
atgcggcgac cgagttgctc ttgcccggcg tcaatacggg ataataccgc gccacatagc   16440
agaactttaa aagtgctcat cattggaaaa cgttcttcgg ggcgaaaact ctcaaggatc   16500
ttaccgctgt tgagatccag ttcgatgtaa cccactcgtg cacccaactg atcttcagca   16560
tcttttactt tcaccagcgt ttctgggtga gcaaaaacag gaaggcaaaa tgccgcaaaa   16620
aagggaataa gggcgacacg gaaatgttga atactcat                          16658

SEQ ID NO: 9         moltype = DNA  length = 16658
FEATURE              Location/Qualifiers
misc_feature         1..16658
                     note = Synthetic: pPBBG-iHelper2.6-HA
source               1..16658
                     mol_type = other DNA
                     organism = synthetic construct
SEQUENCE: 9
actcttcctt tttcaatatt attgaagcat ttatcagggt tattgtctca tgagcggata     60
catatttgaa tgtatttaga aaataaaca aatagggggtt ccgcgcacat ttccccgaaa    120
agtgccacct aaattgtaag cgttaatatt ttgttaaaat tcgcgttaaa tttttgttaa    180
atcagctcat ttttttaacca ataggccgaa atcggcaaaa tcccttataa atcaaaagaa    240
tagaccgaga taggggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt tttgggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taacccctaga aagataatca tattgtgacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaaa caaaaactca   1080
aaattcttct tataaaagtaa caaaacttttt atcgaattcc tgcagcccgg gggatccact   1140
agttctagag ggacagcccc cccccaaaagc cccaggggat gtaattacgt ccctccccg    1200
ctaggggca gcagcgagcc gcccgggggct ccgctccggt ccggcgctcc cccgcatcc    1260
ccgagccggc agcgtgcggg gacagcccgg gcacggggaa ggtggcacgg gatcgctttc   1320
ctctgaacgc ttctcgctgc tctttgagcc tgcagacacc tgggggggata cggggaaaag   1380
gcctccaagg ccagcttccc acaataaggt gggtgaattt tggctcattc ctccttctta   1440
taggattgag gtcagagctt tgtgatggga attctgtgga atgtgtgtca gttagggtgt   1500
ggaaagtccc gcgatcgcta gcgtttaaac ttaagcttgg taccgagctc ggatccacta   1560
gtccagtgtg gtggaattcc tgcttcgcga tgtacgggcc ggtacccaac tccatgctta   1620
acagtcccca ggtacagccc accctgcgtc gcaaccagga acagctctac agcttcctgg   1680
agcgccactc gccctacttc cgcagccaca gtgcgcagat taggagcgcc acttcttttt   1740
gtcacttgaa aaacatgtaa aaataatgta ctaggagaca ctttcaataa aggcaaatgt   1800
tttttatttgt acactctcgg gtgattattt acccccacc cttgccgtct cgcgccgttta   1860
aaaatcaaag gggttctgcc gcgcatcgct atgcgccact ggcagggaca cgttgcgata   1920
ctggtgtttta gtgctccact taaactcagg cacaaccatc cgcggcagct cggtgaagtt   1980
ttcactccac aggctgcgca ccatcaccaa cgcgtttagc aggtcgggcg ccgatatctt   2040
gaagtcgcag ttggggcctc cgccctgcgc gcgcgagttg cgatacacag ggttgcagca   2100
ctggaacact atcagcgccg ggtggtgcac gctggccagc acgctcttgt cggagatcag   2160
atccgcgtcc aggtcctccg cgttgctcag ggcgaacgga gtcaactttg gtagctgcct   2220
tcccaaaaag ggtgcatgcc caggctttga gttgcactcg caccgtagtg gcatcagaag   2280
gtgaccgtgc ccggtctggg cgttaggata cagcgcctgc atgaaagcct tgatctgctt   2340
aaaagccacc tgagcctttg cgccttcaga gaagaacatg ccgcaagact tgccggaaaa   2400
ctgattggcc ggacaggccg cgtcatgcac gcagcacctt gcgtcggtgt tggagatctg   2460
caccacattt cggccccacc ggttcttcac gatcttggcc ttgctagact gctccttcag   2520
cgcgcgctgc ccgttttcgc tcgtcacatc catttcaatc acgtgctcct tatttatcat   2580
aatgctcccg tgtagacact taagctcgcc ttcgatctca gcgcagcggt gcagccacaa   2640
cgcgcagccc gtgggtcgt ggtgcttgta ggttacctct gcaaacgact gcaggtacgc   2700
ctgcaggaat cgcccatca tcgtcacaaa ggtcttgttg ctggtgaagg tacgctgcaa   2760
cccgcgggtgc tcctcgttta gcaggtcttt gcatacggcc gccagagctt ccacttggtc   2820
aggcagtagc ttgaagtttg cctttagatc gttatccacg tggtacttgt ccatcaacgc   2880
gcgcgcagcc tccatgccct tctcccacgc agacacgatc ggcaggctca gcgggttat    2940
caccgtgctt tcactttccg cttcactgga ctcttccttt tcctcttgcg tccgcatacc   3000
cgcgcgccact gggtcgtctt cattcagccg ccgcaccgtg ccttacctc cttgcgttg    3060
cttgattagc accggtgggt tgctgaaacc caccattgt agcgccacat cttctcttc    3120
ttcctgcgtg tccacgatca cctctgggga tggcgggcgc tcgggcttgg gagaggggcg   3180
cttctttttc ttttggacg caatggccaa atcgccgtc gaggtcgatg gccgcgggct    3240
gggtgtgcgc ggcaccagcg catcttgtga cgagtcttct tcgtcctcgg actcgagacg   3300
ccgcctcagc cgcttttttg ggggcgcgcg ggaggcggg gcgacggcg acgggacga    3360
```

```
cacgtcctcc atggttggtg gacgtcgcgc cgcaccgcgt ccgcgctcgg gggtggtttc   3420
gcgctgctcc tcttcccgac tggccatttc cttctcctat aggcagaaaa agatcatgga   3480
gtcagtcgag aaggaggaca gcctaaccgc ccccttgag ttcgccacca ccgcctccac    3540
cgatgccgcc aacgcgccta ccaccttccc cgtcgaggca ccccgcttg aggaggagga    3600
agtgattatc gagcaggacc caggttttgt aagcgaagac gacgaggatc gctcagtacc   3660
aacagaggat aaaaagcaag accaggacga cgcagaggca aacgaggaac aagtcgggcg   3720
gggggaccaa aggcatggcg actacctaga tgtgggagac gacgtgctgt tgaagcatct   3780
gcagcgccag tgcgccatta tctgcgacgc gttgcaagag cgcagcgatg tgcccctcgc   3840
catagcggat gtcagccttg cctacgaacg ccacctgttc tcaccgcgcg tacccccaa    3900
acgccaagaa aacggcacat gcgagcccaa cccgcgcctc aacttctacc ccgtatttgc   3960
cgtgccagag gtgcttgcca cctatcacat ctttttccaa aactgcaaga taccccctatc  4020
ctgccgtgcc aaccgcagcc gagcggacaa gcagctggcc ttgcggcagg cgctgtcat    4080
acctgatatc gcctcgctcg acgaagtgcc aaaaatcttt gagggtcttg gacgcgacga   4140
gaaacgcgcg gcaaacgctc tgcaacaaga aacagcgaa aatgaaagtc actgtggagt    4200
gctggtggaa cttgagggtg acaacgcgcg cctagccgtg ctgaaacgca gcatcgaggt   4260
cacccacttt gcctacccgg cacttaacct acccccccaag gttatgagca cagtcatgag  4320
cgagctgatc gtgcgccgtg cacgacccct ggagagggat gcaaacttgc aagaacaaac   4380
cgaggagggc ctacccgcag ttggcgatga gcagctggcg cgctgcttg agacgccgca    4440
gcctgccgac ttggaggagc gacgcaagct aatgatggcc gcagtgcttg ttaccgtgga   4500
gcttgagtgc atgcagcggt tctttgctga cccggagatg cagcgcaagc tagaggaaac   4560
gttgcactac acctttcgcc agggctacgt gcgccaggcc tgcaaaattt ccaacgtgga   4620
gctctgcaac ctggtctcct accttggaat tttgcacgaa aaccgcctcg ggcaaaacgt   4680
gcttcattcc acgctcaagg gcgaggcgcg ccgcgactac gtccgcgact gcgtttactt   4740
atttctgtgc tacacctggc aaacggccat gggcgtgtgg cagcaatgcc tggaggagcg   4800
caacctaaag gagctgcaga agctgctaaa gcaaaacttg aaggacctat ggacggcctt   4860
caacgagccc tccgtggccg cgcacctggc ggacattatc ttccccgaac gcctgcttaa   4920
aaccctgcaa cagggtctgc cagacttcac cagtcaaagc atgttgcaaa actttaggaa   4980
ctttatcctc gagcgttcag gaattctgcc cgcccactgc tgtgcgcttc ctagcgactt   5040
tgtgcccatt aagtaccgtg aatgccctcc gccgctttgg ggtcactgct accttctgca   5100
gctagccaac taccttgcct accactccga catcatggaa gacgtgagcg gtgacggcct   5160
actggagtgt cactgtcgct gcaacctatg caccccgcac cgctccctgg tctgcaattc   5220
gcaactgctt agcgaaagtc aaattatcgg taccttgag ctgcagggtc cctgcctga    5280
cgaaaagtcc gcggctccgg ggttgaaact cactccgggg ctgtggacgt ccgatctcta   5340
tcactgatag ggagatctct atcactgata gggagagggc ttaccttcgc aaattttgtac  5400
ctgaggacta ccacgcccac gagattaggt tctacgaaga ccaatcccgc ccgccaaatg   5460
cggagcttac cgcctgcgtc attacccagg gccacatcct tggccaattg caagccatca   5520
acaaagcccg ccaagagttt ctgctacgaa agggacgggg ggtttacctg gacccccagt   5580
ccggcgagga gctcaaccca atcccccgc cgccgcagcc ctatcagcag ccgcgggccc    5640
ttgcttccca ggatggcacc caaaaagaag ctgcagctgc cgccgccgcc acccacggac   5700
gaggaggaat actgggacag tcaggcagag gaggttttgg acgaggagga ggagatgatg   5760
gaagactggg acagcctaga cgaagcttcc gaggccgaag aggtgtcaga cgaaacaccg   5820
tcacccctcgg tcgcattccc ctcgccgcg ccccagaaat tggcaaccgt tcccagcatc   5880
gctacaacct ccgctcctca ggcgcgccg gcactgcctc ttcgccgacc caaccgtaga   5940
tgggacacca ctggaaccag ggccggtaag tctaagcagc cgccgccgtt agcccaagag   6000
caacaacagc gccaaggcta ccgctcgtgg cgcgggcaca agaacgccat agttgcttgc   6060
ttgcaagact gtgggggcaa catctccttc gcccgccgct tcttctcta ccatcacggc    6120
gtggccttcc cccgtaacat cctgcattac taccgtcatc tctacagcca ctactgcacc   6180
ggcggcagcg gcagcggcag caacagcagc ggtcacacag aagcaaaggc gaccggatag   6240
caagactctg acaaagcccca agaaatccac agcggcggca gcagcaggag gaggagcgct   6300
gcgtctggcg cccaacgaac ccgtatcgac ccgcgagctt agaaataggg ttttttccac    6360
tctgtatgct atatttcaac aaagcagggg ccaagaacga gagctgaaaa taaaaaacag   6420
gtctctgcgc tccctcaccc gcagctgcct gtatcacaaa agcgaagatc agcttcggcg   6480
cacgctggaa gacgcggagg ctctcttcag caacgatctc tatcactgat agggagatct   6540
ctatcactga tagggagaga tactgcgcgc tgactcttaa ggactagttt cgcgcccttt   6600
ctcaaattta agcgcgaaaa ctacgtcatc tccagcggcc acaccggcg ccagcacctg    6660
tcgtcagcgc cattatgagc aaggaaattc ccacgcccta catgtggagt taccagccac   6720
aaatgggact tgcggctgga gctgcccaag actactcaac ccgaataaac tacatgagcg   6780
cgggacccca catgatatcc cgggtcaacg gaatccgcgc ccaccgaaac cgaattctcc   6840
tcgaacaggc ggctattacc accacacctc gtaataacct taatccccgc agttggccgg   6900
ctgccctggt gtaccaggaa agtcccgctc ccaccactgt ggtacttccc agagacgccc   6960
aggccgaagt tcagatgact aactcagggg cgcagcttgc gggcgctt cgtcacaggg     7020
tgcggtcgcc cccagtggcc aaaaaagcta gcgcagcagc cgccgcgcct ggaaggaagc   7080
caaaaggagc gctcccccgt tgtctgacgt cgcacacctg ggtcgacac gcgggcggta    7140
accgcatgga tcacggcgga cggccggatc cggggttcga accccggtcg tccgccatga   7200
taccccttgcg aattttatcca ccagaccacg gaagagtgcc cgcttacagg ctctccttt   7260
gcacggtcta gagcgtcaac gactgcgcac gccagtggcc aaaaaagcta gcgcagcagc   7320
cgccgcgcct ggaaggaagc caaaaggagc gctcccccgt tgtctgacgt cgcacacctg   7380
ggtcgacac gcgggcggta accgcatgga tcacggcgga cggccggatc cggggttcga    7440
accccggtcg tccgccatga taccccttgcg aattttatcca ccagaccacg gaagagtgcc   7500
cgcttacagg ctctcctttt gcacggtcta gagcgtcaac gactgcgcac gccagtggcc   7560
aaaaaagcta gcgcagcagc cgccgcgcct ggaaggaagc caaaaggagc gctcccccgt   7620
tgtctgacgt cgcacacctg ggtcgacac gcgggcggta accgcatgga tcacggcgga    7680
cggccggatc cggggttcga accccggtcg tccgccatga taccccttgcg aattttatcca   7740
ccagaccacg gaagagtgcc cgcttacagg ctctcctttt gcacggtcta gagcgtcaac   7800
gactgcgcac gccagtggcc aaaaaagcta gcgcagcagc cgccgcgcct ggaaggaagc   7860
caaaaggagc gctcccccgt tgtctgacgt cgcacacctg ggtcgacac gcgggcggta    7920
accgcatgga tcacggcgga cggccggatc cggggttcga accccggtcg tccgccatga   7980
taccccttgcg aattttatcca ccagaccacg gaagagtgcc cgcttacagg ctctcctttt   8040
gcacggtcta gagcgtcaac gactgcgcac ggggcgtttt agggcggagt aacttgcatg   8100
```

```
tattgggaat tgtagttttt ttaaaatggg aagtgacgta tcgtgggaaa acggaagtga   8160
agatttgagg aagttgtggg ttttttggct ttcgtttctg ggcgtaggtt cgcgtgcggt   8220
tttctgggtg ttttttgtgg actttaaccg ttacgtcatt ttttagtcct atatatactc   8280
gctctgtact ctccctatca gtgatagaga tctccctatc agtgatagag atcgcttggc   8340
cctttttaca ctgtgactga ttgagctggt gccgtgtgca gtgtgtttt ttaataggtt    8400
tttttactgg taaggctgac tgttatggct gccgctgtgg aagcgctgta tgttgttctg   8460
gagcgggagg gtgctatttt gcctaggcag gagggttttt caggtgttta tgtgtttttc   8520
tctcctatta attttgttat acctcctatg ggggctgtaa tgttgtctct acgcctgcgg   8580
gtatgtattc ccccgggcta tttcggtcgc tttttagcac tgaccgatgt taaccaacct   8640
gatgtgttta ccgagtctta cattatgact ccgacatga ccgaggaact gtcggtggtg    8700
ctttttaatc acgtgacca gttttttttac ggtcacgccg gcatggccgt agtccgtctt   8760
atgcttataa gggttgtttt tcctgttgta agacaggctt ctaatgttta aatgtttttt   8820
tttttgttat tttatttgt gtttaatgca ggaacccgca gacatgtttg agagaaaaat   8880
ggtgtctttt tctgtggtgg ttccggaact tacctgcctt tatctgcatg agcatgacta   8940
cgatgtgctt gcttttttgc gcgaggcttt gcctgatttt ttgagcagca ccttgcattt   9000
tatatcgccg cccatgcaac aagcttacat aggggctacg ctggttagca tagctccgag   9060
tatgcgtgtc ataatcagtg tgggttcttt tgtcatggtt cctggcgggg aagtggccgc   9120
gctggtccgt gcagacctgc acgattatgt tcagctggcc ctgcgaaggg acctacggga   9180
tcgcggtatt tttgttaatg ttccgctttt gaatcttata caggtctgtg aggaacctga   9240
attttttgcaa tcatgattcg ctgcttgagg ctgaaggtgg agggcgctct ggagcagatt   9300
tttacaatgg ccgacttaa tattcgggat ttgcttagag acatattgat aaggtggcga    9360
gatgaaaatt atttgggcat ggttgaaggt gctggaatgt ttatagagga gattcaccct   9420
gaagggttta gcctttacgt ccacttggac gtgagggcag tttgccttt ggaagccatt    9480
gtgcaacatc ttacaaatgc cattatctgt tctttggctg tagagtttga ccacgccacc   9540
ggaggggagc gcgttcactt aatagatctt cattttgagg ttttggataa tcttttggaa   9600
taaaaaaaaa aaacatggt tcttccagct cttcccgctc ctcccgtgtg tgactcggaa    9660
aacgaatgtg taggttggct gggtgtggct tattctgcgg tggtggatgt tatcagggca   9720
gcggcgcatg aaggagttta catagaaccc gaagccaggg ggcgcctgga tgctttgaga   9780
gagtggatat actacaacta ctacacagag cgagctaagc gacgagaccg gagacgcaga   9840
tctgttttgtc acgcccgcac ctggttttgc ttcaggaaat atgtacccat acgatgttcc   9900
agattacgct ggaggaggcg gaggcactac gtccggcgtt ccatttggca tgacactacg   9960
accaacacga tctcggttgt ctcggcgcac tccgtacagt agggatcgcc tacctccttt  10020
tgagacagag acccgcgcta ccatactgga ggatcatccg ctgctgcccg aatgtaacac  10080
tttgacaatg cacaacgtga gttacgtgcg aggtcttccc tgcagtgtgg gatttacgct  10140
gattcaggaa tgggttgttc cctgggatat ggttctgacg cgggaggagc ttgtaatcct  10200
gaggaagtgt atgcacgtgt gcctgtgttg tgccaacatt gatatcatga cgagcatgat  10260
gatccatggt tacgagtcct gggctctcca ctgtcattgt tccagtcccg gttccctgca  10320
gtgcatagcc ggcgggcagg ttttggccag ctggtttagg atggtggtgg atggcgccat  10380
gtttaatcag aggtttatat ggtaccggga ggtggtgaat tcaacatgc caaaagaggt   10440
aatgtttatg tccagcgtgt ttatgagggg tcgccactta atctacctgc gcttgtggta  10500
tgatggccac gtgggttctg tggtccccgc catgagcttt ggatacagcg ccttgcactg  10560
tgggattttg aacaatattg tggtgctgtg ctgcagttac tgtgctgatt taagtgagat  10620
cagggtgcgc tgctgtgccc ggaggacaag gcgtctcatg ctgcgggtgg tgcgaatcat  10680
cgctgaggag accactgcca tgttgtattc ctgcaggacg gagcggcggc ggcagcagtt  10740
tattcgcgcg ctgctgcagc accaccgcc tatcctgatg cacgattatg actctacccc   10800
catgtaggcg tggacttccc cttcgccgcc cgttgagcaa ccgcaagttg gacagcagcc  10860
tgtggctcag cagctggaca gcgacatgaa cttaagcgag ctgcccggg agtttattaa   10920
tatcactgat gagcgtttgg ctcgacagga aaccgtgtgg aatataacac ctaagaatat   10980
gtctgttacc catgatatga tgctttttaa ggccagccgg ggagaaagga ctgtgtactc  11040
tgtgtgttgg gagggaggtg gcaggttgaa tactagggtt ctgtgagttt gattaaggta   11100
cggtgatcaa tataagctat gtggtggtgg ggctatacta ctgaatgaaa aatgacttga  11160
aattttctgc aattgaaaaa taaacacgtt gaaacataac atgcaacagg ttcacgattc  11220
tttattcctg ggcaatgtag gagaaggtgt aagagttggt agcaaaagtt tcagtggtgt  11280
atttttccact ttcccaggac catgtaaaag acatagagta agtgcttacc tcgctagttt  11340
ctgtggattc actagaatcc actttggccg cggctcgagt gagctattcc agaagtagtg  11400
aagaggcttt tttggaggcc taggcttttg caaaaagctc cggatcgatg cccggggat   11460
ccactagttc tagagggaca gccccccccc aaagccccca gggatgtaat tacgtccctc   11520
ccccgctagg gggcagcagc gagccgcccg gggctccgct ccggtccggc gctccccccg  11580
catcccccgag ccggcagcgt gcggggacag cccgggcacg gggaaggtgg cacgggatcg  11640
cttttcctctg aacgcttctc gctgctcttt gagcctgcag acacctgggg ggatacgggg   11700
aaaaggcctc caaggccagc ttcccacaat aagttgggtg aattttggct gagctattcc   11760
agaagtagtg aagaggcttt tttggaggcc taggcttttg caaaaagctc cggatcgatc   11820
atatatggca gatatacgcg ttgacattga ttattgacta gttattaata gtaatcaatt   11880
acggggtcat tagttcatag cccatatatg gagttccgcg ttacataact taacgtaaat   11940
ggcccgcctg gctgaccgcc caacgacccc cgcccattga cgtcaataat gacgtatgtc  12000
cccatagtaa cgccaatagg gactttccat tgacgtcaat gggtgagta tttacgggtaa  12060
actgcccact tggcagtaca tcaagtgtat catatgccaa gtacgccccc tattgacgtc  12120
aatgacggta aatggcccgc ctggcattat gcccagtaca tgaccttatg gactttcct   12180
acttggcagt acatctacgt attagtcatc gctattacca tggtgatgcg gttttggcag  12240
tacatcaatg ggcgtggata gcggtttgac tcacggggat ttccaagtct ccaccccatt  12300
gacgtcaatg ggagttgtt ttggcaccaa aatcaacggg actttccaaa atgtcgtaac   12360
aactccgccc cattgacgca aatgggcggt aggcgtgtac ggtgggaggt ctatataagc  12420
agagctctct ggctaactat cgtcgacgag ctcgtttagt gaaccgtcag atcgcctgga  12480
gacgccatcc acgctgtttt gacctccata gaagacaccg agccctccgga               12540
ctctagcgtt taaacttaag cttgccacca tgaccgagta caagcccacg gtgcgcctcg  12600
ccaccgcga cgacgtcccc agggccgtac gcaccctcgc cgccgcgttc gccgactacc  12660
ccgccacgcg ccacaccgtc gatccggacc gccacatcga gcgggtcacc gagctgcaag  12720
aactcttcct cacgcgcgtc gggtcgaca tcggcaaggt gtgggtcgcg gacgacggcg   12780
ccgcggtggc ggtctggacc acgccggaga gcgtcgaagc gggggcggtg ttcgccgaga  12840
```

```
tcggcccgcg catggccgag ttgagcggtt cccggctggc cgcgcagcaa cagatggaag  12900
gcctcctggc gccgcaccgg cccaaggagc ccgcgtggtt cctgccacc  gtcggcgtct  12960
cgcccgacca ccagggcaag ggtctgggca gcgccgtcgt gctccccgga gtggaggcgg  13020
ccgagcgcgc cggggtgccc gccttcctgg agacctccgc gccccgcaac ctccccttct  13080
acgagcggct cggcttcacc gtcaccgccg acgtcgaggt gcccgaagga ccgcgcacct  13140
ggtgcatgac ccgcaagccc ggtgcctgaa gcgcggggat ctcatgctgg agttcttcgc  13200
ccaccccaac ttgtttattg cagcttataa tggttacaaa taagcaata  gcatcacaaa  13260
tttcacaaat aaagcatttt tttcactgca ttctagttgt ggtttgtcca aactcatcaa  13320
tgtatcttat catgtctgta gctgatgtat acctaggatc cggccggcct gcaggtgtcc  13380
tcacaggaac gaagtcccta aagaaacagt ggcagccagg tttagccccg gaattgactg  13440
gattcctttt ttagggccca ttggtatggc ttttcccg tatccccca ggtgtctgca  13500
ggctcaaaga gcagcgagaa gcgttcagag gaaagcgatc ccgtgccacc ttccccgtgc  13560
ccgggctgtc cccgcacgct gccggctcgg ggatgcgggg ggagcgccgg accggagcgg  13620
agccccgggc ggctcgctgc tgccccctag cgggggacgg acgtaattac atccctgggg  13680
gctttggggg ggggctgtcc ctctagagcg gccgccaccg cggtggagct ccagcttttg  13740
ttccctttag tgagggttaa ttagatctta atacgactca ctatagggcg aattgggtac  13800
cgggcccccc ctcgaggtcg acggtatcga taagcttgat atctataaca agaaaatata  13860
tatataataa gttatcacgt aagtagaaca tgaaataaca atataattat cgtatgagtt  13920
aaatcttaaa agtcacgtaa aagataatca tgcgtcattt tgactcacgc ggtcgttata  13980
gttcaaaatc agtgacactt accgcattga caagcacgcc tcacgggagc tccaagcggc  14040
gactgagatg tcctaaatgc acagcgacgg attcgcgcta tttagaaaga gagagcaata  14100
tttcaagaat gcatgcgtca attttacgca gactatcttt ctaggggttaa tctagctgca  14160
tcaggatcat atcgtcgggt ctttttttccg gctcagtcat cgcccaagct ggcgctatct  14220
gggcatcggg gaggaagaag cccgtgcctt tccccgcgag gttgaagcgg catggaaaga  14280
gtttgccgag gatgactgct gctgcattga cgttgagcga aaacgcacgt ttaccatgat  14340
gattcgggaa ggtgtggcca tgcacgcctt taacggtgaa ctgttcgttc aggccacctg  14400
ggataccagt tcgtcgcggc ttttccggac acagttccgc atggtcagcc cgaagcgcat  14460
cagcaacccg aacaataccg gcgacagccg gaactgccgt gccggtgtgc agattaatga  14520
cagcggtgcg gcgctgggat attacgtcag cgaggacggg tatcctggct ggatgccgca  14580
gaaatggaca tggataccc  gtgagttacc cggcggggcg gcttggcgta atcatggtca  14640
tagctgtttc ctgtgtgaaa ttgttatccg ctcacaattc cacacaacat acgagccgga  14700
agcataaagt gtaaagcctg gggtgcctaa tgagtgagct aactcacatt aattgcgttg  14760
cgctcactgc ccgctttcca gtcgggaaac ctgtcgtgcc agctgcatta atgaatcggc  14820
caacgcgcgg ggagaggcgg tttgcgtatt gggcgctctt ccgcttcctc gctcactgac  14880
tcgctgcgct cggtcgttcg gctgcggcga gcggtatcag ctcactcaaa ggcggtaata  14940
cggttatcca cagaatcagg ggataacgca ggaaagaaca tgtgagcaaa aggccagcaa  15000
aaggccagga accgtaaaaa ggccgcgttg ctggcgtttt tccataggct ccgcccccct  15060
gacgagcatc acaaaaatcg acgctcaagt cagaggtggc gaaacccgac aggactataa  15120
agataccagg cgtttccccc tggaagctcc ctcgtgcgct ctcctgttcc gaccctgccg  15180
cttaccggat acctgtccgc ctttctccct tcgggaagcg tggcgctttc tcatagctca  15240
cgctgtaggt atctcagttc ggtgtaggtc gttcgctcca agctgggctg tgtgcacgaa  15300
ccccccgttc agcccgaccg ctgcgcctta tccggtaact atcgtcttga gtccaacccg  15360
gtaagacaca cttatcgcc  actggcagca gccactggta acaggattag cagagcgagg  15420
tatgtaggcg gtgctacaga gttcttgaag tggtggccta actacggcta cactagaagg  15480
acagtatttg gtatctgcgc tctgctgaag ccagttacct tcggaaaaag agttggtagc  15540
tcttgatccg gcaaacaaac caccgctggt agcggtggtt ttttttgtttg caagcagcag  15600
attacgcgca gaaaaaaagg atctcaagaa gatcctttga tcttttctac ggggtctgac  15660
gctcagtgga acgaaaactc acgttaaggg attttggtca tgagattatc aaaaaggatc  15720
ttcacctaga tccttttaaa ttaaaaatga agttttaaat caatctaaag tatatatgag  15780
taaacttggt ctgacagtta ccaatgctta atcagtgagg cacctatctc agcgatctgt  15840
ctatttcgtt catccatagt tgcctgactc cccgtcgtgt agataactac gatacgggag  15900
ggcttaccat ctggccccag tgctgcaatg ataccgcgag acccacgctc accggctcca  15960
gatttatcag caataaacca gccagccgga agggccgagc gcagaagtgg tcctgcaact  16020
ttatccgcct ccatccagtc tattaattgt tgccgggaag ctagagtaag tagttcgcca  16080
gttaatagtt tgcgcaacgt tgttgccatt gctacaggca tcgtggtgtc acgctcgtcg  16140
tttggtatgg cttcattcag ctccggttcc caacgatcaa ggcgagttac atgatccccc  16200
atgttgtgca aaaaagcggt tagctccttc ggtcctccga tcgttgtcag aagtaagttg  16260
gccgcagtgt tatcactcat ggttatggca gcactgcata attctcttac tgtcatgcca  16320
tccgtaagat gcttttctgt gactggtgag tactcaacca agtcattctg agaatagtgt  16380
atgcggcgac cgagttgctc ttgcccggcg tcaatacggg ataataccgc gccacatagc  16440
agaactttaa aagtgctcat cattggaaaa cgttcttcgg ggcgaaaact ctcaaggatc  16500
ttaccgctgt tgagatccag ttcgatgtaa cccactcgtg cacccaactg atcttcagca  16560
tcttttactt tcaccagcgt ttctgggtga gcaaaaacag gaaggcaaaa tgccgcaaaa  16620
aagggaataa gggcgacacg gaaatgttga atactcat                          16658

SEQ ID NO: 10          moltype = DNA   length = 17114
FEATURE                Location/Qualifiers
misc_feature           1..17114
                       note = Synthetic: pPBBG-iHelper2.7-HA
source                 1..17114
                       mol_type = other DNA
                       organism = synthetic construct
SEQUENCE: 10
actcttcctt tttcaatatt attgaagcat ttatcagggt tattgtctca tgagcggata   60
catatttgaa tgtatttaga aaaataaaca aataggggtt ccgcgcacat ttccccgaaa  120
agtgccacct aaattgtaag cgttaatatt ttgttaaaat tcgcgttaaa ttttttgtta  180
atcagctcat tttttaacca ataggccgaa atcggcaaaa tcccttataa atcaaaagaa  240
tagaccgaga taggggtgag tgttgttcca gtttggaaca agagtccact attaaagaac  300
gtggactcca acgtcaaagg gcgaaaaacc gtctatcagg gcgatggccc actacgtgaa  360
```

```
ccatcaccct aatcaagttt tttggggtcg aggtgccgta aagcactaaa tcggaaccct   420
aaagggagcc cccgatttag agcttgacgg ggaaagccgg cgaacgtggc gagaaaggaa   480
gggaagaaag cgaaaggagc gggcgctagg gcgctggcaa gtgtagcggt cacgctgcgc   540
gtaaccacca caccgccgc gcttaatgcg ccgctacagg gcgcgtccca ttcgccattc   600
aggctgcgca actgttggga agggcgatcg gtgcgggcct cttcgctatt acgccagctg   660
gcgaaagggg gatgtgctgc aaggcgatta agttgggtaa cgccaggtt ttcccagtca    720
cgacgttgta aaacgacggc cagtgagcgc gcctcgttca ttcacgtttt tgaacccgtg   780
gaggacgggc agactcgcgg tgcaaatgtg ttttacagcg tgatggagca gatgaagatg   840
ctcgacacgc tgcagaacac gcagctagat taaccctaga aagataatca tattgtgacg   900
tacgttaaag ataatcatgc gtaaaattga cgcatgtgtt ttatcggtct gtatatcgag   960
gtttatttat taatttgaat agatattaag ttttattata tttacactta catactaata  1020
ataaattcaa caaacaattt atttatgttt atttattttat taaaaaaaaa caaaaactca  1080
aaatttcttc tataaagtaa caaaacttttt atcgaattcc tgcagcccgg gggatccact  1140
agttctagag ggacagcccc ccccaaagc cccagggat gtaattacgt ccctccccg     1200
ctagggggca gcagcgagcc gcccgggct ccgctccggt ccggcgctcc ccccgcatcc   1260
ccgagccggc agcgtgcggg gacagcccgg gcacggggaa ggtggcacgg gatcgctttc  1320
ctctgaacgc ttctcgctgc tctttgagcc tgcagacacc tgggggata cggggaaaag   1380
gcctccaagg ccagcttccc acaataagtt gggtgaattt tggctcattc ctcctttcta  1440
taggattgag gtcagagctt tgtgatggga attctgtga atgtgtgtca gttagggtgt   1500
ggaaagtccc gcgatcgcta gcgtttaaac ttaagcttgg taccgagctc ggatccacta  1560
gtccagtgtg gtggaattcc tgcttcgcga tgtacgggcc ggtacccaac tccatgctta  1620
acagtcccca ggtacagccc accctgcgtc gcaaccagga acagctctac agcttcctgg  1680
agcgccactc gccctacttc cgcagccaca gtgcgcagat taggagcgcc acttcttttt  1740
gtcacttgaa aaacatgtaa aaataatgta ctaggagaca ctttcaataa aggcaaatgt   1800
ttttatttgt acactctcgg gtgattattt accccccacc cttgccgtct gcgccgttta  1860
aaaatcaaag gggttctgcc gcgcatcgct atgcgccact ggcagggaca cgttgcgata  1920
ctggtgttta gtgctccact taaactcagg cacaaccatc cgcggcagct cggtgaagtt  1980
ttcactccac aggctgcgca ccatcaccaa cgcgtttagc aggtcgggcg ccgatatctt  2040
gaagtcgcag ttggggcctc cgccctgcgc gcgcgagttg cgatacacag ggttgcagca  2100
ctggaacact atcagcgccg ggtggtgcac gctggccagg aagctcttgt cggagatcag  2160
atccgcgtcc aggtcctccg cgttgctcag ggcgaacgga gtcaactttg gtagctgcct  2220
tcccaaaaag ggtgcatgcc caggctttga gttgcactcg caccgtagtg gcatcagaag  2280
gtgaccgtgc ccggtctggg cgttaggata cagcgcctgc atgaaagcct tgatctgctt  2340
aaaagccacc tgagcctttg cgccttcaga gaagaacatg ccgcaagact tgccggaaaa  2400
ctgattggcc ggacaggccg cgtcatgcac gcagcacctt gcgtcggtgt tggagatctg  2460
caccacattt cggccccacc ggttcttcac gatcttggcc ttgctagact gctccttcag  2520
cgcgcgctgc ccgttttcgc tcgtcacatc catttcaatc acgtgctcct tatttatcat  2580
aatgctcccg tgtagacact taagctcgcc ttcgatctca gcgcagcggt gcagccacaa  2640
cgcgcagccc gtgggctcgt ggtgcttgta ggttacctct gcaaacgact gcaggtacgc  2700
ctgcaggaat cgccccatca tcgtcacaaa ggtcttgttg ctggtgaagg tcagctgcaa  2760
cccgcggtgc tcctcgttta gccaggtctt gcatacggcc gccagagctt ccacttggtc  2820
aggcagtagc ttgaagtttg cctttagatc gttatccacg tggtacttgt ccatcaacgc  2880
gcgcgcagcc tccatgccct tctcccacgc agacacgatc ggcaggctca gcgggtttat  2940
caccgtgctt tcacttttccg cttcactgga ctcttccttt tcctcttgcg tccgcatacc  3000
ccgcgccact gggtcgtctt cattcagccg ccgcaccgtg cgcttacctc ccttgccgtg  3060
cttgattagc accggtgggt tgctgaaacc caccatttgt agcgccacat cttctctttc  3120
ttcctcgctg tccacgatca cctctgggga tggcgggcgc tcgggcttgg gagagggggcg 3180
cttctttttc tttttggacg caatggccaa atccgccgtc gaggtcgatg gccgcgggct  3240
gggtgtgcgc ggcaccagcg catcttgtga cgagtcttct tcgtcctcgg actcgagacg  3300
ccgcctcagc cgctttttg ggggcgcgcg ggaggcggc ggcgacggcg acgggacga    3360
cacgtcctcc atggttggtg gacgtcgcgc cgcaccgcgt cgcgctcgg gggtggtttc  3420
gcgctgctcc tcttcccgac tggccatttc cttctcctat aggcagaaaa agatcatgga  3480
gtcagtcgag aaggaggaca gcctaaccgc cccctttgag ttcgccacca ccgcctccac  3540
cgatgccgcc aacgcgccta ccaccttccc cgtcgaggca ccccgcttg aggaggagga   3600
agtgattatc gagcaggacc caggttttgt aagcgaagac gacgaggatc gctcagtacc  3660
aacagaggat aaaagcaag accaggacga cgcagaggca aacgaggaac aagtcgggcg  3720
gggggaccaa aggcatggcg actacctaga tgtgggagac gacgtgctgt tgaagcatct  3780
gcagcgccag tgcgccatta tctgcgacgc gttgcaagag cgcagcgatg tgcccctcgc  3840
catagcggat gtcagcctga cctacgaacg ccacctgttc tcaccgcgcg taccccccaa  3900
acgccaagaa aacggcacat gcgagcccaa cccgcgcctc aacttctacc ccgtatttgc  3960
cgtgccagag gtgcttgcca cctatcacat ctttttccaa aactgcaaga tacccctatc  4020
ctgccgtgcc aaccgcagcc gagcggacaa gcagctggcc ttgcggcagg gcgctgtcat  4080
acctgatatc gcctcgctcg acgaagtgcc aaaaatcttt gagggtcttg gacgcgacga  4140
gaaacgcgcg gcaaacgctc tgcaacaaga aaacagcgaa aatgaaagtc actgtggagt  4200
gctggtggaa cttgagggtg acaacgcgcg cctagccgtg ctgaaacgca gcatcgaggt  4260
cacccacttt gcctacccgg cacttaacct accccccaag gttatgagca cagtcatgag  4320
cgagctgatc gtgcgccgtg cacgacccct ggagagggat gcaaacttgc aagaacaaac  4380
cgaggagggc ctacccgcag ttggcgatga gcagctggcc cgctggcttg agacgcgcga  4440
gcctgccgac ttggaggagc gacgcaagct aatgatggcc gcagtgcttg ttaccgtgga  4500
gcttgagtgc atgcagcggt tctttgctga cccggagatg cagcgcaagc tagaggaaac  4560
gttgcactac accttcgcc agggctacgt gcgccaggcc tgcaaaattt ccaacgtgga  4620
gctctgcaac ctggtctcct accttggaat ttgcacgaa aaccgcctcg gcaaaacgt   4680
gcttcattcc acgctcaagg gcgaggcgcg ccgcgactac gtccgcgact cgtttactt   4740
atttctgtgc tacacctggc aaacggccat gggcgtggc cagcaatgcc tggaggagcg  4800
caacctaaag gagctgcaga agctgctaaa gcaaaacttg aaggacctat ggacggcctt  4860
caacgagcgc tccgtggccg cgcacctggc ggacattatc ttccccgaac gctgcttaa   4920
aaccctgcaa cagggtctgc cagacttcac cagtcaaagc atgttgcaaa actttaggaa  4980
cttttatccta gagcgttcag gaattctgcc cgccacctgc tgtgcgcttc ctagcgactt  5040
tgtgcccatt aagtaccgtg aatgcccctcc gccgctttgg ggtcactgct accttctgca  5100
```

```
gctagccaac taccttgcct accactccga catcatggaa gacgtgagcg gtgacggcct  5160
actggagtgt cactgtcgct gcaacctatg caccccgcac cgctccctgg tctgcaattc  5220
gcaactgctt agcgaaagtc aaattatcgg tacctttgag ctgcagggtc cctcgcctga  5280
cgaaaagtcc gcggctccgg ggttgaaact cactccgggg ctgtggacgt ccgatctcta  5340
tcactgatag ggagatctct atcactgata gggagagggc ttaccttcgc aaatttgtac  5400
ctgaggacta ccacgcccac gagattaggt tctacgaaga ccaatcccgc ccgccaaatg  5460
cggagcttac cgcctgcgtc attacccagg gccacatcct tggccaattg caagccatca  5520
acaaagcccg ccaagagttt ctgctacgaa agggacgggg ggtttacctg gacccccagt  5580
ccggcgagga gctcaaccca atcccccgc cgccgcagcc ctatcagcag ccgcgggcc  5640
ttgcttccca ggatggcacc caaaaagaag ctgcagctgc cgccgccgcc acccacggac  5700
gaggaggaat actgggacag tcaggcagag gaggttttgg acgaggagga ggagatgatg  5760
gaagactggg acagcctaga cgaagcttcc gaggccgaag aggtgtcaga cgaaacaccg  5820
tcaccctcgg tcgcattccc ctcgccggcg ccccagaaat tggcaaccgt tcccagcatc  5880
gctacaacct ccgctcctca ggcgccgccg gcactgcctg ttcgccgacc caaccgtaga  5940
tgggacacca ctggaaccag ggccggtaag tctaagcagc cgccgccgtt agcccaagag  6000
caacaacagc gccaaggcta ccgctcgtgg cgcgggcaca agaacgccat agttgcttgc  6060
ttgcaagact gtgggggcaa catctccttc gcccgccgct tcttctctcta ccatcacggc  6120
gtggccttcc cccgtaacat cctgcattac taccgtcatc tctacagccc ctactgcacc  6180
ggcggcagcg gcagcggcag caacagcagc ggtcacacag aagcaaaggc gaccggatag  6240
caagactctg acaaagccca agaaatccac agcggcggca gcagcaggag gaggagcgct  6300
gcgtctggcg cccaacgaac ccgtatcgac ccgcgagctt agaaatagga ttttttccac  6360
tctgtatgct atatttcaac aaagcagggg ccaagaacaa gagctgaaaa taaaaaacag  6420
gtctctgcgc tccctcaccc gcagctgcct gtatcacaaa agcgaagatc agcttcggcg  6480
cacgctggaa gacgcggagg ctctcttcag caacgatctc tatcactgat agggagatct  6540
ctatcactga tagggagaga tactgcgcgc tgactcttaa ggactagttt cgcgcccttt  6600
ctcaaattta agcgcgaaaa ctacgtcatc tccagcggcc acaccggcg ccagcacctg  6660
tcgtcagcgc cattatgagc aaggaaattc ccacgcccta catgtggagt taccagccac  6720
aaatgggact tgcggctgga gctgcccaag actactcaac ccgaataaac tacatgagcg  6780
cgggacccca catgatatcc cgggtcaacg gaatccgcgc ccaccgaaac cgaattctcc  6840
tcgaacaggc ggctattacc accacacctc gtaataacct taatccccgt agttggccgg  6900
ctgccctggt gtaccaggaa agtcccgctc ccaccactgt ggtacttccc agagacgccc  6960
aggccgaagt tcagatgact aactcagggg cgcagcttgc gggcggcttt cgtcacaggg  7020
tgcggtcgcc cgggcgtttt agggcggagt aacttgcatg tattgggaat tgtagttttt  7080
ttaaaatggg aagtgacgta tcgtgggaaa acggaagtga agatttgagg aagttgtggg  7140
tttttttggct ttcgtttctg ggcgtaggtt cgcgtgcggt tttctgggtg ttttttgtgg  7200
actttaaccg ttacgtcatt ttttagtcct atatatactc gctctgtact ctccctatca  7260
gtgatagaga tctccctatc agtgatagag atcgcttggc ccttttttaca ctgtgactga  7320
ttgagctggt gccgtgtcga gtggtgtttt taatagtt ttttactgg taaggctgac  7380
tgttatggct gccgctgtgg aagcgctgta tgttgttcg gagcgggagg gtgctatttt  7440
gcctaggcag gagggttttt caggtgttta tgtgttttc tctcctatta attttgttat  7500
acctcctatg ggggctgtaa tgttgtctct acgcctgcgg gtatgtattc ccccgggcta  7560
tttcggtcgc ttttttagcac tgaccgatgt taaccaacct gatgtgttta ccgagtctta  7620
cattatgact ccggacatga ccgaggaact gtcggtggtg cttttttaatc acggtgacca  7680
gtttttttac ggtcacgccg gcatggccgt agtccgtcct atgcttataa gggttgtttt  7740
tcctgttgta agacaggctt ctaatgtttta aatgtttttt tttttgttat tttattttgt  7800
gtttaatgca ggaacccgca gacatgtttg agagaaaaat ggtgtctttt tctgtggtgg  7860
ttccggaact tacctgcctt tatctgcatg agcatgactc cgatcgtgct gctttttgc  7920
gcgaggcttt gcctgatttt ttgagcagca ccttgcattt tatatcgccg cccatgcaac  7980
aagcttacat aggggctacg ctggttagca tagctccgag tatgcgtgtc ataatcagtg  8040
tgggttcttt tgtcatggtt cctggcgggg aagtggccgc gctggtccgt gcagacctgc  8100
acgattatgt tcagctggcc ctgcgaaggg acctacggga tcgcggtatt tttgttaatg  8160
ttccgctttt gaatcttata caggtctgtg aggaacctga attttgtcaa tcatgattcg  8220
ctgcttgagg ctgaaggtgg agggcgctct ggagcagatt tttacaatgg ccggacttaa  8280
tattcggat ttgcttagag acatattgat aaggtggcga gatgaaaatt atttgggcat  8340
ggttgaaggt gctggaatgt ttatagagga gattcaccct gaagggttta gccttacgt  8400
ccacttggac gtgagggcag tttgcctttt ggaagccatt gtgcaacatc ttacaaatgc  8460
cattatctgt tctttggctg tagagtttga ccacgccacc ggaggggagc gcgttcactt  8520
aatagatctt cattttgagg ttttggataa tcttttggaa taaaaaaaaa aaacatggt  8580
tcttccagct cttcccgctc ctcccgtgtg tgactgcgca aacgaatgtg taggttggct  8640
gggtgtggct tattctgcgg tggtggatgt tatcagggca gcggcgcatg aaggagttta  8700
catagaaccc gaagccaggg ggcgcctgga tgctttgaga gagtggatat actacaacta  8760
ctacacagag cgagctaagc gacgagaccg gagacgcaga tctgttttgtc acgcccgcac  8820
ctggttttgc ttcaggaaat atgtacccat acgatgttcc agattacgct ggaggaggcg  8880
gaggcactac gtccggcgtt ccatttggca tgacactacg actaacacga tctcggttgt  8940
ctcggcgcac tccgtacagt agggatcgcc tacctccttt tgagacagag acccgcgcta  9000
ccatactgga ggatcatccg ctgctgcccg aatgtaacac tttgcaatg cacaacgtga  9060
gttacgtgcg aggtcttccc tgcagtgtgg gatttacgct gattcaggaa tgggttgttc  9120
cctgggatat ggttctgacg cggaggagc ttgtaatcct gaggaagtgt atgcacgtgt  9180
gcctgtttg tgccaacatt gatatcatga cgagcatgat gatccatgct tacgagtcct  9240
gggctctcca ctgtcattgt tccagtcccg gttccctgca gtgcatagcc ggcgggcagg  9300
ttttggccag ctggtttagg atggtggtgg atggcgccat gtttaatcag aggttttatat  9360
ggtaccggga ggtggtgaat tacaacatgc caaaagaggg aatgtttatg tccagcgtgt  9420
ttatgagggg tcgccactta atctacctgc gcttgtggta tgatgccac gtgggttctg  9480
tggtcccccga catgagcttt ggatacagcg ccttgacctg tgggattttg aacaatattg  9540
tggtgctgtg ctgcagttac tgtgctgatt taagtgagat cagggtcgc tgctgtgccc  9600
ggaggacaag gcgtctcatg ctgcgggcgg tgcgaatcat cgctgaggag accactgcca  9660
tgttgtattc ctgcaggacg gagcggcggc ggcagcagtt tattcgcgcg ctgctgcagc  9720
accaccgccc tatcctgatg cacgattatg actctacccc catgtaggcg tggacttccc  9780
cttcgccgcc cgttgagcaa ccgcaagttg gacagcagcc tgtggctcag cagctggaca  9840
```

```
gcgacatgaa cttaagcgag ctgcccgggg agtttattaa tatcactgat gagcgtttgg   9900
ctcgacagga aaccgtgtgg aatataacac ctaagaatat gtctgttacc catgatatga   9960
tgcttttaa ggccagccgg ggagaaagga ctgtgtactc tgtgtgttgg gagggaggtg  10020
gcaggttgaa tactagggtt ctgtgagttt gattaaggta cggtgatcaa tataagctat  10080
gtggtggtgg ggctatacta ctgaatgaaa aatgacttga aattttctgc aattgaaaaa  10140
taaacacgtt gaaacataac atgcaacagg ttcacgattc tttattcctg ggcaatgtag  10200
gagaaggtgt aagagttggt agcaaaagtt tcagtggtgt attttccact ttcccaggac  10260
catgtaaaag acatagagta agtgcttacc tcgctagttt ctgtggattc actagaacca  10320
gtggccaaaa aagctagcgc agcagccgcc gcgcctggaa ggaagccaaa aggagcgctc  10380
ccccgttgtc tgacgtcgca cacctgggtt cgacacgcgg gcggtaaccg catggatcac  10440
ggcggacggc cggatccggg gttcgaaccc cggtcgtccg ccatgatacc cttgcgaatt  10500
tatccaccag accacggaag agtgccgct tacaggtggt ctcatacaga acttataaga  10560
ttcccaaatc caaagacatt tcacgtttat ggtgatttcc cagaacacat agcgacatgc  10620
aaatattgca gggcgccact cccctgtccg ctctccttt gcacggtcta gagcgtcaac  10680
gactgcgcac gccagtggcc aaaaaagcta gcgcagcagc cgccgcgcct ggaaggaagc  10740
caaaaggagc gctcccccgt tgtctgacgt cgcacacctg ggttcgacac gcgggcggta  10800
accgcatgga tcacggcgga cggccggatc cggggttcga accccggtcg tccgccatga  10860
taccctgcg aattatcca ccagaccacg gaagagtgcc cgcttacagg tggtctcata  10920
cagaacttat aagattccca aatccaaga catttcacgt ttatggtgat ttcccagaac  10980
acatagcgac atgcaaatat tgcagggcgc cactcccctg tccgctctcc ttttgcacgg  11040
tctagagcgt caacgactgc gcacgccagt ggccaaaaaa gctagcgcag cagccgccgc  11100
gcctggaagg aagccaaaag gagcgctccc ccgttgtcg acgtcgcaca cctgggttcg  11160
acacgcgggc ggtaaccgca tggatcacgg cggacggccg gatccggggt tcgaaccccg  11220
gtcgtccgcc atgatacct gcgaattta ccaccagac acggaagag tgcccgctta  11280
caggtggtct catacagaac ttataagatt cccaaatcca aagacatttc acgtttatgg  11340
tgatttccca gaacacatag cgacatgcaa atattgcagg gcgccactcc cctgtccgct  11400
ctccttttgc acgtctaga gcgtcaacga ctgcgcacgc cagtggccaa aaaagctagc  11460
gcagcagccg ccgcgcctgg aaggaagcca aaggagcgc tccccgttg tctgacgtcg  11520
cacacctggg ttcgacacgc gggcggtaac cgcatggatc acggcggacg gccggatccg  11580
gggttcgaac cccggtcgtc cgccatgata cccttgcgaa tttatccacc agaccacgga  11640
agagtgcccg cttacaggtg gtctcataca gaacttataa gattcccaaa tccaaagaca  11700
tttcacgttt atggtgattt cccagaacac atagcgacat gcaaatattg cagggcgcca  11760
ctcccctgtc cgctctcctt ttgcacggtc tagagcgtca acgactgcgc acgtccactt  11820
tggccgcggc tcgagtgagc tattccagaa gtagtgaaga ggcttttttg gaggcctagg  11880
cttttgcaaa aagctccgga tcgatgcccg ggggatccac tagttctaga gggacagccc  11940
ccccccaaag cccccaggga tgtaattacg tccctccccc gctaggggc agcagcgagc  12000
cgcccggggc tccgctccgg tccggcgctc ccccgcatc cccgagccgg cagcgtgcgg  12060
ggacagcccg ggcacgggga aggtggcacg ggatcgcttt cctctgaacg cttctcgctg  12120
ctctttgagc ctgcagacac ctgggggat acggggaaaa ggcctccaag gccagcttcc  12180
cacaataagt tgggtgaatt ttggctgagc tattccagaa gtagtgaaga ggcttttttg  12240
gaggcctagg cttttgcaaa aagctccgga tcgatcatat atggcagata tacgcgttga  12300
cattgattat tgactagtta ttaatagtaa tcaattacgg ggtcattagt tcatagccca  12360
tatatggagt tccgcgttac ataacttacg gtaaatggcc cgcctggctg accgcccaac  12420
gacccccgcc cattgacgtc aataatgacg tatgttccca tagtaacgcc aatagggact  12480
ttccattgac gtcaatgggt ggagtattta cggtaaactg cccacttggc agtacatcaa  12540
gtgtatcata tgccaagtac gccccctatt gacgtcaatg acggtaaatg gcccgcctgg  12600
cattatgccc agtacatgac cttatgggac ttttcctact tggcagtaca ctacgtatta  12660
gtcatcgcta ttaccatggt gatgcggttt tggcagtaca tcaatgggcg tggatagcgg  12720
tttgactcac ggggatttcc aagtctccac cccattgacg tcaatgggag tttgttttgg  12780
caccaaaatc aacgggactt tccaaaatgt cgtaacaact ccgccccatt gacgcaaatg  12840
ggcggtaggc gtgtacggtg ggaggtctat ataagcagag ctctctggct aactatcgtc  12900
gacgagctcg tttagtgaac cgtcagatcg cctggagacg ccatccacgc tgttttgacc  12960
tccatagaag acaccgggac cgatccagcc tccggactct agcgtttaaa cttaagcttg  13020
ccaccatgac cgagtacaag cccacggtgc gcctcgccac ccgcgacgac gtccccaggg  13080
ccgtacgcac cctcgccgcc gcgttcgcg actacccccgc cacgcgccac accgtcgatc  13140
cggaccgcca catcgagcgg gtcaccgagc tgcaagaact cttcctcacg cgcgtcgggc  13200
tcgacatcgg caaggtgtgg gtcgcggacg acggcgccgc ggtggcggtc tggaccacgc  13260
cggagagcgt cgaagcgggg gcggtgttcg ccgagatcgg cccgcgcatg ccgagttga  13320
gcggttcccg gctggccgcg cagcaacaga tggaaggcct cctggcgccg caccggccca  13380
aggagcccgt gggttccctg gccaccgtcg gcgtctcgcc cgaccaccag ggcaagggtc  13440
tgggcagcgc cgtcgtgctc cccggagtgg aggcggccga gcgccgggg tgcccgcct  13500
tcctggagac ctccgcgccc cgcaacctcc ccttctacga gcggctcggc ttcaccgtca  13560
ccgccgacgt cgaggtgccc gaaggaccgc gcacctggtg catgacccgc aagcccggtg  13620
cctgaagcgc gggatctca tgctggagtt cttcgcccac cccaacttgt ttattgcagc  13680
ttataatggt tacaaataaa gcaatagcat cacaaatttc acaaataaag cattttttc  13740
actgcattct agttgtggtt tgtccaaact catcaatgta tcttatcatg tctgtagctg  13800
atgtatacct aggatccggc cggcctgcag gtgtcctcac aggaacgaag tcctaaaga  13860
aacagtggca gccaggttta gccccggaat tgactggatt ccttttttag ggcccattgg  13920
tatggctttt tccccgtatc ccccaggtg tctgcaggct caaagagcag cgagaagcgt  13980
tcagaggaaa gcgatcccgt gccaccttcc ccgtgcccgg gctgtccccg cacgctgccg  14040
gctcggggat gcgggggag gcgcggaccg gagcggagcc ccgggcggct gctgctgcc  14100
ccctagcggg ggagggacgt aattacatcc ctgggggctt tggggggggg ctgtccctct  14160
agagcggccg ccacgcgtt ggagctccag cttttgttcc cttagtgag ggttaattag  14220
atcttaatac gactcactat agggcgaatt gggtaccggg ccccccctcg aggtcgacgg  14280
tatcgataag cttgatatct ataacaagaa aatatatata taataagtta tcacgtaagt  14340
agaacatgaa ataacaatat aattatcgta tgagttaaat cttaaaagtc acgtaaaaga  14400
taatcatgcg tcattttgac tcacgcggtc gttatagttc aaaatcagtg acacttaccg  14460
cattgacaag cacgcctcac gggagctcca agcggcgact gagatgtcct aaatgcacag  14520
cgacggattc gcgctattta gaaagagaga gcaatatttc aagaatgcat gcgtcaattt  14580
```

```
tacgcagact atctttctag ggttaatcta gctgcatcag gatcatatcg tcgggtcttt    14640
tttccggctc agtcatcgcc caagctggcg ctatctgggc atcggggagg aagaagcccg    14700
tgccttttcc cgcgaggttg aagcggcatg gaaagagttt gccgaggatg actgctgctg    14760
cattgacgtt gagcgaaaac gcacgtttac catgatgatt cgggaaggtg tggccatgca    14820
cgccttttaac ggtgaactgt tcgttcaggc cacctggcat accagttcgt cgcggctttt   14880
ccggacacag ttccggatgg tcagcccgaa gcgcatcagc aacccgaaca ataccggcga    14940
cagccggaac tgccgtgccg gtgtgcagat taatgacagc ggtgcggcgc tgggatatta    15000
cgtcagcgag gacgggtatc ctggctggat gccgcagaaa tggacatgga taccccgtga    15060
gttacccggc gggcgcgctt ggcgtaatca tggtcatgac tgtttcctgt gtgaaattgt    15120
tatccgctca caattccaca caacatacga gccggaagca taaagtgtaa agcctgggct    15180
gcctaatgag tgagctaact cacattaatt gcgttgcgct cactgcccgc tttccagtcg    15240
ggaaacctgt cgtgccagct gcattaatga atcggccaac gcgcgggag aggcggtttg    15300
cgtattgggc gctcttccgc ttcctcgctc actgactcgc tgcgctcggt cgttcggctg    15360
cggcgagcgg tatcagctca ctcaaaggcg gtaatacggt tatccacaga atcaggggat    15420
aacgcaggaa agaacatgtg agcaaaaggc cagcaaaagg ccaggaaccg taaaaaggcc    15480
gcgttgctgg cgttttttcca taggctccgc ccccctgacg agcatcacaa aaatcgacgc    15540
tcaagtcaga ggtggcgaaa cccgacagga ctataaagat accaggcgtt tccccctgga    15600
agctccctcg tgcgctctcc tgttccgacc ctgccgctta ccggatacct gtccgccttt    15660
ctcccttcgg gaagcgtggc gctttctcat agctcacgct gtaggtatct cagttcggtg    15720
taggtcgttc gctccaagct gggctgtgtg cacgaacccc ccgttcagcc cgaccgctgc    15780
gccttatccg gtaactatcg tcttgagtcc aacccggtaa gacacgactt atcgccactg    15840
gcagcagcca ctggtaacag gattagcaga gcgaggtatg taggcggtgc tacagagttc    15900
ttgaagtggt ggcctaacta cggctacact agaaggacag tatttggtat ctgcgctctg    15960
ctgaagccag ttaccttcgg aaaaagagtt ggtagctctt gatccggcaa acaaaccacc    16020
gctggtagcg gtggtttttt tgtttgcaag cagcagatta cgcgcagaaa aaaggatct    16080
caagaagatc ctttgatctt ttctacgggg tctgacgctc agtggaacga aaactcacgt    16140
taagggattt tggtcatgag attatcaaaa aggatcttca cctagatcct ttaaattaa     16200
aaatgaagtt ttaaatcaat ctaaagtata tgagtaaa cttggtctga cagttaccaa    16260
tgcttaatca gtgaggcacc tatctcagcg atctgtctat ttcgttcatc catagttgcc    16320
tgactccccg tcgtgtagat aactacgata cgggagggct taccatctgg ccccagtgct    16380
gcaatgatac cgcgagaccc acgctcaccg gctccagatt tatcagcaat aaaccagcca    16440
gccgaaggg ccgagcgcag aagtggtcct gcaactttat ccgcctccat ccagtctatt    16500
aattgttgcc gggaagctag agtaagtagt tcgccagtta atagtttgcg caacgttgtt    16560
gccattgcta caggcatcgt ggtgtcacgc tcgtcgtttg gtatggcttc attcagctcc    16620
ggttccaac gatcaaggcg agttacatga tcccccatgt tgtgcaaaaa agcggttagc    16680
tccttcggtc ctccgatcgt tgtcagaagt aagttggccg cagtgttatc actcatggtt    16740
atggcagcac tgcataattc tcttactgtc atgccatccg taagatgctt ttctgtgact    16800
ggtgagtact caaccaagtc attctgagaa tagtgtatgc ggcgaccgag ttgctcttgc    16860
ccggcgtcaa tacgggataa taccgcgcca catgcagcaa ctttaaaagt gctcatcatt    16920
ggaaaacgtt cttcggggcg aaaactctca aggatcttac cgctgttgag atccagttcg    16980
atgtaaccca ctcgtgcacc caactgatct tcagcatctt ttactttcac cagcgtttct    17040
gggtgagcaa aaacaggaag gcaaaatgcc gcaaaaaagg gaataagggc gacacggaaa    17100
tgttgaatac tcat                                                     17114

SEQ ID NO: 11          moltype = DNA  length = 17114
FEATURE                Location/Qualifiers
misc_feature           1..17114
                       note = Synthetic: pPBBG-iHelper2.8-HA
source                 1..17114
                       mol_type = other DNA
                       organism = synthetic construct
SEQUENCE: 11
actcttccttt tttcaatatt attgaagcat ttatcagggt tattgtctca tgagcggata    60
catatttgaa tgtatttaga aaaataaaca aataggggtt ccgcgcacat ttccccgaaa    120
agtgccacct aaaattgtaag cgttaatatt ttgttaaaat tcgcgttaaa tttttgttaa    180
atcagctcat ttttttaacca ataggccgaa atcggcaaaa tcccttataa atcaaaagaa    240
tagaccgaga taggggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt tttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaaggg gatgtgctgc aagcggatta gttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgt tgcagaacac gcagctagat taaccctaga aagataatca tattgtgacg    900
tacgttaaag ataatcatgc gtaaaattga acgcatgtgt ttatcggtct gtatatcgag    960
gtttattat aattgaat agatattaag ttttattata tttacactta catactaata    1020
ataaattcaa caaacaattt atttatgttt atttatttat taaaaaaaaa caaaaactca    1080
aaatttcttc tataaagtaa caaaacttttt atcgaattcc tgcagcccgg gggatccact    1140
agttctagag gacagccccc cccaaagc cccaggggat gtaattacgt ccctcccccg    1200
ctagggggca gcagcgagcc gcccggggct ccgctccggt ccggcgctcc cccgcatcc    1260
ccgagccgga agcgtgcggg gacaccccgg gcacgggaga ggtggcacgg gatcgctttc    1320
ctctgaacgc ttctcgctgc tctttgagcc tgcagacacc tggggggata cggggaaaag    1380
gcctccaagg ccagcttccc acaataagtt gggtgaattt ggctcattc ctcctttcta    1440
taggattgag tcagagctt tgtgatggga attctgtgga atgtgtgtca gttagggtgt    1500
ggaaagtccc gcgatcgcta gcgttaaac ttaagcttgg taccgagctc ggatccacta    1560
gtccagtgtg gtggaattcc tgcttcgcga tgtacgggcc ggtacccaac tccatgctta    1620
```

-continued

```
acagtcccca ggtacagccc accctgcgtc gcaaccagga acagtctac agcttcctgg  1680
agcgccactc gccctacttc cgcagccaca gtgcgcagat taggagcgcc acttctttt   1740
gtcactttgaa aaacatgtaa aaataatgta ctaggagaca ctttcaataa aggcaaatgt  1800
tttttatttgt acactctcgg gtgattattt acccccccacc cttgccgtct gcgccgttta 1860
aaaatcaaag gggttctgcc gcgcatcgct atgcgccact ggcagggaca cgttgcgata  1920
ctggtgttta gtgctccact taaactcagg cacaaccatc cgcggcagct cggtgaagtt  1980
ttcactccac aggctgcgca ccatcaccaa cgcgtttagc aggtcgggcg ccgatatctt  2040
gaagtcgcag ttggggcctc cgccctgcgc gcgcgagttg cgatacacag ggttgcagca  2100
ctggaacact atcagcgccg ggtggtgcac gctggccagc acgctcttgt cggagatcag  2160
atccgcgtcc aggtcctccg cgttgctcag ggcgaacgga gtcaactttg gtagctgcct  2220
tcccaaaaag ggtgcatgcc caggctttga gttgcactcg caccgtagtg gcatcagaag  2280
gtgaccgtgc ccggtctggg cgttaggata cagcgcctgc atgaaagcct tgatctgctt  2340
aaaagccacc tgagcctttg cgccttcaga gaagaacatg ccgcaagact tgccggaaaa  2400
ctgattggcc ggacaggcg cgtcatgcac gcagcacctt cgtcggttg tggagatctg   2460
caccacattt cggccccacc ggttcttcac gatcttggcc ttgctagact gctccttcag  2520
cgcgcgctgc ccgttttcgc tcgtcacatc catttcaatc acgtgctcct tatttatcat  2580
aatgctcccg tgtagacact taagctcgcc ttcgatctca gcgcagcggt gcagccacaa  2640
cgcgcagccc gtgggctcgt ggtgcttgta ggttaccctc gcaaacgact gcaggtacgc  2700
ctgcaggaat cgcccatca tcgtcacaaa ggtcttgttg ctggtgaagg tcagctgcaa  2760
cccgcggtgc tcctcgttta gccaggtctt gcatacggcc gccagagctt ccacttggtc  2820
aggcagtagc ttgaagtttg cctttagatc gttatccacg tggtacttgt ccatcaacgc  2880
gcgcgcagcc tccatgccct tctcccacgc agacacgatc ggcaggctca gcgggtttat  2940
caccgtgctt tcactttccg cttcactgga ctcttccttt tcctcttgcg tccgcatacc  3000
ccgcgccact gggtcgtctt cattcagccg ccgcaccgtg cgcttacctc ccttgccgtg  3060
cttgattagc accggtgggt tgctgaaacc caccatttgt agcgccacat cttctctttc  3120
ttcctcgctg tccacgatca cctctgggga tggcgggcgc tggcgttgg gagaggggcg   3180
cttcttttc ttttggacg caatggccaa atccgccgtc gaggtcgatg gccgcgggct    3240
gggtgtcgc ggcaccagcg catcttgtga cgagtcttct tcgtcctcgg actcgagacg   3300
ccgcctcagc cgctttttg ggggcgcgcg ggaggcggc ggcgacgcg acggggacga     3360
cacgtcctcc atggttggtg gacgtcgcgc cgcaccgcgt cctcgctcgg gggtggtttc  3420
gcgctgctcc tcttcccgac tggccatttc cttctcctat aggcagaaa agatcatgga   3480
gtcagtcgag aaggaggaca gcctaaccgc ccccttgag ttcgcacca ccgcctccac    3540
cgatgccgcc aacgcgccta ccaccttccc cgtcgaggca ccccgcttg aggaggagga   3600
agtgattatc gagcaggacc caggttttgt aagcgaagac gacgaggatc gctcagtacc  3660
aacagaggat aaaaagcaag accaggacga cgcagaggca aacgaggaac aagtcgggcg  3720
gggggaccaa aggcatggcg actacctaga tgtgggagac gacgtgctgt tgaagcatct  3780
gcagcgccca tgcgccatta tctgcgcacgc gttgcaagag cgcagcgatg tgcccctcgc 3840
catagcggat gtcagccttg cctacgaacg ccacctgttc tcaccgcgcg taccccccaa  3900
acgccaagaa aacggcacat gcgagcccaa cccgcgcctc aacttctacc ccgtatttgc  3960
cgtgccagaa gtgcttgcca cctatcacat cttttttccaa aactgcaaga taccccctatc 4020
ctgccgtgcc aaccgcagcc gagcggacaa gcagctggcc ttgcggcagg gcgctgtcat  4080
acctgatatc gcctcgctcg acgaagtgcc aaaaatcttt gagggtcttg gacgcgacga  4140
gaaacgcgcg gcaaacgctc tgcaacaaga aacagcgaa aatgaaagtc actgtggagt   4200
gctggtggaa cttgagggtg acaacgcgcg cctagccgtg ctgaaacgca gcatcggagtt 4260
cacccacttt gcctaccccgg cacttaacct acccccccaag gttatgagca cagtcatgag 4320
cgagctgatc gtgcgccgtg cacgacccct ggagagggat gcaaacttgc aagaacaaac  4380
cgaggagggc ctacccgcag ttggcgatga gcagctggcg cgctggcttg agacgcgcga  4440
gcctgccgac ttggaggagc gacgcaagct aatgatggcc gcagtgcttg ttaccgtgga  4500
gcttgagtgc atgcagcgt tctttgctga cccggagatg cagcgcaagc tagaggaaac   4560
gttgcactac accttttcgcc agggctacgt gcgccaggcc tgcaaaattt ccaacgtgga  4620
gctctgcaac ctgtctcct accttggaat ttgtcacgaa aaccgcctcg ggcaaaacgt    4680
gcttcattcc acgctcaagg gcgaggcgcg ccgcgactac gtccgcgact gcgtttacttc 4740
atttctgtgc tacacctggc aaacggccat gggcgtgtgg cagcaatgcc tggaggagcg  4800
caacctaaag gagctgcaga agctgctaaa gcaaaacttg aaggacctat ggacggcctt   4860
caacgagcc tccgtggccg cgcacctggc ggacatttac ttccccgaac gcctgcttaa   4920
aaccctgcaa cagggtctgc cagacttcac cagtcaaagc atgttgcaaa actttaggaa  4980
ctttatccta gagcgttcag gaattctgcc cgccaccgtg tgtgcgcttc ctagcgactt   5040
tgtgcccatt aagtaccgtg aatgcctcc gccgctttgg ggtcactgct accttctgca   5100
gctagccaac taccttgcct accactccga catcatgaa gacgtgagcg gtgacggcct    5160
actggagtgt cactgctgct gcaacctatg caccccgcac cgctccctgg tctgcaattc   5220
gcaactgctt agcgaaagtc aaattatcgg taccttgag ctgcagggtc cctcgcctga   5280
cgaaaagtcc gcggctccgg ggttgaaact cactccgggg ctgtgacgt ccgatctcta    5340
tcactgatag ggagatctct atcactgata gggagagggc ttaccttcgc aaatttgtac  5400
ctgaggacta ccacgcccac gagattaggt tctacgaaga ccatcccgc ccgccaaatg    5460
cggagcttac cgcctgcgtc attacccagg gccacatcct tggccaattg caagccatca  5520
acaaagcccg ccaagagtt ctgctacgaa agggacgggg ggtttacctg gacccccagt    5580
ccggcgagga gctcaaccca atccccccgc cgccgcagcc ctatcagcag ccgcgggccc   5640
ttgcttccca ggatggcacc caaaagaag ctgcagctgc cgccgccgcc acccacggac    5700
gaggaggaat actgggacag tcaggcagga gaggttttgg acgaggagga ggagatgatg   5760
gaagactggg acagcctaga cgaagcttcc gaggccgaag aggtgtcaga cgaaacaccg   5820
tcaccctcgg tcgcattccc ctcgccgcgc cccagaaat tggcaaccgt tcccagcatc    5880
gctacaacct ccgctcctca ggcgccgcg gcactgcctg ttcgccgacc caaccgtaga   5940
tgggacacca ctggaaccag ggccggtaag tctaagcagc gccgccgtt agcccaagag    6000
caacaacgc gccaaggcta ccgctcgtgg cgcgggcaca agaacgccat agttgcttgc    6060
ttgcaagact gtgggggcaa catctccttc gcccgccgct tcttctcta ccatcacggc    6120
gtggccttcc cccgtaacat cctgcattac taccgtcatc tctacagccc ctactgcacc   6180
ggcggcagcg gcagcggcag caacagcagc ggtcacacag aagcaaaggc gaccggatag   6240
caagactctg acaaagccca agaaatccac agcggcggca gcagcaggag gaggagcgct   6300
gcgtctggcg cccaacgaac ccgtatcgac ccgcgagctt agaaatagga ttttttcccac  6360
```

```
tctgtatgct atatttcaac aaagcagggg ccaagaacaa gagctgaaaa taaaaaacag  6420
gtctctgcgc tccctcaccc gcagctgcct gtatcacaaa agcgaagatc agcttcggcg  6480
cacgctggaa gacgcggagg ctctcttcag caacgatctc tatcactgat agggagatct  6540
ctatcactga tagggagaga tactgcgcgc tgactcttaa ggactagttt cgcgcccttt  6600
ctcaaattta agcgcgaaaa ctacgtcatc tccagcgacg acaccggcg ccagcacctg   6660
tcgtcagcgc cattatgagc aaggaaattc ccacgcccta catgtggagt taccagccac  6720
aaatgggact tgcggctgga gctgcccaag actactcaac ccgaataaac tacatgagcg  6780
cgggacccca catgatatcc cgggtcaacg gaatccgcgc ccaccgaaac cgaattctcc  6840
tcgaacaggc ggctattacc accacacctc gtaataacct taatcccgt agttggccg     6900
ctgccctggt gtaccaggaa agtcccgctc ccaccactgt ggtacttccc agagacgccc  6960
aggccgaagt tcagatgact aactcagggg cgcagcttgc gggcggcttt cgtcacaggg  7020
tgcggtcgcc cccagtggcc aaaaaagcta gcgcagcagc cgccgcgcct ggaaggaagc  7080
caaaaggagc gctcccccgt tgtctgacgt cgcacacctg ggttcgacac gcgggcggta  7140
accgcatgga tcacgcggga cggccggatc cggggttcga accccggtcg tccgccatga  7200
tacccttgcg aatttatcca ccagaccacg gaagagtgcc cgcttacagg tggtctcata  7260
cagaacttat aagattccca aatccaaaga catttcacgt ttatggtgat ttcccagaac  7320
acatagcgac atgcaaatat tgcagggcgc cactcccctg tccgctctcc ttttgcacgg  7380
tctagagcgt caacgactgc gcacgccagt ggccaaaaaa gctagcgcag cagccgcgc   7440
gcctggaagg aagccaaaag gagcgctccc ccgttgtctg acgtcgcaca cctgggttcg  7500
acacgcgggc ggtaaccgca tggatcacgg cggacggccg gatccggggt tcgaaccccg  7560
gtcgtccgcc atgataccct tgcgaattta tccaccagac cacggaagag tgcccgctta  7620
caggtggtct catacagaac ttataagatt cccaaatcca aagacatttc acgtttatgg  7680
tgatttccca gaacacatag cgacatgcaa atattgcagg gcgccactcc cctgtccgct  7740
ctcctttgc acggtctaga gcgtcaacga ctgcgcacgc cagtggccaa aaaagctagc   7800
gcagcagccg ccgcgcctgg aaggaagcca aaggagcgc tccccgttg tctgacgtcg    7860
cacacctggg ttcgacacgc gggcggtaac cgcatggatc acggcggtaa ccgccgatcg  7920
gggttcgaac cccggtcgtc cgccatgata cccttgcgaa tttatccacc agaccacgga  7980
agagtgcccg cttacaggtg gtctcataca gaacttataa gattcccaaa tccaaagaca  8040
tttcacgttt atggtgattt cccagaacac atagcgacat gcaaatattg cagggcgcca  8100
ctcccctgtc cgctctcctt ttgcacggtc tagagcgtca acgactgcgc acgccagtgg  8160
ccaaaaaagc tagcgcagca gccgccgcgc ctggaaggaa gccaaaagga gcgctccccc  8220
gttgtctgac gtcgcacacc tgggttcgac acgcgggcgg taaccgcatg gatcacggcg  8280
gacggccgga tccggggttc gaaccccggt cgtccgccat gataccctg cgaatttatc    8340
caccagacca cggaagagtg cccgcttaca ggtggtctca tacagaactt ataagattcc  8400
caaatccaaa gacatttcac gtttatggtg atttcccaga acacatagcg acatgcaaat  8460
attgcagggc gccactcccc tgtccgctct ccttttgcac ggtctagagc gtcaacgact  8520
gcgcacgggc cgtttaggg cggagtaact tgcatgtatt gggaattgta gttttttaa    8580
aatgggaagt gacgtatcgt gggaaaacgg aagtgaagat ttgaggaagt tgtgggtttt  8640
ttggctttcg tttctgggcg taggttcgcg tgcggttttc tggtgttttt ttgtggactt  8700
taaccgttac gtcatttttt agtcctatat atactcgctc tgtactctcc ctatcagtga  8760
tagagatctc cctatcagtg atagagatcg cttggccctt tttacactgt gactgattga  8820
gctggtgccg tgtcgagtgg tgtttttaa taggttttt tactggtaag gctgactgtt    8880
atggctgccg ctgtggaagc gctgtatgtt gttctggagc gggagggtgc tattttgcct  8940
aggcaggagg gttttcagg tgtttatgtg ttttctctc ctattaattt tgttatacct     9000
cctatggggg ctgtaatgtt gtctctacgc ctgcgggtat gtattcccc gggctatttc    9060
ggtcgctttt tagcactgac cgatgttaac caacctgatg tgtttaccga gtcttacatt  9120
atgactccgg acatgaccga ggaactgtcg gtggtgcttt ttaatcacgg tgaccagttt  9180
ttttacggtc acgccggcat ggccgtagtc cgtcttatgc ttataagggt tgtttttcct  9240
gttgtaagac aggcttctaa tgtttaaatg tttttttttt tgttatttta ttttgtgttt  9300
aatgcaggaa cccgcagaca tgtttgagag aaaaatggtg tcttttttctg tggtggttcc  9360
ggaacttacc tgccttttatc tgcatgagca tgactacgat gtgcttgctt ttttgcgcag  9420
ggcttttgcct gattttttga gcagcacctt gcatttata tcgccgccca tgcaacaagc    9480
ttacataggg gctacgctgg ttagcatagc tccgagtatg cgtgtcataa tcagtgtggg   9540
ttcttttgtc atggttcctg gcggggaagt ggccgcgctg gtccgtgcag acctgcacga  9600
ttatgttcag ctggccctgc gaagggacct acgggatcgg ggtattttg ttaatgttcc    9660
gcttttgaat cttatacagg tctgtgagga acctgaattt ttgcaatcat gattcgctgc  9720
ttgaggctga aggtggaggg cgctctggag cagattttta caatggccgg acttaatatt  9780
cgggatttgc ttagagacat attgataagg tggcgagatg aaaattattt gggcatggtt  9840
gaaggtgctg gaatgtttat agaggagatt caccctgagg ggtttagcct ttacgtccac  9900
tggacgtga gggcagtttg ccttttgaa gccattgtgc aacatcttac aaatgccatt      9960
atctgttctt tggctgtaga gtttgaccac gccaccggag gggagcgcgt tcacttaata 10020
gatcttcatt ttgaggtttt ggataatctt tggaataaa aaaaaaaaaa catgttctt    10080
ccagctcttc ccgtcctcc cgtgtgtgac tcgcagaacg aatgtgtagg ttggctgggt  10140
gtggcttatt ctgcggtggt ggatgttatc agggacggcg cgcatgaagg agtttacata  10200
gaacccgaag ccaggggcg cctggatgct tgagagagt ggatatacta caactactac     10260
acagagcgag ctaagcgacg agaccggaga cgcagatctg tttgtcacgc ccgcacctgg  10320
ttttgcttca ggaaatatgt acccatacga tgttccagat tacgctggag gaggcggagg  10380
cactacgtcc ggcgttccat ttggcatgac actacgacca acacgatctc ggttgtctcg  10440
gcgcactccg tacagtaggg atcgcctacc tccttttgag acagagaccc gcgctaccat  10500
actggaggat catccgctgc tgcccgaatg taacactttg acaatgcaca acgtgagtta  10560
cgtgcgaggt cttccctgca gtgtgggatt tacgctgatt caggaatggg ttgttccctg  10620
ggatatggtt ctgacgcggg aggagcttgt aatcctgagg aagtgtatgc acgtgtgcct  10680
gtgttgtgcc aacattgata tcatgacgag catgatgatc catggttacg agtcctgggc  10740
tctccactgt cattgttcca gtcccggttc ctgcagtgc atagccggcg ggcaggtttt    10800
ggccagctgg tttaggatgg tggtggatgg cgccatgttt aatcagaggt ttatatggta  10860
ccgggaggtg gtgaattaca acatgccaaa agaggtaatg tttatgtcca gcgtgtttat  10920
gaggggtcgc cacttaatct acctgcgctt gtggtatgat ggcacgtggg ttctgtggt   10980
ccccgccatg agctttggat acagcgcctt gcactgtggg attttgaaca atattgtggt  11040
gctgtgctgc agttactgtg ctgatttaag tgagatcagg gtgcgctgct gtgcccggag  11100
```

```
gacaaggcgt ctcatgctgc gggcggtgcg aatcatcgct gaggagacca ctgccatgtt    11160
gtattcctgc aggacggagc ggcggcggca gcagtttatt cgcgcgctgc tgcagcacca    11220
ccgccctatc ctgatgcacg attatgactc taccccatg taggcgtgga cttcccttc     11280
gccgcccgtt gagcaaccgc aagttggaca gcagcctgtg gctcagcagc tggacagcga    11340
catgaactta agcgagctgc ccggggagtt tattaatatc actgatgagc gtttggctcg    11400
acaggaaacc gtgtggaata taacacctaa gaatatgtct gttacccatg atatgatgct    11460
ttttaaggcc agccggggag aaaggactgt gtactctgtg tgttgggagg gaggtggcag    11520
gttgaatact agggttctgt gagtttgatt aaggtacggt gatcaatata agctatgtgg    11580
tggtggggct atactactga atgaaaaatg acttgaaatt ttctgcaatt gaaaaataaa    11640
cacgttgaaa cataacatgc aacaggttca cgattcttta ttcctgggca atgtaggaga    11700
aggtgtaaga gttggtagca aaagtttcag tggtgtattt tccactttcc caggaccatg    11760
taaaagacat agagtaagtg cttacctcgc tagtttctgt ggattcacta gaatccactt    11820
tggccgcggc tcgagtgagc tattccagaa gtagtgaaga ggcttttttg gaggcctagg    11880
cttttgcaaa aagctccgga tcgatgcccg gggatccac tagttctaga gggacagccc     11940
cccccaaag ccccaggga tgtaattacg tccctccccc gctagggggc agcagcgagc      12000
cgcccgggc tccgctccgg tccggcgctc ccccgcatc cccgagccgg cagcgtgcgg       12060
ggacagcccg ggcacgggga aggtggcacg ggatcgcttt cctctgaacg cttctcgctg    12120
ctctttgagc ctgcagacac ctgggggat acggggaaaa ggcctccaag gccagctcc       12180
cacaataagt tgggtgaatt ttggctgagc tattccagaa gtagtgaaga ggcttttttg    12240
gaggcctagg cttttgcaaa aagctccgga tcgatcatat atggcagata tacgcgttga    12300
cattgattat tgactagtta ttaatagtaa tcaattacgg ggtcattagt tcatagccca    12360
tatatggagt tccgcgttac ataacttacg gtaaatggcc cgcctggctg accgcccaac    12420
gacccccgcc cattgacgtc aataatgacg tatgttccca tagtaacgcc aatagggact    12480
ttccattgac gtcaatgggt ggagtattta cggtaaactg cccacttggc agtacatcaa    12540
gtgtatcata tgccaagtac gccccctatt gacgtcaatg acggtaaatg gcccgcctgg    12600
cattatgccc agtacatgac cttatgggac ttttcctactt gcagtacat ctacgtatta    12660
gtcatcgcta ttaccatggt gatgcggttt tggcagtaca tcaatgggcg tggatagcgg    12720
tttgactcac ggggatttcc aagtctccac cccattgacg tcaatgggag tttgttttgg    12780
caccaaaatc aacgggactt tccaaaatgt cgtaacaact ccgccccatt gacgcaaatg    12840
ggcggtaggc gtgtacggtg ggaggtctat ataagcagag ctctctggct aactatcgtc    12900
gacgagctcg tttagtgaac cgtcagatcc cctggagacg ccatccacgc tgttttgacc    12960
tccatagaag acaccgggac cgatccagcc tccggactct agcgtttaaa cttaagcttg    13020
ccaccatgac cgagtacaag cccacggtgc gcctcgccac ccgcgacgac gtccccaggg    13080
ccgtacgcac cctccgcccc gcgttcgccg actacccgc cacgcgccac accgtcgatc    13140
cggaccgcca catcgagcgg gtcaccgagc tgcaagaact cttcctcacg cgcgtcgtgc    13200
tcgacatcgg caaggtgtgg gtcgcggacg acggcgccgc ggtggcggtc tggaccacgc    13260
cggagagcgt cgaagcgggg gcggtgttcg ccgagatcgg cccgcgcatg ccgagttga     13320
gcggttcccg gctggccgcg cagcaacaga tggaaggcct cctggcgccg caccggccca    13380
aggagcccgc gtggttcctg gccaccgtcg gcgtctccgc cgaccaccag ggcaagggtc    13440
tgggcagcgc cgtcgtgctc cccggagtgg aggcggccga gcgcgccggg gtgcccgcct    13500
tcctggagac ctccgcgccc cgcaacctcc ccttctacga gcggctcggc ttcaccgtca    13560
ccgccgacgt cgaggtgccc gaaggaccgc gcacctggtg catgacccgc aagcccggtg    13620
cctgaagcgc gggatctca tgctggagtt cttcgcccac cccaacttgt ttattgcagc    13680
ttataatggt tacaaataaa gcaatagcat cacaaatttc acaaataaag cattttttc     13740
actgcattct agttgtggtt tgtccaaact catcaatgta tcttatcatg tctgtagctg    13800
atgtatacct aggatccggc cggcctgcag gtgtcctcac aggaacgaag tcctaaaga    13860
aacagtggca gccaggttta gccccggaat tgactggatt cctttttag gggccattgg    13920
tatggctttt tccccgtatc cccccaggtg tctgcaggct caaagagcag cgagaagcgt    13980
tcagaggaaa gcgatcccgt gccaccttcc ccgtgcccgg gctgtccccg cacgctgccg    14040
gctcggggat gcgggggag cgccggaccg gagcggagcc ccgggcggct cgctgctgcc      14100
ccctagcggg ggagggacgt aattacatcc ctgggggctt tgggggggag ctgtccctct    14160
agagcggccg ccaccgcggt ggagctccag ctttttgttcc ctttagtgag ggttaattag   14220
atcttaatac gactcactat agggcgaatt gggtaccggg ccccccctcg aggtcgacgg    14280
tatcgataag cttgatatct ataacaagaa aatatatata taatagtta tcacgtaagt     14340
agaacatgaa ataacaatat aattatcgta tgagttaat cttaaaagtc acgtaaaaga    14400
taatcatgcg tcattttgac tcacgcggtc gttatagttc aaaatcagtg acacttaccg    14460
cattgacaag cacgcctcac gggagctcca agcggcgact gagatgtcct aaatgcacag    14520
cgacggattc gcgctattta gaaagagaga gcaatatttc aagaatgcat gcgtcaattt    14580
tacgcagact atctttctag ggttaatcta gctgcatcag gatcatatcg tcgggtcttt    14640
tttccggctc agtcatcgcc caagctggcg ctatctgggc atcggggagg aagaagcccg    14700
tgcctttttcc cgcgaggttg aagcggcatg gaaagagttt gccgaggatg actgctgctg    14760
cattgacgtt gagcgaaaac gcacgttac catgatgatt cgggaaggtg tggccatgca     14820
cgcctttaac ggtgaactgt tcgttcaggc cacctgggat accagttcgt cgcggctttt    14880
ccggacacag ttccggatgg tcagcccgaa gcgcatcagc aacccgaaca ataccgggca    14940
cagccggaac tgccgtgccg gtgtgcagat taatgacagc ggtgcggcgc tgggatatta    15000
cgtcagcgag gacgggtatc ctggctggat gccgcagaaa tggacatgga taccccgtga    15060
gttaccggc gggcgcgctt ggcgtaatca tggtcatagc tgtttcctgt gtgaaattgt      15120
tatccgctca caattccaca acaatacga gccggaagca taaagtgtaa agcctggggt     15180
gcctaatgag tgagctaact cacattaatt gcgttgcgct cactgcccgc tttccagtcg    15240
ggaaacctgt cgtgccagct gcattaatga atcggccaac gcgcgggga aggcggtttg     15300
cgtattgggc gctcttccgc ttcctcgctc actgactcgc tgcgctcggt cgttcggctg    15360
cggcgagcgg tatcagctca ctcaaaggcg gtaatacggt tatccacaga atcagggat     15420
aacgcaggaa agaacatgtg agcaaaaggc cagcaaaagg ccaggaaccg taaaaaggcc    15480
gcgttgctgg cgtttttcca taggctccgc ccccctgacg agcatcacaa aaatcgacgc    15540
tcaagtcaga ggtggcgaaa cccgacagga ctataaagat accaggcgtt tcccctggaa    15600
gctccctcg tgcgctctcc tgttccgacc ctgccgctta ccggatacct gtccgccttt     15660
ctcccttcgg gaagcgtggc gctttctcat agctcacgct gtaggtatct cagttcggtg    15720
taggtcgttc gctccaagct gggctgtgtg cacgaacccc ccgttcagcc cgaccgctgc    15780
gccttatccg gtaactatcg tcttgagtcc aacccggtaa gacacgactt atcgccactg    15840
```

```
gcagcagcca ctggtaacag gattagcaga gcgaggtatg taggcggtgc tacagagttc   15900
ttgaagtggt ggcctaacta cggctacact agaaggacag tatttggtat ctgcgctctg   15960
ctgaagccag ttaccttcgg aaaaagagtt ggtagctctt gatccggcaa acaaaccacc   16020
gctggtagcg gtggttttt tgtttgcaag cagcagatta cgcgcagaaa aaaggatct    16080
caagaagatc ctttgatctt ttctacgggg tctgacgctc agtggaacga aaactcacgt   16140
taagggattt tggtcatgag attatcaaaa aggatcttca cctagatcct tttaaattaa   16200
aaatgaagtt ttaaatcaat ctaaagtata tatgagtaaa cttggtctga cagttaccaa   16260
tgcttaatca gtgaggcacc tatctcagcg atctgtctat ttcgttcatc catagttgcc   16320
tgactcccg tcgtgtagat aactacgata cgggagggct taccatctgg ccccagtgct   16380
gcaatgatac cgcgagaccc acgctcaccg gctccagatt tatcagcaat aaaccagcca   16440
gccgaaggg ccgagcgcag aagtggtcct gcaactttat ccgcctccat ccagtctatt   16500
aattgttgcc gggaagctag agtaagtagt tcgccagtta atagtttgcg caacgttgtt   16560
gccattgcta caggcatcgt ggtgtcacgc tcgtcgtttg gtatggcttc attcagctcc   16620
ggttcccaac gatcaaggcg agttacatga tcccccagtt gtgcaaaaa agcggttagc   16680
tccttcggtc ctccgatcgt tgtcagaagt aagttggccg cagtgttatc actcatggtt   16740
atggcagcac tgcataattc tcttactgtc atgccatccg taagatgctt ttctgtgact   16800
ggtgagtact caaccaagtc attctgagaa tagtgtatgc ggcgaccgag ttgctcttgc   16860
ccggcgtcaa tacgggataa taccgcgcca catgcagaa ctttaaaagt gctcatcatt   16920
ggaaaacgtt cttcggggcg aaaactctca aggatcttac cgctgttgag atccagttcg   16980
atgtaaccca ctcgtgcacc caactgatct tcagcatctt ttactttcac cagcgtttct   17040
gggtgagcaa aaacaggaag gcaaaatgcc gcaaaaaagg gaataagggc gacacggaaa   17100
tgttgaatac tcat                                                    17114
```

| SEQ ID NO: 12 | moltype = DNA length = 18311 |
|---|---|
| FEATURE | Location/Qualifiers |
| misc_feature | 1..18311 |
| | note = Synthetic: pPBBG-iHelper3.1-HA |
| source | 1..18311 |
| | mol_type = other DNA |
| | organism = synthetic construct |

```
SEQUENCE: 12
actcttcctt tttcaatatt attgaagcat ttatcagggt tattgtctca tgagcggata     60
catatttgaa tgtatttaga aaaataaaca aataggggtt ccgcgcacat ttccccgaaa    120
agtgccacct aaattgtaag cgttaatatt ttgttaaaat tcgcgttaaa tttttgttaa    180
atcagctcat ttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt tttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaaggga tgtgctgc aaggcgatta agttgggtaa cgccagggtt ttcccagtca    720
cgacgttgta aaacgacggc cagtgagcgc gcctcgttca ttcacgtttt tgaacccgtg    780
gaggacggg agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgc gtaaaattga gcatgtgttt ttatcggtct gtatatcgag    960
gtttatttat taatttgaat agatattaag ttttattata tttacactta catactaata   1020
ataaattcaa caaacaattt atttatgttt atttatttat taaaaaaaa caaaaactca   1080
aaatttcttc tataaagtaa caaaacttttt atcgaattcc tgcagcccgg gggatccact   1140
agttctagag ggacagcccc cccccaaagc cccagggat gtaattacgt cccctccccg   1200
ctagggggca gcagcgagcc gcccgggggct ccgctccggt ccggcgctcc ccccgcatcc   1260
ccgagccggc agcgtgcggg gacagcccgg gcacggggaa ggtggcacgg gatcgctttc   1320
ctctgaacgc ttctcgctgc tctttgagcc tgcagacacc tgggggata cggggaaaag   1380
gcctccaagg ccagcttccc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcgttaaac ttaagcttgg taccgagctc ggatccacta   1560
gtccagtgtg tggaattcc tgcttcgcga tgtacgggcc ggtacccaac tccatgctta   1620
acagtcccca ggtacagccc accctcgtc gcaaccagga acagctctcac agcttcctgg   1680
agcgccactc gccctacttc cgcagccaca gtgcgcagat taggagcgcc acttcttttt   1740
gtcacttgaa aacatgtaa aaataatgta ctaggagaca ctttcaataa aggcaaatgt   1800
tttatttgt acactctcgg gtgattattt accccccacc cttgccgtct gcgccgttta   1860
aaaatcaaag gggttctgcc gcgcatcgct atgcgccact ggcagggaca cgttgcgata   1920
ctggtgttta gtgctccact taaactcagg cacaaccatc cgcggcagct cggttgaagtt   1980
ttcactccac aggctgcgca ccatcaccaa cgcgtttagc aggtcgggcg ccgatatctt   2040
gaagtcgcag ttggggcctc cgccctgcgc gcgcgagttg cgatacacag ggttgcagca   2100
ctggaacact atcagcgccg ggtggtgcac gctggccagc acgctcttgt cggagatcag   2160
atccgcgtcc aggtcctccg cgttgctcag ggcgaacgga gtcaactttg gtagctgcct   2220
tcccaaaaag ggtcactgcc caggctttga gttcactcg catcgtagaag gtgatcagaa   2280
gtgaccgtgc ccggtctggg cgttaggata cagcgcctgc atgaaagcct tgatctgctt   2340
aaaagccacc tgagcctttg cgcctcaga gaagaacatg ccgcaagact gccggaaaa   2400
ctgattggcc ggacaggccg cgtcatgcac gcagcacctt gcgtcggtgt ggagatctg   2460
caccacattt cggcccacc ggttcttcac gatcttggcc ttgctagact gctccttcag   2520
cgcgcgctgc cgttttcgc tcgtcacatc catttcaatc acgtgctcct tattatcat   2580
aatgctcccg tgtagacact taagctcgcc ttcgatctca gcgcagcggt gcagccacaa   2640
cgcgcagccc gtgggctcgt ggtgcttgta ggttaccctc gcaaacgact gcaggtacgc   2700
ctgcaggaat cgcccatca tcgtcacaaa ggtcttgttg ctggtgaagg tcagctgcaa   2760
cccgcggtgc tcctcgttta gccaggtctt gcatacggcc gccagagctt ccacttggtc   2820
aggcagtagc ttgaagtttg cctttagatc gttatccacg tggtacttgt ccatcaacgc   2880
```

```
gcgcgcagcc tccatgccct tctcccacgc agacacgatc ggcaggctca gcggggtttat  2940
caccgtgctt tcactttccg cttcactgga ctcttccttt tcctcttgcg tccgcatacc  3000
ccgcgccact gggtcgtctt cattcagccg ccgcaccgtg cgcttacctc ccttgccgtg  3060
cttgattagc accggtgggt tgctgaaacc caccatttgt agcgccacat cttctctttc  3120
ttcctcgctg tccacgatca cctctgggga tggcgggcgc tcgggcttgg gagaggggcg  3180
cttcttttc ttttggacg caatggccaa atccgccgtc gaggtcgatg gccgcgggct  3240
gggtgtcgc ggcaccagcg catccttgtga cgagtcttct tcgtcctcgg actcgagacg  3300
ccgcctcagc cgctttttg ggggcgcgcg gggaggcggc ggcgacggcg acggggacga  3360
cacgtcctcc atggttggtg gacgtcgcgc cgcaccgcgt ccgcgctcgg gggtggtttc  3420
gcgctgctcc tcttcccgac tggccatttc cttctcctat aggcagaaaa agatcatgaa  3480
gtcagtcgag aaggaggaca gcctaaccgc ccccttgaag ttcgccacca ccgcctccac  3540
cgatgccgcc aacgcgccta ccaccttccc cgtcgaggca ccccgcttg aggaggagga  3600
agtgattatc gagcaggacc caggttttgt aagcgaagac gacgaggatc gctcagtacc  3660
aacagaggat aaaaagcaag accaggacga cgcagaggca aacgaggaac aagtcgggcg  3720
gggggaccaa aggcatggcg actacctaga tgtgggagac gacgtgctgt tgaagcatct  3780
gcagcgccca tgcgccatta tctgcgacgc gttgcaagag cgcagcgatg tgcccctcgc  3840
catagcggat gtcagccttg cctacgaacg ccacctgttc tcaccgcgcg tacccccaa  3900
acgccaagaa aacggcacat gcgagcccaa cccgcgccctc aacttctacc ccgtatttgc  3960
cgtgccagag gtgcttgcca cctatcacat cttttttccaa aactgcaaga taccccctatc  4020
ctgccgtgcc aaccgcagcc gagcggacaa gcagctggcc ttgcggcagg cgctgtcat  4080
acctgatatc gcctcgctcg acgaagtgcc aaaaatcttt gagggtcttg gacgcgacga  4140
gaaacgcgcg gcaaacgctc tgcaacaaga aaacagcgaa aatgaaagtc actgtggagt  4200
gctggtggaa cttgagggtg acaacgcgcg cctagccgtg ctgaaacgca gcatcggagt  4260
cacccacttt gcctacccgg cacttaacct accccccaag gttatgagca cagtcatgag  4320
cgagctgatc gtgcgccgtg cacgacccct ggagagggat gcaaacttgc aagaacaaac  4380
cgaggagggc ctacccgcag ttggcgatga gcagctggcg cgctggcttg agacgccgga  4440
gcctgccgac ttggaggagc gacgcaagct aatgatgagc gcagtggcttg ttaccgtgga  4500
gcttgagtgc atgcagcggt tcttttgctga cccggagatg cagcgcaagc tagaggaaac  4560
gttgcactac acctttcgcc agggctacgt gcgccaggtc tgcaaaattt ccaacgtgga  4620
gtctgcaac ctggtctcct accttggaat tttgcacgaa aaccgcctcg ggcaaaacgt  4680
gcttcattcc acgctcaagg gcgaggcgcg ccgcgactac gtccgcgact gcgtttactt  4740
atttctgtgc tacacctggc aaacggccat gggcgtgtgg cagcaatgcc tggaggagcg  4800
caacctaaag gagctgcaga agctgctaaa gcaaaacttg aaggaccat ggacggcctt  4860
caacgagcgc tccgtggccg cgcacctggc ggacattatc ttccccgaac gcctgcttca  4920
aaccctgcaa cagggtctgc cagacttcac cagtcaaagc atgttgcaaa acttttaggaa  4980
ctttatccta gagcgttcag gaattctgcc cgccaccctgc tgtgcgcttc ctagcgactt  5040
tgtgcccatt aagtaccgtg aatgccctcc gccgctttgg ggtcactgct accttctgca  5100
gctagccaac taccttgcct accactccga catcatggaa gacgtgagcg tgacggcct  5160
actggagtgt cactgtcgct gcaacctatg caccccgcac cgctccctgg tctgcaattc  5220
gcaactgctt agcgaaagtc aaattatcgg taccctttgag ctgcagggtc cctcgcctga  5280
cgaaaagtcc gcggctccgg ggttgaaact cactccgggg ctgtgacgt ccgatctcta  5340
tcactgatag ggagatctct atcactgata gggagagggc ttaccttcgc aaatttgtac  5400
ctgaggacta ccacgcccac gagattaggt tctacgaaga ccaatcccgc cgccaaatg  5460
cggagcttac cgcctgcgtc attacccagg gccacatcct tggccaattg caagccatca  5520
acaaagcccg ccaagagttt ctgctacgaa agggacgggg ggtttacctg gacccccagt  5580
ccggcgagga gctcaaccca atcccccgc cgccgcagcc ctatcagcag ccgcgggccc  5640
ttgcttccca ggatggcacc caaaaagaag ctgcagctgc cgccgccgcc acccacggac  5700
gaggaggaat actgggacag tcaggcagag gaggttttgg acgaggagga ggagatgatg  5760
gaagactggg acagcctaga cgaagcttcc gaggccgaag aggtgtcaga cgaaacaccg  5820
tcaccctcgg tcgcattccc ctcgccgcg ccccagaaat tggcaaccgt tcccagcatc  5880
gctacaacct ccgctcctca ggccgccgcg gcactgctcc ttgccgacc caaccgtgga  5940
tgggacacca ctggaaccag ggccggtaag tctaagcagc cgccgccgtt agcccaagag  6000
caacaacagc gccaaggcta ccgctcgtgg cgcgggcaca agaacgccat agttgcttgc  6060
ttgcaagact gtgggggcaa catctccttc gcccgccgt tcttctcta ccatcacggc  6120
gtggccttcc cccgtaacat cctgcattac taccgtcatc tctacagcca ctactgcacc  6180
ggcggcagcg gcagcggcag caacagcagc ggtcacacag aagcaaaggc gaccggatag  6240
caagactctg acaaagccca agaaatccac agcggcggca gcagcaggag gaggagcgct  6300
gcgtctggcc cccaacgaac ccgtatcgac ccgcgagctt agaaataggg ttttttcccac  6360
tctgtatgct atatttcaac aaagcagggg ccaagaacaa gagctgaaaa taaaaaacag  6420
gtctctgcgc tccctcaccc gcagctgcct gtatcacaaa agcgaagatc agcttcggcg  6480
cacgctggaa gacgcggagg ctctcttcag caacgatctc tatcactgat agggagatct  6540
ctatcactga tagggagaga tactgcgcgc tgactcttaa ggactagttt cgcgcccttt  6600
ctcaaattta agcgcgaaaa ctacgtcatc tccagcggcc acaccggcg ccagcacctg  6660
tcgtcacgcg cattatgagc aaggaaattc ccacgccatc catgtggagt taccagccac  6720
aaatgggact tgcggctgga gctgccaagg actactcaac ccgaataaac tacatgagcg  6780
cgggacccca catgatatcc cgggtcaacg gaatccgcgc ccaccgaaac cgaattctcc  6840
tcgaacaggc ggctattacc accacacctc gtaataaccct taatcccgt agttggcccg  6900
ctgccctggt gtaccaggaa agtcccgctc ccaccactgt ggtacttccc agagacgcgt  6960
aggccgaagt tcagatgact aactcagggg cgcagctgc gacggcttt cgtcacaggg  7020
tgcggtcgcc cccagtggcc aaaaaagcta gcgcagcagc cgccgcgcct ggaaggaagc  7080
caaaaggagc gctcccccgt tgtctgacgt cgcacacctg ggttcgacac gcgggcggta  7140
accgcatgga tcacgcgga cggccggatc cggggttcga accccggtcg tccgccatga  7200
tacccttgcg aatttatcca ccagaccacg gaagagtgcc cgcttacagg ctctcctttt  7260
gcacggtcta gagcgtcaac gactgcgcac ggggcgttt agggcggagt aacttgcatg  7320
tattgggaat tgtagttttt ttaaaatggg aagtgacgta tcgtgggaaa acggaagtga  7380
agatttgagg aagttgtggg ttttttggct tcgttctg ggcgtaggtt cgcgtcggt  7440
tttctgggtt tttttgtgg actttaaccg ttacgtcatt ttttagtcct atatatactc  7500
gctctgtact ctccctatca gtgatagaga tctccctatc agtgatagag atcgcttggc  7560
ccttttttaca ctgtgactga ttgagctggt gccgtgtcga gtggtgtttt ttaataggtt  7620
```

```
tttttactgg taaggctgac tgttatggct gccgctgtgg aagcgctgta tgttgttctg   7680
gagcgggagg gtgctatttt gcctaggcag gaggggttttt caggtgttta tgtgttttc   7740
tctcctatta attttgttat acctcctatg ggggctgtaa tgttgtctct acgcctgcgg   7800
gtatgtattc ccccgggcta tttcggtcgc tttttagcac tgaccgatgt taaccaacct   7860
gatgtgttta ccgagtctta cattatgact ccggacatga ccgaggaact gtcggtggtg   7920
cttttaatc acggtgacca gttttttac ggtcacgccg gcatggccgt agtccgtctt    7980
atgcttataa gggttgtttt tcctgttgta agacaggctt ctaatgttta aatgttttt    8040
ttttgttat tttattttgt gtttaatgca ggaacccgca gacatgtttg agagaaaaat   8100
ggtgtctttt tctgtggtgg ttccggaact tacctgcctt tatctgcatg agcatgacta   8160
cgatgtgctt gcttttttgc gcgaggcttt gcctgatttt ttgagcagca ccttgcattt    8220
tatatcgccg cccatgcaac aagcttacat aggggctacg ctggttagca tagctccgag    8280
tatgcgtgtc ataatcagtg tgggttcttt tgtcatggtt cctggcgggg aagtggccgc    8340
gctggtccgt gcagacctgc acgattatgt tcagctggcc ctgcgaaggg acctacggga    8400
tcgcggtatt tttgttaata ttccgctttt gaatcttata ggtactctgt aggaacctga    8460
attttttgcaa tcatgattcg ctgcttgagg ctgaaggtgg agggcgctct ggagcagatt   8520
tttacaatgg ccggacttaa tattcgggat ttgcttagag acatattgat aaggtggcga   8580
gatgaaaatt atttgggcat ggttgaaggt gctggaatgt ttatagagga gattcaccct   8640
gaagggttta gcctttacgt ccacttggac gtgagggcag tttgccttt ggaagccatt    8700
gtgcaacatc ttacaaatgc cattatctgt tcttttggctg tagagtttga ccacgccacc   8760
ggaggggagc gcgttcactt aatagatctt cattttgagg ttttggataa tcttttggaa    8820
taaaaaaaaa aaaacatggt tcttccagct ctttcccgctc ctcccgtgtg tgactcgcag    8880
aacgaatgtg taggttggct gggtgtggct tattctgctg tggtggatgt tatcagggca   8940
gcggcgcatg aaggagttta catagaaccc gaagccaggg ggcgcctgga tgctttgaga    9000
gagtggatat actacaacta ctacacagag cgagctaagc gacgagaccg gagacgcaga    9060
tctgtttgtc acgcccgcac ctggttttgc ttcaggaaat atgtacccat acgatgttcc    9120
agattacgct ggaggaggcg gaggcactac gtccgtcgtt ccatttggca tgacactacg    9180
accaacacga tctcggttgt tccgcgcac tccgtacagt agggatcgcc tacctccttt     9240
tgagacagag acccgcgcta ccatactgga ggatcatccg ctgctgcccg aatgtaacac    9300
tttgacaatg cacaacgtga gttacgtgcg aggtcttccc tgcagtgtgg gatttacgct    9360
gattcaggaa tgggttgttc cctgggatat ggttctgacg gaggagc ttgtaatcct       9420
gaggaagtgt atgcacgtgt gcctgtgttg tgccaacatt gatatcatga cgagcatgat    9480
gatccatggt tacgagtcct gggctctcca ctgtcattgt tccagtcccg gttccctgca    9540
gtgcatagcc ggcgggcagg ttttggccag ctggtttagg atggtggtgg atggcgccat    9600
gtttaatcag aggtttatat ggtaccggga ggtggtgaat tacaacatgc caaaagaggt    9660
aatgtttatg tccagtcgtg ttatgagggg tcgccactta atctacctgc gcttgtggta    9720
tgatggccac gtgggttctg tggtcccgc catgagcttt ggatacacgcg ccttgcactg    9780
tgggattttg aacaatattg tggtgctgtg ctgcagttac tgtgctgatt taagtgagat    9840
cagggtcgcg tgctgtgccc ggaggacaag gcgtctcatg ctgcgggcgg tgcgaatcat    9900
cgctgaggag accactgcca tgtttgtatt ctgcaggacg gagcggcggc ggcagcagttt   9960
tattcgcgcg ctgctgcagc accaccgccc tatcctgatg cacgattatg actctacccc    10020
catgtaggcg tggacttccc ctttgccgcc cgttgagcaa ccgcaagttg cacagcagcc    10080
tgtggctcag cagctggaca gcgacatgaa cttaagcgag ctgcccgggg agtttattaa    10140
tatcactgat gagcgtttgg ctcgacagga aaccgtgtgg aatataacac ctaagaatat    10200
gtctgttacc catgatatga tgctttttaa ggccagccgg ggagaaagga ctgtgtactc    10260
tgtgtgttgg gagggaggtg gcaggttgaa tactaggggtt ctgtgagttt gattaaggta   10320
cggtgatcaa tataagctat gtggtggtgg ggctatacta ctgaatgaaa aatgacttga    10380
aattttctgc aattgaaaaa taaacacgtt gaaacataac atgcaacagg ttcacgattc    10440
tttattcctg ggcaatgtag gagaaggtgt aagagttggt agcaaaagtt tcagtggtgt    10500
attttccact ttcccaggac catgtaaaag acatagagta agtgcttacc tcgctagttt    10560
ctgtggattc actagaatcc acttgggccg cggctcgagg agggacagcc cccccccaaa    10620
gcccccaggg atgtaattac gtcccctcccc cgctagggg cagcagcagg tggcccggtag   10680
ctccgctccg gtccgcgct cccccgcat ccccgagccg gcagcgtgcg gggacagccc      10740
gggcacgggg aaggtggcac gggatcgctt tcctctgaac gcttctcgct gctctttgag    10800
cctgcagaca cctggggga tacggggaaa aggcctccaa ggccagcttc ccacaataag     10860
ttgggtgaat tttggctcat tcctcctttc tataggattg aggtcagagc gacattgatt    10920
attgactagt tattaatagt aatcaattac ggggtcatta gttcatagcc catatatgga    10980
gttccgcgtt acataactta cggtaaatgg cccgcctggc tgaccgccca acgacccccg    11040
cccattgacg tcaataatga cgtatgttcc catagtaacg ccaataggga cttttccattg    11100
acgtcaattgg gtgagtatt tacggtaaac tgcccacttg gcagtacatc aagtgtatca    11160
tatgccaagt acgccccta ttgacgtcaa tgacggtaaa tggcccgcct ggcattatgc     11220
ccagtacatg accttatggg actttcctac ttggcagtac atctacgtat tagtcatcgc    11280
tattaccatg gtgatgcggt tttggcagta catcaatggg cgtggatagc ggtttgactc    11340
acggggattt ccaagtctcc accccattga cgtcaatggg agtttgtttt ggaaccaaaa    11400
tcaacgggac tttccaaaat gtcgtaacaa ctccgcccca ttgacgcaaa tgggcggtag    11460
gcgtgtacgg tgggaggtct atataagcag agctctccct atcagtgata gagatctccc    11520
tatcagtgat agagatcgtc gacgagctcg tttagtgaac cgtcagatcg cctggagacg    11580
ccatccacgc tgttttgacc tccatagaag acacgggac cgatccagcc tgaacgcgca    11640
gccgccatgg actacaaaga cgatgacgac aaggaggag gcggaggcac aactagaaca    11700
aagggcaggg gccatactgc ggccacgact caaaacgaca gaatgccagg ccctgagctt    11760
tcgggctgga tctctgagca gctaatgacc ggaagaattc ctgtaagcga catcttctgt    11820
gatattgaga caatccagg attatgctac gcatcccaaa tgcaacaaac gaagccaaac    11880
ccgaagacgc gcaacagtca aacccaaacg gacccaattt gcaatcatag tttttgaggag   11940
gtagtacaaa cattggcttc attggctact gttgtgcaac aacaaaccat cgcatcagaa    12000
tcattagaac aacgcattac gagtcttgag aaggtcttta agccagttta tgatgcagag    12060
aaaacaatct cctcattgaa cagggttttgt gctgagatgg ttgcaaaata tgatcttctg    12120
gtgatgacaa ccggtcgggc aacagcaacc gctgcggcaa ctgaggctta tgggccgaa    12180
catggtcaac caccacctgg accatcactt tatgaagaaa gtgcgattcg gggtaagatt    12240
gaatctgag atgagaccgt ccctcaaagt gttagggagg cattcaacaa tctaaacagt    12300
accacttcac taactgagga aaattttggg aaacctgaca tttcggcaaa ggatttgaga    12360
```

```
aacattatgt atgatcactt gcctggtttt ggaactgctt tccaccaatt agtacaagtg   12420
atttgtaaat tgggaaaaga tagcaactca ttggacatca ttcatgctga gttccaggcc   12480
agcctggctg aaggagactc tcctcaatgt gccctaattc aaattacaaa aagagttcca   12540
atcttccaag atgctgctcc acctgtcatc cacatccgct ctcgaggtga cattcccga    12600
gcttgccaga aaagcttgcg tccagtccca ccatcgacca agattgatcg aggttgggta   12660
tgtgtttttc agcttcaaga tggtaaaaca cttggactca aaatttgagg atccactagt   12720
ccagtgtggt ggaattctgc agatatccag cacagtggcg gccgctcgag tctagagggc   12780
ccgtttaaac ccgctgatca gcctcgactg tgccttctag ttgccagcca tctgttgttt   12840
gcccctcccc cgtgccttcc ttgacccctg aaggtgccac tcccactgtc ctttcctaat   12900
aaaatgagga aattgcatcg cattgtctga gtaggtgtca ttctattctg gggggtgggg   12960
tgggcagga cagcaagggg gaggattggg aagacaatag caggcatgct ggggatgcgg   13020
tgggctctat ggtgagctat tccagaagta gtgaagaggc ttttttggag cctaggctt    13080
ttgcaaaaag ctccggatcg atgcccgggg gatccactag ttctagaggg acagccccc    13140
cccaaagccc ccagggatgt aattacgtcc ctccccccgct aggggggcagc agcgagccgc  13200
ccggggctcc gctccggtcc ggcgctcccc ccgcatcccc gagccggcag cgtgcgggga   13260
cagcccgggc acggggaagg tggcacggga tcgctttcct ctgaacgctt ctcgctgctc   13320
tttgagcctg cagacacctg gggggatacg gggaaaaggc ctccaaggcc agcttcccac   13380
aataagttgg gtgaattttg gctgaagctat tccagaagta gtgaagaggc tttttttggag  13440
gcctaggctt ttgcaaaaag ctccggatcg atcatatatg gcagatatac gcgttgacat   13500
tgattattga ctagttatta atagtaatca attacgggt cattagttca tagcccatat    13560
atggagttcc gcgttacata acttacggta aatggcccgc ctggctgacc gcccaacgac   13620
ccccgcccat tgacgtcaat aatgacgtat gttcccataag taacgccaat agggactttc   13680
cattgacgtc aatgggtgga gtatttacgg taaactgccc acttggcagt acatcaagtg   13740
tatcatatgc caagtacgcc ccctattgac gtcaatgacg gtaaatggcc cgcctggcat   13800
tatgcccagt acatgacctt atgggactttc ctacttggc agtacatcta cgtattagtc   13860
atcgctatta ccatggtgat gcggttttgg cagtacatca atgggcgtgg atagcggttt   13920
gactcacggg gatttccaag tctccacccc attgacgtca atgggagttt gttttggcac   13980
caaaatcaac gggactttcc aaaatgtcgt aacaactccg ccccattgac gcaaatgggc   14040
ggtaggcgtg tacggtggga ggtctatata agcagagctc tctggctaac tatcgtcgac   14100
gagctcgttt agtgaaccgt cagatcgcct ggagacgcca tccacgctgt tttgacctcc   14160
atagaagaca ccgggaccga tccagcctcc ggactctagc gtttaaactt aagcttgcca   14220
ccatgaccga gtacaagccc acggtgcgcc tcgccacccg cgacgacgtc cccagggccg   14280
tacgcaccct cgccgccgcg ttcgccgact accccgccac gcgccacacc gtcgatccgg   14340
accgccacat cgagcgggtc accgagctgc aagaactctt cctcacgcgc gtcgggctcg   14400
acatcggcaa ggtgtgggtc gcggacgacg gcgccgcggt ggcggtctgg accacgcgg    14460
agagcgtcga agcggggcg tgttcgccg agatcggccc gcgcatggcc gagttgagcg    14520
gttcccggct ggccgcgcag caacagatgg aaggcctcct ggcgccgcac cggcccaagg   14580
agcccgcgtg gttcctggcc accgtcggcg tctcgcccga ccaccagggc aagggtctgg   14640
gcagcgccgt cgtgctcccc ggagtggagg cggccgagcg cgcgggggtg ccgcccttcc   14700
tggagacctc cgcgccccgc aacctcccct tctacgagcg gctcggcttc accgtcaccg   14760
ccgacgtcga ggtgcccgaa ggaccgcgca cctggtgcat gacccgcaag cccggtgcct   14820
gaagcgcggg gatctcatgc tggagttctt cgcccacccc aacttgttta ttgcagctta   14880
taatggttac aaataaagca atagcatcac aaatttcaca aataaagcat tttttttcact   14940
gcattctagt tgtggtttgt ccaaactcat caatgtatct tatcatgtct gtagctgatg   15000
tatacctagg atccggccgg cctgcaggtg tcctcacagg aacgaagtcc ctaaagaaac   15060
agtggcagcc aggtttagcc ccggaattga ctggattcct ttttttagggc ccattggtat   15120
ggcttttttcc ccgtatcccc ccaggtgtct gcaggctcaa agagcagcga gaagcgttca   15180
gaggaaagcg atcccgtgcc accttccccg tgcccgggct gtcccgcac gctgccggct    15240
cggggatgcg gggggagcgc cggaccggag cggagcccccg gcggctcgc tgctgccccc    15300
tagcggggga gggacgtaat tacatccctg ggggctttgg ggggggggctg tccctctaga   15360
gcggccgcca ccgcggtgga gctccagctt ttgttccctt tagtgagggt taattagatc   15420
ttaatacgac tcactatagg gcgaattggg taccgggccc ccctcgagg tcgacgtat    15480
cgataagctt gatatctata acaagaaaat atatatataa taagttatca cgtaagtaga   15540
acatgaaata acaatataat tatcgtatga gttaaatctt aaaagtcacg taaaagataa   15600
tcatcgtca ttttgactca cgcggtcgtt atagttcaaa atcagtgaca cttaccgcat    15660
tgacaagcac gcctcacggg agctccaagc ggcgactgag atgtcctaaa tgcacagcga   15720
cggattcgcg ctatttagaa agagagagca atatttcaag aatgcatgcg tcaattttac   15780
gcagactatc tttctagggt taatctagct gcatcaggat catatcgtcg ggtctttttt   15840
ccggctcagt catcgcccaa gctggcgcta tctgggcatc ggggaggaag aagcccgtgc   15900
cttttcccgc gaggttgaag cggcatgaa agagtttgcc gaggatgact gctgctgcat   15960
tgacgttgag cgaaaacgca cgtttaccat gatgattcgg gaaggtgtgg ccatgcacgc   16020
ctttaacggt gaactgttcg ttcaggccac ctgggatacc agttcgtcgc ggcttttccg   16080
gacacagttc cggatggtca gcccgaagcg catcagcaac ccgaacaata ccggcgacag   16140
ccggaactgc cgtgccggtg tgcagattaa tgacagcggt gcggcgctgg gatattcgt    16200
cagcgaggac gggtatcctg gctggatgcc gcagaaatgg acatggatac ccgtgagtt    16260
acccggcggg cgcgcttggc gtaatcatgg tcatagctgt ttcctgtgtg aaattgttat   16320
ccgctcacaa ttccacacaa catacgagcc ggaagcataa agtgtaaagc ctggggtgcc   16380
taatgagtga gctaactcac attaattgcg ttgcgctcac tgcccgcttt ccagtcggga   16440
aacctgtcgt gccagctgca ttaatgaatc ggccaacgcg cggggagagg cggtttgcgt   16500
attgggcgct cttccgcttc ctcgctcact gactcgctgc gctcggtcgt tcggctgcgg   16560
cgagcggtat cagctcactc aaaggcggta atacggttat ccacagaatc aggggataac   16620
gcaggaaaga acatgtgagc aaaaggccag caaaaggcca ggaaccgtaa aaaggccgcg   16680
ttgctggcgt ttttccatag gctccgcccc cctgacgagc atcacaaaaa tcgacgctca   16740
agtcagaggt ggcgaaaccc gacaggacta taaagatacc aggcgtttcc ccctggaagc   16800
tccctcgtgc gctctcctgt tccgaccctg ccgcttaccg gatacctgtc cgcctttctc   16860
ccttcgggaa gcgtggcgct ttctcatagc tcacgctgta ggtatctcag ttcggtgtag   16920
gtcgttcgct ccaagctggg ctgtgtgcac gaaccccccg ttcagcccga ccgctgcgcc   16980
ttatccggta actatcgtct tgagtccaac ccggtaagac acgacttatc gccactggca   17040
gcagccactg gtaacaggat tagcagagcg aggtatgtag cggtgctac agagttcttg    17100
```

-continued

```
aagtggtggc ctaactacgg ctacactaga aggacagtat ttggtatctg cgctctgctg    17160
aagccagtta ccttcggaaa aagagttggt agctcttgat ccggcaaaca aaccaccgct    17220
ggtagcggtg gttttttgt ttgcaagcag cagattacgc gcagaaaaaa aggatctcaa     17280
gaagatcctt tgatctttc tacggggtct gacgctcagt ggaacgaaaa ctcacgttaa     17340
gggattttgg tcatgagatt atcaaaaagg atccttcacct agatcctttt aaattaaaaa   17400
tgaagtttta aatcaatcta aagtatatat gagtaaactt ggtctgacag ttaccaatgc    17460
ttaatcagtg aggcacctat ctcagcgatc tgtctatttc gttcatccat agttgcctga    17520
ctccccgtcg tgtagataac tacgatacgg gagggcttac catctggccc cagtgctgca    17580
atgataccgc gagacccacg ctcaccggct ccagatttat cagcaataaa ccagccagcc    17640
ggaagggccg agcgcagaag tggtcctgca actttatccg cctccatcca gtctattaat    17700
tgttgccggg aagctagagt aagtagttcg ccagttaata gtttgcgcaa cgttgttgcc    17760
attgctacag gcatcgtggt gtcacgctcg tcgtttggta tggcttcatt cagctccggt    17820
tcccaacgat caaggcgagt tacatgatcc cccatgttgt gcaaaaaagc ggttagctcc    17880
ttcggtcctc cgatcgttgt cagaagtaag ttggccgcag tgttatcact catggttatg    17940
gcagcactgc ataattctct tactgtcatg ccatccgtaa gatgcttttc tgtgactggt    18000
gagtactcaa ccaagtcatt ctgagaatag tgtatgcggc gaccgagttg ctcttgcccg    18060
gcgtcaaatac gggataatac cgcgccacat agcagaactt taaaagtgct catcattgga    18120
aaacgttctt cggggcgaaa actctcaagg atcttaccgc tgttgagatc cagttcgatg    18180
taacccactc gtgcacccaa ctgatcttca gcatctttta ctttcaccag cgtttctggg    18240
tgagcaaaaa caggaaggca aaatgccgca aaaaagggaa taagggcgac acggaaatgt    18300
tgaatactca t                                                         18311

SEQ ID NO: 13             moltype = DNA  length = 18728
FEATURE                   Location/Qualifiers
misc_feature              1..18728
                          note = Synthetic: pPBBG-iHelper3.2-HA
source                    1..18728
                          mol_type = other DNA
                          organism = synthetic construct
SEQUENCE: 13
actcttcctt tttcaatatt attgaagcat ttatcagggt tattgtctca tgagcggata     60
catatttgaa tgtatttaga aaaataaaca aataggggtt ccgcgcacat ttccccgaaa    120
agtgccacct aaattgtaag cgttaatatt ttgttaaaat tcgcgttaaa ttttgttaa     180
atcagctcat tttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt tttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat aacccctaga agataatca tattgtgacg    900
tacgttaaag ataatcatgc gtaaaattga cgcatgtgtt ttatcggtct gtatatcgag    960
gtttatttat taatttgaat agatattaag tttattatata ttacactta catactaata   1020
ataaattcaa caaacaattt atttatgttt atttatttat taaaaaaaaa caaaaactca   1080
aaatttcttc tataaagtaa caaaactttt atcgaattcc tgcagccgg ggatccact    1140
agttctagag gacagcccc ccccaaagc cccagggat gtaattacgt ccctccccg       1200
ctaggggca gcagcagcc gcccggggct cegctccggt ccggcgctcc ccccgcttc      1260
ccgagccggc agcgtgcggg gacagcccgg gcacgggaca ggtggcacgg gatcgctttc   1320
ctctgaacgc ttctcgctgc tcttgagcc tgcagacacc tggggggata cggggaaaag   1380
gcctccaagg ccagcttccc acaataagtt gggtgaattt tggctcattc ctccttcta    1440
taggattgag gtcagagctt tgtgatggga attctgtagca gtgtgtgtca gttagggtgt   1500
ggaaagtccc gcgatcgcta gcgtttaaac ttaagcttgg taccgagctc ggatccacta   1560
gtccagtgtg gtggaattcc tgcttcgcga tgtacgggcc ggtacccaac tccatgctta   1620
acagtcccca ggtacagccc accctgcgtc gcaaccagga acagctctac agcttcctgg   1680
agcgccactc gccctacttc cgcagccaca gtgcgcagat taggacgcgc acttcttttt   1740
gtcacttgaa aaacatgtaa aaataatgta ctaggagaca cttcaataa aggcaaatgt    1800
ttttatttgt acactctcgg gtgattattt acccccccacc cttgccgtct gcgccgttta   1860
aaaatcaaag gggttctgcc gcgcatcgct atgcgccact ggcagggaca cgttgcgata   1920
ctggtgtttta gtgctccact taaactcagg cacaaccatc cgcggcagct cggtgaagtt   1980
ttcactccac aggctgcgca ccatcaccaa cgcgtttagc aggtcgggcg ccgatatctt   2040
gaagtcgcag ttggggcctc cgccctgcgc gcgcgagttg cgatacacag ggttgcagca   2100
ctggaacact atcagcgccg ggtggtgcac gctggccagc acgctcttgt cggagatcag   2160
atccgcgtcc aggtcctccg cgttgctcag ggcgaacgga gtcaactttg gtagctgcct   2220
tcccaaaaag ggtgcatgcc caggctttga gttgcactcg caccgtagtg gcatcagaag   2280
gtgaccgtgc ccggtctggg cgttaggata cagcgcctgc atgaaagcct tgatctgctt   2340
aaaagccacc tgagcctttg gccttcaga aagaacatg ccgcaagact tgccggaaaa    2400
ctgattggcc ggacaggccg cgtcatgcac gcagcacctt cgtcggtgt tggagatctg   2460
caccacattt cggccccacc ggttcttcac gatcttggcc ttgctagact gctccttcag   2520
cgcgcgctgc ccgttttcgc tcgtcacatc catttcaatc acgtgctcct tatttatcat   2580
aatgctcccg tgtagacact taagctcgcc ttcgatctca ggcatcgtcg ccgcacaca    2640
cgcgcagccc gtgggctcgt ggtgcttgta ggttacctct gcaaacgact gcaggtacgc   2700
ctgcaggaat cgcccatca tcgtcacaaa ggtcttgttg ctggtgaagg tcagctgcaa   2760
cccgcggtgc tcctcgttta gccaggtctt gcatacggcc gcagagctt ccacttggtc    2820
aggcagtagc ttgaagtttg cctttagatc gttatccacg tggtacttgt ccatcaacgc   2880
gcgcgcagcc tccatgccct tctcccacgc agacacgatc ggcaggctca gcgggtttat   2940
```

```
caccgtgctt tcactttccg cttcactgga ctcttccttt tcctcttgcg tccgcatacc 3000
ccgcgccact gggtcgtctt cattcagccg ccgcaccgtg cgcttacctc ccttgccgtg 3060
cttgattagc accggtgggt tgctgaaacc caccatttgt agcgccacat cttctctttc 3120
ttcctcgctg tccacgatca cctctgggga tggcgggcgc tcgggcttgg gagaggggcg 3180
cttcttttc ttttggacg caatggccaa atccgccgtc gaggtcgatg gccgcgggct 3240
gggtgtgcgc ggcaccagcg catcttgtga cgagtcttct tcgtcctcgg actcgagacg 3300
ccgcctcagc cgcttttttg ggggcgcgcg gggaggcggc ggcgacggcg acggggacga 3360
cacgtcctcc atggttggtg gacgtcgcgc cgcaccgcgt ccgcgctcgg gggtggtttc 3420
gcgctgctcc tcttcccgac tggccatttc ctttctcctat aggcagaaaa agatcatgga 3480
gtcagtcgag aaggaggaca gcctaaccgc ccccttgag ttcgccacca ccgcctccac 3540
cgatgccgcc aacgcgccta ccaccttccc cgtcgaggca ccccgcttg aggaggagga 3600
agtgattatc gagcaggacc caggttttgt aagcgaagac gacgaggatc gctcagtacc 3660
aacagaggat aaaaagcaag accaggacga cgcagaggca aacgaggaac aagtcggcg 3720
ggggaccaa aggcatggcg actacctaga tgtgggagac gacgtgctgt tgaagcatcc 3780
gcagcgccag tgcgccatta tctgcgacgc gttgcaagag cgcagcgatg tgccctcgc 3840
catagcggat gtcagccttg cctacgaacg ccacctgttc tcaccgcgcg tacccccaa 3900
acgccaagaa aacggcacat gcgagccaa cccgcgcctc aacttctacc ccgtatttgc 3960
cgtgccagag gtgcttgcca cctatcacat cttttccaa aactgcaaga taccctatc 4020
ctgccgtgcc aaccgcagcc gagcggacaa gcagctggcc ttgcggcagg cgctgtcat 4080
acctgatatc gcctcgctcg acgaagtgcc aaaaatcttt gagggtcttg gacgcgacga 4140
gaaacgcgcg caaacgctc tgcaacaaga aaacagcgaa aatgaaagtc actgtggagt 4200
gctggttggaa cttgagggtg acaacgcgcg cctagccgtg ctgaaacgca gcatcgaggt 4260
cacccacttt gcctaccggg cacttaacct accccccaag gttatgagca cagtcatgag 4320
cgagctgatc gtgcgccgtg cacgacccct ggagagggat gcaaacttgc aagaacaaac 4380
cgaggagggc ctacccgcag ttggcgatga gcagctggcg cgctggcttg agacgcgcga 4440
gcctgccgac ttggaggagc gacgcaagct aatgatggcc gcagtgcttg ttaccgtgga 4500
gcttgagtgc atgcagcggt tctttgctga cccggagatg cagcgcaagc tagaggaaac 4560
gttgcactac acctttcgcc agggctacgt gcgccaggcc tgcaaaattt ccaacgtgga 4620
gctctgcaac ctggtctcct accttggaat tttgcacgaa aaccgcctcg gcaaaacgt 4680
gcttcattcc acgctcaagg gcgaggcgcg ccgcgactac gtccgcgact gcgtttactt 4740
atttctgtgc tacacctggc aaacggccat gggcgtgtgg cagcaatgcc tggaggagcg 4800
caacctaaag gagctgcaga agctgctaaa gcaaaacttg aaggacctat ggacggcctt 4860
caacgagcgc tccgtggccg cgcacctggc ggacattatc ttccccgaac gcctgcttaa 4920
aaccctgcaa cagggtctgc cagacttcac cagtcaaagc atgttgcaaa actttaggaa 4980
ctttatccta gagcgttcag gaattctgcc cgccacctgc tgtgcgcttc ctagcgactt 5040
tgtgcccatt aagtaccgtg aatgcctcc gccgctttgg ggtcactgct accttctgca 5100
gctagccaac taccttgcct accactccga catcatggaa gacgtgagcg gtgacggcct 5160
actggagtgt cactgtcgct gcaacctatg cacccccgca cgctcctctgg tctgcaattc 5220
gcaactgctt agcgaaagtc aaattatcgg tacctttgag ctgcaggtgc cctcgcctga 5280
cgaaaagtcc gcggctccgg ggttgaaact cactccgggg ctgtggacgt ccgatctcta 5340
tcactgatag ggagatctct atcactgata gggagagggc ttaccttcgc aaatttgtac 5400
ctgaggacta ccacgcccac gagattaggt tctacgaaga ccaatcccgc ccgccaaatg 5460
cggagcttac cgcctgcgtc attacccagg gccacatcct tggcaattg caagccatca 5520
acaaagcccg ccaagagttt ctgctacgaa agggacgggg ggtttacctg gacccccagt 5580
ccggcgagga gctcaaccca atccccccgc cgccgcagcc ctatcagcag ccgcgggccc 5640
ttgcttccca ggatggcacc caaaagaag ctgcagctgc cgccgccgcc acccacggac 5700
gaggggaat actgggacag tcaggcagag gaggttttgg acgaggagga gggagatgatg 5760
gaagactggg acagcctaga cgaagcttcc gaggccgaag aggtgtcaga cgaaacaccg 5820
tcaccctcgg tcgcattccc ctcgccgcg ccccagaaat tggcaaccgt tccagcatc 5880
gctacaacct ccgctcctca ggcgccgccg gcactgcctg ttcgccgacc caaccgtaga 5940
tgggacacca ctggaaccag ggccggtaag tctaagcagc cgccgccgtt agcccaagag 6000
caacaacagc gccaaggcta ccgctcgtgg cgcgggcaca agaacgccat agttgcttgc 6060
ttgcaagact gtgggggcaa catctccttc gcccgccgct ttcttctcta ccatcacggc 6120
gtggccttcc cccgtaacat cctgcattac taccgtcatc tctacagccc ctactgcacc 6180
ggcggcggc gcagcggcag caacagcgca ggtcacacag aagcaaaggc gaccggatag 6240
caagactctg acaaagcccca agaaatccac agcggcggca gcagcaggag gaggagcgct 6300
gcgtctggcg cccaacgaac ccgtatcgac ccgcgagctt agaaatagga ttttccccac 6360
tctgtatgct atatttcaac aaagcagggg ccaagaacaa gagctgaaaa taaaaaacag 6420
gtctctgcgc tccctcaccc gcagctgcct gtatcacaaa agcgaagatc agcttcggcg 6480
cacgctggaa gacgcggagg ctctcttcag caacgatctc tatcactgat agggagatct 6540
ctatcactga tagggagaga tactgcgcgc tgactcttaa ggactagttt cgcgcccttt 6600
ctcaaattta agcgcgaaaa ctacgtcatc tccagcggcc acaccggcg ccagcacctg 6660
tcgtcagcgc cattatgagc aaggaaattc ccacgcccta catgtggagt taccagccac 6720
aaatgactgc tgcggctgga gctgcccaag actactcaaa ccgaataaac tacatgacgg 6780
cgggaccca catgatatcc cgggtcaacg gaatccgcgc ccaccgaaac cgaattctcc 6840
tcgaacaggc ggctattacc accacactc gtaataacct taatcccgt agttggcccg 6900
ctgccctggt gtaccaggaa agtccccgctc ccaccactgt ggtacttccc agagacgccc 6960
aggccgaagt tcagatgact aactcagggg cgcagcttgc gggcggcttt cgtcacaggg 7020
tgcggtcgcc cccagtggcc aaaaaagcta gcgcagcagc cgccgcgcct ggaaggaagc 7080
caaaaggagc gctccccgt tgtctgacgt cgcacacctg ggttcgacac gcgggcggta 7140
accgcatgga tcacggcgga cggcggatc cggggttcga accccgtcg tccgccatga 7200
taccccttgcg aatttatcca ccagaccacg gaagagtgcc cgcttacagg ctctccttt 7260
gcacggtcta gagcgtcaac gactgcgcac ggggcgtttt agggcggagt aacttgcatg 7320
tattgggaat tgtagttttt ttaaatggg aagtgacgta tcgtgggaaa acgaagtga 7380
agatttgagg aagttgtggg tttttttggct ttcgttctg ggcgtaggtt cgcgtgcggt 7440
tttctgggtg tttttttgtgg actttaaccg ttacgtcatt tttagtcct atatatactc 7500
gctctgtact ctccctatca gtgatagaga tctccctatc agtgatagag atcgcttggc 7560
ccttttaca ctgtgactga ttgagctggt gccgtgtcga gtggtgtttt ttaataggtt 7620
tttttactgg taaggctgac tgttatggct gccgctgtgg aagcgctgta tgttgttctg 7680
```

```
gagcgggagg gtgctatttt gcctaggcag gagggttttt caggtgttta tgtgtttttc  7740
tctcctatta attttgttat acctcctatg ggggctgtaa tgttgtctct acgcctgcgg  7800
gtatgtattc cccgggcta tttcggtcgc tttttagcac tgaccgatgt taaccaacct   7860
gatgtgttta ccgagtctta cattatgact ccggacatga ccgaggaact gtcggtggtg  7920
cttttaatc acggtgacca gttttttac ggtcacgccg gcatggccgt agtccgtctt    7980
atgcttataa gggttgtttt tcctgttgta agacaggctt ctaatgttta aatgtttttt  8040
tttttgttat tttatttgt gtttaatgca ggaacccgca gacatgtttg agagaaaaat   8100
ggtgtctttt tctgtggtgg ttccggaact tacctgcctt tatctgcatg agcatgacta  8160
cgatgtgctt gcttttttgc gcgaggcttt gcctgatttt ttgagcagca ccttgcattt  8220
tatatcgccg cccatgcaac aagcttacat aggggctacg ctggttagca tagctccgag  8280
tatgcgtgtc ataatcagtg tgggttcttt tgtcatggtt cctggcgggg aagtggccgc  8340
gctggtccgt gcagacctgc acgattatgt tcagctggcc ctgcgaaggg acctacggga  8400
tcgcggtatt tttgttaatg ttccgctttt gaatcttata caggtctgtg aggaacctga  8460
atttttgcaa tcatgattcg ctgcttgagg ctgaaggtgg agggcgctct ggagcagatt  8520
tttacaatgg ccggacttaa tattcggat ttgcttagag acatattgat aaggtggcga   8580
gatgaaaatt atttgggcat ggttgaaggt gctggaatgt ttatagagga gattcaccct  8640
gaagggttta gccttacgt ccacttggac gtgagggcag tttgccttt ggaagccatt    8700
gtgcaacatc ttacaaatgc cattatctgt tcttggcta tagagtttga ccacgccacc   8760
ggaggggagc gcgttcactt aatagatctt cattttgagg ttttggataa tcttttggaa  8820
taaaaaaaaa aaaacatggt tcttccagct cttcccgctc ctcccgtgtg tgactcgcag  8880
aacgaatgtg taggttggct gggtgtggct tattctgcgg tggtggatgt tatcagggca  8940
gcggccatg aaggagttta catagaaccc gaagccaggg ggcgcctgga tgctttgaga   9000
gagtggatat actacaacta ctacacagag cgagctaagc gacgagaccg gagacgcaga  9060
tctgtttgtc acgcccgcac ctggttttgc ttcaggaaat atgtacccat acgatgttcc  9120
agattacgct ggaggaggcg gaggcactac gtccggcgtt ccatttggca tgacactacg  9180
accaacacga tctcggttgt ctcggcgcac tccgtacagt agggatcgtc tacctccttt  9240
tgagacagag accccgcgcta ccatactgga ggatcatccg ctgctgcccg aatgtaaac   9300
tttgacaatg cacaacgtga gttacgtgcg aggtcttccc tgcagtgtgg gatttacgct  9360
gattcaggaa tgggttgttc cctgggatat ggttctgacg cgggaggagc ttgtaatcct  9420
gaggaagtgt atgcacgtgt gcctgtgttg tgccaacatt gatatcatga cgagcatgat  9480
gatccatggt tacgagtcct gggctctcca ctgtcattgt tccagtcccg gttccctgca  9540
gtgcatagcc ggcgggcagg ttttggccag ctggtttagg atggtggtgg atggcgccat  9600
gtttaatcag aggtttatat ggtaccggga ggtggtgaat tacaacatgc caaaagaggt  9660
aatgtttatg tccagcgtgt ttatgagggg tcgccactta atctacctgc gcttgtggta  9720
tgatggccac gtgggttctg tggtccccgc catgagcttt ggatacagcg ccttgcactg  9780
tgggattttg aacaatattg tggtgctgtg ctgcagttac tgtgctgatt taagtgagat  9840
cagggtgcgc tgctgtgccc ggaggacaag gcgtctcatg ctgcgggcgg tgcgaatcat  9900
cgctgaggag accactgcca tgttgtattc ctgcaggacg gagcggcggc ggcagcagtt  9960
tattcgccg ctgctgcagc accaccgcc tatcctgcag tcacgattatg actctacccc   10020
catgtaggcg tggacttccc cttgccgcc cgttgagcaa ccgcaagttg gacagcagcc   10080
tgtggctcag cagctggaca gcgacatgaa cttaagcgag ctgcccgggg agtttattaa   10140
tatcactgat gagcgtttgg ctcgacagga aaccgtgtgg aatataacac ctaagaatat   10200
gtctgttacc catgatatga tgcttttaa ggccagccgg ggagaaagga ctgtgtactc    10260
tgtgtgttgg gagggaggtg gcaggttgaa tactagggtt ctgtgagttt gattaaggta   10320
cggtgatcaa tataagctat gtggtggtgg ggctatacta ctgaatgaaa aatgacttga   10380
aattttctgc aattgaaaaa taaacacgtt gaaacataac atgcaacagg ttcacgattc   10440
tttattcctg ggcaatgtag gagaaggtgt aagagttggt agcaaaagtt tcagtggtgt   10500
attttccact ttcccaggac catgtaaaag acatagagta agtgcttacc tcgctagttt   10560
ctgtggattc actagaatcc actttggccg cggctcgagg agggacagcc ccccccaaa    10620
gcccccaggg atgtaattac gtccctcccc cgctagggg cagcagcgag ccgcccgggg    10680
ctccgctccg gtccggcgct cccccccgcat ccccgaccgc gcagcgtcg ggacagccc    10740
gggcacgggg aagtggcac gggatcgctt tcctctgaac gcttctcgct gtctttgag     10800
cctgcagaca cctgggggga tacggggaaa aggcctccaa ggccagcttc cacaataag    10860
ttgggtgaat tttggctcat tcctccttc tataggattg aggtcagagc gacattgatt   10920
attgactagt tattaatagt aatcaattac ggggtcatta gttcatagcc catatatgga   10980
gttccgcgtt acataactta cggtaaatgg cccgcctggc tgaccgccca acgaccccg    11040
cccattgacg tcaataatga cgtatgttcc catagtaacg ccaataggga ctttccattg   11100
acgtcaatgg gtggagtatt tacggtaaac tgcccacttg gcagtacatc aagtgtatca   11160
tatgccaagt acgccccta ttgacgtcaa tgacggtaaa tggcccgcct ggcattatgc    11220
ccagtacatg accttatggg actttcctac ttggcagtac atctacgtat tagtcatcgc    11280
tattaccatg gtgatgcggt tttggcagta catcaatggg cgtggatagc ggtttgactc    11340
acggggattt ccaagtctcc accccattga cgtcaatggg agtttgtttt ggaaccaaaa    11400
tcaacggac tttccaaaat gtcgtaacaa ctccgcccca ttgacgcaaa tgggcggtag      11460
gcgtgtacgg tgggaggtct atataagcag agctctccct atcagtgata gagatctccc    11520
tatcagtgat agagatcgtc gacgagctcg tttagtgaac cgtcagatcg cctggagacg    11580
ccatccacgc tgttttgacc tccatagaag acaccgggac cgatccagcc tgaacgcgca    11640
gccgccatga actacaaaga cgatgacgac aaggaggag gcgaggcgt tccttctcag     11700
agatctcccc gaactagcag catttcctcc aacgaggatc ccgcagagag ccacattgtt    11760
gaactcgaag cggtctcaga caccaacaca gactgcgatc tgtgaccctat ggagggcagc    11820
gaagaacact ccacagatgg agagatttca tcctcagagg aggaggatga agatccaact    11880
ccggcccacg ccataccctgc acggccctcc agcgtggtca taaaccccta ctcggcatcg    11940
tttgtgattc ccagaaagaa gtgggaccta caggacaaga cagtcacatt gcatcgctca     12000
cccctgtgca gggacgagga cgagaaggag gagactggca actcctctta caccagagc     12060
caaaaggc gacgcggaga ggtccatggc tgcaccgata aaggttatgg caagcgcacca    12120
cacctgcccc cggagcaag agcgcccaga gccccaaggg ccccaggt gcctagagca      12180
ccgaggtctc caagagctcc ccgaagcaac agagcaacca gaggtccccg gtcagaatct    12240
cgaggggccg gcaggagcac aaggaagcag gcgaggcaag aacgcagcca gaggcccctg     12300
ccgaacaaac cgtggtttga catgagtctg gttaagcctg tctccaagat tacatttgtc    12360
accttgccca gccccctggc ctctctgacc ctagagccca tccaagaccc gttcctacag    12420
```

```
tcgatgctgg cggtggccgc ccatccagag attggagcct ggcagaaagt gcaacccaga    12480
cacgagctgc gcaggagcta caagacacta cgtgagtttt tcaccaagtc aaccaacaag    12540
gacacatggc tggatgcacg catgcaggcg atccagaacg cggggctctg caccctggtg    12600
gccatgctag aagagaccat cttttggctc caggagatca cctaccacgg cgacctgccc    12660
ctagctcccg cggaagacat cctcctggcc tgcgccataa gtcttagcaa ggtgatcctg    12720
accaagctca aagagctggc accctgcttc cttcctaaca cgcgagacta caactttgtg    12780
aagcaactct tctacatcac ctgtgccacg gcccgtcaaa acaaggtggt ggagaccctg    12840
agcagctcat atgtgaagca gcccctctgt ctcttggcag catatgcggc agtagcccca    12900
gcctacatta acgccaactg cagacggaga cacgatgaag ttgaattcct gggcactac    12960
atcaagaatt acaaccctgg cacgctaagc tcccttttga cagaggccgt ggagactcac    13020
acacgtgact gccgaagtgc atcatgcagc cgacttgtca gggccattct ctctccgggc    13080
actgggtcac taggactgtt ttttgttcct ggattaaatc aataaggatc cactagtcca    13140
gtgtggtgga attctgcaga tatccagcac agtggcggcc gctcgagtct agagggcccg    13200
tttaaacccg ctgatcagcc tcgactgtgc cttctagttg ccagccatct gttgtttgcc    13260
cctccccgt gccttccttg accctggaag gtgccactcc cactgtcctt tcctaataaa    13320
atgaggaaat tgcatcgcat tgtctgagta ggtgtcattc tattctgggg ggtgggtgg    13380
ggcaggacag caaggggggag gattgggaag acaaatagcag gcatgctggg gatgcggtgg    13440
gctctatggt gagctattcc agaagtagtg aagaggcttt tttggaggcc taggcttttg    13500
caaaaagctc cggatcgatg cccgggggat ccactagttc tagagggaca gccccccccc    13560
aaagccccca gggatgtaat tacgtccctc ccccgctagg gggcagcagc gagccgcccg    13620
gggctccgct ccgtccggc gctcccccg catcccgag ccggcagcgt gcggggacag    13680
cccgggcacg gggaaggtgg cacggatcg cttttcctctg aacgcttctc gctgctcttt    13740
gagcctgcag acacctgggg ggatacgggg aaaaggcctc caaggccagc ttcccacaat    13800
aagtggggtg aattttggct gagctattcc agaagtagtg aagaggcttt tttggaggcc    13860
taggcttttg caaaaagctc cggatcgatc atatatggca gatatacgcg ttgacattga    13920
ttattgacta gttattaata gtaatcaatt acggggtcat tagttcatag cccatatatg    13980
gagttccgcg ttacataact tacggtaaat ggcccgcctg gctgaccgcc caacgacccc    14040
cgcccattga cgtcaataat gacgtatgtt cccatagtaa cgccaatagg gactttccat    14100
tgacgtcaat gggtggagta tttacggtaa actgcccact tggcagtaca tcaagtgtat    14160
catatgccaa gtacgccccc tattgacgtc aatgacggta aatggcccgc ctggcattat    14220
gcccagtaca tgaccttatg ggactttcct acttggcagt acatctacgt attagtcatc    14280
gctattacca tggtgatgcg gttttggcag tacatcaatg ggcgtggata gcggtttgac    14340
tcacggggat ttccaagtct ccaccccatt gacgtcaatg ggagtttgtt ttggcaccaa    14400
aatcaacggg actttccaaa atgtcgtaac aactccgccc cattgacgca aatgggcggt    14460
aggcgtgtac ggtgggaggt ctatataagc agagctctct ggctaactat cgtcgacgag    14520
ctcgtttagt gaaccgtcag atcgcctgga gacgccatcc acgctgtttt gacctccata    14580
gaagacaccg ggaccgatcc agcctccgga ctctagcgtt taaacttaag cttgccacca    14640
tgaccgagta caagcccacg gtgcgcctcg ccacccgcga cgacgtcccc agggccgtac    14700
gcaccctcgc cgccgcgttc gccgactacc ccgccacgcg ccacaccgtc gatccggacc    14760
gccacatcga gcgggtcacc gagctgcaag aactcttcct cacgcgcgtc ggcctcgaca    14820
tcggcaaggt gtgggtcgcg gacgacgcg ccgcggtggc ggtctggacc acgcggaga    14880
gcgtcgaagc ggggcggtg ttcgccgaga tcggcccgcg catggccgag ttgagcggtt    14940
cccggctggc cgcgcagcaa cagatggaag gcctcctggc gccgcaccgg ccaaggagc    15000
ccgcgtggtt cctggccacc gtcggcgtct cgcccgacca ccagggcaag gtctgggca    15060
gcgccgtcgt gctcccccgga gtggaggcgg ccgagcgcgc cgggggtgccc gccttcctgg    15120
agacctccgc gccccgcaac ctccccttct acgagcggct cggcttcacc gtcaccgccg    15180
agtcggagt gcccgaagga ccgcgcacct ggtgcatgac ccgcaagccc ggtgccgaa    15240
gcgcggggat ctcatgctgg agttcttcgc ccacccaac ttgttattg cagcttataa    15300
tggttacaaa taaagcaata gcatcacaaa tttcacaaat aaagcatttt tttcactgca    15360
ttctagttgt ggtttgtcca aactcatcaa tgtatcttat catgtctgta gctgatgtat    15420
acctaggatc cggccggcct gcaggtgtcc tcacaggaac gaagtccccta aagaaacagt    15480
ggcagccagg tttagccccg gaattgactg gattcctttt ttaggggccca ttggtatgcc    15540
tttttccccg tatccccca ggtgtctgca ggctcaaaga gcagcgagaa gcgttcagag    15600
gaaagcgatc ccgtgccacc ttccccgtgc ccgggctgtc cccgcacgct gccggctcgg    15660
ggatgcgggg ggagcgccgg accggagcgg agccccggc ggctcgctgc tgccccctag    15720
cgggggaggg acgtaattac atccctgggg gctttgggg ggggctgtcc ctctagagcg    15780
gccgccaccg cggtggagct ccagcttttg ttccctttag tgagggttaa ttagatctta    15840
atacgactca ctatagggcg aattgggtac cgggccccc ctcgaggtcg acggtatcga    15900
taagcttgat atcactaaca agaaaatata tatataataa gttatcacgt aagtagaaca    15960
tgaaataaca atataattat cgtatgagtt aaatcttaaa agtcacgtaa aagataatca    16020
tgcgtcattt tgactcacgc ggtcgttata gttcaaaatc agtgacactt accgcattga    16080
caagcacgcc tcacgggagc tccaagcggc gactgagatg tcctaaatgc acagcgacgg    16140
attcgcgcta tttagaaaga gagagcaata tttcaagaat gcatgcgtca attttacgca    16200
gactatcttt ctaggggtaa tctagctgca tcaggatcat atcgtcggtg cttttttcg    16260
gctcagtcat cgcccaagct ggcgctatct gggcatcggg gaggaagaag cccgtgcctt    16320
tcccgcgag gttgaagcgg catggaaaga gtttgccgag gatgactgct gctgcattga    16380
cgttgagcga aaacgcacgt ttaccatgat gattcgggaa ggtgtggcca tgcacgcctt    16440
taacggtgaa ctgttcgttc aggccacctg ggataccagt tcgtcgcggc ttttccggac    16500
acagttccgg atgttcagcc gcaagcgcat cagcaacccg aacaataccg gcgacagccg    16560
gaactgccgt gccggtgtgc agattaatga cagcggtgcg gcgctgggat attacgtcag    16620
cgaggacggg tatcctggct ggatgccgca gaaatggaca tggataccc gtgagttacc    16680
cggcgggcgc gcttggcgta atcatggtca tagctgtttc ctgtgtgaaa ttgttatccg    16740
ctcacaattc cacacaacat acgagccgga agcataaagt gtaaagcctg ggtgcctaa    16800
tgagtgagct aactcactat aattgcgttg cgctcactgc ccgctttcca gtcgggaaac    16860
ctgtcgtgcc agctgcatta atgaatcggc caacgcgcgg ggagaggcgg tttgcgtatt    16920
gggcgctctt ccgcttcctc gctcactgac tcgctgcgct cggtcgttcg gctgcggcga    16980
gcggtatcag ctcactcaaa ggcggtaata cggttatcca cagaatcagg gataacgca    17040
ggaaagaaca tgtgagcaaa aggccagcaa aaggccagga accgtaaaaa ggccgcgttg    17100
ctggcgtttt tccataggct ccgcccccct gacgagcatc acaaaaatcg acgctcaagt    17160
```

```
cagaggtggc gaaacccgac aggactataa agataccagg cgtttccccc tggaagctcc  17220
ctcgtgcgct ctcctgttcc gaccctgccg cttaccggat acctgtccgc ctttctccct  17280
tcggaagcg tggcgctttc tcatagctca cgctgtaggt atctcagttc ggtgtaggtc   17340
gttcgctcca agctgggctg tgtgcacgaa ccccccgttc agcccgaccg ctgcgcctta  17400
tccggtaact atcgtcttga gtccaacccg gtaagacacg acttatcgcc actggcagca  17460
gccactggta acaggattag cagagcgagg tatgtaggcg gtgctacaga gttcttgaag  17520
tggtggccta actacggcta cactagaagg acagtatttg gtatctgcgc tctgctgaag  17580
ccagttacct tcggaaaaag agttggtagc tcttgatccg gcaaacaaac caccgctggt  17640
agcggtggtt ttttgtttg caagcagcag attacgcgca gaaaaaaagg atctcaagaa    17700
gatcctttga tcttttctac ggggtctgac gctcagtgga acgaaaactc acgttaaggg   17760
attttggtca tgagattatc aaaaaggatc ttcacctaga tccttttaaa ttaaaaatga   17820
agttttaaat caatctaaag tatatatgag taaacttggt ctgacagtta ccaatgctta   17880
atcagtgagg cacctatctc agcgatctgt ctatttcgtt catccatagt tgcctgactc   17940
ccgtcgtgt agataactac gatacgggag ggcttaccat ctggccccag tgctgcaatg    18000
ataccgcgag acccacgctc accggctcca gatttatcag caataaacca gccagccgga   18060
agggccgagc gcagaagtgg tcctgcaact ttatccgcct ccatccagtc tattaattgt   18120
tgccgggaag ctagagtaag tagttcgcca gttaatagtt tgcgcaacgt tgttgccatt   18180
gctacaggca tcgtggtgtc acgctcgtcg tttggtatgg cttcattcag ctccggttcc   18240
caacgatcaa ggcgagttac atgatccccc atgttgtgca aaaaagcggt tagctccttc   18300
ggtcctccga tcgttgtcag aagtaagttg gccgcagtgt tatcactcat ggttatggca   18360
gcactgcata attctcttac tgtcatgcca tccgtaagat gcttttctgt gactggtgag   18420
tactcaacca agtcattctg agaatagtgt atgcggcgac cgagttgctc ttgcccggcg   18480
tcaatacggg ataataccgc gccacatagc agaactttaa aagtgctcat cattggaaaa   18540
cgttcttcgg ggcgaaaact ctcaaggatc ttaccgctgt tgagatccag ttcgatgtaa   18600
cccactcgtg cacccaactg atcttcagca tcttttactt tcaccagcgt ttctgggtga   18660
gcaaaaacag gaaggcaaaa tgccgcaaaa aagggaataa gggcgacacg gaaatgttga   18720
atactcat                                                           18728
SEQ ID NO: 14           moltype = DNA   length = 11866
FEATURE                 Location/Qualifiers
misc_feature            1..11866
                        note = Synthetic: PB-hiRep-1#
source                  1..11866
                        mol_type = other DNA
                        organism = synthetic construct
SEQUENCE: 14
actcttcctt tttcaatatt attgaagcat ttatcagggt tattgtctca tgagcggata    60
catatttgaa tgtatttaga aaaataaaca aataggggtt ccgcgcacat ttccccgaaa   120
agtgccacct aaattgtaag cgttaatatt ttgttaaaat tcgcgttaaa tttttgttaa   180
atcagctcat tttttaacca ataggccgaa atcggcaaaa tcccttataa atcaaaagaa   240
tagaccgaga tagggttgag tgttgttcca gtttggaaca agagtccact attaaagaac   300
gtggactcca acgtcaaagg gcgaaaaacc gtctatcagg gcgatggccc actacgtgaa   360
ccatcaccct aatcaagttt tttggggtcg aggtgccgta agcactaaa tcggaacctc    420
aaagggagcc cccgatttag agcttgacgg ggaaagccgg cgaacgtggc gagaaaggaa   480
gggaagaaag cgaaaggagc gggcgctagg gcgctggcaa gtgtagcggt cacgctgcgc   540
gtaaccacca caccgccgc gcttaatgcg ccgctacagg gcgcgtccca ttcgccattc    600
aggctgcgca actgttggga agggcgatcg gtgcgggcct cttcgctatt acgccagctg   660
gcgaaagggg gatgtgctgc aaggcgatta agttgggtaa cgccagggtt ttcccagtca   720
cgacgttgta aaacgacggc cagtgagcgc gcctcgttca ttcacgtttt tgaacccgtg   780
gaggacgggc agactcgcgg tgcaaatgtg ttttacagcg tgatggagca gatgaagatg   840
ctcgaactga tgcagaacac gcagctagat taaccctaga aagataatca tattgtgacg   900
tacgttaaag ataatcatgc gtaaaattga cgcatgtgtt ttatcggtct gtatatcgag   960
gtttattta taatttgaat agatattaag ttttattata tttacactta catactaata    1020
ataaattcaa caaacaattt atttatgttt atttatttat taaaaaaaa caaaaactca    1080
aaatttcttc tataaagtaa caaaactttt atcgaattcc tgcagcccgg gggatccact   1140
agttctagag gacagcccc ccccaaagc ccccagggat gtaattacgt ccctcccccg     1200
ctaggggca gcagcgagcc gccccgggct ccgtccggt ccggcgctcc ccccgcatcc     1260
ccgagccgga agcgtgcggg gacagcccgg gcacggggaa ggtggcacgg gatcgctttc   1320
ctctgaacgc ttctcgctgc tctttgagcc tgcagacacc tgggggata cgggaaaag    1380
gcctccaagg ccagcttccc acaataagtt gggtgaattt tggctcattc ctcctttcta   1440
taggattgag tcagagctt tgtgatggga attctgtgga atgtgtgtca gttagggtgt    1500
ggaaagtccc gcgatcgcta gcttaagcgc tgatcaattg gcgcgccgaa ttcgttatct   1560
gcagaattcg gcttgacatt gattattgac tagttattaa tagtaatcaa ttacggggtc   1620
attagttcat agcccatata tggagttccg cgttacataa cttacggtaa atggcccgcc   1680
tggctgaccg cccaacgacc cccgcccatt gacgtcaata atgacgtatg ttcccatagt   1740
aacgccaata gggactttcc attgacgtca atgggtggag tatttacggt aaactgccca   1800
cttggcagta catcaagtgt atcatatgcc aagtacgccc cctattgacg tcaatgacgg   1860
taaatggccc gcctggcatt atgcccagta catgacctta tgggactttc ctacttggca   1920
gtacatctac gtattagtca tcgctattac catggtgatg cggttttggc agtacatcaa   1980
tgggcgtgga tagcggtttg actcacgggg atttccaagt ctccacccca ttgacgtcaa   2040
tgggagtttg ttttggaacc aaaatcaacg ggactttcca aaatgtcgta acaactccgc   2100
cccattgacg caaatgggcg gtaggcgtgt acggtgggag gtctatataa gcagagctct   2160
ccctatcagt gatagagatc tccctatcag tgatagagat cgtcgacgag ctcgtttagt   2220
gaaccgtcag atcgcctgga gacgccatcc acgctgtttt gacctccata gaagacaccg   2280
ggaccgatca gcctgaacg cgcagccgcc aatggatgcc ggggttttac gagattgtga    2340
ttaaggtccc cagcgacctt gacgagcatc tgccccggcat ttctgacagc tttgtgaact   2400
gggtggccga gaaggaatgg gagttgccgc cagattctga catggatctg aatctgattg   2460
agcaggcacc cctgaccgtg gccgagaagc tgcagcgcga ctttctgacg gaatggcgcc   2520
gtgtgagtaa ggcccccgga gctcttttct ttgtgcaatt tgagaaggga gagagctact   2580
```

```
tccacatgca cgtgctcgtg gaaaccaccg gggtgaaatc catggttttg ggacgtttcc   2640
tgagtcagat tcgcgaaaaa ctgattcaga gaatttaccg cgggatcgag ccgactttgc   2700
caaactggtt cgcggtcaca aagaccagaa atgcgccgg aggcgggaac aaggtggtgg    2760
atgagtgcta catccccaat tacttgctcc ccaaaaccca gcctgagctc caatgggcat   2820
ggaccaacat ggaacagtac ctcagcgcct gtttgaatct cacggagcgt aaacggttgg   2880
tggcgcagca tctgacgcac gtgtcgcaga cgcaggagca gaacaaagag aatcagaatc   2940
ccaattctga tgcgccggtg atcagatcaa aaacttcagc caggtacatg gagctggtcg   3000
ggtggctcgt ggacaagggg attacctcgg agaagcagtg gatccaggag gaccaggcct   3060
catacatctc cttcaatgcg gcctccaact cgcggtccca aatcaaggct gccttggaca   3120
atgcgggaaa gattatgagc ctgactaaaa ccgcccccga ctacctggtg ggccagcagc   3180
ccgtggagga catttccagc aatcggattt ataaaattt ggaactaaac gggtacgatc    3240
cccaatatgc ggcttccgtc tttctgggat gggccacgaa aaagttcggc aagaggaaca   3300
ccatctggct gtttgggcct gcaactaccg gaagaccaa catcgcggag gccatagccc     3360
acactgtgcc cttctacggg tgcgtaaact ggaccaatga gaactttccc ttcaacgact   3420
gtgtcgacaa gatggtgatc tggtgggagg aggggaagga gaccgccaag gtcgtggagt   3480
cggccaaagc cattctcgga ggaagcaagg tgcgcgtgga ccagaaatgc aagtcctcgg   3540
cccagataga cccgactccc gtgatcgtca cctccaacac caacatgtgc gccgtgattg   3600
acgggaactc aaacgacctc gaacaccagc agccgtttgg agaccggatg ttcaaatttg   3660
aactcacccg ccgtctggat catgactttg gaaggtcac caagcaggaa gtcaaagact    3720
ttttccggtg ggcaaaggat cacgtggttg aggtggagca tgaattctac gtcaaaaagg   3780
gtggagccaa gaaaagaccc gccccagtg acgcagatat aagtgagccc aaacgggtgc    3840
gcgagtcagt tgcgcagcca tcgacgtcag acgcggaagc ttcgatcaac tacgcagaca   3900
ggtaccaaaa caaatgttct cgtcacgtgg gcatgaatct gatgctgttt ccctgcagac   3960
aatgcgagag aatgaatcag aattcaaata tctgcttcac tcacggacag aaagactgtt   4020
tagagtgctt tcccgtgtca gaatctcaac ccgtttctgt cgtcaaaaag gcgtatcaga   4080
aactgtgcta cattcatcat atcatggaga aggtgccaga cgcttgcact gcctgcgctc   4140
tggtcaatgt ggatttggat gactgcatct ttgaacaata aaatggctag gatccggccg   4200
gcctgcaggt gtcctcacag gaacgaagtc cctaaagaaa cagtggcagc caggtttagc   4260
cccggaaaac ttgtttattg cagcttataa tggttacaaa taaagcaata gcatcacaaa   4320
tttcacaaat aaagcatttt tttcactgca ttctagttgt ggtttgtcca aactcatcaa   4380
tgtatcttat tgactggatt gagggacagc ccccccccaa agccccagg gatgtaatta    4440
cgtccctccc ccgctagggg gcagcagcga gccgcccggg gctccgctcc ggtccggcgc   4500
tcccccccgca tccccgagcc ggcagcgtgc ggggacagcc cgggcacggg gaaggtggca   4560
cgggatcgct ttcctctgaa cgcttctcgc tgctcttttga gcctgcagac acctgggggg   4620
atacgggaa aaggcctcca aggccagctt cccacaataa gttgggtgaa ttttggctca    4680
ttcctcctttt ctataggatt gaggtcagag cgacattgat tattgactag ttattaatag   4740
taatcaatta cggggtcatt agttcatagc ccatatatgg agttccgcgt tacataactt   4800
acggtaaatg gcccgcctgg ctgaccgccc aacgaccccc gcccattgac gtcaataatg   4860
acgtatgttc ccatagtaac gccaataggg actttccatt gacgtcaatg ggtggagtat   4920
ttacggtaaa ctgcccactt ggcagtacat caagtgtatc atatgccaag tacgccccct   4980
attgacgtca atgacggtaa atggcccgcc tggcattatg cccagtacat gaccttatgg   5040
gactttccta cttggcagta catctacgta ttagtcatcg ctattaccat ggtgatgcgg   5100
ttttggcagt acatcaatgg gcgtggatag cggtttgact cacggggatt tccaagtctc   5160
caccccattg acgtcaatgg gagtttgttt tggaaccaaa atcaacggga cttttccaaa   5220
tgtcgtaaca actccgcccc attgacgcaa atgggcggta ggcgtgtacg gtgggaggtc   5280
tatataagca gagctctccc tatcagtgat agagatctcc ctatcagtga tagagatcgt   5340
cgacgagctc gtttagtgaa ccgtcagatc gcctggagac gccatccacg ctgttttgac   5400
ctccatagaa gacaccggga ccgatccagc ctatcccaat tctgatgcgc cggtgatcag   5460
atcaaaaact tcagccaggt acgccaccat ggaactggtc ggatggctgg tggataaggg   5520
catcacaagc gagaagcaat ggatccagga ggaccaggcc tcatatattt ctttaacgc   5580
cgctagcaat tccagaagcc agatcaaggc tgctctgaca aacgccggca aaatcatgag   5640
cctgaccaag accgccctg actacctggt gggacagcag cctgtggaag atatcagcag   5700
caacagaatc tataagatcc tggaactgaa cggctacgac ccccagtacg ccgcctccgt   5760
gttcctgggc tgggctacaa agaagttcgg caagcggaac accatctggc tgttcggacc   5820
tgccaccaca ggcaaaacca atatgcccga ggccatccgc cacaccgtgc cttttctacgg   5880
ctgcgtgaac tggacaaacg agaacttccc cttcaacgac tgtgtggaca agatggtgat   5940
ctggtgggag gaaggcaaaa tgacagctaa ggtggtggaa tctgccaagg ctatcctggg   6000
aggctctaag gtcagggtgg atcagaagtg taaaagcagc gcccagattg accctacccc   6060
tgtgatcgtg accagcaata ccaacatgtg cgccgtgatc gacggcaaca gcaacgacct   6120
cgagcatcag cagcctctgc aggaccggat gttcaagttt gagctcacca gacgagctgga   6180
tcacgacttc ggcaaggtga ccaagcagga ggtgaaggat ttcttcagat gggcaaaga   6240
ccacgttgtt gaggtggaac acgagttcta cgtgaagaag gcggcgcca agaaaagacc     6300
cgcccctagc gacgccgaca tcagcgagcc taagagagtg cgggaaagcg tggcccagcc   6360
cagcacatct gatgctgagg ccagcatcaa ctacgccgat agataccaaa acaagtgcag   6420
ccgccacgtg ggcatgaacc tgatgctgtt tccctgcaga cagtgtgaaa gaatgaacca   6480
gaattctaat atctgcttta cacacggcca gaaagattgc tggaatgctt ccctgtgtc    6540
cgagagccaa ccagtgtctg tggtgaaaaa ggcctaccag aagctgtgct acatccacca   6600
catcatgggc aaggtgccag acgcctgtac cgcctgcgac ctggtcaacg tggacctgga   6660
cgactgcatc ttcgagcagt gatttgtgat gggaattctg tgctgtcct tctagttgcc   6720
agccatctgt tgtttgcccc tccccgtgc cttccttgac cctggaaggt gccactccca    6780
ctgtcctttc ctaataaat gaggaaattg catcgcattg tctgagtagg tgtcattcta   6840
ttctgggggg tggggtgggg caggacagca agggggagga ttgggaagac aatagcaggc   6900
atgctgggga tgcggtggc tctatgggac ctttttagg gcccattggt atggcttttt      6960
ccccgtatcc ccccaggtgt ctgcaggctc aaagagcag cagaggaaag                 7020
cgatcccgtc ccaccttccc cgtgcccggg ctgtccccgc acgctgccgg ctcggggatg   7080
cggggggagc gccggaccgg agcggagccc cggcggctc gctgctgccc cctagcgggg   7140
gagggacgta attacatccc tgggggcttt gggggggggc tgtccctcta gagcggccgc   7200
caccgcggtg gagctccagc ttttgttccc tttagtgagg gttaattaga tcttaatacg   7260
actcactata gggcgaattg ggtaccgggc cccctgagg cggaaagaac cagctgggc    7320
```

```
tctaggggt  atccccggg   ttggggttgc  gccttttcca  aggcagccct  gggtttgcgc  7380
agggacgcgg  ctgctctggg  cgtggttccg  ggaaacgcag  cggcgccgac  cctgggtctc  7440
gcacattctt  cacgtccgtt  cgcagcgtca  cccggatctt  cgccgctacc  cttgtgggcc  7500
ccccggcgac  gcttcctgct  ccgcccctaa  gtcgggaagg  ttccttgcgg  ttcgcggcgt  7560
gccggacgtg  acaaacggaa  gccgcacgtc  tcactagtac  cctcgcagac  ggacagcgcc  7620
agggagcaat  ggcagcgcgc  cgaccgcgat  gggctgtggc  caatagcggc  tgctcagcag  7680
ggcgcgccga  gagcagcggc  cgggaagggg  cggtgcggga  ggcggggtgt  ggggcggtag  7740
tgtgggccct  gttcctgccc  gcgcggtgtt  ccgcattctg  caagcctccg  gagcgcacgt  7800
cggcagtcgg  ctccctcgtt  gaccgaatca  ccgacctctc  tccccagaag  ctcccgggag  7860
cttgtatatc  cattttcgga  tctgatcagc  acgtgttgac  aattaatcat  cggcatagta  7920
tatcggcata  gtataatacg  acaaggtgag  gaacgccacc  atggccaagc  ctttgtctca  7980
agaagaatcc  accctcattg  aaagagcaac  ggctacaatc  aacagcatcc  ccatctctga  8040
agactacagc  gtcgccagcg  cagctctctc  tagcgacggc  cgcatcttca  ctggtgtcaa  8100
tgtatatcat  tttactgggg  gaccttgtgc  agaacttgcg  gtgctgggca  ctgctgctgc  8160
tgcggcagct  ggcaacctga  cttgtatcgt  cgcgatcgga  aatgagaaca  ggggcatctt  8220
gagccctgc  ggacggtgcc  gacaggtgct  tctcgatctg  catcctggga  tcaaagccat  8280
agtgaaggac  agtgatggac  agccgacggc  agttgggatt  cgtgaattgc  tgccctctgg  8340
ttatgtgtgg  gagggctaaa  gcgcggggat  ctcatgctgg  agttcttcgc  ccaccccaac  8400
ttgtttattg  cagcttataa  tggttacaaa  taaagcaata  gcatcacaaa  tttcacaaat  8460
aaagcatttt  tttcactgca  ttctagttgt  ggtttgtcca  aactcatcaa  tgtatcttat  8520
catgtctgta  gctgatgtat  acctaggatc  cggccggcct  gcaggtgtcc  tcacaggaac  8580
gaagtcccta  aagaaacagt  ggcagccagg  tttagcccag  gaattgactg  gattcctttt  8640
ttagggccca  ttggtatggc  tttttccccg  tatccccca   ggtgtctgca  ggctcaaaga  8700
gcagcgagaa  gcgttcagag  gaaagcgatc  ccgtgccacc  ttccccgtgc  ccgggctgtc  8760
cccgcacgct  gccggctcgg  ggatgcgggg  ggagcgccgg  accggagcgg  agccccgggc  8820
ggctcgctgc  tgcccctag   cgggggaggg  acgtaattac  atccctgggg  gcttgggg    8880
ggggctgtcc  ctctagagcg  gccgccaccg  cggtggagct  ccagcttttg  ttcccttag   8940
tgagggttaa  ttagatctta  atacgactca  ctatagggcg  aattgggtac  cgggccccc   9000
ctcgaggtcg  acggtatcct  cgaggtcgac  ggtatcgata  agcttgatat  ctataacaag  9060
aaaatatata  tataataagt  tatcacgtaa  gtagaacatg  aaataacaat  ataattatgc  9120
tatgagttaa  atcttaaaag  tcacgtaaaa  gataatcatg  cgtcattttg  actcacgcgg  9180
tcgttatagt  tcaaaatcag  tgacacttac  cgcattgaca  agcacgcctc  acgggagctc  9240
caagcggcga  ctgagatgtc  ctaaatgcac  agcgacggat  tcgcgctatt  tagaaagaga  9300
gagcaatatt  tcaagaatgc  atgcgtcaat  tttacgaca   ctatcttttct ctgggttaatc 9360
tagctgcatc  aggatcatat  cgtcgggtct  tttttccggc  tcagtcatcg  cccaagctgg  9420
cgctatctgg  gcatcggga   ggaagaagcc  cgtgccttt   cccgcgaggt  tgaagcggca  9480
tggaaagagt  ttgccgagga  tgactgctgc  tgcattgacg  ttgagcgaaa  acgcacgttt  9540
accatgatga  ttcgggaagg  tgtggccatg  cacgccttta  acggtgaact  gttcgttcag  9600
gccacctggg  ataccagttc  gtcgcggctt  ttccggacac  agttccggat  ggtcagcccg  9660
aagcgcatca  gcaacccgaa  caataccggc  gacagccgga  actgccgtgc  cggtgtgcag  9720
attaatgaca  gcggtgcggc  gctgggatat  tacgtcagcg  aggacgggta  tcctggctgg  9780
atgccgcaga  aatggacatg  gataccccgt  gagttacccg  gcgggcgcgc  ttggcgtaat  9840
catggtcata  gctgtttcct  gtgtgaaatt  gttatccgct  cacaattcca  cacaacatac  9900
gagccggaag  cataaagtgt  aaagcctggg  gtgcctaatg  agtgagctaa  ctcacattaa  9960
ttgcgttgcg  ctcactgccc  gctttccagt  cgggaaacct  gtcgtgccag  ctgcattaat  10020
gaatcggcca  acgcgcgggg  agaggcggtt  tgcgtattgg  gcgctcttcc  gcttcctcgc  10080
tcactgactc  gctgcgctcg  tcgttcggc   tgcggcgagc  ggtatcagct  cactcaaagg  10140
cggtaatacg  gttatccaca  gaatcagggg  ataacgcagg  aaagaacatg  tgagcaaaag  10200
gccagcaaaa  ggccaggaac  cgtaaaaagg  ccgcgttgct  ggcgtttttc  cataggctcc  10260
gcccccctga  cgagcatcac  aaaaatcgac  gctcaagtca  gaggtggcga  aacccgacag  10320
gactataaag  ataccaggcg  tttccccctg  gaagctccct  cgtgcgctct  cctgttccga  10380
ccctgccgct  taccggatac  ctgtccgcct  ttctcccttc  gggaagcgtg  gcgctttctc  10440
atagctcacg  ctgtaggtat  ctcagttcgg  tgtaggtcgt  tcgctccaag  ctgggctgtg  10500
tgcacgaacc  ccccgttcag  cccgaccgct  gcgccttatc  cggtaactat  cgtcttgagt  10560
ccaacccggt  aagacacgac  ttatcgccac  tggcagcagc  cactggtaac  aggattagca  10620
gagcgaggta  tgtaggcggt  gctacagagt  tcttgaagtg  gtggcctaac  tacggctaca  10680
ctagaaggac  agtatttggt  atctgcgctc  tgctgaagcc  agttaccttc  ggaaaaagag  10740
ttggtagctc  ttgatccggc  aaacaaacca  ccgctggtag  cggtggtttt  tttgtttgca  10800
agcagcagat  tacgcgcaga  aaaaaaggat  ctcaagaaga  tcctttgatc  ttttctacgg  10860
ggtctgacgc  tcagtggaac  gaaaactcac  gttaagggat  tttggtcatg  agattatcaa  10920
aaaggatctt  cacctagatc  cttttaaatt  aaaaatgaag  ttttaaatca  atctaaagta  10980
tatatgagta  aacttggtct  gacagttacc  aatgcttaat  cagtgaggca  cctatctcag  11040
cgatctgtct  atttcgttca  tccatagttg  cctgactccc  cgtcgtgtag  ataactacga  11100
tacgggaggg  cttaccatct  ggccccagtg  ctgcaatgat  accgcgagac  ccacgctcac  11160
cggctccaga  tttatcagca  ataaaccagc  cagccggaag  ggccgagcgc  agaagtggtc  11220
ctgcaacttt  atccgcctcc  atccagtcta  ttaattgttg  ccgggaagct  agagtaagta  11280
gttcgccagt  taatagtttg  cgcaacgttg  ttgccattgc  tacaggcatc  gtggtgtcac  11340
gctcgtcgtt  tggtatggct  tcattcagct  ccggttccca  acgatcaagg  cgagttacat  11400
gatccccat   gttgtgcaaa  aaagcggtta  gctccttcgg  tcctccgatc  gttgtcagaa  11460
gtaagttggc  cgcagtgtta  tcactcatgg  ttatggcagc  actgcataat  tctcttactg  11520
tcatgccatc  cgtaagatgc  ttttctgtga  ctggtgagta  ctcaaccaag  tcattctgag  11580
aatagtgtat  gcggcgaccg  agttgctctt  gcccggcgtc  aatacgggat  aataccgcgc  11640
cacatagcag  aactttaaaa  gtgctcatca  ttggaaaacg  ttcttcgggg  cgaaaactct  11700
caaggatctt  accgctgttg  agatccagtt  cgatgtaacc  cactcgtgca  cccaactgat  11760
cttcagcatc  ttttactttc  accagcgttt  ctgggtgagc  aaaaacagga  aggcaaaatg  11820
ccgcaaaaaa  gggaataagg  gcgacacgga  aatgttgaat  actcat                  11866
```

SEQ ID NO: 15       moltype = DNA   length = 11861
FEATURE             Location/Qualifiers

```
misc_feature      1..11861
                  note = Synthetic: PB-hiRep-2#
source            1..11861
                  mol_type = other DNA
                  organism = synthetic construct
SEQUENCE: 15
actcttcctt tttcaatatt attgaagcat ttatcagggt tattgtctca tgagcggata   60
catatttgaa tgtatttaga aaaataaaca aatagggggtt ccgcgcacat ttccccgaaa  120
agtgccacct aaattgtaag cgttaatatt ttgttaaaat tcgcgttaaa tttttgttaa  180
atcagctcat ttttaaccaa ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaaggggagcc cccgatttag agcttgacgg ggaaagccgg gaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggg agactcgcgg tgcaaatgtg ttttacagcg tgatggagca gatgaagatg  840
ctcgacacgc tgcagaacac gcagctagat taaccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata 1020
ataaattcaa caaacaattt atttatgttt atttatttat taaaaaaaaa caaaaactca 1080
aaatttcttc tataaagtaa caaaacttttt atcgaattcc tgcagcccgg gggatccact 1140
agttctagag ggacagcccc ccccccaaagc cccagggat gtaattacgt ccctccccg  1200
ctagggggca gcagcgagcc gcccgggggct ccgctccggg ccggcgctcc ccccgcatcc 1260
ccgagccggc agcgtgcggg gacagcccgg gcacggggaa ggtggcacgg gatcgctttc 1320
ctctgaacgc ttctcgctgc tctttgagcc tgcagacacc tgggggggata cggggaaaag 1380
gcctccaagg ccagcttccc acaataagtt gggtgaattt tggctcattc ctccttttcta 1440
taggattgag gtcagagctt tgtgatggga attctgtgga atgtgtgtca gttagggtgt 1500
ggaaagtccc gcgatcgcta gcttaagcgc tgatcaattg gcgcgccgaa ttcgttatct 1560
gcagaattcg gcttgacatt gattattgac tagttattaa tagtaatcaa ttacggggtc 1620
attagttcat agcccatata tggagttccg cgttacataa cttacggtaa atggcccgcc 1680
tggctgaccg cccaacgacc cccgcccatt gacgtcaata atgacgtatg ttcccatagt 1740
aacgccaata gggactttcc attgacgtca atgggtggag tatttacggt aaactgccca 1800
cttggcagta catcaagtgt atcatatgcc aagtacgccc cctattgacg tcaatgacgg 1860
taaatggccc gcctggcatt atgcccagta catgacctta tgggactttc ctacttggca 1920
gtacatctac gtattagtca tcgctattac catggtgatg cggttttggc agtacatcaa 1980
tgggcgtgga tagcggtttg actcacgggg atttccaagt ctccacccca ttgacgtcaa 2040
tgggagtttg ttttggaacc aaaatcaacg ggactttcca aaatgtcgta acaactccgc 2100
cccattgacg caaatgggcg gtaggcgtgt acggtgggag gtctatataa gcagagctct 2160
ccctatcagt gatagagatc tccctatcag tgatagagat cgtcgacgag tcgtttagt  2220
gaaccgtcag atcgcctgga gacgccatcc acgctgtttt gacctccata gaagacaccg 2280
ggaccgatcc agcctgaacg cgcagccgcc acgccgggt tttacgagat tgtgattaag 2340
gtccccagca accttgacga gcatctgccc ggcatttctg acagctttgt gaactgggtg 2400
gccgagaagg aatgggagtt gccgcagat tctgacatgg atctgaatct gattgagcag 2460
gcaccctga ccgtggccga gaagctgcag cgcgacttc tgacgaatg gcgccgtgtg 2520
agtaaggcc cggaggctct tttctttgtg caatttgaga agggagagag ctacttccac 2580
atgcacgtgc tcgtggaaac caccggggtg aaatccatgg tttggggacg tttcctgagt 2640
cagattgcg aaaactgat tcagagaatt taccgccgga tcgagccgac ttttgccaaac 2700
tggttcgcgg tcacaaagac cagaaatggc gccggaggcg ggaacaaggt ggtggatgag 2760
tgctacatcc ccaattactt gctccccaaa acccagcctg agctcaatg gcatggaccc 2820
aacatggaac agtacctcag cgcctgtttg aatctcacgg agcgtaaacg gttggtggcg 2880
cagcatctga cgcacgtgtc gcagacgcag gagcagaaca aagagaatca gaatcccaat 2940
tctgatgcgc cggtgatcag atcaaaaact tcagccaggt acatggagct ggtcgggtgg 3000
ctcgtggaca agggattac ctcggagaag cagtggatcc aggaggacca ggcctcatac 3060
atctccttca atgcggcctc caactcgcgg tcccaaatca aggctgcctt ggacaatgcg 3120
ggaaagatta tgagcctgac taaaacgcc cccgactacc tggtgggcca gcagcccgtg 3180
gaggcattt ccagcaatcg gatttataaa atttggaac taaacggta cgatccccaa 3240
tatgcggctt ccgtctttct gggatgggcc acgaaaaagt tcggcaagag gaacaccatc 3300
tggctgtttg ggcctgcaac taccgggaag accaacatcg cggaggccat agcccacact 3360
gtgcccttct acgggtgcgt aaactggacc aatgagaact ttcccttcaa cgactgtgtc 3420
gacaagatg tgatctggtg gaggagggg aagatgaccg ccaaggtgt ggagtcggcc 3480
aaagccattc tcggaggaag caaggtgcgc gtgaccaga atgcaagtc ctcggcccaa 3540
atagaccga ctcccgtgat cgtcacctcc aacaccaaca tgtgcgccgt gattgacggg 3600
aactcaacga ccttcgaaca ccagcagccg ttgcaagacc ggatgttcaa atttgaactc 3660
accccgccgtc tggatcatga ctttgggaag gtcaccaagc aggaagtgaa agacttttt  3720
cggttgcaa aggatcacgt ggttgaggtg agcatgaat tctcagtcaa aaagggtgga 3780
gccaagaaaa gacccgcccc cagtgacgca gatataagtg agcccaaacg ggtgcgcgag 3840
tcagttgcgc agccatcgac gtcagacgcg gaagcttcga tcaactacgc agacaggtac 3900
caaaacaaat gttctcgtca cgtgggcatg aatctgatgc tgtttcctg cagacaatgc 3960
gagagaatga atcagaattc aaatatctgc ttcactcacg acagaaaga ctgtttagag 4020
tgctttcccg tgtcagaatc tcaacccgtt tctgtcgtca aaaggcgta tcagaaactg 4080
tgctacattc atcatatcat gggaaaggtg ccagacgctt gcactgcctg cgatctggtc 4140
aatgtggatt tggatgactg catctttgaa caataaaatg gctaggatcc ggccggcctg 4200
caggtgtcct cacaggaacg aagtccctaa agaaacagtg gcagcaggt ttagccccgg 4260
aaaacttgtt tattgcagct tataatggtt acaaataaag caatagcatc acaaatttca 4320
caaataaagc atttttttca ctgcattcta gttgtggttt gtccaaactc atcaatgtat 4380
```

```
cttattgact ggattgaggg acagccccc cccaaagccc ccagggatgt aattacgtcc    4440
ctcccccgct aggggggcagc agcgagccgc ccggggctcc gctccggtcc ggcgctcccc    4500
ccgcatcccc gagccggcag cgtgcgggga cagcccgggc acggggaagg tggcacggga    4560
tcgctttcct ctgaacgctt ctcgctgctc tttgagcctg cagacacctg gggggatacg    4620
gggaaaaggc ctccaaggcc agcttccac aataagttgg gtgaattttg gctcattcct    4680
cctttctata ggattgaggt cagagcgaca ttgattattg actagttatt aatagtaatc    4740
aattacgggg tcattagttc atagcccata tatggagttc cgcgttacat aacttacggt    4800
aaatggcccg cctggctgac cgcccaacga cccccgccca ttgacgtcaa taatgacgta    4860
tgttcccata gtaacgccaa tagggacttt ccattgacgt caatgggtgg agtatttacg    4920
gtaaactgcc cacttggcag tacatcaagt gtatcatatg ccaagtacgc cccctattga    4980
cgtcaatgac ggtaaatggc ccgcctggca ttatgcccag tacatgacct tatgggactt    5040
tcctacttgg cagtacatct acgtattagt catcgctatt accatggtga tgcggttttg    5100
gcagtacatc aatgggcgtg gatagcggtt tgactcacgg gatttccaa gtctccaccc    5160
cattgacgtc aatgggagtt tgttttggaa ccaaaatcaa cgggactttc caaaatgtcg    5220
taacaactcc gccccattga cgcaaatggg cggtaggcgt gtacggtggg aggtctatat    5280
aagcagagct ctccctatca gtgatagaga tctccctatc agtgatagag atcgtcgacg    5340
agctcgttta gtgaaccgtc agatcgcctg gagacgccat ccacgctgtt ttgacctcca    5400
tagaagacac cgggaccgat ccagcctatc ccaattctga tgccgcggtg atcagatcaa    5460
aaacttcagc caggtacgcc accatgaac tggtcggatg gctggtggat aagggcatca    5520
caagcgagaa gcaatggatc caggaggacc aggcctcata tatttctttt aacgccgcta    5580
gcaattccag aagccagatc aaggctgctc tggacaacgc cggcaaaatc atgagcctga    5640
ccaagacgc ccctgactac ctggtggacg agcagcctgt ggaagatatc agcagcaaca    5700
gaatctataa gatcctggaa ctgaacggct acgaccccca gtacgccgcc tccgtgttcc    5760
tgggctgggc tacaaagaag ttcggcaagc ggaacaccat ctggctgttc ggacctgcca    5820
ccacaggcaa aaccaatatc gccgaggcca tcgcccacac cgtgcctttc tacggctgcg    5880
tgaactggac aaacgagaac ttccccttca acgactgtgt gacaagatg gtgatctgga    5940
gggaggaagg caaaatgaca gctaaggtgg tggaatctgc caaggctatc ctggaggct    6000
ctaaggtcag ggtggatcag aagtgtaaaa gcagcgccca gattgaccct accctgtga   6060
tcgtgaccag caataccaac atgtgcgccg tgatcgacgg caacagcacc accttcgagc    6120
atcagcagcc tctgcaggac cagatggttca agtttgagct caccagacgg ctggatcacg    6180
acttcggcaa ggtgaccaag caggaggtga aggatttctt cagatgggcc aaagaccacg    6240
ttgttgaggt ggaacacgag ttctacgtga agaagggcgg cgccaagaaa agacccgccc    6300
ctagcgacgc cgacatcagc gagcctaaga gagtgcggga agcgtggcc cagcccagca    6360
catctgatgc tgaggccagc aacaactacg ccgatagata ccaaaaacaag tgcagccgca    6420
acgtgggcat gaacctgatg ctgtttccct gcagacagtg tgaaagaatg aaccagaatt    6480
ctaatatctg ctttacacac ggccagaag attgcctgga atgcttccct gtgtccgaga    6540
gccaaccagt gtctgtggtg aaaaaggcct accagaagct gtgctacatc caccacatca    6600
tgggcaaggt gccagacgcc tgtaccgcct gcgacctggt caacgctggac ctggacgact    6660
gcatcttcga gcagtgattt gtgatggaa ttctgtctag ttgccagaca    6720
tctgttgttt gcccctcccc cgtgccttcc ttgaccctgg aaggtgccac tcccactgtc    6780
ctttcctaat aaaatgagga aattgcatcg cattgtctga gtaggtgtca ttctattctg    6840
gggggtgggg tggggcagga cagcaagggg gaggattggg aagacaatag caggcatgct    6900
ggggatgcgg tgggctctat ggaccttttt ttaggggacca ttggtatggc ttttccccg    6960
tatccccca ggtgtctgca ggctcaaaga gcagcgagaa gcgttcagag gaaagcgatc    7020
ccgtgccacc ttccccgtgc ccgggctgtc ccgcacgct gccggctcgg ggatgcgggg    7080
ggagcgccgg accggagcgg agccccgggc ggctcgctgc tgccccctag cggggaggg    7140
acgtaattac atccctgggg gctttggggg gggcgtgtcc ctctagagcg gccgccaccg    7200
cggtggagct ccagcttttg ttccctttag tgagggttaa ttagatctta atacgactca    7260
ctataggcc aattgggtac cggcccccc tgaggcggaa agaaccagct ggggctctag    7320
ggggtatccc cggggtggg gttgcgcctt ttccaaggca gccctgggtt tgcgcaggga    7380
cgcggctgct ctgggcgtgg ttccgggaaa cgcagcgggc ccgaccctgg gtctcgcaca    7440
ttcttcacgt ccgttcgcag cgtcaccccgg atcttcgccg ctaccttgt gggccccccg    7500
gcgacgcttc ctgctccgcc cctaagtcgg gaaggttcct tgcggttcgc ggcgtgccgg    7560
acgtgacaaa cggaagccgc acgtctcact agtaccctcg cagacggaca gcgccaggga    7620
gcaatggcag cgcgccgacc gcgatgggct gtggccaata gcggctgctc agcaggggcc    7680
gccgagagca gcggccggga aggggcggtg cgggaggcgg ggtgtggggc ggtagtgtgg    7740
gccctgttcc tgcccgcgcg gtgttccgca ttctgcaagc ctccggagcg cacgtccggca    7800
gtcggctccc tcgttgaccg aatcaccgac ctctctcccc agaagctccc gggagcttgt    7860
atatccattt tcggatctga tcagcacgtg ttgacaatta atcatcggca tagtatatcg    7920
gcatagtata atacgacaag gtgaggaacg ccaccatggc caagcctttg tctcaagaag    7980
aatccaccct cattgaaaga gcaacggcta caatcaacag catccccatc tctgaagact    8040
acagcgtcgc cagcgcagct ctctctagcg acggccgcat cttcactggt gtcaatgtat    8100
atcatttac tgggggacct tgtgcagaac tcgtggtgct gggcactgct gctgctgcgg    8160
cagctggcaa cctgacttgt atcgtcgcga tcggaaatga gaacaggggc atcgtggaaa    8220
cctgcggacg gtgccgacag gtgcttctcg atctgcatcc tgggatcaaa gccatagtga    8280
aggacagtga tggacagccg acggcagttg ggattcgtga attgctgccc tctggttatg    8340
tgtgggaggg ctaaagcgcg gggatctcat gctgagttc ttcgcccacc caacttgtt    8400
tattgcagct tataatggtt acaaataaag caatagcatc acaaatttca caaataaagc    8460
atttttca ctgcattcta gttgtggttt gtccaaactc atcaatgtat cttatcatgt    8520
ctgtagctga tgtataccta ggatccggcc ggcctgcagg tgtcctcaca ggaacgaagt    8580
ccctaaagaa acagtggcag ccaggtttag ccccggaatt gactggattc cttttttagg    8640
gcccattggt atggcttttt ccccgtatcc ccccaggtgt ctgcaggctc aaagagcagc    8700
gagaagcgtt cagaggaaag cgatcccgtg ccacttcc cgtgccggg ctgtcccgc    8760
acgctgccgg ctcggggatg cgggggggagc accgagccc cggggggcggc    8820
gctgctgccc cctagcgggg gagggacgta attacatccc tgggggcttt ggggggggc    8880
tgtccctcta gagcggccgc caccgcgtgt gagctccagc ttttgttccc tttagtgagg    8940
gttaattaga tcttaatacg actcactata gggcgaattg gtaccgggc cccccctcga    9000
ggtcgacggt atcctcgagg tcgacggtat cgataagctt gatatctata acaagaaaat    9060
atatataaa taagttatca cgtaagtaga acatgaaata acaatataat tatcgtatga    9120
```

| | | | | |
|---|---|---|---|---|
| gttaaatctt | aaaagtcacg | taaaagataa | tcatgcgtca | ttttgactca cgcggtcgtt 9180 |
| atagttcaaa | atcagtgaca | cttaccgcat | tgacaagcac | gcctcacggg agctccaagc 9240 |
| ggcgactgag | atgtcctaaa | tgcacagcga | cggattcgcg | ctatttagaa agagagagca 9300 |
| atatttcaag | aatgcatgcg | tcaattttac | gcagactatc | tttctagggt taatctagct 9360 |
| gcatcaggat | catatcgtcg | ggtctttttt | ccggctcagt | catcgcccca gctggcgcta 9420 |
| tctgggcatc | ggggaggaag | aagcccgtgc | cttttcccgc | gaggttgaag cggcatggaa 9480 |
| agagtttgcc | gaggatgact | gctgctgcat | tgacgttgag | cgaaaacgca cgtttaccat 9540 |
| gatgattcgg | gaaggtgtgg | ccatgcacgc | ctttaacggt | gaactgttcg ttcaggccac 9600 |
| ctgggatacc | agttcgtcgc | ggcttttccg | gacacagttc | cggatggtca gcccgaagcg 9660 |
| catcagcaac | ccgaacaata | ccggcgacag | ccggaactgc | cgtgccggtg tgcagattaa 9720 |
| tgacagcggt | gcggcgctgg | gatattacgt | cagcgaggac | gggtatcctg gctggatgcc 9780 |
| gcagaaatgg | acatggatac | cccgtgagtt | acccggcggg | cgcgcttggc gtaatcatgg 9840 |
| tcatagctgt | ttcctgtgtg | aaattgttat | ccgctcacaa | ttccacacaa catacgagcc 9900 |
| ggaagcataa | agtgtaaagc | ctggggtgcc | taatgagtga | gctaactcac attaattgcg 9960 |
| ttgcgctcac | tgcccgcttt | ccagtcggga | aacctgtcgt | gccagctgca ttaatgaatc 10020 |
| ggccaacgcg | cggggagagg | cggtttgcgt | attgggcgct | cttccgcttc ctcgctcact 10080 |
| gactcgctgc | gctcggtcgt | tcggctgcgg | cgagcggtat | cagctcactc aaaggcggta 10140 |
| atacggttat | ccacagaatc | aggggataac | gcaggaaaga | acatgtgagc aaaaggccag 10200 |
| caaaaggcca | ggaaccgtaa | aaaggccgcg | ttgctggcgt | ttttccatag gctccgcccc 10260 |
| cctgacgagc | atcacaaaaa | tcgacgctca | agtcagaggt | ggcgaaaccc gacaggacta 10320 |
| taaagatacc | aggcgtttcc | ccctggaagc | tccctcgtgc | gctctcctgt tccgaccctg 10380 |
| ccgcttaccg | gatacctgtc | cgcctttctc | ccttcggaag | cgtggcgctt tctcatagc 10440 |
| tcacgctgta | ggtatctcag | ttcggtgtag | gtcgttcgct | ccaagctggg ctgtgtgcac 10500 |
| gaaccccccg | ttcagcccga | ccgctgcgcc | ttatccggta | actatcgtct tgagtccaac 10560 |
| ccggtaagac | acgacttatc | gccactggca | gcagccactg | gtaacaggat tagcagagcg 10620 |
| aggtatgtag | gcggtgctac | agagttcttg | aagtggtggc | ctaactacgg ctacactaga 10680 |
| aggacagtat | ttggtatctg | cgctctgctg | aagccagtta | ccttcggaaa aagagttggt 10740 |
| agctcttgat | ccggcaaaca | aaccaccgct | ggtagcggtg | gtttttttgt ttgcaagcag 10800 |
| cagattacgc | gcagaaaaaa | aggatctcaa | gaagatcctt | tgatcttttc tacggggtct 10860 |
| gacgctcagt | ggaacgaaaa | ctcacgttaa | gggattttgg | tcatgagatt atcaaaaagg 10920 |
| atcttcacct | agatcctttt | aaattaaaaa | tgaagtttta | aatcaatcta agtatatat 10980 |
| gagtaaactt | ggtctgacag | ttaccaatgc | ttaatcagtg | aggcacctat ctcagcgatc 11040 |
| tgtctatttc | gttcatccat | agttgcctga | ctccccgtcg | tgtagataac tacgatacgg 11100 |
| gagggcttac | catctggccc | cagtgctgca | atgataccgc | gagaccacg ctcaccggct 11160 |
| ccagatttat | cagcaataaa | ccagccagcc | ggaagggccg | agcgcagaag tggtcctgca 11220 |
| actttatccg | cctccatcca | gtctattaat | tgttgccggg | aagctagagt aagtagttcg 11280 |
| ccagttaata | gtttgcgcaa | cgttgttgcc | attgctacag | gcatcgtggt gtcacgctcg 11340 |
| tcgtttggta | tggcttcatt | cagctccggt | tcccaacgat | caaggcgagt tacatgatcc 11400 |
| cccatgttgt | gcaaaaaagc | ggttagctcc | ttcggtcctc | cgatcgttgt cagaagtaag 11460 |
| ttggccgcag | tgttatcact | catggttatg | gcagcactgc | ataattctct tactgtcatg 11520 |
| ccatccgtaa | gatgcttttc | tgtgactggt | gagtactcaa | ccaagtcatt ctgagaatag 11580 |
| tgtatgcggc | gaccgagttg | ctcttgcccg | gcgtcaaatac | gggataatac cgcgccacat 11640 |
| agcagaactt | taaaagtgct | catcattgga | aaacgttctt | cggggcgaaa actctcaagg 11700 |
| atcttaccgc | tgttgagatc | cagttcgatg | taacccactc | gtgcacccaa ctgatcttca 11760 |
| gcatctttta | ctttcaccag | cgtttctggg | tgagcaaaaa | caggaaggca aaatgccgca 11820 |
| aaaaagggaa | taagggcgac | acggaaatgt | tgaatactca | t 11861 |

```
SEQ ID NO: 16         moltype = DNA  length = 11580
FEATURE               Location/Qualifiers
misc_feature          1..11580
                      note = Synthetic: PB-hiRep-3#
source                1..11580
                      mol_type = other DNA
                      organism = synthetic construct
SEQUENCE: 16
```

| | | | | |
|---|---|---|---|---|
| actcttcctt | tttcaatatt | attgaagcat | ttatcagggt | tattgtctca tgagcggata 60 |
| catatttgaa | tgtatttaga | aaaataaaca | aatagggggtt | ccgcgcacat ttccccgaaa 120 |
| agtgccacct | aaattgtaag | cgttaatatt | ttgttaaaat | tcgcgttaaa ttttttgtta 180 |
| atcagctcat | tttttaacca | ataggccgaa | atcggcaaaa | tcccttataa atcaaaagaa 240 |
| tagaccgaga | tagggttgag | tgttgttcca | gtttggaaca | agagtccact attaaagaac 300 |
| gtggactcca | acgtcaaagg | gcgaaaaacc | gtctatcagg | gcgatggccc actacgtgaa 360 |
| ccatcaccct | aatcaagttt | tttggggtcg | aggtgccgta | aagcactaaa tcggaaccct 420 |
| aaagggagcc | cccgatttag | agcttgacgg | ggaaagccgg | cgaacgtggc gagaaaggaa 480 |
| gggaagaaag | cgaaaggagc | gggcgctagg | gcgctgcaa | gtgtagcggt cacgctgcgc 540 |
| gtaaccacca | cacccgccgc | gcttaatgcg | ccgctacagg | gcgcgtccca ttcgccattc 600 |
| aggctgcgca | actgttggga | agggcgatcg | gtgcgggcct | cttcgctatt acgccagctg 660 |
| gcgaaagggg | gatgtgctgc | aaggcgatta | agttgggtaa | cgccagggtt ttcccagtca 720 |
| cgacgttgta | aaacgacggc | cagtgagcgc | gcctcgttca | ttcacgtttt tgaacccgtg 780 |
| gaggacgggc | agactcgcgg | tgcaaatgtg | ttttacagcg | tgatggagca gatgaagatg 840 |
| ctcgacacgc | tgcagaacac | gcagctagat | taacctagna | aagataatca tattgtgacg 900 |
| tacgttaaag | ataatcatgc | gtaaaattga | cgcatgtgtt | ttatcggtct gtatatcgag 960 |
| gtttatttat | taatttgaat | agatattaag | ttttattata | tttacactta catactaata 1020 |
| ataaattcaa | caaacaattt | atttatgttt | atttatttat | taaaaaaaa caaaaactca 1080 |
| aaatttcttc | tataaagtaa | caaaactttt | atcgaattcc | tgcagcccgg gggatccatt 1140 |
| agttctagag | ggacagcccc | cccccaaagc | cccaggagat | gtaattacgt ccctcccccg 1200 |
| ctaggggggca | gcagcgagcc | gcccgggggct | ccgtccggt | ccggcgctcc cccgcatcc 1260 |
| ccgagccggca | agcgtgcggg | gacagcccgg | gcacggggaa | ggtggcacgg gatcgctttc 1320 |
| ctctgaacgc | ttctcgctgc | tctttgagcc | tgcagacacc | tgggggggata cggggaaaag 1380 |
| gcctccaagg | ccagcttccc | acaataagtt | gggtgaattt | tggctcattc ctccttttcta 1440 |

```
taggattgag gtcagagctt tgtgatggga attctgtgga atgtgtgtca gttagggtgt   1500
ggaaagtccc gcgatcgcta gcttaagcgc tgatcaattg gcgcgccgaa ttcgttatct   1560
gcagaattcg gcttggcctc cgcgccgggt tttggcgcct cccgcgggcg ccccctcct    1620
cacggcgagc gctgccacgt cagacgaagg gcgcagcgag cgtcctgatc cttccgcccg   1680
gacgctcagg acagcggccc gctgctcata agactcgctt ttagaacccc agtatcagca   1740
gaaggacatt ttaggacggg acttgggtga ctctagggca ctggttttct ttccagagag   1800
cggaacaggc gaggaaaagt agtcccttct cggcgattct gcggagggat ctccgtgggg   1860
cggtgaacgc cgatgattat ataaggacgc gccggtccct atcagtgata gagatctccc   1920
tatcagtgat agagagtgtg gcacagctag ttccgtcgca gccgggattt gggtcgcggt   1980
tcttgttttgt ggatcgctgt gatcgtcact tgacgaacgc gcagccgcca tgccgggtt    2040
ttacgagatt gtgattaagg tccccagcga ccttgacgag catctgcccg gcatttctga   2100
cagctttgtg aactgggtgg ccgagaagga atgggagttg ccgccagatt ctgacatgga   2160
tctgaatctg attgagcagg cacccctgac cgtggccgag aagctgcagc gcgactttct   2220
gacggaatgg cgccgtgtga gtaaggcccc ggaggctctt ttctttgtgc aatttgagaa   2280
gggagagagc tacttccaca tgcacgtgct cgtggaaacc accggggtga atccatggt    2340
tttgggacgt ttcctgagtc agattcgcga aaaactgatt cagagaattt accgcgggat   2400
cgagccgact ttgccaaact ggttcgcggt cacaaagacc agaaatggcg ccggaggcgg   2460
gaacaaggtg gtggatgagt gctacatccc caattacttg ctcccccaaaa ccagcctgga   2520
gctccaatgg gcatggacca acatggaaca gtacctcagc gcctgtttga atctcacgga   2580
gcgtaaacgg ttggtggcgc agcatctgac gcacgtgtcg cagacgcagg agcagaacaa   2640
agagaatcag aatcccaatt ctgatcgcc ggtgatcaga tcaaaaactt cagccaggta   2700
catggagctg gtcgggtggc tcgtggacaa ggggattacc tcggagaagc agtggatcca   2760
ggaggaccag gcctcataca tctccttcaa tgccggcctcc aactcgcggt cccaaaatcaa   2820
ggctgccttg gacaatgcgg gaaagattat gagcctgact aaaaccgccc ccgactacct   2880
ggtgggccag cagcccgtgg aggacatttc cagcaatcgg atttataaaa ttttggaact   2940
aaacgggtac gatccccaat atgcggcttc cgtcttcctg ggatggccca cgaaaaagtt   3000
cggcaagagg aacaccatct ggctgtttgg gcctgcaact accggaaga ccaacatcgc    3060
ggaggccata gcccacactg tgcccttcta cgggtgcgta aactgacca atgaaactt     3120
tcccttcaac gactgtgtcg acaagatggt gatctggtgg gaggagggga agatgaccgc   3180
caaggtcgtg gagtcggcca aagccattct cggaggaagc aaggtgcgcg tggaccagaa   3240
atgcaagtcc tcggcccaga tagacccgac tcccgtgatc gtcacctcca acaccaacat   3300
gtgcgccgtg attgacggga actcaacgac cttcgaacac cagcagccgt tgcaagaccg   3360
gatgttcaaa tttgaactca cccgccgtct ggatcatgac tttgggaagg tcaccaagca   3420
ggaagtcaaa gacttttttcc ggtgggcaaa ggatcacgtg gttgaggtgg agcatgaatt   3480
ctacgtcaaa aagggtggag ccaagaaaag acccgccccc agtgacgcag atataagtga   3540
gcccaaacgg gtgcgcgagt cagttgcgca gccatcgacg tcagacgcgg aagcttcgat   3600
caactacgca gacaggtacc aaaacaaatg ttctcgtcac gtgggcatga atctgatgct   3660
gtttccctgc agacaatgcg agagaatgaa tcagaattca aatatcgct tcactcacgg    3720
acagaaagac tgtttagagt gctttcccgt gtcagaatct caacccgtt ctgtcgtcaa    3780
aaaggcgtat cagaaactgt gctacattca tcatatcatg ggaaaggtgc cagacgcttg   3840
cactgcctgc gatctggtca atgtggattt ggatgactgc atctttgaac aataaaaatgg   3900
ctaggatccg gccggcctgc aggtgtcctc acaggaacga agtccctaaa gaaacagtgg   3960
cagccaggtt tagccccgga aaacttgttt attgcagctt ataatggtta caataaagc    4020
aatagcatca caaatttcac aaataaagca tttttttcac tgcattctag ttgtggtttg   4080
tccaaactca tcaatgtatc ttattgactg gattgaggga cagcccccc ccaaagcccc    4140
cagggatgta attacgtccc tccccgcta ggggcagca gcgagccgcc cggggctccg     4200
ctccgtccg gcgctcccc cgcatccccg agccggcagc gtcggggac agcccgggca      4260
cggggaaggt ggcacgggat cgctttcctc tgaacgcttc tcgctgctct ttgagcctgc   4320
agacacctgg ggggatacgg ggaaaaggcc tccaaggcca gcttcccaca ataagttggg   4380
tgaattttgt ctcattcctc cttctatag gattgaggtc agagcgacat tgattattga   4440
ctagttatta atagtaatca attacggggt cattagttca tagcccatat atggagttcc   4500
gcgttacata acttacggta aatgcccgc ctgctgacc gcccaacgac ccccgcccat     4560
tgacgtcaat aatgacgtat gttcccatag taacgccaat agggactttc cattgacgtc   4620
aatgggtgga gtatttacgg taaactgccc acttggcagt acatcaagtg tatcatatgc   4680
caagtacgcc ccctattgac gtcaatgacg gtaaatgccc gcctggcat tatgcccagt    4740
acatgaccctt atgggacttt cctacttggc agtacatcta cgtattagtc atcgctatta   4800
ccatggtgat gcggttttgg cagtacatca atgggcgtgg atagcggttt gactcacggg   4860
gatttccaag tctccacccc attgacgtca atgggagttt gttttggaac caaaatcaac   4920
gggactttcc aaaatgtcgt aacaactccg ccccattgac gcaaatgggc ggtaggcgtg   4980
tacggtggga ggtctatata agcagagctc tccctatcag tgatagagat ctccctatca   5040
gtgatagaga tcgtcgacga gctcgtttag tgaaccgtca gatcgcctgg agacgccatc   5100
cacgctgttt tgacctccat agaagacacc gggaccgatc cagcctatcc caattctgat   5160
gcgccggtga tcagatcaaa aacttcagcc aggtacgcca ccatgaact ggtcggatgg    5220
ctggtggata agggcatcac aagcgagaag caatgacca ggaggacca ggcctcatat     5280
atttctttta acgccgctag caattccaga agccagatca aggctgctct ggacaacgcc   5340
ggcaaaatca tgagcctgac caagaccgcc cctgactacc tggtgggaca gcagcctgtg   5400
gaagatatca gcagcaacag aatctataag atcctggaac tgaacggcta cgaccccag    5460
tacgccgcct ccgtgttcct gggctgggct acaaagaagt tcggcaagcg gaacaccatc   5520
tggctgttcg gacctgccac cacaggcaaa accaatatcg ccgaggccat cgccacacc    5580
gtgcctttct acggctgcgt gaactggaca aacgagaact tccccttcaa cgactgtgtg   5640
gacaagatgg tgatctggtg gaggaaggc aaaatgacag ctaaggtggt ggaatctgcc    5700
aaggctatcc tgggaggctc taaggtcagg gtggatcaga agtgtaaaag cagcccccag   5760
attgacccta cccctgtgat cgtgaccagc aataccaaca tgtgcgccgt gatcgacggc   5820
aacagcacca ccttcgagca tcagcagcct ctgcaggacc gatgttcaa gtttgagctc   5880
accagacgac tggatcacga cttcggcaag gtgaccaagc aggaggtgaa ggatttcttc   5940
agatgggcca agaccacgt tgttgaggtg aacacgagt tctacgtgaa gaagggcggc     6000
gccaagaaaa gacccgcccc tagcgacgcc gacatcagcg agcctaagag agtgcggaa    6060
agcgtggccc agcccagcac atctgatgct gaggccagca tcaactacgc cgatagatac   6120
caaaacaagt gcagccgcca cgtgggcatg aacctgatgc tgtttccctg cagacagtgt   6180
```

```
gaaagaatga accagaattc taatatctgc tttacacacg gccagaaaga ttgcctggaa    6240
tgcttccctg tgtccgagag ccaaccagtg tctgtggtga aaaaggccta ccagaagctg    6300
tgctacatcc accacatcat gggcaaggtg ccagacgcct gtaccgcctg cgacctggtc    6360
aacgtggacc tggacgactg catcttcgag cagtgatttg tgatgggaat tctgtgctgt    6420
gccttctagt tgccagccat ctgttgtttg ccctccctcc gtgccttcct tgaccctgga    6480
aggtgccact cccactgtcc tttcctaata aaatgaggaa attgcatcgc attgtctgag    6540
taggtgtcat tctattctgg ggggtggggt gggcaggac agcaagggg aggattggga     6600
agacaatagc aggcatgctg gggatgcggt gggctctatg ggacctttt tagggcccat    6660
tggtatggct ttttccccgt atcccccag gtgtctgcag gctcaaagag cagcgagaag    6720
cgttcagagg aaagcgatcc cgtgccacct tccccgtgcc cgggctgtcc ccgcacgctg    6780
ccggctcggg gatgcggggg gagcgccgga ccggagcgga gccccgggcg gctcgctgct    6840
gccccctagc gggggaggga cgtaattaca tccctgggg ctttgggggg gggctgtccc     6900
tctagagcgg ccgccaccgc ggtggagctc cagcttttgt tccctttagt gagggttaat    6960
tagatcttaa tacgactcac tatagggcga attgggtaac gggccccct gaggcggaaa     7020
gaaccagctg gggctctagg gggtatccc ggggttgggg ttgcgccttt tccaaggcag     7080
ccctgggttt gcgcagggac gcggctgctc tgggcgtggt tccgggaaac gcagcggcgc    7140
cgaccctggg tctcgcacat tcttcacgtc cgttcgcagc gtcacccgga tcttcgccgc    7200
tacccttgtg ggccccccgg cgacgcttcc tgctccgccc ctaagtcggg aaggttcctt    7260
gcggttcgcg gcgtgccgga cgtgacaaac ggaagccgca cgtctcacta gtaccctcgc    7320
agacggacag cgccagggag caatggcagc gcgccaccg cgatgggctg tggccaatag     7380
cggctgctca gcagggcgcg ccgagagcag cggccgggaa ggggcggtgc gggaggcggg    7440
gtgtggggca gtagtgtggg ccctgttcct gcccgcggg tgttccgcat tctgcaagcc     7500
tccgagcgc acgtcggcag tcggctccct cgttgaccga atcaccgacc tctctcccca     7560
gaagctcccg ggagcttgta tatccatttt cggatctgat cagcacgtgt tgacaattaa    7620
tcatcggcat agtatatcgg catagtataa tacgacaagg tgaggaacgc caccatggcc    7680
aagcctttgt ctcaagaaga atccaccctc attgaaagag caacggctac aatcaacagc    7740
atccccatct ctgaagacta cagcgtcgcc agcgcagctc tctctagcga cggccgcatc    7800
ttcactggtg tcaatgtata tcattttact gggggacctt gtgcagaact cgtggtgctg    7860
ggcactgctg ctgctgcggc agctggcaac ctgacttgta tcgtcgcgat cggaaatgag    7920
aacaggggca tcttgagccc ctgcggacgg tgccgacagg tgcttctcga tctgcatcct    7980
gggatcaaag ccatagtgaa ggacagtgat ggacagccga cggcagttgg gattcgtgaa    8040
ttgctgccct ctggttatgt gtgggagggc taaagcgcgg ggatcctcatg ctggagttct   8100
tcgcccaccc caacttgttt attgcagctt ataatggtta caaataaagc aatagcatca    8160
caaatttcac aaataaagca ttttttttcac tgcattctag ttgtggtttg tccaaactca   8220
tcaatgtatc ttatcatgtc tgtagctgat gtataccgag atccggccg gcctgcaggt     8280
gtcctcacag gaacgaagtc cctaaagaaa cagtggcagc caggtttagc cccggaattg    8340
actggattcc tttttaggg cccattggta tggctttttc cccgtatccc ccaggtgtc     8400
tgcaggctca aagagcagcg agaagcgttc agaggaaagc gatcccgtgc caccttcccc    8460
gtgccgggc tgtccccgca cgctgccggc tcggggatgc ggggggagcg ccggaccgga    8520
gcggagcccc gggcggctcg ctgctgcccc ctagcggggg agggacgtaa ttacatccc    8580
gggggctttg ggggggggct gtccctag agcggccgcc accgcggtgg agctccagct     8640
tttgttccct ttagtgaggg ttaattagat cttaatacga ctcactatag gcgaattgg    8700
gtaccgggcc cccctcgag gtcgacggta tcctcgaggt cggcgtatc gataagcttg    8760
atatctataa caagaaaata tatatataat aagttatcac gtaagtagaa catgaaataa    8820
caatataatt atcgtatgag ttaatctta aaagtcacgt aaaagataat catgcgtcat     8880
tttgactcac gcggtcgtta tagttcaaaa tcagtgacac ttaccgcatt gacaagcacg    8940
cctcacggga gctccaagcg gcgactgaga tgtcctaaat gcacagcgac ggattcgcgc    9000
tatttagaaa gagagagcaa tattcaaga atgcatgcgt caattttacg cagactatct     9060
ttctagggtt aatctagctg catcaggatc atatcgtcgg gtctttttc cggctcagtc     9120
atcgcccaag ctggcgctat ctgggcatcg ggaggaagaa agcccgtgcc ttttcccgcg    9180
aggttgaagc ggcatggaaa gagtttgccg aggatgactg ctgctgcatt gacgttgagc    9240
gaaaacgcac gtttaccatg atgattcggg aaggtgtggc catgcacgcc tttaacggtg    9300
aactgttcgt tcaggccacc tgggatacca gttcgtcgcg gcttttccgg acacagttcc    9360
ggatggtcag cccgaagcgc atcagcaacc cgaacaatac cggcgacagc cggaactgcc    9420
gtgccggtgt gcagattaat gacagcggtg cggcgctggg atattacgtc agcgaggacg    9480
ggtatcctgg ctggatgcca cagaaatgga catggatacc ccgtgagtta cccggcgggc    9540
gcgcttggcg taatcatggt catagctgtt cctgtgtga aattgttatc cgctcacaat    9600
tccacacaac atacgagccg gaagcataaa gtgtaaagcc tggggtgcct aatgagtgag    9660
ctaactcaca ttaattgcgt tgcgctcact gcccgctttc cagtcgggaa acctgtcgtg    9720
ccagctgcat taatgaatcg gccaacgcgc ggggagaggc ggtttgcgta ttgggcgctc    9780
ttccgcttcc tcgctcactg actcgctgcg ctcggtcgtt cggctgcggc gagcggtatc    9840
agctcactca aaggcggtaa tacggttatc cacagaatca ggggataacg caggaaagaa    9900
catgtgagca aaaggccagc aaaaggccag gaaccgtaaa aaggccgcgt tgctggcgtt    9960
tttccatagg ctccgccccc ctgacgagca tcacaaaaat cgacgctcaa gtcagaggtg   10020
gcgaaacccg acaggactat aaagatacca ggcgtttccc cctggaagct ccctcgtgcg   10080
ctctcctgtt ccgaccctgc cgcttaccgg atacctgtcc gcctttctcc cttcgggaag   10140
cgtggcgctt tctcatagct cacgctgtag gtatctcagt tcggtgtagg tcgttcgctc   10200
caagctgggc tgtgtgcacg aaccccccgt tcagcccgac cgctgcgcct tatccggtaa   10260
ctatcgtctt gagtccaacc cggtaagaca cgacttatcg ccactggcag cagccactgg   10320
taacaggatt agcagagcga ggtatgtagg cggtgctaca gagttcttga agtggtggcc   10380
taactacggc tacactagaa ggacagtatt tggtatctgc gctctgctga gccagttac    10440
cttcggaaaa agagttggta gctcttgatc cggcaaacaa accaccgctg gtagcggtgg   10500
ttttttgtt tgcaagcagc agattacgcg cagaaaaaaa ggatctcaag aagatccttt    10560
gatcttttct acggggtctg acgctcagtg gaacgaaaac tcacgttaag ggattttggt   10620
catgagatta tcaaaaagga tcttcaccta gatcctttta aattaaaaat gaagttttaa   10680
atcaatctaa agtatatatg agtaaacttg gtctgacagt taccaatgct taatcagtga   10740
ggcacctatc tcagcgatct gtctatttcg ttcatccata gttgcctgac tccccgtcgt   10800
gtagataact acgatacggg agggcttacc atctggcccc agtgctgcaa tgataccgcg   10860
agacccacgc tcaccggctc cagatttatc agcaataaac cagccagccg gaagggccga   10920
```

```
gcgcagaagt ggtcctgcaa ctttatccgc ctccatccag tctattaatt gttgccggga   10980
agctagagta agtagttcgc cagttaatag tttgcgcaac gttgttgcca ttgctacagg   11040
catcgtggtg tcacgctcgt cgtttggtat ggcttcattc agctccggtt cccaacgatc   11100
aaggcgagtt acatgatccc ccatgttgtg caaaaaagcg gttagctcct tcggtcctcc   11160
gatcgttgtc agaagtaagt tggccgcagt gttatcactc atggttatgg cagcactgca   11220
taattctctt actgtcatgc catccgtaag atgcttttct gtgactggtg agtactcaac   11280
caagtcattc tgagaatagt gtatgcgcg accgagttgc tcttgcccgg cgtcaatacg    11340
ggataatacc gcgccacata gcagaacttt aaaagtgctc atcattggaa aacgttcttc   11400
ggggcgaaaa ctctcaagga tcttaccgct gttgagatcc agttcgatgt aacccactcg   11460
tgcacccaac tgatcttcag catctttac tttcaccagc gtttctgggt gagcaaaaac    11520
aggaaggcaa aatgccgcaa aaaagggaat aagggcgaca cggaaatgtt gaatactcat   11580

SEQ ID NO: 17            moltype = DNA  length = 11702
FEATURE                  Location/Qualifiers
misc_feature             1..11702
                         note = Synthetic: PB-hiRep-4#
source                   1..11702
                         mol_type = other DNA
                         organism = synthetic construct
SEQUENCE: 17
actcttcctt tttcaatatt attgaagcat ttatcagggt tattgtctca tgagcggata     60
catatttgaa tgtatttaga aaaataaaca aataggggtt ccgcgcacat ttccccgaaa    120
agtgccacct aaattgtaag cgttaatatt ttgttaaaat tcgcgttaaa ttttgttaa    180
atcagctcat ttttaacca ataggccgaa atcggcaaaa tcccttataa atcaaaagaa     240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt ttgggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca caccccgccg gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccaggtt ttcccagtca     720
cgacgttgta aaacgacggc cagtgagcgc gcctcgttca ttcacgtttt tgaacccgtg    780
gaggacgggc agactcgcgg tgcaaatgtg ttttacagcg tgatgagca gatgaagatg     840
ctcgacagc tgcagaacac gcagctagat aaccccagta aagataatca tattgtgacg     900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaaa caaaaactca   1080
aaatttcttc tataaagtaa caaaacttt atcgaattcc tgcagcccgg gggatccact    1140
agttctagag ggacagcccc ccccaaagc ccccagggat gtaattacgt ccctccccg     1200
ctaggggca gcagcgagcc gccgggggct ccgctccggt ccggcgctcc ccccgcatcc    1260
ccgagccggc agcgtgcggg gacagcccgg gcacggggaa ggtggcacgg atcgctttc   1320
ctctgaacgc ttctcgctgc tctttgagcc tgcagacacc tgggggata cgggggaaaag 1380
gcctccaagg ccagcttccc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcttaagcgc tgatcaattg gcgcgccgaa ttcgttatct   1560
gcagaattcg gcttctgctc cctgcttgtg tgttgggagt cgctgagtag tgcgcgagca   1620
aaatttaagc tacaacaagg caaggcttga ccgacaattg catgaagaat ctgcttaggg   1680
ttaggcgttt tgcgctgctt cgcgatgtac gggccagata tacgcgtatc tgaggggact   1740
agggtgtgtt taggcgaaaa gcggggcttc ggttgtacgc ggttaggagt cccctcagga   1800
tatagtagtt tcgcttttgc ataggagggg ggaaatgtag tcttatgcaa tacacttgta   1860
gtcttgcaac atggtaacga tgagttagca acatgcctta caaggagaga aaaagcaccg   1920
tgcatgccga ttggtggaag taaggtggta cgatcgtgcc ttattaggaa ggcaacagac   1980
aggtctgaca tggattggac gaaccactga attccgcatt gcagagataa ttgtatttaa   2040
gtgcctagct ccctatcagt gatagagatc tccctatcag tgatagagat cgatacaata   2100
aacgccattt gaccattcac cacattggtg tgcaccgaac gcgcagccgc catgccgggg   2160
ttttacgaga ttgtgattaa ggtcccagc gaccttgacg agcatctgcc cggcatttct   2220
gacagctttg tgaactgggt ggcgagaag gaatgggagt gccgccaga ttctgacatg    2280
gatctgaatc tgattgagca ggcaccctg accgtggccg agaagctgca gcgcgactt    2340
ctgacggaat ggcgccgtgt gagtaaggcc ccggaggctc ttttcttgt gcaatttgag    2400
aagggagaga gctacttcca catgcacgtg ctcgtgaaa ccaccggggt gaaatccatg     2460
gttttggac gtttcctgag tcagattcgc gaaaactga ttcagagaat ttaccgcggg     2520
atcgagccga ctttgccaaa ctggttcgcg gtcacaaaga ccagaaatgg cgccggaggc    2580
gggaacaagg tggtggatga tgctacatc ccaaattact tgctcccaa aaccagct     2640
gagctccaat gggcatggac caacatgaa cagtacctca gcgcctgttt gaatctcacg    2700
gagcgtaaac ggttggtggc gcagcatctg acgcacgtgt cgcagacgca ggagcagaac    2760
aaagagaatc agaatcccaa ttctgatgcg ccggtgatca gatcaaaaac ttcagccagg    2820
tacatgggagc tggtcgggtg gctcgtggac aaggggatta cctcggagaa gcagtggatc    2880
caggaggacca aggcctcata catctccttc aatgcggtct ccaactcgcg gtcccaaatc    2940
aaggctgcct tggacaatgc gggaaagatt atgagcctga ctaaaaccgc ccccgactac    3000
ctggtgggcc agcagcccgt ggaggacatt ccagcaatc ggattataa aattttggaa      3060
ctaaacgggg acgatcccca atatgcggct tccgtctttc tgggatgggc cacgaaaaag    3120
ttcggcaaga ggaacaccat ctggctgttt gggcctgcaa ctaccgggaa gaccaacatc    3180
gcggacgca tagcccacac tgtgccctc tacgggtgcg taaactgag caatgagaac    3240
tttccttca acgactgtgt cgacaagatg gtgatctggt gggaggaggg gaagatgacc    3300
gccaaggtcg tggagtcggc caagccattc tcggaggaa gcaaggtgcg cgtggaccag    3360
aaatgcaagt cctcggccca gatagacccg actccgtga tcgtcacctc caacaccaac    3420
atgtgcgccc tgattgacgg gaactcaacg accttcgaac accagcagcc gttgcaagac    3480
cggatgttca aatttgaact cacccgcgt ctggatcatg actttgggaa ggtcaccaag    3540
```

```
caggaagtca aagactttttt ccggtgggca aaggatcacg tggttgaggt ggagcatgaa   3600
ttctacgtca aaaagggtgg agccaagaaa agacccgccc ccagtgacgc agatataagt   3660
gagcccaaac gggtgcgcga gtcagttgcg cagccatcga cgtcagacgc ggaagcttcg   3720
atcaactacg cagacaggta ccaaaacaaa tgttctcgtc acgtgggcat gaatctgatg   3780
ctgtttccct gcagacaatg cgagagaatg aatcagaatt caaatatctg cttcactcac   3840
ggacagaaag actgtttaga gtgctttccc gtgtcagaat ctcaacccgt ttctgtcgtc   3900
aaaaaggcgt atcagaaact gtgctacatt catcatatca tgggaaaggt gccagacgct   3960
tgcactgcct gcgatctggt caatgtggat ttggatgact gcatctttga acaataaaat   4020
ggctaggatc cggccggcct gcaggtgtcc tcacaggaac gaagtccta aagaaacagt   4080
ggcagccagg tttagccccg gaaaacttgt ttattgcagc ttataatggt tacaaataaa   4140
gcaatagcat cacaaatttc acaaataaag cattttttc actgcattct agttgtggtt   4200
tgtccaaact catcaatgta tcttattgac tggattgagg acagccccc ccccaaagcc   4260
cccagggatg taattacgtc cctcccccgc taggggcag cagcgagccg cccggggctc   4320
cgctccggtc cggcgctccc cccgcatccc cgagccggca gcgtgcgggg acagcccggg   4380
cacggggaag gtggcacggg atcgcttcc tctgaacgct tctcgctgct ctttgagcct   4440
gcagacacct gggggatac ggggaaaagg cctccaaggc cagcttccca caataagttg   4500
ggtgaatttt ggctcattcc tcctttctat aggattgagg tcagagcgac attgattatt   4560
gactagttat taatagtaat caattacggg gtcattagtt catagcccat atatgagtt   4620
ccgcgttaca taacttacgg taaatgccc gcctggctga ccgcccaacg acccccgccc   4680
attgacgtca ataatgacgt atgttcccat agtaacgcca atagggactt tccattgacg   4740
tcaatgggtg gagtatttac ggtaaactgc ccacttggca gtacatcaag tgtatcatat   4800
gccaagtacg ccccctattg acgtcaatga cggtaaatgg cccgcctggc attatgccca   4860
gtacatgacc ttatgggact ttcctacttg gcagtacatc tacgtattag tcatcgctat   4920
taccatggtg atgcggtttt ggcagtacat caatgggcgt ggatagcggt ttgactcacg   4980
gggatttcca agtctccacc ccattgacgt caatgggagt ttgttttgga accaaaatca   5040
acgggacttt ccaaaatgtc gtaacaactc cgccccattg acgcaaatgg gcggtaggcg   5100
tgtacggtgg gaggtctata taagcagagc tctccctatc agtgatagag atctccctat   5160
cagtgataga gatcgtcgac gagctcgttt agtgaaccgt cagatcgcct ggagacgcca   5220
tccacgctgt tttgacctcc atagaagaca ccgggaccga tccagcctat cccaattctg   5280
atgcgccggt gatcagatca aaaacttcag ccaggtacgc caccatggaa ctggtcggat   5340
ggctggtgga taagggcatc acaagcagga agcaatggat ccaggaggac caggcctcat   5400
atatttcttt taacgccgct agcaattcca gaagccagat caaggctgct ctggacaacg   5460
ccggcaaaat catgagcctg accaagaccg cccctgacta cctggtggga cagcagcctg   5520
tggaagatat cagcagcaac agaatctata agatcctgga actgaacggc tacgaccccc   5580
agtacgccgc ctccgtgttc ctgggctggg ctacaaagaa gttcggcaag cggaacacca   5640
tctggctgtt cggacctgcc accacaggca aaaccaatat cgccgaggcc atcgcccaca   5700
ccgtgccttt ctacgctgc gtgaactgga caaacgagaa cttcccttc aacgactgtg   5760
tggacaagat ggtgatctgg tgggaggaag gcaaaatgac agctaaggtg gtggaatctg   5820
ccaaggctat cctgggaggc tctaaggtca gggtggatca gaagtgtaaa agcagcgccc   5880
agattgaccc taccctgtg atcgtgacca gcaataccaa catgtgcgcc gtgatcgacg   5940
gcaacagcac caccttcgag catcagcagc ctctgcagga ccggatgttc aagtttgagc   6000
tcaccagacg gctggatcac gacttcggca aggtgaccaa gcaggaggtg aaggatttct   6060
tcagatgggc caaagaccac gttgttgagg tggaacacga gttctacgtg aagaagggcg   6120
gcgccaagaa aagacccgcc cctagcgacg ccgacatcag cgagcctaag agagtgcggg   6180
aaagcgtggc ccagcccagc acatctgatg ctgaggccag catcaactac gccgatagat   6240
accaaaacaa gtgcagccgc cacgtgggca tgaacctgat gctgtttccc tgcagacagt   6300
gtgaaagaat gaaccagaat tctaatatct gcttacaca cggccagaaa gattgcctga   6360
aatgcttccc tgtgtccgag agccaaccag tgtctgtggt gaaaaaggcc taccagaagc   6420
tgtgctacat ccaccacatc atgggcaagg tgccagacgc ctgtaccgcc tgcgacctgg   6480
tcaacgtgga cctggacgac tgcatcttcg agcagtgatt tgtgatggga attctgtgct   6540
gtgccttcta gttgccagcc atctgttgtt tgcccctccc cgtgccttc cttgaccctg   6600
gaaggtgcca ctcccactgt cctttcctaa taaaatgagg aaattgcatc gcattgtctg   6660
agtaggtgtc attctattct ggggggtggg gtggggcagg acagcaaggg ggaggattgg   6720
gaagacaata gcaggcatgc tggggatgcg gtgggctcta tgggaccttt tttagggccc   6780
attggtatgg cttttttccc gtatcccccc aggtgtctgc aggctcaaag agcagcgaga   6840
agcgttcaga ggaaagcgat cccgtgccac cttcccgtg cccgggctgt ccccgcacgc   6900
tgccggctcg gggatgcggg gggagcgccg gaccggagcg gagccccggg cggctcgctg   6960
ctgccccta gcggggagg gacgtaatta catccctggg ggctttgggg gggggctgtc   7020
cctctagagc ggccgcacc gcggtggagc tccagctttt gttcccttta gtgagggtta   7080
attagatctt aatacgactc actatagggc gaattggga ccgggccccc ctgaggcgga   7140
aagaaccagc tggggctcta gggggtatcc ccggggttgg ggttgcgcct tttccaaggc   7200
agccctgggt tgcgcaggg acgcggctgc tctgggcgtg gttccgggaa acgcagcggc   7260
gccgaccctg ggtctcgcac attcttcacg tccgttcga gcgtcacccg gatcttcgcc   7320
gctaccccttg tgggccccc ggcgacgctt cctgctccgc cctcaagtcg ggaaggttcc   7380
ttgcggttcg cggcgtgccg gacgtgacaa acggaagccg cacgtctcac tagtaccctc   7440
gcagacggac agcgccaggg agcaatggca gcgcgccgac cgcgatgggc tgtgccaat   7500
agcggctgct cagcagggcg cgccgagagc agcggccggg aaggggcggt gcgggaggcg   7560
gggtgtgggg cggtagtgtg gcgtccggtc cgtccggctc gctgcgcgc ggtgttccgc   7620
cctccgagc gcacgtcgga gtcggctcc ctcgttgacc gaatcaccga cctctctccc   7680
cagaagctcc cgggagcttg tatatccatt ttcggatctg atcagcacgt gttgacaatt   7740
aatcatcggc atagtatatc ggcatagtat aatacgacaa ggtgaggaac gccaccatgg   7800
ccaagccttt gtctcaagaa gaatccaccc tcattgaaag agcaacggct acaatcaaca   7860
gcatcccat ctctgaagac tacagcgtcg ccagcgcagc tctctctagc gacggccgca   7920
tcttcactgg tgtcaatgta tatcatttta ctgggggacc ttgtgcagaa ctcgtggtgc   7980
tgggcactgc tgctgctgcg gcagctggca acctgacttg tatcgtcgcg atcggaaatg   8040
agaacagggg catcttgagc ccctgcggac ggtgccgaca ggtgcttctc gatctgcatc   8100
ctgggatcaa agccatagtg aaggacagtg atggacagcc gacggcagtt gggattcgtg   8160
aattgctgcc ctctggttat gtgtgggagg ctaaagcgc ggggatctca tgctggagtt   8220
cttcgcccac cccaacttgt ttattgcagc ttataatggt tacaaataaa gcaatagcat   8280
```

```
cacaaatttc acaaataaag catttttttc actgcattct agttgtggtt tgtccaaact   8340
catcaatgta tcttatcatg tctgtagctg atgtatacct aggatccggc cggcctgcag   8400
gtgtcctcac aggaacgaag tccctaaaga aacagtggca gccaggttta gccccggaat   8460
tgactggatt cctttttag ggcccattgg tatggctttt tccccgtatc cccccaggtg    8520
tctgcaggct caaagagcag cgagaagcgt tcagaggaac ggatcccgt gccaccttcc    8580
ccgtgcccgg gctgtccccg cacgctgccg gctcggggat gcgggggag cgccggaccg    8640
gagcggagcc ccgggcggct cgctgctgcc cctagcggg ggagggacgt aattacatcc    8700
ctgggggctt tggggggggg ctgtccctct agagcggccg ccaccgcggt ggagctccag   8760
cttttgttcc ctttagtgag ggttaattag atcttaatac gactcactat agggcgaatt   8820
gggtaccggg ccccccctcg aggtcgacgg tatcctcgag gtcgacggta tcgataagct   8880
tgatatctat aacaagaaaa tatatatata ataagttatc acgtaagtag aacatgaaat   8940
aacaatataa ttatcgtatg agttaaatct aaaagtcac gtaaaagata atcatgcgtc    9000
attttgactc acgcggtcgt tatagttcaa aatcagtgac acttaccgca ttgacaagca   9060
cgcctcacgg gagctccaag cggcgactga gatgtcctaa atgcacagcg acggattcgc   9120
gctatttaga aagagagagc aatatttcaa gaatgcatgc gtcaatttta cgcagactat   9180
cttctaggg ttaatctagc tgcatcagga tcatatcgtc gggtcttttt tccggctcag    9240
tcatcgccca agctggcgct atctgggcat cggggaggaa gaagcccgtg ccttttcccg   9300
cgaggttgaa gcggcatgga aagagtttgc cgaggatgac tgctgctgca ttgacgttga   9360
gcgaaaacgc acgtttacca tgatgattcg ggaaggtgtg gccatgcacg cctttaacgg   9420
tgaactgttc gttcaggcca cctgggatac cagttcgtcg cggcttttcc ggacacagtt   9480
ccggatggtc agcccgaagc gcatcagcaa cccgaacaat accggcgaca gccggaactg   9540
ccgtgccggt gtgcagatta atgacagcgg tgcggcgctg gatattacg tcagcgagga    9600
cgggtatcct ggctgatgc cgcagaaatg gacatggata ccccgtgagt tacccggcgg    9660
gcgcgcttgg cgtaatcatg gtcatagctg tttcctgtgt gaaattgtta tccgctcaca   9720
attccacaca acatacgagc cggaagcata aagtgtaaag cctggggtgc ctaatgagtg   9780
agctaactca cattaattgc gttgcgctca ctgccgcttt ccagtcggga aaacctgtcg   9840
tgccagctgc attaatgaat cggccaacgc gcggggagag gcggtttgcg tattgggcgc   9900
tcttccgctt cctcgctcac tgactcgctg cgctcggtcg ttcggctgcg gcgagcggta   9960
tcagctcact caaaggcggt aatacggtta tccacagaat caggggataa cgcaggaaag  10020
aacatgtgag caaaaggcca gcaaaaggcc aggaaccgta aaaaggccgc gttgctgcg   10080
tttttccata ggctccgccc ccctgacgag catcacaaaa atcgacgctc aagtcagagg  10140
tggcgaaacc cgacaggact ataaagatac caggcgtttc ccctggaag ctccctcgtg   10200
cgctctcctg ttccgaccct gccgcttacc ggatacctgt ccgcctttct ccttcggga   10260
agcgtggcgc tttctcatag ctcacgctgt aggtatctca gttcggtgta ggtcgttcgt  10320
tccaagctgg gctgtgtgca cgaacccccc gttcagcccg accgctgcgc cttatccggt  10380
aactatcgtc ttgagtccaa cccggtaaga cacgacttat cgccactggc agcagccact  10440
ggtaacagga ttagcagagc gaggtatgta ggcggtgcta cagagttctt gaagtggtgg  10500
cctaactacg gctacactag aaggacagta tttggtatct gcgctctgct gaagccagtt  10560
accttcggaa aaagagttgg tagctcttga tccggcaaac aaaccaccgc tggtagcggt  10620
ggtttttttg tttgcaagca gcagattacg cgcagaaaaa aaggatctca agaagatcct  10680
ttgatctttt ctacggggtc tgacgctcag tggaacgaaa actcacgtta agggattttg  10740
gtcatgagat tatcaaaaag gatcttcacc tagatccttt taaattaaaa atgaagtttt  10800
aaatcaatct aaagtatata tgagtaaact tggtctgaca gttaccaatg cttaatcagt  10860
gaggcaccta tctcagcgat ctgtctattt cgttcatcca tagttgcctg actccccgtc  10920
gtgtagataa ctacgatacg ggagggctta ccatctggcc ccagtgctgc aatgataccg  10980
cgagacccac gctcaccggc tccagattta tcagcaataa accagccagc cggaagggc   11040
gagcgcagaa gtggtcctgc aactttatcc gcctccatcc agtctattaa ttgttgccgg  11100
gaagctagag taagtagttc gccagttaat agtttgcgca acgttgttgc cattgctaca  11160
ggcatcgtgg tgtcacgctc gtcgtttggt atggcttcat tcagctccgg ttcccaacga  11220
tcaaggcgag ttacatgatc ccccatgttg tgcaaaaag cggttagctc cttcggtcct   11280
ccgatcgttg tcagaagtaa gttggccgca gtgttatcac tcatggttat ggcagcactg  11340
cataattctc ttactgtcat gccatccgta agatgctttt ctgtgactgg tgagtactca  11400
accaagtcat tctgagaata gtgtatgcgg cgaccgagtt gctcttgccc ggcgtcaata  11460
cgggataata ccgcgccaca tagcagaact ttaaaagtgc tcatcattgg aaaacgttct  11520
tcggggcgaa aactctcaag gatcttaccg ctgttgagat ccagttcgat gtaacccact  11580
cgtgcaccca actgatcttc agcatctttt actttcacca gcgtttctgg gtgagcaaaa  11640
acaggaaggc aaaatgccgc aaaaaaggga ataagggcga cacggaaatg ttgaatactc  11700
at                                                                 11702

SEQ ID NO: 18         moltype = DNA   length = 11865
FEATURE               Location/Qualifiers
misc_feature          1..11865
                      note = Synthetic: PB-hiRep-5#
source                1..11865
                      mol_type = other DNA
                      organism = synthetic construct
SEQUENCE: 18
actcttcctt tttcaatatt attgaagcat ttatcagggt tattgtctca tgagcggata     60
catatttgaa tgtatttaga aaaataaaca aatagggggtt ccgcgcacat ttccccgaaa   120
agtgccacct aaattgtaag cgttaatatt ttgttaaaat tcgcgttaaa ttttttgttaa   180
atcagctcat ttttttaacca ataggccgaa atcggcaaaa tcccttataa atcaaaagaa   240
tagaccgaga tagggttgag tgttgttcca gtttggaaca agagtccact attaaagaac   300
gtggactcca acgtcaaagg gcgaaaaacc gtctatcagg gcgatggccc actacgtgaa   360
ccatcaccct aatcaagttt tttggggtcg aggtgccgta agcactaaa tcggaaccct   420
aaagggagcc cccgatttag agcttgacgg ggaaagccgg cgaacgtggc gagaaaggaa   480
gggaagaaag cgaaaggagc gggcgctagg gcgctggcaa gtgtagcggt cacgctgcgc   540
gtaaccacca cacccgccgc gcttaatgcg ccgctacagg gcgcgtccca ttcgccattc   600
aggctgcgca actgttggga agggcgatcg gtgcgggcct cttcgctatt acgccagctg   660
gcgaaagggg gatgtgctgc aaggcgatta agttgggtaa cgccagggtt ttcccagtca   720
```

```
cgacgttgta aaacgacggc cagtgagcgc gcctcgttca ttcacgtttt tgaaccgtgt    780
gaggacgggc agactcgcgg tgcaaatgtg ttttacagcg tgatggagca gatgaagatg    840
ctcgacacgc tgcagaacac gcagctagat taaccctaga aagataatca tatttgtacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttattttat taaaaaaaaa caaaaactca   1080
aaatttcttc tataaagtaa caaaactttt atcgaattcc tgcagccgg gggatccact    1140
agttctagag ggacagcccc cccccaaagc ccccagggat gtaattacgt ccctccccg    1200
ctaggggca gcagcgagcc gcccgggct ccgctccggt ccggcgctcc ccccgcatcc    1260
ccgagccggc agcgtgcggg gacagcccgg gcacgggaa ggtggcacgg gatcgctttc    1320
ctctgaacgc ttctcgctgc tctttgagcc tgcagacacc tggggggata cggggaaaag   1380
gcctccaagg ccagcttccc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcttaagcgc tgatcaattg gcgcgccgaa ttcgttatct   1560
gcagaattcg gcttgacatt gattattgac tagttattaa tagtaatcaa ttacggggtc   1620
attagttcat agcccatata tggagttccg cgttacataa cttacggtaa atggcccgcc   1680
tggctgaccg cccaacgacc cccgcccatt gacgtcaata atgacgtatg ttcccatagt   1740
aacgccaata gggactttcc attgacgtca atgggtggga tatttacggt aaactgccca   1800
cttggcagta catcaagtgt atcatatgcc aagtacgccc cctattgacg tcaatgacgg   1860
taaatggccc gcctggcatt atgcccagta catgacctta tgggactttc ctacttggca   1920
gtacatctac gtattagtca tcgctattac catggtgatg cggttttggc agtacatcaa   1980
tgggcgtgga tagcggtttg actcacgggg atttccaagt ctccacccca ttgacgtcaa   2040
tgggagtttg ttttggaacc aaaatcaacg ggactttcca aaatgtcgta acaactccgc   2100
cccattgacg caaatgggcg gtaggcgtgt acggtgggag gtctatataa gcagagctct   2160
ccctatcagt gatagagatc tccctatcag tgatagagat cgtcgacgag ctcgtttagt   2220
gaaccgtcag atcgcctgga gacgccatcc acgctgtttt gacctccata gaagacaccg   2280
ggaccgatcc agcctgaacg cgcagccgcc aatggatgcc ggggttttac gagattgtga   2340
ttaaggtccc cagcgacctt gacgagcatc tgcccggcat ttctgacagc tttgtgaact   2400
gggtggccga aaggaatgg gagttgccgc cagattctga catggatctg aatctgattg   2460
agcaggcaac cctgaccgtg gccgagaagc tgcagcgcga ctttctgacg gaatggccgc   2520
gtgtgagtaa ggccccggag gctctttct ttgtgcaatt tgagaaggga gagagctact   2580
tccacatgca cgtgctcgtg gaaaccaccg gggtgaaatc catggttttg ggacgtttcc   2640
tgagtcagat tcgcgaaaaa ctgattcaga gaatttaccg cgggatcgag ccgactttgc   2700
caaactggtt cgcggtcaca aagaccagaa atggcgccgg aggcgggaac aaggtggtgg   2760
atgagtgcta catccccaat tacttgctcc ccaaaaccca gcctgagctc caatgggcat   2820
ggaccaacat ggaacagtac ctcagcgcct gtttgaatct cacggagcgt aaacggttgg   2880
tggcgcagca tctgacgcac gtgtcgcaga cgcaggagca gaacaaagag aatcagaatc   2940
ccaattctga tgcgccggtg atcagatcaa aaacttcagc caggtacatg gagctggtcg   3000
ggtggctcgt ggacaagggg attacctcgg agaagcagtg gatccaggag gaccaggcct   3060
catacatctc cttcaatgcg gcctccaact cgcggtccca aatcaaggct gccttggaca   3120
atgcgggaaa gattatgagc ctgactaaaa ccgcccccga ctacctggtg gccagcagc   3180
ccgtggagga catttccagc aatcggattt ataaaatttt ggaactaaac gggtacgatc   3240
cccaatatgc ggcttccgtc ttttctgggat gggccacgaa aagttcggc aagaggaaca   3300
ccatctggct gtttgggcct gcaactaccg ggaagaccaa catcgcggag gccatagccc   3360
acactgtgcc cttctacggg tgcgtaaact ggaccaatga gaactttccc ttcaacgact   3420
gtgtcgacaa gatggtgatc tggtgggagg aggggaagat gaccgccaag gtcgtggagt   3480
cggccaaagc cattctcgga ggaagcaagg tgcgcgtgga ccagaaatgc aagtcctcgg   3540
cccagataga cccgactccc gtgatcgtca cctccaacac caacatgtgc gccgtgattg   3600
acgggaactc aacgacttc gaacaccagc agccgttgca agaccggatg ttcaaatttg   3660
aactcacccg ccgtctggat catgactttg gaaggtcac caagcaggaa gtcaaagact   3720
ttttccggtg ggcaaaggat cacgtggttg aggtggagca tgaattctac gtcaaaaagg   3780
gtggagccaa gaaaagaccc gcccccagtg acgcagatat aagtgagccc aaacgggtgc   3840
gcgagtcagt tgcgcagcca tcgacgtcag acgcggaagc ttcgatcaac tacgcagaca   3900
ggtaccaaaa caaatgttct cgtcacgtgg gcatgaatct gatgctgttt ccctgcagac   3960
aatgcgagag aatgaatcag aattcaaata tctgcttcac tcacggacag aaagactgtt   4020
tagagtgctt tccgtgtca gaatctcaac ccgtttctgt cgtcaaaaag gcgtatcaga   4080
aactgtgcta cattcatcat atcatgggaa aggtgccaga cgcttgcact gcctgcgatc   4140
tggtcaatgt ggatttggat gactgcatct ttgaacaata aaatggctag gatccggccg   4200
gcctgcaggt gtcctcacag gaacgaagtc cctaaagaaa cagtgcagc caggtttagc   4260
cccggaaaac ttgtttattg cagcttataa tggttacaaa taaagcaata gcatcacaaa   4320
tttcacaaat aaagcatttt tttcactgca ttctagttgt ggtttgtcca aactcatcaa   4380
tgtatcttat tgactggatt gagggacagc ccccccccaa agcccccagg gatgtaatta   4440
cgtccctccc ccgctagggg gcagcagcga gccgcccggg gctccgctcc ggtccggcgc   4500
tccccccgca tccccgagcc ggcagcgtgc ggggacacg cccggcacgg gaaggtgtca   4560
cgggatcgct ttcctctgaa cgcttctcgc tgctctttga gcctgcagac acctgggggg   4620
atacggggaa aaggcctcca aggccagctt cccacaataa gttgggtgaa ttttggctca   4680
ttcctccttt ctataggatt gaggtcagag cgacattgat tattgactag ttattaatag   4740
taatcaatta cgggggtcatt agttcatagc ccatatatgg agttccgcgt tacataactt   4800
acggtaaatg gcccgcctgg ctgaccgccc aacgacccc gcccattgac gtcaataatg   4860
acgtatgttc ccatagtaac gccaataggg actttccatt gacgtcaatg ggtggagtat   4920
ttacggtaaa ctgccccactt ggcagtacat caagtgtatc atatgccaag tacgcccct   4980
attgacgtca atgacggtaa atggcccgcc tggcattatg cccagtacat gaccttatgg   5040
gactttccta cttggcagta catctacgta ttagtcatcg ctattaccat ggtgatgcgg   5100
ttttggcagt acatcaatgg gcgtggatag cggtttgact cacggggatt tccaagtctc   5160
caccccattg acgtcaatgg gagtttgttt tggaaccaaa atcaacggga ctttccaaaa   5220
tgtcgtaaca actccgcccc attgacgcaa atgggcggta ggcgtgtacg gtgggaggtc   5280
tatataagca gagctctccc tatcagtgat agagatctcc ctatcagtga tagagatcgt   5340
cgacgagctc gtttagtgaa ccgtcagatc gcctggagac gccatccacg ctgttttgac   5400
ctccatagaa gacaccggga ccgatccagc ctatcccaat tctgatgcgc cggtgatcag   5460
```

```
atcaaaaact tcagccaggt acaatggatg gaactggtcg gatggctggt ggataagggc   5520
atcacaagcg agaagcaatg gatccaggag gaccaggcct catatatttc ttttaacgcc   5580
gctagcaatt ccagaagcca gatcaaggct gctctggaca acgccggcaa aatcatgagc   5640
ctgaccaaga ccgcccctga ctacctggtg ggacagcagc ctgtggaaga tatcagcagc   5700
aacagaatct ataagatcct ggaactgaac ggctacgacc cccagtacgc cgcctccgtg   5760
ttcctgggct gggctacaaa gaagttcggc aagcggaaca ccatctggct gttcggacct   5820
gccaccacag gcaaaaccaa tatcgccgag gccatcgccc acaccgtgcc tttctacggc   5880
tgcgtgaact ggacaaacga gaacttcccc ttcaacgact gtgtggacaa gatggtgatc   5940
tggtgggagg aaggcaaaat gacagctaag gtggtggaat ctgccaaggc tatcctggga   6000
ggctctaagg tcagggtgga tcagaagtgt aaaagcagcg cccagattga ccctaccect   6060
gtgatcgtga ccagcaatac caacatgtgc gccgtgatcg acggcaacag caccaccttc   6120
gagcatcagc agcctctgca ggaccggatg ttcaagtttg agctcaccag acggctggat   6180
cacgacttcg gcaaggtgac caagcaggag gtgaaggatt tcttcagatg ggccaaagac   6240
cacgttgttg aggtggaaca cgagttctac gtgaagaagg gcggcgccaa gaaaagaccc   6300
gcccctagcg acgccgacat cagcgagcct aagagagtgc gggaaagcgt ggcccagccc   6360
agcacatctg atgctgaggc cagcatcaac tacgccgata gataccaaaa caagtgcagc   6420
cgccacgtgg gcatgaacct gatgctgttt ccctgcagac agtgtgaaag aatgaaccag   6480
aattctaata tctgctttac acacggccag aaagattgcc tggaatgctt ccctgtgtcc   6540
gagagccaac cagtgtctgt ggtgaaaaag gcctaccaga agctgtgcta catccaccac   6600
atcatgggca aggtgccaga cgcctgtacc gcctgcgacc tggtcaacgt ggacctggac   6660
gactgcatct tcgagcagtg atttgtgatg ggaattctgt gctgtgcctt ctagttgcca   6720
gccatctgtt gtttgcccct cccccgtgcc ttccttgacc ctggaaggtg ccactcccac   6780
tgtcctttcc taataaaatg aggaaattgc atcgcattgt ctgagtaggt gtcattctat   6840
tctgggggt ggggtggggc aggacagcaa gggggaggat tgggaagaca atagcaggca   6900
tgctgggat gcgtgggct ctatgggacc ttttttaggg cccattggta tggctttttc   6960
cccgtatccc cccaggtgtc tgcaggctca aagagcagcg agaagcgttc agaggaaagc   7020
gatcccgtgc caccttcccc gtgcccgggc tgtcccgcca cgctgccggc tcggggatgc   7080
gggggagcg ccggaccgga gcggagcccc gggcggctcg ctgctgcccc ctagcggggg   7140
agggacgtaa ttacatccct gggggctttg gggggggct gtccctctag agcggccgcc   7200
accgcggtgg agctccagct tttgttcct ttagtgaggg ttaattagat cttaatacga   7260
ctcactatag gcgaattgg gtaccggggc cccctgaggc ggaaagaacc agctggggct   7320
ctaggggta tccccggggt tggggttgcg ccttttccaa ggcagccctg ggtttgcgca   7380
gggacgcggc tgctctgggc gtggttccgg gaaacgcagc ggcgccgacc ctgggtctcg   7440
cacattcttc acgtccgttc gcagcgtcac ccggatcttc gccgctaccc ttgtgggcgg   7500
cccggcgacg cttcctcgct cgcccctaag tcgggaaggt tccttgcggt tcgcggcgtg   7560
ccggacgtga caaacggaag ccgcacgtct cactagtacc ctcgcagacg gacagccgca   7620
gggagcaatg gcagcgcgcc gaccgcgatg ggctgtggcc aatagcggct gctcagcagg   7680
gcgcgccgag agcagcggcc gggaaggggc ggtgcggag gcggggtgtg gggcggtagt   7740
gtgggcccty ttcctgcccg cgcggtgttc cgcattctgc aagcctccgg agcgcacgtc   7800
ggcagtcggc tccctcgttg accgaatcac cgacctctct ccccagaagc tcccgggagc   7860
ttgtatatcc attttcggat ctgatcagca cgtgttgaca attaatcatc ggcatagtat   7920
atcggcatag tataatacga caaggtgagg aacgccacca tggccaagcc tttgtctcaa   7980
gaagaatcca ccctcattga aagagcaacg gctacaatca acagcatccc catctctgaa   8040
gactacagcg tcgccagcgc agctctctct agcgacgcc gcatcttcac tggtgtcaat   8100
gtatatcatt ttactggggg accttgtgca gaactcgtgg tgctgggcac tgctgctgct   8160
gcggcagctg gcaacctgac ttgtatcgtc gcgatcggaa atgagaacag gggcatcttg   8220
agccctgcg gacggtgccg acaggtgctt ctcgatctgc atctgggat caaagccata   8280
gtgaaggaca gtgatggaca gccgacggca gttgggattc gtgaattgct gcctctggtt   8340
tatgtgtggg agggctaaag cgcggggatc tcatgctgga gttcttcgcc cacccaact   8400
tgtttattgc agcttataat ggttacaaat aaagcaatag catcacaaat ttcacaaata   8460
aagcattttt ttcactgcat tctagttgtg gtttgtccaa actcatcaat gtatcttatc   8520
atgtctgtag ctgatgtata cctaggatcc ggcggcctg caggtgtcct cacaggaacg   8580
aagtccctaa agaaacagtg gcagccaggt ttagccccgg aattgactgg attccttttt   8640
tagggcccat tggtatggct ttttccccgt atccccccag gtgtctgcag gctcaaagag   8700
cagcgagaag cgttcagagg aaagcgatcc gtgccacct tccccgtgcc cgggctgtcc   8760
ccgcacgctg ccggctcggg gatgcggggg gagcgccgga ccggagcgga gccccgggcg   8820
gctcgctgct gccccctagc gggggaggga cgtaattaca tccctggggg ctttgggggg   8880
gggctgtccc tctagagcgg ccgccaccgc ggtggagctc cagcttttgt tccctttagt   8940
gagggttaat tagatcttaa tacgactcac tatagggcga attgggtacc gggccccccc   9000
tcgaggtcga cggtatcctc gaggtcgacg gtatcgataa gcttgatatc tataacaaga   9060
aaatatatat ataataagtt atcacgtaag tagaacatga aataacaata taattatcgt   9120
atgagttaaa tcttaaaagt cacgtaaaag ataatcatgc gtcatttgac ctcacgcggt   9180
cgttatagtt caaaatcagt gacacttacc gcattgacaa gcacgcctca cgggagctcc   9240
aagcggcgac tgagatgtcc taaatgcaca gcgacggatt cgcgctattt agaaagagag   9300
agcaatattt caagaatgca tgcgtcaatt ttacgcagac tatctttcta gggttaatct   9360
agctgcatca ggatcatatc gtcggtgtct tttttccggct cagtcatcgc ccaagctggc   9420
gctatctggg catcggggag gaagaagccc gtgccttttc ccgcgaggtt gaagcggcat   9480
ggaaagagtt tgccgaggat gactgctgct gcattgacgt tgagcgaaaa cgcacgttta   9540
ccatgatgat tcgggaaggt gtggccatgc acgcctttaa cggtgaactg ttcgttcagg   9600
ccacctggga taccagttcg tcgcggcttt tccggacaca gttccggatg tcagccga   9660
agcgcatcag caacccgaac aataccgcg cagccggaa ctgccgtgcc ggtgtgcaga   9720
ttaatgacag cggtgcggcg ctgggatatt acgtcagcga ggacgggtat cctgctggga   9780
tgccgcagaa atggacatgg ataccccgtg agttaccgg cgggcgcgct ggcgtaatc   9840
atggtcatag ctgtttcctg tgtgaaattg ttatccgctc acaattccac acaacatacg   9900
agccggaagc ataaagtgta aagcctgggg tgcctaatga gtgagctaac tcacattaat   9960
tgcgttcgc tcactgcccg ctttccagtc gggaaacctg tcgtgccagc tgcattaatg  10020
aatcggccaa cgcgcgggga gaggcggttt gcgtattggg cgctcttccg cttcctcgct  10080
cactgactcg ctgcgctcgg tcgttcggct gcggcgagcg gtatcagctc actcaaaggc  10140
ggtaatacgg ttatccacag aatcagggga taacgcagga agaacatgt gagcaaaagg  10200
```

-continued

```
ccagcaaaag gccaggaacc gtaaaaaggc cgcgttgctg gcgttttcc  ataggctccg  10260
ccccctgac  gagcatcaca aaaatcgacg ctcaagtcag aggtggcgaa acccgacagg  10320
actataaaga taccaggcgt ttccccctgg aagctccctc gtgcgctctc ctgttccgac  10380
cctgccgctt accggatacc tgtccgcctt tctcccttcg ggaagcgtgg cgctttctca  10440
tagctcacgc tgtaggtatc tcagttcggt gtaggtcgtt cgctccaagc tgggctgtgt  10500
gcacgaaccc cccgttcagc ccgaccgctg cgccttatcc ggtaactatc gtcttgagtc  10560
caacccggta agacacgact tatcgccact ggcagcagcc actggtaaca ggattagcag  10620
agcgaggtat gtaggcggtg ctacagagtt cttgaagtgg tggcctaact acggctacac  10680
tagaaggaca gtatttggta tctgcgctct gctgaagcca gttaccttcg gaaaaagagt  10740
tggtagctct tgatccggca aacaaaccac cgctggtagc ggtggttttt ttgtttgcaa  10800
gcagcagatt acgcgcagaa aaaaaggatc tcaagaagat cctttgatct tttctacggg  10860
gtctgacgct cagtggaacg aaaactcacg ttaagggatt ttggtcatga gattatcaaa  10920
aaggatcttc acctagatcc ttttaaatta aaaatgaagt tttaaatcaa tctaaagtat  10980
atatgagtaa acttggtctg acagttacca atgcttaatc agtgaggcac ctatctcagc  11040
gatctgtcta tttcgttcat ccatagttgc ctgactcccc gtcgtgtaga taactacgat  11100
acgggagggc ttaccatctg gccccagtgc tgcaatgata ccgcgagacc cacgctcacc  11160
ggctccagat ttatcagcaa taaaccagcc agccggaagg gccgagcgca gaagtggtcc  11220
tgcaacttta tccgcctcca tccagtctat taattgttgc cgggaagcta gagtaagtag  11280
ttcgccagtt aatagtttgc gcaacgttgt tgccattgct acaggcatcg tggtgtcacg  11340
ctcgtcgttt ggtatggctt cattcagctc cggttcccaa cgatcaaggc gagttacatg  11400
atcccccatg ttgtgcaaaa aagcggttag ctccttcggt cctccgatcg ttgtcagaag  11460
taagttggcc gcagtgttat cactcatggt tatggcagca ctgcataatt ctcttactgt  11520
catgccatcc gtaagatgct tttctgtgac tggtgagtac tcaaccaagt cattctgaga  11580
atagtgtatg cggcgaccga gttgctcttg cccggcgtca atacgggata ataccgcgcc  11640
acatagcaga actttaaaag tgctcatcat tggaaaacgt tcttcgggc  gaaaactctc  11700
aaggatctta ccgctgttga gatccagttc gatgtaaccc actcgtgcac ccaactgatc  11760
ttcagcatct tttactttca ccagcgtttc tgggtgagca aaaacaggaa ggcaaaatgc  11820
cgcaaaaaag ggaataaggg cgacacgaaa atgttgaata ctcat                 11865
```

SEQ ID NO: 19    moltype = DNA length = 11860
FEATURE     Location/Qualifiers
misc_feature    1..11860
          note = Synthetic: PB-hiRep-6#
source       1..11860
          mol_type = other DNA
          organism = synthetic construct

SEQUENCE: 19

```
actcttcctt tttcaatatt attgaagcat ttatcagggt tattgtctca tgagcggata  60
catatttgaa tgtatttaga aaaataaaca aataggggt  ccgcgcacat ttccccgaaa  120
agtgccacct aaattgtaag cgttaatatt tgttaaaat  tcgcgttaaa ttttgttaa   180
atcagctcat ttttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcgag gcgatggccc actacgtgaa  360
ccatcaccct aatcaagttt ttttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctgcaa  gtgtagcggt cacgctgcgc  540
gtaaccacca cacccgccgc gcttaatgcg ccgctacagg cgcgtcccca ttcgccattc  600
aggctgcgca actgttggga agggcgatcg gtgcgggcct cttcgctatt acgccagctg  660
gcgaaagggg gatgtgctgc aaggcgatta agttgggtaa cgccaggtt  tcccagtca   720
cgacgttgta aaacgacggc cagtgagcgc gcctcgttca ttcacgtttt tgaacccgtg  780
gaggacggc  agactcgcgg tgcaaatgtg ttttacagcg tgatggagca gatgaagtag  840
ctcgacacgc tgcagaacac gcagctagat aaccctaga  aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata  1020
ataaattcaa caaacaattt atttatgttt attatttat taaaaaaaaa caaaaactca   1080
aaatttcttc tataaagtaa caaaactttt atcgaattcc tgcagcccgg gggatccact  1140
agttctagag ggacagcccc ccccaaagc  ccccagggat gtaattacgt ccctcccccg   1200
ctaggggca gcagcgagcc gccgggggct ccgctccgt  ccggcgctcc cccgcatcc    1260
ccgagccggc agcgtgcggg gacagccgg  gcacggcagg ggtggcacgg gatcgcttc    1320
ctctgaacgc ttctcgctgc tctttgagcc tgcagacacc tgggggata  cgggaaag    1380
gcctccaagg ccagcttccc acaataagtt gggtgaattt tggctcattc ctcctttcta  1440
taggattgag tcagagcttt tgtgatggga attctgtgga atgtgtgtca gttagggtgt  1500
ggaaagtccc gcgatcgcta gcttaagcgc tgatcaattg gcgcgccgaa ttcgttatct  1560
gcagaattgc gcttgacatt gattattgac tagttattaa ttacgggtc   1620
attagttcat agcccatata tggagttccg cgttacataa cttacggtaa atggcccgcc  1680
tggctgaccg cccaacgacc cccgcccatt gacgtcaata atgacgtatg ttcccatagt  1740
aacgccaata gggactttcc attgacgtca atgggtggag tatttacggt aaactgccca  1800
cttggcagta catcaagtgt atcatatgcc aagtacgccc cctattgacg tcaatgacgg  1860
taaatggccc gcctggcatt atgcccagta catgacctta ctacttggca  1920
gtacatctac gtattagtca tcgctattac catggtgatg cggttttggc agtacatcaa  1980
tgggcgtgga tagcggtttg actcacgggg atttccaagt ctccacccca ttgacgtcaa  2040
tgggagtttg ttttggaacc aaaatcaacg ggactttcca aatgtcgta  acaactccgc   2100
cccattgacg caaatgggcg gtaggcgtgt acggtgggag gtctatataa gcagagctct  2160
ccctatcagt gatagagatc tccctatcag tgatagagat cgtcgacgag ctcgtttagt  2220
gaaccgtcag atcgcctgga gacgccatcc acgctgtttt gacctccata agagacaccg  2280
ggaccgatcc agcctgaacg cgcagccgcc acgccggggt tttacgagat tgtgattaag  2340
gtccccagcg accttgacga gcatctgccc ggcattctg  acagctttgt gaactgggtg   2400
gccgagaagg aatgggagtt gccgccagat tctgacatgg atctgaatct gattgagcag  2460
gcaccctga  ccgtggccga gaagctgcag cgcgactttt gacgaatg  gcgccgtgtg    2520
```

```
agtaaggccc cggaggctct tttctttgtg caatttgaga agggagagag ctacttccac  2580
atgcacgtgc tcgtgaaaac caccggggtg aaatccatgg ttttgggacg tttcctgagt  2640
cagattcgcg aaaaactgat tcagagaatt taccgcggga tcgagccgac tttgccaaac  2700
tggttcgcgg tcacaaagac cagaaatggc gccggaggcg ggaacaaggt ggtggatgag  2760
tgctacatcc ccaattactt gctccccaaa acccagccgc agctccaatg ggcatggacc  2820
aacatggaac agtacctcag cgcctgtttg aatctcacgg agcgtaaacg gttggtggcg  2880
cagcatctga cgcacgtgtc gcagacgcag gagcagaaca aagagaatca gaatcccaat  2940
tctgatgcgc cggtgatcag atcaaaaact tcagccaggt acatggagct ggtcgggtgg  3000
ctcgtggaca aggggattac ctcggagaag cagtggatcc aggaggacca ggcctcatac  3060
atctccttca atgcggcctc caactcgcgg tcccaaatca aggctgcctt ggacaatgcg  3120
ggaaagatta tgagcctgac taaaaccgcc cccgactacc tggtgggcca gcagcccgtg  3180
gaggacattt ccagcaatcg gatttataaa attttggaac taaacgggta cgatccccaa  3240
tatgcggctt ccgtctttct gggatgggcc acgaaaaagt tcggcaagag gaacaccatc  3300
tggctgtttg ggcctgcaac taccgggaag accaacatcg cggaggccat agcccacact  3360
gtgcccttct acgggtgcgt aaactggacc aatgagaact ttcccttcaa cgactgtgtc  3420
gacaagatgg tgatctggtg ggaggagggg aagatgaccg ccaaggtcgt ggagtcggcc  3480
aaagccattc tcggaggaag caaggtgcgc gtggaccaga aatgcaagtc ctcggcccag  3540
atagacccga ctcccgtgat cgtcacctcc aacaccaaca tgtgcgccgt gattgacggg  3600
aactcaacga ccttcgaaca ccagcagccg ttgcaagacc ggatgttcaa atttgaactc  3660
acccgccgtc tggatcatga ctttgggaag gtcaccaagc aggaagtcaa agactttttc  3720
cggtgggcaa aggatcacgt ggttgaggtg gagcatgaat tctacgtcaa aaagggtgga  3780
gccaagaaaa gacccgcccc cagtgacgca gatataagtg agcccaaacg ggtgcgcgag  3840
tcagttcgcg agccatcgac gtcagacgcg gaagcttcga tcaactacgc agacaggtac  3900
caaaacaaat gttctcgtca cgtgggcatg aatctgatgc tgtttccctg cagacaatgc  3960
gagagaatga atcagaattc aaatatctgc ttcactcacg gacagaaaga ctgtttagag  4020
tgctttcccg tgtcagaatc tcaacccgtt tctgtcgtca aaaaggcgta tcagaaactg  4080
tgctacattc atcatatcat gggaaaggtg ccagacgctt gcactgcctg cgatctggtc  4140
aatgtggatt tggatgactg catctttgaa caataaaatg gctaggatcc ggccggcctg  4200
caggtgtcct cacaggaacg aagtccctaa agaaacagtg gcagcaggt ttagccccgg  4260
aaaacttgtt tattgcagct tataatggtt acaaataaag caatagcatc acaaatttca  4320
caaataaagc atttttttca ctgcattcta gttgtggttt gtccaaactc atcaatgtat  4380
cttattgact ggattgaggg acagccccc cccaaagccc cagggatgt aattacgtcc  4440
ctcccccgct aggggcagc agcgagccgc ccggggctcc gctccggtcc ggcgctcccc  4500
ccgcatcccc gagccggcag cgtgcgggga cagcccgggc acggggaagg tggcacggga  4560
tcgctttcct ctgaacgctt ctcgctgctc tttgagcctg cagacacctg gggggatacg  4620
gggaaaaggc ctccaaggcc agcttccacc aataagttgg gtgaattttg gctcattcct  4680
cctttctata ggattgaggt cagagcgaca ttgattattg actagttatt aatagtaatc  4740
aattacgggg tcattagttc atagcccata tatggagttc cgcgttacat aacttacggt  4800
aaatggcccg cctggctgac cgcccaacga ccccgccca ttgacgtcaa taatgacgta  4860
tgttcccata gtaacgccaa tagggacttt ccattgacgt caatgggtgg agtatttacg  4920
gtaaactgcc cacttggcag tacatcaagt gtatcatatg ccaagtacgc ccctattga  4980
cgtcaatgac ggtaaatggc ccgcctggca ttatgcccag tacatgacct tatgggactt  5040
tcctacttgg cagtacatct acgtattagt catcgctatt accatggtga tgcggttttg  5100
gcagtacatc aatgggcgtg atagcggttt tgactcacgg ggatttccaa gtctccaccc  5160
cattgacgtc aatgggagtt tgttttggaa ccaaaatcaa cgggactttc caaaatgtcg  5220
taacaactcc gccccattga cgcaaatggg cggtaggcgt gtacggtggg aggtctatat  5280
aagcagagct ctccctatca gtgatagaga tctccctatc agtgatagag atcgtcgacg  5340
agctcgttta gtgaaccgtc agatcgcctc gagacgccat ccacgctgtt ttgacctcca  5400
tagaagacac cgggaccgat ccagccatc ccaattctga tgcgccggtg atcagatcaa  5460
aaacttcagc caggtacaat ggatggaact ggtcggatgg ctggtggata agggcatcac  5520
aagcagaag caatgatcc aggaggacca ggcctcatat atttcttta acgccgctag  5580
caattccaga agccagatca aggctgctct ggacaacgcc ggcaaaatca tgagcctgac  5640
caagaccgcc cctgactacc tggtgggaca gcagcctgtg gaagatatca gcagcaacag  5700
aatctataag atcctggaac tgaacggcta cgacccccag tacgccgcct ccgtgttcct  5760
gggctgct acaaagaagt tcggcaagcg gaacaccatc tggctgttcg gacctgccac  5820
cacaggcaaa accaatatcg ccgaggccat cgcccacacc gtgcctttct acggctgcgt  5880
gaactggaca aacgagaact tccccttcaa cgactgtgtg gacaagatgg tgatctggtg  5940
ggaggaaggc aaaatgacag ctaaggtggt ggaatctgcc aaggctatcc tgggaggctc  6000
taaggtcagg gtggatcaga agtgtaaaag cagcgcccag attgacccta cccctgtgat  6060
cgtgaccagc aataccaaca tgtgcgccgt gatcgacgc aacagcacca cctcgagca  6120
tcagcagcct ctgcaggacc ggatgttcaa gtttgagctc accagacggc tggatcacga  6180
cttcggcaag gtgaccaagc aggaggtgaa ggatttcttc agatgggcca agaccacgt  6240
tgttgaggtg aacacgagt tctacgtgaa gaagggcggc gccaagaaaa gacccgcccc  6300
tagcgacgcc gacatcagcg agcctaagag agtgcgggaa ggctggccc agaaaaactg  6360
atctgatgct gaggccagca tcaactacgc cgatagatac caaaacaagt gcagccgcca  6420
cgtgggcatg aacctgatgc tgtttccctg cagacagtgt gaaagaatga accagaattc  6480
taatatctgc tttacacacg gccagaaaga ttgcctggaa tgcttccctg tgtccgagag  6540
ccaaccagtg tctgtggtga aaaaggccta ccagaagctg tgctacatcc accacatcat  6600
gggcaaggtg ccagacgcct gtaccgcctg cgacctggtc aacgtggacc tggacgactg  6660
catcttcgag cagtgatttg tgatgggaat tctgtgctgt gccttctagt tgccagccat  6720
ctgttgtttg cccctccccc gtgccttcct tgaccctgga aggtgccact cccactgtcc  6780
tttcctaata aaatgaggaa attgcatcgc attgtctgag taggtgtcat tctattctgg  6840
ggggtgggt gggcaggaca gcaagggggaggattggga agacaatagc aggcatgctg  6900
gggatgcggt gggctctatg ggacctttt ttgggcccat tggtatggct ttttcccgtt  6960
atcccccag gtgtctgcag gctcaaagag cagcgagaag cgttcagagg aaagcgatcc  7020
cgtgccacct tccccgtgcc cgggctgtcc ccgcacgctg ccgctcggg gatgcgggg  7080
gagcgccgga ccgagcgga gccccggcg gctcgctgct gcccctagc ggggaggga  7140
cgtaattaca tccctggggg ctttgggggg gggctgtccc tctagagcgg ccgccaccgc  7200
ggtggagctc cagcttttgt tccctttagt gagggttaat tagatcttaa tacgactcac  7260
```

```
tatagggcga attgggtacc gggcccccct gaggcggaaa gaaccagctg gggctctagg    7320
gggtatcccc ggggttgggg ttgcgccttt tccaaggcag ccctgggttt gcgcagggac    7380
gcggctgctc tgggcgtggt tccgggaaac gcagcggcgc cgaccctggg tctcgcacat    7440
tcttcacgtc cgttcgcagc gtcacccgga tcttcgccgc tacccttgtg ggcccccgg     7500
cgacgcttcc tgctccgccc ctaagtcggg aaggttcctt gcggttcgcg gcgtgccgga    7560
cgtgacaaac ggaagccgca cgtctcacta gtaccctcgc agacggacag cgccagggag    7620
caatggcagc gcgccgaccg cgatgggctg tggccaatag cggctgctca gcagggcgcg    7680
ccgagagcag cggccgggaa ggggcggtgc gggaggcggg gtgtggggcg gtagtgtggg    7740
ccctgttcct gcccgcgcgg tgttccgcat tctgcaagcc tccggagcgc acgtcggcag    7800
tcggctccct cgttgaccga atcaccgacc tctctcccca gaagctcccg ggagcttgta    7860
tatccatttt cggatctgat cagcacgtgt tgacaattaa tcatcggcat agtatatcgg    7920
catagtataa tacgacaagg tgaggaacgc caccatggcc aagcctttgt ctcaagaaga    7980
atccaccctc attgaaagag caacggctac aatcaacagc atcccatct ctgaagacta    8040
cagcgtcgcc agcgcagctc tctctagcga cggccgcatc ttcactggtg tcaatgtata   8100
tcattttact gggggacctt gtgcagaact cgtggtgctg ggcactgctg ctgctgcggc    8160
agctggcaac ctgacttgta tcgtcgcgat cggaaatgag aacaggggca tcttgagccc    8220
ctgcggacgg tgccgacagg tgcttctcga tctgcatcct gggatcaaag ccatagtgaa    8280
ggacagtgat ggacagccga cggcagttgg gattcgtgaa ttgctgccct ctggttatgt    8340
gtgggagggc taaagcgcgg ggatctcatg ctggagttct tcgcccaccc caacttgttt    8400
attgcagctt ataatggtta caaataaagc aatagcatca caaatttcac aaataaagca    8460
tttttttcac tgcattctag ttgtggtttg tccaaactca tcaatgtatc ttatcatgtc    8520
tgtagctgat gtatacctag gatccgccg gcctgcagt gtcctcacag gaacgaagtc     8580
cctaaagaaa cagtggcagc caggtttagc cccggaattg actggattcc ttttttaggg    8640
cccattggta tggcttttc cccgtatccc ccaggtgtc tgcaggctca aagagcagcg     8700
agaagcgttc agaggaaagc gatcccgtgc caccttcccc gtgcccggc tgtccccgca     8760
cgctgccggc tcggggatgc gggggagcg ccggaccgga gcggagcccc gggcggccgc    8820
ctgctgcccc ctagcggggg agggacgtaa ttacatccct gggggctttg gggggggct    8880
gtccctctag agcggccgcc accgcggtgg agctccagct tttgttccct ttagtgaggg    8940
ttaattagat cttaatacga ctcactatag ggcgaattgg gtaccgggcc cccctcgag    9000
gtcgacggta tcctcgaggt cgacggtatc gataagcttg atatctataa caagaaaata    9060
tatatataat aagttatcac gtaagtagaa catgaaataa caatataatt atcgtatgag    9120
ttaaatctta aaagtcacgt aaaagataat catgcgtcat tttgactcac gcggtcgtta    9180
tagttcaaaa tcagtgacac ttaccgcatt gacaagcacg cctcacggga gctccaagcg    9240
gcgactgaga tgtcctaaat gcacagcgac ggattcgcgc tatttagaaa gagagagcaa    9300
tatttcaaga atgcatgcgt caattttacg cagactactt ttctagggtt aatctagctg    9360
catcaggatc atatcgtcgg gtcttttttc cggctcagtc atcgcccaag ctggcgctat    9420
ctgggcatcg gggaggaaga agcccgtgcc ttttcccgcg aggttgaagc ggcatggaaa    9480
gagtttgccg aggatgactg ctgctgcatt gacgttgagc gaaaacgcac gtttaccatg    9540
atgattcggg aaggtgtggc catgcacgcc tttaacggtg aactgttcgt tcaggccac     9600
tgggatacca gttcgtcgcg gctttccgg acacagtcc ggatggtcag cccgaagcgc    9660
atcagcaacc cgaacaatac cggcgacagc cggaactgcc gtgccggtgt gcagattaat    9720
gacagcggtg cggcgctggg atattacgtc agcgaggacg ggtatcctgg ctggatgccg    9780
cagaaatgga catggatacc ccgtgagtta cccggcggc gcgcttggcg taatcatggt    9840
catagctgtt tcctgtgtga aattgttatc cgctcacaat tccacacaac atacgagccg    9900
gaagcataaa gtgtaaagcc tggggtgcct aatgagtgag ctaactcaca ttaattgcgt    9960
tgcgctcact gcccgctttc cagtcgggaa acctgtcgtg ccagctgcat taatgaatcg   10020
gccaacgcgc ggggagaggc ggtttgcgta ttgggcgctc ttccgcttcc tcgctcactg   10080
actcgctgcg ctcggtcgtt cggctgcggc gagcggtatc agctcactca aaggcggtaa   10140
tacggttatc cacagaatca ggggataacg caggaaagaa catgtgagca aaaggccagc   10200
aaaaggccag gaaccgtaaa aaggccgcgt tgctggcgtt tttccatagg ctccgccccc   10260
ctgacgagca tcacaaaaat cgacgctcaa gtcagaggtg gcgaaacccg acaggactat   10320
aaagatacca ggcgtttccc cctggaagct ccctcgtgcg ctctcctgtt ccgaccctgc   10380
cgcttaccgg atacctgtcc gcctttctcc cttcgggaag cgtggcgctt tctcatagct   10440
cacgctgtag gtatctcagt tcggtgtagg tcgttcgctc caagctgggc tgtgtgcacg   10500
aaccccccgt tcagcccgac cgctgcgcct tatccggtaa ctatcgtctt gagtccaacc   10560
cggtaagaca cgacttatcg ccactggcag cagccactgg taacaggatt agcagagcga   10620
ggtatgtagg cggtgctaca gagttcttga agtggtggcc taactacggc tacactagaa   10680
ggacagtatt tggtatctgc gctctgctga gccagttacc ttcggaaaaa gagttggta    10740
gctcttgatc cggcaaacaa accaccgctg gtagcggtgg tttttttgtt tgcaagcagc   10800
agattacgcg cagaaaaaaa ggatctcaag aagatccttt gatcttttct acggggtctg   10860
acgctcagtg gaacgaaaac tcacgttaag ggattttggt catgagatta tcaaaaagga   10920
tcttcaccta gatcctttta aattaaaaat gaagttttaa atcaatctaa agtatatatg   10980
agtaaacttg gtctgacagt taccaatgct taatcagtga ggcaccatc tcagcgatct   11040
gtctatttcg ttcatccata gttgcctgac tccccgtcgt gtagataata ccgatacggg   11100
agggcttacc atctggcccc agtgctgcaa tgataccgcg agaccacgc tcaccggctc    11160
cagatttatc agcaataaac cagccagccg gaagggccga gcgcagaagt ggtcctgcaa   11220
ctttatccgc ctccatccag tctattaatt gttgccggga agctagagta agtagttcgc   11280
cagttaatag tttgcgcaac gttgttgcca ttgctacagg catcgtggtg tcacgctcgt   11340
cgtttggtat ggcttcattc agctccggtt cccaacgatc aaggcgagtt acatgatccc   11400
ccatgttgtg caaaaaagcg gttagctcct tcggtcctcc gatcgttgtc agaagtaagt   11460
tggccgcagt gttatcactc atggttatgg cagcactgca taattctctt actgtcatgc   11520
catccgtaag atgcttttct gtgactggtg agtactcaac caagtcattc tgagaatagt   11580
gtatgcggcg accgagttgc tcttgcccgg cgtcaatacg ggataatacc gcgccacata   11640
gcagaacttt aaaagtgctc atcattggaa aacgttcttc ggggcgaaaa ctctcaagga   11700
tcttaccgct gttgagatcc agttcgatgt aacccactcg tgcacccaac tgatcttcag   11760
catcttttac tttcaccagc gtttctgggt gagcaaaaac aggaaggcaa aatgccgcaa   11820
aaaagggaat aagggcgaca cggaaatgtt gaatactcat                         11860

SEQ ID NO: 20        moltype = DNA  length = 11579
```

```
FEATURE            Location/Qualifiers
misc_feature       1..11579
                   note = Synthetic: PB-hiRep-7#
source             1..11579
                   mol_type = other DNA
                   organism = synthetic construct SEQUENCE: 20
actcttcctt tttcaatatt attgaagcat ttatcagggt tattgtctca tgagcggata   60
catatttgaa tgtatttaga aaaataaaca aatagggggtt ccgcgcacat ttccccgaaa  120
agtgccacct aaattgtaag cgttaatatt ttgttaaaat tcgcgttaaa tttttgttaa  180
atcagctcat tttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
ctcgacacgc tgcagaacac gcagctagat taaccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata 1020
ataaattcaa caaacaattt atttatgttt atttatttat taaaaaaaaa caaaaactca 1080
aaatttcttc tataaagtaa caaaactttt atcgaattcc tgcagcccgg gggatccact 1140
agttctagag ggacagcccc cccccaaagc ccccagggat gtaattacgt ccctccccg  1200
ctaggggggca gcagcgagcc gcccgggggct ccgctccggt ccggcgctcc ccccgcatcc 1260
ccgagccggc agcgtgcggg gacagcccgg gcacggggaa ggtggcacgg gatcgctttc 1320
ctctgaacgc ttctcgctgc tctttgagcc tgcagacacc tgggggggata cggggaaaag 1380
gcctccaagg ccagcttccc acaataagtt gggtgaattt tggctcattc ctcctttcta 1440
taggattgag gtcagagctt tgtgatggga attctgtgga atgtgtgtca gttagggtgt 1500
ggaaagtccc gcgatcgcta gcttaagcgc tgatcaattg gcgcgccgaa ttcgttatct 1560
gcagaattcg gcttggcctc cgcgccgggt tttggcgcct cccgcgggcg cccccctcct 1620
cacggcgagc gctgccacgt cagacgaagg gcgcagcgag cgtcctgatc cttccgcccg 1680
gacgctcagg acagcggccc gctgctcata agactcggcc ttagaacccc agtatcagca 1740
gaaggacatt ttaggacggg acttgggtga ctctagggca ctggttttct ttccagagag 1800
cggaacaggc gaggaaaagt agtcccttct cggcgattct gcggagggat ctccgtgggg 1860
cggtgaacgc cgatgattat ataaggacgc gccgtccct atcagtgata gagatctccc 1920
tatcagtgat agagagtgtg gcacagctag ttccgtcgca gccggatttt gggtcgcggt 1980
tcttgtttgt ggatcgctgt gatcgtcact tgacgaacgc gcagccgcca tgccggggtt 2040
ttacgagatt gtgattaagg tccccagcga ccttgacgag catctgcccg gcatttctga 2100
cagctttgtg aactgggtgg ccgagaagga atgggagttg ccgcagagtt ctgacatgga 2160
tctgaatctg attgagcagg cacccctgac cgtggccgag aagctgcagc gcgactttct 2220
gacgaatgcg cgccgtgtga gtaaggcccc ggaggctctt ttctttgtgc aatttgagaa 2280
gggagagagc tacttccaca tgcacgtgct cgtgaaaacc accggggtga atccatggtt 2340
tttgggacgt ttcctgagtc agattcgcga aaaactgatt cagagaattt accgcgggat 2400
cgagccgact ttgccaaaact ggttcgcggt cacaaagacc agaaatgcg ccggaggcgg 2460
gaacaaggtg gtggatgagt gctacatccc caattacttg ctccccaaaa cccagcctga 2520
gctccaatgg gcatggacca acatggaaca gtacctcagc gcctgtttga atctcacgga 2580
gcgtaaacgg ttggtggcgc agcatctgac gcacgtgtcg cagacgcagg agcagaacaa 2640
agagaatcag aatcccaatt ctgatgcgcc ggtgatcaga tcaaaaactt cagccaggta 2700
catggagctg gtcgggtggc tcgtggacaa gggggattacc tcggagaagc agtgatccaa 2760
ggaggaccag gcctcataca tctccttcaa tgcggcctcc aactcgcggt cccaaatcaa 2820
ggctgccttg gacaatgcgg gaaagattat gagcctgact aaaaccgccc ccgactacct 2880
ggtgggccag cagcccgtgg aggacatttc cagcaatcgg atttataaaa ttttggaact 2940
aaacgggtac gatccccaat atgcggcttc cgtctttctg ggatgggcca cgaaaaagtt 3000
cggcaagagg aacaccatct ggctgtttgg gcctgcaact accggaagga ccaacatcgc 3060
ggaggccata gcccacactg tgcccttcta cgggtgcgta aactgacca atgagaactt 3120
tccctttcaac gactgtgtcg acaagatggt gatctgtgg gaggagggga agataaccgc 3180
caaggtcgtg gagtcggcca aagccattct cggaggaagc aaggtgcgcg tggaccagaa 3240
atgcaagtcc tcggcccaga tagacccgac tcccgtgatc gtcacctcca acaccaacat 3300
gtgcgccgtg attgacggga actcaacgac cttcgaacac cagcagccgt tgcaagaccg 3360
gatgttcaaa tttgaactca cccgccgtct ggatcatgac tttgggaagg tcaccaagca 3420
ggaagtcaaa gactttttcc ggtgggcaaa ggatcacgtg gttgaggtgg agcatgaatt 3480
ctacgtcaaa aaggtgggag ccaagaaaag acccgccccc agtgacgcag atataagtga 3540
gcccaaacgg gtgcgcgagt cagttgcgca gccatcgacg tcagacgcgg aagcttcgat 3600
caactacgca gacaggtacc aaaacaaatg ttctcgtcac gtgggcatga atctgatgct 3660
gtttcctgc agacaatgcg agagaatgaa tcagaattca aatatctgct tcactcacgg 3720
acagaaagac tgtttagagt gctttcccgt gtcagaatct caaccgtttc tgtcgtcaa  3780
aaaggcgtat cagaaactgt gctacattca tcatatcatg gaaaggtgc cagacgcttg  3840
cactgcctgc gatctggtca atgtggattt ggatgactgc atctttgaac aataaaatgg  3900
ctaggatccg gccggcctgc aggtgtcctc acaggaacga agtccctaaa gaaacagtgg  3960
cagccaggtt tagcccggga aaacttgttt attgcagctt ataatggtta caataaaagc  4020
aatagcatca caaatttcac aaataaagca ttttttttcac tgcattctag ttgtggtttg  4080
tccaaactca tcaatgtatc ttattgactg gattgaggga cagccccccc ccaaagcccc  4140
cagggatgta attacgtccc tccccgcta ggggcagca gcgagccgcc cgggctccg    4200
ctccggtccg gcgctcccc cgcatcccg agcggcagc gtgcgggac agcccggca    4260
cggggaaggt ggcacgggat cgctttcctc tgaacgcttc tcgctgctct ttgagcctgc  4320
```

```
agacacctgg ggggatacgg ggaaaaggcc tccaaggcca gcttcccaca ataagttggg   4380
tgaattttgg ctcattcctc ctttctatag gattgaggtc agagcgacat tgattattga   4440
ctagttatta atagtaatca attacggggt cattagttca tagcccatat atggagttcc   4500
gcgttacata acttacggta aatggcccgc ctggctgacc gcccaacgac ccccgcccat   4560
tgacgtcaat aatgacgtat gttcccatag taacgccaat agggactttc cattgacgtc   4620
aatgggtgga gtatttacgg taaactgccc acttggcagt acatcaagtg tatcatatgc   4680
caagtacgcc ccctattgac gtcaatgacg gtaaatggcc cgcctggcat tatgcccagt   4740
acatgacctt atgggacttt cctacttggc agtacatcta cgtattagtc atcgctatta   4800
ccatggtgat gcggttttgg cagtacatca atgggcgtgg atagcggttt gactcacggg   4860
gatttccaag tctccacccc attgacgtca atgggagttt gttttggaac caaaatcaac   4920
gggactttcc aaaatgtcgt aacaactccg ccccattgac gcaaatgggc ggtaggcgtg   4980
tacggtggga ggtctatata agcagagctc tccctatcag tgatagagat ctccctatca   5040
gtgatagaga tcgtcgacga gctcgtttag tgaaccgtca gatcgcctgg agacgccatc   5100
cacgctgttt tgacctccat agaagacacc gggaccgatc cagcctatcc caattctgat   5160
gcgccggtga tcagatcaaa aacttcagcc aggtacaatg gatgaactg gtcggatggc   5220
tggtggataa gggcatcaca agcgagaagc aatggatcca ggaggaccag gcctcatata   5280
tttcttttaa cgccgctagc aattccgaaa gccagatcaa ggctgctctg gacaacgccg   5340
gcaaaatcat gagcctgacc aagaccgccc ctgactacct ggtgggacag cagcctgtgg   5400
aagatatcag cagcaacaga atctataaga tcctggaact gaacggctac gacccccagt   5460
acgccgcctc cgtgttcctg ggctgggcta caaagaagtt cggcaagcgg aacaccatct   5520
ggctgttcgg acctgccacc acaggcaaaa ccaatatcgc cgaggccatc gcccacaccg   5580
tgccttttcta cggctgcgtg aactggacaa acgagaactt ccccttcaac actgtgtgg   5640
acaagatggt gatctggtgg gaggaaggca aatgacagc taaggtggtg aatctgcca   5700
aggctatcct gggaggctct aaggtcaggg tggatcagaa gtgtaaaagc agcgcccaga   5760
ttgaccctac ccctgtgatc gtgaccagca ataccaacat gtgcgccgtg atcgacggca   5820
acagcaccac cttcgagcat cagcagcctc tgcaggacgg gatgttcaag tttgagctca   5880
ccagacggct ggatcacgac ttcggcaagg tgaccaagca ggaggtgaag gatttcttca   5940
gatgggccaa agaccacgtt gttgaggtgg aacacgagtt ctacgtgaag aagggcggcg   6000
ccaagaaaag accccgcccct agcgacgccg acatcagcga gcctaagaga gtgcgggaaa   6060
gcgtggccca gcccagcaca tctgatgctg aggccagact caactacgcc gatagatacc   6120
aaaacaagtg cagccgccac gtgggcatga acctgatgct gttccctgc agacagtgtg   6180
aaagaatgaa ccagaattct aatatctgct ttacacacgg ccagaaagat tgcctggaat   6240
gcttccctgt gtccgagagc caaccagtgt ctgtggtgaa aaaggcctac cagaagctgt   6300
gctacatcca ccacatcatg ggcaaggtgc cagacgcctg taccgcctgc gacctggtca   6360
acgtggacct ggacgactgc atcttcgagc agtgatttgt gatgggaatt ctgtgctgtg   6420
ccttctagtt gccagccatc tgttgtttgc ccctccccg tgccttcctt gaccctggaa   6480
ggtgccactc ccactgtcct ttcctaataa aatgaggaaa ttgcatcgca ttgtctgagt   6540
aggtgtcatt ctattctggg gggtggggtg gggcaggaca gcaaggggga ggattgggaa   6600
gacaatagca ggcatgctgg ggatgcggtg ggctctatgg gacctttttt agggcccatt   6660
ggtatgcgtt tttcccgta tccccccagg tgtctgcagg ctcaaagagc agcgagaagc   6720
gttcagagga aagcgatccc gtgccacctt ccccgtgccc gggctgtccc cgcacgctgc   6780
cggctcgggg atgcgggggg agcgccggac cggagcggag ccccgggcgg ctcgctgctg   6840
cccctagcg ggggagggac gtaattacat ccctggggcc tttgggggg gctgtcccat   6900
ctagagcggc cgccaccgcg gtggagctcc agcttttgtt ccctttagtg agggttaatt   6960
agatcttaat acgactcact atagggcgaa ttgggtaccg gccccccctg aggcggaaag   7020
aaccagctgg ggctctaggg ggtatcccg gggttgggg tgcgccttt ccaaggcagc   7080
cctggggttg cgcagggacg cggctgctct gggcgtgttt ccgggaaacg cagcggcgcc   7140
gaccctgggt ctcgcacatt cttcacgtcc gttcgcagcg tcacccggat cttcgccgct   7200
acccttgtgg gccccccggc gacgcttcct gctccgcccc taagtcggga aggttccttg   7260
cggttcgcgg cgtgccggac gtgacaaacg gaagccgcac gtctcactag taccctgca   7320
gacggacagc gccagggac aatggcagc gccgacgc cgccgacgc gatgggctgt ggccaatgac   7380
ggctgctcag cagggcgcgc cgagagcagc ggccgggaag gggcggtgcg ggaggcgggg   7440
tgtggggcgg tagtgtgggc cctgttcctg cccgcgcggt gttccgcatt ctgcaagcct   7500
ccggagcgca cgtcggcagt cggctccctc gttgaccgaa tcaccgacct ctctcccag   7560
aagctcccgg gagcttgtat atccattttc ggatctgatc agcacgtgtt gacaattaat   7620
catcggcata gtatatcggc atagtataat acgacaaggt gaggaacgcc accatggcca   7680
agcctttgtc tcaagaagaa tccaccctca ttgaaagagc aacggctaca atcaacagca   7740
tccccatctc tgaagactac agcgtcgcca gcgcagctct ctctagcgac ggccgcatct   7800
tcactggtgt caatgtatat cattttactg ggggaccttg tgcagaactc gtggtgctgc   7860
gcactgctgc tgctgcggca gctggcacc tgacttgtat cgtcgcgatc ggaaatgaga   7920
acaggggcat cttgagcccc tgcggacggt gccgacaggt gcttctcgat ctgcatcctg   7980
ggatcaaagc catagtgaag acagtgatg acagccgac ggcagttggg attcgtgaat   8040
tgctgccctc tggttatgtg tgggagggct aaagcgcggg gatctcatgc tggagttctt   8100
cgcccacccc aacttgttta ttgcagctta taatggttac aaataaagca atagcatcac   8160
aaatttcaca aataaagcat ttttttcact gcattctagt tgtggtttgt ccaaactcat   8220
caatgtatct tatcatgtct gtagctgatg tatacctagg atccgccgg cctgcaggtg   8280
tcctcacagg aacgaagtcc ctaaagaaac agtggcagcc aggtttagcc ccggaattga   8340
ctggattcct ttttttagggc ccattggtat ggctttttcc ccgtatcccc ccaggtgtct   8400
gcaggctcaa agagcagcga gaagcgttca gaggaaagcg atcccgtgcc accttcccg   8460
tgcccgggct gtcccgcac gctgccggct cggggatgcg gggagcgc cggaccggag   8520
cggagcccg gcggctcgc tgctgccccc tagcggggga ggacgtaat tacatccctg   8580
ggggctttgg ggggggctg tccctctaga gcggccgcca ccgcggtgga gctccagctt   8640
ttgttcccctt tagtgagggt taattagatc ttaatacgac tcactatagg gcgaattggg   8700
taccgggccc ccctcgagg tcgacggtat cgataagctt gatatcgaat tcctgcagcc   8760
tatctataac aagaaaatat atatataata agttatcacg taagtagaac atgaaataac   8820
aatataatta tcgtatgagt taaatcttaa aagtcacgta aaagataatc atgcgtcatt   8880
ttgactcacg cggtcgttat agttcaaaat cagtgacact taccgcattg acaagcacgc   8940
ctcacgggag ctccaagcgg cgactgagat gtcctaaatg cacagcgacg gattcgcgct   9000
atttagaaag agagagcaat atttcaagaa tgcatgcgtc aattttacgc agactatctt   9060
```

```
tctagggtta atctagctgc atcaggatca tatcgtcggg tcttttttcc ggctcagtca   9120
tcgcccaagc tggcgctatc tgggcatcgg ggaggaagaa gcccgtgcct ttcccgcga    9180
ggttgaagcg gcatggaaag agtttgccga ggatgactgc tgctgcattg acgttgagcg   9240
aaaacgcacg tttaccatga tgattcggga aggtgtggcc atgcacgcct taacggtga    9300
actgttcgtt caggccacct gggataccag ttcgtccgga cttttccgga cacagttccg   9360
gatggtcagc ccgaagcgca tcagcaaccc gaacaatacc ggcgacagcc ggaactgccg   9420
tgccggtgtg cagattaatg acagcggtgc ggcgctggga tattacgtca gcgaggacgg   9480
gtatcctggc tggatgccgc agaaatggac atggataccc cgtgagttac ccggcgggcg   9540
cgcttggcgt aatcatggtc atagctgttt cctgtgtgaa attgttatcc gctcacaatt   9600
ccacacaaca tacgagccgg aagcataaag tgtaaagcct ggggtgccta atgagtgagc   9660
taactcacat taattgcgtt gcgctcactg cccgctttcc agtcgggaaa cctgtcgtgc   9720
cagctgcatt aatgaatcgg ccaacgcgcg gggagaggcg gtttgcgtat gggcgctct    9780
tccgcttcct cgctcactga ctcgctgcgc tcggtcgttc ggctgcggcg agcggtatca   9840
gctcactcaa aggcggtaat acggttatcc acagaatcag gggataacgc aggaaagaac   9900
atgtgagcaa aaggccagca aaaggccagg aaccgtaaaa aggccgcgtt gctggcgttt   9960
ttccataggc tccgccccc tgacgagcat cacaaaaatc gacgctcaag tcagaggtgg    10020
cgaaacccga caggactata agataccag gcgtttcccc ctggaagctc cctcgtgcgc   10080
tctcctgttc cgaccctgcc gcttaccgga tacctgtccg cctttctccc ttcgggaagc   10140
gtggcgcttt ctcatagctc acgctgtagg tatctcagtt cggtgtaggt cgttcgctcc   10200
aagctgggct gtgtgcacga acccccgtt cagcccgacc gctgcgcctt atccggtaac    10260
tatcgtcttg agtccaaccc ggtaagacac gacttatcgc cactggcagc agccactggt   10320
aacaggatta gcagagcgag gtatgtaggc ggtgctacag agttcttgaa gtggtggcct   10380
aactacggct acactagaag gacagtattt ggtatctgcg ctctgctgaa gccagttacc   10440
ttcggaaaaa gagttggtag ctcttgatcc ggcaaacaaa ccaccgctgg tagcggtggt   10500
ttttttgttt gcaagcagca gattacgcgc agaaaaaaag gatctcaaga agatcctttg   10560
atcttttcta cggggtctga cgctcagtgg aacgaaaact cacgttaagg gattttggtc   10620
atgagattat caaaaaggat cttcacctag atccttttaa attaaaaatg aagttttaaa   10680
tcaatctaaa gtatatatga gtaaacttgg tctgacagtt accaatgctt aatcagtgag   10740
gcacctatct cagcgatctg tctatttcgt tcatccatag ttgcctgact ccccgtcgtg   10800
tagataacta cgatacggga gggcttacca tctggcccca gtgctgcaat gataccgcga   10860
gacccacgct caccggctcc agatttatca gcaataaacc agccagccgg aagggccgag   10920
cgcagaagtg gtcctgcaac tttatccgcc tccatccagt ctattaattg ttgccgggaa   10980
gctagagtaa gtagttcgcc agttaatagt ttgcgcaacg ttgttgccat tgctacaggc   11040
atcgtggtgt cacgctcgtc gtttggtatg gcttcattca gctccggttc ccaacgatca   11100
aggcgagtta catgatcccc catgttgtgc aaaaaagcgg ttagctcctt cggtcctccg   11160
atcgttgtca gaagtaagtt ggccgcagtg ttatcactca tggttatggc agcactgcat   11220
aattctctta ctgtcatgcc atccgtaaga tgcttttctg tgactggtga gtactcaacc   11280
aagtcattct gagaatagtg tatgcggcga ccgagttgct cttgcccggc gtcaatacgg   11340
gataataccg cgccacatag cagaacttta aaagtgctca tcattggaaa acgttcttcg   11400
gggcgaaaac tctcaaggat cttaccgctg ttgagatcca gttcgatgta acccactcgt   11460
gcacccaact gatcttcagc atcttttact ttcaccagcg tttctgggtg agcaaaaaca   11520
ggaaggcaaa atgccgcaaa aaagggaata agggcgacac ggaaatgttg aatactcat    11579

SEQ ID NO: 21           moltype = DNA   length = 11701
FEATURE                 Location/Qualifiers
misc_feature            1..11701
                        note = Synthetic: PB-hiRep-8#
source                  1..11701
                        mol_type = other DNA
                        organism = synthetic construct
SEQUENCE: 21
actcttcctt tttcaatatt attgaagcat ttatcagggt tattgtctca tgagcggata   60
catatttgaa tgtatttaga aaaataaaca aataggggtt ccgcgcacat ttccccgaaa   120
agtgccacct aaattgtaag cgttaatatt ttgttaaaat tcgcgttaaa ttttgttaa    180
atcagctcat tttttaacca ataggccgaa atcggcaaaa tcccttataa atcaaaagaa   240
tagaccgaga tagggttgag tgttgttcca gtttggaaca agagtccact attaaagaac   300
gtggactcca acgtcaaagg gcgaaaaacc gtctatcagg gcgatggccc actacgtgaa   360
ccatcaccct aatcaagttt ttttggggtcg aggtgccgta aagcactaaa tcggaaccct   420
aaagggagcc cccgatttag agcttgacgg ggaaagccgg cgaacgtggc gagaaaggaa   480
gggaagaaag cgaaaggagc gggcgctagg gcgctggcaa gtgtagcggt cacgctgcgc   540
gtaaccacca cacccgccgc gcttaatgcg ccgctacagg gcgcgtccca ttcgccattc   600
aggctgcgca actgttggga agggcgatcg gtgcgggcct cttcgctatt acgccagctg   660
gcgaaagggg gatgtgctgc aaggcgatta agttgggtaa cgccagggtt ttcccagtca   720
cgacgttgta aaacgacggc cagtgagcgc gcctcgttca ttcacgtttt tgaaccgtg    780
gaggacgggc agactcgcgg tgcaaatgtg ttttacagcg tgatggagca gatgaagatg   840
ctcgacacgc tgcagaacac gcagctagat taaccctaga aagataatca tattgtgacg   900
tacgttaaag ataatcatgc gtaaaattga cgcatgtgtt ttatcggtct gtatatcgag   960
gtttatttat taatttgaat agatattaag tttttattata tttacactta catactaata   1020
ataaattcaa caaacaattt atttatgttt atttatttat taaaaaaaaa caaaactca    1080
aaatttcttc tataaagtaa caaaacttttt atcgaattcc tgcagcccgg ggatccact   1140
agttctagag gacagcccc cccccaaagc cccagggat gtaattacgt ccctcccccg    1200
ctaggggca gcagcgagcc gcccggggct ccgctccggt ccggcgctcc cccgcatcc    1260
ccgagccggc agcgtgcggg gacagccgg gcacggggaa ggtggcacgg atcgctttc    1320
ctctgaacgc ttctcgctgc tctttgaacc tgcagacacc tggggggata cggggaaaag   1380
gcctccaagg ccagcttccc acaataagtt gggtgaattt tggctcattc ctcctttcta   1440
taggattgag tcagagctt tgtgatggga attctgtgga atgtgtgtca gttaggtgt     1500
ggaaagtccc gcgatcgcta gcttaagcgc tgatcaattg gcgcgccgaa ttcgttatct   1560
gcagaattcg gcttctgctc cctgcttgtg tgttggaggt cgctgagtag tgcgcgagca   1620
aaatttaagc tacaacaagg caaggcttga ccgacaattg catgaagaat ctgcttaggg   1680
```

```
ttaggcgttt tgcgctgctt cgcgatgtac gggccagata tacgcgtatc tgagggact   1740
agggtgtgtt taggcgaaaa gcggggcttc ggttgtacgc ggttaggagt cccctcagga   1800
tatagtagtt tcgcttttgc atagggaggg ggaaatgtag tcttatgcaa tacacttgta   1860
gtcttgcaac atggtaacga tgagttagca acatgcctta caaggagaga aaaagcaccg   1920
tgcatgccga ttggtggaag taaggtggta cgatcgtgcc ttattaggaa ggcaacagac   1980
aggtctgaca tggattggac gaaccactga attccgcatt gcagagataa ttgtatttaa   2040
gtgcctagct ccctatcagt gatagagatc tccctatcag tgatagagat cgatacaata   2100
aacgccattt gaccattcac cacattggtg tgcaccgaac gcgcagccgc catgccgggg   2160
ttttacgaga ttgtgattaa ggtccccagc gaccttgacg agcatctgcc cggcatttct   2220
gacagctttg tgaactgggt ggccgagaag gaatgggagt tgccgccaga ttctgacatg   2280
gatctgaatc tgattgagca ggcacccctg accgtggccg agaagctgca gcgcgacttt   2340
ctgacggaat ggcgccgtgt gagtaaggcc ccggaggctc tttctttgt gcaatttgag    2400
aagggagaga gctacttcca catgcacgtg ctcgtggaaa ccaccggggt gaaatccatg   2460
gttttgggac gtttcctgag tcagattcgc gaaaaactga ttcagagaat ttaccgccgg   2520
atcgagccga ctttgccaaa ctggttcgcg gtcacaaaga ccagaaatgg cgccggaggc   2580
gggaacaagg tggtggatga tgctacatc cccaattact tgctcccaa aacccagcct     2640
gagctccaat gggcatggac caacatgaaa cagtacctgc gcgcctgttt gaatctcacg   2700
gagcgtaaac ggttggtggc gcagcatctg acgcacgtgt cgcagacgca ggagcagaac   2760
aaagagaatc agaatcccaa ttctgatgcg ccggtgatca gatcaaaaac ttcagccagg   2820
tacatggagc tggtcgggtg gctcgtggac aaggggatta cctcggagaa gcagtggatc   2880
caggaggacc aggcctcata catctccttc aatgcggcct ccaactcgcg gtcccaaatc   2940
aaggctgcct tggacaatgc gggaaagatt atgagcctga ctaaaaccgc ccccgactac   3000
ctggtgggcc agcagccgt ggaggacatt tccagcaatc ggatttataa aattttggaa    3060
ctaaacgggt acgatcccca atatgcgct tccgtctttc tgggatgggc cacgaaaaag    3120
ttcggcaaga ggaacaccat ctggctgttt gggcctgcaa ctaccgggaa gaccaacatc   3180
gcggaggcca tagcccacac tgtgcccttc tacgggtgcg taaactggac caatgagaac   3240
tttcccttca acgactgtgt cgacaagatg gtgatctggt gggaggaggg gaagatgacc   3300
gccaaggtcg tggagtcggc caaagccatt tcggaggaa gcaaggtgcg cgtgaccag    3360
aaatgcaagt cctcggccca gatagacccg actcccgtga tcgtcacctc caacaccaac   3420
atgtgcgtca tgattgacgg gaactcaacg accttcgaac accagcagcc gttgcaagac   3480
cggatgttca aatttgaact caccgccgt ctggatcatg actttgggaa ggtcaccaag    3540
caggaagtca aagactttt ccggtgggca aaggatcacg tggttgaggt ggagcatgaa    3600
ttctacgtca aaaagggtgg agccaagaaa agacccgccc ccagtgacgc agatataagt   3660
gagcccaaac gggtgcgcga gtcagttgcg cagccatcga ccatcagacg ggaagcttcg   3720
atcaactacg cagacaggta ccaaaacaaa tgttctcgtc acgtgggcat gaatctgatg   3780
ctgtttccct gcagacaatg cgagagaatg aatcagaatt caaatatctg cttcactcac   3840
ggacagaaag actgtttaga gtgctttccc gtgtcagaat ctcaaccgt ttctgtcgtc    3900
aaaaaggcgt atcagaaact gtgctacatt catcatatca tgggaaaggt gccagacgct   3960
tgcactgcct gcgatctggt caatgtggat ttggatgact gcatctttga acaataaaat   4020
ggctaggatc cggccggcct gcaggtgtcc tcacaggaac gaagtcccta aagaaacagt   4080
ggcagccagg tttagccccg gaaaacttgt ttattgcagc ttataatggt tacaaataaa    4140
gcaatagcat cacaaatttc acaaataaag catttttttc actgcattct agttgtggtt   4200
tgtccaaact catcaatgta tcttattgac tggattgagg acagccccc ccccaaagcc    4260
cccagggatg taattacgtc cctccccgc taggggcag cagcgagccg cccgggctc     4320
cgctccggtc cggcgctccc cccgcatccc cgagccggca gcgtgcgggg acagcccggg   4380
cacgggggaag gtggcacggg atcgcttttc tctgaacgct tctcgctgct ctttgagcct  4440
gcagcacct gggggatac ggggaaaagg cctccaaggc cagcttccca caataagttg    4500
ggtgaattt ggctcattcc tccttttctat aggattgagg tcagagcgac attgattatt   4560
gactagttat taatagtaat caattacggg gtcattagtt catagcccat atatggagtt   4620
ccgcgttaca taacttacgg taaatggccc gcctggctga ccgcccaacg accccgccc   4680
attgacgtca ataatgacgt atgttcccat agtaacgcca atagggactt tccattacg    4740
tcaatgggtg gagtatttac ggtaaactgc ccacttggca gtacatcaag tgtatcatat   4800
gccaagtacg cccccattg acgtcaatga cggtaaatgg cccgcctggc attatgccca   4860
gtacatgacc ttatgggact ttcctacttg gcagtacatc tacgtattag tcatcgctat   4920
taccatggtg atgcggtttt ggcagtacat caatgggcgt ggatagcggt ttgactcacg   4980
gggatttcca agtctccacc ccattgacgt caatgggagt ttgttttgga accaaaatca   5040
acgggacttt ccaaaatgtc gtaacaactc cgccccattg acgcaaatgg gcggtaggcg   5100
tgtacggtgg gaggtctata taagcagagc tctccctatc agtgatagag atctccctat   5160
cagtgataga gatcgtcgac gagctcgttt agtgaaccgt cagatcgcct ggagacgcca   5220
tccacgctgt tttgacctcc atagaagaca ccgggaccga tccagcctat cccaattctg   5280
atgcgccggt gatcagatca aaaacttcag ccaggtacaa tggatggaac tggtcggatg   5340
gctggtggat aagggcatca caagcgagaa gcaatggatc caggaggacc aggcctcata   5400
tatttctttt aacgccgcta gcaattccag aagccagatc aaggctgctc tggacaacgc   5460
cggcaaaatc atgagcctga ccaagaccgc ccctgactac ctggtgggca agcagcccga   5520
ggaagatatc agcagcaaca gaatctataa gatcctggaa ctgaacggct acgaccccca   5580
gtacgccgcc tccgtgttcc tgggctgggc tacaaagaag ttcggcaagc ggaacaccat   5640
ctggctgttc ggacctgcca ccacaggcaa accaatatc gccgaggcca tcgcccacac    5700
cgtgcctttc tacggctgcg tgaactggac aaacgagaac ttcccccttca acgactgtgt   5760
ggacaagatg gtgatctggt gggaggaagg caaaatgaca gctaaggtgg tggaatctgc   5820
caaggctatc ctgggaggct ctaaggtcag ggtggatcag aagtgtaaaa gcagcgccca   5880
gattgaccct acccctgtga tcgtgaccag caataccaac atgtgcgccc tgatcgacgg   5940
caacagcacc accttcgagc atcagcagcc tctgcaggac cggatgttca gtttgagct     6000
caccagacgg ctggatcacg acttcggcaa ggtgaccaag caggaggtga aggatttctt   6060
cagatgggca aaagaccacg ttgttgaggt ggaacactga ttctacgtga agagggcgg    6120
cgccaagaaa agaccgccc ctagcgacgc cgacatcagc gagcctaaga gagtgcgcga    6180
aagcgtggcc cagcccagca catctgatgc tgaggcagc atcaactacg ccgatagata    6240
ccaaaacaag tgcagccgcc acgtgggcat gaacctgatg ctgtttccct gcagacagtg   6300
tgaaagaatg aaccagaatt ctaatatctg ctttacacac ggccagaaag attgcctgga   6360
atgcttccct gtgtccgaga gccaaccagt gtctgtggtg aaaaaggcct accagaagct   6420
```

```
gtgctacatc caccacatca tgggcaaggt gccagacgcc tgtaccgcct gcgacctggt    6480
caacgtggac ctggacgact gcatcttcga gcagtgattt gtgatgggaa ttctgtgctg    6540
tgccttctag ttgccagcca tctgttgttt gcccctcccc cgtgccttcc ttgaccctgg    6600
aaggtgccac tcccactgtc ctttcctaat aaaatgagga aattgcatcg cattgtctga    6660
gtaggtgtca ttctattctg gggggtgggg tggggcagga cagcaagggg gaggattggg    6720
aagacaatag caggcatgct ggggatgcgg tgggctctat gggacctttt ttagggccca    6780
ttggtatggc tttttcccg tatccccca ggtgtctgca ggctcaaaga gcagcgagaa      6840
gcgttcagag gaaagcgatc ccgtgccacc ttccccgtgc ccgggctgtc cccgcacgct    6900
gccggctcgg ggatgcgggg ggagcgccgg accggagcgg agcccgggc ggctcgctgc     6960
tgcccctag cggggaggg acgtaattac atccctgggg gctttggggg ggggctgtcc      7020
ctctagagcg gccgccaccg cggtggagct ccagcttttg ttccctttag tgagggttaa    7080
ttagatctta atacgactca ctatagggcg aattgggtac cggccccc tgaggcgaaa      7140
agaaccagct ggggctctag ggggtatccc cggggttggg gttgcgcctt tccaaggca     7200
gccctgggtt tgcgcaggga cgcggctgct ctgggcgttg ttccgggaaa cgcagcggcg    7260
ccgaccctgg gtctcgcaca ttcttcacgt ccgttcgcag cgtcacccgg atcttcgccg    7320
ctaccctgt gggccccccg gcgacgcttc ctgctccgcc cctaagtcgg aaggttcct      7380
tgcggttcgc ggcgtgccgg acgtgacaaa cggaagccgc acgtctcact agtaccctcg    7440
cagacggaca gcgccaggga gcaatggcag cgcgccgacc gcgatgggct gtggccaata    7500
gcggctgctc agcagggcgc gccgagagca gcggccggga aggggcggtg cgggaggcgg    7560
ggtgtgggc ggtagtgtgg gccctgttcc tgcccgcgcg gtgttccgca ttctgcaagc     7620
ctccggagcg cacgtcggca gtcggctccc tcgttgaccg aatcaccgac ctctctcccc    7680
agaagctccc gggagcttgt atatccattt tcggatctga tcagcacgtg ttgacaatta    7740
atcatcggca tagtatatcg gcatagtata atacgacaag gtgaggaacg ccaccatggc    7800
caagcctttg tctcaagaag aatccaccct cattgaaaga gcaacggcta caatcaacag    7860
catccccatc tctgaagact acagcgtcgc cagcgcagct ctctctagcg acggccgcat    7920
cttcactggt gtcaatgtat atcatttac tgggggacct tgtgcagaac tcgtggtgct    7980
gggcactgct gctgctgcgg cagctggcaa cctgacttgt atcgtcgcga tcggaaatga    8040
gaacagggc atcttgagcc cctgcggacg gtgccgacag gtgcttctcg atctgcatcc    8100
tgggatcaaa gccatagtga aggacagtga tggacagccg acggcagttg ggattcgtga    8160
attgctgcc tctggttatg tgtgggaggg ctaaagccgg ggatctcat gctggagttc      8220
ttcgcccacc ccaacttgtt tattgcagct tataatggtt acaaataaag caatagcatc    8280
acaaatttca caaatgaagc atttttttca ctgcattcta gttgtggttt gtccaaactc    8340
atcaatgtat cttatcatgt ctgtagctga tgtataccta ggatccgcc ggcctgcagg     8400
tgtcctcaca ggaacgaagt ccctaaagaa acagtggcag ccaggtttag ccccggaatt    8460
gactggattc cttttttagg gcccattggt atggcttttt cccgtatcc ccccaggtgt     8520
ctgcaggctc aaagagcagc gagaagcgtt cagaggaaag cgatcccgtg ccaccttccc    8580
cgtgccggg ctgtccccgc acgctgccgg ctcggggatg cgggggagc gccggaccgg      8640
agcggagccc cgggcggctc gctgctgccc cctagcgggg gagggacgta attacatccc    8700
tgggggcttt ggggggggc tgtccctcta gagccgccc caccgcggtg gagctccagc     8760
ttttgttccc tttagtgagg gttaattaga tcttaatacg actcactata gggcgaattg    8820
ggtaccgggc ccccctcga ggtcgacggt atcctcgagg tcgacggtat cgataagctt     8880
gatatctata acaagaaaat atatatataa taagttatca cgtaagtaga acatgaaata    8940
acaatataat tatcgtatga gttaaatctt aaaagtcacg taaaagataa tcatgcgtca    9000
ttttgactca cgcggtcgtt atagttcaaa atcagtgaca cttaccgcat tgacaagcac    9060
gcctcacggg agctccaagc ggcgactgag atgtcctaaa tgcacagcga cggattcgcg    9120
ctatttagaa agagagagca atatttcaag aatgcatgcg tcaattttac gcagactatc    9180
tttctagct taatctagct gcatcaggat catatcgtcg ggtctttttt ccggctcagt     9240
catcgcccaa gctggcgcta tctgggcatc ggggaggaag aagcccgtgc cttttccgg     9300
gaggttgaag cggcatggaa agagtttgcc gaggatgact gctgctgcat tgacgttgag    9360
cgaaaacgca cgtttaccat gatgattcgg gaaggtgtgg ccatgcacgc ctttaacggt    9420
gaactgttcg ttcaggccac ctgggatacc agttcgtcgc ggcttttttc gacacagttc    9480
cggatggtca gcccgaagcg catcagcaac ccgaacaata ccggcgacag ccggaactgc    9540
cgtgccggtg tgcagattaa tgacagcggt gcggcgctgg gatattacgt cagcgaggac    9600
gggtatcctg gctggatgcc gcagaaatgg acatggatac cccgtgagtt acccggcggg    9660
gcgcttggc gtaatcatgg tcatagctgt ttcctgtgtg aaattgttat ccgctcacaa     9720
ttccacacaa catacgagcc ggaagcataa agtgtaaagc ctggggtgcc taatgagtga    9780
gctaactcac attaattgcg ttgcgctcac tgcccgcttt ccagtcggga aacctgtcgt    9840
gccagctgca ttaatgaatc ggccaacgcg cggggagagg cggtttgcgt attgggcgct    9900
cttccgcttc ctcgctcact gactcgctgc gctcggtcgt tcggctgcgg cgagcggtat    9960
cagctcactc aaaggcggta atacggttat ccacagaatc agggggataac gcaggaaaga   10020
acatgtgagc aaaaggccag caaaaggcca ggaaccgtaa aaaggccgcg ttgctggcgt    10080
ttttccatag gctccgcccc cctgacgagc atcacaaaaa tcgacgctca agtcagaggt    10140
ggcgaaaccc gacaggacta taaagatacc aggcgtttcc ccctggaagc tccctcgtgc    10200
gctctcctgt tccgaccctg ccgcttaccg gatacctgtc cgcctttctc ccttcgggaa    10260
gcgtggcgct ttctcatagc tcacgctgta ggtatctcag ttcggtgtag tcgttcgct    10320
ccaagctggg ctgtgtgcac gaaccccccg ttcagcccga ccgctgcgcc ttatccggta    10380
actatcgtct tgagtccaac ccggtaagac acgacttatc gccactggca gcagccactg    10440
gtaacaggat tagcagagcg aggtatgtag gcggtgctac agagttcttg aagtggtggc    10500
ctaactacgg ctacactaga aggacagtat ttggtatctg cgctctgctg aagccagtta    10560
ccttcggaaa aagagttggt agctcttgat ccggcaaaca aaccaccgct ggtagcggtg    10620
gtttttttgt ttgcaagcag cagattacgc gcagaaaaaa aggatctcaa gaagatcctt    10680
tgatcttttc tacggggtct gacgctcagt ggaacgaaaa ctcacgttaa gggattttgg    10740
tcatgagatt atcaaaaagg atcttcacct agatcctttt aaattaaaaa tgaagtttta    10800
aatcaatcta aagtatatat gagtaaactt ggtctgacag ttaccaatgc ttaatcagtg    10860
aggcacctat ctcagcgatc tgtctatttc gttcatccat agttgcctga ctccccgtcg    10920
tgtagataac tacgatacgg gagggcttac catctggccc cagtgctgca atgataccgc    10980
gagacccacg ctcaccggct ccagatttat cagcaataaa ccagccagcc ggaagggccg    11040
agcgcagaag tggtcctgca actttatccg cctccatcca gtctattaat tgttgccggg    11100
aagctagagt aagtagttcg ccagttaata gtttgcgcaa cgttgttgcc attgctacag    11160
```

```
gcatcgtggt gtcacgctcg tcgtttggta tggcttcatt cagctccggt tcccaacgat  11220
caaggcgagt tacatgatcc cccatgttgt gcaaaaaagc ggttagctcc ttcggtcctc  11280
cgatcgttgt cagaagtaag ttggccgcag tgttatcact catggttatg cagcactgc   11340
ataattctct tactgtcatg ccatccgtaa gatgcttttc tgtgactggt gagtactcaa  11400
ccaagtcatt ctgagaatag tgtatgcggc gaccgagttg ctctgccg cgtcaatac    11460
gggataatac cgcgccacat agcagaactt taaaagtgct catcattgga aaacgttctt  11520
cggggcgaaa actctcaagg atcttaccgc tgttgagatc cagttcgatg taacccactc  11580
gtgcacccaa ctgatcttca gcatcttta ctttcaccag cgtttctggg tgagcaaaaa   11640
caggaaggca aatgccgca aaaaagggaa taagggcgac acggaaatgt tgaatactca    11700
t                                                                   11701

SEQ ID NO: 22           moltype = DNA   length = 11861
FEATURE                 Location/Qualifiers
misc_feature            1..11861
                        note = Synthetic: PB-hiRep-9#
source                  1..11861
                        mol_type = other DNA
                        organism = synthetic construct
SEQUENCE: 22
actcttcctt tttcaatatt attgaagcat ttatcagggt tattgtctca tgagcggata     60
catatttgaa tgtatttaga aaaataaaca aataggggtt ccgcgcacat ttccccgaaa    120
agtgccacct aaattgtaag cgttaatatt ttgttaaaat tcgcgttaaa tttttgttaa    180
atcagctcat tttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt tttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccaggggt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacgcc tgcagaacac gcagctagat taaccctaga aagataatca tattgtgacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaa caaaaactca    1080
aaatttcttc tataaagtaa caaaactttt atcgaattcc tgcagcccgg gggatccact   1140
agttctagag ggacagcccc ccccaaagc cccagggat gtaattacgt ccctccccg      1200
ctaggggggca gcagcgagcc gcccggggct ccgctccggt ccggcgctcc ccccgcatcc   1260
ccgagccggc agcgtgcggg gacagcccgg gcacggggaa ggtggcacgg gatcgctttc   1320
ctctgaacgc ttctcgctgc tctttgagcc tgcagacacc tgggggggata cgggggaaaag   1380
gcctccaagg ccagcttccc acaataagt ggggtgaattt tggctcattc ctccttttcta   1440
taggattgag gtcagagctt tgtgatggga attctgtgga atgtgtgtca gttagggtgt    1500
ggaaagtccc gcgatcgcta gcttaagcgc tgatcaattg gcgcgccgaa ttcgttatct    1560
gcagaattcg gcttgacatt gattattgac tagttattaa tagtaatcaa ttacggggtc    1620
attagttcat agcccatata tggagttccg cgttacataa cttacggtaa atggcccgcc    1680
tggctgaccg cccaacgacc cccgcccatt gacgtcaata atgacgtatg ttcccatagt    1740
aacgccaata gggactttcc attgacgtca atgggtggag tatttacggt aaactgccca    1800
cttggcagta catcaagtgt atcatatgcc aagtacgccc cctattgacg tcaatgacgg    1860
taaatggccc gcctggcatt atgcccagta catgacctta tgggactttc ctacttggca    1920
gtacatctac gtattagtca tcgctattac catggtgatg cggttttggc agtacatcaa    1980
tgggcgtgga tagcggtttg actcacgggg atttccaagt ctccacccca ttgacgtcaa    2040
tgggagtttg ttttggaacc aaaatcaacg ggactttcca aaatgtcgta caactccgc     2100
cccattgacg caaatgggcg gtaggcgtgt acggtgggag gtctatataa gcagagctct    2160
ccctatcagt gatagagatc tccctatcag tgatagagat cgtcgacgag ctcgtttagt    2220
gaaccgtcag atcgcctgga gacgccatcc acgctgtttt gacctccata agagacaccg    2280
ggaccgatcc agcctgaacg cgcagccgcc acgccggggt tttacgagat tgtgattaag    2340
gtccccagcg accttgacga gcatctgccc ggcatttctg acagctttgt gaactgggtg    2400
gccgagaagg aatgggagtt gccgccagat tctgacatgg atctgaatct gattgagcag    2460
gcaccctga ccgtggccga aagctgcag cgcgactttc tgacgaatg gcgccgtgtg       2520
agtaaggccc cggaggctct tttctttgtg caatttgaga agggagagag ctacttccac    2580
atgcacgtgc tcgtggaaac caccggggtg aaatccatgg ttttgggacg tttcctgagt    2640
cagattcgcg aaaaactgat tcagagaatt taccgcctgga tcgagccgac tttgccaaac    2700
tggttcgcgg tcacaaagac cagaaatggc gccggaggcg gaacaaggt ggtggatgag     2760
tgctacatcc ccaattactt gctccccaaa acccagcctg agctcaatg ggcatggacc     2820
aacatggaac agtacctcag cgcctgtttg aatctcacgg agcgtaaacg gttggtggcg    2880
cagcatctga cgcacgtgtc gcagacgcag gagcagaaca aagagaatca gaatcccaat    2940
tctgatgcgc cggtgatcag atcaaaaact tcagccaggt acatggagct ggtcgggtgg   3000
ctcgtggaca aggggattac ctcggagaag cagtggatcc aggaggacca ggcctcatac    3060
atctccttca atgcggcctc caactcgcgg tcccaaatca aggctgcctt ggacaatgcg    3120
ggaaagatta tgagcctgac taaaaccgcc ccgactacc tggtgggcca gcagcccgtg    3180
gaggacattt ccagcaatcg gatttataa attttggaac taaacgggta cgatcccaa    3240
tatgcggctt ccgtctttct gggatggcgc acgaaaaagt tcggcaagag gaacaccatc    3300
tggctgtttg ggcctgcaac taccggaaag accaacatcg cggaggccat agcccacact    3360
gtgccttct acgggtgcgt aaactggacc aatgagaact ttcccttcaa cgactgtgtc    3420
gacaagatgg tgatctggtg ggaggagggg aagatgaccg ccaaggtcgt ggagtcggcc   3480
aaagccattc tcggaggaag caaggtcgcg gtgaccaga aatgcaagtc ctcggcccag    3540
atagaccgga ctcccgtgat cgtcacctcc aacaccaaca tgtgcgccgt gattgacggg    3600
```

```
aactcaacga ccttcgaaca ccagcagccg ttgcaagacc ggatgttcaa atttgaactc   3660
acccgccgtc tggatcatga ctttgggaag gtcaccaagc aggaagtcaa agactttttc   3720
cggtgggcaa aggatcacgt ggttgaggtg gagcatgaat tctacgtcaa aaagggtgga   3780
gccaagaaaa gacccgcccc cagtgacgca gatataagtg agcccaaacg ggtgcgcgag   3840
tcagttgcgc agccatcgac gtcagacgcg gaagcttcga tcaactacgc agacaggtac   3900
caaaacaaat gttctcgtca cgtgggcatg aatctgatgc tgtttccctg cagacaatgc   3960
gagagaatga atcagaattc aaatatctgc ttcactcacg gacagaaaga ctgtttagag   4020
tgctttcccg tgtcagaatc tcaacccgtt tctgtcgtca aaaaggcgta tcagaaactg   4080
tgctacattc atcatatcat gggaaaggtg ccagacgctt gcactgcctg cgatctggtc   4140
aatgtggatt tggatgactg catctttgaa caataaaatg gctaggatcc ggccggcctg   4200
caggtgtcct cacaggaacg aagtcccctaa agaaacagtg gcagccaggt ttagccccgg   4260
aaaacttgtt tattgcagct tataatggtt acaaataaag caatagcatc acaaatttca   4320
caaataaagc atttttttca ctgcattcta gttgtggttt gtccaaactc atcaatgtat   4380
cttattgact ggattgaggg acagccccc cccaaagccc ccaggatgt aattacgtcc   4440
ctcccccgct aggggggcagc agcgagccgc ccggggctcc gctccggtcc ggcgctcccc   4500
ccgcatcccc gagccggcag cgtgcgggga cagcccgggc acgggaagg tggcacggga   4560
tcgctttcct ctgaacgctt ctcgctgctc tttgagcctg cagacacctg gggggatacg   4620
gggaaaaggc ctccaaggcc agcttccac aataagttgg gtgaattttg gctcattcct   4680
cctttctata ggattgaggt cagagcgaca ttgattattg actagttatt aatagtaatc   4740
aattacgggg tcattagttc atagcccata tatggagttc cgcgttacat aacttacggt   4800
aaatggcccg cctggctgac cgcccaacga cccccgccca ttgacgtcaa taatgacgta   4860
tgttcccata gtaacgccaa tagggacttt ccattgacgt caatgggtgg agtatttacg   4920
gtaaactgcc cacttggcag tacatcaagt gtatcatatg ccaagtacgc cccctattga   4980
cgtcaatgac ggtaaatggc ccgcctggca ttatgcccag tacatgacct tatgggactt   5040
tcctacttgg cagtacatct acgtattagt catcgctatt accatggtga tgcggttttg   5100
gcagtacatc aatgggcgtg gatagcggtt tgactcactg ggatttccaa gtctccaccc   5160
cattgacgtc aatgggagtt tgttttggaa ccaaaatcaa cgggactttc caaaatgtcg   5220
taacaactcc gccccattga cgcaaatggg cggtaggcgt gtacggtggg aggtctatat   5280
aagcagagct ctccctatca gtgatagaga tctccctatc agtgatagag atcgtcgacg   5340
agctcgttta gtgaaccgtc agatcgcctg gagacgccat ccacgctgtt ttgacctcca   5400
tagaagacac cgggaccgat ccagcctatc caattctga tgcgccggtg atcagatcca   5460
aaacttcagc caggtacgcc accacggaac tggtcggatg gctggtggat aagggcatca   5520
caagcgagaa gcaatggatc caggaggacc aggcctcata tatttctttt aacgccgcta   5580
gcaattccag aagccagatc aaggctgctc tggacaacac cggcaaaatc atgagcctga   5640
ccaagaccgc ccctgactac ctggtggac agcagcctgt ggaagatatc agcgcaaca   5700
gaatctataa gatcctggaa ctgaacggct acgacccccca gtacgccgcc tccgtgttcc   5760
tgggctgggc tacaaagaag ttcggcaagc ggaacaccat ctggctgttc ggacctgcca   5820
ccacaggcaa accaatatc gccgaggcca tcgcccacac cgtgccttc tacggctgcg   5880
tgaactggac aaacgagaac ttccccttca acgactgtgt ggacaagatg tgtatctgc   5940
gggaggaagg caaatgacga gctaaggtgg tggaatctgc caaggctatc ctgggaggct   6000
ctaaggtcag ggtggatcag aagtgtaaaa gcagcgccca gattgaccct accctgtga   6060
tcgtgaccag caataccaac atgtgcgccg tgatcgacgg caacagcacc accttcgagc   6120
atcagcagcc tctgcaggac cggatgttca gtttgagct caccagacgg ctggatcacg   6180
acttcggcaa ggtgaccaag caggaggtga aggatttctt cagatgggcc aaagaccacg   6240
ttgttgaggt ggaacacgag ttctacgtga agaagggcgg cgccaagaaa agacccgccc   6300
ctagcgacgc cgacatcagc gagcctaaga gagtgcggga agcgtggcc cagcccagca   6360
catctgatgc tgaggccagc atcaactacg ccgatagata ccaaaacaag tgcagccgcc   6420
acgtgggcat gaacctgatg ctgtttcccc gcagacagtg tgaaagaatg aaccagaatt   6480
ctaatatctg cttcacacac ggccagaaag attgcctgga atgcttccct gtgtccgaga   6540
gccaaccagt gtctgtggtg aaaaaggcct accagaagct gtgctacatc caccacatca   6600
tgggcaaggt gccagacgcc tgtaccgcct gcgacctggt caacgtggac ctggacgact   6660
gcatcttcga gcagtgattt tgtatggaa ttctgtgctg tgccttctag ttgccagcca   6720
tctgttgttt gcccctcccc cgtgccttcc ttgaccctgg aagtgccac tccactgtc   6780
ctttcctaat aaaatgagga aattgcatcg cattgtctga gtaggtgtca ttctattctg   6840
ggggtgggg tggggcagga cagcaagggg gaggattggg aagacaatag caggcatgct   6900
ggggatgcgg tgggctctat gggacctttt ttagggccca ttggtatggc ttttttcccg   6960
tatccccca ggtgtctgca ggctcaaaga gcagcgagaa gcgttcagag gaaagcgatc   7020
ccgtgccacc ttccccgtgc ccgggctgtc ccgcacgct gccggctcgg ggatgcgggg   7080
ggagcgccgg accggagcgg agccccgggc ggctcgctgc tgccccctag cggggagggg   7140
acgtaattac atccctgggg gctttgggg gggctcgtcc ctctcagagcg gccgccaccg   7200
cggtggagct ccagctttg ttccctttag tgagggttaa ttagatctta atacgactca   7260
ctataggcg aattgggtac cgggcccccc tgaggcggaa agaaccagct ggggctctag   7320
ggggtatccc cgggggttgg gttgcgcctt ttccaaggca gccctgggtt tgcgcaggga   7380
gcggctgct ctgggcgtg ttccgggaaa cgcagcggcg ccgaccctgg gtctcgcaca   7440
ttcttcacgt ccgttcgcag cgtcacccgg atcttcgccg ctaccttgt gggcccccg   7500
gcgacgcttc ctgctccgcc cctaagtcgg gaaggttcct tgcggttcgc ggcgtgccgg   7560
acgtgacaaa cggaagccgc acgtctcact agtaccctcg cagacggaca gcgccaggga   7620
gcaatggcag cgcgccgacc gcgatgggct gtggccaata gcggctgctc agcagggcgc   7680
gccgagagca gcggccggga aggggcggc cggagggcgg ggtgtgggc ggtagtgtgg   7740
gccctgttcc tgcccgcgcg gtgttccgca ttctgcaagc ctccggagcg cacgtcggca   7800
gtcggctccc tcgttgaccg aatcaccgac ctctctcccc agaagctccc gggagcttgt   7860
atatccattt tcggatctga tcagcacgtg ttgacaatta atcatcggca tagtatatcg   7920
gcatagtata atacgacaag gtgaggaacg ccaccatggc caagctttg tctcaagaag   7980
aatccaccct cattgaaaga gcaacggcta caatcaacag catccccatc tctgaagact   8040
acagcgtcgc cagcgcagct ctctctagcg acgccgcat cttcactggt gtcaatgtat   8100
atcattttac tgggggacct tgtgcagaac tcgtggtgct gggcactgct gctgctgcgg   8160
cagctggcaa cctgacttgt atcgtcgcga tcggaaatga gaacagggc atcttgagcc   8220
cctgcggacg tgccgacag gtgcttcctcg atctgcatcc tgggatcaaa gccatagtga   8280
aggacagtga tggacagccg acggcagttg ggattcgtga attgctgccc tctggttatg   8340
```

```
tgtgggaggg ctaaagcgcg gggatctcat gctggagttc ttcgcccacc ccaacttgtt    8400
tattgcagct tataatggtt acaaataaag caatagcatc acaaatttca caaataaagc    8460
attttttca  ctgcattcta gttgtggttt gtccaaactc atcaatgtat cttatcatgt    8520
ctgtagctga tgtataccta ggatccggcc ggcctgcagg tgtcctcaca ggaacgaagt    8580
ccctaaagaa acagtggcag ccaggtttag ccccggaatt gactggattc ctttttaggg    8640
gccattggt  atggcttttt ccccgtatcc ccccaggtgt ctgcaggctc aaagagcagc    8700
gagaagcgtt cagaggaaag cgatcccgtg ccaccttccc cgtgcccggg ctgtccccgc    8760
acgctgccgc ctcggggatg cggggggagc gccggaccgg agcggagccc cgggcggctc    8820
gctgctgccc cctagcgggg gagggacgta attcatccc  tgggggcttt ggggggggc    8880
tgtccctcta gagcggccgc caccgcggtg gagctccagc ttttgttccc tttagtgagg    8940
gttaattaga tcttaatacg actcactata gggcgaattg ggtaccgggc cccccctcga    9000
ggtcgacggt atcctcgagg tcgacggtat cgataagctt gatatctata acaagaaaat    9060
atatatataa taagttatca cgtaagtaga acatgaaata acaatataat tatcgtatga    9120
gttaaatctt aaaagtcacg taaaagataa tcatgcgtca ttttgactca cgcggtcgtt    9180
atagttcaaa atcagtgaca cttaccgcat tgacaagcac gcctcacggg agctccaagc    9240
ggcgactgag atgtcctaaa tgcacagcga cggattcgcg ctatttagaa agagagagca    9300
atatttcaag aatgcatgcg tcaattttac gcagactatc tttctagggt taatctagct    9360
gcatcaggat catatcgtcg ggtctttttt ccggctcagt catcgcccaa gctggcgcta    9420
tctgggcatc ggggaggaag aagcccgtgc cttttcccgc gaggttgaag cggcatggaa    9480
agagtttgcc gaggatgact gctgctgcat tgacgttgag cgaaaacgca cgtttaccat    9540
gatgattcgg gaaggtgtgg ccatgcacgc ctttaacggt gaactgttcg ttcaggccac    9600
ctgggatacc agttcgtcgc ggcttttccg gacacagttc ggatggtca gcccgaagcg    9660
catcagcaac ccgaacaata ccggcgacag ccgaactgcc cgtgccggtg tgcagattaa    9720
tgacagcggt gcggcgctgg gatattacgt cagcgaggac gggtatcctg ctggatgcc    9780
gcagaaatgg acatggatac cccgtgagtt acccggcggg cgcgcttggc gtaatcatgg    9840
tcatagctgt ttcctgtgtg aaattgttat ccgctcacaa ttccacacaa catcgagcc    9900
ggaagcataa agtgtaaagc ctggggtgcc taatgagtga gctaactcac attaattgcg    9960
ttgcgctcac tgcccgcttt ccagtcggga aacctgtcgt gccagctgca ttaatgaatc    10020
ggccaacgcg cggggagagg cggtttgcgt attgggcgct cttccgcttc ctcgctcact    10080
gactcgctgc gctcggtcgt tcggctgcgg cgagcggtat cagctcactc aaaggcggta    10140
atacggttat ccacagaatc aggggataac gcaggaaaga acatgtgagc aaaaggccag    10200
caaaaggcca ggaaccgtaa aaaggccgcg ttgctggcgt ttttccatag gctccgcccc    10260
cctgacgagc atcacaaaaa tcgacgctca agtcagaggt ggcgaaaccc gacaggacta    10320
taaagatacc aggcgtttcc ccctggaagc tccctcgtgc gctctcctgt tccgaccctg    10380
ccgcttaccg gatacctgtc cgcctttctc ccttcgggaa gcgtggcgct ttctcatagc    10440
tcacgctgta ggtatctcag ttcggtgtag tcgttcgct  ccaagctggg ctgtgtgcac    10500
gaaccccccg ttcagcccga ccgctgcgcc ttatccggta actatcgtct tgagtccaac    10560
ccggtaagac acgacttatc gccactggca gcagccactg gtaacaggat tagcagagcg    10620
aggtatgtag gcggtgctac agagttcttg aagtggtggc ctaactacgg ctacactaga    10680
aggacagtat ttggtatctg cgctctgctg aagccagtta ccttcggaaa aagagttggt    10740
agctcttgat ccggcaaaca aaccaccgct ggtagcggtg gtttttttgt ttgcaagcag    10800
cagattacgc gcagaaaaaa aggatctcaa gaagatcctt tgatctttc  tacggggtct    10860
gacgctcagt ggaacgaaaa ctcacgttaa gggattttgg tcatgagatt atcaaaaagg    10920
atcttcacct agatcctttt aaattaaaaa tgaagtttta aatcaatcta agtatatat    10980
gagtaaactt ggtctgacag ttaccaatgc ttaatcagtg aggcacctat ctcagcgatc    11040
tgtctatttc gttcatccat agttgcctga ctccccgtcg tgtagataac tacgatacgg    11100
gagggcttac catctggccc cagtgctgca atgataccgc gagacccacg ctcaccggct    11160
ccagatttat cagcaataaa ccagccagcc ggaagggccg agcgcagaag tggtcctgca    11220
actttatccg cctccatcca gtctattaat tgttgccggg aagctagagt aagtagttcg    11280
ccagttaata gtttgcgcaa cgttgttgcc attgctacag gcatcgtggt gtcacgctcg    11340
tcgtttggta tggcttcatt cagctccggt tcccaacgat caaggcgagt tacatgatcc    11400
cccatgttgt gcaaaaaagc ggttagctcc ttcggtcctc cgatcgttgt cagaagtaag    11460
ttggccgcag tgttatcact catggttatg gcagcactgc ataattctct tactgtcatg    11520
ccatccgtaa gatgcttttc tgtgactggt gagtactcaa ccaagtcatt ctgagaatag    11580
tgtatgcggc gaccgagttg ctcttgcccg gcgtcaatac gggataataa cgcgccacat    11640
agcagaactt taaaagtgct catcattgga aaacgttctt cggggcgaaa actctcaagg    11700
atcttaccgc tgttgagatc cagttcgatg taacccactc gtgcacccaa ctgatcttca    11760
gcatctttta ctttccaccag cgtttctggg tgagcaaaaa caggaaggca aaatgccgca    11820
aaaaagggaa taagggcgac acggaaatgt tgaatactca t                        11861
```

| SEQ ID NO: 23 | moltype = DNA   length = 11580 |
|---|---|
| FEATURE | Location/Qualifiers |
| misc_feature | 1..11580 |
| | note = Synthetic: PB-hiRep-10# |
| source | 1..11580 |
| | mol_type = other DNA |
| | organism = synthetic construct |

SEQUENCE: 23
```
actcttcctt tttcaatatt attgaagcat ttatcagggt tattgtctca tgagcggata     60
catatttgaa tgtatttaga aaaataaaca aataggggtt ccgcgcacat ttccccgaaa    120
agtgccacct aaattgtaag cgttaatatt ttgttaaaat tcgcgttaaa tttttgttaa    180
atcagctcat tttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcacccc aatcaagttt tttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
```

-continued

```
gcgaaaggggg gatgtgctgc aaggcgatta agttgggtaa cgccaggggtt ttcccagtca   720
cgacgttgta aaacgacggc cagtgagcgc gcctcgttca ttcacgtttt tgaacccgtg   780
gaggacgggc agactcgcgg tgcaaatgtg ttttacagcg tgatggagca gatgaagatg   840
ctcgacacgc tgcagaacac gcagctagat taaccctaga aagataatca tattgtgacg   900
tacgttaaag ataatcatgc gtaaaattga cgcatgtgtt ttatcggtct gtatatcgag   960
gtttatttat taatttgaat agatattaag ttttattata tttacactta catactaata  1020
ataaattcaa caaacaattt atttatgttt atttatttat taaaaaaaaa caaaaactca  1080
aaatttcttc tataaagtaa caaaacttttt atcgaattcc tgcagcccgg gggatccact  1140
agttctagag ggacagcccc cccccaaagc ccccagggat gtaattacgt ccctcccccg  1200
ctagggggca gcagcgagcc gcccgggggct ccgctccggt ccggcgctcc ccccgcatcc  1260
ccgagccggc agcgtgcggg gacagcccgg gcacggggaa ggtggcacgg gatcgctttc  1320
ctctgaacgc ttctcgctgc tctttgagcc tgcagacacc tgggggggata cggggaaaag  1380
gcctccaagg ccagcttccc acaataagtt gggtgaattt tggctcattc ctcctttcta  1440
taggattgag gtcagagctt tgtgatggga atttctgtgga atgtgtgtca gttagggtgt  1500
ggaaagtccc gcgatcgcta gcttaagcgc tgatcaattg gcgcgccgaa ttcgttatct  1560
gcagaattcg gcttggcctc cgcgccgggt tttggcgcct cccgcggggcg ccccccctcct  1620
cacggcgagc gctgccacgt cagacgaagg gcgcagcgag cgtcctgatc cttccgcccg  1680
gacgctcagg acagcggccc gctgctcata agactccgcg ttagaacccc agtatcagca  1740
gaaggacatt ttaggacggg acttgggtga ctctagggca ctggtttttct ttccagagag  1800
cggaacaggc gaggaaaagt agtcccttct cggcgattct gcggagggat ctccgtgggg  1860
cggtgaacgc cgatgattat ataaggacgg gccggtccct atcagtgata gagatctccc  1920
tatcagtgat agagagtgtg gcacagctag ttccgtcgca tgccgggattt gggtcgcggt  1980
tcttgtttgt ggatcgctgt gatcgtcact tgacgaacgc gcagccgcca tgccggggtt  2040
ttacgagatt gtgattaagg tccccagcga ccttgacgag catctgcccg gcatttctga  2100
cagctttgtg aactgggtgg ccgagaagga atgggagttg ccgccagatt ctgacatgga  2160
tctgaatctg attgagcagg caccccctgac cgtggccgga agtgcgcagc gcgactttct  2220
gacggaatgg cgccgtgtga gtaaggcccc ggaggctctt ttctttgtgc aatttgagaa  2280
gggagagagc tacttccaca tgcacgtgct cgtggaaacc accggggtga atccatggt  2340
tttgggacgt ttcctgagtc agattcgcga aaaactgatt cagagaattt accgcgggat  2400
cgagccgact ttgccaaact ggttcgcggt cacaaagacc agaaatgccg ccggaggcgg  2460
gaacaaggtc gtggatgagt gctacatccc caattacttg ctccccaaaa cccagcctga  2520
gctcaatgg gcatggacca acatggaaca gtacctcagc gcctgtttga atctcacgga  2580
gcgtaaacgg ttggtggcgc agcatctgac gcacgtgtcg cagacgcagg agcagaacaa  2640
agagaatcag aatcccaatt ctgatcgcc ggtgatcaga tcaaaaactt cagccaggta  2700
catggagctg gtcgggtggc tcgtggacaa ggggattacc tcggagaagc agtggatcca  2760
ggaggaccag gcctcataca tctccttcaa tgccggcctcc aactcgcggt cccaaatcaa  2820
ggctgccttg gacaatgcgg gaaagattat gagcctgact aaaaccgccc ccgactacct  2880
ggtgggccag cagcccgtgg aggacattttc cagcaatcgg atttataaaa ttttggaact  2940
aaacgggtac gatccccaat atgcggcttc cgtctttctg ggatgggcca cgaaaaagtt  3000
cggcaagagg aacaccatct ggctgtttgg gcctgcaact accggaagaa ccaacatcgc  3060
ggaggccata gcccacactg tgcccttcta cgggtgcgta aactggacca atgagaactt  3120
tcccttcaac gactgtgtcg acaagatggt gatctggtgg gaggagggga agatgaccgc  3180
caaggtcgtg gagtcggcca aagccattct cggaggaagc aaggtgcgcg tggaccagaa  3240
atgcaagtcc tcggcccaga tagacccgac tcccgtgatc gtcacctcca acaccaacat  3300
gtgcgccgtg attgacggga actcaacgac cttgaacac cagcagccgt tgcaagaccg  3360
gatgttcaaa tttgaactca cccgccgtct ggatcatgac tttgggaagg tcaccaagca  3420
ggaagtcaaa gacttttttcc ggtgggcaaa ggatcacgtg gttgaggtgg agcatgaatt  3480
ctacgtcaaa aagggtggag ccaagaaaag acccgccccc agtgacgcag atataagtga  3540
gcccaaacgg gtgcgcgagt cagttgcgca gccatcgacg tcagacgcgg aagcttcgat  3600
caactacgca gacaggtacc aaaacaaatg ttctcgtcac gtgggcatga atctgatgct  3660
gttccctgc agacaatgcg agagaatgaa tcagaattca aatatctgct tcactcacgg  3720
acagaaagac tgtttagagt gctttcccgt gtcagaatct caacccgttt ctgtcgtcaa  3780
aaaggcgtat cagaaactgt gctacattca tcatatcatg ggaaaggtgc cagacgcttg  3840
cactgcctgc gatctggtca atgtggattt ggatgactgc atctttgaac aataaaatgg  3900
ctaggatccg gccggcctgc aggtgtcctc acaggaacga agtccctaaa gaaacagtgg  3960
cagccaggtt tagccccgga aaacttgttt attgcagctt ataatggtta caaataaagc  4020
aatagcatca caaattttcac aaataaagca ttttttttcac tgcattctag ttgtggtttg  4080
tccaaactca tcaatgtatc ttattgactg gattgaggga cagcccccc ccaaagcccc  4140
cagggatgta attacgtccc tccccccgcta ggggggcagca gcgagccgcc cgggggctcc gg  4200
ctccggtccg gcgctccccc cgcatccccc agccggcagc gtgcggggac agcccggca  4260
cggggaaggt ggcacgggat cgctttcctc tgaacgcttc tcgctgctct ttgagcctgc  4320
agacacctgg ggggatacgg ggaaaaggcc tccaaggcca gcttcccaca ataagttggg  4380
tgaattttgg ctcattcctc ctttctatag gattgaggtc agacgacat tgattattga  4440
ctagttatta atagtaatca attacggggt cattagttca tagcccatat atggagttcc  4500
gcgttacata acttacggta aatgcccgc ctgctgacc gcccaacgac ccccgcccat  4560
tgacgtcaat aatgacgtat gttcccatag taacgccaat agggactttc cattgacgtc  4620
aatgggtgga gtatttacgg taaactgccc acttggcagt acatcaagtg tatcatatgc  4680
caagtacgcc ccctattgac gtcaatgacg gtaaatggcc cgcctggcat tatgcccagt  4740
acatgacctt atgggactttc cctacttggc agtacatcta cgtattagtc atcgctatta  4800
ccatggtgat gcggttttgg cagtacatca atgggcgtgg atagcggttt gactcacggg  4860
gatttccaag tctccacccc attgacgtca atggagtttt gttttggaac caaaatcaac  4920
gggactttcc aaaatgtcgt aacaactccg ccccattgac gcaaatgggc ggtaggcgtg  4980
tacggtggga ggtctatata agcagagctc tccctatcag tgatagagat ctccctatca  5040
gtgatagaga tcgtcgacga gctcgtttag tgaaccgtca gatcgcctgg agacgccatc  5100
cacgctgttt tgacctccat agaagacacc gggaccgatc cagcctatcc caattctgat  5160
gcgccggtga tcagatcaaa aacttcagcc aggtacgcca ccacgaact ggtcggatgt  5220
ctggtggata agggcatcac aagcgagaag caatggatcc aggaggacca ggcctcatat  5280
atttcttta acgccgctag caattccaga agccagatca aggctgctct ggacaacgcc  5340
ggcaaaatca tgagcctgac caagaccgcc cctgactacc tggtgggaca gcagcctgtg  5400
```

```
gaagatatca gcagcaacag aatctataag atcctggaac tgaacggcta cgacccccag   5460
tacgccgcct ccgtgttcct gggctgggct acaaagaagt tcggcaagcg aacaccatc   5520
tggctgttcg gacctgccac cacaggcaaa accaatatcg ccgaggccat cgcccacacc   5580
gtgcctttct acggctgcgt gaactggaca acgagaact tccccttcaa cgactgtgtg   5640
gacaagatgg tgatctggtg ggaggaaggc aaaatgcag ctaaggtgt ggaatctgcc   5700
aaggctatcc tgggaggctc taaggtcagg gtggatcaga agtgtaaaag cagcgcccag   5760
attgacccta cccctgtgat cgtgaccagc aataccaaca tgtgcgccgt gatcgacggc   5820
aacagcacca ccttcgagca tcagcagcct ctgcaggacc ggatgttcaa gtttgagctc   5880
accagacggc tggatcacga cttcggcaag gtgaccaagc aggaggtgaa ggatttcttc   5940
agatgggcca aagaccacgt tgttgaggtg gaacacgagt tctacgtgaa gaagggcggc   6000
gccaagaaaa gacccgcccc tagcgacgcc gacatcagcg agcctaagag agtgcgggaa   6060
agcgtggccc agcccagcac atctgatgct gaggccagca tcaactacgc cgatagatac   6120
caaaacaagt gcagccgcca cgtgggcatg aacctgatgc tgtttccctg cagacagtgt   6180
gaaagaatga accagaattc taatatctgc tttacacacg gccagaaaga ttgcctggaa   6240
tgcttccctg tgtccgagag ccaaccagtg tctgtggtga aaaaggccta ccagaagctg   6300
tgctacatcc accacatcat gggcaaggtg ccagacgcct gtaccgcctg cgacctggtc   6360
aacgtggacc tggacgactg catcttcgag cagtgatttg tgatgggaat tctgtgctgt   6420
gccttctagt tgccagccat ctgttgtttg ccccctcccc gtgcctcct tgaccctgga   6480
aggtgccact cccactgtcc tttcctaata aaatgaggaa attgcatcgc attgtctgag   6540
taggtgtcat tctattctgg ggggtgggt ggggcaggac agcaagggg aggattggga   6600
agacaatagc aggcatgctg gggatgcggt gggctctatg gaccttttt tagggcccat   6660
tggtatggct ttttccccgt atccccccag gtgtctgcag gctcaaagag cagcgagaag   6720
cgttcagagg aaagcgatcc cgtgccacct tccccgtgcc cgggctgtcc ccgcacgctg   6780
ccggctcggg gatgcggggg gagcgccgga ccggagcgga gccccgggcg gctcgctgct   6840
gcccctagc ggggagga cgtaattaca tccctgggg cttgggggg gggctgtcc   6900
tctagacgg ccgccaccgc ggtgagctc cagcttttgt tcccttttagt gagggttaat   6960
tagatcttaa tacgactcac tatagggcga attgggtacc gggccccct gaggcggaaa   7020
gaaccagctg gggctctagg gggtatcccc gggttgggg ttgcgccttt tccaaggcag   7080
ccctgggttt gcgcagggac gcggctgctc tgggcgtggt tccgggaaac gcagcggcgc   7140
cgaccctggg tctcgcacat tcttcacgtc cgttcgcagc gtcacccgga tcttcgccgc   7200
tacccttgtg ggccccccgg cgacgcttcc tgctccgccc ctaagtcggg aaggttcctt   7260
gcggttcgcg gcgtgccgga cgtgacaaac ggaagccgca cgtctcacta gtaccctcgc   7320
agacggacag cgccagggag caatggcagc gcgccaccg cgatgggctg tggccaatag   7380
cggctgctca gcagggcgcg ccgagagcag cggccgggaa ggggcggtgc gggaggcggg   7440
gtgtggggcg gtagtgtggg ccctgttcct gcccgccggg tgttccgcat tctgcaagcc   7500
tccggagcgc acgtcggcag tcggctcct cgttgaccga atcaccgacc tctctcccca   7560
gaagctcccg ggagcttgta tatccatttt cggatctgat cagcacgtgt tgacaattaa   7620
tcatcggcat agtatatcgg catagtataa tacgacaagg tgaggaacgc caccatggcc   7680
aagcctttgt ctcaagaaga atccacccc attgaaagag caacggctac aatcaacagc   7740
atccccatct ctgaagacta cagcgtcgcc agcgcagctc tctctagcga cggccgcatc   7800
ttcactggtg tcaatgtata tcatttact ggggaccttt gtgcagaact cgtggtgctg   7860
ggcactgctg ctgctgcggc agctggcaac ctgacttgta tcgtcgcgat cggaaatgag   7920
aacaggggca tcttgagccc ctgcggacgg tgccgacagg tgcttctcga tctgcatcct   7980
gggatcaaag ccatagtgaa ggacagtgat ggacagccga cggcagttgg gattcgtgaa   8040
ttgctgccct ctggttatgt gtgggaggc taaagcgcgg ggatctcatg ctggagttct   8100
tcgcccaccc caacttgttt attgcagctt ataatggtta caaataaagc aatagcatca   8160
caaattttcac aaataaagca ttttttttcac tgcattctag ttgtggtttg tccaaactca   8220
tcaatgtatc ttatcatgtc tgtagctgat gtataccaag gatccggccg gcctgcaggt   8280
gtcctcacag gaacgaagtc cctaaagaaa cagtggcagc caggtttagc cccggaattg   8340
actggattcc ttttttaggg cccattggta tggctttttc cccgtatccc ccaggtgtc   8400
tgcaggctca aagagcagcg agaagcgttc agaggaaagc gatcccgtgc caccttccc   8460
gtgcccggc tgtcccgca cgctgccggc tcggggatgc gggggagcg ccggaccgga   8520
gcggagcccc gggcggctcg ctgctgcccc ctagcggggg agggacgtaa ttacatccct   8580
gggggctttg ggggggggct gtccctctag agcggccgcc accgcggtgg agctccagct   8640
tttgttccct ttagtgaggg ttaattagat cttaatacga ctcactatag ggcgaattgg   8700
gtaccgggcc ccccctcgag gtcgacggta tcctcgaggt cgacggtatc gataagcttg   8760
atatctataa caagaaaata tatatataat aagttatcac gtaagtagaa catgaaataa   8820
caatataatt atcgtatgag ttaaatctta aaagtcacgt aaaagataat catgcgtcat   8880
tttgactcac gcggtcgtta tagttcaaaa tcagtgacac ttaccgcatt gacaagcacg   8940
cctcacggga gctccaagcg gcgactgaga tgtcctaaat gcacagcgac ggattcgcgc   9000
tatttagaaa gagagagcaa tatttcaaga atgcatgcgt caattttacg cagactatct   9060
ttctagggtt aatctagctg catcaggatc atatcgtcgg gtctttttc cggctcagtc   9120
atcgcccaag ctggcgctat ctgggcatcg ggaggaagaa gccccgtgcc ttttcccgcg   9180
aggttgaagc ggcatggaaa gagtttgccg aggatgactc ctgctgcatt gacgttgagc   9240
gaaaacgcac gtttaccatg atgattcggg aaggtgtggc catgcacgcc tttaacggtg   9300
aactgttcgt tcaggccacc tgggatacca gttcgtcgcg gcttttccgg acacagttcc   9360
ggatggtcag cccgaagcgc atcagcaacc cgaacaatac cggcgacagc cggaactgcc   9420
gtgccggtgt gcagattaat gacagcggtg cggctgggat atattcgtc agcgaggacg   9480
ggtatcctgg ctggatgccg cagaaatgga catgatacc ggtgagtta cccggcgggc   9540
gcgcttggcg taatcatggt catagctgtt tcctgtgtga aattgttatc cgctcacaat   9600
tccacacaac atacgagccg aagcataaa gtgtaaagcc tggggtgcct aatgagtgag   9660
ctaactcaca ttaattgcgt tgcgctcact gcccgctttc cagtcgggaa acctgtcgtg   9720
ccagctgcat taatgaatcg gccaacgcgc ggggagaggc ggtttgcgta ttgggcgctc   9780
ttccgcttcc tcgctcactg actcgctgcg ctcggtcgtt cggctgcggc gagcggtatc   9840
agctcactca aaggcggtaa tacggttatc cacagaatca ggggataacg caggaaagaa   9900
catgtgagca aaaggccagc aaaaggccag gaaccgtaaa aaggccgcgt tgctggcgtt   9960
tttccatagg ctccgccccc ctgacgagca tcacaaaaat cgacgctcaa gtcagaggtg  10020
gcgaaacccg acaggactat aaagatacca ggcgtttccc cctggaagct ccctcgtgcg  10080
ctctcctgtt ccgaccctgc cgcttaccgg atacctgtcc gcctttctcc cttcgggaag  10140
```

```
cgtggcgctt tctcatagct cacgctgtag gtatctcagt tcggtgtagg tcgttcgctc  10200
caagctgggc tgtgtgcacg aaccccccgt tcagcccgac cgctgcgcct tatccggtaa  10260
ctatcgtctt gagtccaacc cggtaagaca cgacttatcg ccactggcag cagccactgg  10320
taacaggatt agcagagcga ggtatgtagg cggtgctaca gagttcttga agtggtggcc  10380
taactacggc tacactagaa ggacagtatt tggtatctgc gctctgctga agccagttac  10440
cttcggaaaa agagttggta gctcttgatc cggcaaacaa accaccgctg gtagcggtgg  10500
tttttttgtt tgcaagcagc agattacgcg cagaaaaaaa ggatctcaag aagatccttt  10560
gatcttttct acggggtctg acgctcagtg gaacgaaaac tcacgttaag ggattttggt  10620
catgagatta tcaaaaagga tcttcaccta gatcctttta aattaaaaat gaagttttaa  10680
atcaatctaa agtatatatg agtaaacttg gtctgacagt taccaatgct taatcagtga  10740
ggcacctatc tcagcgatct gtctatttcg ttcatccata gttgcctgac tccccgtcgt  10800
gtagataact acgatacggg agggcttacc atctggcccc agtgctgcaa tgataccgcg  10860
agacccacgc tcaccggctc cagatttatc agcaataaac cagccagccg gaagggccga  10920
gcgcagaagt ggtcctgcaa ctttatccgc ctccatccag tctattaatt gttgccggaa  10980
gctagagta agtagttcgc cagttaatag tttgcgcaac gttgttgcca ttgctacagg  11040
catcgtggtg tcacgctcgt cgtttggtat ggcttcattc agctccggtt cccaacgatc  11100
aaggcgagtt acatgatccc ccatgttgtg caaaaaagcg gttagctcct tcggtcctcc  11160
gatcgttgtc agaagtaagt tggccgcagt gttatcactc atggttatgg cagcactgca  11220
taattctctt actgtcatgc catccgtaag atgcttttct gtgactggtg agtactcaac  11280
caagtcattc tgagaatagt gtatgcggcg accgagttgc tcttgcccgg cgtcaatacg  11340
ggataatacc gcgccacata gcagaacttt aaaagtgctc atcattggaa aacgttcttc  11400
ggggcgaaaa ctctcaagga tcttaccgct gttgagatcc agttcgatgt aacccactcg  11460
tgcacccaac tgatcttcag catctttac tttcaccagc gtttctgggt gagcaaaaac  11520
aggaaggcaa aatgccgcaa aaaagggaat aagggcgaca cggaaatgtt gaatactcat  11580

SEQ ID NO: 24       moltype = DNA   length = 11702
FEATURE             Location/Qualifiers
misc_feature        1..11702
                    note = Synthetic: PB-hiRep-11#
source              1..11702
                    mol_type = other DNA
                    organism = synthetic construct
SEQUENCE: 24
actcttcctt tttcaatatt attgaagcat ttatcagggt tattgtctca tgagcggata  60
catatttgaa tgtatttaga aaaataaaca aatagggggtt ccgcgcacat ttccccgaaa  120
agtgccacct aaattgtaag cgttaatatt ttgttaaaat tcgcgttaaa ttttttgttaa  180
atcagctcat tttttaacca ataggccgaa atcggcaaaa tcccttataa atcaaaagaa  240
tagaccgaga taggggttgag tgttgttcca gtttggaaca agagtccact attaaagaac  300
gtggactcca acgtcaaagg gcgaaaaacc gtctatcagg gcgatggccc actacgtgaa  360
ccatcacccct aatcaagttt ttggggtcg aggtgccgta aagcactaaa tcggaaccct  420
aaagggagcc cccgatttag agcttgacgg gaaagccgg cgaacgtggc gagaaaggaa  480
gggaagaaag cgaaaggagc gggcgctagg gcgctgggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
ctcgacacgc tgcagaacac gcagctagat taaccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata  1020
ataaattcaa caaacaattt atttatgttt atttatttat taaaaaaaaa caaaaactca  1080
aaatttcttc tataaagtaa caaaactttt atcgaattcc tgcagcccgg gggatccact  1140
agttctagag ggacagcccc ccccaaagc cccagggat gtaattacgt ccctcccccg  1200
ctagggggca gcagcgagcc gcccgggggct ccgctccggt ccggcgctcc ccccgcatcc  1260
ccgagccggc agcgtgcggg gacagcccgg gcacgggaa ggtggcacgg gatcgctttc  1320
ctctgaacgc ttctcgctgc tcttttgagcc tgcagacacc tggggggata cgggaaaag  1380
gcctccaagg ccagcttccc acaataagtt gggtgaattt tggctcattc ctcctttcta  1440
taggattgag tcagagctt tgtgatggga attctgtgga atgtgtgtca gttagggtgt  1500
ggaaagtccc gcgatcgcta gcttaagcgc tgatcaattg gcgcgccgaa ttcgttatct  1560
gcagaattcg gcttctgctc cctgcttgtg tgttggaggt cgctgagtag tgcgcgagca  1620
aaatttaagc tacaacaagg caaggcttga ccgacaattg catgaagaat ctgcttaggg  1680
ttaggcgttt tgcgctgctt cgcgatgtac gggccagata tacgcgtatc tgaggggact  1740
agggtgtgtt taggcgaaaa gcggggcttc ggttgtacgc ggttaggagt cccctcagga  1800
tatagtagtt tcgctttttgc ataggagggg ggaaatgtag tcttatgcaa tacacttgta  1860
gtcttgcaac atggtaacga tgagttagca acatgcctta caaggagaga aaaagcaccg  1920
tgcatgccga ttggtggaag taaggtggta cgatcgtgcc ttattaggaa ggcaacagac  1980
aggtctgaca tggattggac gaaccactga attccgcatt gcagagataa ttgtatttaa  2040
gtgcctagct ccctatcagt gatagagatc tccctatcag tgatagagat cgatacaata  2100
aacgccattt gaccattcac cacattggtg tgcaccgagc gcgacgcgc catgccgggg  2160
ttttacgaga ttgtgattaa ggtcccccagc gaccttgacg agcatctgcc cggcatttct  2220
gacagctttg tgaactgggt ggccgagaag gaatgggagt gccgccaga ttctgacatg  2280
gatctgaatc tgattgagca ggcacccctg accgtggccg agaagctgca gcgcgacttt  2340
ctgacggaat ggcgccgtgt gagtaaggcc cggaggctc ttttctttgt gcaatttgag  2400
aagggagaga gctacttcca catgcacgtg ctcgtggaag gcggaaatcatg  2460
gtttttgggag gtttcctgag tcagattcgc gaaaaactga ttcagagaat ttaccgcggg  2520
atcgagccga ctttgccaaa ctggttcgcg gtcacaaaga ccagaaatgg cgccggaggc  2580
gggaacaagg tggtggatga gtgctacatc cccaattact tgctccccaa acccagcct  2640
gagctccaat gggcatggac caacatggaa cagtacctca cgcgcctgtt gaatctcacg  2700
gagcgtaaac ggttggtggc gcagcatctg acgcacgtgt cgcagacgca ggagcagaac  2760
```

```
aaagagaatc agaatcccaa ttctgatgcg ccggtgatca gatcaaaaac ttcagccagg  2820
tacatggagc tggtcgggtg gctcgtggac aaggggatta cctcggagaa gcagtggatc  2880
caggaggacc aggcctcata catctccttc aatgcggcct ccaactcgcg gtcccaaatc  2940
aaggctgcct tggacaatgc gggaaagatt atgagcctga ctaaaaccgc ccccgactac  3000
ctggtgggcc agcagcccgt ggaggacatt tccagcaatc ggatttataa aattttggaa  3060
ctaaacgggt acgatcccca atatgcggct tccgtctttc tgggatgggc cacgaaaaag  3120
ttcggcaaga ggaacaccat ctggctgttt gggcctgcaa ctaccgggaa gaccaacatc  3180
gcggaggcca tagcccacac tgtgcccttc tacgggtgcg taaactggac caatgagaac  3240
tttcccttca acgactgtgt cgacaagatg gtgatctggt gggaggaggg gaagatgacc  3300
gccaaggtcg tggagtcggc caaagccatt ctcggaggaa gcaaggtgcg cgtggaccag  3360
aaatgcaagt cctcggccca gatagacccg actcccgtga tcgtcacctc caacaccaac  3420
atgtgcgccg tgattgacgg gaactcaacg accttcgaac accagcagcc gttgcaagac  3480
cggatgttca aatttgaact cacccgccgt ctggatcatg actttgggaa ggtcaccaag  3540
caggaagtca aagactttt ccggtgggca aaggatcacg tggttgaggt ggagcatgaa  3600
ttctacgtca aaaagggtgg agccaagaaa agacccgccc ccagtgacgc agatataagt  3660
gagcccaaac gggtgcgcga gtcagttgcg cagccatcga cgtcagacgc ggaagcttcg  3720
atcaactacg cagacaggta ccaaaacaaa tgttctcgtc acgtgggcat gaatctgatg  3780
ctgtttccct gcagacaatg cgagagaatg aatcagaatt caaatatctg cttcactcac  3840
ggacagaaag actgtttaga gtgctttccc gtgtcagaat ctcaaccgt ttctgtcgtc  3900
aaaaaggcgt atcagaaact gtgctacatt catcatatca tgggaaaggt gccagacgct  3960
tgcactgcct gcgatctggt caatgtggat ttggatgact gcatctttga caataaaat  4020
ggctaggatc cggccggcct gcaggtgtcc tcacaggaac gaagtcccta aagaaacagt  4080
ggcagccagg tttagccccg gaaaacttgt ttattgcagc ttataatggt tacaaataaa  4140
gcaatagcat cacaaatttc acaaataaag cattttttc actgcattct agttgtggtt  4200
tgtccaaact catcaatgta tcttattgac tggattgagg acagccccc ccccaaagcc  4260
cccagggatg taattacgtc cctccccgc taggggcag cagcgagccg cccggggctc  4320
cgctccggtc cggcgctccc ccgcatccc cgagccggca gcgtgcgggg acagccggg  4380
cacggggaag gtggcacggg atcgctttcc tctgaacgct tctcgctgct ctttgagcct  4440
gcagacacct gggggatac ggggaaaagg cctccaaggc cagcttccca caataagttg  4500
ggtgaatttt ggctcattcc tcctttctat aggattgagg tcagagcgac attgattatt  4560
gactagttat taatagtaat caattacggg gtcattagtt catagcccat atatggagtt  4620
ccgcgttaca taacttacgg taaatggccc gcctggctga ccgcccaacg accccgccc  4680
attgacgtca ataatgacgt atgttccat agtaacgcca atagggactt tccattgacg  4740
tcaatgggtg gagtatttac ggtaaactgc ccacttggca gtacatcaag tgtatcatat  4800
gccaagtacg ccccctattg acgtcaatga cggtaaatgg cccgcctggc attatgccca  4860
gtacatgacc ttatgggact ttcctacttg gcagtacatc tacgtattag tcatcgctat  4920
taccatggtg atgcggtttt ggcagtacat caatgggcgt ggatagcggt ttgactcacg  4980
gggatttcca agtctccacc ccattgacgt caatgggagt ttgttttgga accaaaatca  5040
acgggacttt ccaaaatgtc gtaacaactc cgccccattg acgcaaatgg gcggtaggcg  5100
tgtacggtgg gaggtctata taagcagagc tctccctatc agtgatagag atctccctat  5160
cagtgataga gatcgtcgac gagctcgttt agtgaaccgt cagatcgcct ggagacgcca  5220
tccacgctgt tttgacctcc atagaagaca ccgggaccga tccagcctat cccaattctg  5280
atgcgccggt gatcagatca aaaacttcag ccaggtacgc caccacggaa ctggtcggat  5340
ggctggtgga taagggcatc acaagcgaga agcaatggat ccaggaggac caggcctcat  5400
atatttcttt taacgccgct agcaattcca gaagccagat caaggctgct ctggacaacg  5460
ccggcaaaat catgagcctg accaagaccg cccctgacta cctggtggga cagcagcctg  5520
tggaagatat cagcagcaac agaatctata agatcctgga actgaacggc tacgacccc  5580
agtacgccgc ctccgtgttc ctgggctggg ctacaaagaa gttcggcaag cggaacacca  5640
tctggctgtt cggacctgcc accacaggca aaaccaatat cgccgaggcc atcgcccaca  5700
ccgtgccttt ctacgctgc gtgaactgga caaacgagaa cttcccttc aacgactgtg  5760
tggacaagat ggtgatctgg tgggaggaag gcaaaatgac agctaaggtg gtggaatctg  5820
ccaaggctat cctgggaggc tctaaggtca gggtgatca gaagtgtaaa agcagcgccc  5880
agattgaccc taccctgtg atcgtgacca gcaataccaa catgtgcgcc gtgatcgacg  5940
gcaacagcac caccttcgag catcagcagc ctctgcagga ccggatgttc aagtttgagc  6000
tcaccagacg gctggatcac gacttcggca aggtgaccaa gcaggaggtg aaggatttct  6060
tcagatgggc caaagaccac gttgttgagg tggaacacga gttctacgtg aagaagggcg  6120
gcgccaagaa aagacccgcc cctagcgacg ccgacatcag cgagcctaag agagtgcggg  6180
aaagcgtggc ccagcccagc acatctgatg ctgaggccag catcaactac gccgatagat  6240
accaaaacaa gtgcagccgc cacgtgggca tgaacctgat gctgtttccc tgcagacagt  6300
gtgaaagaat gaaccagaat tctaatatct gctttacaca cggccagaaa gattgcctga  6360
aatgcttccc tgtgtccgag agccaaccag tgtctgtggt gaaaaaggcc taccagaagc  6420
tgtgctacat ccaccacatc atgggcaagg tgccagacgc ctgtaccgcc tgcgacctgg  6480
tcaacgtgga cctggacgac tgcatcttcg agcagtgatt tgtgatggga attctgtgct  6540
gtgccttcta gttgccagcc atctgttgtt tgcccctccc ccgtgccttc cttgaccctg  6600
gaaggtgcca ctcccactgt cctttcctaa taaaatgagg aaattgcatc gcattgtctg  6660
agtaggtgtc attctattct ggggggtggg gtggggcagg acagcaaggg gaggattgg  6720
gaagacaata gcaggcatgc tggggatgcg gtgggctcta tgggaccttt tttagggccc  6780
attggtatgg cttttttcccc gtatcccccc aggtgtctgc aggctcaaag agcagcgagg  6840
agcgttcaga ggaaagcgat ccgtgccacc ttccccgctg ccccgcacgc  6900
tgccggctcg gggatgcggg gggagcgccg gaccggagcg gagccccggg cggctcgctg  6960
ctgcccccta gcggggagg gacgtaatta catccctggg ggctttgggg ggggctgtc  7020
cctctagagc ggccgccacc gcggtggagc tccagctttt gttcccttta gtgagggtta  7080
attagatctt aatacgactc actataggc gaattggta ccgggcccc ctgaggcgga  7140
aagaaccagc tggggctcta ggggtatcc ccgggttg ggttgcgcct ttctccaaggc  7200
agccctgggt ttgcgcaggg acgcggctgc tctgggcgtg gttccgggaa acgcagcggc  7260
gccgaccctg ggtctcgcac attcttcacg tccgttcgca gcgtcacccg gatcttcgcc  7320
gctaccttg tgggcccccc ggcgacgctt cctgctccgc ccctaagtcg ggaaggttcc  7380
ttgcggttcg cggcgtgccg gacgtgacaa acggaagccg cacgtctcac tagtaccctc  7440
gcagacggac agcgccaggg agcaatggca gcgcgccgac cgcgatgggc tgtggccaat  7500
```

```
agcggctgct cagcagggcg cgccgagagc agcggccggg aagggcggt gcgggaggcg    7560
gggtgtgggg cggtagtgtg ggccctgttc ctgcccgcgc ggtgttccgc attctgcaag    7620
cctccggagc gcacgtcggc agtcggctcc ctcgttgacc gaatcaccga cctctctccc    7680
cagaagctcc cgggagcttg tatatccatt ttcggatctg atcagcacgt gttgacaatt    7740
aatcatcggc atagtatatc ggcatagtat aatacgcaa ggtgaggaac gccaccatgg    7800
ccaagccttt gtctcaagaa gaatccaccc tcattgaaag agcaacggct acaatcaaca    7860
gcatccccat ctctgaagac tacagcgtcg ccagcgcagc tctctctagc gacggccgca    7920
tcttcactgg tgtcaatgta tatcatttta ctggggacc ttgtgcagaa ctcgtggtgc    7980
tgggcactgc tgctgctgcg gcagctggca acctgacttg tatcgtcgcg atcggaaatg    8040
agaacagggg catcttgagc ccctgcggac ggtgccgaca ggtgcttctc gatctgcatc    8100
ctgggatcaa agccatagtg aaggacagtg atggacagcc gacggcagtt gggattcgtg    8160
aattgctgcc ctctggttat gtgtgggagg gctaaagcgc ggggatctca tgctggagtt    8220
cttcgcccac cccaacttgt ttattgcagc ttataatggt tacaaataaa gcaatagcat    8280
cacaaatttc acaaataaag catttttttc actgcattct agttgtggtt tgtccaaact    8340
catcaatgta tcttatcatg tctgtagctg atgtatacct aggatccggc cggcctgcag    8400
gtgtcctcac aggaacgaag tccctaaaga aacagtggca gccaggttta gccccggaat    8460
tgactggatt cctttttag ggcccattgg tatggctttt tccccgtatc ccccaggtg    8520
tctgcaggct caaagagcag cgagaagcgt tcagaggaag cgatcccgt gccaccttcc    8580
ccgtgcccgg gctgtccccg cacgctgccg gctcggggat gcgggggag cgccggaccg    8640
gagcggagcc ccgggcggct cgctgctgcc cctagcggg ggagggacgt aattacatcc    8700
ctgggggctt tgggggggg ctgtccctct agagcggccg ccaccgcggt ggagctccag    8760
cttttgttcc ctttagtgag ggttaattag atcttaatac gactcactat agggcgaatt    8820
gggtaccggg ccccccctcg aggtcgacgg tatcctcgag gtcgacggta tcgataagct    8880
tgatatctat aacaagaaaa tatatatata ataagttatc acgtaagtag aacatgaaat    8940
aacaataaa ttatcgtatg agttaaatct taaagtcac gtaaagata atcatgcgtc    9000
attttgactc acgcggtcgt tatagttcaa aatcagtgac attaccgca ttgacaagca    9060
cgcctcacgg gagctccaag cggcgactga gatgtcctaa atgcacacg acggattcgc    9120
gctatttaga aagagagagc aatatttcaa gaatgcatgc gtcaattta cgcagactat    9180
cttctctaggg ttaatctagc tgcatcagga tcatatcgtc gggtcttttt tccggctcag    9240
tcatcgccca agctgcgct atctgggcat cggggaggaa gaagcccgtg ccttttcccg    9300
cgaggttgaa gcggcatgga aagagtttgc cgaggatgac tgctgctgca ttgacgttga    9360
gcgaaaacgc acgtttacca tgatgattcg ggaaggtgtg gccatgcacg cctttaacgg    9420
tgaactgttc gttcaggcca cctgggatac cagttcgtcg cggcttttcc ggacacagtt    9480
ccggatggtc agcccgaagc gcatcagcaa cccgaacaat accggcgaca gccggaactg    9540
ccgtgccggt gtgcagatta atgacagcgg tgcggcgctg gatattacg tcagcgagga    9600
cgggtatcct ggctggatgc cgcagaaatg gacatggata cccgtgagt tacccggcgg    9660
gcgcgcttgg cgtaatcatg gtcatagctg tttcctgtgt gaaattgtta tccgctcaca    9720
attccacaca acatacgagc cggaagcata aagtgtaaag cctggggtgc ctaatgagtg    9780
agctaactca cattaattgc gttgcgctca ctgcccgctt tccagtcggg aaacctgtcg    9840
tgccagctgc attaatgaat cggccaacgc gcggggagag gcggtttgcg tattgggcgc    9900
tcttccgctt cctcgctcac tgactcgctg cgctcggtcg ttcggctgcg gcgagcggta    9960
tcagctcact caaaggcggt aatacggtta tccacagaat caggggataa cgcaggaaag   10020
aacatgtgag caaaaggcca gcaaaaggcc aggaaccgta aaaaggccgc gttgctgcgg   10080
tttttccata ggctccgccc ccctgacgag catcacaaaa atcgacgctc aagtcagagg   10140
tggcgaaacc cgacaggact ataaagatac caggcgtttc ccctggaag ctccctcgtg   10200
cgctctcctg ttccgaccct gccgcttacc ggatacctgt ccgcctttct cccttcggga   10260
agcgtggcgc tttctcatag ctcacgctgt aggtatctca gttcggtgta ggtcgttcgc   10320
tccaagctgg gctgtgtgca cgaaccccc gttcagcccg accgctgcgc cttatccggt   10380
aactatcgtc ttgagtccaa cccggtaaga cacgacttat cgccactggc agcagccact   10440
ggtaacagga ttagcagagc gaggtatgta ggcggtgcta cagagttctt gaagtggtgg   10500
cctaactacg gctacactag aaggacagta tttggtatct gcgctctgct gaagccagtt   10560
accttcggaa aaagagttgg tagctcttga tccggcaaac aaaccaccgc tggtagcggt   10620
ggtttttttg tttgcaagca gcagattacg cgcagaaaaa aaggatctca agaagatcct   10680
ttgatctttt ctacgggtc tgacgctcag tggaacgaaa actcacgtta agggattttg   10740
gtcatgagat tatcaaaaag gatcttcacc tagatccttt taaattaaaa atgaagtttt   10800
aaatcaatct aaagtatata tgagtaaact tggtctgaca gttaccaatg cttaatcagt   10860
gaggcaccta tctcagcgat ctgtctattt cgttcatcca tagttgcctg actccccgtc   10920
gtgtagataa ctacgatacg ggagggctta ccatctggcc ccagtgctgc aatgataccg   10980
cgagacccac gctcaccggc tccagattta tcagcaataa accagccagc cggaagggcc   11040
gagcgcagaa gtggtcctgc aactttatcc gcctccatcc agtctattaa ttgttgccgg   11100
gaagctagag taagtagttc gccagttaat agtttgcgca acgttgttgc cattgctaca   11160
ggcatcgtgg tgtcacgctc gtcgtttggt atggcttcat tcagctccgg ttcccaacga   11220
tcaaggcgag ttacatgatc ccccatgttg tgcaaaaaag cggttagctc cttcggtcct   11280
ccgatcgttg tcagaagtaa gttggccgca gtgttatcac tcatggttat ggcagcactg   11340
cataattctc ttactgtcat gccatccgta agatgcttt ctgtgactgg tgagtactca   11400
accaagtcat tctgagaata gtgtatgcgg cgaccgagtt gctcttgccc ggcgtcaata   11460
cgggataata ccgcgccaca tagcagaact ttaaaagtgc tcatcattgg aaaacgttct   11520
tcggggcgaa aactctcaag gatcttaccg ctgttgagat ccagttcgat gtaacccact   11580
cgtgcaccca actgatcttc agcatctttt actttcacca gcgtttctgg gtgagcaaaa   11640
acaggaaggc aaaatgccgc aaaaaaggga ataagggcga cacggaaatg ttgaatactc   11700
at                                                                  11702
```

```
SEQ ID NO: 25          moltype = DNA   length = 11859
FEATURE                Location/Qualifiers
misc_feature           1..11859
                       note = Synthetic: PB-hiRep-12#
source                 1..11859
                       mol_type = other DNA
                       organism = synthetic construct
```

```
SEQUENCE: 25
actcttcctt tttcaatatt attgaagcat ttatcagggt tattgtctca tgagcggata    60
catatttgaa tgtatttaga aaaataaaca aatagggggtt ccgcgcacat ttccccgaaa   120
agtgccacct aaattgtaag cgttaatatt ttgttaaaat tcgcgttaaa tttttgttaa   180
atcagctcat tttttaacca ataggccgaa atcggcaaaa tccctataa atcaaaagaa    240
tagaccgaga tagggttgag tgttgttcca gtttggaaca agagtccact attaaagaac   300
gtggactcca acgtcaaagg gcgaaaaacc gtctatcagg gcgatggccc actacgtgaa   360
ccatcaccct aatcaagttt tttggggtcg aggtgccgta aagcactaaa tcggaaccct   420
aaagggagcc cccgatttag agcttgacgg ggaaagccgg cgaacgtggc gagaaaggaa   480
gggaagaaag cgaaaggagc gggcgctagg gcgctggcaa gtgtagcggt cacgctgcgc   540
gtaaccacca cacccgccgc gcttaatgcg ccgctacagg gcgcgtccca ttcgccattc   600
aggctgcgca actgttggga agggcgatcg gtgcgggcct cttcgctatt acgccagctg   660
gcgaaagggg gatgtgctgc aaggcgatta agttgggtaa cgccagggtt ttcccagtca   720
cgacgttgta aaacgacggc cagtgagcgc gcctcgttca ttcacgtttt tgaacccgtg   780
gaggacgggc agactcgcgg tgcaaatgtg ttttacagcg tgatggagca gatgaagatg   840
ctcgacacgt gcagaacac gcagctagat taacccctaga aagataatca tattgtgacg   900
tacgttaaag ataatcatgc gtaaaattga cgcatgtgtt ttatcggtct gtatatcgag   960
gtttatttat taatttgaat agatattaag ttttattata tttacactta catactaata  1020
ataaattcaa caaacaattt atttatgttt atttattat taaaaaaaaaa caaaaactca  1080
aaatttcttc tataaagtaa caaaactttt atcgaattcc tgcagcccgg gggatccact  1140
agttctagag ggacagcccc cccccaaagc ccccagggat gtaattacgt ccctcccccg  1200
ctaggggggca gcagcgagcc ccgcggggct ccgctccggt ccggcgctcc ccccgcatcc  1260
ccgagccggc agcgtgcggg gacagcccgg gcacggggga ggtggcacgg gatcgctttc  1320
ctctgaacgc ttctcgctgc tctttgagcc tgcagacacc tggggggata cggggaaaag  1380
gcctccaagg ccagcttccc acaataagtt gggtgaattt tggctcattc ctcctttcta  1440
taggattgag gtcagagctt tgtgatggga atttctgtga atgtgtgtca gttagggtgt  1500
ggaaagtccc gcgatcgcta gcttaagcgc tgatcaattg gcgcgccgaa ttcgttatct  1560
gcagaattcg gcttgacatt gattattgac tagttattaa tagtaatcaa ttacggggtc  1620
attagttcat agcccatata tggagttccg cgttacataa cttacggtaa atggcccgcc  1680
tggctgaccg cccaacgacc cccgcccatt gacgtcaata tgacgtatg ttcccatagt  1740
aacgccaata gggactttcc attgacgtca atgggtggag tatttacggt aaactgccca  1800
cttggcagta catcaagtgt atcatatgcc aagtacgccc cctattgacg tcaatgacgg  1860
taaatggccc gcctggcatt atgcccagta catgaccttat gggactttc ctacttggca  1920
gtacatctac gtattagtca tcgctattac catggtgatg cggttttggc agtacatcaa  1980
tgggcgtgga tagcggtttg actcacgggg atttccaagt ctccaccca ttgacgtcaa  2040
tgggagtttg ttttggaacc aaaatcaacg gactttcca aaatgtcgta acaactccgc  2100
cccattgacg caaatgggcg gtaggcgtgt acggtgggag gtctatataa gcagagctct  2160
ccctatcagt gatagagatc tccctatcag tgatagagat cgtcgacgag ctcgtttagt  2220
gaaccgtcag atcgcctgga gacgccatcc acgctgtttt gacctccata gaagacaccg  2280
ggaccgatcc agcctgaacg cgcagccgcc aatggatgcc ggggtttac gagattgtga  2340
ttaaggtccc cagcgacctt gacgagcatc tgcccggcat ttctgacagc tttgtgaact  2400
gggtggccga aaggaatgg gagttgccgc cagattctga catggatctg aatctgattg  2460
agcaggcacc cctgaccgtg gccgagaagc tgcagccgca ctttctgacg gaatggcgcc  2520
gtgtgagtaa ggccccggag gctctttttct ttgtgcaatt tgagaaggga gagagctact  2580
tccacatgca cgtgctcgtg gaaaccaccg gggtgaaatc catggttttg ggacgttttcc  2640
tgagtcgat tcgcgaaaaa ctgattcaga gaatttaccg cgggatcgag ccgactttgc  2700
caaactggtt cgcggtcaca aagaccagaa atggcgcgag aaggtggtgg  2760
atgagtgcta catccccaat tacttgctcc caaaaccca gcctgagctc caatgggcat  2820
ggaccaacat ggaacagtac ctcagcgcct gtttgaatct cacggagcgt aaacggttgg  2880
tggcgcagca tctgacgcac gtgtcgcaga cgcaggagca gaacaaagag aatcagaatc  2940
ccaattctga tgcgccggtg atcagatcaa aaacttcagc caggtacatg agctggtcg   3000
ggtggctcgt ggacaagggg attacctcgg agaagcagtg gatccaggag gaccaggcct  3060
catacatctc cttcaatgcg gcctccaact cgcggtccca aatcaaggct gccttggaca  3120
atgcgggaaa gattatgagc ctgactaaaa ccgcccccga ctacctggtg ggccagcagc  3180
ccgtggagga catttccagc aatcggattt ataaaattttt ggaactaaac gggtacgatc  3240
cccaatatgc ggcttccgtc tttctgggat gggccacgaa aaagttcggc aagaggaaca  3300
ccatctggct gtttgggcct gcaactaccg ggaagaccaa catcgcggag gccatagccc  3360
acactgtgcc cttctacggg tgcgtaaact ggaccaatga gaactttccc ttcaacgact  3420
gtgtcgacaa gatggtgatc tggtgggagg aggggaagat gaccgccaag gtcgttggagt  3480
cggccaaagc cattctcgga ggaagcaagg tgcgcgtgga ccagaaatgc aagtcctcgg  3540
cccagataga cccgactccc gtgatcgtca cctccaacac caacatgtgc gccgtgattg  3600
acgggaactc aacgaccttc gaacaccagc agccgttgca agaccggatg ttcaaatttg  3660
aactcacccg ccgtctggat catgactttg gaaggtcac caagcaggaa gtcaaagact  3720
ttttccggtg ggcaaaggat cacgtggttg agtggaagca tgaattctac ctcaaaaagg  3780
gtggagccaa gaaaagaccc gccccagtg acgcagatat aagtgagccc aaacgggtgc  3840
gcgagtcagt tgcgcagcca tcgacgtcag acgcggaagc ttcgatcaac tacgcagaca  3900
ggtaccaaaa caaatgttct cgtcacgtgg gcatgaatct gatgctgttt ccctgcagac  3960
aatgcgagag aatgaatcag aattcaaata tctgcttcac tcacggacga aaagactgtt  4020
tagagtgctt tccgtgtca gaatctcaac ccgtttctgt cgtcaaaaag gcgtatcaga  4080
aactgtgcta cattcatcat atcatgggaa aggtgccaga gcttgcacct gcctgcgatc  4140
tggtcaatgt ggatttggat gactgcatct tgaacaata aaatggctag gatccggccg  4200
gcctgcaggt gtcctcacag gaacgaagtc cctaaagaaa cagtggcagc caggtttagc  4260
cccggaaaac ttgtttattg cagcttataa tggttacaaa taaagcaata gcatcacaaa  4320
tttcacaaat aaagcatttt tttcactgca ttctagttgt ggtttgtcca aactcatcaa  4380
tgtatcttat tgactggatt gagggacagc ccccccccaa agcccccagg gatgtaatta  4440
cgtccctccc ccgctagggg gcagcagcga gcgcgcccgg gctccgctcc ggtccggcgc  4500
tccccccgca tccccgagcc ggcagcgtgc ggggacagcc cggcacgggg aaggtggca   4560
cgggatcgct ttcctctgaa cgcttctcgc tgctctttga gcctgcagac acctgggggg  4620
atacggggaa aaggcctcca aggccagctt cccacaataa gttgggtgaa ttttggctca  4680
```

```
ttcctcctttctataggattgaggtcagagcgcgttacataacttacggtaaatggcccg    4740
cctggctgaccgcccaacgaccccccgcccattgacgtcaataatgacgtatgttcccata    4800
gtaacgccaatagggactttccattgacgtcaatgggtggagtatttacggtaaactgcc    4860
cacttggcagtacatcaagtgtatcatatgccaagtacgccccctattgacgtcaatgac    4920
ggtaaatggcccgcctggcattatgcccagtacatgacctta tgggactttcctacttgg    4980
cagtacatctacgtattagtcatcgctattaccatggtcgaggtgagcccacgttctgc    5040
ttcactctccccatctccccccctcccaccccaatttgtatttatt tattttttaa    5100
ttattttgtgcagcgatggggcgggggggggggggggcgcgccaggcggggcgggg    5160
cggggcgagggcggggcggggcgaggcggagaggtgcggcggcagccaatcagagcggc    5220
gcgctccgaagtttcctttatggcgaggcggcggcggcggccctataaaagcga    5280
agcgtccctatcagtgatagagatctccctatcagtgatagagacgcggcgggcgggagt    5340
cgctgcgttgccttcgccccgtgccccgctccgcgccgcctcgcgccgcccccggct    5400
ctgactgaccgcgttactcccacagatcccaattctgatgcgccggtgatcagatcaaaa    5460
acttcagccaggtacgccaccatggaactggtcggatggctgctggtggataagggcatcaca    5520
agcgagaagcaatggatccaggaggaccaggcctcatatatttctttaacgccgctagc    5580
aattccagaagccagatcaaggctgctctgacaacgccggcaaaatcatgagcctgacc    5640
aagaccgccctgactacctggtgggacagcagcctgtggaagatatcagcagcaacaga    5700
atctataagatcctggaactgaacgctacgacccccagtacgccgcctccgtgttcctg    5760
ggctgggctacaaagaagttcggcaagcggaacaccatctggctgttcggacctgccacc    5820
acaggcaaaaccaatatcgccgaggccatcgcccacaccgtgcctttctacggctgcgtg    5880
aactggacaaacgagaacttccccttcaacgactgtgtggacaagatggtgatctggtgg    5940
gaggaaggcaaatgacagctaaggtggtggaatctgccaaggctatcctgggaggctct    6000
aaggtcaggggtggatcagaagtgtaaaagcagcgcccagattgaccctaccctgtgatc    6060
gtgaccagcaataccaacatgtgcgccgtgatcgacggcacagcaccaccttcgagcat    6120
cagcagcctctgcaggaccgatgttcaagtttgagctccagacggctggatcacgac    6180
ttcggcaaggtgaccaagcaggaggtgaagatttcttcagatgggccaagaccacgtt    6240
gttgaggtggaacacgagttctacgtgaagaagggcggcgccaagaaaagacccgccccct    6300
agcgacgccgacatcagcgagcctaagagagtgcgggaaagcgtggcccagccccagcaca    6360
tctgatgctgaggccagcatcaactacgccgatagataccaaaacaagtgcagccgccca    6420
gtgggcatgaacctgatgctgttttccctgcagacagtgtgaaagaatgaaccagaattct    6480
aatatctgcttacacacggccagaaagatgcctggaatgcttcctgtgtccgagagc    6540
caaccagtgtctgtggtgaaaaggcctacagaagctgtgctacatccacacatcatg    6600
ggcaaggtgccagacgcctgtaccgcctgcgacctggtcaacgtggacctggacgactgc    6660
atcttcgacagtgatttgtgatgggaattctgtgctgtgccttctagttgccagccatc    6720
tgttgtttgccctccccgtgccttccttgaccctgaaggtgccactcccactgtcct    6780
ttcctaataaaatgaggaaattgcatcgcattgtctgagtaggtgtcattctattctggg    6840
gggtgggtggggcaggacagcaagggggaggattgggaagacaatagcaggcatgctgg    6900
ggatgcggtggctctatggggaccttttttagggcccattggtatggcttttccccgta    6960
tccccccaggtgtctgcaggctcaaagagcagcgagaagcgttcagaggaaaagcgatccc    7020
gtgccacctt ccccgtgcccgggctgtccccgcacgctgccggctcggggatgcggggg    7080
agcgccggaccggagcggagcccgggcggctcgctgctgccccctagcggggaggggac    7140
gtaattacatccctgggggctttggggggggctgtccctctagagcggccgccaccgcg    7200
gtggagctccagcttttgttccctttagtgagggttaattagatcttaatacgactcact    7260
atagggcgaattgggtaccggcccccctaggcggaaagaaccagctggggctctaggg    7320
ggtatccccggggttgggttgcgcctttttccaaggcagccctgggttttgcgcagggacg    7380
cggctgctctgggcgtggttccgggaaacgcagcggcgccgaccctgggtctcgcacatt    7440
cttcacgtccgttcgcagcgtcaccggatctttgcgtggccttgttgtgccccccgc    7500
gacgcttcctgctccgccccttaagtcggggaaggttccttgcggttcgcggcgtgccgac    7560
gtgacaaacggaagccgcacgtctcactagtaccctcgcagacggacagcgccagggagc    7620
aatggcagccgccgaccgcgatgggctgtggccaatagcggctgctcagcagggcgcgc    7680
cgagagcagcggcggaaggggcggtgcggaggcgggtgtggggcggtgtgcgggc    7740
cctgttcctgcccgcgcggttccgcattctgcaagcctccggagcgcagtcggcagt    7800
cggctcctcgttgaccgaatcaccgacctctctccccagaagctcccggagcttgtat    7860
atccatttttcggatctgatcagcacgtgtgacaattaatcatcggcatagtatatcggc    7920
atagtataatacgacaaggtgaggaacgccaccatgccaagcctttgtctcaagaagaa    7980
tccaccctcattgaaagagcaacggctacaatcaacagcatccccactctgaagactac    8040
agcgtcgccagcgcagctctctctagcgacggccgcatctctcactggtgtcaatgtat    8100
cattttactggggggaccttgtgcagaactcgtggtgctggcactgctgctgctgcgca    8160
gctggcaacctgacttgtatcgtgcgatcggaaatgagaacaggcggctcttgagccc    8220
tgccgacggtgccgacaggtgcttctcgatctgcatctggatcaaagccatagtgaag    8280
gacagtgatgacagccgacggcagttgggattcgtgaattgctgccctctggttatgtg    8340
tgggagggctaaagcgcgggatctcatgctggttcttcgcccaccccaacttgttta    8400
ttgcagcttataaatggttacaaataaagcaatagcatcacaaatttcacaaataaagcat    8460
ttttcactgcattctagttgtggtttgtccaaactcatcaatgtatcttatcatgtct    8520
gtagctgatgtatacctaggatccggccggcctgcaggtccctcacaggaacgaagtcc    8580
ctaaagaaacagtggcagccaggtttagcccggaattgactggattccttttttagggc    8640
ccattggtatggcttttccccgtatccccccaggtgtctgcaggctcaaagagcagcga    8700
gaagcgttcagaggaaagcgatcccgtgccaccttccccgtgcccgggctgtccccgcac    8760
gctgccgcggcggggatgcggggggagcgccggaccggagccccgggcggctccgc    8820
tgctgccccctagcggggagggacgtaattacatccctgggggctttgggggggggctg    8880
tccctctagagcggccgccaccgcggtggactccagctttgttcccttagtgagggt    8940
taattagatcttaatacgactcactataggcgaattgggtaccgggccccccctcgagg    9000
tcgacggtatcctcgaggtcgacggtatcgataagcttgatatctataacaagaaaatat    9060
atatataataagttatcacgtaagtagaacaatataattcgtatgagt    9120
taaatcttaaaagtcacgtaaaagataatcatgcgtcattttgactcacggtcgttat    9180
agttcaaaatcagtgacacttaccgcattgacaagcacgcctcacgggagctccaagcgg    9240
cgactgagatgtcctaaatgcacagcgacgattcgcgctatttgaaagagagcaat    9300
atttcaagaatgcatgcgtcaattttacgcagactatcttctagggttaatctagctgc    9360
atcaggatcatatcgtcgggtcttttttccggctcagtcatcgcccaagctggcgctatc    9420
```

```
tgggcatcgg ggaggaagaa gcccgtgcct tttcccgcga ggttgaagcg gcatggaaag    9480
agtttgccga ggatgactgc tgctgcattg acgttgagcg aaaacgcacg tttaccatga    9540
tgattcggga aggtgtggcc atgcacgcct taacggtgaa actgttcgtt caggccacct    9600
gggataccag ttcgtcgcgg cttttccgga cacagttccg gatggtcagc ccgaagcgca    9660
tcagcaaccc gaacaatacc ggcgacagcc ggaactgccg tgccggtgtg cagattaatg    9720
acagcggtgc ggcgctggga tattacgtca gcgaggacgg gtatcctggc tggatgccga    9780
agaaatggac atggataccc cgtgagttac ccggcgggcg cgcttggcgt aatcatggtc    9840
atagctgttt cctgtgtgaa attgttatcc gctcacaatt ccacacaaca tacgagccgg    9900
aagcataaag tgtaaagcct ggggtgccta atgagtgagc taactcacat taattgcgtt    9960
gcgctcactg cccgctttcc agtcgggaaa cctgtcgtgc cagctgcatt aatgaatcgg   10020
ccaacgcgcg gggagaggcg gtttgcgtat tgggcgctct tccgcttcct cgctcactga   10080
ctcgctgcgc tcggtcgttc ggctgcggcg agcggtatca gctcactcaa aggcggtaat   10140
acggttatcc acagaatcag gggataacgc aggaaagaac atgtgagcaa aaggccagca   10200
aaaggccagg aaccgtaaaa aggccgcgtt gctggcgttt ttccataggc tccgcccccc   10260
tgacgagcat cacaaaaatc gacgctcaag tcagaggtgg cgaaacccga caggactata   10320
aagataccag gcgtttcccc ctggaagctc cctcgtgcgc tctcctgttc cgaccctgcc   10380
gcttaccgga tacctgtccg cctttctccc ttcgggaagc gtggcgcttt ctcatagctc   10440
acgctgtagg tatctcagtt cggtgtaggt cgttcgctcc aagctgggct gtgtgcacga   10500
accccccgtt cagcccgacc gctgcgcctt atccggtaac tatcgtcttg agtccaaccc   10560
ggtaagacac gacttatcgc cactggcagc agccactggt aacaggatta gcagagcgag   10620
gtatgtaggc ggtgctacag agttcttgaa gtggtggcct aactacggct acactagaag   10680
gacagtattt ggtatctgcg ctctgctgaa gccagttacc ttcggaaaaa gagttggtag   10740
ctcttgatcc ggcaaacaaa ccaccgctgg tagcggtggt ttttttgttt gcaagcagca   10800
gattacgcgc agaaaaaaag gatctcaaga agatcctttg atcttttcta cggggtctga   10860
cgctcagtgg aacgaaaact cacgttaagg gattttggtc atgagattat caaaaaggat   10920
cttcacctag atccttttaa attaaaaatg aagttttaaa tcaatctaaa gtatatatga   10980
gtaaacttgg tctgacagtt accaatgctt aatcagtgag gcacctatct cagcgatctg   11040
tctatttcgt tcatccatag ttgcctgact ccccgtcgtg tagataacta cgatacggga   11100
gggcttacca tctggcccca gtgctgcaat gataccgcga cccacgct caccggctcc   11160
agatttatca gcaataaacc agccagccgg aagggccgag cgcagaagtg gtcctgcaac   11220
tttatccgcc tccatccagt ctattaattg ttgccggaa gctagagtaa gtagttcgcc   11280
agttaatagt ttgcgcaacg ttgttgccat tgctacaggc atcgtggtgt cacgctcgtc   11340
gtttggtatg gcttcattca gctccggttc caacgatca aggcgagtta catgatcccc   11400
catgttgtgc aaaaaagcgg ttagctcctt cggtcctccg atcgttgtca gaagtaagtt   11460
ggccgcagtg ttatcactca tggttatggc agcactgcat aattctctta ctgtcatgcc   11520
atccgtaaga tgcttttctg tgactggtga gtactcaacc aagtcattct gagaatagtg   11580
tatgcggcga ccgagttgct cttgcccggc gtcaatacgg gataataccg cgccacatag   11640
cagaacttta aaagtgctca tcattggaaa acgttcttcg gggcgaaaac tctcaaggat   11700
cttaccgctg ttgagatcca gttcgatgta acccactcgt gcacccaact gatcttcagc   11760
atcttttact ttcaccagcg tttctgggtg agcaaaaaca ggaaggcaaa atgccgcaaa   11820
aaagggaata agggcgacac ggaaatgttg aatactcat                          11859

SEQ ID NO: 26           moltype = DNA   length = 11854
FEATURE                 Location/Qualifiers
misc_feature            1..11854
                        note = Synthetic: PB-hiRep-13#
source                  1..11854
                        mol_type = other DNA
                        organism = synthetic construct
SEQUENCE: 26
actcttcctt tttcaatatt attgaagcat ttatcagggt tattgtctca tgagcggata     60
catatttgaa tgtatttaga aaaataaaca aataggggtt ccgcgcacat ttccccgaaa    120
agtgccacct aaattgtaag cgttaatatt ttgttaaaat tcgcgttaaa ttttttgttaa    180
atcagctcat ttttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt ttttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cccgccgcgc ttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacaggcg tgatggagca gatgaagatg    840
ctcgacacgc tgcagaacac gcagctagat taacctaga aagataatca tattgtgacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttattttt taaaaaaaaa caaaactca   1080
aaatttcttc tataaagtaa caaaactttt atcgaattcc tgcagcccgg gggatccact   1140
agttctagag gacagcccc cccccaaagc ccccagggat gtaattacgt ccctcccccg   1200
ctaggggca gcagcgagcc gcccggggct ccgctccggt ccggcgctcc ccccgcatcc   1260
ccgagccgga agcgtgcggg gacagcccgg gcacgggaa ggtggcacgg gatcgctttc   1320
ctctgaacgc ttctcgctgc tctttgagcc tgcagacacc tgggggata cggggaaaag   1380
gcctccaagg ccagtcttcc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcttaagcgc tgatcaattg gcgcgccgaa ttcgttatct   1560
gcagaattcg gcttgacatt gattattgac tagttattaa tagtaatcaa ttacggggtc   1620
attagttcat agcccatata tggagttccg cgttacataa cttacggtaa atggcccgcc   1680
tggctgaccg cccaacgacc cccgcccatt gacgtcaata atgacgtatg ttcccatagt   1740
```

```
aacgccaata gggactttcc attgacgtca atgggtggag tatttacggt aaactgccca   1800
cttggcagta catcaagtgt atcatatgcc aagtacgccc cctattgacg tcaatgacgg   1860
taaatggccc gcctggcatt atgcccagta catgacctta tgggactttc ctacttggca   1920
gtacatctac gtattagtca tcgctattac catggtgatg cggttttggc agtacatcaa   1980
tgggcgtgga tagcggtttg actcacgggg atttccaagt ctccacccca ttgacgtcaa   2040
tgggagtttg ttttggaacc aaaatcaacg ggactttcca aaatgtcgta acaactccgc   2100
cccattgacg caaatgggcg gtaggcgtgt acggtgggag gtctatataa gcagagctct   2160
ccctatcagt gatagagatc tccctatcag tgatagagat cgtcgacgag ctcgtttagt   2220
gaaccgtcag atcgcctgga gacgccatcc acgctgtttt gacctccata gaagacaccg   2280
ggaccgatcc agcctgaacg cgcagccgcc acgccgggggt tttacgagat tgtgattaag   2340
gtccccagcg accttgacga gcatctgccc ggcatttctg acagctttgt gaactgggtg   2400
gccgagaagg aatgggagtt gccgccagat tctgacatgg atctgaatct gattgagcag   2460
gcacccctga ccgtggccga aagctgcag cgcgactttc tgacgaatg cgccgtgtg   2520
agtaaggccc cggaggctct tttctttgtg caatttgaga agggagagag ctacttccac   2580
atgcacgtgc tcgtggaaac caccggggtg aaatccatgg ttttgggacg tttcctgagt   2640
cagattcgca aaaactgat tcagagaatt taccgcggga tcgagccgac tttgccaaac   2700
tggttcgcgg tcacaaagac cagaaatggc gccgaggcg ggaacaaggt ggtggatgag   2760
tgctacatcc ccaattactt gctccccaaa acccagccg agctccaatg ggcatggacc   2820
aacatggaac agtacctcag cgcctgtttg aatctcacgg agcgtaaacg gttggtggcg   2880
cagcatctga cgcacgtgtc gcagacgcag gagcagaaca aagagaatca gaatcccaat   2940
tctgatgcgc cggtgatcag atcaaaaact tcagccaggt acatggagct ggtcgggtgg   3000
ctcgtggaca aggggattac tcggagaga cagtggatcc aggaggacca ggcctcatac   3060
atctccttca atgcggcctc caactcgcgg tcccaaatca aggctgcctt ggacaatgcg   3120
ggaaagatta tgagcctgac taaaaccgcc cccgactacc tggtgggcca gcagcccgtg   3180
gaggacattt ccagcaatcg gatttataaa attttggaac taaacgggta cgatccccaa   3240
tatgcggctt ccgtctttct gggatgggcc acgaaaaagt tcggcaagag gaacaccatc   3300
tggctgtttg ggcctgcaac taccgggaag accaacatcc cggaggccat agcccacact   3360
gtgcccttct acgggtgcgt aaactggacc aatgagaact ttcccttcaa cgactgtgtc   3420
gacaagatgg tgatctggtg ggaggagggg aagatgaccg ccaaggtcgt ggagtcggcc   3480
aaagccattc tcggaggaag caaggtgcgc gtggaccaga aatgcaagtc ctcggcccag   3540
atagacccga ctcccgtgat cgtcacctcc aacaccaaca tgtgcgccgt gattgacggg   3600
aactcaacga ccttcgaaca ccagcagccg ttgcaagacc ggatgttcaa atttgaactc   3660
acccgccgtc tggatcatga ctttgggaag gtcaccaagc aggaagtcaa agacttttc   3720
cggtgggcaa aggatcacgt ggttgaggtg gagcatgaat tctacgtcaa aaagggtgga   3780
gccaagaaaa gacccgcccc cagtgacgca gatataagtg agcccaaacg ggtgcgcgag   3840
tcagttgcgc agccatcgac gtcagacgcg gaagcttcga tcaactacgc agacaggtac   3900
caaaacaaat gttctcgtca cgtgggcatg aatctgatgc tgtttccctg cagcaatgc   3960
gagagaatga atcagaattc aaatatctgc ttcactcacg gacagaaaga ctgtttagag   4020
tgctttcccg tgtcagaatc tcaacccgtt tctgtcgtca aaaaggcgta tcagaaactg   4080
tgctacattc atcatatcat gggaaaggtc ccagacgctt gcactgcctg cgatctggtc   4140
aatgtggatt tggatgactg catctttgaa caataaaatg gctaggatcc ggccggcctg   4200
caggtgtcct cacaggaacg aagtccctaa agaaacagtg gcagccaggt ttagccccgg   4260
aaaacttgtt tattgcagct tataatggtt acaaataaag caatagcatc acaaatttca   4320
caaataaagc attttttttca ctgcattcta gttgtggttt gtccaaactc atcaatgtat   4380
cttattgact ggattgaggg acagcccccc cccaaagccc caggatgt aattacgtcc   4440
ctcccccgct aggggcagc agcgagccgc ccggggctcc gctccggtcc ggcgctcccc   4500
ccgcatcccc gagccggcag cgtgcgggga cagcccgggg acggggaagg tggcacggga   4560
tcgctttcct ctgaacgctt ctcgctgctc tttgagcctg cagacacctg gggggatacg   4620
gggaaaaggc ctccaaggcc agcttcccac aataagttgg gtgaattttg gctcattcct   4680
cctttctata ggattgaggt cagagcgcgt tacataactt acggtaaatg gcccgcctgg   4740
ctgaccgccc aacgaccccc gcccattgac gtcaataatg acgtatgttc ccatagtaac   4800
gccaatagg actttccatt gacgtcaatg gtgagtat ttacggtaaa ctgcccactt   4860
ggcagtacat caagtgtatc atatgccaag tacgccccct attgacgtca atgacggtaa   4920
atggcccgcc tggcattatg cccagtacat gaccttatgg gactttccta cttggcagta   4980
catctacgta ttagtcatcg ctattaccat ggtcgaggtg agccccacgt tctgcttcac   5040
tctccccatc tcccccccct ccccaccccc aattttgtat ttatttattt tttaattatt   5100
ttgtgcagcg atggggggcgg gggggggggg gggcgcgcg ccaggcgggg cggggcgggg   5160
cgagggcgg ggcggggcga ggcggagagg tgcggcggca gccaatcaga gcggcgcgct   5220
ccgaaagttt ccttttatgg cgaggcggcg gcggcggcgg ccctataaaa agcgaagcgt   5280
ccctatcagt gatagagatc tccctatcag tgatagagat gcgggggcg ggagtcgctc   5340
cgttgccttc gccccgtgcc ccgctccgcg ccgcctcgcg ccgcccgccc ggctctgac   5400
tgaccgcgtt actcccacag atcccaattc tgatgcgccg gtgatcagat caaaaacttc   5460
agccaggtac gccaccatgg aactggtcgg atggctggtg gataagggca tcacaagcga   5520
gaagcaatgg atccaggagg accaggcctc atatatttct tttaacgccg ctagcaattc   5580
cagaagccag atcaaggctg ctctggacaa cgccggcaaa atcatgagcc tgaccaagac   5640
cgcccctgac tacctggtgg gacagcagcc tgtggaagat atcagcagca acagaatcta   5700
taagatcctg gaactgaacg gctacgaccc ccagtacgcc gcctccgtgt tcctgggctg   5760
ggctacaaag aagttcggca agcggaacac catctggctg ttcggacctg ccaccacagg   5820
caaaccaat atcgccgagg ccatccgcca caccgtgcct ttctacggct gcgtgaactg   5880
gacaaacgag aacttcccct tcaacgactg tgtggacaag atggtgatct ggtgggagga   5940
aggcaaaatg acagctaagg tggtggaatc tgccaaggct atcctgggag gctcaaggt   6000
cagggtggat cagaagtgta aagcagcgc ccagattgac cctacccctg tgatcgtgac   6060
cagcaatacc aacatgtgcg ccgtgatcga cggcaacagc accaccttcg agcatcagca   6120
gcctctgcag gaccggatgt tcaagtttga gctcaccaga gcctggatc acgacttcgg   6180
caaggtgacc aagcaggagg tgaaggattt cttcagatgg gccaagacc acgttgttga   6240
ggtgaacacc gagttctacg tgaagaaggg cggcgccaag aaaagacccg ccctagcga   6300
cgccgacatc agcgagccta agagagtgcg ggaaagcgtg gcccagccca gcacatctga   6360
tgctgaggcc agcatcaact acgccgatag ataccaaaac aagtgcagcc gccacgtggg   6420
catgaacctg atgctgtttc cctgcagaca gtgtgaaaga atgaaccaga attctaatat   6480
```

-continued

```
ctgctttaca cacggccaga aagattgcct ggaatgcttc cctgtgtccg agagccaacc   6540
agtgtctgtg gtgaaaaagg cctaccagaa gctgtgctac atccaccaca tcatgggcaa   6600
ggtgccagac gcctgtaccg cctgcgacct ggtcaacgtg gacctggacg actgcatctt   6660
cgagcagtga tttgtgatgg gaattctgtg ctgtgccttc tagttgccag ccatctgttg   6720
tttgccccte ccccgtgcct tccttgaccc tggaaggtgc cactcccact gtccttttcct  6780
aataaaatga ggaaattgca tcgcattgtc tgagtaggtg tcattctatt ctgggggtg    6840
gggtggggca ggacagcaag ggggaggatt gggaagacaa tagcaggcat gctggggatg   6900
cggtgggctc tatgggacct tttttagggc ccattggtat ggcttttcc ccgtatcccc    6960
ccaggtgtct gcaggctcaa agagcagcga gaagcgttca gaggaaagcg atcccgtgcc   7020
accttcccg tgcccgggct gtccccgcac gctgccggct cggggatgcg ggggagcgc     7080
cggaccggag cggagccccg ggcggctcgc tgctgccccc tagcggggga gggacgtaat   7140
tacatccctg ggggctttgg ggggggctg tccctctaga gcggccgcca ccgcggtgga    7200
gctccagctt ttgttccctt tagtgagggt taattagatc ttaatacgac tcactatagg   7260
gcgaattggg taccgggccc cctgaggcg gaaagaacca gctggggctc tagggggtat    7320
cccccggggtt ggggttgcgc cttttccaag gcagccctgg gtttgcgcag ggacgcggct  7380
gctctgggcg tggttccggg aaacgcagcg gcgccgaccc tgggtctcgc acattcttca   7440
cgtccgttcg cagcgtcacc cggatcttcg ccgctaccct tgtgggcccc ccggcgacgc   7500
ttcctgctcc gccccctaagt cgggaaggtt ccttgcggtt cgcggccgtgc cggacgtgac  7560
aaacggaagc cgcacgtctc actagtaccc tcgcagacgg acagcgccag ggagcaatgg   7620
cagcgcgccc accgcgatgg gctgtgggca atagcggctg ctcagcaggg cgcgccgaga   7680
gcagcggccg ggaaggggcg gtgcgggagg cggggtgtgg ggcggtagtg tgggccctgt   7740
tcctgcccgc gcggtgttcc gcattctgca agcctccgga gcgcacgtcg gcagtcggct   7800
ccctcgttga ccgaatcacc gacctctctc cccagaagct cccgggagct tgtatatcca   7860
ttttcggatc tgatcagcac gtgttgacaa ttaatcatcg gcatagtata tcggcatagt   7920
ataatacgac aaggtgagga acgccaccat ggccaagcct ttgtctcaag aagaatccac   7980
cctcattgaa agagcaacgg ctacaatcaa cagcatccct atctctgaag actacagcgt   8040
cgccagcgca gctctctcta gcgacggccg catcttcact ggtgtcaatg tatatcattt    8100
tactgggga ccttgtgcag aactcgtggt gctgggcact gctgctgctg cggcagctgg     8160
caacctgact tgtatcgtcg cgatcggaaa tgagaacagg ggcatcttga gccctgcgg     8220
acggtgccga caggtgcttc tcgatctgca tcctgggatc aaagccatag tgaaggacag    8280
tgatggacag ccgacggcag ttgggattcg tgaattgctg ccctctggtt atgtgtggga    8340
gggctaaagc gcggggatct catgctggag ttcttcgccc accccaactt gtttattgca    8400
gcttataatg gttacaaata aagcaatagc atcacaaatt tcacaaataa agcatttttt    8460
tcactgcatt ctagttgtgg tttgtccaaa ctcatcatca tatcttatca tgtctgtagc    8520
tgatgtatac ctaggatccg gccggcctgc aggtgtcctc acaggaacga agtccctaaa    8580
gaaacagtgg cagccaggtt tagccccgga attgactgga ttccttttttt agggcccatt   8640
ggtatggctt tttccccgta tcccccagg tgtctgcagg ctcaaagagc agcgagaagc     8700
gttcagagga aagcgatccc gtgccacctt ccccgtgccc gggctgtccc cgcacgctgc    8760
cggctgggcg atgcgggggg agcgccggac cggagccccg gggcgggtcgctgctgcctg    8820
cccctagcg gggagggac gtaattacat ccctgggggc tttgggggg ggctgtccct      8880
ctagagcggc cgccaccgcg gtggagctcc agcttttgtt ccctttagtg agggttaatt    8940
agatcttaat acgactcact ataggggcgaa ttgggtaccg gccccccct cgaggtcgac    9000
ggtatcctcg aggtcgacgg tatcgataag cttgatatct ataacaagaa aatatatata    9060
taataagtta tcacgtaagt agaacatgaa ataacaatat aattatcgta tgagttaaat    9120
cttaaaagtc acgtaaaaga taatcatgcg tcatttttgac tcacgcggtc gttatagttc    9180
aaaatcagtg acacttaccg cattgacaag cacgcctcac gggagctcca gcggcgact    9240
gagatgtcct aaatgcacag cgacggattc gcgctattta gaaagagaga gcaatatttc    9300
aagaatgcat gcgtcaattt tacgcagact atctttctag ggttaatcta gctgcatcag    9360
gatcatatcg tcgggtcttt tttccggctc agtcatcgcc caagctggcg ctatctgggc    9420
atcggggagg aagaagcccg tgccttttcc cgcgaggttg aagcggcatg gaaagagttt    9480
gccgagatga actgctgctg cattgacgtt gagcgaaaac gcacgtttac catgatgatt    9540
cgggaaggtg tggccatgca cgcctttaac ggtgaactgt tcgttcaggc cacctgggat    9600
accagttcgt cgcggctttt ccggacacag ttccggatgg tcagcccgaa gcgcatcagc    9660
aacccgaaca ataccggcga cagccggaac tgccgtgccg gtgtgcagat taatgacagc    9720
ggtgcggcgc tgggatatta cgtcagcgag gacgggtatc ctggctgtga gccgcagaaa    9780
tggacatgga taccccgtga gttaccggcc gggcgcgctt ggcgtaatca tggtcatagc    9840
tgtttcctgt gtgaaattgt tatccgctca caattccaca acatacga gccggaagca    9900
taaagtgtaa agcctgggt gcctaatgag tgagctaact cacattaatt gcgttgcgct    9960
cactgcccgc tttccagtcg ggaaacctgt cgtgccaact gcattaatga atcggccaac  10020
gcgcggggag aggcggtttg cgtattgggc gctcttccgc ttcctcgctc actgactcgc  10080
tgcgctcggt cgttcggctg cggcgagcgg tatcagctca ctcaaaggcg gtaatacggt   10140
tatccacaga atcaggggat aacgcaggaa agaacatgtg agcaaaaggc cagcaaaagg  10200
ccaggaaccg taaaaaggcc gcgttgctgg cgttttttcca taggctccgc cccccctgacg 10260
agcatcacaa aaatcgacgc tcaagtcaga ggtggcgaaa cccgacagga ctataaagat  10320
accaggcgtt tccccctgga agctccctcg tgcgctctcc tgttccgacc ctgccgctta  10380
ccggatacct gtccgccttt ctcccttcgg gaagcgtggc gctttctcat agctcacgct  10440
gtaggtatct cagttcggtg taggtcgttc gctccaagct gggctgtgtg cacgaacccc   10500
ccgttcagcc cgaccgctgc gccttatccg gtaactatcg tcttgagtcc aacccggtaa  10560
gacacgactt atcgccactg gcagcagcca ctggtaacag gattagcaga gcgaggtatg  10620
taggcggtgc tacagagttc ttgaagtggt ggcctaacta cggctacact agaaggacag  10680
tatttggtat ctgcgctctg ctgaagccag ttaccttcgg aaaaagagtt ggtagctctt  10740
gatccggcaa acaaaccacc gctggtagcg gtggtttttt tgtttgcaag cagcagatta  10800
cgcgcagaaa aaaaggatct caagaagatc ctttgatctt ttctacgggg tctgacgctc  10860
agtggaacga aaactcacgt taagggattt tggtcatgag attatcaaaa aggatcttca  10920
cctagatcct tttaaattaa aaatgaagtt ttaaatcaat ctaaagtata tatgagtaaa  10980
cttggtctga cagttaccaa tgcttaatca gtgaggcacc tatctcagcg atctgtctat  11040
ttcgttcatc catagttgcc tgactccccg tcgtgtagat aactacgata cgggagggct  11100
taccatctgg ccccagtgct gcaatgatac gcgagaccc acgctcaccg gctccagatt  11160
tatcagcaat aaaccagcca gccggaaggg ccgagcgcag aagtggtcct gcaactttat  11220
```

```
ccgcctccat ccagtctatt aattgttgcc gggaagctag agtaagtagt tcgccagtta  11280
atagtttgcg caacgttgtt gccattgcta caggcatcgt ggtgtcacgc tcgtcgtttg  11340
gtatggcttc attcagctcc ggttcccaac gatcaaggcg agttacatga tcccccatgt  11400
tgtgcaaaaa agcggttagc tccttcggtc ctccgatcgt tgtcagaagt aagttggccg  11460
cagtgttatc actcatggtt atggcagcac tgcataattc tcttactgtc atgccatccg  11520
taagatgctt ttctgtgact ggtgagtact caaccaagtc attctgagaa tagtgtatgc  11580
ggcgaccgag ttgctcttgc ccggcgtcaa tacgggataa taccgcgcca catagcagaa  11640
ctttaaaagt gctcatcatt ggaaaacgtt cttcggggcg aaaactctca aggatcttac  11700
cgctgttgag atccagttcg atgtaaccca ctcgtgcacc caactgatct tcagcatctt  11760
ttactttcac cagcgtttct gggtgagcaa aacaggaag gcaaaatgcc gcaaaaaagg  11820
gaataagggc gacacgaaa tgttgaatac tcat                               11854

SEQ ID NO: 27        moltype = DNA  length = 11573
FEATURE              Location/Qualifiers
misc_feature         1..11573
                     note = Synthetic: PB-hiRep-14#
source               1..11573
                     mol_type = other DNA
                     organism = synthetic construct
SEQUENCE: 27
actcttcctt tttcaatatt attgaagcat ttatcagggt tattgtctca tgagcggata    60
catatttgaa tgtatttaga aaaataaaca aataggggtt ccgcgcacat ttccccgaaa   120
agtgccacct aaattgtaag cgttaatatt ttgttaaaat tcgcgttaaa ttttttgttaa   180
atcagctcat tttttaacca ataggccgaa atcggcaaaa tcccttataa atcaaaagaa   240
tagaccgaga tagggttgag tgttgttcca gtttggaaca agagtccact attaaagaac   300
gtggactcca acgtcaaagg gcgaaaaacc gtctatcagg gcgatggccc actacgtgaa   360
ccatcaccct aatcaagttt ttggggtcg aggtgccgta aagcactaaa tcggaaccct   420
aaagggagcc cccgatttag agcttgacgg ggaaagccgg cgaacgtggc gagaaaggaa   480
gggaagaaag cgaaaggagc gggcgctagg gcgctggcaa gtgtagcggt cacgctgcgc   540
gtaaccacca cacccgccgc gcttaatgcg ccgctacagg gcgcgtccca ttcgccattc   600
aggctgcgca actgttggga agggcgatcg gtgcgggcct cttcgctatt acgccagctg   660
gcgaaagggg gatgtgctgc aaggcgatta agttgggtaa cgccaggggtt ttcccagtca   720
cgacgttgta aaacgacggc cagtgagcgc gcctcgttca ttcacgtttt tgaacccgtg   780
gaggacgggc agactcgcgg tgcaaatgtg ttttacagcg tgatggagca gatgaagatg   840
ctcgacacga tgcagaacac gcagctagat aagataatca tattgtgacg   900
tacgttaaag ataatcatgc gtaaaattga cgcatgtgtt ttatcggtct gtatatcgag   960
gtttatttat taatttgaat agatattaag ttttattata tttacactta catactaata  1020
ataaattcaa caaacaattt atttatgttt atttatttat taaaaaaaaa caaaaactca  1080
aaatttcttc tataaagtaa caaaacttttt atcgaattcc tgcagcccgg gggatccact  1140
agttctagag ggacagcccc ccccaaagc cccagggat gtaattacgt ccctccccgg   1200
ctaggggca gcagcgagcc gccgggggct ccgctccggt ccggcgctcc cccgcatcc   1260
ccgagccggc agcgtgcggg gacagcccgg gcacggggaa ggtggcacgg gatcgctttc   1320
ctctgaacgc ttctcgctgc tcttgagcc tgcagacacc tgggggata cggggaaaag  1380
gcctccaagg ccagcttccc acaataagtt gggtgaattt tggctcattc ctcctttcta  1440
taggattgag gtcagagctt tgtgatggga attctgtgga atgtgtgtca gttagggtgt  1500
ggaaagtccc gcgatcgcta gcttaagcgc tgatcaattg gcgcgccgaa ttcgttatct  1560
gcagaattcg gcttggcctc cgcgccgggt tttggcgcct cccgcgggcg ccccccctcct  1620
cacggcgagc gctgccacgt cagacgaagg gcgcagcgag cgtcctgatc cttccgcccg  1680
gacgctcagg acagcggccc gctgctcata agactcggcc ttagaacccc agtatcagca  1740
gaaggacatt ttaggacggg acttgggtga ctctagggca ctggttttct ttccagagag  1800
cggaacaggc gaggaaaagt agtcccttct cggcgattct gcggagggat ctccgtgggg  1860
cggtgaacgc cgatgattat ataaggacgc gccggtccct atcagtgata gagatctccc  1920
tatcagtgat agagagtgtg gcacagctag ttccgtcgca gccgggattt gggtcgcggt  1980
tcttgtttgt ggatcgctgt gatcgtcact tgacgaacgc gcagccgcca tgccggggtt  2040
ttacgagatt gtgattaagg tccccagcga ccttgacgag catctgcccg gcatttctga  2100
cagctttgtg aactgggtgg ccgagaagga atgggagttg ccgccagatt ctgacatgga  2160
tctgaatctg attgagcagg cacccctgac cgtggccgag aagctgcagc gcgactttct  2220
gacggaatgc cgccgtgtga gtaaggcccc ggaggctctt ttctttgtgc aatttgagaa  2280
gggagagagc tacttccaca tgcacgtgct cgtggaaacc accggggtga atccatggat  2340
tttgggacgt ttcctgagtc agattcgcga aaaactgatt cagagaattt accgcgggat  2400
cgagccgact ttgccaaact ggttcgcggt cacaaagacc agaaatgcgc cggaggcgg  2460
gaacaaggtg gtggatgagt gctacatccc caattacttg ctccccaaaa cccagcctga  2520
gctccaatgg gcatggacca acatggaaca gtacctcagc gcctgtttga atctcacgga  2580
gcgtaacgga ttggtggcgc agcatctgac gcacgtgtcg cagacgcagg agcagaacaa  2640
agagaatcag aatcccaatt ctgatgcgcc ggtgatcaga tcaaaaactt cagccaggta  2700
catggagctg tcgggtggc tcgtggacaa gggggattac tcggagagc agtggatcca  2760
ggaggaccag gcctcataca tctccttcaa tgcggcctcc aactcgcggt cccaaatcaa  2820
ggctgccttg gacaatgcgg gaaagattat gagcctgact aaaaccgccc ccgactacct  2880
ggtgggccag cagcccgtgg aggacatttc cagcaatcgg atttataaaa ttttggaact  2940
aaacgggtac gatccccaat atgcggcttc cgtctttctg ggatgggcca cgaaaaagtt  3000
cggcaagagg aacaccatct ggctgtttgg gcctgcaact accggaaga ccaacatcgc  3060
ggaggccata gcccacactg tgcccttcta cgggtgcgta aactgaccca atgagaactt  3120
tccccttcaac gactgtgtcg acaagatggt gatctggtgg gaggagggga agatgaccgc  3180
caaggtcgtg agtcggcca aagcattct cggaggaagc aaggtgcgcg tggaccagaa  3240
atgcaagtcc tcgggcccaga tagacccgac tcccgtgatc gtcacctcca acaccaacat  3300
gtgcgccgtg attgacggga actcaacgac cttcgaacac cagcagccgt gcaagaccgg  3360
gatgttcaaa ttgaactca cccgccgtct ggatcatgac tttgggaagg tcaccaagca  3420
ggaagtcaaa gactttttcc ggtgggcaaa ggatcacgtg gttgaggtgg agcatgaatt  3480
ctacgtcaaa aaggggtggag ccaagaaaag acccgccccc agtgacgcag atataagtga  3540
```

```
gcccaaacgg gtgcgcgagt cagttgcgca gccatcgacg tcagacgcgg aagcttcgat  3600
caactacgca gacaggtacc aaaacaaatg ttctcgtcac gtgggcatga atctgatgct  3660
gtttccctgc agacaatgcg agagaatgaa tcagaattca aatatctgct tcactcacgg  3720
acagaaagac tgtttagagt gctttcccgt gtcagaatct caacccgttt ctgtcgtcaa  3780
aaaggcgtat cagaaactgt gctacattca tcatatcatg ggaaaggtgc cagacgcttg  3840
cactgcctgc gatctggtca atgtggattt ggatgactgc atctttgaac aataaaatgg  3900
ctaggatccg gccggcctgc aggtgtcctc acaggaacga agtccctaaa gaaacagtgg  3960
cagccaggtt tagccccgga aaacttgttt attgcagctt ataatggtta caaataaagc  4020
aatagcatca caaatttcac aaataaagca ttttttttcac tgcattctag ttgtggtttg  4080
tccaaactca tcaatgtatc ttattgactg gattgaggga cagcccccc ccaaagcccc  4140
cagggatgta attacgtccc tccccgcta gggggcagca gcgagccgcc cggggctccg  4200
ctccggtccg gcgctccccc cgcatcccg agcggcagc gtgcggggac agcccgggca  4260
cggggaaggt ggcacgggat cgctttcctc tgaacgcttc tcgctgctct ttgagcctgc  4320
agacacctgg ggggatacgg ggaaaaggcc tccaaggcca gcttcccaca ataagttggg  4380
tgaattttgg ctcattcctc ctttctatag gattgaggtc agagcgcgtt acataactta  4440
cggtaaatgg cccgcctggc tgaccgccca acgaccccg cccattgacg tcaatatga  4500
cgtatgttcc catagtaacg ccaataggga cttttccattg acgtcaatgg gtggagtatt  4560
tacggtaaac tgcccacttg gcagtacatc aagtgtatca tatgccaagt acgccccta  4620
ttgacgtcaa tgacggtaaa tggcccgcct ggcattatgc ccagtacatg accttatggg  4680
actttcctac ttggcagtac atctacgtat tagtcatcgc tattaccatg gtcgaggtga  4740
gccccacgtt ctgcttcact ctccccatct ccccccctc cccaccccca attttgtatt  4800
tatttatttt ttaattattt tgtgcagcga tgggggcggg gaggggggg gggcgcgcgc  4860
caggcggggc ggggcgggc gaggggcggg gcggggcgag gcggagaggt gcggcggcag  4920
ccaatcagag cggcgcgctc cgaaagtttc cttttatggc gaggcggcgg cggcggcggc  4980
cctataaaaa gcgaagcgtc cctatcagtg atagagatct ccctatcagt gatagagacg  5040
cggcggggcgg gagtcgctgc gttgccttcg ccccgtgcc cgctccgcgc cgcctcgcgc  5100
cgcccgcccc ggctctgact gaccgcgtta ctcccacaga tcccaattct gatgcgccgg  5160
tgatcagatc aaaaacttca gccaggtacg ccaccatgga actggtcgga tggctggtgg  5220
ataagggcat cacaagcgag aagcaatgga tccaggagga ccaggcctca tatatttctt  5280
ttaacgccgc tagcaattcc agaagccaga tcaaggctgc tctggacaac gccggcaaaa  5340
tcatgagcct gaccaagacc gcccctgact acctggtggg acagcagcct gtggaagata  5400
tcagcagcaa cagaatctat aagatcctgg aactgaacgg ctacgacccc cagtacgccg  5460
cctccgtgtt cctgggctgg gctacaaaga agttcggcaa gcggaacacc atctggctgt  5520
tcggacctgc caccacaggc aaaaccaata tcgccgaggc catcgcccac accgtgcctt  5580
tctacggctg cgtgaactgg acaaacgaga acttcccctt caacgactgt gtggacaaga  5640
tggtgatctg gtgggaggaa ggcaaaatga cagctaaggt ggtggaatct gccaaggcta  5700
tcctgggagg ctctaaggtc agggtggatc agaagtgtaa aagcagcgcc cagattgacc  5760
ctaccctgt gatcgtgacc agcaataccc acatgtgcgc cgtgatcgac ggcaacagca  5820
ccaccttcga gcatcagcag cctctgcagg accggatgtt caagtttgag ctcaccagac  5880
ggctggatca cgacttcggc aaggtgacca agcaggaggt gaaggatttc ttcagatggg  5940
ccaaagacca cgttgttgag gtggaacacg agttctacgt gaagaagggc ggcgccaaga  6000
aaagaccccgc ccctagcgac gccgacatca gcgagcctaa gagagtgcgg gaaagcgtgg  6060
cccagcccag cacatctgat gctgaggcca gcatcaacta cgccgataga taccaaaaca  6120
agtgcagccg ccacgtgggc atgaacctga tgctgttttcc ctgcagacag tgtgaaagaa  6180
tgaaccagaa ttctaatatc tgctttacac acggccagaa agattgcctg gaatgcttcc  6240
ctgtgtccga gagccaacca gtgtctgtgg tgaaaaaggc ctaccagaag ctgtgctaca  6300
tccaccacat catgggcaag gtgccagacg cctgtaccgc ctgcgacctg gtcaacgtgg  6360
acctggacga ctgcatcttc gagcagtgat ttgtgatggg aattctgtgc tgtgccttct  6420
agttgccagc catctgttgt ttgccccctc cccgtgcctt ccttgaccct ggaaggtgcc  6480
actcccactg tccttttccta ataaaatgag gaaattgcat cgcattgtct gagtaggtgt  6540
cattctattc tggggggtgg ggtggggcag gacagcaagg gggaggattg ggaagacaat  6600
agcaggcatg ctggggatgc ggtgggctct atgggacctt ttttagggcc cattggtatg  6660
gcttttttccc cgtatccccc caggtgtctg caggctcaaa gagcagcgag aagcgttcag  6720
aggaaagcga tcccgtgcca ccttcccgt gcccgggctg tccccgcacg ctgccggctc  6780
ggggatgcgg ggggagcgcc ggaccgagc ggagccccgg gggctcgct gctgccccct  6840
agcggggagg ggacgtaatt acatccctgg gggctttggg gggggctgt ccctctagag  6900
cggccgccac cgcggtggag ctccagcttt tgttcccttt agtgagggtt aattagatct  6960
taatacgact cactataggg cgaattgggt accgggcccc cctgaggcgg aaagaaccag  7020
ctggggctct aggggtatc cccggggttg gggttgcgc ttttccaagg cagccctggg  7080
tttgcgcagg gacgcggctg ctctgcggcgt ggttccggga aacgcagcgg cgccgacccc  7140
gggtctcgca cattcttcac gtccgttcgc agcgtcaccc ggatcttcgc cgctaccctt  7200
gtgggccccc cggcgacgct tcctgctccg cccctaagtc gggaaggttc cttgcggttc  7260
gcggcgtgcc ggacgtgaca aacggaagcc gcacgtctca ctagtaccct cgcagacgga  7320
cagcgccagg gagcaatggc agcgcgccga ccgcgatggc ctgtggccaa tagcgcctgc  7380
tcagcagggc gcgccgagag cagcggccgg aaggggcgc tgcggaggc ggggtgtggg  7440
gcggtagtgt gggccctgtt cctgcccgcg cggtgttccg cattctgcaa gcctccggag  7500
cgcacgtcgg cagtcggctc cctcgttgac cgaatcaccg acctctctcc ccagaagctc  7560
ccgggagctt gtatatccat tttcggatct gatcagcacg tgttgacaat taatcatcgg  7620
catagtatat cggcatagta taatacgaca aggtgaggaa cgccaccatg gccaagcctt  7680
tgtctcaaga agaatccacc ctcattgaaa gagcaacggc tacaatcaac agcatcccca  7740
tctctgaaga ctacagcgtc gccagcgcag ctctctctag cgacgccgc atcttcactg  7800
gtgtcaatgt atatcatttt actggggggac cttgtgcaga actcgtggtg ctgggcactg  7860
ctgctgctgc ggcagctggc aacctgactt gtatcgtcgc gatcggaaat gagaacaggg  7920
gcatcttgag ccctgcggga cggtgccgac aggtgctct cgatctgcat cctgggatca  7980
aagccatagt gaaggacagt gatgacagc cgacggcagt tgggattcgt gaattgctgc  8040
cctctggtta tgtgtgggag ggctaaagcg cggggatctc atgctggagt tcttcgccca  8100
ccccaacttg tttattgcag cttataatgg ttacaaataa agcaatagca tcacaaattt  8160
cacaaataaa gcatttttttt cactgcattc tagttgtggt ttgtccaaac tcatcaatgt  8220
atcttatcat gtctgtagct gatgtatacc taggatccgg ccggcctgca ggtgtcctca  8280
```

```
caggaacgaa gtccctaaag aaacagtggc agccaggttt agccccgaa ttgactggat    8340
tccttttta gggcccattg gtatggcttt ttccccgtat ccccccaggt gtctgcaggc    8400
tcaaagagca gcgagaagcg ttcagaggaa agcgatcccg tgccaccttc cccgtgcccg    8460
ggctgtcccc gcacgctgcc ggctcgggga tgcggggga gcgccggacc ggagcggagc    8520
cccggccggc tcgctgctgc ccctagcgg gggagggacg taattacatc cctggggct    8580
ttgggggggg gctgtccctc tagagcggcc gccaccgcgg tggagctcca gcttttgttc    8640
ccttagtga gggttaatta gatcttaata cgactcacta tagggcgaat gggtaccgg    8700
gcccccctc gaggtcgacg gtatcctcga ggtcgacggt atcgataagc ttgatatcta    8760
taacaagaaa atatatat aataagttat cacgtaagta gaacatgaaa taacaatata    8820
attatcgtat gagttaaatc ttaaaagtca cgtaaaagat aatcatgcgt cattttgact    8880
cacgcggtcg ttatagttca aaatcagtga cacttaccgc attgacaagc acgcctcacg    8940
ggagctccaa gcggcgactg agatgtccta aatgcacagc gacggattcg cgctatttag    9000
aaagagagag caatatttca agaatgcatg cgtcaatttt acgcagacta tctttctagg    9060
gttaatcag ctgcatcagg atcatatcgt cgggtctttt ttccggctca gtcatcgccc    9120
aagctggcgc tatctgggca tcggggagga agaagcccgt gccttttccc gcgaggttga    9180
agcggcatgg aaagagtttg ccgaggatga ctgctgctgc attgacgttg agcgaaaacg    9240
cacgtttacc atgatgattc gggaaggtgt ggccatgcac gcctttaacg tgaactgtt    9300
cgttcaggcc acctgggata ccagttcgtc gcggcttttc cggacacagt tccggatggt    9360
cagcccgaag cgcatcagca accccgaacaa taccggcgca agccggaact gccgtgccgg    9420
tgtgcagatt aatgacagcg gtgcggcgct gggatattac gtcagcgagg acgggtatcc    9480
tggctggatg ccgcagaaat ggacatggat accccgtgag ttaccggcg ggcgcgcttg    9540
gcgtaatcat ggtcatagct gtttcctgtg tgaaattgt atccgctcac aattccacac    9600
aacatacgag ccggaagcat aaagtgtaaa gcctggggtg cctaatgagt gagctaactc    9660
acattaattg cgttgcgctc actgcccgct ttccagtcgg gaaacctgtc gtgccagctg    9720
cattaatgaa tcggccaacg cgcggggaga ggcggtttgc gtattgggcg ctcttccgct    9780
tcctcgctca ctgactcgct gcgctcggtc gttcggctgc ggcgagcggt atcagctcac    9840
tcaaaggcgg taatacggtt atccacagaa tcaggggata acgcaggaaa gaacatgtga    9900
gcaaaaggcc agcaaaaggc caggaaccgt aaaaaggccg cgttgctggc gtttttccat    9960
aggctccgcc ccctgacga gcatcacaaa aatcgacgct caagtcagag gtggcgaaac   10020
ccgacaggac tataaagata ccaggcgttt ccccctgag gctccctcgt gcgctctcct   10080
gttccgaccc tgccgcttac cggatacctg tccgcctttc tcccttcggg aagcgtggcg   10140
ctttctcata gctcacgctg taggtatctc agttcggtgt aggtcgttcg ctccaagctg   10200
ggctgtgtgc acgaacccc cgttcagccc gaccgctgcg ccttatccgg taactatcgt   10260
cttgagtcca acccggtaag acacgactta tcgccactgg cagcagccac tggtaacagg   10320
attagcagag cgaggtatgt aggcggtgct acagagttct tgaagtggtg gcctaactac   10380
ggctacacta aggacagt atttggtatc tgcgctctgc tgaagccagt taccttcgga   10440
aaaagagttg gtagctcttg atccggcaaa caaaccaccg ctggtagcgg tggttttttt   10500
gtttgcaagc agcagattac gcgcagaaaa aaggatctc aagaagatcc tttgatcttt   10560
tctacgggt ctgacgctca gtggaacgaa aactcacgtt aagggatttt ggtcatgaga   10620
ttatcaaaaa ggatcttcac ctagatcctt taaattaaa aatgaagttt taaatcaatc   10680
taaagtatat atgagtaaac ttggtctgac agttaccaat gcttaatcag tgaggcacct   10740
atctcagcga tctgtctatt tcgttcatcc atagttgcct gactccccgt cgtgtagata   10800
actacgatac gggagggctt accatctggc cccagtgctg caatgatacc gcgagaccca   10860
cgctcaccgg ctccagattt atcagcaata aaccagccag ccggaaggg cgagcgcaga   10920
agtggtcctg caactttatc cgcctccatc cagtctatta attgttgccg ggaagctaga   10980
gtaagtagtt cgccagttaa tagtttgcgc aacgttgttg ccattgctac aggcatcgtg   11040
gtgtcacgct cgtcgtttgg tatggcttca ttcagctccg gttcccaacg atcaaggcga   11100
gttacatgat ccccccatgtt gtgcaaaaaa gcggttagct ccttcggtcc tccgatcgtt   11160
gtcagaagta agttggccgc agtgttatca ctcatggtta tggcagcact gcataattct   11220
cttactgtca tgccatccgt aagatgcttt tctgtgactg gtgagtactc aaccaagtca   11280
ttctgagaat agtgtatgcg gcgaccgagt tgctcttgcc cggcgtcaat acgggataat   11340
accgcgccac atagcagaac tttaaaagtg ctcatcattg gaaaacgttc ttcggggcga   11400
aaactctcaa ggatcttacc gctgttgaga tccagttcga tgtaacccac tcgtgcaccc   11460
aactgatctt cagcatcttt tactttcacc agcgtttctg ggtgagcaaa aacaggaagg   11520
caaaatgccg caaaaaggg aataagggcg acacggaaat gttgaatact cat           11573

SEQ ID NO: 28         moltype = DNA   length = 11695
FEATURE               Location/Qualifiers
misc_feature          1..11695
                      note = Synthetic: PB-hiRep-15#
source                1..11695
                      mol_type = other DNA
                      organism = synthetic construct
SEQUENCE: 28
actcttcctt tttcaatatt attgaagcat ttatcagggt tattgtctca tgagcggata     60
catatttgaa tgtatttaga aaaataaaca aatagggggtt ccgcgcacat ttccccgaaa    120
agtgccacct aaattgtaag cgttaatatt ttgttaaaat tcgcgttaaa ttttttgttaa    180
atcagctcat tttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt ttttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cccgcacggc gcttaatgcg ccgctacacg ttcgccattc                600
aggctgcgca actgttggga agggcgatcg gtgcgggcct cttcgctatt acgccagctg    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taaccctaga aagataatca tattgtgacg    900
```

```
tacgttaaag ataatcatgc gtaaaattga cgcatgtgtt ttatcggtct gtatatcgag   960
gtttatttat taatttgaat agatattaag ttttattata tttacactta catactaata  1020
ataaattcaa caaacaattt atttatgttt atttattttat taaaaaaaaa caaaaactca  1080
aaatttcttc tataaagtaa caaaactttt atcgaattcc tgcagcccgg gggatccact  1140
agttctagag ggacagcccc cccccaaagc ccccaggagt gtaattacgt ccctcccccg  1200
ctaggggggca gcagcgagcc gcccgggggct ccgctccggt ccggcgctcc ccccgcatcc  1260
ccgagccggc agcgtgcggg gacagcccgg gcacggggaa ggtggcacgg gatcgctttc  1320
ctctgaacgt ttctcgctgc tctttgagcc tgcagacacc tggggggata cggggaaaag  1380
gcctccaagg ccagcttccc acaataagtt gggtgaattt tggctcattc ctcctttcta  1440
taggattgag gtcagagctt tgtgatggga attctgtgga atgtgtgtca gttagggtgt  1500
ggaaagtccc gcgatcgcta gcttaagcgc tgatcaattg gcgcgccgaa ttcgttatct  1560
gcagaattcg gcttctgctc cctgcttgtg tgttggaggt cgctgagtag tgcgcgagca  1620
aaatttaagc tacaacaagg caaggcttga ccgacaattg catgaagaat ctgcttaggg  1680
ttaggcgttt tgcgctgctt cgcgatgtac gggcagata tacgcgtatc tgagggggact  1740
agggtgtgtt taggcgaaaa gcggggcttc ggttgtacgc ggttaggagt cccctcagga  1800
tatagtagtt tcgcttttgc ataggggaggg ggaaatgtag tcttatgcaa tacacttgta  1860
gtcttgcaac atggtaacga tgagttagca acatgccttta caaggagaga aaaagcaccg  1920
tgcatgccga ttggtgggaag taaggtggta cgatcgtgcc ttattaggaa ggcaacagac  1980
aggtctgaca tggattggac gaaccactga attccgcatt gcagagataa ttgtatttaa  2040
gtgcctagct ccctatcagt gatagagatc tccctatcag tgatagagat cgatacaata  2100
aacgccattt gaccattcac cacattggtg tgcaccgaac gcgcagccgc catgccgggg  2160
ttttacgaga ttgtgattaa ggtccccagc gaccttgacg agcatctgcc cggcatttct  2220
gacagctttg tgaactgggt ggccgagaag gaatgggagt tgccgccaga ttctgacatg  2280
gatctgaatc tgattgagca ggcacccctg accgtggccg agaagctgca gcgcgacttt  2340
ctgacgaat ggcgccgtgt gagtaaggcc ccggaggctc ttttctttgt gcaatttgag  2400
aagggagaga gctacttcca catgcacgtg ctcgtgaaca ccaccgggat gaaatccatg  2460
gttttgggac gtttcctgag tcagattcgc gaaaaactga ttcagagaat ttaccgcggg  2520
atcgagccga ctttgccaaa ctggttcgcg gtcacaaaga ccagaaatgg cgccggaggc  2580
gggaacaagg tggtggatga gtgctacatc cccaattact tgctcccaa aacccagcct  2640
gagctccaat gggcatggac caacatgaa cagtacctca ggcctgttt gaatctcacg  2700
gagcgtaaac ggttggtggc gcagcatctg acgcacgtgt cgcagacgca ggagcagaac  2760
aaagagaatc agaatcccaa ttctgatgcg ccggtgatca gatcaaaaac ttcagccagg  2820
tacatggagc tggtcgggtg gctcgtggac aaggggatta cctcggagaa gcagtggatc  2880
caggaggacc aggcctcata catctccttc aatgcggcct ccaactcgcg gtcccaaatc  2940
aaggctgcct tggacaatgc gggaaagatt atgagcctga ctaaaaccgc ccccgactac  3000
ctggtgggcc agcagcccgt ggaggacatt tccagcaatc ggatttataa aatttttggaa  3060
ctaaacgggt acgatcccca atatgcgget tccgtctttc tgggatgggc cacgaaaaag  3120
ttcggcaaga ggaacaccat ctggctgttt gggcctgcaa ctaccgggaa gaccaacatc  3180
gcggaggcca tagcccacac tgtgcccttc tacgggtacg taaactgaca caatgagaac  3240
tttcccttca acgactgtgt cgacaagatg gtgatctggt gggaggaggg gaagatgacc  3300
gccaaggtcg tggagtcggc caaagccatt ctcggaggaa gcaaggtgcg cgtgaccag  3360
aaatgcaagt cctcggccca gatagacccg actcccgtga tcgtcacctc caacaccaac  3420
atgtgccgg tgattgacgg gaactcaacg accttcgaac accgtgcaggac gttgcaagac  3480
cggatgttca aatttgaact cacccgcgct ctggatcatg actttgggaa ggtcaccaag  3540
caggaagtca aagactttt ccggtgggca aaggatcacg tggttgaggt ggagcatgaa  3600
ttctacgtca aaaagggtgg agccaagaaa agacccgccc ccagtgacgc agatataagt  3660
gagcccaaac gggtgcgcga gtcagttgcg cagccatcga cgtcagacgc ggaagcttcg  3720
atcaactacg cagacaggta ccaaaacaaa tgttctcgtc acgtgggcat gaatctgatg  3780
ctgtttccct gcagacaatg cgagagaatg aatcagaatt caaatatctg cttcactcac  3840
ggacagaaag actgtttaga gtgctttccc gtgtcagaat ctcaaccgt ttctgtcgtc  3900
aaaaggcgt atcagaaact gtgctacatt catcatatca tgggaaaggt gccagacgtn  3960
tgcactgcct gcgatctggt caatgtggat ttggatgact gcatctttga caataaaat  4020
ggctaggatc cggccggcct gcaggtgtcc tcacaggaac gaagtcccta agaaacagt  4080
ggcagccagg tttagccccg gaaaacttgt ttattgcagc ttataatggt tacaaataaa  4140
gcaatagcat cacaaatttc acaaataaag cattttttc actgcattct agttgtggtt  4200
tgtccaaact catcaatgta tcttattgac tggattgagg acagccccc cccccaaagcc  4260
cccagggatg taattacgtc cctccccgc taggggcag cagcgagccg cccggggctc  4320
cgctccggtc cggcgctccc cccgcatccc cgagccggca gcgtgcgggg acagcccggg  4380
cacggggaag gtggcacggg atcgctttcc tctgaacgct tctcgctgct ctttgagcct  4440
gcagacacct gggggatac ggggaaaagg cctccaagg cagcttccca caataagttg  4500
ggtgaatttt ggctcattcc tcctttctat aggattgagg tcagagcgcg ttacataact  4560
tacggtaaat ggcccgcctg gctgaccgcc caacgacccc gcccattga cgtcaataat  4620
gacgtatgtt cccatagtaa cgccaatagg gactttccat tgacgtcaat gggtggagta  4680
tttacgtaa actgcccact tggcagtaca tcaagtgtat catatgccaa gtacgccccc  4740
tattgacgtc aatgacggta aatggcccgc ctggcattat gcccagtaca tgaccttatg  4800
ggactttcct acttggcagt acatctacgt attagtcatc gctattacca tggtcgaggt  4860
gagccccacg ttctgcttca ctctccccat ctccccccc tccccacccc caatttttgta  4920
tttatttatt ttttaattat tttgtgcagc gatggggggc ggggggggg ggggcgcgc  4980
gccaggcggg gcggggcggg gcgaggggcg ggggcgggg aggcggagag gtgcggcggc  5040
agccaatcag agcggcgcgc tccgaaagtt tccttttatg gcgaggcggc ggcggcggc  5100
gccctataaa aagcgaagcg tccctatcag tgatagagat ctccctatca gtgatagaga  5160
cgcggcgggc gggagtcgct gcgttgcctt cgccccgtgc cccgctccgc gccgcctcgc  5220
gccgcccgcc ccggctctga ctgaccgcgt tactcccaca gatcccaatt ctgatgcgcc  5280
gtcagaca tcaaaaactt cagccaggta cgccaccatg gatggctggt  5340
ggataagggc atcacaagcg agaagcaatg gatcaggag gaccaggcct catatatttc  5400
ttttaacgcc gctagcaatt ccagaagcca gatcaaggct gctctggaca acgcggcaa  5460
aatcatgagc ctgaccaaga ccgccctga ctacctggtg gacagcagc ctgtggaaga  5520
tatcagcagc aacagaatct ataagatcct ggaactgaac ggctacgacc ccagtacgcg  5580
cgcctccgtg ttcctgggct gggctacaaa gaagttcggc aagcggaaca ccatctggct  5640
```

```
gttcggacct gccaccacag gcaaaaccaa tatcgccgag gccatcgccc acaccgtgcc    5700
tttctacggc tgcgtgaact ggacaaacga gaacttcccc ttcaacgact gtgtggacaa    5760
gatggtgatc tggtgggagg aaggcaaaat gacagctaag gtggtggaat ctgccaaggc    5820
tatcctggga ggctctaagg tcagggtgga tcagaagtgt aaaagcagcg cccagattga    5880
ccctacccct gtgatcgtga ccagcaatac caacatgtgc gcctgcgatc acggcaacag    5940
caccaccttc gagcatcagc agcctctgca ggaccggatg ttcaagtttg agctcaccag    6000
acggctggat cacgacttcg gcaaggtgac caagcaggag gtgaaggatt tcttcagatg    6060
ggccaaagac cacgttgttg aggtggaaca cgagttctac gtgaagaagg gcggcgccaa    6120
gaaaagaccc gccccctagcg acgccgacat cagcgagcct aagagagtgc gggaaagcgt    6180
ggcccagccc agcacatctg atgctgagcc cagcatcaac tacgccgata gataccaaaa    6240
caagtgcagc cgccacgtgg gcatgaacct gatgctgttt ccctgcagac agtgtgaaag    6300
aatgaaccag aattctaata tctgctttac acacggccag aaagattgcc tggaatgctt    6360
ccctgtgtcc gagagccaac cagtgtctgt ggtgaaaaag gccaccagaa agctgtgcta    6420
catccaccac atcatgggca aggtgccaga cgcctgtacc gcctgcgacc tggtcaacgt    6480
ggacctggac gactgcatct tcgagcagtg atttgtgatg gaattctgt gctgtgcctt     6540
ctagttgcca gccatctgtt gttttgccct ccccgtgcc ttccttgacc ctggaaggtg      6600
ccactcccac tgtcctttcc taataaaatg aggaaattgc atcgcattgt ctgagtaggt    6660
gtcattctat tctggggggt ggggtgggggc aggacagaag tgggaagaca                6720
atagcaggca tgctggggat gcggtgggct ctatgggacc ttttttaggg cccattggta    6780
tggcttttc cccgtatccc cccaggtgtc tgcaggctca aagagcagcg agaagcgttc    6840
agaggaaagc gatcccgtgc caccttcccc gtgcccgggc tgtccccgca cgctgccggc    6900
tcggggatgc gggggagcg ccggaccgga gcggagcccc ggcggctcg ctgctgccg        6960
ctagcggggg agggacgtaa ttacatcct gggggctttg ggggggggct gtccctctag     7020
agcggccgcc accgcgtgg agctccagct tttgttccct ttagtgaggg ttaattagat    7080
cttaatacga ctcactatag ggcgaattgg gtaccgggcc ccctgaggc ggaaagaacc      7140
agctgggct ctaggggta tccccggggt tggggttgga ccttttcaa ggcagccgtg       7200
ggtttgcgca gggacgcggc tgctctgggc gtggttccgg gaaacgcagc ggcgccgacc    7260
ctgggtctcg cacattcttc acgtccgttc gcagcgtcac ccggatcttc gccgctaccc    7320
ttgtgggccc cccggcgacg cttcctgctc cgccctaag tcgggaaggt tccttgcggt     7380
tcgccgcgtg ccggacgtga caaacggaag ccgcacgtct cactagtacc tcgcagacg    7440
gacagcgcca gggagcaatg gcagcgcgcc gaccgcgatg ggctgtggcc aatagcggct    7500
gctcagcagg gcgcgccgag agcagcggcc gggaagggc ggtgcgggag gcggggtgtg    7560
gggcggtagt gtgggccctg ttcctgcccg gcgcgtgttc cgcattctgc aagcctccgg    7620
agcgcacgtc ggcagtcggc tccctcgttg accgaatcac cgacctctct ccccagaagc    7680
tcccgggagc ttgtatatcc atttttcggat ctgatcagca cgtgttgaca attaatcatc   7740
ggcatagtat atcggcatag tataatacga caagtgagg aacgccacca tggccaagcc    7800
tttgtctcaa gaagaatcca ccctcattga aagagcaacg gctacaatca acagcatccc    7860
catctctgaa gactacagcg tcgccagcgc agctctctct agcgacggcc gcatcttcac    7920
tggtgtcaat gtatatcatt ttactggggg accttgtgca gaactcgtgg tgctgggcac    7980
tgctgctgct gcggcagctg gcaacctgac ttgtatcgtc gcgatcggaa atgagaacag    8040
gggcatcttg agccctgcg gacggtgccg acaggtgctt ctcgatctgc atcctgggat    8100
caaagccata gtgaaggaca gtgatggaca gccgacggca gttgggattc gtgaattgct    8160
gccctctgtg tatgtgtggg agggctaaag cgcggggatc tcatgctgga gttcttcgcc    8220
cacccaact tgtttattgc agcttataat ggttacaaat aaagcaatag catcacaaat    8280
ttcacaaata aagcattttt ttcactgcat tctagttgtg gtttgtccaa actcatcaat    8340
gtatcttatc atgtctgtag ctgatgtata cctaggatcc ggccggctg caggtgtcct    8400
cacaggaacg aagtccctaa agaaacagtg gcagccaggt ttagccccgg aattgactgg    8460
attccttttt tagggcccat tggtatggct ttttccccgt atcccccag gtgtctgcag     8520
gctcaaagag cagcgagaag cgttcagagg aaagcgatcc cgtgccacct tccccgtgcc    8580
cgggctgtcc ccgcacgctg ccggctcggg gatgcggggg agcgccgga ccggagcgga     8640
gccccggcg gctcgctgct gccccctagc ggggagggga cgtaattaca tccctggggg    8700
cttgggggg gggctgtccc tctagagcgg ccgccaccgc ggtggagctc cagcttttgt    8760
tcccttagt gagggttaat tagatcttaa tacgactcac tataggggcga attgggtacc   8820
gggccccccc tcgaggtcga cggtatcctc gaggtcgacg gtatcgataa gcttgatatc   8880
tataacaaga aaatatatat ataataagtt atcacgtaag tagaacatga aataacaata    8940
taattatcgt atgagttaaa tcttaaaagt cacgtaaaag ataatcatgc gtcattttga    9000
ctcacgcggt cgttatagtt caaaatcagt gacacttacc gcattgacaa gcacgcctca    9060
cgggagctcc aagcggcgac tgagatgtcc taaatgcaca gcgacggatt cgcgctattt    9120
agaaagagag agcaatattt caagaatgca tgcgtcaatt ttacgcagac tatcttcta    9180
gggttaatct agctgcatca ggatcatatc gtcgggtctt ttttccggct cagtcatcgc    9240
ccaagctggc gctatctggg catcggggag aagaagccc gtgccttttc ccgcgaggtt    9300
gaagcggcat ggaaagagtt tgccgaggat gactgctgct gcattgacgt tgagcgaaaa    9360
cgcacgttta ccatgatgat tcgggaaggt gtggccatgc acgcctttaa cggtgaactg    9420
ttcgttcagg ccacctggga taccagttcg tcgcggcttt tccggacaca gttccgatcg    9480
gtcagcccga agcgcatcag caacccgaac aataccggcg acagccggaa ctgccgtgcc    9540
ggtgtgcaga ttaatgacag cggtgcggcg ctgggatatt acgtcagcga ggacgggtat    9600
cctgctggga tgccgcagaa atggacatgg ataccccgtg agttaccgg cgggcgcgct     9660
tggcgtaatc atggtcatag ctgtttcctg tgtgaaattg ttatccgctc acaattccca    9720
acaacatacg agccggaagc ataaagtgta aagcctgggg tgcctaatga gtgagctaac    9780
tcacattaat tgcgttgcgc tcactgcccg ctttccagtc gggaaacctg tcgtgccagc    9840
tgcattaatg aatcggccaa cgcgcgggga gaggcggttt gcgtattggg cgctcttccg    9900
cttcctcgct cactgactcg ctgcgctcgg tcgttcggct gcggcgagcg gtatcagctc    9960
actcaaaggc ggtaatacgg ttatccacag aatcaggggga taacgcagga agaacatgt   10020
gagcaaaagg ccagcaaaag gccaggaacc gtaaaaaggc cgcgttgctg gcgtttttcc   10080
ataggctccg ccccccctgac gagcatcaca aaaatcgacg ctcaagtcag gtggcgaa    10140
acccgacagg actataaaga taccaggcgt ttccccctgg aagctccctc gtgcgctctc   10200
ctgttccgac cctgccgctt accggatacc tgtccgcctt tctcccttcg ggaagcgtgg   10260
cgctttctca tagctcacgc tgtaggtatc tcagttcggt gtaggtcgtt cgctccaagc   10320
tgggctgtgt gcacgaaccc cccgttcagc ccgaccgctg cgccttatcc ggtaactatc   10380
```

```
gtcttgagtc caacccggta agacacgact tatcgccact ggcagcagcc actggtaaca   10440
ggattagcag agcgaggtat gtaggcggtg ctacagagtt cttgaagtgg tggcctaact   10500
acggctacac tagaaggaca gtatttggta tctgcgctct gctgaagcca gttaccttcg   10560
gaaaaagagt tggtagctct tgatccggca aacaaaccac cgctggtagc ggtggttttt   10620
ttgtttgcaa gcagcagatt acgcgcagaa aaaaaggatc tcaagaagat cctttgatct   10680
tttctacggg gtctgacgct cagtggaacg aaaactcacg ttaagggatt ttggtcatga   10740
gattatcaaa aaggatcttc acctagatcc ttttaaatta aaaatgaagt tttaaatcaa   10800
tctaaagtat atatgagtaa acttggtctg acagttacca atgcttaatc agtgaggcac   10860
ctatctcagc gatctgtcta tttcgttcat ccatagttgc ctgactcccc gtcgtgtaga   10920
taactacgat acgggagggc ttaccatctg gccccagtgc tgcaatgata ccgcgagacc   10980
cacgctcacc ggctccagat ttatcagcaa taaaccagcc agccgaagg gccgagcgca    11040
gaagtggtcc tgcaacttta tccgcctcca tccagtctat taattgttgc cgggaagcta   11100
gagtaagtag ttcgccagtt aatagtttgc gcaacgttgt tgccattgct acaggcatcg   11160
tggtgtcacg ctcgtcgttt ggtatggctt cattcagctc cggttcccaa cgatcaaggc   11220
gagttacatg atcccccatg ttgtgcaaaa aagcggttag ctccttcggt cctccgatcg   11280
ttgtcagaag taagttggcc gcagtgttat cactcatggt tatggcagca ctgcataatt   11340
ctcttactgt catgccatcc gtaagatgct tttctgtgac tggtgagtac tcaaccaagt   11400
cattctgaga atagtgtatg cggcgaccga gttgctcttg cccggcgtca atacgggata   11460
ataccgcgcc acatagcaga actttaaaag tgctcatcat tggaaaacgt tcttcgggc    11520
gaaaactctc aaggatctta ccgctgttga gatccagttc gatgtaaccc actcgtgcac   11580
ccaactgatc ttcagcatct tttactttca ccagcgtttc tgggtgagca aaaacaggaa   11640
ggcaaaatgc cgcaaaaaag ggaataaggg cgacacggaa atgttgaata ctcat         11695

SEQ ID NO: 29          moltype = DNA   length = 11421
FEATURE                Location/Qualifiers
misc_feature           1..11421
                       note = Synthetic: PB-hiRep-16#
source                 1..11421
                       mol_type = other DNA
                       organism = synthetic construct
SEQUENCE: 29
actcttcctt tttcaatatt attgaagcat ttatcagggt tattgtctca tgagcggata   60
catatttgaa tgtatttaga aaaataaaca aataggggtt ccgcgcacat ttccccgaaa   120
agtgccacct aaattgtaag cgttaatatt ttgttaaaat tcgcgttaaa tttttgttaa   180
atcagctcat ttttttaacca ataggccgaa atcggcaaaa tcccttataa atcaaaagaa   240
tagaccgaga tagggttgag tgttgttcca gtttggaaca agagtccact attaaagaac   300
gtggactcca acgtcaaagg gcgaaaaacc gtctatcagg gcgatggccc actacgtgaa   360
ccatcaccct aatcaagttt tttggggtcg aggtgccgta agcactaaa tcggaaccct    420
aaagggagcc cccgatttag agcttgacgg ggaaagccgg caacgtggc gagaaaggaa    480
gggaagaaag cgaaaggagc gggcgctagg gcgctggcaa gtgtagcggt cacgctgcgc   540
gtaaccacca cacccgccgc gcttaatgcg ccgctacagg gcgcgtccca ttcgccattc   600
aggctgcgca actgttggga agggcgatcg gtgcgggcct cttcgctatt acgccagctg   660
gcgaaagggg gatgtgctgc aaggcgatta agttgggtaa cgccagggtt ttcccagtca   720
cgacgttgta aaacgacggc cagtgagcgc gcctcgttca ttcacgtttt tgaacccgtg   780
gaggacgggc agactcgcgg tgcaaatgtg ttttacagcg tgatggagca gatgaagatg   840
ctcgacacgc tgcagaacac gcagctagat taaccctaga aagataatca tattgtgacg   900
tacgttaaag ataatcatgc gtaaaattga cgcatgtgtt ttatcggtct gtatatcgag   960
gtttatttat taatttgaat agatattaag ttttattata tttacactta catactaata   1020
ataaattcaa caaacaattt atttatgttt atttatttat taaaaaaaaa caaaaactca   1080
aaatttcttc tataaagtaa caaaacttt atcgaattcc tgcagcccgg gggatccact   1140
agttctagag ggacagcccc cccccaaagc cccagggat gtaattacgt ccctcccccg   1200
ctaggggca gcagcgagcc gcccgggct ccgctccggt ccggcgctcc ccccgcatcc   1260
ccgagccggc agcgtgcggg gacagcccgg gcacggggaa ggtggcacgg gatcgctttc   1320
ctctgaacgc ttctcgctgc tctttgagcc tgcagacacc tggggggata cggggaaaag   1380
gcctccaagg ccagcttccc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcttaagcgc tgatcaattg gcgcgccgaa ttcgttatct   1560
gcagaattcg gcttctgctc cctgcttgtg tgttggaggt cgctgagtag tgcgcgagca   1620
aaatttaagc tacaacaagg caaggcttga ccgacaatta catgaagaat ctgcttaggg   1680
ttaggcgttt tgcgctgctt cgcgatgtac gggccagata tacgcgtatc tgagcggact   1740
agggtgtgtt taggcgaaaa gcggggcttc ggttgtacgc ggttaggagt cccctcagga   1800
tatagtagtt tcgcttttgc ataggggaggg ggaaatgtag tcttatgcaa tacacttgta   1860
gtcttgcaac atggtaacga tgagttagca acatgcctta caaggagaga aaaagcaccg   1920
tgcatgccga ttggtggaag taaggtggta cgatcgtgcc ttattaggaa ggcaacagac   1980
aggtctgaca tggattggac gaaccactga attccgcatt gcagagataa ttgtatttaa   2040
gtgcctagct ccctatcagt gatagagatc ccctatcag tgatagagat cgatacaata   2100
aacgccattt gaccattcac cacattggtg tgcaccgaac gcgcagccgc catgccgggg   2160
ttttacgaga ttgtgattaa ggtccccagc gaccttgacg agcatctgcc cggcatttct   2220
gacagctttg tgaactgggt ggccgagaag gaatggagt tgccgccaga ttctgacatg   2280
gatctgaatc tgattgagca ggcacccctg accgtggccg agaagctgca gcgcgacttt   2340
ctgacggaat ggcgccgtgt gagtaaggcc cggaggctc ttttcttgt gcaatttgag   2400
aagggagaga gctacttcca catgcacgtg ctcgtgaaa ccaccggggt gaaatccatg   2460
gttttgggac gtttcctgag tcagattcgc gaaaaactga ttcagagaat ttaccgcggg   2520
atcgagcgca ctttgccaaa ctggttcgtg gtcacaaaga ccagaaatgg ccgggaggta   2580
gggaacaagg tggtggatga gtgctacatc cccaattact tgctcccaa acccagcct    2640
gagctccaat gggcatggac caacatgaa cagtacctca gcgcctgttt gaatctcacg   2700
gagcgtaaac ggtggtggc gcagcatctg acgcacgtgt cgcagacgca ggagcagaac   2760
aaagagaatc agaatcccaa ttctgatgcg ccggtgatca gatcaaaaac ttcagccagg   2820
tacatggagc tggtcgggtg gctcgtggac aaggggatta cctcggagaa gcagtggatc   2880
```

```
caggaggacc aggcctcata catctccttc aatgcggcct ccaactcgcg gtcccaaatc 2940
aaggctgcct tggacaatgc ggggaaagatt atgagcctga ctaaaaccgc ccccgactac 3000
ctggtgggcc agcagcccgt ggaggacatt tccagcaatc ggatttataa aattttggaa 3060
ctaaacgggt acgatcccca atatgcggct tccgtctttc tgggatgggc cacgaaaaag 3120
ttcggcaaga ggaacaccat ctggctgttt gggcctgcaa ctaccgggaa gaccaacatc 3180
gcggaggcca tagcccacac tgtgcccttc tacgggtgcg taaactggac caatgagaac 3240
tttcccttca acgactgtgt cgacaagatg gtgatctggt gggaggaggg gaagatgacc 3300
gccaaggtcg tggagtcggc caaagccatt ctcggaggaa gcaaggtgcg cgtggaccag 3360
aaatgcaagt cctcggccca gatagacccg actcccgtga tcgtcacctc caacaccaac 3420
atgtgcgccg tgattgacgg gaactcaacg accttcgaac accagcagcc gttgcaagac 3480
cggatgttca aatttgaact cacccgccgt ctggatcatg actttgggaa ggtcaccaag 3540
caggaagtca aagacttttt ccggtgggca aaggatcacg tggttgaggt ggagcatgaa 3600
ttctacgtca aaaaggggtgg agccaagaaa agacccgccc ccagtgacgc agatataagt 3660
gagcccaaac gggtgcgcga gtcagttgcg cagccatcga cgtcagacgc ggaagcttcg 3720
atcaactacg cagacaggta ccaaaacaaa tgttctcgtc acgtgggcat gaatctgatg 3780
ctgtttccct gcagacaatg cgagagaatg aatcagaatt caaatatctg cttcactcac 3840
ggacagaaag actgtttaga gtgctttccc gtgtcagaat ctcaacccgt ttctgtcgtc 3900
aaaaaggcgt atcagaaact gtgctacatt catcatatca tgggaaaggt gccagacgct 3960
tgcactgcct gcgatctggt caatgtggat ttggatgact gcatctttga acaataaaat 4020
ggctaggatc cggccggcct gcaggtgtcc tcacaggaac gaagtcccta agaaacagt 4080
ggcagccagg tttagcccccg gaaaacttgt ttattgcagc ttataatggt tacaaataaa 4140
gcaatagcat cacaaattc acaaataaag catttttttc actgcattct agttgtggtt 4200
tgtccaaact catcaatgta tcttattgac tggattgagg gacagccccc ccccaaagcc 4260
cccagggatg taattacgtc cctcccccgc taggggcag cagcgagccg cccggggctc 4320
cgctccggtc cggcgctccc cccgcatccc cgagccggca gcgtgcgggg acagcccggg 4380
cacggggaag gtggcacggg atcgcttttcc tctgaacgct tctcgctgct ctttgagcct 4440
gcagacacct ggggggatac ggggaaaagg cctccaaggc cagcttccca caataagttg 4500
ggtgaatttt ggctcattcc tccttttctat aggattgagg tcagagcggc ctccgcgccg 4560
ggttttggcg cctcccgcgg gcgcccccct cctcacggcg agcgctgcca cgtcagacga 4620
agggcgcagc gagcgtcctg atccttccgc ccggacgctc aggacagcgg cccgctgctc 4680
ataagactcg gccttagaac cccagtatca gcagaaggac attttaggac gggacttggg 4740
tgactctagg gcactggttt tcttttccaga gagcggaaca ggcgaggaaa agtagtccct 4800
tctcggcgat tctgcggagg gatctccgtg gggcggtgaa cgccgatgat tatataagga 4860
cgcgccggtc cctatcagtg atagagatct ccctatcagt gatagagagt gtggcacagc 4920
tagttccgtc gcagccggga tttgggtcgc ggttcttgtt tgtgatcgc tgtgatcgtc 4980
acttgacatc ccaattctga tgcgccggtc atcagatcaa aaacttcagc caggtacgcc 5040
accatgggaac tggtcggatg gctggtggat aagggcatca caagcgagaa gcaatggatc 5100
caggaggacc aggcctcata tatttctttt aacgccgcta gcaattccag aagccagatc 5160
aaggctgcct tggacaacgc cggcaaaatc atgagcctga ccaagaccgc ccctgactac 5220
ctggtgggac agcagcctgt ggaagatatc agcagcaaca gaatctataa gatcctggaa 5280
ctgaacggct acgaccccca gtacgccgcc tccgtgttcc tgggctgggc tacaaagaag 5340
ttcggcaagc ggaacaccat ctggctgttc ggacctgcca ccacaggcaa aaccaatatc 5400
gccgaggcca tcgcccacac cgtgccttc tacggctgg tgaactggac aaacgagaac 5460
ttcccccttca acgactgtgt ggacaagatg gtgatctggt gggaggaagg caaaatgaca 5520
gctaaggtgg tggaatctgc caaggctatc ctgggaggct ctaaggtcag ggtggatcag 5580
aagtgtaaaa gcagcgccca gattgaccct accctgtga tcgtgaccag caataccaac 5640
atgtgcgccg tgatcgacgg caacagcacc accttcgagc atcagcagcc tctgcaggac 5700
cggatgttca gtttgagct caccagacgg ctggatcacg acttcggcaa ggtgaccaag 5760
caggaggtga aggatttctt cagatgggcc aaagaccacg ttgttgaggt ggaacacgag 5820
ttctacgtga agaagggcgg cgccaagaaa agacccgccc ctagcgacgc cgacatcagc 5880
gagcctaaga gagtgcggga aagcgtgcc cagcccagca catctgatgc tgaggccgac 5940
atcaactacg ccgatagata ccaaaacaag tgcagccgcc acgtgggcat gaacctgatg 6000
ctgtttccct gcagacagtg tgaaagatg aaccagaatt ctaatatctg ctttacacac 6060
ggccagaaag attgcctgga atgcttccct gtgtccgaga ccaaccagt gtctgtggta 6120
aaaaaggcct accagaagct gtgctacatc caccacatca tgggcaaggt gccagacgcc 6180
tgtaccgcct gcgacctggt caacgtggac ctggacgact gcatcttcga gcagtgattt 6240
gtgatgggaa ttctgtgctg tgccttctag ttgccagcca tctgttgttt gcccctcccc 6300
cgtgccttcc ttgaccctgg aaggtgccac tcccactgtc cttttcctaat aaaatgagga 6360
aattgcatcg cattgtctga gtaggtgtca ttctattctg gggggtgggg tggggcagga 6420
cagcaagggg gaggattggg aagacaatag caggcatgct ggggatgcgg tgggctctat 6480
gggaccttt ttagggccca ttggtatggc ttttccccg tatcccccca ggtgtctgca 6540
ggctcaaaga gcagcgagaa gcgttcagag gaaagcgatc ccgtgccacc ttccccgtgc 6600
ccgggctgtc ccgcacgct gccggctcgg ggatgcgggg ggagcgccgg accggagcgg 6660
agccccgggc ggctcgctgc tgccccctag cgggggaggg acgtaattac atccctgggg 6720
gctttggggg ggggctgtcc ctctagagcg gccgccaccg cggtggagct ccagcttttg 6780
ttccctttag tgagggttaa ttagatctta atacgactca ctataggcg aattgggtac 6840
cgggcccccc tgaggcggaa agaaccagct ggggctctag ggggtatccc cggggttggg 6900
gttgcgcctt ttccaaggca gccctgggtt tgcgcaggga cgcggctgct ctgggcgtgg 6960
ttccgggaaa cgcagcggcg ccgaccctgg gtctcgcaca ttcttcacgt ccgttccgag 7020
cgtcacccgg atcttcgccg ctaccccttgt gggcccccg gcgacgcttc ctgctccgcc 7080
cctaagtcgg gaaggttcct tgcggttcgc ggcgtgccgg acgtgacaaa cggaagccgc 7140
acgtctcact agtaccctcg cagacggaca gcgccaggga gcaatggcag cgcgccgacc 7200
gcgatgggct gtggccaata gcggctgctc agcagggcgc gccgagagca gcggccggga 7260
aggggcggtg cggaggcgg ggtgtggggc ggcctgttcc tgcccgcgcg 7320
gtgttccgga ttctgcaagc ctccggagcg cacgtcggca gtcggctccc tcgttgaccg 7380
aatcaccgac ctctctcccc agaagctccc gggagcttgt atatccatt tcggatctga 7440
tcagcacgtg ttgacaatta atcatcggca tagtatatcg gcatagtata atacgacaag 7500
gtgaggaacg ccaccatggc caagcctttg tctcaagaag aatccaccct cattgaaaga 7560
gcaacggcta caatcaacag catccccatc tctgaagact acagcgtcgc cagcgcagct 7620
```

```
ctctctagcg acggccgcat cttcactggt gtcaatgtat atcattttac tgggggacct  7680
tgtgcagaac tcgtggtgct gggcactgct gctgctgcgg cagctggcaa cctgacttgt  7740
atcgtcgcga tcggaaatga gaacaggggc atcttgagcc cctgcggacg gtgccgacag  7800
gtgcttctcg atctgcatcc tgggatcaaa gccatagtga aggacagtga tggacagccg  7860
acggcaggtg ggattcgtga attgctgccc tctggttatg tgtgggaggg ctaaagcgcg  7920
gggatctcat gctggagttc ttcgcccacc ccaacttgtt tattgcagct tataatggtt  7980
acaaataaag caatagcatc acaaatttca caaataaagc attttttca ctgcattcta   8040
gttgtggttt gtccaaactc atcaatgtat cttatcatgt ctgtagctga tgtataccta  8100
ggatccggcc ggcctgcagg tgtcctcaca ggaacgaagt ccctaaagaa acagtggcag  8160
ccaggtttag cccggaatt gactggattc cttttttagg gcccattggt atggcttttt    8220
ccccgtatcc ccccaggtgt ctgcaggctc aaagagcagc gagaagcgtt cagaggaaag  8280
cgatcccgtg ccaccttccc cgtgcccggg ctgtccccgc acgctgccgg ctcggggatg   8340
cggggggagc gccggaccgg agcggagccc cgggcggctc gctgctgccc cctagcgggg  8400
gagggacgta attacatccc tgggggcttt ggggggggtc tgtccctcta gagcggccgc   8460
caccgcggtg gagctccagc ttttgttccc tttagtgagg gttaattaga tcttaatacg  8520
actcactata gggcgaattg ggtaccgggc ccccctcga ggtcgacggt atcctcgagg    8580
tcgacggtat cgataagctt gatatctata acaagaaaat atatatataa taagttatca  8640
cgtaagtaga acatgaaata acaatataat tatcgtatga gttaaatctt aaaagtcacg  8700
taaaagataa tcatgcgtca ttttgactca cgcggtcgtt atagttcaaa atcagtgaca  8760
cttaccgcat tgacaagcac gcctcacggg agctccaagc ggcgactgag atgtcctaaa  8820
tgcacagcga cggattcgcg ctatttagaa agagagagca atatttcaag aatgcatgcg  8880
tcaattttac gcagactatc tttctagggt taatctacgt gcatcaggat catatcgtca  8940
ggtcttttt ccggctcagt catcgcccaa gctggcgcta tctgggcatc ggggaggaag   9000
aagcccgtgc cttttcccgc gaggttgaag cggcatggaa agagtttgcc gaggatgact  9060
gctgctgcat tgacgttgag cgaaaacgca cgtttaccat gatgattcgg gaaggtgtgg  9120
ccatgcacgc ctttaacggt gaactgttcg ttcaggccac ctgggatacc agttcgtcgc  9180
ggcttttccg gacacagttc cggatggtca gcccgaagcg catcagcaac ccgaacaata  9240
ccggcgacag ccggaactgc cgtgccggtg tgcagattaa tgacagcggt gcggcgctgg  9300
gatattacgt cagcgaggac gggtatcctg gctggatgcc gcagaaatgg acatggatac  9360
cccgtgagtt acccggcggg cgcgcttggc gtaatcatgg tcatagctgt ttcctgtgtg  9420
aaattgttat ccgctcacaa ttccacacaa catacgagcc ggaagcataa agtgtaaagc  9480
ctggggtgcc taatgagtga gctaactcac attaattgcg ttgcgctcac tgcccgcttt  9540
ccagtcggga aacctgtcgt gccagctgca ttaatgaatc ggccaacgcg cggggagagg  9600
cggtttgcgt attgggcgct cttccgcttc ctcgctcact gactcgctgc gctcggtcgt  9660
tcggctgcgg cgagcggtat cagctcactc aaaggcggta atacggttat ccacagaatc  9720
aggggataac gcaggaaaga acatgtgagc aaaaggccag caaaaggcca ggaaccgtaa  9780
aaaggccgcg ttgctggcgt ttttccatag gctccgcccc cctgacgagc atcacaaaaa  9840
tcgacgctca agtcagaggt ggcgaaaccc gacaggacta taaagatacc aggcgtttcc  9900
ccctggaagc tccctcgtgc gctctcctgt tccgaccctg ccgcttaccg gatacctgtc  9960
cgcctttctc ccttcgggaa gcgtggcgct ttctcatagc tcacgctgta ggtatctcag 10020
ttcggtgtag tcgttcgct ccaagctggg ctgtgtgcac gaaccccccg ttcagcccga  10080
ccgctgcgcc ttatccggta actatcgtct tgagtccaac ccggtaagac acgacttatc 10140
gccactggca gcagccactg gtaacaggat tagcagagcg aggtatgtag gcggtgctac 10200
agagttcttg aagtggtggc ctaactacgg ctacactaga aggacagtat ttggtatctg 10260
cgctctgctg aagccagtta ccttcggaaa aagagttggt agctcttgat ccggcaaaca 10320
aaccaccgct ggtagcggtg gtttttttgt ttgcaagcag cagattacgc gcagaaaaaa 10380
aggatctcaa gaagatcctt tgatctttc tacggggtct gacgctcagt ggaacgaaaa  10440
ctcacgttaa gggattttgg tcatgagatt atcaaaaagg atcttcacct agatcctttt 10500
aaaattaaaa tgaagtttta aatcaatcta agtatatat gagtaaactt ggtctgacag  10560
ttaccaatgc ttaatcagtg aggcacctat ctcagcgatc tgtctatttc gttcatccat 10620
agttgcctga ctccccgtcg tgtagataac tacgatacgg gagggcttac catctggccc 10680
cagtgctgca atgataccgc gagacccacg ctcaccggct ccagatttat cagcaataaa 10740
ccagccagcc ggaagggccg agcgcagaag tggtcctgca actttatccg cctccatcca 10800
gtctattaat tgttgccggg aagctagagt aagtagttcg ccagttaata gtttgcgcaa 10860
cgttgttgcc attgctacag gcatcgtggt gtcacgctcg tcgtttggta tggcttcatt 10920
cagctccggt tcccaacgat caaggcgagt tacatgatcc cccatgttgt gcaaaaaagc 10980
ggttagctcc ttcggtcctc cgatcgttgt cagaagtaag ttggccgcag tgttatcact 11040
catggttatg gcagcactgc ataattctct tactgtcatg ccatccgtaa gatgcttttc 11100
tgtgactggt gagtactcaa ccaagtcatt ctgagaatag tgtatgcggc gaccgagttg 11160
ctcttgcccg gcgtcaatac gggataatac cgcgccacat agcagaactt taaaagtgct 11220
catcattgga aaacgttctt cggggcgaaa actctcaagg atcttaccgc tgttgagatc 11280
cagttcgatg taacccactc gtgcacccaa ctgatcttca gcatctttta ctttcaccag 11340
cgtttctggg tgagcaaaaa caggaaggca aaatgccgca aaaagggaa taagggcgac  11400
acggaaatgt tgaatactca t                                            11421

SEQ ID NO: 30           moltype = DNA   length = 17121
FEATURE                 Location/Qualifiers
misc_feature            1..17121
                        note = Synthetic: PB-iCap8split-ITRGFP-hygro-1
source                  1..17121
                        mol_type = other DNA
                        organism = synthetic construct
SEQUENCE: 30
actcttcctt tttcaatatt attgaagcat ttatcagggt tattgtctca tgagcggata    60
catatttgaa tgtatttaga aaataaaca aataggggtt ccgcgcacat ttccccgaaa   120
agtgccacct aaattgtaag cgttaatatt ttgttaaaat tcgcgttaaa ttttttgttaa  180
atcagctcat tttttaacca ataggccgaa atcggcaaaa tcccttataa atcaaaagaa   240
tagaccgaga taggggttgag tgttgttcca gtttggaaca agagtccact attaaagaac  300
gtggactcca acgtcaaagg gcgaaaaacc gtctatcagg gcgatggccc actacgtgaa  360
```

```
ccatcaccct aatcaagttt tttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccaggggtt ttcccagtca    720
cgacgttgta aaacgacggc cagtgagcgc gcctcgttca ttcacgtttt tgaacccgtg    780
gaggacgggg agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaaa caaaaactca   1080
aaatttcttc tataaagtaa caaaacttttt atcgaattcc tgcagcccgg gggatccact   1140
agttctagag ggacagcccc ccccaaagc cccagggat gtaattacgt ccctccccg   1200
ctaggggga gcagcgagcc gcccgggct ccgtccggg ccggcgctcc ccccgcatcc   1260
ccgagccggc agcgtgcggg gacagcccgg gcacggggaa ggtggcacgg gatcgctttc   1320
ctctgaacgc ttctcgctgc tctttgagcc tgcagacacc tgggggata cggggaaaag   1380
gcctccaagg ccagcttccc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcgtttaaac ttaagcttgg taccgagctc ggatccacta   1560
gtccagtgtg gtggaattcc tgcttcgcga tgtacgggcc agatatacgc gtgacattga   1620
ttattgacta gttattaata gtaatcaatt acggggtcat tagttcatag cccatatatg   1680
gagttccgcg ttacataact tacggtaaat ggcccgcctg gctgaccgcc caacgacccc   1740
cgcccattga cgtcaataat gacgtatgtt cccatagtaa cgccaatagg gactttccat   1800
tgacgtcaat gggtggagta tttacggtaa actgcccact tggcagtaca tcaagtgtat   1860
catatgccaa gtacgccccc tattgacgtc aatgacggta aatggcccgc ctggcattat   1920
gcccagtaca tgaccttatg ggactttcct acttggcagt acatctacgt attagtcatc   1980
gctattacca tggtgatgcg gttttggcag tacatcaatg ggcgtggata gcggtttgac   2040
tcacgggat ttccaagtct ccaccccatt gacgtcaatg ggagtttgtt ttggaaccaa   2100
aatcaacggg acttttccaa atgtcgtaac aactccgccc cattgacgca aatgggcggt   2160
aggcgtgtac ggtgggaggt ctatataagc agagctctcc ctatcagtga tagagatctc   2220
cctatcagtg atagagatcg tcgacgagct cgtttagtga accgtcagat cgcctggaga   2280
cgccatccac gctgttttga cctccataga agacaccggg accgatccag cctgaacgcg   2340
cagccgccaa tggatggccg ctgatggcta tctgcctgat tggctggaag ataacctgag   2400
tgagggcatc cgggaatggt gggccctgaa gcctggagcc ccgaagccca aagccaacca   2460
gcaaaagcag gacgacggcc ggggtctggt gcttcctggc tacaagtacc tcggaccctt   2520
caacggactc gacaaggggg agcccgtcaa cgcggcggac gcagcggccc tcgagcacga   2580
caaggcctac gaccagcagc tgcaggcggg tgacaatccg tacctgcggt ataaccacgc   2640
cgacgccgag tttcaggagc gtctgcaaga agatacgtct tttgggggca acctcgggcg   2700
agcagtcttc caggccaaga agcgggttct cgaacctctc ggtctggttg aggaaggcgc   2760
taagacggct cctggaaaga gaggccggt agaaacctagc cccagcgat ctccagattc   2820
ttctaccggc atcggcaaaa agggccaaca gcctgcgaga aagcggctga acttcggcca   2880
gaccggagac agcgagagcg tgcccgaccc tcagcctccg ggcgagcccc ctgccgcccc   2940
ttctggcgtg ggcccaaca ccatggccgc cggcggcgga gccctatgg ccgacaacaa   3000
cgagggcgcc gacggcgtgg gaagcagcag cggcaattgg cactgcgact ccacctggct   3060
gggcgacaga gtgatcacca catctacaag aacctgggcc ctgcccacct acaacaatca   3120
cctgtacaag cagatcagca atggaacctc tggaggcgc accaacgata cacctactt   3180
tggctacagc accccttggg gatatttcga cttcaaccgg ttccactgtc acttcagccc   3240
tcgggactgg cagcgtctca ttaacaataa ctggggcttc agaccaaga gactgagctt   3300
caagctgttc aacatccagg tgaaggaagt gacccaaaac gagggcacca agaccatcgc   3360
caataacctc acctccacaa tccaagtgtt caccgattcc gagtaccagc tgcccttacgt   3420
gctgggctcc gcccaccagg gctgcctgcc accattcccc gccgacgtgt tcatgatccc   3480
tcagtacggc tacctgacac tgaacaacgg atctcaagca gtgggcagaa gctccttcta   3540
ctgtctggag tacttcccta gccagatgct gaggacaggc aacaatttcc agttcaccta   3600
cacattcgag gacgtccctt ttcacagctc ttatgcccat agccagagcc tggatagact   3660
gatgaaccct ctgatcgacc agtatctgta ttacctgagc agaacgcaaa caacaggcgg   3720
caccgctaat acccagaccc tgggtttcag ccaaggcggc cctaacacaa tggccaatca   3780
ggccaaaaac tggcttcctg gccctgcta cagacagcaa agagtgagca caaccaccgg   3840
ccagaacaac aactctaact tcgcctggac agccggcacc aaataccacc tgaacggcag   3900
aaacagcctg gccaaccctg gaatcgctat ggctacacac aaggacgatg aggaacggtt   3960
cttcccagc aacggcatcc tgatcttcgg caagcagaac gccgctcgcg acaacgccga   4020
ctacagcgac gtgatgctga ccagcgagga agaaatcaag acaacaaacc cggtcgccac   4080
cgaggaatac ggcattgtgg ccgataacct gcagcagcag aataccgccc ctcagatcgg   4140
caccgtgaac tcccagggag ccctgcctgg catggtgtgg cagaacagag atgtgaact   4200
gcagggccct atctgggcca agatccccca caccgacggg aatttccatc caagccctct   4260
gatgggcgga ttggcctga agcacccccc tccacagatt ctcatcaaaa acacacctgt   4320
gccagccgac cctcccacaa catttaatca gtctaagctg aatagcttca tcacccagta   4380
cagcaccggc caggtgtccg tggaaatcga gtgggagctg cagaaagaga acagcaagga   4440
atggaaccct gagatccagt acaccagcaa ctactacaaa agcaccagcg tggacttcgc   4500
cgttaatact gagggcgtct actcagagcc tcggcccatc ggcactcggt acctgaccag   4560
aaacctgaat ggctaggatc cggccggcct gcaggtgtcc tcacaggaac gaagtcccta   4620
aagaaacagt ggcagccagg tttagccccg gaaaacttgt ttattgcagc ttataatggt   4680
tacaaataaa gcaatagcat cacaaatttc acaaataaag catttttttc actgcattct   4740
agttgtggtt tgtccaaact catcaatgta tcttattagc ttgattgagg gacagcccca   4800
cccaaaagcc cccagggatg taattacgtc cctccccgc taggggggcag cagcgagccc   4860
cccgggctc gctccggtc cggcgctccc ccgcatccc gagccggca gcgtgcggg   4920
acagcccggg cacggggaag gtggcacggg atcgctttcc tctgaacgct tctcgctgct   4980
ctttgagcct gcagacacct gggggatac ggggaaaagg cctccaaggc cagcttccca   5040
caataagttg ggtgaatttt ggctcattcc tcctttctat aggattgagg tcagagcgac   5100
```

```
attgattatt gactagttat taatagtaat caattacggg gtcattagtt catagcccat   5160
atatggagtt ccgcgttaca taacttacgg taaatggccc gcctggctga ccgcccaacg   5220
acccccgccc attgacgtca ataatgacgt atgttcccat agtaacgcca atagggactt   5280
tccattgacg tcaatgggtg gagtatttac ggtaaactgc ccacttggca gtacatcaag   5340
tgtatcatat gccaagtacg ccccctattg acgtcaatga cggtaaatgg cccgcctggc   5400
attatgccca gtacatgacc ttatgggact ttcctacttg gcagtacatc tacgtattag   5460
tcatcgctat taccatggtg atgcggtttt ggcagtacat caatgggcgt ggatagcggt   5520
ttgactcacg gggatttcca agtctccacc ccattgacgt caatgggagt ttgttttgga   5580
accaaaatca acgggacttt ccaaaatgtc gtaacaactc cgccccattg acgcaaatgg   5640
gcggtaggcg tgtacggtgg gaggtctata taagcagagc tctccctatc agtgatagag   5700
atctccctat cagtgataga gatcgtcgac gagctcgttt agtgaaccgt cagatcgcct   5760
ggagacgcca tccacgctgt tttgacctcc atagaagaca ccgggaccga tccagcctat   5820
cccaattctg atgcgccggt gatcagatca aaaacttcag ccaggtacgg cgctaagacg   5880
gctcctggaa agaagaggcc ggtagagcca tcaccccagc gttctccaga ctcctctacg   5940
ggcatcggca agaaaggcca acagcccgcc agaaaaagac tcaattttgg tcagactggc   6000
gactcagagt cagttccaga ccctcaacct ctcggagaac ctcagcagc gccctctggt   6060
gtgggaccta atacaatggc tgcaggcggt ggcgcaccaa tggcagacaa taacgaaggc   6120
gccgacggag tgggtagttc ctcgggaaat tggcattggg attccacatg gctgggcgac   6180
agagtcatca ccaccagcac ccgaacctgg gccctgccca cctacaacaa ccacctctac   6240
aagcaaatct ccaacgggac atcgggagga gccaccaacg acaaccccta cttcggctac   6300
agcacccccc gggggtattt tgactttaac agattccact gccactttc accacgtgac   6360
tggcagcgac tcatcaacaa caactgggga ttccggaaca agactcag cttcaagctc   6420
ttcaacatcc aggtcaagga ggtcacgcag aatgaaggca ccaagaccat cgccaataac   6480
ctcaccagca ccatccaggt gtttacggac tcggagtacc agctgccgta cgttctcggc   6540
tctgccacc agggctgcct gcctccgttc ccggcggacg tgttcatgat tcccagtac   6600
ggctacctaa cactcaacaa cggtagtcag ccgtggcag gctcctcctt ctactgcctg   6660
gaatactttc cttcgcagat gctgagaacc ggcaacaact tccagtttac ttacaccttc   6720
gaggacgtgc ctttccacag cagctacgcc cacagccaga gcttggaccg gctgatgaat   6780
cctctgattg accagtacct gtactacttg tctcggactc aaacaacagg aggcacggca   6840
aatacgacag ctctgggcat cagccaaggt gggcctaata caatggccaa tcaggcaaag   6900
aactggctgc caggaccctg ttaccgccaa caacgcgtct caacgacaac cgggcaaaac   6960
aacaatagca acttgtcctg gactgctggg accaaatacc atctgaatgg aagaaattca   7020
ttggctaatc ctggcatcgc tatggcaaca cacaaagacg acgaggagcg tttttttccc   7080
agtaacgaatc tcctgatttt tggcaaacaa aatgctacgac gagcaatgc ggattacagc   7140
gatgtcatgc tcaccagcga ggaagaaatc aaaaaccactaa acctgtggc tacagaggaa   7200
tacggtatcg tggcagataa cttgcagcag caaaacacgg ctcctcaaat tggaactgtc   7260
aacagccagg gggccttacc cggtatggtc tggcagaacc gggacgtgta cctgcagggt   7320
cccatctggg ccaagattcc tcacacggac ggcaacttcc acccgtctcc gctgatgggc   7380
ggcttttggc tgaaacatcc tccgcctcag atcctgatca agaacacgcc tgtacctgca   7440
gatcctccga ccaccttcaa ccagtcaaag ctgaactctt tcatcacgca atacagcacc   7500
ggacaggtca gcgtggaaat tgaatgggag ctgcagaagg aaaacagcaa gcgctggaac   7560
cccgagatcc agtacacctc caactactac aaatctcaca gtgtggactt tgctgttaat   7620
acagaaggcg tgtactctga accccgcccc attggcaccg gttacctcac ccgtaatctg   7680
taaactagtt tgcttgttaa tcaataaacc gtttaattcg tttcagttga gcggccgtcg   7740
agtctagagg gcccgtttaa acccgctgat cagcctcgac tgtgccttct agttgccagc   7800
catctgttgt ttgcccctcc cccgtgcctt ccttgaccct ggaaggtgcc actcccactg   7860
tcctttccta ataaaatgag gaaattgcat cgcattgtct gagtaggtgt cattctattc   7920
tggggggtgg ggtggggcag gacagcaagg ggaggattg gaagacaat agcaggcatg   7980
ctggggatgc ggtgggctct atggcttctg aggcggaaag aaccagctgg ggctctaggg   8040
ggtatccccg cgcgccgaa ttcgttaaca agctttaatt aacgcgtata cctaggatcc   8100
ggccggctca caggtgtcct cacaggaacg aagtccctaa agaaacagtg gcagccaggt   8160
ttagccccgg aattgactgg attccttttt tagggcccat tggtatggct ttttcccgt   8220
atcccccag gtgtctgcag gctcaaagag cagcgagaag cgttcagagg aaagcgatcc   8280
cgtgccacct tccccgtgcc cgggctgtcc ccgcacgctg ccggctcggg gatgcggggg   8340
gagcgccgga ccggagcgga gccccgggcg gctcgctcgc gccccctagc ggggagggga   8400
cgtaattaca tccctggggg ctttgggggg gggctgtccc tggcctccaa ggcagcttc   8460
ccacaataag ttgggtgaat tttgctcat tcctcctttc tataggattg aggtcagagc   8520
tttgtgatgg gaattctgtg aatgtgtgt cagttagggt gtggaaagtc ccgcgatcgc   8580
tagcaaacgc cagcaacgcg gccttttac ggttcctggc cttttgctgg cctttgctc   8640
acatgcctgc caggcagctg cgcgctcgct cgctcactga ggccgcccgg gcaaagcccg   8700
ggcgtcgggc gacctttggt cgcccggcct cagtgagcga gcgagcgcgc agagagggag   8760
tggccaactc catcactagg ggttcctgcg gccgcacgcg tggagctagt tattaatagt   8820
aatcaattac ggggtcatta gttcatagcc catatatgga gttccgcgtt acataactta   8880
cggtaaatgg cccgcctggc tgaccgccca acgacccccg cccattgacg tcaataatga   8940
cgtatgttcc catagtaacg tcaataggga ctttccattg acgtcaatgg gtggagtatt   9000
tacggtaaac tgcccacttg gcagtacatc aagtgtatca tatgccaagt acgccccta   9060
ttgacgtcaa tgacggtaaa tggcccgcct ggcattatgc ccagtacatg accttatggg   9120
actttcctac ttggcagtac atctacgtat tagtcatcgc tattaccatg gtgatgcggt   9180
tttggcagta catcaatggg cgtggatagc ggtttgactc acggggattt ccaagtctcc   9240
accccattga cgtcaatggg agtttgtttt gcaccaaaat caacgggact ttccaaaatg   9300
tcgtaacaac tccgccccat tgacgcaaat gggcggtagg cgtgtacggt gggaggtcta   9360
tataagcaga gctcgtttag tgaaccgtca gatcgcctgg agacgccatc cacgctgttt   9420
tgacctccat agaagacacc gggaccgatc agcctccgc ggattcgaat cccggccggg   9480
aacggtggaa tgaacgcgg attccccgtg ccaagagtga cgtaagtacc gcctatagag   9540
tctataggcc cacaaaaaat gctttcttct tttaatatac ttttttgttt atcttatttc   9600
taatactttc cctaatctct ttctttcagg gcaataatga tacaatgtat catgcctctt   9660
tgcaccattc taaagaataa cagtgataat ttctgggtta aggcaatagc aatatttctg   9720
catataaata tttctgcata taaattgtaa ctgatgtaag aggtttcata ttgctaatag   9780
cagctacaat ccagctacca ttctgctttt atttttatggt tgggataagg ctggattatt   9840
```

```
ctgagtccaa gctaggccct tttgctaatc atgttcatac ctcttatctt cctcccacag  9900
ctcctgggca acgtgctggt ctgtgtgctg gcccatcact ttggcaaaga attgggattc  9960
gaacatcgat tgaattctga atggtgagca agggcgagga gctgttcacc ggggtggtgc 10020
ccatcctggt cgagctggac ggcgacgtaa acggccacaa gttcagcgtg tccggcgagg 10080
gcgagggcga tgccacctac ggcaagctga ccctgaagtt catctgcacc accggcaagc 10140
tgcccgtgcc ctggcccacc ctcgtgacca ccctgaccta cggcgtgcag tgcttcagcc 10200
gctaccccga ccacatgaag cagcacgact tcttcaagtc cgccatgccc gaaggctacg 10260
tccaggagcg caccatcttc ttcaaggacg acggcaacta caagacccgc gccgaggtga 10320
agttcgaggg cgacaccctg gtgaaccgca tcgagctgaa gggcatcgac ttcaaggagg 10380
acggcaacat cctggggcac aagctggagt acaactacaa cagccacaac gtctatatca 10440
tggccgacaa gcagaagaac ggcatcaagg tgaacttcaa gatccgccac aacatcgagg 10500
acggcagcgt gcagctcgcc gaccactacc agcagaacac ccccatcggc gacggccccg 10560
tgctgctgcc cgacaaccac tacctgagca cccagtccgc cctgagcaaa gaccccaacg 10620
agaagcgcga tcacatggtc ctgctggagt tcgtgaccgc cgcgggatc actctcggca 10680
tggacgagct gtacaagtac tcagatctcg agctcaagta gggatcctct agagtcgacc 10740
tgcagaagct tgcctcgagc agcgctgctc gagagatcta cgggtggcat ccctgtgacc 10800
cctccccagt gcctctcctg gccctggaag ttgccactcc agtgcccacc agccttgtcc 10860
taataaaatt aagttgcatc attttgtctg actaggtgtc cttctataat attatggggt 10920
ggagggggt ggtatggagc aaggggcaag ttgggaagac aacctgtagg gcctgcgggg 10980
tctattggga accaagctgg agtgcagtgg cacaatcttg gctcactgca atctccgcct 11040
cctgggttca agcgattctc ctgcctcagc ctcccgagtt gttgggattc caggcatgca 11100
tgaccaggct cagctaattt ttgttttttt ggtagagacg gagtttcacc atattggcca 11160
ggctggtctc caactcctaa tctcaggtga tctacccacc ttggcctccc aaattgctgg 11220
gattacaggc gtgaaccact gctcccttcc ctgtccttct gatttgtag gtaaccacgt 11280
gcggaccgag cggccgcagg aaccctagt gatggagttg ccactccct ctctgcgcg 11340
tcgctcgctc actgaggccg ggcgaccaaa ggtcgcccga gcccgggct ttgcccggac 11400
ggcctcagtg agcgagcgag cgcgcagctg cctgcagggg cgcctgatgc ggtattttct 11460
ccttacgcat ctgtgcggta tttcacaccg catacgtcgt agctgatcaa ttggcgcgcc 11520
gaattcgtta acaagcttta attaacgcgt atacctagga tccggccggc ctgcaggtgt 11580
cctcacagga acgaagtccc taaagaaaca gtggcagcca ggtttagccc cggaattgac 11640
tggattcctt ttttagggcc cattggtatg gcttttcc cgtatcccc caggtgtctg 11700
caggctcaaa gagcagcgag aagcgttcag aggaaagcga tcccgtgcca ccttccccgt 11760
gcccgggctg tccccgcacg ctgccggctc ggggatgcgg ggggagcgcc ggaccggagc 11820
ggagcccgg gcggctcgct gctgccccct agcggggag ggacgtaatt acatccctgg 11880
gggctttggg gggggctgt ccctggcctc caaggccagc ttcccacaat aagttgggtg 11940
aattttggct cattcctcct ttctatagga ttgaggtcag agcggggttg gggttgcgcc 12000
ttttccaagg cagccctggg tttgcgcagg acgcggctg ctctgggcgt ggttccggga 12060
aacgcagcgg cgccgaccct gggtctgca cattcttcac gtccgttcgc agcgtcaccg 12120
ggatctcgc cgctacccttt gtgggccccc cggcgacgct tcctgctccg ccctaagtc 12180
gggaaggttc cttgcggttc gcggcgtgcc ggacgtgaca aacggaagcc gcacgtctca 12240
ctagtaccct cgcagacgga cagcgccagg gagcaatggc agcgcgccga ccgcgatggg 12300
ctgtggccaa tagcggctgc tcagcagggc gcgccgagag cagcggccgg gaaggggcgg 12360
tgcgggaggc ggggtgtggg gcggtagtgt gggccctgtt cctgcccgcg cggtgttccg 12420
cattctgcaa gcctccggag cgcacgtcgg cagtcggctc cctcgttgac cgaatcaccg 12480
acctctctcc ccagaagctc ccgggagctt gtatatccat tttcggatct gatcagcacg 12540
tgttgacaat taatcatcgg catagtatat cggcatagta taatacgaca aggtgaggaa 12600
cgccaccatg aaaaagcctg aactcaccgc gacgtctgtc gagaagtttc tgatcgaaaa 12660
gttcgacagc gtctccgacc tgatgcagct ctcggagggc gaagaatctc gtgctttcag 12720
cttcgatgta ggagggcgtg gatatgtcct gcggtaaat agctgcgccg atggtttcta 12780
caaagatcgt tatgtttatc ggcactttgc atcggccgcg ctcccgattc cggaagtgct 12840
tgacattggg gaattcagcg agagcctgac ctattgcatc tcccgccgtg cacagggtgt 12900
cacgttgcaa gacctgcctg aaaccgaact gcccgctgtt ctgcagccgg tcgcggaggc 12960
catggatgcg atcgctgcgg ccgatcttag ccagacgagc gggttcggcc cattcggacc 13020
gcaaggaatc ggtcaataca ctacatggcg tgatttcata tgcgcgattg ctgatcccca 13080
tgtgtatcac tggcaaactg tgatggacga caccgtcagt gcgtccgtcg cgcaggctct 13140
cgatgagctg atgctttggg ccgaggactg ccccgaagtc cggcacctcg tgcacgcgga 13200
tttcggctcc aacaatgtcc tgacggacaa tggccgcata acagcggtca ttgactggag 13260
cgaggcgatg ttcgggatt cccaatacga ggtcgccaac atcttcttct ggaggccgtg 13320
gttgcttgt atggagcagc agacgcgcta cttcgagcgg aggcatccgg agcttgcagg 13380
atcgccgcgg ctccgggcgt atatgctccg cattggtctt gaccaactct atcagagctt 13440
ggttgacggc aatttcgatg atgcagcttg ggcgcagggt cgatgcgacg caatcgtccg 13500
atccggagcc gggactgtcg ggcgtacaca atcgcccgc agaagcgcgg ccgtctggac 13560
cgatggctgt gtagaagtac tcgccgatag tggaaaccga cgcccagca ctcgtccgag 13620
ggcaaaggaa tagagcgcgg ggatctcatg ctggagttct tcgcccaccc caacttgttt 13680
attgcagctt ataatggtta caaataaagc aatagcatca caaatttcac aaataaagca 13740
tttttttcac tgcattctag ttgtggtttg tccaaactca tcaatgtatc ttatcatgtc 13800
tgtagctgat gtatacctag gatccggccg gcctgcaggt gtcctcacag gaacgaagtc 13860
cctaaagaaa cagtggcagc caggtttagc cccggaattg actggattcc ttttttaggc 13920
ccattggtat ggcttttttcc ccgtatcccc ccaggtgtct gcaggctcaa agagcagcga 13980
gaagcgttca gaggaaagcg atcccgtgcc accttccccg tgcccgggct gtccccgcac 14040
gctgccggct cggggatgcg gggggagcgc cggaccggag cggagcccg gcggctcgc 14100
tgctgccccc tagcggggga gggacgtaat tacatccctg ggggctttgg ggggggctg 14160
tccctctaga gcggccgcca ccgcggtgga gctccagctt ttgttccctt tagtgagggt 14220
taattagatc ttaatacgac tcactatagg gcgaattggg taccggagcc cccctaagtc 14280
tcgacggtat cgataagctt gatatcctata acaagaaaat atatatataa taagttatca 14340
cgtaagtaga acatgaaata acaatataat tatcgtatga gttaaatctt aaaagtcacg 14400
taaaagataa tcatgcgtca ttttgactca cgcggtcgtt atagttcaaa atcagtgaca 14460
cttaccgcat tgacaagcac gcctcacggg agctccaagc ggcgactgag atgtcctaaa 14520
tgcacagcga cggattcgcg ctatttagaa agagagagca atatttcaag aatgcatgcg 14580
```

```
tcaatttac  gcagactatc  tttctagggt  taatctagct  gcatcaggat  catatcgtcg  14640
ggtctttttt  ccggctcagt  catcgcccaa  gctggcgcta  tctgggcatc  ggggaggaag  14700
aagcccgtgc  cttttcccgc  gaggttgaag  cggcatggaa  agagtttgcc  gaggatgact  14760
gctgctgcat  tgacgttgag  cgaaaacgca  cgtttaccat  gatgattcgg  gaaggtgtgg  14820
ccatgcacgc  ctttaacggt  gaactgttcg  ttcaggccac  ctgggatacc  agttcgtcgc  14880
ggcttttccg  gacacagttc  cggatggtca  gcccgaagcg  catcagcaac  ccgaacaata  14940
ccggcgacag  ccggaactgc  cgtgccggtg  tgcagattaa  tgacagcggt  gcggcgctgg  15000
gatattacgt  cagcgaggac  gggtatcctg  gctggatgcc  gcagaaatgg  acatggatac  15060
cccgtgagtt  accggcggg  cgcgcttggc  gtaatcatgg  tcatagctgt  ttcctgtgtg  15120
aaattgttat  ccgctcacaa  ttccacacaa  catacgagcc  ggaagcataa  agtgtaaagc  15180
ctggggtgcc  taatgagtga  gctaactcac  attaattgcg  ttgcgctcac  tgcccgcttt  15240
ccagtcggga  aacctgtcgt  gccagctgca  ttaatgaatc  ggccaacgcg  cggggagagg  15300
cggtttgcgt  attgggcgct  cttccgcttc  ctcgctcact  gactcgctgc  gctcggtcgt  15360
tcggctgcgg  cgagcggtat  cagctcactc  aaaggcggta  atacggttat  ccacagaatc  15420
aggggataac  gcaggaaaga  acatgtgagc  aaaaggccag  caaaaggcca  ggaaccgtaa  15480
aaaggccgcg  ttgctggcgt  ttttccatag  gctccgcccc  cctgacgagc  atcacaaaaa  15540
tcgacgctca  agtcagaggt  ggcgaaaccc  gacaggacta  taaagatacc  aggcgtttcc  15600
ccctggaagc  tccctcgtgc  gctctcctgt  tccgaccctg  ccgcttaccg  gatacctgtc  15660
cgcctttctc  ccttcgggaa  gcgtggcgct  ttctcatagc  tcacgctgta  ggtatctcag  15720
ttcggtgtag  gtcgttcgct  ccaagctggg  ctgtgtgcac  gaaccccccg  ttcagcccga  15780
ccgctgcgcc  ttatccggta  actatcgtct  tgagtccaac  ccggtaagac  acgacttatc  15840
gccactggca  gcagccactg  gtaacaggat  tagcagagcg  aggtatgtag  gcggtgctac  15900
agagttcttg  aagtggtggc  ctaactacgg  ctacactaga  aggacagtat  ttggtatctg  15960
cgctctgctg  aagccagtta  ccttcggaaa  aagagttggt  agctcttgat  ccggcaaaca  16020
aaccaccgct  ggtagcggtg  gtttttttgt  ttgcaagcag  cagattacgc  gcagaaaaaa  16080
aggatctcaa  gaagatcctt  tgatcttttc  tacggggtct  gacgctcagt  ggaacgaaaa  16140
ctcacgttaa  gggattttgg  tcatgagatt  atcaaaaagg  atcttcacct  agatcctttt  16200
aaattaaaaa  tgaagtttta  aatcaatcta  aagtatatat  gagtaaactt  ggtctgacag  16260
ttaccaatgc  ttaatcagtg  aggcacctat  ctcagcgatc  tgtctatttc  gttcatccat  16320
agttgcctga  ctccccgtcg  tgtagataac  tacgatacgg  gagggcttac  catctggccc  16380
cagtgctgca  atgataccgc  gagacccacg  ctcaccggct  ccagatttat  cagcaataaa  16440
ccagccagcc  ggaagggccg  agcgcagaag  tggtcctgca  actttatccg  cctccatcca  16500
gtctattaat  tgttgccggg  aagctagagt  aagtagttcg  ccagttaata  gtttgcgcaa  16560
cgttgttgcc  attgctacag  gcatcgtggt  gtcacgctcg  tcgtttggta  tggcttcatt  16620
cagctccggt  tcccaacgat  caaggcgagt  tacatgatcc  cccatgttgt  gcaaaaaagc  16680
ggttagctcc  ttcggtcctc  cgatcgttgt  cagaagtaag  ttggccgcag  tgttatcact  16740
catggttatg  gcagcactgc  ataattctct  tactgtcatg  ccatccgtaa  gatgcttttc  16800
tgtgactggt  gagtactcaa  ccaagtcatt  ctgagaatag  tgtatgcggc  gaccgagttg  16860
ctcttgcccg  gcgtcaatac  gggataatac  cgcgccacat  agcagaactt  taaaagtgct  16920
catcattgga  aaacgttctt  cggggcgaaa  actctcaagg  atcttaccgc  tgttgagatc  16980
cagttcgatg  taacccactc  gtgcacccaa  ctgatcttca  gcatctttta  ctttcaccag  17040
cgtttctggg  tgagcaaaaa  caggaaggca  aaatgccgca  aaaaagggaa  taagggcgac  17100
acggaaatgt  tgaatactca  t                                              17121
```

SEQ ID NO: 31        moltype = DNA  length = 17119
FEATURE               Location/Qualifiers
misc_feature       1..17119
                      note = Synthetic: PB-iCap8split-ITRGFP-hygro-2
source               1..17119
                      mol_type = other DNA
                      organism = synthetic construct
SEQUENCE: 31

```
actcttcctt  tttcaatatt  attgaagcat  ttatcagggt  tattgtctca  tgagcggata  60
catatttgaa  tgtatttaga  aaaataaaca  aataggggtt  ccgcgcacat  ttccccgaaa  120
agtgccacct  aaattgtaag  cgttaatatt  ttgttaaaat  tcgcgttaaa  tttttgttaa  180
atcagctcat  tttttaacca  ataggccgaa  atcggcaaaa  tcccttataa  atcaaaagaa  240
tagaccgaga  tagggttgag  tgttgttcca  gtttggaaca  agagtccact  attaaagaac  300
gtggactcca  acgtcaaagg  gcgaaaaacc  gtctatcagg  gcgatggccc  actacgtgaa  360
ccatcaccct  aatcaagttt  tttggggtcg  aggtgccgta  aagcactaaa  tcggaaccct  420
aaagggagcc  cccgatttag  agcttgacgg  ggaaagccgg  cgaacgtggc  gagaaaggaa  480
gggaagaaag  cgaaaggagc  gggcgctagg  gcgctggcaa  gtgtagcggt  cacgctgcgc  540
gtaaccacca  cacccgccgc  gcttaatgcg  ccgctacagg  gcgcgtccca  ttcgccattc  600
aggctgcgca  actgttggga  agggcgatcg  gtgcgggcct  cttcgctatt  acgccagctg  660
gcgaaagggg  gatgtgctgc  aaggcgatta  agttgggtaa  cgccagggtt  ttcccagtca  720
cgacgttgta  aaacgacggc  cagtgagcgc  gcctcgttca  ttcacgtttt  tgaacccgtg  780
gaggacgggc  agactcgcgg  tgcaaatgtg  ttttacagcg  tgatggagca  gatgaagatg  840
ctcgacacgc  tgcagaacac  gcagctagat  taacccctaga  aagataatca  tattgtgacg  900
tacgttaaag  ataatcatgc  gtaaaattga  cgcatgtgtt  ttatcggtct  gtatatcgag  960
gtttatttat  taatttgaat  agatattaag  ttttattata  tttacactta  catactaata  1020
ataaattcaa  caaacaattt  atttatgttt  atttatttat  taaaaaaaaa  caaaaactca  1080
aaatttcttc  tataaagtaa  caaaactttt  atcgaattcc  tgcagcccgg  ggatccact  1140
agttctagag  gacagccccc  ccccaaagc  ccccagggat  gtaattacgt  ccctcccccg  1200
ctaggggca  gcagcgagcc  gcccggggct  ccgctccggt  ccggcgctcc  cccgcatcc  1260
ccgagccgc  agcgtgcggg  gacacccggg  cacgggggtg  gccacggatc  gcttttc  1320
ctctgaacgc  ttctcgctgc  tctttgagcc  tgcagacacc  tggggggata  cggggaaaag  1380
gcctccaagg  ccagcttccc  acaataagtt  gggtgaattt  tggctcattc  ctcctttcta  1440
taggattgag  gtcagagctt  tgtgatggga  attctgtgga  atgtgtgtca  gttagggtgt  1500
ggaaagtccc  cgcgatcgcta  gcgtttaaac  ttaagcttgg  taccgagctc  ggatccacta  1560
gtccagtgtg  gtggaattcc  tgcttcgcga  tgtacgggcc  agatatacgc  gtgacattga  1620
```

-continued

```
ttattgacta gttattaata gtaatcaatt acggggtcat tagttcatag cccatatatg 1680
gagttccgcg ttacataact tacggtaaat ggcccgcctg gctgaccgcc caacgacccc 1740
cgcccattga cgtcaataat gacgtatgtt cccatagtaa cgccaatagg gactttccat 1800
tgacgtcaat gggtggagta tttacggtaa actgcccact tggcagtaca tcaagtgtat 1860
catatgccaa gtacgccccc tattgacgtc aatgacggta aatggcccgc ctggcattat 1920
gcccagtaca tgaccttatg ggactttcct acttggcagt acatctacgt attagtcatc 1980
gctattacca tggtgatgcg gttttggcag tacatcaatg ggcgtggata gcggtttgac 2040
tcacggggat ttccaagtct ccaccccatt gacgtcaatg ggagtttgtt ttggaaccaa 2100
aatcaacggg actttccaaa atgtcgtaac aactccgccc cattgacgca aatgggcggt 2160
aggcgtgtac ggtgggaggt ctatataagc agagctctcc ctatcagtga tagagatctc 2220
cctatcagtg atagagatcg tcgacgagct cgtttagtga accgtcagat cgcctggaga 2280
cgccatccac gctgttttga cctccataga agacaccggg accgatccag cctgaacgcg 2340
caggcgctaa gacggccgct gatggctatc tgcctgattg gctggaagat aacctgagtg 2400
agggcatccg ggaatggtgg gccctgaagc ctggagcccc gaagcccaaa gccaaccagc 2460
aaaagcagga cgacggccgg ggtctggtgc ttcctggcta caagtacctc ggacccttca 2520
acggactcga caagggggag cccgtcaacg cggcggacgc agcggccctc gagcacgaca 2580
aggcctacga ccagcagctg caggcgggtg caatccgta cctgcggtat aaccacgccg 2640
acgccgagtt tcaggagcgt ctgcaagaag atacgtcttt tgggggcaac ctcgggcgag 2700
cagtcttcca ggccaagaag cgggttctcg aacctctcgg tctggttgag gaaggcgcta 2760
agacggctcc tggaaagaag aggccggtag aacctagccc ccagcgatct ccagattctt 2820
ctaccggcat cggcaaaaag ggccaacagc tgcgagaaa cgggctgaac ttcggccaga 2880
ccggagacag cgagagcgtg cccgaccctc agcctctggg cgagcccccct gccgcccctt 2940
ctggcgtggg ccccaacacc atggccgccg cgcgcggagc ccctatggcc gacaacaacg 3000
agggcgccga cggcgtggga agcagcagcg gcaattggca ctgcgactcc acctggctgg 3060
gcgacagagt gatcaccaca tctacaagaa cctgggccct gcccacctac aacaatcacc 3120
tgtacaagca gatcagcaat ggaacctctg gaggcgccaa caacgataac acctactttg 3180
gctacagcac cccttgggga tatttcgact tcaaccggtt ccactgtcac ttcagccctc 3240
gggactggca gcgtctcatt aacaataact ggggcttcag accaaagaga ctgagcttca 3300
agctgttcaa catccaggtg aaggaagtga cccaaaacga gggcaccaag accatcgcca 3360
ataacctcac ctccacaatc caagtgttca ccgattccga gtaccagctc cttacgtgc 3420
tgggctccgc ccaccagggc tgcctgccac cattccccgc cgacgtgttc atgatccctc 3480
agtacggcta cctgacactg aacaacggat tcaagcagt gggcagaagc tccttctact 3540
gtctggagta cttccctagc cagatgctga ggacaggcaa caatttccag ttcacctaca 3600
cattcgagga cgtcccttt cacagctctt atgcccatag ccagagcctg gatagactga 3660
tgaaccctct gatcgaccag tatctgtatt acctgagcag aacgcaaaca acaggcggca 3720
ccgctaatac ccagaccctg gtttcagcc aaggcggccc taacacaatg gccaatcagg 3780
ccaaaaactg gcttcctggc ccctgctaca gacagcaaag agtgagcaca accaccggcc 3840
agaacaacaa ctctaacttc gcctggacag ccggcaccaa atacccctg aacggcagaa 3900
acagcctggc caaccctgga atcgctatgg ctacacacaa ggacgatgag gaacggttct 3960
tcccagcaa cggcatcctg atcttcggca agcagaacgc cgctcgcgac aacgccgact 4020
acagcgacgt gatgctgacc agcgaggaag aaatcaagac aacaaccccg gtcgccaccg 4080
aggaatacgg cattgtggcc gataacctgc agcagcagaa taccgcccct cagatcggca 4140
ccgtgaactc ccagggagcc ctgcctggca tggtgtggca gaacagagat gtgtacctgc 4200
agggccctat ctgggccaag atcccccaca ccgacggaaa tttccatcca gccctctga 4260
tgggcggatt tggcctgaag cacccccctc cacagattct catcaaaaac acacctgtgc 4320
cagccgaccc tccacaaca tttaatcagt ctaagctgaa tagcttcatc acccagtaca 4380
gcaccggcca ggtgtccgtg gaaatggagt gggagctgca gaaagagaac agcaagagat 4440
ggaaccctga gatccagtac accagcaact actacaaaag cacaagcgtg gacttcgccg 4500
ttaatactga gggcgtctac tcagagcctc ggcccatcgg cactcggtac ctgaccagaa 4560
acctgaatgg ctaggatccg gccggcctgc aggtgtcctc acaggaacga agtccctaaa 4620
gaaacagtgg cagccaggtt tagccccgga aaacttgttt attgcagctt ataatggtta 4680
caaataaagc aatagcatca caaatttcac aaataaagca ttttttttcac tgcattctag 4740
ttgtggtttg tccaaactca tcaatgtatc ttattgactg gattgaggga cagcccccc 4800
ccaaagcccc cagggatgta attacgtccc tcccccgcta gggggcagca gcgagccgcc 4860
cggggctccg ctccggtccg gcgctcccc cgcatccccg agccggcagc gtgcggggac 4920
agcccgggca cggggaaggt ggcacgggat cgctttcctc tgaacgcttc tcgctgctct 4980
ttgagcctgc agacacctgg ggggatacgg ggaaaaggcc tccaaggcca gcttcccaca 5040
ataagttggg tgaattttgg ctcattcctc ctttctatag gattgaggtc agagcgacat 5100
tgattattga ctagttatta atagtaatca attacgggt cattagttca tagcccatat 5160
atggagttcc gcgttacata acttacggta aatggcccgc ctggctgacc gcccaacgac 5220
ccccgcccat tgacgtcaat aatgacgtat gttcccatag taacgccaat agggactttc 5280
cattgacgtc aatgggtgga gtatttacgg taaactgccc acttggcagt acatcaagtg 5340
tatcatatgc caagtacgcc ccctattgac gtcaatgacg gtaaatggcc cgcctggcat 5400
tatgcccagt acatgacctt atgggacttt cctacttggc agtacatcta cgtattagtc 5460
atcgctatta ccatggtgat gcggttttgg cagtacatca atgggcgtgg atagcggttt 5520
gactcacggg gatttccaag tctccacccc attgacgtca atgggagttt gttttggaac 5580
caaaatcaac gggactttcc aaaatgtcgt aacaactccg ccccattgac gcaaatgggc 5640
ggtaggcgtg tacggtggga ggtctatata agcagagctc tccctatcag tgatagagat 5700
ctccctatca gtgatagaga tcgtcgacga gctcgtttag tgaaccgtca gatcgcctgg 5760
agacgccatc cacgctgttt tgacctccat agaagacacc gggaccgatc cagcctatcc 5820
caattctgat gcgccggtga tcagatcaaa aacttcagcc aggtacgcg ctaagacggc 5880
tcctggaaag aagaggccgg tagagccatc acccagcgt tctccagact cctctacggg 5940
catcggcaag aaaggccaac agcccgcag aaaagactc aatttggtc agactggcga 6000
ctcagagtca gttcagacc ctcaacctct cggagaaccc cgagcagcgc cctctggtgt 6060
gggacctaat acaatggctg caggcggtgg cgcaccaatg gcagacaata acgaaggcgc 6120
cgacggagtg ggtagttcct cgggaaattg gcattgcgat tccacatggc tgggcgacag 6180
agtcatcacc accagcaccc gaacctgggc cctgcccacc tacaacaacc cctctacaa 6240
gcaaatctcc aacgggacat cgggaggagc caccaacgac aacaccact tcggctacag 6300
cacccccctg gggtatttg actttaacag attccactgc cactttcac cacgtgactg 6360
```

```
gcagcgactc atcaacaaca actgggatt ccggcccaag agactcagct tcaagctctt    6420
caacatccag gtcaaggagg tcacgcagaa tgaaggcacc aagaccatcg ccaataacct    6480
caccagcacc atccaggtgt ttacggactc ggagtaccag ctgccgtacg ttctcggctc    6540
tgcccaccag ggctgcctgc ctccgttccc ggcggacgtg ttcatgattc cccagtacgg    6600
ctacctaaca ctcaacaacg gtagtcaggc cgtgggacgg tcctccttct actgcctgga    6660
atactttcct tcgcagatgc tgagaaccgg caacaacttc cagtttactt acaccttcga    6720
ggacgtgcct ttccacagca gctacgccca cagccagagc ttggaccggc tgatgaatcc    6780
tctgattgac cagtacctgt actacttgtc tcggactcaa acaacaggag gcacggcaaa    6840
tacgcagact ctgggcttca gccaaggtgg gcctaataca atggccaatc aggcaaagaa    6900
ctggctgcca ggaccctgtt accgccaaca acgcgtctca acgacaaccg ggcaaaacaa    6960
caatagcaac tttgcctgga ctgctgggac caaataccat ctgaatggaa gaaattcatt    7020
ggctaatcct ggcatcgcta tggcaacaca caaagacgac gaggagcgtt ttttcccag    7080
taacgggatc ctgatttttg gcaaacaaaa tgctgccaga gacaatgcgg attacagcga    7140
tgtcatgctc accagcgagg aagaaatcaa aaccactaac cctgtggcta cagaggaata    7200
cggtatcgtg gcagataact tgcagcagca aaacacggct cctcaaattg gaactgtcaa    7260
cagccagggg gccttacccg gtatggtctg cagaaccgg gacgtgtacc tgcagggtcc    7320
catctgggcc aagattcctc acacggacgg caacttccac ccgtctccgc tgatgggcgg    7380
ctttggcctg aaacatcctc cgcctcagat cctgatcaag aacacgcctg tacctgcgga    7440
tcctccgacc accttcaacc agtcaaagct gaactctttc atcacgcaat acagcaccgg    7500
acaggtcagc gtggaaattg aatgggagct gcagaaggaa aacagcaagc gctgaaccc    7560
cgagatccag tacacctcca actactacaa atctacaagt gtggactttg ctgttaatac    7620
agaaggcgtg tactctgaac cccgccccat tggcacccgt tacctcaccc gtaatctgta    7680
aactagtttg cttgttaatc aataaaccgt ttaattcgtt tcagttgagc ggccgtcgaa    7740
tctagagggc ccgtttaaac ccgctgatca gcctcgactg tgccttctag ttgccagcca    7800
tctgttgttt gcccctcccc cgtgccttcc ttgaccctgg aaggtgccac tcccactgtc    7860
ctttcctaat aaaatgagga aattgcatcg cattgtctga gtaggtgtca ttctattctg    7920
gggggtgggg tggggcagga cagcaagggg gaggattgga aagacaatag caggcatgct    7980
ggggatgcgg tgggctctat ggcttctgag gcggaaagaa ccagctgggg ctctaggggg    8040
tatccccggc gcgccgaatt cgttaacaag ctttaattaa cgcgtatacc taggatccgg    8100
ccggcctgca ggtgtcctca caggaacgaa gtccctaaaa aaacagtggc agccaggttt    8160
agccccggaa ttgactggat tccttttta gggcccattg gtatggcttt ttccccgtat    8220
cccccaggt gtctgcaggc tcaaagagca gcgagaagcg ttcagaggaa agcgatcccg    8280
tgccaccttc cccgtgcccg ggctgtcccc gcacgctgcc ggctcgggga tgcggggga    8340
gcgccgaccc ggagcgggagc cccggcggc tcgtgctgc cccctagcgg ggagggacg    8400
taattacatc cctgggggct ttgggggggg gctgtccctg gcctccaagg ccagcttccc    8460
acaataagtt gggtgaattt tggctcattc ctcctttcta taggattgag gtcagagctt    8520
tgtgatggga attctgtgga atgtgtgtca gttagggtgt ggaaagtccc gcgatcgcta    8580
gcaaacgcca gcaacgcggc cttttacgg ttcctgcctt tttgctggcc ttttgctcac    8640
atgtcggca ggcagctgcg cgctcgctcg ctcactgagg ccgcccggg aaagcccggg    8700
cgtcgggcga cctttggtcg cccggcctca gtgagcgagc gagcgcgcag agagggagtg    8760
gccaactcca tcactagggg ttcctgcggc cgcacgcgtg gagctagtta ttaatagtaa    8820
tcaattacgg ggtcattagt tcatagccca tatatggagt tccgcgttac ataacttacg    8880
gtaaatggcc cgcctggctg accgcccaac gacccccgcc cattgacgtc aataatgacg    8940
tatgttccca tagtaacgtc aatagggact ttccattgac gtcaatgggt ggagtattta    9000
cggtaaactg cccacttggc agtacatcaa gtgtatcata tgccaagtac gccccctatt    9060
gacgtcaatg acggtaaatg gcccgcctgg cattatgccc agtacatgac cttatgggac    9120
tttcctactt ggcagtacat ctacgtatta gtcatcgcta ttaccatggt gatgcggttt    9180
tggcagtaca tcaatgggcg tggatagcgg tttgactcac ggggatttcc aagtctccac    9240
cccattgacg tcaatgggag tttgttttgc accaaaatca acgggacttt ccaaaatgtc    9300
gtaacaactc cgccccattg acgcaaatgg gcggtaggcg tgtacggtgg gaggtctata    9360
taagcagagc tcgtttagtg aaccgtcaga tcgcctggag acgccatcca cgctgttttg    9420
acctccatag aagacaccgg gaccgatcca gcctccgcgg attcgaatcc cggccgggaa    9480
cggtgcattg aacgcgggat tccccgtgcc aagagtgacg taagtaccgc ctatagagtc    9540
tataggccca caaaaaatgc tttcttcttt taatatactt ttttgtttat ctttattcta    9600
atactttccc taatctcttt cttcagggc aataatgata caattgtatca tgcctctttg    9660
caccattcta aagaataaca gtgataattt ctgggttaag gcaatagcaa tatttctgca    9720
tataaatatt tctgcatata aattgtaact gatgtaagag gtttcatatt gctaatagca    9780
gctacaatcc agctaccatt ctgcttttat tttatggttg ggataaggct ggattattct    9840
gagtccaagc taggccttt tgctaatcat gttcatacct cttatcttcc tcccacagct    9900
cctgggcaac gtgctggtct gtgtgctggc ccatcacttt ggcaaagaat tgggattcga    9960
acatcgattg aattctgaat ggtgagcaag ggcgaggagc tgttcaccgg ggtggtgccc    10020
atcctggtcg agctggacgg cgacgtaaac ggccacaagt tcagcgtgtc cggcgagggc    10080
gagggcgatg ccacctacgg caagctgacc ctgaagttca tctgcaccac cggcaagctg    10140
cccgtgccct ggcccaccct cgtgaccacc ctgacctacg gcgtgcagtg cttcagccgc    10200
taccccgacc acatgaagca gcacgacttc ttcaagtccg ccatgcccga aggctacgtc    10260
caggagcgca ccatcttctt caaggacgac ggcaactaca agacccgcgc cgaggtgaag    10320
ttcgagggcg acacccctgg gaaccgcatc gagctgaagg gcatcgactt caaggaggac    10380
ggcaacatcc tggggcacaa gctggagtac aactacaaca gccacaacgt ctatatcatg    10440
gccgacaagc agaagaacgg catcaaggtg aacttcaaga tccgccacaa catcgaggac    10500
ggcagcgtgc agctcgccga ccactaccag cagaacaccc ccatcggcga cggccccgtg    10560
ctgctgcccg acaaccacta cctgagcacc cagtccgccc tgagcaaaga ccccaacgag    10620
aagcgcgatc acatggtcct gctggagttc gtgaccgccg ccgggatcac tctcggcatg    10680
gacgagctgt acaagtactc agatctcgag ctcaagtagg atcctctag agtcgacctg    10740
cagaagcttg cctcgagcag cgctgctcga gatctcagg ggtggcatcc ctgtgacccc    10800
tccccagtgc ctctcctggc cctggaagtt gccactccag tgcccaccag ccttgtccta    10860
ataaaattaa gttgcatcat tttgtctgac taggtgtcct tctataatat tatggggtgg    10920
aggggggtgg tatggagcaa ggggcaagtt gggaagacaa cctgtagggc ctgcgggtc    10980
tattgggaac caagctggag tgcagtggca caatcttggc tcactgcaat ctccgcctcc    11040
tgggttcaag cgattctcct gcctcagcct cccgagttgt tgggattcca ggcatgcatg    11100
```

-continued

```
accaggctca gctaatttt gtttttttgg tagagacggg gtttcaccat attggccagg   11160
ctggtctcca actcctaatc tcaggtgatc tacccacctt ggcctcccaa attgctggga   11220
ttacaggcgt gaaccactgc tcccttcct gtccttctga ttttgtaggt aaccacgtgc   11280
ggaccgagcg gccgcaggaa cccctagtga tggagttggc cactccctct ctgcgcgctc   11340
gctcgctcac tgaggccggg cgaccaaagg tcgcccgacg cccgggcttt gcccgggcgg   11400
cctcagtgag cgagcgagcg cgcagctgcc tgcaggggcg cctgatgcgg tatttctcc   11460
ttacgcatct gtgcggtatt tcacaccgca tacgtcgtag ctgatcaatt ggcgcgccga   11520
attcgttaac aagctttaat taacgcgtat acctaggatc cggccggcct gcaggtgtcc   11580
tcacaggaac gaagtcccta aagaaacagt ggcagccagt tttagcccg gaattgactg     11640
gattccttt ttagggccca ttggtatggc tttttcccg tatcccccca ggtgtctgca    11700
ggctcaaaga gcagcgagaa gcgttcgag gaaagcgatc ccgtgccacc ttccccgtgc    11760
ccgggctgtc cccgcacgct gccggctcgg ggatgcgggg ggagcgccgg accggagcgg   11820
agccccgggc ggctcgctgc tgcccctag cggggggagg acgtaattac atccctgggg    11880
gcttgggg ggggctgtcc ctggcctcca aggcagtt cccacaataa gttgggtgaa       11940
ttttggctca ttcctccttt ctataggatt gaggtcagag cggggttggg gttgcgcctt   12000
ttccaaggca gccctgggtt tgcgcaggga cgcggctgct ctgggcgtgg ttccgggaaa   12060
cgcagcggcg ccgaccctgg gtctcgcaca ttcttcacgt ccgttcgcag cgtcacccgg   12120
atcttcgccg ctacccttgt gggccccccg gcgacgcttc ctgctccgcc cctaagtcgg   12180
gaaggttcct tgcggttcgc ggcgtgccgg acgtgacaaa cggaagccgc acgtctcact   12240
agtaccctcg cagacggaca gcgccaggga gcaatggcag cgcgccgacc gcgatgggct   12300
gtggccaata gcggctgctc agcagggcgc gccgagagca gcggccggga aggggcggtg   12360
cgggaggcgg ggtgtggggc ggtagtgtgg gccctgttcc tgcccgccgg gtgttccgca   12420
ttctgcaagc ctccggagcg cacgtcggca gtcggctccc tcgttgaccg aatcaccgac   12480
ctctctcccc agaagctccc gggagcttgt atatccattt tcggatctga tcagcacgtg   12540
ttgacaatta atcatcggca tagtatatcg gcatagtata atacgacaag gtgaggaacg   12600
ccaccatgaa aaagcctgaa tcaccgcga cgtctgtcga gaagtttctg atcgaaaagt    12660
tcgacagcgt ctccgacctg atgcagctct cggagggcga agaatctcgt gctttcagct   12720
tcgatgtagg agggcgtgga tatgtcctgc gggtaaatag ctgcgccgat ggtttctaca   12780
aagatcgtta tgtttatcgg cactttgcat cggccgcgct cccgattccg gaagtgcttg   12840
acattgggga attcagcgag agcctgacct attgcatctc ccgccgtgca cagggtgtca   12900
cgttgcaaga cctgcctgaa accgaactgc ccgctgttct gcagccgtc gcggaggcca    12960
tggatgcgat cgctgcggcc gatcttagcc agacgagcgg gttcggccca ttcggaccgc   13020
aaggaatcgg tcaatacact acatggcgtg atttcatatg cgcgattgct gatccccatg   13080
tgtatcactg gcaaactgtg atggacgaca ccgtcagtgc gtccgtcgcg caggctctcg   13140
atgagctgat gctttgggcc gaggactgcc ccgaagtccg gcacctcgtg cacgcggatt   13200
tcggctccaa caatgtcctg acggacaatg gccgcataac agcggtcatt gactgagcg    13260
aggcgatgtt cggggattcc caatacgagg tcgccaacat cttcttctgg aggccgtggt   13320
tggcttgtat ggagcagcag acgcgctact tcgagcggag gcatccggag cttgcaggat   13380
cgccgcggct ccggggcgtat atgctccgca ttggtcttga ccaactctat cagagcttg    13440
ttgacgcaa tttcgatgat gcagcttggg cgcagggtcg atgcgacgca atcgtccgat    13500
ccggagccgg gactgtcggg cgtacacaaa tcgcccgcag aagcgcggcc gtctggaccg   13560
atggctgtgt agaagtactc gccgatagtg gaaaccgacg ccccagcact cgtccgaggg   13620
caaaggaata gagcgcgggg atctcatgct ggagttcttc gcccaccccca acttgtttat   13680
tgcagcttat aatggttaca aataaagcaa tagcatcaca aatttcacaa ataaagcatt   13740
ttttcactg cattctagtt gtggtttgtc caaactcatc aatgtatctt atcatgtctg    13800
tagctgatgt atacctagga tccggccggc ctgcaggtgt cctcacagga acgaagtccc   13860
taaagaaaca gtggcagcca ggtttagccc cggaattgac tggattcctt tttagggccc   13920
attggtatgg cttttccccc gtatccccccc aggtgtctgc aggctcaaag agcagcgaga   13980
agcgttcaga ggaaagcgat cccgtgccac cttccccgtg cccgggctgt ccccgcacgc   14040
tgccggctcg gggatgcggg gggagcgccg gaccggagcg gagccccggg cggctcgctg   14100
ctgcccccta gcggggggagg gacgtaatta catccctggg ggctttgggg ggctttggg   14160
cctctagagc ggccgccacc gcggtggagc tccagctttt gttcccttta gtgagggtta   14220
attagatctt aatacgactc actataggc gaattgggta ccgggccccc cctcgaggtc    14280
gacggtatcg ataagcttga tatctataac aagaaatat atatataata agttatcacg    14340
taagtagaac atgaaataac aatataatta tcgtatgagt taaatcttaa aagtcacgta   14400
aaagataatc atgcgtcatt ttgactcacg cggtcgttat agttcaaaat cagtgacact   14460
taccgcattg acaagcacgc ctcacgggag ctccaagcgg cgactgagat gtcctaaatg   14520
cacagcgacg gattcgcgct atttagaag agagagcaat atttcaagaa tgcatgcgtc    14580
aatttttacgc agactatctt tctagggtta atctagctgc atcaggatca tatcgtcggg   14640
tctttttcc ggctcagtca tcgcccaagc tggcgctatc tgggcatcgg ggaggaagaa    14700
gcccgtgcct tttcccgcga ggttgaagcg gcatggaaag agtttgccga ggatgactgc   14760
tgctgcattg acgttgagcg aaaacgcacg tttaccatga tgattcggga aggtgtggcc   14820
atgcacgcct ttaacggtga actgttcgtt caggccacct gggataccag ttcgtcgcgg   14880
cttttccgga cacagttccg gatggtcagc ccgaagccga tcagcaaccc gaacaatacc   14940
ggcgacagcc ggaactgccg tgccggtgtg cagattaatg acagcggtgc ggcgctggga   15000
tattacgtca gcgaggacgg gtatcctggc tggatgccgc agaaatggac atggataccc   15060
cgtgagttac ccgcgggcg cgcttggcgt aatcatggtc atagctgttt cctgtgtgaa    15120
attgttatcc gctcacaatt ccacacaaca tacgagccgg aagcataaa gtgtaaagcct   15180
ggggtgccta atgagtgagc taactcacat taattgcgt gcgctcactg cccgctttcc    15240
agtcgggaaa cctgtcgtgc cagctgcatt aatgaatcgg ccaacgcgcg gggagaggcg   15300
gtttgcgtat tgggcgctct tccgcttcct cgctcactga ctcgctgcgc tcggtcgttc   15360
ggctgcggcg agcggtatca gctcactcaa aggcggtaat acggttatcc acagaatcag   15420
gggataacgc aggaaagaac atgtgagcaa aaggccagca aaaggccagg aaccgtaaaa   15480
aggccgcgtt gctggcgttt ttccataggc tccgcccccc tgacgagcat cacaaaaatc   15540
gacgctcaag tcagaggtgg cgaaacccga caggactata aagataccag gcgtttcccc   15600
ctggaagctc cctcgtgcgc tctcctgttc cgaccctgcc gcttaccgga tacctgtccg   15660
cctttctccc ttcgggaagc gtggcgcttt ctcatagctc acgctgtagg tatctcagtt   15720
cggtgtaggt cgttcgctcc aagctgggct gtgtgcacga acccccccgtt cagcccgacc   15780
gctgcgcctt atccggtaac tatcgtcttg agtccaaccc ggtaagacac gacttatcgc   15840
```

```
cactggcagc agccactggt aacaggatta gcagagcgag gtatgtaggc ggtgctacag   15900
agttcttgaa gtggtggcct aactacggct acactagaag gacagtattt ggtatctgcg   15960
ctctgctgaa gccagttacc ttcggaaaaa gagttggtag ctcttgatcc ggcaaacaaa   16020
ccaccgctgt tagcggtggt ttttttgttt gcaagcagca gattacgcgc agaaaaaaag   16080
gatctcaaga agatcctttg atcttttcta cggggtctga cgctcagtgg aacgaaaact   16140
cacgttaagg gattttggtc atgagattat caaaaaggat cttcacctag atccttttaa   16200
attaaaaatg aagttttaaa tcaatctaaa gtatatatga gtaaacttgg tctgacagtt   16260
accaatgctt aatcagtgag gcacctatct cagcgatctg tctatttcgt tcatccatag   16320
ttgcctgact ccccgtcgtg tagataacta cgatacggga gggcttacca tctggcccca   16380
gtgctgcaat gataccgcga gacccacgct caccggctcc agatttatca gcaataaacc   16440
agccagccgg aagggccgag cgcagaagtg gtcctgcaac tttatccgcc tccatccagt   16500
ctattaattg ttgccgggaa gctagagtaa gtagttcgcc agttaatagt ttgcgcaacg   16560
ttgttgccat tgctacaggc atcgtggtgt cacgctcgtc gtttggtatg gcttcattca   16620
gctccggttc ccaacgatca aggcgagtta catgatcccc catgttgtgc aaaaaagcgg   16680
ttagctcctt cggtcctccg atcgttgtca gaagtaagtt ggccgcagtg ttatcactca   16740
tggttatggc agcactgcat aattctctta ctgtcatgcc atccgtaaga tgcttttctg   16800
tgactggtga gtactcaacc aagtcattct gagaatagtg tatgcggcga ccgagttgct   16860
cttgcccggc gtcaatacgg gataataccg cgccacatag cagaacttta aaagtgctca   16920
tcattggaaa acgttcttcg gggcgaaaac tctcaaggat cttaccgctg ttgagatcca   16980
gttcgatgta acccactcgt gcacccaact gatcttcagc atcttttact ttcaccagcg   17040
tttctgggtg agcaaaaaca ggaaggcaaa atgccgcaaa aaagggaata agggcgacac   17100
ggaaatgttg aatactcat                                                17119

SEQ ID NO: 32         moltype = DNA  length = 16835
FEATURE               Location/Qualifiers
misc_feature          1..16835
                      note = Synthetic: PB-iCap8split-ITRGFP-hygro-3
source                1..16835
                      mol_type = other DNA
                      organism = synthetic construct
SEQUENCE: 32
actcttcctt tttcaatatt attgaagcat ttatcagggt tattgtctca tgagcggata   60
catatttgaa tgtatttaga aaaataaaca aataggggtt ccgcgcacat ttccccgaaa   120
agtgccacct aaattgtaag cgttaatatt ttgttaaaat tcgcgttaaa tttttgttaa   180
atcagctcat ttttttaacca ataggccgaa atcggcaaaa tcccttataa atcaaaagaa   240
tagaccgaga tagggttgag tgttgttcca gtttggaaca agagtccact attaaagaac   300
gtggactcca acgtcaaagg gcgaaaaacc gtctatcagg gcgatggccc actacgtgaa   360
ccatcaccct aatcaagttt tttggggtcg aggtgccgta aagcactaaa tcggaaccct   420
aaagggagcc cccgatttag agcttgacgg ggaaagccgg cgaacgtggc gagaaaggaa   480
gggaagaaag cgaaaggagc gggcgctagg gcgctggcaa gtgtagcggt cacgctgcgc   540
gtaaccacca cacccgccgc gcttaatgcg ccgctacagg gcgcgtccca ttcgccattc   600
aggctgcgca actgttggga agggcgatcg gtgcgggcct cttcgctatt acgccagctg   660
gcgaaagggg gatgtgctgc aaggcgatta agttgggtaa cgccagggtt ttcccagtca   720
cgacgttgta aaacgacggc cagtgagcgc gcctcgttca ttcacgtttt tgaacccgtg   780
gaggacgggc agactcgcgg tgcaaatgtg ttttacagcg tgatggagca gatgaagatg   840
ctcgacacgc tgcagaacac gcagctagat taaccctaga aagataatca tattgtgacg   900
tacgttaaag ataatcatgc gtaaaattga tgcatgttat ttatcggtct gtatatcgag   960
gtttatttat taatttgaat agatattaag ttttattata tttacactta catactaata   1020
ataaattcaa caaacaattt atttatgttt atttatttat taaaaaaaaa caaaaactca   1080
aaatttcttc tataaagtaa caaaactttt atcgaattcc tgcagcccgg gggatccact   1140
agttctagag ggacagcccc cccccaaagc cccagggat gtaattacgt ccctccccg    1200
ctaggggggca gcagcgagcc gcccggggct ccgctccggt ccggcgctcc cccgcatcc   1260
ccgagccggc agcgtgcggg gacagcccgg gcacggggaa ggtggcacgg gatcgctttc   1320
ctctgaacgc ttctcgctgc tctttgagcc tgcagacacc tggggggata cggggaaaag   1380
gcctccaagg ccagcttccc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcgtttaaac ttaagcttgg taccgagctc ggatccacta   1560
gtccagtgtg gtggaattcc tgcttcgcga tgtacgggcc agatatacgc gtggcctccg   1620
cgccgggttt tggcgcctcc cgcgggcgcc ccctcctca cggcgagcgc tgcacgtca    1680
gacgaagggc gcagcgagcg tcctgatcct tccgcccgga cgctcaggac gcggcccgc   1740
tgctcataag actcggcctt agaacccag tatcagcaga aggacatttt aggacgggac    1800
ttgggtgact ctagggcact ggttttcttt ccagagagcg gaacaggcga ggaaaagtag   1860
tcccttctcg gcgattctgc ggagggatct ccgtgggggc gtgaacgccg atgattatat   1920
aaggacgcgc cggtccctat cagtgataga tcatcccta tcagtgatag agatgtggc    1980
acagtagtt ccgtcgcagc cgggatttgg gtcgcggttc ttgtttgtgg atcgctgtga   2040
tcgtcacttg acgaacgcgc agccgccatg gcgctgatg gctatctgcc tgattggctg   2100
gaagataacc tgagtgaggg catccgggaa tggtgggccc tgaagcctgg agccccgaag   2160
cccaaagcca accagcaaaa gcaggacgac ggccggggtc tggtgcttcc tggctacaag   2220
tacctcggac ccttcaacgg actcgacaag ggggcagcgc tcaacgcagc gcagcagcg   2280
gccctcgagc acgacaaggc ctacgaccag cagctgcagg cggtgacaa tccgtacctg   2340
cggtataacc acgccgacgc cgagtttcag gagcgtctgc aagaagatac gtcttttggg   2400
ggcaacctcg ggcgagcagt cttccaggcc aagaagcggg ttctcgaacc tctcggtctg   2460
gttgaggaag cgctaagac ggctcctgga agaagaggc cggtagaacc tagccccag    2520
cgatctccag attcttctac cggcatcggc aaaaaggcc aacagccca gagaaagtcg    2580
ctgaacttcg gccagaccgg agacagcgag agcgtgccg accctcagcc tctgggcgag   2640
cccctgccg ccccttctgg cgtgggccc aacaccatgg ccgccggcgg cggagccct     2700
atggccgaca caacgagggg cgccgacggc gtggaagca gcagcggcaa ttggcactgc   2760
gactccacct ggctgggcga cagagtgatc accacatcta caagaacctg gccctgccc   2820
acctacaaca tcacctgta caagcagatc agcaatggaa cctctggagg cgccaccaac   2880
```

```
gataacacct actttggcta cagcaccect tggggatatt tcgacttcaa ccggttccac 2940
tgtcacttca gccctcggga ctggcagcgt ctcattaaca ataactgggg cttcagacca 3000
aagagactga gcttcaagct gttcaacatc caggtgaagg aagtgaccca aaacgagggc 3060
accaagacca tcgccaataa cctcacctcc acaatccaag tgttcaccga ttccgagtac 3120
cagctgcctt acgtgctggg ctccgcccac cagggctgcc tgccaccatt ccccgccgac 3180
gtgttcatga tccctcagta cggctacctg acactgaaca acggatctca agcagtgggc 3240
agaagctcct tctactgtct ggagtacttc cctagccaga tgctgaggac aggcaacaat 3300
ttccagttca cctacacatt cgaggacgtc ccttttcaca gctcttatgc ccatagccag 3360
agcctggata gactgatgaa ccctctgatc gaccagtatc tgtattacct gagcagaacg 3420
caaacaacag gcggcaccgc taatacccag accctgggtt tcagccaagg cggcctaac 3480
acaatggcca atcaggccaa aaactggctt cctggcccct gctacagaca gcaaagagtg 3540
agcacaacca ccgccagaa caacaactct aacttcgcct ggacagccgg caccaaatac 3600
cacctgaacg gcagaaacag cctggccaac cctggaatcg ctatggctac acacaaggac 3660
gatgaggaac ggttcttccc cagcaaggc atcctgatct tcggcaagca gaacgccgct 3720
cgcgacaacg ccgactacag cgacgtgatg ctgaccagcg aggaagaaat caagacaaca 3780
aacccggtcg ccaccgagga atacggcatt gtggccgata acctgcagca gcagaatacc 3840
gcccctcaga tcggcaccgt gaactccag ggagccctgc ctggcatggt gtggcagaac 3900
agagatgtgt acctgcaggg ccctatctgg gccaagatcc cccacaccga ccggaaatttc 3960
catccaagcc ctctgatggg cggattggc ctgaagcacc cccctccaca gattctcatc 4020
aaaaacacac ctgtgccagc cgaccctccc acaacattta atcagtctaa gctgaatagc 4080
ttcatcaccc agtacagcac cggccaggtg tccgtgaaa tcgagtggga gctgcagaaa 4140
gagaacacaa agagatggaa ccctgagatc cagtacacca gcaactacta caaaagcaca 4200
agcgtggact tcgccgttaa tactgagggc gtctactcag agcctcggcc catcggcact 4260
cggtacctga ccagaaacct gaatggctag gatccggccg gcctgcaggt gtcctcacag 4320
gaacgaagtc cctaaagaaa cagtggcagc caggtttagc cccggaaaac ttgtttattg 4380
cagcttataa tggttacaaa taaagcaata gcatcacaaa tttcacaaat aaagcatttt 4440
tttcactgca ttctagttgt ggtttgtcca aactcatcaa tgtatcttat tgactggatt 4500
gagggacagc cccccccaa agcccccagg gatgtaatta cgtccctccc ccgctagggg 4560
gcagcagcga gccgccggg gctccgctcc ggtccggcgc tccccccgca tccccgagcc 4620
ggcagcgtgc ggggacagcc cgggcagggg gaaggtgcag cgggatcgct ttcctctgaa 4680
cgcttctcgc tgctctttga gcctgcagac acctggggg atacggggaa aaggcctcca 4740
aggcagctt cccacaataa gttgggtgaa ttttggctca ttcctccttt ctataggatt 4800
gaggtcagag cgacattgat tattgactag ttattaatag taatcaatta cggggtcatt 4860
agttcatagc ccatatatgg agttccgcgt tacataactt acggtaaatg gcccgcctgg 4920
ctgaccgccc aacgaccccc gcccattgac gtcaataatg acgtatgttc ccatagtaac 4980
gccaataggg actttccatt gacgtcaatg ggtggagtat ttacggtaaa ctgcccactt 5040
ggcagtacat caagtgtatc atatgccaag tacgcccct attgacgtca atgacggtaa 5100
atggcccgcc tggcattatg cccagtacat gaccttatgg gactttccta cttggcagta 5160
catctacgta ttagtcatcg ctattaccat ggtgatgcgg ttttggcagt acatcaatgg 5220
gcgtggatag cggtttgact cacggggatt tccaagtctc cacccattg acgtcaatgg 5280
gagtttgttt tggaaccaaa atcaacggga cttttccaaaa tgtcgtaaca actccgcccc 5340
attgacgcaa atgggcggta ggcgtgtacg gtgggaggtc tatataagca gagctctccc 5400
tatcagtgat agagatctcc ctatcagtga tagagatctc cctatcagtga tagagatctc gacgacgctc gtttagtgaa 5460
ccgtcagatc gcctggagac gccatccacg ctgtttgac ctccatagaa gacaccggga 5520
ccgatccagc ctatcccaat tctgatgcgc cggtgatcag atcaaaaact tcagccaggt 5580
acggcgctaa gacggctcct ggaaagaaga ggccggtaga gccatcaccc cagcgttctc 5640
cagactcctc tacgggcatc ggcaagaaag gccaacagcc cgccagaaaa agactcaatt 5700
ttggtcagac tggcgactca gagtcagttc cagaccctca acctctcgga gaacctccag 5760
cagcgccctc tggtgtggga cctaatacaa tggctgcagg cggtgccgca ccaatggcag 5820
acaataacga aggcgccgac ggagtgggta gttcctcggg aaattggcat gcgattcca 5880
catggctggg cgacagagtc atcaccacca gcacccgaac ctgggccctg cccacctaca 5940
acaaccacct ctacaagcaa atctccaacg ggacatcggg aggagccacc aacgacaaca 6000
cctacttcgg ctacagcacc ccctgggggt attttgactt taacagattc cactgccact 6060
tttcaccacg tgactggcag cgactcatca acaacaactg gggattccgg cccaagagac 6120
tcagcttcaa gctcttcaac atccaggtca aggaggtcac gcagaatgaa ggcaccaaga 6180
ccatcgccaa taacctcacc agcaccatcc aggtgtttac ggactcggag taccagctgc 6240
cgtacgttct cggctctgcc caccagggct gcctgcctcc gttccggcg gacgtgttca 6300
tgattcccca gtacggctac ctaacactca acaacgtag tcaggccgtg ggacgctcct 6360
ccttctactg cctggaatac ttccttcgc agatgctgag aaccggcaac aacttccagt 6420
ttacttacac cttcgaggac gtgccttttc acagcagcta cgcccacagc cagagcctgg 6480
accggctgat gaatcctctg attgaccagt acctgtacta cttgtctcgg actcaaacaa 6540
caggaggcac ggcaaatacg cagactctgg gcttcagcca aggtgggcct aatacaatgg 6600
ccaatcaggc aaagaactgg ctgccaggac cctgttaccg ccaacaacgc gtctcaacga 6660
caaccgggca aaacaacaat agcaactttg cctggactgc aggaccaaaa taccatctga 6720
atggaagaaa ttcattggct aatcctggca tcgctatggc aacacacaaa gacgacgagg 6780
agcgttttt tccagtaac gggatcctga ttttggcaa acaaaatgct gccagagaca 6840
atgcggatta cagcgatgtc atgctcacca gcgaggaaga aatcaaaacc actaaccctg 6900
tggctacaga ggaatacggt atcgtggcag ataacttgca ggcaacaaac aggctcctg 6960
aaattggaac tgtcaacagc caggggggcct tacccgtat ggtctggcag aacggggacg 7020
tgtacctgca gggtcccatc tgggccaaga ttcctcacac ggacggcaac ttccaccgt 7080
ctccgctgat gggcggcttt ggcctgaaac atcctccgcc tcagatcctg atcaagaaca 7140
cgcctgtacc tgcggatcct ccgaccacct tcaaccagtc aaagctgaac tctttcatca 7200
cgcaatacag caccggacag gtcagcgtgg aaattgaatg ggagctgcag aaggaaaaca 7260
gcaagcgctg gaaccccgag atccagtaca ccaacaatct acaagtgtgt 7320
actttgctgt taatacagaa ggcgtgtact ctgaacccg cccattggc acccgttacc 7380
tcacccgtaa tctgtaaact agtttgcttg ttaatcaata aaccgtttaa ttcgtttcag 7440
ttgagcggc gtcgagtcta gagggcccgt ttaaacccgc tgatcagcct cgactgtgcc 7500
ttctagttgc cagccatctg ttgtttgccc ctccccccgtg ccttccttga ccctggaagg 7560
tgccactccc actgtccttt cctaataaaa tgaggaaatt gcatcgcatt gtctgagtag 7620
```

```
gtgtcattct attctggggg gtggggtggg gcaggacagc aagggggagg attgggaaga   7680
caatagcagg catgctgggg atgcggtggg ctctatggct tctgaggcgg aaagaaccag   7740
ctggggctct aggggggtatc cccggcgcgc cgaattcgtt aacaagcttt aattaacgcg   7800
tatacctagg atccggccgg cctgcaggtg tcctcacagg aacgaagtcc ctaaagaaac   7860
agtggcagcc aggtttagcc ccggaattga ctggattcct ttttttagggc ccattggtat   7920
ggcttttttcc ccgtatcccc ccaggtgtct gcaggctcaa agagcagcga gaagcgttca   7980
gaggaaagcg atcccgtgcc accttccccg tgcccgggct gtcccgcac gctgccggct   8040
cggggatgcg gggggagcgc cggaccggag cggagcccg gcggctcgc tgctgccccc   8100
tagcggggga gggacgtaat tacatccctg ggggcttttgg ggggggggctg tccctggcct   8160
ccaaggccag cttcccacaa taagttgggt gaattttggc tcattcctcc tttctatagg   8220
attgaggtca gagctttgtg atgggaattc tgtggaatgt gtgtcagtta gggtgtggaa   8280
agtcccgcga tcgctagcaa acgccagcaa cgcggccttt ttacggttcc tggccttttg   8340
ctggcctttt gctcacatgt cctgcaggca gctgcgcgct cgctcgctca ctgaggccgc   8400
ccgggcaaag cccgggcgtc gggcgacctt tggtcgccga gcctcagtga gcgagcgagc   8460
gcgcagagag ggagtggcca actccatcac taggggttcc tgcggccgca cgcgtggagc   8520
tagttattaa tagtaatcaa ttacgggtc attagttcat agcccatata tggagttccg   8580
cgttacataa cttacggtaa atggcccgcc tggctgaccg cccaacgacc cccgcccatt   8640
gacgtcaata atgacgtatg ttcccatagt aacgtcaata gggactttcc attgacgtca   8700
atgggtggag tatttacggt aaactgccca cttggcagta catcaagtgt atcatatgcc   8760
aagtacgccc cctattgacg tcaatgacgg taaatggccc gcctggcatt atgcccagta   8820
catgacctta tgggactttc ctacttggca gtacatctac gtattagtca tcgctattac   8880
catggtgatg cggttttggc agtacatcaa tgggcgtgga tagcggtttg actcacgggg   8940
atttccaagt ctccacccca ttgacgtcaa tgggagtttg ttttgcacca aaatcaacgg   9000
gactttccaa aatgtcgtaa caactccgcc ccattgacgc aaatgggcgg taggcgtgta   9060
cggtgggagg tctatataag cagagctcgt ttagtgaacc gtcagatcgc ctggagacgc   9120
catccacgct gttttgacct ccatagaaga caccgggacc gatccagcct ccgcggattc   9180
gaatcccggc cgggaacggt gcattggaac gcggattccc cgtgccaaga gtgacgtaag   9240
taccgcctat agagtctata ggcccacaaa aaatgctttc ttcttttaat atactttttt   9300
gtttatctta tttctaatac tttccctaat ctctttcttt cagggcaata atgatacaat   9360
gtatcatgcc tctttgcacc atttctaaaga ataacagtaa taatttctgg gttaaggcaa   9420
tagcaatatt tctgcatata aatatttctg catataaatt gtaactgatg taagaggttt   9480
catattgcta atagcagcta caatccagct accattctgc ttttatttta tggttgggat   9540
aaggctggat tattctgagt ccaagctagg ccctttttgct aatcatgttc atacctctta   9600
tcttcctccc acagctcctg ggcaacgtgc tggtctgtgt gctggcccat cactttggca   9660
aagaattggg attcgaacat cgattgaatt ctgaatggtg agcaagggcg aggagctgtt   9720
caccggggtg gtgcccatcc tggtcgagct ggacggcgac gtaaacggcc acaagttcag   9780
cgtgtccggc gagggcgagg gcgatgccac ctacggcaag ctgaccctga agttcatctg   9840
caccaccggc aagctgcccg tgccctggcc caccctcgtg accaccctga cctacggcgt   9900
gcagtgcttc agccgctacc ccgaccacat gaagcagcac gacttcttca agtccgccat   9960
gcccgaaggc tacgtccagg agcgcaccat cttcttcaag gacgacggca actacaagac   10020
ccgcgccgag gtgaagttcg agggcgacac cctggtgaac cgcatcgagc tgaagggcat   10080
cgacttcaag gaggacggca acatcctggg gcacaagctg gagtacaact acaacagcca   10140
caacgtctat atcatgccg acaagcagaa gaacggcatc aaggtgaact tcaagatccg   10200
ccacaacatc gaggacggca gcgtgcagct cgccgaccac taccagcaga caccccccat   10260
cggcgacggc cccgtgctgc tgcccgacaa ccactacctg agcacccagt ccgccctgag   10320
caaagacccc aacgagaagc gcgatcacat ggtcctgctg gagttcgtga ccgccgccgg   10380
gatcactctc ggcatggacg agctgtacaa gtactcagat ctcgagctca agtagggatc   10440
ctctagagtc gacctgcaga agcttgcctc gagcagcgct gctcgagaga tctacggtg   10500
gcatccctgt gacccctccc cagtgcctct cctggccctg gaagttgcca ctccagtgcc   10560
caccagcctt gtcctaataa aattaagttg catcattttg tctgactagg tgtccttcta   10620
taatattatg gggtggaggg gggtggtatg gagcaagggg caagttggga agacaaccta   10680
tagggcctgc ggggtctatt gggaaccaag ctggagtgca gtggcacaat cttggctcac   10740
tgcaatctcc gcctcctggg ttcaagcgat tctcctgcct cagcctcccg agttgttggg   10800
attccaggca tgcatgacca ggctcagcta atttttgttt ttttggtaga gacgggtttt   10860
caccatattg gccaggctgg tctccaactc ctaatctcag gtgatctacc cacccttggcc   10920
tcccaaattg ctgggattac aggcgtgaac cactgctccc ttccctgtcc ttctgatttt   10980
gtaggtaacc acgtgcggac cgagcggccg caggaacccc tagtgatgga gttgccact   11040
ccctctctgc gcgctcgctc gctcactgag gccgggcgac caaaggtcgc ccgacgcccg   11100
ggcttttgccc gggcggcctc agtgagcgag cgagcgcgca gctgcctgca ggggcgcctg   11160
atgcggtatt ttctccttac gcatctgtgc ggtatttcac accgcatacg tcgtagctga   11220
tcaattggcc cgccgaattc gttaacaagc tttaattaac gcgtatacct aggatccggc   11280
cggcctgcag gtgtcctcac aggaacgaag tccctaaaga aacagtggca gccaggttta   11340
gccccggaat tgactggatt cctttttttag ggcccattgg tatggctttt tccccgtatc   11400
cccccaggtg tctgcaggct caaagagcag cgagaagcag tcagaggaaa gcgatcatgg   11460
gccaccttcc ccgtgcccgg gctgtccccg cacgctgccg gctcggggat gcggggggag   11520
cgccggaccg gagcggagcc ccgggcggct cgctgctgcc cctagcgggg gagggacgt   11580
aattacatcc ctgggggctt ggggggggg ctgtccctgg cctccaaggc cagcttccca   11640
caataagttg ggtgaatttt ggctcattcc tcctttctat aggattgagg tcagagcggg   11700
gttggggttg cgccttttcc aaggcagcgc tgggtttgca gggcgcgg gctgctctga   11760
gcgtggttcc gggaaacgca gcggcgccga ccctgggtct cgcacattct tcacgtccgt   11820
tcgcagcgtc acccgatct tcgccgctac ccttgtgggc cccccggcga gcttcctgc    11880
tccgccccta agtcggaag gttccttgcg gttcgcggcg tgccgacgt gacaaacgga   11940
agccgcacgt ctcactagta ccctcgcaga cggacagcgc agggagcaa tggcagcgcg   12000
cgaccgcga tgggctgtgg ccaatagcgg ctgctcagga ggcagcagcg atcgcagcg   12060
ccgggaaggg gcgtgcggg aggcggggtg tggggcggta gtgtgggccc tgttcctgcc   12120
cgcgcggtgt tccgcattct gcaagcctcc ggagcgcacg tcgcagtcg gctccctcgt   12180
tgaccgaatc accgacctct ctccccgaaa gctccgggga gcttgtatat ccattttcgg   12240
atctgatcag cacgtgttga caattaatca tcggcatagt atatcggcat agtataatac   12300
gacaaggtga ggaacgccac catgaaaaag cctgaactca ccgcgacgtc tgtcgagaag   12360
```

```
tttctgatcg aaaagttcga cagcgtctcc gacctgatgc agctctcgga gggcgaagaa    12420
tctcgtgctt tcagcttcga tgtaggaggg cgtggatatg tcctgcgggt aaatagctgc    12480
gccgatggtt tctacaaaga tcgttatgtt tatcggcact ttgcatcggc cgcgctcccg    12540
attccggaag tgcttgacat tggggaattc agcgagagcc tgacctattg catctcccgc    12600
cgtgcacagg gtgtcacgtt gcaagacctg cctgaaaccg aactgcccgc tgttctgcag    12660
ccggtcgcgg aggccatgga tgcgatcgct gcggccgatc ttagccagac gagcgggttc    12720
ggcccattcg gaccgcaagg aatcggtcaa tacactacat ggcgtgattt catatgcgcg    12780
attgctgatc cccatgtgta tcactggcaa actgtgatgg acgacaccgt cagtgcgtcc    12840
gtcgcgcagg ctctcgatga gctgatgctt tgggcgagg actgccccga agtccggcac     12900
ctcgtgcacg cggatttcgg ctccaacaat gtcctgacgg acaatggccg cataacagcg    12960
gtcattgact ggagcgaggc gatgttcggg gattccccaat acgaggtcgc caacatcttc   13020
ttctggaggc cgtggttggc ttgtatggag cagcagacgc gctacttcga gcggaggcat    13080
ccggagcttg caggatcgcc gcggctccgg gcgtatatgc tccgcattgg tcttgaccaa    13140
ctctatcaga gcttggttga cggcaatttc gatgatgcac cttgggcgca gggtcgatgc    13200
gacgcaatcg tccgatccgg agccgggact gtcgggcgta cacaaatcgc ccgcagaagc    13260
gcggccgtct ggaccgatgg ctgtgtagaa gtactcgccg atagtggaaa ccgacgcccc    13320
agcactcgtc cgagggcaaa ggaatagagc gcggggatct catgctggag ttcttcgccc    13380
accccaactt gtttattgca gcttataatg gttacaaata aagcaatagc atcacaaatt    13440
tcacaaataa agcattttt tcactgcatt ctagttgtgg tttgtccaaa ctcatcaatg     13500
tatcttatca tgtctgtagc tgatgtatac ctaggatccg gccggcctgc aggtgtcctc    13560
acaggaacga agtccctaaa gaaacagtgg cagccaggtt tagccccgga attgactgga    13620
ttccttttta gggcccattg gtatgcgttt tccccgtat cccccaggt gctgcaggc       13680
tcaaagagca gcgagaagcg ttcagaggaa agcgatcccg tgccaccttc ccgtgcccg     13740
ggctgtcccc gcacgctgcc ggctcgggga tgcgggggga gcgccggacc ggagcggagc    13800
cccgggcggc tcgctgctgc ccctagcgg gggagggacg taattacatc cctgggggct     13860
ttgggggggg gctgtccctc tagagcggcc gccaccgcgg tggagctcca gcttttgttc    13920
cctttagtga gggttaatta gatcttaata cgactcacta tagggcgaat tgggtaccgg    13980
gccccccctc gaggtcgacg gtatcgataa gcttgatatc tataacaaga aaatatatat    14040
ataataagtt atcacgtaag tagaaacatga aataacaata taattatcgt atgagttaaa   14100
tcttaaaagt cacgtaaaag ataatcatgc gtcattttga ctcacgcgtt cgttatagtt    14160
caaaatcagt gacacttacc gcattgacaa gcacgcctca cgggagctcc aagcggcgac    14220
tgagatgtcc taaatgcaca gcgacggatt cgcgctattt agaaagagag agcaatattt    14280
caagaatgca tgcgtcaatt ttacgcagac tatctttcta gggttaatct agctgcatca    14340
ggatcatatc gtcgggtctt ttttccggct cagtcatcgc ccaagctggc gctatctggg    14400
catcggggag gaagaagccc gtgccttttc ccgcgaggtt gaagcggcat ggaaagagtt    14460
tgccgaggat gactgctgct gcattgacgt tgagcgaaaa cgcacgttta ccatgatgat    14520
tcgggaaggt gtgccatgc acgcctttaa cggtgaactg ttcgttcagg ccacctggga    14580
taccagttcg tcgcggcttt tccggacaca gttccggatg gtcagcccga agcgcatcag    14640
caacccgaac aataccggcg acagccggaa ctgccgtgcc ggtgtgcaga ttaatgacag    14700
cggtgcggcg ctgggatatt acgtcagcga ggacgggtat cctggctgga tgccgcagaa    14760
atggacatgg ataccccgtg agttaccgg cgggcgcgct tggcgtaatc atggtcatag     14820
ctgtttcctg tgtgaaattg ttatccgctc acaattccac acaacatacg agccggaagc    14880
ataaagtgta aagcctgggg tgcctaatga gtgagctaac tcacattaat tgcgttgcgc    14940
tcactgcccg ctttccagtc gggaaacctg tcgtgccagc tgcattaatg aatcggccaa    15000
cgcgcgggga gaggcggttt gcgtattggg cgctcttccg cttcctcgct cactgactcg    15060
ctgcgctcgg tcgttcggct gcggcgagcg gtatcagctc actcaaaggc ggtaatacgg    15120
ttatccacag aatcagggga taacgcagga aagaacatgt gagcaaaagg ccagcaaaag    15180
gccaggaacc gtaaaaaggc cgcgttgctg gcgtttttcc ataggctccg cccccctgac    15240
gagcatcaca aaaatcgacg ctcaagtcag aggtggcgaa acccgacagg actataaaga    15300
taccaggcgt ttccccctgg aagctccctc gtgcgctctc ctgttccgac cctgccgctt    15360
accggatacc tgtccgcctt tctcccttcg ggaagcgtgg cgctttctca tagctcacgc    15420
tgtaggtatc tcagttcggt gtaggtcgtt cgctccaagc tgggctgtgt gcacgaaccc    15480
cccgttcagc ccgaccgctg cgccttatcc ggtaactatc gtcttgagtc caacccggta    15540
agacacgact tatcgccact ggcagcagcc actggtaaca ggattagcag agcgaggtat    15600
gtaggcggtg ctacagagtt cttgaagtgg tggcctaact acggctacac tagaaggaca    15660
gtatttggta tctgcgctct gctgaagcca gttaccttcg aaaaagagt tggtagctct    15720
tgatccggca aacaaaccac cgctggtagc ggtggttttt ttgtttgcaa gcagcagatt    15780
acgcgcagaa aaaaggatc tcaagaagat cctttgatct tttctacggg gtctgacgct    15840
cagtggaacg aaaactcacg ttaagggatt ttggtcatga gattatcaaa aaggatcttc    15900
acctagatcc tttaaatta aaaatgaagt tttaaatcaa tctaaagtat atatgagtaa    15960
acttggtctg acagttacca atgcttaatc agtgaggcac ctatctcagc gatctgtcta    16020
tttcgttcat ccatagttgc ctgactcccc gtcgtgtaga taactacgat acgggagggc    16080
ttaccatctg gccccagtgc tgcaatgata ccgcgagacc cacgctcacc ggctccagat    16140
ttatcagcaa taaaccagcc agccggaagg gccgagcgca gaagtggtcc tgcaacttta   16200
tccgcctcca tccagtctat taattgttgc cgggaagcta gagtaagtag ttcgccagtt    16260
aatagtttgc gcaacgttgt tgccattgct acaggcatcg tggtgtcacg ctcgtcgttt    16320
ggtatggctt cattcagctc cggttcccaa cgatcaaggc gagttacatg atcccccatg    16380
ttgtgcaaaa aagcggttag ctccttcggt cctccgatcg ttgtcagaag taagttggcc    16440
gcagtgttat cactcatggt tatggcagca ctgcataatt ctcttactgt catgccatcc    16500
gtaagatgct tttctgtgac tggtgagtac tcaaccaagt cattctgaga atagtgtatg    16560
cggcgaccga gttgctcttg cccggcgtca atacggata ataccgcgcc acatagcaga     16620
actttaaaag tgctcatcat tggaaaacgt tcttcgggc gaaactctc aaggatctta     16680
ccgctgttga gatccagttc gatgtaaccc actcgtgcac ccaactgatc ttcagcatct    16740
tttactttca ccagcgtttc tgggtgagca aaaacaggaa ggcaaaatgc cgcaaaaaag    16800
ggaataaggg cgacacggaa atgttgaata ctcat                               16835
```

SEQ ID NO: 33        moltype = DNA   length = 17649
FEATURE              Location/Qualifiers
misc_feature         1..17649

| | note = Synthetic: PB-iCap8split-ITRGFP-hygro-4 | |
|---|---|---|
| source | 1..17649 | |
| | mol_type = other DNA | |
| | organism = synthetic construct | |

SEQUENCE: 33

```
actcttcctt tttcaatatt attgaagcat ttatcagggt tattgtctca tgagcggata    60
catatttgaa tgtatttaga aaaataaaca aataggggtt ccgcgcacat ttccccgaaa   120
agtgccacct aaattgtaag cgttaatatt ttgttaaaat tcgcgttaaa ttttttgtta   180
atcagctcat tttttaacca ataggccgaa atcggcaaaa tcccttataa atcaaaagaa   240
tagaccgaga tagggttgag tgttgttcca gtttggaaca agagtccact attaaagaac   300
gtggactcca acgtcaaagg gcgaaaaacc gtctatcagg gcgatggccc actacgtgaa   360
ccatcaccct aatcaagttt ttttggggtcg aggtgccgta aagcactaaa tcggaaccct   420
aaagggagcc cccgatttag agcttgacgg ggaaagccgg cgaacgtggc gagaaaggaa   480
gggaagaaag cgaaaggagc gggcgctagg gcgctggcaa gtgtagcggt cacgctgcgc   540
gtaaccacca cacccgccgc gcttaatgcg ccgctacagg gcgcgtccca ttcgccattc   600
aggctgcgca actgttggga agggcgatcg gtgcgggcct cttcgctatt acgccagctg   660
gcgaaagggg gatgtgctgc aaggcgatta agttgggtaa cgccagggtt ttcccagtca   720
cgacgttgta aaacgacggc cagtgagcgc gcctcgttca ttcacgtttt tgaacccgtg   780
gaggacgggc agactcgcgg tgcaaatgtg ttttacagcg tgatggagca gatgaagatg   840
ctcgacacgt gcagaacac gcagctagat taaccctaga aagataatca tattgtgacg   900
tacgttaaag ataatcatgc gtaaaattga cgcatgtgtt ttatcggtct gtatatcgag   960
gtttatttat taatttgaat agatattaag ttttattata ttacactta catactaata  1020
ataaattcaa caaacaattt atttatgttt atttatttat taaaaaaaaa caaaaactca  1080
aaatttcttc tataaagtaa caaaacttttt atcgaattcc tgcagccgg gggatccact  1140
agttctagag ggacagcccc cccccaaagc ccccagggat gtaattacgt ccctcccccg  1200
ctaggggca gcagcgagcc ccccgggggct cgctccggt ccggcgctcc ccccgcatcc  1260
ccgagccggc agcgtgcggg gacagcccgg gcacgggaca ggtggcacgg gatcgctttc  1320
ctctgaacgc ttctcgctgc tctttgagcc tgcagacacc tgggggggata cggggaaaag  1380
gcctccaagg ccagcttccc acaataagtt gggtgaattt tggctcattc ctcctttcta  1440
taggattgag gtcagagctt tgtgatggga attctgtgga atgtggtgag tagcgggctg  1500
ctgggctggc cggggcttct gtggccgccg gccgctcgg tgggacggaa gcgtgtggag  1560
agaccgccaa gggctgtagt ctgggtccgc gagcaaggtt gccctgaact gggggttggg  1620
gggagcgcag caaaatggcg gctgttccgg agtcttgaat ggaagacgct tgtgaggcgg  1680
gctgtgaggt cgttgaaaca aggtgggggg catggtgggc ggcatggaac caaggtcttg  1740
aggccttcgc taatgcggga aagctcttat tcgggtgaga ttggggctgg ggccaccatcgtg  1800
ggaccctgac gtgaagttg tcactgactg gagaactcgg tttgtcgtct gttgcggggg  1860
cggcagttat ggcggtgccg ttgggcagtg caccgtgcc ttttgggagcg cgcgccctcg  1920
tcgtgtcgtg acgtcacccg ttctgttggc ttataatgca ggtggggggcc acctgccggt  1980
aggtgtgcgg taggctttt cccgtcgcag gacgcaggt tcgggcctag ggtaggctct  2040
cctgaatcga caggcgccgg acctctggtg aggggaggga taagtgaggc gtcagtttct  2100
ttggtcggtt ttatgtacct atcttcttaa gtagctgaag ctccggtttt gaactatgcg  2160
ctcgggggttg gcgagtgtgt tttgtgaagt ttttttaggca ccttttgaaa tgtaatcatt  2220
tgggtcaata tgtaattttc agtgtttagac tagtaaattg tccgctcaaa tctgccgtt  2280
tttggcttttt ttgttagact gtcagttagg gtgtggaaag tcccgcgatc gctagctttt  2340
aaacttaagc ttggtaccga gctcggatcc actagtccag tgtggtggaa ttcctgcttc  2400
gcgatgtacg ggcccagatat acgcgtgcc tccgcgccgg gttttggcgc ctcccgcggg  2460
cgcccccctc ctcacggcga gcgctgccac gtcagacgaa gggcgcagcg agcgtcctga  2520
tccttccgcc cggacgctca ggacagcggc ccgctgctca taagactcgg ccttagaacc  2580
ccagtatcag cagaaggaca ttttaggacg ggacttgggt gactctaggg cactggtttt  2640
cttttccagag agcggaacag gcgaggaaaa gtagtcccct tcgggcgatt ctgcggaggg  2700
atctccgtgg ggcggtgaac gccgatgatt atataaggac gcgccggtcc ctatcagtga  2760
tagagatctc cctatcagtg atagagagtg tggcacagct agttccgtcg cagccgggat  2820
ttgggtcgcg gttcttgttt gtggatcgct gtgatcgtca cttgacgaac gcgcagccgc  2880
catggccgct gatggctatc tgcctgattg gctggaagat aacctgagtg agggcatccg  2940
ggaatggtgg gccctgaagc ctggagcccc gaagcccaaa gccaaccagc aaaagcagga  3000
cgacggccgg ggtctggtgc ttcctggcta caagtacctc ggaccttca acggactcga  3060
caagggggag cccgtcaacg cggcggacgc agcggccctc gagcacgaca aggcctacga  3120
ccagcagctg caggcgggtg acaatccgta cctgcggtat aaccacgccg acgccgagtt  3180
tcaggagcgt ctgcaagaag atacgtcttt tgggggcaac ctcggggcga cagtcttcca  3240
ggccaagaag cgggttctcg aacctctcgg tctggttgag gaaggcgcta agacggctcc  3300
tggaaagaag aggccggtag aacctagccc ccagcgatct ccagattctt ctaccggcat  3360
cggcaaaaag ggcaacagc ctgcgagaaa gcggctgaac ttcggccaga ccggagacag  3420
cgagagcgtg cccgaccctc agcctctggg cgagccccct gccgccct ctggcgtggg  3480
ccccaacacc atggccgccg gcggcggagc cctatgccc gacaacaacg agggcgccga  3540
cggcgtggga agcagcagcg gcaattggca ctgcgactcc acctggctgg gcagagagt  3600
gatcaccaca tctacaagaa cctgggccct gccacctac aacaatacc tgtacaagca  3660
gatcagcaat ggaacctctg gaggcgccac aacgataac acctactttg ctacagcac  3720
cccttgggga tattttgact tcaaccggtt ccactgtcac ttcagccctc gggactggca  3780
gcgtctcatt aacaataact gggcttcag accaaagaga ctgagcttca agctgttcaa  3840
catccaggtg aaggaagtga cccaaaacga gggcaccaag accatcgcca taacctcac  3900
ctccacaatc caagtgttca ccgattccga gtaccagctg ccttacgtgc tgggctccgc  3960
ccaccaggc tgcctgccac cattccccgc cgacgtgttc atgatccctc agtacggcta  4020
cctgacactg aacaacggat tcaagcagt gggcagaagc tccttctact gtctggagta  4080
cttccctagc cagatgctga gacctgggaat caatttccca cattcaccag ttgatcctct  4140
cgtcccttttt cacagctctt atgcccatag ccagagctg atagactga tgaaccctct  4200
gatcgaccaga tatctgtatt acctgagcag aacgcaaaca acaggcggca cctctaatac  4260
ccagaccctg ggtttcagcc aaggcggccc taacacaatg ccaatcagg ccaaaaactg  4320
gcttcctggc cctgctaca gacagcaaag agtgagcaca accaccggcc agaacaacaa  4380
ctctaacttc gcctggacag ccggcaccaa ataccacctg aacggcagaa acagcctggc  4440
```

```
caaccctgga atcgctatgg ctacacacaa ggacgatgag gaacggttct tccccagcaa    4500
cggcatcctg atcttcggca agcagaacgc cgctcgcgac aacgccgact acagcgacgt    4560
gatgctgacc agcgaggaag aaatcaagac aacaaacccg gtcgccaccg aggaatacgg    4620
cattgtggcc gataacctgc agcagcagaa taccgcccct cagatcggca ccgtgaactc    4680
ccagggagcc ctgcctggca tggtgtggca gaacagagat gtgtacctgc agggccctat    4740
ctgggccaag atcccccaca ccgacgaaaa tttccatcca agccctctga tgggcggatt    4800
tggcctgaag caccccctc cacagattct catcaaaaac acacctgtgc cagccgaccc    4860
tcccacaaca tttaatcagt ctaagctgaa tagcttcatc acccagtaca gcaccggcca    4920
ggtgtccgtg gaaatcgagt gggagctgca gaaagagaac agcaagagat ggaaccctga    4980
gatccagtac accagcaact actacaaaag cacaagcgtg gacttcgccg ttaatactga    5040
gggcgtctac tcagagcctc ggcccatcgg cactcggtac ctgaccagaa acctgaatgg    5100
ctaggatccg gccggcctgc aggtgtcctc acaggaacga agtccctaaa gaaacagtgg    5160
cagccaggtt tagccccgga aaacttgttt attgcagctt ataatggtta caatataagc    5220
aatagcatca caaatttcac aaataaagca tttttttcc tgcattctag ttgtggtttg    5280
tccaaactca tcaatgtatc ttattgactg gattgaggga cagccccccc ccaaagcccc    5340
cagggatgta attacgtccc tccccgcta ggggcagca gcgagccgcc cggggctccg    5400
ctccggtccg gcgctccccc cgcatcccg agccggcagc gtgcgggac agcccgggca    5460
cggggaaggt ggcacgggat cgctttcctc tgaacgcttc tcgctgtct ttgagcctgc    5520
agacacctgg ggggatacgg ggaaaaggc tccaaggcca gcttcccaca ataagttggg    5580
tgaattttgg ctcattcctc ctttctatag gattgaggtc agagcgacat tgattattga    5640
ctagttatta atagtaatca attacggggt cattagttca tagcccatat atggagttcc    5700
gcgttacata acttacggta aatgcccgc ctggctgacc caacgac ccccgcccat    5760
tgacgtcaat aatgacgtat gttcccatag taacgccaat agggactttc cattgacgtc    5820
aatgggtgga gtatttacgg taaactgccc acttggcagt acatcaagtg tatcatatgc    5880
caagtacgcc ccctattgac gtcaatgacg gtaaatggcc cgcctggcat tatgcccagt    5940
acatgaccctt atgggacttt cctacttggc agtacatcta cgtattagtc atcgctatta    6000
ccatggtgat gcggttttgg cagtacatca atgggcgtgg atagcggttt gactcacggg    6060
gatttccaag tctccacccc attgacgtca atgggagttt gttttggaac caaaatcaac    6120
gggactttcc aaaatgtcgt aacaactccg ccccattgac gcaaatgggc ggtaggcgtg    6180
tacggtggga ggtctatata agcagagctc tccctatcag tgatagagat ctccctatca    6240
gtgatagaga tcgtcgacga gctcgtttag tgaaccgtca gatcgcctgg agacgccatc    6300
cacgctgttt tgacctccat agaagacacc gggaccgatc cagccatatcc caattctgat    6360
gcgccggtga tcagatcaaa aacttcagcc aggtacggcg ctaagacggc tcctggaaag    6420
aagaggccgg tagagccatc accccagcgt tctccagact cctctacggg catcggcagg    6480
aaaggccaac agcccgccag aaaaagactc aattttggtc agactcagga ctcagagtca    6540
gttccagacc ctcaacctct cggagaacct ccagcagcgc cctctggtgt gggacctaat    6600
acaatggctg caggcggtgg cgcaccaatg gcagacaata acgaaggcgc cgacggagtg    6660
ggtagttcct cgggaaattg gcattgcgat tccacatggc tgggcgacag agtcatcacc    6720
accagcacgc gaacctggcc cctgcccacc tacaacaacc acctctacaa gcaaatctcc    6780
aacgggacat cgggaggagc caccaacgac aacaccctact tcggctacag caccccctgg    6840
gggtattttg acttttaacag attccactgc cacttttcac cacgtgactg gcagcgactc    6900
atcaacaaca actggggatt ccggcccaag agactcagct tcaagctctt caacatccag    6960
gtcaaggagg tcacgcagaa tgaaggcacc aagaccatcg ccaataacct caccagcacc    7020
atccaggtgt ttacggactc ggagtaccag ctgccgtacg ttctcggctc tgcccaccag    7080
ggctgcctgc ctccgttccc ggcggacgtg ttcatgattc cccagtacgg ctacctaaca    7140
ctcaacaacg gtagtcaggc cgtgggacgc tcctccttct actgcctgga atactttcct    7200
tcgcagatgc tgagaaccgg caacaacttc cagtttactt acaccttgga ggacgtgcct    7260
ttccacagca gctacgccca cagccagagc ttggaccggc tgatgaatcc tctgattgac    7320
cagtacctgt actacttgtc tcggactcaa acaacaggag gcacggcaaa tacgcagact    7380
ctgggcttca gccaaggtgg gcctaataca atggccaatc aggcaaagaa ctggctgcca    7440
ggaccctgtt accgccaaca acgcgtctca acgacaaccg ggcaaaacaa caatagcaac    7500
tttgcctgga ctgctgggac caaataccat ctgaatggaa gaaattcatt ggctaatcct    7560
ggcatcgcta tggcaacaca caaagacgac gaggagcgtt ttttcccag taacgggatc    7620
ctgattttt gcaaacaaaa tgctgccaga gacaatgcgg attacagcga tgtcatgctc    7680
accgagagg aagaaatcaa aaccactaac cctgtggcta cagaggaata cggtatcgtg    7740
gcagataact tgcagcagca aaacacggct cctcaaattg aactgtcaa cagccagggg    7800
gccttacccg gtatggtctg gcagaaccgg gacgtgtacc tgcagggtcc catctgggcc    7860
aagattcctc acacggacgg caacttccac ccgtctccgc tgatgggcgg ctttggcctg    7920
aaacatcctc cgcctcagat cctgatcaag aacacgcctg tacctgcgga tcctccgaca    7980
accttcaacc agtcaaagct gaactctttc atcacgcaat acagcaccgg acaggtcagc    8040
gtggaaattg aatgggagct gcagaaggaa aacagcaagc gctggaaccc cgagatccag    8100
tacacctcca actactacaa atctacaagt gtggactttg ctgttaatac agaaggcgtg    8160
tactctgaac ccgcccccat tggcacccgt taccttaccc gtaatctgta aactagtttg    8220
cttgttaatc aataaaccgt ttaattcgtt tcagttgaac ggcgtcgac tctagaggg    8280
ccgtttaaac ccgctgatca gcctcgactg tgccttctag ttgccagcca tctgttgttt    8340
gcccctcccc cgtgccttcc ttgaccctgg aaggtgccac tcccactgtc ctttcctaat    8400
aaaatgagga aattgcatcg cattgtctga gtaggtgtca ttctattctg ggggtgggg    8460
tgggcagga cagcaagggg gaggattggg aagacaatag caggcatgct ggggatgcgg    8520
tgggctctat ggcttctgag gcggaaagaa ccagctgggg ctctagggg tatccccgac    8580
gcgccgaatt cgttaacaag ctttaattaa cgcgtatacc taggatccgg ccggcctgca    8640
ggtgtcctca caggaacgaa gtccctaaag aaacagtggc agcaggtttt agccccggaa    8700
ttgactggat tcctttttta gggccccattg gtatggcttt ttcccccgtat ccccccaggt    8760
gtctgcaggc tcaaagagca gcgagaagcg ttcagaggaa agcgatcccg tgccaccttc    8820
ccccgtgccg ggctgtcccc gcacgctgcc ggctcgggga tgcggggga gcgccgccgc    8880
ggagcggagc cccgggcggc tcgctgctgc ccctagcgg gggagggacg taattacatc    8940
cctggggct tgggggggg gctgtccctg gcctccaagg ccagcttccc acaataagtt    9000
gggtgaattt tggctcattc ctcctttcta taggattgag gtcagagctt tgtgatggga    9060
attctgtgga atgtgtgtca gttagggtgt ggaaagtccc cgcatcgcta gcaaacgcca    9120
gcaacgcggc cttttacgg ttcctggcct tttgctggcc ttttgctcac atgtcctgca    9180
```

```
ggcagctgcg cgctcgctcg ctcactgagg ccgcccgggc aaagcccggg cgtcgggcga  9240
cctttggtcg cccggcctca gtgagcgagc gagcgcgcag agagggagtg gccaactcca  9300
tcactagggg ttcctgcggc cgcacgcgtg gagctagtta ttaatagtaa tcaattacgg  9360
ggtcattagt tcatagccca tatatggagt tccgcgttac ataacttacg gtaaatggcc  9420
cgcctggctg accgcccaac gacccccgcc cattgacgtc aataatgacg tatgttccca  9480
tagtaacgtc aatagggact ttccattgac gtcaatgggt ggagtattta cggtaaactg  9540
cccacttggc agtacatcaa gtgtatcata tgccaagtac gccccctatt gacgtcaatg  9600
acggtaaatg gcccgcctgg cattatgccc agtacatgac cttatgggac tttcctactt  9660
ggcagtacat ctacgtatta gtcatcgcta ttaccatggt gatgcggttt tggcagtaca  9720
tcaatgggcg tggatagcgg tttgactcac ggggatttcc aagtctccac cccattgacg  9780
tcaatgggag tttgttttgc accaaaatca acgggacttt ccaaaatgtc gtaacaactc  9840
cgccccattg acgcaaatgg gcggtaggcg tgtacggtgg gaggtctata taagcagagc  9900
tcgtttagtg aaccgtcaga tcgcctggag acgccatcca cgctgttttg acctccatag  9960
aagacaccgg gaccgatcca gcctccgcgg attcgaatcc cggccgggaa cggtgcattg 10020
gaacgcggat tccccgtgcc aagagtgacg taagtaccgc ctatagagtc tataggccca 10080
caaaaaatgc tttcttcttt taatatactt ttttgtttat cttatttcta atactttccc 10140
taatctcttt ctttcagggc aataatgata caatgtatca tgcctctttg caccattcta 10200
aagaataaca gtgataattt ctgggttaag gcaatagcaa tatttctgca tataaatatt 10260
tctgcatata aattgtaact gatgtaagag gtttcatatt gctaatagca gctacaatcc 10320
agctaccatt ctgcttttat tttatggttg ggataaggct ggattattct gagtccaagc 10380
taggcccttt tgctaatcat gttcatacct cttatcttcc tcccacagct cctgggcaac 10440
gtgctggtct gtgtgctggc ccatcacttt ggcaaagaat tgggattcga acatcgattg 10500
aattctgaat ggtgagcaag ggcgaggagc tgttcaccgg ggtggtgccc atcctggtcg 10560
agctggacgg cgacgtaaac ggccacaagt tcagcgtgtc cggcgagggc gagggcgatg 10620
ccacctacgg caagctgacc ctgaagttca tctgcaccac cggcaagctg cccgtgccct 10680
ggcccaccct cgtgaccacc ctgacctacg gcgtgcagtg cttcagccgc taccccgacc 10740
acatgaagca gcacgacttc ttcaagtccg ccatgcccga aggctacgtc caggagcgca 10800
ccatcttctt caaggacgac ggcaactaca agacccgcgc cgaggtgaag ttcgagggcg 10860
acaccctggt gaaccgcatc gagctgaagg gcatcgactt caaggaggac ggcaacatcc 10920
tggggcacaa gctggagtac aactacaaca gccacaacgt ctatatcatg gccgacaagc 10980
agaagaacgg catcaaggtg aacttcaaga tccgccacaa catcgaggac ggcagcgtgc 11040
agctcgccga ccactaccag cagaacaccc ccatcggcga cggccccgtg ctgctgcccg 11100
acaaccacta cctgagcacc cagtccgccc tgagcaaaga ccccaacgag aagcgcgatc 11160
acatggtcct gctggagttc gtgaccgccg ccgggatcac tctcggcatg gacgagctgt 11220
acaagtactc agatctcgag ctcaagtagg gatcctctag agtcgacctg cagaagcttg 11280
cctcgagcag cgctgctcga gagatctacg ggtggcatcc ctgtgacccc tccccagtgc 11340
ctctcctggc cctggaagtt gccactccag tgcccaccag ccttgtccta taaaattaa 11400
gttgcatcat tttgtctgac taggtgtcct tctataatat tatgggtgg aggggggtgg 11460
tatggagcaa ggggcaagtt gggaagacaa cctgtagggc ctgcgggtc tattgggaac 11520
caagctggag tgcagtggca caatcttggc tcactgcaat ctccgcctcc tgggttcaag 11580
cgattctcct gcctcagcct cccgagttgt gggattcca ggcatgcatg accaggctca 11640
gctaattttt gttttttttgg tagagacggg gttcaccat attggccagg ctggtctcca 11700
actcctaatc tcaggtgatc tacccacctt ggcctcccaa attgctggga ttacaggcgt 11760
gaaccactgc tccttccct gtccttctga ttttgtaggt aaccacgtgc ggaccgagcg 11820
gccgcaggaa cccctagtga tggagttggc cactccctct ctgcgcgctc gctcgctcac 11880
tgaggccggg cgaccaaagg tcgcccgacg cccgggcttt gcccgggcgg cctcagtgag 11940
cgagcgagcg cgcagctgcc tgcaggggcg cctgatgcgg tatttttcct ttacgcatct 12000
gtgcggtatt tcacaccgca tacgtcgtag ctgatcaatt ggcgcgccga attcgttaac 12060
aagctttaat taacgcgtat acctaggatc cggccgcct gcaggtgtcc tcacaggaac 12120
gaagtcccta agaaacagt ggcagccagg tttagccccg gaattgactg gattccttt 12180
ttagggccca ttggtatggc ttttttcccg tatcccccca ggtgtctgca ggctcaaaga 12240
gcagcgagaa gcgttcagag gaaagcgatc ccgtgccacc ttcccgtgc ccgggctgtc 12300
cccgcacgct gccggctcgg ggatgcgggg ggagcgccgg accggagcgg agccccgggc 12360
ggctcgctgc tgcccctag cggggaggg acgtaattac atccctgggg gctttggggg 12420
gggcgtgcc ctggcctcca aggccagctt cccacaataa gttggtgaa ttttggctca 12480
ttcctccttt ctataggatt gaggtcagag cggggttggg gttgcgcctt ttccaaggca 12540
gccctgggtt tgcgcaggga cgcggctgct ctgggcgtgg ttccgggaaa cgcagcggcg 12600
ccgaccctgg gtctcgcaca ttcttcacgt ccgttcgcag cgtcacccgg atcttcgccg 12660
ctaccctgt gggcccccg gcgacgcttc ctgctccgcc cctaagtcgg gaaggttcct 12720
tgcggttcgc ggcgtgccgg acgtgacaaa cggaagccgc acgtctcact agtaccctcg 12780
cagacggaca cgccaggga gcaatggcag cgcgccgacc gcgatgggct gtggccaata 12840
gcggctgctc agcagggcgc gccgagagca gcggccggga aggggcggtg cgggaggcgg 12900
ggtgtggggc ggtagtgtgg gccctgttcc tgcccgcgcg tgttccgca ttctgcaagc 12960
ctccgggacg tccagtcggc agtcggctcc tcgttgaccg aatcaccgac ctctctcccc 13020
agaagctccc gggagcttgt atatccattt tcggatctga tcagcacgtg ttgacaatta 13080
atcatcggca tagtatatcg gcatagtata atacgacaag gtgaggaacg ccaccatgaa 13140
aaagcctgaa ctcaccgcga cgtctgtcga gaagtttctg atcgaaaagt tcgacagcgt 13200
ctccgacctg atgcagctct cggagggcga agaatctcgt gctttcagct tcgatgtagg 13260
agggcgtgga tatgtcctgc gggtaaatag ctgcgccgat ggttctacaa aagatcgtta 13320
tgtttatcgg cactttgcat cggccgcgct cccgattccg gaagtgcttg acattgggga 13380
attcagcgag agcctgacct attgcatctc ccgccgtgca cagggtgtca cgttgcaaga 13440
cctgcctgaa accgaactgc ccgctgttct gcagccggtc gcggaggcca tggatgcgat 13500
cgctgcggcc gatcttagcc agacgagcgg gttcggccca ttcggaccgc aaggaatcgg 13560
tcaatacact acatggcgtg atttcatatg cgcgattgct gatccccatg tgtatcactg 13620
gcaaactgtg atggacgaca ccgtcagtgc gtccgtcgcg caggctctcg atgagctgat 13680
gctttgggcc gaggactgcc ccgaagtccg gcacctcgtg cacgcggatt cggctccaa 13740
caatgtcctg acgacaatg gccgcataac agcggtcatt gactgagcg aggcgatgtt 13800
cggggattcc caatacgagg tcgccaacat cttcttctgg aggccgtggt tggcttgtat 13860
ggagcagcag acgcgctact tcgagcggag gcatccggag cttgcaggat cgccgcggct 13920
```

```
ccgggcgtat atgctccgca ttggtcttga ccaactctat cagagcttgg ttgacggcaa    13980
tttcgatgat gcagcttggg cgcagggtcg atgcgacgca atcgtccgat ccggagccgg    14040
gactgtcggg cgtacacaaa tcgcccgcag aagcgcggcc gtctggaccg atggctgtgt    14100
agaagtactc gccgatagtg gaaaccgacg ccccagcact cgtccgaggg caaaggaata    14160
gagcgcgggg atctcatgct ggagttcttc gcccacccca acttgtttat tgcagcttat    14220
aatggttaca aataaagcaa tagcatcaca aatttcacaa ataaagcatt tttttcactg    14280
cattctagtt gtggtttgtc caaactcatc aatgtatctt atcatgtctg tagctgatgt    14340
atacctagga tccggccggc ctgcaggtgt cctcacagga acgaagtccc taaagaaaca    14400
gtggcagcca ggtttagccc cggaattgac tggattcctt tttagggccc attggtatgg    14460
cttttttcccc gtatcccccc aggtgtctgc aggctcaaag agcagcgaga agcgttcaga    14520
ggaaagcgat cccgtgccac cttcccgtg cccgggctgt ccccgcacgc tgccggctcg    14580
gggatgcggg gggagcgccg gaccggacg gagcccgggg cggctcgctg ctgccccta    14640
gcgggggagg gacgtaatta catccctggg ggctttgggg gggggctgtc cctctagagc    14700
ggccgccacc gcggtggagc tccagctttt gttccttta gtgagggtta attagatctt    14760
aatacgactc actatagggc gaattgggta ccgggccccc cctcgaggtc gacggtatcg    14820
ataagcttga tatctataac aagaaaatat atatataata agttatcacg taagtagaac    14880
atgaaataac aatataatta tcgtatgagt taaatcttaa aagtcacgta aaagataatc    14940
atgcgtcatt ttgactcacg cggtcgttat agttcaaaat cagtgacact taccgcattg    15000
acaagcacgc ctcacgggag ctccaagcgg cgactgagat gtcctaaatg cacagcgacg    15060
gattcgcgct atttagaaag agagagcaat atttcaagaa tgcatgcgtc aattttacgc    15120
agactatctt tctagggtta atctagctgc atcaggatca tatcgtcggg tcttttttcc    15180
ggctcagtca tcgcccaagc tggcgctatc tgggcatggg aggagaaa gcccgtgcct    15240
tttccgcga ggttgaagcg gcatggaaag agtttgccga ggatgactgc tgctgcattg    15300
acgttgagcg aaaacgcacg tttaccatga tgattcggga aggtgtggcc atgcacgcct    15360
ttaacgtga actgttcgtt caggccacct gggataccag ttcgtcgcgg cttttccgga    15420
cacagttccg gatggtcagc ccgaagcgca tcagcaaccc gaacaatacc ggcgacagcc    15480
ggaactgccg tgccggtgtg cagattaatg acagcggtgc ggcgctggga tattacgtca    15540
gcgaggacg gtatcctggc tggatgccgc agaaatggac atggatacccc gtgagttac    15600
ccggcgggcg cgcttggcgt aatcatggtc atagctgttt cctgtgtgaa attgttatcc    15660
gctcacaatt ccacacaaca tacgagccgg aagcataaag tgtaaagcct ggggtgccta    15720
atgagtgagc taactcacat taattgcgtt gcgctcactg cccgctttcc agtcgggaaa    15780
cctgtcgtgc cagctgcatt aatgaatcgg ccaacgcgcg gggagaggcg gtttgcgtat    15840
tgggcgctct tccgcttcct cgctcactga ctcgctgcgc tcggtcgttc ggctgcggcg    15900
agcggtatca gctcactcaa aggcggtaat acggttatcc acagaatcag gggataacgc    15960
aggaaagaac atgtgagcaa aaggccagca aaaggccagg aaccgtaaaa aggccgcgtt    16020
gctggcgttt ttccataggc tccgcccccc tgacgagcat cacaaaaatc gacgctcaag    16080
tcagaggtgg cgaaacccga caggactata aagataccag gcgtttcccc ctggaagctc    16140
cctcgtgcgc tctcctgttc cgaccctgcc gcttaccgga tacctgtccg cctttctccc    16200
ttcgggaagc gtggcgcttt ctcatagctc acgctgtagt tatctcagtt cggtgtaggt    16260
cgttcgctcc aagctgggct gtgtgcacga acccccgtt cagcccgacc gctgcgcctt    16320
atccggtaac tatcgtcttg agtccaaccc ggtaagacac gacttatcgc cactggcagc    16380
agccactggt aacaggatta gcagagcgag gtatgtaggc ggtgctacag agttcttgaa    16440
gtggtggcct aactacggct acactagaag gacagtattt ggtatctgcg ctctgctgaa    16500
gccagttacc ttcggaaaaa gagttggtag ctcttgatcc ggcaaacaaa ccaccgctgg    16560
tagcggtggt ttttttgttt gcaagcagca gattacgcgc agaaaaaaag gatctcaaga    16620
agatcctttg atcttttcta cggggtctga cgctcagtgg aacgaaaact cacgttaagg    16680
gattttggtc atgagattat caaaaaggat cttcacctag atccttttaa attaaaaatg    16740
aagttttaaa tcaatctaaa gtatatatga gtaaacttgg tctgacagtt accaatgctt    16800
aatcagtgag gcacctatct cagcgatctg tctatttcgt tcatccatag ttgcctgact    16860
ccccgtcgtg tagataacta cgatacggga gggcttacca tctggcccca gtgctgcaat    16920
gataccgcga gacccacgct caccggctcc agatttatca gcaataaacc agccagccgg    16980
aagggccgag cgcagaagtg gtcctgcaac tttatccgcc tccatccagt ctattaattg    17040
ttgccgggaa gctagagtaa gtagttcgcc agttaatagt ttgcgcaacg ttgttgccat    17100
tgctacaggc atcgtggtgt cacgctcgtc gtttggtatg gcttcattca gctccggttc    17160
ccaacgatca aggcgagtta catgatcccc catgttgtgc aaaaaagcgg ttagctcctt    17220
cggtcctccg atcgttgtca gaagtaagtt ggccgcagtg ttatcactca tggttatggc    17280
agcactgcat aattctctta ctgtcatgcc atccgtaaga tgcttttctg tgactggtga    17340
gtactcaacc aagtcattct gagaatagtg tatgcggcga ccgagttgct cttgcccggc    17400
gtcatacagg gataataccg cgccacatag cagaacttta aaagtgctca tcattggaaa    17460
acgttcttcg gggcgaaaac tctcaaggat cttaccgctg ttgagatcca gttcgatgta    17520
acccactcgt gcacccaact gatcttcagc atcttttact ttcaccagcg tttctgggtg    17580
agcaaaaaca ggaaggcaaa atgccgcaaa aaagggaata agggcgacac ggaaatgttg    17640
aatactcat                                                           17649
```

SEQ ID NO: 34        moltype = DNA   length = 14262
FEATURE             Location/Qualifiers
misc_feature      1..14262
                     note = Synthetic: pPBBG-iCap8cd-ITRGFP-hygro
source             1..14262
                     mol_type = other DNA
                     organism = synthetic construct
SEQUENCE: 34

```
actcttcctt tttcaatatt attgaagcat ttatcagggt tattgtctca tgagcggata      60
catatttgaa tgtatttaga aaaataaaca aataggggtt ccgcgcacat ttccccgaaa     120
agtgccacct aaattgtaag cgttaatatt ttgttaaaat tcgcgttaaa ttttttgttaa    180
atcagctcat ttttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcacct aatcaagttt ttggggtcg aggtgccgta aagcactaaa tcggaaccct    420
```

```
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa ggccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaaa caaaaactca   1080
aaatttcttc tataaagtaa caaaactttt atcgaattcc tgcagccggg ggatccact    1140
agttctagag ggacagcccc cccccaaagc ccccagggat gtaattacgt ccctcccccg   1200
ctaggggca gcagcgagcc cccgggggct ccgctccggt ccggcgctcc ccccgcatcc   1260
ccgagccggc agcgtgcggg gacagcccgg gcacgggaa ggtggcacgg gatcgctttc    1320
ctctgaacgc ttctcgctgc tctttgaagcc tgcagacacc tggggggata cggggaaaag    1380
gcctccaagg ccagcttccc acaataagtt gggtgaattt tggctcattc ctcctttcta    1440
taggattgag gtcagagctt tgtgatggga attctgtgga atgtgtca gttagggtgt    1500
ggaaagtccc gcgatcgcta gcgtttaaac ttaagcttgg taccgagctc ggatccacta    1560
gtccagtgtg gtggaattcc tgcttcgcga tgtacgggcc agatatacgc gttgacattg    1620
attattgact agttattaat agtaatcaat tacgggtca ttagttcata gcccatatat    1680
ggagttccgc gttacataac ttacggtaaa tggcccgcct ggctgaccgc ccaacgaccc    1740
ccgcccattg acgtcaataa tgacgtatgt tcccatagta acgccaatag ggactttcca    1800
ttgacgtcaa tgggtggagt atttacggta aactgcccac ttggcagtac atcaagtgta    1860
tcatatgcca agtacgcccc ctattgacgt caatgacggt aaatgcccg cctggcatta    1920
tgcccagtac atgaccttat gggactttcc tacttggcag tacatctacg tattagtcat    1980
cgctattacc atggtgatgc ggttttggca gtacatcaat gggcgtggat agcggtttga    2040
ctcacgggga tttccaagtc tccaccccat tgacgtcaat gggagtttgt tttgaaccca    2100
aaatcaacgg gactttccaa aatgtcgtaa caactccgcc ccattgacgc aaatgggcgg    2160
taggcgtgta cggtgggagg tctatataag cagagctctc cctatcagtg atagagatct    2220
ccctatcagt gatagagatc gtcgacgagc tcgtttaagt tgcgcagcca tcgacgtcag    2280
acgcggaagc ttcgatcaac tacgcagaca ggtaagtaaa caaatgttct cgtcacgtgg    2340
gcatgaatct gatgctgttt ccctgcagac aatgcgagag aatgaatcag aattcaaata    2400
tctgcttcac tcacggacag aaagactgtt tagagtgctt tcccgtgtca gaatctcaac    2460
ccgtttctgt cgtcaaaaag gcgtatcaga aactgtgcta cattcatcat atcatgggaa    2520
aggtgccaga cgcttgcact gcctgcgatc tggtcaatgt ggatttggat gactgcatct    2580
ttgaacaata aatgatttaa atcaggtatg gctgccgatg gttatcttcc agattggctc    2640
gaggacaacc tctctgaggg cattcgcgag tggtgggcgc tgaaacctgg agccccgaag    2700
cccaaagcca accagcaaaa gcaggacgac ggccgggctc tggtgcttcc tggctacaag    2760
tacctcggac ccttcaacgg actcgacaag ggggagcccg tcaacgcggc ggacgcagcg    2820
gccctcgagc acgacaaggc ctacgaccag cagctgcagg cggtgacaa tccgtacctg    2880
cggtataacc acgccgacgc cgagtttcag gagcgtctgc aagaagatac gtcttttggg    2940
ggcaacctcg ggcgagcagt cttccaggcc aagaagcggg ttctcgaacc tctcggtctg    3000
gttgaggaag cgctaagac ggctcctgga aagaagaggc cggtagagcc atcacccag    3060
cgttctccag actcctctac gggcatcgg aagaaaggcc aacagccgc cagaaaaaga    3120
ctcaattttg gtcagactgg cgactcagag tcagttccag accctcaacc tctcggagaa    3180
cctccagcag cgccctctgg tgtgggacct aatacaatgg ctgcaggcgg tggcgcacca    3240
atggcagaca ataacgaagg cgccgacgga gtgggtagtt cctcgggaaa ttggcattgc    3300
gattccacat ggctgggcga cagagtcatc accaccagca cccgaacctg ggccctgccc    3360
acctacaaca accacctcta caagcaaatc tccaacggga catcgggagg agccaccaac    3420
gacaacacct acttcggcta cagcaccccc tgggggtatt ttgactttaa cagattccac    3480
tgccactttt caccacgtga ctggcagcga ctcatcaaca caactgggga ttccggccc    3540
aagagactca gcttcaagct cttcaacatc caggtcaagg aggtcacgca gaatgaaggc    3600
accaagacca tcgccaataa cctcaccagc catcaggtg tgtttacgga ctcggagtac    3660
cagctgccgt acgttctcgg ctctgccac cagggctgcc tgcctccgtt cccggcggac    3720
gtgttcatga ttcccagta cggctaccta acactcaaca acggtagtca ggccgtggga    3780
cgctcctcct tctactgcct ggaatacttt ccttcgcaga tgctgagaac cggcaacaac    3840
ttccagttta cttacacctt cgaggacgtg ccttccaca gcagctacgc ccacagccag    3900
agcttggacc ggctgatgaa tcctctgatt gaccagtacc tgtactactt gtctcggact    3960
caaacaacag gaggcacggc aaatacgcag actctgggct tcagccaagg tgggcctaat    4020
acaatggcca atcaggcaaa gaactggctg ccaggaccct gttaccgcca caacgcgtc    4080
tcaacgacaa ccgggcaaaa caacaatagc aactttgcct ggactgctgg gaccaaatac    4140
catctgaatg gaagaaattc attggctaat cctggcatcg ctatgcaac acacaaagac    4200
gacgaggagc gttttttcc cagtaacggg atcctgattt ttggcaaaca aaatgctgac    4260
agagacaatg cggattacag cgatgtcatg ctcaccagca ggaagaaat caaaaccact    4320
aaccctgtgg ctacagagga atacggtatc gtggcagata acttgcagca gcaaaacacg    4380
gctcctcaaa ttgaactgt caacagccag ggggccttac ccgtatggt ctggcagaac    4440
cgggacgtgt acctgcaggg tcccatctgg gccaagatc tcacacgga cggcaacttc    4500
cacccgtctc cgctgatggg cggctttggc ctgaaacatc ctccgcctca gatcctgatc    4560
aagaacacgc ctgtacctgc ggatcctccg accaccttca accagtcaaa gctgaactct    4620
ttcatcacgc aatacagcac cggacaggtc agcgtggaaa ttgaatggga gctgcagaag    4680
gaaaacagca agcgctggaa ccccgagatc cagtacacct ccaactacta caaatctaca    4740
agtgtggact ttgctgttaa tacagaaggc gtgtactctg aacccgccc cattggcacc    4800
cgttacctca cccgtaatct gtaaactagt ttgctttata atcaataaac cgttaattc    4860
gtttcagttg agcggccgtc gagtctagag ggcccgttta aacccgctga tcagcctcga    4920
ctgtgccttc tagttgccag ccatctgttt tttgccctc cccgtgcct tccttgaccc    4980
tggaaggtgc cactcccact gtcctttcct aataaaatga ggaaattgca tcgcattgtc    5040
tgagtaggtg tcattctatt ctgggggtg gggtgggca ggacagcaag ggggaggatt    5100
gggaagacaa tagcaggcat gctggggatg cggtgggctc tatggcttct gaggcggaaa    5160
```

```
gaaccagctg gggctctagg gggtatcccc ggcgcgccga attcgttaac aagctttaat    5220
taacgcgtat acctaggatc cggccggcct gcaggtgtcc tcacaggaac gaagtccta     5280
aagaaacagt ggcagccagg tttagccccg gaattgactg gattccttt ttagggccca    5340
ttggtatggc ttttccccg tatccccca ggtgtctgca ggctcaaaga gcagcgaaa      5400
gcgttcagag gaaagcgatc ccgtgccacc ttccccgtgc ccgggctgtc cccgcacgct    5460
gccggctcgg ggatgcgggg ggagcgccgg accggagcgg agccccgggc ggctcgctgc    5520
tgccccctag cggggaggg acgtaattac atccctgggg gctttgggg ggggctgtcc     5580
ctggcctcca aggccagctt cccacaataa gttgggtgaa ttttggctca ttcctccttt    5640
ctataggatt gaggtcagag cttttgtgatg ggaattctgt ggaatgtgtg tcagttaggg    5700
tgtggaaagt cccgcgatcg ctagcaaacg ccagcaacgc ggcctttta cggttcctgg    5760
ccttttgctg gccttttgct cacatgtcct gcaggcagct gcgcgctcgc tcgctcactg    5820
aggccgcccg ggcaaagccc gggcgtcggg cgacctttgg tcgcccggcc tcagtgagcg    5880
agcgagcgcg cagagaggga gtggccaact ccatcactag ggtttcctgc ggccgcacgc    5940
gtggagctag ttattaatag taatcaatta cggggtcatt agtcatagc ccatatatg     6000
agttccgcgt tacataactt acggtaaatg gcccgcctgg ctgaccgccc aacgaccccc    6060
gcccattgac gtcaataatg acgtatgttc ccatagtaac gtcaatagg actttccatt    6120
gacgtcaatg ggtggagtat ttacggtaaa ctgcccactt ggcagtacat caagtgtatc    6180
atatgccaag tacgcccct attgacgtca atgacggtaa atggcccgcc tggcattatg    6240
cccagtacat gaccttatgg gactttccta cttggcagta catctacgta ttagtcatcg    6300
ctattaccat ggtgatgcgg ttttggcagt acatcaatgg gcgtggatag cggtttgact    6360
cacgggatt tccaagtctc cacccccattg acgtcaatgg gagtttgttt tgcaccaaaa    6420
tcaacgggac tttccaaaat gtcgtaacaa ctccgcccca ttgacgcaaa tgggcggtaa    6480
gcgtgtacgg tgggaggtct ataagcag agctcgttta gtgaaccgtc agatcgcctg    6540
gagacgccat ccacgctgtt ttgacctcca tagaagacac cgggaccgat ccagcctccg    6600
cggattcgaa tcccggccgg gaacggtgca ttggaacgcg gattcccgt gccaagagtg    6660
acgtaagtac cgcctataga gtctataggc ccacaaaaaa tgcttttcttc ttttaatata    6720
ctttttttgtt tatcttattt ctaatacttt ccctaatctc tttctttcag ggcaataatg    6780
atacaatgta tcatgcctct ttgcaccatt ctaaagaata acagtgataa tttctgggtt    6840
aaggcaatag caatatttct gcatataaat atttctgcat ataaattgta actgatgtaa    6900
gaggttttcat attgctaata gcagctacaa tccagctacc attctgcttt tatttatgg    6960
ttgggataag gctggattat tctgagtcca agctaggccc ttttgctaat catgttcata    7020
cctcttatct tcctcccaca gctcctgggc aacgtgctgg tctgtgtgct ggcccatcac    7080
tttggcaaag aattgggatt cgaacatcga ttgaattctg aatggtgagc aagggcgagg    7140
agctgttcac cggggtggtg cccatcctgg tcgagctgga cggcgacgta aacggccaca    7200
agttcagcgt gtccggcgag ggcgagggcg atgccaccta cggcaagctg accctgaagt    7260
tcatctgcac caccggcaag ctgcccgtgc cctggcccac cctcgtgacc accctgacct    7320
acggcgtgca gtgcttcagc cgctacccc accacatgaa gcagcacgac ttcttcaagt    7380
ccgccatgcc cgaaggctac gtccaggagc gcaccatctt cttcaaggac gacggcaact    7440
acaagacccg cgccgaggtg aagttcgagg gcgacaccct ggtgaaccgc atcgagctga    7500
agggcatcga cttcaaggag gacggcaaca tcctggggca caagctggag tacaactaca    7560
acagccacaa cgtctatatc atggccgaca agcagaagaa cggcatcaag gtgaacttca    7620
agatccgcca caacatcgag gacggcagcg tgcagctcgc cgaccactac cagcagaaca    7680
ccccatcgg cgacggcccc gtgctgctgc ccgacaacca ctacctgagc acccagtccg    7740
ccctgagcaa agaccccaac gagaagcgcg atcacatgat cctgctggag ttcgtgaccg    7800
ccgccgggat cactctcggc atggacgagc tgtacaagta ctcagatctc gagctcaagt    7860
agggatccta tagagtcgac ctgcagaagc ttgcctcgag cagcgctgct cgagagatct    7920
acgggtggca tccctgtgac ccctccccag tgcctctcct ggccctggaa gttgccactc    7980
cagtgcccac cagccttgtc ctaataaaat taagttgcat cattttgtct gactaggtgt    8040
ccttctataa tattatgggg tggaggggg tggtatggag caaggggcaa gttgggaaga    8100
caacctgtag ggcctgcggg gtctattggg aaccaagctg gagtgcagtg gcacaatctt    8160
ggctcactgc aatctccgcc tcctgggttc aagcgattct cctgcctcag cctcccagt    8220
tgttgggatt ccaggcatgc atgaccagge tcagctaatt tttgtttttt tggtagagac    8280
ggggttcac catattggcc aggctggtct ccaactccta atctcaggtg atctacccac    8340
cttggcctcc caaattgctg ggattacagg cgtgaaccac tgctcccttc cctgtccttc    8400
tgatttttgta ggtaaccacg tgcggaccga gcggccgaga gaacccctag tgatggagtt    8460
ggccactccc tctctgcgcg ctcgctcgct cactgaggcc gggcgaccaa aggtcgcccg    8520
acgcccgggc tttgccccggg cggcctcagt gagcgagcga gcgcgcagct gcctgcaggg    8580
gcgcctgatg cggtattttc tccttacgca tctgtgcggt atttcacacc gcatacgtcg    8640
tagctgatca attggcgcg cgaattcgtt aacaagcttt aattaacgtc tatacctagg    8700
atccggccgg cctgcaggtg tcctcacagg aacgaagtcc ctaaagaaac agtggcagcc    8760
aggtttagcc ccggaattga ctggattcct ttttagggcc ccattggtat ggcttttcc    8820
ccgtatcccc caggtgtct gcaggctcaa agagcagcga gaagcgttca gaggaaagcg    8880
atcccgtgcc accttccccg tgcccgggct gtccccgcac gctgccggct cggggatgcg    8940
gggggagcgc cggaccggag cggagccccg ggcggctcgc tgctgccccc tagcggggga    9000
gggacgtaat tacatccctg ggggctttgg ggggggctg tccctggcct ccaaggccag    9060
cttcccacaa taagttgggt gaattttggc tcattcctcc tttctatagg attgaggtca    9120
gagcggggtt ggggttgcgc cttttccaag gcagcctgg gtttgcgcag gacgcggct    9180
gctctgggcg tggttccggg aaacgcagcg gcgccgatcc tgggctctcgc acattcttca    9240
cgtccgttcg cagcgtcacc cggatcttcc gcgctaccct tgtgggcccc ccggcgacgc    9300
ttcctgctcc gccctaagt cgggaaggtt ccttgcggtt gcggcgtgc cggacgtgac    9360
aaacggaagc cgcacgtctc actagtaccc tcgcagacgg acagcgccag ggagcaatgg    9420
cagcgcgcc accgcgatgg gctgtggcca atagcggctc tcagcaggg cgcgccgaga    9480
gcagcggccg ggaaggggcg gtgcgggagg cggggtgtgg ggcggtagtg tgggccctgt    9540
tcctgcccgc gcggtgttcc gcattctgca agcctccgtc gcagtcggt                9600
ccctcgttga ccgaatcacc gacctctctc cccagaagct cccggagct tgtatatcca    9660
ttttcggatc tgatcagcac gtgttgacaa ttaatcatcg gcatagtata tcggcatagt    9720
ataatacgac aaggtgagga acgccaccat gaaaagcct gaactcaccg cgacgtctgt    9780
cgagaagttt ctgatcgaaa agttcgacag cgtctccgac ctgatgcagc tctcggaggg    9840
cgaagaatct cgtgctttca gcttcgatgt aggagggcgt ggatatgtcc tgcgggtaaa    9900
```

-continued

```
tagctgcgcc gatggtttct acaaagatcg ttatgtttat cggcactttg catcggccgc   9960
gctcccgatt ccggaagtgc ttgacattgg ggaattcagc gagagcctga cctattgcat  10020
ctcccgccgt gcacaggagtg tcacgttgca agacctgcct gaaaccgaac tgcccgctgt  10080
tctgcagccg gtcgcggagg ccatggatgc gatcgctgcg gccgatctta gccagacgag  10140
cgggttcggc ccattcggac cgcaaggaat cggtcaatac actacatggc gtgatttcat  10200
atgcgcgatt gctgatcccc atgtgtatca ctggcaaact gtgatggacg acaccgtcag  10260
tgcgtccgtc gcgcaggctc tcgatgagct gatgctttgg gccgaggact gccccgaagt  10320
ccggcacctc gtgcacgcgg atttcggctc caacaatgtc ctgacggaca atggccgcat  10380
aacagcggtc attgactgga gcgaggcgat gttcggggat tcccaatacg aggtcgccaa  10440
catcttcttc tggaggccgt ggttggcttg tatggagcag cagacgcgct acttcgagcg  10500
gaggcatccg gagcttgcag gatcgccgcg gctccgggcg tatatgctcc gcattggtct  10560
tgaccaactc tatcagagct tggttgacgg caatttcgat gatgcagctt gggcgcaggg  10620
tcgatgcgac gcaatcgtcc gatccggagc cgggactgtc gggcgtacac aaatcgcccg  10680
cagaagcgcg gccgtctgga ccgatggctg tgtagaagta ctcgccgata gtggaaaccg  10740
acgcccagc actcgtccga gggcaaagga atagagcgcg gggatctcat gctggagttc  10800
ttcgcccacc ccaacttgtt tattgcagct tataatggtt acaaataaag caatagcatc  10860
acaaatttca caaataaagc atttttttca ctgcattcta gttgtggttt gtccaaactc  10920
atcaatgtat cttatcatgt ctgtagctga tgtataccta ggatccgcc ggcctgcagg  10980
tgtcctcaca ggaacgaagt ccctaaagaa acagtggcag ccaggtttag ccccggaatt  11040
gactggattc ctttttaggg cccattggta tggcttttc cccgtatccc ccaggtgtc   11100
tgcaggctca aagagcagcg agaagcgttc agaggaaagc gatcccgtgc caccttcccc  11160
gtgcccgggc tgtccccgca cgctgccggc tcgggagtcg ccggaccgga  11220
gcggagcccc gggcggctcg ctgctgcccc ctagcgggg agggacgtaa ttacatccct  11280
gggggctttg gggggggggct gtccctctag agcggccgcc accgcggtgg agctccagct  11340
tttgttccct ttagtgaggg ttaattagat cttaatacga ctcactatag ggcgaattgg  11400
gtaccgggcc ccccctcgag gtcgacggta tcgataagct tgatatctat aacaagaaaa  11460
tatatatata ataagttatc acgtaagtag aacatgaaat aacaatataa ttatcgtatg  11520
agttaaatct taaaagtcac gtaaaagata atcatgcgtc attttgactc acgcggtcgt  11580
tatagttcaa aatcagtgac acttaccgca ttgacaagca cgcctcacgg gagctccaag  11640
cggcgactga gatgtcctaa atgcacagcg acggattcgc gctatttaga aagagagagc  11700
aatatttcaa gaatgcatgc gtcaatttta cgcagactat cttttctaggg ttaatctagc  11760
tgcatcagga tcatatcgtc gggtctttt tccggctcag tcatcgccca agctggcgct  11820
atctgggcat cggggaggaa gaagcccgtg cctttttccg cgaggttgaa gcggcatgga  11880
aagagtttgc cgaggatgac tgctgctgca ttgacgttga gcgaaaacgc acgtttacca  11940
tgatgattcg ggaaggtgtg gccatgcacg cctttaacgg tgaactgttc gttcaggcca  12000
cctgggatac cagttcgtcg cggcttttcc ggacacagtt ccggatggtc agcccgaagc  12060
gcatcagcaa cccgaacaat accggcgaca gccggaactg ccgtgccggt gtgcagatta  12120
atgacagcgg tgcgcgctg ggatattacg tcagcgagca cgggtatcct ggctggatgc  12180
cgcagaaatg gacatggata ccccgtgagt taccccggcgg gcgcgcttgg cgtaatcatg  12240
gtcatagctg tttcctgtgt gaaattgtta tccgctcaca attccacaca acatacgagc  12300
cggaagcata aagtgtaaag cctggggtgc ctaatgagtg agctaactca cattaattgc  12360
gttgcgctca ctgcccgctt tccagtcggg aaacctgtcg tgccagctgc attaatgaat  12420
cggccaacgc gcggggagag gcggtttgcg tattgggcgc tcttccgctt cctcgctcac  12480
tgactcgctg cgctcggtcg ttcggctgcg gcgagcggta tcagctcact caaaggcggt  12540
aatacggtta tccacagaat caggggataa cgcaggaaag aacatgtgag caaaaggcca  12600
gcaaaaggcc aggaaccgta aaaaggccgc gttgctggcg ttttttccata ggctccgccc  12660
ccctgacgag catcacaaaa atcgacgctc aagtcagagg tggcgaaacc cgacaggact  12720
ataaagatac caggcgtttc ccctggaag ctccctcgtg cgctctcctg ttccgaccct  12780
gccgcttacc ggatacctgt ccgcctttct cccttcggga agcgtggcgc tttctcatag  12840
ctcacgctgt aggtatctca gttcggtgta ggtcgttcgc tccaagctgg gctgtgtgca  12900
cgaaccccc gttcagcccg accgctgcgc cttatccggt aactatcgtc ttgagtccaa  12960
cccggtaaga cacgacttat cgccactggc agcagccact ggtaacagga ttagcagagc  13020
gaggtatgta ggcggtgcta cagagttctt gaagtggtgg cctaactacg gctacactag  13080
aaggacagta tttggtatct gcgctctgct gaagccagtt accttcggaa aaagagttgg  13140
tagctcttga tccggcaaac aaaccaccgc tggtagcggt ggttttttg tttgcaagca  13200
gcagattacg cgcagaaaaa aaggatctca agaagatcct ttgatctttt ctacgggtc   13260
tgacgctcag tggaacgaaa actcacgtta agggattttg gtcatgagat tatcaaaaag  13320
gatctttcacc tagatccttt taaattaaaa atgaagtttt aaatcaatct aaagtatata  13380
tgagtaaact tggtctgaca gttaccaatg cttaatcagt gaggcaccta tctcagcgat  13440
ctgtctattt cgttcatcca tagttgcctg actccccgtc gtgtagataa ctacgatacg  13500
ggagggctta ccatctggcc ccagtgctgc aatgataccg cgagacccac gctcaccggc  13560
tccagattta tcagcaataa accagccagc cggaagggcc gagcgcagaa gtggtcctgc  13620
aactttatcc gcctccatcc agtctattaa ttgttgccgg gaagctagag taagtagttc  13680
gccagttaat agtttgcgca acgttgttgc cattgctaca ggcatcgtgg tgtcacgctc  13740
gtcgtttggt atggcttcat tcagctccgg ttcccaacga tcaaggcgag ttacatgatc  13800
ccccatgttg tgcaaaaaag cggttagctc cttcggtcct ccgatcgttg tcagaagtaa  13860
gttggccgca gtgttatcac tcatggttat ggcagcactg cataattctc ttactgtcat  13920
gccatccgta agatgctttt ctgtgactgg tgagtactca accaagtcat tctgagaata  13980
gtgtatgcgg cgaccgagtt gctcttgccc ggcgtcaata cgggataata ccgcgccaca  14040
tagcagaact taaaagtgc tcatcattgg aaaacgttct tcggggcgaa aactctcaag  14100
gatcttaccg ctgttgagat ccagttcgat gtaacccact cgtgcaccca actgatcttc  14160
agcatctttt actttcacca gcgtttctgg gtgagcaaaa acaggaaggc aaaatgccgc  14220
aaaaaaggga ataagggcga cacggaaatg ttgaatactc at                      14262
```